US008691555B2

(12) United States Patent
Bailey et al.

(10) Patent No.: US 8,691,555 B2

(45) Date of Patent: Apr. 8, 2014

(54) PRODUCTION OF CAROTENOIDS IN OLEAGINOUS YEAST AND FUNGI

(75) Inventors: Richard B. Bailey, South Natick, MA (US); Kevin T. Madden, Arlington, MA (US); Joshua Trueheart, Concord, MA (US); Reed Doten, Framingham, MA (US); Maria Mayorga, Medford, MA (US); Joshua Griffin Dunn, San Francisco, CA (US); Dan Dueppen, Woburn, MA (US)

(73) Assignee: DSM IP Assests B.V., Heerlen (NL)

( * ) Notice: Subject to any disclaimer, the term of this patent is extended or adjusted under 35 U.S.C. 154(b) by 923 days.

(21) Appl. No.: 12/443,362

(22) PCT Filed: Sep. 28, 2007

(86) PCT No.: PCT/US2007/021092

§ 371 (c)(1), (2), (4) Date: May 5, 2010

(87) PCT Pub. No.: WO2008/042338

PCT Pub. Date: Apr. 10, 2008

(65) Prior Publication Data

US 2011/0039299 A1 Feb. 17, 2011

Related U.S. Application Data

(60) Provisional application No. 60/902,145, filed on Feb. 16, 2007, provisional application No. 60/848,062, filed on Sep. 28, 2006.

(51) Int. Cl.

| | |
|---|---|
| *C12N 1/19* | (2006.01) |
| *C12N 1/15* | (2006.01) |
| *C12P 21/00* | (2006.01) |

(52) U.S. Cl.

USPC ................... 435/254.2; 435/254.11; 435/71.1

(58) Field of Classification Search

None

See application file for complete search history.

(56) References Cited

U.S. PATENT DOCUMENTS

| | | | |
|---|---|---|---|
| 4,318,987 | A | 3/1982 | Murillo Araujo et al. |
| 4,439,629 | A | 3/1984 | Ruegg |
| 4,680,314 | A | 7/1987 | Nonomura |
| 4,851,339 | A | 7/1989 | Hills |
| 4,870,011 | A | 9/1989 | Suzuki et al. |
| 4,880,741 | A | 11/1989 | Davidow et al. |
| 4,937,189 | A | 6/1990 | Davidow et al. |
| 5,071,764 | A | 12/1991 | Davidow et al. |
| 5,164,308 | A | 11/1992 | Kyle |
| 5,182,208 | A | 1/1993 | Johnson et al. |
| 5,212,088 | A | 5/1993 | Prevatt |
| 5,310,554 | A | 5/1994 | Haigh |
| 5,328,845 | A | 7/1994 | Finkelstein et al. |
| 5,349,126 | A | 9/1994 | Chappell et al. |
| 5,356,809 | A | 10/1994 | Johnson et al. |
| 5,356,810 | A | 10/1994 | Fleno et al. |
| 5,360,730 | A | 11/1994 | Orndorff et al. |
| 5,365,017 | A | 11/1994 | Chappell et al. |
| 5,374,657 | A | 12/1994 | Kyle |
| 5,378,369 | A | 1/1995 | Rose et al. |
| 5,422,247 | A | 6/1995 | Finkelstein et al. |
| 5,429,939 | A | 7/1995 | Misawa et al. |
| 5,460,949 | A | 10/1995 | Saunders et al. |
| 5,466,599 | A | 11/1995 | Jacobson et al. |
| 5,550,156 | A | 8/1996 | Kyle |
| 5,583,019 | A | 12/1996 | Barclay |
| 5,589,581 | A | 12/1996 | Misawa et al. |
| 5,589,619 | A | 12/1996 | Chappell et al. |
| 5,591,343 | A | 1/1997 | Kitaoka et al. |
| 5,599,711 | A | 2/1997 | Fleno et al. |
| 5,607,839 | A | 3/1997 | Tsubokura et al. |
| 5,643,719 | A | 7/1997 | Cerda-Olmedo et al. |
| 5,648,261 | A | 7/1997 | De Boer et al. |
| 5,679,567 | A | 10/1997 | Fleno et al. |
| 5,691,190 | A | 11/1997 | Girard et al. |
| 5,709,856 | A | 1/1998 | Fleno et al. |
| 5,712,110 | A | 1/1998 | Fleno et al. |
| 5,766,911 | A | 6/1998 | Koike et al. |
| 5,773,265 | A | 6/1998 | Koike et al. |
| 5,773,273 | A | 6/1998 | Nishino et al. |
| 5,786,193 | A | 7/1998 | Greene et al. |
| 5,786,212 | A | 7/1998 | James et al. |
| 5,792,903 | A | 8/1998 | Hirschberg et al. |
| 5,807,725 | A | 9/1998 | Ohto et al. |
| 5,811,273 | A | 9/1998 | Misawa et al. |
| 5,840,528 | A | 11/1998 | Van Ooyen |
| 5,849,524 | A | 12/1998 | Kondo et al. |
| 5,858,700 | A | 1/1999 | Ausich et al. |
| 5,858,761 | A | 1/1999 | Tsubokura et al. |
| 5,879,927 | A | 3/1999 | De Boer et al. |

(Continued)

FOREIGN PATENT DOCUMENTS

| | | |
|---|---|---|
| EP | 0005277 A2 | 11/1979 |
| EP | 0138508 A1 | 4/1985 |

(Continued)

OTHER PUBLICATIONS

Abe, Y. et al., "Effect of increased dosage of the ML-236B (compactin) biosynthetic gene cluster on ML-236B production in *Penicillium citrinum*" Mol Genet Genomics, 268:130-137 (2002).

Abe, Y. et al., "Functional analysis of micR, a regulatory gene for ML-236B (compactin) biosynthesis in *Penicillium citrinum*" Mol Genet Genomics, 268:352-361 (2002).

Abe, Y. et al., "Molecular basis of ML-236B production in the high-producing mutant No. 41520 of *Penicillium citrinum*" J. Gen. Appl. Microbial., 50:169-176 (2004).

Abe, Y. et al., "Molecular cloning and characterization of an ML-236B (compactin) biosynthetic gene cluster in *Penicillium citrinum*" Mol Genet Genomics, 267:636-646 (2002).

Adams, I. et al., "The distinctiveness of ATP:citrate lyase from *Aspergillus nidulans*" Biochim Biophys Acta, 1597:36-41 (2002).

Aharonowitz, Y. et al., "Penicillin and cephalosporin biosynthetic genes: structure, organization, regulation, and evolution" Annu. Rev. Microbiol., 46:461-95 (1992).

(Continued)

*Primary Examiner* — Michele K Joike

(74) *Attorney, Agent, or Firm* — Choate, Hall & Stewart, LLP

(57) ABSTRACT

The present invention provides systems for producing engineered oleaginous yeast or fungi that express carotenoids.

20 Claims, 52 Drawing Sheets

(56) References Cited

U.S. PATENT DOCUMENTS

| | | | |
|---|---|---|---|
| 5,882,909 | A | 3/1999 | Ohto et al. |
| 5,885,810 | A | 3/1999 | Ohto et al. |
| 5,910,433 | A | 6/1999 | Kajiwara et al. |
| 5,916,791 | A | 6/1999 | Hirschberg et al. |
| 5,922,560 | A | 7/1999 | Jacobson et al. |
| 5,928,696 | A | 7/1999 | Best et al. |
| 5,928,924 | A | 7/1999 | Greene et al. |
| 5,935,808 | A | 8/1999 | Hirschberg et al. |
| 5,935,832 | A | 8/1999 | Nakane et al. |
| 5,965,795 | A | 10/1999 | Hirschberg et al. |
| 5,972,642 | A | 10/1999 | Fleno et al. |
| 5,972,690 | A | 10/1999 | Misawa et al. |
| 6,020,177 | A | 2/2000 | Koike et al. |
| 6,040,165 | A | 3/2000 | Narita et al. |
| 6,071,733 | A | 6/2000 | Muramatsu et al. |
| 6,087,152 | A | 7/2000 | Hohmann et al. |
| 6,107,072 | A | 8/2000 | Ishida |
| 6,124,113 | A | 9/2000 | Hohmann et al. |
| 6,150,130 | A | 11/2000 | Misawa et al. |
| 6,166,231 | A | 12/2000 | Hoeksema |
| 6,207,409 | B1 | 3/2001 | Hohmann et al. |
| 6,218,599 | B1 | 4/2001 | Hirschberg et al. |
| 6,225,096 | B1 | 5/2001 | Narita et al. |
| 6,255,505 | B1 | 7/2001 | Bijl et al. |
| 6,265,185 | B1 | 7/2001 | Muller et al. |
| 6,284,506 | B1 | 9/2001 | Hoshino et al. |
| 6,291,204 | B1 | 9/2001 | Pasamontes et al. |
| 6,316,216 | B1 | 11/2001 | Ohto et al. |
| 6,329,141 | B1 | 12/2001 | Van Ooijen et al. |
| 6,365,386 | B1 | 4/2002 | Hoshino et al. |
| 6,407,306 | B1 | 6/2002 | Peter et al. |
| 6,410,288 | B1 | 6/2002 | Knutzon et al. |
| 6,413,736 | B1 | 7/2002 | Jacobson et al. |
| 6,420,135 | B1 | 7/2002 | Kunsch et al. |
| 6,448,043 | B1 | 9/2002 | Choi et al. |
| 6,531,292 | B1 | 3/2003 | Rine et al. |
| 6,531,303 | B1 | 3/2003 | Millis et al. |
| 6,541,049 | B2 | 4/2003 | Barclay |
| 6,551,807 | B1 | 4/2003 | Cunningham |
| 6,582,951 | B1 | 6/2003 | Nicaud et al. |
| 6,586,202 | B2 | 7/2003 | Hoshino et al. |
| 6,596,538 | B1 | 7/2003 | Lardizabal et al. |
| 6,600,089 | B1 | 7/2003 | Cahoon et al. |
| 6,613,543 | B2 | 9/2003 | Hohmann et al. |
| 6,627,795 | B1 | 9/2003 | Coughlan et al. |
| 6,645,767 | B1 | 11/2003 | Villa et al. |
| 6,660,507 | B2 | 12/2003 | Cheng et al. |
| 6,677,134 | B2 | 1/2004 | Pasamontes et al. |
| 6,689,593 | B2 | 2/2004 | Millis et al. |
| 6,696,293 | B2 | 2/2004 | Hoshino et al. |
| 6,709,688 | B1 | 3/2004 | Breivik et al. |
| 6,727,373 | B2 | 4/2004 | Bijl et al. |
| 6,750,048 | B2 | 6/2004 | Ruecker et al. |
| 6,753,459 | B2 | 6/2004 | Keller et al. |
| 6,753,460 | B2 | 6/2004 | Fabijanski et al. |
| 6,812,001 | B2 | 11/2004 | Sibeijn et al. |
| 6,812,009 | B2 | 11/2004 | Gladue et al. |
| 6,818,239 | B2 | 11/2004 | Kagan et al. |
| 6,818,424 | B2 | 11/2004 | DiCosimo et al. |
| 6,821,749 | B1 | 11/2004 | Kajiwara et al. |
| 6,849,434 | B2 | 2/2005 | Ingram et al. |
| 6,863,914 | B1 | 3/2005 | Auweter et al. |
| 6,869,773 | B2 | 3/2005 | Hoshino et al. |
| 6,872,556 | B2 | 3/2005 | Hoshino et al. |
| 6,929,928 | B2 | 8/2005 | Cheng et al. |
| 6,969,595 | B2 | 11/2005 | Brzostowicz et al. |
| 6,972,191 | B2 | 12/2005 | Muramatsu et al. |
| 7,015,014 | B2 | 3/2006 | Schaap et al. |
| 7,064,196 | B2 | 6/2006 | Cheng et al. |
| 7,070,952 | B2 | 7/2006 | Cheng et al. |
| 7,125,672 | B2 | 10/2006 | Picataggio et al. |
| 7,202,356 | B2 | 4/2007 | Pollak et al. |
| 7,214,491 | B2 | 5/2007 | Yadav et al. |
| 7,238,482 | B2 | 7/2007 | Picataggio et al. |
| 7,335,476 | B2 | 2/2008 | Picataggio et al. |
| 7,384,788 | B2 | 6/2008 | Van Dyk |
| 7,511,128 | B2 | 3/2009 | Picataggio et al. |
| 7,553,628 | B2 | 6/2009 | Picataggio et al. |
| 2002/0039758 | A1 | 4/2002 | De Laat et al. |
| 2002/0051998 | A1 | 5/2002 | Schmidt-Dannert et al. |
| 2002/0146784 | A1 | 10/2002 | Suzuki et al. |
| 2002/0147371 | A1 | 10/2002 | Hohmann et al. |
| 2002/0168703 | A1 | 11/2002 | Hoshino et al. |
| 2003/0022273 | A1 | 1/2003 | Pasamontes et al. |
| 2003/0033626 | A1 | 2/2003 | Hahn et al. |
| 2003/0044499 | A1 | 3/2003 | Zelkha et al. |
| 2003/0049720 | A1 | 3/2003 | Hoshino et al. |
| 2003/0054070 | A1 | 3/2003 | Bridges et al. |
| 2003/0054523 | A1 | 3/2003 | Hoshino et al. |
| 2003/0077691 | A1 | 4/2003 | Hoshino et al. |
| 2003/0087337 | A1 | 5/2003 | Giraud et al. |
| 2003/0092144 | A1 | 5/2003 | Millis et al. |
| 2003/0096385 | A1 | 5/2003 | Muramatsu et al. |
| 2003/0134353 | A1 | 7/2003 | Wolff et al. |
| 2003/0143705 | A1 | 7/2003 | Roberts et al. |
| 2003/0148319 | A1 | 8/2003 | Brzostowicz et al. |
| 2003/0148416 | A1 | 8/2003 | Berry et al. |
| 2003/0157592 | A1 | 8/2003 | Lerchl et al. |
| 2003/0190734 | A1 | 10/2003 | Hoshino et al. |
| 2003/0207947 | A1 | 11/2003 | DeSouza et al. |
| 2004/0058410 | A1 | 3/2004 | Pasamontes et al. |
| 2004/0067550 | A1 | 4/2004 | Costa Perez et al. |
| 2004/0077068 | A1 | 4/2004 | Brzostowicz et al. |
| 2004/0078846 | A1 | 4/2004 | Desouza et al. |
| 2004/0091958 | A1 | 5/2004 | Van Ooijen et al. |
| 2004/0115309 | A1 | 6/2004 | Harris |
| 2004/0116514 | A1 | 6/2004 | Nishino et al. |
| 2004/0127554 | A1 | 7/2004 | Ghisalberti |
| 2004/0152154 | A1 | 8/2004 | Perez et al. |
| 2004/0191877 | A1 | 9/2004 | Roberts et al. |
| 2004/0219629 | A1 | 11/2004 | Cheng et al. |
| 2004/0224383 | A1 | 11/2004 | Cheng et al. |
| 2004/0234579 | A1 | 11/2004 | Finke |
| 2004/0241672 | A1 | 12/2004 | Goldsmith et al. |
| 2004/0248266 | A1 | 12/2004 | Barclay |
| 2004/0253621 | A1 | 12/2004 | Picataggio et al. |
| 2004/0259959 | A1 | 12/2004 | Sharoni et al. |
| 2004/0268439 | A1 | 12/2004 | Cheng et al. |
| 2004/0268442 | A1 | 12/2004 | Miller et al. |
| 2005/0003474 | A1 | 1/2005 | Desouza et al. |
| 2005/0014219 | A1 | 1/2005 | Cheng et al. |
| 2005/0014270 | A1 | 1/2005 | Picataggio et al. |
| 2005/0019852 | A1 | 1/2005 | Cheng et al. |
| 2005/0037995 | A1 | 2/2005 | Lockwood et al. |
| 2005/0049248 | A1 | 3/2005 | Lockwood et al. |
| 2005/0071764 | A1 | 3/2005 | Jaeger |
| 2005/0096477 | A1 | 5/2005 | Gloor et al. |
| 2005/0124031 | A1 | 6/2005 | Rodriguez Saiz et al. |
| 2005/0182208 | A1 | 8/2005 | Chung et al. |
| 2005/0212088 | A1 | 9/2005 | Akaki |
| 2005/0266132 | A1 | 12/2005 | Temelli et al. |
| 2006/0015684 | A1 | 1/2006 | Schnapp et al. |
| 2006/0022701 | A1 | 2/2006 | Tokuhiro et al. |
| 2006/0040165 | A1 | 2/2006 | Uchiyama et al. |
| 2006/0071733 | A1 | 4/2006 | Hsu |
| 2006/0099670 | A1 | 5/2006 | Matuschek et al. |
| 2006/0148049 | A1 | 7/2006 | Fukuchi et al. |
| 2006/0150130 | A1 | 7/2006 | Allen et al. |
| 2006/0218599 | A1 | 9/2006 | Tannenbaum |
| 2006/0225096 | A1 | 10/2006 | Walker et al. |
| 2006/0234333 | A1 | 10/2006 | Matuschek et al. |
| 2006/0284506 | A1 | 12/2006 | Kim et al. |
| 2007/0238160 | A1 | 10/2007 | Millis et al. |
| 2008/0020438 | A1 | 1/2008 | Matsuda et al. |
| 2008/0233620 | A1 | 9/2008 | Okubo et al. |
| 2009/0233346 | A1 | 9/2009 | Picataggio et al. |
| 2009/0233347 | A1 | 9/2009 | Picataggio et al. |

FOREIGN PATENT DOCUMENTS

| | | | |
|---|---|---|---|
| EP | 0166659 | A2 | 1/1986 |
| EP | 0367765 | A1 | 5/1990 |
| EP | 0427405 | A1 | 5/1991 |
| EP | 0436562 | A1 | 7/1991 |

(56) References Cited

FOREIGN PATENT DOCUMENTS

| | | | |
|---|---|---|---|
| EP | 0438182 | A1 | 7/1991 |
| EP | 0454024 | A2 | 10/1991 |
| EP | 0474347 | A1 | 3/1992 |
| EP | 0551676 | A1 | 7/1993 |
| EP | 0587872 | A1 | 3/1994 |
| EP | 0590707 | A1 | 4/1994 |
| EP | 0670306 | A1 | 9/1995 |
| EP | 0674000 | A2 | 9/1995 |
| EP | 0719866 | A1 | 7/1996 |
| EP | 0725137 | A1 | 8/1996 |
| EP | 0735137 | | 10/1996 |
| EP | 0747483 | A2 | 12/1996 |
| EP | 0769551 | A1 | 4/1997 |
| EP | 812360 | A1 | 12/1997 |
| EP | 0812914 | A2 | 12/1997 |
| EP | 0832258 | A1 | 4/1998 |
| EP | 0870042 | A1 | 10/1998 |
| EP | 0872554 | A2 | 10/1998 |
| EP | 0877811 | A1 | 11/1998 |
| EP | 0955363 | A2 | 11/1999 |
| EP | 1035206 | A1 | 9/2000 |
| EP | 1070759 | A1 | 1/2001 |
| EP | 1111067 | A2 | 6/2001 |
| EP | 1140043 | | 10/2001 |
| EP | 1158051 | A1 | 11/2001 |
| EP | 1196583 | A2 | 4/2002 |
| EP | 1203818 | A2 | 5/2002 |
| EP | 1219704 | A2 | 7/2002 |
| EP | 1306444 | A1 | 5/2003 |
| EP | 1367131 | A1 | 12/2003 |
| EP | 1471151 | A1 | 10/2004 |
| EP | 1476546 | A2 | 11/2004 |
| EP | 1510583 | A1 | 3/2005 |
| EP | 1947189 | | 7/2008 |
| JP | 2006008712 | A | 1/2006 |
| JP | 2006008713 | A | 1/2006 |
| JP | 2006008714 | A | 1/2006 |
| JP | 2006008715 | A | 1/2006 |
| JP | 2006008716 | A | 1/2006 |
| JP | 2006008717 | A | 1/2006 |
| JP | 2006008718 | A | 1/2006 |
| JP | 2006008719 | A | 1/2006 |
| JP | 2006008720 | A | 1/2006 |
| JP | 2006016407 | A | 1/2006 |
| JP | 2006016408 | A | 1/2006 |
| JP | 2006016409 | A | 1/2006 |
| JP | 2006022121 | A | 1/2006 |
| WO | WO-8808025 | | 10/1988 |
| WO | WO-9001552 | | 2/1990 |
| WO | WO-9102060 | | 2/1991 |
| WO | WO-9221764 | | 12/1992 |
| WO | WO-9320183 | | 10/1993 |
| WO | WO-9406918 | | 3/1994 |
| WO | WO-9612013 | | 4/1996 |
| WO | WO-9621736 | A1 | 7/1996 |
| WO | WO-9628014 | | 9/1996 |
| WO | WO-9628545 | | 9/1996 |
| WO | WO-9633276 | A1 | 10/1996 |
| WO | WO-9707219 | | 2/1997 |
| WO | WO-9723633 | A1 | 7/1997 |
| WO | WO-9739114 | | 10/1997 |
| WO | WO-9807830 | A2 | 2/1998 |
| WO | WO-9820138 | A1 | 5/1998 |
| WO | WO-9837179 | | 8/1998 |
| WO | WO-9843620 | | 10/1998 |
| WO | WO-9858943 | A1 | 12/1998 |
| WO | WO-9906585 | | 2/1999 |
| WO | WO-9964618 | | 12/1999 |
| WO | WO-0001650 | | 1/2000 |
| WO | WO-0005382 | A2 | 2/2000 |
| WO | WO-0012725 | A2 | 3/2000 |
| WO | WO-0037660 | A1 | 6/2000 |
| WO | WO-0047746 | A1 | 8/2000 |
| WO | WO-0053768 | | 9/2000 |
| WO | WO-0061764 | A1 | 10/2000 |
| WO | WO-0065062 | A2 | 11/2000 |
| WO | WO-0078935 | A1 | 12/2000 |
| WO | WO-0112832 | A1 | 2/2001 |
| WO | WO-0120011 | | 3/2001 |
| WO | WO-0142455 | A1 | 6/2001 |
| WO | WO-0144276 | A2 | 6/2001 |
| WO | WO-0148163 | | 7/2001 |
| WO | WO-0166703 | A1 | 9/2001 |
| WO | WO-0183437 | A1 | 11/2001 |
| WO | WO-0218617 | | 3/2002 |
| WO | WO-0220733 | | 3/2002 |
| WO | WO-0220815 | | 3/2002 |
| WO | WO-0226933 | | 4/2002 |
| WO | WO-0241833 | | 5/2002 |
| WO | WO-02053745 | | 7/2002 |
| WO | WO-02053746 | | 7/2002 |
| WO | WO-02053747 | | 7/2002 |
| WO | WO-02059290 | | 8/2002 |
| WO | WO-02059297 | | 8/2002 |
| WO | WO-02070721 | | 9/2002 |
| WO | WO-02079395 | | 10/2002 |
| WO | WO-02088365 | | 11/2002 |
| WO | WO-02094867 | | 11/2002 |
| WO | WO-02094868 | | 11/2002 |
| WO | WO-02099095 | | 12/2002 |
| WO | WO-03000902 | A1 | 1/2003 |
| WO | WO-03012056 | | 2/2003 |
| WO | WO-03020936 | A1 | 3/2003 |
| WO | WO-03023016 | | 3/2003 |
| WO | WO-03027293 | | 4/2003 |
| WO | WO-03031642 | | 4/2003 |
| WO | WO-03038064 | | 5/2003 |
| WO | WO-03044205 | A1 | 5/2003 |
| WO | WO-03047547 | | 6/2003 |
| WO | WO-03062419 | | 7/2003 |
| WO | WO-03076575 | | 9/2003 |
| WO | WO-03097798 | | 11/2003 |
| WO | WO-2004001057 | | 12/2003 |
| WO | WO-2004013345 | | 2/2004 |
| WO | WO-2004016791 | | 2/2004 |
| WO | WO-2004018385 | | 3/2004 |
| WO | WO-2004018688 | | 3/2004 |
| WO | WO-2004018694 | | 3/2004 |
| WO | WO-2004022765 | | 3/2004 |
| WO | WO-2004029232 | | 4/2004 |
| WO | WO-2004029255 | | 4/2004 |
| WO | WO-2004029261 | | 4/2004 |
| WO | WO-2004029263 | | 4/2004 |
| WO | WO-2004029275 | | 4/2004 |
| WO | WO-2004039991 | | 5/2004 |
| WO | WO-2004047763 | | 6/2004 |
| WO | WO-2004056972 | A2 | 7/2004 |
| WO | WO-2004056974 | | 7/2004 |
| WO | WO-2004056975 | | 7/2004 |
| WO | WO-2004057012 | | 7/2004 |
| WO | WO-2004063358 | A1 | 7/2004 |
| WO | WO-2004063359 | | 7/2004 |
| WO | WO-2004063366 | | 7/2004 |
| WO | WO-2004067709 | A2 | 8/2004 |
| WO | WO-2004070035 | | 8/2004 |
| WO | WO-2004074440 | | 9/2004 |
| WO | WO-2004074490 | | 9/2004 |
| WO | WO-2004087883 | | 10/2004 |
| WO | WO-2004098530 | | 11/2004 |
| WO | WO-2004101753 | | 11/2004 |
| WO | WO-2004101757 | | 11/2004 |
| WO | WO-2004104167 | | 12/2004 |
| WO | WO-2004104180 | | 12/2004 |
| WO | WO-2004111214 | | 12/2004 |
| WO | WO-2005001024 | | 1/2005 |
| WO | WO-2005007826 | | 1/2005 |
| WO | WO-2005010156 | | 2/2005 |
| WO | WO-2005010174 | | 2/2005 |
| WO | WO-2005011712 | | 2/2005 |
| WO | WO-2005014828 | | 2/2005 |
| WO | WO-2005019467 | | 3/2005 |
| WO | WO-2006014837 | | 2/2006 |
| WO | WO-2006091924 | | 8/2006 |
| WO | WO-2006096392 | | 9/2006 |

(56) References Cited

FOREIGN PATENT DOCUMENTS

| | | |
|---|---|---|
| WO | WO-2006102342 A2 | 9/2006 |
| WO | WO-2007095007 | 8/2007 |
| WO | WO-2008042338 | 4/2008 |
| WO | WO-2008073367 | 6/2008 |
| WO | WO-2008076758 | 6/2008 |
| WO | WO-2009010826 | 1/2009 |

OTHER PUBLICATIONS

Alberts, A.W. et al., "Mevinolin: A Highly Potent Competitive Inhibitor of Hydroxymethylglutaryl-Coenzyme A Reductase and a Cholesterol-Lowering Agent" Proc. Natl. Acad. Sci USA, 77(7):3957-3961 (1980).
Alexander, N.J. et al., "TRI12, a trichothecene efflux pump from *Fusarium sporotrichioides*: gene isolation and expression in yeast" Mol Gen Genet, 261:977-984 (1999).
Appel, K.F. et al., "A multicopy vector system for genetic studies in *Mucor circinelloides* and other zygomycetes" Mol Genet Genomics, 271:595-602 (2004).
Arrach, N. et al., "Mutants of the carotene cyclase domain of al-2 from *Neurospora crassa*" Mol Genet Genomics, 266:914-21 (2002).
Arst, H.N. et al., "Do the Tightly Linked Structural Genes for Nitrate and Nilritie Reductases in *Aspergillus nidulans* Form an Operon? Evidence from an Insertional Translocation Which Separates Them" Molec gen Genet, 174: 89-100 (1979).
Atalla, M.M. et al., "Mycotoxin production in wheat grains by different Aspergilli in relation to different relative humidities and storage periods" Nahrung/Food, 47:6-10 (2003).
Athenstaedt, K. et. al., "Identification and characterization of major lipid particle proteins of the yeast *Saccharomyces cerevisiae*" J Bacteriol, 181(20):6441-6448 (1999).
Baddley, J.W. et al., "Epidemiology of *Aspergillus terreus* at a University Hospital" Journal of Clinical Microbiology, 41(12):5525-5529 (2003).
Baillie, G.S. and Douglas, L.J., "*Candida* Biofilms and Their Susceptibility to Antifungal Agents" Methods in Enzymology, 310: 644-657 (1999).
Ballance, D.J. et al., "Transformation of *Aspergillus nidulans* by the Orotidine-5'-Phosphate Decarboxylase Gene of *Neurospora crassa*" Biochemical and Biophysical Research Communications, 112(1): 284-289 (1983).
Barth et al., "*Yarrowia lipolytica*" Nonconventional Yeasts in Genetics, Biochemistry and Biotechnology, (Springer-Verlag, Berlin, Germany) 335-406 (2003).
Barth, G. and Gaillardin, C., "Physiology and genetics of the dimorphic fungus *Yarrowia lipolytica*" FEMS Microbiol Rev., 19:219-237 (1997).
Bauernfeind, "Carotenoids as colorants and vitamin A precursors" Academic Press, NY, 1&2 (1981).
Bentley, R., "Secondary Metabolite Biosynthesis: The First Century" Critical Reviews in Biotechnology, 19(1):1-40 (1999).
Bertram, J.S., "Carotenoids and Gene Regulation" Nutr. Rev., 57(6):182-191 (1999).
Bhosale, P.B. and Gadre, R.V., "Production of β-carotene by a mutant of *Rhodotorula glutinis*" Applied Microbiology and Biotechnology, 55(4):423-427 (2001).
Boeke, J.D. et al.,"Fluoroorotic Acid as a Selective Agent in Yeast Molecular Genetics" Methods Enzymol., 154:164-175 (1987).
Bok, J.W. and Keller, N.P., "LaeA, a Regulator of Secondary Metabolism in *Aspergillus* spp." Eukaryotic Cell, 3:527-535 (2004).
Boone, A.N. et al., "Bimodal activation of acetyl-GoA carboxylase by glutamate", J Biol Chem, 275:10819-25 (2000).
Borel, J.F., "Editorial: Ciclosporin and Its Future" Prog. Allergy, 38:9-18 (1986).
Boyum, R. and Guidotti, G., "Effect of ATP Binding Casselle/ Multidrug Resistance Proteins on ATP Efflux of *Saccharomyces cerevisiae*" Biochemical and Biophysical Research Communications, 230(1):22-26 (1997).
Bradamante, S. et al., "Production of Lovastatin Examined by an Integrated Approach Based on Chemometrics and DOSY-NMR" Biotechnology and Bioengineering, 80:589-593, 2002.
Bray, H.G. et al., "Kinetic Studies of the Metabolism of Foreign Organic Compounds" Kinetics of Glucuronide Formation in vivo, 52: 416-419 (1952).
Brock, M. et al., "Methylcitrate synthase from *Aspergillus nidulans*: implications for propionate as an antifungal agent" Molecular Microbiology, 35:961-973 (2000).
Brown, D.W. et al., "Twenty-five coregulaled transcripts define a sterigmatocystin gene cluster in *Aspergillus nidulans*" Proc. Natl. Acad. Sci. USA, 93: 1418-1422 (1996).
Buchholz, A. et al., "Quantification of Intracellular Metabolites in *Escherichia coli* K12 Using Liquid Chromatographic-Elctrospray Ionization Tandem Mass Spectrometric Techniques" Analytical Biochemistry, 295: 129-137 (2001).
Bundgaard, H. and Ilver, K., "A new spectrophotometric method for the determination of penicillins" J. Pharm. Pharmac., 24:790-794 (1972).
Buxton, F.P. and Radford, A., "Cloning of the Structural Gene for Orolidine 5'-Phosphate Carboxylase of *Neurospora crassa* by Expression in *Escherichia coli*" Mol Gen Genet, 190(3): 403-405 (1983).
Cannizzaro, C. et al., "Metabolic network analysis on *Phaffia rhodozyma* yeast using 13C-labeled glucose and gas chromatography-mass spectrometry" Metab Eng, 6:340-51 (2004).
Cardenas, M.E. et al., "Targets of immunophilin-immunosuppressant complexes are distinct highly conserved regions of calcineurin A" The EMBO Journal, 14:2772-2783 (1995).
Carroll, B.J. et al., "Identification of a Set of Genes Involved in the Formation of the Substrate for the Incorporation of the Unusual 'Glycolate' Chain Extension Unit in Ansamitocin Biosynthesis" J. Am. Chem. Soc., 124:4176-4177 (2002).
Casqueiro, J. et al., "Gene Targeting in *Penicillium chrysogenum*: Disruption of the lys2 Gene Leads to Penicillin Overproduction" Journal of Bacteriology, 181:1181-1188 (1999).
Cerda-Olmedo, E. and Avalos, J., "Oleaginous Fungi: Carotene-rich oil from *Phycomyces*" Progress in Lipid Res., 33(1-2): 185-192 (1994).
Chakravarti, R. and Sahai, V. "Compactin—a review" Appl Microbiol Biotechnol, 64(5):618-624 (2004).
Chen, Y. et al., "Mapping Mutations in Genes Encoding the Two Large Subunits of *Drosophila* RNA Polymerase II Defines Domains Essential for Basic Transcription Functions and for Proper Expression of Developmental Genes" Molecular and Cellular Biology, 13:4212-4222 (1993).
Chew, B.P. et al., "A Comparison of the Anticancer Activities of Dietary β-Carotene, Canthaxanthin and Astaxanthin in Mic in Vivo*" Anticancer Res., 19:1849 (1999).
Cooke, F.J. et al., "Disseminated *Aspergillus terreus* infection arising from cutaneous inoculation treated with caspofungin" Clinical Microbiology and Infection, 9: 1238-1241 (2003.
Cove, D.J., "The induction and repression of nitrate reductase in the fungus *Aspergillus nidulans*" Biochimica et Biophysica Acta, 113:51-56 (1966).
Dannaoui, E. et al., "In Vitro Evaluation of Double and Triple Combinations of Antifungal Drugs against *Aspergillus fumigatus* and *Aspergillus terreus*" Antimicrobial Agents and Chemotherapy, 48:970-978 (2004).
Davies, R.W., "Chapter 21, Heterologous Gene Expression and Protein Secretion in *Aspergillus*" Prog Ind Microbiol. 29:527-560 (1994).
Decottignies, A. and Goffeau, A., "Complete inventory of the yeast ABC proteins" nature genetics, 15:137-145 (1997.
Del Campo et al., "Accumulation of astaxanthin and lutein in *Chlorella zofingiensis* (Chlorophyta)" Appl Microbiol Biotechnol, 64:848-854 (2004).
Demain, A.L., "Microbial secondary metabolism: a new theoretical frontier for academia, a new opportunity for industry" Microbial secondary metabolism for academia and industry, 171:3-23 (1992).
Devchand, M. and Gwynne, D.I, "Expression of heterologous proteins in *Aspergillus*" Journal of Biotechnology, 17(1):3-10 (1991).

(56) References Cited

OTHER PUBLICATIONS

Dominguez-Bochanegra, A.R., et al., "Influence of environmental and nutritional factors in the production of astaxanthin from *Haematococcus pluvialis*" BioresourTechnol, 92:209-14 (2004).

Downing et al., "The isolation of two mutants of *Saccharomyces cerevisiae* which demonstrate increased activity of 3-hydroxy-3-methylglutaryl coenzyme A reductase" Chem. Abs., 93:65791y, 484 (1980).

Dowzer, C.E. and Kelly, J.M., "Analysis of the creA Gene, a Regulatro of Carbon Catabolite Repression in *Aspergillus nidulans*" Molecular and Cellular Biology, 11(11):5701-5709 (1991).

Drake, H.L. and Daniel, S.L., "Physiology of the thermophilic acetogen *Moorella thermoacetica*" Research in Microbiology, 155:422-436 (2004).

Drgonova et al., "Rho1p, a Yeast Protein at the Interface Between Cell Polarization and Morphogenesis" Science, 272:277-279 (1996).

Durand, N. et al., "Randomly amplified polymorphic DNAs assess recombination following an induced parasexual cycle in *Penicillium roqueforti*" Current Genetics, 24:417-420 (1993).

Dyal, S,.D. and Narine, S.S., "Implications for the use of *Mortierella* fungi in the industrial production of essential fatty acids" Food Res. Int., 38(4):445-467 (May 2005).

Echavarri-Erasun, C. and Johnson, E.A., "Stimulation of astaxanthin formation in the yeast *Xanthophyllomyces dendrorhous* by the fungus *Epicoccum nigrum*" FEMS Yeast Res, 4(45):511-519 (2004).

Edge, R. et al., The Carotenoids as anti-oxidants—a review J. Photochem Photobiol, 41:189-200 (1997).

Edwards, K. et al., "A simple and rapid method for the preparation of plant genomic DNA for PCR analysis" Nucleic Acids Research, 19:1349 (1991).

Endo et al., "The Synthesis of Compactin (ML-236B) and Monacolin Kin Fungi" The Journal of Antibiotics, 39:1609-1610 (1986).

Evans, C.T. and Ratledge, C., "A Comparison of the Oleaginous Yeast, *Candida curvata*, Grown on Different Carbon Sources in Continuous and Balch Culture" Lipids, 18(9):623-629 (1983).

Fabre, E. et al., "Role of the proregion in the production and secretion of the *Yarrowia lipolytica* alkaline extracellular protease" J Biol Chem, 266:3782-90 (1991).

Fauser, S. and Wissinger, B., "Simultaneous Detection of Multiple Point Mutations Using Fluorescence-Coupled Competitive Primer Extension" BioTechniques, 22:964-968 (1997).

Fickers, P. et al., "New disruption cassettes for rapid gene disruption and marker rescue in the yeast *Yarrowia lipolytica*" J Microbiol Methods, 55:727-37 (2003).

Fierro, F. et al., "High efficiency transformation of *Penicillium nalgiovense* with integrative and autonomously replicating plasmids" International Journal of Food Microbiology 90:237-248 (2004).

Flikweert, M.T. et al., "Pyruvate decarboxylase: an indispensable enzyme for growth of *Saccharomyces cerevisiae* on glucose" Yeast 12(3):247-57 (1996).

Flores, C.L. et al., "Carbohydrate and energy-yielding metabolism in non-conventional yeasts" FEMS Microbiol Rev, 24:507-29 (2000).

Gadanho, M. and Sampaio, J.P. et al., "Polyphasic taxonomy of the basidiomycetous yeast genus *Rhodolorula: Rh. glutinis* sensu stricto and *Rh. dairenensis* comb. nov" FEMS Yeast Res, 2:47-58 (2002).

Gil, G. et al., "Membrane-bound domain of HMG GoA reductase is required for sterol-enhanced degradation of the enzyme" Cell, 41:249-258 (1985).

Giovannucci, E. et al., "Intake of Carotenoids and Retinol in Relation to Risk of Prostate Cancer" J. Natl. Cancer Inst., 87(23):1767-1776 (1995).

Golubev, "Perfect state of *Rhodomyces dendrorhous* (Phaffia rhodozyma)" Yeast, 11:101-10 (1995).

Guo, J. and Frost, J.W., "Synthesis of Aminoshikimic Acid" Org Lett, 6:1585-8 (2004).

Gutierrez, S. et al., "The cefG Gene of *Cephalosporium acremonium* Is Linked to the cefEF Gene and Encodes a Deacetylcephalosporin C Acetyltransferase Closely Related to Homoserine 0-Acetyltransferase" Journal of Bacteriology, 174: 3056-3064 (1992).

Hacia, J.G., "Resequencing and mutational analysis using oligonucleotide microarrays" nature genetics supplement, 21:41-47 (1999).

Hall, D.A. et al., "Regulation of gene expression by a metabolic enzyme" Science, 306:482-4 (2004).

Han, K.H. et al., "A putative G protein-coupled receptor negatively controls sexual development in *Aspergillus nidulans*" Molecular Microbiology, 51:1333-1345 (2004).

Hancock, R.D. and Viola, R., "Biotechnological approaches for L-ascorbic acid production" Trends in Biotechnology, 20:299-305 (2002).

Hasper, A.A. et al., "Functional analysis of the transcriptional activator XInR from *Aspergillus niger*" Microbiology, 150:1367-75 (2004).

Helmuth, L., "Microbiology: Bakers' Yeast Blooms Into Biofilms" Science, 291:806-807 (2001).

Hendrickson, L. et al., "Lovastatin biosynthesis in *Aspergillus terreus*: characterization of blocked mutants, enzyme activities and a multifunctional polyketide synthase gene" Chemistry and Biology, 6:429-439 (1999).

Hundle, B.S. et al., "In vitro expression and activity of lycopene cyclase and β-carotene hydroxylase from *Erwinia herbicola*" Fed. of Eur. Biochem. Soc., 315(3):329-334 (1993).

Hutchinson, C.R. et al., "Aspects of the biosynthesis of non-aromatic fungal polykelides by iterative polykelide synthases" Antonie van Leeusenhoek, 78:287-295 (2000).

Inoue, K. "Carotenoid hydroxylation—P450 finally!" Trends Plant Sci, 9(11):515-517 (2004).

International Search Report, PCT/US2006/010271, date of mailing Jul. 31, 2007.

International Search Report, PCT/US2006/010271, filed on Sep. 27, 2007.

International Search Report, PCT/US2007/021092, date of mailing Aug. 11, 2008.

Iturriaga, E.A. et al., "Structure and function of the genes involved in the biosynthesis of carotenoids in the mucorales" Biotech. Bioprocess Eng. 5(4):263-274 (2000).

Jadoun, J. et al., "Disruption of the *Aspergillus fumigatus* argB gene using a novel in vitro transposon-based mutagenesis approach" Curr Genet, 45:235-241 (2004).

Jensen and Demain, Chapter 8, Beta-Lactams, 239-268.

Jin, Z.H. et al., "Improvement of industry-applied rifamycin B-producing strain, *Amycolatopsis mediterranei*, by rational screening" J. Gen. Appl. Microbiol., 48:329-334 (2002).

Jitrapakdee, S. and Wallace, J.C., "The Biotin Enzyme Family: Conserved Structural Motifs and Domain Rearrangements" Curr Protein Pept Sci., 4:217-229 (2003).

Johnson, E.A., "*Phaffia rhodozyma*: colorful odyssey" Int. Microbiol, 6:169-174 (2003).

Junker, B.H. et al., "Early Phase Process Scale-Up Challenges for Fungal and Filamentous Bacterial Cultures" Applied Biochemistry and Biotechnology 119:241-277 (2004).

Juretzek, T. et al., "Vectors for gene expression and amplification in the yeast *Yarrowia lipolytica*" Yeast 2001, 18:97-113 (2001).

Jyonouchi, H. et al., "Studies of Immunomodulating Actions of Carotenoids. I. Effects of β-Carotene and Astaxanthin on Murine Lymphocyte Functions and Cell Surface Marker Expression in In Vitro Culture System" Nutr. Cancer, 16(2):93-105 (1991).

Kamisaka, Y. and Noda, N., "Intracellular transport of phosphatidic acid and phosphatidylcholine into lipid bodies: use of ftuorescent lipids to study lipid-body formation in an oleaginous fungus" Biochem Soc Trans, 28:723-5 (2000).

Kanamasa, S. et al., "Transformation of *Aspergillus aculeatus* Using the Drug Resistance Gene of *Aspergillus oryzae* and the pyrG Gene of *Aspergillus nidulans*" Biosci. Biotechnol. Biochem., 67(12):2661-2663 (2003).

Kaster, K.R. et al., "Analysis of a bacterial hygromycin B resistance gene by transcriptional and translational fusions and by DNA sequencing" Nucleic Acids Research, 11:6895-6911 (1983).

(56) References Cited

OTHER PUBLICATIONS

Kato, N. et al., "The Expression of Sterigmatocystin and Penicillin Genes in *Aspergillus nidulans* Is Controlled by veA, a Gene Required for Sexual Development" Eukaryotic Cell, 2:1178-1186 (2003).
Kato, Y. et al., "Functional Expression of Genes Involved in the Biosynthesis of the Novel Polyketide Chain Extension Unit, Methoxymalonyi-Acyl Carrier Protein, and Engineered Biosynthesis of 2-Desmethyi-2-Methoxy-6- Deoxyerythronolide B" JACS Communications, 124:5268-5269 (2002).
Katzmann, D.J. et al., "Transcriptional Control of the Yeast PDR5 Gene by the PDR3 Gene Product" Molecular and Cellular Biology, 14:4653-4661 (1994).
Kelly, J.M. and Hynes, M.J., "Transformation of *Aspergillus niger* by the amdS gene of *Aspergillus nidulans*" EMBO Journal, 4:475-479 (1985).
Kendrick, A. and Ratledge, C., "Desaturation of polyunsaturated fatty acids in *Mucor circinelloides* and the involvement of a novel membrane-bound malic enzyme" Eur J Biochem, 209:667-73 (1992).
Kholsa, C. and Keasling, J.D., "Metabolic engineering for drug discovery and development" Nature, 2:1019-1025 (2003).
Kim, I.G. et al., "Cloning of the Ribosomal Protein L41 Gene of *Phaffia rhodozyma* and Its Use as a Drug Resistance Marker for Transformation" Appl Environ Microbiol., 64(5):1947-1949 (1998).
Kim, W.G. et al., "Terreulactones A, B, C, and D: Novel Acetylcholinesterase Inhibitors Produced by *Aspergillus terreus*" The Journal of Antibiotics, 56:351-357 (2003).
Kimura, E., "Metabolic Engineering of Glutamate Production" Advances in Biochemical Engineering, 79:37-57 (2003).
Kimura, K. et al., "Rapid estimation of lipids in oleaginous fungi and yeasts using Nile red fluorescence" Journal of Microbiological Methods 56:331-338 (2004).
Kimura, M. et al., "Trichothecene 3-0-Acetyltransferase Protects Both the Producing Organism and Transformed Yeast from Related Mycotoxins" The Journal of Biological Chemistry, 273:1654-1661 (1998).
Kloosterman, H. et al., "(De)regulation if key enzyme steps in the shikimate pathway and phenylalanine-specific pathway of the actinomycete *Amycolatopsis methanolica*" Microbiology, 149: 3321-3330 (2003).
Koyama, Y. "New Trends in Photobiology: Structures and functions of carotenoids in photosynthetic systems" J. Photochem Photobiol, 9:265-280 (1991).
Krinsky, N.I., "The biological properities of carotenoids" Pure Appl. Chem., 66(5):1003-1010 (1994).
Kroken, S. et al., "Phylogenomic analysis of type I polykelide synthase genes in pathogenic and saprobic ascomycetes" PNAS, 100:15670-15675 (2003).
Kumari, M. et al., "Secretion of ligninperoxidase by *Penicillium citrinum, Fusarium oxysporum* and *Aspergillus terreus*" Indian Journal of Experimental Biology, 40:802-806 (2002).
Kurischko, C., "The MATA locus of the dimorphic yeast *Yarrowia lipolytica* consists of two divergently oriented genes" Mol Gen Genet, 262:180-8 (1999).
Kyte, J. and Doolitile, R.F., "A Simple Method for Displaying the Hydropathic Character of a Protein" J. Mol. Biol., 157:105-132 (1982).
Lee, P.C. and Schmidt-Dannert, C., "Metabolic engineering towards biotechnical production of carotenoids in microorganisms" Applied Microbiology and Biotechnology, 60:1-11 (2002).
Leman, J., "Oleaginous microorganisms: an assessment of the potential" Adv Appl Microbiol, 43:195-243 (1997).
Levert, K.L. and Waldrop, G.L., "A bisubslrate analog inhibitor of the carboxyltransferase component of Acetyl-CoA carboxylase" Biochem Biophys Res Commun, 291:1213-1217 (2002).
Li, Y.G. et al., "Identification and chemical profiling of monacolins in red yeast rice using high-performance liquid chromatography with photodiode array detector and mass spectrometry" Journal of Pharaceutical and Biomedical Analysis, 35(5):1101-1112 (2004).
Liras, P. et al., "Evolution of the clusters of genes for B-lactam antibiotics: a model for evolutive combinatorial assembly of new B-lactams" Internatl Microbial, 1:271-278 (1998).
Liu, W. et al., "Extra Copies of the *Aspergillus fumigaus* Squalene Epoxidase Gene Confer Resistance to Terbinafine: Genetic Approach to Studying Gene Dose-Dependent Resistance to Antifungals in *A. fumigatus*" Antimicrobial Agents and Chemotherapy, 48:2490-2496 (2004).
Lodato, P. et al., "Study of the expression of carotenoid biosynthesis genes in wild-type and deregulated strains of *Xanthophyllomyces dendrorhous*(Ex.: *Phaffia rhodozyma*)" Biol. Res. 37(1):83-93 (2004).
Lopez-Nieto, M.J. et al., "Biotechnologicallycopene production by mated fermentation of *Blakeslea trispora*" Appl Microbiol Biotechnol (2004).
Luengo and Penalva, Chapter 23, Penicillin Biosynthesis, 603-638.
Lum, P.Y. et al., "Molecular, functional and evolutionary characterization of the gene encoding HMG-CoA reductase in the fission yeast, *Schizosaccharomyces pombe*" Yeast:1107-24 (1996).
Madzak, C. et al., "Heterologous protein expression and secretion in the non-conventional yeast *Yarrowia lipolytica*: a review" J Biotechnol., 109:63-81 (2004).
Madzak, C. et al., "Strong Hybrid Promoters and Integrative Expression/Secretion Vectors for Quasi-Constitutive Expression of Heterologous Proteins in the Yeast *Yarrowia lipolytica*" J. Mol. Microbiol. Biotechnol., 2(2):207-216 (2000).
Madzak, C. et. al., "Functional analysis of upstream regulating regions from the *Yarrowia lipolytica* XPR2 promoter" Microbiology, 145:75-87 (1999).
Maggio-Hall, L.A. and Keller, N.P., "Mitochondrial B-oxidation in *Aspergillus nidulans*" Molecular Microbiology, 54(5):1173-1185 (2004).
Malmstrom, J. et al., "Secondary metabolites characteristic of *Penicillium citrinum, Penicillium steckii* and related species" Phytochemistry, 54:301-309 ( 2000).
Mannhaupt, G. et al., "What's in the genome of a filamentous fungus? Analysis of the *Neurospora* genome sequence" Nucleic Acids Research, 31(7) :1944-1954 (2003).
Manzoni, M. and Rollini, M., "Biosynthesis and biotechnoligical production of statins by filamentous fungi and application of these cholesterol-lowering drugs" Appl Microbiol Biotechnol, 58:555-564 (2002).
Martinez, C. et al., "Genetic transformation of astaxanthin mutants of *Phaffia rhodozyma*" Antonie Van Leeuwenhoek, 73(2):147-153 (1998).
Matsumoto, G. et al., "The Trichothecene Biosynthesis Regulatory Gene from the Type B Producer *Fusarium* Strains: Sequence ofTri6 and It's Expression in *Escherichia coli*" Biosci. Biotechnol. Biochem., 63:2001-2004 (1999).
McCluskey, K. "The Fungal Genetics Stock Center: From Molds to Molecules" Advances in Applied Microbiology, 52:245-263 (2003).
Mehta, B.J. et al., "New Mutants of *Phycomyces blakesleeanus* for β-Carotene Production" Applied and Environmental Microbiology 63(9):3657-3661 (1997).
Miki, W., "Biological functions and activities of animal carotenoids" Pure Appl. Chem., 63(1):141-146 (1991).
Misawa, N. and Shimada, H., "Metabolic engineering for the production of carotenoids in noncarotenogenic bacteria and yeasts" J. Biotechnol., 59:169-181 (1998).
Miura, Y. et al., "Production of lycopene by the food yeast, *Candida utilis* that does not naturally synthesize carotenoid" Biotechnol Bioeng, 58:306-308 (1998).
Miura, Y. et al., "Production of the Carotenoids Lycopene, β-Carotene, and Astaxanthin in the Food Yeast *Candida utilis*" Appl. Environ. Microbiol., 64(4):1226-1229 (1998).
Mlickova, K. et al., "Lipid Accumulation, Lipid Body Formation, and Acyl Coenzyme A Oxidases of the Yeast *Yarrowia lipolytica*" Applied and Environmental Microbiology, 70(7):3918-3924 (2004).
Muhlrad, D. and Parker, R., "Aberrant mRNAs with extended 3' UTRs are substrates for rapid degradation by mRNA surveillance" RNA 5:1299-1307 (1999).
Muhlrad, D. et al., "A Rapid Method for Localized Mutagenesis of Yeast Genes" Yeast, 8:79-82 (1992).

(56) References Cited

OTHER PUBLICATIONS

Mullaney, E.J. et al., "Primary structure of the trpC gene from *Aspergillus nidulans*" Mol Gen Genet, 199(1):37-45 (1985).
Murphy, K.C. et al., "PCR-mediated gene replacement in *Escherichia coli*" Gene, 246:321-330 (2000).
Nakagawa, M. and Misawa, N., "Analysis of Carotenoid Glycosides Produced in Gram-negative Bacteria by Introduction of the *Erwinia uredovora* Carotenoid Biosynthesis Genes" Agric. Biol. Chem., 55(8):2147-2148 (1991).
Nannini, E.C. et al., "Peritonitis due to *Aspergillus* and zygomycetes in patients undergoing peritoneal dialysis: report of 2 cases and review of the literature" Diagnostic Microbiology and Infectious Disease, 46:49-54 (2003).
Nelissen, B. et al., "Classification of all putative permeases and other membrane plurispanners of the major facilitator superfamily encoded by the complete genome of *Saccharomyces cerevisiae*" FEMS Microbiology Reviews, 21:113-134 (1997).
Nicaud, J.M. et al., "Protein expression and secretion in the yeast *Yarrowia lipolytica*" FEMS Yeast Res, 2:371-379 (2002).
Nikolaev, I. et al., "Nuclear Import of Zinc Binuclear Cluster Proteins Proceeds through Multiple, Overlapping Transport Pathways" Eukaryotic Cell, 2(2):209-221 (2003).
Nobbs, T.J. and Halford, S.E., "DNA Cleavage at Two Recoginition Sites by the SfiI Restriction Endonuclease: Salt Dependence of Cis and Trans Interactions between Distant DNA Sites" J. Mol. Bioi., 252(4):399-411 (1995).
Nonaka, H. et al., "A downstream target of RH01 small GTP-binding protein is PKC1, a homolog of protein kinase C, which leads to activation of the MAP kinase cascade in *Saccharomyces cerevisiae*" EMBO Journal, 14:5931-5938 (1995).
Nowrousian, M. et al., "The fungal acl1 and acl2 genes encode two polypeptides with homology to the N-and C- terminal parts of the animal ATP citrate lyase polypeptide" Curr Genet, 37:189-93 (2000).
O'Toole, G.A. et al., "Genetic Approaches to Study of Biofilms" Genetic Approaches, 310:91-109 (1999).
Oda S. and Ohta, H., "Coupling of Fermentation and Esterification:Microbial Esterification of Decanoic Acid with Ethanol Produced via Fermentation" Biosci Biotechnol Biochem, 65:1388-1390 (2001).
Ohara, T. et al., "REN1 is Required for Development of Microconidia and Macroconidia, but Not of Chlamydospores, in the Plant Pathogenic Fungus *Fusarium oxysporum*" Genetics Society of America, 166:113-124 (2004).
Oskouian, B. and Saba, J.D., "YAP1 confers resistance to the fatty acid synthase inhibitor cerulenin through the transporter Flr1p in *Saccharomyces cerevisiae*" Mol Gen Genet, 261:346-353 (1999).
Palozza, P. and Krinsky, N.I., "Antioxidant Effects of Carotenoids in Vivo and in Vitro: An Overview" Meth. Enzymol., 213:403-420 (1992).
Papanikolaou, S. et al., "Accumulation of a cocoa-buller-like lipid by *Yarrowia lipolytica* cultivated on agro-industrial residues" Curr Microbiol, 46:124-30 (2003).
Papanikolaou, S. et al., "Repression of reserve lipid turnover in *Cunninghamella echinulata* and *Mortierella isabellina* cultivated in multiple-limited media" J Appl Microbiol, 97:867-75 (2004).
Papanikolaou, S. et al., "Single cell oil (SCO) production by *Mortierella isabellina* grown on high-sugar content media" Bioresour Technol., 95(3):287 (2004).
Parekh, S. et al., "Improvement of microbial strains and fermentation processes" Appl Microbiol Biotechnol, 54:287-301 (2000).
Park, C.S. et al., "Expression, Secretion, and Processing of Rice α-Amylase in the Yeast *Yarrowia lipolytica*" J Biol Chem, 272:6876-81 (1997).
Park, J.W. et al., "Bioconverstion of compactin into pravastatin by *Streptomyces* sp." Biotechnology Letters, 25:1827-1831 (2003).
Penalva, M.A. et al., "The optimization of penicillin boisynthesis in fungi" Tibetch, 16:483-489 (1998).
Peng, F.C. et al., "Production of Plyclonal Antibodies against Territrem Band Detection of Territrem Bin the Conidia of *Aspergillus terreus* 23-1 by Immunelectron Microscopy" J. Agric. Food Chem., 52(11):3360-3365 (2004).
Peng, Y. et al., "Biotransformation of Compactin to Pravastatin by *Actinomadura* sp. 2966" The Journal of Antibiotics, 50(12):1032-1035 (1997).
Perry, K.L. et al., "Cloning and Regulation of *Erwinia herbicola* Pigment Genes" J of Bacteriology, 168(2):607-612 (1986).
Pines et al. "The cytosolic pathway of L-malic acid synthesis in *Saccharomyces cerevisiae*: the role of fumarase" Appl Microbial Biotechnol, 46:393-399 (1996).
Pines, O. et al., "Overexpression of cytosolic malate dehydrogenase (MDH2) causes overproduction of specific organic acids in *Saccharomyces cerevisiae*" Appl Microbiol Biotechnol, 48:248-55 (1997).
Pisano, M.A. and Vellozzi, E.M., "Production of Cephalosporin C by *Paecilimyces persicinus* P-10" Antimicrobial Agents and Chemotherapy, 6:447-451 (1974).
Poteete, A.R., "What makes the bacteriophage Red system useful for genetic engineering: molecular mechanism and biological function" Fems Microbiology Letters, 201(1):9-14 (2001).
Prado-Cabrero, A., et al., "Retinal biosynthesis in fungi: Characterization of the carotenoid oxygenase CarX from *Fusarium fujikuroi*" Eukaryotic Cell, 6(4):650-657 (2007).
Prasad, R.A. et al., "Tryptophan Accumulation in *Saccharomyces cerevisiae* Under the Influence of an Artificial Yeast TRP Gene Cluster" Yeast, 3:95-105 (1987).
Qadota, H. et al., "Identification of Yeast Rho1p GTPase as a Regulatory Subunit of 1,3-$/beta$-Glucan Synthase" Science, 272:279-281 (1996).
Rand, K.N. and Arst, H.N. Jr., "A Mutation in *Aspergillus nidulans* which Affects the Regulation of Nitrite Reductase and is Tightly Linked to Its Structural Gene" Molec. Gen. Genet., 155(1):67-75 (1977).
Ratledge, C., "Fatty acid biosynthesis in microorganisms being used for Single Cell Oil Production" Biochimie, 86:207 (2004).
Ratledge, C., "Regulation of lipid accumulation in oleaginous microorganisms" Biochem Soc Trans, 30:1047-50 (2002).
Roberts, R.L. and Fink, G.R., "Elements of a single MAP kinase cascade in *Saccharomyces cerevisiae* mediate two developmental programs in the same cell type: mating and invasive growth" Genes and Development, 8:2974-2985 (1994).
Robertson, D.E. et al., "Exploring Nitrilase Sequence Sapce for Enantioselective Catalysis" Applied and Environmental Microbiology, 70:2429-2436 (2004).
Rock, C., "Carotenoids: Biology and Treatment" Pharmacol. Ther., 75(3):185-197 (1997).
Rodriguez-Saiz, M. et al., "*Biakeslea trispora* genes for carotene biosynthesis" Appl Environ Microbiol, 70:5589-94 (2004).
Roncal, T. and Ugalde, U., "Conidiation induction in *Penicillium*" Research in Microbiology, 154:539-546 (2003).
Sagami, I. et al., "Aspulvinone Dimethylallyltransferase" Methods in Enzymology, 110:320-327 (1985).
Sallam, L.A.R. et al., "Role of some fermentation parameters on cyclosporin A production by a new isolate of *Aspergillus terreus*" J Gen Appl Microbial, 49:321-8 (2003).
Samson, S.M. et al., "Isolation, sequence determination and expression in *Escherichia coli* of the isopenicilln n. synthetase gene from *Cephalosporium acremonium*" Nature, 318:191-194 (1985).
Schimmel, T.G. and Parsons, S.J., "High purity, high yield procedure for butyrolactone I production from *Aspergillus terreus*" Biotechnology Techniques, 13:379-384 (1999).
Schmidt-Dannert, C. "Engineering novel carotenoids in microorganisms" Current Opin. in Biotechnology, 11(3): 255-261 (2000).
Schmidt-Dannert, C. et al., "Molecular breeding of carotenoid biosynthetic pathways" Nat Biotechnol, 18: 750-3 (2000).
Schmitt, E.K. and Kuck, U., "The Fungal CPCR1 Protein, Which Binds Specifically to B-Lactam Biosynthesis Genes, Is Related to Human Regulatory Factor X Transcription Factors" The Journal of Biological Chemistry, 275(13):9348-9357 (2000).

(56) References Cited

OTHER PUBLICATIONS

Schuldiner, M. et al., "Exploration of the Function and Organization of the Yeast Early Secretory Pathway through an Epistatic Miniarray Profile" Cell 123:507-519 (2005).
Search Report and Written Opinion from the Austrian Patent Office Service and Information Center received in Singapore App. No. 200706626-9, Date of Mailing Dec. 10, 2009.
Seng, T.W. et al., "Cyclohexanedione Herbicides are Inhibitors of Rat Heart Acetyl-GoA Carboxylase" Bioorganic and Medicinal Chemistry Letters, 13:3237-3242 (2003).
Seo, J.A. et al., "Suppressor Mutations Bypass the Requirement offtuG for Asexual Sporulation and Sterigmatocystin Production in *Aspergillus nidulans*" Genetics Society of America, 165:1083-1093 (2003).
Shearer, A.G. and Hampton, R., "Lipid-mediated, reversible misfolding of a sterol-sensing domain protein" The EMBO Journal, 24:149-159 (2005).
Sherman, D. et al., "Génolevures: comparative genomics and molecular evolution of hemiascomycetous yeasts" Nucleic Acids Res. 32 (Database Issue): D315-D318 (2004).
Shimada, H. et al., "Increased carotenoid production by the food yeast *Candida utilis* through metabolic engineering of the isoprenoid pathway" Appl Environ Microbiol, 64:2676-80 (1998).
Shimizu, K. et al., "Pka, Ras and RGS Protein Interactions Regulate Activity of AftR, a Zn(II)2Cys6 Transcription Factor in *Aspergillus nidulans*" Genetics, 165:1095-1104 (2003).
Silva, E.M. and Yang, S.T., "Production of Amylases from Rice by Solid-Slate Fermentation in a Gas-Solid Spouted-Bed Bioreactor" Biotechnol Prog, 14:580-587 (1998).
Singh, D.K. and Lippman, S.M., "Cancer Chemoprevention Part 1: Retinoids and Carotenoids and Other Classic Antioxidants" Oncology, 12(11):1643-1658 (1998).
Skatrud, P.L. et al., "Efficient integrative transformation of *Cephalosporium acremonium*" Current Genetics, 12:337-348 (1987).
Song, L., "Detection of farnesyl diphosphate accumulation in yeast ERG9 mutants" Anal Biochem, 317:180-5,2003).
Spiteller, P. et al., "The Post-Polyketide Synthase Modification Steps in the Biosynthesis of the Antitumor Agent Ansamitocin by *Actinosynnema pretiosum*" J. Am. Chem. Soc., 125:14236-14237 (2003).
Steiger, S. and Sandmann, G., "Cloning of two carotenoid ketolase genes from *Nostoc punctiforme* for the heterologous production of canthaxanthin and astaxanthin" Biotechnol Lett, 26:813-7 (2004).
Su, S.S. and Mitchell, A.P., "Identification of Functionally Related Genes That Stimulate Early Meiotic Gene Expression in Yeast" Genetics, 133:67-77 (1993).
Suarez, T. and Penalva, N.A. "Characterization of a *Penicillium chrysogenum* gene encoding a Pace transcription factor and its binding sites in the divergent pcbAB-pcbC promoter of the penicillin biosynthetic cluster" Molecular Microbiolgy, 20: 529-540 (1996).
Swart, K. et al., "Genetic Analysis in the Asexual Fungus *Aspergillus niger*" Acta Biiologica Hungarica, 52:335-343 (2001).
Takahashi, I. et al., "Purification and Characterization of Dimethylallyl Pyrophosphate: Aspulvinone Dimethylallyltransferase from *Aspergillus terreus*" Biochemistry, 17:2696-2702 (1978).
Takahasi, T. et al., "Efficient gene disruption in the koji-mold *Aspergillus sojae* using a novel variation of the positive-negative method" Mol Genet Genomics, 272:344-52 (2004).
Taylor, G.R. and Deeble, J. "Enzymatic methods for mutation scanning" Genetic Analysis, 14:181-186 (1999).
Thaker, P. and Yadav, N.K., "Lipid production by *Candida* Y-1" Indian J. Exp. Biol., 35(3):313-314 (1997).
Thampy, G.K. et al., "Troglitazone stimulates acetyl-GoA carboxylase activity through a posttranslational mechanism" Life Sciences, 68:699-708 (2000).
Tilburn, J. et al., "The *Aspergillus* Pace zinc finger transcription factor mediates regulation of both acid- and alkaline-expressed genes by ambient pH" The EMBO Journal, 14:779-790 (1995).
Tilburn, J. et al., "Transformation by intergration in *Aspergillus nidulans*" Gene, 914:205-221 (1983).
Titorenko, V.I. and Rachubinski, R.A., "Dynamics of peroxisome assembly and function" Trends in Cell Biology, 11:22-29 (2001).
Titorenko, V.I. et al., "Peroxisome biogenesis in the yeast *Yarrowia lipolytica*" Cell Biochem Biophys, 32:21-6 (2000).
Todd, R.B. and Andrianopoulos, A., "Evolution of a Fungal Regulatory Gene Family: The Zn(II)2Cys6 Binuclear Cluster DNA Binding Motif" Fungal Genetics and Biology, 21(13):388-405 (1997).
Townsend, C.A. "New reactions in clavulanic acid biosynthesis" Current Opinion in Chemical Biology, 6:583-589 (2002).
Trapp, S.C. et al., "Characterizaion of the gene cluster for biosynthesis of macrocyclic trichothecenes in *Myrothecium roridum*" Mol Gen Genet, 257:421-432 (1998).
Tuveson, R.W. et al., "Role of Cloned Carotenoid Genes Expressed in *Escherichia coli* in Protecting against Inactivation by Near-UV Light and Specific Phototoxic Molecules" J. of Bacteriology, 170(10):4675-4680 (1988).
Vahlensieck, H.F. et al., "Identification of the yeast ACC1 gene product (acetyl-GoA carboxylase) as the target of the polykelide fungicide soraphen A" Curr Genet, 25:95-100 (1994).
van der Giezen et al., "A mitochondrial-like targeting signal on the hydrogenosomal malic enzyme from the anaerobic fungus *Neocallimastix frontalis*: support for the hypothesis that hydrogenosomes are modified mitochondria" Mol Microbiol, 23(1):11-21 (1997).
Varga, J. et al., "Diversity of polyketide synthase gene sequences in *Aspergillus* species" Research in Microbiology, 154:593-600 (2003).
Verdoes, J.C. et al., "Metabolic Engineering of the Carotenoid Biosynthetic Pathway in Yeast *Xanthophyllomyces dendromous* (*Phaffia rhodzyma*)" Appl Environ Microbiol, 69:3728-38 (2003).
Visser, H. et al.,"Metabolic engineering of the astaxanthin-biosynthetic pathway of *Xanthophyllomyces dendrorhous*" FEMS Yeast Res, 4:221-231 (2003).
Wang, G.Y. and Keasling, J.D., "Amplification of HMG-CoA reductase production enhances carotenoid accumulation in *Neurospora crassa*" Melab Eng, 4:193-201 (2002).
Wang, L.H. et al., "A bacterial cell-cell communication signal with cross-kingdom structural analogues" Molecular Biology, 51(3):903-912 (2004).
Wang, W. et al., "A novel Two-Component System amrB-amkB Involved in the Regulation of Central Carbohydrate Metabolism in Rifamycin SV-Producting *Amycolatopsis medilerranei* U32" Current Microbiology, 48:14-19 (2004).
Wang, X et al., "Astaxanthin-Rich Algal Meal and Vitamin C Inhibit *Helicobacter pylori* Infection in BALB/cA Mice" Antimicrob. Agents Chemother., 44(9):2452-2457 (2000).
Watanabe, I. et al., "Cloning, characterization and expression of the gene encoding cytochrome P-450sca-2 from *Streptomyces carbophilus* involved in production of pravastatin, a specific HMG-CoA reductatse inhibitor" Gene, 163:81-85 (1995).
Wentzell, L.M. et al., "The SfiI Restriction Endonuclease Makes a Four-strand DNA Break at Two Copies of its Recognition Sequence" J. Mol. Biol., 248:581-595 (1995).
Wery, J. et al., "High copy number integration into the ribosomal DNA of the yeast *Phaffia rhodozyma*" Gene., 184(1):89-97 (1997).
Willinger, B. et al., "Detection and Identification of Fungi from Fungus Balls of the Maxillary Sinus by Molecular Techniques" Journal of Clinical Microbiology, 41:581-585 (2003).
Woloshuk, C.P. et al., "Genetic Transformation System for the Aflatoxin-Producing Fungus *Aspergillus flavus*" Applied and Environmental Microbiology, 55:86-90 (1989).
Woloshuk, C.P. et al., "Molecular Characterization of aftR, a Regulatory Locus fo Aftatoxin Biosynthesis" Applied and Environmental Microbiology, 60:2408-2414 (1994).
Written Opinion of International Searching Authority, PCT/US2006/010271, date of mailing Jul. 31, 2007.
Written Opinion of the International Searching Authority, PCT/US2007/021092, date of mailing Aug. 11, 2008.
Wynn et al., "The role of malic enzyme in the regulation of lipid accumulation in filamentous fungi" Microbiol, 145:1911 (1999).
Wynn, J.P. et al., "Biochemical events leading to the diversion of carbon into storage lipids in the oleaginous fungi *Mucor circinelloides* and *Mortierella alpina*" Microbiology, 147:2857-64 (2001).

(56) References Cited

OTHER PUBLICATIONS

Yamano, S. et al., "Metabolic engineering for production of beta-carotene and lycopene in *Saccharomyces cerevisiae*" Biosci Biotechnol Biochem, 58:1112-4 (1994).

Yelton, M.M. et al., "A Cosmid for Selecting Genes by Complementation is *Aspergillus nidulans*: Selection of the Developmentally Regulated yA Locus" Proceedings of the National Academy of Sciences of the USA, 70:834-838 (1985).

Yelton, M.M. et al., "Transformation of *Aspergillus nidulans* by using a trpC plasmid" Proc. Nail. Acad. Sci. USA, 81:1470-1474 (1984).

Zhang, H. et al., "Molecular basis for the inhibition of the carboxyltransferase domain of acetyl-coenzyme-A carboxylase by haloxyfop and diclofop" Proc Nail Acad Sci US A, 101:5910-5 (2004).

Zhang, Y.Q. and Keller, N.P., "Blockage of methylcitrate cycle ingibils polykelide production in *Aspergillus nidulans*" Molecular Microbiology, 52(2):541-550 (2004).

Zhu, M. et al., "An inexpensive medium for production of arachidonic acid by *Mortierella alpina*" J. Ind. Microbiol. Biotechnol., 30(1):75-79 (2003).

antheraxanthin canthaxanthin

β-carotene

γ-carotene astaxanthin

α-carotene

ε-carotene

ζ-carotene

α-cryptoxanthin diatoxanthin 7,8-didehydroastaxanthin fucoxanthin fucoxanthinol lactucaxanthin lutein lycopene neoxanthin peridinin rhodopin neurosporene phytoene siphonaxanthin

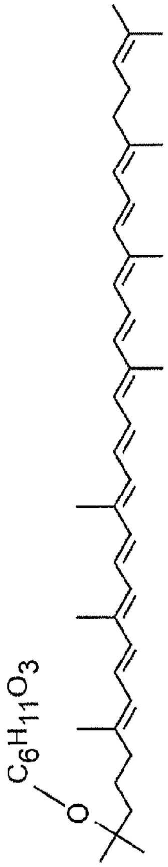
rhodopin glucoside
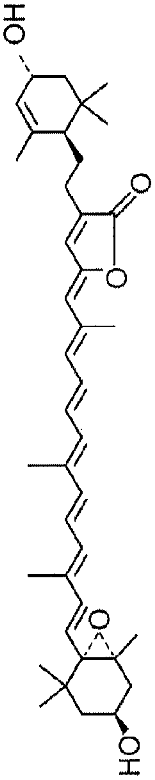
uriolide
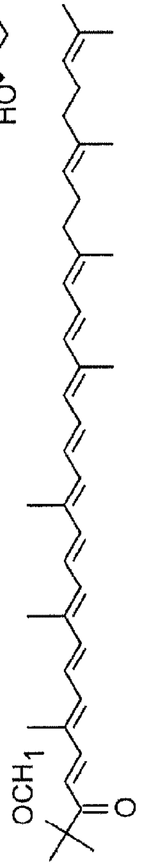
spheroidenone
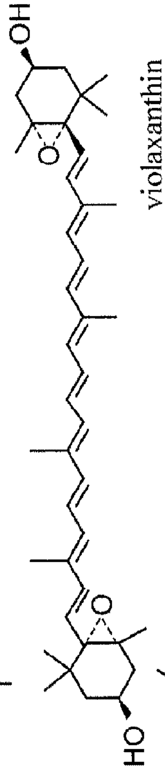
violaxanthin
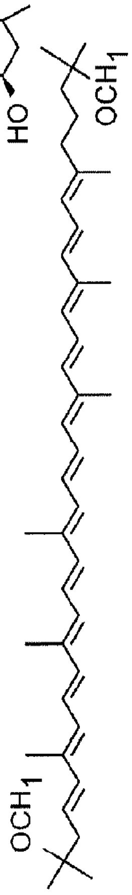
spirilloxanthin
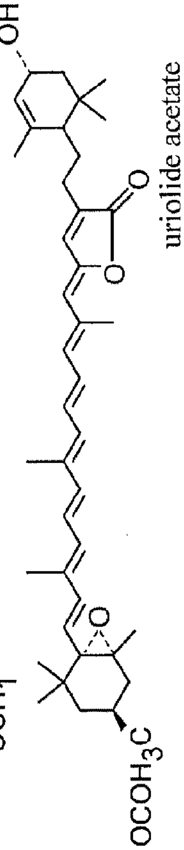
uriolide acetate
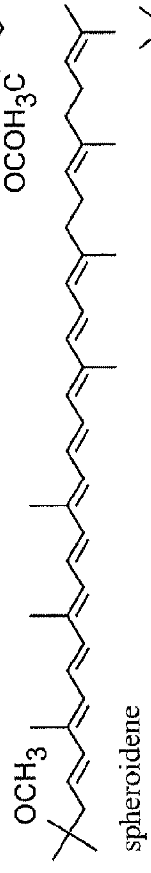
spheroidene
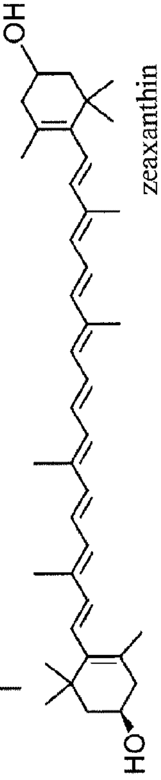
zeaxanthin
FIG. 1D

MEVALONATE PATHWAY TO ISOPRENOIDS

β-Carotene

Echinenone

β-Cryptoxanthin

Canthaxanthin

3'-Hydroxyechinenone

3'-Hydroxyechinenone

Zeaxanthin

Phoenicoxanthin (Adonirubin)

Adonixanthin (4-ketozeaxanthin)

Astaxanthin neurosporene

α-zeacarotene lycopene

β-zeacarotene

δ-carotene

γ-carotene

β-carotene

α-carotene

β-carotene

α-cryptoxanthin zeinoxanthin

β-cryptoxanthin lutein zeaxanthin

Alignment of representative fungal HMG-CoA reductase polypeptides.

```
                          1                                                  50
      A. nidulans HMG  (1) -MASVLIRRKFGTE--GGSDAEPSWLKRQVTGCLQSISRRACIHPIHTIV
          G. zeae HMG  (1) -MASILLPKKFRGETAPAEKTTPSWASKRLTPIAQFISRLACSHPIHTVV
       N. crassa HMG  (1) MIASSLLPSKFRGEQPATQAATPSWINKKVTPPLQKLSKITSSNPIHTIV
   S. cerevisea HMG2  (1) -------------------MSLPLKTIVHLVKPFACTARFSARYPIHVIV
  S. cereviseae HMG1  (1) -------------------MPPLFKGLKQMAKPLAYVSRFSAKPPIHIIL
  Y. lipolytica HMG  (1) ----------------------------MLQAAIGKIVGFAVNRPIHTVV
            Consensus  (1)  MAS LL  RF  E       A PSW  K LT PIQ ISRFAA HPIHTIV
                          51                                                 100
      A. nidulans HMG (48) VIALLASTTYVGLLEGSLFDSFRNSNNVAGHVDVDSLLLGNRSLRLGEGT
          G. zeae HMG (50) LVAVLASTSYVGLLQESFFSTDLP---TVGKADWSSLVEGSRVLRAGPET
       N. crassa HMG (51) IVALLASSSYIGLLQNSLFNVTR----SVRKAEWESLQAGSRMLRAGANT
   S. cerevisea HMG2 (32) VAVLLSAAAYLSVTQSYLNEWKLDSN-----QYSTYLSIKPDELFEKCTH
  S. cereviseae HMG1 (32) FSLIISAFAYLSVIQYYFNGWQLDSNS----VFETAPNKDSNTLFQECSH
  Y. lipolytica HMG (23) LTSIVASTAYLALLDIAIPGEEG--------TQPISYYHPAAKSYDNPAD
            Consensus (51) LVALLASTAYLGLLQ SLF W L SN       D TSL  GSR LR G  T
```

```
                             101                                              150
A. nidulans HMG       (98)  SWKWQVEDSLNQDDQKVGNPELKREVDQHLALTTLIFPDSISKS-ASTAP
G. zeae HMG           (97)  AWNWKAIEQDSIQ--------HAGADADHLALLTLVFPDTHSAESSSTAP
N. crassa HMG         (97)  EWNWQNHDPEAP----------VPANANHLALLTLVFPDTAES--GPVVA
S. cerevisea HMG2     (77)  YYRSPVSDTWKLLS------SKEAADIYTPFHYYLSTISFQSKDNSTTLP
S. cereviseae HMG1    (78)  YYRDSSLDGWVSIT------AHEASELPAPHHYYLLNLNFSPNETDSIP
Y. lipolytica HMG     (65)  ---WTHIAEADIP-----------SDAYRLAFAQIRVSDVQGGE-APTIP
Consensus            (101)   WRW  ID   I           AADA HLAL TLVFPDTQS E ASTIP
                             151                                              200
A. nidulans HMG      (147)  AADALPVPANASAQLLPHTPNLFSPFSHDSSLVFTLPFDQVPQFLRAVQE
G. zeae HMG          (139)  RSSHVPVPQNLSITPLPSTKNSFTAYSQDSILAYSLPYAEG---------
N. crassa HMG        (135)  QTNTVPLPSNLSITPLPSTAISFT-YSQDSALAFSLPYSQAPEFLANAQE
S. cerevisea HMG2    (121)  SLDDVIYSVDHTRYLLSEEPKIPTELVSENGTKWRLRNNSN---------
S. cereviseae HMG1   (122)  ELANTVFEKDNTKYLLQEDLSVSKEISSTDGTKWRLRSDRK---------
Y. lipolytica HMG    (100)  GAVAVSDLDHRIVMDYKQWAPWTASNEQIASENHIWKHSFK-------D-
Consensus            (151)   A  VPVP N SI LLP T  IFT YSQDSSL FSLPYS
                             201                                              250
A. nidulans HMG      (197)  LPDPTLEDDEGEQKR---WIMRATRGPVSGPNGTISSWLSDAWSSFVDLI
G. zeae HMG          (180)  --------------------------------PDVVQWANNAWTEFLDLL
N. crassa HMG        (184)  IPNAVSSQETIETERGHEKKMWIMKAARVQTRSSTVKWVQNAWVEFTDLL
S. cerevisea HMG2    (162)  ------------------------------FILDLHNIYRNMVKQFSNKT
S. cereviseae HMG1   (163)  ------------------------------SLFDVKTLAYSLYDVFSENV
Y. lipolytica HMG    (142)  -----------------------------HVAFSWIKWFRWAYLRLSTLI
Consensus            (201)                                DIV W  NAW  FSDLI
```

FIG. 7B

```
                                251                                               300
      A. nidulans HMG  (244)  KHAETIDIIIMTLGYLAMYLSFASLEFSMKQLGSKFWLATTVLFSGMFAF
          G. zeae HMG  (198)  KNAETLDIVIMFLGYTAMHLTFVSLFLSMRKIGSKFWLGICTLFSSVFAF
        N. crassa HMG  (234)  RNAETLDIIIMALGYISMHLTFVSLFLSMRRMGSNFWLATSVIFSSIFAF
   S. cerevisea HMG2  (182)  SEFDQFDLFIILAAYLTILFYTLCCLFNDMRKIGSKFWLSFSALSNSACAL
  S. cereviseae HMG1  (183)  TQADPFDVLIMVTAYLMMFYTIFGLFNDMRKTGSNFWLSASTVVNSASSL
   Y. lipolytica HMG  (163)  QGADNFDIAVVALGYLAMHYTFFSLFRSKRKVGSHFWLASMALVSSFFAF
            Consensus  (251)  KNADTFDIIIM LGYLAMHYTF SLF SMRKLGSKFWLATS LFSSIFAF
                                301                                               350
      A. nidulans HMG  (294)  LFGLIVTTKFG-VPLNLLLLSEGLPFLVTTIGFEKPIILTRAVLSASIDK
          G. zeae HMG  (248)  LFGLIVTTKLG-VPISVILLSEGLPFLVVTIGFEKNIVLTRAVMSHAIEH
        N. crassa HMG  (284)  LFGLLVTTKLG-VPMNMVLLSEGLPFLVVTIGFEKNIVLTRAVLSHAIDH
   S. cerevisea HMG2  (232)  YLSLYTTHSLLKKPASLLSLVIGLPFTVVIIGEKHKVRLAAFSLQKFHRI
  S. cereviseae HMG1  (233)  FLALYVTQCILGKEVSALTLFEGLPFLVVVVGFKHKIKIAQYALEKFERV
   Y. lipolytica HMG  (213)  LLAVVASSSLG-YRPSMITMSEGLPFLVVAIGFDRKVNLASEVLTSKSSQ
            Consensus  (301)  LLGLLVTTKLG VPISMLLLSEGLPFLVVTIGFEKKIVLTRAVLS AID
                                351                                               400
      A. nidulans HMG  (343)  KRQGS---------ATSTPSSIQDSIQTAIREQGFEIIRDYCIEISILIA
          G. zeae HMG  (297)  RRQIQNSKSGKGSPERSMQNVIQYAVQSAIKEKGFEIMRDYAIEIVILAL
        N. crassa HMG  (333)  RRPTE--KSGKPSKQADSAHSIQSAIQLAIKEKGFDIVKDYAIEAGILVL
   S. cerevisea HMG2  (282)  S--------------IDKKITVSNIIYEAMFQEGAYLIRDYLFYISSFIG
  S. cereviseae HMG1  (283)  G--------------LSKRITTDEIVFESVSEEGGRLIQDHLLCIFAFIG
   Y. lipolytica HMG  (262)  ----------------------LAPMVQVITKIASKALFEYSLFVAALFA
            Consensus  (351)  RR              S    SIQ AIQ AIKE GFEIIRDYAIEISILIA
```

FIG. 7C

```
                                 401                                              450
       A. nidulans HMG   (384)   GAASGVQGG-LQQFCFLAAWILFFDCILLFTFYTTIICIKLEITRIRRHV
           G. zeae HMG   (347)   GAASGVQGG-LQHFCFLAAWTLFFDFILLFTFYTAILSIKLEINRIKRHV
         N. crassa HMG   (381)   GAASGVQGG-LQQFCFLAAWILFFDCILLFSFYTAILCIKLFINRIKRHV
    S. cerevisea HMG2    (318)   CAIYARHLPGLVNFCILSTFMLVFDLLLSATFYSAILSMKLFINIIHRST
   S. cereviseae HMG1    (319)   CSMYAHQLKTLTNFGILSAFILIFELILTPTFYSAILALRLFMNVIHRST
    Y. lipolytica HMG    (290)   GAYTGVPR--LSQFCFLSAWILIEDYMFLLTFYSAVIAIKFLINHIKFNR
             Consensus   (401)   GAASGVQGG L QFCFLAAWILFFD ILLFTFYSAILAIKLEINRIKRHV
                                 451                                              500
       A. nidulans HMG   (433)   TLRKALEEDGTTQSVAEKVASSN-DWFGAGSDNSDADDASVFGRKIKSNN
           G. zeae HMG   (396)   DMRMALFDDGVSRRVAENVAKSDGDWTRVKGDSSLFG--------RKSSS
         N. crassa HMG   (430)   QMRKALEEDCVSRRVAEKVAQSN-DWPRADGKDQPGTTI--FGRQLKSTH
    S. cerevisea HMG2    (368)   VIRQTLEEDGVVPTTADIIYKDE------TASEPHFLR--------SNVA
   S. cereviseae HMG1    (369)   IIKQTLEEDGVVPSTARIISKAE------KKSVSSFLN--------LSVV
    Y. lipolytica HMG    (338)   MIQDALKEDGVSAAVAEKVADSSPDAKLDRKSDVSLFG--------ASGA
             Consensus   (451)   IIR ALEEDGVS SVAEKVAKSE DW   KGSDS F          KS A
                                 501                                              550
       A. nidulans HMG   (482)   VRRFKFLMVGGFVLVNVVNMTAIPFRNS-S-------LSPLCNVFSPTPI
           G. zeae HMG   (438)   VPTFKVLMILGFIFVNIVNICSIPFRNPRSLSTIRTWASSLGGVVAPLSV
         N. crassa HMG   (477)   IPKFKVMMVTGFVLINVLNLCTIPFRSANSISSISSWARGLGGVVTPPPV
    S. cerevisea HMG2    (404)   IILGKASVIGLLILINIYVFTDKLNATILN---------------TVYFD
   S. cereviseae HMG1    (405)   VITMKLSVILLFVFINFYNFGANWVNDAFN---------------SLYFD
    Y. lipolytica HMG    (380)   IAVFKIFMVLGFIGLNLINLTAIPHLGK--------------AAAAAQSV
             Consensus   (501)   I IFKVLMILGFVLINLVNLTAIPFR A S          L GV SP  V
```

FIG. 7D

```
                                551                                               600
     A. nidulans HMG   (524)   DPFKVAENGLDATYVSAKSQKLETLVTVVPPIKVKLEYPSVHYAKLGES-
          G. zeae HMG  (488)   DPFKVASNGLDAILAAAKSNNRPTLVTVLTPIKYELEYPSIHYALGSAIN
       N. crassa HMG   (527)   DPFKVASNGLDIILEAARADGRETTVTVLTPIRYELEYPSTHYDLPQKS-
  S. cerevisea HMG2    (439)   S---TIYSLPNFINYKDIGNLSNQVIISVLPKQYYTPLKKYHQIEDSVL-
 S. cereviseae HMG1    (440)   K---ERVSLPDFITSNASENFKEQAIVSVTPLLYYKPIKSYQRIEDMVL-
  Y. lipolytica HMG    (416)   TPITLSPELLHAIPASVP-----VVVTFVPSVVYEHSQLILQLEDALTE-
            Consensus  (551)   DPFKVA NLLDAI AAAKSN RETLVTVVTPIKYELEYPSIHY E   S
                                601                                               650
     A. nidulans HMG   (573)   ----QSIEIEYTDQLLDAVGGHVLNGVLKSIEDPVISKWITAVLTLSIVL
          G. zeae HMG  (538)   GNNAEYTDAFHHHFQGYGVGGRMVGGILKSLEDPVLSKWIVIALALSVAL
       N. crassa HMG   (576)   -----AEVEGGDYANLGGYGGRMVGSILKSLEDPTLSKWIVVALALSVAL
  S. cerevisea HMG2    (485)   ---------L--------------IIDSVSNAIRDQFISKLLFFAFAVSISI
 S. cereviseae HMG1    (486)   ---------L--------------LLRNVSVAIRDRFVSKLVLSALVCSAVI
  Y. lipolytica HMG    (460)   -----------------------FLAACSKTIGDPVISKYIFLCLMVSTAL
            Consensus  (601)            L         G GG MLGSVSKSIEDPVISKWIVIALALSIAL
                                651                                               700
     A. nidulans HMG   (619)   NGYLFNAARWSIKEPQAAPAPKEP--------------------------
          G. zeae HMG  (588)   NGYLFNVARWGIKDPNVPEHNIDRNELARAQQFNDTGSATLPLGEYVPPT
       N. crassa HMG   (621)   NGYLFNAARWGIKDPNVPDHPINPKELDEAQKFNDTASATLPLGEYMKPT
  S. cerevisea HMG2    (514)   NVYLLNAAKIHTGYMNFQPQSNKIDDLVVQQKSATIEFSETRSMPLASGL
 S. cereviseae HMG1    (515)   NVYLLNAARIHTSYTADQLVKTEVTKKSFTAPVQKASTPVLTNKTVISGS
  Y. lipolytica HMG    (488)   NVYLFGATREVVRTQSVKVVEKHMPIVIE----K----------------
            Consensus  (651)   NVYLFNAARW IKDPNV      EV EL   Q  N   SA L      I  T
```

FIG. 7E

```
                                 701                                              750
      A. nidulans HMG    (643)   ----------------------AKPKVYPKTDLNAGPKRSMEECEAMLKA
            G. zeae HMG    (638)   PMR--TEPSTPAITDDEAEGLQMTKARSDKLPNRPNEE-----LEKLIAE
        N. crassa HMG    (671)   APSSPVAPLTPSSTDDENDAQAKENRAVTLAAQRATTIRSQGELDKMTAE
   S. cerevisea HMG2    (564)   E----TPVTAKDIIISEEIQNN---ECVYALSSQDEPIRPLSNLVELMEK
 S. cereviseae HMG1    (565)   K----VKSLSSAQSSSSGPSSSSEEDDSRDIESLDKKIRPLEELEALLSS
   Y. lipolytica HMG    (518)   ----------PSEKEEDTSSEDSIELTVGKQPKPVTETRSLDDLEATMKA
             Consensus    (701)            TPA TDDE  S  S    V KI      IRSLEELEALLAA
                                 751                                              800
      A. nidulans HMG    (671)   KKAAYLSDELLIELSLSGKLPGYALLKSLENEELMSRVDAFLRAVKLRRA
            G. zeae HMG    (681)   KRVKEMSDEELVSLSMRCKIPGYALLKTLG---------DFTRAVKIRRS
        N. crassa HMG    (721)   KRTHELNDEETVHLSLKGKIPGYALEKTLK---------DFTRAVKVRRS
   S. cerevisea HMG2    (607)   EQLKNMNNTEVSNLVVNGKLPLYSLEKKLE---------DTLRAVLVRRK
 S. cereviseae HMG1    (611)   GNTKQLKNKEVAALVIHGKLPLYALEKKLG---------DTTRAVAVRRK
   Y. lipolytica HMG    (558)   GKTKLLEDHEVVKLSLEGKLPLYALFKQLG---------DNTRAVGIRRS
             Consensus    (751)   KKTK L DEEVV LSL GKLPLYALEKTLG         DFTRAVKIRRS
                                 801                                              850
      A. nidulans HMG    (721)   VVSRTPATSAVTSSLETSKLPYKDYNYALVHGACCENVIGTLPLPLGVAG
            G. zeae HMG    (722)   IIARNRATSDLTHSLERSKLPFEKYNWERVFCACCENVIGYMPLPVGVAG
        N. crassa HMG    (762)   IISRTKATTELTNILDRSKLPYQNVNWAQVHGACCENVIGYMPLPVGVAG
   S. cerevisea HMG2    (648)   ALST---L-AESPILVSEKLPFRNYDYDRVFGACCENVIGYMPIPVGVIG
 S. cereviseae HMG1    (652)   ALSI---L-AEAPVLASDRLPYKNYDYDRVFGACCENVIGYMPLPVGVIG
   Y. lipolytica HMG    (599)   IISQ---Q-SNTKTLETSKLPYLHYDYDRVFGACCENVIGYMPLPVGVAG
             Consensus    (801)   IISR  ATSALT SLESSKLPYKNYNYDRVFGACCENVIGYMPLPVGVAG
```

FIG. 7F

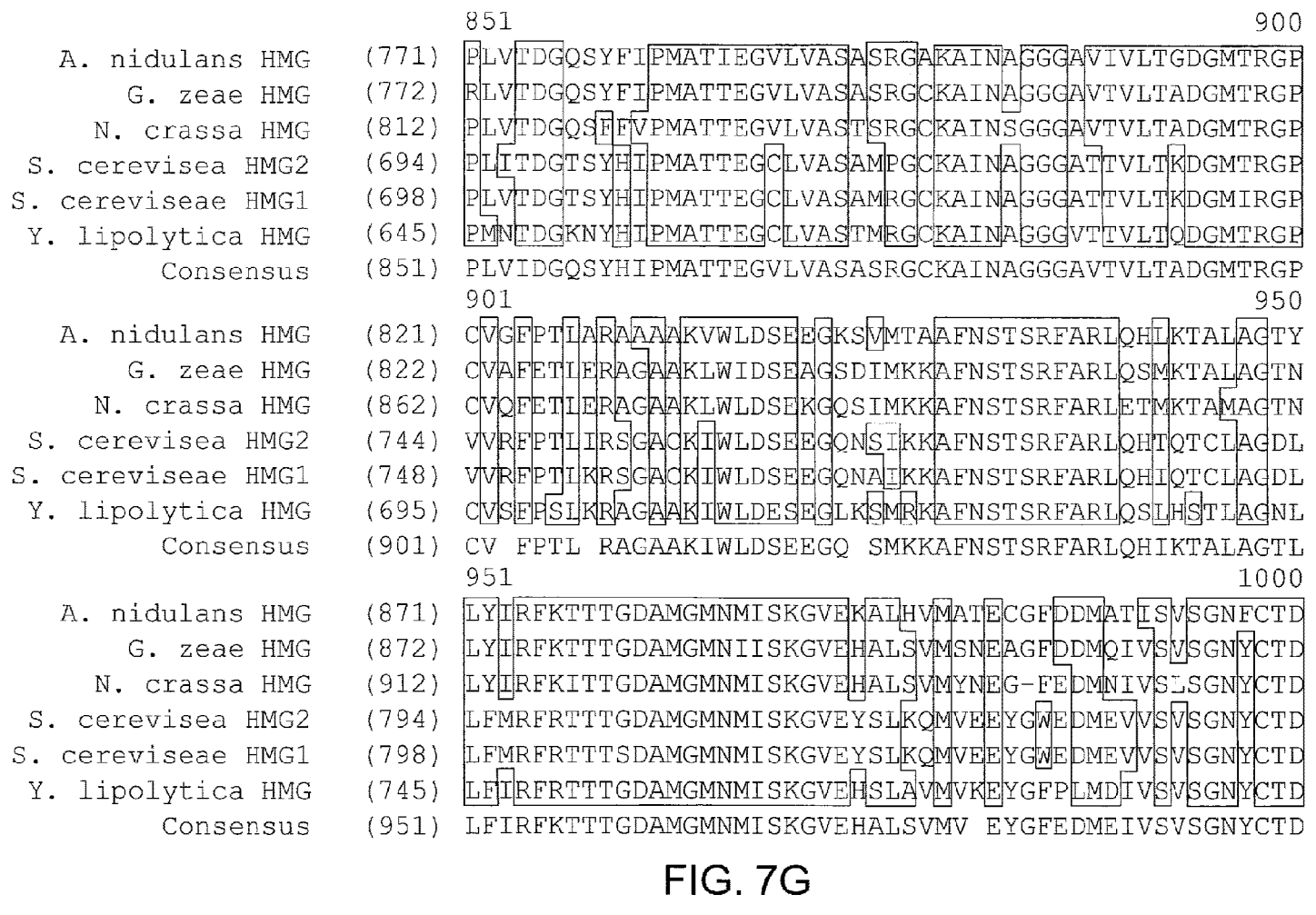

```
                               851                                              900
   A. nidulans HMG     (771)  PLVTDGQSYFIPMATIEGVLVASASRGAKAINAGGGAVIVLTGDGMTRGP
          G. zeae HMG  (772)  RLVTDGQSYFIPMATTEGVLVASASRGCKAINAGGGAVTVLTADGMTRGP
       N. crassa HMG   (812)  PLVTDGQSFFVPMATTEGVLVASTSRGCKAINSGGGAVTVLTADGMTRGP
  S. cerevisea HMG2    (694)  PLITDGTSYHIPMATTEGCLVASAMPGCKAINAGGGATTVLTKDGMTRGP
 S. cereviseae HMG1    (698)  PLVTDGTSYHIPMATTEGCLVASAMRGCKAINAGGGATTVLTKDGMIRGP
  Y. lipolytica HMG    (645)  PMNTDGKNYHIPMATTEGCLVASTMRGCKAINAGGGVTTVLTQDGMTRGP
          Consensus    (851)  PLVIDGQSYHIPMATTEGVLVASASRGCKAINAGGGAVTVLTADGMTRGP
                               901                                              950
   A. nidulans HMG     (821)  CVGFPTLARAAAAKVWLDSEEGKSVMTAAFNSTSRFARLQHLKTALAGTY
          G. zeae HMG  (822)  CVAFETLERAGAAKLWIDSEAGSDIMKKAFNSTSRFARLQSMKTALAGTN
       N. crassa HMG   (862)  CVQFETLERAGAAKLWLDSEKGQSIMKKAFNSTSRFARLETMKTAMAGTN
  S. cerevisea HMG2    (744)  VVRFPTLIRSGACKIWLDSEEGQNSIKKAFNSTSRFARLQHTQTCLAGDL
 S. cereviseae HMG1    (748)  VVRFPTIKRSGACKIWLDSEEGQNAIKKAFNSTSRFARLQHIQTCLAGDL
  Y. lipolytica HMG    (695)  CVSFPSLKRAGAAKIWLDESEGLKSMRKAFNSTSRFARLQSLHSTLAGNL
          Consensus    (901)  CV FPTL RAGAAKIWLDSEEGQ SMKKAFNSTSRFARLQHIKTALAGTL
                               951                                             1000
   A. nidulans HMG     (871)  LYIRFKTTTGDAMGMNMISKGVEKALHVMATECGFDDMATISVSGNFCTD
          G. zeae HMG  (872)  LYIRFKTTTGDAMGMNIISKGVEHALSVMSNEAGFDDMQIVSVSGNYCTD
       N. crassa HMG   (912)  LYIRFKITTGDAMGMNMISKGVEHALSVMYNEG-FEDMNIVSLSGNYCTD
  S. cerevisea HMG2    (794)  LFMRFRTTTGDAMGMNMISKGVEYSLKQMVEEYGWEDMEVVSVSGNYCTD
 S. cereviseae HMG1    (798)  LFMRFRTTTSDAMGMNMISKGVEYSLKQMVEEYGWEDMEVVSVSGNYCTD
  Y. lipolytica HMG    (745)  LFIRFRTTTGDAMGMNMISKGVEHSLAVMVKEYGFPLMDIVSVSGNYCTD
          Consensus    (951)  LFIRFKTTTGDAMGMNMISKGVEHALSVMV EYGFEDMEIVSVSGNYCTD
```

FIG. 7G

```
                                   1001                                              1050
     A. nidulans HMG     (921)   KKAAALNWIDGRGKSVVAEAIIPGDVVRNVLKSDVDALVELNTSKNLIGS
            G. zeae HMG  (922)   KKAAALNWIDGRGKGVVAEAIIPGDVVRSVLKSDVDALVELNISKNIIGS
         N. crassa HMG   (961)   KKAAAINVIDGRGKSVVAEAIIPADVVKNVLKTDVDTLVELNVNKNTIGS
   S. cerevisea HMG2     (844)   KKPAAINWIEGRGKSVVAEATIPGDVVKSVLKSDVSALVELNISKNIVGS
  S. cereviseae HMG1     (848)   KKPAAINWIEGRGKSVVAEATIPGDVVRKVLKSDVSALVELNIAKNLVGS
   Y. lipolytica HMG     (795)   KKPAAINWIEGRGKSVVAEATIPAHIVKSVLKSEVDALVELNISKNLIGS
           Consensus    (1001)   KKPAAINWIDGRGKSVVAEATIPGDVVKSVLKSDVDALVELNISKNLIGS
                                   1051                                              1100
     A. nidulans HMG     (971)   AMAGSLGGFNAHASNIVTAIFLATGQDPAQNVESSSCITTMKNTNGNLQT
            G. zeae HMG  (972)   AMAGSVGGFNAHAANIVAAIFLATGQDPAQVVESANCITLMKNLRGALQT
         N. crassa HMG  (1011)   AMAGSMGGFNAHAANIVAAIFLATGQDPAQVVESANCITLMRNLRGNLQI
   S. cerevisea HMG2     (894)   AMAGSVGGFNAHAANLVTALFLALGQDPAQNVESSNCITLMKEVDGDLRI
  S. cereviseae HMG1     (898)   AMAGSVGGENAHAANLVTAVFLALGQDPAQNVESSNCITLMKEVDGDLRI
   Y. lipolytica HMG     (845)   AMAGSVGGFNAHAANLVTAIYLATGQDPAQNVESSNCITLMSNVDGNLLI
           Consensus    (1051)   AMAGSVGGFNAHAANIVTAIFLATGQDPAQNVESSNCITLMKNVDGNLQI
                                   1101                                              1150
     A. nidulans HMG    (1021)   AVSMPSIEVGTIGGGTILEAQGAMLDLLGVRGSHPTNPGDNARQLARIVA
            G. zeae HMG (1022)   SVSMPSLEVGTLGGGTILEPQSAMIDILGVRGSHPTNPGDNSRRLARIIG
         N. crassa HMG  (1061)   SVSMPSIEVGTLGGGTILEPQSAMLDMLGVRGPHPTNPGENARRLARIVA
   S. cerevisea HMG2     (944)   SVSMPSIEVGTIGGGTVLEPQGAMLDLLGVRGPHPTEPGANARQLARIIA
  S. cereviseae HMG1     (948)   SVSMPSIEVGTIGGGTVLEPQGAMLDLLSVRGPHATAPGTNARQLARIVA
   Y. lipolytica HMG     (895)   SVSMPSIEVGTIGGGTILEPQGAMLEMLGVRGPHIETPGANAQQLARIIA
           Consensus    (1101)   SVSMPSIEVGTIGGGTILEPQGAMLDLLGVRGPHPTNPGDNARQLARIIA
```

FIG. 7H

| | | |
|---|---|---|
| | | 1151 1200 |
| A. nidulans HMG | (1071) | AAVLAGFLSLCSALAAGHLVRAHMAHNRSAAPTRSATPVSAAVGATRGLS |
| G. zeae HMG | (1072) | ASVLAGELSLCSALAAGHLVRAHMQHNRSAAPSRSTTPAPMTPVRSFDTK |
| N. crassa HMG | (1111) | AAVLAGFLSLCSALAAGHLVKAHMAHNRSAPPTRTSTPAPAAAAGLTMTS |
| S. cerevisea HMG2 | (994) | CAVLAGELSLCSALAAGHLVQSHMIHNRKTNKANELP----QPSNKGPPC |
| S. cereviseae HMG1 | (998) | CAVLAGELSLCAALAAGHLVQSHMIHNRKPAEPTKPNNLDATDINRLKDG |
| Y. lipolytica HMG | (945) | SGVLAAELSLCSALAAGHLVQSHMIHNRSQAPTPAKQSQADLQRLQNGSN |
| Consensus | (1151) | AAVLAGELSLCSALAAGHLVQAHMTHNRSAAPTRS TP A T |
| | | 1201 1250 |
| A. nidulans HMG | (1121) | MTSSR--------------------------------------------- |
| G. zeae HMG | (1122) | VRCQPNNKDIRNILLTQHPSKPTITYSKRVIKSTIHLNPLILALFDNSVQ |
| N. crassa HMG | (1161) | S-------------N---PNAAAVERSRR--------------------- |
| S. cerevisea HMG2 | (1040) | KTSALL-------------------------------------------- |
| S. cereviseae HMG1 | (1048) | SVTCIKS------------------------------------------- |
| Y. lipolytica HMG | (995) | ICIRS--------------------------------------------- |
| Consensus | (1201) | I S |
| | | 1251 1289 |
| A. nidulans HMG | (1126) | --------------------------------------- |
| G. zeae HMG | (1172) | TRDVQLGDQVSTRGTLDAVGGPQGGGVAAGGVARRVVGS |
| N. crassa HMG | (1174) | --------------------------------------- |
| S. cerevisea HMG2 | (1046) | --------------------------------------- |
| S. cereviseae HMG1 | (1055) | --------------------------------------- |
| Y. lipolytica HMG | (1000) | --------------------------------------- |
| Consensus | (1251) | |

FIG. 7I

Figure 9a. β-Carotene and phytoene production of Strain MF760 when grown in glycerol, glucose or olive oil
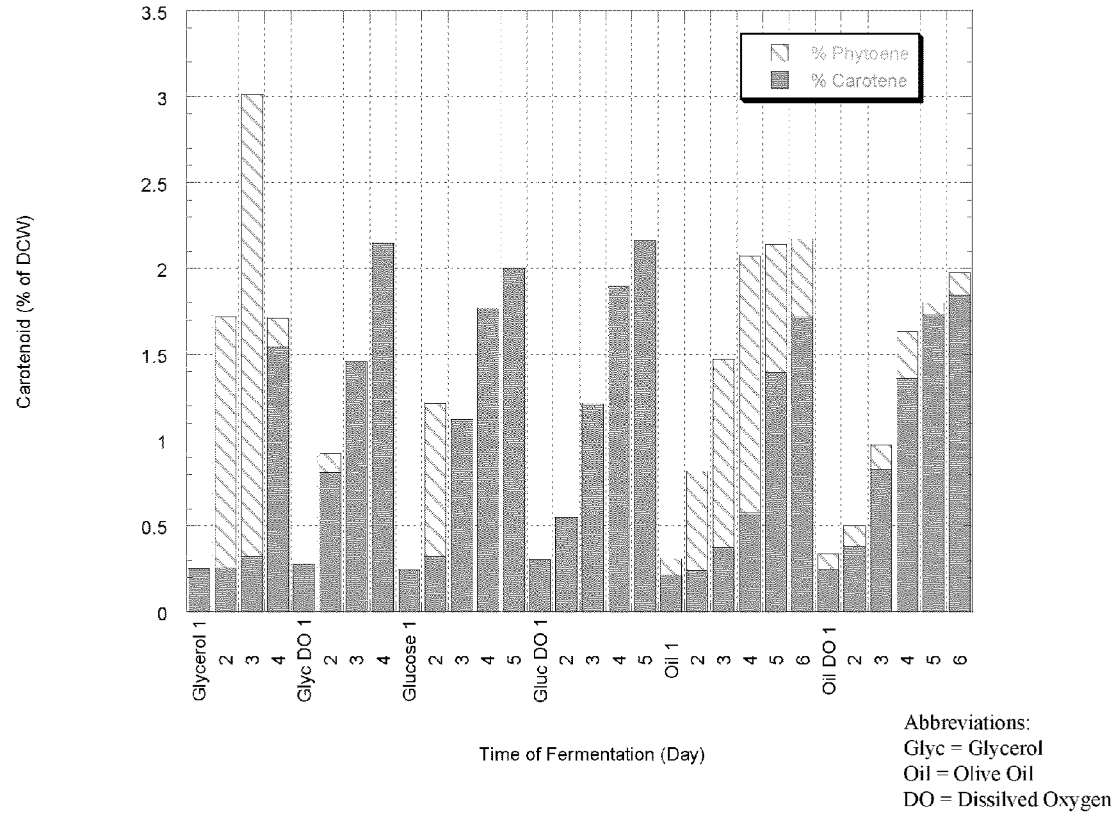
Abbreviations:
Glyc = Glycerol
Oil = Olive Oil
DO = Dissilved Oxygen
Carotene= β-Carotene Figure 9b. Dry cell weight accumulation of strain MF760 when grown in glycerol, glucose or olive oil
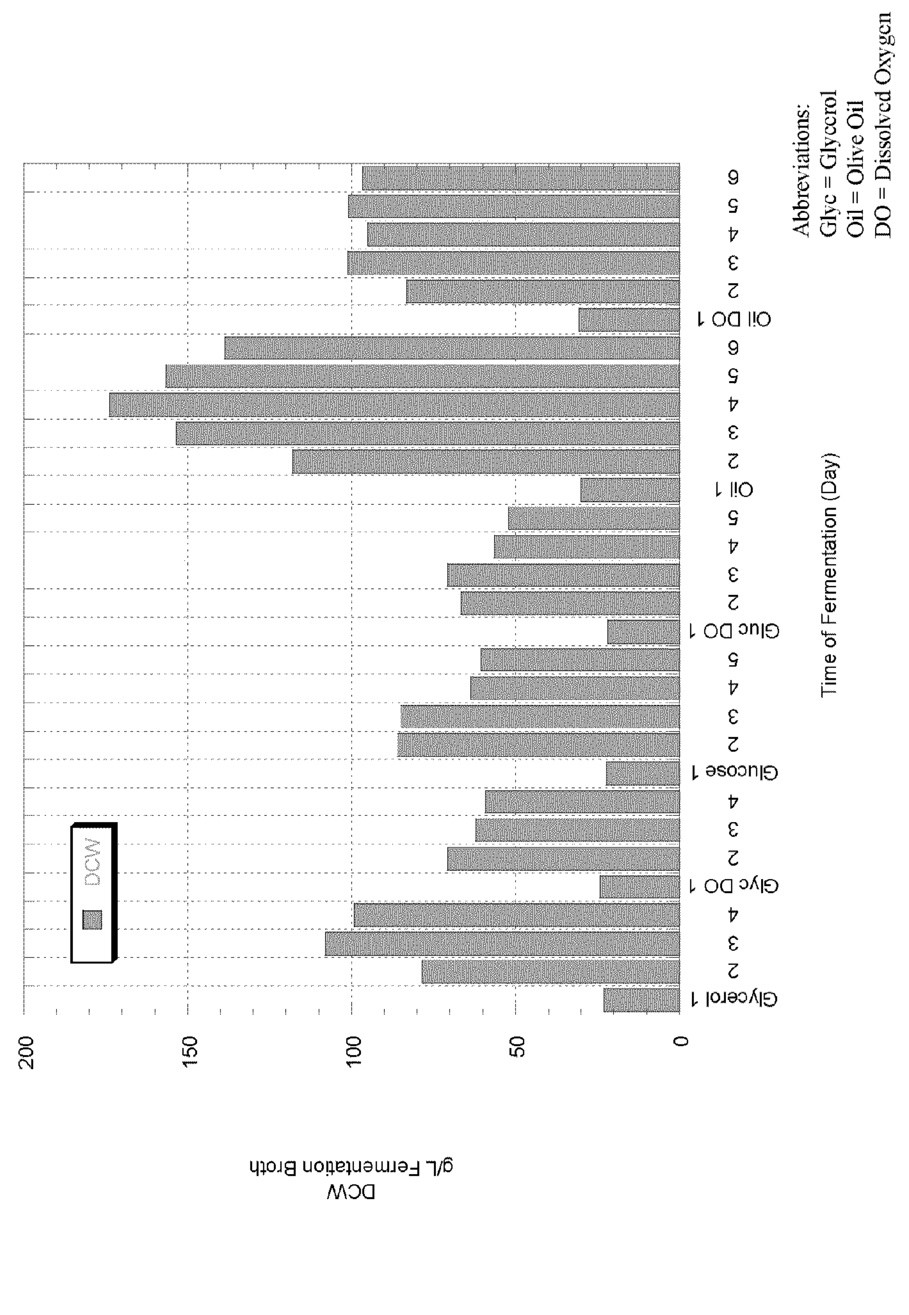

Figure 9c. β-Carotene and dry cell weight analysis of strain MF760 when grown in the presence of a combination of olive oil and glucose
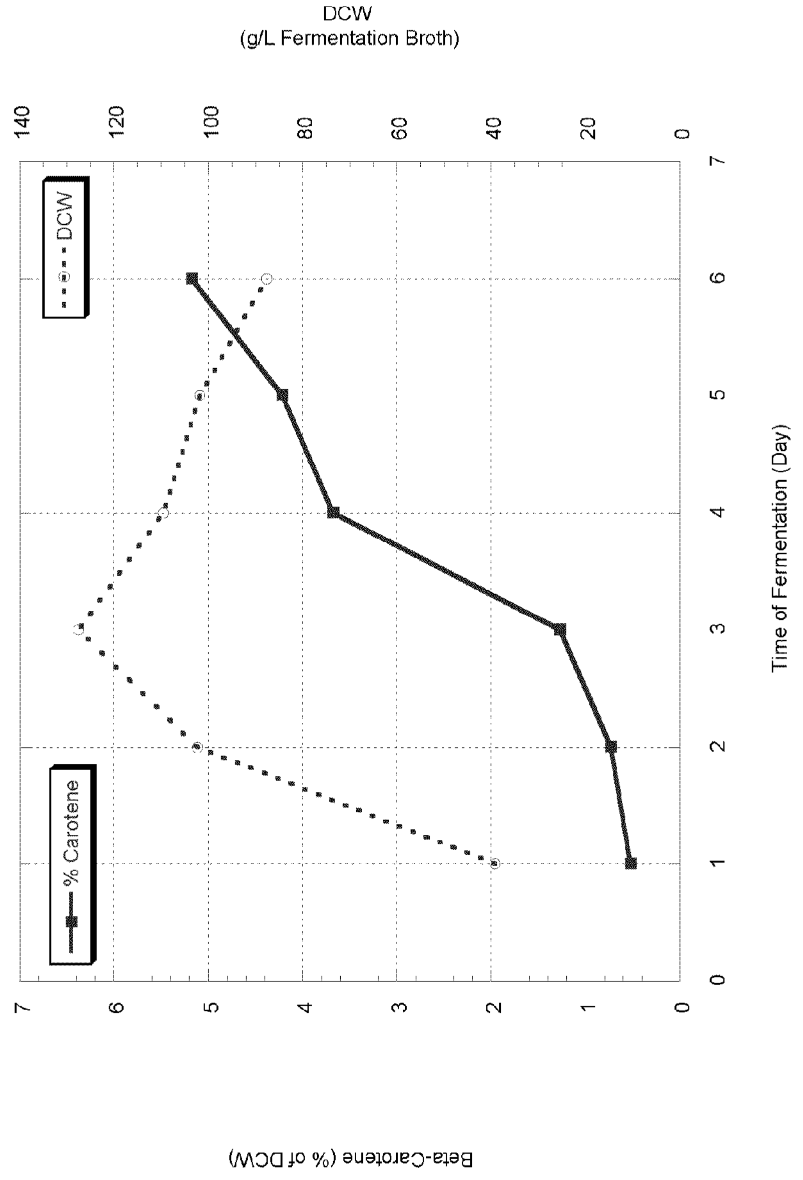

Figure 9d. Canthaxanthin, echinenone and β -carotene production of strain MF840
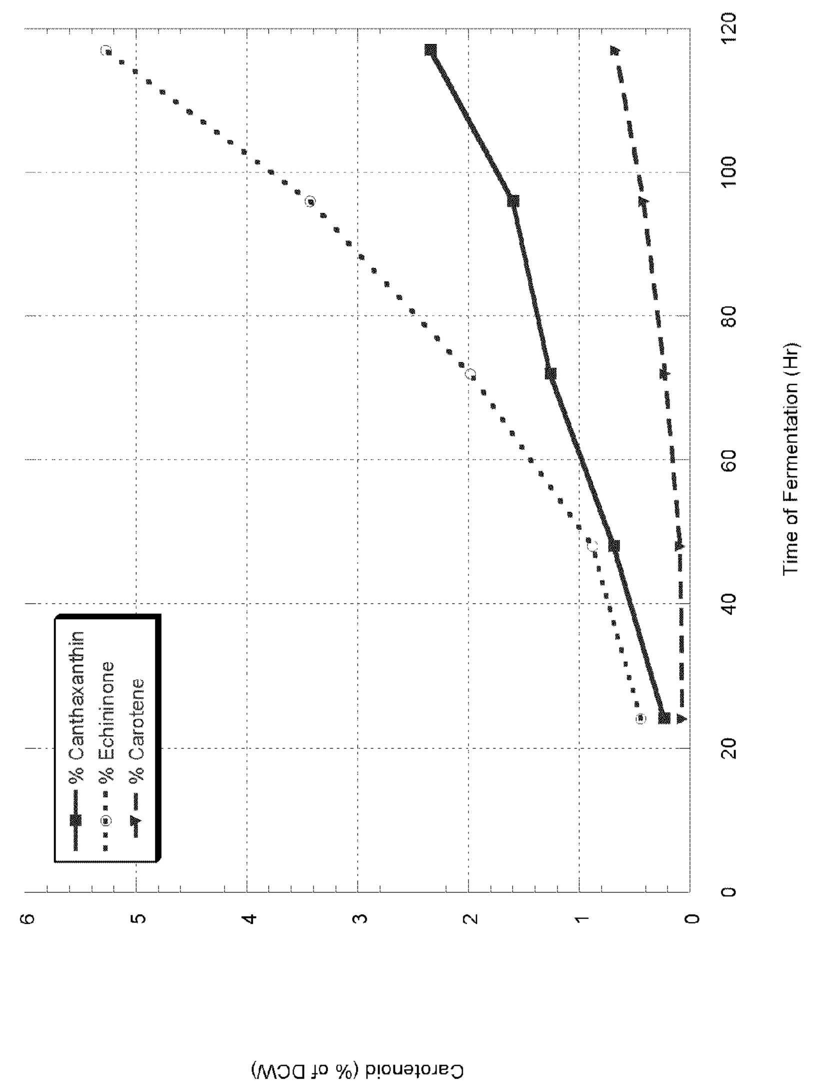

Figure 9e. Canthaxanthin and echinenone production of strain MF838 in a 2 phase feeding protocol
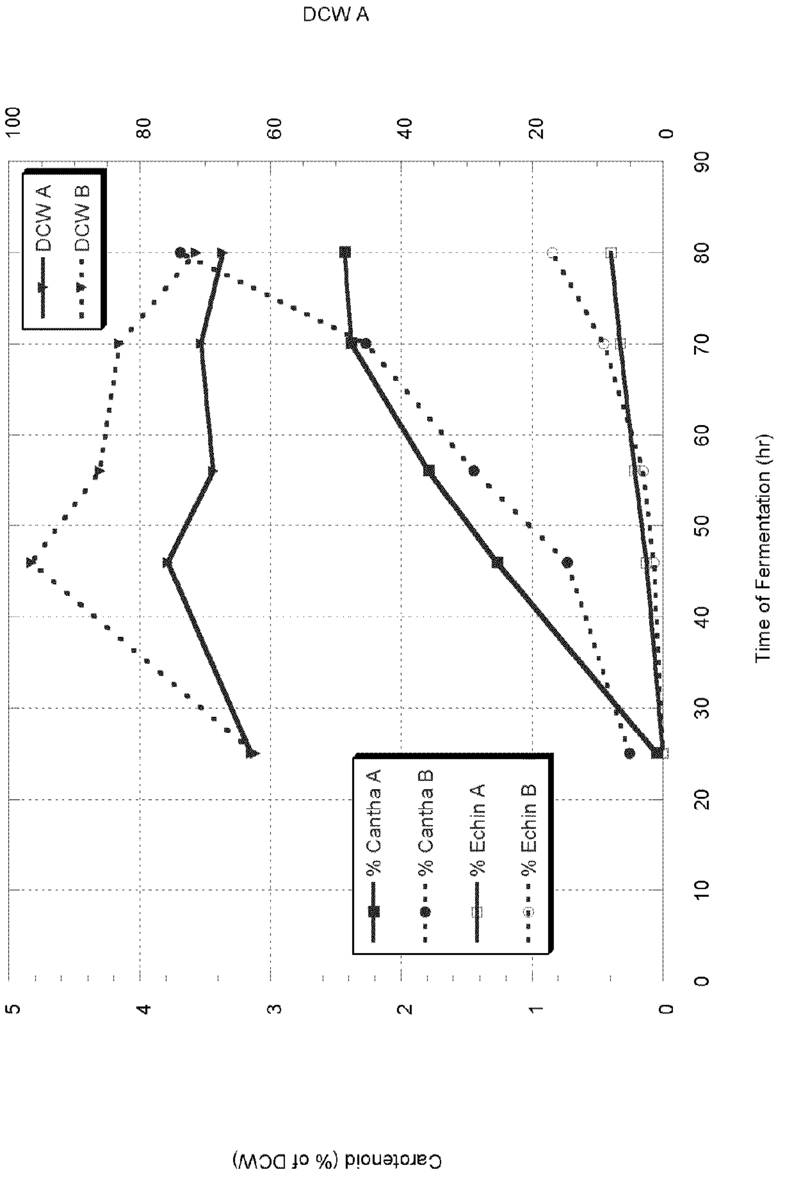

Figure 10. *Y. Lipolytica* Genes

| Genbank protein GI number | Genbank protein Accession Number | polypeptide | Y. lipolytica gene | Oligo 1 | Oligo 2 |
|---|---|---|---|---|---|
| 50557288 | XP_506052 | HMG-CoA synthase | YALI0F30481g | MO4890-<br>5'ctctagacacaaaaatgtcgcaaccccagaacgt<br>(SEQ ID NO:183) | MO4891-<br>5'cacgcgtctactgcttgatctcgtact<br>(SEQ ID NO:184) |
| 50546973 | XP_500956 | Mevalonate Kinase | YALI0B16038g | MO4982-<br>5'cgctagccacaaaaatggactacatcatttcggcg<br>c (SEQ ID NO:185) | MO4983-<br>5'cacgcgtctaatgggtccagggaccga<br>(SEQ ID NO:186) |
| 50552418 | XP_503619 | Phosphomevalonate kinase | YALI0E06193g | MO4984-<br>5'ctctagacacaaaaatgaccacctattcggctccg<br>(SEQ ID NO:187) | MO4985-<br>5'cggcgcgccctacttgaaccccttctcga<br>(SEQ ID NO:188) |
| 50555265 | XP_505041 | Mevalonate Pyrophosphate Decarboxylase | YALI0F05632g | MO4986-<br>5'ctctagacacaaaaatgatccaccaggcctccacc<br>a (SEQ ID NO:189) | MO4987-<br>5'cacgcgtctacttgctgttcttcagag<br>(SEQ ID NO:190) |
| 50555131 | XP_504974 | IPP Isomerase | YALI0F04015g | MO4988-<br>5'ctctagacacaaaaatgacgacgtcttacagcga<br>(SEQ ID NO:191) | MO4989-<br>5'cacgcgtctacttgatccaccgccgaa<br>(SEQ ID NO:192) |
| 50552378 | XP_503599 | FPP synthase | YALI0E05753 | MO4990-<br>5'ctctagacacaaaaatgtccaaggcgaaattcgaa<br>(SEQ ID NO:193) | MO4991-<br>5'cacgcgtctacttctgtcgcttgtaaa<br>(SEQ ID NO:194) |
| 50553402 | XP_504112 | Malic Enzyme | YALI0E18634g | MO4992-<br>5'ctctagacacaaaaatgttacgactacgaaccat<br>(SEQ ID NO:195) | MO4993-<br>5'cacgcgtctagtcgtaatcccgcacat<br>(SEQ ID NO:196) |

Figure 10. *Y. Lipolytica* Genes (Cont.)

| | | | | | |
|---|---|---|---|---|---|
| 50552824 | XP_503822 | AMP Deaminase | YALI0E11495g | MO4996-<br>5'cgctagccacaaaaatgccgcagcaagcaatgga<br>(SEQ ID NO:197) | MO4997-<br>5'cacgcgtttaaccatgcagccgctcaa<br>(SEQ ID NO:198) |
| 50550873 | XP_502909 | Malate Dehydrogenase Homolog | YALI0D16753g | MO5000-<br>5'ctctagacacaaaaatgttccgaacccgagttac<br>(SEQ ID NO:199) | MO5001-<br>5'cacgcgtttaagggttctgcttgacaa<br>(SEQ ID NO:200) |
| 50550839 | XP_502892 | Isocitrate Dehydrogenase | YALI0D16247g | MO5004-<br>5'ctctagacacaaaaatgacacaaacgcacaatct<br>(SEQ ID NO:201) | MO5005-<br>5'cacgcgtttacatcttgtacgcagggt<br>(SEQ ID NO:202) |
| 50545147 | XP_500111 | Fructose 1,6 bisphosphatase | YALI0A15972g | MO5008-<br>5'ctctagacacaaaaatggaagccaaccccgaagt<br>(SEQ ID NO:203) | MO5009-<br>5'cacgcgttcatttcagaaggtacttct<br>(SEQ ID NO:204) |
| 50552796 | XP_503808 | Acetoacetyl CoA thiolase | YALI0E11099g | MO4852-<br>5'ctctagacacaaaaatgcgactcactctgccc<br>(SEQ ID NO:205) | MO4853-<br>5'cacgcgtctactcgacagaagagaccttc<br>(SEQ ID NO:206) |
| 50554757 | XP_504787 | ATP citrate lyase subunit 1 | YALI0E34793g | MO4741-<br>5'ttctagacccaaaaatgtctgccaacgagaacatct<br>c (SEQ ID NO:207) | MO4743-<br>5'aacgcgtctatgatcgagtcttggccttg<br>(SEQ ID NO:208) |
| 50551515 | XP_503231 | ATP citrate lyase subunit 2 | YALI0D24431g | MO4760-<br>5'ttctagacacaaaaatgtcagcgaaatccattcacg<br>a (SEQ ID NO:209) | MO4861-<br>5'cacgcgttaaactccgagaggagtgg<br>(SEQ ID NO:210) |
| 50553046 | XP_503933 | Malate Dehydrogenase | YALI0E14190g | MO4994-<br>5'ctctagacacaaaagtggttaaagctgtcgttgc<br>(SEQ ID NO:211) | MO4995-<br>5'cacgcgtttacttggcaggaggagggt<br>(SEQ ID NO:212) |

Figure 10. *Y. Lipolytica* Genes (Cont.)

| | | | | | |
|---|---|---|---|---|---|
| 50553728 | XP_504275 | Glucose 6 Phosphate Dehydrogenase | YALI0E22649g | MO4998-<br>5'ctctagacacaaaaatgactggcaccttacccaa<br>(SEQ ID NO:213) | MO4999-<br>5'cacgcgttcacgaggagcccttggtga<br>(SEQ ID NO:214) |
| 50546937 | XP_500938 | 6-phosphogluconate dehydrogenase | YALI0B15598g | MO5002-<br>5'ctctagacacaaaaatgactgacacttcaaacat<br>(SEQ ID NO:215) | MO5003-<br>5'cacgcgtttaagcatcgtaagtggaag<br>(SEQ ID NO:216) |
| 50550013 | XP_502479 | Isocitrate dehydrogenase | YALI0D06303g | MO5006-<br>5'ctctagacacaaaaatgctcaaccttagaaccgc<br>(SEQ ID NO:217) | MO5007-<br>5'cacgcgtctacttgagtcgcttgataa<br>(SEQ ID NO:218) |

Vitamin A Biosynthesis from Beta-Carotene

C02094 beta-Carotene

C00376 All-trans-Retinal

C00473 all-trans-Retinol (vitamin A)

Figure 12a. Total carotenoid accumulation in ML1011 grown under varying pH conditions
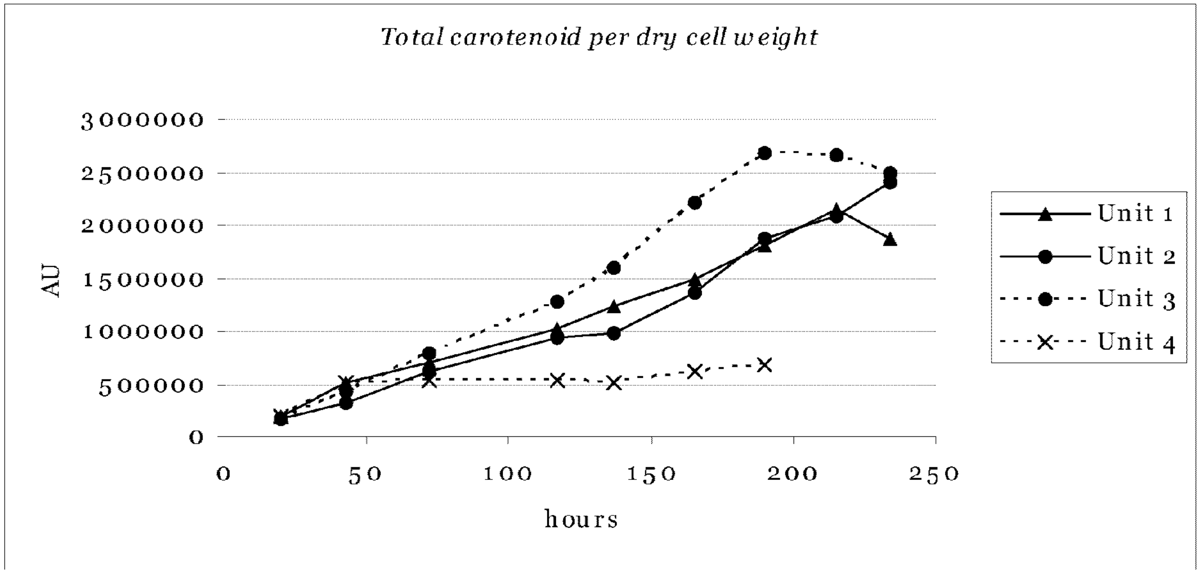
| | | |
|---|---|---|
| | Unit 1 | pH 5.5 |
| | Unit 2 | pH 7.0 |
| | Unit 3 | pH 7.0, rising to pH 8.0 at 0.021 pH units / hour until 48 hours |
| | Unit 4 | pH 7.0, rising to pH 9.0 at 0.042 pH units / hour until 48 hours |

Figure 12b. Zeaxanthin accumulation in ML1011 grown under varying pH conditions
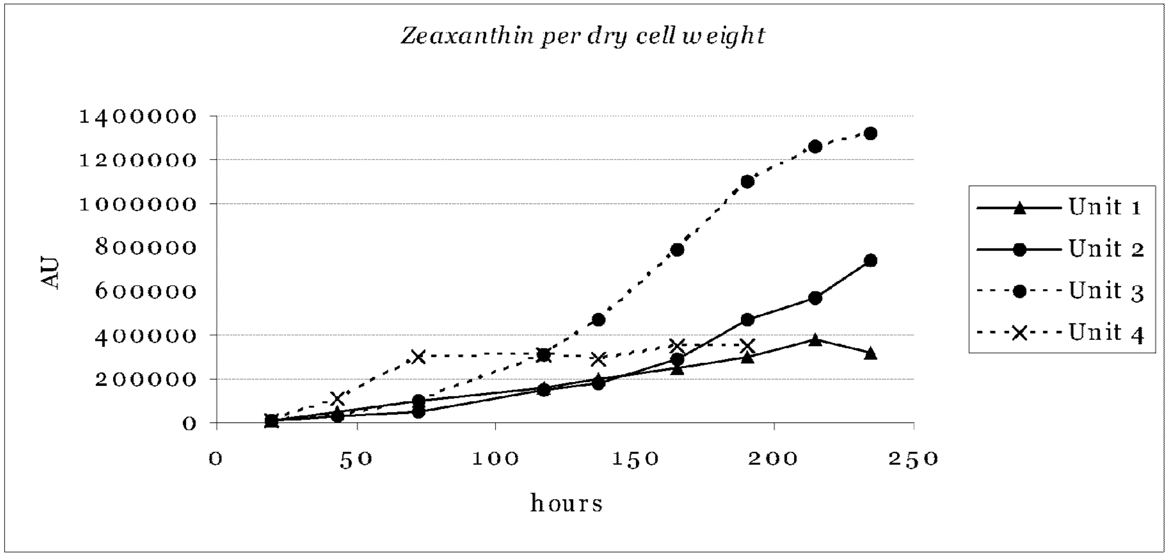
| | | |
|---|---|---|
| —▲— | Unit 1 | pH 5.5 |
| —●— | Unit 2 | pH 7.0 |
| - -●- - | Unit 3 | pH 7.0, rising to pH 8.0 at 0.021 pH units / hour until 48 hours |
| - -X- - | Unit 4 | pH 7.0, rising to pH 9.0 at 0.042 pH units / hour until 48 hours |

Figure 12c. Fraction of carotenoid as zeaxanthin in ML1011 grown under varying pH conditions
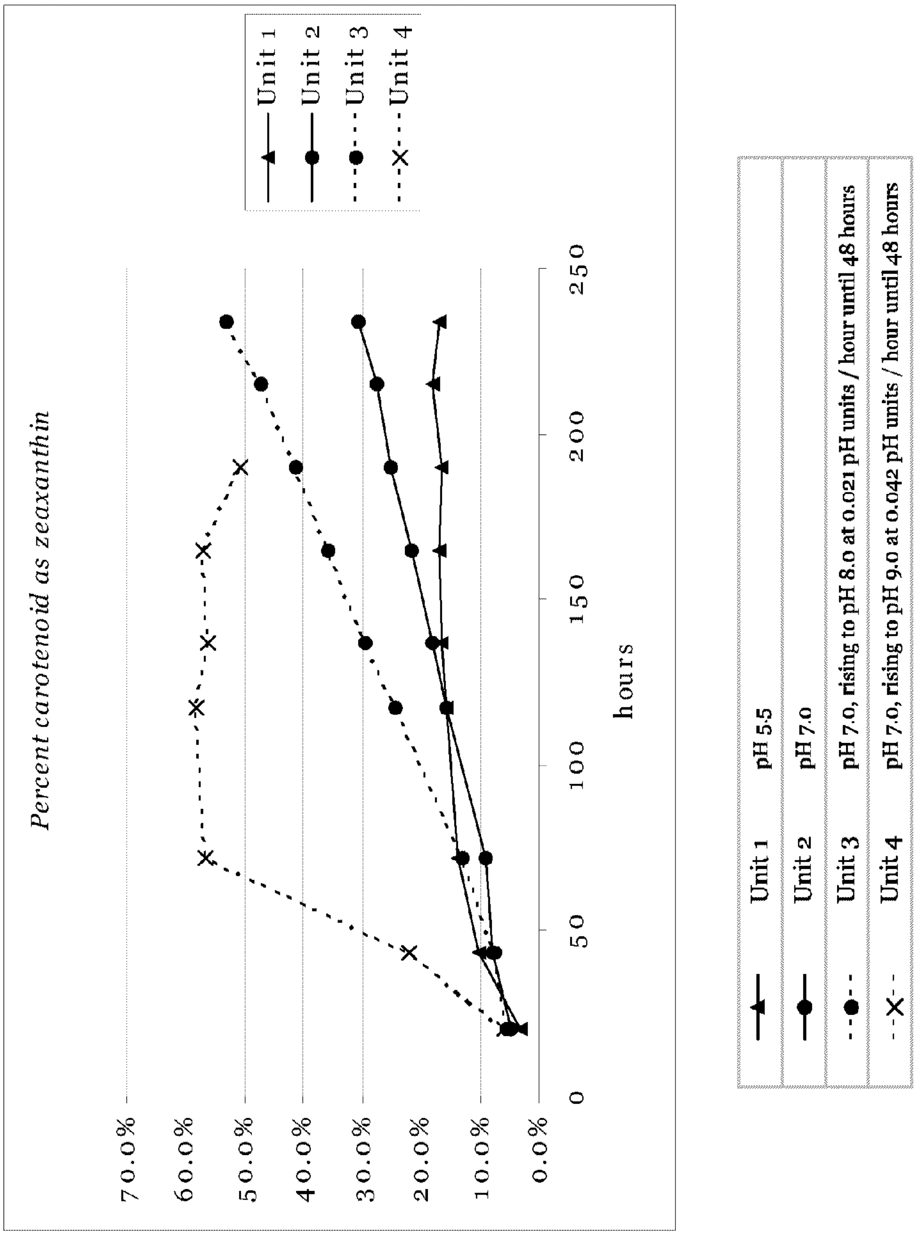

Figure 12d. Carbon dioxide evolution of ML1011 grown under varying pH conditions
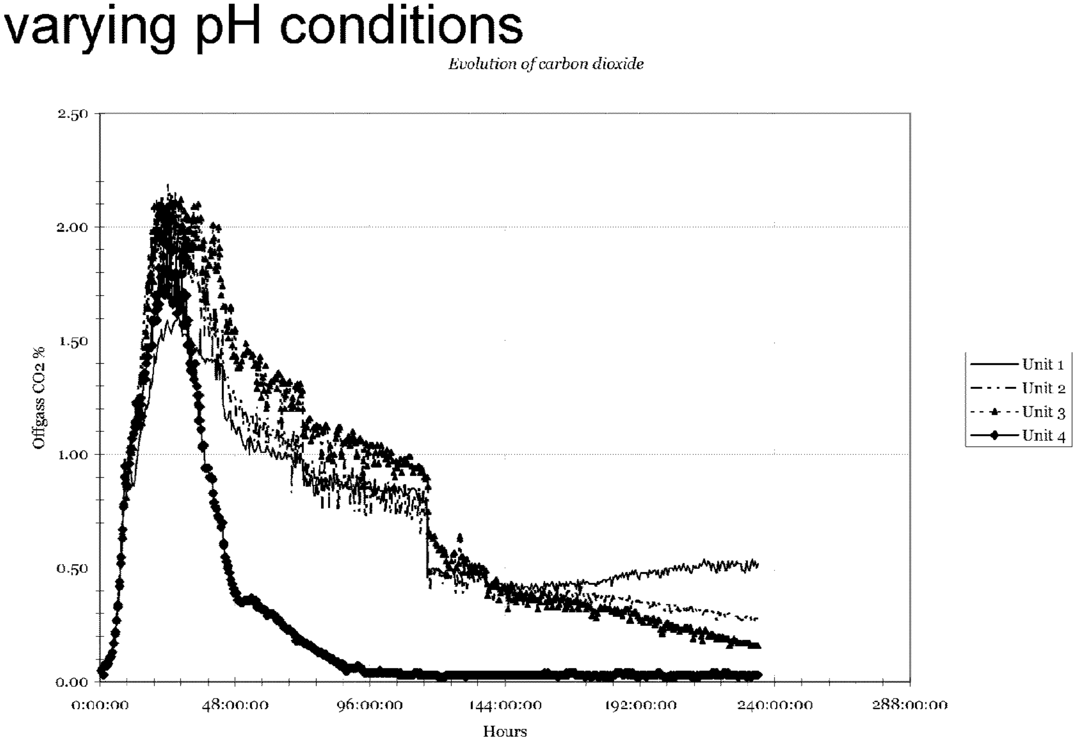
| | | |
|---|---|---|
| | Unit 1 | pH 5.5 |
| | Unit 2 | pH 7.0 |
| | Unit 3 | pH 7.0, rising to pH 8.0 at 0.021 pH units / hour until 48 hours |
| | Unit 4 | pH 7.0, rising to pH 9.0 at 0.042 pH units / hour until 48 hours |

Figure 12e. Biomass accumulation in ML1011 grown under varying pH conditions
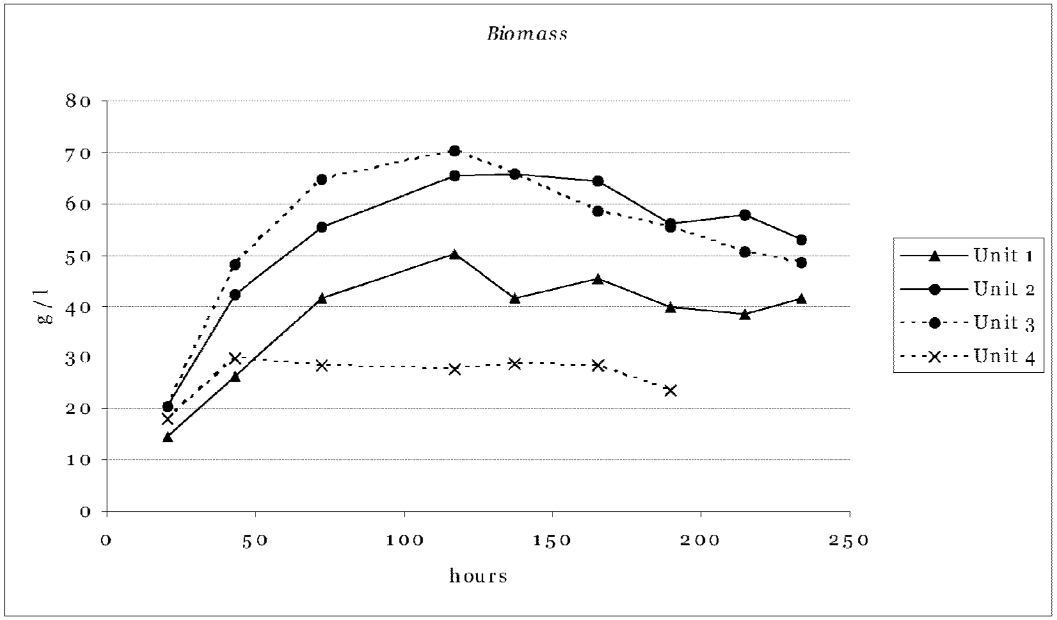
| | | |
|---|---|---|
| | Unit 1 | pH 5.5 |
| | Unit 2 | pH 7.0 |
| | Unit 3 | pH 7.0, rising to pH 8.0 at 0.021 pH units / hour until 48 hours |
| | Unit 4 | pH 7.0, rising to pH 9.0 at 0.042 pH units / hour until 48 hours |

PRODUCTION OF CAROTENOIDS IN OLEAGINOUS YEAST AND FUNGI

CROSS REFERENCE TO RELATED APPLICATIONS

This application is a national phase application under 35 U.S.C. §371 of PCT International Application No. PCT/US2007/021092, filed Sep. 28, 2007, which is copending with, shares at least one common inventor with, and claims priority to U.S. provisional patent application No. 60/848,062, filed Sep. 28, 2006. This application is also copending with, shares at least one common inventor with, and claims priority to U.S. provisional patent application No. 60/902,145, filed Feb. 16, 2007. The entire contents of each of these applications are hereby incorporated by reference.

SEQUENCE LISTING

In accordance with 37 CFR 1.52(e)(5), a Sequence Listing in the form of a text file (entitled "2005862-0053_SL.txt," created on Feb. 11, 2013, and 329,074 bytes in size) is incorporated herein by reference in its entirety.

BACKGROUND OF THE INVENTION

Carotenoids are organic pigments ranging in color from yellow to red that are naturally produced by certain organisms, including photosynthetic organisms (e.g., plants, algae, cyanobacteria), and some fungi. Carotenoids are responsible for the orange color of carrots, as well as the pink in flamingos and salmon, and the red in lobsters and shrimp. Animals, however, cannot produce carotenoids and must receive them through their diet.

Carotenoid pigments (e.g., β-carotene and astaxanthin) are used industrially as ingredients for food and feed stocks, both serving a nutritional function and enhancing consumer acceptability. For example, astaxanthin is widely used in salmon aquaculture to provide the orange coloration characteristic of their wild counterparts. Some carotenoids are also precursors of vitamin A. Also, carotenoids have antioxidant properties, and may have various health benefits (see, for example, Jyonouchi et al., *Nutr. Cancer* 16:93, 1991; Giovannucci et al., *J. Natl. Cancer Inst.* 87:1767, 1995; Miki, *Pure Appl. Chem* 63:141, 1991; Chew et al., *Anticancer Res.* 19:1849, 1999; Wang et al., *Antimicrob. Agents Chemother.* 44:2452, 2000). Some carotenoids such as β-carotene, lycopene, and lutein are currently sold as nutritional supplements.

In general, the biological systems that produce carotenoids are industrially intractable and/or produce the compounds at such low levels that commercial scale isolation is not practicable. Thus, most carotenoids used in industry are produced by chemical synthesis. There is a need for improved biological systems that produce carotenoids. Some efforts have previously been made to genetically engineer certain bacteria or fungi to produce higher levels of carotenoids (see, for example, Misawa et al., *J. Biotechnol.* 59:169, 1998; Visser et al., *FEMS Yeast Research* 4:221, 2003). However, improved systems, allowing higher levels of production and greater ease of isolation, are needed.

SUMMARY OF THE INVENTION

The present invention provides improved systems for the biological production of carotenoids and/or retinolic compounds. In one aspect, the invention encompasses the discovery that it is desirable to produce carotenoids and/or retinolic compounds in oleaginous organisms. Without wishing to be bound by any particular theory, the present inventors propose that biological systems may be able to accumulate higher levels of carotenoids and/or retinolic compounds if the compounds are sequestered in lipid bodies. Regardless of whether absolute levels are higher, however, carotenoids and/or retinolic compounds that are accumulated within lipid bodies in oleaginous organisms are readily isolatable through isolation of the lipid bodies.

The present invention therefore provides oleaginous fungi (including, for example, yeast) that produce one or more carotenoids and/or retinolic compounds. The present invention also provides methods of constructing such yeast and fungi, methods of using such yeast and fungi to produce carotenoids and/or retinolic compounds, and methods of preparing carotenoid-containing compositions and/or retinolic compound-containing compositions, such as food or feed additives, or nutritional supplements, using carotenoids and/or retinolic compounds produced in such oleaginous yeast or fungi. In particular, the present invention provides systems and methods for generating yeast and fungi containing one or more oleaginic and/or carotenogenic and/or retinologenic modifications that increase the oleaginicity and/or alter their carotenoid-producing and/or retinolic compound-producing capabilities as compared with otherwise identical organisms that lack the modification(s).

The present invention further encompasses the general recognition that lipid-accumulating systems are useful for the production and/or isolation of lipophilic agents (such as, but not limited to isoprenoids, or isoprenoid-derived compounds such as retinolic compounds, carotenoids, ubiquinones, lanosterol, zymosterol, ergosterol, vitamins (e.g., vitamins A, E, D, K, specifically 7-dehydrocholesterol (provitamin D3), sterols (e.g., squalene), etc.). According to the present invention, it is desirable to engineer organisms to produce such lipophilic agents and/or to accumulate lipid.

Indeed, one aspect of the present invention is the recognition that host cells can be engineered to accumulate in lipid bodies any of a variety of hydrophilic and/or fat soluble compounds (e.g., retinolic compounds, carotenoids, ubiquinones, vitamins, squalene, etc.) having negligible solubility in water (whether hot or cold) and an appropriate solubility in oil. In some embodiments of the invention, modified host cells are engineered to produce one or more lipophilic agents characterized by negligible solubility in water and detectable solubility in one or more oils. In some embodiments, such lipophilic agents (including, but not limited to carotenoids and/or retinolic compounds) have a solubility in oil below about 0.2%. In some embodiments, such lipophilic agents have a solubility in oil within the range of about <0.001%-0.2%.

The present invention therefore provides engineered host cells (and methods of making and using them) that contain lipid bodies and that further contain one or more compounds accumulated in the lipid bodies, where the compounds are characterized by a negligible solubility in water and a solubility in oil within the range of about <0.001%-0.2%; 0.004%-0.15%; 0.005-0.1%; or 0.005-0.5%. For example, in some embodiments, such lipophilic agents have a solubility in oil below about 0.15%, 0.14%, 0.13%, 0.12%, 0.11%, 0.10%, 0.09, 0.08%, 0.07%, 0.06%, 0.05%, 0.04%, 0.03%, 0.02%, 0.01%, 0.05%, or less. In some embodiments, the lipophilic agents show such solubility in an oil selected from the group consisting of sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose;

orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and mixtures thereof.

In some embodiments, the present invention provides a recombinant fungus. In certain embodiments, the recombinant fungus is oleaginous in that it can accumulate lipid to at least about 20% of its dry cell weight; and produces at least one carotenoid and/or retinolic compound, and can accumulate the produced carotenoid and/or retinolic compound to at least about 1% of its dry cell weight; wherein the recombinant fungus comprises at least one modification as compared with a parental fungus, which parental fungus both is not oleaginous and does not accumulate the carotenoid and/or retinolic compound to at least about 1% of its dry cell weight, the at least one modification being selected from the group consisting of retinologenic modifications, carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one carotenoid and/or retinolic compound to a level at least about 1% of its dry cell weight, or confers to the recombinant fungus the ability to produce at least one carotenoid and/or retinolic compound which the parental fungus does not produce.

In other embodiments, the recombinant fungus is oleaginous in that it can accumulate lipid to at least about 20% of its dry cell weight; and produces at least one carotenoid selected from the group consisting of antheraxanthin, adonirubin, adonixanthin, astaxanthin, canthaxanthin, capsorubrin, β-cryptoxanthin, α-carotene, β,ψ-carotene, δ-carotene, ϵ-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, a C30 carotenoid, and combinations thereof, and can accumulate the produced carotenoid to at least about 1% of its dry cell weight; wherein the recombinant fungus comprises at least one modification as compared with a parental fungus, the at least one modification being selected from the group consisting of carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one carotenoid to a level at least about 1% of its dry cell weight, or confers to the recombinant fungus the ability to produce at least one carotenoid which the parental fungus does not naturally produce.

In other embodiments, the recombinant fungus is oleaginous in that it can accumulate lipid to at least about 20% of its dry cell weight; and produces at least one retinolic compound selected from the group consisting of retinol, retinal, retinoic acid, and combinations thereof, and can accumulate the produced retinolic compound to at least about 1% of its dry cell weight; wherein the recombinant fungus comprises at least one modification as compared with a parental fungus, the at least one modification being selected from the group consisting of retinologenic modifications, carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one retinolic compound to a level at least about 1% of its dry cell weight, or confers to the recombinant fungus the ability to produce at least one retinolic compound which the parental fungus does not naturally produce.

In some embodiments, the recombinant fungus is oleaginous in that it can accumulate lipid to at least about 20% of its dry cell weight; and produces at least one carotenoid and/or retinolic compound, and can accumulate the produced carotenoid and/or retinolic compound to at least about 1% of its dry cell weight; wherein the recombinant fungus is a member of a genus selected from the group consisting of: *Aspergillus, Blakeslea, Botrytis, Candida, Cercospora, Cryptococcus, Cunninghamella, Fusarium* (*Gibberella*), *Kluyveromyces, Lipomyces, Mortierella, Mucor, Neurospora, Penicillium, Phycomyces, Pichia* (*Hansenula*), *Puccinia, Pythium, Rhodosporidium, Rhodotorula, Saccharomyces, Sclerotium, Trichoderma, Trichosporon, Xanthophyllomyces* (*Phaffia*), and *Yarrowia*; or is a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi* (*Gibberella zeae*), *Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous* (*Phaffia rhodozyma*), and *Yarrowia lipolytica*, wherein the recombinant fungus comprises at least one modification as compared with a parental fungus, the at least one modification being selected from the group consisting of retinologenic modifications, carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one carotenoid and/or retinolic compound to a level at least about 1% of its dry cell weight, or confers to the recombinant fungus the ability to produce at least one carotenoid and/or retinolic compound which the parental fungus does not naturally produce.

In other embodiments, the recombinant fungus is oleaginous in that it can accumulate lipid to at least about 20% of its dry cell weight; and produces at least one carotenoid selected from the group consisting of antheraxanthin, adonirubin, adonixanthin, astaxanthin, canthaxanthin, capsorubrin, β-cryptoxanthin, α-carotene, β,ψ-carotene, δ-carotene, ϵ-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, a C30 carotenoid, and combinations thereof, and can accumulate the produced carotenoid to at least about 1% of its dry cell weight; wherein the recombinant fungus is a member of a genus selected from the group consisting of: *Aspergillus, Blakeslea, Botrytis, Candida, Cercospora, Cryptococcus, Cunninghamella, Fusarium* (*Gibberella*), *Kluyveromyces, Lipomyces, Mortierella, Mucor, Neurospora, Penicillium, Phycomyces, Pichia* (*Hansenula*), *Puccinia, Pythium, Rhodosporidium, Rhodotorula, Saccharomyces, Sclerotium, Trichoderma, Trichosporon, Xanthophyllomyces* (*Phaffia*), and *Yarrowia*, or is of a species selected from the group consisting of *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi* (*Gibberella zeae*), *Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous* (*Phaffia rhodozyma*), and *Yarrowia lipolytica*, wherein the recombinant fungus comprises at least one modification as compared with a parental fungus, the at least one modification being selected from the group consisting of carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one carotenoid to a level at least about 1% of its dry cell weight, or confers to the recombinant fungus the ability to produce at least one carotenoid which the parental fungus does not naturally produce.

In other embodiments, the recombinant fungus is oleaginous in that it can accumulate lipid to at least about 20% of its dry cell weight; and produces at least one retinolic compound selected from the group consisting of retinol, retinal, retinoic acid, and combinations thereof, and can accumulate the produced retinolic compound to at least about 1% of its dry cell weight; wherein the recombinant fungus is a member of a genus selected from the group consisting of: *Aspergillus, Blakeslea, Botrytis, Candida, Cercospora, Cryptococcus, Cunninghamella, Fusarium* (*Gibberella*), *Kluyveromyces, Lipomyces, Mortierella, Mucor, Neurospora, Penicillium, Phycomyces, Pichia* (*Hansenula*), *Puccinia, Pythium, Rhodosporidium, Rhodotorula, Saccharomyces, Sclerotium, Trichoderma, Trichosporon, Xanthophyllomyces* (*Phaffia*), and *Yarrowia*, or is of a species selected from the group consisting of *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi* (*Gibberella zeae*), *Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous* (*Phaffia rhodozyma*), and *Yarrowia lipolytica*, wherein the recombinant fungus comprises at least one modification as compared with a parental fungus, the at least one modification being selected from the group consisting of retinologenic modifications, carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one retinolic compound to a level at least about 1% of its dry cell weight, or confers to the recombinant fungus the ability to produce at least one retinolic compound which the parental fungus does not naturally produce.

In certain embodiments, the recombinant fungus is oleaginous in that it can accumulate lipid to at least about 20% of its dry cell weight; and the recombinant fungus produces at least one small molecule lipophilic agent selected from the group consisting of retinolic compounds, carotenoids, ubiquinone, vitamin K, vitamin E, squalene, lanosterol, zymosterol, ergosterol, 7-dehydrocholesterol (provitamin D3), and combinations thereof and can accumulate the produced carotenoid and/or retinolic compound to at least about 1% of its dry cell weight; wherein the recombinant fungus comprises at least one modification as compared with a parental fungus, the at least one modification being selected from the group consisting of retinologenic modifications, carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one carotenoid and/or retinolic compound to a level at least about 1% of its dry cell weight, or confers to the recombinant fungus the ability to produce at least one carotenoid and/or retinolic compound which the parental fungus does not naturally produce.

In some embodiments, the recombinant fungus is oleaginous in that it can accumulate lipid to at least about 20% of its dry cell weight; and the recombinant fungus produces at least one small molecule lipophilic agent characterized by a negligible solubility in water and solubility in oil within the range of about <0.001%-0.2%; 0.004%-0.15%; 0.005-0.1%; or 0.005-0.5%, and combinations thereof and can accumulate the produced small molecule lipophilic agent to at least about 1% of its dry cell weight; wherein the recombinant fungus comprises at least one modification as compared with a parental fungus, the at least one modification being selected from the group consisting of retinologenic modifications, carotenogenic modifications, oleaginic modifications, and combinations thereof, and wherein the at least one modification alters oleaginicity of the recombinant fungus, confers to the recombinant fungus oleaginy, confers to the recombinant fungus the ability to produce the at least one small molecule lipophilic agent to a level at least about 1% of its dry cell weight, or confers to the recombinant fungus the ability to produce at least one small molecule lipophilic agent which the parental fungus does not naturally produce.

In other embodiments the recombinant fungus is oleaginous in that it can accumulate lipid to at least about 20% of its dry cell weight; and the recombinant fungus produces at least one small molecule lipophilic agent selected from the group consisting of retinolic compounds, carotenoids, ubiquinone, vitamin K, vitamin E, squalene, lanosterol, zymosterol, ergosterol, 7-dehydrocholesterol (provitamin D3), and can accumulate the produced small molecule lipophilic agent to at least about 1% of its dry cell weight; wherein the recombinant fungus is a member of a genus selected from the group consisting of *Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium* (*Gibberella*), *Kluyveromyces, Neurospora, Penicillium, Pichia* (*Hansenula*), *Puccinia, Saccharomyces, Schizosaccharomyces, Sclerotium, Trichoderms, Ustilago*, and *Xanthophyllomyces* (*Phaffia*) and comprises at least one genetic modification as compared with a parental fungus, wherein the at least one modification alters oleaginicity of the recombinant fungus, confers to the recombinant fungus oleaginy, confers to the recombinant fungus the ability to produce the at least one small molecule lipophilic agent to a level at least about 1% of its dry cell weight, or confers to the recombinant fungus the ability to produce at least one small molecule lipophilic agent which the parental fungus does not naturally produce.

In some embodiments, the present invention provides a strain of *Yarrowia lipolytica* comprising one or more modifications selected from the group consisting of an oleaginic modification, a carotenogenic modification, and combinations thereof, such that the strain accumulates from 1% to 15% of its dry cell weight as at least one carotenoid. In some embodiments, the present invention provides a strain of *Yarrowia lipolytica* comprising one or more modifications selected from the group consisting of an oleaginic modification, a retinologenic modification, and combinations thereof, such that the strain accumulates from 1% to 15% of its dry cell weight as at least one retinolic compound.

In some embodiments, the present invention provides an engineered *Y. lipolytica* strain that produces β-carotene, the strain containing one or more carotenogenic modifications selected from the group consisting of: increased expression or activity of a *Y. lipolytica* GGPP synthase polypeptide; expression or activity of a truncated HMG CoA reductase polypeptide; expression or activity of a phytoene dehydrogenase polypeptide; expression or activity of a phytoene synthase/lycopene cyclase polypeptide; increased expression or activity of an FPP synthase polypeptide; increased expression or activity of an IPP isomerase polypeptide; increased expression or activity of an HMG synthase polypeptide; increased expression or activity of a mevalonate kinase polypeptide; increased expression or activity of a phosphomevalonate kinase polypeptide; increased expression or activity of a mevalonate pyrophosphate decarboxylate polypeptide; increased expression or activity of a malic enzyme polypeptide; increased expression or activity of a malate dehydrogenase polypeptide; increased expression or activity of an AMP deaminase polypeptide; increased expression or activity of a glucose 6 phosphate dehydrogenase polypeptide; increased expression or activity of a malate dehydrogenase homolog2 polypeptide; increased expression or activity of a GND1-6-phosphogluconate dehydrogenase polypeptide; increased expression or activity of a isocitrate dehydrogenase polypeptide; increased expression or activity of a IDH2-isocitrate dehydrogenase polypeptide; increased expression or activity of a fructose 1,6 bisphosphatase polypeptide; increased expression or activity of a Erg10-acetoacetyl CoA thiolase polypeptide; increased expression or activity of a ATP citrate lyase subunit 2 polypeptide; increased expression or activity of a ATP citrate lyase subunit 1 polypeptide; decreased expression or activity of a squalene synthase polypeptide; decreased expression or activity of a prenyldiphosphate synthase polypeptide; or decreased expression or activity of a PHB polyprenyltransferase polypeptide; and combinations thereof.

In some embodiments, the present invention provides an engineered *Y. lipolytica* strain that produces Vitamin A, the strain containing one or more retinologenic modifications selected from the group consisting of: increased expression or activity of a beta-carotene 15,15'-monooxygenase polypeptide; increased expression or activity of a retinol dehydrogenase polypeptide; and combinations thereof.

In some embodiments, the present invention provides an engineered *Y. lipolytica* strain containing a truncated HMG CoA reductase polypeptide. In some embodiments, the present invention provides an engineered *Y. lipolytica* strain having increased expression or activity of a GGPP synthase gene. In some embodiments, the present invention provides an engineered *Y. lipolytica* strain having decreased expression or activity of a squalene synthase polypeptide. In some embodiments, the present invention provides an engineered *Y. lipolytica* strain containing a heterologous phytoene dehydrogenase (carB) polypeptide and a heterologous phytoene synthase/lycopene cyclase (carRP) polypeptide.

In some embodiments, the present invention provides a genetically modified *Y. lipolytica* strain comprising an altered activity or expression of one or more enzymes when compared to an unmodified strain, wherein the altered activity or expression of one or more enzymes is selected from the group consisting of: increased activity or expression of a beta-carotene 15,15'-monooxygenase polypeptide; increased activity or expression of a retinol dehydrogenase polypeptide; increased activity or expression of acetyl-CoA thiolase, increased activity or expression of HMG-CoA synthase, increased activity or expression of HMG-CoA reductase, increased activity or expression of mevalonate kinase, increased activity or expression of phosphomevalonate kinase, increased activity or expression of mevalonate PP decarboxylase, decreased activity or expression of acetyl-CoA carboxylase, increased activity or expression of IPP isomerase, increased activity or expression of GPP synthase, increased activity or expression of FPP synthase, increased activity or expression of squalene synthase, decreased activity or expression of squalene synthase, increased activity or expression of GGPP synthase, decreased activity or expression of GGPP synthase, increased activity or expression of glucose-6-phosphate dehydrogenase, increased activity or expression of 6-phosphogluconate dehydrogenase, increased activity or expression of fructose 1,6 bisphosphatase, increased activity or expression of NADH kinase, increased activity or expression of transhydrogenase, and combinations thereof.

In certain embodiments, the present invention provides a genetically modified *Candida utilis* strain comprising an altered activity or expression of one or more enzymes when compared to an unmodified strain, wherein the altered activity or expression of one or more enzymes is selected from the group consisting of: increased activity or expression of a beta-carotene 15,15'-monooxygenase polypeptide; increased activity or expression of a retinol dehydrogenase polypeptide; increased activity or expression of acetyl-CoA thiolase, increased activity or expression of HMG-CoA synthase, increased activity or expression of HMG-CoA reductase, increased activity or expression of mevalonate kinase, increased activity or expression of phosphomevalonate kinase, increased activity or expression of mevalonate PP decarboxylase, decreased activity or expression of acetyl-CoA carboxylase, increased activity or expression of IPP isomerase, increased activity or expression of GPP synthase, increased activity or expression of FPP synthase, increased activity or expression of squalene synthase, decreased activity or expression of squalene synthase, increased activity or expression of GGPP synthase, decreased activity or expression of GGPP synthase, increased activity or expression of glucose-6-phosphate dehydrogenase, increased activity or expression of 6-phosphogluconate dehydrogenase, increased activity or expression of fructose 1,6 bisphosphatase, increased activity or expression of NADH kinase, increased activity or expression of transhydrogenase, and combinations thereof.

In other embodiments, the present invention provides a genetically modified *Saccharomyces cerevisiae* strain comprising an altered activity or expression of one or more enzymes when compared to an unmodified strain, wherein the altered activity or expression of one or more enzymes is selected from the group consisting of: increased activity or expression of a beta-carotene 15,15'-monooxygenase polypeptide; increased activity or expression of a retinol dehydrogenase polypeptide; increased activity or expression of acetyl-CoA thiolase, increased activity or expression of HMG-CoA synthase, increased activity or expression of HMG-CoA reductase, increased activity or expression of mevalonate kinase, increased activity or expression of phosphomevalonate kinase, increased activity or expression of mevalonate PP decarboxylase, decreased activity or expression of acetyl-CoA carboxylase, increased activity or expression of IPP isomerase, increased activity or expression of GPP synthase, increased activity or expression of FPP synthase, increased activity or expression of squalene synthase, decreased activity or expression of squalene synthase, increased activity or expression of GGPP synthase, decreased activity or expression of GGPP synthase, increased activity or expression of glucose-6-phosphate dehydrogenase, increased activity or expression of 6-phosphogluconate dehydrogenase, increased activity or expression of fructose 1,6 bisphosphatase, increased activity or expression of NADH kinase, increased activity or expression of transhydrogenase, and combinations thereof.

In some embodiments, the present invention provides a genetically modified *Xanthophyllomyces dendrorhous* (*Phaffia rhodozyma*) strain comprising an altered activity or expression of one or more enzymes when compared to an unmodified strain, wherein the altered activity or expression of one or more enzymes is selected from the group consisting of: increased activity or expression of a beta-carotene 15,15'-monooxygenase polypeptide; increased activity or expression of a retinol dehydrogenase polypeptide; increased activity or expression of acetyl-CoA thiolase, increased activity or expression of HMG-CoA synthase, increased activity or expression of HMG-CoA reductase, increased activity or expression of mevalonate kinase, increased activity or expression of phosphomevalonate kinase, increased activity or expression of mevalonate PP decarboxylase, decreased activity or expression of acetyl-CoA carboxylase, increased activity or expression of IPP isomerase, increased activity or expression of GPP synthase, increased activity or expression of FPP synthase, increased activity or expression of squalene synthase, decreased activity or expression of squalene synthase, increased activity or expression of GGPP synthase, decreased activity or expression of GGPP synthase, increased activity or expression of glucose-6-phosphate dehydrogenase, increased activity or expression of 6-phosphogluconate dehydrogenase, increased activity or expression of fructose 1,6 bisphosphatase, increased activity or expression of NADH kinase, increased activity or expression of transhydrogenase, and combinations thereof.

In other embodiments, the present invention provides a method of producing a carotenoid, the method comprising steps of cultivating a fungus under conditions that allow production of the carotenoid; and isolating the produced carotenoid. In other embodiments, the present invention provides a method of producing a retinolic compound, the method comprising steps of cultivating a fungus under conditions that allow production of the retinolic compound; and isolating the produced retinolic compound.

In certain embodiments, the present invention provides an isolated carotenoid composition, prepared by a method comprising steps of cultivating the fungus under conditions that allow production of a carotenoid; and isolating the produced carotenoid. In certain embodiments, the present invention provides an isolated retinolic compound composition, prepared by a method comprising steps of cultivating the fungus under conditions that allow production of a retinolic compound; and isolating the produced retinolic compound.

In other embodiments, the present invention provides a composition comprising lipid bodies; at least one carotenoid compound; and intact fungal cells. In other embodiments, the present invention provides a composition comprising lipid bodies; at least one retinolic compound; and intact fungal cells.

In some embodiments, the present invention provides a composition comprising: an oil suspension comprising: lipid bodies; at least one carotenoid compound; intact fungal cells; and a binder or filler. In some embodiments, the present invention provides a composition comprising: an oil suspension comprising: lipid bodies; at least one retinolic compound; intact fungal cells; and a binder or filler.

In certain embodiments, the present invention provides a composition comprising: an oil suspension comprising: lipid bodies; at least one carotenoid compound; intact fungal cells; and one or more other agents selected from the group consisting of chelating agents, pigments, salts, surfactants, moisturizers, viscosity modifiers, thickeners, emollients, fragrances, preservatives, and combinations thereof. In certain embodiments, the present invention provides a composition comprising: an oil suspension comprising: lipid bodies; at least one retinolic compound; intact fungal cells; and one or more other agents selected from the group consisting of chelating agents, pigments, salts, surfactants, moisturizers, viscosity modifiers, thickeners, emollients, fragrances, preservatives, and combinations thereof.

In some embodiments, the present invention provides a feedstuff comprising a carotenoid in lipid bodies. In other embodiments, the present invention provides a feedstuff comprising a carotenoid in lipid bodies; wherein the carotenoid is selected from the group consisting of astaxanthin, β-carotene, canthaxanthin, zeaxanthin, lutein, lycopene, echinenone, β-cryptoxanthin and combinations thereof. In some embodiments, the present invention provides a feedstuff comprising a retinolic compound in lipid bodies. In other embodiments, the present invention provides a feedstuff comprising a retinolic compound in lipid bodies; wherein the retinolic compound is selected from the group consisting of retinol, retainal, retinoic acid, and combinations thereof.

In certain embodiments, the present invention provides a carotenoid composition comprising a *Y. lipolytica* cell containing at least 1% carotenoids by weight. In other embodiments, the present invention provides a carotenoid composition comprising *Y. lipolytica* lipid bodies; and at least one carotenoid compound, wherein the at least one carotenoid compound is present at a level that is at least 1% by weight of the lipid bodies. In certain embodiments, the present invention provides a retinolic compound composition comprising a *Y. lipolytica* cell containing at least 1% retinolic compounds by weight. In other embodiments, the present invention provides a retinolic compound composition comprising *Y. lipolytica* lipid bodies; and at least one retinolic compound, wherein the at least one retinolic compound is present at a level that is at least 1% by weight of the lipid bodies.

Additional aspects of the present invention will be apparent to those of ordinary skill in the art from the present description, including the appended claims.

BRIEF DESCRIPTION OF THE DRAWING

FIG. 1A-1D depicts certain common carotenoids.

FIG. 6A highlights branches leading to various cyclic and acyclic xanthophylls; FIG. 6B shows certain *X. dendrorhous* pathways that generate dicyclic and monocyclic carotenoids, including astaxanthin; FIG. 6C shows interconnecting pathways for converting β-carotene into any of a variety of other carotenoids, including astaxanthin; FIG. 6D depicts possible routes of synthesis of cyclic carotenoids and common plant and algal xanthophylls from neurosporene.

FIG. 7 and subparts FIGS. 7A-7I show an alignment of certain representative fungal HMG-CoA reductase polypeptides (SEQ ID NOs 176-182, respectively, in order of appearance). As can be seen, these polypeptides show very high identity across the catalytic region, and also have complex membrane spanning domains. In some embodiments of the invention, these membrane-spanning domains are disrupted or are removed, so that, for example, a hyperactive version of the polypeptide may be produced.

FIGS. 9A-E show production characteristics of certain engineered cells according to the present invention. Specifically, Panel A shows β-Carotene and phytoene production by Strain MF760 when grown in glycerol, glucose or olive oil; Panel B shows dry cell weight accumulation of strain MF760 when grown in glycerol, glucose or olive oil; Panel C shows β-Carotene and dry cell weight analysis of strain MF760 when grown in the presence of a combination of olive oil and glucose; Panel D shows canthaxanthin, echinenone and β-carotene production of strain MF840; and Panel E shows canthaxanthin and echinenone production of strain MF838 in a 2 phase feeding protocol.

FIG. 10 is a Table listing certain *Y. lipolytica* genes representing various polypeptides (e.g., oleaginic and isoprenoid biosynthesis peptides) useful in engineering cells in accordance with the present invention. Figure discloses SEQ ID NOs 183-218, respectively, in order of appearance.

FIG. 12 depicts various characteristics of strain ML1011 (MF740 transformed with multiple integrated copies of the *X. autotrophicus* crtZ gene) grown under different pH conditions. FIG. 12*a* depicts accumulation of total carotenoid (absorbance units per unit dry cell weight) over the course of the fermentation. FIG. 12*b* depicts accumulation of zeaxanthin (absorbance units per dry cell weight; AU) over the course of the fermentation. FIG. 12*c* depicts the fraction of carotenoid as zeaxanthin (AU zeaxanthin/AU total carotenoid) over the course of the fermentation. FIG. 12*d* depicts carbon dioxide evolution over the course of the fermentation. FIG. 12*e* depicts biomass accumulation over the course of the fermentation.

DEFINITIONS

Figure 1A:
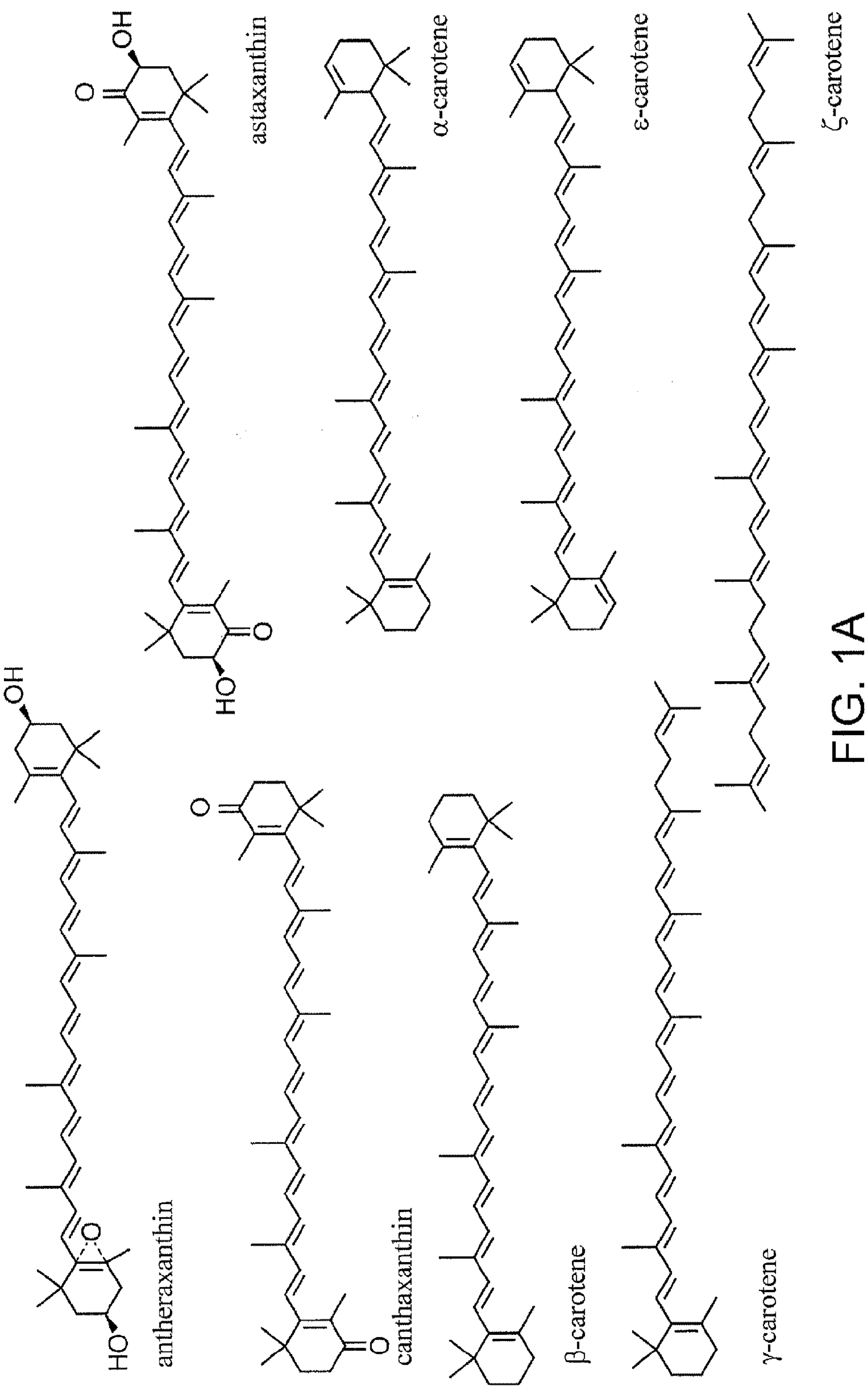

Aromatic amino acid biosynthesis polypeptide: The term "aromatic amino acid biosynthesis polypeptide" refers to any polypeptide that is involved in the synthesis of aromatic amino acids in yeast and/or bacteria through chorismate and the shikimate pathway. For example, as discussed herein, anthranilate synthase, enzymes of the shikimate pathway, chorismate mutase, chorismate synthase, DAHP synthase, and transketolase are all aromatic amino acid biosynthesis polypeptides. Each of these polypeptides is also a ubiquinone biosynthesis polypeptide or a ubiquinone biosynthesis competitor for purposes of the present invention, as production of chorismate is a precursor in the synthesis of para-hydroxybenzoate for the biosynthesis of ubiquinone.

Biosynthesis polypeptide: The term "biosynthesis polypeptide" as used herein (typically in reference to a particular compound or class of compounds), refers to polypeptides involved in the production of the compound or class of compounds. In some embodiments of the invention, biosynthesis polypeptides are synthetic enzymes that catalyze particular steps in a synthesis pathway that ultimately produces a relevant compound. In some embodiments, the term "biosynthesis polypeptide" may also encompass polypeptides that do not themselves catalyze synthetic reactions, but that regulate expression and/or activity of other polypeptides that do so. Biosynthesis polypeptides include, for example, aromatic amino acid biosynthesis polypeptides, $C_{5-9}$ quinone biosynthesis polypeptides, carotenoid biosynthesis polypeptides, retinolic compound biosynthesis polypeptides, FPP biosynthesis polypeptides, isoprenoid biosynthesis polypeptides, PHB biosynthesis polypeptides, quinone biosynthesis polypeptides, sterol biosynthesis polypeptides, ubiquinone biosynthesis polypeptides, Vitamin D biosynthesis polypeptides, Vitamin E biosynthesis polypeptides, and Vitamin K biosynthesis polypeptides.

$C_{5-9}$ quinone biosynthesis polypeptide: The term "$C_{5-9}$ quinone biosynthesis polypeptide" refers to any polypeptide that is involved in the synthesis of a $C_{5-9}$ quinone, for example a polyprenyldiphosphate synthase polypeptide. To mention but a few, these include, for example, pentaprenyl, hexaprenyl, heptaprenyl, octaprenyl, and/or solanesyl (nonaprenyl) diphosphate synthase polypeptides (i.e., polypeptides that perform the chemical reactions performed by the pentaprenyl, hexaprenyl, heptaprenyl, octaprenyl, and solanesyl (nonaprenyl) polypeptides, respectively (see also Okada et al., *Biochim. Biophys. Acta* 1302:217, 1996; Okada et al., *J. Bacteriol.* 179:5992, 1997). As will be appreciated by those of ordinary skill in the art, in some embodiments of the invention, $C_{5-9}$ quinone biosynthesis polypeptides include polypeptides that affect the expression and/or activity of one or more other $C_{5-9}$ quinone biosynthesis polypeptides.

Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, an inventive carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the carotenogenic modification comprises at least one chemical, physiological, genetic, or other modification; in other embodiments, the carotenogenic modification comprises more than one chemical, physiological, genetic, or other modification. In certain aspects where more than one modification is utilized, such modifications can comprise any combination of chemical, physiological, genetic, or other modification (e.g., one or more genetic, chemical, and/or physiological modification(s)). In some embodiments, the selected carotenoid is one or more of astaxanthin, β-carotene, canthaxanthin, lutein, lycopene, phytoene, zeaxanthin, and/or modifications of zeaxanthin or astaxanthin (e.g., glucoside, esterified zeaxanthin or astaxanthin). In some embodiments, the selected carotenoid is one or more xanthophylls, and/or a modification thereof (e.g., glucoside, esterified xanthophylls). In certain embodiments, the selected xanthophyl is selected from the group consisting of astaxanthin, lutein, zeaxanthin, lycopene, and modifications thereof. In some embodiments, the selected carotenoid is one or more of astaxanthin, β-carotene, canthaxanthin, lutein, lycopene, and zeaxanthin and/or modifications of zeaxanthin or astaxanthin. In some embodiments, the carotenoid is β-carotene. In some embodiments, the selected carotenoid is astaxanthin. In some embodiments, the selected carotenoid is other than β-carotene.

Carotenogenic polypeptide: The term "carotenogenic polypeptide", as used herein, refers to any polypeptide that is involved in the process of producing carotenoids in a cell, and may include polypeptides that are involved in processes other than carotenoid production but whose activities affect the extent or level of production of one or more carotenoids, for example by scavenging a substrate or reactant utilized by a carotenoid polypeptide that is directly involved in carotenoid production. Carotenogenic polypeptides include isoprenoid biosynthesis polypeptides, carotenoid biosynthesis polypeptides, and isoprenoid biosynthesis competitor polypeptides, as those terms are defined herein. The term also encompasses polypeptides that may affect the extent to which carotenoids are accumulated in lipid bodies.

Figure 1B:
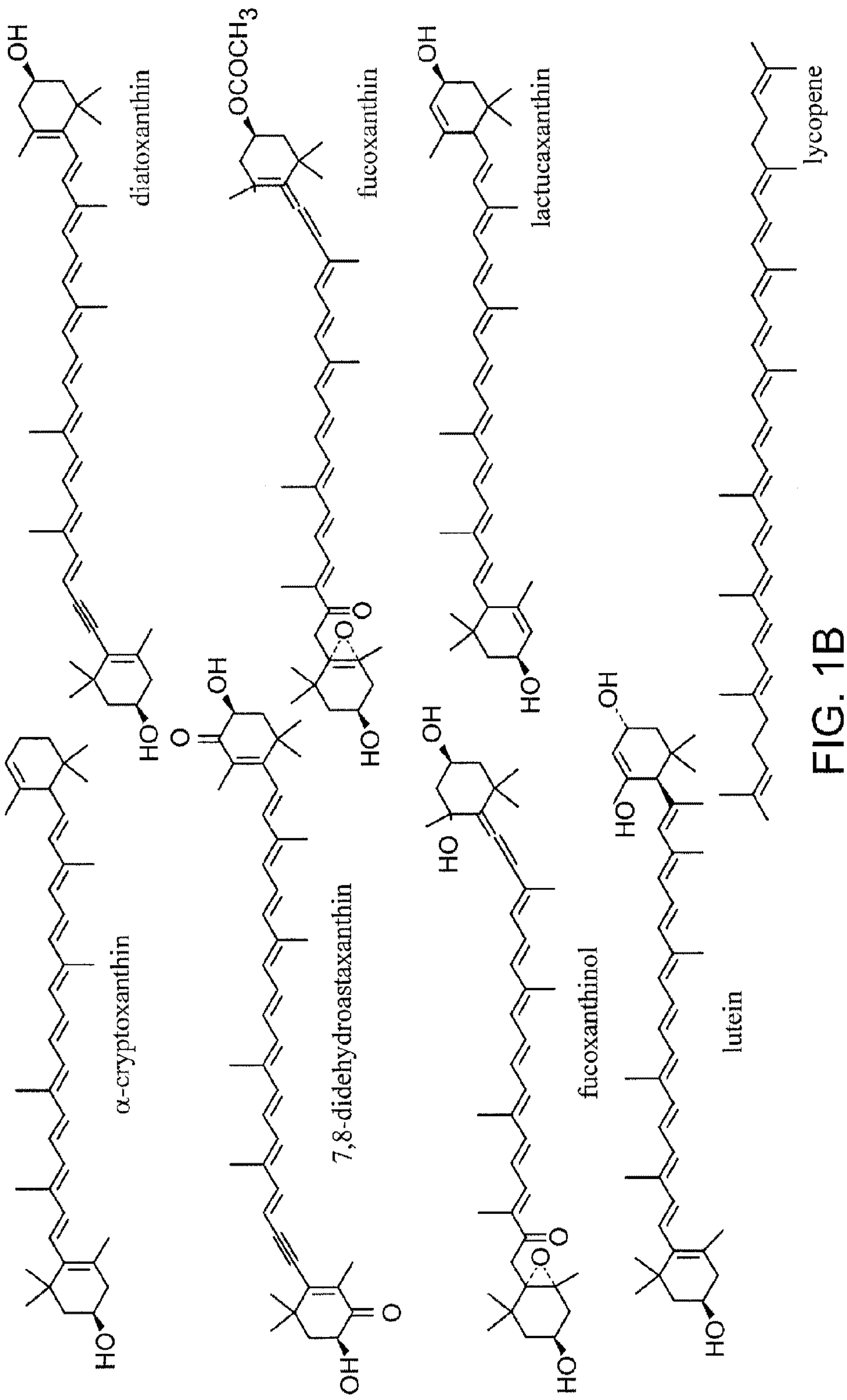
Figure 1C:
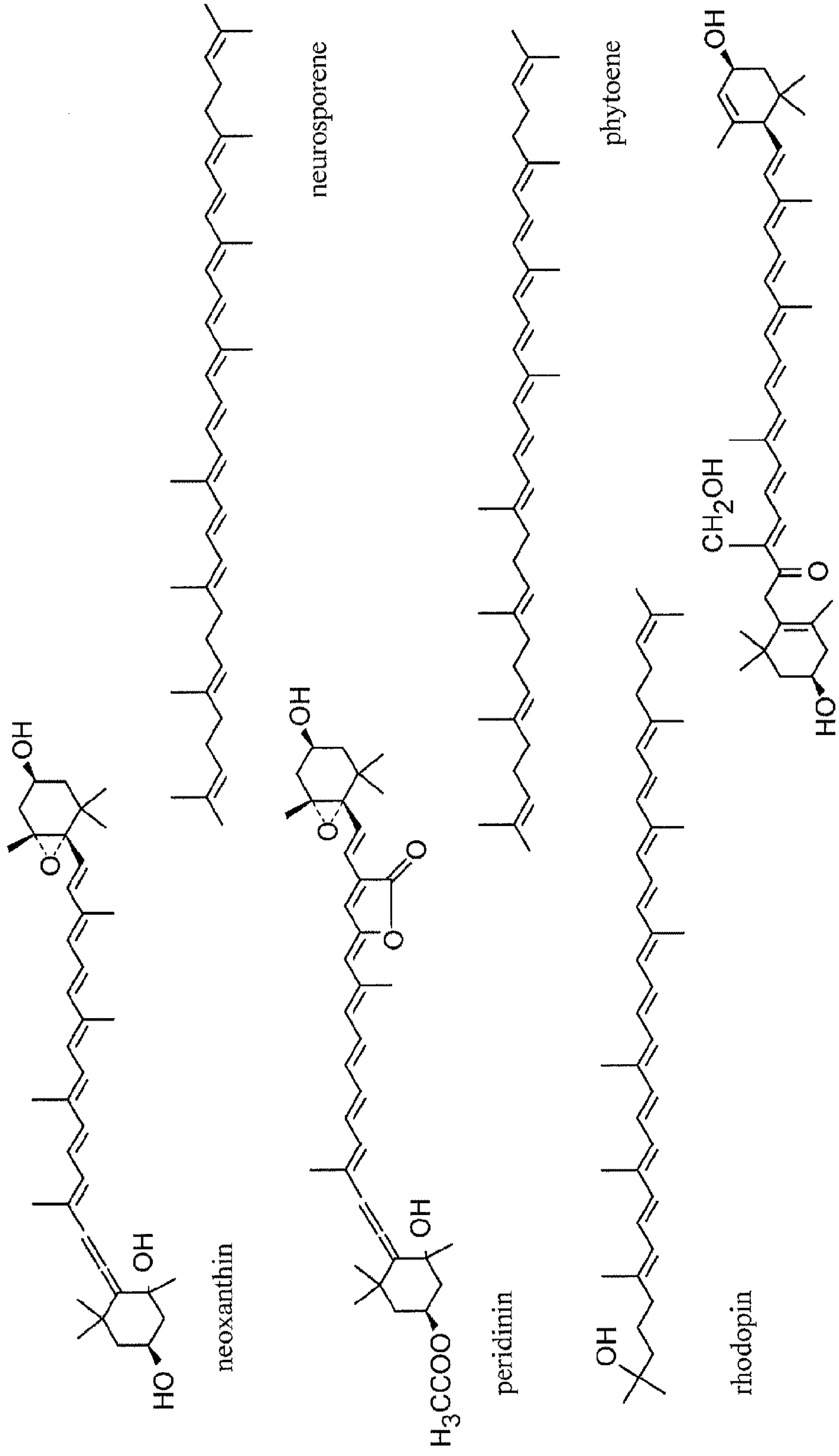

Carotenoid: The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{200}$. $C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature; certain common carotenoids are depicted in FIG. 1. Carotenoids include but are not limited to: antheraxanthin, adonirubin, adonixanthin, astaxanthin, canthaxanthin, capsorubrin, β-cryptoxanthin, α-carotene, β-carotene, β,ψ-carotene, δ-carotene, ϵ-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

Carotenoid biosynthesis polypeptide: The term "carotenoid biosynthesis polypeptide" refers to any polypeptide that is involved in the synthesis of one or more carotenoids. To mention but a few, these carotenoid biosynthesis polypeptides include, for example, polypeptides of phytoene synthase, phytoene dehydrogenase (or desaturase), lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, and acyl CoA:diacyglycerol acyltransferase. In some instances, a single gene may encode a protein with multiple carotenoid biosynthesis polypeptide activities. Representative examples of carotenoid biosynthesis polypeptide sequences are presented in Tables 17a-25. As will be appreciated by those of ordinary skill in the art, in some embodiments of the invention, carotenoid biosynthesis polypeptides include polypeptides that affect the expression and/or activity of one or more other carotenoid biosynthesis polypeptides.

FPP biosynthesis polypeptides: The term "FPP biosynthesis polypeptide" refers to any polypeptide that is involved in the synthesis of farnesyl pyrophosphate. As discussed herein, farnesyl pyrophosphate represents the branchpoint between the sterol biosynthesis pathway and the carotenoid and other biosynthesis pathways. One specific example of an FPP biosynthesis polypeptide is FPP synthase. Representative examples of FPP synthase polypeptide sequences are presented in Table 14. As will be appreciated by those of ordinary skill in the art, in some embodiments of the invention, FPP biosynthesis polypeptides include polypeptides that affect the expression and/or activity of one or more other FPP biosynthesis polypeptides.

Gene: The term "gene", as used herein, generally refers to a nucleic acid encoding a polypeptide, optionally including certain regulatory elements that may affect expression of one or more gene products (i.e., RNA or protein).

Heterologous: The term "heterologous", as used herein to refer to genes or polypeptides, refers to a gene or polypeptide that does not naturally occur in the organism in which it is being expressed. It will be understood that, in general, when a heterologous gene or polypeptide is selected for introduction into and/or expression by a host cell, the particular source organism from which the heterologous gene or polypeptide may be selected is not essential to the practice of the present invention. Relevant considerations may include, for example, how closely related the potential source and host organisms are in evolution, or how related the source organism is with other source organisms from which sequences of other relevant polypeptides have been selected. Where a plurality of different heterologous polypeptides are to be introduced into and/or expressed by a host cell, different polypeptides may be from different source organisms, or from the same source organism. To give but one example, in some cases, individual polypeptides may represent individual subunits of a complex protein activity and/or may be required to work in concert with other polypeptides in order to achieve the goals of the present invention. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell. For example, when the host cell is a *Yarrowia* strain (e.g., *Yarrowia lipolytica*), it will often be desirable to alter the gene sequence encoding a given polypeptide such that it conforms more closely with the codon preferences of such a *Yarrowia* strain. In certain embodiments, a gene sequence encoding a given polypeptide is altered to conform more closely with the codon preference of a species related to the host cell. For example, when the host cell is a *Yarrowia* strain (e.g., *Yarrowia lipolytica*), it will often be desirable to alter the gene sequence encoding a given polypeptide such that it conforms more closely with the codon preferences of a related fungal strain. Such embodiments are advantageous when the gene sequence encoding a given polypeptide is difficult to optimize to conform to the codon preference of the host cell due to experimental (e.g., cloning) and/or other reasons. In certain embodiments, the gene sequence encoding a given polypeptide is optimized even when such a gene sequence is derived from the host cell itself (and thus is not heterologous). For example, a gene sequence encoding a polypeptide of interest may not be codon optimized for expression in a given host cell even though such a gene sequence is isolated from the host cell strain. In such embodiments, the gene sequence may be further optimized to account for codon preferences of the host cell. Those of ordinary skill in the art will be aware of host cell codon preferences and will be able to employ inventive methods and compositions disclosed herein to optimize expression of a given polypeptide in the host cell.

Host cell: As used herein, the "host cell" is a fungal cell or yeast cell that is manipulated according to the present invention to accumulate lipid and/or to express one or more carotenoids as described herein. A "modified host cell", as used herein, is any host cell which has been modified, engineered, or manipulated in accordance with the present invention as compared with a parental cell. In some embodiments, the modified host cell has at least one carotenogenic and/or at least one oleaginic modification. In some embodiments, the modified host cell containing at least one oleaginic modification and/or one carotenogenic modification further has at least one sterologenic modification and/or at least one quinonogenic modification. In some embodiments, the parental cell is a naturally occurring parental cell.

Isolated: The term "isolated", as used herein, means that the isolated entity has been separated from at least one component with which it was previously associated. When most other components have been removed, the isolated entity is "purified" or "concentrated". Isolation and/or purification and/or concentration may be performed using any techniques known in the art including, for example, fractionation, extraction, precipitation, or other separation.

Isoprenoid biosynthesis competitor: The term "isoprenoid biosynthesis competitor", as used herein, refers to an agent whose presence or activity in a cell reduces the level of geranylgeranyl diphosphate (GGPP) available to enter the carotenoid biosynthesis pathway. The term "isoprenoid biosynthesis competitor" encompasses both polypeptide and non-polypeptide (e.g., small molecule) inhibitor agents. Those of ordinary skill in the art will appreciate that certain competitor agents that do not act as inhibitors of isoprenoid biosynthesis generally can nonetheless act as inhibitors of biosynthesis of a particular isoprenoid compound. Particular examples of isoprenoid biosynthesis competitor agents act on isoprenoid intermediates prior to GGPP, such that less GGPP is generated (see, for example, FIG. 5). Squalene synthase is but one isoprenoid biosynthesis competitor polypeptide according to the present invention; representative squalene synthase sequences are presented in Table 16. Prenyldiphosphate synthase enzymes and para-hydroxybenzoate (PHB) polyprenyltransferase are yet additional isoprenoid biosynthesis competitor polypeptides according to the present invention; representative prenyldiphosphate synthase enzymes and PHB polyprenyltransferase polypeptides are presented in Tables 29 and 30, respectively. In certain embodiments, one or more polypeptide components of the SAGA complex are isoprenoid biosynthesis competitors according to the present invention. Genes encoding SAGA complex polypeptides are presented in Table 69. In certain embodiments, a polypeptide encoded by these and other SAGA complex genes is an isoprenoid biosynthesis competitor polypeptide according to the present invention. Those of ordinary skill in the art, considering the known metabolic pathways relating to isoprenoid production and/or metabolism (see, for example, FIGS. 3-6 and other Figures and references herein) will readily appreciate a variety of other particular isoprenoid biosynthesis competitors, including isoprenoid biosynthesis polypeptides.

Isoprenoid biosynthesis polypeptide: The term "isoprenoid biosynthesis polypeptide" refers to any polypeptide that is involved in the synthesis of isoprenoids. For example, as discussed herein, acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase, are all involved in the mevalonate pathway for isoprenoid biosynthesis. Each of these proteins is also an isoprenoid biosynthesis polypeptide for purposes of the present invention, and sequences of representative examples of these enzymes are provided in Tables 7-15. As will be appreciated by those of ordinary skill in the art, in some embodiments of the invention, isoprenoid biosynthesis polypeptides include polypeptides that affect the expression and/or activity of one or more other isoprenoid biosynthesis polypeptides (e.g., of one or more enzymes that participates in isoprenoid synthesis). Thus, for instance, transcription factors that regulate expression of isoprenoid biosynthesis enzymes can be isoprenoid biosynthesis polypeptides for purposes of the present invention. To give but a couple of examples, the *S. cerevisae* Upc2 and YLR228c genes, and the *Y. lipolytica* YALI0B00660g gene encode transcription factors that are isoprenoid biosynthesis polypeptides according to certain embodiments of the present invention. For instance, the semi-dominant upc2-1 point mutant (G888D) exhibits increases sterol levels (Crowley et al. J Bacteriol. 180: 4177-4183, 1998). Corresponding YLR228c mutants have been made and tested (Shianna et al. J Bacteriology 183:830-834, 2001); such mutants may be useful in accordance with the present invention, as may be YALI0B00660g derivatives with corresponding upc2-1 mutation(s).

Isoprenoid pathway: The term "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway". The term "isoprenoid pathway" is sufficiently general to encompass both of these types of pathway. Biosynthesis of isoprenoids from IPP occurs by polymerization of several five-carbon isoprene subunits. Isoprenoid metabolites derived from IPP are of varying size and chemical structure, including both cyclic and acyclic molecules. Isoprenoid metabolites include, but are not limited to, monoterpenes, sesquiterpenes, diterpenes, sterols, and polyprenols such as carotenoids.

Oleaginic modification: The term "oleaginic modification", as used herein, refers to a modification of a host organism that adjusts the desirable oleaginy of that host organism, as described herein. In some cases, the host organism will already be oleaginous in that it will have the ability to accumulate lipid to at least about 20% of its dry cell weight. It may nonetheless be desirable to apply an oleaginic modification to such an organism, in accordance with the present invention, for example to increase (or, in some cases, possibly to decrease) its total lipid accumulation, or to adjust the types or amounts of one or more particular lipids it accumulates (e.g., to increase relative accumulation of triacylglycerol). In other cases, the host organism may be non-oleaginous (though may contain some enzymatic and regulatory components used in other organisms to accumulate lipid), and may require oleaginic modification in order to become oleaginous in accordance with the present invention. The present invention also contemplates application of oleaginic modification to non-oleaginous host strains such that their oleaginicity is increased even though, even after being modified, they may not be oleaginous as defined herein. In principle, the oleaginic modification may be any chemical, physiological, genetic, or other modification that appropriately alters oleaginy of a host organism as compared with an otherwise identical organism not subjected to the oleaginic modification. In most embodiments, however, the oleaginic modification will comprise a genetic modification, typically resulting in increased production and/or activity of one or more oleaginic polypeptides. In some embodiments, the oleaginic modification comprises at least one chemical, physiological, genetic, or other modification; in other embodiments, the oleaginic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Oleaginic polypeptide: The term "oleaginic polypeptide", as used herein, refers to any polypeptide that is involved in the process of lipid accumulation in a cell and may include polypeptides that are involved in processes other than lipid biosynthesis but whose activities affect the extent or level of accumulation of one or more lipids, for example by scavenging a substrate or reactant utilized by an oleaginic polypeptide that is directly involved in lipid accumulation. For example, as discussed herein, acetyl-CoA carboxylase, pyruvate decarboxylase, isocitrate dehydrogenase, ATP-citrate lyase, malic enzyme, malate dehydrogenase, and AMP deaminase, among other proteins, are all involved in lipid accumulation in cells. In general, reducing the activity of pyruvate decarboxylase or isocitrate dehydrogenase, and/or increasing the activity of acetyl CoA carboxylase, ATP-citrate lyase, malic enzyme, malate dehydrogenase, and/or AMP deaminase is expected to promote oleaginy. Each of these proteins is an oleaginic peptide for the purposes of the present invention, and sequences of representative examples of these enzymes are provided in Tables 1-6, and 30. Other peptides that can be involved in regenerating NADPH may include, for example, 6-phosphogluconate dehydrogenase (gnd); Fructose 1,6 bisphosphatase (fbp); Glucose 6 phosphate dehydrogenase (g6pd); NADH kinase (EC 2.7.1.86); and/or transhydrogenase (EC 1.6.1.1 and 1.6.1.2). Alternative or additional strategies to promote oleaginy may include one or more of the following: (1) increased or heterologous expression of one or more of acyl-CoA:diacylglycerol acyltransferase (e.g., DGA1; YALI0E32769g); phospholipid:diacylglycerol acyltransferase (e.g., LRO1; YALI0E16797g); and acyl-CoA:cholesterol acyltransferase (e.g., ARE genes such as ARE1, ARE2, YALI0F06578g), which are involved in triglyceride synthesis (Kalscheuer et al. *Appl Environ Microbiol* p. 7119-7125, 2004; Oelkers et al. *J Biol Chem* 277:8877-8881, 2002; and Sorger et al. *J Biol Chem* 279:31190-31196, 2004), (2) decreased expression of triglyceride lipases (e.g., TGL3 and/or TGL4; YALI0D17534g and/or YALI0F10010g (Kurat et al. *J Biol Chem* 281:491-500, 2006); and (3) decreased expression of one or more acyl-coenzyme A oxidase activities, for example encoded by POX genes (e.g. POX1, POX2, POX3, POX4, POX5; YALI0C23859g, YALI0D24750g, YALI0E06567g, YALI0E27654g, YALI0E32835g, YALI0F10857g; see, for example, Mlickova et al. *Appl Environ Microbiol* 70: 3918-3924, 2004; Binns et al. *J Cell Biol* 173:719, 2006). Each of these proteins is an oleaginic peptide for the purposes of the present invention, and sequences of representative examples of these enzymes are provided in Tables 31-43 and 45-47.

Oleaginous: The term "oleaginous", refers to the ability of an organism to accumulate lipid to at least about 20% of its dry cell weight. In certain embodiments of the invention, oleaginous yeast or fungi accumulate lipid to at least about 25% of their dry cell weight. In other embodiments, inventive oleaginous yeast or fungi accumulate lipid within the range of about 20-45% (e.g., about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, or more) of their dry cell weight. In some embodiments, oleaginous organisms may accumulate lipid to as much as about 70% of their dry cell weight. In some embodiments of the invention, oleaginous organisms may accumulate a large fraction of total lipid accumulation in the form of triacylglycerol. In certain embodiments, the majority of the accumulated lipid is in the form of triacylglycerol. Alternatively or additionally, the lipid may accumulate in the form of intracellular lipid bodies, or oil bodies. In certain embodiments, the present invention utilizes yeast or fungi that are naturally oleaginous. In some aspects, naturally oleaginous organisms are manipulated (e.g., genetically, chemically, or otherwise) so as to further increase the level of accumulated lipid in the organism. In other embodiments, yeast or fungi that are not naturally oleaginous are manipulated (e.g., genetically, chemically, or otherwise) to accumulate lipid as described herein. For example, for the purposes of the present invention, *Saccharomyces cerevisiae, Xanthophyllomyces dendrorhous* (*Phaffia rhodozyma*), and *Candida utilis* are not naturally oleaginous fungi.

PHB polypeptide or PHB biosynthesis polypeptide: The terms "PHB polypeptide" or "PHB biosynthesis polypeptide" as used herein refers to a polypeptide that is involved in the synthesis of para-hydroxybenzoate from chorismate. In prokaryotes and lower eukaryotes, synthesis of para-hydroxybenzoate occurs by the action of chorismate pyruvate lyase. Biosynthesis of para-hydroxybenzoate from tyrosine or phenylalanine occurs through a five-step process in mammalian cells. Lower eukaryotes such as yeast can utilize either method for production of para-hydroxybenzoate. For example, enzymes of the shikimate pathway, chorismate synthase, DAHP synthase, and transketolase are all PHB biosynthesis polypeptides. Each of these polypeptides is also a ubiquinone biosynthesis polypeptide or a ubiquinone biosynthesis competitor polypeptide for purposes of the present invention.

Polypeptide: The term "polypeptide", as used herein, generally has its art-recognized meaning of a polymer of at least three amino acids. However, the term is also used to refer to specific functional classes of polypeptides, such as, for example, oleaginic polypeptides, carotenogenic polypeptides, isoprenoid biosynthesis polypeptides, carotenoid biosynthesis polypeptides, etc. For each such class, the present specification provides several examples of known sequences of such polypeptides. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions (e.g., isocitrate dehydrogenase polypeptides often share a conserved AMP-binding motif; HMG-CoA reductase polypeptides typically include a highly conserved catalytic domain (see, for example, FIG. 7); acetyl coA carboxylase typically has a carboxyl transferase domain; see, for example, Downing et al., *Chem. Abs.* 93:484, 1980; Gil et al., *Cell* 41:249, 1985; Jitrapakdee et al. *Curr Protein Pept Sci.* 4:217, 2003; U.S. Pat. No. 5,349,126, each of which is incorporated herein by reference in its entirety), usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides presented in the Tables herein.

Quinone biosynthesis polypeptide: A "quinone biosynthesis polypeptide", as that term is used herein, refers to any polypeptide involved in the synthesis of one or more quinone derived compound, as described herein. In particular, quinone biosynthesis polypeptides include ubiquinone biosynthesis polypeptides, $C_{5-9}$ quinone biosynthesis polypeptides, vitamin K biosynthesis polypeptides, and vitamin E biosynthesis polypeptides.

Quinonogenic modification: The term "quinonogenic modification", as used herein, refers to a modification of a host organism that adjusts production of one or more quinone derived compounds (e.g., ubiquinone, vitamin K compounds, vitamin E compounds, etc.), as described herein. For example, a quinonogenic modification may increase the production level of a particular quinone derived compound, or of a variety of different quinone derived compounds. In some embodiments of the invention, production of a particular quinone derived compound may be increased while production of other quinone derived compounds is decreased. In some embodiments of the invention, production of a plurality of different quinone derived compounds is increased. In principle, an inventive quinonogenic modification may be any chemical, physiological, genetic, or other modification that appropriately alters production of one or more quinone derived compounds in a host organism produced by that organism as compared with the level produced in an otherwise identical organism not subject to the same modification. In most embodiments, however, the quinonogenic modification will comprise a genetic modification, typically resulting in increased production of one or more quinone derived compounds (e.g., ubiquinone, vitamin K compounds, vitamin E compounds). In some embodiments, the quinonogenic modification comprises at least one chemical, physiological, genetic, or other modification; in other embodiments, the quinonogenic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Retinologenic modification: The term "retinologenic modification", as used herein, refers to a modification of a host organism that adjusts production of one or more retinolic compounds, as described herein. For example, a retinologenic modification may increase the production level of one or more retinolic compounds, and/or may alter relative production levels of different retinolic compounds. In principle, an inventive retinologenic modification may be any chemical, physiological, genetic, or other modification that appropriately alters production of one or more retinolic compounds in a host organism produced by that organism as compared with the level produced in an otherwise identical organism not subject to the same modification. In most embodiments, however, the retinologenic modification will comprise a genetic modification, typically resulting in increased production of one or more selected retinolic compounds. In some embodiments, the retinologenic modification comprises at least one chemical, physiological, genetic, or other modification; in other embodiments, the retinologenic modification comprises more than one chemical, physiological, genetic, or other modification. In certain aspects where more than one modification is utilized, such modifications can comprise any combination of chemical, physiological, genetic, or other modification (e.g., one or more genetic, chemical, and/or physiological modification(s)). In some embodiments, the selected retinolic compound is one or more of retinol, retinal, and retinoic acid. In some embodiments, the selected retinolic compound is retinol or esters of retinol, including but not limited to retinyl palmitate or retinyl acetate. In some embodiments, the selected retinolic compound is retinoic acid. In some embodiments, the selected retinolic compound is other than retinol.

Retinologenic polypeptide: The term "retinologenic polypeptide", as used herein, refers to any polypeptide that is involved in the process of producing retinolic compounds in a cell, and may include polypeptides that are involved in processes other than retinolic compound production but whose activities affect the extent or level of production of one or more retinolic compounds, for example by scavenging a substrate or reactant utilized by a retinologenic polypeptide that is directly involved in retinolic compound production. Retinologenic polypeptides include retinolic compound biosynthesis polypeptides, isoprenoid biosynthesis polypeptides, carotenoid biosynthesis polypeptides, and isoprenoid biosynthesis competitor polypeptides, as those terms are defined herein. The term also encompasses polypeptides that may affect the extent to which retinolic compounds are accumulated in lipid bodies.

Retinolic compounds: The term "retinolic compound" is understood in the art to refer to a structurally similar class of compounds derived from certain carotenoids, collectively referred to as Vitamin A. All forms of Vitamin A have a beta-ionone ring to which an isoprenoid chain is attached. Retinolic compounds include, for example, retinol (the alcohol form), retinal (the aldehyde form), and retinoic acid (the acid form). Many different geometric isomers of retinol, retinal and retinoic acid are possible as a result of either a trans or cis configuration of four of the five double bonds found in the polyene chain. The cis isomers are less stable and can readily convert to the all-trans configuration. Nevertheless, some cis isomers are found naturally and carry out essential functions. For example, the 11-cis-retinal isomer is the chromophore of rhodopsin, the vertebrate photoreceptor molecule. The term retinolic compound also includes esters of retinol such as retinyl palmitate or retinyl acetate. Hydrolysis of retinyl esters results in retinol. Retinal, also known as retinaldehyde, can be reversibly reduced to produce retinol or it can be irreversibly oxidized to produce retinoic acid. The best described active retinoid metabolites are 11-cis-retinal and the all-trans and 9-cis-isomers of retinoic acid.

Retinolic compound biosynthesis polypeptides: The term "retinolic compound biosynthesis polypeptide" refers to any polypeptide that is involved in the synthesis of one or more retinolic compounds. To mention but a few, these retinolic compound biosynthesis polypeptides include, for example, polypeptides of beta-carotene 15,15'-monooxygenase (also known as beta-carotene dioxygenase) and/or beta-carotene retinol dehydrogenase. In some instances, a single gene may encode a protein with multiple retinolic compound biosynthesis polypeptide activities. Representative examples of retinolic compound biosynthesis polypeptide sequences are presented in Tables 67 and 68. As will be appreciated by those of ordinary skill in the art, in some embodiments of the invention, retinolic compound biosynthesis polypeptides include polypeptides that affect the expression and/or activity of one or more other retinolic compound biosynthesis polypeptides.

Small Molecule: In general, a small molecule is understood in the art to be an organic molecule that is less than about 5 kilodaltons (Kd) in size. In some embodiments, the small molecule is less than about 3 Kd, 2 Kd, or 1 Kd. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Source organism: The term "source organism", as used herein, refers to the organism in which a particular polypeptide sequence can be found in nature. Thus, for example, if one or more heterologous polypeptides is/are being expressed in a host organism, the organism in which the polypeptides are expressed in nature (and/or from which their genes were originally cloned) is referred to as the "source organism". Where multiple heterologous polypeptides are being expressed in a host organism, one or more source organism(s) may be utilized for independent selection of each of the heterologous polypeptide(s). It will be appreciated that any and all organisms that naturally contain relevant polypeptide sequences may be used as source organisms in accordance with the present invention. Representative source organisms include, for example, animal, mammalian, insect, plant, fungal, yeast, algal, bacterial, cyanobacterial, archaebacterial and protozoal source organisms.

Sterol biosynthesis polypeptide: The term "sterol biosynthesis polypeptide", as used herein, refers to any polypeptide that is involved in the synthesis of one or more sterol compounds. Thus, sterol biosynthesis polypeptides can include isoprenoid biosynthesis polypeptides to the extent that they are involved in production of isopentyl pyrophosphate. Moreover, the term refers to any polypeptide that acts downstream of farnesyl pyrophosphate and in involved in the production of one or more sterol compounds. For example, sterol biosynthesis polypeptides include squalene synthase, which catalyses conversion of farnesyl pyrophosphate to presqualene pyrophosphate, and further catalyzes conversion of presqualene pyrophosphate to squalene, e.g., the enzyme with EC number 2.5.1.21. In some embodiments of the invention, sterol biosynthesis polypeptides further include one or more polypeptides involved in metabolizing squalene into a vitamin D compound. Thus, sterol biosynthesis polypeptides can include one or more of the polypeptides designated by EC number 1.14.99.7, 5.4.99.7, 5.4.99.8, 5.3.3.5, 1.14.21.6, 1.14.15.-, and/or 1.14.13.13, as well as other enzyme polypeptides involved in the sterol biosynthesis pathways. Furthermore, sterol biosynthesis polypeptides can include one or more enzyme polypeptides including, for example, C-14 demethylase (ERG9), squalene monooxygenase (ERG1), 2,3-oxidosqualene-lanosterol synthase (ERG7), C-1 demethylase (ERG11), C-14 reductase (ERG24), C-4 methyloxidase (ERG25), C-4 decarboxylase (ERG26), 3-ketoreductase (ERG27), C-24 methyltransferase (ERG6), Δ8-7 isomerase (ERG2), C-5 desaturase (ERG3), C-22 desaturase (ERG5) and/or C-24 reductase (ERG4) polypeptides, and/or other polypeptides involved in producing one or more vitamin D compounds (e.g., vitamin D2, vitamin D3, or a precursor thereof). As will be appreciated by those of ordinary skill in the art, in some embodiments of the invention, sterol biosynthesis polypeptides include polypeptides that affect the expression and/or activity of one or more other sterol biosynthesis polypeptides. Thus, for instance, transcription factors that regulate expression of sterol biosynthesis enzymes can be sterol biosynthesis polypeptides for purposes of the present invention. To give but a couple of examples, the *S. cerevisiae* Upc2 and YLR228c genes, and the *Y. lipolytica* YALI0B00660g gene encode transcription factors that are sterol biosynthesis polypeptides according to certain embodiments of the present invention. For instance, the semidominant upc2-1 point mutation (G888D) exhibits increased sterol levels (Crowley et al., *J. Bacteriol* 180:4177-4183, 1998). Corresponding YLR228c mutants have been made and tested (Shianna et al., *J Bacteriol* 183:830, 2001); such mutants may be useful in accordance with the present invention, as may be YALI0B00660g derivatives with corresponding upc2-1 mutation(s). Representative examples of sterol biosynthesis polypeptide sequences are presented in Tables 53-66. As will be appreciated by those of ordinary skill in the art, in some embodiments of the invention, sterol biosynthesis polypeptides include polypeptides that affect the expression and/or activity of one or more other sterol biosynthesis polypeptides.

Sterologenic modification: The term "sterologenic modification", as used herein, refers to a modification of a host organism that adjusts production of one or more sterol compounds (e.g., squalene, lanosterol, zymosterol, ergosterol, 7-dehydrocholesterol (provitamin D3), vitamin D compound(s), etc.), as described herein. For example, a sterologenic modification may increase the production level of a particular sterol compound, or of a variety of different sterol compounds. In some embodiments of the invention, production of a particular sterol compound may be increased while production of other sterol compounds is decreased. In some embodiments of the invention, production of a plurality of different sterol compounds is increased. In principle, an inventive sterologenic modification may be any chemical, physiological, genetic, or other modification that appropriately alters production of one or more sterol compounds in a host organism produced by that organism as compared with the level produced in an otherwise identical organism not subject to the same modification. In most embodiments, however, the sterologenic modification will comprise a genetic modification, typically resulting in increased production of one or more sterol compounds (e.g., squalene, lanosterol, zymosterol, ergosterol, 7-dehydrocholesterol (provitamin D3) or vitamin D compound(s)). In certain aspects where more than one modification is utilized, such modifications can comprise any combination of chemical, physiological, genetic, or other modification (e.g., one or more genetic modification and chemical or physiological modification).

Ubiquinone biosynthesis polypeptide: The term "ubiquinone biosynthesis polypeptide" refers to any polypeptide that is involved in the synthesis of ubiquinone. To mention but a few, these ubiquinone biosynthesis polypeptides include, for example, polypeptides of prenyldiphosphate synthase, PHB-polyprenyltransferase, and O-methyltransferase, as well as $C_{5-9}$ quinone biosynthesis polypeptides. As will be appreciated by those of ordinary skill in the art, in some embodiments of the invention, ubiquinone biosynthesis polypeptides include polypeptides that affect the expression and/or activity of one or more other ubiquinone biosynthesis polypeptides.

Ubiquinogenic modification: The term "ubiquinogenic modification", as used herein, refers to a modification of a host organism that adjusts production of ubiquinone (e.g., CoQ10), as described herein. For example, a ubiquinogenic modification may increase the production level of ubiquinone (e.g., CoQ10), and/or may alter relative levels of ubiquinone and/or ubiquinol. In principle, an inventive ubiquinogenic modification may be any chemical, physiological, genetic, or other modification that appropriately alters production of ubiquinone (e.g., CoQ10) in a host organism produced by that organism as compared with the level produced in an otherwise identical organism not subject to the same modification. In most embodiments, however, the ubiquinogenic modification will comprise a genetic modification, typically resulting in increased production of ubiquinone (CoQ10).

Vitamin D biosynthesis polypeptide: The term "vitamin D biosynthesis polypeptide" refers to any polypeptide that is involved in the synthesis of one or more vitamin D compounds. To mention but a few, these include, for example, polypeptides enzymes with EC numbers the 1.14.99.7, 5.4.99.7, 5.4.99.8, 5.3.3.5, and/or 1.14.21.6. They further can include the hydroxylases that convert vitamin $D_3$ to calcitriol (e.g., polypeptides enzymes with EC numbers 1.14.15.- and 1.14.13.13). As will be appreciated by those of ordinary skill in the art, in some embodiments of the invention, vitamin D biosynthesis polypeptides include polypeptides that affect the expression and/or activity of one or more other vitamin D biosynthesis polypeptides.

Vitamin E biosynthesis polypeptide: The term "vitamin E biosynthesis polypeptide" refers to any polypeptide that is involved in the synthesis of vitamin E. To mention but a few, these include, for example, tyrA, pds1(hppd), VTE1, HPT1 (VTE2), VTE3, VTE4, and/or GGH polypeptides (i.e., polypeptides that perform the chemical reactions performed by tyrA, pds1(hppd), VTE1, HPT1(VTE2), VTE3, VTE4, and/or GGH, respectively). As will be appreciated by those of ordinary skill in the art, in some embodiments of the invention, vitamin E biosynthesis polypeptides include polypeptides that affect the expression and/or activity of one or more other vitamin E biosynthesis polypeptides.

Vitamin K biosynthesis polypeptide: The term "vitamin K biosynthesis polypeptide" refers to any polypeptide that is involved in the synthesis of vitamin K. To mention but a few, these include, for example, MenF, MenD, MenC, MenE, MenB, MenA, UbiE, and/or MenG polypeptides (i.e., polypeptides that perform the chemical reactions performed by MenF, MenD, MenC, MenE, MenB, MenA, UbiE, and/or MenG, respectively). As will be appreciated by those of ordinary skill in the art, in some embodiments of the invention, vitamin K biosynthesis polypeptides include polypeptides that affect the expression and/or activity of one or more other carotenoid biosynthesis polypeptides.

DETAILED DESCRIPTION OF CERTAIN PREFERRED EMBODIMENTS OF THE INVENTION

As noted above, the present invention encompasses the discovery that carotenoids and/or retinolic compounds can desirably be produced in oleaginous yeast and fungi. According to the present invention, strains that both (i) accumulate lipid, often in the form of cytoplasmic oil bodies and typically to at least about 20% of their dry cell weight; and (ii) produce carotenoid(s) and/or retinolic compound(s) at a level at least about 1%, and in some embodiments at least about 3-20%, of their dry cell weight, are generated through manipulation of host cells (i.e., strains, including, e.g., naturally-occurring strains, strains which have been previously modified, etc.).

These manipulated host cells are then used to produce carotenoids and/or retinolic compounds, so that carotenoids and/or retinolic compounds that partition into the lipid bodies can readily be isolated.

In general, it will be desirable to balance oleaginy and carotenoid production in inventive cells such that, as soon as a minimum desirable level of oleaginy is achieved, substantially all further carbon which is capable of being utilized and diverted into biosynthesis of products is diverted into a carotenoid and/or retinolic compounds production pathway. In some embodiments of the invention, this strategy involves engineering cells to be oleaginous; in other embodiments, it involves engineering cells to accumulate a higher level of lipid, particularly cytoplasmic lipid, than they would accumulate in the absence of such engineering even though the engineered cells may not become "oleaginous" as defined herein. In other embodiments, the extent to which an oleaginous host cell accumulates lipid is actually reduced so that remaining carbon can be utilized in carotenoid and/or retinolic compound production. According to the present invention, the extent of lipid accumulation in a host cell can be adjusted by modifying the level and/or activity of one or more polypeptides involved in lipid accumulation. Such modification can take the form of genetic engineering and/or exposure to particular growth conditions that induce or inhibit lipid accumulation.

To give but one example of adjustments that could be made to achieve a desired balance between oleaginy and carotenoid and/or retinolic compound production, we note that, while increasing acetyl CoA carboxylase expression (and/or activity) promotes oleaginy, decreasing its expression and/or activity can promote carotenoid and/or retinolic compound production. Those of ordinary skill in the art will appreciate that the expression and/or activity of acetyl CoA carboxylase, or of other polypeptides may be adjusted up or down as desired according to the characteristics of a particular host cell of interest.

We note that engineered cells and processes of using them as described herein may provide one or more advantages as compared with unmodified cells. Such advantages may include, but are not limited to: increased yield (e.g., carotenoid and/or retinolic compound content expressed as either % dry cell weight (mg/mg) or parts per million), titer (g carotenoid/L and/or g retinolic compound/L), specific productivity (mg carotenoid $g^{-1}$ biomass $hour^{-1}$ and/or mg retinolic compound $g^{-1}$ biomass $hour^{-1}$), and/or volumetric productivity (g carotenoid $liter^{-1}$ $hour^{-1}$ and/or g retinolic compound $liter^{-1}$ $hour^{-1}$)) of the desired carotenoid and/or retinolic compound (and/or intermediates thereof), and/or decreased formation of undesirable side products (for example, undesirable intermediates).

Thus, for example, the specific productivity for one or more desired carotenoids (e.g. β-carotene, astaxanthin), retinolic compound (e.g., retinol, retinal, retinoic acid), total carotenoids and/or total retinolic compounds may be at or about 0.1, at or about 0.11, at or about 0.12, at or about 0.13, at or about 0.14, at or about 0.15, at or about 0.16, at or about 0.17, at or about 0.18, at or about 0.19, at or about 0.2, at or about 0.21, at or about 0.22, at or about 0.23, at or about 0.24, at or about 0.25, at or about 0.26, at or about 0.27, at or about 0.28, at or about 0.29, at or about 0.3, at or about 0.31, at or about 0.32, at or about 0.33, at or about 0.34, at or about 0.35, at or about 0.36, at or about 0.37, at or about 0.38, at or about 0.39, at or about 0.4, at or about 0.41, at or about 0.42, at or about 0.43, at or about 0.44, at or about 0.45, at or about 0.46, at or about 0.47, at or about 0.48, at or about 0.49, at or about 0.5, at or about 0.51, at or about 0.52, at or about 0.53, at or about 0.54, at or about 0.55, at or about 0.56, at or about 0.57, at or about 0.58, at or about 0.59, at or about 0.6, at or about 0.61, at or about 0.62, at or about 0.63, at or about 0.64, at or about 0.65, at or about 0.66, at or about 0.67, at or about 0.68, at or about 0.69, at or about 0.7, at or about 0.71, at or about 0.72, at or about 0.73, at or about 0.74, at or about 0.75, at or about 0.76, at or about 0.77, at or about 0.78, at or about 0.79, at or about 0.8, at or about 0.81, at or about 0.82, at or about 0.83, at or about 0.84, at or about 0.85, at or about 0.86, at or about 0.87, at or about 0.88, at or about 0.89, at or about 0.9, at or about 0.91, at or about 0.92, at or about 0.93, at or about 0.94, at or about 0.95, at or about 0.96, at or about 0.97, at or about 0.98, at or about 0.99, at or about 1, 1.05, at or about 1.1, at or about 1.15, at or about 1.2, at or about 1.25, at or about 1.3, at or about 1.35, at or about 1.4, at or about 1.45, at or about 1.5, at or about 1.55, at or about 1.6, at or about 1.65, at or about 1.7, at or about 1.75, at or about 1.8, at or about 1.85, at or about 1.9, at or about 1.95, at or about 2 mg $g^{-1}$ $hour^{-1}$ or more.

Thus, for example, the volumetric productivity for one or more desired carotenoids (e.g. β-carotenoid, astaxanthin), retinolic compound (e.g., retinol, retinal, retinoic acid), total carotenoids and/or total retinolic compounds may be at or about 0.01, at or about 0.011, at or about 0.012, at or about 0.013, at or about 0.014, at or about 0.015, at or about 0.016, at or about 0.017, at or about 0.018, at or about 0.019, at or about 0.02, at or about 0.021, at or about 0.022, at or about 0.023, at or about 0.024, at or about 0.025, at or about 0.026, at or about 0.027, at or about 0.028, at or about 0.029, at or about 0.03, at or about 0.031, at or about 0.032, at or about 0.033, at or about 0.034, at or about 0.035, at or about 0.036, at or about 0.037, at or about 0.038, at or about 0.039, at or about 0.04, at or about 0.041, at or about 0.042, at or about 0.043, at or about 0.044, at or about 0.045, at or about 0.046, at or about 0.047, at or about 0.048, at or about 0.049, at or about 0.05, at or about 0.051, at or about 0.052, at or about 0.053, at or about 0.054, at or about 0.055, at or about 0.056, at or about 0.057, at or about 0.058, at or about 0.059, at or about 0.06, at or about 0.061, at or about 0.062, at or about 0.063, at or about 0.064, at or about 0.065, at or about 0.066, at or about 0.067, at or about 0.068, at or about 0.069, at or about 0.07, at or about 0.071, at or about 0.072, at or about 0.073, at or about 0.074, at or about 0.075, at or about 0.076, at or about 0.077, at or about 0.078, at or about 0.079, at or about 0.08, at or about 0.081, at or about 0.082, at or about 0.083, at or about 0.084, at or about 0.085, at or about 0.086, at or about 0.087, at or about 0.088, at or about 0.089, at or about 0.09, at or about 0.091, at or about 0.092, at or about 0.093, at or about 0.094, at or about 0.095, at or about 0.096, at or about 0.097, at or about 0.098, at or about 0.099, at or about 0.1, 0.105, at or about 0.110, at or about 0.115, at or about 0.120, at or about 0.125, at or about 0.130, at or about 0.135, at or about 0.14, at or about 0.145, at or about 0.15, at or about 0.155, at or about 0.16, at or about 0.165, at or about 0.17, at or about 0.175, at or about 0.18, at or about 0.185, at or about 0.19, at or about 0.195, at or about 0.20 grams $liter^{-1}$ $hour^{-1}$ or more.

Host Cells

Those of ordinary skill in the art will readily appreciate that a variety of yeast and fungal strains exist that are naturally oleaginous or that naturally produce carotenoids. Yeast and fungal strains do not naturally produce retinolic compounds. Any of such strains may be utilized as host strains according to the present invention, and may be engineered or otherwise manipulated to generate inventive oleaginous, carotenoid-producing strains and/or oleaginous, retinolic acid compound-producing strains. Alternatively, strains that naturally are neither oleaginous nor: i) carotenoid-producing and/or ii) retinolic compound-producing may be employed. Furthermore, even when a particular strain has a natural capacity for oleaginy or for carotenoid production, its natural capabilities may be adjusted as described herein, so as to change the production level of lipid, carotenoid and/or retinolic compound. In certain embodiments engineering or manipulation of a strain results in modification of a type of lipid, carotenoid and/or retinolic compound which is produced. For example, a strain may be naturally oleaginous and/or carotenogenic, however engineering or modification of the strain may be employed so as to change the type of lipid which is accumulated and or to change the type of carotenoid which is produced. Additionally or alternatively, naturally oleaginous strain may be engineered to permit retinolic compound production. Moreover, further engineering or modification of the strain may be employed so as to change the type of lipid which is accumulated and/or to change the type of retinolic compound which is produced.

When selecting a particular yeast or fungal strain for use in accordance with the present invention, it will generally be desirable to select one whose cultivation characteristics are amenable to commercial scale production. For example, it will generally (though not necessarily always) be desirable to avoid filamentous organisms, or organisms with particularly unusual or stringent requirements for growth conditions. However, where conditions for commercial scale production can be applied which allow for utilization of filamentous organisms, these may be selected as host cells. In some embodiments of the invention, it will be desirable to utilize edible organisms as host cells, as they may optionally be formulated directly into food or feed additives, or into nutritional supplements, as desired. For ease of production, some embodiments of the invention utilize host cells that are genetically tractable, amenable to molecular genetics (e.g., can be efficiently transformed, especially with established or available vectors; optionally can incorporate and/or integrate multiple genes, for example sequentially; and/or have known genetic sequence; etc), devoid of complex growth requirements (e.g., a necessity for light), mesophilic (e.g., prefer growth temperatures with in the range of about 20-32° C.) (e.g. 20, 21, 22, 23, 24, 25, 26, 27, 28, 29, 30, 31, 32° C.), able to assimilate a variety of carbon and nitrogen sources and/or capable of growing to high cell density. Alternatively or additionally, various embodiments of the invention utilize host cells that grow as single cells rather than multicellular organisms (e.g., as mycelia).

In general, when it is desirable to utilize a naturally oleaginous organism in accordance with the present invention, any modifiable and cultivatable oleaginous organism may be employed. In certain embodiments of the invention, yeast or fungi of genera including, but not limited to, *Blakeslea, Candida, Cryptococcus, Cunninghamella, Lipomyces, Mortierella, Mucor, Phycomyces, Pythium, Rhodosporidium, Rhodotorula, Trichosporon*, and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium irregulare, Rhodosporidium toruloides, Rhodotorula glutinis, R. gracilis, R. graminis, R. mucilaginosa, R. pinicola, Trichosporon pullans, T. cutaneum*, and *Yarrowia lipolytica* are used.

Of these naturally oleaginous strains, some also naturally produce carotenoids and some do not; these strains do not naturally produced retinolic compounds. In most cases, only low levels (less than about 0.05% dry cell weight) of carotenoids are produced by naturally-occurring carotenogenic, oleaginous yeast or fungi. Higher levels of β-carotene are sometimes produced, but high levels of other carotenoids are generally not observed.

In general, any organism that is naturally oleaginous and non-carotenoid-producing (e.g., produce less than about 0.05% dry cell weight, do not produce the carotenoid of interest) may be utilized as a host cell in accordance with the present invention. Additionally or alternatively, any organism that is naturally oleaginous and non-retinolic compound-producing (e.g., produce less than about 0.05% dry cell weight, do not produce the retinolic compound of interest) may be utilized as a host cell in accordance with the present invention. For example, introduction of one or more retinologenic modifications (e.g., increased expression of one or more endogenous or heterologous retinologenic polypeptides), in accordance with the present invention, can achieve the goals for retinolic compound production. In some embodiments, the organism is a yeast or fungus from a genus such as, but not limited to, *Candida, Cryptococcus, Cunninghamella, Lipomyces, Mortierella, Pythium, Trichosporon*, and *Yarrowia*; in some embodiments, the organism is of a species including, but not limited to, *Mortierella alpina* and *Yarrowia lipolytica*.

Comparably, the present invention may utilize any naturally oleaginous, carotenoid-producing organism as a host cell. In general, the present invention may be utilized to increase carbon flow into the isoprenoid pathway in naturally carotenoid-producing organisms (particularly for organisms other than *Blakeslea* and *Phycomyces*), and/or to shift production from one carotenoid (e.g., β-carotene) to another (e.g., astaxanthin). Introduction of one or more carotenogenic modifications (e.g., increased expression of one or more endogenous or heterologous carotenogenic polypeptides), in accordance with the present invention, can achieve these goals. Additionally or alternatively, the present invention may be utilized to introduce the ability to produce one or more retinolic compounds in such naturally carotenoid-producing host cells.

In certain embodiments of the invention, the utilized oleaginous, carotenoid-producing organism is a yeast or fungus, for example of a genus such as, but not limited to, *Blakeslea, Mucor, Phycomyces, Rhodosporidium*, and *Rhodotorula*; in some embodiments, the organism is of a species such as, *Mucor circinelloides* and *Rhodotorula glutinis*.

When it is desirable to utilize strains that are naturally non-oleaginous as host cells in accordance with the present invention, genera of non-oleaginous yeast or fungi include, but are not limited to, *Aspergillus, Botrytis, Cercospora, Fusarium* (*Gibberella*), *Kluyveromyces, Neurospora, Penicillium, Pichia* (*Hansenula*), *Puccinia, Saccharomyces, Sclerotium, Trichoderma*, and *Xanthophyllomyces* (*Phaffia*); in some embodiments, the organism is of a species including, but not limited to, *Candida utilis, Aspergillus nidulans, A. niger, A. terreus, Botrytis cinerea, Cercospora nicotianae, Fusarium fujikuroi* (*Gibberella zeae*), *Kluyveromyces lactis, K. lactis, Neurospora crassa, Pichia pastoris, Puccinia distincta, Saccharomyces cerevisiae, Sclerotium rolfsii, Trichoderma reesei*, and *Xanthophyllomyces dendrorhous* (*Phaffia rhodozyma*).

It will be appreciated that the term "non-oleaginous", as used herein, encompasses both strains that naturally have some ability to accumulate lipid, especially cytoplasmically, but do not do so to a level sufficient to qualify as "oleaginous"

as defined herein, as well as strains that do not naturally have any ability to accumulate extra lipid, e.g., extra-membranous lipid. It will further be appreciated that, in some embodiments of the invention, it will be sufficient to increase the natural level of oleaginy of a particular host cell, even if the modified cell does not qualify as oleaginous as defined herein. In some embodiments, the cell will be modified to accumulate at least about 19%, 18%, 17%, 16%, 15%, 14%, 13%, 12%, 11%, 10%, 9%, 8%, 7%, 6%, or 5% in dry cell weight as lipid, so long as the accumulation level is more than that observed in the unmodified parental cell.

As with the naturally oleaginous organisms, some of the naturally non-oleaginous fungi naturally produce carotenoids, whereas others do not; these strains do not naturally produced retinolic compounds. Genera of naturally non-oleaginous fungi that do not naturally produce carotenoids (e.g., produce less than about 0.05% dry cell weight, do not produce a carotenoid or retinolic compound of interest) may desirably be used as host cells in accordance with the present invention include, but are not limited to, *Aspergillus, Kluyveromyces, Penicillium, Saccharomyces*, and *Pichia*; species include, but are not limited to, *Candida utilis, Aspergillus niger* and *Saccharomyces cerevisiae*. Genera of naturally non-oleaginous fungi that do naturally produce carotenoids or retinolic compounds and that may desirably be used as host cells in accordance with the present invention include, but are not limited to, *Botrytis, Cercospora, Fusarium* (*Gibberella*), *Neurospora, Puccinia, Sclerotium, Trichoderma*, and *Xanthophyllomyces* (*Phaffia*); species include, but are not limited to, *Xanthophyllomyces dendrorhous* (*Phaffia rhodozyma*).

As discussed above, any of a variety of organisms may be employed as host cells in accordance with the present invention. In certain embodiments of the invention, host cells will be *Yarrowia lipolytica* cells. Advantages of *Y. lipolytica* include, for example, tractable genetics and molecular biology, availability of genomic sequence (see, for example. Sherman et al. *Nucleic Acids Res.* 32(Database issue):D315-8, 2004), suitability to various cost-effective growth conditions, and ability to grow to high cell density. In addition, *Y. lipolytica* is naturally oleaginous, such that fewer manipulations may be required to generate an oleaginous, carotenoid-producing and/or retinolic compound-producing *Y. lipolytica* strain than might be required for other organisms. Furthermore, there is already extensive commercial experience with *Y. lipolytica.*

*Saccharomyces cerevisiae* is also a useful host cell in accordance with the present invention, particularly due to its experimental tractability and the extensive experience that researchers have accumulated with the organism. Although cultivation of *Saccharomyces* under high carbon conditions may result in increased ethanol production, this can generally be managed by process and/or genetic alterations.

Additional useful hosts include *Xanthophyllomyces dendrorhous* (*Phaffia rhodozyma*), which is experimentally tractable and naturally carotenogenic. *Xanthophyllomyces dendrorhous* (*Phaffia rhodozyma*) strains can produce several carotenoids, including astaxanthin.

*Aspergillus niger* and *Mortierella alpina* accumulate large amounts of citric acid and fatty acid, respectively; *Mortierella alpina* is also oleaginous.

*Neurospora* or *Gibberella* are also useful. They are not naturally oleaginous and tend to produce very low levels of carotenoids, thus extensive modification may be required in accordance with the present invention. *Neurospora* and *Gibberella* are considered relatively tractable from an experimental standpoint. Both are filamentous fungi, such that production at commercial scales can be a challenge necessary to overcome in utilization of such strains.

*Mucor circinelloides* is another available useful species. While its molecular genetics are generally less accessible than are those of some other organisms, it naturally produces β-carotene, thus may require less modification than other species available.

*Candida utilis* is a further useful species. Although it is not naturally oleaginous and produces little or no carotenoids, it is amenable to genetic manipulation (for example, see Iwakiri et al. (2006) Yeast 23:23-34, Iwakiri et al. (2005) Yeast 2005 22:1079-87, Iwakiri et al. (2005) Yeast 22:1049-60, Rodriquez et al. (1998) Yeast 14:1399-406, Rodriquez et al. (1998) FEMS Microbiol Lett. 165:335-40, and Kondo et al. (1995) J Bacteriol. 177:7171-7) and furthermore is edible.

Molecular genetics can be performed in *Blakeslea*, though significant effort may be required. Furthermore, cost-effective fermentation conditions can be challenging, as, for example, it may be required that the two mating types are mixed. Fungi of the genus *Phycomyces* are also possible sources which have the potential to pose fermentation process challenges, and these fungi may be less amenable to manipulate than several other potential host organisms.

Additional useful hosts include strains such as *Schizosaccharomyces pombe, Saitoella complicata*, and *Sporidiobolus ruineniae.*

Those of ordinary skill in the art will appreciate that the selection of a particular host cell for use in accordance with the present invention will also affect, for example, the selection of expression sequences utilized with any heterologous polypeptide to be introduced into the cell, codon bias that can optionally be engineered into any nucleic acid to be expressed in the cell, and will also influence various aspects of culture conditions, etc. Much is known about the different gene regulatory requirements, protein targeting sequence requirements, and cultivation requirements, of different host cells to be utilized in accordance with the present invention (see, for example, with respect to *Yarrowia*, Barth et al. *FEMS Microbiol Rev.* 19:219, 1997; Madzak et al. *J Biotechnol.* 109:63, 2004; see, for example, with respect to *Xanthophyllomyces*, Verdoes et al. *Appl Environ Microbiol* 69: 3728-38, 2003; Visser et al. FEMS Yeast Res 4: 221-31, 2003; Martinez et al. Antonie Van Leeuwenhoek. 73(2):147-53, 1998; Kim et al. Appl Environ Microbiol. 64(5):1947-9, 1998; Wery et al. Gene. 184(1):89-97, 1997; see, for example, with respect to *Saccharomyces*, Guthrie and Fink *Methods in Enzymology* 194:1-933, 1991). In certain aspects, for example, targeting sequences of the host cell (or closely related analogs) may be useful to include for directing heterologous proteins to subcellular localization. Thus, such useful targeting sequences can be added to heterologous sequence for proper intracellular localization of activity. In other aspects (e.g., addition of mitochondrial targeting sequences), heterologous targeting sequences may be eliminated or altered in the selected heterologous sequence (e.g., alteration or removal of source organism plant chloroplast targeting sequences).

To give but a few specific examples, of promoters and/or regulatory sequences that may be employed in expression of polypeptides according to the present invention, useful promoters include, but are not limited to, the Leu2 promoter and variants thereof (see, for example, see U.S. Pat. No. 5,786,212); the EF1alpha protein and ribosomal protein S7 gene promoters (see, for example, PCT Application WO 97/44470); the Gpm (see US20050014270), Xpr2 (see U.S. Pat. No. 4,937,189), Tef1, Gpd1 (see, for example, US Application 2005-0014270A1), Cam1 (YALI0C24420g), YALI0D16467g, Tef4 (YALI0B12562g), Yef3

(YALI0E13277g), Pox2, Yat1 (see, for example US Application 2005-0130280; PCT Application WO 06/052754), Fba1 (see, for example WO05049805), and/or Gpat (see WO06031937) promoters; the sequences represented by SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, subsequences thereof, and hybrid and tandem derivatives thereof (e.g., as disclosed in US Application 2004-0146975); the sequences represented by SEQ ID NO: 1, 2, or 3 including fragments (e.g. by 462-1016 and by 197-1016 of SEQ ID NO: 1; by 5-523 of SEQ ID NO:3) and complements thereof (e.g., as disclosed in U.S. Pat. No. 5,952,195); CYP52A2A (see, for example, US Application 2002-0034788); promoter sequences from fungal (e.g., *C. tropicalis*) catalase, citrate synthase, 3-ketoacyl-CoA thiolase A, citrate synthase, O-acetylhornserine sulphydrylase, protease, carnitine O-acetyltransferase, hydratase-dehydrogenase, epimerase genes; promoter sequences from Pox4 genes (see, for example, US application 2004-0265980); and/or promoter sequences from Met2, Met3, Met6, Met25 and YALI0D12903g genes. Any such promoters can be used in conjunction with endogenous genes and/or heterologous genes for modification of expression patterns of endogenous polypeptides and/or heterologous polypeptides in accordance with the present invention.

Alternatively or additionally, regulatory sequences useful in accordance with the present invention may include one or more Xpr2 promoter fragments, for example as described in U.S. Pat. No. 6,083,717 (e.g. SEQ ID NOS: 1-4 also including sequences with 80% or more identity to these SEQ ID NOs) (e.g., see Example 11) in one or more copies either in single or in tandem. Similarly, exemplary terminator sequences include, but are not limited to, *Y. lipolytica* Xpr2 (see U.S. Pat. No. 4,937,189) and Pox2 (YALI0F10857g) terminator sequences.

In some embodiments of this invention, it may be desirable to fused sequences encoding specific targeting signals to bacterial source genes. For example, in certain embodiments mitochondrial signal sequences are useful in conjunction with, e.g., bacterial polypeptides for effective targeting of polypeptides for proper functioning. Mitochondrial signal sequences are known in the art, and include, but are not limited to example, mitochondrial signal sequences provided in Table 52 below. In other embodiments, it may be desirable to utilize genes from other source organisms such as animals, plants, alga, or microalgae, fungi, yeast, insect, protozoa, and mammals.

Engineering Oleaginy

All living organisms synthesize lipids for use in their membranes and various other structures. However, most organisms do not accumulate in excess of about 10% of their dry cell weight as total lipid, and most of this lipid generally resides within cellular membranes.

Significant biochemical work has been done to define the metabolic enzymes necessary to confer oleaginy on microorganisms (primarily for the purpose of engineering single cell oils as commercial sources of arachidonic acid and docosahexaenoic acid; see for example Ratledge *Biochimie* 86:807, 2004, the entire contents of which are incorporated herein by reference). Although this biochemical work is compelling, there only have been a limited number of reports of de novo oleaginy being established through genetic engineering with the genes encoding the key metabolic enzymes. It should be noted that oleaginous organisms typically accumulate lipid only when grown under conditions of carbon excess and nitrogen limitation. The present invention further establishes that the limitation of other nutrients (e.g. phosphate and/or magnesium) can also induce lipid accumulation. The present invention establishes, for example, that limitation of nutrients such as phosphate and/or magnesium can induce lipid accumulation, much as is observed under conditions of nitrogen limitation. Under these conditions, the organism readily depletes the limiting nutrient but continues to assimilate the carbon source. The "excess" carbon is channeled into lipid biosynthesis so that lipids (usually triacylglycerols) accumulate in the cytosol, typically in the form of bodies. It should be noted that oleaginous organisms typically only accumulate lipid when grown under conditions of carbon excess and nitrogen or other nutrient limitation (e.g. phosphate or magnesium). Under these conditions, the organism readily depletes the limiting nutrient but continues to assimilate the carbon source. The "excess" carbon is channeled into lipid biosynthesis so that lipids (usually triacylglycerols) accumulate in the cytosol, typically in the form of bodies.

In general, it is thought that, in order to be oleaginous, an organism must produce both acetyl-CoA and NADPH in the cytosol, which can then be utilized by the fatty acid synthase machinery to generate lipids. In at least some oleaginous organisms, acetyl-CoA is generated in the cytosol through the action of ATP-citrate lyase, which catalyzes the reaction:

$$\text{citrate+CoA+ATP}\rightarrow\text{acetyl-CoA+oxaloacetate+ADP+}P_i. \quad (1)$$

Of course, in order for ATP-citrate lyase to generate appropriate levels of acetyl-CoA in the cytosol, it must first have an

TABLE 52

Examples of mitochondrial targeting sequences.

| Species | Protein (residues) | GI | Sequence |
|---|---|---|---|
| *Yarrowia lipoylitica* | NUAM (AA 1-34) | 6689648 | MLSRNLSKFARAGLIRPATTSTHTRLFSVSARR L (SEQ ID NO: 171) |
| *Yarrowia lipoylitica* | NUHM (AA 1-32) | 50549567 | MLRLIRPRLAALARPTTRAPQALNARTHIVSV (SEQ ID NO: 172) |
| *Saccharomyces cerevisiae* | Coq1 (AA 1-53) | 536190 | MFQRSGAAHHIKLISSRRCRFKSSFAVALNAA SKLVTPKILWNNPISLVSKEM (SEQ ID NO: 173) |
| *Yarrowia lipoylitica* | Coq1 (AA 1-77) | 60389562 | MLRVGRIGTKTLASSSLRFVAGARPKSTLTEA VLETTGLLKTTPQNPEWSGAVKQASRLVETD TPIRDPFSIVSQEM (SEQ ID NO: 174) |

available pool of its substrate citric acid. Citric acid is generated in the mitochondria of all eukaryotic cells through the tricarboxylic acid (TCA) cycle, and can be moved into the cytosol (in exchange for malate) by citrate/malate translocase.

In most oleaginous organisms, and in some non-oleaginous organisms, the enzyme isocitrate dehydrogenase, which operates as part of the TCA cycle in the mitochondria, is strongly AMP-dependent. Thus, when AMP is depleted from the mitochondria, this enzyme is inactivated. When isocitrate dehydrogenase is inactive, isocitrate accumulates in the mitochondria. This accumulated isocitrate is then equilibrated with citric acid, presumably through the action of aconitase. Therefore, under conditions of low AMP, citrate accumulates in the mitochondria. As noted above, mitochondrial citrate is readily transported into the cytosol.

Figure 2:
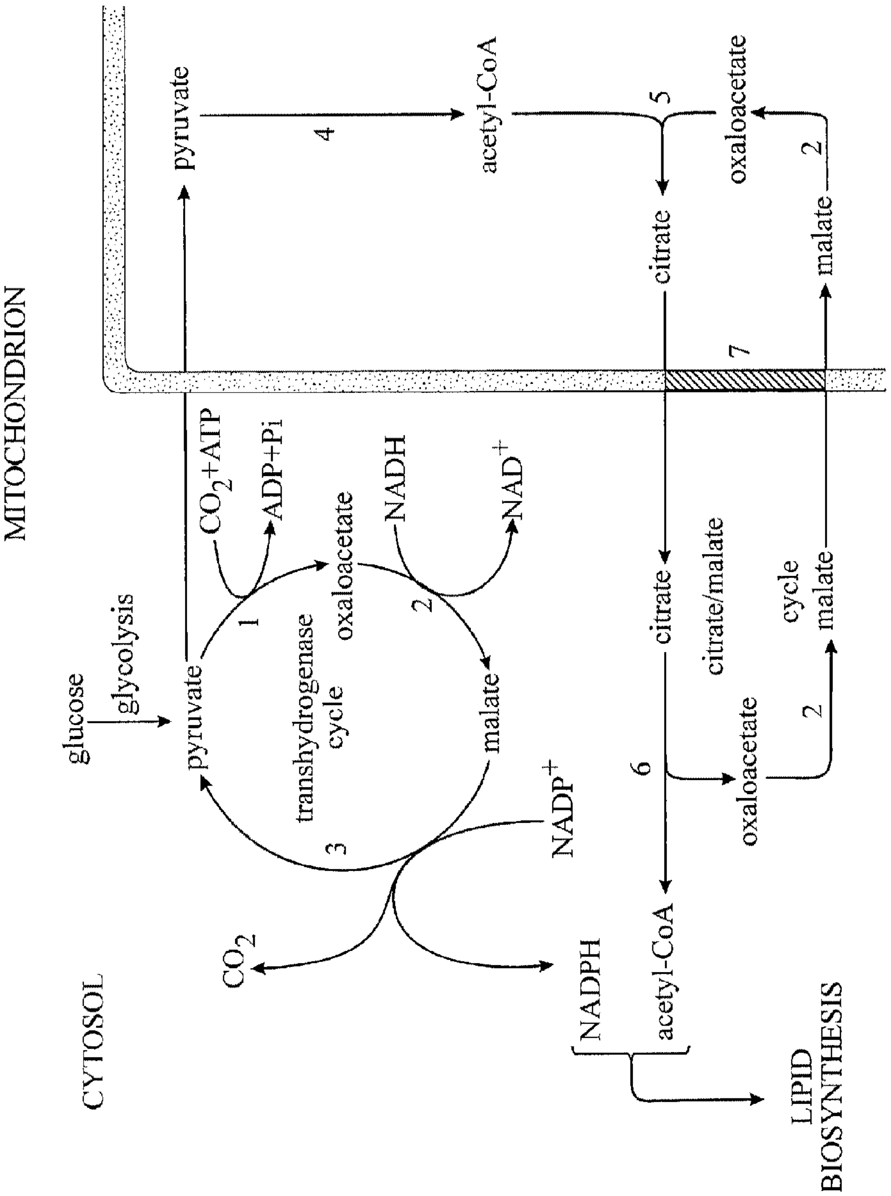
FIG. 2 depicts how sufficient levels of acetyl-CoA and NADPH may be accumulated in the cytosol of oleaginous organisms to allow for production of significant levels of cytosolic lipids. Enzymes: 1, pyruvate decarboxylase; 2, malate dehydrogenase; 3, malic enzyme; 4, pyruvate dehydrogenase; 5, citrate synthase; 6, ATP-citrate lyase; 7, citrate/malate translocase.

AMP depletion, which in oleaginous organisms is believed to initiate the cascade leading to accumulation of citrate (and therefore acetyl-CoA) in the cytoplasm, occurs as a result of the nutrient depletion mentioned above. When oleaginous cells are grown in the presence of excess carbon source but under conditions limiting for nitrogen or some other nutrient(s) (e.g., phosphate or magnesium), the activity of AMP deaminase, which catalyzes the reaction:

$$AMP \rightarrow inosine\ 5'\text{-}monophosphate + NH_3 \quad (2)$$

is strongly induced. The increased activity of this enzyme depletes cellular AMP in both the cytosol and the mitochondria. Depletion of AMP from the mitochondria is thought to inactivate the AMP-dependent isocitrate dehydrogenase, resulting in accumulation of citrate in the mitochondria and, therefore, the cytosol. This series of events is depicted diagrammatically in FIG. 2.

As noted above, oleaginy requires both cytosolic acetyl-CoA and cytosolic NADPH. It is believed that, in many oleaginous organisms, appropriate levels of cytosolic NADPH are provided through the action of malic enzyme (Enzyme 3 in FIG. 2). Some oleaginous organisms (e.g., *Lipomyces* and some *Candida*) do not appear to have malic enzymes, however, so apparently other enzymes can provide comparable activity, although it is expected that a dedicated source of NADPH is probably required for fatty acid synthesis (see, for example, Wynn et al., *Microbiol* 145:1911, 1999; Ratledge *Adv. Appl. Microbiol.* 51:1, 2002, each of which is incorporated herein by reference in its entirety).

Other activities which can be involved in regenerating NADPH include, for example, 6-phosphogluconate dehydrogenase (gnd); Fructose 1,6 bisphosphatase (fbp); Glucose 6 phosphate dehydrogenase (g6pd); NADH kinase (EC 2.7.1.86); and/or transhydrogenase (EC 1.6.1.1 and 1.6.1.2).

Gnd is part of the pentose phosphate pathway and catalyses the reaction:

$$6\text{-phospho-D-gluconate} + NADP+ \rightarrow \text{D-ribulose 5-phosphate} + CO_2 + NADPH$$

Fbp is a hydrolase that catalyses the gluconeogenic reaction:

$$\text{D-fructose 1,6-bisphosphate} + H_2O \rightarrow \text{D-fructose 6-phosphate} + \text{phosphate}$$

Fbp redirects carbon flow from glycolysis towards the pentose phosphate pathway. The oxidative portion of the pentose phosphate pathway, which includes glucose 6 phosphate dehydrogenase and 6-phosphogluconate dehydrogenase, enables the regeneration of NADPH. G6pd is part of the pentose phosphate pathway and catalyses the reaction:

$$\text{D-glucose 6-phosphate} + NADP^+ \rightarrow \text{D-glucono-1,5-lactone 6-phosphate} + NADPH + H^+\ NADH$$

kinase catalyzes the reaction:

$$ATP + NADH \rightarrow ADP + NADPH$$

Transhydrogenase catalyzes the reaction:

$$NADPH + NAD^+ \leftrightarrow NADP^+ + NADH$$

Thus, enhancing the expression and/or activity of any of these enzymes can increase NADPH levels and promote anabolic pathways requiring NADPH.

Alternative or additional strategies to promote oleaginy may include one or more of the following: (1) increased or heterologous expression of one or more of acyl-CoA:diacylglycerol acyltransferase (e.g., DGA1; YALI0E32769g); phospholipid:diacylglycerol acyltransferase (e.g., LRO1; YALI0E16797g); and acyl-CoA:cholesterol acyltransferase (e.g., ARE genes such as ARE1, ARE2, YALI0F06578g), which are involved in triglyceride synthesis (Kalscheuer et al. *Appl Environ Microbiol* p. 7119-7125, 2004; Oelkers et al. *J Biol Chem* 277:8877-8881, 2002; and Sorger et al. *J Biol Chem* 279:31190-31196, 2004), (2) decreased expression of triglyceride lipases (e.g., TGL3 and/or TGL4; YALI0D17534g and/or YALI0F10010g (Kurat et al. *J Biol Chem* 281:491-500, 2006); and (3) decreased expression of one or more acyl-coenzyme A oxidase activities, for example encoded by POX genes (e.g. POX1, POX2, POX3, POX4, POX5; YALI0C23859g, YALI0D24750g, YALI0E06567g, YALI0E27654g, YALI0E32835g, YALI0F10857g; see for example Mlickova et al. *Appl Environ Microbiol* 70: 3918-3924, 2004; Binns et al. *J Cell Biol* 173:719, 2006).

Thus, according to the present invention, the oleaginy of a host organism may be enhanced by modifying the expression or activity of one or more polypeptides involved in generating cytosolic acetyl-CoA and/or NADPH and/or altering lipid levels through other mechanisms. For example, modification of the expression or activity of one or more of acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1,6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, acyl-coenzyme A oxidase can enhance oleaginy in accordance with the present invention. Exemplary polypeptides which can be utilized or derived so as to enhance oleaginy in accordance with the present invention include, but are not limited to those acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1,6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, acyl-coenzyme A oxidase polypeptides provided in Tables 1-6, and 31-47, respectively.

In some embodiments of the invention, where an oleaginous host cell is employed, enzymes and regulatory components relevant to oleaginy are already in place but could be modified, if desired, by for example altering expression or activity of one or more oleaginic polypeptides and/or by introducing one or more heterologous oleaginic polypeptides. In those embodiments of the invention where a non-oleaginous host cell is employed, it is generally expected that at least one or more heterologous oleaginic polypeptides will be introduced.

The present invention contemplates not only introduction of heterologous oleaginous polypeptides, but also adjustment of expression or activity levels of heterologous or endogenous oleaginic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) and/or regulatory factors (e.g., polypeptides that modulate transcription, splicing, translation, modification, etc.) may be utilized to confer particular regulation of expression patterns. Such genetic modifications may be utilized in conjunction with endogenous genes (e.g., for regulation of endogenous oleaginic polypeptide(s)); alternatively, such genetic modifications may be included so as to confer regulation of expression of at least one heterologous polypeptide (e.g., oleaginic polypeptide(s)).

In some embodiments, at least one oleaginic polypeptide is introduced into a host cell. In some embodiments of the invention, a plurality (e.g., two or more) of different oleaginic polypeptides is introduced into the same host cell. In some embodiments, the plurality of oleaginic polypeptides contains polypeptides from the same source organism; in other embodiments, the plurality includes polypeptides independently selected from different source organisms.

Representative examples of a variety of oleaginic polypeptides that may be introduced into or modified within host cells according to the present invention, include, but are not limited to, those provided in Tables 1-6, and Tables 31-47. As noted above, it is expected that at least some of these polypeptides (e.g., malic enzyme and ATP-citrate lyase) should desirably act in concert, and possibly together with one or more components of fatty acid synthase, such that, in some embodiments of the invention, it will be desirable to utilize two or more oleaginic polypeptides from the same source organism.

In certain embodiments, the oleaginy of a host organism is enhanced by growing the organism on a carbon source comprising one or more oils. For example, an organism may be grown on a carbon source comprising one or more oils selected from the group consisting of, for example, olive, canola, corn, sunflower, soybean, cottonseed, rapeseed, etc., and combinations thereof. In certain embodiments, the oleaginy of a host organism is enhanced by growing the organism on a carbon source comprising one or more oils in combination with modifying the expression or activity of one or more polypeptides such as any of those described above (e.g., oleaginic polypeptides such as polypeptides involved in generating cytosolic acetyl-CoA and/or NADPH) and/or altering lipid levels through other mechanisms.

In general, source organisms for oleaginic polypeptides to be used in accordance with the present invention include, but are not limited to, *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium* (*Gibberella*), *Kluyveromyces, Neurospora, Penicillium, Pichia* (*Hansenula*), *Puccinia, Saccharomyces, Sclerotium, Trichoderma*, and *Xanthophyllomyces* (*Phaffia*). In some embodiments, the source species for acetyl CoA carboxylase, ATP-citrate lyase, malice enzyme and/or AMP deaminase polypeptides include, but are not limited to, *Aspergillus nidulans, Cryptococcus neoformans, Fusarium fujikuroi, Kluyveromyces lactis, Neurospora crassa, Saccharomyces cerevisiae, Schizosaccharomyces pombe, Ustilago maydis*, and *Yarrowia lipolytica*; in some embodiments, source species for pyruvate decarboxylase or isocitrate dehydrogenase polypeptides include, but are not limited to *Neurospora crassa, Xanthophyllomyces dendrorhous* (*Phaffia rhodozyma*), *Aspergillus niger, Saccharomyces cerevisiae, Mucor circinelloides, Rhodotorula glutinis, Candida utilis, Mortierella alpina*, and *Yarrowia lipolytica.*

*Aspergillus niger* accumulates large amounts of citric acid, whereas *Mortierella alpina* and *Thraustochytrium* sp. accumulate large amounts of fatty acid, respectively; *Mortierella alpina* and *Thraustochytrium* are also oleaginous.

To give but one particular example of a host cell engineered to be oleaginous (or at least to accumulate increased levels of lipid) in accordance with the present invention, *S. cerevisiae* can be engineered to express one or more oleaginic polypeptides, e.g., from heterologous source organisms. In some embodiments, a plurality of different oleaginic polypeptides are expressed, optionally from different source organisms. For instance, in some embodiments, *S. cerevisiae* cells are engineered to express (and/or to increase expression of) ATP-citrate lyase (e.g., from *N. crassa*), AMP deaminase (e.g., from *S. cerevisiae*), and/or malic enzyme (e.g., from *M. circinelloides*). In other embodiments, *Candida utilis* and *Phaffia rhodozyma* can be similarly modified. Modified *S. cerevisiae, C. utilis*, and *P. rhodozyma* strains can be further modified as described herein to increase production of one or more carotenoids.

In certain embodiments, host cells are engineered to be olegaginous by introducing one or more oleaginic polypeptides. In general, any oleaginic polypeptide can be introduced into any host cell of the present invention. In certain embodiments, such oleaginic polypeptides are codon-optimized to accommodate the codon preferences of the host cell. In certain embodiments, an oleaginic polypeptide introduced into a host cell is from the same organism as the host cell and/or a related organism. For example, without limitation, the present invention encompasses the recognition that it may be desirable to introduce a fungal oleaginic polypeptide into a fungal host cell (e.g., from the same and/or a related fungal species). In certain embodiments, the host cell is a *Y. lipolytica* host cell. In certain aspects of such embodiments, a *Y. lipolytica* olegainic polypeptide is introduced into the *Y. lipolytica* host cell. In certain aspects, a *S. cerevisiae* olegainic polypeptide is introduced into the *Y. lipolytica* host cell. In certain aspects, any of a variety of fungal olegainic polypeptides is introduced into the *Y. lipolytica* host cell.

Engineering Carotenoid Production

Figure 3A:
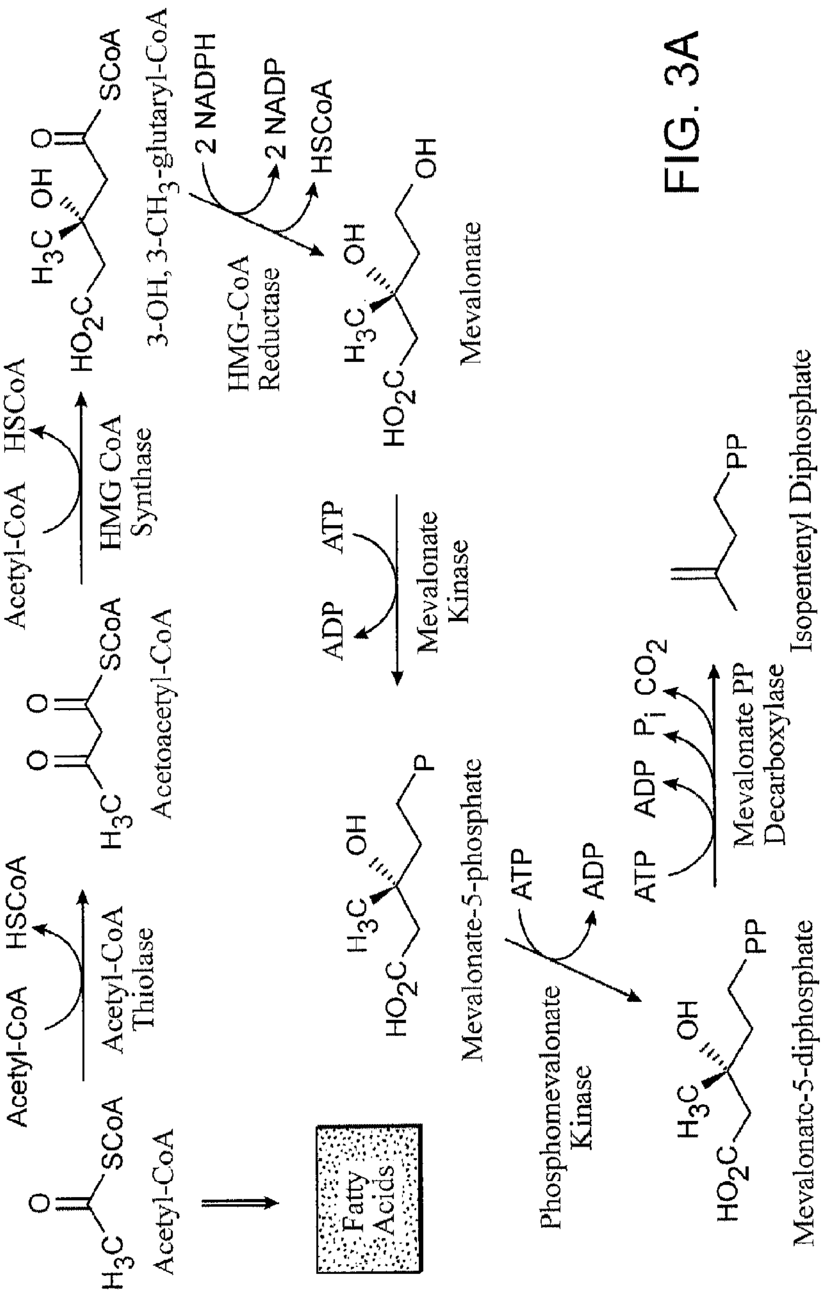
FIGS. 3A and 3B depict the mevalonate isoprenoid biosynthesis pathway, which typically operates in eukaryotes, including fungi.
Figure 3B:
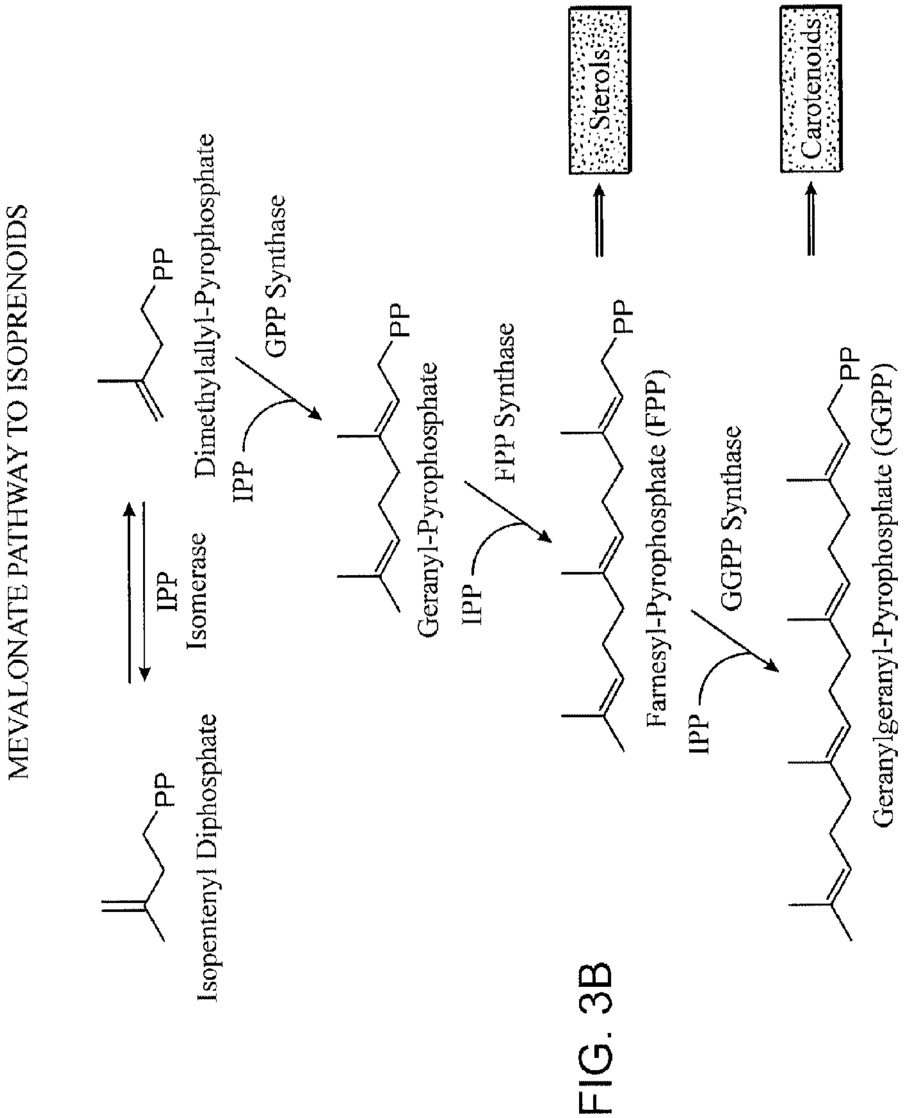

Carotenoids are synthesized from isoprenoid precursors, some of which are also involved in the production of steroids and sterols. The most common isoprenoid biosynthesis pathway, sometimes referred to as the "mevalonate pathway", is generally depicted in FIG. 3. As shown, acetyl-CoA is converted, via hydroxymethylglutaryl-CoA (HMG-CoA), into mevalonate. Mevalonate is then phosphorylated and converted into the five-carbon compound isopentenyl pyrophosphate (IPP). Following isomerization of IPP into dimethylallyl pyrophosphate (DMAPP), three sequential condensation reactions with additional molecules of IPP generate the ten-carbon molecule geranyl pyrophosphate (GPP), followed by the fifteen-carbon molecule farnesyl pyrophosphate (FPP), and finally the twenty-carbon compound geranylgeranyl pyrophosphate (GGPP).

Figure 4:
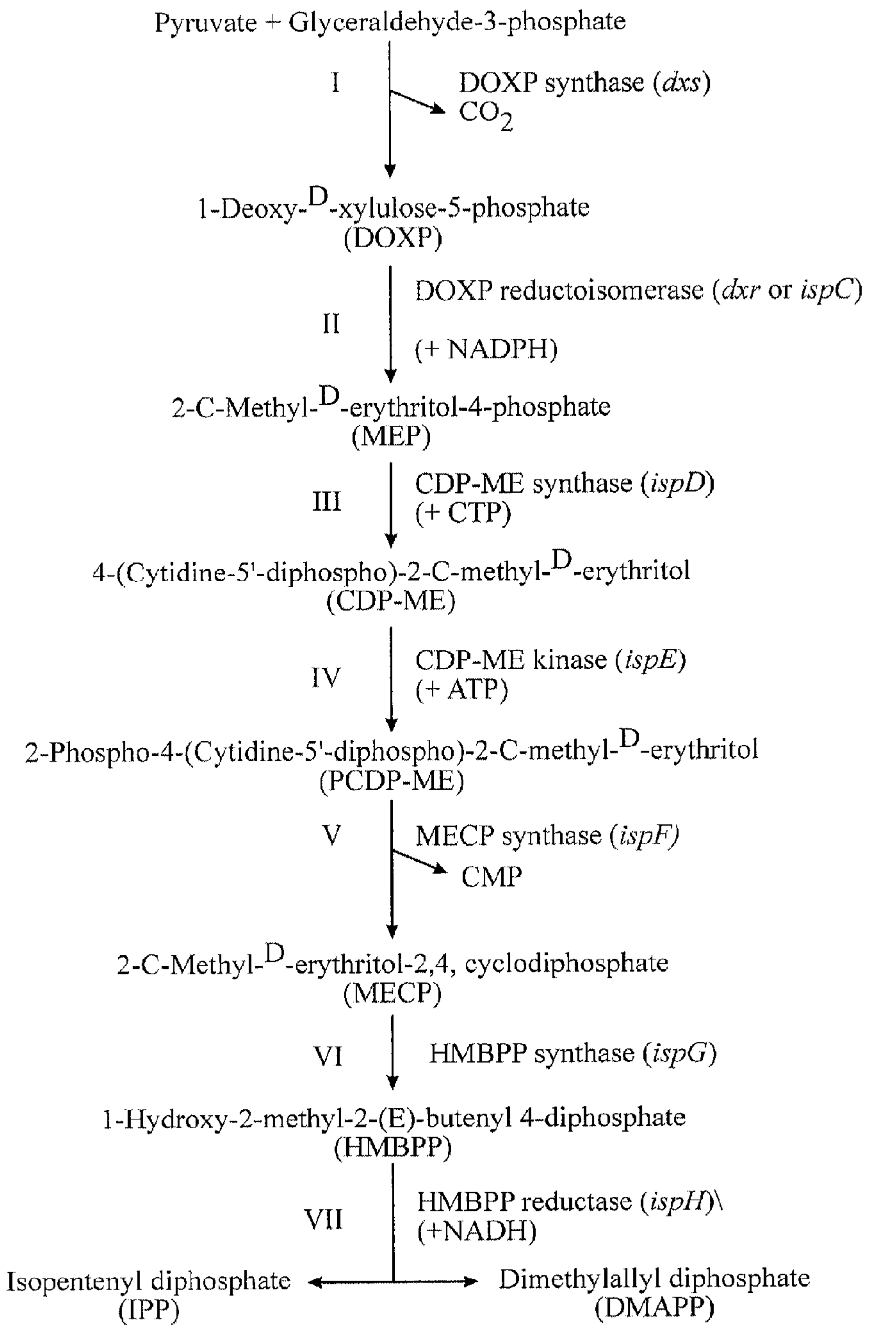
FIG. 4 depicts the mevalonate-independent isoprenoid biosynthesis pathway, also known as the DXP pathway, which typically operates in bacteria and in the plastids of plants.
Figure 5:
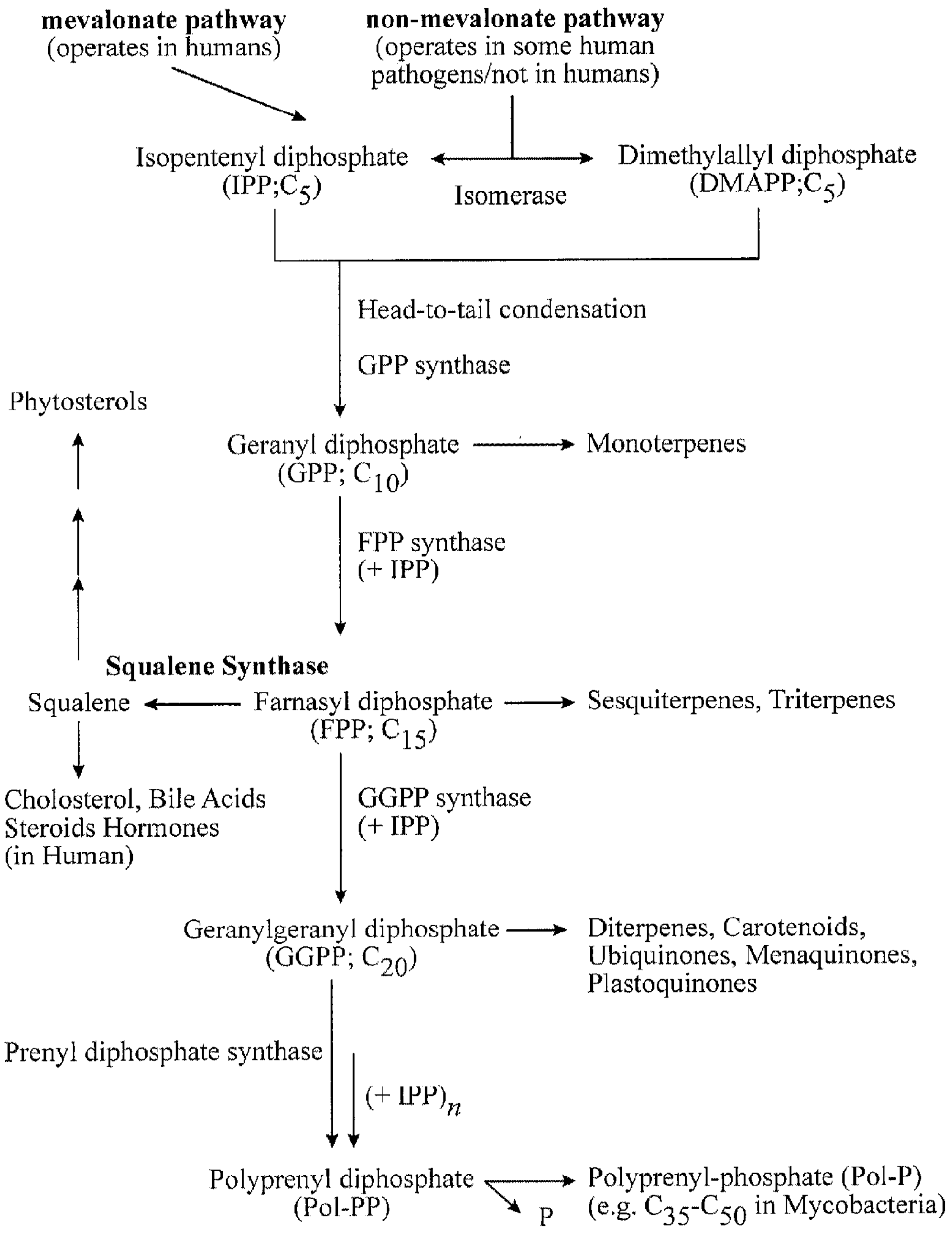
FIG. 5 depicts intermediates in the isoprenoid biosynthesis pathway and how they feed into biosynthetic pathways of other biomolecules, including carotenoids as well as non-carotenoid compounds such as sterols, steroids, and vitamins, such as vitamin E or vitamin K.
Figure 6A:
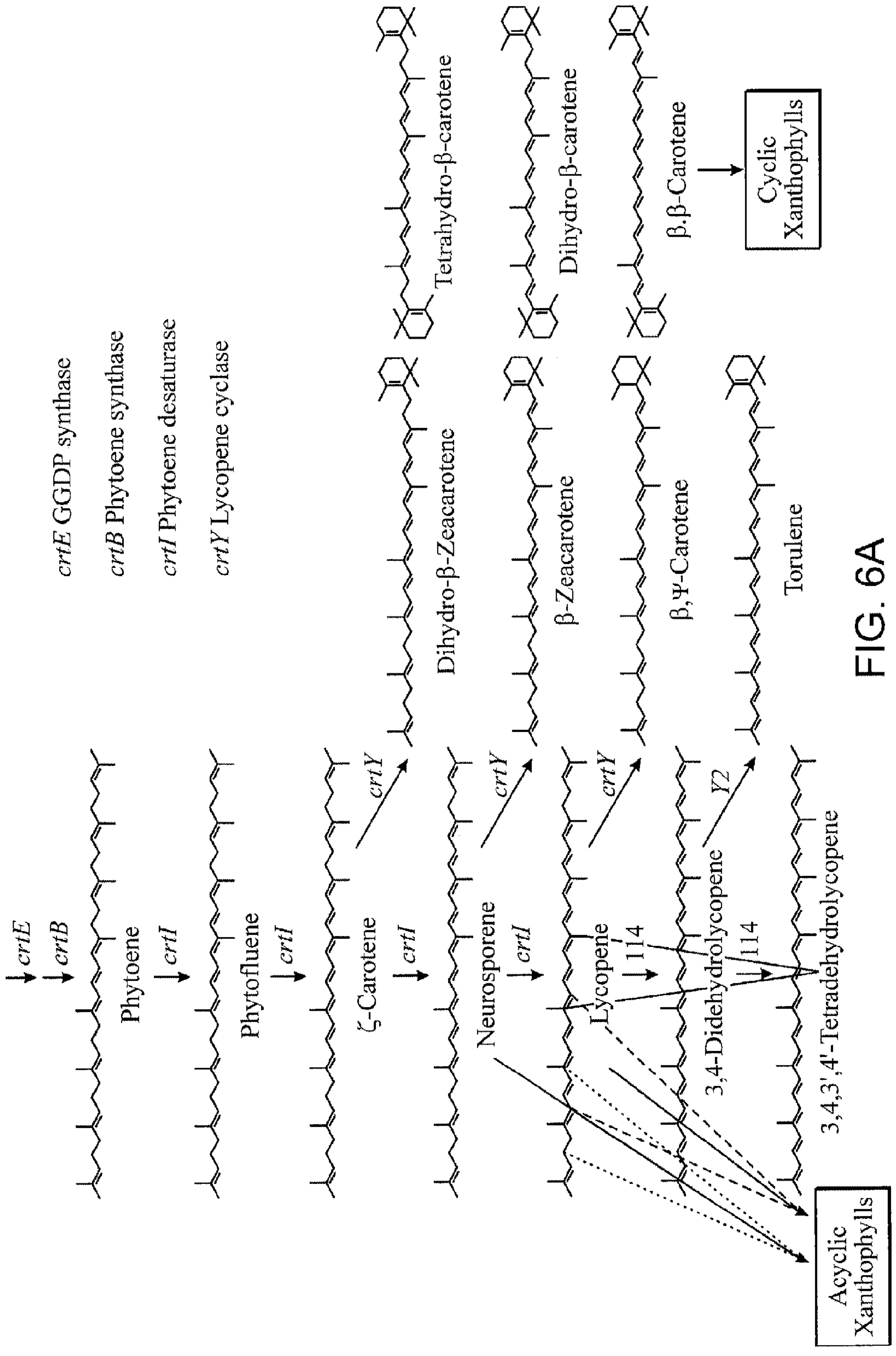
FIGS. 6A-6D illustrate various carotenoid biosynthetic pathways.
Figure 6B:
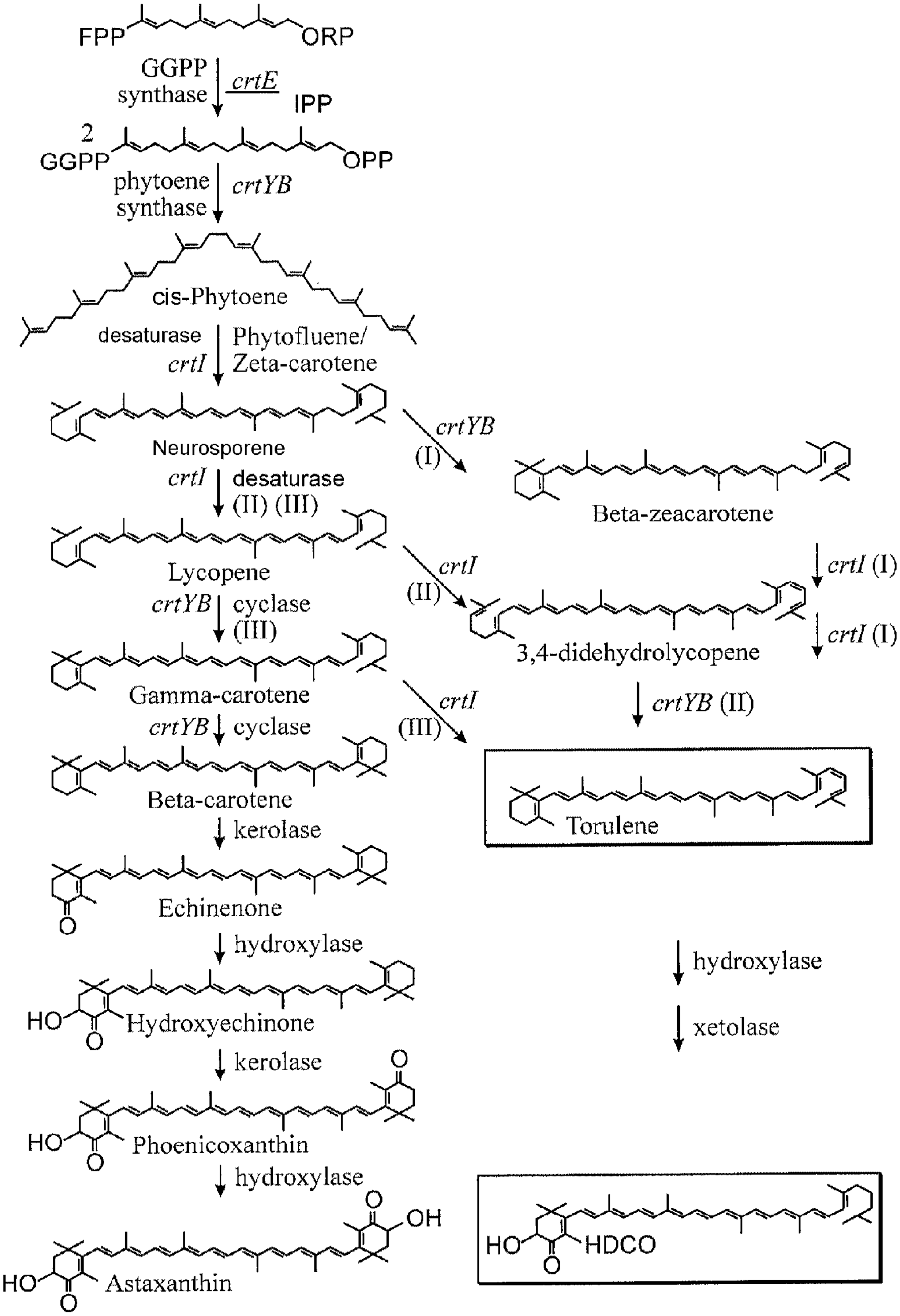
Figure 6C:
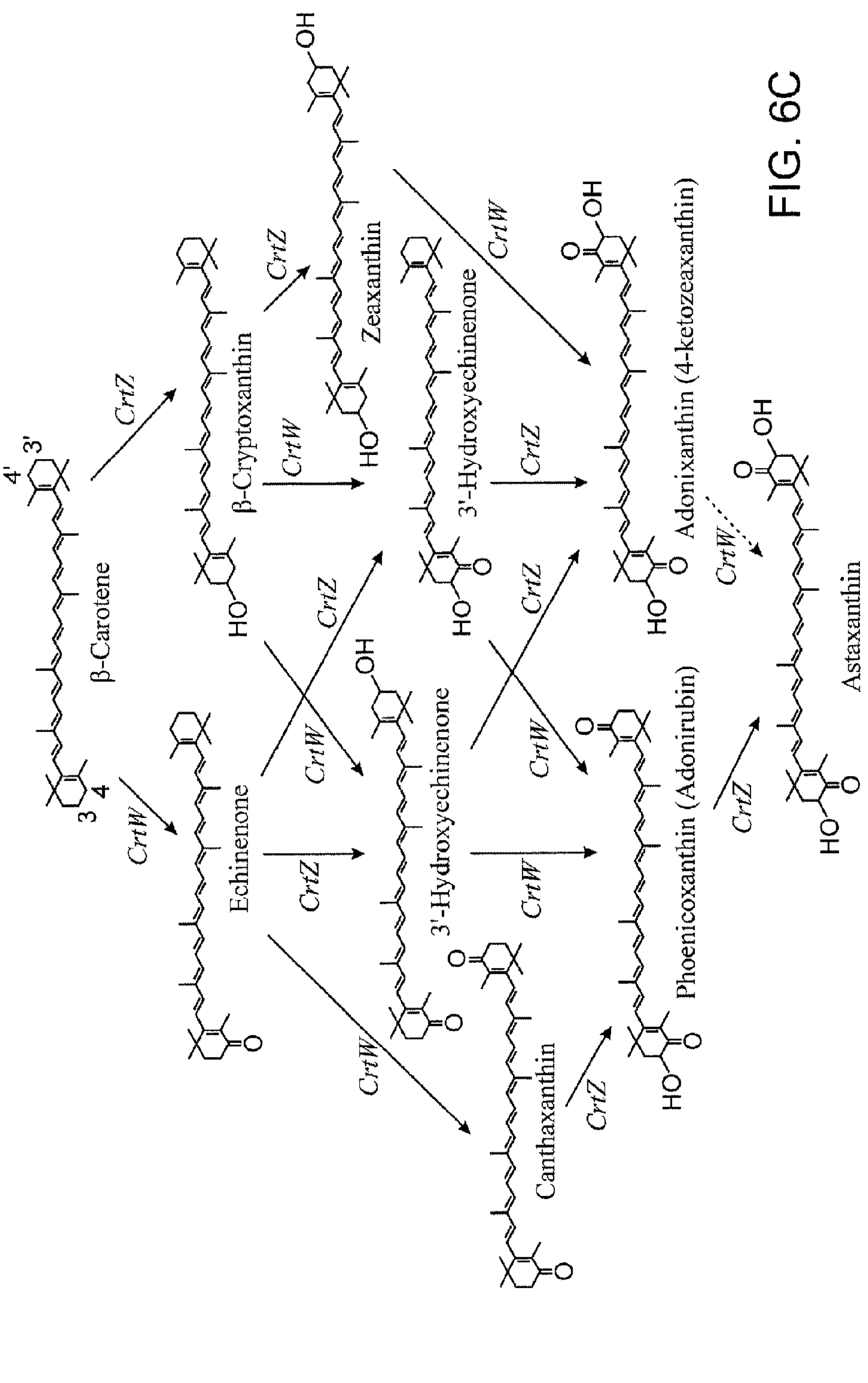
Figure 6D:
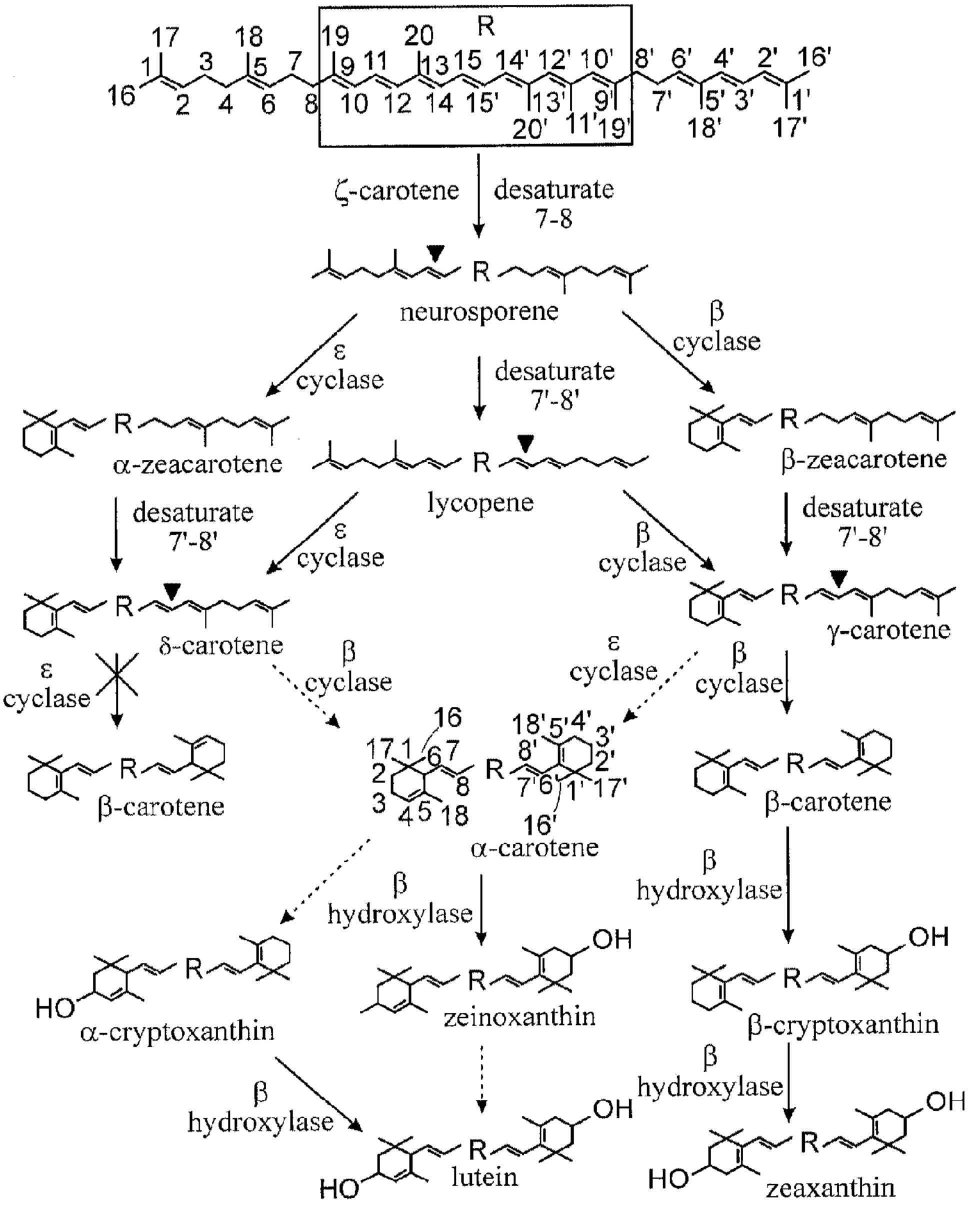
Figure 8A:
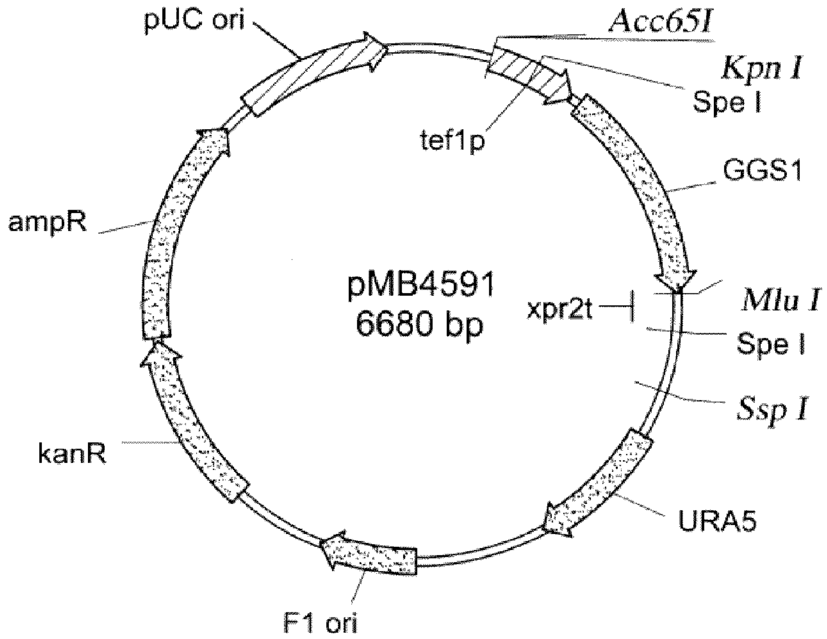
FIGS. 8A-8P depict schematic representations of plasmids generated and described in detail in the exemplification.
Figure 8B:
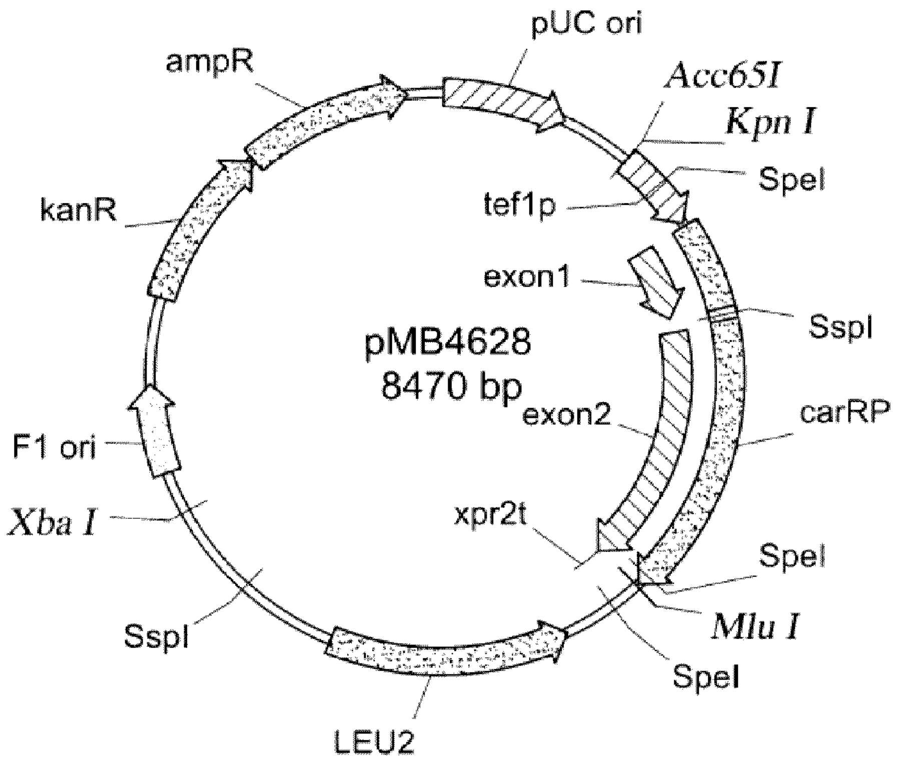
Figure 8C:
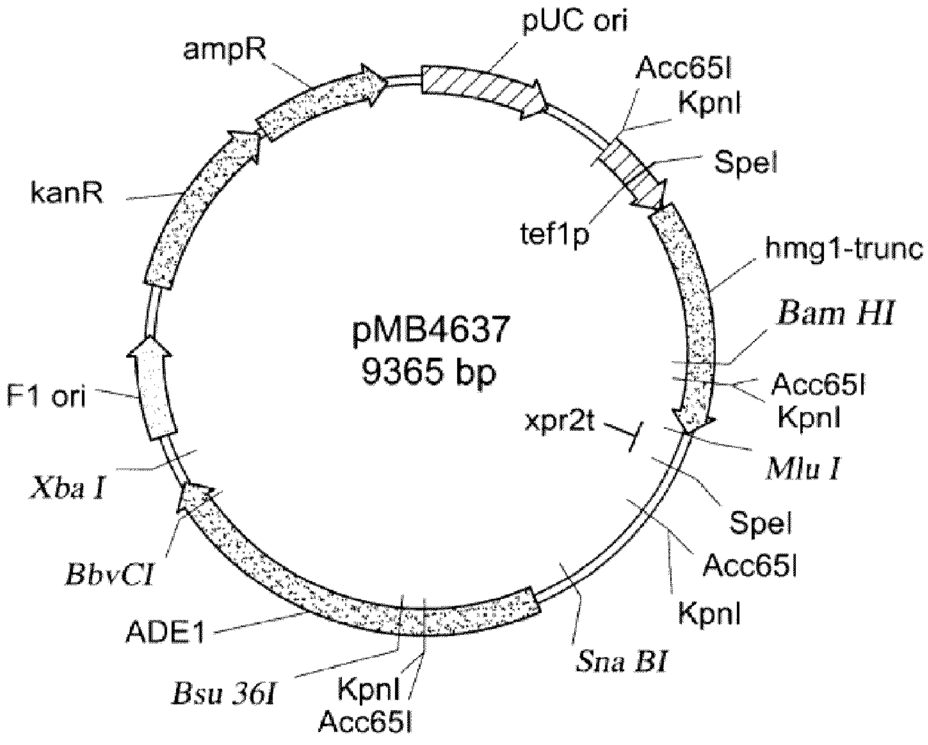
Figure 8D:
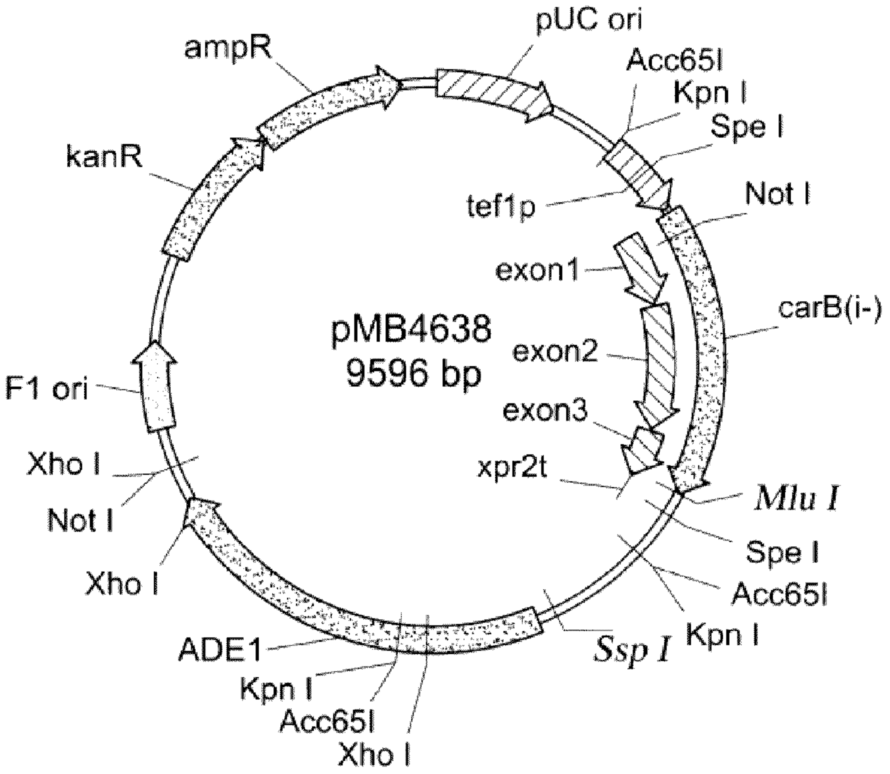
Figure 8E:
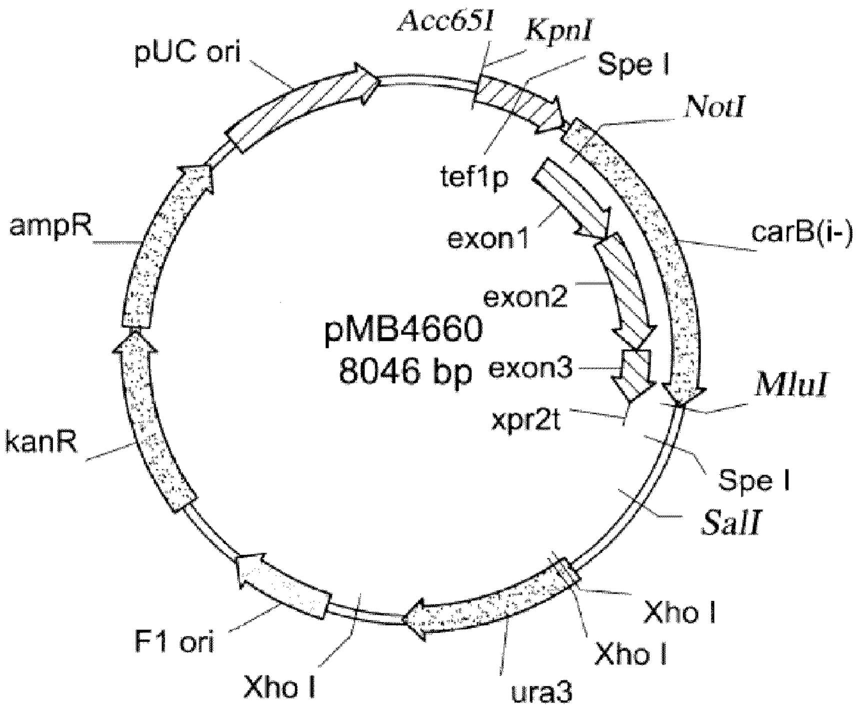
Figure 8F:
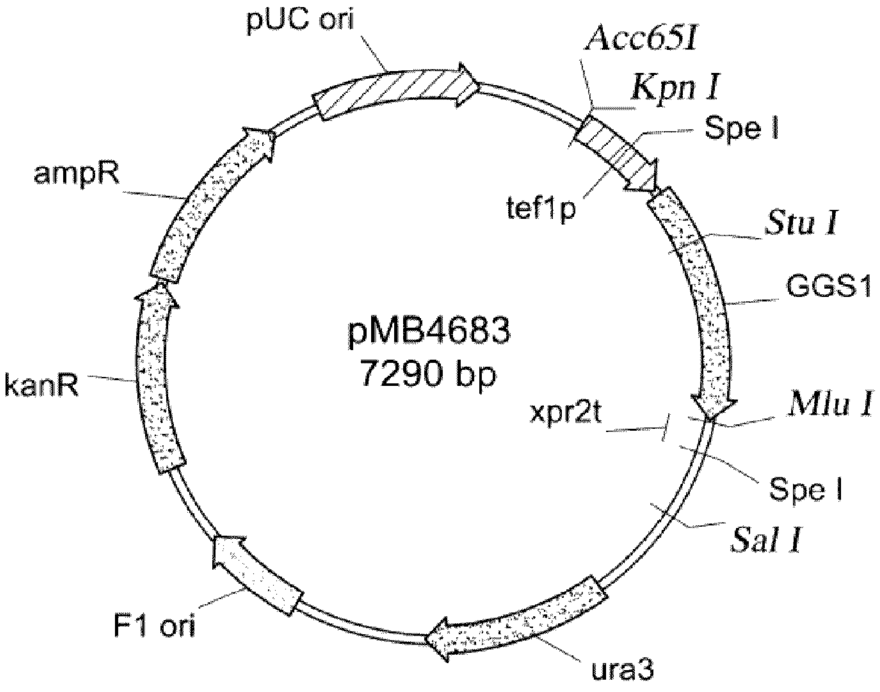
Figure 8G:
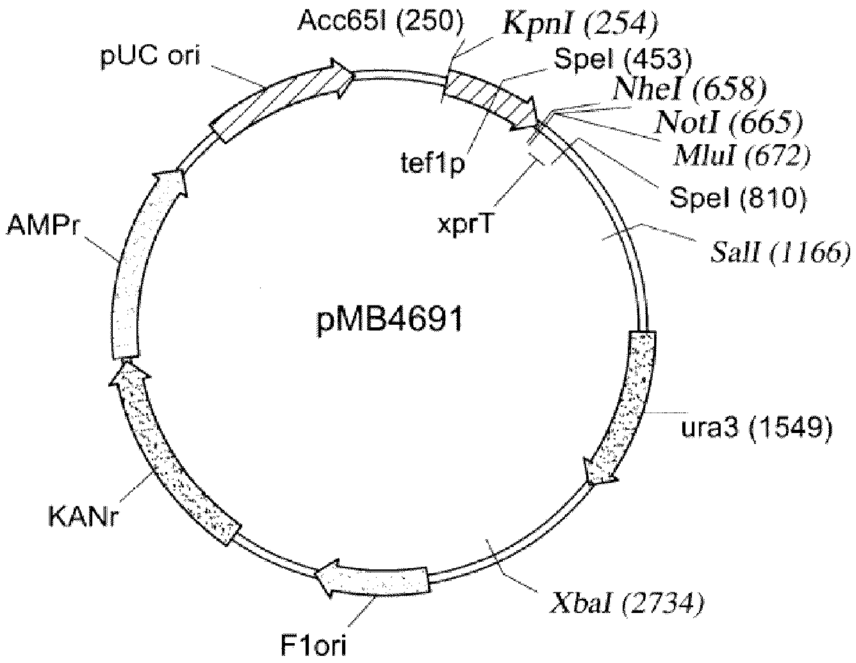
Figure 8H:
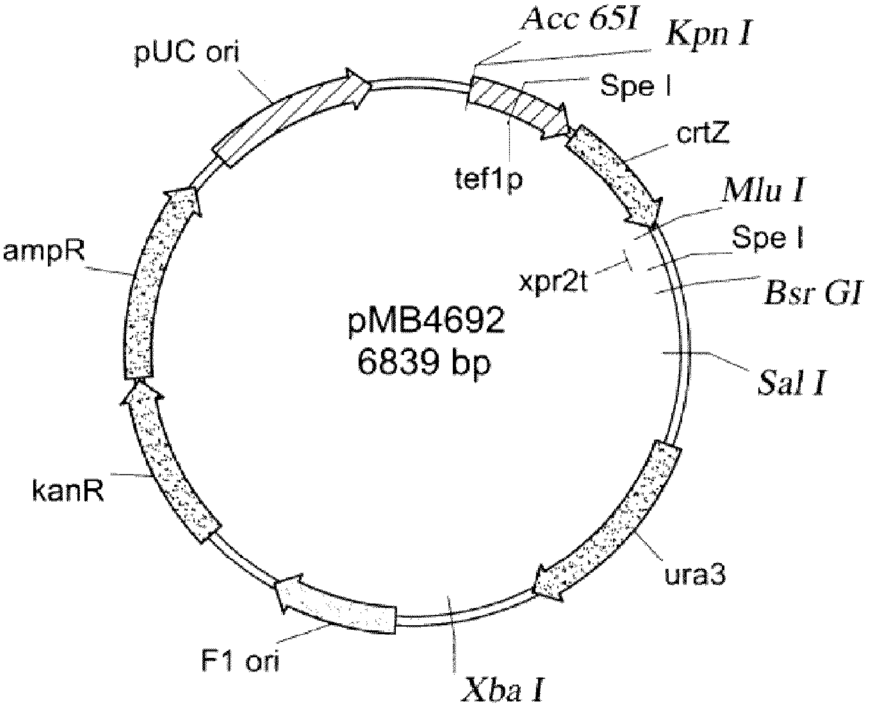
Figure 8I:
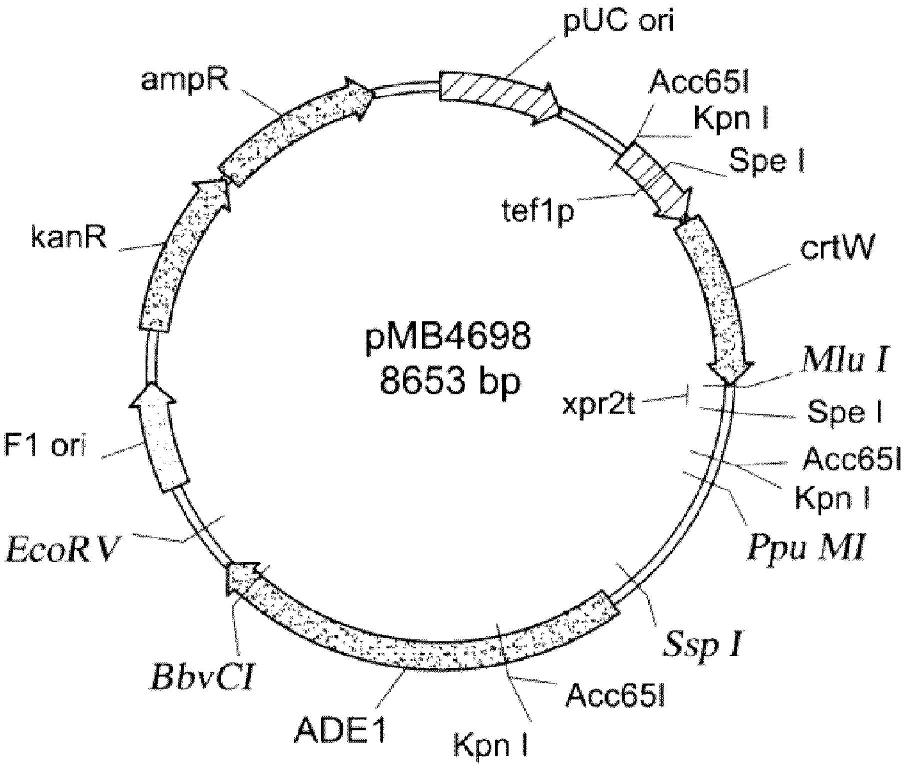
Figure 8J:
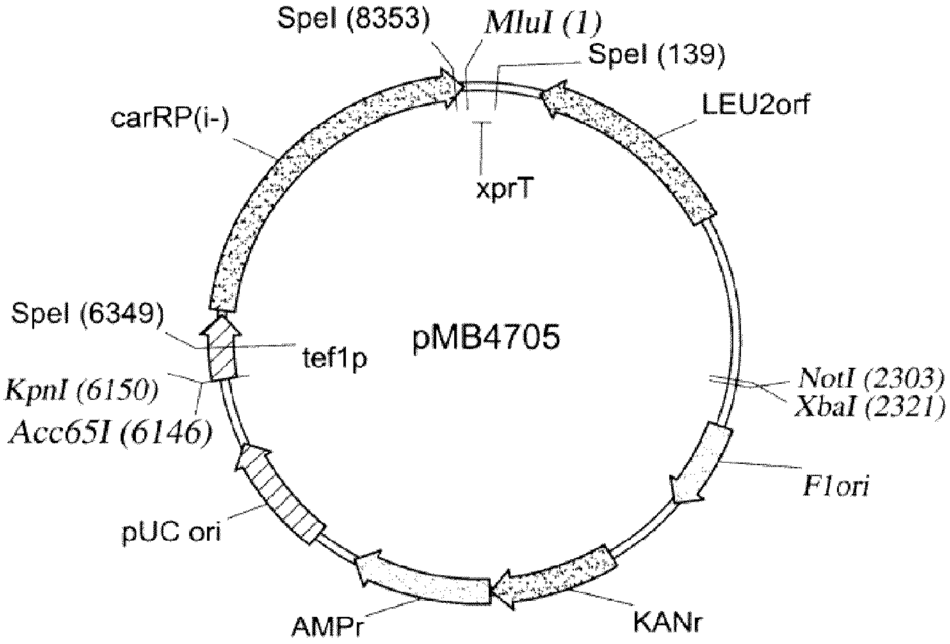
Figure 8K:
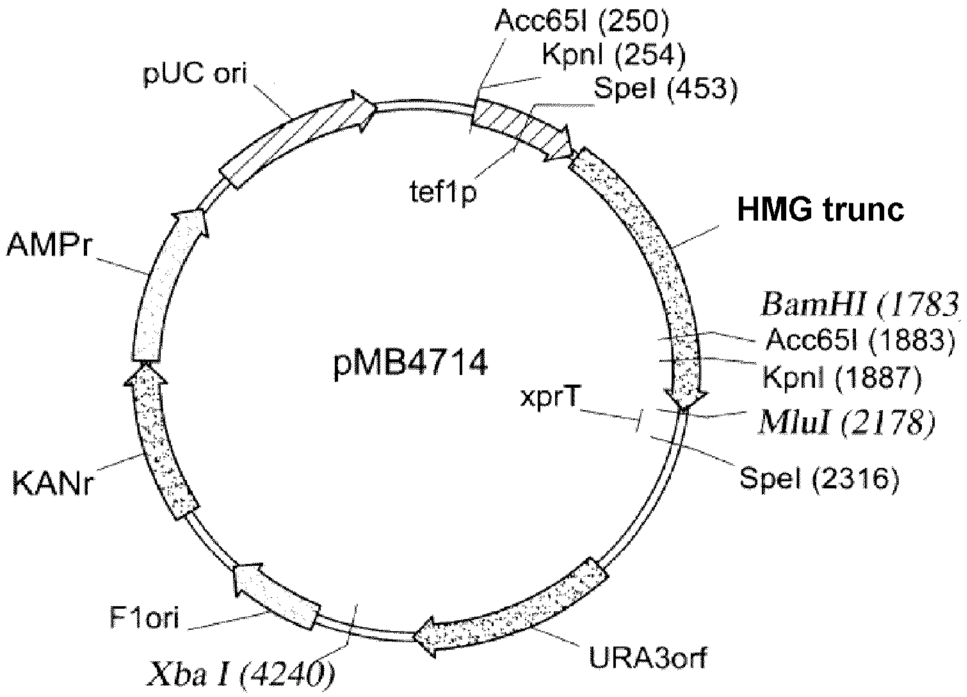
Figure 8L:
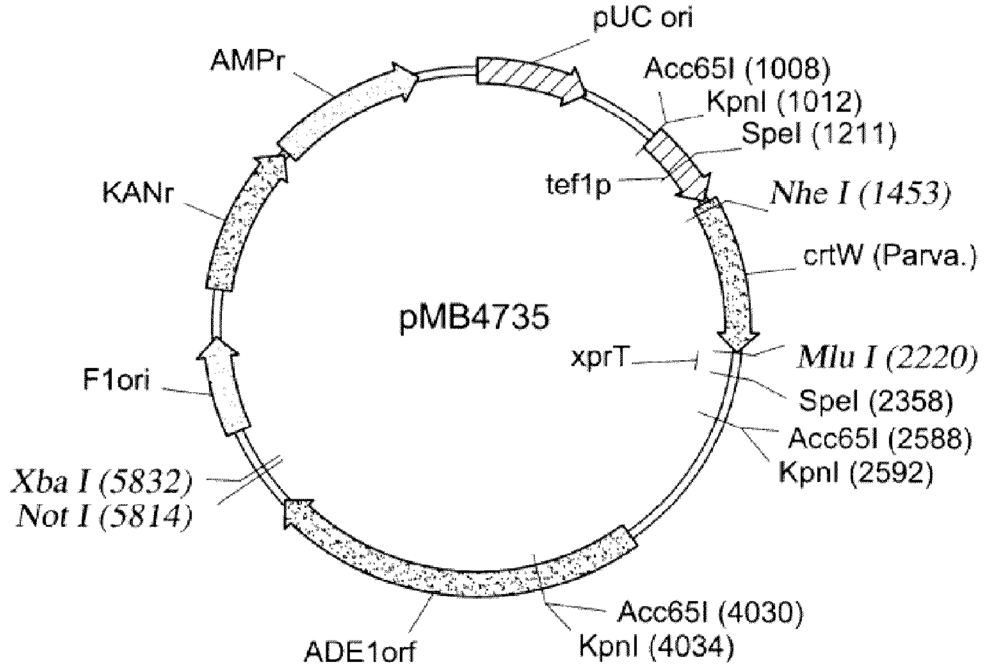
Figure 8M:
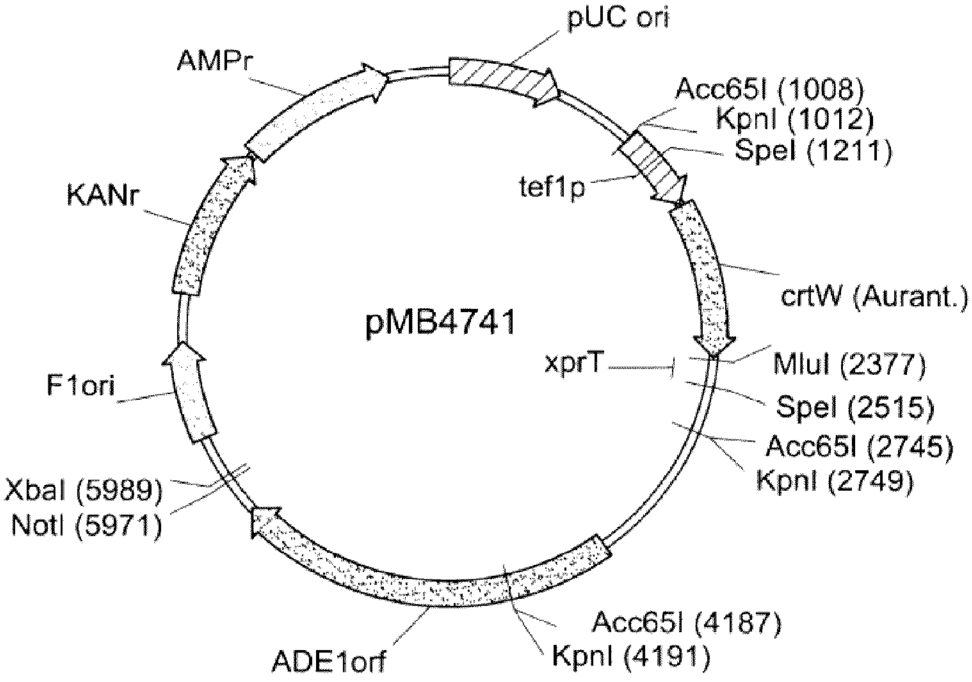
Figure 8N:
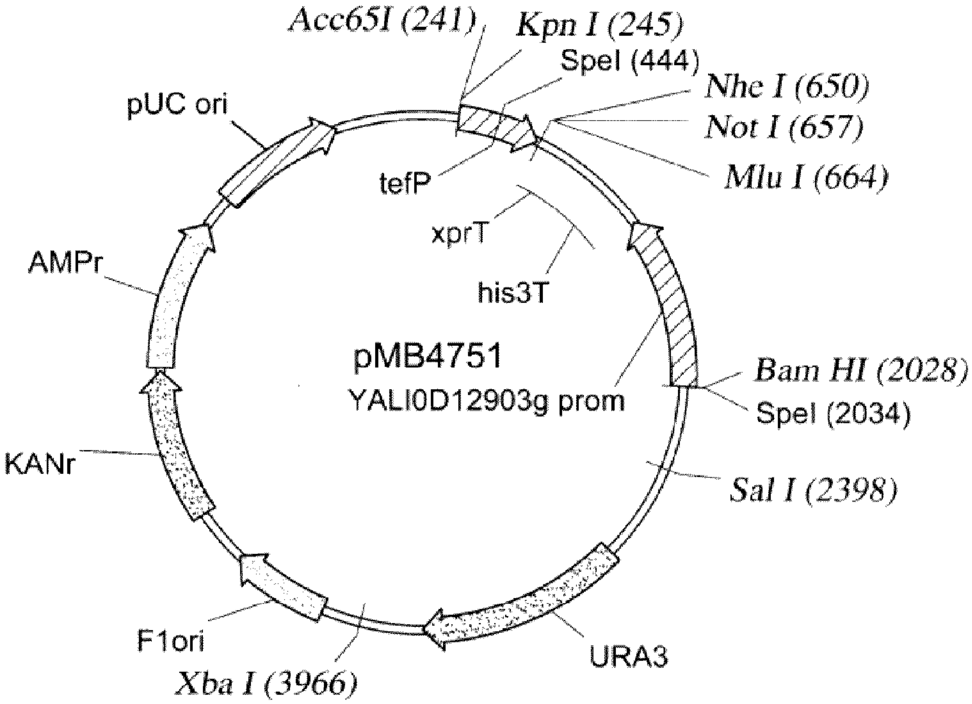
Figure 8O:
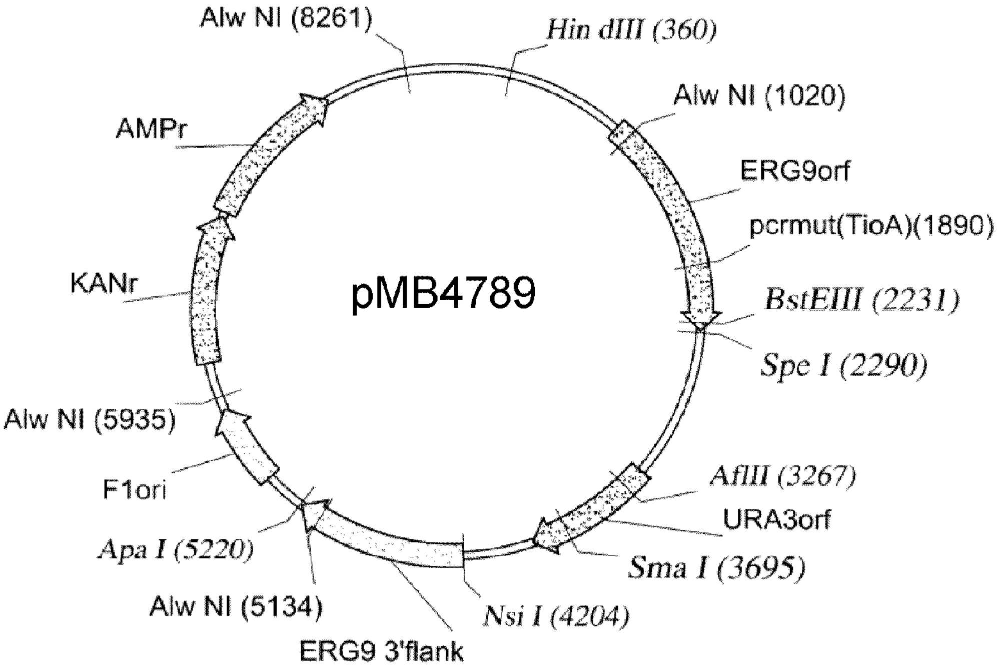
Figure 8P:
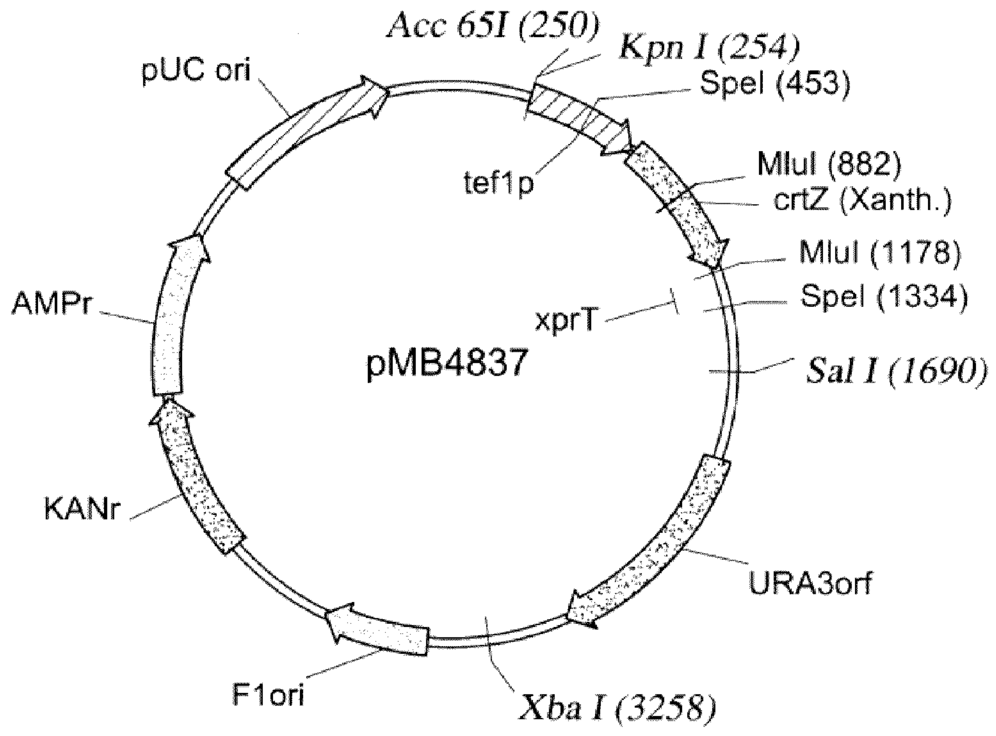

An alternative isoprenoid biosynthesis pathway, that is utilized by some organisms (particularly bacteria) and is sometimes called the "mevalonate-independent pathway", is depicted in FIG. 4. This pathway is initiated by the synthesis of 1-deoxy-D-xyloglucose-5-phosphate (DOXP) from pyruvate and glyceraldehyde-3-phosphate. DOXP is then converted, via a series of reactions shown in FIG. 4, into IPP, which isomerizes into DMAPP and is then converted, via GPP and FPP, into GGPP as shown in FIG. 3 and discussed above.

Various proteins involved in isoprenoid biosynthesis have been identified and characterized in a number of organisms. Moreover, various aspects of the isoprenoid biosynthesis pathway are conserved throughout the fungal, bacterial, plant and animal kingdoms. For example, polypeptides corresponding to the acetoacetyl-CoA thiolase, HMG-CoA synthase, HMG-CoA reductase, mevalonate kinase, phosphomevalonate kinase, mevalonate pyrophosphate decarboxylase, IPP isomerase, FPP synthase, and GGPP synthase shown in FIG. 3 have been identified in and isolated from a wide variety of organisms and cells. Representative examples of a wide variety of such polypeptides are provided in Tables 7-15. One or more of the polypeptides selected from those provided in any one of Tables 7-15 may be utilized or derived for use in the methods and compositions in accordance with the present invention.

Alternatively or additionally, modified mevalonate kinase polypeptides that exhibit decreased feedback inhibition properties (e.g. to farnesyl pyrophosphate (FPP)) may be utilized in accordance with the present invention. Such modified mevalonate kinase polypeptides may be of eukaryotic or prokaryotic origin. For example, modified versions of mevalonate kinase polypeptides from animals (including humans), plants, algae, fungi (including yeast), and/or bacteria may be employed; for instance, modified versions of mevalonate kinase polypeptides disclosed in Table 10 herein may be utilized.

Particular examples of modified mevalonate kinase polypeptides include "feedback-resistant mevalonate kinases" disclosed in PCT Application WO 2006/063752. Thus, for example, a modified mevalonate kinase polypeptide may include one or more mutation (s) at one or more amino acid position (s) selected from the group consisting of amino acid positions corresponding to positions 17, 47, 93, 94, 132, 167, 169, 204, and 266 of the amino acid sequence of *Paracoccus zeaxanthinifaciens* mevalonate kinase as shown in SEQ ID NO: 1 of PCT Application WO 2004/111214. For example, the modified mevalonate kinase polypeptide may contain one or more substitutions at positions corresponding to one or more of I17T, G47D, K93E, V94I, R204H and C266S.

To give but a few specific examples, when a modified mevalonate kinase polypeptide comprises 2 amino acid changes as compared with a parent mevalonate kinase polypeptide, it may comprise changes at positions corresponding to the following positions 132/375, 167/169, 17/47 and/or 17/93 of SEQ ID NO: 1 of WO/2004/111214 (e.g. P132A/P375R, R167W/K169Q, I17T/G47D or I17T/K93E); when a modified mevalonate kinase polypeptide comprises 3 amino acid changes as compared with a parent mevalonate kinase, it may comprise changes at positions corresponding to the following positions 17/167/169, 17/132/375, 93/132/375, and/or 17/47/93 of SEQ ID NO: 1 of WO/2004/111214 (e.g., I17T/R167W/K169Q, I17T/P132A/P375R, K93E/P132A/P375R, I17T/R167W/K169H, I17T/R167T/K169M, I17T/R167T/K169Y, I17T/R167F/K169Q, I17T/R167I/K169N, I17T/R167H/K169Y, I17T/G47D/K93E or I17T/G47D/K93Q).

Thus, for example, a modified mevalonate kinase polypeptide may include one or more mutation(s) (particularly substitutions), as compared with a parent mevalonate kinase polypeptide, at one or more amino acid position (s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO: 1 of PCT application WO 2006/063752. For example, such corresponding substitutions may comprise one or more of P55L, F59S, N66K, C117S, or I152M. A modified mevalonate kinase may comprise a substitution corresponding to F59S substitution. A modified mevalonate kinase polypeptide comprising 2 amino acid changes as compared with its parent mevalonate kinase polypeptide may, for example, comprise changes at positions corresponding to the following positions 55/117, 66/152, 83/249, 111/375 or 106/218 of to SEQ ID NO: 1 of WO2006/063752 (e.g. P55L/C117S, N66K/I152M, K83E/S249P, H111N/K375N or L106P/S218P). A modified mevalonate kinase may comprise a substitution corresponding to N66K/I152M. A modified mevalonate kinase polypeptide comprising 4 amino acid changes as compared with its parent mevalonate kinase polypeptide may have changes at positions corresponding to one or more of the following positions 42/158/231/367 of SEQ ID NO:1 of WO2006/063752 (e.g. I142N/L158S/L231I/T367S).

According to the present invention, carotenoid production in a host organism may be adjusted by modifying the expression or activity of one or more proteins involved in isoprenoid biosynthesis. In some embodiments, such modification involves introduction of one or more heterologous isoprenoid biosynthesis polypeptides into the host cell; alternatively or additionally, modifications may be made to the expression or activity of one or more endogenous or heterologous isoprenoid biosynthesis polypeptides. Given the considerable conservation of components of the isoprenoid biosynthesis polypeptides, it is expected that heterologous isoprenoid biosynthesis polypeptides will often function even in significantly divergent organisms. Furthermore, should it be desirable to introduce more than one heterologous isoprenoid biosynthesis polypeptide (e.g., more than one version of the same polypeptide and/or more that one different polypeptides), in many cases polypeptides from different source organisms will function together. In some embodiments of the invention, a plurality of different heterologous isoprenoid biosynthesis polypeptides is introduced into the same host cell. In some embodiments, this plurality contains only polypeptides from the same source organism (e.g., two or more sequences of, or sequences derived from, the same source organism); in other embodiments the plurality includes polypeptides independently selected from from different source organisms (e.g., two or more sequences of, or sequences derived from, at least two independent source organisms).

In some embodiments of the present invention that utilize heterologous isoprenoid biosynthesis polypeptides, the source organisms include, but are not limited to, fungi of the genera *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium* (*Gibberella*), *Kluyveromyces, Neurospora, Penicillium, Pichia* (*Hansenula*), *Puccinia, Saccharomyces, Schizosaccharomyces, Sclerotium, Trichoderms, Ustilago*, and *Xanthophyllomyces* (*Phaffia*). In certain embodiments, the source organisms are of a species including, but not limited to, *Cryptococcus neoformans, Fusarium fujikuroi, Kluyveromyces lactis, Neurospora crassa, Saccharomyces cerevisiae, Schizosaccharomyces pombe, Ustilago maydis*, and *Yarrowia lipolytica.*

As noted above, the isoprenoid biosynthesis pathway is also involved in the production of non-carotenoid compounds, such as sterols, steroids, and vitamins, such as vitamin E or vitamin K. Proteins that act on isoprenoid biosynthesis pathway intermediates, and divert them into biosynthesis of non-carotenoid compounds are therefore indirect inhibitors of carotenoid biosynthesis (see, for example, FIG. 5, which illustrates points at which isoprenoid intermediates are channeled into other biosynthesis pathways). Such proteins are therefore considered isoprenoid biosynthesis competitor polypeptides. Reductions of the level or activity of such isoprenoid biosynthesis competitor polypeptides are expected to increase carotenoid production in host cells according to the present invention. Additionally or alternatively, since disruption of the SAGA complex component SPT-8 increases carotenoid production (see e.g., Example 16), increased expression or activity of one or more components of the SAGA complex such as, without limitation, the SPT8 gene, may decrease production of carotenoids and/or retinolic compounds. Thus, polypeptides that comprise the SAGA complex can be considered competitor polypeptides in the situation where they decrease production of carotenoids and/or retinolic compounds. Without wishing to be bound by theory, the present invention encompasses the recognition that increased expression or activity of one or more components of the SAGA complex may act as isoprenoid biosynthesis competitors, thus reducing the amount of carotenoid produced. For example, one or more components of the SAGA complex may act on isoprenoid intermediates prior to GGPP, such that less GGPP is generated and available for the carotenoid generation pathway. In such embodiments, it will be understood that the SAGA polypeptide(s) components whose activity or expression is increased functions as isoprenoid biosynthesis competitor polypeptide(s). Thus, for example, one or more of the polypeptides encoded by the genes listed in Table 69 may function as isoprenoid biosynthesis competitor polypeptides. Such SAGA polypeptides can be expressed individually or in combination with one another. In certain embodiments, SAGA isoprenoid biosynthesis competitor polypeptides are expressed (and/or their activity increased) in combination with an increase in expression and/or activity of one or more additional isoprenoid biosynthesis competitor polypeptides, such as, without limitation, those isoprenoid biosynthesis competitor polypeptides listed in Tables 7-15.

In some embodiments of the present invention, production or activity of endogenous isoprenoid biosynthesis competitor polypeptides may be reduced or eliminated in host cells. In some embodiments, this reduction or elimination of the activity of an isoprenoid biosynthesis competitor polypeptide can be achieved by treatment of the host organism with small molecule inhibitors of enzymes of the ergosterol biosynthetic pathway. Enzymes of the ergosterol biosynthetic pathway include, for example, squalene synthase (Erg9), squalene epoxidase (Erg1), 2,3-oxidosqualene-lanosterol cyclase (Erg7), cytochrome P450 lanosterol 14α-demethylase (Erg11), C-14 sterol reductase (Erg24), C-4 sterol methyl oxidase (Erg25), SAM:C-24 sterol methyltransferase (Erg6), C-8 sterol isomerase (Erg2), C-5 sterol desaturase (Erg3), C-22 sterol desaturase (Erg5), and C-24 sterol reductase (Erg4) polypeptides. Each of these enzymes is considered an isoprenoid biosynthesis competitor polypeptide. Regulators of these enzymes may also be considered isoprenoid biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms.

In other embodiments, reduction or elimination of the activity of an isoprenoid biosynthesis competitor polypeptide can be achieved by decreasing activity of the ubiquinone biosynthetic pathway. The commitment step in ubiquinone biosynthesis is the formation of para-hydroxybenzoate (PHB) from tyrosine or phenylalanine in mammals or chorismate in bacteria, followed by condensation of PHB and isoprene precursor, resulting in addition of the prenyl group. This reaction is catalyzed by PHB-polyprenyltransferase. The isoprenoid side chain of ubiquinone, which can be of varying length in different organisms, is determined by the prenyldiphosphate synthase enzyme. In organisms that produce the coenzyme Q10 form of ubiquinone, the 3-decaprenyl-4-hydroxybenzoic acid resulting from the condensation of PHB and decaprenyldiphosphate reaction undergoes further modifications, which include hydroxylation, methylation and decarboxylation, in order to form ubiquinone (CoQ10). Thus, reducing the activity of prenyldiphosphate synthase leading from farnesyldiphosphate to extended isoprenoids, or reducing the activity of PHB polyprenyltransferase may be useful in increasing the amount of isoprenoid available for carotenoid biosynthesis. (Examples of prenyldiphosphate synthase and PHB-polyprenyltransferase enzymes are depicted in Tables 29 and 30, respectively).

Known small molecule inhibitors of isoprenoid biosynthesis competitor enzymes include, but are not limited to, zaragosic acid (including analogs thereof such as TAN1607A (Biochem Biophys Res Commun 1996 Feb. 15; 219(2):515-520)), RPR 107393 (3-hydroxy-3-[4-(quinolin-6-yl)phenyl]-1-azabicyclo[2-2-2]octane dihydrochloride; J Pharmacol Exp Ther. 1997 May; 281(2):746-52), ER-28448 (5-{N-[2-butenyl-3-(2-methoxyphenyl)]-N-methylamino}-1,1-penthylidenebis(phosphonic acid) trisodium salt; Journal of Lipid Research, Vol. 41, 1136-1144, July 2000), BMS-188494 (The Journal of Clinical Pharmacology, 1998; 38:1116-1121), TAK-475 (1-[2-[(3R,5S)-1-(3-acetoxy-2,2-dimethylpropyl)-7-chloro-1,2,3,5-tetrahydro-2-oxo-5-(2,3-dimethoxyphenyl)-4,1-benzoxazepine-3-yl]acetyl]piperidin-4-acetic acid; Eur J. Pharmacol. 2003 Apr. 11; 466(1-2):155-61), YM-53601 ((E)-2-[2-fluoro-2-(quinuclidin-3-ylidene) ethoxy]-9H-carbazole monohydrochloride; Br J Pharmacol. 2000 September; 131(1):63-70), or squalestatin I that inhibit squalene synthase; terbinafine (e.g., LAMISIL®), naftifine (NAFTIN®), S-allylcysteine, garlic, resveratrol, NB-598 (e.g., from Banyu Pharmaceutical Co), and/or green tea phenols that inhibit squalene epoxidase (see, for example, *J. Biol Chem* 265:18075, 1990; *Biochem. Biophys. Res. Commun.* 268:767, 2000); various azoles that inhibit cytochrome P450 lanosterol 14α-demethylase; and fenpropimorph that inhibits the C-14 sterol reductase and the C-8 sterol isomerase. In other embodiments, heterologous isoprenoid biosynthesis competitor polypeptides may be utilized (whether functional or non-functional; in some embodiments, dominant negative mutants are employed).

One particular isoprenoid biosynthesis competitor polypeptide useful according to the present invention is squalene synthase which has been identified and characterized from a variety of organisms; representative examples of squalene synthase polypeptide sequences are included in Table 16. In some embodiments of the invention that utilize squalene synthase (or modifications of squalene synthase) source organisms include, but are not limited to, *Neurospora crassa, Xanthophyllomyces dendrorhous* (*Phaffia rhodozyma*), *Aspergillus niger, Saccharomyces cerevisiae, Mucor circinelloides, Rhotorula glutinis, Candida utilis, Mortierella alpina*, and *Yarrowia lipolytica.*

The carotenoid biosynthesis pathway branches off from the isoprenoid biosynthesis pathway at the point where GGPP is formed. The commitment step in carotenoid biosynthesis is the formation of phytoene by the head-to-head condensation of two molecules of GGPP, catalyzed by phytoene synthase (often called crtB; see FIG. 6). A series of dehydrogenation reactions, each of which increases the number of conjugated double bonds by two, converts phytoene into lycopene via neurosporene. The pathway branches at various points, both before and after lycopene production, so that a wide range of carotenoids can be generated. For example, action of a cyclase enzyme on lycopene generates γ-carotene; action of a desaturase instead produces 3,4-didehydrolycopene. γ-carotene is converted to β-carotene through the action of a cyclase. β-carotene can be processed into any of a number of products (see, for example, FIG. 6C), including astaxanthin (via echinenone, hydroxyechinenone, and phoenicoxanthin).

According to the present invention, carotenoid production in a host organism may be adjusted by modifying the expression or activity of one or more proteins involved in carotenoid biosynthesis. As indicated, in some embodiments, it will be desirable to utilize as host cells organisms that naturally produce one or more carotenoids. In some such cases, the focus will be on increasing production of a naturally-produced carotenoid, for example by increasing the level and/or activity of one or more proteins involved in the synthesis of that carotenoid and/or by decreasing the level or activity of one or more proteins involved in a competing biosynthetic pathway. Alternatively or additionally, in some embodiments it will be desirable to generate production of one or more carotenoids not naturally produced by the host cell.

According to some embodiments of the invention, it will be desirable to introduce one or more heterologous carotenogenic polypeptides into a host cell. As will be apparent to those of ordinary skill in the art, any of a variety of heterologous polypeptides may be employed; selection will consider, for instance, the particular carotenoid whose production is to be enhanced. The present invention contemplates not only introduction of heterologous carotenogenic polypeptides, but also adjustment of expression or activity levels of heterologous or endogenous carotenogenic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous carotenogenic); alternatively, such genetic modifications may be included so as to confer regulation of expression of at least one heterologous polypeptide (e.g., carotenogenic polypeptide(s)). For example, promoters including, but not limited to those described herein, such as Tef1, Gpd1 promoters can be used in conjunction with endogenous genes and/or heterologous genes for modification of expression patterns of endogenous carotenogenic polypeptide(s) and/or heterologous carotenogenic polypeptide(s). Similarly, exemplary terminator sequences include, but are not limited to, use of *Y. lipolytica* XPR2 terminator sequences.

As indicated in FIG. 6 and in the literature, proteins involved in carotenoid biosynthesis include, but are not limited to, phytoene synthase, phytoene dehydrogenase, lycopene cyclase, carotenoid ketolase, carotenoid hydroxylase, astaxanthin synthase (a single multifunctional enzyme found in some source organisms that typically has both ketolase and hydroxylase activities), carotenoid epsilon hydroxylase, lycopene cyclase (beta and epsilon subunits), carotenoid glucosyltransferase, and acyl CoA:diacyglycerol acyltransferase. Representative example sequences for these carotenoid biosynthesis polypeptides are provided in Tables 17a-25.

Alternatively or additionally, modified carotenoid ketolase polypeptides that exhibit improved carotenoid production activity may be utilized in accordance with the present invention. For example, carotenoid ketolase polypeptides comprising one more mutations to corresponding to those identified *Sphingomonas* sp. DC18 which exhibited improved astaxanthin production (Tao et al. 2006 Metab Eng. 2006 Jun. 27) and *Paracoccus* sp. strain N81106 which exhibited altered carotenoid production (Ye et al. 2006 Appl Environ Microbiol 72:5829-37).

Xanthophylls can be distinguished from other carotenoids by the presence of oxygen containing functional groups on their cyclic end groups. For instance, lutein and zeaxanthin contain a single hydroxyl group on each of their terminal ring structures, while astaxanthin contains both a keto group and a hydroxyl on each terminal ring. This property makes xanthophylls more polar than carotenes such as beta-carotene and lycopene, and thus dramatically reduces their solubility in fats and lipids. Naturally occurring xanthophylls are often found as esters of the terminal hydroxyl groups, both mono- and diesters of fatty acids. They also occur as glucosides in certain species of bacteria. The solubility and dispersibility of xanthophylls can be greatly modified by the addition of ester moieties, and it is known that esterification can also affect the absorbability and/or bioavailability of a given carotenoid. It is an objective of this invention to maximize the amount of a particular xanthophyll accumulating within the intracellular triacylglyceride fraction of oleaginous yeasts, and one mechanism for achieving this goal is to increase the hydrophobic nature of the xanthophyll product that accumulates. One way of achieving this is to engineer the production of fatty-acyl mono- and/or diesters of the target xanthophyll compound.

A variety of enzymes can function to esterify carotenoids. For example, carotenoid glucosyltransferases have been identified in several bacterial species (see, e.g., Table 24). In addition, acyl CoA:diacyglycerol acyltransferase (DGAT) and acyl CoA:monoacylglycerol acyltransferases (MGAT), which function in the final steps of triacylglycerol biosynthesis, are likely to serve an additional role in the esterification of xanthophylls. Representative DGAT polypeptides are shown in Table 25. Furthermore, other enzymes may specifically modify carotenoids and molecules of similar structure (e.g. sterols) and be available for modification and ester production.

In some embodiments of the invention, potential source organisms for carotenoid biosynthesis polypeptides include, but are not limited to, genera of naturally oleaginous or non-oleaginous fungi that naturally produce carotenoids. These include, but are not limited to, *Botrytis, Cercospora, Fusarium* (*Gibberella*), *Mucor, Neurospora, Phycomyces, Puccina, Rhodotorula, Sclerotium, Trichoderma*, and *Xanthophyllomyces*. Exemplary species include, but are not limited to, *Neurospora crassa, Xanthophyllomyces dendrorhous* (*Phaffia rhodozyma*), *Mucor circinelloides*, and *Rhodotorula glutinis*. Of course, carotenoids are produced by a wide range of diverse organisms such as plants, algae, yeast, fungi, bacteria, cyanobacteria, etc. Any such organisms may be source organisms for carotenoid biosynthesis polypeptides according to the present invention.

In certain embodiments of the invention, carotenoid production in a host organism may be adjusted by modifying the activity of one or more endogenous genes that affect carotenoid biosynthesis. For example, as shown in Example 16, disruption of the endogenous SPT8 gene (YALI0E23804g) in *Yarrowia lipolytica* results in increased carotenoid production. SPT8 functions as part of the SAGA histone acetyltransferase complex, which is required for normal expression of some fungal genes and is thought to function as a coactivator complex in a multistep pathway leading to gene activation. Thus, without wishing to be bound by theory, the present invention encompasses the recognition that alteration of the expression and/or activity of one or more components of the SAGA histone acetyltransferase complex result in increased carotenoid production. Additionally, it will be appreciated by those of ordinary skill in the art that by increasing production of carotenoid(s) in a host organism by altering the expression and/or activity of one or more components of the SAGA histone acetyltransferase complex, production of a retinolic compound(s) in a host organism able to utilize such a carotenoid(s) as a substrate may also be increased since more of the cartenoid substrate will be available.

In *Saccharomyces cerevisiae*, the SAGA complex is a 1.8-MDa complex comprising a variety of components including distinct classes of transcription factors, such as Ada proteins (Ada1p, Ada2p, Ngg1p/Ada3p, and Ada4p/Gcn5p), TATA-binding protein (TBP)-related SPT proteins (Spt3p, Spt7p, Spt8p, and Spt20p/Ada5p), and TBP-associated factors or (TAFIIs) (TAFII90, TAFII68/61, TAFII60, TAFII25/23, and TAFII17). The SAGA complex also comprises the DNA-dependent protein kinase related molecule Tra1p, acetyltransferase and ubiquitin protease activities. The SAGA complex core comprises Ada and Spt subunits, a subset of Tafs, acetyltransferase and ubiquitin protease activities, the essential factor Tra1p, and two factors related to TBP function, Spt3 and Spt8. Several components of the *Saccharomyces cerevisiae* SAGA complex and their corresponding *Yarrowia lipolytica* homologs, are listed in Table 69. Each of these SAGA complex components is encompassed by the recombinant fungal strains, methods and compositions of the present invention. Those of ordinary skill in the art will be aware of these and other SAGA components, and will be able to modify such components in accordance with the present invention.

Certain SAGA components are essential. For example, in *Saccharomyces cerevisiae*, the TRA1 gene is essential. Thus, in certain embodiments, production of a carotenoid is increased by altering expression and/or activity of the TRA1 such that the host organism remains viable. For example, the expression and/or activity of the TRA1 gene or gene product may be decreased to a level below the expression and/or activity of wild type TRA1, but not to such an extent as to result in lethality. Those of ordinary skill in the art will be aware of tra1 mutations that result in decreased expression and/or activity but that do not result in lethality. Furthermore, it will be within the capability of one of ordinary skill in the art to identify such mutations without undue experimentation, for example by employing standard mutatgenesis/screening techniques.

In certain embodiments of the present invention, production of one or more carotenoids is increased by alteration of the expression and/or activity of one or more components of the SAGA histone acetyltransferase complex in one or more of the following host organisms: *Aspergillus, Blakeslea, Botrytis, Candida, Cercospora, Cryptococcus, Cunninghamella, Fusarium* (*Gibberella*), *Kluyveromyces, Lipomyces, Mortierella, Mucor, Neurospora, Penicillium, Phycomyces, Pichia* (*Hansenula*), *Puccinia, Pythium, Rhodosporidium, Rhodotorula, Saccharomyces, Sclerotium, Trichoderma, Trichosporon, Xanthophyllomyces* (*Phaffia*), and *Yarrowia*; or is a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi* (*Gibberella zeae*), *Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous* (*Phaffia rhodozyma*), and/or *Yarrowia lipolytica*.

In certain embodiments, production of one or more carotenoids is increased by altering expression and/or activity of one or more components of the SAGA histone acetyltransferase complex in a host organism, in combination with one or more additional carotenogenic modifications as described herein. For example, such one or more additional carotenogenic modifications may comprise heterologous expression of one or more carotenogenic polypeptides, isoprenoid biosynthesis polypeptides, carotenoid biosynthesis polypeptides, etc.

In certain embodiments, production of one or more carotenoids is increased by altering expression and/or activity of one or more components of the SAGA histone acetyltransferase complex in a host organism, in combination with one or more oleaginic modifications, as described herein. In certain embodiments, production of one or more carotenoids is increased by altering expression and/or activity of one or more components of the SAGA histone acetyltransferase complex in a host organism that is not naturally oleaginous. In certain embodiments, production of one or more carotenoids is increased by altering expression and/or activity of one or more components of the SAGA histone acetyltransferase complex in a host organism that is naturally oleaginous.

It will be appreciated that the particular carotenogenic modification to be applied to a host cell in accordance with the present invention will be influenced by which carotenoid(s) is desired to be produced. For example, isoprenoid biosynthesis polypeptides are relevant to the production of most carotenoids. Carotenoid biosynthesis polypeptides are also broadly relevant. Carotenoid ketolase activity is particularly relevant for production of canthaxanthin, as carotenoid hydroxylase activity is for production of lutein and zeaxanthin, among others. Both carotenoid hydroxylase and ketolase activities (and astaxanthin synthase) are particularly useful for production of astaxanthin.

In certain embodiments, host cells are engineered to produce carotenoids by introducing one or more carotenoid biosynthesis polypeptides. In general, any carotenoid biosynthesis polypeptide can be introduced into any host cell of the present invention. In certain embodiments, such carotenoid biosynthesis polypeptides are codon-optimized to accommodate the codon preferences of the host cell. In certain embodiments, a carotenoid biosynthesis polypeptide introduced into a host cell is from the same organism as the host cell and/or a related organism. For example, without limitation, the present invention encompasses the recognition that it may be desirable to introduce a fungal carotenoid biosynthesis polypeptide into a fungal host cell (e.g., from the same and/or a related fungal species). In certain embodiments, the host cell is a *Y. lipolytica* host cell. In certain aspects of such embodiments, a *Y. lipolytica* carotenoid biosynthesis polypeptide is introduced into the *Y. lipolytica* host cell. In certain aspects, a *S. cerevisiae* carotenoid biosynthesis polypeptide is introduced into the *Y. lipolytica* host cell. In certain aspects, any of a variety of fungal carotenoid biosynthesis polypeptides is introduced into the *Y. lipolytica* host cell.

Engineering Retinolic Compound Production

Retinolic compounds are synthesized from certain carotenoid precursors, which are themselves synthesized from isoprenoid precursors, some of which are also involved in the production of steroids and sterols (see description under section entitled "Engineering Carotenoid Production"). Thus, any carotenogenic modification that results in the increased production of a carotenoid from which a retinolic compound can be produced may similarly result in an increased production of a retinolic compound. Retinolic compounds comprise retinol, retinal, and retinoic acid, which together are collectively referred to as "Vitamin A". In certain embodiments, the retinolic compound retinol is synthesized from the carotenoid precursor beta-carotene. Other carotenoid compounds that contain at least one beta-ionone ring structure, such as alpha-carotene and beta-cryptoxanthin, can be precursor compounds for synthesis of retinolic compounds.

According to the present invention, retinolic compound production in a host organism may be adjusted by modifying the expression or activity of one or more proteins involved in retinolic compound biosynthesis. As indicated, in some embodiments, it will be desirable to utilize as host cells organisms that naturally produce one or more retinolic compounds. In some such cases, the focus will be on increasing production of a naturally-produced retinolic compound, for example by increasing the level and/or activity of one or more proteins involved in the synthesis of that retinolic compound and/or by decreasing the level or activity of one or more proteins involved in a competing biosynthetic pathway. Alternatively or additionally, in some embodiments it will be desirable to generate production of one or more retinolic compounds not naturally produced by the host cell.

According to some embodiments of the invention, it will be desirable to introduce one or more heterologous retinologenic polypeptides into a host cell. As will be apparent to those of ordinary skill in the art, any of a variety of heterologous polypeptides may be employed; selection will consider, for instance, the particular retinolic compound whose production is to be enhanced. The present invention contemplates not only introduction of heterologous retinologenic polypeptides, but also adjustment of expression or activity levels of heterologous retinologenic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous carotenogenic); alternatively, such genetic modifications may be included so as to confer regulation of expression of at least one heterologous polypeptide (e.g., retinologenic polypeptide(s)). For example, promoters including, but not limited to those described herein, such as Tef1, Gpd1 promoters can be used in conjunction with endogenous genes and/or heterologous genes for modification of expression patterns of endogenous retinologenic polypeptide(s) and/or heterologous retinologenic polypeptide(s). Similarly, exemplary terminator sequences include, but are not limited to, use of *Y. lipolytica* XPR2 terminator sequences.

Figure 11:
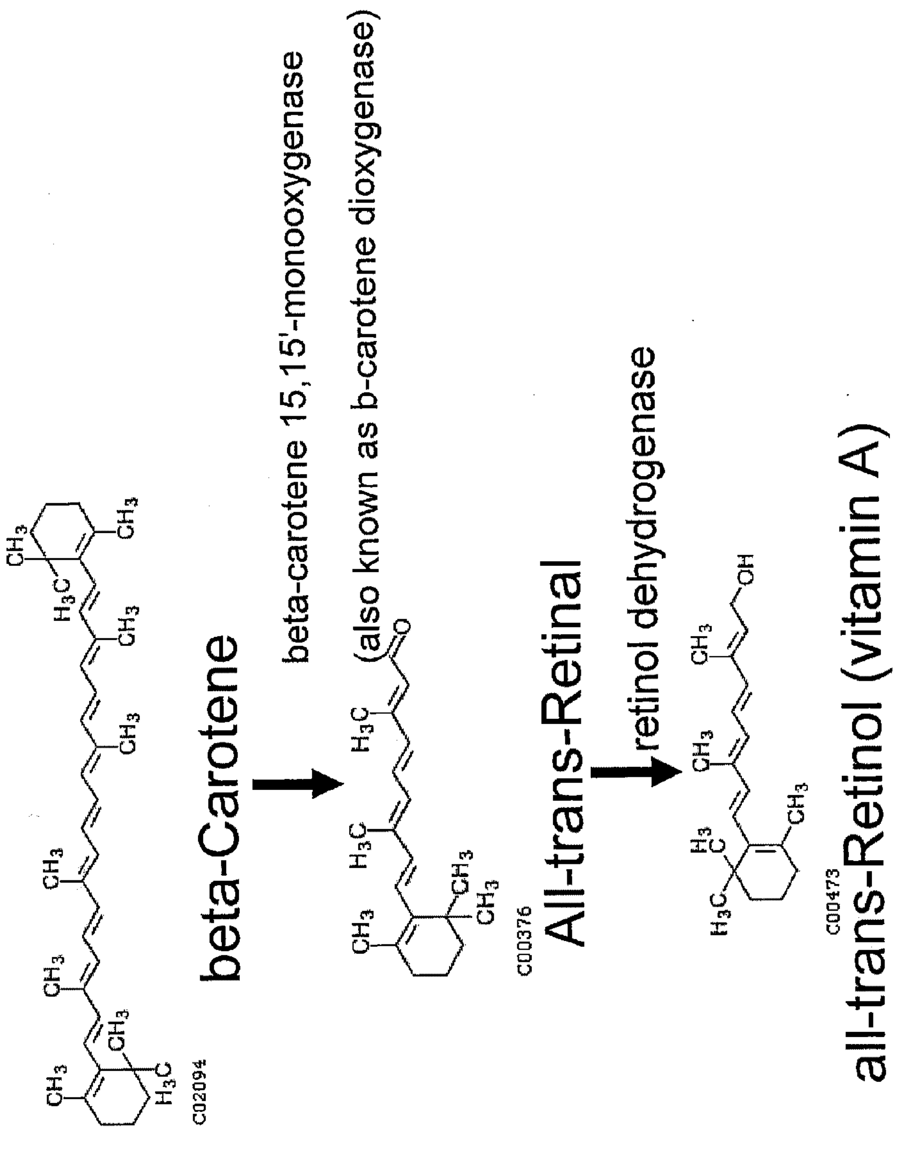
FIG. 11 depicts the all-trans-retinol (Vitamin A) biosynthesis pathway, starting with beta-carotene as a substrate.

As indicated in FIG. 11 and in the literature, proteins involved in retinologenic biosynthesis include, but are not limited to, beta-carotene 15,15'-monooxygenase (also known as beta-carotene dioxygenase) and beta carotene retinol dehydrogenase. Representative example sequences for these retinolic compound biosynthesis polypeptides are provided in Tables 67-68.

In some embodiments of the invention, potential source organisms for retinolic compound biosynthesis polypeptides include, but are not limited to, genera of naturally oleaginous or non-oleaginous fungi that naturally produce carotenoids. These include, but are not limited to, *Botrytis, Cercospora, Fusarium* (*Gibberella*), *Mucor, Neurospora, Phycomyces, Puccina, Rhodotorula, Sclerotium, Trichoderma*, and *Xanthophyllomyces*. Exemplary species include, but are not limited to, *Neurospora crassa, Xanthophyllomyces dendrorhous* (*Phaffia rhodozyma*), *Mucor circinelloides*, and *Rhodotorula glutinis*. Of course, retinolic compounds are produced by a wide range of diverse organisms such as mammals, bacteria, cyanobacteria, etc. Any such organisms may be source organisms for retinolic compound biosynthesis polypeptides according to the present invention.

In certain embodiments of the invention, retinolic compound production in a host organism that is able to produce retinolic compounds from carotenoid substrates is adjusted by modifying the activity of one or more endogenous genes that affect carotenoid biosynthesis. For example, as shown in Example 16, disruption of the endogenous SPT8 gene (YALI0E23804g) in *Yarrowia lipolytica* results in increased carotenoid production. As will be appreciated by those of ordinary skill in the art, increasing production of a carotenoid(s) in a host organism by altering the expression and/or activity of one or more components of the SAGA histone acetyltransferase complex will result in a greater abundance of such a carotenoid(s); hence, production of a retinolic compound(s) in a host organism able to utilize such a carotenoid(s) as a substrate may similarly be increased.

Without wishing to be bound by theory, the present invention contemplates that alteration of the expression and/or activity of one or more components of the SAGA histone acetyltransferase complex may result in increased retinolic compound production. In certain embodiments, retinolic compound production is increased in a host organism by altering the expression and/or activity of one or more of: Ada proteins (Ada1p, Ada2p, Ngg1p/Ada3p, and Ada4p/Gcn5p), TATA-binding protein (TBP)-related SPT proteins (Spt3p, Spt7p, Spt8p, and Spt20p/Ada5p), TBP-associated factors or (TAFIIs) (TAFII90, TAFII68/61, TAFII60, TAFII25/23, and TAFII17), Tra1p, and/or proteins encoding the acetyltransferase and/or ubiquitin protease activities. In certain embodiments, retinolic compound production is increased in a host organism by altering the expression and/or activity of one or more polypeptides listed in Table 69. Those of ordinary skill in the art will be aware of these and other SAGA components, and will be able to modify such components in accordance with the present invention.

In certain embodiments, host cells are engineered to produce retinolic compounds by introducing one or more carotenoid biosynthesis polypeptides. In general, any retinolic compound biosynthesis polypeptide can be introduced into any host cell of the present invention. In certain embodiments, such retinolic compound biosynthesis polypeptides are codon-optimized to accommodate the codon preferences of the host cell. In certain embodiments, a retinolic compound biosynthesis polypeptide introduced into a host cell is from the same organism as the host cell and/or a related organism. For example, without limitation, the present invention encompasses the recognition that it may be desirable to introduce a fungal retinolic compound biosynthesis polypeptide into a fungal host cell (e.g., from the same and/or a related fungal species). In certain embodiments, the host cell is a *Y. lipolytica* host cell. In certain aspects of such embodiments, a *Y. lipolytica* retinolic compound biosynthesis polypeptide is introduced into the *Y. lipolytica* host cell. In certain aspects, a *S. cerevisiae* retinolic compound biosynthesis polypeptide is introduced into the *Y. lipolytica* host cell. In certain aspects, any of a variety of fungal retinolic compound biosynthesis polypeptides is introduced into the *Y. lipolytica* host cell.

Production and Isolation of Carotenoids and/or Retinolic Compounds

As discussed above, accumulation of lipid bodies in oleaginous organisms is generally induced by growing the relevant organism in the presence of excess carbon source and limiting nitrogen and/or other nutrients (eg. phosphate and magnesium). Specific conditions for inducing such accumulation have previously been established for a number of different oleaginous organisms (see, for example, Wolf (ed.) *Nonconventional yeasts in biotechnology* Vol. 1, Springer-Verlag, Berlin, Germany, pp. 313-338; *Lipids* 18(9):623, 1983; *Indian J. Exp. Biol.* 35(3):313, 1997; *J. Ind. Microbiol. Biotechnol.* 30(1):75, 2003; *Bioresour Technol.* 95(3):287, 2004, each of which is incorporated herein by reference in its entirety).

In general, it will be desirable to cultivate inventive modified host cells under conditions that allow accumulation of at least about 20% of their dry cell weight as lipid. In other embodiments, the inventive modified host cells are grown under conditions that permit accumulation of at least about 15%, 16%, 17%, 18%, 19%, 20%, 21%, 22%, 23%, 24%, 25%, 30%, 35%, 40%, 45%, 50%, 55%, 60%, 65%, 70%, 75%, or even 80% or more of their dry cell weight as lipid. In certain embodiments, the host cells utilized are cells which are naturally oleaginous, and induced to produce lipid to the desired levels. In other embodiments, the host cells are cells which naturally produce lipid, but have been engineered to increase production of lipid such that desired levels of lipid production and accumulation are achieved.

In certain embodiments, the host cells of the invention are not naturally oleaginous, but have been engineered to produce lipid such that desired levels of lipid production are obtained. Those of ordinary skill in the art will appreciate that, in general, growth conditions that are effective for inducing lipid accumulation in a source organism, may well also be useful for inducing lipid accumulation in a host cell into which the source organism's oleaginic polypeptides have been introduced. Of course, modifications may be required in light of characteristics of the host cell, which modifications are within the skill of those of ordinary skill in the art.

It will also be appreciated by those of ordinary skill in the art that it will often be desirable to ensure that production of the desired carotenoid and/or retinolic compound by the inventive modified host cell occurs at an appropriate time in relation to the induction of oleaginy such that the carotenoid(s) and/or retinolic compound(s) accumulate(s) in the lipid bodies. In some embodiments, it will be desirable to induce production of the carotenoid(s) and/or retinolic compound(s) in a host cell which does not naturally produce the carotenoid(s) and/or retinolic compound(s), such that detectable levels of the carotenoid(s) and/or retinolic compound(s) is/are produced. In certain aspects the host cells which do not naturally produce a certain carotenoid(s) and/or retinolic compound(s) are capable of production of other carotenoid(s) (e.g. certain host cells may, for example, naturally produce β-carotene but may not naturally produce astaxanthin) and/or retinolic compound(s), (e.g. certain host cells may, for example, naturally produce retinal but may not naturally produce retinol); in other aspects the host cells do not naturally produce any carotenoid(s) and/or retinolic compound(s). In other embodiments, it will be desirable to increase production levels of carotenoid(s) and/or retinolic compound(s) in a host cell which does naturally produce low levels of the carotenoid(s) and/or retinolic compound(s), such that increased detectable levels of the carotenoid(s) and/or retinolic compound(s) are produced. In certain aspects, the host cells which do naturally produce the carotenoid(s) (e.g., β-carotene) also produce additional carotenoid(s) (e.g., astaxanthin, etc.) and/or retinolic compound(s) (e.g., retinal); in still other aspects, the cells which naturally produce the carotenoid(s) (e.g., β-carotene) do not produce additional carotenoid(s) and/or retinolic compound(s).

In certain embodiments of the invention, it will be desirable to accumulate carotenoids and/or retinolic compounds to levels (i.e., considering the total amount of all produced carotenoids and/or retinolic compounds together or considering a particular carotenoid and/or retinolic compound) that are greater than at least about 1% of the dry weight of the cells. In some embodiments, the total carotenoid and/or retinolic compound accumulation will be to a level at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells.

In some embodiments of the invention, a particular carotenoid and/or retinolic compound may not accumulate to a level as high as 1% of the total dry weight of the cells; appropriately engineered cells according to the present invention, and any lipid bodies, carotenoids and/or retinolic compounds they produce, remain within the scope of the present invention. Thus, in some embodiments, the cells accumulate a given carotenoid and/or retinolic compound to a level below about 1% of the dry weight of the cells. In some embodiments, the carotenoid and/or retinolic compound accumulates to a level below about 0.9%, 0.8%, 0.7%, 0.6%, 0.5%, 0.4%, 0.3%, 0.2%, 0.1%, 0.05%, or lower, of the dry cell weight of the cells.

In some embodiments of the invention, carotenoids and/or retinolic compounds accumulate both within lipid bodies and elsewhere in the cells. In some embodiments, carotenoids and/or retinolic compounds accumulate primarily within lipid bodies. In some embodiments, carotenoids and/or retinolic compounds accumulate substantially exclusively within lipid bodies. In some embodiments, at least about 10%, 15%, 20%, 25%, 30%, 35%, 40%, 45%, 50%, 55%, 60%, 65%, 70%, 75%, 80%, 85%, 90%, 95% or more of a desired produced carotenoid and/or retinolic compound accumulates in lipid bodies.

In some embodiments of the invention, modified host cells are engineered to produce one or more carotenoid compound(s) and/or retinolic compound(s) characterized by negligible solubility in water (whether hot or cold) and detectable solubility in one or more oils. In some embodiments, such compounds have a solubility in oil below about 0.2%. In some embodiments, such compounds have a solubility in oil within the range of about <0.001%-0.2%.

The present invention therefore provides engineered host cells (and methods of making and using them) that contain lipid bodies and that further contain one or more carotenoid compounds and/or retinolic compounds accumulated in the lipid bodies, where the compounds are characterized by a negligible solubility in water and a solubility in oil within the range of about <0.001%-0.2%; 0.004%-0.15%; 0.005-0.1%; or 0.005-0.5%. For example, in some embodiments, such compounds have a solubility in oil below about 0.15%, 0.14%, 0.13%, 0.12%, 0.11%, 0.10%. 0.09, 0.08%, 0.07%, 0.06%, 0.05%, 0.04%, 0.03%, 0.02%, 0.01%, 0.05%, or less. In some embodiments, the compounds show such solubility in an oil selected from the group consisting of sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and mixtures thereof.

Bacterial carotenogenic genes have already been demonstrated to be transferable to other organisms, and are therefore particularly useful in accordance with the present invention (see, for example, Miura et al., *Appl. Environ. Microbiol.* 64:1226, 1998). In other embodiments, it may be desirable to utilize genes from other source organisms such as plant, alga, or microalgae; these organisms provide a variety of potential sources for ketolase and hydroxylase polypeptides. Still additional useful source organisms include fungal, yeast, insect, protozoal, and mammalian sources of polypeptides.

In some embodiments of the present invention, isoprenoid production is increased in host cells (e.g., in *Y. lipolytica* cells) through expression of a truncated variant of a hydroxymethylglutaryl-CoA (HMG CoA) reductase polypeptide. In some embodiments, the truncated variant is a truncated variant of a *Y. lipolytica* HMG CoA reductase polypeptide. According to the present invention, expression of such a truncated HMG CoA reductase polypeptide can result in increased isoprenoid and/or carotenoid production in host cells (e.g., *Y. lipolytica* cells).

Alternatively or additionally, in some embodiments of the present invention, isoprenoid production is increased in host cells (e.g., in *Y. lipolytica* cells) through application of one or more carotenogenic modification(s) that increase(s) level and/or activity of a polypeptide selected from the group consisting of farnesyl pyrophosphate synthase polypeptides, geranylgeranylpyrophosphate synthase polypeptides, and combinations thereof. In some embodiments, the source organism for the selected polypeptide is *Y. lipolytica.*

Alternatively or additionally, in some embodiments of the present invention, isoprenoid production is increased in host cells (e.g., in *Y. lipolytica* cells) through application of one or more carotenogenic modification(s) that decrease(s) expression or activity of an isoprenoid biosynthesis competitor polypeptide (e.g., of a squalene synthase polypeptide), for example thereby reducing diversion of one or more intermediates away from the isoprenoid and/or carotenoid biosynthesis pathways. In some embodiments, the polypeptide whose expression or activity is reduced is endogenous to the host cell.

In some embodiments of the present invention, more than one carotenogenic modification is applied to the same host cell. For example, isoprenoid production may be increased in host cells (e.g., *Y. lipolytica* cells) through application of at least two or more carotenogenic modifications selected from the group consisting of: expression of a truncated HMG CoA reductase polypeptide, increase in expression and/or activity of farnesyl pyrophosphate synthase polypeptide, increase in expression and/or activity of a geranylgeranylpyrophosphate synthase polypeptide, decrease in expression and/or activity of a squalene synthase polypeptide, and combinations thereof.

Furthermore, in some embodiments of the invention, carotenoid production (e.g., production of β-carotene) is increased in host cells (e.g., in *Y. lipolytica* cells) through application of one or more carotenogenic modification(s) that increase(s) expression and/or activity of a polypeptide selected from the group consisting of phytoene synthase, lycopene cyclase, phytoene dehydrogenase, and combinations thereof. In some embodiments, such increase in expression comprises introduction of one or more genes encoding heterologous polypeptides. In some embodiments, phytoene synthase and lycopene cyclase activities are provided in a single polypeptide or complex (e.g., by the *Mucor circinelloides* or *Neurospora crassa* multifunctional phytoene synthase/lycopene cyclase). In some embodiments, phytoene dehydrogenase from *Mucor circinelloides* or *Neurospora crassa* is utilized.

In some embodiments, production of one or more carotenoids downstream of β-carotene (e.g., of one or more hydroxylated xanthophylls) is increased in host cells that produce β-carotene (including host cells that have been engineered to produce β-carotene, e.g., through application of one or more carotenogenic modifications as described herein) through application of one or more carotenogenic modifications that increase(s) level and/or activity of one or more carotenoid ketolase polypeptides (e.g., from *Parvularcula bermudensis* and/or *Aurantimonase* sp. SI85-9A1) to produce one or more ketone-containing carotenoids (e.g., canthaxanthin, echinenone, astaxanthin, and combinations thereof).

In some embodiments, production of one or more hydroxylated carotenoids is increased in host cells that produce (including having been engineered to produce) β-carotene and/or one or more ketone-containing carotenoids though application of one or more carotenogenic modifications that increase(s) the level and/or activity of one or more carotenoid hydroxylase polypeptides (e.g., from *Xanthobacter autotrophicus* and/or *Erythrobacter litoralis*) to increase production of one or more hydroxylated carotenoids (e.g., zeaxanthin, lutein, β-cryptoxanthin, astaxanthin, and combinations thereof).

Similar approaches to enhance carotenoid production may be employed in other oleaginous or non-oleaginous host organisms (e.g. *S. cerevisiae, C. utilis, P. rhodozyma*) can be undertaken, using the same, homologous, or functionally similar carotogenic polypeptides.

In some embodiments, the present invention provides modified *Y. lipolytica* strains that have been engineered to express one or more carotenoid biosynthesis polypeptides and/or isoprenoid biosynthesis polypeptides. For example, in some embodiments, a modified *Y. lipolytica* strain is engineered to increase expression and/or activity of one or more of phytoene synthase, phytoene dehydrogenase, lycopene cyclase, and GGPP synthase, and/or to decrease expression and/or activity of squalene synthase. In some embodiments, a modified *Y. lipolytica* strain is engineered to express all of these polypeptides. Such a modified *Y. lipolytica* strain produces β-carotene (see, for example, Example 2).

In some embodiments, inventive modified *Y. lipolytica* strains that have been engineered to produce β-carotene are further engineered to express a truncated HMG CoA reductase; in some such embodiments, the strains are engineered so that expression of the truncated HMG CoA reductase increases β-carotene several fold (for example, 3-4 fold or more).

In some embodiments, inventive modified *Y. lipolytica* strains that have been engineered to produce β-carotene are further engineered to express a beta-carotene 15,15'-monooxygenase and/or a retinol dehydrogenase to increase retinolic compound production.

In some embodiments, inventive modified *Y. lipolytica* strains that have been engineered to produce β-carotene are further engineered to express carotenoid hydroxylase (to achieve production of zeaxanthin and/or β-cryptoxanthin), carotenoid ketolase (to achieve production of canthaxanthin and/or echinenone), or both (to achieve production of astaxanthin).

In some embodiments, inventive modified *Y. lipolytica* strains that have been engineered to produce, for example, β-carotene, zeaxanthin, canthaxanthin, echinenone, and/or astaxanthin are also engineered to have increased expression of, for example, malic enzyme, mevalonate kinase, etc.

It will be appreciated that, in some embodiments of the invention, it may be desirable to engineer a particular host cell by expressing more than one version of a given polypeptide (e.g., isoprenoid biosynthesis polypeptide, carotenoid biosynthesis polypeptide, oleaginic polypeptide, isoprenoid biosynthesis competitor polypeptides, retinolic compound biosynthesis polypeptide, etc.). For example, a given host cell may be engineered to express versions of a given polypeptide from two or more different sources. Where a particular enzyme may be comprised of more than one polypeptide chains, it will often be desirable to utilize all chains from a single source, although this is not required so long as activity is achieved. Also, whenever a host cell is engineered to express a polypeptide from a different source, it may be desirable to alter the gene sequence encoding the polypeptide to account for codon preferences of the host cell.

To give but a few specific examples, the present invention provides modified *Y. lipolytica* strains that have been engineered to express the phytoene synthase/lycopene cyclase bifunctional (carB) polypeptide from *M. circinelloides* (see, for example, Example 1B), and also to express the phytoene dehydrogenase (carRP) polypeptide from *M. circinelloides* (see, for example, Example 1A). In some embodiments, the present invention provides such carB+carRP-expressing *Y. lipolytica* strains that have been engineered to modify expression and/or activity of a truncated HMG-CoA reductase polypeptide from *Y. lipolytica* and/or one or more *Y. lipolytica* polypeptides selected from the group consisting of GGPP synthase, FPP synthase (Erg20), IPP isomerase (IDI), HMG synthase (Erg13), mevalonate kinase (Erg12), squalene synthase (Erg9), phosphimevalonate kinase (Erg8), mevalonate pyrophosphate decarboxylase (MVD1), malic enzyme, malate dehydrogenase, glucose 6 phosphate dehydrogenase, malate dehydrogenase homolog 2,6-phosphogluconate dehydrogenase (GND1), isocitrate dehydrogenase, fructose 1,6 bisphosphatase, acetoacetyl CoA thiolase (Erg10), ATP citrate lyase subunit 1, ATP citrate lyase subunit 2, and combinations thereof. The present invention therefore specifically provides *Y. lipolytica* strains that have been engineered to produce β-carotene.

The present invention also specifically provides modified *Y. lipolytica* strains that have been engineered to express at least one carotenoid ketolase (e.g., crtO/crtW) polypeptide, and in some embodiments more than one, for example from a source selected from the group consisting of *Parvularcula bermudensis* (see, for example, Example 1H), *Aurantimonas* (see, for example, Example 1G), and/or an environmental isolate identified from the Sargasso Sea (see, for example, Example 1F). The present invention therefore specifically provides *Y. lipolytica* strains that have been engineered to produce canthaxanthin, astaxanthin, and/or echinenone.

The present invention further specifically provides modified *Y. lipolytica* strains that have been engineered to express at least one carotenoid hydroxylase (e.g., crtZ) polypeptide, and in some embodiments more than one, from *Erythrobacter litoralis* (see, for example, Examples 1J and 1L), *Novosphingobium aromaticivarans* (see, for example, Example 1E), *Parvularcula bermudensis* (see, for example, Example 1I), *Xanthobacter autotrophicus* (see, for example, Example 1O), *Sphingopyxis alaskensis* (see, for example, Example 1M), *Chlamydomonas rheinhardtii, Erythrobacter longus, Robiginitalea biformata* (see, or example, Example 1N) and/or *Pseudomonas putida* (see, for example, Example 1P). The present invention therefore specifically provides *Y. lipolytica* strains that have been engineered to produce zeaxanthin, lutein, β-cryptoxanthin, and/or astaxanthin.

The present invention further specifically provides modified *Y. lipolytica* strains that have been engineered to express at least one carotenoid ketolase (e.g., crtO/crtW) polypeptide in combination with at least one carotenoid hydroxylase (e.g., crtZ) polypeptide. In certain embodiments, the at least one carotenoid ketolatse polypeptide and at least one carotenoid hydroxylase polypeptide are encoded by nucleic acid sequences present in separate nucleic acid molecules. In certain embodiments, the at least one carotenoid ketolatse polypeptide and at least one carotenoid hydroxylase polypeptide are encoded by nucleic acid sequences present in the same nucleic acid molecule. For example, a host organism may be transformed or transfected with a single expression vector, which expression vector comprises both a carotenoid ketolatse polypeptide and a carotenoid hydroxylase polypeptide, each of which comprises sequences sufficient to direct their expression in the host organism.

In certain embodiments, the at least one carotenoid ketolase (e.g., crtO/crtW) polypeptide and the at least one carotenoid hydroxylase (e.g., crtZ) polypeptide are expressed as a fusion protein. A representative example of such embodiments is presented in Example 17. In certain embodiments, such a fusion polypeptide is designed such that the carotenoid ketolatse polypeptide is positioned N-terminal to the carotenoid hydroxylase polypeptide. In certain embodiments, such a fusion polypeptide is designed such that the carotenoid ketolatse polypeptide is positioned C-terminal to the carotenoid hydroxylase polypeptide.

In embodiments in which the carotenoid ketolatse polypeptide and the carotenoid hydroxylase polypeptide are expressed concurrently (whether from separate nucleic acid molecules or from the same nucleic acid molecule), the polypeptides may be selected from any of a variety of source organisms. As non-limiting examples, the carotenoid hydroxylase polypeptide may be selected from an organism such as *Erythrobacter litoralis* (see, for example, Examples 1J and 1L), *Novosphingobium aromaticivarans* (see, for example, Example 1E), *Parvularcula bermudensis* (see, for example, Example 1I), *Xanthobacter autotrophicus* (see, for example, Example 1O), *Sphingopyxis alaskensis* (see, for example, Example 1M), *Chlamydomonas rheinhardtii, Erythrobacter longus, Robiginitalea biformata* (see, or example, Example 1N) and/or *Pseudomonas putida* (see, for example, Example 1P). As further non-limiting examples, the carotenoid ketolase polypeptide may be selected from an organism such as *Parvularcula bermudensis* (see, for example, Example 1H), *Aurantimonas* (see, for example, Example 1G), and/or an environmental isolate identified from the Sargasso Sea (see, for example, Example 1F).

It should be noted that, for inventive organisms that produce more than one carotenoid, it will sometimes be possible to adjust the relative amounts of individual carotenoids produced by adjusting growth conditions. For example, it has been reported that controlling the concentration of dissolved oxygen in a culture during cultivation can regulate relative production levels of certain carotenoids such as β-carotene, echinenone, β-cryptoxanthin, 3-hydroxyechinenone, asteroidenone, canthaxanthin, zeaxanthin, adonirubin, adonixanthin and astaxanthin (see, for example, U.S. Pat. No. 6,825,002 to Tsubokura et al., the entire contents of which are incorporated herein by reference). Additionally or alternatively, the present invention encompasses the recognition that controlling the pH in a culture during cultivation can regulate relative production levels of these and/or other carotenoids (see e.g., Example 18).

Particularly for embodiments of the present invention directed toward production of astaxanthin, it will often be desirable to utilize one or more genes from a natural astaxanthin-producing organism. Where multiple heterologous polypeptides are to be expressed, it may be desirable to utilize the same source organism for all, or to utilize closely related source organisms.

Inventive modified cells, that have been engineered to produce carotenoids and/or to accumulate lipid (including to be oleaginous), can be cultured under conditions that achieve carotenoid production and/or oleaginy. In some embodiments, it will be desirable to control growth conditions so in order to maximize production of a particular carotenoid or set of carotenoids (including all carotenoids) and/or to optimize accumulation of the particular carotenoid(s) in lipid bodies. In some embodiments it will be desirable to control growth conditions to adjust the relative amounts of different carotenoid products produced.

Inventive modified cells, that have been engineered to produce retinolic compounds and/or to accumulate lipid (including to be oleaginous), can be cultured under conditions that achieve retinolic compound production and/or oleaginy. In some embodiments, it will be desirable to control growth conditions so in order to maximize production of a particular retinolic compound or set of retinolic compounds (including all retinolic compounds) and/or to optimize accumulation of the particular retinolic compound (s) in lipid bodies. In some embodiments it will be desirable to control growth conditions to adjust the relative amounts of different retinolic compound products produced.

In some embodiments, it will be desirable to limit accumulation of a particular intermediate, for example ensuring that substantially all of a particular intermediate compound is converted so that accumulation is limited. For example, particularly in situations where a downstream enzyme may be less efficient than an upstream enzyme and it is desirable to limit accumulation of the product of the upstream enzyme (e.g., to avoid its being metabolized via a competitive pathway and/or converted into an undesirable product), it may be desirable to grow cells under conditions that control (e.g., slow) activity of the upstream enzyme so that the downstream enzyme can keep pace.

Those of ordinary skill in the art will appreciate that any of a variety of growth parameters, including for example amount of a particular nutrient, pH, temperature, pressure, oxygen concentration, timing of feeds, content of feeds, etc can be adjusted as is known in the art to control growth conditions as desired.

To give but a few examples, in some embodiments, growth and/or metabolism is/are limited by limiting the amount of biomass accumulation. For example, growth and/or metabolism can be limited by growing cells under conditions that are limiting for a selected nutrient. The selected limiting nutrient can then be added in a regulated fashion, as desired. In some embodiments, the limiting nutrient is carbon, nitrogen (e.g., via limiting ammonium or protein), phosphate, magnesium, one or more trace metals, or combinations thereof. In some embodiments, the limiting nutrient is carbon. In some embodiments, the limiting nutrient is one or more trace metals.

In some embodiments, use of a limiting nutrient can by utilized to control metabolism of a particular intermediate and/or to adjust relative production of particular carotenoid compounds and/or retinolic compounds. In some embodiments, this result can be achieved by controlling metabolism of a particular intermediate as discussed above; in some embodiments, it can be achieved, for example, by limiting progress through the carotenoid and/or retinolic compound biosynthesis pathway so that a desired carotenoid product (e.g., β-carotene, canthaxanthin, astaxanthin, etc.) or retinolic compound (e.g., retinal) is not converted to a downstream compound. To give but one example, phosphate limitation can slow the overall rate of clux through the carotenoid biosynthesis pathway and can be utilized to change the ratio of canthaxanthin to echinenone produced.

In some embodiments, cells are grown in the presence of excess carbon source and limiting nitrogen, phosphate, and/or magnesium to induce oleaginy. In some embodiments cells are grown in the presence of excess carbon source and limiting nitrogen. In some embodiments, the carbon:nitrogen ratio is within the range of about 200:1, 150:1, 125:1, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, or less. Those of ordinary skill in the art are aware of a wide variety of carbon sources, including, for example, glycerol, glucose, galactose, dextrose, any of a variety of oils (e.g., olive, canola, corn, sunflower, soybean, cottonseed, rapeseed, etc., and combinations thereof) that may be utilized in accordance with the present invention. Combinations of such may also be utilized. For example, common carbon source compositions contain oil: glucose in a ratio within the range of about 5:95 to 50:50 (e.g. about 5:95, about 10:90, about 15:85, about 20:80, about 25:75, about 30:70, about 35:65, about 40:60, about 45:55, about 50:50).

Those of ordinary skill in the art are also aware of a variety of different nitrogen sources (e.g., ammonium sulfate, proline, sodium glutamate, soy acid hydrolysate, yeast extract-peptone, yeast nitrogen base, corn steep liquor, etc, and combinations thereof) that can be utilized in accordance with the present invention.

In some embodiments, cultures are grown at a selected oxygen concentration (e.g., within a selected range of oxygen concentrations). In some embodiments, oxygen concentration may be varied during culture. In some embodiments, oxygen concentration may be controlled during some periods of culture and not controlled, or controlled at a different point, during others. In some embodiments, oxygen concentration is not controlled. In some embodiments, cultures are grown at an oxygen concentration within the range of about 5-30%, 5-20%, 10-25%, 10-30%, 15-25%, 15-30%, including at about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or more. In some embodiments, oxygen concentration is maintained above about 20%, at least for some period of the culture.

In some embodiments, cells are grown via fed-batch fermentation. In some embodiments, feed is continued until feed exhaustion and/or the feed is controlled to initiate or increase once a certain level of dissolved oxygen is detected in the culture medium (e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more dissolved oxygen). The feed rate can be modulated to maintain the dissolved oxygen at a specific level (e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more dissolved oxygen).

In some embodiments, inventive modified cells are grown in a two-phase feeding protocol in which the first phase is designed to maintain conditions of excess carbon and limiting oxygen, and the second phase results in conditions of excess oxygen and limiting carbon. The carbon sources in each phase can be the same (e.g., both glucose) or different (e.g., glucose then glucose-oil mixture, oil then glucose, or glucose-oil mixture then glucose). The present invention demonstrates that such conditions can achieve high levels of carotenoid production (see, for example, Example 5D). Additionally or alternatively, such conditions also result in high levels of retinolic compound production. For example, high levels of retinolic compound(s) production may be achieved by increasing the levels of a particular carotenoid that is used as a substrate for the production of such a retinolic compound(s).

In some embodiments, inventive modified cells are cultivated at constant temperature (e.g., between about 20-40, or 20-30 degrees, including for example at about 20, 20.5, 21, 21.5, 22, 22.5, 23, 23.5, 24, 24.5, 25, 25.5, 26, 26.5, 27, 27.5, 28, 28.5, 29, 29.5, 30° C. or above) and/or pH (e.g., within a range of about 4-7.5, or 4-6.5, 3.5-7, 3.5-4, 4-4.5, 4.5-5, 5-5.5, 5.5-6, 6-6.5, 6.5-7, 7-7.5, 7-8, etc., including at about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5 or above); in other embodiments, temperature and/or pH may be varied during the culture period, either gradually or in a stepwise fashion.

For example, in some embodiments, the pH is 7.0 at inoculation and is increased to pH 8.0 during the course of the fermentation. The pH may be increased either continuously or in discrete steps. For example, in Example 19, the pH of the culture in increased continuously. In certain embodiments, the pH in increased continuously by increasing the pH at a rate of 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050 or more units/hour.

In certain embodiments, the pH in increased in discrete steps by increasing the pH by 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050 or more at each step.

In certain embodiments, the pH is increased employing a combination of continuous increase and discrete steps.

In certain embodiments, increasing the pH during the course of fermentation results in one or more beneficial effects such as, without limitation, an increase in total biomass accumulation, an increase in the percentage of biomass representing carotenoid accumulation, and, in the case of zeaxanthin production, an increase in the hydroxylation of beta-carotene to zeaxanthin. Those of ordinary skill in the art will be able to select without undue experimentation an appropriate rate of increase, an appropriate type of increase (e.g. continuous, discrete steps or a combination of the two), and/or an optimum pH within the selected range to maximize these and/or other beneficial effects.

In some embodiments, the temperature at which inventive cells are cultivated is selected so that production of one or more particular carotenoid compound(s) and/or retinolic compound(s) is adjusted (e.g., so that production of one or more particular compound(s) is increased and/or production of one or more other compound(s) is decreased). In some embodiments, the temperature at which inventive cells are cultivated is selected so that the ratio of one carotenoid compound and/or retinolic compound to another, is adjusted. To give but one example, in some embodiments, a temperature is selected to be sufficiently low that β-carotene levels are reduced and the level of at least one other carotenoid compound(s) (e.g., zeaxanthin) is increased.

In some embodiments, cultures are grown at about pH 5.5, at about pH 7.0, and or at a temperature between about 28-30° C. In some embodiments, it may be desirable to grow inventive modified cells under low pH conditions, in order to minimize growth of other cells. In some embodiments, it will be desirable to grow inventive modified cells under relatively higher temperature conditions in order to slow growth rate and/or increase the ultimate dry cell weight output of carotenoids and/or retinolic compounds. In some embodiments, it will be desirable to grow inventive modified cells under conditions in which the pH in increased (e.g. continuously, in discrete steps, or both) during the course of fermentation (e.g. increased from pH 7.0 to pH 8.0). In some embodiments, it will be desirable to grow inventive modified cells under two or more of these conditions. For example, inventive modified cells can be grown under relatively higher temperature conditions while simultaneously increasing the pH over the course of the fermentation. Those of ordinary skill in the art will be able to select appropriate growth conditions to achieve their experimental, production and/or other cell culture goals.

One advantage provided by the present invention is that, in addition to allowing the production of high levels of carotenoids and/or retinolic compounds, certain embodiments of the present invention allow produced compounds to be readily isolated because they accumulate in the lipid bodies within oleaginous organisms. Methods and systems for isolating lipid bodies have been established for a wide variety of oleaginous organisms (see, for example, U.S. Pat. Nos. 5,164,308; 5,374,657; 5,422,247; 5,550,156; 5,583,019; 6,166,231; 6,541,049; 6,727,373; 6,750,048; and 6,812,001, each of which is incorporated herein by reference in its entirety). In brief, cells are typically recovered from culture, often by spray drying, filtering or centrifugation.

Of course, it is not essential that lipid bodies be specifically isolated in order to collect carotenoid compounds and/or retinolic compounds produced according to the present invention. Any of a variety of approaches can be utilized to isolate and/or purify carotenoids and/or retinolic compounds. Many useful extraction and/or purification procedures for particular carotenoid compounds, and/or for carotenoids generally, are known in the art (see, for example, EP670306, EP719866, U.S. Pat. No. 4,439,629, U.S. Pat. No. 4,680,314, U.S. Pat. No. 5,310,554, U.S. Pat. No. 5,328,845, U.S. Pat. No. 5,356,810, U.S. Pat. No. 5,422,247, U.S. Pat. No. 5,591,343, U.S. Pat. No. 6,166,231, U.S. Pat. No. 6,750,048, U.S. Pat. No. 6,812,001, U.S. Pat. No. 6,818,239, U.S. Pat. No. 7,015,014, US2003/0054070, US2005/0266132, each of which is incorporated herein by reference).

In many typical isolation procedures, cells are disrupted (e.g., mechanically (for example using a bead mill, mashing), enzymatically (e.g. using zymolyase or a β-1,3 glucanase such as Glucanex 200G (Novozyme), chemically (e.g., by exposure to a mild caustic agent such as a detergent or 0.1 N NaOH, for example at room temperature or at elevated temperature), using a reducing agent (e.g. dithiothreitol, β-mercaptoethanol), using high pressure homogenization/shearing, by changing pH, etc. and combinations thereof) to allow access of intracellular carotenoid and/or retinolic compound(s) to an extraction solvent, and are then extracted one or more times. In certain embodiments, cells are disrupted mechanically using a bead mill/mashing at high pressure (e.g. at 25K, 10K-30K, 15K-25K, or 20-25K, pound-force per square inch (psi)). Cells may optionally be concentrated (e.g., to at least about 100 g/L or more, including to at least about 120 g/l, 150 g/l, 175 g/L, 200 g/L or more) and/or dried (e.g., with a spray dryer, double drum dryer (e.g. Blaw Knox double drum dryer), single drum vacuum dryer, etc.), prior to exposure to extraction solvent (and/or prior to disruption or homogenization). Disruption can, of course, be performed prior to and/or during exposure to extraction solvent. After extraction, solvent is typically removed (e.g., by evaporation, for example by application of vacuum, change of temperature, etc.).

In some instances, cells are disrupted and then subjected to supercritical liquid extraction or solvent extraction. Typical liquids or solvents utilized in such extractions include, for example, organic or non-organic liquids or solvents. To give but a few specific examples, such liquids or solvents may include acetone, supercritical fluids (e.g. carbon dioxide, propane, xenon, ethane, propylene, methane, ethylene, ethanol), carbon dioxide, chloroform, ethanol, ethyl acetate, heptane, hexane, isopropanol, methanol, methylene chloride, octane, tetrahydrofuran (THF), cyclohexane, isobutyl acetate, methyl ketone, ethyl ketone, toluene, cyclohexanone, benzene, propylene glycol, vegetable oils (e.g. soybeen soybean oil, rapeseed oil, corn oil, cottonseed oil, canola oil, etc.) and combinations thereof (e.g. hexane:ethyl acetate, combination of a polar and non-polar solvent, combination of an alcohol with either hexane or ethyl acetate). Particular solvents may be selected, for example, based on their ability to solubilize particular carotenoid compounds and/or retinolic compounds, or sets of carotenoid compounds (e.g., all carotenoids) and/or retinolic compounds (e.g., all retinolic compounds), and/or based on regulatory or other considerations (e.g., toxicity, cost, ease of handling, ease of removal, ease of disposal, etc.). For example, more polar carotenoids (e.g., xanthophylls) are known to be extracted more efficiently into extraction solvents with increased polarity. Craft (1992) J. Agric. Food Chem 40, 431-434 which is herein incorporated by reference discusses the relative solubility of two carotenoids, lutein and β-carotene in different solvents.

In some embodiments, combinations of solvents may be utilized. In some embodiments, combinations of a relatively polar solvent (e.g., alcohols, acetone, chloroform, methylene chloride, ethyl acetate, etc.) and a relatively non-polar solvent (e.g., hexane, cyclohexane, oils, etc.) are utilized for extraction. Those of ordinary skill in the art will readily appreciate that different ratios of polar to non-polar solvent may be employed as appropriate in a particular situation. Just to give a few examples, common ratios include 1:1, 2:1, 3:1, 3:2, 95:5, 90:10, 85:15, 80:20, 75:25, 70:30, 65:45, 60:40, 55:45, and 50:50. It will be appreciated that solvents or solvent mixtures of different polarities may be more effective at extracting particular carotenoids (e.g., based on their polarities and/or as a function of other attributes of the host cell material from which they are being extracted). Those of ordinary skill in the art are well able to adjust the overall polarity of the extracting solvent, for instance by adjusting the relative amounts of polar and non-polar solvents in a solvent blend, in order to achieve more efficient extraction.

Extraction may be performed under any of a variety of environmental conditions, including any of a variety of temperatures. For example, extraction may be performed on ice (for example at 4° C., 0° C., less than 0° C.), at room temperature, or at any of a variety of other temperatures. For example, a solvent may be maintained at a selected temperature (e.g., about less than 0, 0, 4, 25, 28, 30, 37, 68, 70, 75, 80, 85, 90, 95, or 100° C.) in order to improve or adjust extraction of a particular desired carotenoid.

Extraction typically yields a crude oil suspension. In some embodiments, the crude oil suspension contains some intact host cells but is at least about 95% free of intact host cells. In some embodiments, the crude oil suspension is at least about 96%, 97%, 98%, or 99% or more free of intact host cells. In some embodiments, the suspension is substantially free of water-soluble cell components (e.g., nucleic acids, cell wall or storage carbohydrates, etc.). In some embodiments, the suspension contains less than about 5%, 4%, 3%, 2%, or 1% or less water-soluble cell components.

Extraction conditions that yield a crude oil suspension will enrich for lipophilic components that accumulate in the lipid bodies within oleaginous organisms. In general, the major components of the lipid bodies consist of triacylglycerols, ergosteryl esters, other steryl esters, free ergosterol, phospholipids, and some proteins, which often function in the synthesis or regulation of the levels of other lipid body components. C16 and C18 (e.g. C16:0, C16:1, C18:0, C18:1, and C18:2) are generally the major fatty acids present in lipid bodies, mainly as components of triacylglycerol and steryl esters.

In some embodiments of the invention, the crude oil suspension contains at least about 2.5% by weight carotenoid compound(s) and/or retinolic compound(s); in some embodiments, the crude oil suspension contains at least about 5% by weight carotenoid compound(s) and/or retinolic compound(s), at least about 10% by weight carotenoid compound(s) and/or retinolic compound(s), at least about 20% by weight carotenoid compound(s) and/or retinolic compound(s), at least about 30% by weight carotenoid compound(s) and/or retinolic compound(s), at least about 40% by weight carotenoid compound(s) and/or retinolic compound(s), or at least about 50% by weight carotenoid compound(s) and/or retinolic compound(s).

The crude oil suspension may optionally be refined as known in the art. Refined oils may be used directly as feed or food additives. Alternatively or additionally, carotenoids and/or retinolic compound can be isolated from the oil using conventional techniques.

Given the sensitivity of carotenoids and retinolic compounds generally to oxidation, many embodiments of the invention employ oxidative stabilizers (e.g., ascorbyl palmitate, tocopherols, vitamin C (e.g. sodium ascorbate), ethoxyquin, vitamin E, BHT, BHA, TBHQ, etc., or combinations thereof) during and/or after carotenoid isolation. Alternatively or additionally, nitrogen or an inert gas can be utilized to purge oxygen from the process lines of any tanks or equipment. Alternatively or additionally, microencapsulation, (for example with a microencapsulation ingredients such as proteins, carbohydrates (e.g. maltodextrin, gum acacia, xanthan gum, starches/sugars like sucrose), or gelatins, or any other substance which creates a physical barrier to air and/or light) may be employed to add a physical barrier to oxidation and/or to improve handling (see, for example, U.S. Patent Applications 2004/0191365 and 2005/0169999). For example, carotenoids and/or retinolic compounds produced according to the present invention may be microencapsulated after isolation during the formulation of commercial products (e.g. pharmaceuticals, food supplements, electro-optic applications, animal feed additives, cosmetics, etc.) to minimize or eliminate oxidation during production, storage, transport, etc.

Extracted carotenoids and/or retinolic compounds may be further isolated and/or purified, for example, by crystallization, washing, recrystallization, and/or other purification strategies. In some embodiments, carotenoid and/or retinolic compound crystals are collected by filtration and/or centrifugation. Isolated or purified carotenoids and/or retinolic compound may be dried and/or formulated for storage, transport, sale, and/or ultimate use. To give but a few specific examples, carotenoids and/or retinolic compounds may be prepared as a water (e.g. cold water) dispersible powder (e.g. 1%-20% carotenoid: microencapsulation ingredient), as a suspension of crystals in oil (e.g., vegetable oil, e.g., about 1%-30%, 5%-30%, 10%-30% w/w), etc.

Uses

Carotenoids and/or retinolic compounds produced according to the present invention can be utilized in any of a variety of applications, for example exploiting their biological or nutritional properties (e.g., anti-oxidant, anti-proliferative, etc.) and/or their pigment properties. For example, according to the present invention, carotenoids may be used in pharmaceuticals (see, for example, Bertram, *Nutr. Rev.* 57:182, 1999; Singh et al., *Oncology* 12:1643, 1998; Rock, *Pharmacol. Ther.* 75:185, 1997; Edge et al, *J. Photochem Photobiol* 41:189, 1997; U.S. Patent Application 2004/0116514; U.S. Patent Application 2004/0259959), food supplements (see, for example, Koyama et al, *J. Photochem Photobiol* 9:265, 1991; Bauernfeind, *Carotenoids as colorants and vitamin A precursors*, Academic Press, NY, 1981; U.S. Patent Application 2004/0115309; U.S. Patent Application 2004/0234579), electro-optic applications, animal feed additives (see, for example, Krinski, *Pure Appl. Chem.* 66:1003, 1994; Polazza et al., *Meth. Enzymol.* 213:403, 1992), cosmetics (as anti-oxidants and/or as cosmetics, including fragrances; see for example U.S. Patent Application 2004/0127554), etc. Carotenoids produced in accordance with the present invention may also be used as intermediates in the production of other compounds (e.g., steroids, etc.).

For example, astaxanthin and/or esters thereof may be useful in a variety of pharmaceutical applications and health foods including treatment of inflammatory diseases, asthma, atopic dermatitis, allergies, multiple myeloma, arteriosclerosis, cardiovascular disease, liver disease, cerebrovascular disease, thrombosis, neoangiogenesis-related diseases, including cancer, rheumatism, diabetic retinopathy; macular degeneration and brain disorder, hyperlipidemia, kidney ischemia, diabetes, hypertension, tumor proliferation and metastasis; and metabolic disorders. Additionally, carotenoids and astaxanthin may be useful in the prevention and treatment of fatigue, for improving kidney function in nephropathy from inflammatory diseases, as well as prevention and treatment of other life habit-related diseases. Still further, astaxanthin has been found to play a role as inhibitors of various biological processes, including interleukin inhibitors, phosphodiesterase inhibitors, phospholipase A2 inhibitors, cyclooxygenase-2 inhibitors, matrix metalloproteinase inhibitors, capillary endothelium cell proliferation inhibitors, lipoxygenase inhibitors. See, e.g., Japanese Publication No. 2006022121, published 2006 Jan. 26 (JP Appl No. 2005-301156 filed 2005 Oct. 17); Japanese Publication No. 2006016408, published 2006 Jan. 19 (JP Appl No. 2005-301155 filed 2005 Oct. 17); Japanese Publication No. 2006016409, published 2006 Jan. 19 (JP Appl No. 2005-301157 filed 2005 Oct. 17); Japanese Publication No. 2006016407, published 2006 Jan. 19 (JP Appl No. 2005-301153 filed 2005 Oct. 17); Japanese Publication No. 2006008717, published 2006 Jan. 12 (JP Appl No. 2005-301151 filed 2005 Oct. 17); Japanese Publication No. 2006008716, published 2006 Jan. 12 (JP Appl No. 2005-301150 filed 2005 Oct. 17); Japanese Publication No. 2006008720, published 2006 Jan. 12 (JP Appl No. 2005-301158 filed 2005 Oct. 17); Japanese Publication No. 2006008719, published 2006 Jan. 12 (JP Appl No. 2005-301154 filed 2005 Oct. 17); Japanese Publication No. 2006008718, published 2006 Jan. 12 (JP Appl No. 2005-301152 filed 2005 Oct. 17); Japanese Publication No. 2006008713, published 2006 Jan. 12 (JP Appl No. 2005-301147 filed 2005 Oct. 17); Japanese Publication No. 2006008715, published 2006 Jan. 12 (JP Appl No. 2005-301149 filed 2005 Oct. 17); Japanese Publication No. 2006008714, published 2006 Jan. 12 (JP Appl No. 2005-301148 filed 2005 Oct. 17); and Japanese Publication No. 2006008712, published 2006 Jan. 12 (JP Appl No. 2005-301146 filed 2005 Oct. 17).

As other non-limiting examples, retinolic compounds produced according to the present invention may be used in pharmaceuticals, foodstuff, dietary supplements, electro-optic applications, animal feed additives, cosmetics, etc.

It will be appreciated that, in some embodiments of the invention, carotenoids and/or retinolic compounds produced by manipulated host cells as described herein are incorporated into a final product (e.g., food or feed supplement, pharmaceutical, cosmetic, dye-containing item, etc.) in the context of the host cell. For example, host cells may be lyophilized, freeze dried, frozen or otherwise inactivated, and then whole cells may be incorporated into or used as the final product. The host cell may also be processed prior to incorporation in the product to increase bioavailability (e.g., via lysis). Alternatively or additionally, a final product may incorporate only a portion of the host cell (e.g., fractionated by size, solubility), separated from the whole. For example, in some embodiments of the invention, lipid droplets are isolated from the host cells and are incorporated into or used as the final product. For instance, inventive carotenoid-containing and/or retinolic compound-containing lipid bodies (e.g., from engineered cells, and particularly from engineered fungal cells) may be substituted for the plant oil bodies described in U.S. Pat. No. 6,599,513 (the entire contents of which are hereby incorporated by reference) and incorporated into emulsion or emulsion formulations, as described therein. In other embodiments, the carotenoids and/or retinolic compounds themselves, or individual carotenoid and/or retinolic compounds are isolated and reformulated into a final product.

As stated above, fatty acid and glucoside esters are the predominant carotenoid esters found in nature, whereas additional esters (e.g. with organic acids or inorganic phosphate) can be synthesized to generate useful product forms. For delivery, carotenoid esters can also be formulated as salts of the ester form. See, e.g., US Publication No. 20050096477.

The amount of carotenoid and/or retinolic compound incorporated into a given product may vary dramatically depending on the product, and the particular carotenoid(s) and/or retinolic compound(s) involved. Amounts may range, for example, from less than 0.01% by weight of the product, to more than 1%, 10%, 20%, 30% or more; in some cases the carotenoid and/or retinolic compound may comprise 100% of the product. Thus, amount of carotenoid and/or retinolic compound incorporated into a given product may be, for example, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%.

In some embodiments of the invention, one or more produced carotenoids and/or retinolic compounds is incorporated into a component of food or feed (e.g., a food supplement). Types of food products into which carotenoids and/or retinolic compounds can be incorporated according to the present invention are not particularly limited, and include beverages such as milk, water, sports drinks, energy drinks, teas, juices, and liquors; confections such as jellies and biscuits; fat-containing foods and beverages such as dairy products; processed food products such as rice and soft rice (or porridge); infant formulas; breakfast cereals; or the like. In some embodiments, one or more produced carotenoids and/or retinolic compounds is incorporated into a dietary supplements, such as for example a multivitamin. In certain embodiments, beta-carotene produced according to the present invention is included in a dietary supplement. In certain embodiments, lutein produced according to the present invention is included in a dietary supplement. In certain embodiments, retinol, retinal, retinyl palmitate, retinyl acetate, and/or retinoic acid produced according to the present invention is included in a dietary supplement. In some embodiments of this aspect of the invention, it may be useful to incorporate the carotenoids and/or retinolic compounds within bodies of edible lipids as it may facilitate incorporation into certain fat-containing food products. Thus, for example, when the edible fungus, *Candida utilis* is used as a host, its' carotenoid and/or retinolic compound containing lipids may be directly incorporated into a component of food or feed (e.g., a food supplement).

Examples of feedstuffs into which carotenoids and/or retinolic compounds produced in accordance with the present invention may be incorporated include, for instance, pet foods such as cat foods, dog foods and the like, feeds for aquarium fish, cultured fish or crustaceans, etc., feed for farm-raised animals (including livestock and further including fish or crustaceans raised in aquaculture). Food or feed material into which the carotenoid(s) and/or retinolic compound(s) produced in accordance with the present invention is incorporated is preferably palatable to the organism which is the intended recipient. This food or feed material may have any physical properties currently known for a food material (e.g., solid, liquid, soft).

In some embodiments, feedstuffs containing carotenoids and/or retinolic compounds produced in accordance with the present invention are substantially free of intact host cells. For example, feedstuffs of the present invention may be at least about 95% free of intact host cells. In some embodiments, feedstuffs of the present invention are at least about 96%, 97%, 98%, or 99% or more free of intact host cells. Such embodiments are typical when the carotenoids and/or retinolic compounds are highly purified away from the host cell in which they were produced (see section entitled "Production and Isolation of Carotenoids and/or Retinolic Compounds").

In some embodiments, feedstuffs containing carotenoids and/or retinolic compounds produced in accordance with the present invention are not substantially free of intact host cells. For example, feedstuffs of the present invention may comprise greater than about 95% intact host cells. In certain embodiments, feedstuffs of the present invention comprise greater than about 70%, 75%, 85%, or 90% intact host cells. In certain embodiments, feedstuffs of the present invention comprise nearly intact host cells. For example, feedstuffs of the present invention may comprise greater than about 70%, 75%, 85%, 90%, or 95% nearly intact host cells. As will be appreciated by those of ordinary skill in the art, carotenoid and/or retinolic compound-containing feedstuffs of the present invention that contain intact cells and/or nearly intact cells will have great utility in providing the carotenoids and/or retinolic compounds of interest present in such host cells to an animal. Such embodiments are advantageous when host cells that produce the carotenoids and/or retinolic compounds of interest contain additional vitamins, nutrients, etc. that benefit the animal.

In some embodiments of the invention, one or more produced carotenoids and/or retinolic compounds is incorporated into a cosmetic product. Examples of such cosmetics include, for instance, skin cosmetics (e.g., lotions, emulsions, creams and the like), lipsticks, anti-sunburn cosmetics, makeup cosmetics, fragrances, products for daily use (e.g., toothpastes, mouthwashes, bad breath preventive agents, solid soaps, liquid soaps, shampoos, conditioners), etc.

In some embodiments, one or more produced carotenoids and/or retinolic compounds is incorporated into a pharmaceutical. Examples of such pharmaceuticals include, for instance, various types of tablets, capsules, drinkable agents, troches, gargles, etc. In some embodiments, the pharmaceutical is suitable for topical application. Dosage forms are not particularly limited, and include capsules, oils, granula, granula subtilae, pulveres, tabellae, pilulae, trochisci, or the like. Oils and oil-filled capsules may provide additional advantages both because of their lack of ingredient decomposition during manufacturing, and because inventive carotenoid-containing and/or retinolic compound-containing lipid droplets may be readily incorporated into oil-based formulations.

Pharmaceuticals according to the present invention may be prepared according to techniques established in the art including, for example, the common procedure as described in the United States Pharmacopoeia, for example.

Carotenoids and/or retinolic compounds produced according to the present invention may be incorporated into any pigment-containing product including, for example, fabric, paint, etc. They may also be incorporated into a product which is an environmental indicator, or an instrument such as a biosensor for use as a detection agent.

Carotenoids and/or retinolic compounds produced according to the present invention (whether isolated or in the context of lipid droplets or of cells, e.g., fungal cells) may be incorporated into products as described herein by combinations with any of a variety of agents. For instance, such carotenoids and/or retinolic compounds may be combined with one or more binders or fillers. In some embodiments, inventive products will include one or more chelating agents, pigments, salts, surfactants, moisturizers, viscosity modifiers, thickeners, emollients, fragrances, preservatives, etc., and combinations thereof.

Useful surfactants include, for example, anionic surfactants such as branched and unbranched alkyl and acyl hydrocarbon compounds, sodium dodecyl sulfate (SDS); sodium lauryl sulfate (SLS); sodium lauryl ether sulfate (SLES); sarconisate; fatty alcohol sulfates, including sodium, potassium, ammonium or triethanolamine salts of $C_{10}$ to $C_{18}$ saturated or unsaturated forms thereof; ethoxylated fatty alcohol sulfates, including alkyl ether sulfates; alkyl glyceryl ether sulfonate, alpha sulpho fatty acids and esters; fatty acid esters of isethionic acid, including Igepon A; acyl (fatty) N-methyltaurides, including Igepon T; dialkylsulfo succinate esters, including $C_8$, $C_{10}$ and $C_{12}$ forms thereof; Miranot BT also referred to as lauroamphocarboxyglycinate and sodium tridecath sulfate; N-acylated amino acids, such as sodium N-lauroyl sarconisate or gluconate; sodium coconut monoglyceride sulfonate; and fatty acid soaps, including sodium, potassium, DEA or TEA soaps.

Among the cationic surfactants that are useful are monoalkyl trimethyl quartenary salts; dialkyl dimethyl quartenary salts; ethoxylated or propoxylated alkyl quaternary ammonium salts, also referred to in the art as ethoquats and propoquats; cetyl benzylmethylalkyl ammonium chloride; quaternized imidazolines, which are generally prepared by reacting a fat or fatty acid with diethylenetriamine followed by quaternization, and non-fat derived cationic polymers such as the cellulosic polymer, Polymer JR (Union Carbide).

Further useful cationic surfactants include lauryl trimethyl ammonium chloride; cetyl pyridinium chloride; and alkyltrimethylammonium bromide. Cationic surfactants are particularly useful in the formulation of hair care products, such as shampoos, rinses and conditioners.

Useful nonionic surfactants include polyethoxylated compounds and polypropoxylated products. Examples of ethoxylated and propoxylated non-ionic surfactants include ethoxylated anhydrohexitol fatty esters, for example Tween 20; mono- and diethanolamides; Steareth-20, also known as Volpo20; polyethylene glycol fatty esters (PEGs), such as PEG-8-stearate, PEG-8 distearate; block co-polymers, which are essentially combinations of hydrophylic polyethoxy chains and lipophilic polypropoxy chains and generically known as Poloaxamers.

Still other useful non-ionic surfactants include fatty esters of polyglycols or polyhydric alcohols, such as mono and diglyceride esters; mono- and di-ethylene glycol esters; diethylene glycol esters; sorbitol esters also referred to as Spans; sucrose esters; glucose esters; sorbitan monooleate, also referred to as Span80; glyceryl monostearate; and sorbitan monolaurate, Span20 or Arlacel 20.

Yet other useful nonionic surfactants include polyethylene oxide condensates of alkyl phenols and polyhydroxy fatty acid amide surfactants which may be prepared as for example disclosed in U.S. Pat. No. 2,965,576.

Examples of amphoteric surfactants which can be used in accordance with the present invention include betaines, which can be prepared by reacting an alkyldimethyl tertiary amine, for example lauryl dimethylamine with chloroacetic acid. Betaines and betaine derivatives include higher alkyl betaine derivatives including coco dimethyl carboxymethyl betaine; sulfopropyl betaine; alkyl amido betaines; and cocoamido propyl betaine. Sulfosultaines which may be used include for example, cocoamidopropyl hydroxy sultaine. Still other amphoteric surfactants include imidazoline derivatives and include the products sold under the trade name "Miranol" described in U.S. Pat. No. 2,528,378 which is incorporated herein by reference in its entirety. Still other amphoterics include phosphates for example, cocamidopropyl PG-dimonium chloride phosphate and alkyldimethyl amine oxides.

Suitable moisturizers include, for example, polyhydroxy alcohols, including butylene glycol, hexylene glycol, propylene glycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example aloe vera gel; sugars and starches; sugar and starch derivatives, for example alkoxylated glucose; hyaluronic acid; lactamide monoethanolamine; acetamide monoethanolamine; glycolic acid; alpha and beta hydroxy acids (e.g. lactic, glycolic salicylic acid); glycerine; pantheol; urea; vaseline; natural oils; oils and waxes (see: the emollients section herein) and mixtures thereof.)

Viscosity modifiers that may be used in accordance with the present invention include, for example, cetyl alcohol; glycerol, polyethylene glycol (PEG); PEG-stearate; and/or Keltrol.

Appropriate thickeners for use in inventive products include, for example, gelling agents such as cellulose and derivatives; Carbopol and derivatives; carob; carregeenans and derivatives; xanthane gum; sclerane gum; long chain alkanolamides; bentone and derivatives; Kaolin USP; Veegum Ultra; Green Clay; Bentonite NFBC; etc.

Suitable emollients include, for example, natural oils, esters, silicone oils, polyunsaturated fatty acids (PUFAs), lanoline and its derivatives and petrochemicals.

Natural oils which may be used in accordance with the present invention may be obtained from sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and mixtures thereof.

Esters which may be used include, for example, $C_8$-$C_{30}$ alklyl esters of $C_8$-$C_{30}$ carboxylic acids; $C_1$-$C_6$ diol monoesters and diesters of $C_8$-$C_{30}$ carboxylic acids; $C_{10}$-$C_{20}$ alcohol monosorbitan esters, $C_{10}$-$C_{20}$ alcohol sorbitan di- and tri-esters; $C_{10}$-$C_{20}$ alcohol sucrose mono-, di-, and tri-esters and $C_{10}$-$C_{20}$ fatty alcohol esters of $C_2$-$C_6$ 2-hydroxy acids and mixtures thereof. Examples of these materials include isopropyl palmitate; isopropyl myristate; isopropyl isononate; $C_{12}$/$C_{14}$ benzoate ester (also known as Finesolve); sorbitan palmitate, sorbitan oleate; sucrose palmitate; sucrose oleate; isostearyl lactate; sorbitan laurate; lauryl pyrrolidone carboxylic acid; panthenyl triacetate; and mixtures thereof.

Further useful emollients include silicone oils, including non-volatile and volatile silicones. Examples of silicone oils that may be used in the compositions of the present invention are dimethicone; cyclomethycone; dimethycone-copolyol; aminofunctional silicones; phenyl modified silicones; alkyl modified silicones; dimethyl and diethyl polysiloxane; mixed $C_1$-$C_{30}$ alkyl polysiloxane; and mixtures thereof. Additionally useful silicones are described in U.S. Pat. No. 5,011,681 to Ciotti et al., incorporated by reference herein.

A yet further useful group of emollients includes lanoline and lanoline derivatives, for example lanoline esters.

Petrochemicals which may be used as emollients in the compositions of the present invention include mineral oil; petrolatum; isohexdecane; permethyl 101; isododecanol; $C_{11}$-$C_{12}$ Isoparrafin, also known as Isopar H.

Among the waxes which may be included in inventive products are animal waxes such as beeswax; plant waxes such as carnauba wax, candelilla wax, ouricurry wax, Japan wax or waxes from cork fibres or sugar cane. Mineral waxes, for example paraffin wax, lignite wax, microcrystalline waxes or ozokerites and synthetic waxes may also be included.

Exemplary fragrances for use in inventive products include, for instance, linear and cyclic alkenes (i.e. terpenes); primary, secondary and tertiary alcohols; ethers; esters; ketones; nitrites; and saturated and unsaturated aldehydes; etc.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranellal; phenyl ethyl acetate; phenylethylisobutarate; gamma methyl ionone; geraniol; anethole; benzaldehyde; benzyl acetate; benzyl salicate; linalool; cinnamic alcohol; phenyl acetaldehyde; amyl cinnamic aldehyde; caphore; p-tertiairy butyl cyclohexyl acetate; citral; cinnamyl acetate; citral diethyl acetal; coumarin; ethylene brasslate; eugenol; 1-menthol; vanillin; etc.

Examples of natural fragrances of use herein include without limitation lavandin; heliotropin; sandlewood oil; oak moss; pathouly; ambergris tincture; ambrette seed absolute; angelic root oil; bergamont oil; benzoin Siam resin; buchu leaf oil; *cassia* oil; cedarwood oil; *cassia* oil; castoreum; civet absolute; chamomile oil; geranium oil; lemon oil; lavender oil; Ylang Ylang oil; etc.

A list of generally used fragrance materials can be found in various reference sources, for example, "Perfume and Flavor Chemicals", Vols. I and II; Steffen Arctander Allured Pub. Co. (1994) and "Perfumes: Art, Science and Technology"; Muller, P. M. and Lamparsky, D., Blackie Academic and Professional (1994) both incorporated herein by reference.

Suitable preservatives include, among others, (e.g., sodium metabisulfite; Glydant Plus; Phenonip; methylparaben; Germall 115; Germaben II; phytic acid; sodium lauryl sulfate (SLS); sodium lauryl ether sulfate (SLES); Neolone; Kathon; Euxyl and combinations thereof), anti-oxidants (e.g., butylated hydroxytoluened (BHT); butylated hydroxyanisol (BHA); ascorbic acid (vitamin C); tocopherol; tocopherol acetate; phytic acid; citric acid; pro-vitamin A.

In some embodiments, inventive products will comprise an emulsion (e.g., containing inventive lipid bodies), and may include one or more emulsifying agents (e.g., Arlacel, such as Alacel 165; Glucamate; and combinations thereof) and/or emulsion stabilizing agents.

In some embodiments, inventive products will include one or more biologically active agents other than the carotenoid(s).To give but a few examples, inventive cosmetic or pharmaceutical products may include one or more biologically active agents such as, for example, sunscreen actives, anti-wrinkle actives, anti-aging actives, whitening actives, bleaching actives, sunless tanning actives, anti-microbial actives, anti-acne actives, anti-psoriasis actices, anti-eczema actives, antioxidants, anesthetics, vitamins, protein actives, etc.

EXEMPLIFICATION

Table 26 below describes certain *Yarrowia lipolytica* strains used in the following exemplification:

TABLE 26

*Yarrowia lipolytica* strains.

| | | |
|---|---|---|
| NRRL Y-1095 | Wild type diploid | |
| ATCC76861 | MATB ura2-21 lyc1-5 LYS1-5B | |
| ATCC76982 | MATB ade1 leu2-35 lyc1-5 xpr2 | |
| ATCC201249 | MATA ura3-302 leu2-270 lys8-11 PEX17-HA | |
| MF346 | MATA ura2-21 | ATCC76861 x ATCC201249 |
| MF350 | MATB ura2-21 leu2-35 ade1 | ATCC76982 x MF346 |

(The genotypes at LYC1, LYS1, XPR2, and PEX17 were not determined in crosses nor verified for ATCC strains.)

All basic molecular biology and DNA manipulation procedures described herein are generally performed according to Sambrook et al. or Ausubel et al. (Sambrook J, Fritsch E F, Maniatis T (eds). 1989. *Molecular Cloning: A Laboratory Manual*. Cold Spring Harbor Laboratory Press: New York; Ausubel F M, Brent R, Kingston R E, Moore D D, Seidman J G, Smith J A, Struhl K (eds). 1998. *Current Protocols in Molecular Biology*. Wiley: New York).

Example 1

Production of Plasmids for Carotenoid Strain Construction

Plasmids were generated for construction of carotenoid producing strains. The following subparts describe production of plasmids encoding carotenogenic polypeptides. Plasmids used in these studies and details of their construction are described in Table 27. Additional plasmid construction details and descriptions of their use are found in the text of the relevant subsection. All PCR amplifications used NRRL Y-1095 genomic DNA as template unless otherwise specified. The URA5 gene described below is allelic with the ura2-21 auxotrophy above. The GPD1 and TEF1 promoters are from *Y. lipolytica* as is the XPR2 terminator.

GGS1 is the gene encoding the *Y. lipolytica* gene encoding geranylgeranylpyrophosphate synthase. The nucleic acid coding sequence, and encoded Ggs1 protein of pMB4591 and pMB4683 are as follows:

(SED ID NO: 1)
atggattataacagcgcggatttcaaggagatatggggcaaggccgccgacaccgcgctgctgggaccgtacaactacc tcgccaacaaccggggccacaacatcagagaacacttgatcgcagcgttcggagcggttatcaaggtggacaagagcgatctcgagaccatttcg cacatcaccaagattttgcataactcgtcgctgcttgttgatgacgtggaagacaactcgatgctccgacgaggcctgccggcagcccattgtctgttt ggagtcccccaaaccatcaactccgccaactacatgtactttgtggctctgcaggaggtgctcaagctcaagtcttatgatgccgtctccattttcaccga ggaaatgatcaacttgcatagaggtcagggtatggatctctactggagagaaacactcacttgcccctcggaagacgagtatctggagatggtg gtgcacaagaccggtggactgtttcggctggctctgagacttatgctgtcggtggcatcgaaacaggaggaccatgaaaagatcaactttgatctca cacaccttaccgacacactgggagtcatttaccagattctggatgattacctcaacctgcagtccacggaattgaccgagaacaagggattctgcga agatatcagcgaaggaaagttttcgtttccgctgattcacagcatacgcaccaacccggataaccacgagattctcaacattctcaaacagcgaaca agcgacgcttcactcaaaaagtacgccgtggactacatgagaacagaaaccaagagtttcgactactgcctcaagaggatacaggccatgtcactc aaggcaagttcgtacattgatgatctagcagcagctggccacgatgtctccaagctacgagccattttgcattattttgtgtccacctctgactgtgagg agagaaagtactttgaggatgcgcagtga (SEQ ID NO: 2)
mdynsadfkeiwgkaadtallgpynylannrghnirehliaafgavikvdksdletishitkilhnssllvddvednsm lrrglpaahclfgvpqtinsanymyfvalqevlklksydavsifteeminlhrgqgmdlywretltcpsedeylemvvhktgglfrlalrlmlsv askqedhekinfdlthltdtlgviyqilddylnlqsteltenkgfcedisegkfsfplihsirtnpdnheilnilkqrtsdaslkkyavdymrtetksf dyclkriqamslkassyiddlaaaghdvsklrailhyfvstsdceerkyfedaq

TABLE 27

| Plasmids | | | |
|---|---|---|---|
| Plasmid | Backbone | Insert | Oligos or source |
| pMB4529 | PCR2.1 | 3.4 kb ADE1 PCR product | MO4475 & MO4476 |
| pMB4534 | PCR2.1 | 2.1 kb LEU2 PCR product | MO4477 & MO4478 |
| pMB4535 | PCR2.1 | 1.2 kb URA5 PCR product | MO4471 & MO4472 |
| pMB4589 | pMB4535 (KpnI + SpeI) | 1.2 kb GPD1 promoter (KpnI + NotI); 0.14 kb XPR2 terminator (NotI + SpeI) | MO4568 & MO4591; MO4566 & MO4593 |
| pMB4590 | pMB4535 (KpnI + SpeI) | 0.4 kb TEF1 promoter (KpnI + NotI); 0.14 kb XPR2 terminator (NotI + SpeI) | MO4571 & MO4592; MO4566 & MO4593 |
| pMB4591 | pMB4590 (NheI + MluI) | 1.0 kb GGS1 ORF (XbaI + MluI) | MO4534 & MO4544 |
| pMB4597 | pMB4534 (Acc65I + SpeI) | GPD1 promoter & XPR2 terminator (Acc65I + SpeI) | From pMB4589 |
| pMB4603 | pMB4597 (RsrII + MluI) | Residual backbone & TEF1 promoter (RsrII + MluI) | From pMB4590 |
| pMB4616 | pMB4529 (RsrII + SpeI) | Residual backbone & GPD1 promoter & XPR2 terminator (RsrII + SpeI) | From pMB4589 |
| pMB4629 | pMB4616 (RsrII + MluI) | Residual backbone & TEF1 promoter (RsrII + MluI) | From pMB4590 |
| pMB4631 | pMB4603 (KpnI + NheI) | 1.2 kb GPD1 promoter (KpnI + NheI); | MO4568 & MO4659 |
| pMB4628 | pMB4603 | carRP | See 1A |
| pMB4637 | pMB4629 (NheI + MluI) | 1.5 kb hmg1$^{trunc}$ ORF (XbaI + MluI) | See 1D |
| pMB4714 | pMB4691 (NheI + MluI) | 1.5 kb hmg1$^{trunc}$ ORF (XbaI + MluI) | See 1D |
| pMB4638 | pMB4629 | carB(i$^-$) | See 1B |
| pMB4660 | pMB4638 (+URA3) | carB(i$^-$) | See 1C |
| pMB4662 | pMB4631 (SpeI + XhoI) | 1.8 kb URA3 fragment (SpeI + BsaI | See 1C |

TABLE 27-continued

| Plasmids | | | |
|---|---|---|---|
| Plasmid | Backbone | Insert | Oligos or source |
| pMB4683 | pMB4662 (Acc65I + MluI) | 1.4 kb tef1p-GGS1 fragment (Acc65I + MluI) | From pMB4591 |
| pMB4692 | pMB4662 (Acc65I + MluI) | 0.4 kb TEF1 promoter (Acc65I + NheI); 0.55 kb crtZ ORF (XbaI + MluI) | See 1E |
| pMB4698 | pMB4629 (NheI + MluI) | 0.9 kb crtW ORF (XbaI + MluI) | See 1F |
| pMB4599 | pBluescriptSKII-(EcoRV) | 1.9 kb carRP gene | See 1A |
| pMB4606 | pBluescriptSKII-(EcoRV) | 1.9 kb carB gene | See 1A |
| pMB4613 | pMB4599 (Acc65I + PpuMI) | carRP(i$^-$) | See 1A |
| pMB4619 | pBluescriptSKII-(BamHI + Acc65I)) | carB(i$^-$) | See 1A |
| pMB4705 | pMB4603 (NheI + MluI) | carRP(i$^-$) | See 1A |
| pMB4691 | pMB4662 (Acc65I + MluI) | 0.4 kb TEF1 promoter (Acc65I + MluI) | From pMB4629 |
| pMB4751 | pMB4691 | 0.75 kb YALI0D12903g promoter + 0.45 *Y. lipoltyica* HIS3 terminator | Inserted between TEF1p/XPRt and URA3 |
| pMB4719 | pMB4691 (NheI + MluI) | crtZ (*E. litoralis*) | See 1J |
| pMB4778 | pMB4751 (NheI + MluI) | crtZ (*P. bermudensis*) | See 1I |
| pMB4741 | pMB4629 (NheI + MluI) | crtW (*Aurantimonas*) | See 1G |
| pMB4735 | pMB4629 (NheI + MluI) | crtW (*P. bermudensis*) | See 1H |
| pMB4812 | pMB4603 (NheI + MluI) | al-2 (*N. crassa*) | See 1K |
| pMB4846 | pMB4691 (NheI + MluI) | crtZ (*Erythrobacter* sp. NAP1) | See 1L |
| pMB4835 | pMB4691 (NheI + MluI) | *S. alaskensis*) | See 1M |
| pMB4845 | pMB4691 (NheI + MluI) | crtZ (R. *biformata*) | See 1N |
| pMB4837 | pMB4691 (NheI + MluI) | crtZ (X. *autrophicus*) | See 1O |
| pMB4850 | pMB4691 (NheI + MluI) | crtZ (*P. putida*) | See 1P |

Certain oligonucleotides referred to in Table 27 above are as follows:

```
                                    (SEQ ID NO: 3)
MO4471 5'-CTGGGTGACCTGGAAGCCTT

                                    (SEQ ID NO: 4)
MO4472 5'-AAGATCAATCCGTAGAAGTTCAG

                                    (SEQ ID NO: 5)
MO4475 5'-AAGCGATTACAATCTTCCTTTGG

                                    (SEQ ID NO: 6)
MO4476 5'-CCAGTCCATCAACTCAGTCTCA

                                    (SEQ ID NO: 7)
MO4477 5'-GCATTGCTTATTACGAAGACTAC

                                    (SEQ ID NO: 8)
MO4478 5'-CCACTGTCCTCCACTACAAACAC

                                    (SEQ ID NO: 9)
MO4534 5'-CACAAACGCGTTCACTGCGCATCCTCAAAGT

                                   (SEQ ID NO: 10)
MO4544 5'-CACAATCTAGACACAAATGGATTATAACAGCGCGGAT

                                   (SEQ ID NO: 11)
MO4566 5'-CACAAACTAGTTTGCCACCTACAAGCCAGAT

                                   (SEQ ID NO: 12)
MO4568 5'-CACAAGGTACCAATGTGAAAGTGCGCGTGAT

                                   (SEQ ID NO: 13)
MO4571 5'-CACAAGGTACCAGAGACCGGGTTGGCGG
```

-continued

```
                                   (SEQ ID NO: 14)
MO4591 5'-CACAAGCGGCCGCGCTAGCATGGGGATCGATCTCTTATAT

                                   (SEQ ID NO: 15)
MO4592 5'-CACAAGCGGCCGCGCTAGCGAATGATTCTTATACTCAGAAG

                                   (SEQ ID NO: 16)
MO4593 5'-CACAAGCGGCCGCACGCGTGCAATTAACAGATAGTTTGCC

                                   (SEQ ID NO: 17)
MO4659 5'-CACAAGCTAGCTGGGGATGCGATCTCTTATATC
```

1A: Production of pMB4628 (tef1p-carRP LEU2) and pMB4705 (tef1p-carRP[i$^-$] LEU2) Encoding Phytoene Synthase/Lycopene Cyclase:

Intron-containing carRP was amplified from *M. circinelloides* (ATCC 90680) genomic DNA using MO4525 and MO4541:

```
                                   (SEQ ID NO: 18)
MO4525 5'-CACAAACGCGTTTAAATGGTATTTAGATTTCTCATT

                                   (SEQ ID NO: 19)
MO4541 5'-CACAATCTAGACACAAATGCTGCTCACCTACATGGA
```

and the resulting 1.9 kb fragment was phosphorylated with T4 polynucleotide kinase. The resulting fragment was blunt-end ligated into pBluescriptSKII– cleaved with EcoRV, yielding pMB4599. The 1.9 kb XbaI-MluI fragment from pMB4599 was inserted into NheI- and MluI-cleaved pMB4603, yielding pMB4628. The intron containing nucleic acid coding sequence, and encoded CarRP protein (assuming correctly predicted splicing) of pMB4628 are as follows:

(SEQ ID NO: 20)

atgctgctcacctacatggaagtccacctctactacacgctgcctgtgctgggcgtcctgtcctggctgtcgcggccgtact acacagccaccgatgcgctcaaattcaaatttctgacactggttgccttcacgaccgcctccgcctgggacaactacattgtctaccacaaggcgtg gtcctactgccccacctgcgtcaccgctgtcattggctacgtgcccttggaggagtacatgttcttcatcatcatgactctgttgaccgtggcattcaccaa tctggtgatgcgctggcacctgcacagcttctttatcaggcctgaaacgcccgtcatgcagtccgtcctggtccgtcttgtccccataacagcctta ttaatcactgcatacaaggcttgggtaagcaaacaaacaaatgatgtgccgcatcgcattttaatattaaccattgcatacacagcatttggcggtccct ggaaagccactgttctacggatcatgcattttgtggtacgcctgtccggttttggccttattgtggtttggtgctggcgagtacatgatgcgtcgtccgct ggcggtgctcgtctccattgcgctgcccacgctgtttctctgctgggtcgatgtcgtcgctattggcgccggcacatgggacatttcgctggccacaa gcaccggcaagttcgtcgtgccccacctgcccgtggaggaattcatgttctttgcgctaattaataccgttttggtatttggtacgtgtgcgatcgatcg cacgatggcgatcctccacctgttcaaaaacaagagtccttatcagcgcccataccagcacagcaagtcgttcctccaccagatcctcgagatgacc tgggccttctgtttacccgaccaagtgctgcattcagacacattccacgacctgtccgtcagctgggacatcctgcgcaaggcctccaagtcctttac acggcctctgctgtctttcccggcgacgtgcgccaagagctcggtgtgctatacgccttttgcagagccacggacgatctctgcgacaacgagcag gtccctgtgcagacgcgaaaggagcagctgatactgacacatcagttcgtcagcgatctgtttggccaaaagacaagcgcgccgactgccattga ctgggacttttacaacgaccaactgcctgcctcgtgcatctctgccttcaagtcgttcacccgtttgcgccatgtgctggaagctggagccatcaagg aactgctcgacgggtacaagtgggatttggagcgtcgctccatcagggatcaggaggatctcagatattactcagcttgtgtcgccagcagtgttgg tgaaatgtgcactcgcatcatactggcccacgccgacaagcccgcctcccgccagcaaacacagtggatcattcagcgtgcgcgtgaaatgggtc tggtactccaatatacaaacattgcaagagacattgtcaccgacagcgaggaactgggcagatgctacctgcctcaggattggcttaccgagaagg aggtggcgctgattcaaggcggccttgcccgagaaattggcgaggagcgattgctctcactgtcgcatcgcctcatctaccaggcagacgagctc atggtggttgccaacaagggcatcgacaagctgcccagccattgtcaaggcggcgtgcgtgcggcctgcaacgtctatgcttccattggcaccaa gctcaagtcttacaagcaccactatcccagcagagcacatgtcggcaattcgaaacgagtggaaattgctcttcttagcgtatacaacctttacaccg cgccaattgcgactagtagtaccacacattgcagacagggaaaaatgagaaatctaaataccatttaa (SEQ ID NO: 21)

mlltymevhlyytlpvlgvlswlsrpyytatdalkfkfltlvafttasawdnyivyhkawsycptcvtavigyvpleey mffiimtlltvaftnlvmrwhlhsffirpetpvmqsvlvrlvpitallitaykawhlavpgkplfygscilwyacpvlallwfgageymmrrpla vlvsialptlflcwvdvvaigagtwdislatstgkfvvphlpveefmffalintvlvfgtcaidrtmailhlfknkspyqrpyqhsksflhqilemt wafclpdqvlhsdtfhdlsvswdilrkasksfytasavfpgdvrqelgvlyafcratddlcdneqvpvqtrkeqlilthqfvsdlfgqktsaptaid wdfyndqlpascisafksftrlrhvleagaikelldgykwdlerrsirdqedlryysacvassvgemctriilahadkpasrqqtqwiiqrarem glvlqytniardivtdseelgrcylpqdwltekevaliqgglareigeerllslshrliyqadelmvvankgidklpshcqggvraacnvyasigt klksykhhypsrahvgnskrveiallsvynlytapiatssthcrqgkmrnlnti Alternatively, pMB4599 was also used as a template for PCR amplification using MO4318, MO4643, MO4644, and MO4639:

(SEQ ID NO: 22)
MO4318 5'-GTAAAACGACGGCCAGT (SEQ ID NO: 23)
MO4643 5'-CACACGGTCTCATGCCAAGCCTTGTATGCAGTGATTAA (SEQ ID NO: 24)
MO4639 5'-CCACTGTGTTTGCTGGCGG

-continued (SEQ ID NO: 25)
MO4644 5'-CACACGGTCTCTGGCATTTGGCGGTCCCTGGAAA producing fragments of 0.5 and 0.95 kb, that were subsequently cleaved with Acc65I and BsaI, and BsaI and PpuMI, respectively. These fragments were ligated to pMB4599 that had been digested with Acc65I and PpuMI, yielding pMB4613, harboring intronless carRP. The 1.85 kb XbaI-MluI fragment from pMB4613 was inserted into NheI- and MluI-cleaved pMB4603 to yield pMB4705.

The intronless nucleic acid coding sequence of pMB4705 is as follows, and encodes the same CarRP protein as above:

(SEQ ID NO: 26)

atgctgctcacctacatggaagtccacctctactacacgctgcctgtgctgggcgtcctgtcctggctgtcgcggccgtact acacagccaccgatgcgctcaaattcaaatttctgacactggttgccttcacgaccgcctccgcctgggacaactacattgtctaccacaaggcgtg gtcctactgccccacctgcgtcaccgctgtcattggctacgtgcccttggaggagtacatgttcttcatcatcatgactctgttgaccgtggcattcacc -continued

```
aatctggtgatgcgctggcacctgcacagcttctttatcaggcctgaaacgcccgtcatgcagtccgtcctggtccgtcttgtccccataacagcctta

ttaatcactgcatacaaggcttggcatttggcggtccctggaaagccactgttctacggatcatgcattttgtggtacgcctgtccggttttggccttattgt

ggtttggtgctggcgagtacatgatgcgtcgtccgctggcggtgctcgtctccattgcgctgcccacgctgtttctctgctgggtcgatgtcgtcgc

tattggcgccggcacatgggacatttcgctggccacaagcaccggcaagttcgtcgtgccccacctgcccgtggaggaattcatgttctttgcgcta

attaataccgttttggtatttggtacgtgtgcgatcgatcgcacgatggcgatcctccacctgttcaaaaacaagagtccttatcagcgcccataccag

cacagcaagtcgttcctccaccagatcctcgagatgacctgggccttctgtttacccgaccaagtgctgcattcagacacattccacgacctgtccgt

cagctgggacatcctgcgcaaggcctccaagtccttttacacggcctctgctgtctttcccggcgacgtgcgccaagagctcggtgtgctatacgcc

ttttgcagagccacggacgatctctgcgacaacgagcaggtccctgtgcagacgcgaaaggagcagctgatactgacacatcagttcgtcagcga

tctgtttggccaaaagacaagcgcgccgactgccattgactgggacttttacaacgaccaactgcctgcctcgtgcatctctgccttcaagtcgttcac

ccgtttgcgccatgtgctggaagctggagccatcaaggaactgctcgacgggtacaagtgggatttggagcgtcgctccatcagggatcaggagg

atctcagatattactcagcttgtgtcgccagcagtgttggtgaaatgtgcactcgcatcatactggcccacgccgacaagcccgcctcccgccagca

aacacagtggatcattcagcgtgcgcgtgaaatgggtctggtactccaatatacaaacattgcaagagacattgtcaccgacagcgaggaactggg

cagatgctacctgcctcaggattggcttaccgagaaggaggtggcgctgattcaaggcggccttgcccgagaaattggcgaggagcgattgctct

cactgtcgcatcgcctcatctaccaggcagacgagctcatggtggttgccaacaagggcatcgacaagctgcccagccattgtcaaggcggcgtg

cgtgcggcctgcaacgtctatgcttccattggcaccaagctcaagtcttacaagcaccactatcccagcagagcacatgtcggcaattcgaaacga

gtggaaattgctcttcttagcgtatacaacctttacaccgcgccaattgcgactagtagtaccacacattgcagacagggaaaaatgagaaatctaaat

accatttaa
```

1B: Production of pMB4638 (tef1p-carB ADE1), Encoding Phytoene Dehydrogenase:

Intron-containing carB was amplified from *M. circinelloides* (ATCC 90680) genomic DNA using MO4530 and MO4542:

```
                                              (SEQ ID NO: 27)
MO4530   5'-CACAAACGCGTTTAAATGACATTAGAGTTATGAAC

                                              (SEQ ID NO: 28)
MO4542   5'-CACAATCTAGACACAAATGTCCAAGAAACACATTGTC
```

and the resulting 1.9 kb fragment was phosphorylated with T4 polynucleotide kinase and blunt-end ligated into pBS-SKII− cleaved with EcoRV, yielding pMB4606. pMB4606 was then used as a template for PCR amplification using MO4318 and MO4648, and MO4646 and MO4647, and MO4343 and MO4645:

```
                                              (SEQ ID NO: 29)
MO4318 5'-GTAAAACGACGGCCAGT
```

-continued

```
                                              (SEQ ID NO: 30)
MO4648 5'-CACAAGGTCTCAAGCACGCATCCCGGAACTG

                                              (SEQ ID NO: 31)
MO4646 5'-CACACGGTCTCAGGCATGTCGCCCTACGATGC

                                              (SEQ ID NO: 32)
MO4647 5'-CACACGGTCTCATGCTTGCACCCCACAAAGAATAGG

                                              (SEQ ID NO: 33)
MO4343 5'-CAGGAAACAGCTATGAC

                                              (SEQ ID NO: 34)
MO4645 5'-CACACGGTCTCTTGCCCATATACATGGTCTGAAACG
```

producing fragments of 0.4 and 0.85 and 0.7 kb, that were subsequently cleaved with Acc65I and BsaI, and BsaI, and BsaI and BamHI, respectively. These fragments were ligated to pBS-SKII− that had been cut with Acc65I and BamHI, yielding pMB4619, harboring intronless carB. The 1.75 kb XbaI-MluI fragment from pMB4619 was inserted into NheI- and MluI-cleaved pMB4629, yielding pMB4638. The resulting nucleic acid coding sequence and encoded CarB protein of pMB4638 are as follows:

```
                                                                    (SEQ ID NO: 35)
atgtccaagaaacacattgtcattatcggtgctggcgtgggtggcacggctacagctgctcgtttggcccgcgaaggcttca

aggtcactgtggtggagaaaaacgactttggtggcggccgctgctccttgatccatcaccagggccatcgctttgatcagggcccgtcgctctacct

gatgcccaagtactttgaggacgcctttgccgatctggacgagcgcattcaagaccacctggagctgctgcgatgcgacaacaactacaaggtgc

actttgacgacggtgagtcgatccagctgtcgtctgacttgacacgcatgaaggctgaattggaccgcgtggagggcccccttggttttggccgatt

cctggatttcatgaaagagacacacatccactacgaaagcggcaccctgattgcgctcaagaagaatttcgaatccatctgggacctgattcgcatc

aagtacgctccagagatctttcgcttgcacctgtttggcaagatctacgaccgcgcttccaagtacttcaagaccaagaagatgcgcatggcattcac

gtttcagaccatgtatatgggcatgtcgccctacgatgcgcctgctgtctacagcctgttgcagtacaccgagttcgctgaaggcatctggtatcccc
```

-continued gtggcggcttcaacatggtggttcagaagctagaggcgattgcaaagcaaaagtacgatgccgagtttatctacaatgcgcctgttgccaagattaa
caccgatgatgccaccaaacaagtgacaggtgtaaccttggaaaatggccacatcatcgatgccgatgcggttgtgtgtaacgcagatctggtctat
gcttatcacaatctgttgcctccctgccgatggacgcaaaacacactggcttccaagaaattgacgtcttcttccatttccttctactggtccatgtccac
caaggtgcctcaattggacgtgcacaacatctttttggccgaggcttatcaggagagctttgacgaaatcttcaaggactttggcctgccttctgaagc
ctccttctacgtcaatgtgccctctcgcatcgatccttctgctgctcccgacggcaaggactctgtcattgtcttggtgcctattggtcatatgaagagca
agacgggcgatgcttccaccgagaactacccggccatggtggacaaggcacgcaagatggtgctggctgtgattgagcgtcgtctgggcatgtc
gaatttcgccgacttgattgagcatgagcaagtcaatgatcccgctgtatggcagagcaagttcaatctgtggagaggctcaattctgggtttgtctca
tgatgtgcttcaggtgctgtggttccgtcccagcacaaaggattctaccggtcgttatgataacctattctttgtgggtgcaagcacgcatcccggaact
ggtgttcccattgtccttgcaggaagcaagctcacctctgaccaagttgtcaagagctttggaaagacgcccaagccaagaaagatcgagatggag
aacacgcaagcacctttggaggagcctgatgctgaatcgacattccctgtgtggttctggttgcgcgctgccttttgggtcatgtttatgttcttttacttct
tccctcaatccaatggccaaacgcccgcatcttttatcaataatttgttacctgaagtattccgcgttcataactctaatgtcatttaa (SEQ ID NO: 36)

mskkhiviigagvggtataarlaregfkvtvvekndfgggrcslihhqghrfdqgpslylmpkyfedafadlderiqdh
lellrcdnnykvhfddgesiqlssdltrmkaeldrvegplgfgrfldfmkethihyesgtlialkknfesiwdlirikyapeifrlhlfgkiydrask
yfktkkmrmaftfqtmymgmspydapavysllqytefaegiwyprggfnmvvqkleaiakqkydaefiynapvakintddatkqvtgvtl
enghiidadavvcnadlvyayhnllppcrwtqntlaskkltsssisfywsmstkvpqldvhniflaeayqesfdeifkdfglpseasfyvnvps
ridpsaapdgkdsvivlvpighmksktgdastenypamvdkarkmvlavierrlgmsnfadlieheqvndpavwqskfnlwrgsilglshd
vlqvlwfrpstkdstgrydnlffvgasthpgtgvpivlagskltsdqvvksfgktpkprkiementqapleepdaestfpvwfwlraafwvmf
mffyffpqsngqtpasfinnllpevfrvhnsnvi

1C. Production of pMB4660 (tef1p-carB URA3) Encoding Phytoene Dehydrogenase:

The 4.3 kb XhoI-NotI fragment and the 1.8 kb NotI-SpeI fragment from pMB4638 were ligated to the 1.9 kb BsaI- and SpeI-cleaved URA3 gene generated by PCR amplification of *Y. lipolytica* genomic DNA using MO4684 and MO4685 to create pMB4660:

(SEQ ID NO: 37)
MO4684 5'-CATTCACTAGTGGTGTGTTCTGTGGAGCATTC (SEQ ID NO: 38)
MO4685 5'-CACACGGTCTCATCGAGGTGTAGTGGTAGTGCAGTG

The resulting nucleic acid coding sequence and encoded CarB(i) protein of pMB4660 are as follows:

(SEQ ID NO: 39)

atgtccaagaaacacattgtcattatcggtgctggcgtgggtggcacggctacagctgctcgtttggcccgcgaaggcttca
aggtcactgtggtggagaaaaacgactttggtggcggccgctgctccttgatccatcaccagggccatcgctttgatcagggcccgtcgctctacct
gatgcccaagtactttgaggacgcctttgccgatctggacgagcgcattcaagaccacctggagctgctgcgatgcgacaacaactacaaggtgc
actttgacgacggtgagtcgatccagctgtcgtctgacttgacacgcatgaaggctgaattggaccgcgtggagggcccccttggttttggccgatt
cctggatttcatgaaagagacacacatccactacgaaagcggcaccctgattgcgctcaagaagaatttcgaatccatctgggacctgattcgcatc
aagtacgctccagagatctttcgcttgcacctgtttggcaagatctacgaccgcgcttccaagtacttcaagaccaagaagatgcgcatggcattcac
gtttcagaccatgtatatgggcatgtcgccctacgatgcgcctgctgtctacagcctgttgcagtacaccgagttcgctgaaggcatctggtatcccc
gtggcggatcaacatggtggttcagaagctagaggcgattgcaaagcaaaagtacgatgccgagtttatctacaatgcgcctgttgccaagattaa
caccgatgatgccaccaaacaagtgacaggtgtaaccttggaaaatggccacatcatcgatgccgatgcggttgtgtgtaacgcagatctggtctat
gcttatcacaatctgttgcctccctgccgatggacgcaaaacacactggcttccaagaaattgacgtcttcttccatttccttctactggtccatgtccac
caaggtgcctcaattggacgtgcacaacattctttttggccgaggcttatcaggagagctttgacgaaatcttcaaggactttggcctgccttctgaagc
ctccttctacgtcaatgtgccctctcgcatcgatccttctgctgctcccgacggcaaggactctgtcattgtcttggtgcctattggtcatatgaagagca
agacgggcgatgcttccaccgagaactacccggccatggtggacaaggcacgcaagatggtgctggctgtgattgagcgtcgtctgggcatgtc -continued gaatttcgccgacttgattgagcatgagcaagtcaatgatcccgctgtatggcagagcaagttcaatctgtggagaggctcaattctgggtttgtctca tgatgtgcttcaggtgctgtggttccgtcccagcacaaaggattctaccggtcgttatgataacctattctttgtgggtgcaagcacgcatcccggaact ggtgttcccattgtccttgcaggaagcaagctcacctctgaccaagttgtcaagagctttggaaagacgcccaagccaagaaagatcgagatggag aacacgcaagcacctttggaggagcctgatgctgaatcgacattccctgtgtggttctggttgcgcgctgccttttgggtcatgtttatgttcttttacttct tccctcaatccaatggccaaacgcccgcatcttttatcaataatttgttacctgaagtattccgcgttcataactctaatgtcatttaa (SEQ ID NO: 40)

mskkhiviigagvggtataarlaregfkvtvveknd fgggrcslihhqghrfdqgpslylmpkyfedafadlderiqdh lellrcdnnykvhfddgesiqlssdltrmkaeldrvegplgfgrfldfmkethihyesgtlialkknfesiwdlirikyapeifrlhlfgkiydrask yfktkkmrmaftfqtmymgmspydapavysllqytefaegiwyprggfnmvvqkleaiakqkydaefiynapvakintddatkqvtgvtl enghiidadavvcnadlvyayhnllppcrwtqntlaskkltsssisfywsmstkvpqldvhniflaeayqesfdeifkdfglpseasfyvnvps ridpsaapdgkdsvivlvpighmksktgdastenypamvdkarkmvlavierrlgmsnfadliehеqvndpavwqskfnlwrgsilglshd vlqvlwfrpstkdstgrydnlffvgasthpgtgvpivlagskltsdqvvksfgktpkprkiementqapleepdaestfpvwfwlraafwvmf mffyffpqsngqtpasfinnllpevfrvhnsnvi 1D. Production of pMB4637, pMB4714 and pTef-HMG Encoding a Truncated HMG1.

For production of a truncated variant of the HMG-CoA reductase gene, which also encodes a 77 amino acid leader sequence derived from *S. cerevisiae*, the following oligonucleotides are synthesized:

(SEQ ID NO: 41)
PRIMER O 5'-TTCTAGACACAAAAATGGCTGCAGACCAATTGGTGA (SEQ ID NO: 42)
PRIMER P 5'-CATTAATTCTTCTAAAGGACGTATTTTCTTATC (SEQ ID NO: 43)
PRIMER Q 5'-GTTCTCTGGACGACCTAGAGG (SEQ ID NO: 44)
MO4658 5'-CACACACGCGTACACCTATGACCGTATGCAAAT

Primers O and P are used to amplify a 0.23 kb fragment encoding Met-Ala followed by residues 530 to 604 of the Hmg1 protein of *S. cerevisiae*, using genomic DNA as template. Primers Q and MO4658 are used to amplify a 1.4 kb fragment encoding the C-terminal 448 residues of the Hmg1 protein of *Y. lipolytica*, using genomic DNA as template. These fragments are ligated to the appropriate cloning vector, and the resultant plasmids, designated pOP and pQMO4658, are verified by sequencing. The OP fragment is liberated with XbaI and AseI, and the QMO4658 fragment is liberated with MaeI and MluI. These fragments are then ligated to the ADE1 TEF1p expression vector pMB4629 cut with XbaI and MluI to produce pTefHMG.

Alternatively, the native HMG1 gene from *Y. lipolytica* was amplified without *S. cerevisiae* sequences using primers MO4658 (described above) and MO4657 (5'-CACACTCTAGACACAAAAATGACCCAGTCTGTGAAGGTGG (SEQ ID NO:45)). The 1.5 kb product was phosphorylated and ligated to pBluescriptSK$^-$ that had been cleaved with EcoRV to create pMB4623. The XbaI-MluI fragment containing hmg1$^{trunc}$ was ligated both to NheI-MluI-cleaved MB4629 and to NheI-MluI-cleaved pMB4691 to create pMB4637 and pMB4714, respectively.

The resulting nucleic acid coding sequence and encoded Hmg1$^{trunc}$ protein of pMB4637 and pMB4714 are as follows:

(SEQ ID NO: 46)

atgacccagtctgtgaaggtggttgagaagcacgttcctatcgtcattgagaagcccagcgagaaggaggaggacacctc ttctgaagactccattgagctgactgtcggaaagcagcccaagcccgtgaccgagacccgttctctggacgacctagaggctatcatgaaggcag gtaagaccaagcttctggaggaccacgaggttgtcaagctctctctcgagggcaagcttcctttgtatgctcttgagaagcagcttggtgacaacacc cgagctgttggcatccgacgatctatcatctcccagcagtctaataccaagactttagagacctcaaagcttccttacctgcactacgactacgaccgt gtttttggagcctgttgcgagaacgttattggttacatgcctctccccgttggtgttgctggccccatgaacattgatggcaagaactaccacattcctat ggccaccactgagggttgtcttgttgcctcaaccatgcgaggttgcaaggccatcaacgccggtggcggtgttaccactgtgcttactcaggacggt atgacacgaggtccttgtgtttccttcccctctctcaagcgggctggagccgctaagatctggcttgattccgaggagggtctcaagtccatgcgaaa ggccttcaactccacctctcgatttgctcgtctccagtctcttcactctacccttgctggtaacctgctgtttattcgattccgaaccaccactggtgatgc catgggcatgaacatgatctccaagggcgtcgaacactctctggccgtcatggtcaaggagtacggcttccctgatatggacattgtgtctgtctcgg gtaactactgcactgacaagaagcccgcagcgatcaactggatcgaaggccgaggcaagagtgttgttgccgaagccaccatccctgctcacatt gtcaagtctgttctcaaaagtgaggttgacgctcttgttgagctcaacatcagcaagaatctgatcggtagtgccatggctggctctgtgggaggtttc aatgcacacgccgcaaacctggtgaccgccatctaccttgccactggccaggatcctgctcagaatgtcgagtcttccaactgcatcacgctgatga gcaacgtcgacggtaacctgctcatctccgtttccatgccttctatcgaggtcggtaccattggtggaggtactattttggagccccagggggctatgc -continued tggagatgcttggcgtgcgaggtcctcacatcgagacccccggtgccaacgcccaacagcttgctcgcatcattgcttctggagttcttgcagcgga gctttcgctgtgttctgctcttgctgccggccatcttgtgcaaagtcatatgacccacaaccggtcccaggctcctactccggccaagcagtctcagg ccgatctgcagcgtctacaaaacggttcgaatatttgcatacggtcatag (SEQ ID NO: 47)

mtqsvkvvekhvpiviekpsekeedtssedsieltvgkqpkpvtetrslddleaimkagktklledhevvklslegklp lyalekqlgdntravgirrsiisqqsntktletsklpylhydydrvfgaccenvigymplpvgvagpmnidgknyhipmattegclvastmrg ckainagggvttvltqdgmtrgpcvsfpslkragaakiwldseeglksmrkafnstsrfarlqslhstlagnllfirfrtttgdamgmnmiskgve hslavmvkeygfpdmdivsvsgnyctdkkpaainwiegrgksvvaeatipahivksvlksevdalvelnisknligsamagsvggfnahaa nlvtaiylatgqdpaqnvessncitlmsnvdgnllisvsmpsievgtigggtilepqgamlemlgvrgphietpganaqqlariiasgvlaaelsl csalaaghlvqshmthnrsqaptpakqsqadlqrlqngsnicirs 1E. Production of pMB4692 (URA3 tef1p-crtZ) Encoding *N. aromaticovans* Carotene Hydroxylase.

The following carotene hydroxylase (CrtZ) ORF sequence was synthesized de novo based on protein sequence of *Novosphingobium aromaticivorans*, using *Y. lipolytica* codon bias:

(SEQ ID NO: 48)

5'-ttctagacacaaaaatgggtggagccatgcagaccctcgctgctatc ctgatcgtcctcggtacagtgctcgctatggagtttgtcgcttggtcttc tcataagtatatcatgcatggcttcggatggggatggcatagagaccatc acgagccccatgagggatttcttgagaagaatgacttatacgccatcgtt ggcgctgccctctcgatactcatgtttgccctcggctctcccatgatcat gggcgctgacgcctggtggcccggaacctggatcggactcggtgtcctct tctatggtgtcatctataccctcgtgcacgacggtctggtgcaccaacga tggtttagatgggtgcctaaacgaggttacgccaaacgactcgtgcaggc ccataagctgcaccacgccaccattggcaaggaaggaggcgtctcattcg gtttcgtgttcgcccgagatcccgccgttctgaagcaggagcttcgagct caacgagaagcaggtatcgccgtgctgcgagaggctgtggacggctagac gcgt

This sequence was cleaved using XbaI and MluI and ligated, along with an Acc65I-NheI TEF1 promoter fragment from pMB4629, to pMB4662 cut with Acc65I and MIA to produce pMB4692. The nucleic acid coding sequence is depicted in bold underline above. The resulting encoded CrtZ protein of pMB4692 is as follows:

(SEQ ID NO: 49)

mggamqtlaailivlgtvlamefvawsshkyimhgfgwgwhrdhhepheg flekndlyaivgaalsilmfalgspmimgadawwpgtwiglgvlfygviy tlvhdglvhqrwfrwvpkrgyakrlvqahklhhatigkeggvsfgfvfar dpavlkqelraqreagiavlreavdg 1F. Production of pMB4698 (ADE1 tef1p-crtW), Encoding Carotene Ketolase Derived from an Environmental Sample.

The following carotene ketolase (CrtW) ORF sequence was synthesized de novo, based on protein sequence of an environmental sequence isolated from the Sargasso Sea (Genbank accession AACY01034193.1):

(SEQ ID NO: 50)

5'-ttctagacacaaaaatgactcgatctatttcctggccttccacctac tggcacctccagccctcctgttcttcttgggtcgcaaacgaattctctcc tcaagcccgaaaaggtctcgtcctcgctggtctcattggttccgcttggc tgcttactctcggacttggcttttcccttcccctccatcaaacgagctgg cttctcatcggttgtctcgttctccttagatctttcctgcacaccggact ttttatcgttgcccatgacgctatgcacgcttctcttgttcctgaccacc ctggccttaaccgttggattggacgtgtctgtcttctcatgtatgctgga ctctcctacaaaagatgctgccgaaatcaccgtcgacaccaccaagcccc tgaaacagttgaagaccctgactaccaacgatgcactaacaacaatatcc tcgactggtacgttcactttatgggaaattacctcggatggcaacaattg cttaatctctcttgcgtttggctcgctctcaccttccgtgtttctgacta ctctgctcaattcttccacctgctccttttctctgtccttcctctcatcg tctcctcctgtcaactcttcctcgtgggaacctggctgccacaccgacga ggcgctactactcgacccggcgttaccactcgatccctgaacttccaccc tgctctttccttcgctgcttgctaccacttcggttaccaccgtgaacacc atgaatctccctctactccttggttccaacttcctaaactccgagaaggt tctctcatctaaacgcgt

This sequence was cleaved using XbaI and MluI and ligated to pMB4629 cut with NheI and MluI to produce pMB4698. The nucleic acid coding sequence is depicted in bold underline above. The resulting encoded CrtW protein of pMB4698 is as follows:

(SEQ ID NO: 51)

mtrsiswpstywhlqpscsswvanefspqarkglvlagligsawlltlgl gfslplhqtswlligclvllrsflhtglfivahdamhaslvpdhpglnrw igrvcllmyaglsykrccrnhrrhhqapetvedpdyqrctnnnildwyvh fmgnylgwqqllnlscvwlaltfrvsdysaqffhlllfsvlplivsscql flvgtwlphrrgattrpgvttrslnfhpalsfaacyhfgyhrehhespst pwfqlpklregsli Mutant alleles of this protein (e.g. L200M, F238L/I/V, including combinations thereof) can also be constructed and tested.

1G. Production of pMB4741 (ADE1 tef-crtW), Encoding *Aurantimonas* Carotene Ketolase.

The following carotene ketolase (CrtW) ORF sequence was synthesized de novo based on protein sequence of *Aurantimonas* sp. 5185-9A1, using *Y. lipolytica* codon bias:

(SEQ ID NO: 52)

ctctagacacaaaaatgtcttcctttgcccctatgaatgatgttgctatt cctgccggtcaagctcctttctctgcctgtactagaaaacctgtcctgag accttttcaagctgccatcggtcttacactcgccggatgtgttatctctg cttggattgcaatccacgttggagctgtctttttcctcgatgtcggttgg cgaacccttcctgttgttcctgtcctcattgccgttcagtgctggctcac ggtcggtctttttattgtcgcacacgatgctatgcacggctccctcgctc ctggttggccacgacttaacgctcgaattggtgccttcatcctcaccatc tacgctggattcgcttggagacgtgtccgaggagctcacatggcccatca cgacgcccctggtactgccgatgaccctgacttctttgttgatgaacctg accgattttggccttggtttcgagctttcttccttagatattttggacgt cgatctattctctttgtttgcacagttgtcaccgtttacattctggtcct tggagcccctgttcttaatgttgttctcttttacggtcttccttcccttc tgtcttctcttcaactcttttactttggaacttttcgtcctcaccgtcat gaagaagatgatttcgttgacgcccataatgcccgatctaatgaatttg gttacatcgcctccctcctttcttgctttcactttggataccatcacgaa catcatgccgagccgtgggtcccttggtggggtcttccttctcaatggcg ccagagacaagcctcttcttcccgacaggtcccgggcggccgagacgctg ctgacgccgctggagcatctcgacaacctgccggacgataccgatctgtt tcttctcgaggtcgaaatcaggcccgttctcccgcttctggtcgaaa cgaacaaatgagataaacgcgt

This sequence was cleaved using XbaI and MluI and ligated to pMB4629 cut with NheI and MluI to produce pMB4741. The nucleic acid coding sequence is depicted in bold underline above. The resulting encoded CrtW protein of pMB4741 is as follows:

(SEQ ID NO: 53)

mssfapmndvaipagqapfsactrkpvlrpfqaaigltlagcvisawiai hvgavffldvgwrtlpvvpvliavqcwltvglfivahdamhgslapgwpr lnarigafiltiyagfawrrvrgahmahhdapgtaddpdffvdepdrfwp wfrafflryfgrrsilfvctvvtvyilvlgapvlnvvlfyglpsllsslq lfyfgtfrphrheeddfvdahnarsnefgyiasllscfhfgyhhehhaep wvpwwglpsqwrqrqasssrqvpggrdaadaagasrqpag ryrsvssrgrnqarspasgrneqmr Mutant alleles of this protein (e.g. L201M, A232V/I/L, F240L/I/V, including combinations thereof) can also be constructed and tested.

1H. Production of pMB4735 (ADE1 tef-crtW), Encoding *P. bermudensis* Carotene Ketolase.

The following carotene ketolase (CrtW) ORF sequence was synthesized de novo based on protein sequence of *Parvularcula bermudensis*, using *Y. lipolytica* codon bias:

(SEQ ID NO: 54)

ctctagacacaaaaatggaccctaccggagacgttactgctagccctcga cctcaaaccaccattcctgtccgacaagcactctggggacttagccttgc tggagccatcatcgccgcatgggtttttatgcacattggtttcgtttttt ttgccccccttgatcctatcgttctcgccctcgccccagttattattctt cttcaatcctggctttctgttggtctttttattatttctcacgacgcaat tctccctcgcccctggacgacccgcctttaatagagccatgggacgactc tgcatgacactttacgccggtttcgactttgaccgtatggccgctgcaca tcaccgacatcacagatcccctggaaccgccgctgaccccgatttttctg ttgactcccctgatcgacctctcccttggtttggagctttcttccgacct actttggctggagaccttttcttaccgttaacgctgtcgtctttacctac tggcttgttcttggagctaaccctgttaatattgttctcttttatggcgt tcctgcactcctttccgccggacagctattttactttggtacatttctcc ctcaccgacacgaacgacaaggctttgctgatcaccaccgagcacgatcc gtccgatccccttacatgctttctcttgttacttctaccactttggaggc tatcatcacgaacatcatctctttccacacgaaccctggtggcgcctgcc tcaacgaggaggttgggaacgtgacagacgaaagagaaccggcccttaac gcgt

This sequence was cleaved using XbaI and MluI and ligated to pMB4629 cut with NheI and MluI to produce pMB4735. The nucleic acid coding sequence is depicted in bold underline above. The resulting encoded CrtW protein of pMB4735 is as follows:

(SEQ ID NO: 55)

mdptgdvtasprpqttipvrqalwglslagaiiaawvfmhigfvffapld pivlalapviillqswlsvglfiishdaihgslapgrpafnramgrlcmt lyagfdfdrmaaahhrhhrspgtaadpdfsvdspdrplpwfgaffrryfg wrpfltvnavvftywlvlganpvnivlfygvpallsagqlfyfgtflphr herqgfadhhrarsvrspymlslvtcyhfggyhhehhlfphepwwrlp qrggwerdrrkrtgp Mutant alleles of this protein (e.g. L190M, M110I/V/L, F229L/I/V, including combinations thereof) can also be constructed and tested.

1I. Production of pMB4778 (URA3 tef-crtZ), Encoding *P. bermudensis* Carotene Hydroxylase.

The following carotene hydroxylase (CrtZ) ORF sequence was synthesized de novo based on protein sequence of *Parvularcula bermudensis*, using *Y. lipolytica* codon bias:

(SEQ ID NO: 56)

ctctagacacaaaaatgactctcgctctctggcaaagatcaccctcgtcc ttggttccgctgctctgatggaaggatttgcttggtgggcccatagatat attatgcacggttggggatgggcttggcatagagatcatcatgaacctca cgacaaagtttttgaaaaaaatgacctgtttgctgtggtttttggctcgt tcgcatttggtttgttcatcgtcggttacctttattggccacctgtttgg tacgttgctgctggcatcactctttacggacttctttacgcatttgttca

-continued tgacggtttggttcatcaacgttggccctggcatttcatgcctaaacgag gatacctccgaagactggttcaagctcacaaacttcatcatgctgttaca acacaaggcggaaatgtttcgtttggattcgtccttgcccctgaccctag acatcttagagaaaaacttagacaatttcgtgctgaaagacatcgtgcc cttgccgccgaaggtgcttcctcctctgaccctcgtgttccccattttcg aaaagttcaagacgtttaaacgcgt

This sequence was cleaved using XbaI and MluI and ligated to pMB4751 cut with NheI and MluI to produce pMB4778. The nucleic acid coding sequence is depicted in bold underline above. The resulting encoded CrtZ protein of pMB4778 is as follows:

(SEQ ID NO: 57)

mtlalwqkitlvlgsaalmegfawwahryimhgwgwawhrdhhephdkvf ekndlfavvfgsfafglfivgylywppywyvaagitlygllyafvhdglv hqrwpwhfmpkrgylrrlvqahklhhavttqggnvsfgfvlapdprhlre klrqfraerhralaaegasssdprvppfrkvqdv 1J. Production of pMB4719 (URA3 tef-crtZ), Encoding *E. litoralis* Carotene Hydroxylase.

The following carotene hydroxylase (CrtZ) ORF sequence was synthesized de novo based on protein sequence of *Erythrobacter litoralis*, using *Y. lipolytica* codon bias:

(SEQ ID NO: 58)

ctctagacacaaaaatgagctggtgggctatcgctcttattgtctttggt gctgtcgttggaatggaatttttttgcttggttcgctcataagtacattat gcatggttggggatggagctggcaccgagatcatcacgaacctcacgata atactcttgaaaaaaacgaccttttcgccgttgtctttggctcggttgcc gcacttctgtttgttattggagctctctggtctgatcctctctggtgggc agcagttggtattacattgtatggcgtcatttacactctggttcacgacg gacttgttcatcaacgttactggcgttggacccctaagcgaggttatgct aagagacttgtccaggcccatcgacttcatcacgctactgttggaaagga aggaggtgtttcttttggttttgtgttcgcccgagatcctgctaagttga

-continued aagccgaattgaaacaacaaagagaacagggacttgccgtcgttcgaga ttctatgggagcataaacgcgt

This sequence was cleaved using XbaI and MluI and ligated to pMB4691 cut with NheI and MluI to produce pMB4719. The nucleic acid coding sequence is depicted in bold underline above. The resulting encoded CrtZ protein of pMB4719 is as follows:

(SEQ ID NO: 59)

mswwaialivfgavvgmeffawfahkyimhgwgwswhrdhhephdntlek ndlfavvfgsvaallfvigalwsdplwwaavgitlygviytlvhdglvhq rywrwtpkrgyakrlvqahrlhhatvgkeggvsfgfvfardpaklkaelk qqreqglavvrdsmga 1K. Production of pMB4812, Encoding *N. crassa* Phytoene Synthase/Lycopene Cyclase, al-2.

Exon 1 of al-2 was synthesized by annealing the following oligonucleotides:

(SEQ ID NO: 60)

MO5017: 5'-CTAGACACAAAAATGTACGACTACGCCTTCGT;

(SEQ ID NO: 61)

MO5018: 5'-GCACCTGAAGTTCACCGTGCCCGCGGTTCCAA;

(SEQ ID NO: 62)

MO5019: 5'-GTGCACGAAGGCGTAGTCGTACATTTTTGTGT;

(SEQ ID NO: 63)

MO5020: 5'-CGCGTTGGAACCGCGGGCACGGTGAACTTCAG, and ligating them to pMB4603 that had been cleaved with NheI and MluI, to create pMB4811. Exon2 was amplified from *N. crassa* (Fungal Genetic Stock Center #3200) genomic DNA, using MO5016 (5'-CCCGCGGCGGTACTTCT (SEQ ID NO:64)) and MO5013 (5'-CCGTCTCTACAGCAGGATCAGGTCAATGC (SEQ ID NO:65)), and inserted into pCR-TOPO (Invitrogen), to create pMB4809. Exon 3 was similarly amplified with MO5014 (5'-CCGTCTCACTGTACTCCTTCTGTCGCCTG (SEQ ID NO:66)) and MO5015 (5'-CACGCGTCTACTGCTCATACAACGCCCT (SEQ ID NO:67)), and cloned into the same vector to create pMB4810. The 0.9 kb SacII-BsmBI fragment from pMB4809 was ligated together with the 0.9 kb BsmBI-MluI fragment from pMB4810 into SacII-MluI-cleaved pMB4811, to create pMB4812, which expresses al-2 from the TEF1 promoter. The resulting nucleic acid coding sequence and encoded al-2 protein of pMB4812 are as follows:

(SEQ ID NO: 68)

atgtacgactacgccttcgtgcacctgaagttcaccgtgcccgcggcggtacttctcaccgctatcgcctaccccattctcaa
caggatacatctcatccaaacaggcttcctcgtcgtcgtcgcctttaccgccgctctgccatgggatgcctacttgattaagcacaaagtatggtcttac
ccaccagaagccattgttgggccgcgtttgcttggaattccctttgaagagctgttcttctttgtgatacagacttacatcacggcgctcgtatacatcct
cttcaacaagccggtgctgcacgcgttgcacctcaacaatcaacaaaacccgccagcatggatgagggttgtcaaggttaccggccaggtagtcct
cgtagccttgtcggtatggggatggaatgccgctcaggttcatcaggaaacaagctatctcggcttgatccttgtttgggcttgtccgttcttactggct
atctggaccctcgctgggcgcttcattctcagcctaccctggtacgcgacggtgctcccgatgttcctacccaccttctatctttgggcggtagacgag
tttgccttgcacaggggtacttggtccatcggatcggggacgaagctcgatttttgtctgtttggcaagttggacattgaagaagccacgttcttcctgg
tgaccaacatgctcatcgttggcggtatggccgcgttcgatcaatatctggccgtcatttacgctttcccaactctgttccccaaggtcaaccggtatcc
gacaactcatatgcttcttcaaagccgtcttatcaacacttccaggtacgatcttgagcgcattgagggcctgagagaagcggtcgagagactgcgc
ctgaagagcaggagtttttacctggccaattcgctcttttctggtcgactccgcattgacctgatcctgctgtactccttctgtcgcctggctgatgatcta
gtcgacgacgccaaatctcgccgtgaggtcttgtcctggaccgcgaagctgaaccacttccttgatctgcactacaaggacgcggacgccaccga
ggaccccaagaaaaaggcggagcgaatcgacgcctacatcaagacagcgttccctccctgtgcctaccaagccctccacctcctgcccactcaca
ttcttcctcccaagcctctttacgatctcatcaagggtttcgagatggactctcaattcaccttccacggtacttccgactctacggatctccaatacccc
atcgccgacgacaaggaccttgagaactacgctatctatgtcgccggtaccgtcggcgagctctgcatcgccctcatcatctaccactgcctgccag
acatgtcggacactcagaagcgcgagctcgagaccgccgcgtgccggatgggcatcgcgctgcagtacgtcaacatcgctcgtgacatcgtcgt
cgacgcacgtatcgggcgcgtttacttgcctaccacctggctcaagaaggaagggttgacgcacaagatggtcttggagaaccccgagggtcccg
aggtcattgagcggatgagaagacggcttttggaaaatgcgtttgagctgtatgggggcgcgaggcctgagatgcaacggataccgagcgaggc
taggggcccgatgattggtgccgttgaaaattacatggcgattggaagggtgttgagggagaggaaggaggggacggtgtttgtgaggatggag
gggagggctacggtcccgaagcgaaggaggttgagcacgctgttgagggcgttgtatgagcagtag;

(SEQ ID NO: 69)

mydyafvhlkftvpaavlltaiaypilnrihliqtgflvvvaftaalpwdaylikhkvwsyppeaivgprllgipfeelfff
viqtyitalvyilfnkpvlhalhlnnqqnppawmrvvkvtgqvvlvalsvwgwnaaqvhqetsylglilvwacpfllaiwtlagrfilslpwya
tvlpmflptfylwavdefalhrgtwsigsgtkldfclfgkldieeatfflvtnmlivggmaafdqylaviyafptlfpkvnryptthmllqsrlints
rydlerieglreaverlrlksrsfylanslfsgrlridlillysfcrladdlvddaksrrevlswtaklnhfldlhykdadatedpkkkaeridayiktaf
ppcayqalhllpthilppkplydlikgfemdsqftfhgtsdstdlqypiaddkdlenyaiyvagtvgelcialiiyhclpdmsdtqkreletaacr
mgialqyvniardivvdarigrvylpttwlkkeglthkmvlenpegpeviermrrrllenafelyggarpemqripseargpmigavenyma
igrvlrerkegtvfvrmegratvpkrrrlstllralyeq 1L. Production of pMB4846 (URA3 tef-crtZ), Encoding an *Erythrobacter* Carotene Hydroxylase.

The following carotene hydroxylase (CrtZ) ORF sequence was synthesized de novo based on protein sequence of *Erythrobacter* sp. NAP1, using *Y. lipolytica* codon bias:

(SEQ ID NO: 70)

ctctagacacaaaaatgtcttggcctgccgctattgcagttacacttggtgcccttatttttatggaattctttgcttggta
cgctcacaaatacattatgcatggatggggatggggttggcacagagaccatcacgaacctcacgacaacaaactggaaaaaaatgacc
tgttcgctgtggttttcggaacaattaacgctggtatgtatatttttggtgctctttattgggatgctttgtggtgggctgcacttggagttaat
ctttacggagtgatttacgcccttgttcatgacggactggttcatcaaagatttggaagatacgtccctaaaaacgcatacgctaaacgacttgt
tcaagcacacagattgcatcacgctactatcggtaaagaaggaggagtgtccttcggattcgttcttgctcgagaccctgctaaacttaaag
ccgaacttaaacgacaatctcaatccggagaagctattgttcgagaatccgccggagcctaaacgcgt This sequence was cleaved using XbaI and MluI and ligated to pMB4691 cut with NheI and MluI to produce pMB4846. The nucleic acid coding sequence is depicted in bold underline above. The resulting encoded CrtZ protein of pMB4846 is as follows:

(SEQ ID NO: 71)

mswpaaiavtlgalifmeffawyahkyimhgwgwgwhrdhhephdnk lekndlfavvfgtinagmyifgalywdalwwaalgvnlygviyalvhdg -continued lvhqrfgryvpknayakrlvqahrlhhatigkeggvsfgfvlardpaklk aelkrqsqsgeaivresaga 1M. Production of pMB4835 (URA3 tef-crtZ), Encoding an *S. alaskensis* Carotene Hydroxylase.

The following carotene hydroxylase (CrtZ) ORF sequence was synthesized de novo based on protein sequence of *Sphingopyxis alaskensis*, using *Y. lipolytica* codon bias:

(SEQ ID NO: 72)

ctctagacacaaaaatgagccaccgaagagatccaggacttagaagagacgacgcacgatctatggcctcctgtctca gacgagcttacaacccccacatgtccctgcctgcaattttgtttttggttcttgctactgtcattgcaatggaaggagtcgcctgggcatcc cacaaatacatcatgcacggatttggatgggcctggcacagagaccaccatgaaccccacgacaatcgactcgagaaaaacgacctgtttgc cctgttcggagccgctatgtctatttctgccttcgctattggttctcctatgattatgggtgcagctgcctggaagcctggaacttggattgg acttggtattcttctttacggtattatctacacactcgttcacgacggccttgtgcaccaaagatactttcgatgggtcccacgacgaggtt acgcaaaacgacttgttcaagcacacaaacttcatcacgctacaatcggaaaagagggaggagtttctttcggatttgtttttgctcgtg accctgctaaacttaaagccgaactgaaagcacaacgagaagctggtattgcagtcgtcagagaagcccttgctgactaaacgcgt This sequence was cleaved using XbaI and MluI and ligated to pMB4691 cut with NheI and MluI to produce pMB4835. The nucleic acid coding sequence is depicted in bold underline above. The resulting encoded CrtZ protein of pMB4835 is as follows:

mshrrdpglrrddarsmasclrrayn-phmslpailflylatviamegvawashkyimhgfgwawhrdhhephdnr lekndlfalfgaamsisafaigspmim-gaaawkpgtwiglgillygiiytivhdg-lvhqryfrwvprrgyakrlvqahklhhatigkeggvsfg fvfardpakl-kaelkaqreagiavvrealad (SEQ ID NO:73)

1N. Production of pMB4845 (URA3 tef-crtZ), Encoding an *R. biformata* Carotene Hydroxylase.

The following carotene hydroxylase (CrtZ) ORF sequence was amplified from genomic DNA extracted from *Robiginitalea biformata*:

(SEQ ID NO: 74)

cacaatctagacacaaaaatgacagtcttgatttggatcgcaattttcctggccaccttctgcttcatggaattcatggc ctggtttacgcataaatatatcatgcacggtttcctctggagccttcataaggaccaccataaaaaggaccacgacagttggtttgagcgaa acgacgccttctttctattttatgcgatagtctccatgtcctttatcggggccgccgtgaacacgggattctggcaggggtggcccatcggcct gggcatcctcgcttacgggattgcctactttatcgtacacgatatctttatccatcagcggttcaagctctttcgcaatgcgaataactggtac gcgcggggtatccgcagggcccataaaatccaccacaagcacctgggaaaagaggaaggggaatgcttcgggatgctgtttgtcccattt aagtacttccggaagacctgaacgcgtttgtg

This sequence was phosphorylated and ligated to pBluescriptSK⁻ that had been cleaved with EcoRV and dephosphorylated, to create pMB4824. The XbaI-MluI fragment from pMB4824 that contains crtZ was ligated to pMB4691 cut with NheI and MluI to produce pMB4845. The nucleic acid coding sequence is depicted in bold underline above. The resulting encoded CrtZ protein of pMB4845 is as follows:

(SEQ ID NO: 75)

mtvliwiaiflatfcfmefmawfthkyimhgflwslhkdhhkkdhdswf erndafflfyaivsmsfigaavntgfwqgwpiglgilaygiayfivhdif -continued ihqrfklfrnannwyargirrahkihhkhlgkeegecfgmlfvpfkyfr kt 1O. Production of pMB4837 (URA3 tef-crtZ), Encoding an *X. autotrophicus* Carotene Hydroxylase.

The following carotene hydroxylase (CrtZ) ORF sequence was amplified from genomic DNA extracted from *Xanthobacter autotrophicus*:

(SEQ ID NO: 76)

cacaatctagacacaaaaatgtccaccagcctcgccttcctcgtcaacgcgctcatcgtgatcgccacggtcgccgcc atggaaggggtggcctgggccgcgcacaaatatgtcatgcacggcttcggctggggctggcacaagtcccaccacgagccgcgcgaggg cgtgttcgagcgcaacgacctttatgcgctgctgttcgcaggcatcgccatcgccctcatctacgcgttccgcaatggcggcgcgctgctgtg ggtgggcgtggggatgacggtctacggcttcctttatttcttcgtgcacgacggcatcacccaccagcgctggccgttccgctacgtgccgc gcaacggctatctcaagcgcctggtgcaggcccaccggctgcaccatgcggtggatggcaaggagggctgcgtctccttcggcttcatcta tgccccgccgcctgccgacctgaaggccaagctgaagaagctgcacggcagcctgaacagaacgaggcggcggaatagacgcgt ttgtg This sequence was phosphorylated and ligated to pBluescriptSK⁻ that had been cleaved with EcoRV and dephosphorylated, to create pMB4823. The XbaI-HindIII (filled in with Klenow) fragment from pMB4823 that contains crtZ was ligated to pMB4691 cut with NheI and MluI (filled in with Klenow) to produce pMB4837. The nucleic acid coding sequence is depicted in bold underline above. The resulting encoded CrtZ protein of pMB4837 is as follows:

mstslaflvnalivi-atvaamegvawaahkyvmhgfgwgwhk-shhepregvferndlyallfagiaialiyafrngg allwvgvgmtvygfly-ffvhdgithqrwpfryvprngylkrlvqahrlhhavdgkegcvsfgfiy apppadlkaklkklhggslkqneaae (SEQ ID NO:77)

1P. Production of pMB4850 (URA3 tef-crtZ), Encoding a *P. putida* Carotene Hydroxylase.

The following carotene hydroxylase (CrtZ) ORF sequence was amplified from genomic DNA extracted from *Pseudomonas putida* (this sequence encodes a valine rather than a leucine at the second position, due to N-end rule considerations):

(SEQ ID NO: 78)

tctctctagacacaaaaatggtgttcaatctcgccatattgttcggcaccctggtggccatggagggcgttggtacgct ggctcacaagtacatcatgcatggctggggctggtggctgcaccgatcgcaccatgagccacacctgggcatgctcgaaaccaacgacct gtacctggtggccctggggctgatcgccacggcgctggtggcgctgggcaaaagtggttatgcgcctttgcagtgggtgggcggtggtgtg gcaggctatggagcactgtatgtactggcccacgacggtttctttcaccggcactggccgcgcaagccgcggccggtcaaccgctacctga aacgcttgcaccgcgcgcaccgcttgcaccatgcggtgaaggggcgcacggggagcgtgtcgttcgggttcttctatgcgccgccgctgaa ggtgttgaagcagcaattgcgcagcaggcgcagccaatcgtgaacgcgtgagacgttgtg

This sequence was phosphorylated and ligated to pBluescriptSK$^-$ that had been cleaved with EcoRV and dephosphorylated, to create pMB4847. The XbaI-MluI fragment from pMB4847 that contains crtZ was ligated to pMB4691 cut with NheI and MluI to produce pMB4850. The nucleic acid coding sequence is depicted in bold underline above. The resulting encoded CrtZ protein of pMB4850 is as follows:

```
                                        (SEQ ID NO: 79)
mvfnlailfgtlvamegvgtlahkyimhgwgwwlhrshhephlgmletn

dlylvalgliatalvalgksgyaplqwvgggvagygalyvlahdgffhrh

wprkprpvnrylkrlhrahrlhhavkgrtgsvsfgffyapplkvlkqqlr

srrsqs
```

Example 2

Engineering *Yarrowia lipolytica* for Increased Carotenoid Production

2A. Production of *Y. lipolytica* Expressing Geranylgeranylpyrophosphate Synthase and Phytoene Dehydrogenase:

MF350 (MATB ura2-21 leu2-35 ade1) was transformed with pMB4591 (tef1p-GGS1) that had been cleaved upstream of URA5 with SspI; a Ura$^+$ transformant carrying the plasmid at the ura2 locus was identified and named MF364. It was subsequently transformed with pMB4638 (tef1p-carB) that had been cleaved at ADE1 with SspI and a prototrophic transformant was chosen that harbored the plasmid at the ade1 locus. This strain was named MF502.

2B. Production of *Y. lipolytica* Expressing Geranylgeranylpyrophosphate Synthase, Phytoene Dehydrogenase and Phytoene Synthase/Lycopene Cyclase MF502 was transformed with pMB4705 (tef1p-carRP[i$^-$]) that had been treated with SspI. Ninety percent of the prototrophic transformants were very orange on YPD agar plates, and one, MF719, produced greater than 10 mg carotene per g dry cell weight (DCW) after four days of growth in YPD at 30° C.

2C. Production of *Y. lipolytica* Expressing Phytoene Synthase/Lycopene Cyclase and Phytoene Dehydrogenase:

ATCC201249 (MATA ura3-302 leu2-270 lys8-11) was transformed with SspI-cleaved pMB4628. Hundreds of Leu$^+$ colonies were pooled, re-grown, and transformed with pMB4660 (tef1p-carB) that had been cleaved upstream of URA3 with SalI. One colony that was noticeably yellow after 5 days at 30° C. on YNBglut media (per liter: 1.7 g yeast nitrogen base, 1 g monosodium glutamate, 1% glucose) plus 0.6 mM lysine was selected, named MF447, and found to produce 0.2 mg carotene per gram dry cell weight after 4 days of growth in YPD.

MF447 was challenged with 1 g/L 5-fluoroorotic acid and Ura$^-$ segregants selected. Surprisingly, they were all found to retain the identical yellow appearance of their parent, implying that the loss of a functional URA3 gene did not coincide with the loss of a functional CarB enzyme. Southern analysis demonstrates that two fragments from a KpnI-HindIII digest of MF447 DNA contain URA3p-hybridizing sequences, only one of which also hybridizes to carB. The other is absent in MF578, the Ura3$^-$ segregant chosen for further manipulation. Plasmid rescue and analysis of the DNA sequence surrounding tef-carB in MF578 confirmed the absence of nearby URA3 sequences. Plasmid rescue and analysis of the DNA sequence encompassing the carRP intron in MF447 revealed that exons 1 and 2 were contiguous and were each separated by an intron sequence that lacked the original internal SspI site (present in pMB4628). The sequence of this region shows a seven-base pair deletion (AATATTA) that would restore the proper frame to an unspliced message. Partial intron sequence comprising the sequence where the deletion occurred is shown as follows:

(SEQ ID NO: 80)

<u>ACAAACAAATGATGTGCCGCATCGCATTTTAATATTAACCATTGCATACA CAG</u>.

Predicted partial amino acid sequence comprising this intron, if unspliced, is as follows:

(SEQ ID NO: 219)

*KAW*<u>VSKQTNDVPHRILIPLHTQ</u>*HLA*....
(VSKQTNDVPHRILIPLHTQ is intron encoded)

2D. Production of *Y. lipolytica* Expressing Phytoene Synthase/Lycopene Cyclase, Phytoene Dehydrogenase and Geranylgeranylpyrophosphate Synthase:

MF578 was transformed with pMB4683 (tef1p-GGS1) that had been cleaved with SalI (upstream of URA3) or with StuI (within the GGS1 ORF). Ura$^+$ Leu$^+$ colonies in both cases appeared bright orange on YNBglut+Lysine and on YPD, and several produced greater than 4 mg carotene per gram of dry cell weight when grown as above. One, MF633, contained a single copy of the plasmid at the GGS1 locus, as inferred from Southern analysis. The others arose by non-homologous or more complex integrations.

2E. Production of *Y. lipolytica* Expressing Phytoene Synthase/Lycopene Cyclase, Phytoene Dehydrogenase and Geranylgeranylpyrophosphate Synthase:

MF364 was crossed with MF578, and spores from the resulting diploid were plated on YPD for two to three days at 30° C. White Leu$^-$ Ade$^-$ Ura$^-$ colonies were screened for the presence of tefp-carB and tefp-GGS1 and for the absence of tefp-carRP by PCR. Thirteen colonies meeting these criteria, as well as displaying resistance to 5-fluorootic acid, an indication that they harbor the ura3-302 allele, were chosen as hosts for further modifications.

One such strain, MF731, was transformed with pMB4705 cut with BbvCI, and one Leu$^+$ orange colony, MF740, produced 6 mg of β-carotene per g DCW after four days of growth in YPD at 30° C.

Another tefp-carB tefp-GGS1 strain from the same cross, MF739, was transformed with pMB4705 cut with BbvCI, and one Leu$^+$ orange colony, MF746, produced 8 mg of β-carotene per g DCW after four days of growth in YPD at 30° C. When this strain was transformed with pMB4812 (expressing *N. crassa* al-2 protein) treated with SspI, the Leu$^+$ transformants were less orange than parallel pMB4705 Leu$^+$ transformants, and after 4 days of growth in YPD, produced about half the amount of β-carotene as pMB4705 transformants. In addition, the pMB4812 transformants produced significant amounts of γ-carotene (~40% of total carotene.).

2F. Expression of a Truncated Form of HMG-CoA Reductase Results in Increased Carotenoid Production in *Y. lipolytica* Expressing Phytoene Synthase/Lycopene Cyclase, Phytoene Dehydrogenase, and Geranylgeranylpyrophosphate Synthase:

In order to increase carotenoid production, carbon flow through the isoprenoid pathway is enhanced by introducing a truncated variant of the HMG-CoA reductase gene.

MF740 was transformed with pMB4637 treated with SnaBI, and Ade$^+$ colonies were selected. One such colony, MF760, was shown to produce about 20 mg β-carotene per g DCW after four days of growth in YPD at 30° C. This strain was also the subject of several fermentor studies outlined in Example 5. In addition, MF740 was also transformed with MB4714 treated with AflII and $Ura^+$ colonies, were selected. One such colony was designated MF779 (see Example 2G). MF746 was also transformed with pMB4637 treated with SnaBI, and $Ade^+$ colonies were selected. One such colony, MF946, was shown to produce greater than 35 mg β-carotene per g DCW after four days of growth in YPD at 30° C.

MF760 was also transformed with pMB4691 (empty vector) cut with SalI, creating the prototroph MF858.

2G. Production of *Y. lipolytica* Expressing Carotene Ketolase, a Truncated Form of HMG-CoA Reductase, Phytoene Synthase/Lycopene Cyclase, Phytoene Dehydrogenase and Geranylgeranylpyrophosphate Synthase:

MF779 was transformed with either pMB4735 or pMB4741 cleaved with SnaBI, and a red prototrophic colony was chosen from each transformation: MF838 (pMB4735) and MF840 (pMB4741). After 4 days of growth in YPD, MF838 produced 25 mg canthaxanthin per g DCW, and MF840 produced 14 mg canthaxanthin and 30 mg echinenone per g DCW. Only trace levels of β-carotene were produced. These strains are the subject of fermentor studies described in Example 5.

In addition, MF740 was transformed with pMB4735 cleaved with SnaBI, and a red $Ade^+$ colony was chosen for further manipulation and designated MF889 (See example 2I).

2H. Manipulation of the *Y. lipolytica* ERG9 Gene to Enhance Carotenoid Production.

In order to decrease the expression of Erg9 (squalene synthase) in a carotenoid-producing yeast, pMB4789, containing the following cassette, was constructed using standard molecular techniques. The 4.8 kb fragment contains the *Y. lipolytica* URA3 gene flanked by the ERG9 ORF and the ERG9 terminator.

Thus this fragment comprises the sequence: GATCtcgttctgctcgggtagatc (SEQ ID NO: 82)-ERG9 (promoter and ORF)-gtgctctgcggtaagatcgACTAGTggtgtgttctgtggagcattc (SEQ ID NO:83)-URA3 (promoter, ORF, and terminator)-ccaccactgcactaccactacacCTCGAGCATGCATcaggaaggactctccctgtggt (SEQ ID NO:84)-ERG9 terminator-gtgttatggctctacgtgaagGGGCCC (SEQ ID NO:85). (Capital letters: restriction sites [engineered for assembly]) In addition, it was found that a mutation was generated during cloning that changed the coding sequence of ERG9 as follows: (cccgacgttAtccagaagaac (SEQ ID NO:86); F317I in the encoded protein).

Two overlapping fragments from this cassette, a 2.4 kb AlwNI-SmaI fragment and a 1.9 kb AlwNI-AflII fragment, were cotransformed into MF760 and $Ura^+$ colonies were selected. PCR analysis showed that one, designated MF921, contains the erg9::URA3 cassette replacing the wild type ERG9 gene. MF921 produced greater than 30 mg β-carotene per g DCW after 4 days of growth at 30° C. in YPD.

2I. Production of *Y. lipolytica* Expressing Carotene Hydroxylase, Phytoene Synthase/Lycopene Cyclase, Phytoene Dehydrogenase and Geranylgeranylpyrophosphate Synthase:

MF740 was transformed with pMB4837 cleaved with SalI, and a $Ura^+$ colony was selected and designated MF1011. MF1011 produced 6 mg of zeaxanthin and 1.5 mg of β-carotene per g DCW after 4 days of growth at 30° C. in YPD.

2J. Production of *Y. lipolytica* Expressing Carotene Hydroxylase, Carotene Ketolase, Phytoene Synthase/Lycopene Cyclase, Phytoene Dehydrogenase and Geranylgeranylpyrophosphate Synthase:

MF889 was transformed with pMB4837 cleaved with SalI, and a prototrophic colony was selected and designated MF1016. MF1016 produced 1.5 mg of astaxanthin and 3 mg of canthaxanthin per g DCW after 4 days of growth at 30° C. in YPD.

Example 3

Extraction of Carotenoids

3a: Total Extraction of Carotenoids from *Yarrowia lipolytica* Cells

*Yarrowia lipolytica* cultures to be tested for carotenoid production were grown in 20 ml YPD medium (1% yeast extract, 2% peptone, 2% glucose) in 125 flasks at 30° C. Following incubation for 72-96 hr, the cultures were harvested by centrifugation and the solvent extractions were performed to determine carotenoid form and quantity. Dry cell weights were determined by transferring 1.8 ml of each culture to an Eppendorf tube, which was then centrifuged to pellet the cells, and then the pellet washed twice with 1 ml water. After the second wash, the cells were resuspended in water and transferred to a pre-weighed snap-cap tube with a hole poked in the top, frozen, and then lyophilized overnight. After drying to constant weight, the tube was weighed in order to calculate dry cell weight (mg dry cell weight/ml).

The carotenoid content of the culture was calculated by solvent extraction from 0.25 ml of culture from the same shake flask culture. This 0.25 ml culture sample was transferred to a 2 ml screw-cap tube, the cells pelleted, and the supernatant aspirated. Such pelleted cells may be extracted immediately or frozen at −80° C. and stored.

An equal volume of cubic zirconia beads was added to cell pellets, along with 1 ml ice-cold extraction solvent (a 50/50 v/v mix of hexane and ethyl acetate containing 0.01% butylhydroxytoluene (BHT)). The mixture was then agitated (Mini-BeadBeater-8, BioSpec Products, Inc.) at maximum speed for 5 minutes at 4° C. The mixture was then spun at maximum speed for 1 minute, and the supernatant was collected and deposited in a cold 16 ml glass vial.

The remaining cell debris was re-extracted at least three times, without the addition of zirconia beads; all supernatants were pooled in the 16 ml glass vial. Following extraction, the glass vial was spun for 5 minutes at 2000 rpm at 4° C. in a Sorvall tabletop centrifuge, and the supernatant was transferred to a new cold 16 ml glass vial. A Speed Vac was used to concentrate the supernatant (room temperature in dark), and the samples were stored at −20° C. or −80° C. until immediately before HPLC analysis. Prior to HPLC analysis, the samples were resuspended in 1 ml ice-cold solvent and then transferred to a cold amber vial. Throughout the protocol, care was taken to avoid contact with oxygen, light, heat, and acids.

The use of a hexane:ethyl acetate (50:50) mixture to extract carotenoids efficiently extracted all carotenoids analyzed from *Yarrowia* even though the carotenoids possessed different polarity levels. For instance, in a strain containing β-carotene, γ-carotene, echinenone, and canthaxanthin, a hexane: ethyl acetate (50:50) mixture efficiently extracted all carotenoids even though echinenone and canthaxanthin, respectively, are progressively more polar than either β-carotene or γ-carotene. Given the high efficiency of extraction observed for all carotenoids with 50:50 hexane:ethyl acetate, these conditions were chosen as a "100%" standard against which the extraction efficiency of other conditions could be compared.

3B. Extraction of β-carotene from *Y. lipolytica* MF858.

*Y. lipolytica* strain MF858 was grown as described in Example 3a and found to contain β-carotene as the dominant carotenoid. Extraction and breakage with hexane yielded an equal amount of β-carotene as was observed with a 50:50 hexane:ethyl acetate mixture.

3C. Extraction of Mixed Carotenoids from *Y. lipolytica* MF838.

*Y. lipolytica* strain MF838 (example 2g) had previously been found to contain the following types carotenoids when extracted as described in Example 3a: β-carotene, γ-carotene, echinenone, and canthaxanthin. Extraction with 750 μl of hexane resulted in the following extraction efficiencies for each of the carotenoids (extraction efficiency is reported independently for each of the carotenoid species based on the total amount found by hexane:ethyl acetate extraction): β-carotene (79.3%), γ-carotene (82.4%), echinenone (42.6%), and canthaxanthin (8.0%).

When an identical aliquot of MF838 was extracted with 1 ml of ethanol (95%), the extraction efficiency of the same four carotenoids was as follows: β-carotene (53.6%), γ-carotene (71.3%), echinenone (39.9%), and canthaxanthin (28.0%). Thus ethanol can be used to extract both polar and nonpolar carotenoids from fungi (e.g. *Y. lipolytica*).

Example 4

Quantification of Carotenoid Production by HPLC

For carotenoid analysis, samples were resuspended in ice-cold extraction solvent (a 50/50 v/v mix of hexane and ethyl acetate containing 0.01% butylhydroxytoluene (BHT)). An Alliance 2795 HPLC (Waters) equipped with a Waters XBridge C18 column (3.5 pa, 2.1×50 mm) and Thermo Basic 8 guard column (2.1×10 mm) was used to resolve carotenoid at 25° C.; authentic carotenoid samples were used as standards. The mobile phases and flow rates are shown below (Solvent A=Ethyl Acetate; Solvent B=Water; Solvent C=Methanol; Solvent D=Acetonitrile). The injection volume was 10 μL. The detector is a Waters 996 photodiode array detector. The retention times for lipophilic molecules include astaxanthin (1.159 min), zeaxanthin (1.335), β-apo-8'-carotenal (2.86 min), ergosterol (3.11 min), lycopene (3.69 min), β-carotene (4.02 min), Canthaxanthin (2.50 min), Echinenone (3.38 min), and phytoene (4.13 min). Astaxanthin, zeaxanthin, β-apo-8'-carotenal, lycopene, β-carotene, canthaxanthin, and echinenone are detected at 475 nm, whereas ergosterol and phytoene were detected at 286 nm.

TABLE 28

Retention Times for Lipophilic Molecules

| Time (min) | Flow (mL/min) | % A | % B | % C | % D | Curve |
|---|---|---|---|---|---|---|
| | 0.50 | 0.0 | 20.0 | 0.0 | 80.0 | |
| 3.00 | 1.00 | 20.0 | 0.0 | 0.0 | 80.0 | 6 |
| 4.50 | 1.00 | 80.0 | 0.0 | 20.0 | 0.0 | 6 |
| 5.00 | 1.00 | 0.0 | 0.0 | 100.0 | 0.0 | 6 |
| 6.00 | 1.00 | 0.0 | 0.0 | 100.0 | 0.0 | 6 |
| 6.50 | 1.00 | 0.0 | 20.0 | 0.0 | 80.0 | 6 |
| 7.00 | 0.50 | 0.0 | 20 | 0.0 | 80.0 | 6 |

Example 5A

2 Liter Fed-Batch Fermentation of β-Carotene Producing Strain MF760

FIG. 9A depicts the production and intracellular accumulation of phytoene and β-carotene by strain MF760 (Example 2F) when grown in fed-batch fermentation on various carbon sources. Fermentation medium and process parameters are described below. Carbon sources used were glucose, glycerol, or olive oil. Feeding was initiated during the early exponential growth phase at a rate of 15.2 ml/hr. This feed rate either continued until feed exhaustion or, when the dissolved oxygen (dO2) level of the culture reached 20% saturation, feed was added to maintain the dO2 at 20% (DO controlled feed). As seen in FIG. 9*a*, β-carotene accumulates in all fermentations from 1.5 to 2.2% of DCW weight. Substantial phytoene accumulation was observed in the constant feed fermentations but not in the DO controlled feed fermentations.

FIG. 9B depicts dry cell weight accumulation during the course of the fermentations. For each carbon source examined, constant feeding resulted in greater biomass production relative to the DO controlled feed fermentation. This was especially true for the olive oil fed-batch fermentations where the constant feed fermentation reached greater than 150 g/L DCW. This was expected as *Y. lipolytica* has been reported to accumulate greater than 40% its biomass as lipid when grown on oils under conditions of excess carbon and oxygen limitation (Pananikolaou et al., Appl. Microbiol. Biotechnol. 58:p308, 2002) and was independent of nitrogen concentration.

Batch Medium—1 L

| | | |
|---|---|---|
| Carbon Source (one of the following): | Glucose | 60 g |
| | Glycerol | 75 g |
| | Olive Oil | 50 ml |
| Yeast Nitrogen Base w/o Amino Acids and $(NH_4)_2SO_4$ | | 4.1 g |
| $(NH_4)_2SO_4$ | | 6 g |
| Uracil | | 72 mg |
| Antifoam 204 (Sigma catalog A6426) | | 5 ml |

Feed Medium—1 L

| Carbon Source (one of the following): | |
|---|---|
| Glucose | 500 g |
| Glycerol | 500 g |
| Olive Oil | 500 ml |
| $(NH_4)_2SO_4$ | 72 g |
| $KH_2PO_4$ | 13.5 g |
| $MgSO_4$ | 5 g |
| Inositol | 70 mg |
| Thiamine | 10 mg |
| Uracil | 900 mg |
| Trace Metal Solution | 40 ml |
| $FeCl_3•6H_2O$ | 2.7 g/L |
| $ZnCl_2•4H_2O$ | 2.0 g/L |
| $CaCl_2•2H_2O$ | 2.0 g/L |
| $Na_2MoO_4•2H_2O$ | 2.0 g/L |
| $CuSO_4•5H_2O$ | 1.9 g/L |
| $H_3BO_3$ | 0.5 g/L |
| $MnSO_4•H_2O$ | 2.23 g/L |
| Concentrated HCl | 10 ml/L |
| Vitamins Solution | 40 ml |
| Pantothenic acid | 5.4 g/L |
| Pyridoxine | 1.4 g/L |
| Niacin | 6.1 g/L |
| Folic acid | 0.04 g/L |
| Biotin | 0.06 g/L |

Fermentation Parameters:
- pH 5.5, controlled
- Temp—30° C.
- Air Flow—1.4 lpm
- Agitation—1200 rpm Inoculum—200 ml overnight culture grown in YEP+5% glucose Example 5B 2 Liter Fed-Batch of β-Carotene Producing Strain MF760

FIG. 9*c* depicts the production and intracellular accumulation of β-carotene by strain MF760 when grown in fed-batch fermentation. In this fermentation, additions of olive oil were combined with a glucose feeding protocol. Medium and process parameters are described below. Both glucose and olive oil were present in the batch medium. Feeding of the glucose containing feed medium was initiated during the early exponential growth phase at a rate of 15.2 ml/hr, this feed rate continued until feed exhaustion. 25 ml of olive oil was added at 24, 48, and 72 hr.

As shown in FIG. 9*c*, this combined glucose and oil feeding protocol resulted in substantially higher DCW production when compared to glucose as the sole carbon source (example 5a). In addition, β-carotene accumulated to over 5% of the DCW at the end of the fermentation, higher then either the glucose or oil fermentations of example 5a.

Batch Medium—1 L

| | |
|---|---|
| Glucose | 40 g |
| Olive Oil | 50 ml |
| Yeast Nitrogen Base w/o Amino Acids and $(NH_4)_2SO_4$ | 4.1 g |
| $(NH_4)_2SO_4$ | 6 g |
| Uracil | 72 mg |
| Antifoam 204 | 5 ml |

Feed Medium—1 L

| | |
|---|---|
| Glucose | 500 g |
| $(NH_4)_2SO_4$ | 72 g |
| $KH_2PO_4$ | 13.5 g |
| $MgSO_4$ | 5 g |
| Inositol | 70 mg |
| Thiamine | 10 mg |
| Uracil | 900 mg |
| Trace Metal Solution | 40 ml |
| Vitamins Solution | 40 ml |

Olive Oil Additions - 25 ml at 24, 48, and 72 hr

Fermentation Parameters:
- pH 5.5, controlled
- Temp—30° C.
- Air Flow—1.4 lpm
- Agitation—1150 rpm Inoculum—200 ml overnight culture grown in YEP+5% glucose 2.5% olive oil Example 5C 2 Liter Fed-Batch of Canthaxanthin Producing Strain MF840

FIG. 9*d* depicts the production and intracellular accumulation of canthaxanthin, echinenone and β-carotene by strain 840 (Example 2g) when grown in fed-batch fermentation. Medium and process parameters are described below. Both glucose and olive oil were present in the batch medium. Feeding of the glucose containing feed medium was initiated during the early exponential growth phase at a rate of 15.2 ml/hr; this feed rate continued until the dissolved oxygen reached 20%, at which time feed was added to maintain the dO2 at 20% (DO controlled feed) for the remainder of the fermentation.

As seen in FIG. 9*d*, the combined total amount of canthaxanthin, echinenone and β-carotene represented over 8% of the DCW at the end of the fermentation and demonstrates the ability of genetically engineered *Y. lipolytica* to produce and accumulate significant amounts of carotenoids.

Batch Medium—1 L

| | |
|---|---|
| Glucose | 40 g |
| Olive Oil | 50 ml |
| Yeast Nitrogen Base w/o Amino Acids and $(NH_4)_2SO_4$ | 4.1 g |
| $(NH_4)_2SO_4$ | 6 g |
| Antifoam 204 | 5 ml |

Feed Medium—1 L

| | |
|---|---|
| Glucose | 500 g |
| $(NH_4)_2SO_4$ | 72 g |
| $KH_2PO_4$ | 13.5 g |
| $MgSO_4$ | 5 g |
| Inositol | 70 mg |
| Thiamine | 10 mg |
| Trace Metal Solution | 40 ml |
| Vitamins Solution | 40 ml |

Fermentation Parameters:
- pH 5.5, controlled
- Temp—30° C.
- Air Flow—1.4 lpm
- Agitation—1150 rpm Inoculum—200 ml overnight culture grown in YEP+5% glucose+2.5% olive oil.

Example 5D

2 Liter Fed-Batch of Canthaxanthin Producing Strain MF838

FIG. 9*e* depicts the production and intracellular accumulation of canthaxanthin and echinenone by strain MF838 (Example 2g) in fed-batch fermentation together with DCW levels. This example demonstrates the advantage of a two phase feeding protocol in which the first phase of feeding is designed to maintain excess carbon and oxygen limited conditions, while the second phase of feeding results in oxygen excess conditions via carbon limitation.

Fermentations A and B are depicted on FIG. 9*e*. Medium and process parameters are described below. In both fermentations, feeding of the glucose containing feed medium was initiated during the early exponential growth phase at a rate of 22.8 ml/hr. In fermentation A, this feed rate continued until the dissolved oxygen reached 20%, at which time feed was added to maintain the dO2 at 20% (DO controlled feed) for the remainder of the fermentation. In fermentation B, the constant feed rate was maintained such that glucose was in excess, and dO2 level was essential zero, until approximately hour 40 of the fermentation. At that time feed was added to maintain the dO2 at 20% (DO controlled feed) for the remainder of the fermentation. As seen in FIG. 9*e*, the extended period of carbon excess and oxygen limitation resulted in higher peak DCW, altered kinetics of canthaxanthin production, and produced a higher final level canthaxanthin—over 3.5% of DCW.

Batch Medium—1 L

| | |
|---|---|
| Glucose | 40 g |
| Yeast Nitrogen Base w/o Amino Acids and (NH$_4$)$_2$SO$_4$ | 8.2 g |
| (NH$_4$)$_2$SO$_4$ | 6 g |
| Antifoam 204 | 5 ml |

Feed Medium—1 L

| | |
|---|---|
| Glucose | 500 g |
| (NH$_4$)$_2$SO$_4$ | 72 g |
| KH$_2$PO$_4$ | 13.5 g |
| MgSO$_4$ | 5 g |
| Inositol | 70 mg |
| Thiamine | 10 mg |
| Trace Metal Solution | 40 ml |
| Vitamins Solution | 40 ml |

Fermentation Parameters:
 pH 5.5, controlled
 Temp—30 C
 Air Flow—1.4 lpm
 Agitation—1150 rpm
Inoculum—200 ml overnight culture grown in YEP+5% glucose Example 6

Introduction of Heterologous Carotene Hydroxylase and Carotene Ketolase Genes into *Y. lipolytica* Strains Producing Carotenoid for Production of Astaxanthin For introduction of carotene hydroxylase and carotene ketolase into carotenoid producing *Y. lipolytica*, pMB4692 and pMB4698, described as in Example 1E and 1F above, can be sequentially introduced into MF740 or MF746 (described in Example 2E). For the introduction of pMB4692, the plasmid may be cleaved with SalI or BsrGI to direct integration at the ura3 locus, or with XbaI to promote random integration, selecting for uracil prototrophy. Ura$^+$ transformants from MF740 or MF746 harboring pMB4692 are screened for zeaxanthin production in YPD. Zeaxanthin-producing cells are transformed with pMB4698 (which can be cleaved with PpuMI, SspI or BbvCI to direct integration at the ade1 locus, or with EcoRV to promote random integration) and prototrophic colonies are screened for astaxanthin production.

Alternatively, the order of plasmid transformation may be reversed wherein pMB4698 is transformed first and transformants are selected for adenine prototrophy. Ade$^+$ transformants from MF740 or MF746 harboring pMB4698 are screened for canthaxanthin production. Canthaxanthin-producing MF740[pMB4698] or MF746[pMB4698] cells are transformed with pMB4692 and prototrophic colonies are screened for astaxanthin production.

In another approach, the carotenoid ketolase and carotenoid hydroxylase genes from *P. marcusii* can be introduced into a Leu2$^-$ version of MF740 or MF746, in order to convert β-carotene into astaxanthin. *P. marcusii* genomic DNA is amplified with two primers.

```
                                              (SEQ ID NO: 87)
CrtZfwd: 5' CACACCGTCTCAAatgaccaatttcctgatcgtcgtc
                                              (SEQ ID NO: 88)
CrtZrev: 5' CACACAGATCtcacgtgcgctcctgcgcc,
```

and the resulting fragment is cleaved with BsmBI, modified with the Klenow fragment of DNA polymerase, and cleaved with BglII. This fragment is inserted into PmlI- and BamHI-cleaved pINA1269 (J. Mol. Microbiol. Biotechnol. 2 (2000): 207-216), containing the hp4d promoter, the XPR2 terminator, the selectable LEU2 gene, and sequences necessary for selection and propagation in *E. coli*. The resulting plasmid "pA" contains sequences encoding carotene hydroxylase from *P. marcusii* (crtZ gene) (Genbank accession: CAB56060.1) under the control of the hp4d promoter.

"pYEG1TEF" is modified by substituting the LIP2 terminator for the XPR2 terminator as follows. pINA1291 is digested with AvrII, modified with the Klenow fragment of DNA polymerase, and cleaved with EcoRI, and the small LIP2t containing fragment is ligated to "pYEG1TEF" that has been digested with SacII, modified with T4 DNA polymerase in the presence of dNTP, and cleaved with EcoRI. The resulting plasmid is named "pYEG1TEF-LIP2t".

In order to amplify the carotenoid ketolase gene, *P. marcusii* genomic DNA is amplified with two primers.

```
                                              (SEQ ID NO: 89)
CrtWfwd: 5' CACACCCTAGGCCatgagcgcacatgccctgc
                                              (SEQ ID NO: 90)
CrtWrev: 5' CACACAAGCTTtcatgcggtgtcccccttg,
```

and the resulting fragment is cleaved with AvrII and HindIII, and inserted into AvrII- and HindIII-cleaved "pYEG1TEF-LIP2t". The resulting plasmid, "pBt", contains sequences encoding the carotene ketolase (crtW gene) (Genbank accession: CAB56059.1) under the control of the constitutive TEF1 promoter.

In order to combine the two expression cassettes into a single plasmid, "pBt" is cleaved with ClaI, modified with the Klenow fragment of DNA polymerase, and cleaved with EcoRI, and the crtW-containing fragment is isolated, mixed with the phosphorylated oligonucleotide adaptor pair:

```
5' AATTCGCGGCCGCT        (SEQ ID NO: 91)
and

5' AGCGGCCGCG,           (SEQ ID NO: 92)
```

cleaved with NotI, and ligated to NotI-digested "pA". The resulting plasmid, "pABt", contains both the TEF1p/crtW/LIP2t cassette and the hp4d/crtZ/XPR2t cassette as well as the selectable LEU2 gene.

"pABt" can be introduced into MF740 or MF746 and transformants selected for leucine prototrophy.

Example 7

Partial Inactivation of *Y. lipolytica* ERG9 Gene Encoding Squalene Synthase Results in Increased Carotenoid Production 7A. In order to partially inactivate the ERG9 gene encoding squalene synthase, the neighboring FOL3 gene is disrupted, resulting in a folinic acid requirement. This strain is then transformed with a mutagenized fragment of DNA partially spanning the two genes, and Fol+ transformants are screened for decreased squalene synthase activity.

The following oligonucleotides are synthesized:

```
                                   (SEQ ID NO: 93)
PRIMER K 5'-CCTTCTAGTCGTACGTAGTCAGC;

                                   (SEQ ID NO: 94)
PRIMER L 5'-CCACTGATCTAGAATCTCTTTCTGG
```

and used to amplify a 2.3 kb fragment from *Y. lipolytica* genomic DNA spanning most of the FOL3 gene, using Pfu polymerase. The resulting fragment is cleaved with XbaI and phosphorylated, then ligated into pBluescriptSK− that has been cleaved with KpnI, treated with T4 DNA polymerase (T4pol) in the presence of dNTPs, and subsequently cleaved with XbaI. The resultant plasmid, designated pBS-fol3, is then cleaved with Acc65I and EcoRI, treated with T4pol as above, and ligated to the 3.4 kb EcoRV-SpeI ADE1 fragment (treated with T4pol) from pMB4529.

The resulting plasmid, pBSfol3Δade, can be cleaved with BsiWI and XbaI to liberate a 5.5 kb fragment that is used to transform MF740 or MF746 to adenine prototrophy. Resulting Ade+ transformants are screened for a folinic acid requirement, and for homologous integration by PCR analysis.

Strains that harbor the resultant fol3ΔADE1 allele can be transformed with a 3.5 kb DNA fragment generated by mutagenic PCR amplification using the primers:

```
                                   (SEQ ID NO: 95)
PRIMER M 5'-GGCTCATTGCGCATGCTAACATCG;

                                   (SEQ ID NO: 96)
PRIMER N 5'-CGACGATGCTATGAGCTTCTAGACG,
```

and *Y. lipolytica* genomic DNA as template. The resulting fragment containing the N-terminal three-quarters of the FOL3 ORF and the C-terminal nine-tenths of the ERG9 ORF is used to transform strains. The resulting Fol+ Ade− transformants are screened for decreased squalene synthase activity by sensitivity to agents such as zaragozic acid, itraconazole, or fluconazole. Additionally, the resulting transformants are screened for increased carotenoid production.

7B. Alternatively, the PCR fragment produced in 7A could be cloned and altered in such a way as to remove the 3'-untranslated region of ERG9 gene. Replacement of the fol3ΔADE1 disruption by this fragment results in decreased expression of squalene synthase [Schuldiner et al. (2005), Cell 123:507-519] [Muhlrad and Parker (1999), RNA 5:1299-1307], which can be confirmed as in 7A. This approach may also be used in a Fol+ Ade− strain, using the ADE1 marker to disrupt the ERG9 3'-UTR.

7C. In still another approach, partially defective ERG9 alleles can be identified in *S. cerevisiae* using plasmid shuffling techniques [Boeke et al. (1987), Methods Enzymol. 154:164-175], and using drug sensitivities as a phenotype. Defective genes can be transferred to *Y. lipolytica* using standard molecular genetic techniques.

Example 8

Treatment of *Y. lipolytica* Strains Producing Carotenoid with Inhibitor of an Isoprenoid Biosynthesis Competitor Polypeptide Results in Increased Carotenoid Production Cultures produced in Example 2 are treated with the squalene synthase inhibitor, zaragozic acid (zaragozic acid at 0.5 μM) and monitored for β-carotene production, as described above.

Example 9

Constructing an Oleaginous Strain of *Saccharomyces cerevisiae*

The genes encoding the two subunits of ATP-citrate lyase from *N. crassa*, the AMP deaminase from *Saccharomyces cerevisiae*, and the cytosolic malic enzyme from *M. circinelloides* are overexpressed in *S. cereviseae* strains in order to increase the total lipid content. Similar approaches to enhance lipid production could be employed in other host organisms such as *Xanthophyllomyces dendrorhous* (*Phaffia rhodozyma*), using the same, homologous, or functionally similar oleaginic polypeptides.

Qiagen RNAEasy kits (Qiagen, Valencia, Calif.) are used to prepare messenger RNA from lyophilized biomass prepared from cultures of *N. crassa*. Subsequently, RT-PCR is performed in two reactions containing the mRNA template and either of the following primer pairs. acl1:

```
                                        (SEQ ID NO: 97)
1fwd: 5' CACACGGATCCTATAatgccttccgcaacgaccg
                                        (SEQ ID NO: 98)
1rev: 5' CACACACTAGttaaatttggacctcaacacgaccc

acl2:
                                        (SEQ ID NO: 99)
2fwd: 5' CACACGGATCCAATATAAatgtctgcgaagagcatcctcg
                                       (SEQ ID NO: 100)
2rev: 5' CACACGCATGCttaagcttggaactccaccgcac
```

The resulting fragment from the acl1 reaction is cleaved with SpeI and BamHI, and that from the acl2 reaction is cleaved with BamHI and SphI, and both are ligated together into YEp24 that has been digested with NheI and SphI, creating the plasmid "p12". The bi-directional GAL1-10 promoter is amplified from *S. cerevisiae* genomic DNA using the primers.

```
                                       (SEQ ID NO: 101)
gal10: 5' CACACGGATCCaattttcaaaaattcttacttt

ttttttggatggac
                                       (SEQ ID NO: 102)
gal1: 5' CACACGGATCCtttttctccttgacgttaaagtataga

gg,
```

and the resulting 0.67 kb fragment is cleaved with BamHI and ligated in either orientation to BamHI-digested "p12" to create "p1gal2" and "p2gal1", containing GAL1-acl1/GAL10-acl2 and GAL10-acl1/GAL1-acl2, respectively (Genbank accession: acl1: CAB91740.2; acl2: CAB91741.2).

In order to amplify the *S. cereviseae* gene encoding AMP deaminase and a promoter suitable for expressing this gene, *S. cerevisiae* genomic DNA is amplified using two primer pairs in separate reactions:

AMD1 ORF:

(SEQ ID NO: 103)
AMD1FWD: 5' CACACGAGCTCAAAAatggacaatcaggctacacagag (SEQ ID NO: 104)
AMD1rev: 5' CACACCCTAGGtcacttttcttcaatggttctcttg aaattg GAL7p:

(SEQ ID NO: 105)
gal7prox: 5' CACACGAGCTCggaatattcaactgtttttttttatc atgttgatg (SEQ ID NO: 106)
gal7dist: 5' CACACGGAtccttcttgaaaatatgcactctatat cttttag, and the resulting fragment from the AMD1 reaction (2.4 kb) is cleaved with SacI and AvrII, and that from the GAL7 reaction (0.7 kb) is cleaved with BamHI and SphI, and both are ligated together into YEp13 that has been digested with NheI and BamHI, creating the plasmid "pAMPD". This plasmid carries the *S. cerevisiae* gene, AMD1, encoding AMP deaminase, under the control of the galactose-inducible GAL7 promoter.

Messenger RNA is prepared from lyophilized biomass of *M. circinelloides*, as described above, and the mRNA template is used in a RT-PCR reaction with two primers:

(SEQ ID NO: 107)
MAEfwd: 5' CACACGCTAGCTACAAAatgttgtcactcaaacgcata gcaac (SEQ ID NO: 108)
MAErev: 5' CACACGTCGACttaatgatctcggtatacgagaggaac, and the resulting fragment is cleaved with NheI and SalI, and ligated to XbaI- and XhoI-digested pRS413TEF (Mumberg, D. et al. (1995) Gene, 156:119-122), creating the plasmid "pTEFMAE", which contains sequences encoding the cytosolic $NADP^+$-dependant malic enzyme from *M. circinelloides* (E.C. 1.1.1.40; mce gene; Genbank accession: AY209191) under the control of the constitutive TEF1 promoter.

The plasmids "p1gal2", "pAMPD", and "pTEFMAE" are sequentially transformed into a strain of *S. cereviseae* to restore prototrophy for uracil ("p1gal2"), leucine ("pAMPD"), and histidine ("pTEFMAE") (Guthrie and Fink *Methods in Enzymology* 194:1-933, 1991). The resulting transformants are tested for total lipid content following shake flask testing in either synthetic complete (SC) medium lacking uracil, leucine and histidine, as described in Example 3, or in a 2-step fermentation process. In the 2-step process, 1.5 ml of cells from an overnight 2 ml roll tube culture containing SC medium lacking uracil, leucine and histidine are centrifuged, washed in distilled water, and resuspended in 20 ml of a nitrogen-limiting medium suitable for lipid accumulation (30 g/L glucose, 1.5 g/L yeast extract, 0.5 g/L $NH_4Cl$, 7 g/L $KH_2PO_4$, 5 g/L $Na_2HPO_4$-$12H_2O$, 1.5 g/L $MgSO_4$-$7H_2O$, 0.08 g/L $FeCl_3$-$6H_2O$, 0.01 g/L $ZnSO_4$-$7H_2O$, 0.1 g/L $CaCl_2$-$2H_2O$, 0.1 mg/L $MnSO_4$-$5H_2O$, 0.1 mg/L $CuSO_4$-$5H_2O$, 0.1 mg/L $Co(NO_3)_2$-$6H_2O$; pH 5.5 (J Am Oil Chem Soc 70:891-894 (1993)).

Intracellular lipid content of the modified and control *S. cerevisiae* strains is analyzed using the fluorescent probe, Nile Red (J Microbiol Meth (2004) 56:331-338). In brief, cells diluted in buffer are stained with Nile Red, excited at 488 nm, and the fluorescent emission spectra in the wavelength region of 400-700 nm are acquired and compared to the corresponding spectra from cells not stained with Nile Red. To confirm results from the rapid estimation method, the total lipid content is determined by gas chromatographic analysis of the total fatty acids directly transmethylesterified from dried cells, as described (Appl Microbiol Biotechnol. 2002 November; 60(3):275-80). Non-transformed *S. cerevisiae* strains produce 6% and 10% total lipid (dry cell weight basis) after growth in YPD and lipid accumulation medium, respectively. Yeast strains expressing the multiple oleaginic polypeptides produce 17% and 25% total lipid following growth in YPD and lipid accumulation medium, respectively.

Example 10

Introduction of Heterologous Carotene Hydroxylase into *Y. lipolytica* Strains Producing Carotenoid for Production of Zeaxanthin MF578 (tef-carRP tef-carB) was transformed with pMB4692 that had been cleaved with SalI. Several $Ura^+$ colonies inferred to contain tef-crtZ by PCR analysis were able to produce zeaxanthin in YPD shake flasks, and in one case, all of the β-carotene was depleted.

Example 11

Regulatory Sequences

Sequences which consist of, consist essentially of, and comprise the following regulatory sequences (e.g. promoters and terminator sequences, including functional fragments thereof) may be useful to control expression of endogenous and heterologous genes in engineered host cells, and particularly in engineered fungal cells described herein.

Met2 promoter (SEQ ID NO: 109)
5'cctctcactttgtgaatcgtgaaacatgaatcttcaagccaagaatgttaggcaggggaagctttctttcagactttttggaattggtcctcttttggac attattgacgatattattatttttccccgtccaatgttgacccttgtaagccattccggttctggagcgcatctcgtctgaaggagtcttcgtgtggctata actacaagcgttgtatggtggatcctatgaccgtctatatagggcaacttttgctcttgttcttccccctccttgagggacgtatggcaatggctatgaca actatcgtagtgagcctctataacccattgaagtacaagtcctccaccttgctgccaaactcgcgagaaaaaaagtccaccaactccgccgggaaat actggagaacacctctaagacgtgggcttctgcacctgtgtggcttgggtctgggttttgcgagctctgagccacaacctaaggacggtgtgattgg -continued gagataagtagtcgttggttttctaatcgcacgtgatatgcaagccacacttataacacaatgaagacaggccgatgaactgcatgtcattgtacaggt gcggagagcaagaaactctggggcggaggtgaaagatgagacaaaaagcctcaggtgcaaggtagggagttgatcaacgtcaaacacaaataa tctaggttgttaggcagctaaacatgtatataactgggctgccaccgagtgttacttgtcattaacgtcgcattttcgcctacacaaaatttgggttactcg ccactacactgctcaaatctttcagctgtgcaacaagctttcaggtcacacatagactcgcataaggacccgggtcatctgttattctccactggtaaac caatagtcctagctgatttgggtacagaagctcactttcacatcttttcatcttcttctacaaccatc Met3 promoter (SEQ ID NO: 110)

5'atctgtgaggagcccctggcgtcactgtcgactgtgccggcatttctgatggtatttccagccccgcagttctcgagacccccgaacaaatgtgcc acacccttgccaaaatgacgaatacacggcgtcgcggccgggaatcgaactcttggcaccgccacaggagtgaaatttgaaatttgaaatttgaaa aataattcacattttgagtttcaataatatatcgatgaccctcccaaaagacccaagtcgagacgcaaaaaaacacccagacgacatggatgcggtc acgtgaccgcaaaaaccgccccggaaatccgtttgtgacgtgttcaattccatctctatgtttttctgcggtttctacgatgccgcaatggtggccaatg tgcgtttcactgccgtagtggctggaacaagccacagggggtcgtcgggccaatcagacggtccctgacatggttctgcgccctaacccgggaac tctaacccccgtggtggcgcaatcgctgtcttcatgtgctttatctcacgtgacggctggaatctggcagaagacggagtatgtacattttgtcgttggt cacgttatccctaaaacgtggtgtttaaactggtcgaatgcttggcccagaacacaagaagaaaaaaaacgagacaacttgatcagtttcaacgccac agcaagcttgtcttcactgtggttggtcttctccacgccacaagcaacacgtacatgtcaattacgtcagggtcttttaagttctgtggcttttgaaccagt tataaagaaccaaccacccttttttcaaagctaatcaagacggggaaattttttttttgatatttttcgaca Met6 promoter (SEQ ID NO: 111)

5'gatactgcagacggtgcattacttacccgtgtcgactgagagtctacttggtacttggccctgtggctaagcagtatttgagcaacaatgcaatgca gttgctgactcggttccagatccccttgccccgatgtgtggaagcgttgtttttggggcaagggcatgtgggggctgcatcatactgtggctggggcc gttggaagagccgtcggcagcgagcctgagtcgcttctcggggccttattcccccgcctctaggtcagcggcggccgaagtgtcgtactcagctc gcctgtacagtatgacgtgaccgaatagcctctggaaggttggagaagtacagtgcaaaaaaaagttgcaaaatttcattttagcgttcgatccgacg tggcagttggacaatgaatcgatggagacatgatcatgggcagaaatagaaggtctccatgttcaatggcagtaccaattgagcaacagacgggtc gacaggcggcgggcacaccatccgccctccacatggcgcaatcgtcagtgcagcgattcgtactcggattgcatcatgttgcaccgaaagttggg gcccgcacgttggagaggcgaggagccagggttagctttggtggggtcctttgttgtcacgtggcatcagcgaatggcgtcctccaatcagggcc gtcagcgaagtcggcgtgtgatagtgcgtggggagcgaatagagtttctggggggggcggcccaaaacgtgaaatccgagtacgcatgtaga gtgtaaattgggtgtatagtgacattgtttgactctgaccctgagagtaatatataatgtgtacgtgtccccctccgttggtcttcttttttttctcctttt ctcctaaccaacacccaaactaatcaatc Met25 promoter (SEQ ID NO: 112)

5'aagtcgtattaacataactttccttacatttttttaaagcacgtcactatccacgtgacctagccacgcgataccaagtattcatccataatgacacact catgacgtccggaggacgtcatcatcgtccagtcacgtgccaaggcacatgactaatcataacaccttatgactagcttctgaatcgctacacagttc caattcgcaaataaactcgaaatgacgaaatgccataataaaaatgacgaaactcgagattgagagcagcacatgcactgaagtggtggacaacc agcgtatccggagacacgacggatccagcaccatggaagctggccgaaaaagagatccccagcacattgagcaaccaagtcagctcaattgagt aacatcacacactcagatcgagtctgatggtggtcccctttgttccttcacttgaaaaataattgaaaataacaataacaataaaaataaaaacaaaat aaaaataaaaataaaaataaaaataaaaaaatatataaaaaaaccttgccgcatttagcgtcagccacccccgcattgacctgagtacgttggattgacc ccgatcctgcacgtcgagcgtggtcggccaaaaagcgcccgtggctggtgagtcagaaatagcagggttgcaagagagagctgcgcaacgagc aataaacggtgtttttttcgcttctgtgctgcttagagtggagagccgaccctcgccatgctcacgtgaccattcacgtggttgcaaactccaccttagt atagccgtgtccctctcgctacccattatcgcatcgtactccagccacatttttttgttccccgctaaatccggaaccttatctgggtcacgtgaaattgc aatctcgacaggaggttatacttatagagtgagacactccacgcaaggtgttgcaagtcaattgacaccacctcacctcagactaacatccaca Pox2 promoter (SEQ ID NO: 113)

5'gaatctgcccccacatttatctccgcttttgactgtttttctccccccctttcacactctgcttttggctacataaaccccgcac cgtttggaactctg ttggtccggggaagccgccgttaggtgtgtcagatggagagcgccagacgagcagaaccgagggacagcggatcgggggagggctgtcacgtga cgaagggcactgttgacgtggtgaatgtcgcccgttctcacgtgacccgtctcctctatatgtgtatccgcctctttgtttggtttttttttctgcttcccccc -continued cccccccccccaccccaatcacatgctcagaaagtagacatctgcatcgtcctgcatgccatcccacaagacgaacaagtgataggccgagagccg aggacgaggtggagtgcacaaggggtaggcgaatggtacgattccgccaagtgagactggcgatcgggagaagggttggtggtcatgggggat agaatttgtacaagtggaaaaaccactacgagtagcggatttgataccacaagtagcagagatatacagcaatggtgggagtgcaagtatcggaat gtactgtacctcctgtactcgtactcgtacggcactcgtagaaacggggcaatacgggggagaagcgatcgcccgtctgttcaatcgccacaagtc cgagtaatgctcgagtatcgaagtcttgtacctccctgtcaatcatggcaccactggtcttgacttgtctattcatactggacaagcgccagagttaagc ttgtagcgaatttcgccctcggacatcaccccatacgacggacacacatgcccgacaaacagcctctcttattgtagctgaaagtatattgaatgtgaa cgtgtacaatatcaggtaccagcgggaggttacggccaaggtgataccggaataaccctggcttggagatggtcggtccattgtactgaagtgtcc gtgtcgtttccgtcactgccccaattggacatgtttgtttttccgatctttcgggcgccctctccttgtctccttgtctgtctcctggactgttgctacc ccatttctttggcctccattggttcctccccgtctttcacgtcgtctatggttgcatggtttcccttatacttttccccacagtcacatgttatggaggggt ctagatggaggcctaattttgacgtgcaaggggcgaattggggcgagaaacacgtcgtggacatggtgcaaggcccgcagggttgattcgacgc ttttccgcgaaaaaaacaagtccaaatacccccgtttattctccctcggctctcggtatttcacatgaaaactataacctagactacacgggcaac cttaaccccagagtatacttatataccaaagggatgggtcctcaaaaatcacacaagcaacg Yef3 (YALI0E13277g) promoter (SEQ ID NO: 114)

5'cgccattcggttccttccagaccattccagatcaatccacctcttcttatctcaggtgggtgtgctgacatcagaccccgtagcccttctcccagtgg cgaacagcaggcataaaacagggccattgagcagagcaaacaaggtcggtgaaatcgtcgaaaaagtcggaaaacggttgcaagaaattggag cgtcacctgccaccctccaggctctatataaagcattgccccaattgctaacgcttcatatttacacctttggcaccccagtccatccctccaataaaat gtactacatgggacacaacaagagaggatgcgcgcccaaaccctaacctagcacatgcacgatgattctctttgtctgtgaaaaaatttttccaccaa aatttccccattgggatgaaaccctaaccgcaaccaaaagtttttaactatcatcttgtacgtcacggtttccgattcttctcttctctttcatcatc atcacttgtgacc Cam1 (YALI0C24420g) promoter (SEQ ID NO: 115)

5'aactaccataaagtaccgagaaatataggcaattgtacaaattgtccacctccttcacttacattaccgaaccatggccatatcaccaaaatacccc gagtgctaaaacacctccctccaaatgttctcttaccttccaccgaaaaccgatcttattatcccaacgcttgttgtggcttgacgcgccgcacccgctg ggcttgccatttcgataccaatccaagaggaaaagctcatgagaaacaatcggaatatcacgagaacggcctggcgaaccaacaggatatttttga atataattaccccctcgaatctagtcatatctatgtctactgtagacttgggcggcatcatgatgtacattatttttagcgtctggaaccctaaagttcacgta caatcatgtgacaaacgaggctaaaaaatgtcaatttcgtatattagtgttattacgtggctcacatttccgaatcatctaccacccccccacctaaaaa YALI0D16467g promoter (SEQ ID NO: 116)

5'tttttttaattttcatatttattttcatatttattttcatatttattttcatttatttattcatgtatttatttattacttttaagtattttaaactcc tcactaaaccgtcgattgcacaatattaaccttcattacacctgcagcgtggtttttgtggtcgttagccgaagtcttccaacgtgggtataagtaggaac aattgggccgatttttttgagccgtctaaatctctcgactcaattgatctgctgtcgaaaatccggctctctagctccttttccccgtccgctggagctcctc ttcattgtgccgtttttccaacatttaactttgccacccaccaccaccccccactaccatcacccactcgatctctgttcgtgtcaccacgactttgtcttctc acacatactctgtttgtgcaccacacattgcgaa Tef4 (YALI0B12562g) promoter (SEQ ID NO: 117)

5'gctacaatagctttattggccctattgagcacgctacaattcggtccagtatgtacaacgtctatgcgcactaacggccatacagtgagttacagca cacccaaaagtaaccctgcctgacctgtctgcctgagacaggaagattaactcttgtagtgaccgagctcgataagactcaagccacacaattttttta tagccttgcttcaagagtcgccaaaatgacattacacaactccacggaccgtcggttccatgtccacacccttggatgggtaagcgctccacgcacg taccacgtgcattgagtttaaccacaaacataggtctgtgtcccagagttaccctgctgcatcagccaagtcttgaaagcaaaatttattgcacaatttt cctcttcttttcttcactgatcgcagtccaaacacaaaca YALI0D12903g promoter (SEQ ID NO: 118)

5'gcgctctgatccacttgtatggctccaagttcagtgtaccaagtagttggtgatgcagggagggatgtctctatccaccaataatgaactcatgggcgaa attgtttctgttaaacactccaactgtcgttttaaatctcattctctttgcatttggactccattcgcttccgttgggccaatataatccatcgtaacgtac -continued tttagatggaaatttagttacctgctacttgtctcaacaccccaacaggggctgttcgacagaggtaatagagcgtcaatgggttaataaaaacacactgtc gattttcactcattgtctttatgatattacctgttttccgctgttatcaatgccgagcatcgtgttatatcttccaccccaactacttgcatttacttaact attacctcaactatttacaccccgaattgttacctcccaataagtaactttatttcaaccaatgggacgagagcatctctgagaacatcgatctatctctgt caatattgcccagaatcgttcgaaaaaaaacaccaaaaggtttacagcgccattataaatataaattcgttgtcaattcccccgcaatgtctgttgaaat ctcattttgagaccttccaacattaccctctctcccgtctggtcacatgacgtgactgcttcttcccaaaacgaacactcccaactcttcccccccgtca gtgaaaagtatacatccgacctccaaatcttttcttcactcaac Tef1 (YALI0C09141g) promoter (SEQ ID NO: 119)

5'agagacgggttggcggcgtatttgtgtcccaaaaaacagccccaattgccccaattgaccccaaattgacccagtagcgggcccaaccccggc gagagcccccttcaccccacatatcaaacctcccccggttcccacacttgccgttaagggcgtagggtactgcagtctggaatctacgcttgttcaga ctttgtactagtttctttgtctggccatccgggtaacccatgccggacgcaaaatagactactgaaaatttttttgctttgtggttgggactttagccaagg gtataaaagaccaccgtccccgaattacctttcctcttcttttctctctctccttgtcaactcacacccgaaatcgttaagcatttccttctgagtataaga atcattc Fba1 (YALI0E26004g) promoter (SEQ ID NO: 120)

5'gctgcgctgatctggacaccacagaggttccgagcactttaggttgcaccaaatgtcccaccaggtgcaggcagaaaacgctggaacagcgtg tacagtttgtcttagcaaaaagtgaaggcgctgaggtcgagcagggtggtgtgacttgttatagcctttagagctgcgaaagcgcgtatggatttggc tcatcaggccagattgagggtctgtggacacatgtcatgttagtgtacttcaatcgccccctggatatagccccgacaataggccgtggcctcatttttt tgccttccgcacatttccattgctcggtacccacaccttgcttctcctgcacttgccaaccttaatactggtttacattgaccaacatcttacaagcgggg ggcttgtctagggtatatataaacagtggctctcccaatcggttgccagtctcttttttcctttctttccccacagattcgaaatctaaactacacatc Pox2 terminator:

(SEQ ID NO: 121)

5'gatgaggaatagacaagcgggtatttattgtatgaataaagattatgtattgattgcaaaaaagtgcatttgtagatgtggtttattgtagagagtacg gtatgtactgtacgaacattaggagctacttctacaagtagattttcttaacaagggtgaaatttactaggaagtacatgcatatttcgttagtagaatcac aaaagaaatgtacaagcacgtactacttgtactccacaatgtggagtgggagcaaaaaaattggacgacaccggaatcgaaccggggacctcgc gcatgctaagcgcatgtgataaccaactacaccagacgcccaagaactttcttggtgattatggaatacgtggtctgctatatctcaattttgctgtaatg aatcattagaattaaaaaaaaaaccccattttgtgtgattgtcggccaagagatggaacaggaagaatacgtgaacaagcgagcacgaatgccata tgctcttctgaacaaccgagtccgaatccgatttgtgggtatcacatgtctcaagtagctgaaatgtatttcgctagaataaaataaatgagattaagaatt aaaaatattggaatatattttcctagaatagaaactttggatttttttttcggctattacagtctgaactggacaaacggctgactatatataaatattattgg gtctgttttcttgtttatgtcgaaattatctgggttttactactgtgtcgtcgagtatagagtggcctgactggagaaaatgcagtagtatggacagtaggt actgccagccagagaagtttttggaattgatacttgagtcatttttccattccccattccccattccaacacaatcaactgtttctgaacattttccaaaacg cggagatgtatgtcacttggcactgcaagtctcgattcaaaatgcatctctttcagaccaaagtgtcatcagctttgtttggccccaaattaccgcaaat acttgtcgaaattgaagtgcaatacggcctcgtctgccatgaaacctgcctattctcttcaaattggcgtcaggtttcacgtccagcattcctcgcccag acagagttgctatggttgaatcgtgtactgttaatatatgtatgtattatactcgtactacgatatactgttcaatagagtctcttataatcgtacgacgatt ctgggca

Example 12

*Y. lipolytica* Oleaginic and Isoprenoid Biosynthesis Genes

FIG. 10 is a list of *Y. lipolytica* genes representing various polypeptides (e.g. oleaginic and isoprenoid biosynthesis peptides) useful in the fungal strains and methods described herein. The Genbank accession number and GI number is given for each polypeptide in addition to oligo pairs which can be used to amplify the coding region for each gene from *Y. lipolytica* genomic DNA or cDNA. Resulting PCR fragments can be cleaved with restriction enzyme pairs (e.g. depending on what site is present within the oligo sequence, XbaI/MluI or NheI/MluI or XbaI/AscI or NheI/AscI) and inserted into expression vectors (e.g. fungal expression vectors including *Y. lipolytica* expression vectors such as MB4629 and MB4691 described herein).

The DNA and proteins they encode of the *Y. lipolytica* genes represented in FIG. 10 are as follows (intron sequence is underlined):

YALI0F30481g
DNA:

(SEQ ID NO: 122)

atgtcgcaaccccagaacgttggaatcaaagccctcgagatctacgtgccttctcgaattgtcaaccaggctgagctcgagaagcacgacggtgtc gctgctggcaagtacaccattggtcttggtcagaccaacatggcctttgtcgacgacagagaggacatctattcctttgccctgaccgccgtctctcg actgctcaagaacaacaacatcgaccctgcatctattggtcgaatcgaggttggtactgaaacccttctggacaagtccaagtccgtcaagtctgtgc tcatgcagctctttggcgagaacagcaacattgagggtgtggacaacgtcaacgcctgctacggaggaaccaacgccctgttcaacgctatcaact gggttgagggtcgatcttgggacggccgaaacgccatcgtcgttgccggtgacattgccctctacgcaaagggcgctgcccgacccaccggagg tgccggctgtgttgccatgctcattggccccgacgctcccctggttcttgacaacgtccacggatcttacttcgagcatgcctacgatttctacaagcct gatctgacctccgagtacccctatgttgatggccactactccctgacctgttacacaaaggccctcgacaaggcctacgctgcctacaacgcccgag ccgagaaggtcggtctgttcaaggactccgacaagaagggtgctgaccgatttgactactctgccttccacgtgcccacctgcaagcttgtcaccaa gtcttacgctcgacttctctacaacgactacctcaacgacaagagcctgtacgagggccaggtccccgaggaggttgctgccgtctcctacgatgc ctctctcaccgacaagaccgtcgagaagaccttccttggtattgccaaggctcagtccgccgagcgaatggctccttctctccagggacccaccaa caccggtaacatgtacaccgcctctgtgtacgcttctctcatctctctgctgacttttgtccccgctgagcagctgcagggcaagcgaatctctctcttct cttacggatctggtcttgcttccactcttttctctctgaccgtcaagggagacatttctcccatcgtcaaggcctgcgacttcaaggctaagctcgatgac cgatccaccgagactcccgtcgactacgaggctgccaccgatctccgagagaaggcccacctcaagaagaactttgagccccagggagacatca agcacatcaagtctggcgtctactacctcaccaacatcgatgacatgttccgacgaaagtacgagatcaagcagtag Protein:

(SEQ ID NO: 123)

Msqpqnvgikaleiyvpsrivnqaelekhdgvaagkytiglgqtnmafvddrediysfaltavsrllknnnidpasigrievgtetlldksksvk svlmqlfgensniegvdnvnacyggtnalfnainwvegrswdgrnaivvagdialyakgaarptggagcvamligpdaplvldnvhgsyfe haydfykpdltseypyvdghysltcytkaldkayaaynaraekvglfkdsdkkgadrfdysafhvptcklvtksyarllyndylndkslyegq vpeevaavsydasltdktvektflgiakaqsaermapslqgptntgnmytasvyaslisllltfvpaeqlqgkrislfsygsglastlfsltvkgdisp ivkacdfkaklddrstetpvdyeaatdlrekahlkknfepqgdikhiksgvyyltniddmfrrkyeikq YALI0B16038g
DNA:

(SEQ ID NO: 124)

atggactacatcatttcggcgccaggcaaagtgattctatttggtgaacatgccgctgtgtttggtaagcctgcgattgcagcagccatcgacttgcga acatacctgcttgtcgaaaccacaacatccgacaccccgacagtcacgttggagtttccagacatccacttgaacttcaaggtccaggtggacaagc tggcatctctcacagcccagaccaaggccgaccatctcaattggtcgactcccaaaactctggataagcacattttcgacagcttgtctagcttggcg cttctggaagaacctgggctcactaaggtccagcaggccgctgttgtgtcgttcttgtacctctacatccacctatgtccccccttctgtgtgcgaagatt catcaaactgggtagttcgatcaacgctgcctatcggcgcgggcctgggctcttccgcatccatttgtgtctgtttggctgcaggtcttctggttctcaa cggccagctgagcattgaccaggcaagagatttcaagtccctgaccgagaagcagctgtctctggtggacgactggtccttcgtcggtgaaatgtg cattcacggcaacccgtcgggcatcgacaatgctgtggctactcagggaggtgctctgttgttccagcgacctaacaaccgagtccctcttgttgac attcccgagatgaagctgctgcttaccaatacgaagcatcctcgatctaccgcagacctggttggtggagtcggagttctcactaaagagtttggctc catcatggatcccatcatgacttcagtaggcgagatttccaaccaggccatggagatcatttctagaggcaagaagatggtggaccagtctaaccttg agattgagcagggtatcttgcctcaacccacctctgaggatgcctgcaacgtgatggaagatggagctactcttcaaaagttgagagatatcggttcg gaaatgcagcatctagtgagaatcaatcacggcctgcttatcgctatgggtgtttcccacccgaagctcgaaatcattcgaactgcctccattgtccac aacctgggtgagaccaagctcactggtgctggaggaggaggttgcgccatcactctagtcacttctaaagacaagactgcgacccagctggagga aaatgtcattgctttcacagaggagatggctacccatggcttcgaggtgcacgagactactattggtgccagaggagttggtatgtgcattgaccatc cctctctcaagactgttgaagccttcaagaaggtggagcgggcggatctcaaaaacatcggtccctggacccattag Protein:

(SEQ ID NO: 125)

mdyiisapgkvilfgehaavfgkpaiaaaidlrtyllvetttsdtptvtlefpdihlnfkvqvdklasltaqtkadhlnwstpktldkhifdslsslall eepgltkvqqaavvsflylyihlcppsvcedssnwvvrstlpigaglgssasicyclaagllvlngqlsidqardfksltekqlslvddwsfvgem cihgnpsgidnavatqggallfqrpnnrvplvdipemkllltntkhprstadlvggvgvltkefgsimdpimtsvgeisnqameiisrgkkmv -continued dqsnleieqgilpqptsedacnvmedgatlqklrdigsemqhlvrinhglliamgvshpkleiirtasivhnlgetkltgaggggcaitlvtskdk tatqleenviafteemathgfevhettigargvgmcidhpslktveafkkkveradlknigpwth YALI0E06193g
DNA:

(SEQ ID NO: 126)

atgaccacctattcggctccgggaaaggccctcctttgcggcggttatttggttattgatccggcgtattcagcatacgtcgtgggcctctcggcgcgt atttacgcgacagtttcggcttccgaggcctccaccacctctgtccatgtcgtctctccgcagtttgacaagggtgaatggacctacaactacacgaa cggccagctgacggccatcggacacaacccatttgctcacgcggccgtcaacaccgttctgcattacgttcctcctcgaaacctccacatcaacatc agcatcaaaagtgacaacgcgtaccactcgcaaattgacagcacgcagagaggccagtttgcataccacaaaaaggcgatccacgaggtgccta aaacgggcctcggtagctccgctgctcttaccaccgttcttgtggcagctttgctcaagtcatacggcattgatcccttgcataacacccacctcgttca caacctgtcccaggttgcacactgctcggcacagaagaagattgggtctggatttgacgtggcttcggccgtttgtggctctctagtctatagacgttt cccggcggagtccgtgaacatggtcattgcagctgaagggacctccgaatacggggctctgttgagaactaccgttaatcaaaagtggaaggtga ctctggaaccatccttcttgccgccgggaatcagcctgcttatgggagacgtccagggaggatctgagactccaggtatggtggccaaggtgatgg catggcgaaaagcaaagccccgagaagccgagatggtgtggagagatctcaacgctgccaacatgctcatggtcaagttgttcaacgacctgcgc aagctctctctcactaacaacgaggcctacgaacaacttttggccgaggctgctcctctcaacgctctaaagatgataatgttgcagaaccctctcgg agaactagcacgatgcattatcactattcgaaagcatctcaagaagatgacacgggagactggtgctgctattgagccggatgagcagtctgcattg ctcaacaagtgcaacacttatagtggagtcattggaggtgttgtgcctggagcaggaggctacgatgctatttctcttctggtgatcagctctacggtg aacaatgtcaagcgagagagccagggagtccaatggatggagctcaaggaggagaacgagggtctgcggctcgagaaggggttcaagtag Protein:

(SEQ ID NO: 127)

mttysapgkalleggylvidpaysayvvglsariyatvsaseasttsvhvvspqfdkgewtynytngqltaighnpfahaavntvlhyvpprnl hinisiksdnayhsqidstqrgqfayhkkaihevpktglgssaalttvlvaallksygidplhnthlvhnlsqvahcsaqkkigsgfdvasavcgs lvyrrfpaesvnmviaaegtseygallrttvnqkwkvtlepsflppgisllmgdvqggsetpgmvakvmawrkakpreaemvwrdlnaan mlmvklfildlrklsltnneayeqllaeaaplnalkmimlqnplgelarciitirkhlkkmtretgaaiepdeqsallnkcntysgviggvvpgag gydaisllvisstvnnvkresqgvqwmelkeeneglrlekgfk YALI0F05632g
DNA:

(SEQ ID NO: 128)

atgatccaccaggcctccaccaccgctccggtgaacattgcgacactcaagtactggggcaagcgagaccctgctctcaatctgcccactaacaac tccatctccgtgactttgtcgcaggatgatctgcggaccctcaccacagcctcgtgttcccctgatttcacccaggacgagctgtggctcaatggcaa gcaggaggacgtgagcggcaaacgtctggttgcgtgtttccgagagctgcgggctctgcgacacaaaatggaggactccgactcttctctgcctaa gctggccgatcagaagctcaagatcgtgtccgagaacaacttccccaccgccgctggtctcgcctcatcggctgctggctttgccgccctgatccg agccgttgcaaatctctacgagctccaggagacccccgagcagctgtccattgtggctcgacagggctctggatccgcctgtcgatctctctacgga ggctacgtggcatgggaaatgggcaccgagtctgacggaagcgactcgcgagcggtccagatcgccaccgccgaccactggcccgagatgcg agccgccatcctcgttgtctctgccgacaagaaggacacgtcgtccactaccggtatgcaggtgactgtgcacacttctcccctcttcaaggagcga gtcaccactgtggttcccgagcggtttgcccagatgaagaagtcgattctggaccgagacttccccacctttgccgagctcaccatgcgagactcaa accagttccacgccacctgtctggactcgtatcctcccatttttctacctcaacgacgtgtcgcgagcctccattcgggtagttgaggccatcaacaag gctgccggagccaccattgccgcctacacctttgatgctggacccaactgtgtcatctactacgaggacaagaacgaggagctggttctgggtgct ctcaaggccattctgggccgtgtggagggatgggagaagcaccagtctgtggacgccaagaagattgatgttgacgagcggtgggagtccgagc tggccaacggaattcagcgggtgatccttaccaaggttggaggagatcccgtgaagaccgctgagtcgcttatcaacgaggatggttctctgaaga acagcaagtag Protein:

(SEQ ID NO: 129)

mihqasttapvniatlkywgkrdpalnlptnnsisvtlsqddlrtlttascspdftqdelwlngkqedvsgkrlvacfrelralrhkmedsdsslpk ladqklkivsennfptaaglassaagfaaliravanlyelqetpeqlsivarqgsgsacrslyggyvawemgtesdgsdsravqiatadhwpem -continued raailvvsadkkdtssttgmqvtvhtsplfkervttvvperfaqmkksildrdfptfaeltmrdsnqfhatcldsyppifylndvsrasirvveain kaagatiaaytfdagpncviyyedkneelvlgalkailgrvegwekhqsvdakkidvderweselangiqrviltkvggdpvktaeslinedg slknsk YALI0F04015g
DNA:

(SEQ ID NO: 130)

Atgacgacgtcttacagcgacaaaatcaagagtatcagcgtgagctctgtggctcagcagtttcctgaggtggcgccgattgcggacgtgtccaag gctagccggcccagcacggagtcgtcggactcgtcggccaagctatttgatggccacgacgaggagcagatcaagctgatggacgagatctgtg tggtgctggactgggacgacaagccgattggcggcgcgtccaaaaagtgctgtcatctgatggacaacatcaacgacggactggtgcatcgggc cttttccgtgttcatgttcaacgaccgcggtgagctgcttctgcagcagcgggcggcggaaaaaatcacctttgccaacatgtggaccaacacgtgc tgctcgcatcctctggcggtgcccagcgagatgggcgggctggatctggagtcccggatccagggcgccaaaaacgccgcggtccggaagctt gagcacgagctgggaatcgaccccaaggccgttccggcagacaagttccatttcctcacccggatccactacgccgcgccctcctcgggcccctg gggcgagcacgagattgactacattctgtttgtccggggcgaccccgagctcaaggtggtggccaacgaggtccgcgataccgtgtgggtgtcgc agcagggactcaaggacatgatggccgatcccaagctggttttcaccccttggttccggctcatttgtgagcaggcgctgtttccctggtgggacca gttggacaatctgcccgcgggcgatgacgagattcggcggtggatcaagtag Protein:

(SEQ ID NO: 131)

mttsysdkiksisyssvaqqfpevapiadvskasrpstessdssaklfdghdeeqiklmdeicvvldwddkpiggaskkcchlmdnindglv hrafsvfmfndrgelllqqraaekitfanmwtntccshplavpsemggldlesriqgaknaavrklehelgidpkavpadkfhfltrihyaapss gpwgeheidyilfvrgdpelkvvanevrdtvwvsqqglkdmmadpklvftpwfrliceqalfpwwdqldnlpagddeirrwik

YALI0E05753
DNA:

(SEQ ID NO: 132)

atgtccaaggcgaaattcgaaagcgtgttcccccgaatctccgaggagctggtgcagctgctgcgagacgagggtctgccccaggatgccgtgc agtggttttccgactcacttcagtacaactgtgtgggtggaaagctcaaccgaggcctgtctgtggtcgacacctaccagctactgaccggcaagaa ggagctcgatgacgaggagtactaccgactcgcgctgctcggctggctgattgagctgctgcaggcgtttttcctcgtgtcggacgacattatggat gagtccaagacccgacgaggccagccctgctggtacctcaagcccaaggtcggcatgattgccatcaacgatgctttcatgctagagagtggcat ctacattctgcttaagaagcatttccgacaggagaagtactacattgaccttgtcgagctgttccacgacatttcgttcaagaccgagctgggccagct ggtggatcttctgactgcccccgaggatgaggttgatctcaaccggttctctctggacaagcactccttttattgtgcgatacaagactgcttactactcc ttctacctgcccgttgttctagccatgtacgtggccggcattaccaaccccaaggacctgcagcaggccatggatgtgctgatccctctcggagagt acttccaggtccaggacgactaccttgacaactttggagaccccgagttcattggtaagatcggcaccgacatccaggacaacaagtgctcctggct cgttaacaaagcccttcagaaggccacccccgagcagcgacagatcctcgaggacaactacggcgtcaaggacaagtccaaggagctcgtcatc aagaaactgtatgatgacatgaagattgagcaggactaccttgactacgaggaggaggttgttggcgacatcaagaagaagatcgagcaggttga cgagagccgaggcttcaagaaggaggtgctcaacgctttcctcgccaagatttacaagcgacagaagtag Protein:

(SEQ ID NO: 133)

mskakfesvfpriseelvqllrdeglpqdavqwfsdslqyncvggklnrglsvvdtyqlltgkkelddeeyyrlallgwliellqafflvsddim desktrrgqpcwylkpkvgmiaindafmlesgiyillkkhfrqekyyidlvelfhdisfktelgqlvdlltapedevdlnrfsldkhsfivrykta yysfylpvvlamyvagitnpkdlqqamdvliplgeyfqvqddyldnfgdpefigkigtdiqdnkcswlvnkalqkatpeqrqilednygvk dkskelvikklyddmkieqdyldyeeevvgdikkkieqvdesrgfkkevlnaflakiykrqk YALI0E18634g
DNA:

(SEQ ID NO: 134)

atgttacgactacgaaccatgcgacccacacagaccagcgtcagggcggcgcttgggcccaccgccgcggcccgaaacatgtcctcctccagc ccctccagcttcgaatactcgtcctacgtcaagggcacgcgggaaatcggccaccgaaaggcgcccacaacccgtctgtcggttgagggcccca tctacgtgggcttcgacggcattcgtcttctcaacctgccgcatctcaacaagggctcgggattccccctcaacgagcgacgggaattcagactcag tggtcttctgccctctgccgaagccaccctggaggaacaggtcgaccgagcataccaacaattcaaaaagtgtggcactcccttagccaaaaacgg -continued gttctgcacctcgctcaagttccaaaacgaggtgctctactacgccctgctgctcaagcacgttaaggaggtcttccccatcatctatacaccgactca gggagaagccattgaacagtactcgcggctgttccggcggcccgaaggctgcttcctcgacatcaccagtccctacgacgtggaggagcgtctg ggagcgtttggagaccatgacgacattgactacattgtcgtgactgactccgagggtattctcggaattggagaccaaggagtgggcggtattggta tttccatcgccaagctggctctcatgactctatgtgctggagtcaacccctcacgagtcattcctgtggttctggatacgggaaccaacaaccaggag ctgctgcacgaccccctgtatctcggccgacgaatgccccgagtgcgaggaaagcagtacgacgacttcatcgacaactttgtgcagtctgcccga aggctgtatcccaaggcggtgatccatttcgaggactttgggctcgctaacgcacacaagatcctcgacaagtatcgaccggagatcccctgcttca acgacgacatccagggcactggagccgtcactttggcctccatcacggccgctctcaaggtgctgggcaaaaatatcacagatactcgaattctcgt gtacggagctggttcggccggcatgggtattgctgaacaggtctatgataacctggttgcccagggtctcgacgacaagactgcgcgacaaaacat ctttctcatggaccgaccgggtctactgaccaccgcacttaccgacgagcagatgagcgacgtgcagaagccgtttgccaaggacaaggccaatt acgagggagtggacaccaagactctggagcacgtggttgctgccgtcaagccccatattctcattggatgttccactcagcccggcgcctttaacga gaaggtcgtcaaggagatgctcaaacacacccctcgacccatcattctccctctttccaaccccacacgtcttcatgaggctgtccctgcagatctgt acaagtggaccgacggcaaggctctggttgccaccggctcgccctttgacccagtcaacggcaaggagacgtctgagaacaataactgctttgtttt ccccggaatcgggctgggagccattctgtctcgatcaaagctcatcaccaacaccatgattgctgctgccatcgagtgcctcgccgaacaggcccc cattctcaagaaccacgacgagggagtacttcccgacgtagctctcatccagatcatttcggcccgggtggccactgccgtggttcttcaggccaag gctgagggcctagccactgtcgaggaagagctcaagcccggcaccaaggaacatgtgcagattcccgacaactttgacgagtgtctcgcctgggt cgagactcagatgtggcggcccgtctaccggcctctcatccatgtgcgggattacgactag Protein:

(SEQ ID NO: 135)

mlrlrtmrptqtsvraalgptaaarnmsssspssfeyssyvkgtreighrkapttrlsvegpiyvgfdgirllnlphlnkgsgfplnerrefrlsgllp saeatleeqvdrayqqfkkcgtplakngfctslkfqnevlyyalllkhvkevfpiiytptqgeaieqysrlfrrpegcflditspydveerlgafgdh ddidyivvtdsegilgigdqgvggigisiaklalmtlcagvnpsrvipvvldtgtnnqellhdplylgrrmprvrgkqyddfidnfvqsarrlyp kavihfedfglanahkildkyrpeipcfnddiqgtgavtlasitaalkvlgknitdtrilvygagsagmgiaeqvydnlvaqglddktarqniflm drpglltta ltdeqmsdvqkpfakdkanyegvdtktlehvvaavkphiligcstqpgafnekvvkemlkhtprpiilplsnptrlheavpadly kwtdgkalvatgspfdpvngketsennncfvfpgiglgailsrsklitntmiaaaieclaeqapilknhdegvlpdvaliqiisarvatavvlqak aeglatveeelkpgtkehvqipdnfdeclawvetqmwrpvyrplihvrdyd YALI0E11495g
DNA:

(SEQ ID NO: 136)

atgccgcagcaagcaatggatatcaagggcaaggccaagtctgtgcccatgcccgaagaagacgacctggactcgcattttgtgggtcccatctct ccccgacctcacggagcagacgagattgctggctacgtgggctgcgaagacgacgaagacgagcttgaagaactgggaatgctgggccgatct gcgtccacccacttctcttacgcggaagaacgccacctcatcgaggttgatgccaagtacagagctcttcatggccatctgcctcatcagcactctca gagtcccgtgtccagatcttcgtcatttgtgcgggccgaaatgaaccacccccctcccccacctccagccacacccaccaacagccagaggacg atgacgcatcttccactcgatctcgatcgtcgtctcgagcttctggacgcaagttcaacagaaacagaaccaagtctggatcttcgctgagcaagggt ctccagcagctcaacatgaccggatcgctcgaagaagagccctacgagagcgatgacgatgcccgactatctgcggaagacgacattgtctatga tgctacccagaaagacacctgcaagcccatatctcctactctcaaacgcacccgcaccaaggacgacatgaagaacatgtccatcaacgacgtca aaatcaccaccaccacagaagatcctcttgtggcccaggagctgtccatgatgttcgaaaaggtgcagtactgccgagacctccgagacaagtacc aaaccgtgtcgctacagaaggacggagacaaccccaaggatgacaagacacactggaaaatttaccccgagcctccaccaccctcctggcacga gaccgaaaagcgattccgaggctcgtccaaaaaggagcaccaaaagaaagacccgacaatggatgaattcaaattcgaggactgcgaaatcccc ggacccaacgacatggtcttcaagcgagatcctacctgtgtctatcaggtctatgaggatgaaagctctctcaacgaaaataagccgtttgttgccatc ccctcaatccgagattactacatggatctggaggatctcattgtggcttcgtctgacggacctgccaagtcttttgctttccgacgactgcaatatctag aagccaagtggaacctctactacctgctcaacgagtacacggagacaaccgagtccaagaccaacccccatcgagacttttacaacgtacgaaag gtcgacacccacgttcaccactctgcctgcatgaaccagaagcatctgctgcgattcatcaaatacaagatgaagaactgccctgatgaagttgtcat ccaccgagacggtcgggagctgacactctcccaggtgtttgagtcacttaacttgactgcctacgacctgtctatcgatacccttgatatgcatgctca -continued caaggactcgttccatcgatttgacaagttcaacctcaagtacaaccctgtcggtgagtctcgactgcgagaaatcttcctaaagaccgacaactaca tccagggtcgatacctagctgagatcacaaaggaggtgttccaggatctcgagaactcgaagtaccagatggcggagtaccgtatttccatctacg gtcggtccaaggacgagtgggacaagctggctgcctgggtgctggacaacaaactgttttcgcccaatgttcggtggttgatccaggtgcctcgact gtacgacatttacaagaaggctggtctggttaacacctttgccgacattgtgcagaacgtctttgagcctcttttcgaggtcaccaaggatcccagtac ccatcccaagctgcacgtgttcctgcagcgagttgtgggctttgactctgtcgatgacgagtcgaagctggaccgacgtttccaccgaaagttccca actgcagcatactgggacagcgcacagaaccctccctactcgtactggcagtactatctatacgccaacatggcctccatcaacacctggagacag cgtttgggctataatacttttgagttgcgaccccatgctggagaggctggtgacccagagcatcttctgtgcacttatctggttgctcagggtatcaacc acggtattctgttgcgaaaggtgcccttcattcagtacctttactacctggaccagatccccattgccatgtctcctgtgtccaacaatgcgctgttcctc acgttcgacaagaaccccttctactcatacttcaagcggggtctcaacgtgtccttgtcatcggatgatcctctgcagtttgcttacactaaggaggctc tgattgaggagtactctgtggctgcgctcatttacaagctttccaacgtggatatgtgtgagcttgctcgaaactcggtactgcaatctggctttgagcg aatcatcaaggagcattggatcggcgaaaactacgagatccatggccccgagggcaacaccatccagaagacaaacgtgcccaatgtgcgtctg gccttccgagacgagactttgacccacgagcttgctctggtggacaagtacaccaatcttgaggagtttgagcggctgcatggttaa Protein:

(SEQ ID NO: 137)

mpqqamdikgkaksvpmpeeddldshfvgpisprphgadeiagyvgceddedeleelgmlgrsasthfsyaeerhlievdakyralhghl phqhsqspvsrsssfvraemnhppppsshthqqpedddasstrsrsssrasgrkfnrnrtksgsslskglqqlnmtgsleeepyesdddarls aeddivydatqkdtckpisptlkrtrtkddmknmsindvkittttedplvaqelsmmfekvqycrdlrdkyqtvslqkdgdnpkddkthwki ypeppppswhetekrfrgsskkehqkkdptmdefkfedceipgpndmvfkrdptcvyqvyedesslnenkpfvaipsirdyymdledliv assdgpaksfafrrlqyleakwnlyyllneytettesktnphrdfynvrkvdthvhhsacmnqkhllrfikykmkncpdevvihrdgreltlsq vfeslnltaydlsidtldmhahkdsfhrfdkfnlkynpvgesrlreiflktdnyiqgrylaeitkevfqdlenskyqmaeyrisiygrskdewdkl aawvldnklfspnvrwliqvprlydiykkaglvntfadivqnvfeplfevtkdpsthpklhvflqrvvgfdsvddeskldrrfhrkfptaaywd saqnppysywqyylyanmasintwrqrlgyntfelrphageagdpehllctylvaqginhgillrkvpfiqylyyldqipiamspvsnnalflt fdknpfysyfkrglnyslssddplqfaytkealieeysvaaliyklsnvdmcelarnsvlqsgferiikehwigenyeihgpegntiqktnvpnv rlafrdetlthelalvdkytnleeferlhg YALI0D16753g
DNA:

(SEQ ID NO: 138)

atgttccgaacccgagttaccggctccaccctgcgatccttctccacctccgctgcccgacagcacaaggttgtcgtccttggcgccaacggaggc attggccagcccctgtctctgctgctcaagctcaacaagaacgtgaccgacctcggtctgtacgatctgcgaggcgcccccggcgttgctgccgat gtctcccacatccccaccaactccaccgtggccggctactctcccgacaacaacggcattgccgaggccctcaagggcgccaagctggtgctgat ccccgccggtgtcccccgaaagcccggcatgacccgagacgatctgttcaacaccaacgcctccattgtgcgagacctggccaaggccgtcggt gagcacgcccccgacgcctttgtcggagtcattgctaaccccgtcaactccaccgtccccattgtcgccgaggtgctcaagtccaagggcaagtac gaccccaagaagctcttcggtgtcaccaccctcgacgtcatccgagccgagcgattcgtctcccagctcgagcacaccaaccccaccaaggagta cttccccgttgttggcggccactccggtgtcaccattgtccccctcgtgtcccagtccgaccaccccgacattgccggtgaggctcgagacaagctt gtccaccgaatccagtttggcggtgacgaggttgtcaaggccaaggacggtgccggatccgccaccctttccatggcccaggctgccgcccgatt cgccgactctctcctccgaggtgtcaacggcgagaaggacgttgttgagcccactttcgtcgactctcctctgttcaagggtgagggcatcgacttct tctccaccaaggtcactcttggccctaacggtgttgaggagatccaccccatcggaaaggtcaacgagtacgaggagaagctcatcgaggctgcc aaggccgatctcaagaagaacattgagaagggtgtcaactttgtcaagcagaacccttaa Protein:

(SEQ ID NO: 139)

mfrtrvtgstlrsfstsaarqhkvvvlganggigqplsllllklnknvtdlglydlrgapgvaadvshiptnstvagyspdnngiaealkgaklvlip agvprkpgmtrddlfntnasivrdlakavgehapdafvgvianpvnstvpivaevlkskgkydpkklfgvttldviraerfvsqlehtnptkey fpvvgghsgvtivplvsqsdhpdiageardklvhriqfggdevvkakdgagsatlsmaqaaarfadsllrgvngekdvveptfvdsplfkgeg idffstkvtlgpngveeihpigkvneyeeklieaakadlkkniekgvnfvkqnp -continued YALI0D16247g
DNA:

(SEQ ID NO: 140)

atgacacaaacgcacaatctgttttcgccaatcaaagtgggctcttcggagctccagaaccggatcgttctcgcacccttgactcgaaccagagctct gcccggaaacgtgccctcggatcttgccacagagtactacgcacaaagagcagcatctccaggcactctcctcatcaccgaggccacatacatctc cccggatctgctggagtgcccattccaggagacggaatcgttccgggcatctggagtgacgagcagctcgaagcatggaaaaaggtgttcaag gccgtgcacgaccgaggatccaaaatctacgtccagctgtgggacattggacgtgtcgcatggtaccacaagctgcaggaactgggcaactactt ccctacaggcccctcagctatccccatgaagggagaggagagcgagcatctcaaggctctgactcactgggagatcaagggcaaggtggccctc tacgtcaacgctgccaagaacgccattgccgcaggcgctgatggcgtcgagatccactcggccaacggctaccttcccgacacatttctgagaag cgcctccaaccaacgaacagacgaatatggaggaagcatcgagaaccgggcccgattctcgctggagattgtcgacgctatcaccgaggccatt ggagcagacaaaaccgccatccgtctgtctccctggtccactttccaggacattgaggtgaatgacaccgagacccccgcacagttcacatacctg tttgagcagctgcagaagcgagccgacgagggaaagcagctggcctacgtgcatgtagttgagccccgactgtttggtcccccgagccctggg ccaccaatgagcattcagaaaaatttggaagggtaacttcattagagcaggtggatacgatagagagactgctcttgaggatgcagacaagtcaga caacaccctgattgcctttggtcgagacttcattgccaatcctgatctcgtccaacgcctcaagaataacgagccttggccaagtacgacagaacaa ccttctacgttccaggtgccaagggctacactgattaccctgcgtacaagatgtaa Protein:

(SEQ ID NO: 141)

mtqthnlfspikvgsselqnrivlapltrtralpgnvpsdlateyyaqraaspgtlliteatyispgsagvpipgdgivpgiwsdeqleawkkvfk avhdrgskiyvqlwdigrvawyhklqelgnyfptgpsaipmkgeesehlkalthweikgkvalyvnaaknaiaagadgveihsangylpdt flrsasnqrtdeyggsienrarfsleivdaiteaigadktairlspwstfqdievndtetpaqftylfeqlqkradegkqlayvhvveprlfgppep watnepfrkiwkgnfiraggydretaledadksdntliafgrdfianpdlvqrlknneplakydrttfyvpgakgytdypaykm YALI0A15972g
DNA:

(SEQ ID NO: 142)

atggaagccaaccccgaagtccagaccgatatcatcacgctgacccggttcattctgcaggaacagaacaaggtgggcgcgtcgtccgcaatccc caccggagacttcactctgctgctcaactcgctgcagtttgccttcaagttcattgcccacaacatccgacgatcgaccctggtcaacctgattggcct gtcgggaaccgccaactccaccggcgacgaccagaagaagctggacgtgatcggagacgagatcttcatcaacgccatgaaggcctccggtaa ggtcaagctggtggtgtccgaggagcaggaggacctcattgtgtttgagggcgacggccgatacgccgtggtctgcgaccccatcgacggatcct ccaacctcgacgccggcgtctccgtcggcaccattttcggcgtctacaagctccccgagggctcctccggatccatcaaggacgtgctccgaccc ggaaaggagatggttgccgccggctacaccatgtacggtgcctccgccaacctggtgctgtccaccggaaacggctgcaacggcttcactctcga tgaccctctgggagagttcatcctgacccaccccgatctcaagctccccgatctgcgatccatctactccgtcaacgagggtaactcctccctgtggt ccgacaacgtcaaggactacttcaaggccctcaagttccccgaggacggctccaagccctactcggcccgatacattggctccatggtcgccgac gtgcaccgaaccattctctacggaggtatgtttgcctaccccgccgactccaagtccaagaagggcaagctccgacttttgtacgagggtttccccat ggcctacatcattgagcaggccggcggtcttgccatcaacgacaacggcgagcgaatcctcgatctggtccccaccgagatccacgagcgatcc ggcgtctggctgggctccaagggcgagattgagaaggccaagaagtaccttctgaaatga Protein:

(SEQ ID NO: 143)

meanpevqtdiitltrfilqeqnkvgassaiptgdftlllnslqfafkfiahnirrstlvnliglsgtanstgddqkkldvigdeifinamkasgkvkl vvseeqedlivfegdgryavvcdpidgssnldagvsvgtifgvyklpegssgsikdvlrpgkemvaagytmygasanlvlstgngcngftld dplgefilthpdlklpdlrsiysvnegnsslwsdnvkdyfkalkfpedgskpysaryigsmvadvhrtilyggmfaypadskskkgklrllye gfpmayiieqagglaindngerildlvpteihersgvwlgskgeiekakkyllk YALI0E11099g
DNA:

(SEQ ID NO: 144)

atgcgactcactctgccccgacttaacgccgcctacattgtaggagccgcccgaactcctgtcggcaagttcaacggagccctcaagtccgtgtctg ccattgacctcggtatcaccgctgccaaggccgctgtccagcgatccaaggtccccgccgaccagattgacgagtttctgtttggccaggtgctgac cgccaactccggccaggcccccgcccgacaggtggttatcaagggtggtttccccgagtccgtcgaggccaccaccatcaacaaggtgtgctctt -continued ccggcctcaagaccgtggctctggctgcccaggccatcaaggccggcgaccgaaacgttatcgtggccggtggaatggagtccatgtccaacac cccctactactccggtcgaggtcttgttttcggcaaccagaagctcgaggactccatcgtcaaggacggtctctgggacccctacaacaacatccac atgggcaactgctgcgagaacaccaacaagcgagacggcatcacccgagagcagcaggacgagtacgccatcgagtcctaccgacgggccaa cgagtccatcaagaacggcgccttcaaggatgagattgtccccgttgagatcaagacccgaaagggcaccgtgactgtctccgaggacgaggag cccaagggagccaacgccgagaagctcaagggcctcaagcctgtctttgacaagcagggctccgtcactgccggtaacgcctcccccatcaacg atggtgcttctgccgttgtcgttgcctctggcaccaaggccaaggagctcggtacccccgtgctcgccaagattgtctcttacgcagacgccgccac cgcccccattgactttaccattgctccctctctggccattcccgccgccctcaagaaggctggccttaccaaggacgacattgccctctgggagatca acgaggccttctccggtgtcgctctcgccaacctcatgcgactcggaattgacaagtccaaggtcaacgtcaagggtggagctgttgctctcggcc accccattggtgcctccggtaaccgaatctttgtgactttggtcaacgccctcaaggagggcgagtacggagttgccgccatctgcaacggtggag gagcttccaccgccatcgtcatcaagaaggtctcttctgtcgagtag Protein:

(SEQ ID NO: 145)

mrltlprlnaayivgaartpvgkfngalksvsaidlgitaakaavqrskvpadqideflfgqvltansgqaparqvvikggfpesveattinkvcs sglktvalaaqaikagdrnvivaggmesmsntpyysgrglvfgnqkledsivkdglwdpynnihmgnccentnkrdgitreqqdeyaiesy rranesikngafkdeivpveiktrkgtvtvsedeepkganaeklkglkpvfdkqgsvtagnaspindgasavvvasgtkakelgtpvlakivsy adaatapidftiapslaipaalkkagltkddialweineafsgvalanlmrlgidkskvnvkggavalghpigasgnrifvtlvnalkegeygva aicngggastaivikkvssve YALI0E34793g
DNA:

(SEQ ID NO: 146)

atgtctgccaacgagaacatctcccgattcgacgcccctgtgggcaaggagcaccccgcctacgagctcttccataaccacacacgatctttcgtct atggtctccagcctcgagcctgccagggtatgctggacttcgacttcatctgtaagcgagagaacccctccgtggccggtgtcatctatcccttcggc ggccagttcgtcaccaagatgtactggggcaccaaggagactcttctccctgtctaccagcaggtcgagaaggccgctgccaagcaccccgaggt cgatgtcgtggtcaactttgcctcctctcgatccgtctactcctctaccatggagctgctcgagtacccccagttccgaaccatcgccattattgccgag ggtgtccccgagcgacgagcccgagagatcctccacaaggcccagaagaagggtgtgaccatcattggtcccgctaccgtcggaggtatcaagc ccggttgcttcaaggttggaaacaccggaggtatgatggacaacattgtcgcctccaagctctaccgacccggctccgttgcctacgtctccaagtc cggaggaatgtccaacgagctgaacaacattatctctcacaccaccgacggtgtctacgagggtattgctattggtggtgaccgataccctggtact accttcattgaccatatcctgcgatacgaggccgaccccaagtgtaagatcatcgtcctccttggtgaggttggtggtgttgaggagtaccgagtcat cgaggctgttaagaacggccagatcaagaagcccatcgtcgcttgggccattggtacttgtgcctccatgttcaagactgaggttcagttcggccac gccggctccatggccaactccgacctggagactgccaaggctaagaacgccgccatgaagtctgctggcttctacgtccccgataccttcgagga catgcccgaggtccttgccgagctctacgagaagatggtcgccaagggcgagctgtctcgaatctctgagcctgaggtccccaagatccccattga ctactcttgggcccaggagcttggtcttatccgaaagcccgctgctttcatctccactatttccgatgaccgaggccaggagcttctgtacgctggcat gcccatttccgaggttttcaaggaggacattggtatcggcggtgtcatgtctctgctgtggttccgacgacgactccccgactacgcctccaagtttctt gagatggttctcatgcttactgctgaccacggtcccgccgtatccggtgccatgaacaccattatcaccacccgagctggtaaggatctcatttcttcc ctggttgctggtctcctgaccattggtacccgattcggaggtgctcttgacggtgctgccaccgagttcaccactgcctacgacaagggtctgtcccc ccgacagttcgttgataccatgcgaaagcagaacaagctgattcctggtattggccatcgagtcaagtctcgaaacaaccccgatttccgagtcgag cttgtcaaggactttgttaagaagaacttcccctccacccagctgctcgactacgcccttgctgtcgaggaggtcaccacctccaagaaggacaacc tgattctgaacgttgacggtgctattgctgtttcttttgtcgatctcatgcgatcttgcggtgcctttactgtggaggagactgaggactacctcaagaac ggtgttctcaacggtctgttcgttctcggtcgatccattggtctcattgcccaccatctcgatcagaagcgactcaagaccggtctgtaccgacatcctt gggacgatatcacctacctggttggccaggaggctatccagaagaagcgagtcgagatcagcgccggcgacgtttccaaggccaagactcgatc atag Protein:

-continued (SEQ ID NO: 147)

msanenisrfdapvgkehpayelfhnhtrsfvyglqpracqgmldfdfickrenpsvagviypfggqfvtkmywgtketllpvyqqvekaa akhpevdvvvnfassrsvysstmelleypqfrtiaiiaegvperrareilhkaqkkgvtiigpatvggikpgcfkvgntggmmdnivasklyr pgsvayvsksggmsnelnniishttdgvyegiaiggdrypgttfidhilryeadpkckiivllgevggveeyrvieavkngqikkpivawaigt casmfktevqfghagsmansdletakaknaamksagfyvpdtfedmpevlaelyekmvakgelsrisepevpkipidyswaqelglirkp aafistisddrgqellyagmpisevfkedigiggvmsllwfrrrlpdyaskflemvlmltadhgpavsgamntiittragkdlisslvaglltigtrf ggaldgaateftta ydkglsprqfvdtmrkqnklipgighrvksrnnpdfrvelvkdfvkknfpstqlldyalaveevttskkdnlilnvdgaia vsfvdlmrscgaftveetedylkngvlnglfvlgrsigliahhldqkrlktglyrhpwdditylvgqeaiqkkrveisagdvskaktrs YALI0D24431g
DNA:

(SEQ ID NO: 148)

atgtcagcgaaatccattcacgaggccgacggcaaggccctgctcgcacactttctgtccaaggcgcccgtgtgggccgagcagcagcccatca acacgtttgaaatgggcacacccaagctggcgtctctgacgttcgaggacggcgtggcccccgagcagatcttcgccgccgctgaaaagacctac ccctggctgctggagtccggcgccaagtttgtggccaagcccgaccagctcatcaagcgacgaggcaaggccggcctgctggtactcaacaagt cgtgggaggagtgcaagccctggatcgccgagcgggccgccaagcccatcaacgtggagggcattgacggagtgctgcgaacgttcctggtcg agccctttgtgccccacgaccagaagcacgagtactacatcaacatccactccgtgcgagagggcgactggatcctcttctaccacgagggagga gtcgacgtcggcgacgtggacgccaaggccgccaagatcctcatccccgttgacattgagaacgagtacccctccaacgccacgctcaccaagg agctgctggcacacgtgcccgaggaccagcaccagaccctgctcgacttcatcaaccggctctacgccgtctacgtcgatctgcagtttacgtatct ggagatcaacccccctggtcgtgatccccaccgcccagggcgtcgaggtccactacctggatcttgccggcaagctcgaccagaccgcagagtttg agtgcggccccaagtgggctgctgcgcggtcccccgccgctctgggccaggtcgtcaccattgacgccggctccaccaaggtgtccatcgacgc cggccccgccatggtcttccccgctcctttcggtcgagagctgtccaaggaggaggcgtacattgcggagctcgattccaagaccggagcttctct gaagctgactgttctcaatgccaagggccgaatctggacccttgtggctggtggaggagcctccgtcgtctacgccgacgccattgcgtctgccgg ctttgctgacgagctcgccaactacggcgagtactctggcgctcccaacgagacccagacctacgagtacgccaaaaccgtactggatctcatgac ccggggcgacgctcaccccgagggcaaggtactgttcattggcggaggaatcgccaacttcacccaggttggatccaccttcaagggcatcatcc gggccttccgggactaccagtcttctctgcacaaccacaaggtgaagatttacgtgcgacgaggcggtcccaactggcaggagggtctgcggttg atcaagtcggctggcgacgagctgaatctgcccatggagatttacggccccgacatgcacgtgtcgggtattgttcctttggctctgcttggaaagcg gcccaagaatgtcaagccttttggcaccggaccttctactgaggcttccactcctctcggagtttaa Protein:

(SEQ ID NO: 149)

Msaksiheadgkallahflskapvwaeqqpintfemgtpklasltfedgvapeqifaaaektypwllesgakfvakpdqlikrrgkagllvlnk sweeckpwiaeraakpinvegidgvlrtflvepfvphdqkheyyinihsvregdwilfyheggvdvgdvdakaakilipvdieneypsnatl tkellahvpedqhqtlldfinrlyavyvdlqftyleinplvviptaqgvevhyldlagkldqtaefecgpkwaaarspaalgqvvtidagstkvsi dagpamvfpapfgrelskeeayiaeldsktgaslkltvlnakgriwtlvagggasvvyadaiasagfadelanygeysgapnetqtyeyaktvl dlmtrgdahpegkvlfigggianftqvgstfkgiirafrdyqsslhnhkvkiyvrrggpnwqeglrliksagdelnlpmeiygpdmhvsgivp lallgkrpknvkpfgtgpsteastplgv YALI0E14190g
DNA:

(SEQ ID NO: 150)

atggttattatgtgtgtgggacctcagcacacgcatcatcccaacacagggtgcagtatatatagacagacgtgttccttcgcaccgttcttcacatatc aaaacactaacaaattcaaaagtgagtatcatggtgggagtcaattgattgctcggggagttgaacaggcaacaatggcatgcacagggccagtga aggcagactgcagtcgctgcacatggatcgtggttctgaggcgttgctatcaaaagggtcaattacctcacgaaacacagctggatgttgtgcaatc gtcaattgaaaaacccgacacaatgcaagatctctttgcgcgcattgccatcgctgttgccatcgctgtcgccatcgccaatgccgctgcggattatta tccctaccttgttccccgcttccgcacaaccggcgatgtctttgtatcatgaactctcgaaactaactcagtggttaaagctgtcgttgccggagccgct ggtggtattggccagcccctttctcttctcctcaaactctctccttacgtgaccgagcttgctctctacgatgtcgtcaactcccccggtgttgccgctga cctctcccacatctccaccaaggctaaggtcactggctacctccccaaggatgacggtctcaagaacgctctgaccggcgccaacattgtcgttatc -continued cccgccggtatcccccgaaagcccggtatgacccgagacgatctgttcaagatcaacgctggtatcgtccgagatctcgtcaccggtgtcgcccag tacgcccctgacgcctttgtgctcatcatctccaaccccgtcaactctaccgtccctattgctgccgaggtcctcaagaagcacaacgtcttcaaccct aagaagctcttcggtgtcaccacccttgacgttgtccgagcccagaccttcaccgccgctgttgttggcgagtctgaccccaccaagctcaacatcc ccgtcgttggtggccactccggagacaccattgtccctctcctgtctctgaccaagcctaaggtcgagatccccgccgacaagctcgacgacctcgt caagcgaatccagtttggtggtgacgaggttgtccaggctaaggacggtcttggatccgctaccctctccatggcccaggctggtttccgatttgccg aggctgtcctcaagggtgccgctggtgagaagggcatcatcgagcccgcctacatctaccttgacggtattgatggcacctccgacatcaagcgag aggtcggtgtcgccttcttctctgtccctgtcgagttcggccctgagggtgccgctaaggcttacaacatccttcccgaggccaacgactacgagaa gaagcttctcaaggtctccatcgacggtctttacggcaacattgccaagggcgaggagttcattgttaaccctcctcctgccaagtaa Protein:

(SEQ ID NO: 152)

vvkavvagaaggigqplslllklspyvtelalydvvnspgvaadlshistkakvtgylpkddglknaltganivvipagiprkpgmtrddlfkin agivrdlvtgvaqyapdafvliisnpvnstvpiaaevlkkhnvfnpkklfgvttldvvraqtftaavvgesdptklnipvvgghsgdtivpllsltk pkveipadklddlvkriqfggdevvqakdglgsatlsmaqagfrfaeavlkgaagekgiiepayiyldgidgtsdikrevgvaffsvpvefgpe gaakaynilpeandyekkllkvsidglygniakgeefivnpppak YALI0E22649g
DNA:

(SEQ ID NO: 151)

atgactggcaccttacccaagttcggcgacggaaccaccattgtggttcttggagcctccggcgacctcgctaagaagaagaccgtgagtattgaa ccagactgaggtcaattgaagagtaggagagtctgagaacattcgacggacctgattgtgctctggaccactcaattgactcgttgagagccccaat gggtcttggctagccgagtcgttgacttgttgacttgttgagcccagaaccccccaacttttgccaccatacaccgccatcaccatgacacccagatgt gcgtgcgtatgtgagagtcaattgttccgtggcaaggcacagcttattccaccgtgttccttgcacaggtggtctttacgctctcccactctatccgagc aataaaagcggaaaaacagcagcaagtcccaacagacttctgctccgaataaggcgtctagcaagtgtgcccaaaactcaattcaaaaatgtcaga aacctgatatcaacccgtcttcaaaagctaaccccagttccccgccctcttcggcctttaccgaaacggcctgctgcccaaaaatgttgaaatcatcg gctacgcacggtcgaaaatgactcaggaggagtaccacgagcgaatcagccactacttcaagacccccgacgaccagtccaaggagcaggcca agaagttccttgagaacacctgctacgtccagggccccttacgacggtgccgagggctaccagcgactgaatgaaaagattgaggagtttgagaag aagaagcccgagccccactaccgtcttttctacctggctctgcccccagcgtatccttgaggctgccaacggtctgaagaagtatgtctaccccg gcgagggcaaggcccgaatcatcatcgagaagccctttggccacgacctggcctcgtcacgagagctccaggacggccttgctcctctctggaa ggagtctgagatcttccgaatcgaccactacctcggaaaggagatggtcaagaacctcaacattctgcgatttggcaaccagttcctgtccgccgtgt gggacaagaacaccatttccaacgtccagatctccttcaaggagccctttggcactgagggccgaggtggatacttcaacgacattggaatcatcc gagacgttattcagaaccatctgttgcaggttctgtccattctagccatggagcgacccgtcactttcggcgccgaggacattcgagatgagaaggtc aaggtgctccgatgtgtcgacattctcaacattgacgacgtcattctcggccagtacggcccctctgaagacggaaagaagcccggatacaccgat gacgatggcgttcccgatgactcccgagctgtgacctttgctgctctccatctccagatccacaacgacagatgggagggtgttcctttcatcctccg agccggtaaggctctggacgagggcaaggtcgagatccgagtgcagttccgagacgtgaccaagggcgttgtggaccatctgcctcgaaatgag ctcgtcatccgaatccagccctccgagtccatctacatgaagatgaactccaagctgcctggccttactgccaagaacattgtcaccgacctggatct gacctacaaccgacgatactcggacgtgcgaatccctgaggcttacgagtctctcattctggactgcctcaagggtgaccacaccaactttgtgcga aacgacgagctggacatttcctggaagattttcaccgatctgctgcacaagattgacgaggacaagagcattgtgcccgagaagtacgcctacggc tctcgtggccccgagcgactcaagcagtggctccgagaccgaggctacgtgcgaaacggcaccgagctgtaccaatggcctgtcaccaagggct cctcgtga Protein:

(SEQ ID NO: 153)

mtgtlpkfgdgttivvlgasgdlakkktfpalfglyrngllpknveiigyarskmtqeeyherishyfktpddqskeqakkflentcyvqgpyd gaegyqrlnekieefekkkpephyrlfylalppsvfleaanglkkyvypgegkariiiekpfghdlassrelqdglaplwkeseifridhylgke mvknlnilrfgnqflsavwdkntisnvqisfkepfgtegrggyfndigiirdviqnhllqvlsilamerpvtfgaedirdekvkvlrcvdilnidd vilgqygpsedgkkpgytdddgvpddsravtfaalhlqihndrwegvpfilragkaldegkveirvqfrdvtkgvvdhlprnelviriqpsesi -continued ymkmnsklpgltaknivtdldltynrrysdvripeayeslildclkgdhtnfvrndeldiswkiftdllhkidedksivpekyaygsrgperlkq wlrdrgyvrngtelyqwpvtkgss YALI0B15598g
DNA:

(SEQ ID NO: 154)

atgactgacacttcaaacatcaagtgagtattgccgcacacaattgcaatcaccgccgggctctacctcctcagctctcgacgtcaatgggccagca gccgccatttgaccccaattacactggttgtgtaaaaccctcaaccacaatcgcttatgctcaccacagactacgacttaaccaagtcatgtcacaggt caaagtaaagtcagcgcaacacccccctcaatctcaacacacttttgctaactcaggcctgtcgctgacattgccctcatcggtctcgccgtcatgggc cagaacctgatcctcaacatggccgaccacggtaagtatcaattgactcaagacgcaccagcaagatacagagcatacccagcaatcgctcctctg ataatcgccattgtaacactacgttggttagattgatctaaggtcgttgctggttccatgcacttccacttgctcatatgaagggagtcaaactctattttg atagtgtcctctcccatccccgaaatgtcgcattgttgctaacaataggctacgaggttgttgcctacaaccgaaccacctccaaggtcgaccacttcc tcgagaacgaggccaagggtgagtatccgtccagctatgctgtttacagccattgacccccacttcccccacaattgctacgtcaccattaaaaaaca aaattaccggtatcggcaagctagactttcatgcaacctacgcagggtaacaagttgagtttcagccgtgcaccttacaggaaaaccagtcatacgc cgaggcagtgtgaaagcgaaagcacacagcctacggtgattgattgcatttttttgacataggagggaaacacgtgacatggcaagtgcccaacac gaatactaacaaacaggaaagtccattattggtgctcactctatcaaggagctgtgtgctctgctgaagcgaccccgacgaatcattctgctcgttaag gccggtgctgctgtcgattctttcatcgaacagctcctgccctatctcgataagggtgatatcatcattgacggtggtaactcccacttccccgactcca accgacgatacgaggagcttaacgagaagggaatcctctttgttggttccggtgtttccggcggtgaggagggtgcccgatacggtccctccatcat gcccggtggaaacaaggaggcctggccccacattaagaagattttccaggacatctctgctaaggctgatggtgagccctgctgtgactgggtcgg tgacgctggtgccggccactttgtcaagatggttcacaacggtattgagtatggtgacatgcagcttatctgcgaggcttacgacctcatgaagcgag gtgctggtttcaccaatgaggagattggagacgttttcgccaagtggaacaacggtatcctcgactccttcctcattgagatcacccgagacatcttca agtacgacgacggctctggaactcctctcgttgagaagatctccgacactgctggccagaagggtactggaaagtggaccgctatcaacgctcttg accttggtatgcccgtcaccctgatcggtgaggccgtcttcgctcgatgcattctgccctcaagcaggagcgtgtccgagcttccaaggttcttgatg gccccgagcccgtcaagttcactggtgacaagaaggagtttgtcgaccagctcgagcaggccctttacgcctccaagatcatctcttacgcccagg gtttcatgcttatccgagaggccgccaagacctacggctgggagctcaacaacgccggtattgccctcatgtggcgaggtggttgcatcatccgatc cgtcttccttgctgacatcaccaaggcttaccgacaggaccccaacctcgagaacctgctgttcaacgacttcttcaagaacgccatctccaaggcc aacccctcttggcgagctaccgtggccaaggctgtcacctggggtgttcccactcccgcattgcctcggctctggctttctacgacggttaccgatct gccaagctccccgctaacctgctccaggcccagcgagactacttcggcgcccacacctaccagctcctcgatggtgatggaaagtggatccacac caactggaccggccgaggtggtgaggtttcttcttccacttacgatgcttaa Protein:

(SEQ ID NO: 155)

mtdtsnikpvadialiglavmgqnlilnmadhgyevvaynrttskvdhfleneakgksiigahsikelcallkrprriillvkagaavdsfieqll pyldkgdiiidggnshfpdsnrryeelnekgilfvgsgvsggeegarygpsimpggnkeawphikkifqdisakadgepccdwvgdagag hfvkmvhngieygdmqliceaydlmkrgagftneeigdvfakwnngildsflieitrdifkyddgsgtplvekisdtagqkgtgkwtainald lgmpvtligeavfarclsalkqervraskvldgpepvkftgdkkefvdqleqalyaskiisyaqgfmlireaaktygwelnnagialmwrggci irsvfladitkayrqdpnlenllfndffknaiskanpswratvakavtwgvptpafasalafydgyrsaklpanllqaqrdyfgahtyqlldgdgk wihtnwtgrggevssstyda YALI0D06303g
DNA:

(SEQ ID NO: 156)

atgctcaaccttagaaccgcccttcgagctgtgcgacccgtcactctggtgagtatctcggagcccgggacggctaccaacacacaagcaagatg caacagaaaccggacttttttaaatgcggattgcggaaaatttgcatggcggcaacgactcggagaaggagcgggacaattgcaatggcaggatgc cattgacgaactgagggtgatgagagaccgggcctccgatgacgtggtggtgacgacagcccggctggtgttgccgggactgtctctgaaaagc aatttctctatctccggtctcaacagactccccttctctagctcaattggcattgtcttcagaaggtgtcttagtggtatccccattgttatcttcttttc cccaatgtcaatgtcaatgtcaatggctccgacctctttcacattaacacggcgcaaacacagataccacggaaccgactcaaacaaatccaaagagacg cagcggaataattggcatcaacgaacgatttgggatactctggcgagaatgccgaaatatttcgcttgtcttgttgtttctcttgagtgagttgtttgtgaa -continued

```
gtcgtttggaagaaggttcccaatgtcacaaaccataccaactcgttacagccagcttgtaatcccccacctcttcaatacatactaacgcagacccg

atcctacgccacttccgtggcctctttcaccggccagaagaactccaacggcaagtacactgtgtctctgattgagggagacggtatcggaaccga

gatctccaaggctgtcaaggacatctaccatgccgccaaggtccccatcgactgggaggttgtcgacgtcacccccactctggtcaacggcaaga

ccaccatccccgacagcgccattgagtccatcaaccgaaacaaggttgccctcaagggtcccctcgccacccccatcggtaagggccacgtttcc

atgaacctgactctgcgacgaaccttcaacctgttcgccaacgtccgaccttgcaagtccgtcgtgggctacaagaccccttacgagaacgtcgac

accctgctcatccgagagaacactgagggtgagtactccggtatcgagcacaccgtcgtccccggtgtcgttcagtccatcaagctgatcacccga

gaggcttccgagcgagtcatccggtacgcttacgagtacgccctgtcccgaggcatgaagaaggtccttgttgtccacaaggcctctattatgaagg

tctccgatggtcttttccttgaggttgctcgagagctcgccaaggagtacccctccattgacctttccgtcgagctgatcgacaacacctgtctgcgaat

ggtccaggaccccgctctctaccgagatgtcgtcatggtcatgcccaacctttacggtgacattctgtccgatcttgcctccggtcttatcggtggtctt

ggtctgacccccctccggtaacatgggtgacgaggtctccatcttcgaggccgtccacggatccgctcccgacattgctggcaagggtcttgctaac

cccactgctctgctgctctcctccgtgatgatgctgcgacacatgggtctcaacgacaacgccaccaacatcgagcaggccgtctttggcaccattg

cttccggccccgagaaccgaaccaaggatcttaagggtaccgccaccacttctcactttgctgagcagattatcaagcgactcaagtag

Protein:
                                                                                   (SEQ ID NO: 157)
mlnlrtalravrpvtltrsyatsvasftgqknsngkytvsliegdgigteiskavkdiyhaakvpidwevvdvtptlvngkttipdsaiesinrnkv

alkgplatpigkghvsmnltlrrtfnlfanvrpcksvvgyktpyenvdtllirentegeysgiehtvvpgvvqsiklitreaserviryayeyalsrg

mkkvlvvhkasimkvsdglflevarelakeypsidlsvelidntclrmvqdpalyrdvvmvmpnlygdilsdlasgligglgltpsgnmgde

vsifeavhgsapdiagkglanptalllssvmmlrhmglndnatnieqavfgtiasgpenrtkdlkgtattshfaeqiikrlk
```

Example 13

Determination of Lipid Levels of *Y. lipolytica*

12A. Determination of Lipid Levels of *Y. lipolytica* in Various Growth Conditions of Varying Carbon to Nitrogen Ratios.

Shake flask testing was conducted using carbon to nitrogen (C/N) ratios of 160, 80, 60, 40, 30, 20, and 10 with yeast nitrogen base being the base medium providing vitamins, trace elements and salts. Ammonium sulfate (which contains 21% nitrogen) was used as the nitrogen source and glucose (which contains 40% carbon) was used as the carbon source at a concentration of 30 g/L. The concentrations of ammonium sulfate corresponding to these ratios are: 0.36, 0.71, 0.95, 1.43, 1.91, 2.86, and 4.6 g/L, respectively. Uracil was supplemented at 0.2 mM. As controls, strains were also grown in yeast extract-peptone with 50 g/L of glucose (media in which lipids do not accumulate at high levels) and yeast extract-peptone with 5% olive oil (v/v) (media in which lipids accumulate at high levels).

Strain MF760 (10-14 ml of culture) was harvested after 4 days of growth at 30° C., during which time the cultures were shaking at 250 rpm. Following harvesting, cells were washed three times with water, with the exception of the oil-grown cells which were washed three times in 0.5% BSA and one time with water before lipid extractions. Lipids were extracted as described in Folch J, Lees, M, and Stanley, G. H. S. *J. Biol. Chem.* 226: 497-509, 1957. In brief, cell pellets were resuspended in 6 ml of water. A 1 ml aliquot was transferred to a pre-weighed tube with a hole on the lid, spun down and the cell pellet lyophilized overnight to determine the dry cell weight. The remaining 5 ml were placed in a 15 ml Falcon tube and spun down. Cell pellets were frozen at −20° C. until extractions were performed.

Two to three volumes of a Zymolyase solution (2 mg/ml Zymolyase 100T in 1M Sorbitol, 50 mM EDTA and 0.01% β-mercaptoethanol) was added to each cell pellet and placed at 37° C. with constant agitation for 1 hr. Two volumes of cubic zirconia beads were added to each tube and vortexed for 15-20 min. Samples were viewed under a microscope to ensure cell breakage before continuing with extractions. After cell breakage was complete, 6 ml of extraction solvent was added (a 2:1 mix of chloroform and methanol) and mixed. The mixture was spun down for 5 min at 3000 rpm and the organic layer was transferred to a clean tube. NaCl was added to the remaining aqueous layer to make it a 0.29% NaCl solution. 6 ml of extraction solvent was added and mixed, and the mixture was spun down for 5 min. The organic layers were pooled and filtered through a 0.2 μm filter to get rid of any cell debris. The extract was washed with 0.2 volumes of 0.29% NaCl solution and another 6 ml of extraction solvent added and mixed. Mixtures were spun and the organic layer was placed in a pre-weighed glass vial, the solvent was evaporated under a flow on nitrogen and the vial was weighed again to determine the weight of the lipid extracted. The dry cell weight is used to determine the percentage of lipid per dry cell weight. The lipid accumulation results are in the Table 48 below:

TABLE 48

Lipid accumulation under various carbon:nitrogen ratio growth conditions

| | C/N Ratio | % lipid |
|---|---|---|
| YNB | 160 | 61 |
| 3% Glucose | 80 | 49 |
| | 60 | 34 |
| | 40 | 17 |
| | 30 | 16 |
| | 20 | 14 |
| | 10 | 15 |
| YEP | 5% Glucose | 22 |
| | 5% olive oil | 38 |

Other nitrogen sources tested were proline (12% nitrogen), sodium glutamate (7% nitrogen), soy acid hydrolysate (12% nitrogen), and yeast extract-peptone (26.8% nitrogen). All nitrogen sources tested at C/N ratios of 80 (with glucose as a carbon source), had significantly larger lipid bodies than at C/N ratios of 10 (also with glucose as a carbon source).

Strains MF858 and MF921 (example 2F and 2H) were harvested after 4 days of growth at 30° C. (3% glucose was used as the carbon source). Cells were washed three times with water and lipids extracted as described above. Lipid accumulation data for soy hydrolysate, yeast extract-peptone and yeast nitrogen base, used as a control, are listed in Table 49 below.

TABLE 49

Lipid accumulation under different carbon and nitrogen conditions with various nitrogen sources

| | | % lipid | |
|---|---|---|---|
| | C/N Ratio | MF858 | MF921 |
| Soy hydrolysate | 80 | 36 | 36 |
| | 60 | 36 | 35 |
| | 10 | 14 | 15 |
| Yeast Extract- | 80 | 37 | 37 |
| Peptone | 10 | 15 | 14 |
| Yeast Nitrogen | 80 | 37 | 38 |
| Base | 10 | 13 | 11 |

12b. Determination of Lipid Levels Under High Carbon and Phosphate or Magnesium Limiting Conditions.

To test whether other nutrient limitations, under high carbon conditions, will allow for higher lipid accumulation, phosphate or magnesium limiting conditions were tested. For phosphate limiting conditions, yeast nitrogen base medium without phosphate was prepared. Shake flask testing was performed using carbon to phosphate ratios ranging from 5376 down to 42. This range corresponds to 7.8 mg/L up to 1 g/L, respectively, and the latter concentration corresponds to that are commonly used in yeast nitrogen base medium. Glucose, at 30 g/L, was used at the carbon source. Potassium phosphate monobasic (containing 28.7% phosphate) was used as the phosphate source.

For magnesium limiting conditions, yeast nitrogen base medium without magnesium was prepared. Shake flask testing was conducted using carbon to magnesium ratios ranging from 31360 down to 245. This range corresponds to 0.375 mg/L up to 0.5 g/L, and the latter magnesium concentration corresponds to that commonly used in yeast nitrogen base. Glucose, at 30 g/L, was used as the carbon source. Magnesium sulfate (containing 9.8% magnesium) was used as the magnesium source.

Strains MF858 and MF921 were harvested after 4 days of growth at 30° C., during which time the cultures were shaking at 250 rpm. Cells were washed three times with water before lipid extraction. Lipids were extracted as described above. Lipid accumulation data is listed in the Table 50 below:

TABLE 50

Lipid accumulation in phosphate or magnesium limiting growth conditions

| | | % Lipid | |
|---|---|---|---|
| | g/L | MF858 | MF921 |
| phosphate | 1 | 14 | 14 |
| | 0.0625 | 18 | 20 |
| | 0.0313 | 34 | 41 |
| | 0.0156 | 62 | 63 |
| | 0.0078 | 83 | 76 |
| magnesium | 0.5 | 12 | 11 |
| | 0.0313 | NA | 16 |
| | 0.0156 | NA | 25 |
| | 0.0078 | NA | 42 |
| | 0.0039 | 48 | 48 |

Example 14

Effect of Temperature on Carotenoid Production

MF740 was transformed with pMB4719 with SalI, and a $Ura^+$ colony was designated ML878. MF740 was transformed with pMB4629 cleaved with SalI, an $Ade^+$ colony was designated ML857, and subsequently transformed with pMB4719 cleaved with SalI, to create ML836. ML878 and ML836 were grown for 4 days in YPD at 20° C., 24° C., and 28° C., and carotenoids were extracted and analyzed by HPLC. β-carotene or zeaxanthin yield (% dry cell weight) at 20° C. was chosen as a standard against which yields at other temperatures were compared. In addition, the ratio of zeaxanthin/carotenoid (% dry cell weight) was calculated for each temperature. Whereas the β-carotene levels fell with decreasing temperatures, the ratio of zeaxanthin to β-carotene increased with lower temperatures (Table 51).

TABLE 51

Effect of Temperature on carotenoid production

| Strain | Temperature (° C.) | β-carotene yield* | Zeaxanthin yield** | Zeaxanthin/β-carotene ratio (% dry cell weight)*** |
|---|---|---|---|---|
| MF878 | 20 | 1.0 | 1.0 | 2.4 |
| MF878 | 24 | 1.3 | 1.0 | 1.9 |
| MF878 | 28 | 3.2 | 1.5 | 1.1 |
| MF836 | 20 | 1.0 | 1.0 | 1.0 |
| MF836 | 24 | 1.9 | 1.2 | 0.7 |
| MF836 | 28 | 3.4 | 1.1 | 0.4 |

*β-carotene yield is calculated as % DCW β-carotene at 20° C. divided by % DCW β-carotene at each temperature
**Zeaxanthin yield is calculated as % DCW zeaxanthin at 20° C. divided by % DCW zeaxanthin at each temperature
***Zeaxanthin/β-carotene ratio is calculated as % DCW zeaxanthin divided by % DCW β-carotene Example 15

Construction of a Recyclable URA3 Marker Plasmid pMB5082

To create a selectively excisable ("recyclable") URA3 marker, an 860 bp SpeI-SacI (blunt ended with T4 DNA ligase) fragment (containing the URA3 promoter and the first 121 nucleotides of the URA3 gene) from plasmid pMB4691 was inserted into the SpeI-NotI sites of plasmid pMB4534 to create pMB5055.

The URA3 promoter was excised from pMB5055 as an 878 bp fragment by XbaI-SpeI digest, and was ligated into XbaI-cleaved pMB4691. Orientation of the promoter was verified by restriction digest. The resulting plasmid, designated pMB5082, contained the URA3 promoter both upstream of the URA3 gene and downstream of its terminator. This cassette, once integrated into the *Yarrowia* genome, permits excision of the URA3 marker by homologous recombination between the two copies of the URA3 promoter. Colonies containing the excision may be selected on 5-FOA.

Example 16

Effects of Mutations in the Transcriptional Regulator, SPT8 on Carotenoid Production

*Y. Lipolytica* strain ML1018 was isolated by plasmid insertion mutagenesis. ML1018 was darker in hue, shiny, exclusively yeast-form rather than partial mycelial morphology and exhibited increased carotenoid levels when compared to its sibling transformants. Sequence analysis identified the site of ML1018 plasmid insertion between base pairs 701 and 702 of the SPT8 coding sequence. Experiments were undertaken to examine carotenoid levels in a targeted SPT8 disruption strain.

A 2.5 kb fragment containing the SPT8 gene (YALI0E23804g) with its endogenous promoter and terminator was amplified from genomic DNA isolated from *Y. lipolytica* strain NRRL Y-1095 using primers: MO5651 (5'-CACAAACTAGTGTCAGGAATATGAAACCAGG-3') (SEQ ID NO:158) and MO5652 (5'-CACAAACTAGTG-CATGTGATAGGAAGGAGGA-3') (SEQ ID NO:159). Plasmid pMB5083 was constructed by phosphorylating the 2.5 kb SPT8 fragment with T4 polynucleotide kinase and ligating the phosphorylated fragment with desphosphorylated, EcoRV-digested pBluescriptSK−.

A 3.4 kb fragment containing the TEF1 promoter, XPR terminator, and a recyclable URA3 marker was isolated from plasmid pMB5082 by Acc65I and XbaI (subsequently made blunt with Klenow) digestion. This fragment was cloned into the BsiWI and SmaI sites of pMB5083 to create pMB5086. BamHI-XbaI digestion of pMB5086 yields a 5.6 kb *Y. Lipolytica* SPT8 disruption fragment containing the TEF1 promoter and XPR terminators followed by a recyclable URA3 marker between base pairs 752 and 753 of the SPT8 coding sequence (SPT8::URA3 disruption cassette).

A 3.6 kb fragment containing the XPR terminator and ADE1 gene was excised from plasmid pMB4629 by MluI and EcoRV digest and subsequently cloned into MulI-PmlI-digested pMB5086. The resulting plasmid, pMB5124, contains a 5.8 kb BamHI-XbaI SPT8 disruption cassette similar to that in pMB5086, with the distinction that the recyclable URA3 marker is replaced with a non-recyclable ADE1 marker (SPT8::ADE1 disruption cassette).

*Y. lipolytica* strains MF740 and MF746 (both ade1 ura3) are transformed with a 5.8 kb BamHI-XbaI fragment from pMB5124 (spt8::ADE1). spt8 disruptants are distinguished from ectopic integrants by colony morphology, as spt8 strains are shinier, darker in hue, and less mycelial than SPT8 strains. Correct integration may be assayed by PCR or by Southern blotting. Carotenoid yield is assayed in spt8 disrupted and SPT8' strains by harvesting carotenoids after a four-day fermentation in YPD shake flasks at 30° C.

Example 17

Construction plasmid pMB4844 Encoding a Chimeric β-carotene Hydroxylase-Ketolase (crtZW)

A β-carotene hydroxylase:β-carotene ketolase chimera is constructed as follows. First, a 0.5 kb fragment containing crtZ from *Erythrobacter litoralis* is amplified from pMB4715, a plasmid containing a copy of the crtZ gene, using primers MO4814: 5'-CACAACGTCTCTCTAGACA-CAAAAATGAGCT-3' (SEQ ID NO:160) and MO4816: 5'-CACAACGTCTCAGCCGGCACCTGCTC-CCATAGAATCTCG-3' (SEQ ID NO:161) and the resulting fragment is digested with XbaI and BsmBI. Similarly, a 0.8 kb fragment containing crtW from *Parvularcula bermudensis* is amplified from pMB4731, a plasmid containing a copy of the crtW gene, with primers MO5060: 5'-CACAAGAAGA-CAACGGCGCAGGAGCCATGGACCCTAC-CGGAGACG-3' (SEQ ID NO:162) and MO5061: 5'-CA-CAAGAAGACAACGCGTTTAAGGGCCGGTTCTCTTTC-3' (SEQ ID NO:163) and the resulting fragment is digested with BbsI and MluI. The digested fragments containing the crtZ and crtW genes are then ligated in a three-piece reaction into NheI-MluI cleaved vector pMB4691 to create pMB4844. Sequence analysis confirms the creation of an in-frame fusion of crtZ and crtW placed under control of the TEF1 promoter and the XPR terminator. The chimeric sequence is designated crtZW. The amino acid sequence of crtZW is:

```
                                        (SEQ ID NO: 175)
mswwaialivfgavvgmeffawfahkyimhgwgwswhrdhhephdntlek
ndlfavvfgsvaallfvigalwsdplwwaavgitlygviytlvhdglvhq
rywrwtpkrgyakrlvqahrlhhatvgkeggvsfgfvfardpaklkaelk
qqreqglavvrdsmgagagagamdptgdvtasprpqttipvrqalwglsl
agaiiaawvfmhigfvffapldpivlalapviillqswlsvglfiishda
ihgslapgrpafnramgrlcmtlyagfdfdrmaaahhrhhrspgtaadpd
fsvdspdrplpwfgaffrryfgwrpfltvnavvftywlvlganpvnivlf
ygvpallsagqlfyfgtflphrherqgfadhhrarsvrspymlslvtcyh
fggyhhehhlfphepwwrlpqrggwerdrrkrtgp
```

Example 18 pH Effects on Total Carotenoid Yield and Hydroxylation of Beta-Carotene

The effect of altering pH on total carotenoid yield and relative amount of individual carotenoids was investigated. Strain ML1011 (MF740 transformed with multiple integrated copies of the *X. autotrophicus* crtZ gene) which accumulates a mixture of carotenoids comprising beta-carotene, beta-cryptoxanthin, and zeaxanthin was fermented under the following parameters.

Batch medium: YPD
Temperature setpoint: 30° C.
Initial volume: 210 ml
Vessel volume: 400 ml
Agitation rate: 1000 rpm
Feed: 40% glucose
Feed rate: 2 ml/hour, starting at 24th hour after inoculation Four separate fermentor units were setup and the pH was controlled as follows:

Unit 1: pH 5.5
Unit 2: pH 7.0
Unit 3: pH 7.0 at inoculation, continuously rising to a setpoint of pH 8.0 at 48 hours (change of 0.021 pH units/hour)

Unit 4: pH 7.0 at inoculation, continuously rising to a setpoint of pH 9.0 at 48 hours (change of 0.042 pH units/hour Additionally, the glucose feed of unit 4 was halted at 64 hours (see below). FIG. 12*a* depicts accumulation of total carotenoid (absorbance units per unit dry cell weight) throughout the fermentation. Excluding the last timepoint, units 1 and 2 accumulated similar amounts of carotenoid throughout the run. This result, consistent with previous experiments, suggests that varying the pH in the range of 5.5-7.0 does not affect total carotenoid yield. During this same period, fermentor unit 3 accumulated more carotenoid than units 1 and 2, suggesting setting pH to be within the range of 7.0-8.0 improves the rate of carotenoid biosynthesis. In unit 4, carbon dioxide evolution (indicating metabolic activity) and carotenoid accumulation started to fall precipitiously when the unit reached pH 8.3 at approximately 31 hours (FIG. 12*d*), suggesting toxicity due to high pH. The feed to this unit was therefore stopped at 64 hours. Together, these results suggest that carotenoid yield may be maximized by maintaining pH within the range 7.0-8.0, while pH levels below or above this range were ineffective or toxic, respectively.

FIG. 12*b* depicts accumulation of zeaxanthin (absorbance units per dry cell weight; AU) over the course of the fermentation. As seen in FIG. 12*b*, zeaxanthin accumulation improves with increasing pH. Unit 4, at highest pH, shows superior zeaxanthin accumulation compared to all other units until hour 64, when its feed was terminated. Likewise, unit 3, maintained at pH 8.0 after hour 48, shows significantly improved zeaxanthin accumulation over units 1 and 2, maintained at pH 5.5 and 7.0, respectively. These results indicate that hydroxylation of beta carotene to zeaxanthin is favored by higher pH.

FIG. 12*c* depicts the fraction of carotenoid as zeaxanthin (AU zeaxanthin/AU total carotenoid) throughout the course of the fermentation. Unit 3 hydroxylated a greater fraction of beta-carotene than units 1 and 2, in addition to producing more total carotenoid (FIG. 12*a*) and more total zeaxanthin (FIG. 12*b*). This result demonstrates that at pH 8.0, zeaxanthin accumulation outpaced the global increase in carotenoid biosynthesis also seen at this pH As seen in FIG. 12*e*, biomass accumulated fastest in unit 3 and remained above all other units until the hundred-thirtieth or so hour of fermentation. This unit similarly was the most metabolically active, as shown by its increased rate of carbon dioxide evolution compared to the other units over the same time period (FIG. 12*d*). The subsequent decline in biomass in this unit may be attributed to accelerated metabolism of carbon stored as intracellular oil, relative to the other three units. Thus, it appears that the pH range of 7.0-8.0 enables *Yarrowia lipolytica* both to accumulate biomass and metabolize stored carbon at rates faster than it is able at lower pH.

Together, these results indicate that total biomass accumulation, percentage of biomass representing carotenoid accumulation, and the hydroxylation of beta-carotene to zeaxanthin may be manipulated by maintaining fermentation pH in the approximate range of 7.0-8.0. Moreover, these results suggest that within this same range, an optimum pH may be selected at which to maximize production of both non-oxygenated carotenoids and xanthophylls (e.g. hydroxylation of b-carotene to zeaxanthin and total carotenoid production.

Example 19

Lycopene Epsilon Cyclase Sequences

The DNA and proteins they encode of the certain lycopene epsilon cyclase sequences are provided below. Corresponding Genbank Accession and GI numbers are found in table 23.

*Ostreococcus lucimarinus* sequence XP_001422490
DNA (SEQ ID NO: 164)

ATGAAGGATGATCGCGAATGGATTGCGTTTCAACAGCGCAAGGTGTTTAGTGAGCAAAA

GCAAATCAAAGAGTACCTCAGTGCTTTGAACGACCGCGACAAGGTCGACGTTCTCGTTGT

CGGTGCGGGCCCCGCAGGTCTGGCGATCGCAGCGGAGACGGCGAAGAAGGGTCTTTCTG

TTGGTCTCGTCGCACCAGACACCCCGTTCGTGAACAACTACGGAGTATGGCTCGACGAGT

TCAAAGATCTAGGGCTCGAACACTGCTTGCTTCATAAGTATGACGACGCATTGGTTTGGT

TCGATGATTCTGATCCTGCGAGTGGAACTGAACTCGGTCGACCTTACGGTCAAGTGTGCC

GCAGGCGTCTTCGCGACCATTTGTTGAAGGAGTGCGCGGCGGCTGGCGTCAAGTATTTAC

CAGGCCTGGTAGATTTTGTGCGTCACGGTGACGTCGAAAAGAACGAGTTAGCCGAAGCA

AACAGAGGCCAGCAATTCACGTTGAATTCGCGTCTCGTCGTTGCCGGCACCGGTCACAAC

CGCGACATGCTCAGCTACGAAGAGGGTGCGCCGCCGGGCTGGCAGACTGCGTATGGCGT

TGAGGTGCGCATTCCGAACCACGGTTTTCCCGTGAACAAGGCCGTGTTCATGGATTTTCG

TCAAAGCGATCCGGAGGCGATGAAAGAGGAACAAGACGAGGGCGTTTGGCGCGTGCCG

TCTTTCCTTTACGTGTTACCCGTGGACAAGGATGTGGTGTTCGTCGAGGAGACGTGCCTC

GTCGCGCGCGTACAAGTGCCGTTCGATGAACTCAAACGGCGATTGTATCGTCGTATGAAG

CGGATGGGTATGGAAATCGTCGAAGAAGACATCTTGGAAGTCGAGGCGAGTTGGATTCC

ACTGGGCGGTACCCCGCCGGTTGCCCCGCAACGCACCATCGCGTACGGTGCAGCAGCCG

GCATGGTCCACCCTGCGTCTGGCTACTCCGTCGTAAACAGTATTAGCAAAGCTCCGCGTG

TTGCGACGGCCATGGCCGAAGGCTTGAAGGAGGGTGGCGAGATTGAGGCGAGCCGAAG

-continued

AGCGTGGGAAATCCTTTGGGGTGCGGAGCCACGAAGACAAATCGGTTTCTACCAGTTCG

GTATGGAGCTTCTCATGTCGCTTCGCATCGAGCAGATGCGCAACTTCTTTAGTACCTTCTT

TGCGCTTCCAACAAATCTGAGCAGAGGATTTTTGGGTAACAGATTGTCGAGCTCAGAGTT

GATCATGTTTGCTCTCACTACGTTCGCAATTGGTAACAACGAACTTCGTGGGTTGTTGCTC

GCTCACCTGGTTTCA

Protein (SEQ ID NO: 165)

MKDDREWIAFQQRKVFSEQKQIKEYLSALNDRDKVDVLVVGAGPAGLAIAAETAKKGLSVG

LVAPDTPFVNNYGVWLDEFKDLGLEHCLLHKYDDALVWFDDSDPASGTELGRPYGQVCRR

RLRDHLLKECAAAGVKYLPGLVDFVRHGDVEKNELAEANRGQQFTLNSRLVVAGTGHNRD

MLSYEEGAPPGWQTAYGVEVRIPNHGFPVNKAVFMDFRQSDPEAMKEEQDEGVWRVPSFL

YVLPVDKDVVFVEETCLVARVQVPFDELKRRLYRRMKRMGMEIVEEDILEVEASWIPLGGTP

PVAPQRTIAYGAAAGMVHPASGYSVVNSISKAPRVATAMAEGLKEGGEIEASRRAWEILWG

AEPRRQIGFYQFGMELLMSLRIEQMRNFFSTFFALPTNLSRGFLGNRLSSSELIMFALTTFAIGN

NELRGLLLAHLVS lycopene epsilon cyclase (*Diospyros kaki*) sequence BAE94036
DNA (SEQ ID NO: 166)

ACTACGGCGTATGGGAGGATGAATTTAGAGATCTTGGACTTGAAAGGTGTATTGAACAT

GTTTGGAGAGACACAATTGTATATCTTGATGACAATGATCCCATTCTGATTGGTCGTGCT

TATGGACGAGTTAGTCGTCACTTGCTCCACGAGGAGCTATTAAGAAGGTGTGTGGAGTCA

GGTGTTTCATATTTGAGCTCAAAAGTGGAAAGAATTATTGAAACTACGAATGGGCAGAG

TCTCATAGAGTGCGGAACTGATGTTGTTGTCCCATGCAGGCTTGCTACTGTTGCTTCGGG

AGCAGCTTCTGGGAAACTTTTGAAGTTTGAGGTGGGAGGACCCAGAGTTTCTGTTCAAAC

AGCTTATGGTGTGGAGGTTGAGGTGGAAAACAATCCATATGACCCCAACTTGATGGTTTT

CATGGATTACAGAGACTATGCCAAACAAAAAGTTCAGCCTTTGGAAGCACAATATCCAA

CATTTCTTTATGCCATGCCTATGTCCCCTACAAGAGTCTTCTTTGAGGAAACTTGTTTGGC

TTCAAAGGATGCCATGCCTTTTGATCTATTAAAGAGGAAACTCATGGACAGATTAGAGAC

AATGGGAGTCCATGTTCTAAAAACGTATGAGGAGGAATGGTCTT

Protein (SEQ ID NO: 167)

YGVWEDEFRDLGLERCIEHVWRDTIVYLDDNDPILIGRAYGRVSRHLLHEELLRRCVESGVS

YLSSKVERIIETTNGQSLIECGTDVVVPCRLATVASGAASGKLLKFEVGGPRVSVQTAYGVEV

EVENNPYDPNLMVFMDYRDYAKQKVQPLEAQYPTFLYAMPMSPTRVFFEETCLASKDAMP

FDLLKRKLMDRLETMGVHVLKTYEEEWS

Example 20

Construction of a Lutein Producing Strain

The following sequence, optimized for *Y. lipolytica* codon bias and encoding a putative lycopene epsilon cyclase from *Ostreococcus lucimarinus* CCE9901, is synthesized de novo:

(SEQ ID NO: 168)

TTCTAGAACAAAATGAAGGACGACCGAGAGTGGATCGCCTTCCAGCAGCGAAAG

GTGTTCTCTGAGCAGAAGCAGATCAAGGAGTACCTGTCTGCCCTGAACGACCGA

-continued

```
GACAAGGTGGACGTGCTGGTGGTGGGCGCCGGCCCCGCCGGCCTGGCCATCGCC

GCCGAGACCGCCAAGAAGGGCCTGTCTGTGGGCCTGGTGGCCCCCGACACCCCC

TTCGTGAACAACTACGGCGTGTGGCTGGACGAGTTCAAGGACCTGGGCCTGGAG

CACTGTCTGCTGCACAAGTACGACGACGCCCTGGTGTGGTTCGACGACTCTGACC

CCGCCTCTGGCACCGAGCTGGGCCGACCCTACGGCCAGGTGTGTCGACGACGAC

TGCGAGACCACCTGCTGAAGGAGTGTGCCGCCGCCGGCGTGAAGTACCTGCCCG

GCCTGGTGGACTTCGTGCGACACGGCGACGTGGAGAAGAACGAGCTGGCCGAGG

CCAACCGAGGCCAGCAGTTCACCCTGAACTCTCGACTGGTGGTGGCCGGCACCG

GCCACAACCGAGACATGCTGTCTTACGAGGAGGGCGCCCCCCCCGGCTGGCAGA

CCGCCTACGGCGTGGAGGTGCGAATCCCCAACCACGGCTTCCCCGTGAACAAGG

CCGTGTTCATGGACTTCCGACAGTCTGACCCCGAGGCCATGAAGGAGGAGCAGG

ACGAGGGCGTGTGGCGAGTGCCCTCTTTCCTGTACGTGCTGCCCGTGGACAAGGA

CGTGGTGTTCGTGGAGGAGACCTGTCTGGTGGCCCGAGTGCAGGTGCCCTTCGAC

GAGCTGAAGCGACGACTGTACCGACGAATGAAGCGAATGGGCATGGAGATCGTG

GAGGAGGACATCCTGGAGGTGGAGGCCTCTTGGATCCCCCTGGGCGGCACCCCC

CCCGTGGCCCCCCAGCGAACCATCGCCTACGGCGCCGCCGCCGGCATGGTGCAC

CCCGCCTCTGGCTACTCTGTGGTGAACTCTATCTCTAAGGCCCCCCGAGTGGCCACCGC

CATGGCCGAGGGCCTGAAGGAGGGCGGCGAGATCGAGGCCTCTCGACGAG

CCTGGGAGATCCTGTGGGGCGCCGAGCCCCGACGACAGATCGGCTTCTACCAGTT

CGGCATGGAGCTGCTGATGTCTCTGCGAATCGAGCAGATGCGAAACTTCTTCTCT

ACCTTCTTCGCCCTGCCCACCAACCTGTCTCGAGGCTTCCTGGGCAACCGACTGT

CTTCTTCTGAGCTGATCATGTTCGCCCTGACCACCTTCGCCATCGGCAACAACGAGCTGC

GAGGCCTGCTGCTGGCCCACCTGGTGTCTTAAACGCGT
```

This fragment, liberated with XbaI and MluI, is cloned into NheI- and MluI-cleaved pMB5082 to produce pEpCyOs1.

A second putative lycopene epsilon cyclase from *Ostreococcus lucimarinus* CCE9901 is similarly codon-optimized and synthesized de novo:

```
                                              (SEQ ID NO: 169)
TTCTAGAACAAAATGCGAGCCCGACGAGCCCCCGCCGCCCGAGTGACCCGAGCC

ATCCGAGCCCGAGGCGACGCCGGCACCCGAGCCCGAGACGTGGCCCCCGGCGCC

ACCCGACGAGGCGCCTCTGCCACCCCCCGAGCCACCCGACGACCCTCTGCCCGA

GAGACCCGACCCGAGCTGTACGGCCTGGACGCCTCTTGGGACCCCCTGACCTCTG

GCGACCGACGAGAGTCTGAGGAGTCTCGAACCCCCCTGCCCGAGACCCTGCCCA

ACGTGCGATGGGGCACCTCTGCCTCTGAGGCCTACGACCTGGTGATCGTGGGCTG

TGGCCCCGCCGGCCTGACCGCCGCCGACGAGGCCTCTAAGCGAGGCCTGCGAGT

GGCCCTGATGGACCCCTCTCCCCTGGCCCCCTGGATGAACAACTACGGCGTGTGG

TGTGACGAGTTCAAGTCTCTGGGCTTCGACGACTGTTACCGAGCCGTGTGGAACA

AGGCCCGAGTGATCATCGACGACGGCGACGCCGACGGCAAGATGCTGGACCGAG

CCTACGCCCAGGTGGACCGAAAGAAGCTGAAGCAGAAGCTGATCGCCCGATCTG

TGACCCAGGGCGTGGAGTTCGGCATCGCCGCCGTGGACTCTTGTGACAACTCTGA

CCCCAACCACTCTGTGGTGACCCTGTCTGACGGCCGAAAGGTGTACGCCAAGATG
```

-continued

GTGCTGGACGCCACCGGCCACTCTCGAAAGCTGGTGGACTTCGACCGAGACTTCA

CCCCCGGCTACCAGGCCGCCTTCGGCATCGTGTGTACCGTGGAGAAGCACGACTT

CCCCCTGGACACCATGCTGTTCATGGACTGGCGAGACGAGCACCTGTCTCCCGAG

TTCAAGCGAGCCAACGACCGACTGCCCACCTTCCTGTACGCCATGCCCTTCTCTG

AGACCGAGGTGTTCCTGGAGGAGACCTCTCTGGTGGCCCGACCCGGCCTGGAGTT

CGACGACCTGAAGCTGAAGCTGAAGGAGCGACTGGACTACCTGGGCGTGAAGGT

GACCAAGGTGCACGAGGAGGAGTACTGTCTGATCCCCATGGGCGGCGTGCTGCCCAC

CTTCCCCCAGCGAACCCTGGGCATCGGCGGCACCGCCGGCATGGTGCACCCC

TCTACCGGCTTCATGGTGGCCAAGACCATGCTGTGTGTGCGAACCCTGGTGGGCA

CCCTGGACGAGGCCCTGAAGGCCGGCAAGCGAGGCGACATCACCGGCGCCCTGG

AGGCCGCCGAGGCCGCCCAGATGAACAACGGCAAGTTCGACGCCGACGCCACCGCC

GCCCTGGTGTGGAACTCTATCTGGCCCGAGAACGACCTGCGAATGCGAACCTT

CATGTGTTTCGGCATGGAGACCCTGATGCAGCTGGACATCGACGGCACCCGACAGTTC

TTCGACACCTTCTTCGACCTGCCCAAGGACGTGTGGGCCGGCTTCCTGTCTT

GGCGAATCCAGCCCGTGGGCCTGCTGTCTCTGGGCGTGAACCTGTTCGCCCTGTT

CTCTAACTACATGCGAGTGAACTTCGTGAAGTCTGCCCTGCCCTTCATGGGCTCTTTCTT

CGCCAACTAAACGCGT

This fragment, liberated with XbaI and MluI, is cloned into NheI- and MluI-cleaved pMB5082 to produce pEpCyOs2.

The following sequence, optimized for *Y. lipolytica* codon bias and encoding a putative carotene epsilon hydroxylase from *Ostreococcus tauri*, is synthesized de novo:

(SEQ ID NO: 170)

TTCTAGAACAAAATGAAGGACGGCCAGGACGAGGACTCTGACGAGATCTGGGGC

GGCCAGCGACACGCCTCTGAGATGAAGACCCCCACCCGACGAAAGGCCCGAACC

AAGGCCGAGCGAGAGGCCTCTGCCGCCTCTTACGAGTGGTCTGCCTGGGCCTCTTCT

TGTGGCGTGATCTCTGTGGCCATCACCGCCACCTACTTCCGAATCCTGCGAGA

GGTGGACGTGAACGGCGGCGTGTTCCCCGTGGCCGAGCTGGTGGCCCAGCTGGC

CCTGATCGCCGGCGCCGCCGTGGGCATGGAGTTCTACGCCCGATACGCCCACAA

GCACCTGTGGCACGGCTCTTGGTGGACCATGTCTAACAAGTACCGACAGGAGTG

GAACCGACCCATCTGGCTGCTGCACGAGTCTCACCACCTGCCCCGAGAGGGCGC

CTTCGAGGCCAACGACGTGTTCGCCCTGATGAACGGCGTGCCCGCCTTCGCCCTG

TGTGCCTTCGGCTTCTTCACCCCCGGCGTGTTCGGCGGCCTGTGTTTCGGCGCCGGCC

TGGGCATCACCCTGTTCGGCATCGCCTACATGTACGTGCACGACGGCCTGGTG

CACAAGCGATTCCCCACCGGCCCCCTGGGCAAGCTGCCCGTGATGCGACGAATC

GCCGCCGGCCACACCATCCACCACACCGAGGCCTTCGAGGGCGTGCCCTGGGGCCTG

TTCCTGGGCATCCAGGAGCTGGCCGCCGTGCCCGGCGGCCTGGAGGAGCTG

GAGAAGGTGGTGATCGCCGCCGAGCGAAAGGAGAAGCGAGACGAGCTGGAGCT

GGCCCGACGAGCCTCTGTGGGCCTGGTGACCGAGGGCGCCCACATCCCCTCTATGAAG

GAGGCCCCCCAGTGTAAGCTGCCCGAGGACCCCTAAACGCGT

This fragment, liberated with XbaI and MluI, is cloned into NheI- and MluI-cleaved pMB5082 to produce pEpHyOs1.

The 1.9 kb KpnI-SacI TEF1p-crtZ fragment from pMB4837 (example 10) is cloned into KpnI- and SacI-cleaved pMB5082 to create pCrtZ-Ub.

A strain expressing carRP, carB, GGS, and HMG1$_{trunc}$ and auxotrophic for ura3 (MF946; example 2F) is transformed successively, in any order, with the URA3 plasmids pEpCyOs1 (or pEpCyOs2), pEpHyOs1, and pCrtZ-Ub, with the recycling of the ura3 marker between each step, as described in Example 15. Such a strain is expected to produce >1 mg/gDCW lutein. This strain may be further modified by transformation with pMB4789 (erg9[F317I]-3'UTR::URA3), as described in example 2H.

The following tables are referenced throughout the description. Each reference and information designated by each of the Genbank Accession and GI numbers are hereby incorporated by reference in their entirety. The order of genes, polypeptides and sequences presented in the tables is not indicative of their relative importance and/or suitability to any of the embodiments disclosed herein.

TABLE 1

Examples of acetyl-CoA carboxylase polypeptides.

| ACCESSION | GI | PROTEIN DESCRIPTION |
|---|---|---|
| XP_410263 | 49097606 | hypothetical protein AN6126.2 [*Aspergillus nidulans* FGSC A4] |
| XP_329580 | 32418204 | hypothetical protein [*Neurospora crassa*] |
| XP_386756 | 46124405 | hypothetical protein FG06580.1 [*Gibberella zeae* PH-1] |
| XP_367702 | 39972623 | hypothetical protein MG07613.4 [*Magnaporthe grisea* 70-15] |
| XP_501721 | 50548503 | hypothetical protein [*Yarrowia lipolytica*] |
| EAK99708 | 46440402 | hypothetical protein CaO19.7466 [*Candida albicans* SC5314] |
| XP_457211 | 50413128 | unnamed protein product [*Debaryomyces hansenii*] |
| NP_982612 | 45184894 | AAR071Wp [*Eremothecium gossypii*] |
| XP_449236 | 50293649 | unnamed protein product [*Candida glabrata*] |
| NP_593271 | 19114183 | acetyl-coa carboxylase [*Schizosaccharomyces pombe*] |
| NP_014413 | 6324343 | Acc1p [*Saccharomyces cerevisiae*] |
| XP_455355 | 50310667 | unnamed protein product [*Kluyveromyces lactis*] |
| T42531 | 11272737 | acetyl-CoA carboxylase (EC 6.4.1.2) - fission yeast (*Schizosaccharomyces pombe*) |
| AAA20073 | 171504 | acetyl-CoA carboxylase |
| EAL20176 | 50257469 | hypothetical protein CNBF2520 [*Cryptococcus neoformans* var. *neoformans* B-3501A] |
| XP_571316 | 58268320 | acetyl-CoA carboxylase, putative [*Cryptococcus neoformans* var. *neoformans* JEC21] |
| XP_402244 | 49076566 | hypothetical protein UM04629.1 [*Ustilago maydis* 521] |
| S60200 | 2133343 | acetyl-CoA carboxylase (EC 6.4.1.2) - smut fungus (*Ustilago maydis*) |
| BAA24410 | 2804173 | acetyl-coenzyme A carboxylase like carboxylase [*Saccharomyces cerevisiae*] |
| P32874 | 1708192 | HFA1 protein |
| S55089 | 7438088 | probable acetyl-CoA carboxylase (EC 6.4.1.2) HFA1 - yeast (*Saccharomyces cerevisiae*) |
| NP_990836 | 45382859 | acetyl-Coenzyme A carboxylase alpha [*Gallus gallus*] |
| CAE01471 | 32526576 | Acetyl-CoA carboxylase 2 [*Homo sapiens*] |
| AAR37018 | 40019048 | acetyl-CoA carboxylase 2 [*Homo sapiens*] |
| NP_001 . . . | 57164283 | acetyl-CoA carboxylase [*Ovis aries*] |
| NP_776649 | 27806341 | acetyl-coenzyme A carboxylase alpha [acetyl-coA carboxylase] [*Bos taurus*] |
| CAI25271 | 56205878 | acetyl-Coenzyme A carboxylase [*Mus musculus*] |
| XP_109883 | 51828611 | PREDICTED: acetyl-Coenzyme A carboxylase [*Mus musculus*] |
| NP_942134 | 38679971 | acetyl-Coenzyme A carboxylase alpha isoform 3 [*Homo sapiens*] |
| NP_942131 | 38679960 | acetyl-Coenzyme A carboxylase alpha isoform 1 [*Homo sapiens*] |
| NP_942135 | 38679974 | acetyl-Coenzyme A carboxylase alpha isoform 4 [*Homo sapiens*] |
| NP_942136 | 38679977 | acetyl-Coenzyme A carboxylase alpha isoform 2 [*Homo sapiens*] |
| AAP94122 | 33112885 | acetyl-CoA carboxylase 1 [*Homo sapiens*] |
| NP_071529 | 11559962 | acetyl-coenzyme A carboxylase alpha [*Rattus norvegicus*] |
| 2006242A | 740964 | Ac-CoA carboxylase |
| AAS13685 | 42405896 | acetyl-CoA carboxylase 1 [*Mus musculus*] |
| NP_598665 | 48976025 | acetyl-Coenzyme A carboxylase beta [*Mus musculus*] |
| Q13085 | 2493311 | Acetyl-CoA carboxylase 1 (ACC-alpha) [Includes: Biotin carboxylase] |
| XP_548250 | 57091783 | PREDICTED: similar to acetyl-CoA carboxylase [*Canis familiaris*] |
| XP_314071 | 58385597 | ENSANGP00000015662 [*Anopheles gambiae* str. PEST] |
| CAG08536 | 47226520 | unnamed protein product [*Tetraodon nigroviridis*] |
| NP_724636 | 24586460 | CG11198-PB, isoform B [*Drosophila melanogaster*] |
| NP_610342 | 24586458 | CG11198-PA, isoform A [*Drosophila melanogaster*] |
| NP_001084 | 4501855 | acetyl-Coenzyme A carboxylase beta [*Homo sapiens*] |
| NP_446374 | 16758804 | acetyl-Coenzyme A carboxylase beta [*Rattus norvegicus*] |
| EAL63219 | 60465120 | acetyl-CoA carboxylase [*Dictyostelium discoideum*] |
| NP_921034 | 37533464 | putative acetyl-CoA carboxylase [*Oryza sativa* (*japonica* cultivar-group)] |
| T07084 | 7438099 | acetyl-CoA carboxylase (EC 6.4.1.2) A - soybean |
| AAP78896 | 32264940 | acetyl-coenzyme A carboxylase ACC1A [*Zea mays*] |
| AAO62903 | 29123370 | acetyl-coenzyme A carboxylase [*Setaria italica*] |
| BAA07012 | 1100253 | acetyl-CoA carboxylase [*Arabidopsis thaliana*] |
| AAL02056 | 15558947 | acetyl-coenzyme A carboxylase [*Setaria italica*] |
| AAG40563 | 11869927 | acetyl-CoA carboxylase 1 [*Arabidopsis thaliana*] |
| D86483 | 25293894 | protein F5J5.19 [imported] - *Arabidopsis thaliana* |
| T07920 | 7438090 | probable acetyl-CoA carboxylase (EC 6.4.1.2) - rape |
| A57710 | 2130099 | acetyl-CoA carboxylase (EC 6.4.1.2) - wheat |

TABLE 1-continued

| Examples of acetyl-CoA carboxylase polypeptides. | | |
|---|---|---|
| ACCESSION | GI | PROTEIN DESCRIPTION |
| AAO62902 | 29123376 | acetyl-coenzyme A carboxylase [*Setaria italica*] |
| 2208491A | 1588584 | Ac-CoA carboxylase |
| T09538 | 7438102 | acetyl-CoA carboxylase (EC 6.4.1.2) - alfalfa |
| CAC19875 | 12057067 | acetyl-CoA carboxylase [*Brassica napus*] |
| AAP78897 | 32264942 | acetyl-coenzyme A carboxylase ACC1B [*Zea mays*] |
| T02235 | 7438095 | acetyl-CoA carboxylase (EC 6.4.1.2) - maize |
| AAG40564 | 11869928 | acetyl-CoA carboxylase 2 [*Arabidopsis thaliana*] |
| E86483 | 25293893 | probable acetyl-CoA carboxylase, 9984-22276 [mported] - *Arabidopsis thaliana* |
| CAC84161 | 20975574 | acetyl-coenzyme A carboxylase [*Alopecurus myosuroides*] |
| T07081 | 7438097 | acetyl-CoA carboxylase (EC 6.4.1.2) B - soybean (fragment) |
| CAC19876 | 12057069 | acetyl-CoA carboxylase [*Brassica napus*] |

TABLE 2

| Examples of pyruvate decarboxylase polypeptides. | | |
|---|---|---|
| ACCESSION | GI | PROTEIN DESCRIPTION |
| 1QPBB | 7245977 | Chain B, Pyruvate Decarboyxlase From Yeast (Form B) Complexed With Pyruvamide |
| CAA54522 | 871533 | pyruvate decarboxylase [*Saccharomyces cerevisiae*] |
| 1PYDB | 515237 | Chain B, Pyruvate Decarboxylase (Pdc) (E.C.4.1.1.1) |
| CAA28380 | 4109 | pyruvate decarboxylase [*Saccharomyces cerevisiae*] |
| 1PVDB | 1127233 | Chain B, Pyruvate Decarboxylase (Pdc) (E.C.4.1.1.1) |
| CAA33709 | 4114 | unnamed protein product [*Saccharomyces cerevisiae*] |
| AAN77243 | 25992752 | pyruvate decarboxylase [*Candida glabrata*] |
| NP_013235 | 6323163 | Minor isoform of pyruvate decarboxylase, key enzyme in alcoholic fermentation [*Saccharomyces cerevisiae*] |
| Q6FJA3 | 57012668 | Pyruvate decarboxylase |
| S36363 | 486942 | pyruvate decarboxylase (EC 4.1.1.1) - yeast (*Kluyveromyces marxianus*) |
| Q12629 | 52788279 | Pyruvate decarboxylase |
| AAP75898 | 37359468 | pyruvate decarboxylase [*Saccharomyces kluyveri*] |
| S70684 | 2131152 | pyruvate decarboxylase (EC 4.1.1.1) - yeast (*Kluyveromyces marxianus* var. *lactis*) |
| NP_011601 | 6321524 | Minor isoform of pyruvate decarboxylase, key enzyme in alcoholic fermentation [*Saccharomyces cerevisiae*] |
| AAQ73618 | 34500072 | pyruvate decarboxylase [*Saccharomyces kluyveri*] |
| NP_983270 | 45185554 | ACL134Cp [*Eremothecium gossypii*] |
| AAF78895 | 8745337 | putative pyruvate decarboxylase [*Saccharomyces kluyveri*] |
| CAB65554 | 6689662 | putative pyruvate decarboxylase [*Zygosaccharomyces bisporus*] |
| AAP75899 | 37359470 | pyruvate decarboxylase [*Saccharomyces kluyveri*] |
| NP_982469 | 45184751 | AAL073Wp [*Eremothecium gossypii*] |
| CAA97091 | 1945321 | PDC6 [*Saccharomyces cerevisiae*] |
| S50700 | 1086157 | pyruvate decarboxylase (EC 4.1.1.1) - yeast (*Hanseniaspora uvarum*) |
| XP_446491 | 50288125 | unnamed protein product [*Candida glabrata*] |
| XP_462338 | 50427451 | unnamed protein product [*Debaryomyces hansenii*] |
| AAC03164 | 17066784 | pyruvate decarboxylase 1 [*Pichia stipitis*] |
| EAK96569 | 46437219 | hypothetical protein CaO19.10395 [*Candida albicans* SC5314] |
| XP_457131 | 50412425 | unnamed protein product [*Debaryomyces hansenii*] |
| AAC03165 | 2734883 | pyruvate decarboxylase 2 [*Pichia stipitis*] |
| XP_459224 | 50421349 | unnamed protein product [*Debaryomyces hansenii*] |
| CAH56494 | 52673248 | pyruvate decarboxylase [*Pichia anomala*] |
| XP_502647 | 50550349 | hypothetical protein [*Yarrowia lipolytica*] |
| NP_010203 | 6320123 | Probable decarboxylase, [*Saccharomyces cerevisiae*] |
| BAA04886 | 1786148 | THI3 regulatory protein [*Saccharomyces cerevisiae*] |
| XP_449074 | 50293325 | unnamed protein product [*Candida glabrata*] |
| EAL04098 | 46444826 | hypothetical protein CaO19.12078 [*Candida albicans* SC5314] |
| CAD60727 | 27803024 | unnamed protein product [*Podospora anserina*] |
| T38759 | 25777585 | probable pyruvate decarboxylase (EC 4.1.1.1) - fission yeast (*Schizosaccharomyces pombe*) |
| XP_331173 | 32421459 | hypothetical protein [*Neurospora crassa*] |
| NP_594083 | 19114995 | pyruvate decarboxylase [*Schizosaccharomyces pombe*] |
| XP_401609 | 49075036 | hypothetical protein UM03994.1 [*Ustilago maydis* 521] |
| XP_390010 | 46136637 | hypothetical protein FG09834.1 [*Gibberella zeae* PH-1] |
| XP_409025 | 49095128 | DCPY_EMENI Pyruvate decarboxylase [*Aspergillus nidulans* FGSC A4] |
| NP_984350 | 45188127 | ADR254Wp [*Eremothecium gossypii*] |
| AAD16178 | 4323053 | pyruvate decarboxylase [*Aspergillus oryzae*] |
| P87208 | 2501326 | Pyruvate decarboxylase |
| EAL18331 | 50255598 | hypothetical protein CNBJ2540 [*Cryptococcus neoformans* var. *neoformans* B-3501A] |

TABLE 2-continued

Examples of pyruvate decarboxylase polypeptides.

| ACCESSION | GI | PROTEIN DESCRIPTION |
|---|---|---|
| XP_567475 | 58260130 | pyruvate decarboxylase, putative [*Cryptococcus neoformans* var. *neoformans* JEC21] |
| AAM73540 | 21666011 | pyruvate decarboxylase PdcB [*Rhizopus oryzae*] |
| AAM73539 | 21666009 | pyruvate decarboxylase PdcA [*Rhizopus oryzae*] |
| XP_502508 | 50550071 | hypothetical protein [*Yarrowia lipolytica*] |
| CAA93158 | 1177659 | SPAC3H8.01 [*Schizosaccharomyces pombe*] |
| XP_412533 | 49123327 | hypothetical protein AN8396.2 [*Aspergillus nidulans* FGSC A4] |
| P51844 | 1706333 | Pyruvate decarboxylase |
| XP_455842 | 50311631 | unnamed protein product [*Kluyveromyces lactis*] |
| CAA61155 | 3688422 | pyruvate decarboxylase [*Kluyveromyces lactis*] |
| XP_444902 | 50284947 | unnamed protein product [*Candida glabrata*] |
| CAA47319 | 4118 | pyruvate decarboxylase [*Saccharomyces cerevisiae*] |

TABLE 3

Examples of isocitrate dehydrogenase polypeptides.

| ACCESSION | GI | PROTEIN DESCRIPTION |
|---|---|---|
| O13285 | 3023996 | Isocitrate dehydrogenase [NADP], mitochondrial precursor (IDH) (NADP+-specific ICDH) (IDP) (CtIDP1) |
| EAK91676 | 46432179 | hypothetical protein CaO19.5211 [*Candida albicans* SC5314] |
| O13285 | 3023996 | Isocitrate dehydrogenase [NADP], mitochondrial precursor (IDH) (NADP+-specific ICDH) (IDP) (CtIDP1) |
| EAK94305 | 46434909 | hypothetical protein CaO19.3733 [*Candida albicans* SC5314] |
| XP_451683 | 50303483 | unnamed protein product [*Kluyveromyces lactis*] |
| XP_459772 | 50422415 | unnamed protein product [*Debaryomyces hansenii*] |
| O13294 | 27805482 | Isocitrate dehydrogenase [NADP] peroxisomal (Oxalosuccinate decarboxylase) (IDH) (PS-NADP-IDH) (CtIDP2) |
| XP_460289 | 50423413 | unnamed protein product [*Debaryomyces hansenii*] |
| XP_390523 | 46137663 | hypothetical protein FG10347.1 [*Gibberella zeae* PH-1] |
| XP_367343 | 39971905 | hypothetical protein MG07268.4 [*Magnaporthe grisea* 70-15] |
| XP_323176 | 32405126 | hypothetical protein [*Neurospora crassa*] |
| XP_445447 | 50286037 | unnamed protein product [*Candida glabrata*] |
| AAK76730 | 15027826 | mitochondrial NADP-dependent isocitrate dehydrogenase [*Aspergillus nidulans*] |
| NP_010217 | 6320137 | Idp1p [*Saccharomyces cerevisiae*] |
| NP_984921 | 45190667 | AER061Cp [*Eremothecium gossypii*] |
| AAK76731 | 15027827 | peroxisomal NADP-dependent isocitrate dehydrogenase [*Aspergillus nidulans*] |
| P79089 | 3023999 | Isocitrate dehydrogenase [NADP], mitochondrial precursor (IDH) (NADP+-specific ICDH) (IDP) |
| NP_013275 | 6323203 | Cytosolic NADP-specific isocitrate dehydrogenase [*Saccharomyces cerevisiae*] |
| XP_407136 | 49091350 | IDHP_ASPNG ISOCITRATE DEHYDROGENASE [NADP], MITOCHONDRIAL PRECURSOR (IDP) [*Aspergillus nidulans* FGSC A4] |
| NP_982520 | 45184802 | AAL022Wp [*Eremothecium gossypii*] |
| XP_446953 | 50289047 | unnamed protein product [*Candida glabrata*] |
| XP_445184 | 50285511 | unnamed protein product [*Candida glabrata*] |
| XP_455638 | 50311227 | unnamed protein product [*Kluyveromyces lactis*] |
| AAA64516 | 736722 | isocitrate dehydrogenase |
| NP_970434 | 42525054 | isocitrate dehydrogenase (NADP) [*Bdellovibrio bacteriovorus* HD100] |
| AAT93173 | 51013759 | YNL009W [*Saccharomyces cerevisiae*] |
| XP_569233 | 58264154 | isocitrate dehydrogenase (NADP+), putative [*Cryptococcus neoformans* var. *neoformans* JEC21] |
| XP_569234 | 58264156 | isocitrate dehydrogenase (NADP+), putative [*Cryptococcus neoformans* var. *neoformans* JEC21] |
| XP_403726 | 49080406 | hypothetical protein UM06111.1 [*Ustilago maydis* 521] |
| XP_503571 | 50552322 | |
| XP_458151 | 50428131 | unnamed protein product [*Debaryomyces hansenii*] |
| O13302 | 13124301 | Isocitrate dehydrogenase [NAD] subunit 1, mitochondrial precursor (NAD+-specific ICDH) |
| XP_409927 | 49096934 | IDH1_AJECA Isocitrate dehydrogenase [NAD] subunit 1, mitochondrial precursor[*Aspergillus nidulans* FGSC A4] |
| XP_385909 | 46122711 | IDH1_AJECA Isocitrate dehydrogenase [NAD] subunit 1, mitochondrial precursor [*Gibberella zeae* PH-1] |
| XP_365293 | 39967489 | hypothetical protein MG01995.4 [*Magnaporthe grisea* 70-15] |
| NP_983873 | 45187650 | ADL223Wp [*Eremothecium gossypii*] |
| XP_455266 | 50310493 | IDH1_KLULA [*Kluyveromyces lactis*] |
| NP_594397 | 19115309 | putative isocitrate dehydrogenase (EC 1.1.1.41) [*Schizosaccharomyces pombe*] |

TABLE 3-continued

| Examples of isocitrate dehydrogenase polypeptides. | | |
|---|---|---|
| ACCESSION | GI | PROTEIN DESCRIPTION |
| XP_324955 | 32408949 | hypothetical protein [*Neurospora crassa*] |
| CAE81942 | 38636405 | probable isocitrate dehydrogenase [NAD] subunit 1, mitochondrial precursor [*Neurospora crassa*] |
| NP_014361 | 6324291 | Idh1p [*Saccharomyces cerevisiae*] |
| XP_446479 | 50288101 | unnamed protein product [*Candida glabrata*] |
| XP_567378 | 58259936 | isocitrate dehydrogenase (NAD+), putative [*Cryptococcus neoformans* var. *neoformans* JEC21] |
| XP_398944 | 49069310 | hypothetical protein UM01329.1 [*Ustilago maydis* 521] |
| XP_502479 | 50550013 | hypothetical protein [*Yarrowia lipolytica*] |
| EAK96238 | 46436883 | hypothetical protein CaO19.13213 [*Candida albicans* SC5314] |
| EAK96305 | 46436951 | hypothetical protein CaO19.5791 [*Candida albicans* SC5314] |
| XP_461797 | 50426401 | unnamed protein product [*Debaryomyces hansenii*] |
| XP_328403 | 32415850 | hypothetical protein [*Neurospora crassa*] |
| CAF31997 | 42820684 | isocitrate dehydrogenase, putative [*Aspergillus fumigatus*] |
| XP_389756 | 46136129 | hypothetical protein FG09580.1 [*Gibberella zeae* PH-1] |
| XP_363786 | 39952139 | hypothetical protein MG01712.4 [*Magnaporthe grisea* 70-15] |
| AAL73035 | 18463935 | isocitrate dehydrogenase [*Coccidioides immitis*] |
| XP_405140 | 49086142 | hypothetical protein AN1003.2 [*Aspergillus nidulans* FGSC A4] |
| NP_595203 | 19111995 | probable isocitrate dehydrogenase [nad] subunit 2, mitochondrial precursor [*Schizosaccharomyces pombe*] |
| NP_014779 | 6324709 | Idh2p [*Saccharomyces cerevisiae*] |
| XP_447564 | 50290265 | unnamed protein product [*Candida glabrata*] |
| NP_985684 | 45198655 | AFR137Cp [*Eremothecium gossypii*] |
| XP_566837 | 58258849 | isocitrate dehydrogenase, putative [*Cryptococcus neoformans* var. *neoformans* JEC21] |
| XP_454086 | 50308171 | IDH2_KLULA [*Kluyveromyces lactis*] |
| XP_398943 | 49069308 | hypothetical protein UM01328.1 [*Ustilago maydis* 521] |

TABLE 4

| Examples of ATP-citrate lyase polypeptides. | | |
|---|---|---|
| ACCESSION | GI | PROTEIN DESCRIPTION |
| XP_327071 | 32413182 | hypothetical protein [*Neurospora crassa*] |
| O93988 | 30912679 | ATP-citrate synthase subunit 1 (ATP-citrate (pro-S-)-lyase 1) (Citrate cleavage enzyme subunit 1) |
| XP_370222 | 39977669 | hypothetical protein MG06719.4 [*Magnaporthe grisea* 70-15] |
| XP_406573 | 49090008 | ACL1_NEUCR Probable ATP-citrate synthase subunit 1 [*Aspergillus nidulans* FGSC A4] |
| XP_504787 | 50554757 | hypothetical protein [*Yarrowia lipolytica*] |
| Q9P7W3 | 30912748 | Probable ATP-citrate synthase subunit 1 (ATP-citrate (pro-S-)-lyase 1) (Citrate cleavage enzyme subunit 1) |
| XP_398620 | 49068662 | hypothetical protein UM01005.1 [*Ustilago maydis* 521] |
| NP_596202 | 19112994 | probable ATP citrate lyase [*Schizosaccharomyces pombe*] |
| XP_567460 | 58260100 | conserved hypothetical protein [*Cryptococcus neoformans* var. *neoformans* JEC21] |
| NP_001008 | 56118260 | acly-prov protein [*Xenopus tropicalis*] |
| XP_418154 | 50760837 | PREDICTED: similar to ATP citrate lyase [*Gallus gallus*] |
| AAH84253 | 54038148 | LOC495086 protein [*Xenopus laevis*] |
| NP_942127 | 38569423 | ATP citrate lyase isoform 2 [*Homo sapiens*] |
| NP_001087 | 38569421 | ATP citrate lyase isoform 1 [*Homo sapiens*] |
| P53396 | 20141248 | ATP-citrate synthase (ATP-citrate (pro-S-)-lyase) (Citrate cleavage enzyme) |
| AAL34316 | 17028103 | ATP-citrate lyase [*Rattus norvegicus*] |
| NP_001002 | 50540366 | zgc: 92008 [*Danio rerio*] |
| AAH84776 | 54311201 | LOC495316 protein [*Xenopus laevis*] |
| S21173 | 105392 | ATP citrate (pro-S)-lyase - human |
| AAT94429 | 51092031 | RE70805p [*Drosophila melanogaster*] |
| AAD34754 | 28372804 | LD21334p [*Drosophila melanogaster*] |
| AAH21502 | 18204829 | Acly protein [*Mus musculus*] |
| XP_319323 | 58392375 | ENSANGP00000012364 [*Anopheles gambiae* str. PEST] |
| NP_725514 | 24653990 | CG8322-PB, isoform B [*Drosophila melanogaster*] |
| EAL26601 | 54637198 | GA20986-PA [*Drosophila pseudoobscura*] |
| CAE56725 | 39579419 | Hypothetical protein CBG24512 [*Caenorhabditis briggsae*] |
| CAE64663 | 39593194 | Hypothetical protein CBG09435 [*Caenorhabditis briggsae*] |
| XP_511495 | 55645405 | PREDICTED: similar to ATP citrate lyase isoform 1 [*Pan troglodytes*] |
| CAF95829 | 47210997 | unnamed protein product [*Tetraodon nigroviridis*] |
| AAO22565 | 27754223 | putative ATP citrate lyase [*Arabidopsis thaliana*] |
| AAL33788 | 17065616 | putative ATP citrate lyase [*Arabidopsis thaliana*] |
| CAB46077 | 5304837 | ATP citrate lyase [*Cyanophora paradoxa*] |
| CAF96044 | 47204726 | unnamed protein product [*Tetraodon nigroviridis*] |
| AAK13318 | 13160653 | ATP:citrate lyase [*Capsicum annuum*] |

TABLE 4-continued

Examples of ATP-citrate lyase polypeptides.

| ACCESSION | GI | PROTEIN DESCRIPTION |
|---|---|---|
| AAQ75159 | 34558815 | citrate lyase subunit 2 [*Alvinella pompejana* epibiont 7G3] |
| AAQ75128 | 34558783 | citrate lyase subunit 2 [*Alvinella pompejana* epibiont 6C6] |
| XP_537640 | 57091075 | PREDICTED: similar to ATP citrate lyase isoform 2 [*Canis familiaris*] |
| XP_327069 | 32413178 | hypothetical protein ((AJ243817) ATP citrate lyase, subunit 2 [*Sordaria macrospora*]) [*Neurospora crassa*] |
| CAB76164 | 7160184 | ATP citrate lyase, subunit 2 [*Sordaria macrospora*] |
| XP_370223 | 39977671 | hypothetical protein MG06720.4 [*Magnaporthe grisea* 70-15] |
| XP_386215 | 46123323 | hypothetical protein FG06039.1 [*Gibberella zeae* PH-1] |
| CAA10666 | 7159697 | ATP-citrat-lyase [*Gibberella pulicaris*] |
| XP_406572 | 49090004 | conserved hypothetical protein [*Aspergillus nidulans* FGSC A4] |
| XP_503231 | 50551515 | hypothetical protein [*Yarrowia lipolytica*] |
| NP_593246 | 19114158 | putative ATP-citrate (pro-S-) lyase (EC 4.1.3.8) [*Schizosaccharomyces pombe*] |
| XP_398620 | 49068662 | hypothetical protein UM01005.1 [*Ustilago maydis* 521] |
| XP_567460 | 58260100 | conserved hypothetical protein [*Cryptococcus neoformans* var. *neoformans* JEC21] |
| AAT94429 | 51092031 | RE70805p [*Drosophila melanogaster*] |
| NP_725514 | 24653990 | CG8322-PB, isoform B [*Drosophila melanogaster*] |
| AAD34754 | 28372804 | LD21334p [*Drosophila melanogaster*] |
| EAL26601 | 54637198 | GA20986-PA [*Drosophila pseudoobscura*] |
| XP_319323 | 58392375 | ENSANGP00000012364 [*Anopheles gambiae* str. PEST] |
| AAH84776 | 54311201 | LOC495316 protein [*Xenopus laevis*] |
| BAB00624 | 9229902 | ATP citrate-lyase [*Ciona intestinalis*] |
| NP_001008 | 56118260 | acly-prov protein [*Xenopus tropicalis*] |
| AAH84253 | 54038148 | LOC495086 protein [*Xenopus laevis*] |
| AAH56378 | 38614162 | ATP citrate lyase [*Mus musculus*] |
| NP_001087 | 38569421 | ATP citrate lyase isoform 1 [*Homo sapiens*] |
| NP_942127 | 38569423 | ATP citrate lyase isoform 2 [*Homo sapiens*] |
| P53396 | 20141248 | ATP-citrate synthase (ATP-citrate (pro-S-)-lyase) (Citrate cleavage enzyme) |
| XP_511495 | 55645405 | PREDICTED: similar to ATP citrate lyase isoform 1 [*Pan troglodytes*] |
| NP_058683 | 8392839 | ATP citrate lyase [*Rattus norvegicus*] |
| NP_001002 | 50540366 | zgc: 92008 [*Danio rerio*] |
| S21173 | 105392 | ATP citrate (pro-S)-lyase - human |
| NP_508280 | 17551266 | atp citrate lyase (XC101) [*Caenorhabditis elegans*] |
| CAE64663 | 39593194 | Hypothetical protein CBG09435 [*Caenorhabditis briggsae*] |
| CAE56725 | 39579419 | Hypothetical protein CBG24512 [*Caenorhabditis briggsae*] |
| NP_506267 | 17557344 | ATP citrate lyase (120.6 kD) (5N599) [*Caenorhabditis elegans*] |
| XP_537640 | 57091075 | PREDICTED: similar to ATP citrate lyase isoform 2 [*Canis familiaris*] |
| CAF96059 | 47204551 | unnamed protein product [*Tetraodon nigroviridis*] |
| F96633 | 25404292 | hypothetical protein F8A5.32 [imported]- *Arabidopsis thaliana* |
| AAM91141 | 22136126 | similar to ATP-citrate-lyase [*Arabidopsis thaliana*] |
| NP_849634 | 30681854 | expressed protein [*Arabidopsis thaliana*] |
| AAO23582 | 27764922 | At1g09430/F19J9_9 [*Arabidopsis thaliana*] |
| AAM65078 | 21593129 | ATP citrate-lyase, putative [*Arabidopsis thaliana*] |
| CAC86996 | 15919089 | ATP citrate lyase b-subunit [*Lupinus albus*] |
| AAQ75158 | 34558814 | citrate lyase subunit 1 [*Alvinella pompejana* epibiont 7G3] |
| AAQ75127 | 34558782 | citrate lyase subunit 1 [*Alvinella pompejana* epibiont 6C6] |

TABLE 5

Examples of malic enzyme polypeptides.

| ACCESSION | GI | PROTEIN DESCRIPTION |
|---|---|---|
| NP_012896 | 6322823 | Mae1p [*Saccharomyces cerevisiae*] |
| XP_448858 | 50292851 | unnamed protein product [*Candida glabrata*] |
| XP_454793 | 50309563 | unnamed protein product [*Kluyveromyces lactis*] |
| NP_986598 | 45201028 | AGL068Wp [*Eremothecium gossypii*] |
| XP_460887 | 50424595 | unnamed protein product [*Debaryomyces hansenii*] |
| EAK97738 | 46438407 | hypothetical protein CaO19.3419 [*Candida albicans* SC5314] |
| XP_504112 | 50553402 | hypothetical protein [*Yarrowia lipolytica*] |
| XP_330094 | 32419237 | hypothetical protein [*Neurospora crassa*] |
| XP_380981 | 46107844 | hypothetical protein FG00805.1 [*Gibberella zeae* PH-1] |
| XP_411070 | 49102552 | hypothetical protein AN6933.2 [*Aspergillus nidulans* FGSC A4] |
| XP_362875 | 39946676 | hypothetical protein MG08562.4 [*Magnaporthe grisea* 70-15] |
| NP_587760 | 19075260 | malate oxidoreductase [nad] [*Schizosaccharomyces pombe*] |
| NP_978189 | 42780942 | malate oxidoreductase [*Bacillus cereus* ATCC 10987] |
| YP_035982 | 49481098 | NAD-dependent malic enzyme [*Bacillus thuringiensis* serovar konkukian str. 97-27] |
| YP_027934 | 49184682 | malate oxidoreductase [*Bacillus anthracis* str. Sterne] |
| YP_018438 | 47527089 | malate oxidoreductase [*Bacillus anthracis* str. 'Ames Ancestor'] |
| ZP_002365 | 47565532 | malate oxidoreductase VC1188 [*Bacillus cereus* G9241] |

TABLE 5-continued

Examples of malic enzyme polypeptides.

| ACCESSION | GI | PROTEIN DESCRIPTION |
|---|---|---|
| YP_083209 | 52143619 | NAD-dependent malic enzyme [*Bacillus cereus* ZK] |
| XP_571672 | 58269032 | malate dehydrogenase, putative [*Cryptococcus neoformans* var. *neoformans JEC21*] |
| NP_391586 | 16080758 | hypothetical protein BSU37050 [*Bacillus subtilis* subsp. *subtilis* str. 168] |
| YP_092693 | 52786864 | MalS [*Bacillus licheniformis* ATCC 14580] |
| NP_831516 | 30019885 | NAD-dependent malic enzyme [*Bacillus cereus* ATCC 14579] |
| YP_093460 | 52787631 | YwkA [*Bacillus licheniformis* ATCC 14580] |
| YP_081030 | 52082239 | Malic oxidoreductase [*Bacillus licheniformis* ATCC 14580] |
| NP_822689 | 29828055 | putative malate dehydrogenase [*Streptomyces avermitilis* MA-4680] |
| O34389 | 33517449 | Probable NAD-dependent malic enzyme 3 (NAD-ME 3) |
| EAL19111 | 50256386 | hypothetical protein CNBH2110 [*Cryptococcus neoformans* var. *neoformans* B-3501A] |
| NP_825047 | 29830413 | putative malate dehydrogenase [*Streptomyces avermitilis* MA-4680] |
| ZP_002340 | 47096498 | NADP-dependent malic enzyme [*Listeria monocytogenes* str. ½a F6854] |
| NP_928837 | 37525493 | malate dehydrogenase (oxaloacetate-decarboxylating) [*Photorhabdus luminescens* subsp. *laumondii* TTO1] |
| NP_230833 | 15641201 | malate oxidoreductase [*Vibrio cholerae* O1 biovar eltor str. N16961] |
| NP_934257 | 37679648 | malic enzyme [*Vibrio vulnificus* YJ016] |
| NP_761613 | 27366085 | Malic enzyme [*Vibrio vulnificus* CMCP6] |
| AC1314 | 25283688 | malolactic enzyme (malate dehydrogenase) homolog lmo1915 - *Listeria monocytogenes* (strain EGD-e) |
| YP_055602 | 50842375 | NAD-dependent malic enzyme [*Propionibacterium acnes* KPA171202] |
| YP_095310 | 52841511 | malate oxidoreductase [*Legionella pneumophila* subsp. *pneumophila* str. Philadelphia 1] |
| ZP_002315 | 47093832 | NADP-dependent malic enzyme [*Listeria monocytogenes* str. 4b H7858] |
| AC1686 | 25283689 | malolactic enzyme (malate dehydrogenase) homolog lin2029 [imported] - *Listeria innocua* (strain Clip11262) |
| YP_126594 | 54294179 | malate oxidoreductase [*Legionella pneumophila* str. Lens] |
| YP_123567 | 54297198 | malate oxidoreductase [*Legionella pneumophila* str. Paris] |
| EAJ76260 | 44510091 | unknown [environmental sequence] |
| YP_114273 | 53803890 | malate oxidoreductase [*Methylococcus capsulatus* str. Bath] |
| NP_797637 | 28898032 | malate oxidoreductase [*Vibrio parahaemolyticus* RIMD 2210633] |
| YP_040250 | 49483026 | putative malolactic enzyme [*Staphylococcus aureus* subsp. *aureus* MRSA252] |
| ZP_001276 | 53693400 | COG0281: Malic enzyme [*Pseudomonas syringae* pv. *syringae* B728a] |
| YP_044961 | 50083451 | NAD-linked malate dehydrogenase, Rossman fold [*Acinetobacter* sp. ADP1] |
| YP_128226 | 54295811 | hypothetical protein lpl2901 [*Legionella pneumophila* str. Lens] |
| NP_719387 | 24375344 | malate oxidoreductase [*Shewanella oneidensis* MR-1] |
| XP_572853 | 58271394 | nad-dependent malic enzyme, putative [*Cryptococcus neoformans* var. *neoformans* JEC21] |
| NP_252161 | 15598667 | probable malic enzyme [*Pseudomonas aeruginosa* PAO1] |
| ZP_001368 | 46164263 | COG0281: Malic enzyme [*Pseudomonas aeruginosa* UCBPP-PA14] |
| YP_125345 | 54298976 | hypothetical protein lpp3043 [*Legionella pneumophila* str. Paris] |
| NP_793695 | 28871076 | malate dehydrogenase [*Pseudomonas syringae* pv. tomato str. DC3000] |
| YP_096964 | 52843165 | malate dehydrogenase (NAD-linked) [*Legionella pneumophila* subsp. *pneumophila* str. Philadelphia 1] |
| EAH92280 | 44245125 | unknown [environmental sequence] |
| YP_154988 | 56459707 | Malic enzyme [*Idiomarina loihiensis* L2TR] |
| EAI68195 | 44354928 | unknown [environmental sequence] |
| YP_070054 | 51595863 | NAD-dependent malic enzyme [*Yersinia pseudotuberculosis* IP 32953] |
| YP_133025 | 54303032 | putative malate oxidoreductase [*Photobacterium profundum* SS9] |
| NP_969623 | 42524243 | NAD-dependent malic enzyme [*Bdellovibrio bacteriovorus* HD100] |
| NP_856009 | 31793516 | PROBABLE [NAD] DEPENDENT MALATE OXIDOREDUCTASE MEZ (MALIC ENZYME) (NAD-MALIC ENZYME) (MALATE DEHYDROGENASE TATE |
| DECARBOXY | ATING)) | PYRUVIC-MALIC CARBOXYLASE) (NAD-ME) [*Mycobacterium bovis* AF2122/97] |
| NP_935035 | 37680426 | malic enzyme [*Vibrio vulnificus* YJ016] |
| YP_050922 | 50121755 | NAD-dependent malic enzyme [*Erwinia carotovora* subsp. *atroseptica* SCRI1043] |
| E70705 | 7431223 | probable malate oxidoreductase - *Mycobacterium tuberculosis* (strain H37RV) |
| NP_216848 | 57116971 | PROBABLE [NAD] DEPENDENT MALATE OXIDOREDUCTASE MEZ (MALIC ENZYME) (NAD-MALIC ENZYME) (MALATE DEHYDROGENASE TATE |
| DECARBOXY | ATING)) | PYRUVIC-MALIC CARBOXYLASE) (NAD-ME) [*Mycobacterium tuberculosis* H37Rv] |
| YP_143786 | 55980489 | NAD-dependent malic enzyme (malate dehydrogenase) [*Thermus thermophilus* HB8] |
| YP_130202 | 54309182 | putative malate oxidoreductase [*Photobacterium profundum* SS9] |
| NP_415996 | 16129438 | NAD-linked malate dehydrogenase [*Escherichia coli* K12] |
| NP_819843 | 29654151 | malate oxidoreductase [*Coxiella burnetii* RSA 493] |

TABLE 5-continued

Examples of malic enzyme polypeptides.

| ACCESSION | GI | PROTEIN DESCRIPTION |
|---|---|---|
| NP_753809 | 26247769 | NAD-dependent malic enzyme [*Escherichia coli* CFT073] |
| NP_707611 | 56479957 | NAD-linked malate dehydrogenase (malic enzyme) [*Shigella flexneri* 2a str. 301] |
| F85728 | 25283682 | NAD-linked malate dehydrogenase (malic enzyme) - *Escherichia coli* (strain O157:H7, substrain EDL933) |
| YP_163690 | 56552851 | malic enzyme [*Zymomonas mobilis* subsp. *mobilis* ZM4] |
| YP_150562 | 56413487 | NAD-linked malic enzyme [*Salmonella enterica* subsp. *enterica* serovar Paratypi A str. ATCC 9150] |
| NP_720610 | 24378655 | malolactic enzyme [*Streptococcus mutans* UA159] |
| NP_460525 | 16764910 | NAD-linked malate dehydrogenase [*Salmonella typhimurium* LT2] |
| ZP_003193 | 48865537 | COG0281: Malic enzyme [*Oenococcus oeni* PSU-1] |
| NP_784797 | 28377905 | malolactic enzyme [*Lactobacillus plantarum* WCFS1] |
| T13496 | 7431227 | malolactic enzyme (EC 1.1.1.- ) - *Leuconostoc oenos* |
| AAV65766 | 55793550 | malolactic enzyme [*Oenococcus oeni*] |
| A97096 | 25283683 | malic enzyme [imported] - *Clostridium acetobutylicum* |
| YP_193951 | 58337366 | malolactic enzyme [*Lactobacillus acidophilus* NCFM] |
| H97096 | 25283684 | malic enzyme [imported] - *Clostridium acetobutylicum* |
| ZP_003237 | 48870993 | COG0281: Malic enzyme [*Pediococcus pentosaceus* ATCC 25745] |
| ZP_001460 | 41689468 | COG0281: Malic enzyme [*Psychrobacter* sp. 273-4] |
| D86737 | 25283676 | malolactic enzyme [imported] - *Lactococcus lactis* subsp. *lactis* (strain IL1403) |
| ZP_002870 | 48825851 | COG0281: Malic enzyme [*Enterococcus faecium*] |
| ZP_001439 | 34762975 | Malolactic enzyme [*Fusobacterium nucleatum* subsp. *vincentii* ATCC 49256] |
| 1922245A | 737262 | malolactic enzyme |
| YP_169914 | 56708018 | NAD-dependent malic enzyme [*Francisella tularensis* subsp. *tularensis* Schu 4] |
| YP_055027 | 50841800 | putative malate oxidoreductase [*Propionibacterium acnes* KPA171202] |
| ZP_000625 | 23023297 | COG0281: Malic enzyme [*Leuconostoc mesenteroides* subsp. mesenteroides ATCC 8293] |
| NP_296302 | 15807565 | malate oxidoreductase [*Deinococcus radiodurans* R1] |
| NP_285599 | 15807938 | malate oxidoreductase [*Deinococcus radiodurans* R1] |
| YP_132069 | 54302076 | hypothetical malate oxidoreductase [*Photobacterium profundum* SS9] |
| CAA50716 | 467569 | malolactic enzyme [*Lactococcus lactis*] |
| ZP_002906 | 48833596 | COG0281: Malic enzyme [*Magnetococcus* sp. MC-1] |
| ZP_003155 | 48861632 | COG0281: Malic enzyme [*Microbulbifer degradans* 2-40] |
| NP_773109 | 27381580 | malic enzyme [*Bradyrhizobium japonicum* USDA 110] |
| AAQ95658 | 37622953 | malic enzyme [*Dictyostelium discoideum*] |
| CAC19505 | 56204311 | malic enzyme 1, NADP(+)-dependent, cytosolic [*Homo sapiens*] |
| AAH80660 | 51873855 | Mod1 protein [*Mus musculus*] |
| P40927 | 729986 | NADP-dependent malic enzyme (NADP-ME) |
| AAT02533 | 46850200 | NADP-dependent malic enzyme 1 [*Hydrilla verticillata*] |
| BAC37086 | 26346875 | unnamed protein product [*Mus musculus*] |
| T02763 | 7431235 | probable malate dehydrogenase (oxaloacetate-decarboxylating) (NADP) (EC 1.1.1.40) - maize |
| XP_387367 | 46125627 | hypothetical protein FG07191.1 [*Gibberella zeae* PH-1] |
| AAC50613 | 1465733 | cytosolic NADP(+)-dependent malic enzyme |
| CAA39421 | 669118 | sbcA8 recE fusion [*Escherichia coli*] |
| CAA39420 | 669117 | sbcA8 recE fusion [*Escherichia coli*] |
| NP_032641 | 6678912 | malic enzyme, supernatant [*Mus musculus*] |
| CAA39419 | 581228 | sbcA8 recE fusion [*Escherichia coli*] |
| AAB01380 | 1335389 | NADP-dependent malic enzyme |
| JC4160 | 1085347 | malate dehydrogenase (oxaloacetate-decarboxylating) (NADP) (EC 1.1.1.40) - human |
| E96828 | 25283677 | probable malate oxidoreductase, 93001-96525 [imported] - *Arabidopsis thaliana* |
| BAD87910 | 57899974 | cytosolic NADP malic enzyme [*Oryza sativa* (*japonica* cultivar-group)] |
| EAJ77083 | 44511304 | unknown [environmental sequence] |
| P13697 | 266504 | NADP-dependent malic enzyme (NADP-ME) (Malic enzyme 1) |
| NP_036732 | 7106353 | malic enzyme 1 [*Rattus norvegicus*] |
| YP_065939 | 51246055 | related to NAD-dependent malic enzyme [*Desulfotalea psychrophila* LSv54] |
| CAC18164 | 16944467 | related to malate dehydrogenase (oxaloacetate-decarboxylating) (NADP+) [*Neurospora crassa*] |
| XP_322953 | 32404680 | hypothetical protein [*Neurospora crassa*] |
| AAK91502 | 18460985 | NADP-dependent malic enzyme [*Zea mays*] |
| AAQ88396 | 37147841 | non-photosynthetic NADP-malic enzyme [*Zea mays*] |
| NP_001003 | 57525624 | zgc: 100941 [*Danio rerio*] |
| 1GQ2P | 21465488 | Chain P, Malic Enzyme From Pigeon Liver |
| AAO26053 | 28195290 | malic enzyme [*Mucor circinelloides*] |
| AAH84250 | 54038006 | Me2 protein [*Xenopus laevis*] |
| XP_362590 | 39946106 | hypothetical protein MG08173.4 [*Magnaporthe grisea* 70-15] |
| AAH03287 | 13096987 | Mod1 protein [*Mus musculus*] |
| Q29558 | 2497785 | NADP-dependent malic enzyme (NADP-ME) (Malic enzyme 1) |
| XP_532217 | 57094622 | PREDICTED: similar to malate dehydrogenase decarboxylase (NADP+) [*Canis familiaris*] |

TABLE 5-continued

Examples of malic enzyme polypeptides.

| ACCESSION | GI | PROTEIN DESCRIPTION |
|---|---|---|
| P28227 | 126734 | NADP-dependent malic enzyme (NADP-ME) |
| NP_496968 | 17537199 | malic enzyme nadp-dependent (2O518) [*Caenorhabditis elegans*] |
| NP_914533 | 34906372 | unnamed protein product [*Oryza sativa* (*japonica* cultivar-group)] |
| AAD10504 | 4096786 | NADP-malic enzyme [*Zea mays*] |
| AAO67523 | 50897495 | mitochondrial malic enzyme 2 [*Xenopus laevis*] |
| P43279 | 1170871 | NADP-dependent malic enzyme, chloroplast precursor (NADP-ME) |
| AAK83074 | 15077109 | putative cytosolic NADP-malic enzyme [*Flaveria pringlei*] |
| AAP33011 | 30575690 | NADP-malic enzyme [*Zea mays*] |
| AAN86690 | 27357017 | malic enzyme [*Mastigamoeba balamuthi*] |
| P78715 | 41017288 | Malic enzyme, hydrogenosomal precursor (ME) |
| AAP32204 | 30526303 | NADP-dependent malic enzyme [*Sorghum bicolor*] |
| AAV31249 | 54287505 | NADP malic enzyme [*Oryza sativa* (*japonica* cultivar-group)] |
| T06402 | 7431232 | malate dehydrogenase (oxaloacetate-decarboxylating) (NADP) (EC 1.1.1.40) 2, cytosolic - tomato |
| Q99KE1 | 55583978 | NAD-dependent malic enzyme, mitochondrial precursor (NAD-ME) (Malic enzyme 2) |
| XP_399922 | 49071266 | hypothetical protein UM02307.1 [*Ustilago maydis* 521] |
| P36444 | 547886 | NADP-dependent malic enzyme, chloroplast precursor (NADP-ME) |
| AAO30034 | 28059162 | malate oxidoreductase (malic enzyme) [*Arabidopsis thaliana*] |
| AAK83073 | 15077107 | putative cytosolic NADP-malic enzyme [*Flaveria pringlei*] |
| NP_002387 | 4505145 | malic enzyme 2, NAD(+)-dependent, mitochondrial [*Homo sapiens*] |
| AAA33487 | 168528 | NADP-dependent malic enzyme (EC 1.1.1.40) |
| BAA74735 | 4239891 | NADP-malic enzyme [*Aloe arborescens*] |
| NP_989634 | 45383538 | malic enzyme 1, NADP(+)-dependent, cytosolic [*Gallus gallus*] |
| 1GZ3D | 31615316 | Chain D, The Regulation Of Human Mitochondrial Nad(P)+-Dependent Malic Enzyme By Atp And Fumarate |
| AAW56450 | 57791240 | chloroplast NADP-dependent malic enzyme precursor [*Flaveria bidentis*] |
| AAT02534 | 46850202 | NADP-dependent malic enzyme 2 [*Hydrilla verticillata*] |
| S29742 | 422339 | malate dehydrogenase (oxaloacetate-decarboxylating) (NADP) (EC 1.1.1.40) - pig roundworm |
| 1O0SB | 34811253 | Chain B, Crystal Structure Of *Ascaris Suum* Malic Enzyme Complexed With Nadh |
| P27443 | 126732 | NAD-dependent malic enzyme, mitochondrial precursor (NAD-ME) |
| T06401 | 7431231 | malate dehydrogenase (oxaloacetate-decarboxylating) (NADP) (EC 1.1.1.40) precursor - tomato |
| AAL16175 | 16226466 | AT5g11670/T22P22_60 [*Arabidopsis thaliana*] |
| AAF73006 | 8118507 | NADP-dependent malic protein [*Ricinus communis*] |
| AAK97530 | 15420975 | malic enzyme [*Meleagris gallopavo*] |
| EAI90348 | 44385841 | unknown [environmental sequence] |
| P51615 | 1708924 | NADP-DEPENDENT MALIC ENZYME (NADP-ME) |
| AAA19575 | 169327 | NADP-dependent malic enzyme |
| S43718 | 1084300 | malate dehydrogenase (oxaloacetate-decarboxylating) (NADP) (EC 1.1.1.40) - common ice plant |
| P34105 | 1346485 | NADP-DEPENDENT MALIC ENZYME (NADP-ME) |
| AAS38597 | 42733630 | similar to *Mastigamoeba balamuthi* Malic enzyme (EC 1.1.1.38) [Dictyostelium discoideum] |
| BAC54101 | 27530932 | cytosolic NADP-malic enzyme [*Lithospermum erythrorhizon*] |
| AAT02535 | 46850204 | NADP-dependent malic enzyme 3 [*Hydrilla verticillata*] |
| CAB66003 | 6706333 | NADP-dependent malate dehydrogenase (decarboxylating) [*Apium graveolens*] |
| AAH84860 | 54311418 | LOC495390 protein [*Xenopus laevis*] |
| CAA39422 | 669119 | sbcA8 recE fusion [*Escherichia coli*] |
| NP_916713 | 34910732 | P0022F10.12 [*Oryza sativa* (*japonica* cultivar-group)] |
| CAA56354 | 510876 | NADP dependent malic enzyme [*Phaseolus vulgaris*] |
| DEFBC | 7427668 | malate dehydrogenase (oxaloacetate-decarboxylating) (NADP) (EC 1.1.1.40) - kidney bean |
| JC5967 | 7431234 | malate dehydrogenase (oxaloacetate-decarboxylating) (NADP) (EC 1.1.1.40) - aloe |
| NP_197960 | 15239517 | malate oxidoreductase, putative [*Arabidopsis thaliana*] |
| NP_651959 | 21356279 | CG5889-PA [*Drosophila melanogaster*] |
| CAB64263 | 6634090 | malate dehydrogenase (NADP-dependent oxaloacetate decarboxylating), malic enzyme [*Drosophila melanogaster*] |
| BAB20887 | 54606800 | NADP dependent malic enzyme [*Oryza sativa* (*japonica* cultivar-group)] |
| EAL27424 | 54638022 | GA19206-PA [*Drosophila pseudoobscura*] |
| NP_006671 | 5729920 | malic enzyme 3, NADP(+)-dependent, mitochondrial [*Homo sapiens*] |
| AAB08874 | 1561774 | malate dehydrogenase [*Vitis vinifera*] |
| 1PJLH | 33358128 | Chain H, Crystal Structure Of Human M-Nad-Me In Ternary Complex With Nad And Lu3+ |
| 1GZ4D | 22218682 | Chain D, The Regulation Of Human Mitochondrial Nad(P)+-Dependent Malic Enzyme By Atp And Fumarate |
| 1QR6B | 5822327 | Chain B, Human Mitochondrial Nad(P)-Dependent Malic Enzyme |
| 1PJ3D | 39654475 | Chain D, Crystal Structure Of Human Mitochondrial Nad(P)+-Dependent Malic Enzyme |

TABLE 5-continued

| Examples of malic enzyme polypeptides. | | |
|---|---|---|
| ACCESSION | GI | PROTEIN DESCRIPTION |
| P22178 | 126736 | NADP-dependent malic enzyme, chloroplast precursor (NADP-ME) |
| XP_410305 | 49097690 | hypothetical protein AN6168.2 [*Aspergillus nidulans* FGSC A4] |
| AAH22472 | 18490280 | Malic enzyme 3, NADP(+)-dependent, mitochondrial [*Homo sapiens*] |

TABLE 6

| Examples of AMP deaminase polypeptides. | | |
|---|---|---|
| ACCESSION | GI | PROTEIN DESCRIPTION |
| AAA34420 | 171053 | AMP deaminase (EC 3.5.4.6) |
| XP_446684 | 50288509 | unnamed protein product [*Candida glabrata*] |
| NP_983153 | 45185436 | ABR204Cp [*Eremothecium gossypii*] |
| XP_453337 | 50306727 | unnamed protein product [*Kluyveromyces lactis*] |
| EAL02322 | 46443037 | adenosine/AMP deaminase [*Candida albicans SC5314*] |
| XP_460211 | 50423261 | unnamed protein product [*Debaryomyces hansenii*] |
| XP_503822 | 50552824 | hypothetical protein [*Yarrowia lipolytica*] |
| XP_413009 | 49131023 | hypothetical protein AN8872.2 [*Aspergillus nidulans* FGSC A4] |
| XP_360256 | 39941438 | hypothetical protein MG05630.4 [*Magnaporthe grisea* 70-15] |
| XP_381547 | 46108978 | hypothetical protein FG01371.1 [*Gibberella zeae* PH-1] |
| XP_330167 | 32419447 | probable AMP deaminase [MIPS] [*Neurospora crassa*] |
| CAB97316 | 16945394 | probable AMP deaminase [*Neurospora crassa*] |
| T50996 | 11359582 | probable AMP deaminase [imported] - *Neurospora crassa* |
| NP_595153 | 19111945 | amp deaminase [*Schizosaccharomyces pombe*] |
| EAL22226 | 50259553 | hypothetical protein CNBC3640 [*Cryptococcus neoformans* var. *neoformans* B-3501A] |
| XP_402237 | 49076548 | hypothetical protein UM04622.1 [*Ustilago maydis* 521] |
| CAA62797 | 995562 | AMP deaminase [*Schizosaccharomyces pombe*] |
| AAF65407 | 7638159 | AMP deaminase [*Dictyostelium discoideum*] |
| XP_537039 | 57088163 | PREDICTED: similar to AMP deaminase 2 (AMP deaminase isoform L) [*Canis familiaris*] |
| AAH49119 | 29145073 | Adenosine monophosphate deaminase 2 (isoform L) [*Mus musculus*] |
| XP_569691 | 58265070 | AMP deaminase, putative [*Cryptococcus neoformans var. neoformans* JEC21] |
| AAD56303 | 5922018 | AMP deaminase isoform L [*Homo sapiens*] |
| NP_004028 | 21264318 | adenosine monophosphate deaminase 2 (isoform L) isoform 1 [*Homo sapiens*] |
| A44313 | 345738 | AMP deaminase (EC 3.5.4.6) isoform L - human |
| CAI19307 | 56206061 | adenosine monophosphate deaminase 2 (isoform L) [*Homo sapiens*] |
| AAA62126 | 644509 | AMP deaminase isoform L splicing variant |
| CAI19305 | 56206059 | adenosine monophosphate deaminase 2 (isoform L) [*Homo sapiens*] |
| XP_310497 | 58424203 | ENSANGP00000017310 [*Anopheles gambiae* str. PEST] |
| CAI19306 | 56206060 | adenosine monophosphate deaminase 2 (isoform L) [*Homo sapiens*] |
| AAC50308 | 608499 | AMP deaminase |
| CAG06825 | 47229629 | unnamed protein product [*Tetraodon nigroviridis*] |
| NP_727741 | 45551453 | CG32626-PD, isoform D [*Drosophila melanogaster*] |
| NP_727739 | 45551452 | CG32626-PA, isoform A [*Drosophila melanogaster*] |
| NP_727740 | 24641890 | CG32626-PB, isoform B [*Drosophila melanogaster*] |
| AAN09337 | 22832227 | CG32626-PC, isoform C [*Drosophila melanogaster*] |
| T01259 | 7484807 | AMP deaminase homolog F16M14.21 - *Arabidopsis thaliana* |
| XP_506591 | 51963676 | PREDICTED P0034A04.129 gene product [*Oryza sativa* (*japonica* cultivar-group)] |
| NP_850294 | 30687456 | AMP deaminase, putative/myoadenylate deaminase, putative [*Arabidopsis thaliana*] |
| CAG07509 | 47228777 | unnamed protein product [*Tetraodon nigroviridis*] |
| NP_494974 | 32564190 | Adenosine/AMP deaminase (85.4 kD) (2F499) [*Caenorhabditis elegans*] |
| T15771 | 7497030 | hypothetical protein C34F11.3 - *Caenorhabditis* elegans |
| CAE59064 | 39596837 | Hypothetical protein CBG02349 [*Caenorhabditis briggsae*] |
| NP_494973 | 32564194 | Adenosine/AMP deaminase family member (2F499) [*Caenorhabditis elegans*] |
| BAA06505 | 1321635 | erythrocyte-type AMP deaminase [*Homo sapiens*] |
| NP_000471 | 4502079 | adenosine monophosphate deaminase (isoform E) [*Homo sapiens*] |
| S68147 | 2134756 | AMP deaminase (EC 3.5.4.6), erythrocte, splice form 1c - human |
| AAH56380 | 38614134 | Ampd3 protein [*Mus musculus*] |
| O08739 | 2494043 | AMP DEAMINASE 3 (AMP DEAMINASE ISOFORM E) (AMP DEAMINASE H-TYPE) (HEART-TYPE AMPD) |
| NP_113732 | 13928736 | adenosine monophosphate deaminase 3 [*Rattus norvegicus*] |
| O09178 | 2494044 | AMP deaminase 3 (AMP deaminase isoform E) |
| XP_420973 | 50747746 | PREDICTED: similar to AMP deaminase 3 (Erythrocyte AMP deaminase) [*Gallus gallus*] |
| NP_956142 | 41054127 | AMP deaminase 3 [*Danio rerio*] |
| CAG01709 | 47222742 | unnamed protein product [*Tetraodon nigroviridis*] |
| NP_957187 | 41053780 | hypothetical protein MGC77905 [*Danio rerio*] |

TABLE 6-continued

| Examples of AMP deaminase polypeptides. | | |
|---|---|---|
| ACCESSION | GI | PROTEIN DESCRIPTION |
| XP_392957 | 48104570 | similar to ENSANGP00000017310 [*Apis mellifera*] |
| AAH07183 | 13938134 | Ampd3 protein [*Mus musculus*] |
| CAG05605 | 47220579 | unnamed protein product [*Tetraodon nigroviridis*] |
| NP_620231 | 20302047 | adenosine monophosphate deaminase 1 (isoform M) [*Rattus norvegicus*] |
| XP_540247 | 57098851 | PREDICTED: similar to AMP deaminase 1 (AMP deaminase isoform M) [*Canis familiaris*] |
| CAF99638 | 47230445 | unnamed protein product [*Tetraodon nigroviridis*] |
| XP_513671 | 55587796 | PREDICTED: adenosine monophosphate deaminase 1 (isoform M) [*Pan troglodytes*] |
| CAI18828 | 56203368 | adenosine monophosphate deaminase 1 (isoform M) [*Homo sapiens*] |
| CAI18829 | 56203369 | OTTHUMP00000059283 [*Homo sapiens*] |
| CAI18830 | 56203370 | adenosine monophosphate deaminase 1 (isoform M) [*Homo sapiens*] |
| EAA19931 | 23484684 | AMP deaminase homolog [*Plasmodium yoelii yoelii*] |
| CAH99706 | 56500932 | AMP deaminase, putative [*Plasmodium berghei*] |
| XP_131103 | 38076931 | similar to AMP deaminase 1 (Myoadenylate deaminase) (AMP deaminase isoform M) [*Mus musculus*] |
| CAH77387 | 56523366 | AMP deaminase, putative [*Plasmodium chabaudi*] |

TABLE 7

| Examples of acetoacetyl-CoA thiolase polypeptides. | | |
|---|---|---|
| ACCESSION | GI | PROTEIN DESCRIPTION |
| P10551 | 135758 | Acetyl-CoA acetyltransferase (Acetoacetyl-CoA thiolase) |
| Q04677 | 418002 | Acetyl-CoA acetyltransferase IB (Peroxisomal acetoacetyl-CoA thiolase) (Thiolase IB) |
| Q12598 | 34925109 | Acetyl-CoA acetyltransferase IA (Peroxisomal acetoacetyl-CoA thiolase) (Thiolase IA) |
| T10247 | 7433657 | acetyl-CoA C-acetyltransferase (EC 2.3.1.9), cytosolic - radish |
| T42741 | 11257345 | probable acetyl-CoA C-acetyltransferase (EC 2.3.1.9) - fission yeast (*Schizosaccharomyces pombe*) |
| AAL18924 | 16417944 | acetyl Co-A acetyltransferase [*Hevea brasiliensis*] |
| AAM67058 | 21618008 | acetoacyl-CoA-thiolase [*Arabidopsis thaliana*] |
| AAO51605 | 28829030 | similar to acetyl-coa acetyltransferase (EC 2.3.1.9) [*Schizosaccharomyces pombe*] |
| AAU95618 | 53854350 | cytosolic acetoacetyl-coenzyme A thiolase [*Nicotiana tabacum*] |
| AAU95619 | 53854352 | peroxisomal acetoacetyl-coenzyme A thiolase [*Nicotiana tabacum*] |
| BAA97003 | 8777413 | acetyl-CoA C-acetyltransferase [*Arabidopsis thaliana*] |
| CAE76429 | 38567134 | probable acetoacetyl-CoA thiolase [*Neurospora crassa*] |
| EAK90852 | 46431255 | hypothetical protein CaO19.1591 [*Candida albicans* SC5314] |
| EAL32264 | 54643520 | GA10651-PA [*Drosophila pseudoobscura*] |
| NP_015297 | 6325229 | Acetyl-CoA C-acetyltransferase (acetoacetyl-CoA thiolase) [*Saccharomyces cerevisiae*] |
| NP_568694 | 30695411 | acetyl-CoA C-acyltransferase, putative/3-ketoacyl-CoA thiolase, putative [*Arabidopsis thaliana*] |
| NP_572414 | 24640423 | CG10932-PA [*Drosophila melanogaster*] |
| NP_596686 | 19113478 | acetyl-coa acetyltransferase (EC 2.3.1.9) [*Schizosaccharomyces pombe*] |
| NP_851154 | 30695409 | acetyl-CoA C-acyltransferase, putative/3-ketoacyl-CoA thiolase, putative [*Arabidopsis thaliana*] |
| NP_908411 | 34894172 | putative acetoacetyl-coenzyme A thiolase [*Oryza sativa* (*japonica* cultivar-group)] |
| NP_974900 | 42573608 | acetyl-CoA C-acyltransferase, putative/3-ketoacyl-CoA thiolase, putative [*Arabidopsis thaliana*] |
| NP_974901 | 42573610 | acetyl-CoA C-acyltransferase, putative/3-ketoacyl-CoA thiolase, putative [*Arabidopsis thaliana*] |
| NP_984262 | 45188039 | ADR165Cp [*Eremothecium gossypii*] |
| XP_389497 | 46134945 | hypothetical protein FG09321.1 [*Gibberella zeae* PH-1] |
| XP_401186 | 49074048 | hypothetical protein UM03571.1 [*Ustilago maydis* 521] |
| XP_405546 | 49087148 | hypothetical protein AN1409.2 [*Aspergillus nidulans* FGSC A4] |
| XP_449306 | 50293789 | unnamed protein product [*Candida glabrata*] |
| XP_449306 | 50293789 | unnamed protein product [*Candida glabrata*] |
| XP_450298 | 50899020 | putative acetyl-CoA C-acyltransferase [*Oryza sativa* (*japonica* cultivar-group)] |
| XP_453599 | 50307241 | unnamed protein product [*Kluyveromyces lactis*] |
| XP_460741 | 50424309 | unnamed protein product [*Debaryomyces hansenii*] |
| XP_500646 | 50546253 | hypothetical protein [*Yarrowia lipolytica*] |

TABLE 8

Examples of HMG-CoA synthase polypeptides.

| ACCESSION | GI | PROTEIN DESCRIPTION |
|---|---|---|
| B55729 | 1083370 | hydroxymethylglutaryl-CoA synthase (EC 4.1.3.5), mitochondrial - mouse |
| P54869 | 1708235 | Hydroxymethylglutaryl-CoA synthase, mitochondrial precursor (HMG-CoA synthase) |
| S13887 | 86312 | hydroxymethylglutaryl-CoA synthase (EC 4.1.3.5) - chicken |
| S27197 | 284048 | hydroxymethylglutaryl-CoA synthase (EC 4.1.3.5), cytosolic, fibroblast isoform - human |
| AAA37076 | 387072 | 3-hydroxy-3-methylglutaryl coenzyme A synthase (HMG CoA) |
| AAF89580 | 9621905 | 3-hydroxy-3-methylglutaryl coenzyme A synthase [*Dendroctonus jeffreyi*] |
| AAH00297 | 33991031 | HMGCS1 protein [*Homo sapiens*] |
| AAH31363 | 21618633 | 3-hydroxy-3-methylglutaryl-Coenzyme A synthase 1 [*Mus musculus*] |
| AAH42929 | 27552834 | Hmgcs1-prov protein [*Xenopus laevis*] |
| AAH79694 | 50925193 | MGC80816 protein [*Xenopus laevis*] |
| AAH83543 | 54035469 | 3-hydroxy-3-methylglutaryl-Coenzyme A synthase 2 [*Rattus norvegicus*] |
| AAO52569 | 28830079 | similar to *Homo sapiens* (*Human*). *Hypothetical protein FLJ40785* [*Dictyostelium discoideum*] |
| AAP35966 | 30583443 | 3-hydroxy-3-methylglutaryl-Coenzyme A synthase 1 (soluble) [*Homo sapiens*] |
| BAB23657 | 12836439 | unnamed protein product [*Mus musculus*] |
| BAC04559 | 21754758 | unnamed protein product [*Homo sapiens*] |
| BAC05233 | 21758044 | unnamed protein product [*Mus musculus*] |
| CAA52032 | 1772495 | hydroxymethylglutaryl-CoA synthase [*Blattella germanica*] |
| CAC18553 | 11602786 | putative 3-hydroxy-3-methylglutaryl coenzyme A synthase [*Phycomyces blakesleeanus*] |
| CAG33131 | 48145817 | HMGCS2 [*Homo sapiens*] |
| CAH92111 | 55730782 | hypothetical protein [*Pongo pygmaeus*] |
| CAI22408 | 56205097 | 3-hydroxy-3-methylglutaryl-Coenzyme A synthase 2 (mitochondrial) [*Homo sapiens*] |
| EAK97451 | 46438115 | hypothetical protein CaO19.7312 [*Candida albicans* SC5314] |
| EAL25034 | 54635631 | GA18098-PA [*Drosophila pseudoobscura*] |
| NP_002121 | 54020720 | 3-hydroxy-3-methylglutaryl-Coenzyme A synthase 1 (soluble) [*Homo sapiens*] |
| NP_013580 | 6323509 | 3-hydroxy-3-methylglutaryl-CoA (HMG-CoA) synthase [*Saccharomyces cerevisiae*] |
| NP_032282 | 31560689 | 3-hydroxy-3-methylglutaryl-Coenzyme A synthase 2 [*Mus musculus*] |
| NP_058964 | 8393538 | 3-hydroxy-3-methylglutaryl-Coenzyme A synthase 1 [*Rattus norvegicus*] |
| NP_593859 | 19114771 | hydroxymethylglutaryl-coa synthase (EC 4.1.3.5) [*Schizosaccharomyces pombe*] |
| NP_666054 | 31981842 | 3-hydroxy-3-methylglutaryl-Coenzyme A synthase 1 [*Mus musculus*] |
| NP_725570 | 24654139 | CG4311-PE, isoform E [*Drosophila melanogaster*] |
| NP_775117 | 27465521 | 3-hydroxy-3-methylglutaryl-Coenzyme A synthase 2 [*Rattus norvegicus*] |
| NP_957379 | 41055180 | similar to 3-hydroxy-3-methylglutaryl-Coenzyme A synthase 1 [*Danio rerio*] |
| NP_983739 | 45187516 | ADL356Cp [*Eremothecium gossypii*] |
| NP_990742 | 45382279 | 3-hydroxy-3-methylglutaryl-CoA synthase [*Gallus gallus*] |
| NP_999545 | 47523816 | hydroxymethylglutaryl-CoA synthase [*Sus scrofa*] |
| XP_315872 | 58387870 | ENSANGP00000017491 [*Anopheles gambiae* str. PEST] |
| XP_323241 | 32405256 | probable hydroxymethylglutaryl-CoA synthase [MIPS] [*Neurospora crassa*] |
| XP_368218 | 39973655 | hypothetical protein MG01026.4 [*Magnaporthe grisea* 70-15] |
| XP_389442 | 46134253 | conserved hypothetical protein [*Gibberella zeae* PH-1] |
| XP_397202 | 48141273 | similar to CG4311-PA [*Apis mellifera*] |
| XP_402977 | 49078452 | hypothetical protein UM05362.1 [*Ustilago maydis* 521] |
| XP_409060 | 49095198 | hypothetical protein AN4923.2 [*Aspergillus nidulans* FGSC A4] |
| XP_446972 | 50289085 | unnamed protein product [*Candida glabrata*] |
| XP_453529 | 50307101 | unnamed protein product [*Kluyveromyces lactis*] |
| XP_456470 | 50405663 | unnamed protein product [*Debaryomyces hansenii*] |
| XP_506052 | 50557288 | hypothetical protein [*Yarrowia lipolytica*] |
| XP_513693 | 55587844 | PREDICTED: 3-hydroxy-3-methylglutaryl-Coenzyme A synthase 2 (mitochondrial) [*Pan troglodytes*] |
| XP_536483 | 57085299 | PREDICTED: similar to HMGCS1 protein [*Canis familiaris*] |
| XP_569805 | 58265298 | hydroxymethylglutaryl-CoA synthase, putative [*Cryptococcus* |
| XP_571930 | 58269548 | conserved hypothetical protein [*Cryptococcus neoformans* var. *neoformans* JEC21] |

TABLE 9

| Examples of HMG-CoA reductase polypeptides. | | |
|---|---|---|
| ACCESSION | GI | PROTEIN DESCRIPTION |
| A23586 | 90238 | hydroxymethylglutaryl-CoA reductase (EC 1.1.1.88) - golden hamster |
| O74164 | 11132850 | 3-hydroxy-3-methylglutaryl-coenzyme A reductase (HMG-CoA reductase) |
| P51639 | 1708252 | 3-hydroxy-3-methylglutaryl-coenzyme A reductase (HMG-CoA reductase) |
| P54960 | 1708251 | 3-hydroxy-3-methylglutaryl-coenzyme A reductase (HMG-CoA reductase) |
| Q12649 | 18276268 | 3-hydroxy-3-methylglutaryl-coenzyme A reductase (HMG-CoA reductase) |
| Q29512 | 2495262 | 3-hydroxy-3-methylglutaryl-coenzyme A reductase (HMG-CoA reductase) |
| Q9Y7D2 | 11133211 | 3-hydroxy-3-methylglutaryl-coenzyme A reductase (HMG-CoA reductase) |
| S30338 | 422383 | hydroxymethylglutaryl-CoA reductase (NADPH2) (EC 1.1.1.34) - German cockroach |
| S72194 | 7450066 | hydroxymethylglutaryl-CoA reductase (EC 1.1.1.88) - fission yeast (*Schizosaccharomyces pombe*) |
| AAA36989 | 387052 | 3-hydroxy-3-methylglutaryl coenzyme A [*Mesocricetus auratus*] |
| AAA37077 | 305355 | 3-hydroxy-3-methylglutaral coenzyme A reductase (EC 1.1.1.34) |
| AAA49740 | 214237 | 3-hydroxy-3-methylglutaryl-coenzyme A reductase |
| AAD20975 | 9817458 | 3-hydroxy-3-methylglutaryl coenzyme A reductase [*Ips paraconfusus*] |
| AAH74197 | 49257596 | Unknown (protein for MGC: 82101) [*Xenopus laevis*] |
| AAL09351 | 15824453 | 3-hydroxy-3-methylglutaryl coenzyme A reductase [*Ips pini*] |
| AAO85434 | 29468180 | HMG-CoA reductase [*Aspergillus nidulans*] |
| AAP72015 | 32165622 | 3-hydroxy-3-methylglutaryl-Coenzyme A reductase [*Homo sapiens*] |
| AAR02862 | 45272118 | HMG-CoA reductase [*Dicentrarchus labrax*] |
| AAT92819 | 51013051 | YLR450W [*Saccharomyces cerevisiae*] |
| BAC20567 | 23574646 | HMG-CoA reductase [*Penicillium citrinum*] |
| CAA63970 | 4376229 | HMG-CoA-reductase; hydroxymethylglutaryl-CoA reductase (NADPH) [*Gibberella fujikuroi*] |
| CAE47850 | 41581201 | 3-hydroxy-3-methylglutaryl-coenzyme a reductase, putative [*Aspergillus fumigatus*] |
| CAF92135 | 47213283 | unnamed protein product [*Tetraodon nigroviridis*] |
| CAH92577 | 55731745 | hypothetical protein [*Pongo pygmaeus*] |
| EAK94577 | 46435190 | hypothetical protein CaO19.8633 [*Candida albicans* SC5314] |
| EAL20195 | 50257490 | hypothetical protein CNBF0070 [*Cryptococcus neoformans* var. *neoformans* B-3501A] |
| AAF80374 | 8886086 | HMG-CoA reductase [*Dendroctonus jeffreyi*] |
| NP_013555 | 6323483 | Hmg2p [*Saccharomyces cerevisiae*] |
| NP_013636 | 6323565 | Hmg1p [*Saccharomyces cerevisiae*] |
| NP_032281 | 56119096 | 3-hydroxy-3-methylglutaryl-Coenzyme A reductase [*Mus musculus*] |
| NP_037266 | 40538852 | 3-hydroxy-3-methylglutaryl-Coenzyme A reductase [*Rattus norvegicus*] |
| NP_588235 | 19075735 | 3-hydroxy-3-methylglutaryl-coenzyme a reductase [*Schizosaccharomyces pombe*] |
| NP_985010 | 45190756 | AER152Wp [*Eremothecium gossypii*] |
| NP_989816 | 45383193 | 3-hydroxy-3-methylglutaryl-CoA reductase [*Gallus gallus*] |
| NP_999724 | 47551099 | HMGCoA reductase [*Strongylocentrotus purpuratus*] |
| XP_324892 | 32408825 | hypothetical protein [*Neurospora crassa*] |
| XP_364130 | 39955070 | hypothetical protein MG08975.4 [*Magnaporthe grisea* 70-15] |
| XP_389373 | 46134115 | hypothetical protein FG09197.1 [*Gibberella zeae* PH-1] |
| XP_400629 | 49072680 | hypothetical protein UM03014.1 [*Ustilago maydis* 521] |
| XP_405730 | 49087632 | hypothetical protein AN1593.2 [*Aspergillus nidulans* FGSC A4] |
| XP_407954 | 49092986 | hypothetical protein AN3817.2 [*Aspergillus nidulans* FGSC A4] |
| XP_449268 | 50293713 | unnamed protein product [*Candida glabrata*] |
| XP_451740 | 50303597 | unnamed protein product [*Kluyveromyces lactis*] |
| XP_458872 | 50420671 | unnamed protein product [*Debaryomyces hansenii*] |
| XP_503558 | 50552167 | hypothetical protein [*Yarrowia lipolytica*] |
| XP_536323 | 57084803 | PREDICTED: similar to 3-hydroxy-3-methylglutaryl-coenzyme A reductase (HMG-CoA reductase) [*Canis* s] |
| XP_571450 | 58268588 | hydroxymethylglutaryl-CoA reductase (NADPH), putative [*Cryptococcus neoformans* var. *neoformans* JEC21] |

TABLE 10

| Examples of mevalonate kinase polypeptides. | | |
|---|---|---|
| ACCESSION | GI | PROTEIN DESCRIPTION |
| XP_386088 | 46123069 | hypothetical protein FG05912.1 [*Gibberella zeae* PH-1] |
| XP_408006 | 49093090 | hypothetical protein AN3869.2 [*Aspergillus nidulans* FGSC A4] |
| XP_370449 | 39978123 | hypothetical protein MG06946.4 [*Magnaporthe grisea* 70-15] |
| EAL04797 | 46445529 | hypothetical protein CaO19.4809 [*Candida albicans* SC5314] |

TABLE 10-continued

Examples of mevalonate kinase polypeptides.

| ACCESSION | GI | PROTEIN DESCRIPTION |
|---|---|---|
| XP_322935 | 32404644 | hypothetical protein ((AL513444) related to MEVALONATE KINASE [*Neurospora crassa*]) |
| NP_001007 | 55925207 | zgc: 103473 [*Danio rerio*] |
| XP_460851 | 50424525 | unnamed protein product [*Debaryomyces hansenii*] |
| XP_567851 | 58260882 | cystathionine beta-lyase, putative [*Cryptococcus neoformans* var. *neoformans* JEC21] |
| XP_567850 | 58260880 | cystathionine beta-lyase, putative [*Cryptococcus neoformans* var. *neoformans* JEC21] |
| AAQ02416 | 33303805 | mevalonate kinase [synthetic construct] |
| CAA53059 | 450346 | unnamed protein product [Hepatitis B virus] |
| AAH16140 | 16359371 | MVK protein [*Homo sapiens*] |
| AAH05606 | 13542811 | Mevalonate kinase [*Mus musculus*] |
| XP_403111 | 49078786 | hypothetical protein UM05496.1 [*Ustilago maydis* 521] |
| XP_452532 | 50305147 | unnamed protein product [*Kluyveromyces lactis*] |
| CAG08527 | 47226511 | unnamed protein product [*Tetraodon nigroviridis*] |
| XP_446138 | 50287417 | unnamed protein product [*Candida glabrata*] |
| AAO51522 | 28828936 | similar to *Rattus norvegicus* (Rat). Mevalonate kinase (EC 2.7.1.36) (MK) [*Dictyostelium discoideum*] |
| NP_985191 | 45190937 | AER335Wp [*Eremothecium gossypii*] |
| XP_500956 | 50546973 | hypothetical protein [*Yarrowia lipolytica*] |
| NP_013935 | 6323864 | Erg12p [*Saccharomyces cerevisiae*] |
| AAD45421 | 5578718 | mevalonate kinase [*Arabidopsis thaliana*] |
| NP_920723 | 37532842 | putative mevalonate kinase [*Oryza sativa* (*japonica* cultivar-group)] |
| NP_851084 | 30690651 | mevalonate kinase (MK) [*Arabidopsis thaliana*] |
| AAL18925 | 16417946 | mevalonate kinase [*Hevea brasiliensis*] |
| NP_788338 | 28573850 | CG33009-PA, isoform A [*Drosophila melanogaster*] |
| AAU20834 | 51988124 | Hypothetical protein Y42G9A.4b [*Caenorhabditis elegans*] |
| AAU87813 | 52839819 | Hypothetical protein Y42G9A.4d [*Caenorhabditis elegans*] |
| AAU20835 | 51988125 | Hypothetical protein Y42G9A.4c [*Caenorhabditis elegans*] |
| YP_183887 | 57641409 | mevalonate kinase [*Thermococcus kodakaraensis* KOD1] |
| NP_143478 | 14591399 | mevalonate kinase [*Pyrococcus horikoshii* OT3] |
| BAA24409 | 2804172 | mevalonate kinase [*Saccharomyces cerevisiae*] |
| NP_126232 | 14520757 | mevalonate kinase [*Pyrococcus abyssi* GE5] |
| XP_522574 | 55639331 | PREDICTED: similar to Mevalonate kinase (MK) [*Pan troglodytes*] |
| NP_071114 | 11499870 | mevalonate kinase (mvk) [*Archaeoglobus fulgidus* DSM 4304] |
| XP_423949 | 50797461 | PREDICTED: similar to mevalonate kinase [*Gallus gallus*] |
| NP_633786 | 21227864 | Mevalonate kinase [*Methanosarcina mazei* Go1] |
| ZP_002971 | 48840229 | COG1577: Mevalonate kinase [*Methanosarcina barkeri* str. *fusaro*] |
| EAH50787 | 44170778 | unknown [environmental sequence] |
| NP_615566 | 20089491 | mevalonate kinase [*Methanosarcina acetivorans* C2A] |
| 1VISA | 40890012 | Chain A, Crystal Structure Of Mevalonate Kinase |
| EAK03559 | 44549994 | unknown [environmental sequence] |
| NP_248080 | 15669275 | mevalonate kinase [*Methanocaldococcus jannaschii* DSM 2661] |
| 1KKHA | 20150886 | Chain A, Crystal Structure Of The *Methanococcus Jannaschii* Mevalonate Kinase |
| Q50559 | 2497518 | Mevalonate kinase (MK) |
| CAF88123 | 47200914 | unnamed protein product [*Tetraodon nigroviridis*] |
| NP_275189 | 15678075 | mevalonate kinase [*Methanothermobacter thermautotrophicus* str. Delta H] |
| EAI88745 | 44383877 | unknown [environmental sequence] |
| ZP_002040 | 46141948 | COG1577: Mevalonate kinase [*Methanococcoides burtonii* DSM 6242] |
| XP_543435 | 57105916 | PREDICTED: similar to Mevalonate kinase (MK) [*Canis familiaris*] |
| EAI38920 | 44313360 | unknown [environmental sequence] |
| NP_148611 | 14602065 | mevalonate kinase [*Aeropyrum pernix* K1] |
| EAD08953 | 43286228 | unknown [environmental sequence] |
| EAD45697 | 43361720 | unknown [environmental sequence] |
| YP_134862 | 55377012 | mevalonate kinase [*Haloarcula marismortui* ATCC 43049] |
| NP_720650 | 24378695 | putative mevalonate kinase [*Streptococcus mutans* UA159] |
| NP_614276 | 20094429 | Mevalonate kinase [*Methanopyrus kandleri* AV19] |
| E84270 | 25409931 | mevalonate kinase [imported] - *Halobacterium* sp. NRC-1 |
| NP_691146 | 23097680 | mevalonate kinase [*Oceanobacillus iheyensis* HTE831] |
| ZP_003233 | 48870579 | COG1577: Mevalonate kinase [*Pediococcus pentosaceus* ATCC 25745] |
| AAG02440 | 9937386 | mevalonate kinase [*Enterococcus faecalis*] |
| EAD12278 | 43292898 | unknown [environmental sequence] |
| NP_498328 | 17555862 | mevalonate kinase (64.1 kD) (3H214) [*Caenorhabditis elegans*] |
| EAB31483 | 42928976 | unknown [environmental sequence] |
| ZP_003319 | 50590618 | COG1577: Mevalonate kinase [*Streptococcus suis* 89/1591] |
| NP_814642 | 29375488 | mevalonate kinase [*Enterococcus faecalis* V583] |
| AC1434 | 25514495 | mevalonate kinase homolog lin0010 [imported] - *Listeria innocua* (strain Clip11262) |
| ZP_003577 | 53796847 | COG1577: Mevalonate kinase [*Chloroflexus aurantiacus*] |
| EAD82048 | 43454743 | unknown [environmental sequence] |
| CAE73618 | 39586491 | Hypothetical protein CBG21109 [*Caenorhabditis briggsae*] |
| YP_012624 | 46906235 | mevalonate kinase [*Listeria monocytogenes* str. 4b F2365] |
| NP_988455 | 45358898 | Mevalonate kinase [*Methanococcus maripaludis* S2] |
| ZP_002348 | 47097293 | mevalonate kinase [*Listeria monocytogenes* str. ½a F6854] |

TABLE 10-continued

| Examples of mevalonate kinase polypeptides. | | |
|---|---|---|
| ACCESSION | GI | PROTEIN DESCRIPTION |
| ZP_002862 | 48824993 | COG1577: Mevalonate kinase [*Enterococcus faecium*] |
| ZP_002307 | 47093020 | mevalonate kinase [*Listeria monocytogenes* str. 4b H7858] |
| NP_597102 | 19173299 | MEVALONATE KINASE [*Encephalitozoon cuniculi*] |
| CAD24422 | 20429111 | phosphomevalonate kinase [*Paracoccus zeaxanthinifaciens*] |
| NP_785308 | 28378416 | mevalonate kinase [*Lactobacillus plantarum* WCFS1] |
| EAA39098 | 29247539 | GLP_305_18405_19430 [*Giardia lamblia* ATCC 50803] |
| NP_819638 | 29653946 | phosphomevalonate kinase, putative [*Coxiella burnetii* RSA 493] |
| EAH49746 | 44168765 | unknown [environmental sequence] |
| EAH49745 | 44168764 | unknown [environmental sequence] |
| NP_378182 | 15922513 | hypothetical protein ST2185 [*Sulfolobus tokodaii* str. 7] |
| ZP_000459 | 23002259 | COG1577: Mevalonate kinase [*Lactobacillus gasseri*] |
| H90181 | 25393827 | mevalonate kinase [imported] - *Sulfolobus solfataricus* |
| YP_054120 | 50405028 | Mevalonate kinase, putative [*Paramecium tetraurelia*] |
| BAB07790 | 9695270 | mevalonate kinase [*Streptomyces* sp. CL190] |
| AAG02435 | 9937379 | mevalonate kinase [*Staphylococcus epidermidis*] |
| NP_560495 | 18313828 | mevalonate kinase [*Pyrobaculum aerophilum* str. IM2] |
| YP_187834 | 57866187 | mevalonate kinase [*Staphylococcus epidermidis* RP62A] |
| EAK40782 | 44602942 | unknown [environmental sequence] |
| CAC51370 | 15212070 | mevalonate kinase [*Lactobacillus helveticus*] |
| AAG02424 | 9937364 | mevalonate kinase [*Staphylococcus aureus*] |
| YP_185521 | 57651465 | mevalonate kinase [*Staphylococcus aureus* subsp. *aureus* COL] |
| YP_040044 | 49482820 | mevalonate kinase [*Staphylococcus aureus* subsp. *aureus* MRSA252] |
| YP_194037 | 58337452 | mevalonate kinase [*Lactobacillus acidophilus* NCFM] |
| D86675 | 25400965 | mevalonate kinase [imported] - *Lactococcus lactis* subsp. *lactis* (strain IL1403) |
| NP_763916 | 27467279 | mevalonate kinase [*Staphylococcus epidermidis* ATCC 12228] |
| CAF89434 | 47197810 | unnamed protein product [*Tetraodon nigroviridis*] |
| EAF38333 | 43767792 | unknown [environmental sequence] |
| EAK46841 | 44611394 | unknown [environmental sequence] |
| H89827 | 25507776 | mevalonate kinase [imported] - *Staphylococcus aureus* (strain N315) |
| ZP_003149 | 48861061 | COG0153: Galactokinase [*Microbulbifer degradans* 2-40] |
| EAK17824 | 44570143 | unknown [environmental sequence] |
| EAH86276 | 44235719 | unknown [environmental sequence] |
| YP_118418 | 54024176 | putative mevalonate kinase [*Nocardia farcinica* IFM 10152] |
| ZP_003196 | 48865749 | COG1577: Mevalonate kinase [*Oenococcus oeni* PSU-1] |
| AAG02430 | 9937372 | mevalonate kinase [*Staphylococcus haemolyticus*] |
| NP_269075 | 15674901 | mevalonate kinase [*Streptococcus pyogenes* M1 GAS] |
| NP_802520 | 28896170 | putative mevalonate kinase [*Streptococcus pyogenes* SSI-1] |
| AAL97579 | 19748102 | mevalonate kinase [*Streptococcus pyogenes* MGAS8232] |
| ZP_003666 | 56808907 | COG1577: Mevalonate kinase [*Streptococcus pyogenes* M49 591] |
| NP_965060 | 42519130 | mevalonate kinase [*Lactobacillus johnsonii* NCC 533] |
| NP_819639 | 29653947 | mevalonate kinase, putative [*Coxiella burnetii* RSA 493] |
| EAD97024 | 43484567 | unknown [environmental sequence] |
| BAD86800 | 57753870 | mevalonate kinase [*Streptomyces* sp. KO-3988] |

TABLE 11

| Examples of phosphomevalonate kinase polypeptides. | | |
|---|---|---|
| ACCESSION | GI | PROTEIN DESCRIPTION |
| AAA34596 | 171479 | phosphomevalonate kinase |
| XP_452514 | 50305111 | unnamed protein product [*Kluyveromyces lactis*] |
| NP_985210 | 45190956 | AER354Wp [*Eremothecium gossypii*] |
| XP_446144 | 50287429 | unnamed protein product [*Candida glabrata*] |
| XP_462340 | 50427455 | unnamed protein product [*Debaryomyces hansenii*] |
| EAL04096 | 46444824 | hypothetical protein CaO19.12076 [*Candida albicans* SC5314] |
| EAL03941 | 46444668 | hypothetical protein CaO19.4606 [*Candida albicans* SC5314] |
| XP_503619 | 50552418 | hypothetical protein [*Yarrowia lipolytica*] |
| XP_389940 | 46136497 | hypothetical protein FG09764.1 [*Gibberella zeae* PH-1] |
| XP_329795 | 32418634 | hypothetical protein [*Neurospora crassa*] |
| XP_369652 | 39976529 | hypothetical protein MG05812.4 [*Magnaporthe grisea* 70-15] |
| XP_406448 | 49089559 | hypothetical protein AN2311.2 [*Aspergillus nidulans* FGSC A4] |
| NP_593421 | 19114333 | putative phosphomevalonate kinase [*Schizosaccharomyces pombe*] |
| XP_568385 | 58261950 | expressed protein [*Cryptococcus neoformans* var. *neoformans* JEC21] |
| EAL17628 | 50254887 | hypothetical protein CNBM0120 [*Cryptococcus neoformans* var. *neoformans* B-3501A] |
| AAL18926 | 16417948 | phosphomevalonate kinase [*Hevea brasiliensis*] |
| BAD43274 | 51969164 | hypothetical protein [*Arabidopsis thaliana*] |
| BAD44652 | 51971975 | hypothetical protein [*Arabidopsis thaliana*] |
| XP_398375 | 49068172 | hypothetical protein UM00760.1 [*Ustilago maydis* 521] |
| BAD44486 | 51971643 | hypothetical protein [*Arabidopsis thaliana*] |

TABLE 11-continued

| Examples of phosphomevalonate kinase polypeptides. | | |
|---|---|---|
| ACCESSION | GI | PROTEIN DESCRIPTION |
| F90479 | 25393214 | (Phospho) mevalonate kinase, probable [imported] - *Sulfolobus solfataricus* |
| YP_194039 | 58337454 | phosphomevalonate kinase [*Lactobacillus acidophilus* NCFM] |

TABLE 12

| Examples of mevalonate pyrophosphate decarboxylase polypeptides. | | |
|---|---|---|
| ACCESSION | GI | PROTEIN DESCRIPTION |
| AAT93171 | 51013755 | YNR043W [*Saccharomyces cerevisiae*] |
| 1FI4A | 13786942 | Chain A, The X-Ray Crystal Structure Of Mevalonate 5-Diphosphate Decarboxylase At 2.3 Angstrom Resolution. |
| XP_455548 | 50311049 | unnamed protein product [*Kluyveromyces lactis*] |
| XP_445335 | 50285813 | unnamed protein product [*Candida glabrata*] |
| XP_456912 | 50409853 | unnamed protein product [*Debaryomyces hansenii*] |
| NP_986435 | 45200865 | AGL232Cp [*Eremothecium gossypii*] |
| AAF19399 | 6625790 | diphosphomevalonate decarboxylase MVD1 [*Candida albicans*] |
| XP_328845 | 32416734 | hypothetical protein [*Neurospora crassa*] |
| XP_505041 | 50555265 | hypothetical protein [*Yarrowia lipolytica*] |
| NP_594027 | 19114939 | diphosphomevalonate decarboxylase [*Schizosaccharomyces pombe*] |
| XP_364905 | 39963452 | hypothetical protein MG09750.4 [*Magnaporthe grisea* 70-15] |
| XP_390600 | 46137817 | hypothetical protein FG10424.1 [*Gibberella zeae* PH-1] |
| XP_408551 | 49094180 | hypothetical protein AN4414.2 [*Aspergillus nidulans* FGSC A4] |
| AAA34506 | 7544604 | ORF [*Saccharomyces cerevisiae*] |
| EAL18927 | 50256200 | hypothetical protein CNBI1880 [*Cryptococcus neoformans* var. *neoformans* B-3501A] |
| XP_568247 | 58261674 | diphosphomevalonate decarboxylase, putative [*Cryptococcus neoformans* var. *neoformans* JEC21] |
| XP_402794 | 49077992 | hypothetical protein UM05179.1 [*Ustilago maydis* 521] |
| AAH81784 | 51980639 | Mevalonate (diphospho) decarboxylase [*Rattus norvegicus*] |
| EAL00166 | 46440864 | hypothetical protein CaO19.6105 [*Candida albicans* SC5314] |
| NP_619597 | 20149736 | mevalonate (diphospho) decarboxylase [*Mus musculus*] |
| NP_112324 | 13592005 | mevalonate (diphospho) decarboxylase [*Rattus norvegicus*] |
| BAC40852 | 26354448 | unnamed protein product [*Mus musculus*] |
| XP_546783 | 57087071 | Mevalonate pyrophosphate decarboxylase [*Canis familiaris*] |
| Q99JF5 | 23814095 | Diphosphomevalonate decarboxylase (Mevalonate pyrophosphate decarboxylase) |
| AAH63907 | 39645379 | LOC394871 protein [*Xenopus tropicalis*] |
| CAF99534 | 47230341 | unnamed protein product [*Tetraodon nigroviridis*] |
| AAP35576 | 30582699 | mevalonate (diphospho) decarboxylase [*Homo sapiens*] |
| AAP36301 | 30584105 | Homo sapiens mevalonate (diphospho) decarboxylase [synthetic construct] |
| AAL18927 | 16417950 | mevalonate disphosphate decarboxylase [*Hevea brasiliensis*] |
| AAV32433 | 54292590 | mevalonate disphosphate decarboxylase [*Ginkgo biloba*] |
| AAP68208 | 31711704 | At2g38700 [*Arabidopsis thaliana*] |
| AAM64988 | 21593039 | mevalonate diphosphate decarboxylase [*Arabidopsis thaliana*] |
| NP_566995 | 18410026 | mevalonate diphosphate decarboxylase, putative [*Arabidopsis thaliana*] |
| XP_423130 | 50771155 | PREDICTED: similar to mevalonate pyrophosphate decarboxylase [*Gallus gallus*] |
| AAM65192 | 21593243 | diphosphomevalonate decarboxylase-like protein [*Arabidopsis thaliana*] |
| NP_001007 | 55925435 | zgc: 100824 [*Danio rerio*] |
| NP_573068 | 28571205 | CG8239-PA [*Drosophila melanogaster*] |
| BAD27942 | 50252009 | putative mevalonate disphosphate decarboxylase [*Oryza sativa* (*japonica cultivar-group*)] |
| T47584 | 11281655 | diphosphomevalonate decarboxylase (EC 4.1.1.33) F24B22.210 [similarity] - *Arabidopsis thaliana* |
| XP_307373 | 31196851 | ENSANGP00000013738 [*Anopheles gambiae* str. PEST] |
| CAE73245 | 39591192 | Hypothetical protein CBG20661 [*Caenorhabditis briggsae*] |
| NP_496966 | 17537201 | mevalonate decarboxylase (41.5 kD) (2O512) [*Caenorhabditis elegans*] |
| XP_393230 | 48121058 | similar to mevalonate pyrophosphate decarboxylase [*Apis mellifera*] |
| G90479 | 25393662 | diphosphomevalonate decarboxylase, probable [imported] - *Sulfolobus solfataricus* |
| NP_496967 | 17537203 | mevalonate decarboxylase (2O512) [*Caenorhabditis elegans*] |
| NP_691147 | 23097681 | mevalonate diphosphate decarboxylase [*Oceanobacillus iheyensis* HTE831] |
| EAL29282 | 54640164 | GA20922-PA [*Drosophila pseudoobscura*] |
| AD1434 | 25515042 | mevalonate diphosphate decarboxylase homolog lin0011 [imported] - *Listeria innocua* (*strain Clip11262*) |
| ZP_002308 | 47093021 | diphosphomevalonate decarboxylase [*Listeria monocytogenes* str. 4b H7858] |
| YP_012625 | 46906236 | diphosphomevalonate decarboxylase [*Listeria monocytogenes* str. 4b F2365] |

TABLE 12-continued

| Examples of mevalonate pyrophosphate decarboxylase polypeptides. | | |
|---|---|---|
| ACCESSION | GI | PROTEIN DESCRIPTION |
| ZP_002348 | 47097294 | diphosphomevalonate decarboxylase [*Listeria monocytogenes* str. ½a F6854] |
| NP_819637 | 29653945 | diphosphomevalonate decarboxylase [*Coxiella burnetii* RSA 493] |
| NP_376888 | 15921219 | hypothetical diphosphomevalonate decarboxylase [*Sulfolobus tokodaii* str. 7] |
| ZP_003319 | 50590617 | COG3407: Mevalonate pyrophosphate decarboxylase [*Streptococcus suis* 89/1591] |
| NP_585805 | 19074299 | MEVALONATE PYROPHOSPHATE DECARBOXYLASE [*Encephalitozoon cuniculi*] |
| YP_187835 | 57866188 | mevalonate diphosphate decarboxylase [*Staphylococcus epidermidis* RP62A] |
| CAD24423 | 20429112 | mevalonate diphosphate decarboxylase [*Paracoccus zeaxanthinifaciens*] |
| AAG02431 | 9937373 | mevalonate diphosphate decarboxylase [*Staphylococcus haemolyticus*] |
| NP_763917 | 27467280 | mevalonate diphosphate decarboxylase [*Staphylococcus epidermidis* ATCC 12228] |
| AAG02446 | 9937394 | mevalonate diphosphate decarboxylase [*Enterococcus faecium*] |
| ZP_002863 | 48824994 | COG3407: Mevalonate pyrophosphate decarboxylase [*Enterococcus faecium*] |
| AAG02441 | 9937387 | mevalonate diphosphate decarboxylase [*Enterococcus faecalis*] |
| YP_185522 | 57651466 | mevalonate diphosphate decarboxylase [*Staphylococcus aureus* subsp. *aureus* COL] |
| A89828 | 25505863 | mevalonate diphosphate decarboxylase [imported] - Staphylococcus *aureus* (strain N315) |
| NP_814641 | 29375487 | mevalonate diphosphate decarboxylase [*Enterococcus faecalis* V583] |
| YP_040045 | 49482821 | mevalonate diphosphate decarboxylase [*Staphylococcus aureus* subsp. *aureus* MRSA252] |
| NP_785307 | 28378415 | diphosphomevalonate decarboxylase [*Lactobacillus plantarum* WCFS1] |
| ZP_003196 | 48865750 | COG3407: Mevalonate pyrophosphate decarboxylase [*Oenococcus oeni* PSU-1] |
| ZP_003233 | 48870580 | COG3407: Mevalonate pyrophosphate decarboxylase [*Pediococcus pentosaceus* ATCC 25745] |
| E86675 | 25400967 | diphosphomevalonate decarboxylase [imported] - *Lactococcus lactis* subsp. *lactis* (strain IL1403) |
| EAE31110 | 43552684 | unknown [environmental sequence] |
| BAB07791 | 9695271 | diphosphomevalonate decarboxylase [*Streptomyces* sp. CL190] |
| CAC51371 | 15212071 | mevalonate diphosphate decarboxylase [*Lactobacillus helveticus*] |
| ZP_000459 | 23002258 | COG3407: Mevalonate pyrophosphate decarboxylase [*Lactobacillus gasseri*] |
| NP_965061 | 42519131 | mevalonate pyrophosphate decarboxylase [*Lactobacillus johnsonii* NCC 533] |
| BAD86801 | 57753871 | mevalonate diphosphate decarboxylase [*Streptomyces* sp. KO-3988] |
| YP_194038 | 58337453 | mevalonate diphosphate decarboxylase [*Lactobacillus acidophilus* NCFM] |
| YP_118419 | 54024177 | putative diphosphomevalonate decarboxylase [*Nocardia farcinica* IFM 10152] |
| EAK18820 | 44571499 | unknown [environmental sequence] |
| EAI85935 | 44379784 | unknown [environmental sequence] |
| NP_721336 | 24379381 | putative mevalonate diphosphate decarboxylase [*Streptococcus mutans* UA159] |
| D95044 | 25388338 | diphosphomevalonate decarboxylase [imported] - *Streptococcus pneumoniae* (strain TIGR4) |
| AAG02456 | 9937408 | mevalonate diphosphate decarboxylase [*Streptococcus pneumoniae*] |
| C97914 | 25511486 | diphosphomevalonate decarboxylase (EC 4.1.1.33) [imported] - *Streptococcus pneumoniae* (strain R6) |
| EAK47683 | 44612560 | unknown [environmental sequence] |
| EAB86425 | 43039778 | unknown [environmental sequence] |
| YP_140971 | 55822530 | mevalonate pyrophosphate decarboxylase [*Streptococcus thermophilus* CNRZ1066] |
| YP_139081 | 55820639 | mevalonate pyrophosphate decarboxylase [*Streptococcus thermophilus* LMG 18311] |
| BAD07376 | 40882372 | mevalonate diphosphate decarboxylase [*Actinoplanes* sp. A40644] |
| NP_968512 | 42523132 | Diphosphomevalonate decarboxylase [*Bdellovibrio bacteriovorus* HD100] |
| EAI06705 | 44265427 | unknown [environmental sequence] |
| YP_060018 | 50914046 | Diphosphomevalonate decarboxylase [*Streptococcus pyogenes* MGAS10394] |
| AAG02451 | 9937401 | mevalonate diphosphate decarboxylase [*Streptococcus pyogenes*] |
| NP_269076 | 15674902 | mevalonate pyrophosphate decarboxylase [*Streptococcus pyogenes* M1 GAS] |
| ZP_003666 | 56808906 | COG3407: Mevalonate pyrophosphate decarboxylase [*Streptococcus pyogenes* M49 591] |
| NP_688323 | 22537472 | diphosphomevalonate decarboxylase [*Streptococcus agalactiae* 2603V/R] |
| NP_735832 | 25011437 | hypothetical protein gbs1395 [*Streptococcus agalactiae* NEM316] |
| EAC40267 | 43149093 | unknown [environmental sequence] |

TABLE 12-continued

| Examples of mevalonate pyrophosphate decarboxylase polypeptides. | | |
|---|---|---|
| ACCESSION | GI | PROTEIN DESCRIPTION |
| AAL97580 | 19748103 | mevalonate pyrophosphate decarboxylase [*Streptococcus pyogenes* MGAS8232] |
| EAI76915 | 44367119 | unknown [environmental sequence] |
| EAD35042 | 43339207 | unknown [environmental sequence] |
| YP_073129 | 51598941 | mevalonate pyrophosphate decarboxylase [*Borrelia garinii* PBi] |
| EAI90092 | 44385501 | unknown [environmental sequence] |
| BAB07818 | 9711347 | mevalonate diphosphate decaroboxylase [*Kitasatospora griseola*] |
| EAD72850 | 43433025 | unknown [environmental sequence] |
| NP_212820 | 15595031 | mevalonate pyrophosphate decarboxylase [*Borrelia burgdorferi* B31] |
| YP_124337 | 54297968 | hypothetical protein lpp2023 [*Legionella pneumophila* str. Paris] |
| YP_096056 | 52842257 | mevalonate diphosphate decarboxylase [*Legionella pneumophila* subsp. *pneumophila* str. Philadelphia 1] |
| EAA39903 | 29248368 | GLP_479_14176_13169 [*Giardia lamblia* ATCC 50803] |
| EAH06252 | 44088237 | unknown [environmental sequence] |
| YP_127354 | 54294939 | hypothetical protein lpl2018 [*Legionella pneumophila* str. Lens] |
| EAD45753 | 43361830 | unknown [environmental sequence] |
| NP_802519 | 28896169 | putative mevalonate pyrophosphate decarboxylase [*Streptococcus pyogenes* SSI-1] |

TABLE 13

| Examples of IPP isomerase polypeptides. | | |
|---|---|---|
| ACCESSION | GI | PROTEIN DESCRIPTION |
| NP_015208 | 6325140 | Idi1p [*Saccharomyces cerevisiae*] |
| XP_448008 | 50291151 | unnamed protein product [*Candida glabrata*] |
| NP_983828 | 45187605 | ADL268Cp [*Eremothecium gossypii*] |
| XP_455121 | 50310203 | unnamed protein product [*Kluyveromyces lactis*] |
| XP_462358 | 50427491 | unnamed protein product [*Debaryomyces hansenii*] |
| EAL01685 | 46442395 | potential isopentenyl diphosphate isomerase [*Candida albicans* SC5314] |
| XP_504974 | 50555131 | hypothetical protein [*Yarrowia lipolytica*] |
| XP_328425 | 32415894 | hypothetical protein [*Neurospora crassa*] |
| XP_367200 | 39971619 | hypothetical protein MG07125.4 [*Magnaporthe grisea* 70-15] |
| XP_389898 | 46136413 | conserved hypothetical protein [*Gibberella zeae* PH-1] |
| XP_404716 | 49085144 | hypothetical protein AN0579.2 [*Aspergillus nidulans* FGSC A4] |
| CAD37150 | 21627818 | isopentenyl-diphosphate delta-isomerase [*Aspergillus fumigatus*] |
| NP_595164 | 19111956 | isopentenyl-diphosphate delta-isomerase [*Schizosaccharomyces pombe*] |
| XP_566641 | 58258457 | isopentenyl-diphosphate delta-isomerase, putative [*Cryptococcus neoformans* var. *neoformans* JEC21] |
| XP_402453 | 49077100 | hypothetical protein UM04838.1 [*Ustilago maydis* 521] |
| O35586 | 6225528 | Isopentenyl-diphosphate delta-isomerase 1 (IPP isomerase 1) |
| AAP36609 | 30584713 | *Homo sapiens* isopentenyl-diphosphate delta isomerase [synthetic construct] |
| AAF37873 | 7188790 | isopentenyl pyrophosphate isomerase [*Dictyostelium discoideum*] |
| NP_445991 | 16758306 | isopentenyl-diphosphate delta isomerase [*Rattus norvegicus*] |
| O42641 | 6225529 | Isopentenyl-diphosphate delta-isomerase (IPP isomerase) (Isopentenyl pyrophosphate isomerase) |
| BAA33979 | 3790386 | IPP isomerase [*Xanthophyllomyces dendrorhous*] |
| Q13907 | 6225527 | Isopentenyl-diphosphate delta-isomerase 1 (IPP isomerase 1) |
| AAH22418 | 48257241 | IDI1 protein [*Homo sapiens*] |
| AAH19227 | 48257312 | IDI1 protein [*Homo sapiens*] |
| AAH57827 | 35505325 | IDI1 protein [*Homo sapiens*] |
| NP_004499 | 40018633 | isopentenyl-diphosphate delta isomerase [*Homo sapiens*] |
| AAH89786 | 58477715 | Unknown (protein for MGC: 108635) [*Rattus norvegicus*] |
| CAH91844 | 55730243 | hypothetical protein [*Pongo pygmaeus*] |
| XP_418561 | 50732281 | PREDICTED: similar to isopentenyl-diphosphate delta isomerase; IPP isomerase [*Gallus gallus*] |
| AAH06999 | 48257093 | IDI1 protein [*Homo sapiens*] |
| CAF98782 | 47225155 | unnamed protein product [*Tetraodon nigroviridis*] |
| NP_808875 | 29366820 | isopentenyl-diphosphate delta isomerase [*Mus musculus*] |
| XP_507622 | 55633353 | PREDICTED: similar to isopentenyl-diphosphate delta isomerase; IPP isomerase [*Pan troglodytes*] |
| AAH82648 | 52139082 | LOC494671 protein [*Xenopus laevis*] |
| NP_001011 | 58332496 | hypothetical LOC496783 [*Xenopus tropicalis*] |
| AAF29976 | 6856556 | isopentenyl pyrophosphate:dimethyllallyl pyrophosphate isomerase [*Lactuca sativa*] |
| AAG10423 | 9971806 | isopentenyl pyrophosphate:dimethyllallyl pyrophosphate isomerase [*Tagetes erecta*] |
| O48964 | 6225525 | Isopentenyl-diphosphate delta-isomerase I (IPP isomerase I) (Isopentenyl pyrophosphate isomerase I) |
| AAF29973 | 6856550 | isopentenyl pyrophosphate:dimethyllallyl pyrophosphate isomerase [*Adonis palaestina*] |

TABLE 13-continued

Examples of IPP isomerase polypeptides.

| ACCESSION | GI | PROTEIN DESCRIPTION |
|---|---|---|
| AAF29977 | 6856558 | isopentenyl pyrophosphate:dimethyllallyl pyrophosphate isomerase [*Tagetes erecta*] |
| AAQ84167 | 35186998 | isopentenyl pyrophosphate isomerase [*Pueraria montana* var. *lobata*] |
| AAF29974 | 6856552 | isopentenyl pyrophosphate:dimethyllallyl pyrophosphate isomerase [*Adonis palaestina*] |
| Q39472 | 6225526 | Isopentenyl-diphosphate delta-isomerase I (IPP isomerase I) (Isopentenyl pyrophosphate isomerase I) |
| S49588 | 1085973 | isopentenyl-diphosphate Delta-isomerase (EC 5.3.3.2) 1 - *Clarkia breweri* (fragment) |
| AAL91980 | 19568939 | isopentenyl pyrophosphate isomerase IDI1 [*Melaleuca alternifolia*] |
| BAB40973 | 13603406 | isopentenyl diphosphate isomerase 1 [*Nicotiana tabacum*] |
| AAF29975 | 6856554 | isopentenyl pyrophosphate:dimethyllallyl pyrophosphate isomerase [*Lactuca sativa*] |
| T52027 | 25493162 | isopentenyl-diphosphate Delta-isomerase (EC 5.3.3.2) 1 [validated] - *Haematococcus pluvialis* |
| AAL91979 | 19568937 | isopentenyl pyrophosphate isomerase IDI2 [*Melaleuca alternifolia*] |
| T46812 | 11362218 | isopentenyl-diphosphate Delta-isomerase (EC 5.3.3.2) [imported] - *Haematococcus pluvialis* |
| T51248 | 11362217 | isopentenyl-diphosphate Delta-isomerase (EC 5.3.3.2) 2 [validated] - *Haematococcus pluvialis* |
| BAB40974 | 13603408 | isopentenyl diphosphate isomerase 2 [*Nicotiana tabacum*] |
| O48965 | 6225532 | Isopentenyl-diphosphate delta-isomerase II (IPP isomerase II) (Isopentenyl pyrophosphate isomerase II) |
| XP_225509 | 34877710 | similar to isopentenyl diphosphate delta-isomerase type 2 [*Rattus norvegicus*] |
| XP_506401 | 51963472 | PREDICTED OJ1612_A04.101 gene product [*Oryza sativa* (*japonica* cultivar-group)] |
| AAF29978 | 6856560 | isopentenyl pyrophosphate:dimethyllallyl pyrophosphate isomerase [*Oryza sativa*] |
| AAH76541 | 50369278 | Unknown (protein for IMAGE: 7037641) [*Danio rerio*] |
| AAT94033 | 51038230 | putative isopentenyl-diphosphate delta-isomerase [*Oryza sativa* (*japonica* cultivar-group)] |
| XP_225502 | 34876517 | similar to isopentenyl diphosphate delta-isomerase type 2 [*Rattus norvegicus*] |
| Q39471 | 6225533 | Isopentenyl-diphosphate delta-isomerase II (IPP isomerase II) (Isopentenyl pyrophosphate isomerase II) |
| AAB67743 | 1213450 | isopentenyl pyrophosphate isomerase [*Clarkia breweri*] |
| NP_197148 | 22326844 | isopentenyl-diphosphate delta-isomerase I [*Arabidopsis thaliana*] |
| BAB09611 | 9759126 | isopentenyl pyrophosphate:dimethyllallyl pyrophosphate isomerase [*Arabidopsis thaliana*] |
| AAD41766 | 5305669 | isopentenyl pyrophosphate isomerase [*Hevea brasiliensis*] |
| AAB67741 | 1213442 | isopentenyl pyrophosphate isomerase [*Arabidopsis thaliana*] |
| XP_395125 | 48101420 | similar to CG8646-PA [*Apis mellifera*] |
| AAN28784 | 23505849 | At3g02780/F13E7_28 [*Arabidopsis thaliana*] |
| AAF36996 | 7110585 | isopentenyl pyrophosphate:dimethylallyl pyrophosphate isomerase [*Brassica oleracea* var. *botrytis*] |
| BAB16690 | 15289752 | putative IPP isomerase [*Eucommia ulmoides*] |
| AAQ14869 | 33340598 | isopentenyl pyrophosphate isomerase [*Zea mays*] |
| BAC65421 | 28971819 | isopentenyl-diphosphate delta-isomerase [*Periploca sepium*] |
| S71369 | 2129625 | isopentenyl-diphosphate Delta-isomerase (EC 5.3.3.2) 1 - *Arabidopsis thaliana* |
| AAF29979 | 6856562 | isopentenyl pyrophosphate:dimethyllallyl pyrophosphate isomerase [*Arabidopsis thaliana*] |
| AAF29980 | 6856564 | isopentenyl pyrophosphate:dimethyllallyl pyrophosphate isomerase [*Arabidopsis thaliana*] |
| AAP21674 | 30267831 | isopentenyl diphosphate delta-isomerase type 2 [*Mus musculus*] |
| Q39664 | 6225534 | Isopentenyl-diphosphate delta-isomerase II (IPP isomerase II) (Isopentenyl pyrophosphate isomerase II) |
| NP_650962 | 24648688 | CG5919-PA [*Drosophila melanogaster*] |
| AAM50284 | 21429130 | RE22306p [*Drosophila melanogaster*] |
| XP_321388 | 58395620 | ENSANGP00000011643 [*Anopheles gambiae* str. PEST] |
| Q9BXS1 | 20978506 | Isopentenyl-diphosphate delta-isomerase 2 (IPP isomerase 2)) |
| T07979 | 7484383 | isopentenyl-diphosphate Delta-isomerase (EC 5.3.3.2) ipi1 - *Chlamydomonas reinhardtii* |
| XP_225508 | 34876527 | similar to diphosphate dimethylallyl diphosphate isomerase 2 [*Rattus norvegicus*] |
| AAT92102 | 51011386 | isopentenyl-diphosphate delta-isomerase [*Ixodes pacificus*] |
| XP_225507 | 34876555 | similar to isopentenyl diphosphate delta-isomerase type 2 [*Rattus norvegicus*] |
| XP_344623 | 34876537 | similar to isopentenyl diphosphate delta-isomerase type 2 [*Rattus norvegicus*] |
| S44843 | 630677 | K06H7.3 protein - *Caenorhabditis elegans* |
| XP_225498 | 27687955 | similar to diphosphate dimethylallyl diphosphate isomerase 2 [*Rattus norvegicus*] |
| AAT08468 | 47013849 | isopentenyl-diphosphate isomerase [*Caenorhabditis elegans*] |
| EAI79636 | 44370808 | unknown [environmental sequence] |

TABLE 13-continued

Examples of IPP isomerase polypeptides.

| ACCESSION | GI | PROTEIN DESCRIPTION |
|---|---|---|
| CAE75055 | 39587401 | Hypothetical protein CBG22969 [*Caenorhabditis briggsae*] |
| EAL04047 | 46444775 | potential isopentenyl diphosphate isomerase fragment [*Candida albicans* SC5314] |
| XP_225528 | 34876543 | similar to isopentenyl diphosphate delta-isomerase type 2 [*Rattus norvegicus*] |
| XP_544282 | 57040602 | PREDICTED: similar to isopentenyl-diphosphate delta isomerase [*Canis familiaris*] |
| XP_225511 | 27688013 | similar to diphosphate dimethylallyl diphosphate isomerase 2 [*Rattus norvegicus*] |
| P26173 | 114853 | Isopentenyl-diphosphate delta-isomerase (IPP isomerase) (Bacteriochlorophyll synthase 20 kDa chain) |
| EAJ04069 | 44405322 | unknown [environmental sequence] |
| EAH27496 | 44127513 | unknown [environmental sequence] |
| AAF91499 | 9653280 | isopentenyl pyrophosphate isomerase [*Daucus carota*] |
| AAM48661 | 21328655 | isopentyl-diphosphate delta-isomerase [uncultured proteobacterium] |
| EAK17826 | 44570145 | unknown [environmental sequence] |
| EAD59515 | 43391069 | unknown [environmental sequence] |
| YP_128702 | 54307682 | hypothetical isopentenyldiphosphate isomerase [*Photobacterium profundum* SS9] |
| EAK66656 | 44639203 | unknown [environmental sequence] |
| YP_118189 | 54023947 | putative isopentenyldiphosphate isomerase [*Nocardia farcinica* IFM 10152] |
| T50740 | 11282665 | isopentenyl diphosphate isomerase homolog [imported] - *Rhodobacter sphaeroides* |
| ZP_002077 | 46193541 | COG1443: Isopentenyldiphosphate isomerase [*Rhodobacter sphaeroides* 2.4.1] |
| EAK16470 | 44568229 | unknown [environmental sequence] |
| YP_165403 | 56695056 | isopentyl-diphosphate delta-isomerase [*Silicibacter pomeroyi* DSS-3] |
| EAD08775 | 43285885 | unknown [environmental sequence] |
| YP_195623 | 58616494 | putative isopentenyl-diphosphate delta-isomerase [*Azoarcus* sp. EbN1] |
| EAI38918 | 44313358 | unknown [environmental sequence] |
| NP_930583 | 37527239 | hypothetical protein plu3365 [*Photorhabdus luminescens* subsp. *laumondii* TTO1] |
| YP_160254 | 56478665 | isopentenyl-diphosphate delta-isomerase [*Azoarcus* sp. EbN1] |
| EAH69842 | 44206571 | unknown [environmental sequence] |
| EAK26254 | 44582307 | unknown [environmental sequence] |
| AAR24381 | 38569721 | isopentyl-diphosphate delta isomerase [*Sus scrofa*] |
| AAM48607 | 21328600 | isopentenyl-diphosphate delta-isomerase, putative [uncultured proteobacterium] |
| EAD82049 | 43454744 | unknown [environmental sequence] |
| ZP_001924 | 45914126 | COG1443: Isopentenyldiphosphate isomerase [*Mesorhizobium* sp. BNC1] |
| YP_056780 | 50843553 | isopentenyl-diphosphate delta-isomerase [*Propionibacterium acnes* KPA171202] |
| YP_050880 | 50121713 | putative isopentenyl-diphosphate delta-isomerase [*Erwinia carotovora* subsp. *atroseptica* SCRI1043] |
| EAF29235 | 43749645 | unknown [environmental sequence] |
| NP_630823 | 21225044 | putative IPP isomerase [*Streptomyces coelicolor* A3(2)] |
| Q82MJ7 | 34582349 | Isopentenyl-diphosphate delta-isomerase (IPP isomerase) (Isopentenyl pyrophosphate isomerase) |
| ZP_003374 | 52010110 | COG1443: Isopentenyldiphosphate isomerase [*Silicibacter* sp. TM1040] |
| AAS75819 | 45737905 | isopentenyl/dimethylallyl diphosphate isomerase [*Nicotiana benthamiana*] |
| Q8KP37 | 30913023 | Isopentenyl-diphosphate delta-isomerase (IPP isomerase) (Isopentenyl pyrophosphate isomerase) |
| XP_507621 | 55633351 | PREDICTED: similar to isopentenyl-diphosphate delta isomerase 2 [*Pan troglodytes*] |
| XP_344621 | 34876521 | similar to diphosphate dimethylallyl diphosphate isomerase 2 [*Rattus norvegicus*] |
| XP_346322 | 34880719 | similar to diphosphate dimethylallyl diphosphate isomerase 2 [*Rattus norvegicus*] |
| YP_152060 | 56414985 | probable isomerase [*Salmonella enterica* subsp. *enterica* serovar Paratypi A str. ATCC 9150] |
| AAT42442 | 48429280 | putative isopentenyl diphosphate isomerase [*Edwardsiella ictaluri*] |
| Q9KK75 | 13878536 | Isopentenyl-diphosphate delta-isomerase (IPP isomerase) (Isopentenyl pyrophosphate isomerase) |
| NP_806649 | 29143307 | probable isomerase [*Salmonella enterica* subsp. *enterica* serovar Typhi Ty2] |
| YP_063124 | 50955836 | isopentenyldiphosphate isomerase [*Leifsonia xyli* subsp. *xyli* str. CTCB07] |
| Q8FND7 | 46395593 | Isopentenyl-diphosphate delta-isomerase (IPP isomerase) (Isopentenyl pyrophosphate isomerase) |
| CAF20647 | 41326485 | ISOPENTENYLDIPHOSPHATE ISOMERASE [*Corynebacterium glutamicum* ATCC 13032] |
| Q8NN99 | 23821718 | Isopentenyl-diphosphate delta-isomerase (IPP isomerase) (Isopentenyl pyrophosphate isomerase) |

TABLE 13-continued

Examples of IPP isomerase polypeptides.

| ACCESSION | GI | PROTEIN DESCRIPTION |
|---|---|---|
| Q7X5H2 | 46395586 | Isopentenyl-diphosphate delta-isomerase (IPP isomerase) (Isopentenyl pyrophosphate isomerase) |
| NP_336246 | 15841209 | isopentenyl-diphosphate delta-isomerase [*Mycobacterium tuberculosis* CDC1551] |
| Q83MJ9 | 46395588 | Isopentenyl-diphosphate delta-isomerase (IPP isomerase) (Isopentenyl pyrophosphate isomerase) |
| P60923 | 46395576 | Isopentenyl-diphosphate delta-isomerase (IPP isomerase) (Isopentenyl pyrophosphate isomerase) |
| Q8FE75 | 31563050 | Isopentenyl-diphosphate delta-isomerase (IPP isomerase) (Isopentenyl pyrophosphate isomerase) |
| 1R67A | 38493022 | Chain A, Y104a Mutant Of *E. Coli* Ipp Isomerase |
| Q9KWD1 | 13878537 | Isopentenyl-diphosphate delta-isomerase (IPP isomerase) |
| Q7VEU0 | 46395585 | Isopentenyl-diphosphate delta-isomerase (IPP isomerase) |
| B84333 | 25410326 | isopentenyl pyrophosphate isomerase [imported] - *Halobacterium* sp. NRC-1 |
| NP_417365 | 16130791 | isopentenyl diphosphate isomerase [*Escherichia coli* K12] |
| E85944 | 25355426 | probable enzyme Z4227 [imported] - *Escherichia coli* (strain O157:H7, substrain EDL933) |
| 1HZTA | 15826050 | Chain A, Crystal Structure Of Metal-Free Isopentenyl Diphosphate:dimethylallyl Diphosphate Isomerase |
| 1PVFB | 50513321 | Chain B, *E. Coli* Ipp Isomerase In Complex With Diphosphate |
| EAD63579 | 43403471 | unknown [environmental sequence] |
| 1I9AB | 13786886 | Chain B, Mevalonate 5-Diphosphate Decarboxylase And Isopentenyl Diphosphate Isomerase |
| YP_012992 | 46906603 | MutT/nudix family protein [*Listeria monocytogenes* str. 4b F2365] |
| ZP_002293 | 47091503 | MutT/nudix family protein [*Listeria monocytogenes* str. 4b H7858] |
| EAI37194 | 44310821 | unknown [environmental sequence] |
| YP_137864 | 55380014 | probable isopentenyl-diphosphate delta-isomerase [*Haloarcula marismortui* ATCC 43049] |
| CAD92056 | 42516867 | putative isopentenyl diphosphate isomerase type 1 [*Haloferax mediterranei*] |
| 1OW2B | 42543244 | Chain B, Isopentenylpyrophosphate-Dimethylallylpyrophosphate Isomerase: Complex Of C67a Mutant With Eipp |

TABLE 14

Examples of FPP synthase polypeptides.

| ACCESSION | GI | PROTEIN DESCRIPTION |
|---|---|---|
| Q92250 | 2497455 | Farnesyl pyrophosphate synthetase (FPP synthetase) (FPS) (Farnesyl diphosphate synthetase) |
| XP_363065 | 39948036 | hypothetical protein MG08649.4 [*Magnaporthe grisea* 70-15] |
| XP_386960 | 46124813 | FPPS_GIBFU Farnesyl pyrophosphate synthetase (FPP synthetase) (FPS) [*Gibberella zeae* PH-1] |
| Q92235 | 3122099 | Farnesyl pyrophosphate synthetase (FPP synthetase) (FPS) (Farnesyl diphosphate synthetase) |
| XP_412149 | 49116518 | hypothetical protein AN8012.2 [*Aspergillus nidulans* FGSC A4] |
| XP_503599 | 50552378 | hypothetical protein [*Yarrowia lipolytica*] |
| NP_593299 | 19114211 | farnesyl pyrophosphate synthetase [*Schizosaccharomyces pombe*] |
| CAD42869 | 21955860 | farnesyl pyrophosphate synthase [*Mucor circinelloides f. lusitanicus*] |
| XP_448787 | 50292709 | unnamed protein product [*Candida glabrata*] |
| NP_012368 | 6322294 | Erg20p [*Saccharomyces cerevisiae*] |
| T42081 | 7433997 | farnesyl-pyrophosphate synthetase - fission yeast (*Schizosaccharomyces pombe*) (fragment) |
| EAK93751 | 46434339 | likely farnesyl diphosphate synthetase [*Candida albicans* SC5314] |
| XP_451300 | 50302727 | FPPS_KLULA [*Kluyveromyces lactis*] |
| XP_571137 | 58267962 | isoprenoid biosynthesis-related protein, putative [*Cryptococcus neoformans* var. *neoformans* JEC21] |
| XP_460720 | 50424267 | unnamed protein product [*Debaryomyces hansenii*] |
| NP_984739 | 45190485 | AEL122Wp [*Eremothecium gossypii*] |
| BAD15361 | 46367743 | farnesyl diphosphate synthase [*Lactarius chrysorrheus*] |
| S71433 | 7433991 | farnesyl-pyrophosphate synthetase - ergot fungus (fragment) |
| CAA65643 | 1523990 | farnesyl pyrophosphate synthetase [*Claviceps purpurea*] |
| XP_399061 | 49069544 | hypothetical protein UM01446.1 [*Ustilago maydis* 521] |
| S71432 | 7433990 | farnesyl-pyrophosphate synthetase - *Sphaceloma manihoticola* (fragment) |
| AAH68912 | 46249832 | MGC83119 protein [*Xenopus laevis*] |
| 1FPS | 1065289 | Chain, Avian Farnesyl Diphosphate Synthase (Fps) (E.C.2.5.1.10) |
| P08836 | 3915686 | Farnesyl pyrophosphate synthetase (FPP synthetase) (FPS) (Farnesyl diphosphate synthetase) |
| AAH83515 | 53733369 | Unknown (protein for IMAGE: 7049076) [*Danio rerio*] |
| 1UBX | 1942050 | Chain, Structure Of Farnesyl Pyrophosphate Synthetase |

TABLE 14-continued

Examples of FPP synthase polypeptides.

| ACCESSION | GI | PROTEIN DESCRIPTION |
|---|---|---|
| 1UBY | 1942051 | Chain, Structure Of Farnesyl Pyrophosphate Synthetase |
| AAF37872 | 7188788 | farnesyl diphosphate synthase [*Dictyostelium discoideum*] |
| NP_803463 | 29135293 | farnesyl diphosphate synthase [*Bos taurus*] |
| AAK63847 | 14488053 | farnesyl diphosphate synthase [*Mentha* X *piperita*] |
| AAV58896 | 55710092 | farnesyl diphosphate synthase [*Centella asiatica*] |
| T06272 | 7433988 | farnesyl-pyrophosphate synthetase FPS1 - tomato |
| JC4846 | 2117737 | farnesyl-pyrophosphate synthetase - *Artemisia annua* |
| P05369 | 120478 | Farnesyl pyrophosphate synthetase (FPP synthetase) (FPS) (Farnesyl diphosphate synthetase) |
| O24241 | 25452945 | Farnesyl pyrophosphate synthetase 1 (FPP synthetase 1) |
| O24242 | 25452946 | Farnesyl pyrophosphate synthetase 2 (FPP synthetase 2) |
| AAH59125 | 37590777 | Testis-specific farnesyl pyrophosphate synthetase [*Rattus norvegicus*] |
| AAH48497 | 28913418 | Farnesyl diphosphate synthetase [*Mus musculus*] |
| AAP74720 | 32329199 | farnesyl diphosphate synthase [*Artemisia tridentata* subsp. *spiciformis*] |
| CAG11850 | 47225367 | unnamed protein product [*Tetraodon nigroviridis*] |
| AAM51429 | 21436457 | putative farnesyl-pyrophosphate synthetase FPS2 [*Arabidopsis thaliana*] |
| AAP74719 | 32329197 | farnesyl diphosphate synthase [*Artemisia tridentata* subsp. *spiciformis*] |
| AAM08927 | 20135548 | farnesyl pyrophosphate synthase [*Malus* X *domestica*] |
| XP_537252 | 57089113 | PREDICTED: similar to farnesyl diphosphate synthase [*Canis familiaris*] |
| AAQ56011 | 34013692 | farnesyl diphosphate synthase [*Hevea brasiliensis*] |
| AAQ14872 | 33340604 | truncated geranylgeranyl-diphosphate synthase [*Zea mays*] |
| AAQ14871 | 33340602 | geranylgeranyl-diphosphate synthase [*Zea mays*] |
| AAD17204 | 4324960 | farnesyl diphosphate synthase [*Artemisia annua*] |
| AAH87886 | 56789674 | Farnesyl diphosphate synthetase [*Mus musculus*] |
| AAK68152 | 14573639 | farnesyldiphosphate synthase [X *Citrofortunella microcarpa*] |
| AAA52423 | 182399 | farnesyl pyrophosphate synthetase (EC 2.5.1.1) |
| S66470 | 2129849 | farnesyl-pyrophosphate synthetase fps1 - white lupine |
| CAA29064 | 4725 | unnamed protein product [*Saccharomyces cerevisiae*] |
| CAI12715 | 55957735 | farnesyl diphosphate synthase [*Homo sapiens*] |
| BAA03523 | 40788949 | KIAA1293 [*Homo sapiens*] |
| P14324 | 1346031 | Farnesyl pyrophosphate synthetase (FPP synthetase) |
| S66471 | 2129850 | farnesyl-pyrophosphate synthetase fps2 - white lupine |
| AAA35820 | 182405 | farnesyl pyrophosphate synthetase |
| CAA59170 | 1491641 | dimethylallyltransferase [*Capsicum annuum*] |
| BAB16687 | 15289750 | putative FPP synthase 1 [*Eucommia ulmoides*] |
| CAA72793 | 1922251 | farnesyl pyrophosphate synthase [*Gossypium arboreum*] |
| CAH91070 | 55728661 | hypothetical protein [*Pongo pygmaeus*] |
| AAK58594 | 14279425 | farnesyl pyrophosphate synthase [*Humulus lupulus*] |
| AAB07264 | 1146159 | farnesyl diphosphate synthase short form [*Arabidopsis thaliana*] |
| Q09152 | 21431776 | Farnesyl pyrophosphate synthetase 1, mitochondrial precursor (FPP synthetase 1) |
| O64905 | 6016044 | Farnesyl pyrophosphate synthetase (FPP synthetase) |
| BAB60822 | 14422406 | putative FPP synthase 2 [*Eucommia ulmoides*] |
| S52009 | 1076319 | farnesyl-pyrophosphate synthetase FPS1 - *Arabidopsis thaliana* |
| NP_917118 | 34911542 | putative farnesyl-pyrophosphate synthetase [*Oryza sativa* (*japonica* cultivar-group)] |
| AAD32648 | 4894899 | farnesyl diphosphate synthase [*Artemisia annua*] |
| AAA40960 | 203582 | cholesterol-regulated protein CR39 |
| AAR27053 | 38684029 | farnesyl diphosphate synthetase [*Ginkgo biloba*] |
| AAU43998 | 52353430 | putative farnesyl pyrophosphate synthase [*Oryza sativa* (*japonica* cultivar-group)] |
| AAL82595 | 18958450 | farnesyl pyrophosphare synthase [*Musa acuminata*] |
| NP_917069 | 34911444 | putative farnesyl-pyrophosphate synthetase [*Oryza sativa* (*japonica* cultivar-group)] |
| XP_228802 | 34879769 | similar to testis-specific farnesyl pyrophosphate synthetase [*Rattus norvegicus*] |
| BAD81810 | 56785155 | putative farnesyl-pyrophosphate synthetase fps2 [*Oryza sativa* (*japonica* cultivar-group)] |
| AAN62522 | 24796660 | farnesyl pyrophosphate synthetase [*Eucommia ulmoides*] |
| NP_595334 | 19112126 | farnesyl pyrophosphate synthetase [*Schizosaccharomyces pombe*] |
| T52066 | 25458583 | probable farnesyl pyrophosphate synthase [imported] - rice |
| AAL49067 | 17946048 | RE52884p [*Drosophila melanogaster*] |
| CAA08919 | 3395483 | dimethylallyltransferase; farnesyl pyrophosphate synthase [*Drosophila melanogaster*] |
| XP_547662 | 57089869 | PREDICTED: similar to farnesyl diphosphate synthase [*Canis familiaris*] |
| EAL26135 | 54636732 | GA11601-PA [*Drosophila pseudoobscura*] |
| BAB60821 | 14422404 | putative FPP synthase 1 [*Eucommia ulmoides*] |
| AAP74721 | 32329201 | chrysanthemyl diphosphate synthase [*Artemisia tridentata* subsp. *spiciformis*] |
| XP_496902 | 51466663 | PREDICTED: similar to Farnesyl pyrophosphate synthetase (FPP synthetase) [*Homo sapiens*] |
| XP_474182 | 50929309 | OSJNBa0071I13.18 [*Oryza sativa* (*japonica* cultivar-group)] |
| CAA87327 | 1160178 | partial sequence [*Homo sapiens*] |
| BAD20729 | 47776234 | farnesyl pyrophosphate synthase [*Candida glabrata*] |

TABLE 14-continued

Examples of FPP synthase polypeptides.

| ACCESSION | GI | PROTEIN DESCRIPTION |
|---|---|---|
| BAC53873 | 30984142 | farnesyl pyrophosphate synthase [*Phaseolus lunatus*] |
| BAB69490 | 15991313 | farnesyl pyrophosphate syntase [*Bombyx mori*] |
| NP_974565 | 42572937 | farnesyl pyrophosphate synthetase 2 (FPS2)/FPP synthetase 2 [*Arabidopsis thaliana*] |
| CAA08918 | 5678609 | dimethylallyltransferase; farnesyl pyrophosphate synthase [*Agrotis ipsilon*] |
| AAP86267 | 32527731 | Ac2-125 [*Rattus norvegicus*] |
| AAO17735 | 30522953 | farnesyl pyrophosphate synthase [*Trypanosoma brucei*] |
| AAK71861 | 14647139 | farnesyl pyrophosphate synthase [*Trypanosoma cruzi*] |
| AAL73357 | 18478919 | farnesyl diphosphate synthase precursor [*Trypanosoma cruzi*] |
| AAO63552 | 29124957 | putative farnesyl pyrophosphate synthase [*Plasmodium falciparum*] |
| CAI00471 | 56498227 | farnesyl pyrophosphate synthase, putative [*Plasmodium berghei*] |
| NP_701155 | 23508486 | farnesyl pyrophosphate synthase, putative [*Plasmodium falciparum* 3D7] |
| XP_474180 | 50929305 | OSJNBa0071I13.16 [*Oryza sativa* (*japonica* cultivar-group)] |
| AAL73358 | 18478922 | farnesyl diphosphate synthase precursor [*Trypanosoma cruzi*] |
| EAH48995 | 44167328 | unknown [environmental sequence] |
| NP_493027 | 17508563 | farnesyl pyrophosphate synthetase (1M510) [*Caenorhabditis elegans*] |
| CAE71711 | 39580204 | Hypothetical protein CBG18688 [*Caenorhabditis briggsae*] |
| XP_487220 | 51766977 | similar to farnesyl pyrophosphate synthase [*Mus musculus*] |

TABLE 15

Examples of GGPP synthase polypeptides.

| ACCESSION | GI | PROTEIN DESCRIPTION |
|---|---|---|
| AAT92871 | 51013155 | YPL069C [*Saccharomyces cerevisiae*] |
| XP_447025 | 50289191 | unnamed protein product [*Candida glabrata*] |
| NP_984623 | 45190369 | AEL238Cp [*Eremothecium gossypii*] |
| XP_390273 | 46137163 | GGPP_GIBFU Geranylgeranyl pyrophosphate synthetase (GGPP synthetase) [*Gibberella zeae* PH-1] |
| XP_404791 | 49085320 | hypothetical protein AN0654.2 [*Aspergillus nidulans* FGSC A4] |
| XP_368486 | 39974191 | hypothetical protein MG00758.4 [*Magnaporthe grisea* 70-15] |
| Q92236 | 6831550 | Geranylgeranyl pyrophosphate synthetase (GGPP synthetase) |
| AAO85432 | 29468176 | geranylgeranyl diphosphate synthase [*Aspergillus nidulans*] |
| XP_572774 | 58271236 | farnesyltranstransferase, putative [*Cryptococcus neoformans* var. *neoformans* JEC21] |
| XP_502923 | 50550901 | hypothetical protein [*Yarrowia lipolytica*] |
| AAK11525 | 13021716 | geranylgeranyl pyrophosphate synthase [*Penicillium paxilli*] |
| XP_326920 | 32412880 | GERANYLGERANYL PYROPHOSPHATE SYNTHETASE (GGPP SYNTHETASE) [*Neurospora crassa*] |
| CAF32032 | 42820719 | geranylgeranyl pyrophosphate synthetase, putative [*Aspergillus fumigatus*] |
| BAD29965 | 50355599 | Phoma betae geranylgeranyl diphosphate synthase |
| XP_384767 | 46117498 | hypothetical protein FG04591.1 [*Gibberella zeae* PH-1] |
| BAD29970 | 50355631 | geranylgeranyldiphosphate synthase [*Phoma betae*] |
| CAB89115 | 7649674 | geranylgeranyl pyrophosphate synthase [*Mucor circinelloides f. lusitanicus*] |
| CAG09545 | 47229030 | unnamed protein product [*Tetraodon nigroviridis*] |
| CAI13753 | 55960163 | geranylgeranyl diphosphate synthase 1 [*Homo sapiens*] |
| AAH69913 | 47124116 | Geranylgeranyl diphosphate synthase 1 [*Mus musculus*] |
| AAH67768 | 45709211 | GGPS1 protein [*Homo sapiens*] |
| XP_455003 | 50309979 | unnamed protein product [*Kluyveromyces lactis*] |
| P56966 | 9296978 | Geranylgeranyl pyrophosphate synthetase (GGPP synthetase) |
| NP_001007 | 56090562 | geranylgeranyl diphosphate synthase 1 [*Rattus norvegicus*] |
| AAT65717 | 49409613 | geranylgeranyl diphosphate synthase [*Aspergillus flavus*] |
| NP_956329 | 41053321 | geranylgeranyl diphosphate synthase 1 [*Danio rerio*] |
| BAA90525 | 6899844 | geranylgeranyl diphosphate synthase [*Nigrospora sphaerica*] |
| XP_405729 | 49087630 | hypothetical protein AN1592.2 [*Aspergillus nidulans* FGSC A4] |
| AAK11531 | 13021724 | geranylgeranyl pyrophosphate synthase [*Penicillium paxilli*] |
| XP_412280 | 49119197 | hypothetical protein AN8143.2 [*Aspergillus nidulans* FGSC A4] |
| AAC05273 | 2944400 | geranylgeranyl pyrophosphate synthase [*Drosophila melanogaster*] |
| NP_523958 | 24660002 | CG8593-PA [*Drosophila melanogaster*] |
| XP_402074 | 49076128 | hypothetical protein UM04459.1 [*Ustilago maydis* 521] |
| EAL30191 | 54641441 | GA21189-PA [*Drosophila pseudoobscura*] |
| XP_536340 | 57084951 | PREDICTED: hypothetical protein XP_536340 [*Canis familiaris*] |
| XP_424685 | 50811194 | PREDICTED: similar to geranylgeranyl diphosphate synthase 1, partial [*Gallus gallus*] |
| AAH06798 | 13905030 | Ggps1 protein [*Mus musculus*] |
| AAP06018 | 29841005 | similar to NM_010282 geranylgeranyl diphosphate synthase 1; GGPP synthase [*Schistosoma japonicum*] |
| XP_460338 | 50423511 | unnamed protein product [*Debaryomyces hansenii*] |
| AAC05595 | 2957271 | geranylgeranyl pyrophosphate synthase [*Drosophila melanogaster*] |

TABLE 15-continued

Examples of GGPP synthase polypeptides.

| ACCESSION | GI | PROTEIN DESCRIPTION |
|---|---|---|
| EAK92197 | 46432727 | hypothetical protein CaO19.6674 [*Candida albicans* SC5314] |
| XP_535573 | 57108760 | PREDICTED: similar to geranylgeranyl diphosphate synthase 1 [*Canis familiaris*] |
| AAH83212 | 53734594 | Zgc: 56514 protein [*Danio rerio*] |
| XP_486466 | 51827552 | similar to geranylgeranyl diphosphate synthase 1; GGPP synthase [*Mus musculus*] |
| CAH18006 | 51469024 | geranylgeranyl diphosphate synthase [*Fusarium proliferatum*] |
| CAA75568 | 3549881 | geranylgeranyl diphosphate synthase [*Gibberella fujikuroi*] |
| XP_397455 | 48143654 | similar to CG8593-PA [*Apis mellifera*] |
| XP_410947 | 49101294 | hypothetical protein AN6810.2 [*Aspergillus nidulans* FGSC A4] |
| XP_381914 | 46109712 | hypothetical protein FG01738.1 [*Gibberella zeae* PH-1] |
| XP_364478 | 39959279 | hypothetical protein MG09448.4 [*Magnaporthe grisea* 70-15] |
| XP_360889 | 39942704 | hypothetical protein MG03432.4 [*Magnaporthe grisea* 70-15] |
| XP_369218 | 39975655 | hypothetical protein MG00026.4 [*Magnaporthe grisea* 70-15] |
| XP_406544 | 49089926 | hypothetical protein AN2407.2 [*Aspergillus nidulans* FGSC A4] |
| XP_367595 | 39972409 | hypothetical protein MG07506.4 [*Magnaporthe grisea* 70-15] |
| XP_363775 | 39952117 | hypothetical protein MG01701.4 [*Magnaporthe grisea* 70-15] |
| XP_368486 | 39974191 | hypothetical protein MG00758.4 [*Magnaporthe grisea* 70-15] |
| XP_390273 | 46137163 | GGPP_GIBFU Geranylgeranyl pyrophosphate synthetase (GGPP synthetase) [*Gibberella zeae* PH-1] |
| Q92236 | 6831550 | Geranylgeranyl pyrophosphate synthetase (GGPP synthetase) |
| AAK11525 | 13021716 | geranylgeranyl pyrophosphate synthase [*Penicillium paxilli*] |
| CAF32032 | 42820719 | geranylgeranyl pyrophosphate synthetase, putative [*Aspergillus fumigatus*] |
| XP_404791 | 49085320 | hypothetical protein AN0654.2 [*Aspergillus nidulans* FGSC A4] |
| AAO85432 | 29468176 | geranylgeranyl diphosphate synthase [*Aspergillus nidulans*] |
| BAD29965 | 50355599 | Phoma betae geranylgeranyl diphosphate synthase |
| BAD29970 | 50355631 | geranylgeranyldiphosphate synthase [*Phoma betae*] |
| BAA90525 | 6899844 | geranylgeranyl diphosphate synthase [*Nigrospora sphaerica*] |
| AAT65717 | 49409613 | geranylgeranyl diphosphate synthase [*Aspergillus flavus*] |
| XP_384767 | 46117498 | hypothetical protein FG04591.1 [*Gibberella zeae* PH-1] |
| CAB89115 | 7649674 | geranylgeranyl pyrophosphate synthase [*Mucor circinelloides f. lusitanicus*] |
| XP_572774 | 58271236 | farnesyltranstransferase, putative [*Cryptococcus neoformans* var. *neoformans* JEC21] |
| AAK11531 | 13021724 | geranylgeranyl pyrophosphate synthase [*Penicillium paxilli*] |
| XP_502923 | 50550901 | hypothetical protein [*Yarrowia lipolytica*] |
| CAI13753 | 55960163 | geranylgeranyl diphosphate synthase 1 [*Homo sapiens*] |
| CAG09545 | 47229030 | unnamed protein product [*Tetraodon nigroviridis*] |
| XP_412280 | 49119197 | hypothetical protein AN8143.2 [*Aspergillus nidulans* FGSC A4] |
| P56966 | 9296978 | Geranylgeranyl pyrophosphate synthetase (GGPP synthetase) |
| NP_001007 | 56090562 | geranylgeranyl diphosphate synthase 1 [*Rattus norvegicus*] |
| AAH69913 | 47124116 | Geranylgeranyl diphosphate synthase 1 [*Mus musculus*] |
| AAH67768 | 45709211 | GGPS1 protein [*Homo sapiens*] |
| NP_956329 | 41053321 | geranylgeranyl diphosphate synthase 1 [*Danio rerio*] |
| EAL30191 | 54641441 | GA21189-PA [*Drosophila pseudoobscura*] |
| XP_424685 | 50811194 | PREDICTED: similar to geranylgeranyl diphosphate synthase 1, partial [*Gallus gallus*] |
| XP_536340 | 57084951 | PREDICTED: hypothetical protein XP_536340 [*Canis familiaris*] |
| NP_523958 | 24660002 | CG8593-PA [*Drosophila melanogaster*] |
| AAC05273 | 2944400 | geranylgeranyl pyrophosphate synthase [*Drosophila melanogaster*] |
| XP_405729 | 49087630 | hypothetical protein AN1592.2 [*Aspergillus nidulans* FGSC A4] |
| AAC05595 | 2957271 | geranylgeranyl pyrophosphate synthase [*Drosophila melanogaster*] |
| XP_402074 | 49076128 | hypothetical protein UM04459.1 [*Ustilago maydis* 521] |
| AAP06018 | 29841005 | similar to NM_010282 geranylgeranyl diphosphate synthase 1; GGPP synthase [*Schistosoma japonicum*] |
| AAH06798 | 13905030 | Ggps1 protein [*Mus musculus*] |
| XP_535573 | 57108760 | PREDICTED: similar to geranylgeranyl diphosphate synthase 1 [*Canis familiaris*] |
| AAH83212 | 53734594 | Zgc: 56514 protein [*Danio rerio*] |
| AAP21085 | 30097620 | albino-3 [*Neurospora crassa*] |
| NP_984623 | 45190369 | AEL238Cp [*Eremothecium gossypii*] |
| XP_447025 | 50289191 | unnamed protein product [*Candida glabrata*] |
| AAT92871 | 51013155 | YPL069C [*Saccharomyces cerevisiae*] |
| XP_486466 | 51827552 | similar to geranylgeranyl diphosphate synthase 1; GGPP synthase [*Mus musculus*] |
| XP_410947 | 49101294 | hypothetical protein AN6810.2 [*Aspergillus nidulans* FGSC A4] |
| XP_397455 | 48143654 | similar to CG8593-PA [*Apis mellifera*] |
| XP_455003 | 50309979 | unnamed protein product [*Kluyveromyces lactis*] |
| EAK92197 | 46432727 | hypothetical protein CaO19.6674 [*Candida albicans* SC5314] |
| XP_381914 | 46109712 | hypothetical protein FG01738.1 [*Gibberella zeae* PH-1] |
| XP_460338 | 50423511 | unnamed protein product [*Debaryomyces hansenii*] |
| CAH18006 | 51469024 | geranylgeranyl diphosphate synthase [*Fusarium proliferatum*] |
| XP_360889 | 39942704 | hypothetical protein MG03432.4 [*Magnaporthe grisea* 70-15] |
| XP_406544 | 49089926 | hypothetical protein AN2407.2 [*Aspergillus nidulans* FGSC A4] |
| XP_364478 | 39959279 | hypothetical protein MG09448.4 [*Magnaporthe grisea* 70-15] |
| XP_363775 | 39952117 | hypothetical protein MG01701.4 [*Magnaporthe grisea* 70-15] |

TABLE 15-continued

Examples of GGPP synthase polypeptides.

| ACCESSION | GI | PROTEIN DESCRIPTION |
|---|---|---|
| XP_367595 | 39972409 | hypothetical protein MG07506.4 [*Magnaporthe grisea* 70-15] |
| XP_369218 | 39975655 | hypothetical protein MG00026.4 [*Magnaporthe grisea* 70-15] |
| C39273 | 483124 | phytoene synthase - *Erwinia herbicola* |
| BAB79600 | 18143445 | crtE [*Pantoea agglomerans* pv. *milletiae*] |
| BAA14124 | 216682 | crtE [*Pantoea ananatis*] |
| AAN85596 | 27228290 | Geranylgeranyl Pyrophosphate Synthase [*Pantoea stewartii*] |
| AAA32797 | 413730 | geranylgeranyl pyrophosphate synthase |
| Q08291 | 585326 | Geranyltranstransferase (Farnesyl-diphosphate synthase) (FPP synthase) |
| S52584 | 1073293 | crtE protein - *Erwinia herbicola* |
| S53722 | 1076576 | farnesyltranstransferase (EC 2.5.1.29) precursor - pepper |
| AAC44848 | 1842242 | geranylgeranyl synthase |
| BAA19583 | 1944371 | geranylgeranyl pyrophosphate synthase [*Arabidopsis thaliana*] |
| S71230 | 2129674 | geranylgeranyl pyrophosphate synthase (EC 2.5.1.—) 2 precursor - *Arabidopsis thaliana* |
| BAA23157 | 2578822 | geranyl geranyl pyrophosphate synthase [*Arabidopsis thaliana*] |
| AAC77874 | 3885426 | geranylgeranyl pyrophosphate synthase [*Helianthus annuus*] |
| CAB38744 | 4490594 | geranylgeranyl pyrophosphate synthase [*Rhodobacter sphaeroides*] |
| BAA78047 | 4958920 | GGPP synthase [*Daucus carota*] |
| BAA82613 | 5631295 | geranylgeranyl diphosphate synthase (SelGGPS) [*Synechococcus elongatus*] |
| CAB56064 | 5912297 | geranylgeranyl pyrophosphate synthase [*Paracoccus marcusii*] |
| BAA86284 | 6277254 | geranylgeranyl pyrophosphate synthase [*Croton sublyratus*] |
| T11021 | 7447356 | farnesyltranstransferase (EC 2.5.1.29) - white lupine |
| AAF78199 | 8650415 | geranylgeranyl synthase [*Bradyrhizobium* sp. ORS278] |
| AAG10424 | 9971808 | GGDP synthase [*Tagetes erecta*] |
| CAC10561 | 10637876 | gpp synthase large subunit [*Mentha* × *piperita*] |
| T50879 | 11279298 | phytoene synthase [imported] - *Rubrivivax gelatinosus* |
| BAB01343 | 11994221 | geranyl geranyl pyrophosphate synthase-like protein [*Arabidopsis thaliana*] |
| Q42698 | 13431546 | Geranylgeranyl pyrophosphate synthetase, chloroplast precursor (GGPP synthetase) |
| Q43133 | 13431547 | Geranylgeranyl pyrophosphate synthetase, chloroplast precursor (GGPP synthetase) |
| P54976 | 13878921 | Geranylgeranyl pyrophosphate synthetase (GGPP synthetase) (Farnesyltranstransferase) |
| BAB50600 | 14023995 | geranyltranstransferase; farnesyl-diphosphate synthase [*Mesorhizobium loti* MAFF303099] |
| BAB60678 | 14325238 | geranylgeranyl diphosphate synthase [*Hevea brasiliensis*] |
| BAB60820 | 14422402 | putative GGPP synthase [*Eucommia ulmoides*] |
| NP_189589 | 15228704 | geranylgeranyl pyrophosphate synthase, putative/GGPP synthetase [*Arabidopsis thaliana*] |
| NP_188651 | 15231055 | geranylgeranyl pyrophosphate synthase, putative/GGPP synthetase [*Arabidopsis thaliana*] |
| NP_188069 | 15231869 | geranylgeranyl pyrophosphate synthase, putative/GGPP synthetase [*Arabidopsis thaliana*] |
| NP_188073 | 15231881 | geranylgeranyl pyrophosphate synthase, putative/GGPP synthetase [*Arabidopsis thaliana*] |
| AAL01997 | 15553715 | farnesyl diphosphate synthase [*Xanthobacter* sp. Py2] |
| AAL01998 | 15553717 | geranylgeranyl diphosphate synthase [*Xanthobacter* sp. Py2] |
| NP_252732 | 15599238 | geranyltranstransferase [*Pseudomonas aeruginosa* PAO1] |
| NP_245470 | 15602398 | IspA [*Pasteurella multocida* subsp. *multocida* str. Pm70] |
| NP_390308 | 16079484 | hypothetical protein BSU24280 [*Bacillus subtilis* subsp. *subtilis* str. 168] |
| NP_440010 | 16329282 | geranylgeranyl pyrophosphate synthase [*Synechocystis* sp. PCC 6803] |
| NP_440010 | 16329282 | geranylgeranyl pyrophosphate synthase [*Synechocystis* sp. PCC 6803] |
| AAL17614 | 17352451 | geranylgeranyl diphosphate synthase [*Abies grandis*] |
| NP_520343 | 17546941 | PROBABLE GERANYLTRANSTRANSFERASE (FARNESYL-DIPHOSPHATE SYNTHASE) PROTEIN [*Ralstonia solanacearum* GM |
| AAL76349 | 18645048 | geranyltranstransferase [uncultured proteobacterium] |
| AAM21638 | 20386366 | geranylgeranyl pyrophosphate synthase [*Cistus incanus* subsp. *creticus*] |
| AAM21639 | 20386368 | geranylgeranyl pyrophosphate synthase [*Cistus incanus* subsp. *creticus*] |
| NP_622916 | 20807745 | Geranylgeranyl pyrophosphate synthase [*Thermoanaerobacter tengcongensis* MB4] |
| AAM48650 | 21328644 | geranylgeranyl pyrophosphate synthetase [uncultured proteobacterium] |
| NP_659794 | 21492720 | probable polyprenyl synthetase. [*Rhizobium etli*] |
| AAM64496 | 21592547 | putative geranylgeranyl pyrophosphate synthase GGPS3 [*Arabidopsis thaliana*] |
| AAM65107 | 21593158 | geranylgeranyl pyrophosphate synthase [*Arabidopsis thaliana*] |
| NP_680811 | 22297564 | geranylgeranyl pyrophosphate synthase [*Thermosynechococcus elongatus* BP-1] |
| ZP_000474 | 23003800 | COG0142: Geranylgeranyl pyrophosphate synthase [*Lactobacillus gasseri*] |
| ZP_001252 | 23469933 | COG0142: Geranylgeranyl pyrophosphate synthase [*Pseudomonas syringae* pv. *syringae* B728a] |
| NP_698760 | 23502633 | geranyltranstransferase [*Brucella suis* 1330] |
| E84566 | 25313373 | probable geranylgeranyl pyrophosphate synthase [imported] - *Arabidopsis thaliana* |

TABLE 15-continued

| Examples of GGPP synthase polypeptides. | | |
|---|---|---|
| ACCESSION | GI | PROTEIN DESCRIPTION |
| F85434 | 25313385 | geranylgeranyl pyrophosphate synthase [imported] - *Arabidopsis thaliana* |
| AC1245 | 25313389 | geranyltranstransferase homolog lmo1363 [imported] - *Listeria monocytogenes* (strain EGD-e) |
| E83997 | 25313393 | geranyltranstransferase BH2781 [imported] - *Bacillus halodurans* (strain C-125) |
| G84566 | 25313395 | probable geranylgeranyl pyrophosphate synthase [imported] - *Arabidopsis thaliana* |
| AH2910 | 25315863 | geranyltranstransferase [imported] - *Agrobacterium tumefaciens* (strain C58, Dupont) |
| D87505 | 25398795 | geranyltranstransferase [imported] - *Caulobacter crescentus* |
| A89932 | 25505949 | hypothetical protein ispA [imported] - *Staphylococcus aureus* (strain N315) |
| F97685 | 25520741 | geranyltransferase (AF203881) [imported] - *Agrobacterium tumefaciens* (strain C58, Cereon) |
| AI3285 | 25527013 | geranyltranstransferase (EC 2.5.1.10) [imported] - *Brucella melitensis* (strain 16M) |
| BAC42571 | 26450928 | putative geranylgeranyl pyrophosphate synthase GGPS3 [*Arabidopsis thaliana*] |
| NP_785195 | 28378303 | geranyltranstransferase [*Lactobacillus plantarum* WCFS1] |
| NP_790546 | 28867927 | geranyltranstransferase [*Pseudomonas syringae* pv. tomato str. DC3000] |
| AAO63392 | 28950937 | At2g23800 [*Arabidopsis thaliana*] |
| AAO93113 | 29893480 | geranylgeranyl pyrophosphate synthetase; CrtE [*Rubrivivax gelatinosus*] |
| NP_833891 | 30022260 | Dimethylallyltransferase [*Bacillus cereus* ATCC 14579] |
| AAP59037 | 31621279 | CrtE [*Thiocapsa roseopersicina*] |
| ZP_001374 | 32039216 | COG0142: Geranylgeranyl pyrophosphate synthase [*Pseudomonas aeruginosa* UCBPP-PA14] |
| NP_864766 | 32471772 | geranylgeranyl pyrophosphate synthetase [precursor] [*Rhodopirellula baltica* SH 1] |
| NP_875521 | 33240579 | Geranylgeranyl pyrophosphate synthase [*Prochlorococcus marinus* subsp. *marinus* str. CCMP1375] |
| NP_881399 | 33593755 | probable geranyltranstransferase [*Bordetella pertussis* Tohama I] |
| NP_884694 | 33597051 | probable geranyltranstransferase [*Bordetella parapertussis* 12822] |
| NP_888456 | 33600896 | probable geranyltranstransferase [*Bordetella bronchiseptica* RB50] |
| NP_893187 | 33861626 | Polyprenyl synthetase [*Prochlorococcus marinus* subsp. *pastoris* str. CCMP1986] |
| NP_894940 | 33863380 | Polyprenyl synthetase [*Prochlorococcus marinus* str. MIT 9313] |
| NP_896835 | 33865276 | geranylgeranyl pyrophosphate synthase [*Synechococcus* sp. WH 8102] |
| NP_896835 | 33865276 | geranylgeranyl pyrophosphate synthase [*Synechococcus* sp. WH 8102] |
| AAQ65086 | 34365549 | At3g14530 [*Arabidopsis thaliana*] |
| NP_945877 | 39933601 | putative geranyltranstransferase (farnesyl-diphosphate synthase) [*Rhodopseudomonas palustris* CGA009] |
| NP_946867 | 39934591 | geranylgeranyl pyrophosphate synthase [*Rhodopseudomonas palustris* CGA009] |
| NP_952815 | 39996864 | geranyltranstransferase [*Geobacter sulfurreducens* PCA] |
| AAR37805 | 40062934 | polyprenyl synthetase [uncultured bacterium 442] |
| AAR37858 | 40062988 | geranylgeranyl pyrophosphate synthetase [uncultured bacterium 443] |
| AAR98495 | 41018904 | geranyl geranyl synthase [*Bradyrhizobium* sp. ORS278] |
| AAR99082 | 41059107 | geranylgeranyl pyrophosphate synthase [*Plectranthus barbatus*] |
| NP_965349 | 42519419 | geranyltranstransferase [*Lactobacillus johnsonii* NCC 533] |
| NP_980544 | 42783297 | geranyltranstransferase [*Bacillus cereus* ATCC 10987] |
| EAA96348 | 42858148 | unknown [environmental sequence] |
| EAB36506 | 42939031 | unknown [environmental sequence] |
| EAB36642 | 42939300 | unknown [environmental sequence] |
| EAC39208 | 43146996 | unknown [environmental sequence] |
| EAD26007 | 43320598 | unknown [environmental sequence] |
| EAE43084 | 43576643 | unknown [environmental sequence] |
| EAE70061 | 43630884 | unknown [environmental sequence] |
| EAF70308 | 43832107 | unknown [environmental sequence] |
| EAG88494 | 44055952 | unknown [environmental sequence] |
| EAH52060 | 44173220 | unknown [environmental sequence] |
| EAH78354 | 44221788 | unknown [environmental sequence] |
| EAH84117 | 44231960 | unknown [environmental sequence] |
| EAI11762 | 44272832 | unknown [environmental sequence] |
| EAI49391 | 44328289 | unknown [environmental sequence] |
| EAI54846 | 44336042 | unknown [environmental sequence] |
| EAI68356 | 44355138 | unknown [environmental sequence] |
| EAI68713 | 44355672 | unknown [environmental sequence] |
| EAI69401 | 44356609 | unknown [environmental sequence] |
| EAI73873 | 44362658 | unknown [environmental sequence] |
| EAJ73634 | 44506168 | unknown [environmental sequence] |
| EAJ77351 | 44511694 | unknown [environmental sequence] |
| EAK70639 | 44644254 | unknown [environmental sequence] |
| ZP_001751 | 45523854 | COG0142: Geranylgeranyl pyrophosphate synthase [*Crocosphaera watsonii* WH 8501] |

TABLE 15-continued

| Examples of GGPP synthase polypeptides. | | |
|---|---|---|
| ACCESSION | GI | PROTEIN DESCRIPTION |
| AAS76253 | 45752710 | At1g49530 [*Arabidopsis thaliana*] |
| ZP_001957 | 45916757 | COG0142: Geranylgeranyl pyrophosphate synthase [*Mesorhizobium* sp. BNC1] |
| 1RTRB | 46015556 | Chain B, Crystal Structure Of *S. Aureus* Farnesyl Pyrophosphate Synthase |
| ZP_001863 | 46105954 | COG0142: Geranylgeranyl pyrophosphate synthase [*Rubrobacter xylanophilus* DSM 9941] |
| ZP_002002 | 46107045 | COG0142: Geranylgeranyl pyrophosphate synthase [*Rubrobacter xylanophilus* DSM 9941] |
| ZP_001711 | 46132567 | COG0142: Geranylgeranyl pyrophosphate synthase [*Ralstonia eutropha* JMP134] |
| ZP_002073 | 46192680 | COG0142: Geranylgeranyl pyrophosphate synthase [*Rhodobacter sphaeroides* 2.4.1] |
| ZP_002074 | 46192861 | COG0142: Geranylgeranyl pyrophosphate synthase [*Rhodobacter sphaeroides* 2.4.1] |
| AAS82860 | 46241274 | geranyl diphosphate synthase large subunit [*Antirrhinum majus*] |
| ZP_002108 | 46308696 | COG0142: Geranylgeranyl pyrophosphate synthase [*Ehrlichia canis* str. Jake] |
| YP_010568 | 46579760 | geranylgeranyl diphosphate synthase [*Desulfovibrio vulgaris* subsp. *vulgaris* str. Hildenborough] |
| BAD18313 | 47076770 | geranyltranstransferase [*Geobacillus stearothermophilus*] |
| ZP_002315 | 47093750 | geranyltranstransferase [*Listeria monocytogenes* str. 4b H7858] |
| ZP_002335 | 47095946 | geranyltranstransferase [*Listeria monocytogenes* str. ½a F6854] |
| AAT35222 | 47531118 | fusion of carotene synthesis proteins [synthetic construct] |
| ZP_002401 | 47569437 | geranyltranstransferase [*Bacillus cereus G9241*] |
| ZP_002435 | 47573473 | COG0142: Geranylgeranyl pyrophosphate synthase [*Rubrivivax gelatinosus* PM1] |
| ZP_002626 | 48728941 | COG0142: Geranylgeranyl pyrophosphate synthase [*Pseudomonas fluorescens* PfO-1] |
| ZP_002702 | 48765678 | COG0142: Geranylgeranyl pyrophosphate synthase [*Rhodospirillum rubrum*] |
| ZP_002705 | 48766028 | COG0142: Geranylgeranyl pyrophosphate synthase [*Rhodospirillum rubrum*] |
| ZP_002732 | 48768894 | COG0142: Geranylgeranyl pyrophosphate synthase [*Ralstonia metallidurans* CH34] |
| ZP_002914 | 48834438 | COG0142: Geranylgeranyl pyrophosphate synthase [*Magnetococcus* sp. MC-1] |
| ZP_003024 | 48848203 | COG0142: Geranylgeranyl pyrophosphate synthase [*Novosphingobium aromaticivorans* DSM 12444] |
| ZP_003129 | 48858958 | COG0142: Geranylgeranyl pyrophosphate synthase [*Clostridium thermocellum* ATCC 27405] |
| ZP_003177 | 48863841 | COG0142: Geranylgeranyl pyrophosphate synthase [*Microbulbifer degradans* 2-40] |
| ZP_003225 | 48869790 | COG0142: Geranylgeranyl pyrophosphate synthase [*Pediococcus pentosaceus* ATCC 25745] |
| AAT51323 | 49086036 | PA4043 [synthetic construct] |
| ZP_003301 | 49236117 | COG0142: Geranylgeranyl pyrophosphate synthase [*Moorella thermoacetica* ATCC 39073] |
| YP_034222 | 49476181 | Geranyltranstransferase (farnesyl-diphosphate synthase) [*Bartonella henselae* str. Houston-1] |
| YP_040995 | 49483771 | putative geranyltranstransferase [*Staphylococcus aureus* subsp. *aureus* MRSA252] |
| YP_043579 | 49486358 | putative geranyltranstransferase [*Staphylococcus aureus* subsp. *aureus* MSSA476] |
| AAT71982 | 50253560 | At3g32040 [*Arabidopsis thaliana*] |
| AAT90315 | 50952782 | putative geranylgeranyl pyrophosphate synthetase [uncultured proteobacterium eBACred25D05] |
| YP_066435 | 51246551 | probable geranylgeranyl pyrophosphate synthase [*Desulfotalea psychrophila* LSv54] |
| YP_075673 | 51892982 | geranylgeranyl pyrophosphate synthase [*Symbiobacterium thermophilum* IAM 14863] |
| YP_085511 | 52141318 | geranyltranstransferase [*Bacillus cereus* ZK] |
| YP_092166 | 52786337 | YqiD [*Bacillus licheniformis* ATCC 14580] |
| ZP_001298 | 53691368 | COG0142: Geranylgeranyl pyrophosphate synthase [*Desulfovibrio desulfuricans* G20] |
| YP_105136 | 53716444 | geranyltranstransferase [*Burkholderia mallei* ATCC 23344] |
| YP_111769 | 53722784 | geranyltranstransferase [*Burkholderia pseudomallei* K96243] |
| ZP_003630 | 54030933 | COG0142: Geranylgeranyl pyrophosphate synthase [*Polaromonas* sp. JS666] |
| YP_129021 | 54308001 | putative geranyltranstransferase [*Photobacterium profundum* SS9] |
| AAV74395 | 56122554 | geranylgeranyl diphosphate synthase [*Adonis palaestina*] |
| AAV74396 | 56122556 | geranylgeranyl diphosphate synthase [*Adonis palaestina*] |
| YP_148246 | 56420928 | geranyltranstransferase (farnesyl-diphosphate synthase) [*Geobacillus kaustophilus* HTA426] |
| YP_156518 | 56461237 | Geranylgeranyl pyrophosphate synthase [*Idiomarina loihiensis* L2TR] |
| YP_162590 | 56551751 | geranyltranstransferase [*Zymomonas mobilis* subsp. *mobilis* ZM4] |

TABLE 15-continued

Examples of GGPP synthase polypeptides.

| ACCESSION | GI | PROTEIN DESCRIPTION |
|---|---|---|
| YP_171470 | 56750769 | geranylgeranyl pyrophosphate synthase [*Synechococcus elongatus* PCC 6301] |
| YP_175959 | 56964228 | geranyltranstransferase [*Bacillus clausii* KSM-K16] |
| YP_186407 | 57650478 | geranyltranstransferase [*Staphylococcus aureus* subsp. *aureus* COL] |
| YP_190690 | 58038726 | Dimethylallyltransferase [*Gluconobacter oxydans* 621H] |
| AAW66658 | 58201026 | geranyl diphosphate synthase [*Picrorhiza kurrooa*] |
| YP_194187 | 58337602 | geranylgeranyl diphosphate (GGPP) synthase [*Lactobacillus acidophilus* NCFM] |
| YP_197469 | 58579257 | Possible geranyltranstransferase [*Ehrlichia ruminantium* str. Welgevonden] |
| YP_201938 | 58582922 | geranyltranstransferase; farnesyl-diphosphate synthase [*Xanthomonas oryzae* pv. *oryzae* KACC10331] |
| YP_196510 | 58617311 | Possible geranyltranstransferase [*Ehrlichia ruminantium* str. Gardel] |

TABLE 16

Examples of squalene synthetase polypeptides.

| ACCESSION | GI | PROTEIN DESCRIPTION |
|---|---|---|
| AAA34597 | 171481 | squalene synthetase |
| CAA42583 | 3686 | farnesyl-diphosphate farnesyltransferase [*Saccharomyces cerevisiae*] |
| Q9HGZ6 | 51704336 | Farnesyl-diphosphate farnesyltransferase (Squalene synthetase) (SQS) (SS) (FPP:FPP farnesyltransferase) |
| BAB12207 | 9955387 | squalene synthase [*Candida glabrata*] |
| XP_453457 | 50306959 | unnamed protein product [*Kluyveromyces lactis*] |
| Q752X9 | 51701405 | Farnesyl-diphosphate farnesyltransferase (Squalene synthetase) (SQS) (SS) (FPP:FPP farnesyltransferase) |
| O74165 | 51701378 | Farnesyl-diphosphate farnesyltransferase (Squalene synthetase) (SQS) (SS) (FPP:FPP farnesyltransferase) |
| XP_458579 | 50420093 | unnamed protein product [*Debaryomyces hansenii*] |
| EAK95451 | 46436082 | hypothetical protein CaO19.11099 [*Candida albicans* SC5314] |
| P78589 | 2499979 | Farnesyl-diphosphate farnesyltransferase (Squalene synthetase) (SQS) (SS) (FPP:FPP farnesyltransferase) |
| Q9Y753 | 51701459 | Farnesyl-diphosphate farnesyltransferase (Squalene synthetase) (SQS) (SS) (FPP:FPP farnesyltransferase) |
| XP_407513 | 49092104 | hypothetical protein AN3376.2 [*Aspergillus nidulans* FGSC A4] |
| XP_364394 | 39958237 | hypothetical protein MG09239.4 [*Magnaporthe grisea* 70-15] |
| Q7S4Z6 | 51701416 | Probable farnesyl-diphosphate farnesyltransferase (Squalene synthetase) |
| CAD60581 | 27764301 | unnamed protein product [*Podospora anserina*] |
| XP_389557 | 46135731 | hypothetical protein FG09381.1 [*Gibberella zeae* PH-1] |
| NP_595363 | 19112155 | farnesyl-diphosphate farnesyltransferase [*Schizosaccharomyces pombe*] |
| B48057 | 477750 | farnesyl-diphosphate farnesyltransferase (EC 2.5.1.21) - fission yeast (*Schizosaccharomyces pombe*) |
| NP_034321 | 34328173 | farnesyl diphosphate farnesyl transferase 1 [*Mus musculus*] |
| CAH92517 | 55731622 | hypothetical protein [*Pongo pygmaeus*] |
| AAF00038 | 6002565 | squalene synthase [*Mus musculus*] |
| P53798 | 1706773 | Farnesyl-diphosphate farnesyltransferase (Squalene synthetase) (SQS) (SS) (FPP:FPP farnesyltransferase) |
| NP_004453 | 31542632 | farnesyl-diphosphate farnesyltransferase 1 [*Homo sapiens*] |
| AAP36671 | 30584837 | *Homo sapiens* farnesyl-diphosphate farnesyltransferase 1 [synthetic construct] |
| 1EZFC | 11514497 | Chain C, Crystal Structure Of Human Squalene Synthase |
| AAH09251 | 14328083 | Farnesyl-diphosphate farnesyltransferase 1 [*Homo sapiens*] |
| AAH84016 | 54035372 | LOC494973 protein [*Xenopus laevis*] |
| I52090 | 2136196 | squalene synthase - human |
| XP_420043 | 50745256 | PREDICTED: similar to Farnesyl-diphosphate farnesyltransferase 1 [*Gallus gallus*] |
| AAH81810 | 51858605 | Farnesyl diphosphate farnesyl transferase 1 [*Rattus norvegicus*] |
| CAE48363 | 50841455 | TPA: FDFT1 protein [*Bos taurus*] |
| XP_569783 | 58265254 | farnesyl-diphosphate farnesyltransferase, putative [*Cryptococcus neoformans* var. *neoformans* JEC21] |
| XP_569782 | 58265252 | farnesyl-diphosphate farnesyltransferase, putative [*Cryptococcus neoformans* var. *neoformans* JEC21] |
| XP_534557 | 57105080 | PREDICTED: similar to FDFT1 protein [*Canis familiaris*] |
| XP_401989 | 49075920 | FDFT_USTMA Farnesyl-diphosphate farnesyltransferase (Squalene synthetase) [*Ustilago maydis* 521] |

TABLE 17a

Examples of phytoene dehydrogenase polypeptides.

| ACCESSION | PROTEIN DESCRIPTION |
|---|---|
| 1613414B | crtI gene |
| 1613414F | crtD gene |
| 1904206A | methoxyneurosporene dehydrogenase |
| 2121278A | zeta carotene desaturase |
| A86203 | hypothetical protein [imported] - *Arabidopsis thaliana* |
| A96612 | hypothetical protein F12K22.18 [imported] - *Arabidopsis thaliana* |
| A99470 | phytoene dehydrogenase (desaturase) (crtI) [imported] - *Sulfolobus solfataricus* |
| AAA24820 | phytoene dehydrogenase [*Pantoea agglomerans*] |
| AAA34001 | phytoene desaturase |
| AAA50313 | photoprotective pigment |
| AAA64981 | phytoene dehydrogenase [*Pantoea agglomerans*] |
| AAA91161 | zeta-carotene desaturase precursor |
| AAA99519 | phytoene desaturase |
| AAC44798 | hydroxyneurosporene and rhodopin dehydrogenase [*Rubrivivax gelatinosus*] |
| AAC44850 | phytoene desaturase |
| AAC48983 | phytoene dehydrogenase precursor |
| AAF78201 | phytoene desaturase [*Bradyrhizobium* sp. ORS278] |
| AAG10426 | phytoene desaturase [*Tagetes erecta*] |
| AAG14399 | zeta-carotene desaturase precursor [*Oryza sativa*] |
| AAG28700 | CrtI [*Streptomyces griseus*] |
| AAG50743 | hypothetical protein [*Arabidopsis thaliana*] |
| AAH85048 | Unknown (protein for MGC: 97898) [*Xenopus laevis*] |
| AAK51545 | phytoene desaturase [*Citrus* × *paradisi*] |
| AAK51557 | zeta-carotene desaturase precursor [*Citrus* × *paradisi*] |
| AAK64299 | phytoene desaturase [*Corynebacterium glutamicum*] |
| AAL02000 | phytoene dehydrogenase [*Xanthobacter* sp. Py2] |
| AAL15300 | AT4g14210/dl3145c [*Arabidopsis thaliana*] |
| AAL38046 | phytoene desaturase [*Hordeum vulgare*] |
| AAL73986 | hypothetical protein MMT-7 [*Mus musculus*] |
| AAL80005 | phytoene desaturase [*Sandersonia aurantiaca*] |
| AAL91366 | carotenoid isomerase [*Lycopersicon esculentum*] |
| AAM45380 | phytoene desaturase [*Tagetes erecta*] |
| AAM48646 | phytoene dehydrogenase [uncultured proteobacterium] |
| AAM63349 | putative zeta-carotene desaturase precursor [*Arabidopsis thaliana*] |
| AAM94364 | phytoene desaturase [*Agromyces mediolanus*] |
| AAN75037 | CrtD [*Rhodospirillum rubrum*] |
| AAN85599 | Phytoene Desaturase [*Pantoea stewartii*] |
| AAO24235 | phytoene desaturase [*Crocus sativus*] |
| AAO46892 | phytoene dehydrogenase [*Blakeslea trispora*] |
| AAO46894 | phytoene dehydrogenase [*Blakeslea trispora*] |
| AAO53257 | phytoene desaturase [*Xanthophyllomyces dendrorhous*] |
| AAO53258 | phytoene desaturase splice variant [*Xanthophyllomyces dendrorhous*] |
| AAO64750 | At5g49550/K6M13_10 [*Arabidopsis thaliana*] |
| AAO93135 | phytoene dehydrogenase; CrtI [*Rubrivivax gelatinosus*] |
| AAP59036 | CrtD [*Thiocapsa roseopersicina*] |
| AAP79175 | phytoene dehydrogenase [*Bigelowiella natans*] |
| AAQ04224 | zeta-carotene desaturase ZDS1 [*Malus* × domestica] |
| AAQ04225 | zeta-carotene desaturase ZDS2 [*Malus* × domestica] |
| AAQ65246 | phytoene desaturase [*Methylobacterium extorquens*] |
| AAQ65246 | phytoene desaturase [*Methylobacterium extorquens*] |
| AAQ88931 | WLPL439 [*Homo sapiens*] |
| AAR37797 | methoxyneurosporene dehydrogenase [uncultured bacterium 442] |
| AAR37802 | phytoene dehydrogenase [uncultured bacterium 442] |
| AAR37850 | methoxyneurosporene dehydrogenase [uncultured bacterium 443] |
| AAR37855 | phytoene dehydrogenase [uncultured bacterium 443] |
| AAR86105 | phytoene desaturase [*Momordica charantia* var. *abbreviata*] |
| AAR98491 | phytoene desaturase [*Bradyrhizobium* sp. ORS278] |
| AAR98494 | phytoene dehydrogenase [*Bradyrhizobium* sp. ORS278] |
| AAR98733 | phytoene desaturase [*Lilium longiflorum*] |
| AAS17750 | phytoene desaturase [*Solanum tuberosum*] |
| AAT01639 | phytoene desaturase [*Petunia* × *hybrida*] |
| AAT35222 | fusion of carotene synthesis proteins [synthetic construct] |
| AAT74579 | PDS [*Citrus sinensis*] |
| AAT74580 | ZDS [*Citrus sinensis*] |
| AAT76050 | zeta-carotene desaturase [*Citrus clementina*] |
| AAT76434 | phytoene desaturase [*Hydrilla verticillata*] |
| AAT90316 | putative methoxyneurosporene dehydrogenase [uncultured proteobacterium eBACred25D05] |
| AAU34019 | retina and RPE/choroid [*Macaca fascicularis*] |
| AAW23161 | phytoene dehydrogenase [*Rhodococcus erythropolis*] |
| AB2035 | phytoene desaturase [imported] - *Nostoc* sp. (strain PCC 7120) |
| AB2064 | hypothetical protein alr2064 [imported] - *Nostoc* sp. (strain PCC 7120) |
| AC2446 | hypothetical protein all5123 [imported] - *Nostoc* sp. (strain PCC 7120) |
| AF1557 | phytoene dehydrogenase homolog lin0999 [imported] - *Listeria innocua* (strain Clip11262) |

TABLE 17a-continued

Examples of phytoene dehydrogenase polypeptides.

| ACCESSION | PROTEIN DESCRIPTION |
|---|---|
| AF2029 | hypothetical protein alr1788 [imported] - *Nostoc* sp. (strain PCC 7120) |
| AG2103 | zeta-carotene desaturase [imported] - *Nostoc* sp. (strain PCC 7120) |
| AG2509 | zeta-carotene desaturase [imported] - *Nostoc* sp. (strain PCC 7120) plasmid pCC7120alpha |
| AH1199 | phytoene dehydrogenase homolog lmo1000 [imported] - *Listeria monocytogenes* (strain EGD-e) |
| AI2185 | hypothetical protein all3040 [imported] - *Nostoc* sp. (strain PCC 7120) |
| AI2273 | hypothetical protein all3744 [imported] - *Nostoc* sp. (strain PCC 7120) |
| B55548 | crtN protein - *Staphylococcus aureus* |
| B84327 | phytoene dehydrogenase [imported] - *Halobacterium* sp. NRC-1 |
| B90061 | squalene synthase [imported] - *Staphylococcus aureus* (strain N315) |
| BAA14127 | crtI [*Pantoea ananatis*] |
| BAA20276 | phytoene desaturase [*Erythrobacter longus*] |
| BAA76534 | Phytoene disaturase [*Acidiphilium rubrum*] |
| BAB10768 | phytoene dehydrogenase-like [*Arabidopsis thaliana*] |
| BAB50520 | phytoene dehydrogenase [*Mesorhizobium loti* MAFF303099] |
| BAB51896 | mlr5446 [*Mesorhizobium loti* MAFF303099] |
| BAB68552 | zeta-carotene desaturase [*Citrus unshiu*] |
| BAB79603 | crtI [*Pantoea agglomerans* pv. milletiae] |
| BAB82461 | phytoene desaturase [*Gentiana lutea*] |
| BAB82462 | phytoene desaturase [*Gentiana lutea*] |
| BAB98016 | Phytoene dehydrogenase and related proteins [*Corynebacterium glutamicum* ATCC 13032] |
| BAC75676 | putative phytoene desaturase [*Gordonia* sp. TM414] |
| BAC77668 | phytoene desaturase [marine bacterium P99-3] |
| BAC77671 | gamma-carotene desaturase [marine bacterium P99-3] |
| BAD07279 | phytoene desaturase [*Citrus sinensis*] |
| BAD07280 | zeta-carotene desaturase [*Citrus sinensis*] |
| BAD07287 | phytoene desaturase [*Citrus limon*] |
| BAD07288 | zeta-carotene desaturase [*Citrus limon*] |
| CAA52098 | squalene synthase [*Staphylococcus aureus*] |
| CAA60479 | Phytoene desaturase [*Haematococcus pluvialis*] |
| CAA66626 | unnamed protein product [*Staphylococcus aureus*] |
| CAB38739 | phytoene dehydrogenase [*Rhodobacter sphaeroides*] |
| CAB38743 | methoxyneurosporene dehydrogenase [*Rhodobacter sphaeroides*] |
| CAB40843 | phytoene dehydrogenase [*Mucor circinelloides f. lusitanicus*] |
| CAB56041 | zeta-carotene desaturase [*Nostoc* sp. PCC 7120] |
| CAB56062 | phytoene desaturase [*Paracoccus marcusii*] |
| CAB59726 | phytoene desaturase [*Lycopersicon esculentum*] |
| CAB65434 | zeta carotene desaturase [*Synechococcus leopoliensis*] |
| CAB94794 | phytoene dehydrogenase [*Mycobacterium aurum*] |
| CAC85667 | zeta-carotene desaturase [*Citrus sinensis*] |
| CAD19989 | phytoene dehydrogenase [*Gibberella fujikuroi*] |
| CAD27442 | putative zeta-carotene desaturase [*Helianthus annuus*] |
| CAD55814 | putative zeta-carotene desaturase [*Helianthus annuus*] |
| CAE00192 | phytoene desaturase [*Nicotiana benthamiana*] |
| CAE83576 | phytoene desaturase [*Nicotiana tabacum*] |
| CAF19330 | PHYTOENE DEHYDROGENASE (DESATURASE) [*Corynebacterium glutamicum* ATCC 13032] |
| CAF21094 | PHYTOENE DEHYDROGENASE (DESATURASE) (N-terminal fragment) [*Corynebacterium glutamicum* ATCC 13032] |
| CAF21337 | phytoene desaturase [*Pisum sativum*] |
| CAH91165 | hypothetical protein [*Pongo pygmaeus*] |
| E90061 | hypothetical protein SA2351 [imported] - *Staphylococcus aureus* (strain N315) |
| EAA90383 | unknown [environmental sequence] |
| EAA98598 | unknown [environmental sequence] |
| EAB09790 | unknown [environmental sequence] |
| EAB14136 | unknown [environmental sequence] |
| EAB18725 | unknown [environmental sequence] |
| EAB29729 | unknown [environmental sequence] |
| EAB30992 | unknown [environmental sequence] |
| EAB41377 | unknown [environmental sequence] |
| EAB54727 | unknown [environmental sequence] |
| EAB76679 | unknown [environmental sequence] |
| EAB87028 | unknown [environmental sequence] |
| EAB92587 | unknown [environmental sequence] |
| EAB94459 | unknown [environmental sequence] |
| EAB96864 | unknown [environmental sequence] |
| EAC01884 | unknown [environmental sequence] |
| EAC38895 | unknown [environmental sequence] |
| EAC60360 | unknown [environmental sequence] |
| EAD05874 | unknown [environmental sequence] |
| EAD05999 | unknown [environmental sequence] |
| EAD20520 | unknown [environmental sequence] |
| EAE06978 | unknown [environmental sequence] |
| EAE70773 | unknown [environmental sequence] |

TABLE 17a-continued

Examples of phytoene dehydrogenase polypeptides.

| ACCESSION | PROTEIN DESCRIPTION |
|---|---|
| EAF04985 | unknown [environmental sequence] |
| EAF51354 | unknown [environmental sequence] |
| EAF62819 | unknown [environmental sequence] |
| EAF75453 | unknown [environmental sequence] |
| EAG09111 | unknown [environmental sequence] |
| EAG19412 | unknown [environmental sequence] |
| EAG23070 | unknown [environmental sequence] |
| EAG25053 | unknown [environmental sequence] |
| EAG25054 | unknown [environmental sequence] |
| EAG29279 | unknown [environmental sequence] |
| EAG39845 | unknown [environmental sequence] |
| EAG56100 | unknown [environmental sequence] |
| EAG63013 | unknown [environmental sequence] |
| EAG68633 | unknown [environmental sequence] |
| EAG71574 | unknown [environmental sequence] |
| EAG89835 | unknown [environmental sequence] |
| EAH04928 | unknown [environmental sequence] |
| EAH04936 | unknown [environmental sequence] |
| EAH08586 | unknown [environmental sequence] |
| EAH22597 | unknown [environmental sequence] |
| EAH22853 | unknown [environmental sequence] |
| EAH31648 | unknown [environmental sequence] |
| EAH55579 | unknown [environmental sequence] |
| EAH68071 | unknown [environmental sequence] |
| EAH73302 | unknown [environmental sequence] |
| EAH79041 | unknown [environmental sequence] |
| EAH86965 | unknown [environmental sequence] |
| EAH97108 | unknown [environmental sequence] |
| EAH99977 | unknown [environmental sequence] |
| EAI01660 | unknown [environmental sequence] |
| EAI03576 | unknown [environmental sequence] |
| EAI06784 | unknown [environmental sequence] |
| EAI11087 | unknown [environmental sequence] |
| EAI15261 | unknown [environmental sequence] |
| EAI15547 | unknown [environmental sequence] |
| EAI17521 | unknown [environmental sequence] |
| EAI21398 | unknown [environmental sequence] |
| EAI29728 | unknown [environmental sequence] |
| EAI38468 | unknown [environmental sequence] |
| EAI43591 | unknown [environmental sequence] |
| EAI51589 | unknown [environmental sequence] |
| EAI58453 | unknown [environmental sequence] |
| EAI72974 | unknown [environmental sequence] |
| EAI77885 | unknown [environmental sequence] |
| EAI78272 | unknown [environmental sequence] |
| EAI80262 | unknown [environmental sequence] |
| EAI83937 | unknown [environmental sequence] |
| EAI86664 | unknown [environmental sequence] |
| EAJ00517 | unknown [environmental sequence] |
| EAJ05570 | unknown [environmental sequence] |
| EAJ08238 | unknown [environmental sequence] |
| EAJ15524 | unknown [environmental sequence] |
| EAJ18144 | unknown [environmental sequence] |
| EAJ20649 | unknown [environmental sequence] |
| EAJ21683 | unknown [environmental sequence] |
| EAJ24413 | unknown [environmental sequence] |
| EAJ28774 | unknown [environmental sequence] |
| EAJ30522 | unknown [environmental sequence] |
| EAJ35157 | unknown [environmental sequence] |
| EAJ37407 | unknown [environmental sequence] |
| EAJ39929 | unknown [environmental sequence] |
| EAJ54356 | unknown [environmental sequence] |
| EAJ54959 | unknown [environmental sequence] |
| EAJ56207 | unknown [environmental sequence] |
| EAJ58447 | unknown [environmental sequence] |
| EAJ59958 | unknown [environmental sequence] |
| EAJ63347 | unknown [environmental sequence] |
| EAJ66054 | unknown [environmental sequence] |
| EAJ67637 | unknown [environmental sequence] |
| EAJ69812 | unknown [environmental sequence] |
| EAJ74441 | unknown [environmental sequence] |
| EAJ76472 | unknown [environmental sequence] |
| EAJ76473 | unknown [environmental sequence] |
| EAJ80355 | unknown [environmental sequence] |
| EAJ80839 | unknown [environmental sequence] |
| EAJ81408 | unknown [environmental sequence] |

TABLE 17a-continued

Examples of phytoene dehydrogenase polypeptides.

| ACCESSION | PROTEIN DESCRIPTION |
|---|---|
| EAJ86174 | unknown [environmental sequence] |
| EAJ87600 | unknown [environmental sequence] |
| EAJ88203 | unknown [environmental sequence] |
| EAJ88682 | unknown [environmental sequence] |
| EAJ92341 | unknown [environmental sequence] |
| EAJ94774 | unknown [environmental sequence] |
| EAJ97555 | unknown [environmental sequence] |
| EAJ97958 | unknown [environmental sequence] |
| EAK07654 | unknown [environmental sequence] |
| EAK08513 | unknown [environmental sequence] |
| EAK08529 | unknown [environmental sequence] |
| EAK10609 | unknown [environmental sequence] |
| EAK10614 | unknown [environmental sequence] |
| EAK12902 | unknown [environmental sequence] |
| EAK13034 | unknown [environmental sequence] |
| EAK15092 | unknown [environmental sequence] |
| EAK22483 | unknown [environmental sequence] |
| EAK23222 | unknown [environmental sequence] |
| EAK24187 | unknown [environmental sequence] |
| EAK24674 | unknown [environmental sequence] |
| EAK28785 | unknown [environmental sequence] |
| EAK34731 | unknown [environmental sequence] |
| EAK34742 | unknown [environmental sequence] |
| EAK36883 | unknown [environmental sequence] |
| EAK37522 | unknown [environmental sequence] |
| EAK42705 | unknown [environmental sequence] |
| EAK43213 | unknown [environmental sequence] |
| EAK52580 | unknown [environmental sequence] |
| EAK53452 | unknown [environmental sequence] |
| EAK58759 | unknown [environmental sequence] |
| EAK62665 | unknown [environmental sequence] |
| EAK63558 | unknown [environmental sequence] |
| F84187 | phytoene dehydrogenase [imported] - *Halobacterium* sp. NRC-1 |
| F90272 | phytoene dehydrogenase related protein [imported] - *Sulfolobus solfataricus* |
| G87635 | phytoene dehydrogenase-related protein [imported] - *Caulobacter crescentus* |
| G90413 | phytoene dehydrogenase related protein [imported] - *Sulfolobus solfataricus* |
| H83880 | hypothetical protein BH1848 [imported] - *Bacillus halodurans* (strain C-125) |
| H84320 | phytoene dehydrogenase [imported] - *Halobacterium* sp. NRC-1 |
| JC7723 | phytoene desaturase (EC 1.14.99.—) 1 - *citrus* |
| NP_060220 | all-trans-13,14-dihydroretinol saturase [*Homo sapiens*] |
| NP_080435 | all-trans-13,14-dihydroretinol saturase [*Mus musculus*] |
| NP_193157 | phytoene dehydrogenase, chloroplast/phytoene desaturase (PDS) [*Arabidopsis thaliana*] |
| NP_214383 | protoporphyrinogen oxidase [*Aquifex aeolicus* VF5] |
| NP_276913 | phytoene dehydrogenase [*Methanothermobacter thermautotrophicus* str. Delta H] |
| NP_293819 | phytoene dehydrogenase, putative [*Deinococcus radiodurans* R1] |
| NP_294534 | dehydrogenase, putative [*Deinococcus radiodurans* R1] |
| NP_294585 | phytoene dehydrogenase [*Deinococcus radiodurans* R1] |
| NP_295972 | methoxyneurosporene dehydrogenase [*Deinococcus radiodurans* R1] |
| NP_338490 | oxidoreductase, putative [*Mycobacterium tuberculosis* CDC1551] |
| NP_376437 | hypothetical protein ST0549 [*Sulfolobus tokodaii* str. 7] |
| NP_377056 | hypothetical protein ST1130 [*Sulfolobus tokodaii* str. 7] |
| NP_388895 | protoporphyrinogen IX and coproporphyrinogen III oxidase [*Bacillus subtilis* subsp. *subtilis* str. 168] |
| NP_441167 | phytoene desaturase [*Synechocystis* sp. PCC 6803] |
| NP_441254 | hypothetical protein sll0254 [*Synechocystis* sp. PCC 6803] |
| NP_442491 | b-carotene ketolase [*Synechocystis* sp. PCC 6803] |
| NP_442727 | hypothetical protein sll0033 [*Synechocystis* sp. PCC 6803] |
| NP_562475 | probable diapophytoene dehydrogenase [*Clostridium perfringens* str. 13] |
| NP_568712 | amine oxidase-related [*Arabidopsis thaliana*] |
| NP_601630 | hypothetical protein NCgl2346 [*Corynebacterium glutamicum* ATCC 13032] |
| NP_601630 | hypothetical protein NCgl2346 [*Corynebacterium glutamicum* ATCC 13032] |
| NP_616426 | phytoene dehydrogenase family protein [*Methanosarcina acetivorans* C2A] |
| NP_624522 | putative phytoene dehydrogenase (phytoene desaturase) (putative secreted protein) [*Streptomyces coelicolor* A3(2)] |
| NP_626360 | putative carotenoid dehydrogenase (putative secreted protein) [*Streptomyces coelicolor* A3(2)] |
| NP_630834 | putative phytoene dehydrogenase [*Streptomyces coelicolor* A3(2)] |
| NP_643053 | phytoene dehydrogenase [*Xanthomonas axonopodis* pv. *citri* str. 306] |
| NP_647302 | hypothetical protein MW2485 [*Staphylococcus aureus* subsp. *aureus* MW2] |
| NP_659552 | all-trans-13,14-dihydroretinol saturase [*Rattus norvegicus*] |
| NP_661086 | lycopene cyclase, putative [*Chlorobium tepidum* TLS] |
| NP_661546 | carotenoid isomerase, putative [*Chlorobium tepidum* TLS] |
| NP_661701 | phytoene desaturase [*Chlorobium tepidum* TLS] |
| NP_662300 | zeta-carotene desaturase [*Chlorobium tepidum* TLS] |
| NP_681023 | putative phytoene dehydrogenase [*Thermosynechococcus elongatus* BP-1] |

TABLE 17a-continued

Examples of phytoene dehydrogenase polypeptides.

| ACCESSION | PROTEIN DESCRIPTION |
|---|---|
| NP_681127 | zeta-carotene desaturase [*Thermosynechococcus elongatus* BP-1] |
| NP_682351 | phytoene dehydrogenase/phytoene desaturase [*Thermosynechococcus elongatus* BP-1] |
| NP_693380 | phytoene dehydrogenase [*Oceanobacillus iheyensis* HTE831] |
| NP_693382 | phytoene dehydrogenase [*Oceanobacillus iheyensis* HTE831] |
| NP_737250 | phytoene desaturase [*Corynebacterium efficiens* YS-314] |
| NP_763380 | hypothetical protein VV21505 [*Vibrio vulnificus* CMCP6] |
| NP_786524 | squalene synthase [*Lactobacillus plantarum* WCFS1] |
| NP_822198 | phytoene desaturase [*Streptomyces avermitilis* MA-4680] |
| NP_822828 | squalene/phytoene dehydrogenase [*Streptomyces avermitilis* MA-4680] |
| NP_827278 | putative phytoene dehydrogenase [*Streptomyces avermitilis* MA-4680] |
| NP_851528 | putative phytoene dehydrogenase [*Streptomyces rochei*] |
| NP_857496 | PUTATIVE DEHYDROGENASE [*Mycobacterium bovis* AF2122/97] |
| NP_868798 | probable phytoene dehydrogenase [*Rhodopirellula baltica* SH 1] |
| NP_869339 | phytoene dehydrogenase [*Rhodopirellula baltica* SH 1] |
| NP_870237 | phytoene dehydrogenase [*Rhodopirellula baltica* SH 1] |
| NP_874530 | Zeta-carotene desaturase [*Prochlorococcus marinus* subsp. *marinus* str. CCMP1375] |
| NP_874561 | Phytoene dehydrogenase, phytoene desaturase [*Prochlorococcus marinus* subsp. *marinus* str. CCMP1375] |
| NP_874977 | Phytoene dehydrogenase/carotenoid isomerase [*Prochlorococcus marinus* subsp. *marinus* str. CCMP1375] |
| NP_892236 | zeta-carotene desaturase [*Prochlorococcus marinus* subsp. *pastoris* str. CCMP1986] |
| NP_892265 | phytoene desaturase [*Prochlorococcus marinus* subsp. *pastoris* str. CCMP1986] |
| NP_892458 | Bacterial-type phytoene dehydrogenase [*Prochlorococcus marinus* subsp. *pastoris* str. CCMP1986] |
| NP_893232 | putative carotenoid isomerase [*Prochlorococcus marinus* subsp. *pastoris* str. CCMP1986] |
| NP_894882 | putative carotenoid isomerase [*Prochlorococcus marinus* str. MIT 9313] |
| NP_895385 | NAD binding site [*Prochlorococcus marinus* str. MIT 9313] |
| NP_895793 | zeta-carotene desaturase [*Prochlorococcus marinus* str. MIT 9313] |
| NP_895829 | phytoene desaturase [*Prochlorococcus marinus* str. MIT 9313] |
| NP_896854 | hypothetical protein SYNW0761 [*Synechococcus* sp. WH 8102] |
| NP_896994 | Carotenoid isomerase [*Synechococcus* sp. WH 8102] |
| NP_898304 | zeta-carotene desaturase [*Synechococcus* sp. WH 8102] |
| NP_898346 | phytoene desaturase [*Synechococcus* sp. WH 8102] |
| NP_902647 | hypothetical protein CV2977 [*Chromobacterium violaceum* ATCC 12472] |
| NP_923340 | beta-carotene ketolase [*Gloeobacter violaceus* PCC 7421] |
| NP_923639 | hypothetical protein gll0693 [*Gloeobacter violaceus* PCC 7421] |
| NP_923813 | phytoene dehydrogenase [*Gloeobacter violaceus* PCC 7421] |
| NP_925079 | hypothetical protein gvip293 [*Gloeobacter violaceus* PCC 7421] |
| NP_931515 | phytoene dehydrogenase (phytoene desaturase) [*Photorhabdus luminescens* subsp. *laumondii* TTO1] |
| NP_936379 | hypothetical protein VVA0323 [*Vibrio vulnificus* YJ016] |
| NP_940208 | phytoene dehydrogenase related enzyme [*Corynebacterium diphtheriae* NCTC 13129] |
| NP_945754 | NAD binding site:Amine oxidase [*Rhodopseudomonas palustris* CGA009] |
| NP_946860 | phytoene dehydrogenase CrtI [*Rhodopseudomonas palustris* CGA009] |
| NP_946866 | methoxyneurosporene dehydrogenase [*Rhodopseudomonas palustris* CGA009] |
| NP_948851 | phytoene dehydrogenase-related protein [*Rhodopseudomonas palustris* CGA009] |
| NP_962004 | hypothetical protein MAP3070 [*Mycobacterium avium* subsp. *paratuberculosis* str. k10] |
| NP_968600 | Phytoene dehydrogenase [*Bdellovibrio bacteriovorus* HD100] |
| NP_974222 | zeta-carotene desaturase (ZDS1)/carotene 7,8-desaturase [*Arabidopsis thaliana*] |
| NP_974545 | phytoene dehydrogenase, chloroplast/phytoene desaturase (PDS) [*Arabidopsis thaliana*] |
| O49901 | Zeta-carotene desaturase, chloroplast precursor (Carotene 7,8-desaturase) |
| P17059 | Methoxyneurosporene dehydrogenase |
| P54971 | Phytoene dehydrogenase (Phytoene desaturase) |
| P54978 | Phytoene dehydrogenase (Phytoene desaturase) |
| P54979 | Phytoene dehydrogenase (Phytoene desaturase) |
| P54981 | Phytoene dehydrogenase (Phytoene desaturase) |
| P54982 | Phytoene dehydrogenase (Phytoene desaturase) |
| P74306 | Zeta-carotene desaturase (Carotene 7,8-desaturase) |
| Q01671 | Methoxyneurosporene dehydrogenase |
| Q02861 | Phytoene dehydrogenase (Phytoene desaturase) |
| Q38893 | Zeta-carotene desaturase, chloroplast precursor (Carotene 7,8-desaturase) |
| Q40406 | Phytoene dehydrogenase, chloroplast precursor (Phytoene desaturase) |
| Q9FV46 | Zeta-carotene desaturase, chloroplast precursor (Carotene 7,8-desaturase) |
| Q9SE20 | Zeta-carotene desaturase, chloroplast precursor (Carotene 7,8-desaturase) |
| Q9SMJ3 | Zeta-carotene desaturase, chloroplast precursor (Carotene 7,8-desaturase) |
| Q9ZTN9 | Phytoene dehydrogenase, chloroplast precursor (Phytoene desaturase) |
| Q9ZTP4 | Zeta-carotene desaturase, chloroplast precursor (Carotene 7,8-desaturase) |
| S29314 | phytoene dehydrogenase (EC 1.3.—.—) - pepper |
| S32171 | hydroxyneurosporene dehydrogenase (EC 1.3.—.—) - *Myxococcus xanthus* |
| S49624 | methoxyneurosporene dehydrogenase (EC 1.3.—.—) CrtD - *Rhodobacter sphaeroides* |
| S52586 | phytoene dehydrogenase (EC 1.3.—.—) - *Erwinia herbicola* |

TABLE 17a-continued

| Examples of phytoene dehydrogenase polypeptides. | |
|---|---|
| ACCESSION | PROTEIN DESCRIPTION |
| S65060 | phytoene desaturase precursor - maize |
| T10701 | probable phytoene dehydrogenase (EC 1.3.—.—) - green alga (*Dunaliella bardawil*) |
| T31463 | probable diapophytoene dehydrogenase crtN - *Heliobacillus mobilis* |
| T46822 | phytoene desaturase (EC 1.3.—.—) [validated] - *Xanthophyllomyces dendrorhous* |
| T48646 | phytoene dehydrogenase (EC 1.—.—.—) [validated] - *Cercospora nicotianae* |
| T50745 | phytoene dehydrogenase (EC 1.3.—.—) [imported] - *Rhodobacter sphaeroides* |
| T50749 | methoxyneurosporene dehydrogenase (EC 1.3.—.—) crtD [imported] - *Rhodobacter sphaeroides* |
| T50893 | methoxyneurosporene dehydrogenase [imported] - *Rubrivivax gelatinosus* |
| T50910 | phytoene dehydrogenase [imported] - *Rubrivivax gelatinosus* |
| T51119 | phytoene desaturase crtI [imported] - *Brevibacterium linens* |
| T51123 | betacarotene desaturase [imported] - *Brevibacterium linens* |
| XP_324732 | PHYTOENE DEHYDROGENASE (PHYTOENE DESATURASE) (ALBINO-1 PROTEIN) [*Neurospora crassa*] |
| XP_383241 | hypothetical protein FG03065.1 [*Gibberella zeae* PH-1] |
| XP_401825 | hypothetical protein UM04210.1 [*Ustilago maydis* 521] |
| XP_470568 | Putative phytoene dehydrogenase precursor [*Oryza sativa*] |
| XP_473486 | OSJNBa0084K11.8 [*Oryza sativa* (*japonica* cultivar-group)] |
| XP_477063 | putative zeta-carotene desaturase precursor [*Oryza sativa* (*japonica* cultivar-group)] |
| XP_525801 | PREDICTED: hypothetical protein XP_525801 [*Pan troglodytes*] |
| XP_540198 | PREDICTED: hypothetical protein XP_540198 [*Canis familiaris*] |
| YP_006049 | phytoene dehydrogenase [*Thermus thermophilus* HB27] |
| YP_013621 | phytoene dehydrogenase, putative [*Listeria monocytogenes* str. 4b F2365] |
| YP_024310 | phytoene dehydrogenase [*Picrophilus torridus* DSM 9790] |
| YP_041986 | squalene synthase [*Staphylococcus aureus* subsp. *aureus* MRSA252] |
| YP_041988 | putative phytoene dehydrogenase related protein [*Staphylococcus aureus* subsp. *aureus* MRSA252] |
| YP_044561 | squalene synthase [*Staphylococcus aureus* subsp. *aureus* MSSA476] |
| YP_044564 | putative phytoene dehydrogenase related protein [*Staphylococcus aureus* subsp. *aureus* MSSA476] |
| YP_062471 | phytoene dehydrogenase [*Leifsonia xyli* subsp. *xyli* str. CTCB07] |
| YP_117947 | putative phytoene desaturase [*Nocardia farcinica* IFM 10152] |
| YP_120612 | putative phytoene desaturase [*Nocardia farcinica* IFM 10152] |
| YP_135077 | phytoene dehydrogenase [*Haloarcula marismortui* ATCC 43049] |
| YP_136483 | phytoene dehydrogenase [*Haloarcula marismortui* ATCC 43049] |
| YP_145331 | probable phytoene dehydrogenase [*Thermus thermophilus* HB8] |
| YP_145348 | phytoene dehydrogenase [*Thermus thermophilus* HB8] |
| YP_171014 | carotene isomerase [*Synechococcus elongatus* PCC 6301] |
| YP_172823 | phytoene dehydrogenase [*Synechococcus elongatus* PCC 6301] |
| YP_173078 | carotene isomerase [*Synechococcus elongatus* PCC 6301] |
| YP_173207 | zeta-carotene desaturase [*Synechococcus elongatus* PCC 6301] |
| YP_184572 | predicted oxidoreductase [*Thermococcus kodakaraensis*] |
| YP_187368 | dehydrosqualene desaturase [*Staphylococcus aureus* subsp. *aureus* COL] |
| YP_187371 | phytoene dehydrogenase [*Staphylococcus aureus* subsp. *aureus* COL] |
| YP_187371 | phytoene dehydrogenase [*Staphylococcus aureus* subsp. *aureus* COL] |
| YP_187371 | phytoene dehydrogenase [*Staphylococcus aureus* subsp. *aureus* COL] |
| ZP_000490 | COG1233: Phytoene dehydrogenase and related proteins [*Magnetospirillum magnetotacticum* MS-1] |
| ZP_000509 | COG1233: Phytoene dehydrogenase and related proteins [*Magnetospirillum magnetotacticum* MS-1] |
| ZP_000518 | COG1233: Phytoene dehydrogenase and related proteins [*Magnetospirillum magnetotacticum* MS-1] |
| ZP_000566 | COG0562: UDP-galactopyranose mutase [*Magnetospirillum magnetotacticum* MS-1] |
| ZP_000627 | COG1233: Phytoene dehydrogenase and related proteins [*Leuconostoc mesenteroides* subsp. *mesenteroides* ATCC 8293] |
| ZP_000627 | COG1233: Phytoene dehydrogenase and related proteins [*Leuconostoc mesenteroides* subsp. *mesenteroides* ATCC 8293] |
| ZP_001073 | COG1233: Phytoene dehydrogenase and related proteins [*Nostoc punctiforme* PCC 73102] |
| ZP_001081 | COG1233: Phytoene dehydrogenase and related proteins [*Nostoc punctiforme* PCC 73102] |
| ZP_001091 | COG3349: Uncharacterized conserved protein [*Nostoc punctiforme* PCC 73102] |
| ZP_001116 | COG1233: Phytoene dehydrogenase and related proteins [*Nostoc punctiforme* PCC 73102] |
| ZP_001117 | COG3349: Uncharacterized conserved protein [*Nostoc punctiforme* PCC 73102] |
| ZP_001119 | COG3349: Uncharacterized conserved protein [*Nostoc punctiforme* PCC 73102] |
| ZP_001124 | COG1233: Phytoene dehydrogenase and related proteins [*Nostoc punctiforme* PCC 73102] |
| ZP_001510 | COG1233: Phytoene dehydrogenase and related proteins [*Dechloromonas aromatica* RCB] |
| ZP_001591 | COG3349: Uncharacterized conserved protein [*Anabaena variabilis* ATCC 29413] |
| ZP_001593 | COG1233: Phytoene dehydrogenase and related proteins [*Anabaena variabilis* ATCC 29413] |
| ZP_001602 | COG3349: Uncharacterized conserved protein [*Anabaena variabilis* ATCC 29413] |
| ZP_001614 | COG3349: Uncharacterized conserved protein [*Anabaena variabilis* ATCC 29413] |

TABLE 17a-continued

| Examples of phytoene dehydrogenase polypeptides. | |
|---|---|
| ACCESSION | PROTEIN DESCRIPTION |
| ZP_001645 | COG3349: Uncharacterized conserved protein [*Synechococcus elongatus* PCC 7942] |
| ZP_001650 | COG3349: Uncharacterized conserved protein [*Synechococcus elongatus* PCC 7942] |
| ZP_001722 | COG1233: Phytoene dehydrogenase and related proteins [*Methylobacillus flagellatus* KT] |
| ZP_001746 | COG3349: Uncharacterized conserved protein [*Crocosphaera watsonii* WH 8501] |
| ZP_001752 | COG3349: Uncharacterized conserved protein [*Crocosphaera watsonii* WH 8501] |
| ZP_001770 | COG1232: Protoporphyrinogen oxidase [*Crocosphaera watsonii* WH 8501] |
| ZP_001777 | COG1233: Phytoene dehydrogenase and related proteins [*Crocosphaera watsonii* WH 8501] |
| ZP_001787 | COG3349: Uncharacterized conserved protein [*Crocosphaera watsonii* WH 8501] |
| ZP_001837 | COG1233: Phytoene dehydrogenase and related proteins [*Exiguobacterium* sp. 255-15] |
| ZP_001867 | COG1233: Phytoene dehydrogenase and related proteins [*Rubrobacter xylanophilus* DSM 9941] |
| ZP_002073 | COG1233: Phytoene dehydrogenase and related proteins [*Rhodobacter sphaeroides* 2.4.1] |
| ZP_002077 | COG1233: Phytoene dehydrogenase and related proteins [*Rhodobacter sphaeroides* 2.4.1] |
| ZP_002339 | phytoene dehydrogenase, putative [*Listeria monocytogenes* str. ½a F6854] |
| ZP_002680 | COG1233: Phytoene dehydrogenase and related proteins [*Rhodospirillum rubrum*] |
| ZP_002705 | COG1233: Phytoene dehydrogenase and related proteins [*Rhodospirillum rubrum*] |
| ZP_002771 | COG1232: Protoporphyrinogen oxidase [*Burkholderia fungorum* LB400] |
| ZP_002892 | hypothetical protein Mmc102002317 [*Magnetococcus* sp. MC-1] |
| ZP_002916 | COG3349: Uncharacterized conserved protein [*Thermobifida fusca*] |
| ZP_002963 | COG1233: Phytoene dehydrogenase and related proteins [*Methanosarcina barkeri* str. fusaro] |
| ZP_003022 | COG1233: Phytoene dehydrogenase and related proteins [*Novosphingobium* aromaticivorans DSM 12444] |
| ZP_003036 | COG1233: Phytoene dehydrogenase and related proteins [*Novosphingobium aromaticivorans* DSM 12444] |
| ZP_003107 | COG1233: Phytoene dehydrogenase and related proteins [*Cytophaga hutchinsonii*] |
| ZP_003202 | COG1233: Phytoene dehydrogenase and related proteins [*Oenococcus oeni* PSU-1] |
| ZP_003258 | COG1233: Phytoene dehydrogenase and related proteins [*Trichodesmium erythraeum* IMS101] |
| ZP_003268 | COG3349: Uncharacterized conserved protein [*Trichodesmium erythraeum* IMS101] |
| ZP_003269 | COG3349: Uncharacterized conserved protein [*Trichodesmium erythraeum* IMS101] |
| ZP_003276 | COG1233: Phytoene dehydrogenase and related proteins [*Trichodesmium erythraeum* IMS101] |
| ZP_003283 | COG1233: Phytoene dehydrogenase and related proteins [*Trichodesmium erythraeum* IMS101] |
| ZP_003557 | COG1233: Phytoene dehydrogenase and related proteins [*Exiguobacterium* sp. 255-15] |
| ZP_003559 | COG3349: Uncharacterized conserved protein [*Chloroflexus aurantiacus*] |
| ZP_003565 | COG1233: Phytoene dehydrogenase and related proteins [*Chloroflexus aurantiacus*] |
| ZP_003577 | COG1233: Phytoene dehydrogenase and related proteins [*Chloroflexus aurantiacus*] |
| ZP_003593 | COG1233: Phytoene dehydrogenase and related proteins [*Chloroflexus aurantiacus*] |
| ZP_003595 | COG1233: Phytoene dehydrogenase and related proteins [*Chloroflexus aurantiacus*] |
| ZP_003685 | carotenoid isomerase, putative [*Campylobacter lari* RM2100] |

TABLE 17b

| Examples of phytoene dehydrogenase polypeptides. | | | |
|---|---|---|---|
| Row | Accession | GI | Protein Description |
| 1 | 1613414B | 227039 | crtI gene |
| 2 | CAA36533 | 45998 | unnamed protein product [*Rhodobacter capsulatus*] |
| 3 | ABP69925 | 145555312 | Phytoene dehydrogenase-related protein [*Rhodobacter sphaeroides* ATCC 17025] |
| 4 | ABG29855 | 109453650 | phytoene dehydrogenase [*Roseobacter denitrificans* OCh 114] |
| 5 | YP_001 . . . | 126462676 | Phytoene dehydrogenase-related protein [*Rhodobacter sphaeroides* ATCC 17029] |
| 6 | CAB38739 | 4490589 | phytoene dehydrogenase [*Rhodobacter sphaeroides*] |
| 7 | AAF24289 | 6690721 | CrtI [*Rhodobacter sphaeroides*] |
| 8 | ZP_019 . . . | 149914257 | Phytoene dehydrogenase [*Roseobacter* sp. AzwK-3b] |
| 9 | ZP_018 . . . | 149203764 | Phytoene dehydrogenase [*Roseovarius* sp. TM1035] |
| 10 | ZP_017 . . . | 126734359 | Phytoene dehydrogenase [*Roseobacter* sp. CCS2] |
| 11 | ZP_015 . . . | 118735466 | Phytoene dehydrogenase-related protein [*Dinoroseobacter shibae* DFL 12] |
| 12 | EBA75398 | 134340305 | hypothetical protein GOS_348183 [marine metagenome] |
| 13 | ZP_010 . . . | 85703533 | Phytoene dehydrogenase [*Roseovarius* sp. 217] |
| 14 | ZP_010 . . . | 84514966 | Phytoene dehydrogenase [*Loktanella vestfoldensis* SKA53] |
| 15 | EDJ26541 | 144155062 | hypothetical protein GOS_1726264 [marine metagenome] |

TABLE 17b-continued

Examples of phytoene dehydrogenase polypeptides.

| Row | Accession | GI | Protein Description |
|---|---|---|---|
| 16 | AAM48646 | 21328640 | phytoene dehydrogenase [uncultured proteobacterium] |
| 17 | EBF29285 | 135068871 | hypothetical protein GOS_9621672 [marine metagenome] |
| 18 | EDH88525 | 143962357 | hypothetical protein GOS_524801 [marine metagenome] |
| 19 | ABD53060 | 88862183 | phytoene dehydrogenase [*Jannaschia* sp. CCS1] |
| 20 | ECX23858 | 142320992 | hypothetical protein GOS_2574166 [marine metagenome] |
| 21 | EDD83467 | 143241615 | hypothetical protein GOS_1236491 [marine metagenome] |
| 22 | ECW60413 | 142235101 | hypothetical protein GOS_2690740 [marine metagenome] |
| 23 | EDB24382 | 142880994 | hypothetical protein GOS_1857800 [marine metagenome] |
| 24 | EDC65629 | 143078396 | hypothetical protein GOS_1437717 [marine metagenome] |
| 25 | EDC66763 | 143079940 | hypothetical protein GOS_1435710 [marine metagenome] |
| 26 | EBF73535 | 135137918 | hypothetical protein GOS_9549173 [marine metagenome] |
| 27 | EDB61897 | 142933299 | hypothetical protein GOS_1624464 [marine metagenome] |
| 28 | EDH58399 | 143920581 | hypothetical protein GOS_579274 [marine metagenome] |
| 29 | ECV46406 | 142084909 | hypothetical protein GOS_2893885 [marine metagenome] |
| 30 | EBG03643 | 135184853 | hypothetical protein GOS_9500102 [marine metagenome] |
| 31 | ECW11301 | 142170256 | hypothetical protein GOS_2778421 [marine metagenome] |
| 32 | EDG30167 | 143690631 | hypothetical protein GOS_805431 [marine metagenome] |
| 33 | EBF89344 | 135162533 | hypothetical protein GOS_9523433 [marine metagenome] |
| 34 | EDG14791 | 143664156 | hypothetical protein GOS_832322 [marine metagenome] |
| 35 | ECW44302 | 142213461 | hypothetical protein GOS_2720548 [marine metagenome] |
| 36 | EDC28179 | 143027347 | hypothetical protein GOS_1503868 [marine metagenome] |
| 37 | EBF91518 | 135165888 | hypothetical protein GOS_9519783 [marine metagenome] |
| 38 | EBG06098 | 135188689 | hypothetical protein GOS_9496261 [marine metagenome] |
| 39 | YP_001 . . . | 121998398 | Phytoene dehydrogenase-related protein [*Halorhodospira halophila* SL1] |
| 40 | ABC21298 | 83574747 | Phytoene desaturase [*Rhodospirillum rubrum* ATCC 11170] |
| 41 | EDD45555 | 143188703 | hypothetical protein GOS_1301547 [marine metagenome] |
| 42 | EBF89879 | 135163364 | hypothetical protein GOS_9522488 [marine metagenome] |
| 43 | EDA94958 | 142836512 | hypothetical protein GOS_1907603 [marine metagenome] |
| 44 | EBE40240 | 134934911 | hypothetical protein GOS_9769793 [marine metagenome] |
| 45 | ABQ38355 | 146409849 | Phytoene dehydrogenase (Phytoene desaturase) [*Bradyrhizobium* sp. BTAi1] |
| 46 | ECV53668 | 142093711 | hypothetical protein GOS_2880588 [marine metagenome] |
| 47 | EDJ05722 | 144126667 | hypothetical protein GOS_1762374 [marine metagenome] |
| 48 | EDJ52003 | 144189327 | hypothetical protein GOS_1681048 [marine metagenome] |
| 49 | CAL75489 | 146191484 | Phytoene dehydrogenase (Phytoene desaturase) [*Bradyrhizobium* sp. ORS278] |
| 50 | ZP_011 . . . | 88706670 | phytoene dehydrogenase [gamma proteobacterium KT 71] |
| 51 | ABD86823 | 90104786 | amine oxidase [*Rhodopseudomonas palustris* BisB18] |
| 52 | ZP_019 . . . | 149922641 | amine oxidase [*Plesiocystis pacifica* SIR-1] |
| 53 | ECW14126 | 142173943 | hypothetical protein GOS_2773516 [marine metagenome] |
| 54 | ABJ05267 | 115517283 | amine oxidase [*Rhodopseudomonas palustris* BisA53] |
| 55 | ZP_020 . . . | 156449192 | Zeta-phytoene desaturase [*Methylobacterium chloromethanicum* CM4] |
| 56 | ZP_020 . . . | 153900167 | FAD-dependent pyridine nucleotide-disulphide oxidoreductase [*Methylobacterium extorquens* PA1] |
| 57 | EDO75157 | 157409160 | Zeta-phytoene desaturase [*Methylobacterium populi* BJ001] |
| 58 | EBF26787 | 135064945 | hypothetical protein GOS_9625603 [marine metagenome] |
| 59 | EBM47492 | 136188235 | hypothetical protein GOS_8404015 [marine metagenome] |
| 60 | BAA94063 | 7416814 | phytoene dehydrogenase [*Rubrivivax gelatinosus*] |
| 61 | AAO93135 | 29893506 | phytoene dehydrogenase; CrtI [*Rubrivivax gelatinosus*] |
| 62 | ABE40987 | 91684685 | amine oxidase [*Rhodopseudomonas palustris* BisB5] |
| 63 | ABC44467 | 83756354 | phytoene dehydrogenase [*Salinibacter ruber* DSM 13855] |
| 64 | NP_946860 | 39934584 | phytoene dehydrogenase CrtI [*Rhodopseudomonas palustris* CGA009] |
| 65 | EDK95498 | 148522573 | Phytoene dehydrogenase-related protein [*Methylobacterium* sp. 4-46] |
| 66 | AAX48189 | 61653236 | phytoene dehydrogenase [uncultured proteobacterium DelRiverFos06H03] |
| 67 | ABD08704 | 86574147 | Amine oxidase [*Rhodopseudomonas palustris* HaA2] |
| 68 | ECV97125 | 142151708 | hypothetical protein GOS_2803067 [marine metagenome] |
| 69 | EBF91320 | 135165576 | hypothetical protein GOS_9520100 [marine metagenome] |
| 70 | EDG74671 | 143780072 | hypothetical protein GOS_728533 [marine metagenome] |
| 71 | AAR37802 | 40062931 | phytoene dehydrogenase [uncultured bacterium 442] |
| 72 | ZP_016 . . . | 119504131 | amine oxidase [marine gamma proteobacterium HTCC2080] |
| 73 | EBY63975 | 138260458 | hypothetical protein GOS_5033312 [marine metagenome] |
| 74 | ECW52975 | 142225047 | hypothetical protein GOS_2704529 [marine metagenome] |
| 75 | EDB07926 | 142858428 | hypothetical protein GOS_1885673 [marine metagenome] |
| 76 | ECX08477 | 142300457 | hypothetical protein GOS_2602107 [marine metagenome] |
| 77 | EBE08763 | 134887517 | hypothetical protein GOS_9823078 [marine metagenome] |
| 78 | EDG53739 | 143740094 | hypothetical protein GOS_764800 [marine metagenome] |
| 79 | AAR37855 | 40062985 | phytoene dehydrogenase [uncultured bacterium 443] |
| 80 | EBE55393 | 134957668 | hypothetical protein GOS_9744377 [marine metagenome] |
| 81 | EBK49247 | 135888345 | hypothetical protein GOS_8723699 [marine metagenome] |
| 82 | YP_001 . . . | 154247504 | Zeta-phytoene desaturase [*Xanthobacter autotrophicus* Py2] |
| 83 | EBJ38620 | 135714057 | hypothetical protein GOS_8907038 [marine metagenome] |

TABLE 17b-continued

Examples of phytoene dehydrogenase polypeptides.

| Row | Accession | GI | Protein Description |
|---|---|---|---|
| 84 | EBO29607 | 136458570 | hypothetical protein GOS_8104065 [marine metagenome] |
| 85 | EDI63495 | 144067673 | hypothetical protein GOS_399405 [marine metagenome] |
| 86 | ECH51213 | 139794606 | hypothetical protein GOS_4963038 [marine metagenome] |
| 87 | ZP_014 . . . | 113941052 | amine oxidase [*Herpetosiphon aurantiacus* ATCC 23779] |
| 88 | P54978 | 85700409 | Phytoene dehydrogenase (Phytoene desaturase) |
| 89 | AAY28420 | 63034218 | phytoene desaturase [*Paracoccus haeundaensis*] |
| 90 | YP_001 . . . | 148655097 | Phytoene dehydrogenase-related protein [*Roseiflexus* sp. RS-1] |
| 91 | AAT35222 | 47531118 | fusion of carotene synthesis proteins [synthetic construct] |
| 92 | CAB56062 | 5912295 | phytoene desaturase [*Paracoccus marcusii*] |
| 93 | ZP_016 . . . | 119484684 | phytoene dehydrogenase CrtI [*Lyngbya* sp. PCC 8106] |
| 94 | YP_001 . . . | 156932562 | hypothetical protein ESA_00343 [*Enterobacter sakazakii* ATCC BAA-894] |
| 95 | CAL34121 | 112702901 | phytoene dehydrogenase CRTI [*Enterobacter sakazakii*] |
| 96 | ZP_014 . . . | 114705593 | phytoene dehydrogenase (phytoene desaturase) [*Fulvimarina pelagi* HTCC2506] |
| 97 | ABU57678 | 156232895 | Zeta-phytoene desaturase [*Roseiflexus castenholzii* DSM 13941] |
| 98 | EDJ24172 | 144151864 | hypothetical protein GOS_1730347 [marine metagenome] |
| 99 | EBP04886 | 136575764 | hypothetical protein GOS_7976019 [marine metagenome] |
| 100 | EDJ19941 | 144146057 | hypothetical protein GOS_1737754 [marine metagenome] |
| 101 | EDE02809 | 143268695 | hypothetical protein GOS_1202430 [marine metagenome] |
| 102 | EDA02972 | 142711842 | hypothetical protein GOS_2076612 [marine metagenome] |
| 103 | AAC44850 | 1842244 | phytoene desaturase |
| 104 | ECI48880 | 139936452 | hypothetical protein GOS_4592564 [marine metagenome] |
| 105 | ECW29436 | 142194003 | hypothetical protein GOS_2746710 [marine metagenome] |
| 106 | CAE79593 | 39575425 | Phytoene dehydrogenase [*Bdellovibrio bacteriovorus* HD100] |
| 107 | EDJ16294 | 144141089 | hypothetical protein GOS_1744028 [marine metagenome] |
| 108 | ABC50114 | 84043362 | phytoene desaturase [*Brevundimonas vesicularis*] |
| 109 | CAE16714 | 36787607 | phytoene dehydrogenase (phytoene desaturase) [*Photorhabdus luminescens* subsp. *laumondii* TTO1] |
| 110 | AAZ73142 | 72536076 | phytoene desaturase [*Enterobacteriaceae bacterium* DC416] |
| 111 | ECC15254 | 138850366 | hypothetical protein GOS_5005338 [marine metagenome] |
| 112 | EBF96527 | 135173721 | hypothetical protein GOS_9511771 [marine metagenome] |
| 113 | AAZ73130 | 72536062 | phytoene desaturase [*Enterobacteriaceae bacterium* DC260] |
| 114 | AAW72814 | 92430259 | CrtI [*Pantoea* sp. C1B1Y] |
| 115 | EBF63722 | 135122709 | hypothetical protein GOS_9565260 [marine metagenome] |
| 116 | EDJ33653 | 144164568 | hypothetical protein GOS_1713484 [marine metagenome] |
| 117 | BAB79603 | 18143448 | crtI [*Pantoea agglomerans* pv. *milletiae*] |
| 118 | AAZ73136 | 72536069 | phytoene desaturase [*Enterobacteriaceae bacterium* DC404] |
| 119 | ABD73281 | 89475493 | phytoene dehydrogenase [*Pantoea agglomerans*] |
| 120 | AAF78201 | 8650417 | phytoene desaturase [*Bradyrhizobium* sp. ORS278] |
| 121 | ZP_010 . . . | 84704558 | phytoene dehydrogenase (phytoene desaturase) [*Parvularcula bermudensis* HTCC2503] |
| 122 | EBF30985 | 135071529 | hypothetical protein GOS_9618780 [marine metagenome] |
| 123 | EDJ11107 | 144133947 | hypothetical protein GOS_1752989 [marine metagenome] |
| 124 | YP_001 . . . | 146284185 | phytoene desaturase [*Pseudomonas stutzeri* A1501] |
| 125 | EDB39933 | 142902995 | hypothetical protein GOS_1830750 [marine metagenome] |
| 126 | ZP_013 . . . | 94496006 | amine oxidase [*Sphingomonas* sp. SKA58] |
| 127 | P22871 | 117514 | Phytoene dehydrogenase (Phytoene desaturase) |
| 128 | ECD12151 | 139058277 | hypothetical protein GOS_4688757 [marine metagenome] |
| 129 | AAA64981 | 551855 | phytoene dehydrogenase [*Pantoea agglomerans*] |
| 130 | ECS36705 | 141558903 | hypothetical protein GOS_4990354 [marine metagenome] |
| 131 | ECJ26724 | 140055135 | hypothetical protein GOS_5004115 [marine metagenome] |
| 132 | ECY06051 | 142435846 | hypothetical protein GOS_2424849 [marine metagenome] |
| 133 | ZP_007 . . . | 76261240 | Amine oxidase: FAD dependent oxidoreductase [*Chloroflexus aurantiacus* J-10-fl] |
| 134 | BAD99408 | 67003497 | phytoene desaturase [*Brevundimonas* sp. SD212] |
| 135 | ZP_015 . . . | 118048084 | amine oxidase [*Chloroflexus aggregans* DSM 9485] |
| 136 | EAS49801 | 90336053 | phytoene dehydrogenase [*Aurantimonas* sp. SI85-9A1] |
| 137 | EDF88410 | 143616932 | hypothetical protein GOS_877736 [marine metagenome] |
| 138 | AAN85599 | 27228293 | Phytoene Desaturase [*Pantoea stewartii*] |
| 139 | EDI65706 | 144070706 | hypothetical protein GOS_395761 [marine metagenome] |
| 140 | AAA21263 | 148397 | phytoene dehydrogenase [*Pantoea agglomerans*] |
| 141 | P21685 | 117515 | Phytoene dehydrogenase (Phytoene desaturase) |
| 142 | AAZ73149 | 72536084 | phytoene desaturase [*Enterobacteriaceae bacterium* DC413] |
| 143 | ZP_016 . . . | 119476622 | phytoene dehydrogenase [marine gamma proteobacterium HTCC2143] |
| 144 | ABL97778 | 119713729 | crtI phytoene dehydrogenase [uncultured marine bacterium HF10_29C11] |
| 145 | ABL97829 | 119713781 | crtI/crtB [uncultured marine bacterium HF10_49E08] |
| 146 | EDB02259 | 142846369 | hypothetical protein GOS_1894993 [marine metagenome] |
| 147 | ECQ63324 | 141245988 | hypothetical protein GOS_4882732 [marine metagenome] |
| 148 | EAS48195 | 90333025 | phytoene dehydrogenase [marine gamma proteobacterium HTCC2207] |
| 149 | EAU13549 | 113732481 | Amine oxidase: FAD dependent oxidoreductase [*Caulobacter* sp. K31] |

TABLE 17b-continued

Examples of phytoene dehydrogenase polypeptides.

| Row | Accession | GI | Protein Description |
|---|---|---|---|
| 150 | ECV72481 | 142118377 | hypothetical protein GOS_2846587 [marine metagenome] |
| 151 | ECZ41342 | 142625145 | hypothetical protein GOS_2188322 [marine metagenome] |
| 152 | EDF61582 | 143556399 | hypothetical protein GOS_924048 [marine metagenome] |
| 153 | EBN79105 | 136382241 | hypothetical protein GOS_8187951 [marine metagenome] |
| 154 | YP_001 . . . | 156974447 | hypothetical protein VIBHAR_02162 [*Vibrio harveyi* ATCC BAA-1116] |
| 155 | BAA20276 | 2130971 | phytoene desaturase [*Erythrobacter longus*] |
| 156 | EBC81369 | 134685202 | hypothetical protein GOS_10270 [marine metagenome] |
| 157 | ECS97023 | 141726243 | hypothetical protein GOS_8923124 [marine metagenome] |
| 158 | ECY38926 | 142480300 | hypothetical protein GOS_2368541 [marine metagenome] |
| 159 | YP_632230 | 108758926 | putative phytoene dehydrogenase [*Myxococcus xanthus* DK 1622] |
| 160 | EDB72930 | 142948834 | hypothetical protein GOS_1603748 [marine metagenome] |
| 161 | EDJ54243 | 144192357 | hypothetical protein GOS_1677113 [marine metagenome] |
| 162 | EAR55130 | 89049570 | phytoene dehydrogenase [*Photobacterium* sp. SKA34] |
| 163 | EDF01226 | 143447606 | hypothetical protein GOS_1030671 [marine metagenome] |
| 164 | EDD12651 | 143142675 | hypothetical protein GOS_1354831 [marine metagenome] |
| 165 | EDI08258 | 143990952 | hypothetical protein GOS_491661 [marine metagenome] |
| 166 | EDI22441 | 144010457 | hypothetical protein GOS_467843 [marine metagenome] |
| 167 | ABF54837 | 98978686 | amine oxidase [*Sphingopyxis alaskensis* RB2256] |
| 168 | EBL74107 | 136074962 | hypothetical protein GOS_8521797 [marine metagenome] |
| 169 | EBX98247 | 138142760 | hypothetical protein GOS_6427327 [marine metagenome] |
| 170 | ECV76618 | 142124100 | hypothetical protein GOS_2839194 [marine metagenome] |
| 171 | EBP18308 | 136596794 | hypothetical protein GOS_7953009 [marine metagenome] |
| 172 | YP_265547 | 71082828 | phytoene dehydrogenase [*Candidatus Pelagibacter ubique* HTCC1062] |
| 173 | EAS85201 | 91718551 | phytoene dehydrogenase [*Candidatus Pelagibacter ubique* HTCC1002] |
| 174 | EDG91241 | 143827295 | hypothetical protein GOS_699208 [marine metagenome] |
| 175 | ECV24805 | 142059343 | hypothetical protein GOS_2935833 [marine metagenome] |
| 176 | AAY87313 | 68164584 | predicted phytoene desaturase [uncultured bacterium BAC17H8] |
| 177 | EBD43768 | 134788236 | hypothetical protein GOS_9929916 [marine metagenome] |
| 178 | EDG35515 | 143701587 | hypothetical protein GOS_796054 [marine metagenome] |
| 179 | ZP_018 . . . | 149185744 | Phytoene dehydrogenase [*Erythrobacter* sp. SD-21] |
| 180 | ABL60986 | 119094156 | phytoene dehydrogenase CrtI [uncultured marine bacterium HF10_19P19] |
| 181 | ECZ18273 | 142592252 | hypothetical protein GOS_2227647 [marine metagenome] |
| 182 | ABD26256 | 87135514 | amine oxidase [*Novosphingobium aromaticivorans* DSM 12444] |
| 183 | EDG45712 | 143723898 | hypothetical protein GOS_778645 [marine metagenome] |
| 184 | EBE76519 | 134988930 | hypothetical protein GOS_9708797 [marine metagenome] |
| 185 | EDC75856 | 143092398 | hypothetical protein GOS_1419598 [marine metagenome] |
| 186 | EDF35075 | 143504771 | hypothetical protein GOS_970643 [marine metagenome] |
| 187 | ZP_014 . . . | 114771897 | phytoene dehydrogenase [alpha proteobacterium HTCC2255] |
| 188 | EDG12368 | 143659594 | hypothetical protein GOS_836451 [marine metagenome] |
| 189 | AAT90320 | 50952787 | putative phytoene dehydrogenase [uncultured proteobacterium eBACred25D05] |
| 190 | EBV02567 | 137608266 | hypothetical protein GOS_6968229 [marine metagenome] |
| 191 | ECB29435 | 138684670 | hypothetical protein GOS_4941392 [marine metagenome] |
| 192 | EDI67354 | 144073017 | hypothetical protein GOS_393156 [marine metagenome] |
| 193 | AAY78594 | 67633343 | predicted phytoene dehydrogenase [uncultured bacterium MedeBAC82F10] |
| 194 | ECY07797 | 142438219 | hypothetical protein GOS_2421570 [marine metagenome] |
| 195 | EDI16519 | 144002234 | hypothetical protein GOS_477455 [marine metagenome] |
| 196 | EDH58504 | 143920724 | hypothetical protein GOS_579102 [marine metagenome] |
| 197 | EAU52387 | 114549505 | phytoene dehydrogenase CrtI [alpha proteobacterium HTCC2255] |
| 198 | ECX42733 | 142346738 | hypothetical protein GOS_2540243 [marine metagenome] |
| 199 | EBE06505 | 134884139 | hypothetical protein GOS_9826927 [marine metagenome] |
| 200 | EDB92338 | 142976670 | hypothetical protein GOS_1568269 [marine metagenome] |
| 201 | EBN30363 | 136310418 | hypothetical protein GOS_8268666 [marine metagenome] |

TABLE 18

Examples of phytoene synthase and lycopene cyclase polypeptides.

| Accession Number | GI Number | Description |
|---|---|---|
| 1613414C | 227040 | crtB gene |
| A49558 | 1076590 | phytoene synthase 2 precursor - tomato (fragment) |
| AAA19428 | 506623 | phytoene synthase [*Neurospora crassa*] |
| AAA32836 | 413732 | phytoene synthase |
| AAA64982 | 148413 | phytoene synthase [*Pantoea agglomerans*] |
| AAB87738 | 29893495 | phytoene synthase [*Rubrivivax gelatinosus*] |
| AAC44849 | 1842243 | phytoene synthase |

TABLE 18-continued

Examples of phytoene synthase and lycopene cyclase polypeptides.

| Accession Number | GI Number | Description |
|---|---|---|
| AAD38051 | 13542332 | phytoene synthase [*Citrus* × *paradisi*] |
| AAF78202 | 8650418 | phytoene synthase [*Bradyrhizobium* sp. ORS278] |
| AAF82616 | 9081847 | phytoene synthase [*Tagetes erecta*] |
| AAG10427 | 9971814 | phytoene synthase [*Tagetes erecta*] |
| AAG28701 | 11066678 | CrtB [*Streptomyces griseus*] |
| AAK07734 | 18476085 | phytoene synthase [*Oryza sativa* (*japonica* cultivar-group)] |
| AAK07735 | 18476089 | phytoene synthase [*Oryza sativa* (*japonica* cultivar-group)] |
| AAK15621 | 13195243 | phytoene synthase [*Haematococcus pluvialis*] |
| AAL02001 | 15553721 | phytoene synthase [*Xanthobacter* sp. Py2] |
| AAL76346 | 18645045 | phytoene synthase [uncultured proteobacterium] |
| AAL82578 | 21326700 | phytoene synthase radicle isoform [*Oryza sativa* (*indica* cultivar-group)] |
| AAM45379 | 21360353 | phytoene synthase [*Tagetes erecta*] |
| AAM48647 | 21328641 | phytoene synthase [uncultured proteobacterium] |
| AAM62787 | 21553694 | phytoene synthase [*Arabidopsis thaliana*] |
| AAM94363 | 22296799 | phytoene synthase [*Agromyces mediolanus*] |
| AAN85600 | 27228294 | Phytoene Synthase [*Pantoea stewartii*] |
| AAO24767 | 27903500 | phytoene synthase [*Citrus maxima*] |
| AAO39835 | 28403302 | phytoene synthase [*Citrus sinensis*] |
| AAO46895 | 37729028 | lycopene cyclase/phytoene synthase [*Blakeslea trispora*] |
| AAO47570 | 33465823 | phytoene-beta carotene synthase [*Xanthophyllomyces dendrorhous*] |
| AAO73816 | 33465821 | crtYB [*Xanthophyllomyces dendrorhous*] |
| AAP22038 | 30349414 | phytoene synthase 2 [*Zea mays*] |
| AAP55451 | 32350232 | phytoene synthase 2 [*Zea mays*] |
| AAP55453 | 32350236 | phytoene synthase 2 [*Zea mays*] |
| AAP55461 | 32350252 | phytoene synthase 2 [*Zea mays*] |
| AAP55471 | 32350272 | phytoene synthase 2 [*Zea mays*] |
| AAP55484 | 32350298 | phytoene synthase 2 [*Zea mays*] |
| AAP55486 | 32350302 | phytoene synthase 2 [*Zea mays*] |
| AAP56083 | 32349564 | phytoene synthase [*Zea mays*] |
| AAP56124 | 32349646 | phytoene synthase [*Zea mays*] |
| AAP56127 | 32349652 | phytoene synthase [*Zea mays*] |
| AAP56136 | 32349670 | phytoene synthase [*Zea mays*] |
| AAP56148 | 32349694 | phytoene synthase [*Zea mays*] |
| AAP56155 | 32349708 | phytoene synthase [*Zea mays*] |
| AAP56156 | 32349710 | phytoene synthase [*Zea mays*] |
| AAP56157 | 32349712 | phytoene synthase [*Zea mays*] |
| AAP56158 | 32349714 | phytoene synthase [*Zea mays*] |
| AAP79176 | 32307542 | phytoene synthase [*Bigelowiella natans*] |
| AAQ91837 | 37499616 | phytoene synthase 2 [*Zea mays*] |
| AAR08445 | 38037628 | chloroplast phytoene synthase 1 [*Zea mays*] |
| AAR31885 | 39842609 | chloroplast phytoene synthase [*Zea mays*] |
| AAR37803 | 40062932 | phytoene synthase [uncultured bacterium 442] |
| AAR37856 | 40062986 | phytoene synthase [uncultured bacterium 443] |
| AAR86104 | 40456029 | phytoene synthase [*Momordica charantia* var. *abbreviata*] |
| AAR87868 | 40557193 | phytoene synthase [*Oncidium* cv. ‘Gower Ramsey’] |
| AAR98492 | 41018901 | phytoene synthase [*Bradyrhizobium* sp. ORS278] |
| AAS02284 | 41394357 | phytoene synthase 2 [*Zea mays*] |
| AAS17009 | 42491736 | phytoene synthase 2 [*Oryza sativa* (*japonica* cultivar-group)] |
| AAS18307 | 42521626 | phytoene synthase 1; PSY1 [*Oryza sativa* (*indica* cultivar-group)] |
| AAT28184 | 47498515 | phytoene synthase [*Dunaliella salina*] |
| AAT35222 | 47531118 | fusion of carotene synthesis proteins [synthetic construct] |
| AAT38473 | 47779181 | chloroplast phytoene synthase precursor [*Chlamydomonas reinhardtii*] |
| AAT46069 | 48686711 | phytoene synthase [*Dunaliella salina*] |
| AAT74581 | 50313418 | PSY [*Citrus sinensis*] |
| AAT90319 | 50952786 | putative phytoene synthase [uncultured proteobacterium eBACred25D05] |
| AAV74394 | 56122551 | phytoene synthase [*Adonis palaestina*] |
| AAW23162 | 56698928 | phytoene synthase [*Rhodococcus erythropolis*] |
| AC2035 | 25366683 | phytoene synthase [imported] - *Nostoc* sp. (strain PCC 7120) |
| AC2035 | 25366683 | phytoene synthase [imported] - *Nostoc* sp. (strain PCC 7120) |
| BAB18514 | 11344507 | phytoene synthase [*Citrus unshiu*] |
| BAB79604 | 18143449 | crtB [*Pantoea agglomerans* pv. *milletiae*] |
| BAD07278 | 40809739 | phytoene synthase [*Citrus sinensis*] |
| BAD07286 | 40809755 | phytoene synthase [*Citrus limon*] |
| BAD62106 | 54291340 | phytoene synthase [*Oryza sativa* (*japonica* cultivar-group)] |
| BAD62107 | 54291341 | phytoene synthase-like [*Oryza sativa* (*japonica* cultivar-group)] |
| C90061 | 25506636 | squalene desaturase [imported] - *Staphylococcus aureus* (strain N315) |
| CAA47625 | 19347 | mutant phytoene synthase [*Lycopersicon esculentum*] |
| CAA68575 | 19341 | unnamed protein product [*Lycopersicon esculentum*] |
| CAB07958 | 1934837 | unknown [*Bacillus subtilis*] |
| CAB38740 | 4490590 | phytoene synthase [*Rhodobacter sphaeroides*] |
| CAB51949 | 5690074 | phytoene-beta carotene synthase [*Xanthophyllomyces dendrorhous*] |

TABLE 18-continued

Examples of phytoene synthase and lycopene cyclase polypeptides.

| Accession Number | GI Number | Description |
|---|---|---|
| CAB56063 | 5912296 | phytoene synthase [*Paracoccus marcusii*] |
| CAB86388 | 7453011 | phytoene synthase/lycopene cyclase [*Phycomyces blakesleeanus*] |
| CAB93661 | 8250520 | lycopene cyclase/phytoene synthase [*Phycomyces blakesleeanus*] |
| CAB94795 | 8574392 | phytoene synthase [*Mycobacterium aurum*] |
| CAC19567 | 11990226 | phytoene synthase [*Helianthus annuus*] |
| CAC27383 | 12584564 | phytoene synthase [*Helianthus annuus*] |
| CAD19988 | 18307500 | carotene cyclase [*Gibberella fujikuroi*] |
| CAD29284 | 57282088 | putative phytoene synthase [*Oryza sativa*] |
| CAE76609 | 38567321 | geranylgeranyl-diphosphate geranylgeranyltransferase (AL-2) [*Neurospora crassa*] |
| E37802 | 95606 | crtB protein - *Erwinia uredovora* |
| E84320 | 25410251 | phytoene synthase [imported] - *Halobacterium* sp. NRC-1 |
| EAA98758 | 42863045 | unknown [environmental sequence] |
| EAB01965 | 42869439 | unknown [environmental sequence] |
| EAB04170 | 42873822 | unknown [environmental sequence] |
| EAB07138 | 42879858 | unknown [environmental sequence] |
| EAB09791 | 42885235 | unknown [environmental sequence] |
| EAB19826 | 42905452 | unknown [environmental sequence] |
| EAB35029 | 42936011 | unknown [environmental sequence] |
| EAB41375 | 42948740 | unknown [environmental sequence] |
| EAB78706 | 43024004 | unknown [environmental sequence] |
| EAB92586 | 43052355 | unknown [environmental sequence] |
| EAC06949 | 43081493 | unknown [environmental sequence] |
| EAC18360 | 43104624 | unknown [environmental sequence] |
| EAC25793 | 43119723 | unknown [environmental sequence] |
| EAC29883 | 43128092 | unknown [environmental sequence] |
| EAC32813 | 43133973 | unknown [environmental sequence] |
| EAC33105 | 43134560 | unknown [environmental sequence] |
| EAC38486 | 43145552 | unknown [environmental sequence] |
| EAC52233 | 43173313 | unknown [environmental sequence] |
| EAC60029 | 43189028 | unknown [environmental sequence] |
| EAC68026 | 43204953 | unknown [environmental sequence] |
| EAC96197 | 43261031 | unknown [environmental sequence] |
| EAD08701 | 43285745 | unknown [environmental sequence] |
| EAD20866 | 43310220 | unknown [environmental sequence] |
| EAD32755 | 43334458 | unknown [environmental sequence] |
| EAD38008 | 43345761 | unknown [environmental sequence] |
| EAD50152 | 43370658 | unknown [environmental sequence] |
| EAD50402 | 43371147 | unknown [environmental sequence] |
| EAD81123 | 43452903 | unknown [environmental sequence] |
| EAD93882 | 43478303 | unknown [environmental sequence] |
| EAE12860 | 43516265 | unknown [environmental sequence] |
| EAE16121 | 43522884 | unknown [environmental sequence] |
| EAE31084 | 43552634 | unknown [environmental sequence] |
| EAE35665 | 43561764 | unknown [environmental sequence] |
| EAE44717 | 43579862 | unknown [environmental sequence] |
| EAE46627 | 43583580 | unknown [environmental sequence] |
| EAE47846 | 43586023 | unknown [environmental sequence] |
| EAE72264 | 43635190 | unknown [environmental sequence] |
| EAE76009 | 43642573 | unknown [environmental sequence] |
| EAE86335 | 43662748 | unknown [environmental sequence] |
| EAE89581 | 43669163 | unknown [environmental sequence] |
| EAF18881 | 43728007 | unknown [environmental sequence] |
| EAF64277 | 43819669 | unknown [environmental sequence] |
| EAF67931 | 43827263 | unknown [environmental sequence] |
| EAF84745 | 43861327 | unknown [environmental sequence] |
| EAF94004 | 43880040 | unknown [environmental sequence] |
| EAG06083 | 43903395 | unknown [environmental sequence] |
| EAG21950 | 43933540 | unknown [environmental sequence] |
| EAG43625 | 43973477 | unknown [environmental sequence] |
| EAG50171 | 43985555 | unknown [environmental sequence] |
| EAG57517 | 43999205 | unknown [environmental sequence] |
| EAG62787 | 44009110 | unknown [environmental sequence] |
| EAG65580 | 44014171 | unknown [environmental sequence] |
| EAG68110 | 44018715 | unknown [environmental sequence] |
| EAG72283 | 44026322 | unknown [environmental sequence] |
| EAG78750 | 44037938 | unknown [environmental sequence] |
| EAG80445 | 44041116 | unknown [environmental sequence] |
| EAG93220 | 44064453 | unknown [environmental sequence] |
| EAH04927 | 44085694 | unknown [environmental sequence] |
| EAH08972 | 44093217 | unknown [environmental sequence] |
| EAH10377 | 44095788 | unknown [environmental sequence] |
| EAH22151 | 44117864 | unknown [environmental sequence] |
| EAH31461 | 44134654 | unknown [environmental sequence] |
| EAH50033 | 44169323 | unknown [environmental sequence] |

TABLE 18-continued

Examples of phytoene synthase and lycopene cyclase polypeptides.

| Accession Number | GI Number | Description |
|---|---|---|
| EAH64480 | 44196848 | unknown [environmental sequence] |
| EAH79040 | 44223009 | unknown [environmental sequence] |
| EAH99976 | 44255671 | unknown [environmental sequence] |
| EAI02786 | 44259828 | unknown [environmental sequence] |
| EAI02787 | 44259829 | unknown [environmental sequence] |
| EAI03575 | 44260943 | unknown [environmental sequence] |
| EAI05900 | 44264266 | unknown [environmental sequence] |
| EAI61004 | 44344824 | unknown [environmental sequence] |
| EAI70669 | 44358327 | unknown [environmental sequence] |
| EAI83938 | 44377067 | unknown [environmental sequence] |
| EAJ05110 | 44406802 | unknown [environmental sequence] |
| EAJ05569 | 44407471 | unknown [environmental sequence] |
| EAJ08876 | 44412338 | unknown [environmental sequence] |
| EAJ35156 | 44449986 | unknown [environmental sequence] |
| EAJ38900 | 44455130 | unknown [environmental sequence] |
| EAJ49645 | 44470504 | unknown [environmental sequence] |
| EAJ54357 | 44477026 | unknown [environmental sequence] |
| EAJ60475 | 44485647 | unknown [environmental sequence] |
| EAJ64125 | 44492007 | unknown [environmental sequence] |
| EAJ67499 | 44497025 | unknown [environmental sequence] |
| EAJ76471 | 44510405 | unknown [environmental sequence] |
| EAJ76950 | 44511114 | unknown [environmental sequence] |
| EAJ78637 | 44513596 | unknown [environmental sequence] |
| EAJ78787 | 44513824 | unknown [environmental sequence] |
| EAJ79616 | 44515082 | unknown [environmental sequence] |
| EAJ80356 | 44516200 | unknown [environmental sequence] |
| EAJ81914 | 44518489 | unknown [environmental sequence] |
| EAJ87417 | 44526623 | unknown [environmental sequence] |
| EAK08514 | 44557109 | unknown [environmental sequence] |
| EAK08523 | 44557119 | unknown [environmental sequence] |
| EAK12901 | 44563097 | unknown [environmental sequence] |
| EAK22180 | 44576315 | unknown [environmental sequence] |
| EAK24859 | 44580262 | unknown [environmental sequence] |
| EAK28345 | 44585276 | unknown [environmental sequence] |
| EAK34732 | 44594324 | unknown [environmental sequence] |
| EAK34736 | 44594329 | unknown [environmental sequence] |
| EAK37296 | 44597942 | unknown [environmental sequence] |
| EAK37521 | 44598256 | unknown [environmental sequence] |
| EAK56335 | 44624430 | unknown [environmental sequence] |
| G84363 | 25410528 | hypothetical protein ggt [imported] - *Halobacterium* sp. NRC-1 |
| NP_274195 | 15677043 | phytoene synthase, putative [*Neisseria meningitidis* MC58] |
| NP_284085 | 15794263 | poly-isoprenyl transferase [*Neisseria meningitidis* Z2491] |
| NP_294586 | 15805888 | phytoene synthase [*Deinococcus radiodurans* R1] |
| NP_388961 | 16078144 | hypothetical protein BSU10810 [*Bacillus subtilis* subsp. *subtilis* str. 168] |
| NP_441168 | 16330440 | phytoene synthase [*Synechocystis* sp. PCC 6803] |
| NP_443763 | 16519643 | Y4aC [*Rhizobium* sp. NGR234] |
| NP_624523 | 21218744 | putative phytoene synthase [*Streptomyces coelicolor* A3(2)] |
| NP_630832 | 21225053 | putative phytoene synthase [*Streptomyces coelicolor* A3(2)] |
| NP_662273 | 21674208 | phytoene desaturase [*Chlorobium tepidum* TLS] |
| NP_682350 | 22299103 | phytoene synthase [*Thermosynechococcus elongatus* BP-1] |
| NP_693381 | 23099915 | phytoene synthase [*Oceanobacillus iheyensis* HTE831] |
| NP_786525 | 28379633 | phytoene synthase [*Lactobacillus plantarum* WCFS1] |
| NP_822199 | 29827565 | phytoene synthase [*Streptomyces avermitilis* MA-4680] |
| NP_822829 | 29828195 | squalene/phytoene synthase [*Streptomyces avermitilis* MA-4680] |
| NP_851527 | 30795077 | putative phytoene synthase [*Streptomyces rochei*] |
| NP_868799 | 32475805 | probable phytoene synthase [*Rhodopirellula baltica* SH 1] |
| NP_874560 | 33239618 | Phytoene synthase, CrtB [*Prochlorococcus marinus* subsp. *marinus* str. CCMP1375] |
| NP_879992 | 33592348 | putative phytoene synthase [*Bordetella pertussis* Tohama I] |
| NP_884101 | 33596458 | putative phytoene synthase [*Bordetella parapertussis* 12822] |
| NP_889809 | 33602249 | putative phytoene synthase [*Bordetella bronchiseptica* RB50] |
| NP_892264 | 33860703 | Squalene and phytoene synthases [*Prochlorococcus marinus* subsp. *pastoris* str. CCMP1986] |
| NP_895828 | 33864268 | Squalene and phytoene synthases [*Prochlorococcus marinus* str. MIT 9313] |
| NP_898345 | 33866786 | phytoene synthases [*Synechococcus* sp. WH 8102] |
| NP_902648 | 34498433 | probable geranylgeranyl-diphosphate geranylgeranyltransferase [*Chromobacterium violaceum* ATCC 12472 |
| NP_902649 | 34498434 | probable phytoene synthase-related protein [*Chromobacterium violaceum* ATCC 12472] |
| NP_924690 | 37521313 | phytoene synthase [*Gloeobacter violaceus* PCC 7421] |
| NP_931516 | 37528171 | phytoene synthase [*Photorhabdus luminescens* subsp. *laumondii* TTO1] |

TABLE 18-continued

Examples of phytoene synthase and lycopene cyclase polypeptides.

| Accession Number | GI Number | Description |
|---|---|---|
| NP_946861 | 39934585 | CrtB phytoene synthase [*Rhodopseudomonas palustris* CGA009] |
| NP_949079 | 39936803 | putative poly-isoprenyl transferase [*Rhodopseudomonas palustris* CGA009] |
| NP_962005 | 41409169 | hypothetical protein MAP3071 [*Mycobacterium avium* subsp. *paratuberculosis* str. k10] |
| NP_968601 | 42523221 | phytoene synthase [*Bdellovibrio bacteriovorus* HD100] |
| O07333 | 3913360 | Phytoene synthase |
| P08196 | 585746 | Phytoene synthase 1, chloroplast precursor (Fruit ripening specific protein pTOM5) |
| P21683 | 30923192 | Phytoene synthase |
| P37269 | 585009 | Phytoene synthase |
| P37271 | 27735222 | Phytoene synthase, chloroplast precursor |
| P37272 | 585749 | Phytoene synthase, chloroplast precursor |
| P53797 | 1709885 | Phytoene synthase, chloroplast precursor |
| P54975 | 1706137 | Phytoene synthase |
| P54977 | 1706139 | Phytoene synthase |
| P65860 | 54041032 | Probable phytoene synthase |
| Q9SSU8 | 8928282 | Phytoene synthase, chloroplast precursor |
| Q9UUQ6 | 34922667 | CarRP protein [Includes: Lycopene cyclase; Phytoene synthase] |
| S22474 | 7489041 | phytoene synthase (EC 2.5.1.—) - tomato |
| S32170 | 321671 | phytoene synthetase - *Myxococcus xanthus* |
| S52587 | 1073300 | prephytoene pyrophosphate synthase - *Erwinia herbicola* |
| S56668 | 2129505 | geranylgeranyl-diphosphate geranylgeranyltransferase (EC 2.5.1.32) precursor - muskmelon |
| S68307 | 2130144 | phytoene synthase - maize |
| T10702 | 7484346 | phytoene synthase (EC 2.5.1.—) - green alga (*Dunaliella bardawil*) |
| T46594 | 11291807 | phytoene synthase (EC 2.5.1.—) [validated] - *Mycobacterium marinum* |
| T50746 | 11356347 | phytoene synthase (EC 2.5.1.—) [imported] - *Rhodobacter sphaeroides* |
| T50895 | 11291816 | prephytoene pyrophosphate synthase [imported] - *Rubrivivax gelatinosus* |
| XP_324765 | 32408567 | PHYTOENE SYNTHASE [*Neurospora crassa*] |
| XP_383242 | 46114448 | hypothetical protein FG03066.1 [*Gibberella zeae* PH-1] |
| XP_403902 | 49080862 | hypothetical protein UM06287.1 [*Ustilago maydis* 521] |
| YP_006040 | 46255128 | phytoene synthase [*Thermus thermophilus* HB27] |
| YP_103126 | 53723680 | phytoene synthase, putative [*Burkholderia mallei* ATCC 23344] |
| YP_112342 | 53723357 | squalene/phytoene synthase [*Burkholderia pseudomallei* K96243] |
| YP_117945 | 54023703 | putative phytoene synthase [*Nocardia farcinica* IFM 10152] |
| YP_120611 | 54026369 | putative phytoene synthase [*Nocardia farcinica* IFM 10152] |
| YP_136628 | 55378778 | lycopene cyclase [*Haloarcula marismortui* ATCC 43049] |
| YP_136629 | 55378779 | phytoene synthase [*Haloarcula marismortui* ATCC 43049] |
| YP_145340 | 55978284 | phytoene synthase [*Thermus thermophilus* HB8] |
| YP_145343 | 55978287 | phytoene synthase-related protein [*Thermus thermophilus* HB8] |
| YP_160917 | 56479328 | probable terpenoid synthase-related protein [*Azoarcus* sp. EbN1] |
| YP_160918 | 56479329 | putative terpenoid synthase [*Azoarcus* sp. EbN1] |
| YP_162605 | 56551766 | phytoene/squalene synthetase [*Zymomonas mobilis* subsp. *mobilis* ZM4] |
| YP_172822 | 56752121 | phytoene synthase [*Synechococcus elongatus* PCC 6301] |
| YP_187369 | 57652299 | dehydrosqualene synthase [*Staphylococcus aureus* subsp. *aureus* COL] |
| YP_192648 | 58040684 | Putative phytoene synthase [*Gluconobacter oxydans* 621H] |
| ZP_000044 | 22956752 | COG1562: Phytoene/squalene synthetase [*Rhodobacter sphaeroides* 2.4.1] |
| ZP_001091 | 53688068 | COG1562: Phytoene/squalene synthetase [*Nostoc punctiforme* PCC 73102] |
| ZP_001591 | 53763709 | COG1562: Phytoene/squalene synthetase [*Anabaena variabilis* ATCC 29413] |
| ZP_001657 | 45514234 | COG1562: Phytoene/squalene synthetase [*Ralstonia eutropha* JMP134] |
| ZP_001690 | 46132223 | COG1562: Phytoene/squalene synthetase [*Ralstonia eutropha* JMP134] |
| ZP_001746 | 45523280 | COG1562: Phytoene/squalene synthetase [*Crocosphaera watsonii* WH 8501] |
| ZP_001837 | 53771530 | COG1562: Phytoene/squalene synthetase [*Exiguobacterium* sp. 255-15] |
| ZP_001867 | 45546711 | COG1562: Phytoene/squalene synthetase [*Rubrobacter xylanophilus* DSM 9941] |
| ZP_002096 | 46204978 | COG1562: Phytoene/squalene synthetase [*Magnetospirillum magnetotacticum* MS-1] |
| ZP_002248 | 46324513 | COG1562: Phytoene/squalene synthetase [*Burkholderia cepacia* R1808] |
| ZP_002450 | 47575031 | COG1562: Phytoene/squalene synthetase [*Rubrivivax gelatinosus* PM1] |
| ZP_002680 | 48763469 | COG1562: Phytoene/squalene synthetase [*Rhodospirillum rubrum*] |
| ZP_002710 | 48766450 | COG1562: Phytoene/squalene synthetase [*Rhodospirillum rubrum*] |

TABLE 18-continued

| Examples of phytoene synthase and lycopene cyclase polypeptides. | | |
|---|---|---|
| Accession Number | GI Number | Description |
| ZP_002791 | 48782680 | COG1562: Phytoene/squalene synthetase [*Burkholderia fungorum* LB400] |
| ZP_002892 | 48832182 | COG1562: Phytoene/squalene synthetase [*Magnetococcus* sp. MC-1] |
| ZP_002916 | 48834623 | COG1562: Phytoene/squalene synthetase [*Thermobifida fusca*] |
| ZP_003036 | 48849426 | COG1562: Phytoene/squalene synthetase [*Novosphingobium aromaticivorans* DSM 12444] |
| ZP_003269 | 48893702 | COG1562: Phytoene/squalene synthetase [*Trichodesmium erythraeum* IMS101] |
| ZP_003351 | 52007802 | COG1562: Phytoene/squalene synthetase [*Thiobacillus denitrificans* ATCC 25259] |
| ZP_003487 | 53730362 | COG1562: Phytoene/squalene synthetase [*Dechloromonas aromatica* RCB] |
| ZP_003501 | 53759405 | COG1562: Phytoene/squalene synthetase [*Methylobacillus flagellatus* KT] |
| ZP_003591 | 53798896 | COG1562: Phytoene/squalene synthetase [*Chloroflexus aurantiacus*] |
| ZP_003628 | 54030691 | COG1562: Phytoene/squalene synthetase [*Polaromonas* sp. JS666] |

TABLE 19

| Examples of carotenoid ketolase polypeptides. | | |
|---|---|---|
| Accession Number | GI Number | Description |
| AAA99932 | 609575 | fatty acid desaturase |
| AAB48668 | 1870215 | ORF [*Emericella nidulans*] |
| AAC25611 | 2541936 | unknown [*Pseudomonas syringae*] |
| AAF78203 | 8650419 | beta-carotene ketolase [*Bradyrhizobium* sp. ORS278] |
| AAH16427 | 16741158 | 2210008A03Rik protein [*Mus musculus*] |
| AAN03484 | 22597194 | BKT [*Haematococcus pluvialis*] |
| AAN85497 | 26541510 | putative fatty acid desaturase [*Streptomyces atroolivaceus*] |
| AAN86030 | 33439708 | beta-carotene C4 oxygenase [*Brevundimonas aurantiaca*] |
| AAO64399 | 28976134 | putative beta-carotene ketolase [*Nodularia spumigena*] |
| AAQ23139 | 33621091 | CrtW/CrtY fusion protein [synthetic construct] |
| AAT35222 | 47531118 | fusion of carotene synthesis proteins [synthetic construct] |
| AAT35555 | 47558911 | beta-carotene ketolase [*Haematococcus pluvialis*] |
| AAV41372 | 55139370 | beta-carotene ketolase/oxygenase ['*Chlorella*' *zofingiensis*] |
| AB2307 | 25530134 | hypothetical protein alr4009 [imported] - *Nostoc* sp. (strain PCC 7120) |
| AF2204 | 25533132 | beta-carotene ketolase [imported] - *Nostoc* sp. (strain PCC 7120) |
| BAB54999 | 14028447 | mlr9395 [*Mesorhizobium loti* MAFF303099] |
| BAB58879 | 14270087 | membrane fatty acid desaturase [*Toxoplasma gondii*] |
| BAC98366 | 37360914 | alkane hydroxylase [*Alcanivorax borkumensis*] |
| CAA60478 | 2654318 | beta-carotene C-4 oxygenase (ketolase) [*Haematococcus pluvialis*] |
| CAB56059 | 5912292 | beta-carotene C-4-oxygenase (ketolase) [*Paracoccus marcusii*] |
| D87673 | 25398945 | conserved hypothetical protein CC3422 [imported] - *Caulobacter crescentus* |
| EAA79304 | 42823978 | unknown [environmental sequence] |
| EAA80363 | 42826055 | unknown [environmental sequence] |
| EAA81403 | 42828115 | unknown [environmental sequence] |
| EAA84711 | 42834481 | unknown [environmental sequence] |
| EAB82380 | 43031476 | unknown [environmental sequence] |
| EAB86624 | 43040184 | unknown [environmental sequence] |
| EAC05755 | 43079085 | unknown [environmental sequence] |
| EAD12219 | 43292778 | unknown [environmental sequence] |
| EAD71182 | 43427899 | unknown [environmental sequence] |
| EAD94927 | 43480380 | unknown [environmental sequence] |
| EAF11582 | 43712986 | unknown [environmental sequence] |
| EAF98072 | 43888329 | unknown [environmental sequence] |
| EAG19345 | 43928738 | unknown [environmental sequence] |
| EAG38273 | 43963688 | unknown [environmental sequence] |
| EAG79800 | 44039853 | unknown [environmental sequence] |
| EAG96474 | 44070318 | unknown [environmental sequence] |
| EAH00349 | 44077315 | unknown [environmental sequence] |
| EAH36448 | 44143633 | unknown [environmental sequence] |
| EAH40683 | 44151265 | unknown [environmental sequence] |
| EAH53180 | 44175316 | unknown [environmental sequence] |
| EAH96648 | 44250729 | unknown [environmental sequence] |
| EAI05260 | 44263397 | unknown [environmental sequence] |
| EAI17468 | 44281329 | unknown [environmental sequence] |
| EAI53009 | 44333409 | unknown [environmental sequence] |
| EAI54054 | 44334878 | unknown [environmental sequence] |

TABLE 19-continued

Examples of carotenoid ketolase polypeptides.

| Accession Number | GI Number | Description |
|---|---|---|
| EAI67818 | 44354362 | unknown [environmental sequence] |
| EAI68153 | 44354875 | unknown [environmental sequence] |
| EAI89684 | 44384943 | unknown [environmental sequence] |
| EAJ27674 | 44439188 | unknown [environmental sequence] |
| EAJ45589 | 44464684 | unknown [environmental sequence] |
| EAJ45589 | 44464684 | unknown [environmental sequence] |
| EAJ67118 | 44496466 | unknown [environmental sequence] |
| EAJ74221 | 44507022 | unknown [environmental sequence] |
| EAJ74653 | 44507662 | unknown [environmental sequence] |
| EAJ88396 | 44528064 | unknown [environmental sequence] |
| EAJ88887 | 44528792 | unknown [environmental sequence] |
| EAK06069 | 44553531 | unknown [environmental sequence] |
| EAK11467 | 44561166 | unknown [environmental sequence] |
| EAK16824 | 44568733 | unknown [environmental sequence] |
| EAK28828 | 44585942 | unknown [environmental sequence] |
| EAK28828 | 44585942 | unknown [environmental sequence] |
| EAK31112 | 44589271 | unknown [environmental sequence] |
| EAK42591 | 44605441 | unknown [environmental sequence] |
| NP_045063 | 11465545 | fatty-acid desaturase [*Cyanidium caldarium*] |
| NP_081575 | 27754029 | sphingolipid delta 4 desaturase/C-4 hydroxylase [*Mus musculus*] |
| NP_338204 | 15843167 | fatty acid desaturase, putative/ferredoxin reductase, electron transfer component [*Mycobacterium tuberculosis* CDC1551] |
| NP_440788 | 16330060 | b-carotene hydroxylase [*Synechocystis* sp. PCC 6803] |
| NP_441220 | 16330492 | hypothetical protein sl11611 [*Synechocystis* sp. PCC 6803] |
| NP_682690 | 22299443 | beta-carotene hydroxylase [*Thermosynechococcus elongatus* BP-1] |
| NP_770721 | 27379192 | hypothetical protein blr4081 [*Bradyrhizobium japonicum* USDA 110] |
| NP_848964 | 30468077 | beta-carotene hydroxylase [*Cyanidioschyzon merolae* strain 10D] |
| NP_857223 | 31794730 | POSSIBLE ELECTRON TRANSFER PROTEIN FDXB [*Mycobacterium bovis* AF2122/97] |
| NP_881760 | 33594116 | putative fatty acid desaturase [*Bordetella pertussis* Tohama I] |
| NP_882469 | 33594826 | putative fatty acid desaturase [*Bordetella parapertussis* 12822] |
| NP_886657 | 33599097 | putative fatty acid desaturase [*Bordetella bronchiseptica* RB50] |
| NP_895643 | 33864083 | beta carotene hydroxylase [*Prochlorococcus marinus* str. MIT 9313] |
| NP_896386 | 33864827 | beta-carotene hydroxylase [*Synechococcus* sp. WH 8102] |
| NP_897461 | 33865902 | possible beta-carotene ketolase [*Synechococcus* sp. WH 8102] |
| NP_924674 | 37521297 | beta-carotene ketolase [*Gloeobacter violaceus* PCC 7421] |
| NP_927525 | 37524181 | hypothetical protein plu0159 [*Photorhabdus luminescens* subsp. *laumondii* TTO1] |
| NP_947075 | 39934799 | Fatty acid desaturase family [*Rhodopseudomonas palustris* CGA009] |
| P54972 | 1706150 | Beta-carotene ketolase (Beta-carotene oxygenase) |
| Q39982 | 2498257 | Beta-carotene ketolase (Beta-carotene oxygenase) |
| Q44261 | 2498256 | Beta-carotene ketolase (Beta-carotene oxygenase) |
| T31123 | 11361063 | hypothetical protein 15 - *Sphingomonas aromaticivorans* plasmid pNL1 |
| XP_330780 | 32420673 | hypothetical protein [*Neurospora crassa*] |
| XP_368852 | 39974923 | hypothetical protein MG00392.4 [*Magnaporthe grisea* 70-15] |
| XP_380194 | 46102628 | hypothetical protein FG00018.1 [*Gibberella zeae* PH-1] |
| XP_383758 | 46115480 | hypothetical protein FG03582.1 [*Gibberella zeae* PH-1] |
| XP_405100 | 49086048 | hypothetical protein AN0963.2 [*Aspergillus nidulans* FGSC A4] |
| XP_409222 | 49095522 | hypothetical protein AN5085.2 [*Aspergillus nidulans* FGSC A4] |
| YP_102417 | 53725671 | alkane-1 monooxygenase [*Burkholderia mallei* ATCC 23344] |
| YP_108945 | 53719959 | putative alkane monooxygenase [*Burkholderia pseudomallei* K96243] |
| YP_132414 | 54302421 | hypothetical putative delta-9 fatty acid desaturase [*Photobacterium profundum* SS9] |
| YP_154670 | 56459389 | Fatty-acid desaturase [*Idiomarina loihiensis* L2TR] |
| YP_166682 | 56696325 | fatty acid desaturase family protein [*Silicibacter pomeroyi* DSS-3] |
| YP_168846 | 56698471 | fatty acid desaturase family protein [*Silicibacter pomeroyi* DSS-3] |
| YP_172377 | 56751676 | beta-carotene hydroxylase [*Synechococcus elongatus* PCC 6301] |
| ZP_001068 | 23124870 | COG3239: Fatty acid desaturase [*Nostoc punctiforme* PCC 73102] |
| ZP_001112 | 53688676 | COG3239: Fatty acid desaturase [*Nostoc punctiforme* PCC 73102] |
| ZP_001607 | 53764743 | COG3239: Fatty acid desaturase [*Anabaena variabilis* ATCC 29413] |
| ZP_001757 | 46118877 | COG3239: Fatty acid desaturase [*Crocosphaera watsonii* WH 8501] |
| ZP_001787 | 53736018 | COG3239: Fatty acid desaturase [*Crocosphaera watsonii* WH 8501] |
| ZP_002218 | 46321435 | COG3239: Fatty acid desaturase [*Burkholderia cepacia* R1808] |
| ZP_002456 | 47575608 | COG3239: Fatty acid desaturase [*Rubrivivax gelatinosus* PM1] |
| ZP_003028 | 48848557 | COG3239: Fatty acid desaturase [*Novosphingobium aromaticivorans* DSM 12444] |
| ZP_003107 | 48856640 | COG3239: Fatty acid desaturase [*Cytophaga hutchinsonii*] |
| ZP_003264 | 48893204 | COG3239: Fatty acid desaturase [*Trichodesmium erythraeum* IMS101] |
| ZP_003458 | 53688805 | hypothetical protein Npun02000865 [*Nostoc punctiforme* PCC 73102] |
| ZP_003513 | 53763576 | COG3239: Fatty acid desaturase [*Anabaena variabilis* ATCC 29413] |

TABLE 20

| Examples of carotenoid hydroxylase polypeptides. | | |
|---|---|---|
| Accession Number | GI Number | Description |
| AAC44852 | 1842246 | b-carotene hydroxylase |
| AAC49443 | 1575296 | beta-carotene hydroxylase [*Arabidopsis thaliana*] |
| AAD54243 | 5852870 | carotenoid hydroxylase [*Haematococcus pluvialis*] |
| AAG10430 | 9971820 | beta hydroxylase [*Tagetes erecta*] |
| AAG10793 | 9988836 | beta-carotene hydroxylase [*Citrus unshiu*] |
| AAG33636 | 11245486 | beta-carotene hydroxylase [*Citrus unshiu*] |
| AAL80006 | 19071768 | beta carotene hydroxylase [*Sandersonia aurantiaca*] |
| AAM44971 | 21280903 | putative beta-carotene hydroxylase [*Arabidopsis thaliana*] |
| AAM51300 | 21436107 | putative beta-carotene hydroxylase [*Arabidopsis thaliana*] |
| AAM77007 | 21734857 | beta-carotene hydroxylase [*Vitis vinifera*] |
| AAN85601 | 27228295 | Beta-Carotene Hydroxylase [*Pantoea stewartii*] |
| AAO53295 | 28911949 | carotenoid hydroxylase [*Haematococcus pluvialis*] |
| AAS48097 | 44887642 | beta-carotene hydroxylase [*Citrus sinensis*] |
| AAS55552 | 45184599 | putative beta-carotene hydroxylase [*Brassica rapa*] |
| AAS88426 | 46326968 | beta-carotene hydroxylase [*Glycine max*] |
| AAT48741 | 49036137 | beta-carotene hydroxylase [*Citrus sinensis*] |
| AAT84408 | 50844570 | beta carotene hydroxylase [*Crocus sativus*] |
| AAV85452 | 56267980 | beta-ring oxygenase AdKeto1 [*Adonis palaestina*] |
| AAV85453 | 56267982 | beta-ring oxygenase AdKeto2 [*Adonis palaestina*] |
| BAA14129 | 216687 | crtZ [*Pantoea ananatis*] |
| BAB79605 | 18143450 | crtZ [*Pantoea agglomerans* pv. *milletiae*] |
| BAC77670 | 31790567 | gamma-carotene hydroxylase [*marine bacterium* P99-3] |
| BAD07283 | 40809749 | beta-ring hydroxylase [*Citrus sinensis*] |
| BAD07291 | 40809765 | beta-ring hydroxylase [*Citrus limon*] |
| CAA70427 | 2956671 | beta-carotene hydrolase [*Capsicum annuum*] |
| CAA70888 | 2956717 | beta-carotene hydroxylase 2 [*Capsicum annuum*] |
| CAB55625 | 5870598 | beta-carotene hydroxylase [*Lycopersicon esculentum*] |
| CAB55626 | 5870600 | beta-carotene hydroxylase [*Lycopersicon esculentum*] |
| CAB56060 | 5912293 | carotene hydroxylase [*Paracoccus marcusii*] |
| CAC06712 | 9968545 | beta-carotene hydroxylase [*Narcissus pseudonarcissus*] |
| CAC95130 | 33145986 | beta-carotene hydroxylase [*Crocus sativus*] |
| EAB30128 | 42926157 | unknown [environmental sequence] |
| EAC49462 | 43167766 | unknown [environmental sequence] |
| EAC86129 | 43241003 | unknown [environmental sequence] |
| EAD61089 | 43395962 | unknown [environmental sequence] |
| EAD76156 | 43443111 | unknown [environmental sequence] |
| EAD88640 | 43467793 | unknown [environmental sequence] |
| EAE27903 | 43546376 | unknown [environmental sequence] |
| EAE28203 | 43546980 | unknown [environmental sequence] |
| EAE78743 | 43647896 | unknown [environmental sequence] |
| EAF12173 | 43714211 | unknown [environmental sequence] |
| EAH29370 | 44130906 | unknown [environmental sequence] |
| EAH44202 | 44158360 | unknown [environmental sequence] |
| EAI00766 | 44256844 | unknown [environmental sequence] |
| EAI29017 | 44298625 | unknown [environmental sequence] |
| EAJ30844 | 44443849 | unknown [environmental sequence] |
| EAJ72524 | 44504516 | unknown [environmental sequence] |
| EAK10611 | 44559981 | unknown [environmental sequence] |
| EAK53455 | 44620561 | unknown [environmental sequence] |
| EAK63955 | 44635271 | unknown [environmental sequence] |
| H90469 | 25394049 | beta carotene hydroxylase (crtZ) [imported] - *Sulfolobus solfataricus* |
| NP_745389 | 26989964 | beta-carotene hydroxylase [*Pseudomonas putida* KT2440] |
| NP_922503 | 37536402 | putative beta-carotene hydroxylase [*Oryza sativa* (*japonica* cultivar-group)] |
| P54973 | 1706152 | Beta-carotene hydroxylase |
| Q44262 | 2498258 | Beta-carotene hydroxylase |
| S52982 | 1073291 | beta-carotene hydroxylase - *Erwinia herbicola* |
| XP_473611 | 50928167 | OSJNBa0011J08.7 [*Oryza sativa* (*japonica* cultivar-group)] |
| YP_024309 | 48478603 | beta carotene hydroxylase [*Picrophilus torridus* DSM 9790] |
| ZP_003055 | 48851297 | COG3000: Sterol desaturase [*Novosphingobium aromaticivorans* DSM 12444] |
| ZP_003107 | 48856620 | COG3000: Sterol desaturase [*Cytophaga hutchinsonii*] |

TABLE 21

Examples of astaxanthin synthase polypeptides and putative astaxanthin synthase polypeptides.

| ACCESSION | GI | PROTEIN DESCRIPTION |
|---|---|---|
| AAM56288 | 21501451 | Astaxanthin synthase [*Xanthophyllomyces dendrorhous*] |
| XP_571276 | 58268240 | Cytochrome P450, putative [*Cryptococcus neoformans* var. *neoformans* JEC21] |
| EAL20013 | 50257304 | hypothetical protein CNBF3400 [*Cryptococcus neoformans* var. *neoformans* B-3501A] |
| XP_401804 | 49075484 | hypothetical protein UM04189.1 [*Ustilago maydis* 521] |
| XP_397817 | 49067054 | hypothetical protein UM00202.1 [*Ustilago maydis* 521] |
| XP_399595 | 49070612 | hypothetical protein UM01980.1 [*Ustilago maydis* 521] |
| XP_403279 | 49079218 | hypothetical protein UM05664.1 [*Ustilago maydis* 521] |
| XP_382294 | 46110473 | hypothetical protein FG02118.1 [*Gibberella zeae* PH-1] |
| XP_406021 | 49088382 | hypothetical protein AN1884.2 [*Aspergillus nidulans* FGSC A4] |
| XP_381224 | 46108332 | hypothetical protein FG01048.1 [*Gibberella zeae* PH-1] |
| XP_391479 | 46139577 | hypothetical protein FG11303.1 [*Gibberella zeae* PH-1] |
| XP_569261 | 58264210 | conserved hypothetical protein [*Cryptococcus neoformans* var. *neoformans* JEC21] |
| EAL22841 | 50260180 | hypothetical protein CNBB0620 [*Cryptococcus neoformans* var. *neoformans* B-3501A] |
| XP_359866 | 39940658 | hypothetical protein MG04911.4 [*Magnaporthe grisea* 70-15] |

TABLE 22

Examples of carotenoid epsilon hydroxylase polypeptides.

| ACCESSION | GI | PROTEIN DESCRIPTION |
|---|---|---|
| ABB52076 | 79155148 | putative epsilon-ring carotene hydroxylase [*Daucus carota* subsp. *sativus*] |
| BAD94136 | 62319017 | Cytochrom P450-like protein [*Arabidopsis thaliana*] |
| ABD28565 | 87162770 | E-class P450, group I [*Medicago truncatula*] |
| AAT28222 | 47498772 | putative 97B2-like cytochrome P450 [*Ginkgo biloba*] |
| ABC68396 | 85001685 | cytochrome P450 monooxygenase CYP97A [*Glycine max*] |
| ABC59110 | 84514203 | cytochrome P450 monooxygenase CYP97B [*Medicago truncatula*] |
| NP_190881 | 42565881 | LUT1 (LUTEIN DEFICIENT 1); oxygen binding [*Arabidopsis thaliana*] |
| ABB47954 | 78708979 | cytochrome P450 monooxygenase, putative [*Oryza sativa* (*japonica* cultivar-group)] |
| NP_922604 | 37536604 | putative cytochrome P450 monooxygenase [*Oryza sativa* (*japonica* cultivar-group)] |

TABLE 23

Examples of lycopene cyclase polypeptides, beta and epsilon subunits.

| ACCESSION | GI | PROTEIN DESCRIPTION |
|---|---|---|
| XP_001422490 | 145356548 | predicted protein [*Ostreococcus lucimarinus* CCE9901] |
| BAE94036 | 94481238 | lycopene epsilon cyclase (*Diospyros kaki*) |
| AAK07431 | 12746307 | lycopene epsilon-cyclase [*Adonis palaestina*] |
| ABB52073 | 79154988 | putative lycopene epsilon cyclase [*Daucus carota* subsp. *sativus*] |
| Q38932 | 27735211 | Lycopene epsilon cyclase, chloroplast precursor |
| AAB53336 | 1399181 | lycopene epsilon cyclase |
| AAG10428 | 9971816 | epsilon cyclase [*Tagetes erecta*] |
| AAK07434 | 12746313 | lycopene epsilon-cyclase [*Lactuca sativa*] |
| AAM45382 | 21360359 | epsilon cyclase [*Tagetes erecta*] |
| O65837 | 11132841 | Lycopene epsilon cyclase, chloroplast precursor |
| AAL69394 | 18419661 | lycopene epsilon-cyclase [*Spinacia oleracea*] |
| BAE79549 | 87299433 | lycopene epsilon-cyclase [*Chrysanthemum* x *morifolium*] |
| XP_463351 | 50901836 | putative lycopene epsilon-cyclase [*Oryza sativa* (*japonica* cultivar-group)] |
| AAS48096 | 44887640 | epsilon lycopene cyclase [*Citrus sinensis*] |
| AAX92679 | 62638188 | lycopene epsilon cyclase [*Citrus maxima*] |
| AAL92114 | 19569601 | lycopene epsilon-cyclase [*Citrus* x *paradisi*] |
| AAK07433 | 12746311 | lycopene epsilon-cyclase [*Solanum tuberosum*] |
| AAL47019 | 17864021 | lycopene epsilon-cyclase [*Citrus sinensis*] |
| AAT46065 | 48686703 | chloroplast lycopene epsilon-cyclase precursor [*Chlamydomonas reinhardtii*] |
| BAD07293 | 40809769 | lycopene epsilon-cyclase [*Citrus limon*] |
| BAD07285 | 40809753 | lycopene epsilon-cyclase [*Citrus sinensis*] |

TABLE 23-continued

| Examples of lycopene cyclase polypeptides, beta and epsilon subunits. | | |
|---|---|---|
| ACCESSION | GI | PROTEIN DESCRIPTION |
| BAD07277 | 40809737 | lycopene epsilon-cyclase [*Citrus unshiu*] |
| EAJ62839 | 44489138 | unknown [environmental sequence] |
| BAE43547 | 73993068 | putative lycopene beta cyclase [*Taxodium distichum* var. *distichum*] |
| BAE43550 | 73993074 | putative lycopene beta cyclase [*Taxodium distichum* var. *distichum*] |
| BAE43557 | 73993088 | putative lycopene beta cyclase [*Taxodium distichum* var. *imbricarium*] |
| BAE43558 | 73993090 | putative lycopene beta cyclase [*Taxodium distichum* var. *imbricarium*] |
| BAE43553 | 73993080 | putative lycopene beta cyclase [*Taxodium distichum* var. *imbricarium*] |
| BAE43545 | 73993064 | putative lycopene beta cyclase [*Taxodium distichum* var. *distichum*] |
| BAE43556 | 73993086 | putative lycopene beta cyclase [*Taxodium distichum* var. *imbricarium*] |
| BAE43552 | 73993078 | putative lycopene beta cyclase [*Taxodium distichum* var. *distichum*] |
| BAE43560 | 73993094 | putative lycopene beta cyclase [*Taxodium distichum* var. *imbricarium*] |
| BAE43554 | 73993082 | putative lycopene beta cyclase [*Taxodium distichum* var. *imbricarium*] |
| BAE43551 | 73993076 | putative lycopene beta cyclase [*Taxodium distichum* var. *distichum*] |
| BAE43519 | 73993012 | putative lycopene beta cyclase [*Cryptomeria japonica*] |
| BAE43535 | 73993044 | putative lycopene beta cyclase [*Cryptomeria japonica*] |
| BAE43541 | 73993056 | putative lycopene beta cyclase [*Cryptomeria japonica*] |
| BAE43542 | 73993058 | putative lycopene beta cyclase [*Cryptomeria japonica*] |
| BAE43517 | 73993008 | putative lycopene beta cyclase [*Cryptomeria japonica*] |
| BAE43534 | 73993042 | putative lycopene beta cyclase [*Cryptomeria japonica*] |
| BAE43537 | 73993048 | putative lycopene beta cyclase [*Cryptomeria japonica*] |
| BAE43533 | 73993040 | putative lycopene beta cyclase [*Cryptomeria japonica*] |
| BAD02774 | 38603277 | putative lycopene beta cyclase [*Cryptomeria japonica*] |
| BAD02766 | 38603261 | putative lycopene beta cyclase [*Cryptomeria japonica*] |
| BAE43540 | 73993054 | putative lycopene beta cyclase [*Cryptomeria japonica*] |
| BAE43514 | 73993002 | putative lycopene beta cyclase [*Cryptomeria japonica*] |
| BAE43544 | 73993062 | putative lycopene beta cyclase [*Cryptomeria japonica*] |
| BAE43538 | 73993050 | putative lycopene beta cyclase [*Cryptomeria japonica*] |
| BAE43528 | 73993030 | putative lycopene beta cyclase [*Cryptomeria japonica*] |
| BAE43546 | 73993066 | putative lycopene beta cyclase [*Taxodium distichum* var. *distichum*] |
| BAE43526 | 73993026 | putative lycopene beta cyclase [*Cryptomeria japonica*] |
| BAE43543 | 73993060 | putative lycopene beta cyclase [*Cryptomeria japonica*] |
| BAD02742 | 38603213 | putative lycopene beta cyclase [*Cryptomeria japonica*] |
| BAD02770 | 38603269 | putative lycopene beta cyclase [*Cryptomeria japonica*] |
| BAE43522 | 73993018 | putative lycopene beta cyclase [*Cryptomeria japonica*] |
| BAE43559 | 73993092 | putative lycopene beta cyclase [*Taxodium distichum* var. *imbricarium*] |
| BAE43527 | 73993028 | putative lycopene beta cyclase [*Cryptomeria japonica*] |
| BAE43548 | 73993070 | putative lycopene beta cyclase [*Taxodium distichum* var. *distichum*] |
| AAF44700 | 14550425 | lycopene beta-cyclase [*Citrus sinensis*] |
| BAE43555 | 73993084 | putative lycopene beta cyclase [*Taxodium distichum* var. *imbricarium*] |
| BAE43549 | 73993072 | putative lycopene beta cyclase [*Taxodium distichum* var. *distichum*] |
| AAU14144 | 51922063 | lycopene beta-cyclase [*Citrus sinensis*] |
| AAN86060 | 27261727 | lycopene cyclase [*Citrus unshiu*] |
| AAR89632 | 40756518 | lycopene-beta-cyclase [*Citrus maxima*] |
| AAM21152 | 20530862 | lycopene beta-cyclase [*Citrus sinensis*] |
| AAD38049 | 13959731 | lycopene cyclase [*Citrus* x *paradisi*] |
| AAU05146 | 51511939 | lycopene beta-cyclase [*Citrus sinensis*] |
| AAU05145 | 51511937 | lycopene beta-cyclase [*Citrus sinensis*] |
| AAK07430 | 12746305 | lycopene beta-cyclase [*Adonis palaestina*] |
| ABB72443 | 82394885 | lycopene beta-cyclase [*Citrus sinensis*] |
| BAE79544 | 87299423 | lycopene beta-cyclase [*Chrysanthemum* x *morifolium*] |
| BAE78471 | 85717882 | lycopene beta cyclase [*Taraxacum officinale*] |
| Q43415 | 11133019 | Lycopene beta cyclase, chloroplast precursor |
| AAF23013 | 6665782 | lycopene epsilon-cyclase [*Daucus carota*] |
| ABB52071 | 79154899 | putative lycopene beta cyclase [*Daucus carota* subsp. *sativus*] |
| AAW88382 | 59665024 | lycopene beta-cyclase [*Lycium barbarum*] |
| AAG10429 | 9971818 | beta cyclase [*Tagetes erecta*] |
| AAM45381 | 21360357 | beta cyclase [*Tagetes erecta*] |
| AAM14335 | 20259239 | putative lycopene beta cyclase [*Arabidopsis thaliana*] |
| AAO18661 | 27728515 | lycopene beta-cyclase [*Zea mays*] |

TABLE 23-continued

Examples of lycopene cyclase polypeptides, beta and epsilon subunits.

| ACCESSION | GI | PROTEIN DESCRIPTION |
|---|---|---|
| AAA81880 | 735882 | lycopene cyclase |
| Q43503 | 11133022 | Lycopene beta cyclase, chloroplast precursor |
| S66350 | 2129931 | lycopene beta-cyclase (EC 5.5.1. - ) - tomato |
| XP_464409 | 50905841 | putative lycopene beta-cyclase [*Oryza sativa* (*japonica* cultivar-group)] |
| CAD70565 | 45237491 | lycopene cyclase [*Bixa orellana*] |
| Q43578 | 11133025 | Lycopene beta cyclase, chloroplast precursor |
| AAL92175 | 19569782 | beta-lycopene cyclase [*Sandersonia aurantiaca*] |
| AAX54906 | 61742130 | putative chloroplast lycopene beta cyclase precursor [*Chlamydomonas reinhardtii*] |
| S66349 | 2129954 | lycopene beta-cyclase (EC 5.5.1. - ) - common tobacco |
| AAG21133 | 10644119 | chromoplast-specific lycopene beta-cyclase [*Lycopersicon esculentum*] |
| CAB92977 | 8247354 | neoxanthin synthase [*Solanum tuberosum*] |
| CAB93342 | 8249885 | neoxanthin synthase [*Lycopersicon esculentum*] |
| Q9SEA0 | 11131528 | Capsanthin/capsorubin synthase, chloroplast precursor |
| Q42435 | 12643508 | Capsanthin/capsorubin synthase, chloroplast precursor |
| AAO64977 | 37730608 | lycopene beta cyclase [*Haematococcus pluvialis*] |
| Q40424 | 11133011 | Lycopene beta cyclase, chloroplast precursor |
| ABB52072 | 79154940 | putative capsanthin-capsorubin synthase [*Daucus carota* subsp. *sativus*] |
| AAQ02668 | 33304511 | lycopene cyclase [*Setaria italica*] |
| CAA54961 | 840729 | putative chromoplastic oxydo-reductase [*Capsicum annuum*] |
| EAJ62838 | 44489136 | unknown [environmental sequence] |
| YP_401079 | 81300871 | Lycopene cyclase, beta and epsilon [*Synechococcus elongatus* PCC 7942] |
| YP_172741 | 56752040 | lycopene cyclase [*Synechococcus elongatus* PCC 6301] |
| ZP_011 . . . | 88808972 | lycopene beta cyclase [*Synechococcus* sp. WH 7805] |
| EAK50052 | 44615956 | unknown [environmental sequence] |
| NP_892751 | 33861190 | putative lycopene epsilon cyclase [*Prochlorococcus marinus* subsp. *pastoris* str. CCMP1986] |
| NP_875182 | 33240240 | Lycopene epsilon cyclase [*Prochlorococcus marinus* subsp. *marinus* str. CCMP1375] |
| YP_382237 | 78213458 | Lycopene cyclase, beta and epsilon [*Synechococcus* sp. CC9605] |
| YP_397130 | 78779018 | Lycopene cyclase, beta and epsilon [*Prochlorococcus marinus* str. MIT 9312] |
| NP_896821 | 33865262 | lycopene beta cyclase [*Synechococcus* sp. WH 8102] |
| YP_397570 | 78779458 | Lycopene cyclase, beta and epsilon [*Prochlorococcus marinus* str. MIT 9312] |
| ZP_010 . . . | 87302144 | lycopene cyclase [*Synechococcus* sp. WH 5701] |
| EAK17149 | 44569190 | unknown [environmental sequence] |
| YP_291882 | 72382527 | lycopene cyclase, beta and epsilon [*Prochlorococcus marinus* str. NATL2A] |
| NP_875528 | 33240586 | Lycopene beta cyclase related dehydrogenase [*Prochlorococcus marinus* subsp. *marinus* str. CCMP1375] |
| NP_893181 | 33861620 | putative lycopene beta cyclase [*Prochlorococcus marinus* subsp. *pastoris* str. CCMP1986] |
| NP_895600 | 33864040 | putative lycopene epsilon cyclase [*Prochlorococcus marinus* str. MIT 9313] |
| EAI47456 | 44325573 | unknown [environmental sequence] |
| YP_291268 | 72381913 | lycopene cyclase, beta and epsilon [*Prochlorococcus marinus* str. NATL2A] |
| ZP_010 . . . | 84517806 | Lycopene beta cyclase related dehydrogenase [*Prochlorococcus marinus* str. MIT 9211] |
| AAF34191 | 6970079 | lycopene epsilon cyclase [*Daucus carota*] |
| ZP_010 . . . | 84518202 | Lycopene epsilon cyclase [*Prochlorococcus marinus* str. MIT 9211] |
| YP_376736 | 78184301 | Lycopene cyclase, beta and epsilon [*Synechococcus* sp. CC9902] |
| ZP_003 . . . | 66796756 | Lycopene cyclase, beta and epsilon [*Deinococcus geothermalis* DSM 11300] |
| NP_894954 | 33863394 | putative lycopene beta cyclase [*Prochlorococcus marinus* str. MIT 9313] |
| AAT76051 | 50365502 | lycopene cyclase [*Citrus clementina*] |
| EAK22047 | 44576122 | unknown [*environmental sequence*] |
| NP_294525 | 15805827 | lycopene cyclase [*Deinococcus radiodurans* R1] |

TABLE 24

Examples of carotenoid glucosyltransferase polypeptides.

| ACCESSION | GI | PROTEIN DESCRIPTION |
|---|---|---|
| AAA21261 | 148395 | CrtX [*Pantoea agglomerans*] |
| AAN85597 | 27228291 | Zeaxanthin Glucosyl Transferase [*Pantoea stewartii*] |
| BAB79601 | 18143446 | crtX [*Pantoea agglomerans* pv. *milletiae*] |
| AAZ73147 | 72536082 | zeaxanthin glucosyl transferase [*Enterobacteriaceae bacterium* DC413] |
| AAZ73128 | 72536060 | zeaxanthin glucosyl transferase [*Enterobacteriaceae bacterium* DC260] |
| AAZ73140 | 72536074 | zeaxanthin glucosyl transferase [*Enterobacteriaceae bacterium* DC416] |
| Q01330 | 231911 | Zeaxanthin glucosyl transferase |
| ZP_006 . . . | 71674312 | UDP-glycosyltransferase, MGT [*Trichodesmium erythraeum* IMS101] |
| NP_439972 | 16329244 | zeaxanthin glucosyl transferase [*Synechocystis* sp. PCC 6803] |
| EAH29368 | 44130903 | unknown [environmental sequence] |
| ZP_005 . . . | 67926135 | zeaxanthin glucosyl transferase, hypothetical protein [*Crocosphaera watsonii* WH 8501] |
| YP_378763 | 78188425 | hypothetical protein Cag_0447 [*Chlorobium chlorochromatii* CaD3] |
| ZP_005 . . . | 68549418 | Glycosyl transferase, group 1 [*Pelodictyon phaeoclathratiforme* BU-1] |
| ZP_010 . . . | 85713606 | glycosyl transferase, group 1 [*Nitrobacter* sp. Nb-311A] |
| YP_317171 | 75674750 | glycosyl transferase, group 1 [*Nitrobacter winogradskyi* Nb-255] |
| ZP_006 . . . | 69929171 | Glycosyl transferase, group 1 [*Nitrobacter hamburgensis* X14] |
| ZP_009 . . . | 84500589 | hypothetical protein OB2597_11541 [*Oceanicola batsensis* HTCC2597] |
| ZP_009 . . . | 83953176 | hypothetical protein NAS141_12746 [*Sulfitobacter* sp. NAS-14.1] |
| ZP_009 . . . | 83942121 | hypothetical protein EE36_07793 [*Sulfitobacter* sp. EE-36] |
| YP_508020 | 89052569 | glycosyl transferase, group 1 [*Jannaschia* sp. CCS1] |
| ZP_010 . . . | 85704103 | hypothetical protein ROS217_13931 [*Roseovarius* sp. 217] |
| ZP_009 . . . | 83370850 | probable glycosyltransferase [*Rhodobacter sphaeroides* ATCC 17025] |
| ZP_006 . . . | 69934465 | Glycosyl transferase, group 1 [*Paracoccus denitrificans* PD1222] |
| ZP_009 . . . | 83949880 | probable glycosyltransferase [*Roseovarius nubinhibens* ISM] |
| YP_376237 | 78183803 | putative glycosyltransferase [*Synechococcus* sp. CC9902] |
| YP_376129 | 78183695 | probable glycosyltransferase [*Synechococcus* sp. CC9902] |
| YP_374296 | 78186253 | hypothetical protein Plut_0365 [*Pelodictyon luteolum* DSM 273] |
| ZP_010 . . . | 87301651 | Putative glycosyltransferase [*Synechococcus* sp. WH 5701] |
| ZP_011 . . . | 88809938 | Putative glycosyltransferase [*Synechococcus* sp. WH 7805] |
| BAE47471 | 78483937 | carotenoid glucosyltransferase [*Paracoccus* sp. N81106] |
| ZP_010 . . . | 87303273 | probable glycosyltransferase [*Synechococcus* sp. WH 5701] |
| YP_376127 | 78183693 | probable glycosyltransferase [*Synechococcus* sp. CC9902] |
| YP_501334 | 88196509 | hypothetical protein SAOUHSC_02880 [*Staphylococcus aureus* subsp. *aureus* NCTC 8325] |
| YP_187370 | 57652300 | glycosyl transferase, group 2 family protein [*Staphylococcus aureus* subsp. *aureus* COL] |
| CAA66627 | 1340131u | nnamed protein product [*Staphylococcus aureus*] |
| YP_041987 | 49484763 | putative glycosyl transferase [*Staphylococcus aureus* subsp. *aureus* MRSA252] |
| YP_417885 | 82752144 | hypothetical protein SAB2436c [*Staphylococcus aureus* RF122] |
| YP_252404 | 70725490 | hypothetical protein SH0489 [*Staphylococcus haemolyticus* JCSC1435] |
| NP_693379 | 23099913 | hypothetical protein OB2458 [*Oceanobacillus iheyensis* HTE831] |
| ZP_008 . . . | 82501285 | conserved hypothetical protein [*Caldicellulosiruptor* saccharolyticus DSM 8903] |
| ZP_010 . . . | 87303565 | hypothetical protein WH5701_09900 [*Synechococcus* sp. WH 5701] |

TABLE 25

Examples of acyl CoA:diacyglycerol acyltransferase (DGAT) polypeptides.

| ACCESSION | GI | PROTEIN DESCRIPTION |
|---|---|---|
| XP_957022 | 85082953 | hypothetical protein [*Neurospora crassa* N150] |
| XP_386864 | 46124621 | hypothetical protein FG06688.1 [*Gibberella zeae* PH-1] |
| XP_755172 | 71000982 | diacylglycerol O-acyltransferase DGAT [*Aspergillus fumigatus* Af293] |

TABLE 25-continued

Examples of acyl CoA:diacyglycerol acyltransferase (DGAT) polypeptides.

| ACCESSION | GI | PROTEIN DESCRIPTION |
|---|---|---|
| XP_663763 | 67539978 | hypothetical protein AN6159.2 [*Aspergillus nidulans* FGSC A4] |
| BAE65302 | 83775179 | unnamed protein product [*Aspergillus oryzae*] |
| XP_502557 | 50550169 | hypothetical protein [*Yarrowia lipolytica*] |
| AAS78662 | 56199782 | diacylglycerol acyltransferase [*Glycine max*] |
| ABB84383 | 82582915 | diacylglycerol acyltransferase [*Jatropha curcas*] |
| AAV31083 | 54145459 | 1,2-diacyl-sn-glycerol:acyl-CoA acyltransferase [*Euonymus alatus*] |
| AAG23696 | 10803053 | diacylglycerol acyltransferase [*Perilla frutescens*] |
| AAF64065 | 7576941 | putative diacylglycerol acyltransferase [*Brassica napus*] |
| AAS01606 | 41387497 | acyl-CoA:diacylglycerol acyltransferase 1 [*Olea europaea*] |
| AAT73629 | 50299542 | acyl CoA:diacylglycerol acyltransferase [*Glycine max*] |
| AAM03340 | 67043496 | putative diacylglycerol acyltransferase [*Tropaeolum majus*] |
| XP_645633 | 66824557 | hypothetical protein DDB0202877 [*Dictyostelium discoideum*] |
| AAF19345 | 6625653 | diacylglycerol acylCoA acyltransferase [*Nicotiana tabacum*] |
| AAY40785 | 63376239 | diacylglycerol acyltransferase DGAT2 [*Brassica juncea*] |
| AAW47581 | 57231736 | diacylglycerol acyltransferase [*Oryza sativa* (japonica cultivar-group)] |
| AAR11479 | 38146080 | diacylglycerol acyltransferase [*Ricinus communis*] |
| AAY40784 | 63376226 | diacylglycerol acyltransferase DGAT1 [*Brassica juncea*] |
| AAP68322 | 31711932 | At2g19450 [*Arabidopsis thaliana*] |
| AAW51456 | 57545061 | diacylglycerol acyltransferase [*Lotus corniculatus* var. *japonicus*] |
| AAD45536 | 5579408 | putative diacylglycerol acyltransferase [*Brassica napus*] |
| BAD53762 | 53791817 | putative acyl-CoA:diacylglycerol acyltransferase [*Oryza sativa* (japonica cultivar-group)] |
| NP_956024 | 41054343 | hypothetical protein LOC325875 [*Danio rerio*] |
| AAL49962 | 18642598 | diacylglycerol acyltransferase 1 [*Bos taurus*] |
| XP_930884 | 89028385 | similar to Diacylglycerol O-acyltransferase 1 (Diglyceride acyltransferase) (ACAT-related gene) [*Homo sapiens*] |
| NP_777118 | 27819636 | diacylglycerol O-acyltransferase 1 [*Bos taurus*] |
| Q9GMF1 | 18202926 | Diacylglycerol O-acyltransferase 1 (Diglyceride acyltransferase) |
| NP_036211 | 6912332 | diacylglycerol O-acyltransferase 1 [*Homo sapiens*] |
| AAH06263 | 34782946 | DGAT1 protein [*Homo sapiens*] |
| XP_780515 | 72006039 | similar to Diacylglycerol O-acyltransferase 1 [*Strongylocentrotus purpuratus*] |
| AAD40881 | 5225382 | putative diacylglycerol acyltransferase [*Brassica napus*] |
| XP_539214 | 73974769 | similar to Diacylglycerol O-acyltransferase 1 (ACAT related gene product 1) isoform 1 [*Canis familiaris*] |
| AAZ22403 | 71063860 | diacylglycerol O-acyltransferase 1 [*Bubalus bubalis*] |
| NP_999216 | 47522918 | diacylglycerol acyltransferase [*Sus scrofa*] |
| NP_001... | 50539976 | hypothetical protein LOC436731 [*Danio rerio*] |
| XP_849176 | 73974767 | similar to Diacylglycerol O-acyltransferase 1 (ACAT related gene product 1) isoform 2 [*Canis familiaris*] |
| NP_505828 | 71997360 | H19N07.4 [*Caenorhabditis elegans*] |
| AAF82410 | 9049538 | diacylglycerol acyltransferase [*Caenorhabditis elegans*] |
| CAE75170 | 39591950 | Hypothetical protein CBG23107 [*Caenorhabditis briggsae*] |
| XP_626337 | 66358318 | diacylglycerol acyltransferase 1 [*Cryptosporidium parvum* Iowa II] |
| XP_668402 | 67624239 | acyl-CoA:diacylglycerol acyltransferase 1-related enzyme [*Cryptosporidium hominis* TU502] |
| AAP94208 | 33113253 | acyl-CoA:diacylglycerol acyltransferase 1-related enzyme [*Toxoplasma gondii*] |
| AAP94209 | 33113255 | acyl-CoA:diacylglycerol acyltransferase 1-related enzyme [*Toxoplasma gondii*] |
| XP_579557 | 62652535 | PREDICTED: diacylglycerol O-acyltransferase 1 [*Rattus norvegicus*] |
| BAC66171 | 29170489 | diacylglycerol acyltransferase [*Mus musculus*] |
| Q9ERM3 | 18202872 | Diacylglycerol O-acyltransferase 1 (Diglyceride acyltransferase) |
| AAL78366 | 18698659 | acyl coenzyme A:diacylglycerol acyltransferase [*Drosophila melanogaster*] |
| NP_995724 | 45552403 | CG31991-PD, isoform D [*Drosophila melanogaster*] |
| NP_724017 | 24584734 | CG31991-PC, isoform C [*Drosophila melanogaster*] |
| XP_858062 | 73974765 | similar to Diacylglycerol O-acyltransferase 1 (ACAT related gene product 1) isoform 3 [*Canis familiaris*] |
| XP_728984 | 82915156 | hypothetical protein PY01256 [*Plasmodium yoelii yoelii* str. 17XNL] |
| CAG11944 | 47225461 | unnamed protein product [*Tetraodon nigroviridis*] |
| BAD27526 | 50199438 | acyl-CoA:diacylglycerol acyltransferase [eukaryotic synthetic construct] |
| XP_317656 | 31226099 | ENSANGP00000002281 [*Anopheles gambiae* str. PEST] |
| AAV59457 | 55733950 | putative diacylglycerol acyltransferase [*Oryza sativa* (japonica cultivar-group)] |

TABLE 25-continued

Examples of acyl CoA:diacyglycerol acyltransferase (DGAT) polypeptides.

| ACCESSION | GI | PROTEIN DESCRIPTION |
|---|---|---|
| EAL33593 | 54644853 | GA16599-PA [*Drosophila pseudoobscura*] |
| XP_678753 | 68073677 | diacylglycerol O-acyltransferase [*Plasmodium berghei* strain ANKA] |
| XP_520014 | 55631434 | PREDICTED: similar to Diacylglycerol O-acyltransferase 1 (Diglyceride acyltransferase) [*Pan troglodytes*] |
| CAG10815 | 47219451 | unnamed protein product [*Tetraodon nigroviridis*] |
| XP_624754 | 66522700 | PREDICTED: similar to ENSANGP00000002281 [*Apis mellifera*] |
| CAC69884 | 15620769 | diacylglycerol acyltransferase I [*Rattus norvegicus*] |
| XP_686181 | 68363630 | PREDICTED: similar to Diacylglycerol O-acyltransferase 1 (Diglyceride acyltransferase) [*Danio rerio*] |
| XP_734008 | 70921323 | diacylglycerol O-acyltransferase [*Plasmodium chabaudi chabaudi*] |
| XP_673128 | 68062248 | hypothetical protein PB300300.00.0 [*Plasmodium berghei* strain ANKA] |
| AAS72376 | 45642963 | acyl-CoA:cholesterol acyltransferase beta [*Toxoplasma gondii*] |
| AAS72375 | 45642961 | acyl-CoA:cholesterol acyltransferase alpha [*Toxoplasma gondii*] |
| NP_586145 | 19074639 | STEROL O-ACYLTRANSFERASE [*Encephalitozoon cuniculi* GB-M1] |
| XP_640280 | 66812202 | hypothetical protein DDB0205259 [*Dictyostelium discoideum*] |
| AAY40783 | 63376221 | diacylglycerol acyltransferase [*Brassica juncea*] |
| XP_765774 | 71032265 | diacylglycerol O-acyltransferase [*Theileria parva* strain *Muguga*] |
| Q876L2 | 34582301 | Sterol O-acyltransferase 2 (Sterol-ester synthase 2) |
| XP_571260 | 58268208 | sterol O-acyltransferase [*Cryptococcus neoformans* var. *neoformans* JEC21] |
| EAL20032 | 50257323 | hypothetical protein CNBF3580 [*Cryptococcus neoformans* var. *neoformans* B-3501A] |
| XP_954478 | 84999514 | acyl transferase [*Theileria annulata* strain *Ankara*] |
| XP_505086 | 50555355 | hypothetical protein [*Yarrowia lipolytica*] |
| NP_588558 | 19076058 | hypothetical protein SPCP1E11.05c [*Schizosaccharomyces pombe* 972h-] |
| AAC49441 | 1389739 | acyl-CoA: sterol acyltransferase |
| NP_014416 | 6324346 | Acyl-CoA: sterol acyltransferase, isozyme of Are1p; Are2p [*Saccharomyces cerevisiae*] |
| XP_750354 | 70991010 | sterol o-acyltransferase APE2 [*Aspergillus fumigatus* Af293] |
| XP_382192 | 46110268 | hypothetical protein FG02016.1 [*Gibberella zeae* PH-1] |
| BAE54934 | 83764790 | unnamed protein product [*Aspergillus oryzae*] |
| XP_885914 | 76617939 | similar to Sterol O-acyltransferase 2 (Cholesterol acyltransferase 2) (ACAT-2) isoform 2 [*Bos taurus*] |
| XP_591251 | 76617937 | similar to Sterol O-acyltransferase 2 (Cholesterol acyltransferase 2) (ACAT-2) isoform 1 [*Bos taurus*] |
| BAC00846 | 21392392 | AcylCoA: Cholesterol Acyltransferase 2 [*Rattus norvegicus*] |
| NP_649816 | 28571583 | CG8112-PA [*Drosophila melanogaster*] |
| NP_666176 | 22122547 | sterol O-acyltransferase 2 [*Mus musculus*] |
| O88908 | 18202245 | Sterol O-acyltransferase 2 (Cholesterol acyltransferase 2) (ACAT-2) |
| XP_761502 | 71022545 | hypothetical protein UM05355.1 [*Ustilago maydis* 521] |
| NP_714950 | 40254723 | sterol O-acyltransferase 2 [*Rattus norvegicus*] |
| EAQ86094 | 88178626 | hypothetical protein CHGG_07347 [*Chaetomium globosum* CBS 148.51] |
| XP_461395 | 50425599 | hypothetical protein DEHA0F25652g [*Debaryomyces hansenii* CBS767] |
| XP_661812 | 67527926 | hypothetical protein AN4208.2 [*Aspergillus nidulans* FGSC A4] |
| AAH96091 | 64654094 | Sterol O-acyltransferase 2 [*Homo sapiens*] |
| O75908 | 18202149 | Sterol O-acyltransferase 2 (Cholesterol acyltransferase 2) (ACAT-2) |
| AAH96090 | 64652990 | Sterol O-acyltransferase 2 [*Homo sapiens*] |
| AAK48829 | 13898623 | acyl coenzyme A: cholesterol acyltransferase-2 [*Homo sapiens*] |
| XP_543637 | 73996435 | PREDICTED: similar to sterol O-acyltransferase 2 [*Canis familiaris*] |
| O77759 | 18202176 | Sterol O-acyltransferase 2 (Cholesterol acyltransferase 2) (ACAT-2) |
| AAO32474 | 28564191 | ARE2 [*Saccharomyces castellii*] |
| XP_323485 | 32405744 | hypothetical protein [*Neurospora crassa*] |
| NP_982606 | 45184888 | AAR065Cp [*Eremothecium gossypii*] |
| NP_593708 | 19114620 | hypothetical protein SPAC13G7.06 [*Schizosaccharomyces pombe* 972h-] |
| AAO32554 | 28564940 | ARE2 [*Saccharomyces kluyveri*] |
| EAL28962 | 54639560 | GA20833-PA [*Drosophila pseudoobscura*] |

TABLE 25-continued

Examples of acyl CoA:diacyglycerol acyltransferase (DGAT) polypeptides.

| ACCESSION | GI | PROTEIN DESCRIPTION |
|---|---|---|
| XP_449806 | 50294790 | hypothetical protein CAGL0M10571g [*Candida glabrata* CBS138] |
| NP_033256 | 84619697 | sterol O-acyltransferase 1 [*Mus musculus*] |
| Q61263 | 18202591 | Sterol O-acyltransferase 1 (Cholesterol acyltransferase 1) (ACAT-1) |
| BAC34925 | 26342537 | unnamed protein product [*Mus musculus*] |
| XP_452607 | 50305295 | unnamed protein product [*Kluyveromyces lactis*] |
| NP_001 . . . | 77735363 | hypothetical protein LOC504287 [*Bos taurus*] |
| Q60457 | 18202585 | Sterol O-acyltransferase 1 (Cholesterol acyltransferase 1) (ACAT-1) |
| XP_320321 | 58393811 | ENSANGP00000016512 [*Anopheles gambiae* str. PEST] |
| XP_320320 | 58393809 | ENSANGP00000016486 [*Anopheles gambiae* str. PEST] |
| O70536 | 18202126 | Sterol O-acyltransferase 1 (Cholesterol acyltransferase 1) (ACAT-1) |
| XP_714776 | 68482533 | acyl-CoA cholesterol acyltransferase [*Candida albicans* SC5314] |
| P84285 | 56404462 | Sterol O-acyltransferase 2 (Sterol-ester synthase) (ASAT) |
| AAH77916 | 50416229 | Soat1-prov protein [*Xenopus laevis*] |
| XP_692855 | 68364838 | PREDICTED: similar to Soat1-prov protein [*Danio rerio*] |
| CAI13574 | 55960156 | sterol O-acyltransferase (acyl-Coenzyme A: cholesterol acyltransferase) 1 [*Homo sapiens*] |
| AAL56227 | 18028942 | cholesterol acyltransferase 1 [*Gorilla gorilla*] |
| AAL56228 | 18028944 | cholesterol acyltransferase 1 [*Pongo pygmaeus*] |
| AAC37532 | 4878022 | acyl-coenzyme A: cholesterol acyltransferase [*Homo sapiens*] |
| 2201440A | 1585676 | acyl-CoA/cholesterol acyltransferase |
| Q876L3 | 34582302 | Sterol O-acyltransferase 1 (Sterol-ester synthase 1) |
| BAE01048 | 67969393 | unnamed protein product [*Macaca fascicularis*] |
| XP_514030 | 55588858 | PREDICTED: hypothetical protein XP_514030 [*Pan troglodytes*] |
| XP_547445 | 73961286 | similar to Sterol O-acyltransferase 1 (Cholesterol acyltransferase 1) (ACAT-1) [*Canis familiaris*] |
| EAQ84619 | 88177151 | hypothetical protein CHGG_08633 [*Chaetomium globosum* CBS 148.51] |
| O77761 | 18202178 | Sterol O-acyltransferase 1 (Cholesterol acyltransferase 1) (ACAT-1) |
| XP_422267 | 50751122 | PREDICTED: similar to Sterol O-acyltransferase 1 (Cholesterol acyltransferase 1) (ACAT-1) [*Gallus gallus*] |
| XP_693284 | 68392980 | PREDICTED: similar to Sterol O-acyltransferase 1 (Cholesterol acyltransferase 1) (ACAT-1) [*Danio rerio*] |
| AAT92940 | 51013293 | YCR048W [*Saccharomyces cerevisiae*] |
| XP_956576 | 85080625 | hypothetical protein [*Neurospora crassa* N150] |
| XP_624691 | 66564061 | PREDICTED: similar to ENSANGP00000016486 [*Apis mellifera*] |
| CAF96514 | 47222847 | unnamed protein product [*Tetraodon nigroviridis*] |
| XP_788209 | 72085563 | PREDICTED: similar to sterol O-acyltransferase 1 [*Strongylocentrotus purpuratus*] |
| XP_445307 | 50285757 | unnamed protein product [*Candida glabrata*] |
| CAE70002 | 39596364 | Hypothetical protein CBG16409 [*Caenorhabditis briggsae*] |
| CAG07990 | 47225647 | unnamed protein product [*Tetraodon nigroviridis*] |
| NP_510623 | 17549960 | B0395.2 [*Caenorhabditis elegans*] |
| AAX28331 | 76157393 | SJCHGC04421 protein [*Schistosoma japonicum*] |
| CAI96158 | 66347204 | Diacylglycerol O-acyltransferase [*Bubalus bubalis*] |
| XP_390039 | 46136695 | hypothetical protein FG09863.1 [*Gibberella zeae* PH-1] |
| XP_643169 | 66819019 | hypothetical protein DDB0203882 [*Dictyostelium discoideum*] |
| AAO53095 | 28850306 | hypothetical protein [*Dictyostelium discoideum*] |
| AAB06959 | 1515472 | acyl-CoA: cholesterol acyltransferase [*Oryctolagus cuniculus*] |
| NP_945619 | 39933343 | putative alginate o-acetyltransferase AlgI [*Rhodopseudomonas palustris* CGA009] |
| ZP_008 . . . | 77691302 | Membrane bound O-acyl transferase, MBOAT [*Rhodopseudomonas palustris* BisB5] |
| XP_465546 | 50908115 | putative wax synthase [*Oryza sativa* (japonica cultivar-group)] |

TABLE 29

| Examples of Prenyldiphosphate synthase polypeptides | | |
|---|---|---|
| Accession | GI | Description |
| 29A: Bacteria Proteins that require a mitochondrial targeting sequence | | |
| ZP_009 . . . | 83373595 | Trans-hexaprenyltranstransferase [*Rhodobacter sphaeroides* ATCC 17029] |
| ZP_009 . . . | 83371280 | Trans-hexaprenyltranstransferase [*Rhodobacter sphaeroides* ATCC 17025] |
| CAD24417 | 20429105 | decaprenyl diphosphate synthase [*Paracoccus zeaxanthinifaciens*] |
| ZP_010 . . . | 85705714 | Geranylgeranyl pyrophosphate synthase/Polyprenyl synthetase [*Roseovarius* sp. 217] |
| ZP_010 . . . | 84515724 | decaprenyl diphosphate synthase [*Loktanella vestfoldensis* SKA53] |
| YP_165582 | 56695234 | decaprenyl diphosphate synthase [*Silicibacter pomeroyi* DSS-3] |
| ZP_010 . . . | 86139019 | decaprenyl diphosphate synthase [*Roseobacter* sp. MED193] |
| ZP_009 . . . | 83941379 | decaprenyl diphosphate synthase [*Sulfitobacter* sp. EE-36] |
| ZP_009 . . . | 83854856 | decaprenyl diphosphate synthase [*Sulfitobacter* sp. NAS-14.1] |
| ZP_006 . . . | 69299873 | Farnesyltranstransferase [*Silicibacter* sp. TM1040] |
| ZP_010 . . . | 84683979 | Geranylgeranyl pyrophosphate synthase/Polyprenyl synthetase [*Rhodobacterales* bacterium HTCC2654] |
| ZP_009 . . . | 84500217 | decaprenyl diphosphate synthase [*Oceanicola batsensis* HTCC2597] |
| ZP_009 . . . | 83952381 | decaprenyl diphosphate synthase [*Roseovarius nubinhibens* ISM] |
| ZP_006 . . . | 69937106 | Trans-hexaprenyltranstransferase [*Paracoccus denitrificans* PD1222] |
| ZP_005 . . . | 68180845 | Trans-hexaprenyltranstransferase [*Jannaschia* sp. CCS1] |
| ZP_008 . . . | 78495595 | Polyprenyl synthetase [*Rhodopseudomonas palustris* BisB18] |
| AAY82368 | 67866738 | decaprenyl diphosphate synthase [*Agrobacterium tumefaciens*] |
| NP_353656 | 15887975 | hypothetical protein AGR_C_1125 [*Agrobacterium tumefaciens* str. C58] |
| ZP_008 . . . | 77688465 | Farnesyltranstransferase [*Rhodopseudomonas palustris* BisB5] |
| NP_531334 | 17934544 | octaprenyl-diphosphate synthase [*Agrobacterium tumefaciens* str. C58] |
| YP_484709 | 86748213 | Farnesyltranstransferase [*Rhodopseudomonas palustris* HaA2] |
| AAP56240 | 37903500 | decaprenyl diphosphate synthase [*Agrobacterium tumefaciens*] |
| YP_192388 | 58040424 | Decaprenyl diphosphate synthase [*Gluconobacter oxydans* 621H] |
| 29B: Subunit 1 - Proteins that contain mitochondrial targeting sequence | | |
| T43193 | 11279237 | trans-pentaprenyltranstransferase homolog - fission yeast (*Schizosaccharomyces pombe*) |
| AAD28559 | 4732024 | trans-prenyltransferase [*Homo sapiens*] |
| AAI07275 | 78070698 | Trans-prenyltransferase [*Mus musculus*] |
| BAE48216 | 81157931 | subunit 1 of decaprenyl diphosphate synthase [*Homo sapiens*] |
| AAH49211 | 29165656 | PDSS1 protein [*Homo sapiens*] |
| Q33DR2 | 85700953 | Decaprenyl-diphosphate synthase subunit 1 (Solanesyl-diphosphate synthase subunit 1) (Trans-prenyltransferase) |
| XP_507706 | 55633583 | PREDICTED: similar to TPRT protein [*Pan troglodytes*] |
| XP_586717 | 76632198 | PREDICTED: similar to trans-prenyltransferase [*Bos taurus*] |
| XP_849908 | 73948851 | PREDICTED: similar to trans-prenyltransferase [*Canis familiaris*] |
| 29C: Subunit 2 - Proteins that contain mitochondrial targeting sequence | | |
| O13851 | 60389474 | Decaprenyl-diphosphate synthase subunit 2 (Decaprenyl pyrophosphate synthetase subunit 2) |
| BAE48218 | 81157935 | subunit 2 of solanesyl diphosphate synthase [*Mus musculus*] |
| BAE48217 | 81157933 | subunit 2 of decaprenyl diphosphate synthase [*Homo sapiens*] |

TABLE 30

| Examples of PHB-Polyprenyltransferase polypeptides | |
|---|---|
| GI | PROTEIN DESCRIPTION |
| 51013645 | YNR041C [*Saccharomyces cerevisiae*] |
| 50285815 | unnamed protein product [*Candida glabrata*] |
| 50311051 | unnamed protein product [*Kluyveromyces lactis*] |
| 45200866 | AGL231Wp [*Eremothecium gossypii*] |
| 50555263 | hypothetical protein [*Yarrowia lipolytica*] |
| 68473193 | para-hydroxybenzoate: polyprenyl transferase [*Candida albicans* SC5314] |
| 50410039 | hypothetical protein DEHA0A14212g [*Debaryomyces hansenii* CBS767] |
| 83769349 | unnamed protein product [*Aspergillus oryzae*] |
| 70994900 | para-hydroxybenzoate-polyprenyltransferase precursor [*Aspergillus fumigatus* Af293] |
| 19114131 | hypothetical protein SPAC56F8.04c [*Schizosaccharomyces pombe* 972h-] |
| 39973573 | hypothetical protein MG01067.4 [*Magnaporthe grisea* 70-15] |
| 85078920 | protein related to para-hydroxybenzoate polyprenyltransferase precursor [*Neurospora crassa* N150] |
| 76660839 | PREDICTED: similar to para-hydroxybenzoate-polyprenyltransferase, mitochondrial [*Bos taurus*] |

TABLE 30-continued

| Examples of PHB-Polyprenyltransferase polypeptides | |
|---|---|
| GI | PROTEIN DESCRIPTION |
| 52138578 | para-hydroxybenzoate-polyprenyltransferase, mitochondrial [*Homo sapiens*] |
| 18088424 | COQ2 protein [*Homo sapiens*] |
| 47221448 | unnamed protein product [*Tetraodon nigroviridis*] |
| 58385249 | ENSANGP00000012220 [*Anopheles gambiae* str. PEST] |
| 50746583 | PREDICTED: similar to hypothetical protein CL640 [*Gallus gallus*] |
| 54638587 | GA21912-PA [*Drosophila pseudoobscura*] |
| 21355567 | CG9613-PA [*Drosophila melanogaster*] |
| 71005862 | hypothetical protein UM01450.1 [*Ustilago maydis* 521] |

TABLE 31

Examples of soluble transydrogenase polypeptides.

| Row | ACCESSION | GI | PROTEIN DESCRIPTION |
|---|---|---|---|
| 1 | AAD40691 | 5163507 | soluble pyridine nucleotide transhydrogenase [*Azotobacter vinelandii* |
| 2 | ZP_013 . . . | 107102541 | hypothetical protein PaerPA_01003605 [*Pseudomonas aeruginosa* PACS2] |
| 3 | ZP_012 . . . | 94416745 | hypothetical protein PaerP_01001583 [*Pseudomonas aeruginosa* PA7] |
| 4 | O05139 | 11135075 | Soluble pyridine nucleotide transhydrogenase (STH) (NAD(P)(+) transhydrogenase [B-specific]) |
| 5 | YP_259077 | 70729340 | soluble pyridine nucleotide transhydrogenase [*Pseudomonas fluorescens* Pf-5] |
| 6 | YP_349590 | 77460083 | soluble pyridine nucleotide transhydrogenase [*Pseudomonas fluorescens* PfO-1] |
| 7 | YP_274087 | 71735155 | soluble pyridine nucleotide transhydrogenase [*Pseudomonas syringae* pv. *phaseolicola* 1448A] |
| 8 | YP_234983 | 66045142 | soluble pyridine nucleotide transhydrogenase [*Pseudomonas syringae* pv. *syringae* B728a] |
| 9 | YP_609219 | 104782721 | soluble pyridine nucleotide transhydrogenase (NAD(P)(+) transhydrogenase [B-specific]) [*Pseudomonas entomophila* L48] |
| 10 | Q884I6 | 38258471 | Soluble pyridine nucleotide transhydrogenase (STH) (NAD(P)(+) transhydrogenase [B-specific]) |
| 11 | ZP_009 . . . | 82739140 | soluble pyridine nucleotide transhydrogenase [*Pseudomonas putida* F1] |
| 12 | YP_573629 | 92113701 | pyridine nucleotide-disulphide oxidoreductase dimerisation region [*Chromohalobacter salexigens* DSM 3043] |
| 13 | ZP_008 . . . | 77951906 | NAD(P) transhydrogenase [*Marinobacter aquaeolei* VT8] |
| 14 | YP_433907 | 83645472 | Pyruvate/2-oxoglutarate dehydrogenase complex, dihydrolipoamide dehydrogenase (E3) component, and related enzyme [*Hahella chejuensis* KCTC 2396] |
| 15 | ZP_011 . . . | 89094310 | soluble pyridine nucleotide transhydrogenase [*Oceanospirillum* sp. MED92] |
| 16 | ZP_013 . . . | 94499566 | Pyruvate/2-oxoglutarate dehydrogenase complex, dihydrolipoamide dehydrogenase (E3) component, and related enzyme [*Oceanobacter* sp. RED65] |
| 17 | ZP_011 . . . | 88800089 | soluble pyridine nucleotide transhydrogenase [*Reinekea* sp. MED297] |
| 18 | ZP_010 . . . | 87121312 | soluble pyridine nucleotide transhydrogenase [*Marinomonas* sp. MED121] |
| 19 | ZP_012 . . . | 90417525 | soluble pyridine nucleotide transhydrogenase [marine gamma proteobacterium HTCC2207] |
| 20 | Q7MQ83 | 47606104 | Soluble pyridine nucleotide transhydrogenase (STH) (NAD(P)(+) transhydrogenase [B-specific]) |
| 21 | YP_527277 | 90021450 | regulatory protein, ArsR [*Saccharophagus degradans* 2-40] |
| 22 | ZP_009 . . . | 83586194 | COG1249: Pyruvate/2-oxoglutarate dehydrogenase complex, dihydrolipoamide dehydrogenase (E3) component, and related enzymes [*Escherichia coli* 101-1] |
| 23 | YP_219002 | 62182585 | soluble pyridine nucleotide transhydrogenase [*Salmonella enterica* subsp. *enterica serovar Choleraesuis* str. SC-B67] |
| 24 | YP_543498 | 91213512 | soluble pyridine nucleotide transhydrogenase [*Escherichia coli* UTI89] |
| 25 | Q87KN5 | 33301640 | Soluble pyridine nucleotide transhydrogenase (STH) (NAD(P)(+) transhydrogenase [B-specific]) |
| 26 | YP_153038 | 56415963 | soluble pyridine nucleotide transhydrogenase [*Salmonella enterica* subsp. *enterica serovar Paratyphi* A str. ATCC 9150] |
| 27 | YP_672034 | 110644304 | soluble pyridine nucleotide transhydrogenase [*Escherichia coli* 536] |
| 28 | ZP_013 . . . | 106883834 | FAD-dependent pyridine nucleotide-disulphide oxidoreductase:Pyridine nucleotide-disulphide oxidoreductase |

TABLE 31-continued

| Row | ACCESSION | GI | PROTEIN DESCRIPTION |
|---|---|---|---|
| Examples of soluble transydrogenase polypeptides. | | | |
| | | | dimerisation region:FAD dependent oxidoreductase [*Psychromonas ingrahamii* 37] |
| 29 | ZP_006 . . . | 75176647 | COG1249: Pyruvate/2-oxoglutarate dehydrogenase complex, dihydrolipoamide dehydrogenase (E3) component, and related enzymes [*Shigella boydii* BS512] |
| 30 | Q8FB93 | 38258590 | Soluble pyridine nucleotide transhydrogenase (STH) (NAD(P)(+) transhydrogenase [B-specific]) |
| 31 | ZP_007 . . . | 75197835 | COG1249: Pyruvate/2-oxoglutarate dehydrogenase complex, dihydrolipoamide dehydrogenase (E3) component, and related enzymes [*Escherichia coli* HS] |
| 32 | ZP_007 . . . | 75513852 | COG1249: Pyruvate/2-oxoglutarate dehydrogenase complex, dihydrolipoamide dehydrogenase (E3) component, and related enzymes [*Escherichia coli* 53638] |
| 33 | Q8X727 | 21362954 | Soluble pyridine nucleotide transhydrogenase (STH) (NAD(P)(+) transhydrogenase [B-specific]) |
| 34 | YP_267100 | 71278420 | soluble pyridine nucleotide transhydrogenase [*Colwellia psychrerythraea* 34H] |
| 35 | Q83MI1 | 39932373 | Soluble pyridine nucleotide transhydrogenase (STH) (NAD(P)(+) transhydrogenase [B-specific]) |
| 36 | ZP_007 . . . | 75238410 | COG1249: Pyruvate/2-oxoglutarate dehydrogenase complex, dihydrolipoamide dehydrogenase (E3) component, and related enzymes [*Escherichia coli* E110019] |
| 37 | ZP_007 . . . | 75854141 | COG1249: Pyruvate/2-oxoglutarate dehydrogenase complex, dihydrolipoamide dehydrogenase (E3) component, and related enzymes [*Vibrio* sp. Ex25] |
| 38 | YP_052329 | 50123162 | soluble pyridine nucleotide transhydrogenase [*Erwinia carotovora* subsp. *atroseptica* SCRI1043] |
| 39 | ZP_008 . . . | 77973002 | COG1249: Pyruvate/2-oxoglutarate dehydrogenase complex, dihydrolipoamide dehydrogenase (E3) component, and related enzymes [*Yersinia frederiksenii* ATCC 33641] |
| 40 | ZP_008 . . . | 77957412 | COG1249: Pyruvate/2-oxoglutarate dehydrogenase complex, dihydrolipoamide dehydrogenase (E3) component, and related enzymes [*Yersinia bercovieri* ATCC 43970] |
| 41 | ZP_008 . . . | 78702791 | NAD(P) transhydrogenase (B-specific) [*Alkalilimnicola ehrlichei* MLHE-1] |
| 42 | YP_645986 | 108810219 | soluble pyridine nucleotide transhydrogenase [*Yersinia pestis* Nepal516] |
| 43 | ZP_007 . . . | 75828016 | COG1249: Pyruvate/2-oxoglutarate dehydrogenase complex, dihydrolipoamide dehydrogenase (E3) component, and related enzymes [*Vibrio cholerae* O395] |
| 44 | Q7MBG9 | 47606102 | Soluble pyridine nucleotide transhydrogenase (STH) (NAD(P)(+) transhydrogenase [B-specific]) |
| 45 | ZP_008 . . . | 77976809 | COG1249: Pyruvate/2-oxoglutarate dehydrogenase complex, dihydrolipoamide dehydrogenase (E3) component, and related enzymes [*Yersinia intermedia* ATCC 29909] |
| 46 | ZP_008 . . . | 77961066 | COG1249: Pyruvate/2-oxoglutarate dehydrogenase complex, dihydrolipoamide dehydrogenase (E3) component, and related enzymes [*Yersinia mollaretii* ATCC 43969] |
| 47 | ZP_010 . . . | 86148649 | soluble pyridine nucleotide transhydrogenase [*Vibrio* sp. MED222] |
| 48 | YP_205822 | 59713046 | soluble pyridine nucleotide transhydrogenase [*Vibrio fischeri* ES114] |
| 49 | ZP_009 . . . | 84394322 | pyridine nucleotide-disulfide oxidoreductase, class I [*Vibrio splendidus* 12B01] |
| 50 | ZP_011 . . . | 89074500 | soluble pyridine nucleotide transhydrogenase [*Photobacterium* sp. SKA34] |
| 51 | YP_154714 | 56459433 | soluble pyridine nucleotide transhydrogenase [*Idiomarina loihiensis* L2TR] |
| 52 | YP_046885 | 50085375 | soluble pyridine nucleotide transhydrogenase [*Acinetobacter* sp. ADP1] |
| 53 | ZP_012 . . . | 90581098 | soluble pyridine nucleotide transhydrogenase [*Vibrio angustum* S14] |
| 54 | YP_693290 | 110834431 | NAD(P) transhydrogenase [*Alcanivorax borkumensis* SK2] |
| 55 | ZP_011 . . . | 88795508 | soluble pyridine nucleotide transhydrogenase [*Alteromonas macleodii* 'Deep ecotype'] |
| 56 | ZP_012 . . . | 90407259 | soluble pyridine nucleotide transhydrogenase [*Psychromonas* sp. CNPT3] |
| 57 | E65203 | 7431869 | probable dehydrogenase (EC 1.8.1.—) udhA - *Escherichia coli* (strain K-12) |
| 58 | YP_410260 | 82546313 | putative oxidoreductase [*Shigella boydii* Sb227] |
| 59 | YP_312883 | 74314464 | putative oxidoreductase [*Shigella sonnei* Ss046] |
| 60 | YP_131541 | 54310521 | soluble pyridine nucleotide transhydrogenase [*Photobacterium profundum* SS9] |
| 61 | AAC43068 | 396309 | ORF_f444 [*Escherichia coli*] |
| 62 | H86087 | 25284914 | probable oxidoreductase udhA [imported] - *Escherichia coli* (strain O157:H7, substrain EDL933) |

TABLE 31-continued

Examples of soluble transydrogenase polypeptides.

| Row | ACCESSION | GI | PROTEIN DESCRIPTION |
|---|---|---|---|
| 63 | ZP_012 . . . | 90414698 | soluble pyridine nucleotide transhydrogenase [*Photobacterium profundum* 3TCK] |
| 64 | NP_709766 | 56480495 | soluble pyridine nucleotide transhydrogenase [*Shigella flexneri* 2a str. 301] |
| 65 | YP_405233 | 82778884 | putative oxidoreductase [*Shigella dysenteriae* Sd197] |
| 66 | YP_691341 | 110807821 | putative oxidoreductase [*Shigella flexneri* 5 str. 8401] |
| 67 | NP_667661 | 22124238 | soluble pyridine nucleotide transhydrogenase [*Yersinia pestis* KIM] |
| 68 | YP_341375 | 77361800 | soluble pyridine nucleotide transhydrogenase [*Pseudoalteromonas haloplanktis* TAC125] |
| 69 | YP_455837 | 85060135 | soluble pyridine nucleotide transhydrogenase [*Sodalis glossinidius* str. 'morsitans'] |
| 70 | ZP_012 . . . | 91771448 | FAD-dependent pyridine nucleotide-disulphide oxidoreductase:Pyridine nucleotide-disulphide oxidoreductase dimerisation region:FAD dependent oxidoreductase [*Psychrobacter* sp. PRwf-1] |
| 71 | ZP_011 . . . | 88861405 | soluble pyridine nucleotide transhydrogenase [*Pseudoalteromonas tunicata* D2] |
| 72 | YP_264617 | 71065890 | soluble pyridine nucleotide transhydrogenase [*Psychrobacter arcticus* 273-4] |
| 73 | YP_580301 | 93005864 | pyridine nucleotide-disulphide oxidoreductase dimerisation region [*Psychrobacter cryohalolentis* K5] |
| 74 | ZP_010 . . . | 85710769 | soluble pyridine nucleotide transhydrogenase [*Idiomarina baltica* OS145] |
| 75 | ZP_012 . . . | 91227486 | soluble pyridine nucleotide transhydrogenase [*Vibrio alginolyticus* 12G01] |
| 76 | ZP_007 . . . | 75814072 | COG1249: Pyruvate/2-oxoglutarate dehydrogenase complex, dihydrolipoamide dehydrogenase (E3) component, and related enzymes [*Vibrio cholerae* V52] |
| 77 | YP_666832 | 110670275 | soluble pyridine nucleotide transhydrogenase [*Francisella tularensis* subsp. *tularensis* FSC 198] |
| 78 | YP_169700 | 56707804 | soluble pyridine nucleotide transhydrogenase [*Francisella tularensis* subsp. *tularensis* SCHU S4] |
| 79 | YP_513671 | 89256309 | soluble pyridine nucleotide transhydrogenase [*Francisella tularensis* subsp. *holarctica*] |
| 80 | CAA46822 | 43237 | udhA [*Escherichia coli*] |
| 81 | ZP_005 . . . | 67929855 | FAD-dependent pyridine nucleotide-disulphide oxidoreductase:Pyridine nucleotide-disulphide oxidoreductase dimerisation region [*Solibacter usitatus* Ellin6076] |
| 82 | YP_592298 | 94970250 | pyridine nucleotide-disulphide oxidoreductase [*Acidobacteria bacterium* Ellin345] |
| 83 | NP_961763 | 41408927 | soluble pyridine nucleotide transhydrogenase [*Mycobacterium avium* subsp. *paratuberculosis* K-10] |
| 84 | P66006 | 54042093 | Probable soluble pyridine nucleotide transhydrogenase (STH) (NAD(P)(+) transhydrogenase [B-specific]) |
| 85 | ZP_007 . . . | 76783189 | COG1249: Pyruvate/2-oxoglutarate dehydrogenase complex, dihydrolipoamide dehydrogenase (E3) component, and related enzymes [*Mycobacterium tuberculosis* F11] |
| 86 | YP_716291 | 111225497 | soluble pyridine nucleotide transhydrogenase [*Frankia alni* ACN14a] |
| 87 | ZP_005 . . . | 68235154 | FAD-dependent pyridine nucleotide-disulphide oxidoreductase:Pyridine nucleotide-disulphide oxidoreductase dimerisation domain [*Frankia* sp. EAN1pec] |
| 88 | ZP_012 . . . | 90205475 | FAD-dependent pyridine nucleotide-disulphide oxidoreductase:Pyridine nucleotide-disulphide oxidoreductase dimerisation region [*Mycobacterium vanbaalenii* PYR-1] |
| 89 | YP_482962 | 86742562 | pyridine nucleotide-disulphide oxidoreductase dimerisation region [*Frankia* sp. CcI3] |
| 90 | NP_532346 | 17935556 | soluble pyridine nucleotide transhydrogenase [*Agrobacterium tumefaciens* str. C58] |
| 91 | AAY87873 | 68165826 | pyridine nucleotide-disulfide oxidoreductase class I [*Vibrio cholerae*] |
| 92 | AAY87863 | 68165806 | pyridine nucleotide-disulfide oxidoreductase class I [*Vibrio cholerae*] |
| 93 | AAY87865 | 68165810 | pyridine nucleotide-disulfide oxidoreductase class I [*Vibrio cholerae*] |
| 94 | YP_469365 | 86357473 | probable pyridine nucleotide transhydrogenase protein [*Rhizobium etli* CFN 42] |
| 95 | ZP_010 . . . | 85706062 | soluble pyridine nucleotide transhydrogenase [*Roseovarius* sp. 217] |
| 96 | ZP_014 . . . | 113873124 | putative soluble pyridine nucleotide transhydrogenase [*Sinorhizobium medicae* WSM419] |
| 97 | NP_385835 | 15965482 | soluble pyridine nucleotide transhydrogenase [*Sinorhizobium meliloti* 1021] |
| 98 | YP_169016 | 56698639 | soluble pyridine nucleotide transhydrogenase [*Silicibacter pomeroyi* DSS-3] |

TABLE 31-continued

Examples of soluble transydrogenase polypeptides.

| Row | ACCESSION | GI | PROTEIN DESCRIPTION |
|---|---|---|---|
| 99 | ZP_009 . . . | 83951172 | soluble pyridine nucleotide transhydrogenase [*Roseovarius nubinhibens* ISM] |
| 100 | YP_611681 | 99078423 | pyridine nucleotide-disulphide oxidoreductase dimerisation region [*Silicibacter* sp. TM1040] |
| 101 | ZP_010 . . . | 86140117 | soluble pyridine nucleotide transhydrogenase [*Roseobacter* sp. MED193] |
| 102 | BAB53939 | 14027670 | soluble pyridine nucleotide transhydrogenase [*Mesorhizobium loti* MAFF303099] |
| 103 | YP_630631 | 108762684 | NAD(P) transhydrogenase (B-specific) [*Myxococcus xanthus* DK 1622] |
| 104 | YP_467034 | 86160249 | FAD-dependent pyridine nucleotide-disulphide oxidoreductase [*Anaeromyxobacter dehalogenans* 2CP-C] |
| 105 | YP_007724 | 46446359 | soluble pyridine nucleotide transhydrogenase [*Candidatus* Protochlamydia amoebophila UWE25] |
| 106 | YP_433307 | 83644872 | Pyruvate/2-oxoglutarate dehydrogenase complex, dihydrolipoamide dehydrogenase (E3) component, and related enzyme [*Hahella chejuensis* KCTC 2396] |
| 107 | YP_527988 | 90022161 | soluble pyridine nucleotide transhydrogenase [*Saccharophagus degradans* 2-40] |
| 108 | ZP_005 . . . | 67931474 | FAD-dependent pyridine nucleotide-disulphide oxidoreductase:Pyridine nucleotide-disulphide oxidoreductase dimerisation region [*Solibacter usitatus* Ellin6076] |
| 109 | YP_575887 | 92116158 | Dihydrolipoamide dehydrogenase [*Nitrobacter hamburgensis* X14] |
| 110 | NP_539063 | 17986429 | dihydrolipoamide dehydrogenase [*Brucella melitensis* 16M] |
| 111 | NP_698895 | 23502768 | dihydrolipoamide dehydrogenase [*Brucella suis* 1330] |
| 112 | YP_415258 | 82700684 | Pyridine nucleotide-disulphide oxidoreductase, class-II:NAD binding site:Adrenodoxin reductase:Mercuric reductase:Pyridine nu... [*Brucella melitensis biovar Abortus* 2308] |
| 113 | ZP_011 . . . | 88945707 | Dihydrolipoamide dehydrogenase [*Desulfotomaculum reducens* MI-1] |
| 114 | YP_675936 | 110635728 | dihydrolipoamide dehydrogenase [*Mesorhizobium* sp. BNC1] |
| 115 | YP_483896 | 86747400 | Dihydrolipoamide dehydrogenase [*Rhodopseudomonas palustris* HaA2] |
| 116 | ZP_006 . . . | 71836831 | Dihydrolipoamide dehydrogenase [*Pelobacter propionicus* DSM 2379] |
| 117 | BAB50985 | 14024381 | ferric leghemoglobin reductase-2 precursor, dihydrolipoamide dehydrogenase [*Mesorhizobium loti* MAFF303099] |
| 118 | ZP_011 . . . | 88946629 | Dihydrolipoamide dehydrogenase [*Desulfotomaculum reducens* MI-1] |
| 119 | YP_032854 | 49474812 | dihydrolipoamide dehydrogenase [*Bartonella quintana* str. Toulouse] |
| 120 | YP_317044 | 75674623 | dihydrolipoamide dehydrogenase [*Nitrobacter winogradskyi* Nb-255] |
| 121 | ZP_012 . . . | 90421039 | 2-oxoglutarate dehydrogenase, E3 component, lipoamide dehydrogenase [*Aurantimonas* sp. SI85-9A1] |
| 122 | NP_533297 | 17936507 | dihydrolipoamide dehydrogenase [*Agrobacterium tumefaciens* str. C58] |
| 123 | AAR21288 | 38489206 | 2-oxoglutarate dehydrogenase E3 component [*Bartonella henselae*] |
| 124 | YP_034342 | 49476301 | dihydrolipoamide dehydrogenase [*Bartonella henselae* str. Houston-1] |
| 125 | ZP_008 . . . | 78694497 | Dihydrolipoamide dehydrogenase [*Bradyrhizobium* sp. BTAi1] |
| 126 | ZP_010 . . . | 85713709 | dihydrolipoamide dehydrogenase [*Nitrobacter* sp. Nb-311A] |
| 127 | YP_471355 | 86359463 | dihydrolipoamide dehydrogenase protein [*Rhizobium etli* CFN 42] |
| 128 | ZP_008 . . . | 77739670 | Dihydrolipoamide dehydrogenase [*Rhodopseudomonas palustris* BisA53] |
| 129 | NP_387154 | 15966801 | dihydrolipoamide dehydrogenase [*Sinorhizobium meliloti* 1021] |
| 130 | YP_567689 | 91975030 | Dihydrolipoamide dehydrogenase [*Rhodopseudomonas palustris* BisB5] |
| 131 | ZP_009 . . . | 83750811 | COG1249: Pyruvate/2-oxoglutarate dehydrogenase complex, dihydrolipoamide dehydrogenase (E3) component, and related enzymes [*Bartonella bacilliformis* KC583] |
| 132 | NP_767089 | 27375560 | dihydrolipoamide dehydrogenase [*Bradyrhizobium japonicum* USDA 110] |
| 133 | ZP_014 . . . | 113873546 | dihydrolipoamide dehydrogenase [*Sinorhizobium medicae* WSM419] |
| 134 | ZP_011 . . . | 88801370 | Pyruvate/2-oxoglutarate dehydrogenase complex [*Polaribacter irgensii* 23-P] |
| 135 | AAN03817 | 22652790 | dihydrolipoamide dehydrogenase [*Methylobacterium extorquens*] |
| 136 | NP_945538 | 39933262 | dihydrolipoamide dehydrogenase [*Rhodopseudomonas palustris* CGA009] |
| 137 | ZP_010 . . . | 86142639 | Dihydrolipoyl dehydrogenase [*Flavobacterium* sp. MED217] |
| 138 | YP_005669 | 46200002 | dihydrolipoamide dehydrogenase [*Thermus thermophilus* HB27] |

TABLE 31-continued

Examples of soluble transydrogenase polypeptides.

| Row | ACCESSION | GI | PROTEIN DESCRIPTION |
|---|---|---|---|
| 139 | ZP_012 . . . | 90589077 | Dihydrolipoamide dehydrogenase [*Flavobacterium johnsoniae* UW101] |
| 140 | YP_143553 | 55980256 | 2-oxoglutarate dehydrogenase E3 component (dihydrolipoamide dehydrogenase) [*Thermus thermophilus* HB8] |
| 141 | YP_679939 | 110639729 | dihydrolipoyl dehydrogenanse [*Cytophaga hutchinsonii* ATCC 33406] |
| 142 | YP_530077 | 90421707 | Dihydrolipoamide dehydrogenase [*Rhodopseudomonas palustris* BisB18] |
| 143 | YP_681916 | 110678909 | dihydrolipoamide dehydrogenase [*Roseobacter denitrificans* OCh 114] |
| 144 | ZP_010 . . . | 86135035 | dihydrolipoamide dehydrogenase [*Tenacibaculum* sp. MED152] |
| 145 | ZP_011 . . . | 89068141 | 2-oxoglutarate dehydrogenase, E3 component, dihydrolipoamide dehydrogenase [*Oceanicola granulosus* HTCC2516] |
| 146 | ZP_007 . . . | 75761004 | Dihydrolipoamide dehydrogenase [*Bacillus thuringiensis* serovar israelensis ATCC 35646] |
| 147 | ZP_010 . . . | 84684243 | 2-oxoglutarate dehydrogenase, E3 component, dihydrolipoamidedehydrogenase [*Rhodobacterales bacterium* HTCC2654] |
| 148 | ZP_009 . . . | 84500199 | 2-oxoglutarate dehydrogenase, E3 component, dihydrolipoamidedehydrogenase [*Oceanicola batsensis* HTCC2597] |
| 149 | ZP_006 . . . | 71900956 | Dihydrolipoamide dehydrogenase [*Xylella fastidiosa* Ann-1] |
| 150 | XP_829730 | 74026328 | dihydrolipoyl dehydrogenase [*Trypanosoma brucei* TREU927] |
| 151 | ZP_010 . . . | 86132778 | dihydrolipoamide dehydrogenase [*Cellulophaga* sp. MED134] |
| 152 | P71317 | 11135239 | Soluble pyridine nucleotide transhydrogenase (STH) (NAD(P)(+) transhydrogenase [B-specific]) |
| 153 | ZP_012 . . . | 89891405 | dihydrolipoyl dehydrogenase (pyruvate 2-oxoglutarate dehydrogenase) [*Flavobacteria bacterium* BBFL7] |
| 154 | ZP_009 . . . | 83950445 | 2-oxoglutarate dehydrogenase, E3 component, dihydrolipoamidedehydrogenase [*Roseovarius nubinhibens* ISM] |
| 155 | AAA21748 | 472330 | dihydrolipoamide dehydrogenase |
| 156 | Q04933 | 416906 | Dihydrolipoyl dehydrogenase (Dihydrolipoamide dehydrogenase) |
| 157 | ZP_011 . . . | 88805521 | Pyruvate/2-oxoglutarate dehydrogenase complex [*Robiginitalea biformata* HTCC2501] |
| 158 | YP_351398 | 77461891 | dihydrolipoamide dehydrogenase [*Pseudomonas fluorescens* PfO-1] |
| 159 | ZP_006 . . . | 71900678 | Dihydrolipoamide dehydrogenase [*Xylella fastidiosa* Ann-1] |
| 160 | ZP_011 . . . | 88936095 | Dihydrolipoamide dehydrogenase [*Geobacter uraniumreducens* Rf4] |
| 161 | YP_430607 | 83590598 | Dihydrolipoamide dehydrogenase [*Moorella thermoacetica* ATCC 39073] |
| 162 | YP_165603 | 56695257 | 2-oxoglutarate dehydrogenase, E3 component, dihydrolipoamide dehydrogenase [*Silicibacter pomeroyi* DSS-3] |
| 163 | ZP_011 . . . | 89359154 | Dihydrolipoamide dehydrogenase [*Xanthobacter autotrophicus* Py2] |
| 164 | YP_007150 | 46445785 | dihydrolipoamide dehydrogenase [*Candidatus Protochlamydia amoebophila* UWE25] |
| 165 | YP_632394 | 108758911 | alpha keto acid dehydrogenase complex, E3 component, lipoamide dehydrogenase [*Myxococcus xanthus* DK 1622] |
| 166 | ZP_010 . . . | 85704799 | 2-oxoglutarate dehydrogenase, E3 component, dihydrolipoamidedehydrogenase [*Roseovarius* sp. 217] |
| 167 | NP_778978 | 28198664 | dihydrolipoamide dehydrogenase [*Xylella fastidiosa* Temecula1] |
| 168 | ZP_011 . . . | 88949385 | Dihydrolipoamide dehydrogenase [*Halorhodospira halophila* SL1] |
| 169 | XP_749345 | 70988990 | dihydrolipoamide dehydrogenase [*Aspergillus fumigatus* Af293] |
| 170 | YP_359567 | 78044229 | alpha keto acid dehydrogenase complex, E3 component, lipoamide dehydrogenase [*Carboxydothermus hydrogenoformans* Z-2901] |
| 171 | XP_959535 | 85092766 | hypothetical protein [*Neurospora crassa* OR74A] |
| 172 | ZP_009 . . . | 83856665 | Dihydrolipoyl dehydrogenase [*Croceibacter atlanticus* HTCC2559] |
| 173 | ZP_006 . . . | 69259929 | Dihydrolipoamide dehydrogenase [*Magnetococcus* sp. MC-1] |
| 174 | NP_298837 | 15838149 | dihydrolipoamide dehydrogenase [*Xylella fastidiosa* 9a5c] |
| 175 | YP_508779 | 89053328 | Dihydrolipoamide dehydrogenase [*Jannaschia* sp. CCS1] |
| 176 | CAA72131 | 1854569 | dihydrolipoamide dehydrogenase [*Trypanosoma cruzi*] |
| 177 | ZP_011 . . . | 88713490 | Dihydrolipoyl dehydrogenase [*Flavobacteriales bacterium* HTCC2170] |
| 178 | P90597 | 6166121 | Dihydrolipoyl dehydrogenase (Dihydrolipoamide dehydrogenase) |
| 179 | ZP_009 . . . | 83944432 | 2-oxoglutarate dehydrogenase, E3 component, dihydrolipoamidedehydrogenase [*Sulfitobacter* sp. EE-36] |
| 180 | ZP_009 . . . | 83953473 | 2-oxoglutarate dehydrogenase, E3 component, dihydrolipoamidedehydrogenase [*Sulfitobacter* sp. NAS-14.1] |

TABLE 31-continued

| Examples of soluble transydrogenase polypeptides. | | | |
|---|---|---|---|
| Row | ACCESSION | GI | PROTEIN DESCRIPTION |
| 181 | ZP_010 . . . | 86141935 | dihydrolipoamide dehydrogenase, E3 component of 2-oxoglutarate and pyruvate dehydrogenase complexes [*Flavobacterium* sp. MED217] |
| 182 | XP_818792 | 71663602 | dihydrolipoyl dehydrogenase [*Trypanosoma cruzi* strain CL Brener] |
| 183 | XP_812294 | 71422952 | dihydrolipoyl dehydrogenase [*Trypanosoma cruzi* strain CL Brener] |
| 184 | CAA72132 | 1854571 | dihydrolipoamide dehydrogenase [*Trypanosoma cruzi*] |
| 185 | NP_623271 | 20808100 | Dihydrolipoamide dehydrogenase/glutathione oxidoreductase and related enzyme [*Thermoanaerobacter tengcongensis* MB4] |
| 186 | YP_265659 | 71082940 | Dihydrolipoyl dehydrogenase [*Candidatus Pelagibacter ubique* HTCC1062] |
| 187 | ZP_012 . . . | 91762636 | Dihydrolipoyl dehydrogenase [*Candidatus Pelagibacter ubique* HTCC1002] |
| 188 | CAA11554 | 4210334 | 2-oxoglutarate dehydrogenase, E3 subunit [*Arabidopsis thaliana*] |
| 189 | NP_566570 | 30684428 | LPD2 (LIPOAMIDE DEHYDROGENASE 2); FAD binding/dihydrolipoyl dehydrogenase/disulfide oxidoreductase/oxidoreductase [*Arabidopsis thaliana*] |
| 190 | ZP_010 . . . | 84515869 | 2-oxoglutarate dehydrogenase, E3 component, dihydrolipoamidedehydrogenase [*Loktanella vestfoldensis* SKA53] |
| 191 | YP_355777 | 77917962 | 2-oxoglutarate dehydrogenase complex, E3 component, lipoamide dehydrogenase [*Pelobacter carbinolicus DSM 2380*] |
| 192 | AAS47708 | 44804791 | dihydrolipoamide dehydrogenase [*Leishmania major*] |
| 193 | AAC26053 | 3309269 | ferric leghemoglobin reductase-2 precursor [*Glycine max*] |
| 194 | XP_712334 | 68487571 | putative mitochondrial matrix dihydrolipoamide dehydrogenase Lpd1p [*Candida albicans* SC5314] |
| 195 | ZP_008 . . . | 78702525 | Dihydrolipoamide dehydrogenase [*Alkalilimnicola ehrlichei* MLHE-1] |
| 196 | YP_002403 | 45658317 | dihydrolipoamide dehydrogenase [*Leptospira interrogans serovar Copenhageni* str. Fiocruz L1-130] |
| 197 | ZP_008 . . . | 82736566 | Dihydrolipoamide dehydrogenase [*Pseudomonas putida* F1] |
| 198 | CAD60736 | 27803033 | unnamed protein product [*Podospora anserina*] |
| 199 | NP_747467 | 26992042 | dihydrolipoamide dehydrogenase [*Pseudomonas putida* KT2440] |
| 200 | ZP_013 . . . | 106891371 | Dihydrolipoamide dehydrogenase [*Roseiflexus* sp. RS-1] |
| 201 | EAQ92192 | 88184724 | conserved hypothetical protein [*Chaetomium globosum* CBS 148.51] |

TABLE 32

| Examples of transhydrogenase subunit alpha polypeptides. | | | |
|---|---|---|---|
| Row | ACCESSION | GI | PROTEIN DESCRIPTION |
| 1 | NP_416120 | 16129561 | NAD(P) transhydrogenase subunit alpha [*Escherichia coli* K12]. |
| 2 | ZP_007 . . . | 75512964 | COG3288: NAD/NADP transhydrogenase alpha subunit [*Escherichia coli* 53638] |
| 3 | ZP_009 . . . | 83587938 | COG3288: NAD/NADP transhydrogenase alpha subunit [*Escherichia coli* 101-1] |
| 4 | YP_669455 | 110641725 | NAD(P) transhydrogenase subunit alpha [*Escherichia coli* 536] |
| 5 | YP_540800 | 91210814 | NAD(P) transhydrogenase subunit alpha [*Escherichia coli* UTI89] |
| 6 | ZP_007 . . . | 75236686 | COG3288: NAD/NADP transhydrogenase alpha subunit [*Escherichia coli* F11] |
| 7 | NP_753890 | 26247850 | NAD(P) transhydrogenase subunit alpha [*Escherichia coli* CFT073] |
| 8 | YP_310491 | 74312072 | pyridine nucleotide transhydrogenase, alpha subunit [*Shigella sonnei* Ss046] |
| 9 | ZP_007 . . . | 75234916 | COG3288: NAD/NADP transhydrogenase alpha subunit [*Escherichia coli* E110019] |
| 10 | YP_403177 | 82776828 | pyridine nucleotide transhydrogenase, alpha subunit [*Shigella dysenteriae* Sd197] |
| 11 | ZP_007 . . . | 75190643 | COG3288: NAD/NADP transhydrogenase alpha subunit [*Escherichia coli* E24377A] |
| 12 | ZP_009 . . . | 83570993 | COG3288: NAD/NADP transhydrogenase alpha subunit [*Shigella dysenteriae* 1012] |
| 13 | ZP_007 . . . | 75257022 | COG3288: NAD/NADP transhydrogenase alpha subunit [*Escherichia coli* E22] |
| 14 | YP_407977 | 82544030 | pyridine nucleotide transhydrogenase, alpha subunit [*Shigella boydii* Sb227] |
| 15 | ZP_006 . . . | 75178502 | COG3288: NAD/NADP transhydrogenase alpha subunit [*Shigella boydii* BS512] |

TABLE 32-continued

Examples of transhydrogenase subunit alpha polypeptides.

| Row | ACCESSION | GI | PROTEIN DESCRIPTION |
|---|---|---|---|
| 16 | YP_689096 | 110805576 | pyridine nucleotide transhydrogenase, alpha subunit [*Shigella flexneri* 5 str. 8401] |
| 17 | NP_310336 | 15831563 | NAD(P) transhydrogenase subunit alpha [*Escherichia coli* O157:H7 str. Sakai] |
| 18 | YP_216484 | 62180067 | NAD(P) transhydrogenase subunit alpha [*Salmonella enterica* subsp. *enterica serovar Choleraesuis* str. SC-B67] |
| 19 | NP_460439 | 16764824 | NAD(P) transhydrogenase subunit alpha [*Salmonella typhimurium* LT2] |
| 20 | NP_805194 | 29141852 | NAD(P) transhydrogenase subunit alpha [*Salmonella enterica* subsp. *enterica serovar Typhi* Ty2] |
| 21 | ABF71058 | 102621428 | NADP transhydrogenase alpha subunit [*Enterobacter cloacae*] |
| 22 | ZP_008 . . . | 77963333 | COG3288: NAD/NADP transhydrogenase alpha subunit [*Yersinia mollaretii* ATCC 43969] |
| 23 | ZP_008 . . . | 77958020 | COG3288: NAD/NADP transhydrogenase alpha subunit [*Yersinia bercovieri* ATCC 43970] |
| 24 | ZP_008 . . . | 77975377 | COG3288: NAD/NADP transhydrogenase alpha subunit [*Yersinia frederiksenii* ATCC 33641] |
| 25 | YP_647693 | 108811926 | NAD(P) transhydrogenase alpha subunit [*Yersinia pestis* Nepal516] |
| 26 | YP_070740 | 51596549 | NAD(P) transhydrogenase subunit alpha [*Yersinia pseudotuberculosis* IP 32953] |
| 27 | ZP_007 . . . | 77629299 | COG3288: NAD/NADP transhydrogenase alpha subunit [*Yersinia pseudotuberculosis* IP 31758] |
| 28 | YP_050297 | 50121130 | NAD(P) transhydrogenase subunit alpha [*Erwinia carotovora* subsp. *atroseptica* SCRI1043] |
| 29 | ZP_008 . . . | 77979498 | COG3288: NAD/NADP transhydrogenase alpha subunit [*Yersinia intermedia* ATCC 29909] |
| 30 | NP_929427 | 37526083 | NAD(P) transhydrogenase subunit alpha [*Photorhabdus luminescens* subsp. *laumondii* TTO1] |
| 31 | YP_455168 | 85059466 | pyridine nucleotide transhydrogenase alpha subunit [*Sodalis glossinidius* str. 'morsitans'] |
| 32 | YP_206544 | 59713769 | NAD(P) transhydrogenase subunit alpha [*Vibrio fischeri* ES114] |
| 33 | ZP_007 . . . | 75831475 | COG3288: NAD/NADP transhydrogenase alpha subunit [*Vibrio cholerae* MO10] |
| 34 | ZP_010 . . . | 86147993 | NAD(P) transhydrogenase subunit alpha [*Vibrio* sp. MED222] |
| 35 | ZP_009 . . . | 84393928 | NAD(P) transhydrogenase subunit alpha [*Vibrio splendidus* 12B01] |
| 36 | ZP_007 . . . | 75857576 | COG3288: NAD/NADP transhydrogenase alpha subunit [*Vibrio* sp. Ex25] |
| 37 | ZP_012 . . . | 91226112 | NAD(P) transhydrogenase subunit alpha [*Vibrio alginolyticus* 12G01] |
| 38 | NP_936868 | 37676472 | NAD(P) transhydrogenase subunit alpha [*Vibrio vulnificus* YJ016] |
| 39 | NP_800432 | 28900777 | NAD(P) transhydrogenase subunit alpha [*Vibrio parahaemolyticus* RIMD 2210633] |
| 40 | NP_762287 | 27366760 | NAD(P) transhydrogenase subunit alpha [*Vibrio vulnificus* CMCP6] |
| 41 | ZP_012 . . . | 90577759 | NAD(P) transhydrogenase subunit alpha [*Vibrio angustum* S14] |
| 42 | ZP_011 . . . | 89073747 | NAD(P) transhydrogenase subunit alpha [*Photobacterium* sp. SKA34] |
| 43 | NP_245690 | 15602618 | NAD(P) transhydrogenase subunit alpha [*Pasteurella multocida* subsp. *multocida* str. Pm70] |
| 44 | YP_088416 | 52425279 | NAD(P) transhydrogenase subunit alpha [*Mannheimia succiniciproducens* MBEL55E] |
| 45 | YP_718440 | 113460378 | NAD(P)(+) transhydrogenase, alpha subunit (pyridine nucleotide transhydrogenase) [*Haemophilus somnus* 129PT] |
| 46 | ZP_001 . . . | 32030098 | COG3288: NAD/NADP transhydrogenase alpha subunit [*Haemophilus somnus* 2336] |
| 47 | ZP_005 . . . | 68545628 | NAD(P) transhydrogenase, alpha subunit [*Shewanella amazonensis* SB2B] |
| 48 | ZP_012 . . . | 90412639 | NAD(P) transhydrogenase subunit alpha [*Photobacterium profundum* 3TCK] |
| 49 | ZP_007 . . . | 75429914 | NAD/NADP transhydrogenase alpha subunit [*Actinobacillus succinogenes* 130Z] |
| 50 | YP_249235 | 68250123 | NAD(P) transhydrogenase subunit alpha [*Haemophilus influenzae* 86-028NP] |
| 51 | YP_132574 | 54302581 | NAD(P) transhydrogenase subunit alpha [*Photobacterium profundum* SS9] |
| 52 | NP_439513 | 16273272 | NAD(P) transhydrogenase subunit alpha [*Haemophilus influenzae* Rd KW20] |
| 53 | ZP_009 . . . | 82741968 | NAD(P) transhydrogenase, alpha subunit [*Shewanella* sp. W3-18-1] |
| 54 | ZP_014 . . . | 113949477 | NAD(P) transhydrogenase, alpha subunit [*Shewanella baltica* OS195] |
| 55 | YP_561942 | 91792291 | NAD(P) transhydrogenase, alpha subunit [*Shewanella denitrificans* OS217] |

TABLE 32-continued

Examples of transhydrogenase subunit alpha polypeptides.

| Row | ACCESSION | GI | PROTEIN DESCRIPTION |
|---|---|---|---|
| 56 | NP_719279 | 24375236 | NAD(P) transhydrogenase subunit alpha [*Shewanella oneidensis* MR-1] |
| 57 | NP_874046 | 33152693 | NAD(P) transhydrogenase subunit alpha [*Haemophilus ducreyi* 35000HP] |
| 58 | YP_735209 | 113971416 | NAD(P) transhydrogenase, alpha subunit [*Shewanella* sp. MR-4] |
| 59 | ZP_008 . . . | 78686308 | NAD(P) transhydrogenase, alpha subunit [*Shewanella* sp. ANA-3] |
| 60 | YP_736947 | 114046397 | NAD(P) transhydrogenase, alpha subunit [*Shewanella* sp. MR-7] |
| 61 | ZP_006 . . . | 69950756 | NAD(P) transhydrogenase, alpha subunit [*Shewanella frigidimarina* NCIMB 400] |
| 62 | ZP_007 . . . | 75818840 | COG3288: NAD/NADP transhydrogenase alpha subunit [*Vibrio cholerae* V51] |
| 63 | ZP_013 . . . | 106883669 | NAD(P) transhydrogenase, alpha subunit [*Psychromonas ingrahamii* 37] |
| 64 | NP_283944 | 15794122 | NAD(P) transhydrogenase subunit alpha [*Neisseria meningitidis* Z2491] |
| 65 | YP_434236 | 83645801 | NAD(P) transhydrogenase, alpha subunit [*Hahella chejuensis* KCTC 2396] |
| 66 | NP_274017 | 15676872 | NAD(P) transhydrogenase subunit alpha [*Neisseria meningitidis* MC58] |
| 67 | YP_208522 | 59801810 | NAD(P) transhydrogenase subunit alpha [*Neisseria gonorrhoeae* FA 1090] |
| 68 | ZP_012 . . . | 90408904 | PntA [*Psychromonas* sp. CNPT3] |
| 69 | YP_268514 | 71281713 | NAD(P) transhydrogenase subunit alpha [*Colwellia psychrerythraea* 34H] |
| 70 | ZP_001 . . . | 32035329 | COG3288: NAD/NADP transhydrogenase alpha subunit [*Actinobacillus pleuropneumoniae* serovar 1 str. 4074] |
| 71 | ZP_012 . . . | 90202099 | NAD(P) transhydrogenase, alpha subunit [*Mycobacterium vanbaalenii* PYR-1] |
| 72 | YP_342322 | 77163797 | NAD(P) transhydrogenase subunit alpha [*Nitrosococcus oceani* ATCC 19707] |
| 73 | ZP_009 . . . | 84495285 | NAD(P) transhydrogenase subunit alpha [*Janibacter* sp. HTCC2649] |
| 74 | AAY87755 | 68165590 | NAD(P) transhydrogenase alpha subunit [*Vibrio cholerae*] |
| 75 | ZP_011 . . . | 89340414 | NAD(P) transhydrogenase, alpha subunit [*Mycobacterium flavescens* PYR-GCK] |
| 76 | AAY87751 | 68165582 | NAD(P) transhydrogenase alpha subunit [*Vibrio cholerae*] |
| 77 | AAY87754 | 68165588 | NAD(P) transhydrogenase alpha subunit [*Vibrio cholerae*] |
| 78 | AAY87762 | 68165604 | NAD(P) transhydrogenase alpha subunit [*Vibrio cholerae*] |
| 79 | YP_422187 | 83311923 | NAD/NADP transhydrogenase alpha subunit [*Magnetospirillum magneticum* AMB-1] |
| 80 | YP_637279 | 108797082 | NAD(P) transhydrogenase, alpha subunit [*Mycobacterium* sp. MCS] |
| 81 | YP_115165 | 53803088 | NAD(P) transhydrogenase subunit alpha [*Methylococcus capsulatus* str. Bath] |
| 82 | NP_821578 | 29826944 | NAD(P) transhydrogenase subunit alpha [*Streptomyces avermitilis* MA-4680] |
| 83 | ZP_006 . . . | 69261416 | NAD(P) transhydrogenase, alpha subunit [*Magnetococcus* sp. MC-1] |
| 84 | NP_440856 | 16330128 | NAD(P) transhydrogenase subunit alpha [*Synechocystis* sp. PCC 6803] |
| 85 | ZP_002 . . . | 46202292 | COG3288: NAD/NADP transhydrogenase alpha subunit [*Magnetospirillum magnetotacticum* MS-1] |
| 86 | YP_298860 | 73538493 | NAD(P) transhydrogenase subunit alpha [*Ralstonia eutropha* JMP134] |
| 87 | ZP_004 . . . | 66966825 | NAD(P) transhydrogenase, alpha subunit [*Arthrobacter* sp. FB24] |
| 88 | ZP_006 . . . | 71366730 | NAD(P) transhydrogenase, alpha subunit [*Nocardioides* sp. JS614] |
| 89 | YP_524985 | 89902514 | NAD(P) transhydrogenase, alpha subunit [*Rhodoferax ferrireducens* T118] |
| 90 | YP_055339 | 50842112 | NAD(P) transhydrogenase subunit alpha [*Propionibacterium acnes* KPA171202] |
| 91 | NP_631664 | 21225885 | NAD(P) transhydrogenase subunit alpha [*Streptomyces coelicolor* A3(2)] |
| 92 | ZP_006 . . . | 74018096 | NAD(P) transhydrogenase, alpha subunit [*Burkholderia ambifaria* AMMD] |
| 93 | CAJ96500 | 113530153 | NAD(P) transhydrogenase subunit alpha [*Ralstonia eutropha* H16] |
| 94 | YP_366916 | 78060341 | NAD(P) transhydrogenase subunit alpha [*Burkholderia* sp. 383] |
| 95 | YP_574538 | 92114610 | NAD(P) transhydrogenase, alpha subunit [*Chromohalobacter salexigens* DSM 3043] |
| 96 | ZP_004 . . . | 67542770 | NAD(P) transhydrogenase, alpha subunit [*Burkholderia vietnamiensis* G4] |

TABLE 32-continued

Examples of transhydrogenase subunit alpha polypeptides.

| Row | ACCESSION | GI | PROTEIN DESCRIPTION |
|---|---|---|---|
| 97 | YP_702683 | 111019711 | NAD(P) transhydrogenase alpha subunit [*Rhodococcus* sp. RHA1] |
| 98 | ZP_007 . . . | 75821435 | COG3288: NAD/NADP transhydrogenase alpha subunit [*Vibrio cholerae* RC385] |
| 99 | ZP_011 . . . | 88798022 | NAD(P) transhydrogenase subunit alpha [*Reinekea* sp. MED297] |
| 100 | ZP_009 . . . | 83371049 | NAD(P) transhydrogenase, alpha subunit [*Rhodobacter sphaeroides* ATCC 17025] |
| 101 | ZP_006 . . . | 69933435 | NAD(P) transhydrogenase, alpha subunit [*Paracoccus denitrificans* PD1222] |
| 102 | YP_353313 | 77463809 | NAD(P) transhydrogenase subunit alpha [*Rhodobacter sphaeroides* 2.4.1] |
| 103 | ZP_009 . . . | 83373326 | NAD(P) transhydrogenase, alpha subunit [*Rhodobacter sphaeroides* ATCC 17029] |
| 104 | ZP_010 . . . | 85704984 | NAD(P) transhydrogenase subunit alpha [*Roseovarius* sp. 217] |
| 105 | YP_612703 | 99080549 | NAD(P) transhydrogenase, alpha subunit [*Silicibacter* sp. TM1040] |
| 106 | YP_683504 | 110680497 | NAD(P) transhydrogenase, alpha subunit [*Roseobacter denitrificans* OCh 114] |
| 107 | AAQ87369 | 36958944 | NAD(P) transhydrogenase subunit alpha [*Rhizobium* sp. NGR234] |
| 108 | ZP_010 . . . | 86137634 | NAD(P) transhydrogenase subunit alpha [*Roseobacter* sp. MED193] |
| 109 | XP_799127 | 72030333 | PREDICTED: similar to nicotinamide nucleotide transhydrogenase [*Strongylocentrotus purpuratus*] |
| 110 | ZP_010 . . . | 84503572 | NAD(P) transhydrogenase subunit alpha [*Oceanicola batsensis* HTCC2597] |
| 111 | ZP_010 . . . | 84516763 | NAD(P) transhydrogenase subunit alpha [*Loktanella vestfoldensis* SKA53] |
| 112 | NP_533164 | 17936374 | NAD(P) transhydrogenase subunit alpha [*Agrobacterium tumefaciens* str. C58] |
| 113 | XP_562937 | 57968100 | ENSANGP00000025507 [*Anopheles gambiae* str. PEST] |
| 114 | YP_511224 | 89055773 | NAD(P) transhydrogenase, alpha subunit [*Jannaschia* sp. CCS1] |
| 115 | ZP_009 . . . | 83942708 | NAD(P) transhydrogenase subunit alpha [*Sulfitobacter* sp. EE-36] |
| 116 | YP_168028 | 56697658 | NAD(P) transhydrogenase subunit alpha [*Silicibacter pomeroyi* DSS-3] |
| 117 | EAT35199 | 108870974 | nadp transhydrogenase [*Aedes aegypti*] |
| 118 | ZP_009 . . . | 83953947 | NAD(P) transhydrogenase subunit alpha [*Sulfitobacter* sp. NAS-14.1] |
| 119 | ZP_009 . . . | 83949483 | NAD(P) transhydrogenase subunit alpha [*Roseovarius nubinhibens* ISM] |
| 120 | XP_367628 | 39972475 | hypothetical protein MG07539.4 [*Magnaporthe grisea* 70-15] |
| 121 | NP_999921 | 47550793 | nicotinamide nucleotide transhydrogenase [*Danio rerio*] |
| 122 | XP_961047 | 85100871 | hypothetical protein (mitochondrial nicotinamide nucleotide transhydrogenase-related protein [imported] - *Neurospora crassa* OR74A) |
| 123 | AAH81117 | 51703526 | MGC83563 protein [*Xenopus laevis*] |
| 124 | CAF99322 | 47223713 | unnamed protein product [*Tetraodon nigroviridis*] |
| 125 | CAB88572 | 16416047 | related to mitochondrial nicotinamide nucleotide transhydrogenase [*Neurospora crassa*] |
| 126 | AAI10544 | 83405154 | Nicotinamide nucleotide transhydrogenase [*Homo sapiens*] |
| 127 | AAI10545 | 83405537 | Nicotinamide nucleotide transhydrogenase [*Homo sapiens*] |
| 128 | NP_509028 | 17550456 | Nicotinamide Nucleotide Transhydrogenase family member (nnt-1) [*Caenorhabditis elegans*] |
| 129 | 2211247B | 1589396 | nicotinamide nucleotide transhydrogenase |
| 130 | ZP_010 . . . | 84686399 | NAD(P) transhydrogenase subunit alpha [*Rhodobacterales bacterium* HTCC2654] |
| 131 | NP_776368 | 27806831 | nicotinamide nucleotide transhydrogenase [*Bos taurus*] |
| 132 | AAA21440 | 163397 | nicotinamide nucleotide transhydrogenase |
| 133 | P11024 | 128400 | NAD(P) transhydrogenase, mitochondrial precursor (Pyridine nucleotide transhydrogenase) (Nicotinamide nucleotide transhydrogenase) |
| 134 | XP_536481 | 73953769 | PREDICTED: similar to NAD(P) transhydrogenase, mitochondrial precursor (Pyridine nucleotide transhydrogenase) (Nicotinamide nucleotide transhydrogenase) isoform 1 [*Canis familiaris*] |
| 135 | XP_970382 | 91083631 | PREDICTED: similar to nicotinamide nucleotide transhydrogenase [*Tribolium castaneum*] |
| 136 | NP_001 . . . | 61557127 | nicotinamide nucleotide transhydrogenase [*Rattus norvegicus*] |
| 137 | NP_892022 | 33695086 | nicotinamide nucleotide transhydrogenase [*Homo sapiens*] |
| 138 | XP_867928 | 73953777 | PREDICTED: similar to NAD(P) transhydrogenase, mitochondrial precursor (Pyridine nucleotide transhydrogenase) (Nicotinamide nucleotide transhydrogenase) isoform 5 [*Canis familiaris*] |

TABLE 32-continued

| Examples of transhydrogenase subunit alpha polypeptides. | | | |
|---|---|---|---|
| Row | ACCESSION | GI | PROTEIN DESCRIPTION |
| 139 | NP_036475 | 33695084 | nicotinamide nucleotide transhydrogenase [*Homo sapiens*] |
| 140 | XP_424784 | 50761621 | PREDICTED: similar to nicotinamide nucleotide transhydrogenase [*Gallus gallus*] |
| 141 | XP_646840 | 66826971 | NAD(P)+ transhydrogenase (AB-specific) [*Dictyostelium discoideum* AX4] |
| 142 | BAC40113 | 26352966 | unnamed protein product [*Mus musculus*] |
| 143 | EAS31570 | 90301939 | conserved hypothetical protein [*Coccidioides immitis* RS] |
| 144 | XP_867922 | 73953775 | PREDICTED: similar to NAD(P) transhydrogenase, mitochondrial precursor (Pyridine nucleotide transhydrogenase) (Nicotinamide nucleotide transhydrogenase) isoform 4 [*Canis familiaris*] |
| 145 | CAF99856 | 47230663 | unnamed protein product [*Tetraodon nigroviridis*] |
| 146 | Q61941 | 51338804 | NAD(P) transhydrogenase, mitochondrial precursor (Pyridine nucleotide transhydrogenase) (Nicotinamide nucleotide transhydrogenase) |
| 147 | 2211247A | 1589395 | nicotinamide nucleotide transhydrogenase |
| 148 | NP_032736 | 31543330 | nicotinamide nucleotide transhydrogenase [*Mus musculus*] |
| 149 | BAE35294 | 74198248 | unnamed protein product [*Mus musculus*] |
| 150 | XP_748064 | 70985116 | nicotinamide nucleotide transhydrogenase [*Aspergillus fumigatus* Af293] |
| 151 | XP_389182 | 46130902 | hypothetical protein FG09006.1 [*Gibberella zeae* PH-1] |
| 152 | CAE68875 | 39598183 | Hypothetical protein CBG14838 [*Caenorhabditis briggsae*] |
| 153 | AAK18179 | 13310152 | nicotinamide nucleotide transhydrogenase [*Acetabularia acetabulum*] |
| 154 | AAG02246 | 11597233 | NAD(P)H transhydrogenase [*Acetabularia acetabulum*] |
| 155 | AAC41577 | 6478876 | pyridine nucleotidetranshydrogenase [*Entamoeba histolytica*] |
| 156 | XP_627136 | 66359916 | pyridine nucleotide/NAD(P) transhydrogenase alpha plus beta subunits, duplicated gene, [*Cryptosporidium parvum* Iowa II] |
| 157 | XP_666495 | 67602649 | transhydrogenase 7B2 [*Cryptosporidium hominis* TU502] |
| 158 | BAE40577 | 74219995 | unnamed protein product [*Mus musculus*] |
| 159 | CAH90079 | 55726630 | hypothetical protein [*Pongo pygmaeus*] |
| 160 | AAA80188 | 571367 | nicotinamide nucleotide transhydrogenase |
| 161 | EAQ86424 | 88178956 | conserved hypothetical protein [*Chaetomium globosum* CBS 148.51] |
| 162 | AAA29077 | 305062 | transhydrogenase |
| 163 | AAA29081 | 158904 | transhydrogenase |
| 164 | YP_724141 | 113478080 | NAD(P)(+) transhydrogenase (AB-specific) [*Trichodesmium erythraeum* IMS101] |
| 165 | NP_487450 | 17230902 | nicotinamide nucleotide transhydrogenase, subunit alpha [*Nostoc* sp. PCC 7120] |
| 166 | YP_323932 | 75909636 | Alanine dehydrogenase/PNT-like [*Anabaena variabilis* ATCC 29413] |
| 167 | ZP_005 . . . | 67924536 | NAD(P)(+) transhydrogenase (AB-specific) [*Crocosphaera watsonii* WH 8501] |
| 168 | ZP_013 . . . | 110607624 | Alanine dehydrogenase/PNT-like [*Maricaulis maris* MCS10] |
| 169 | ZP_012 . . . | 91222948 | NAD(P) transhydrogenase subunit alpha [*Psychroflexus torquis* ATCC 700755] |
| 170 | ZP_009 . . . | 82737423 | NAD/NADP transhydrogenase, NAD(H)-binding DI subunit [*Pseudomonas putida* F1] |
| 171 | YP_000046 | 45655960 | proton-translocating transhydrogenase, subunit alpha part 1 [*Leptospira interrogans serovar Copenhageni* str. Fiocruz L1-130] |
| 172 | YP_257267 | 70733627 | NAD(P) transhydrogenase, alpha subunit part 1 [*Pseudomonas fluorescens* Pf-5] |
| 173 | ZP_001 . . . | 23130320 | COG3288: NAD/NADP transhydrogenase alpha subunit [*Nostoc punctiforme* PCC 73102] |
| 174 | ZP_013 . . . | 110593183 | NAD(P)(+) transhydrogenase (AB-specific) [*Acidovorax* sp. JS42] |
| 175 | ZP_009 . . . | 83859916 | nicotinamide nucleotide transhydrogenase, subunit [*Oceanicaulis alexandrii* HTCC2633] |
| 176 | YP_526430 | 90020603 | Glycogen/starch/alpha-glucan phosphorylase [*Saccharophagus degradans* 2-40] |
| 177 | ZP_012 . . . | 89362826 | nicotinamide nucleotide transhydrogenase, subunit alpha1 [*Xanthobacter autotrophicus* Py2] |
| 178 | YP_277175 | 71737873 | NAD(P) transhydrogenase, subunit alpha part 1 [*Pseudomonas syringae* pv. *phaseolicola* 1448A] |
| 179 | YP_238081 | 66048240 | Alanine dehydrogenase/PNT, C-terminal:Alanine dehydrogenase/PNT, N-terminal [*Pseudomonas syringae* pv. *syringae* B728a] |
| 180 | YP_675347 | 110635139 | alanine dehydrogenase/PNT-like [*Mesorhizobium* sp. BNC1] |
| 181 | YP_345847 | 77456342 | NAD(P)(+) transhydrogenase (AB-specific) [*Pseudomonas fluorescens* PfO-1] |
| 182 | AAQ87237 | 36958769 | NAD(P) transhydrogenase subunit alpha [*Rhizobium* sp. NGR234] |
| 183 | ZP_013 . . . | 94499798 | pyridine nucleotide transhydrogenase alpha subunit [*Oceanobacter* sp. RED65] |

TABLE 32-continued

Examples of transhydrogenase subunit alpha polypeptides.

| Row | ACCESSION | GI | PROTEIN DESCRIPTION |
|---|---|---|---|
| 184 | NP_881481 | 33593837 | NAD(P) transhydrogenase, subunit alpha part 1 [*Bordetella pertussis Tohama* I] |
| 185 | P0C186 | 91207608 | NAD(P) transhydrogenase subunit alpha part 1 (Pyridine nucleotide transhydrogenase subunit alpha 1) (Nicotinamide nucleotide transhydrogenase subunit alpha 1) (Proton-translocating transhydrogenase component 1) (dI) |
| 186 | 1PTJB | 37927621 | Chain B, Crystal Structure Analysis Of The Di And Diii Complex Of Transhydrogenase With A Thio-Nicotinamide Nucleotide Analogue |
| 187 | YP_485056 | 86748560 | NAD(P)(+) transhydrogenase (AB-specific) [*Rhodopseudomonas palustris* HaA2] |
| 188 | YP_620103 | 107021776 | alanine dehydrogenase/PNT-like [*Burkholderia cenocepacia* AU 1054] |
| 189 | ZP_008 . . . | 77952426 | pyridine nucleotide transhydrogenase alpha subunit [*Marinobacter aquaeolei* VT8] |
| 190 | NP_840933 | 30248863 | Alanine dehydrogenase and pyridine nucleotide transhydrogenase [*Nitrosomonas europaea* ATCC 19718] |
| 191 | 2FRDB | 90109601 | Chain B, Structure Of Transhydrogenase (Di.S138a.Nadh)2(Diii.Nadph)1 Asymmetric Complex |
| 192 | NP_888491 | 33600931 | NAD(P) transhydrogenase, subunit alpha part 1 [*Bordetella bronchiseptica* RB50] |
| 193 | XP_726447 | 82596885 | NAD(P) transhydrogenase subunit beta [*Plasmodium yoelii yoelii* str. 17XNL] |
| 194 | YP_551329 | 91790377 | NAD(P)(+) transhydrogenase (AB-specific) [*Polaromonas* sp. JS666] |
| 195 | ZP_006 . . . | 71548985 | NAD(P)(+) transhydrogenase (AB-specific) [*Nitrosomonas eutropha* C71] |
| 196 | YP_568553 | 91975894 | NAD(P)(+) transhydrogenase (AB-specific) [*Rhodopseudomonas palustris* BisB5] |
| 197 | 2FSVB | 90109621 | Chain B, Structure Of Transhydrogenase (Di.D135n.Nad+) 2(Diii.E155w.Nadp+)1 Asymmetric Complex |
| 198 | 1NM5B | 42543078 | Chain B, *R. Rubrum* Transhydrogenase (Di.Q132n)2(Diii)1 Asymmetric Complex |
| 199 | 1L7DB | 27065343 | Chain B, Crystal Structure Of *R. Rubrum* Transhydrogenase Domain I Without Bound Nad(H) |
| 200 | ZP_012 . . . | 90418769 | NAD(P) transhydrogenase, subunit alpha part 1 [*Aurantimonas* sp. SI85-9A1] |
| 201 | 2FR8B | 90109598 | Chain B, Structure Of Transhydrogenase (Di.R127a.Nad+)2(Diii.Nadp+)1 Asymmetric Complex |

TABLE 33

Examples of transhydrogenase subunit beta polypeptides.

| Row | ACCESSION | GI | PROTEIN DESCRIPTION |
|---|---|---|---|
| 1 | NP_416119 | 16129560 | pyridine nucleotide transhydrogenase [*Escherichia coli* K12]. |
| 2 | YP_669454 | 110641724 | NAD(P) transhydrogenase subunit beta [*Escherichia coli* 536] |
| 3 | ZP_007 . . . | 75234915 | COG1282: NAD/NADP transhydrogenase beta subunit [*Escherichia coli* E110019] |
| 4 | ZP_007 . . . | 75230949 | COG1282: NAD/NADP transhydrogenase beta subunit [*Escherichia coli* B7A] |
| 5 | YP_407978 | 82544031 | pyridine nucleotide transhydrogenase, beta subunit [*Shigella boydii* Sb227] |
| 6 | YP_150630 | 56413555 | pyridine nucleotide transhydrogenase [*Salmonella enterica* subsp. *enterica serovar Paratyphi* A str. ATCC 9150] |
| 7 | YP_216485 | 62180068 | pyridine nucleotide transhydrogenase [*Salmonella enterica* subsp. *enterica serovar Choleraesuis* str. SC-B67] |
| 8 | ABF71059 | 102621429 | NADP transhydrogenase beta subunit [*Enterobacter cloacae*] |
| 9 | NP_929428 | 37526084 | pyridine nucleotide transhydrogenase [*Photorhabdus luminescens* subsp. *laumondii* TTO1] |
| 10 | YP_050298 | 50121131 | pyridine nucleotide transhydrogenase [*Erwinia carotovora* subsp. *atroseptica* SCRI1043] |
| 11 | ZP_008 . . . | 77979497 | COG1282: NAD/NADP transhydrogenase beta subunit [*Yersinia intermedia* ATCC 29909] |
| 12 | ZP_008 . . . | 77975378 | COG1282: NAD/NADP transhydrogenase beta subunit [*Yersinia frederiksenii* ATCC 33641] |
| 13 | ZP_008 . . . | 77958019 | COG1282: NAD/NADP transhydrogenase beta subunit [*Yersinia bercovieri* ATCC 43970] |
| 14 | ZP_008 . . . | 77963332 | COG1282: NAD/NADP transhydrogenase beta subunit [*Yersinia mollaretii* ATCC 43969] |
| 15 | YP_647692 | 108811925 | NAD(P) transhydrogenase subunit beta [*Yersinia pestis* Nepal516] |

TABLE 33-continued

Examples of transhydrogenase subunit beta polypeptides.

| Row | ACCESSION | GI | PROTEIN DESCRIPTION |
|---|---|---|---|
| 16 | YP_455167 | 85059465 | pyridine nucleotide transhydrogenase beta subunit [*Sodalis glossinidius* str. 'morsitans'] |
| 17 | NP_719280 | 24375237 | pyridine nucleotide transhydrogenase [*Shewanella oneidensis* MR-1] |
| 18 | YP_736946 | 114046396 | NAD(P) transhydrogenase, beta subunit [*Shewanella* sp. MR-7] |
| 19 | ZP_009 . . . | 82741967 | NAD(P) transhydrogenase, beta subunit [*Shewanella* sp. W3-18-1] |
| 20 | NP_245689 | 15602617 | pyridine nucleotide transhydrogenase [*Pasteurella multocida* subsp. *multocida* str. Pm70] |
| 21 | ZP_005 . . . | 68541685 | NAD(P) transhydrogenase, beta subunit [*Shewanella baltica* OS155] |
| 22 | ZP_012 . . . | 90412640 | putative NAD(P) transhydrogenase, beta subunit [*Photobacterium profundum* 3TCK] |
| 23 | ZP_001 . . . | 53732668 | COG1282: NAD/NADP transhydrogenase beta subunit [*Haemophilus influenzae* R2846] |
| 24 | YP_249234 | 68250122 | pyridine nucleotide transhydrogenase [*Haemophilus influenzae* 86-028NP] |
| 25 | NP_439514 | 16273273 | pyridine nucleotide transhydrogenase [*Haemophilus influenzae* Rd KW20] |
| 26 | ZP_005 . . . | 68545629 | NAD(P) transhydrogenase, beta subunit [*Shewanella amazonensis* SB2B] |
| 27 | YP_132575 | 54302582 | pyridine nucleotide transhydrogenase [*Photobacterium profundum* SS9] |
| 28 | ZP_011 . . . | 89073748 | pyridine nucleotide transhydrogenase [*Photobacterium* sp. SKA34] |
| 29 | NP_800431 | 28900776 | pyridine nucleotide transhydrogenase [*Vibrio parahaemolyticus* RIMD 2210633] |
| 30 | ZP_012 . . . | 90577760 | pyridine nucleotide transhydrogenase [*Vibrio angustum* S14] |
| 31 | ZP_007 . . . | 75857577 | COG1282: NAD/NADP transhydrogenase beta subunit [*Vibrio* sp. Ex25] |
| 32 | NP_936867 | 37676471 | pyridine nucleotide transhydrogenase [*Vibrio vulnificus* YJ016] |
| 33 | ZP_007 . . . | 75818461 | COG1282: NAD/NADP transhydrogenase beta subunit [*Vibrio cholerae* V51] |
| 34 | ZP_007 . . . | 75831476 | COG1282: NAD/NADP transhydrogenase beta subunit [*Vibrio cholerae* MO10] |
| 35 | ZP_012 . . . | 91226113 | pyridine nucleotide transhydrogenase [*Vibrio alginolyticus* 12G01] |
| 36 | YP_206543 | 59713768 | pyridine nucleotide transhydrogenase [*Vibrio fischeri* ES114] |
| 37 | YP_088415 | 52425278 | pyridine nucleotide transhydrogenase [*Mannheimia succiniciproducens* MBEL55E] |
| 38 | ZP_001 . . . | 32035330 | COG1282: NAD/NADP transhydrogenase beta subunit [*Actinobacillus pleuropneumoniae serovar* 1 str. 4074] |
| 39 | ZP_006 . . . | 69950757 | NAD(P) transhydrogenase, beta subunit [*Shewanella frigidimarina* NCIMB 400] |
| 40 | ZP_010 . . . | 86147992 | pyridine nucleotide transhydrogenase [*Vibrio* sp. MED222] |
| 41 | ZP_009 . . . | 84393927 | NAD(P) transhydrogenase, beta subunit [*Vibrio splendidus* 12B01] |
| 42 | ZP_007 . . . | 75429915 | NAD/NADP transhydrogenase beta subunit [*Actinobacillus succinogenes* 130Z] |
| 43 | NP_274015 | 15676870 | pyridine nucleotide transhydrogenase [*Neisseria meningitidis* MC58] |
| 44 | NP_283942 | 15794120 | pyridine nucleotide transhydrogenase [*Neisseria meningitidis* Z2491] |
| 45 | YP_208524 | 59801812 | pyridine nucleotide transhydrogenase [*Neisseria gonorrhoeae* FA 1090] |
| 46 | YP_718441 | 113460379 | NAD(P)(+) transhydrogenase, beta subunit (pyridine nucleotide transhydrogenase) [*Haemophilus somnus* 129PT] |
| 47 | NP_874045 | 33152692 | pyridine nucleotide transhydrogenase [*Haemophilus ducreyi* 35000HP] |
| 48 | YP_561941 | 91792290 | NAD(P) transhydrogenase, beta subunit [*Shewanella denitrificans* OS217] |
| 49 | YP_434235 | 83645800 | NAD/NADP transhydrogenase beta subunit [*Hahella chejuensis* KCTC 2396] |
| 50 | YP_268515 | 71280969 | pyridine nucleotide transhydrogenase [*Colwellia psychrerythraea* 34H] |
| 51 | ZP_013 . . . | 106883670 | NAD(P) transhydrogenase, beta subunit [*Psychromonas ingrahamii* 37] |
| 52 | ZP_009 . . . | 84495284 | pyridine nucleotide transhydrogenase [*Janibacter* sp. HTCC2649] |
| 53 | YP_637278 | 108797081 | NAD(P) transhydrogenase, beta subunit [*Mycobacterium* sp. MCS] |
| 54 | ZP_012 . . . | 90408905 | NAD(P) transhydrogenase subunit beta [*Psychromonas* sp. CNPT3] |
| 55 | ZP_011 . . . | 89340413 | NAD(P) transhydrogenase, beta subunit [*Mycobacterium flavescens* PYR-GCK] |

TABLE 33-continued

Examples of transhydrogenase subunit beta polypeptides.

| Row | ACCESSION | GI | PROTEIN DESCRIPTION |
|---|---|---|---|
| 56 | ZP_012 . . . | 90202100 | NAD(P) transhydrogenase, beta subunit [*Mycobacterium vanbaalenii* PYR-1] |
| 57 | NP_631663 | 21225884 | NAD(P) transhydrogenase beta subunit [*Streptomyces coelicolor* A3(2)] |
| 58 | NP_821577 | 29826943 | pyridine nucleotide transhydrogenase, beta subunit [*Streptomyces avermitilis* MA-4680] |
| 59 | YP_702682 | 111019710 | NAD(P) transhydrogenase beta subunit [*Rhodococcus* sp. RHA1] |
| 60 | YP_422186 | 83311922 | NAD/NADP transhydrogenase beta subunit [*Magnetospirillum magneticum* AMB-1] |
| 61 | ZP_006 . . . | 71366731 | NAD(P) transhydrogenase, beta subunit [*Nocardioides* sp. JS614] |
| 62 | YP_115164 | 53803089 | NAD(P) transhydrogenase, beta subunit [*Methylococcus capsulatus* str. Bath] |
| 63 | YP_524984 | 89902513 | NAD(P) transhydrogenase, beta subunit [*Rhodoferax ferrireducens* T118] |
| 64 | NP_440860 | 16330132 | pyridine nucleotide transhydrogenase beta subunit [*Synechocystis* sp. PCC 6803] |
| 65 | ZP_004 . . . | 66966824 | NAD(P) transhydrogenase, beta subunit [*Arthrobacter* sp. FB24] |
| 66 | ZP_011 . . . | 88798021 | pyridine nucleotide transhydrogenase [*Reinekea* sp. MED297] |
| 67 | YP_342321 | 77163796 | NAD(P) transhydrogenase, beta subunit [*Nitrosococcus oceani* ATCC 19707] |
| 68 | ZP_006 . . . | 69261415 | NAD(P) transhydrogenase, beta subunit [*Magnetococcus* sp. MC-1] |
| 69 | ZP_004 . . . | 67542769 | NAD(P) transhydrogenase, beta subunit [*Burkholderia vietnamiensis* G4] |
| 70 | YP_366915 | 78060340 | NAD(P) transhydrogenase, beta subunit [*Burkholderia* sp. 383] |
| 71 | ZP_006 . . . | 74018097 | NAD(P) transhydrogenase, beta subunit [*Burkholderia ambifaria* AMMD] |
| 72 | YP_298859 | 73538492 | NAD(P) transhydrogenase, beta subunit [*Ralstonia eutropha* JMP134] |
| 73 | YP_055340 | 50842113 | NAD(P) transhydrogenase subunit beta [*Propionibacterium acnes* KPA171202] |
| 74 | ZP_009 . . . | 83949482 | NAD(P)+ transhydrogenase, beta subunit [*Roseovarius nubinhibens* ISM] |
| 75 | CAJ96499 | 113530152 | NAD(P) transhydrogenase subunit beta [*Ralstonia eutropha* H16] |
| 76 | ZP_006 . . . | 69933434 | NAD(P) transhydrogenase, beta subunit [*Paracoccus denitrificans* PD1222] |
| 77 | YP_168027 | 56697657 | NAD(P)+ transhydrogenase, beta subunit [*Silicibacter pomeroyi* DSS-3] |
| 78 | NP_533165 | 17936375 | NAD(P)+ transhydrogenase beta chain [*Agrobacterium tumefaciens* str. C58] |
| 79 | AAQ87370 | 36958945 | NAD(P) transhydrogenase subunit beta [*Rhizobium* sp. NGR234] |
| 80 | ZP_009 . . . | 83942707 | NAD(P)+ transhydrogenase, beta subunit [*Sulfitobacter* sp. EE-36] |
| 81 | ZP_009 . . . | 83953946 | NAD(P)+ transhydrogenase, beta subunit [*Sulfitobacter* sp. NAS-14.1] |
| 82 | ZP_007 . . . | 75813705 | COG1282: NAD/NADP transhydrogenase beta subunit [*Vibrio cholerae* V52] |
| 83 | ZP_010 . . . | 84503573 | NAD(P)+ transhydrogenase, beta subunit [*Oceanicola batsensis* HTCC2597] |
| 84 | ZP_010 . . . | 84686400 | NAD(P)+ transhydrogenase, beta subunit [*Rhodobacterales bacterium* HTCC2654] |
| 85 | YP_612702 | 99080548 | NAD(P) transhydrogenase, beta subunit [*Silicibacter* sp. TM1040] |
| 86 | ZP_010 . . . | 84516762 | NAD(P)+ transhydrogenase, beta subunit [*Loktanella vestfoldensis* SKA53] |
| 87 | ZP_010 . . . | 86137633 | NAD(P)+ transhydrogenase, beta subunit [*Roseobacter* sp. MED193] |
| 88 | YP_511223 | 89055772 | NAD(P) transhydrogenase, beta subunit [*Jannaschia* sp. CCS1] |
| 89 | ZP_010 . . . | 85704983 | NAD(P)+ transhydrogenase, beta subunit [*Roseovarius* sp. 217] |
| 90 | ZP_007 . . . | 75822802 | COG1282: NAD/NADP transhydrogenase beta subunit [*Vibrio cholerae* RC385] |
| 91 | YP_683503 | 110680496 | NAD(P) transhydrogenase, beta subunit [*Roseobacter denitrificans* OCh 114] |
| 92 | NP_949516 | 39937240 | nicotinamide nucleotide transhydrogenase, subunit beta [*Rhodopseudomonas palustris* CGA009] |
| 93 | YP_418478 | 83269187 | NAD(P) transhydrogenase, beta subunit [*Brucella melitensis biovar Abortus* 2308] |
| 94 | YP_485058 | 86748562 | NAD(P) transhydrogenase, beta subunit [*Rhodopseudomonas palustris* HaA2] |
| 95 | ZP_009 . . . | 83859918 | nicotinamide nucleotide transhydrogenase, subunit beta [*Oceanicaulis alexandrii* HTCC2633] |

TABLE 33-continued

Examples of transhydrogenase subunit beta polypeptides.

| Row | ACCESSION | GI | PROTEIN DESCRIPTION |
|---|---|---|---|
| 96 | ZP_008 . . . | 77740973 | NAD(P) transhydrogenase, beta subunit [*Rhodopseudomonas palustris* BisA53] |
| 97 | ZP_012 . . . | 89362731 | NAD(P) transhydrogenase, beta subunit [*Xanthobacter autotrophicus* Py2] |
| 98 | ZP_008 . . . | 77814001 | NAD(P) transhydrogenase, beta subunit [*Shewanella putrefaciens* CN-32] |
| 99 | ZP_010 . . . | 84704197 | PntB, NAD(P) transhydrogenase, beta subunit [*Parvularcula bermudensis* HTCC2503] |
| 100 | YP_533811 | 90425441 | NAD(P) transhydrogenase, beta subunit [*Rhodopseudomonas palustris* BisB18] |
| 101 | P0C188 | 91207612 | NAD(P) transhydrogenase subunit beta (Pyridine nucleotide transhydrogenase subunit beta) (Nicotinamide nucleotide transhydrogenase subunit beta) (Proton-translocating transhydrogenase NADP(H)-binding component) (dIII) |
| 102 | YP_568555 | 91975896 | NAD(P) transhydrogenase, beta subunit [*Rhodopseudomonas* palustris BisB5] |
| 103 | ZP_012 . . . | 90418771 | NAD(P) transhydrogenase, subunit beta [*Aurantimonas* sp. SI85-9A1] |
| 104 | YP_526432 | 90020605 | NAD(P) transhydrogenase, beta subunit [*Saccharophagus degradans* 2-40] |
| 105 | ZP_008 . . . | 78699497 | NAD(P)+ transhydrogenase beta chain [*Bradyrhizobium* sp. BTAi1] |
| 106 | XP_424784 | 50761621 | PREDICTED: similar to nicotinamide nucleotide transhydrogenase [*Gallus gallus*] |
| 107 | XP_799127 | 72030333 | PREDICTED: similar to nicotinamide nucleotide transhydrogenase [*Strongylocentrotus purpuratus*] |
| 108 | ZP_010 . . . | 85716091 | NAD/NADP transhydrogenase beta subunit [*Nitrobacter* sp. Nb-311A] |
| 109 | YP_605919 | 104779421 | pyridine nucleotide transhydrogenase, beta subunit [*Pseudomonas entomophila* L48] |
| 110 | YP_457359 | 85373297 | PntB, NAD(P) transhydrogenase, beta subunit [*Erythrobacter litoralis* HTCC2594] |
| 111 | XP_970382 | 91083631 | PREDICTED: similar to nicotinamide nucleotide transhydrogenase [*Tribolium castaneum*] |
| 112 | BAB51677 | 14025075 | nicotinamide nucleotide transhydrogenase, subunit beta [*Mesorhizobium loti* MAFF303099] |
| 113 | ZP_012 . . . | 94413536 | hypothetical protein PaerP_01004711 [*Pseudomonas aeruginosa* PA7] |
| 114 | ZP_011 . . . | 88938736 | NAD/NADP transhydrogenase beta subunit-like [*Acidiphilium cryptum* JF-5] |
| 115 | NP_795188 | 28872569 | NAD(P) transhydrogenase, beta subunit [*Pseudomonas syringae* pv. tomato str. DC3000] |
| 116 | YP_257265 | 70733625 | NAD(P) transhydrogenase, beta subunit [*Pseudomonas fluorescens* Pf-5] |
| 117 | NP_773764 | 27382235 | NAD(P)+ transhydrogenase beta chain [*Bradyrhizobium japonicum* USDA 110] |
| 118 | YP_576517 | 92116788 | NAD(P) transhydrogenase, beta subunit [*Nitrobacter hamburgensis* X14] |
| 119 | ZP_013 . . . | 107099186 | hypothetical protein PaerPA_01000196 [*Pseudomonas aeruginosa* PACS2] |
| 120 | YP_557045 | 91781839 | Putative NAD(P) transhydrogenase, beta subunit [*Burkholderia xenovorans* LB400] |
| 121 | ZP_009 . . . | 82737421 | pyridine nucleotide transhydrogenase, beta subunit [*Pseudomonas putida* F1] |
| 122 | YP_345845 | 77456340 | NAD(P) transhydrogenase, beta subunit [*Pseudomonas fluorescens* PfO-1] |
| 123 | NP_999921 | 47550793 | nicotinamide nucleotide transhydrogenase [*Danio rerio*] |
| 124 | YP_411848 | 82702282 | NAD(P) transhydrogenase, beta subunit [*Nitrosospira multiformis* ATCC 25196] |
| 125 | CAF99856 | 47230663 | unnamed protein product [*Tetraodon nigroviridis*] |
| 126 | YP_675345 | 110635137 | NAD(P) transhydrogenase, beta subunit [*Mesorhizobium* sp. BNC1] |
| 127 | EAT35199 | 108870974 | nadp transhydrogenase [*Aedes aegypti*] |
| 128 | YP_277177 | 71736851 | NAD(P) transhydrogenase, beta subunit [*Pseudomonas syringae* pv. *phaseolicola* 1448A] |
| 129 | YP_263852 | 71065125 | NAD(P) transhydrogenase, beta subunit [*Psychrobacter arcticus* 273-4] |
| 130 | NP_840935 | 30248865 | NAD(P) transhydrogenase beta subunit [*Nitrosomonas europaea* ATCC 19718] |
| 131 | XP_867922 | 73953775 | PREDICTED: similar to NAD(P) transhydrogenase, mitochondrial precursor (Pyridine nucleotide transhydrogenase) (Nicotinamide nucleotide transhydrogenase) isoform 4 [*Canis familiaris*] |
| 132 | XP_867916 | 73953773 | PREDICTED: similar to NAD(P) transhydrogenase, mitochondrial precursor (Pyridine nucleotide transhydrogenase) |

TABLE 33-continued

| Row | ACCESSION | GI | PROTEIN DESCRIPTION |
|---|---|---|---|
| Examples of transhydrogenase subunit beta polypeptides. | | | |
| | | | (Nicotinamide nucleotide transhydrogenase) isoform 3 [*Canis familiaris*] |
| 133 | XP_536481 | 73953769 | PREDICTED: similar to NAD(P) transhydrogenase, mitochondrial precursor (Pyridine nucleotide transhydrogenase) (Nicotinamide nucleotide transhydrogenase) isoform 1 [*Canis familiaris*] |
| 134 | XP_867928 | 73953777 | PREDICTED: similar to NAD(P) transhydrogenase, mitochondrial precursor (Pyridine nucleotide transhydrogenase) (Nicotinamide nucleotide transhydrogenase) isoform 5 [*Canis familiaris*] |
| 135 | NP_001 . . . | 61557127 | nicotinamide nucleotide transhydrogenase [*Rattus norvegicus*] |
| 136 | YP_238083 | 66048242 | NAD(P) transhydrogenase, beta subunit [*Pseudomonas syringae* pv. *syringae* B728a] |
| 137 | BAE40577 | 74219995 | unnamed protein product [*Mus musculus*] |
| 138 | BAC39226 | 26351179 | unnamed protein product [*Mus musculus*] |
| 139 | ZP_013 . . . | 94494989 | NAD(P) transhydrogenase, beta subunit [*Sphingomonas* sp. SKA58] |
| 140 | NP_032736 | 31543330 | nicotinamide nucleotide transhydrogenase [*Mus musculus*] |
| 141 | BAC40113 | 26352966 | unnamed protein product [*Mus musculus*] |
| 142 | ZP_004 . . . | 67155631 | NAD(P) transhydrogenase, beta subunit [*Azotobacter vinelandii* AvOP] |
| 143 | YP_579812 | 93005375 | NAD(P) transhydrogenase, beta subunit [*Psychrobacter cryohalolentis* K5] |
| 144 | YP_297031 | 73542511 | NAD(P) transhydrogenase, beta subunit [*Ralstonia eutropha* JMP134] |
| 145 | YP_585107 | 94311897 | NAD(P) transhydrogenase, beta subunit [*Ralstonia metallidurans* CH34] |
| 146 | YP_497119 | 87199862 | NAD(P) transhydrogenase, beta subunit [*Novosphingobium* aromaticivorans DSM 12444] |
| 147 | AAQ87239 | 36958771 | NAD(P) transhydrogenase subunit beta [*Rhizobium* sp. NGR234] |
| 148 | NP_888489 | 33600929 | NAD(P) transhydrogenase subunit beta [*Bordetella bronchiseptica* RB50] |
| 149 | Q61941 | 51338804 | NAD(P) transhydrogenase, mitochondrial precursor (Pyridine nucleotide transhydrogenase) (Nicotinamide nucleotide transhydrogenase) |
| 150 | NP_776368 | 27806831 | nicotinamide nucleotide transhydrogenase [*Bos taurus*] |
| 151 | NP_884728 | 33597085 | NAD(P) transhydrogenase subunit beta [*Bordetella parapertussis* 12822] |
| 152 | AAA21440 | 163397 | nicotinamide nucleotide transhydrogenase |
| 153 | YP_441808 | 83721084 | NAD(P) transhydrogenase, beta subunit [*Burkholderia thailandensis* E264] |
| 154 | AAI10544 | 83405154 | Nicotinamide nucleotide transhydrogenase [*Homo sapiens*] |
| 155 | NP_899769 | 34495554 | NAD(P) transhydrogenase, beta subunit [*Chromobacterium violaceum* ATCC 12472] |
| 156 | NP_422097 | 16127533 | NAD(P) transhydrogenase, beta subunit [*Caulobacter crescentus* CB15] |
| 157 | XP_312859 | 58383882 | ENSANGP00000016622 [*Anopheles gambiae* str. PEST] |
| 158 | ZP_009 . . . | 84360819 | COG1282: NAD/NADP transhydrogenase beta subunit [*Burkholderia dolosa* AUO158] |
| 159 | ZP_014 . . . | 113935785 | NAD(P) transhydrogenase, beta subunit [*Caulobacter* sp. K31] |
| 160 | ZP_006 . . . | 71548983 | NAD(P) transhydrogenase, beta subunit [*Nitrosomonas eutropha* C71] |
| 161 | AAH81117 | 51703526 | MGC83563 protein [*Xenopus laevis*] |
| 162 | CAH90079 | 55726630 | hypothetical protein [*Pongo pygmaeus*] |
| 163 | BAE35294 | 74198248 | unnamed protein product [*Mus musculus*] |
| 164 | ZP_014 . . . | 113872300 | probable NAD(P) transhydrogenase subunit beta transmembrane protein [*Sinorhizobium medicae* WSM419] |
| 165 | AAI10545 | 83405537 | Nicotinamide nucleotide transhydrogenase [*Homo sapiens*] |
| 166 | NP_036475 | 33695084 | nicotinamide nucleotide transhydrogenase [*Homo sapiens*] |
| 167 | YP_727574 | 113869085 | NAD(P) transhydrogenase subunit beta [*Ralstonia eutropha* H16] |
| 168 | 2211247B | 1589396 | nicotinamide nucleotide transhydrogenase |
| 169 | 2211247A | 1589395 | nicotinamide nucleotide transhydrogenase |
| 170 | AAN62246 | 24461677 | putative pyridine nucleotide transhydrogenase, beta subunit [*Pseudomonas aeruginosa*] |
| 171 | P11024 | 128400 | NAD(P) transhydrogenase, mitochondrial precursor (Pyridine nucleotide transhydrogenase) (Nicotinamide nucleotide transhydrogenase) |
| 172 | NP_892022 | 33695086 | nicotinamide nucleotide transhydrogenase [*Homo sapiens*] |
| 173 | NP_386966 | 15966613 | PROBABLE NAD(P) TRANSHYDROGENASE SUBUNIT BETA TRANSMEMBRANE PROTEIN [*Sinorhizobium meliloti* 1021] |
| 174 | YP_299910 | 73539543 | NAD(P) transhydrogenase, beta subunit [*Ralstonia eutropha* JMP134] |

TABLE 33-continued

Examples of transhydrogenase subunit beta polypeptides.

| Row | ACCESSION | GI | PROTEIN DESCRIPTION |
|---|---|---|---|
| 175 | ZP_012 . . . | 91769178 | NAD(P) transhydrogenase, beta subunit [*Psychrobacter* sp. PRwf-1] |
| 176 | YP_293241 | 72383887 | NAD(P) transhydrogenase, beta subunit [*Ralstonia eutropha* JMP134] |
| 177 | YP_299480 | 73539113 | NAD(P) transhydrogenase, beta subunit [*Ralstonia eutropha* JMP134] |
| 178 | YP_293567 | 72384213 | NAD(P) transhydrogenase, beta subunit [*Ralstonia eutropha* JMP134] |
| 179 | YP_725774 | 113867285 | NAD(P) transhydrogenase subunit beta [*Ralstonia eutropha* H16] |
| 180 | YP_620105 | 107021778 | NAD(P) transhydrogenase, beta subunit [*Burkholderia cenocepacia* AU 1054] |
| 181 | YP_725367 | 113866878 | NAD(P) transhydrogenase subunit beta [*Ralstonia eutropha* H16] |
| 182 | NP_520854 | 17547452 | PROBABLE TRANSMEMBRANE NADP TRANSHYDROGENASE (BETA SUBUNIT) OXIDOREDUCTASE PROTEIN [*Ralstonia solanacearum* GMI1000] |
| 183 | ZP_009 . . . | 83746755 | PntB [*Ralstonia solanacearum* UW551] |
| 184 | ZP_013 . . . | 100235717 | hypothetical protein Bpse4_03000891 [*Burkholderia pseudomallei* 406e] |
| 185 | YP_334763 | 76809085 | NAD(P) transhydrogenase subunit beta [*Burkholderia pseudomallei* 1710b] |
| 186 | ZP_013 . . . | 100917505 | hypothetical protein Bmal10_03001254 [*Burkholderia mallei* 10399] |
| 187 | ZP_004 . . . | 67667725 | NAD(P) transhydrogenase, beta subunit [*Burkholderia cenocepacia* HI2424] |
| 188 | ZP_012 . . . | 91762289 | NAD(p) transhydrogenase subunit beta [*Candidatus Pelagibacter ubique* HTCC1002] |
| 189 | YP_471093 | 86359201 | NAD(P)(+) transhydrogenase (AB-specific), beta subunit protein [*Rhizobium etli* CFN 42] |
| 190 | ZP_010 . . . | 85707884 | PntB, NAD(P) transhydrogenase, beta subunit [*Erythrobacter* sp. NAP1] |
| 191 | YP_293266 | 72383912 | NAD(P) transhydrogenase, beta subunit [*Ralstonia eutropha* JMP134] |
| 192 | ZP_009 . . . | 84356795 | COG1282: NAD/NADP transhydrogenase beta subunit [*Burkholderia cenocepacia* PC184] |
| 193 | YP_266000 | 71083281 | NAD(p) transhydrogenase subunit beta [*Candidatus Pelagibacter ubique* HTCC1062] |
| 194 | CAE68875 | 39598183 | Hypothetical protein CBG14838 [*Caenorhabditis briggsae*] |
| 195 | YP_368033 | 78065264 | NAD(P) transhydrogenase, beta subunit [*Burkholderia* sp. 383] |
| 196 | YP_616428 | 103486867 | NAD(P) transhydrogenase, beta subunit [*Sphingopyxis alaskensis* RB2256] |
| 197 | YP_246075 | 67458451 | NAD(p) transhydrogenase subunit beta [*Rickettsia felis* URRWXCal2] |
| 198 | YP_537194 | 91204839 | NAD(p) transhydrogenase subunit beta [*Rickettsia bellii* RML369-C] |
| 199 | XP_646840 | 66826971 | NAD(P)+ transhydrogenase (AB-specific) [*Dictyostelium discoideum* AX4] |
| 200 | ZP_009 . . . | 83747817 | NAD(P) transhydrogenase subunit beta [*Ralstonia solanacearum* UW551] |
| 201 | YP_047599 | 50086089 | pyridine nucleotide transhydrogenase, beta subunit [*Acinetobacter* sp. ADP1] |

TABLE 34

Examples of pox2 polypeptides.

| Row | ACCESSION | GI | PROTEIN DESCRIPTION |
|---|---|---|---|
| 1 | XP_505264.1 | 50555712 | YlPOX2 [*Yarrowia lipolytica*]. |
| 2 | O74936 | 59799074 | Acyl-coenzyme A oxidase 3 (Acyl-CoA oxidase 3) |
| 3 | XP_504475 | 50554133 | YlPOX4 [*Yarrowia lipolytica*] |
| 4 | XP_502199 | 50549457 | YlPOX5 [*Yarrowia lipolytica*] |
| 5 | O74934 | 59799072 | Acyl-coenzyme A oxidase 1 (Acyl-CoA oxidase 1) |
| 6 | XP_504703 | 50554589 | YlPOX1 [*Yarrowia lipolytica*] |
| 7 | XP_503632 | 50552444 | hypothetical protein [*Yarrowia lipolytica*] |
| 8 | XP_760471 | 71020481 | hypothetical protein UM04324.1 [*Ustilago maydis* 521] |
| 9 | XP_571768 | 58269224 | Acyl-coenzyme A oxidase I [*Cryptococcus neoformans* var. *neoformans* JEC21] |
| 10 | XP_717995 | 68475844 | putative fatty-acyl coenzyme A oxidase [*Candida albicans* SC5314] |

TABLE 34-continued

Examples of pox2 polypeptides.

| Row | ACCESSION | GI | PROTEIN DESCRIPTION |
|---|---|---|---|
| 11 | P08790 | 17373073 | Acyl-coenzyme A oxidase 5 (Acyl-CoA oxidase 5) (PXP-5) |
| 12 | Q6BRD5 | 59799027 | Acyl-coenzyme A oxidase (Acyl-CoA oxidase) |
| 13 | OXCKX5 | 66061 | acyl-CoA oxidase (EC 1.3.3.6) POX5, peroxisomal - yeast (*Candida tropicalis*) |
| 14 | BAA83482 | 5763520 | acyl-CoA oxidase [*Candida tropicalis*] |
| 15 | XP__457726 | 50417804 | hypothetical protein DEHA0C01155g [*Debaryomyces hansenii* CBS767] |
| 16 | BAA83483 | 5763522 | acyl-CoA oxidase [*Candida tropicalis*] |
| 17 | OXCKPM | 66060 | acyl-CoA oxidase (EC 1.3.3.6) PXP4, peroxisomal - yeast (*Candida maltosa*) |
| 18 | AAA34362 | 170912 | acyl-coenzyme A oxidase II precursor |
| 19 | Q9Y7B1 | 60391213 | Acyl-coenzyme A oxidase (Acyl-CoA oxidase) |
| 20 | XP__721610 | 68468582 | putative fatty-acyl coenzyme A oxidase [*Candida albicans* SC5314] |
| 21 | AAA34361 | 170910 | PXP-2 protein |
| 22 | 1306283A | 225549 | oxidase, fatty acyl |
| 23 | P06598 | 17373023 | Acyl-coenzyme A oxidase 4 (Acyl-CoA oxidase 4) (PXP-4) (Peroxisomal fatty acyl-CoA oxidase) |
| 24 | XP__721613 | 68468588 | putative fatty-acyl coenzyme A oxidase [*Candida albicans* SC5314] |
| 25 | XP__459232 | 50421365 | hypothetical protein DEHA0D18667g [*Debaryomyces hansenii* CBS767] |
| 26 | Q00468 | 2498206 | Acyl-coenzyme A oxidase 2 (Acyl-CoA oxidase 2) (AOX 2) |
| 27 | Q6CKK7 | 59799028 | Acyl-coenzyme A oxidase (Acyl-CoA oxidase) |
| 28 | NP__011310 | 6321233 | Fatty-acyl coenzyme A oxidase, involved in the fatty acid beta-oxidation pathway; localized to the peroxisomal matrix; Pox1p [*Saccharomyces cerevisiae*] |
| 29 | AAA34891 | 172217 | acyl-coenzyme A oxidase |
| 30 | Q6FY63 | 59799032 | Acyl-coenzyme A oxidase (Acyl-CoA oxidase) |
| 31 | Q756A9 | 60391210 | Acyl-coenzyme A oxidase (Acyl-CoA oxidase) |
| 32 | O65202 | 62286589 | Acyl-coenzyme A oxidase 1, peroxisomal (AOX 1) (Long-chain acyl-CoA oxidase) (AtCX1) |
| 33 | 1W07B | 58177067 | Chain B, Arabidopsis Thaliana Acyl-Coa Oxidase 1 |
| 34 | NP__567513 | 18414744 | ACX1 (ACYL-COA OXIDASE 1) [*Arabidopsis thaliana*] |
| 35 | H71434 | 7488059 | probable apetala2 domain TINY - *Arabidopsis thaliana* |
| 36 | XP__001 . . . | 109118312 | PREDICTED: similar to acyl-Coenzyme A oxidase isoform b [*Macaca mulatta*] |
| 37 | Q5RC19 | 62286600 | Acyl-coenzyme A oxidase 1, peroxisomal (Palmitoyl-CoA oxidase) (AOX) |
| 38 | Q15067 | 17380467 | Acyl-coenzyme A oxidase 1, peroxisomal (Palmitoyl-CoA oxidase) (AOX) (Straight-chain acyl-CoA oxidase) (SCOX) |
| 39 | NP__009223 | 30089974 | acyl-Coenzyme A oxidase isoform b [*Homo sapiens*] |
| 40 | AAB30019 | 7689914 | peroxisomal acyl-coenzyme A oxidase [*Homo sapiens*] |
| 41 | CAH90691 | 55727877 | hypothetical protein [*Pongo pygmaeus*] |
| 42 | AAL01888 | 15553480 | acyl-CoA oxidase [*Glycine max*] |
| 43 | AAA19113 | 458119 | acyl-CoA oxidase |
| 44 | AAA18595 | 495475 | peroxisomal fatty acyl-coA oxidase |
| 45 | XP__540441 | 73965013 | PREDICTED: similar to acyl-Coenzyme A oxidase isoform a [*Canis familiaris*] |
| 46 | NP__001 . . . | 54400372 | hypothetical protein LOC449662 [*Danio rerio*] |
| 47 | NP__001 . . . | 78369480 | acyl-Coenzyme A oxidase 1, palmitoyl [*Bos taurus*] |
| 48 | NP__004026 | 30089972 | acyl-Coenzyme A oxidase isoform a [*Homo sapiens*] |
| 49 | AAH08767 | 14250616 | Acyl-Coenzyme A oxidase 1, palmitoyl [*Homo sapiens*] |
| 50 | CAD97622 | 31873262 | hypothetical protein [*Homo sapiens*] |
| 51 | I38095 | 2117541 | acyl-CoA oxidase (EC 1.3.3.6), peroxisomal - human |
| 52 | NP__001 . . . | 55741614 | acyl-Coenzyme A oxidase 1, palmitoyl [*Gallus gallus*] |
| 53 | CAA68660 | 2673 | acyl-coenzyme A oxidase [*Candida tropicalis*] |
| 54 | Q8HYL8 | 34098564 | Acyl-coenzyme A oxidase 1, peroxisomal (Palmitoyl-CoA oxidase) (AOX) |
| 55 | B54942 | 1082171 | acyl-CoA oxidase (EC 1.3.3.6), peroxisomal splice form II - human |
| 56 | AAH10425 | 14714578 | Acyl-Coenzyme A oxidase 1, palmitoyl [*Homo sapiens*] |
| 57 | CAJ83302 | 89271321 | acyl-Coenzyme A oxidase 2, branched chain [*Xenopus tropicalis*] |
| 58 | AAO15577 | 27462768 | acyl-CoA oxidase type 2 [*Phascolarctos cinereus*] |
| 59 | XP__414406 | 50754485 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Gallus gallus*] |
| 60 | AAH97101 | 67678187 | Zgc: 92584 protein [*Danio rerio*] |
| 61 | AAH85743 | 55249685 | Acyl-Coenzyme A oxidase 1, palmitoyl [*Rattus norvegicus*] |
| 62 | 2DDHA | 93279231 | Chain A, Crystal Structure Of Acyl-Coa Oxidase Complexed With 3-Oh-Dodecanoate |
| 63 | Q9ZQP2 | 62286640 | Putative acyl-coenzyme A oxidase 1.2, peroxisomal |
| 64 | AAH63727 | 39795632 | MGC68531 protein [*Xenopus laevis*] |
| 65 | NP__001 . . . | 62751552 | MGC108278 protein [*Xenopus tropicalis*] |

TABLE 34-continued

Examples of pox2 polypeptides.

| Row | ACCESSION | GI | PROTEIN DESCRIPTION |
|---|---|---|---|
| 66 | AAH68891 | 46250227 | MGC83074 protein [*Xenopus laevis*] |
| 67 | AAW78689 | 58531948 | peroxisomal acyl-CoA oxidase 1A [*Lycopersicon esculentum*] |
| 68 | 2FONC | 109157678 | Chain C, X-Ray Crystal Structure Of Leacx1, An Acyl-Coa Oxidase From *Lycopersicon Esculentum* (Tomato) |
| 69 | ABE83706 | 92875906 | acyl-CoA oxidase [*Medicago truncatula*] |
| 70 | XP_511690 | 55645995 | PREDICTED: similar to hypothetical protein [*Pan troglodytes*] |
| 71 | AAW78691 | 58531952 | peroxisomal acyl-CoA oxidase 1A [*Lycopersicon cheesmaniae*] |
| 72 | AAL01887 | 15553478 | acyl-CoA oxidase [*Glycine max*] |
| 73 | Q9Z1N0 | 17367267 | Acyl-coenzyme A oxidase 1, peroxisomal (Palmitoyl-CoA oxidase) (AOX) |
| 74 | BAA86870 | 6429156 | peroxisomal acyl-CoA oxidase [*Mus musculus*] |
| 75 | Q9R0H0 | 51338830 | Acyl-coenzyme A oxidase 1, peroxisomal (Palmitoyl-CoA oxidase) (AOX) |
| 76 | BAF18456 | 113594582 | Os06g0103500 [*Oryza sativa* (*japonica* cultivar-group)] |
| 77 | AAI08648 | 83318302 | Unknown (protein for MGC: 131363) [*Xenopus laevis*] |
| 78 | AAB62926 | 2253380 | peroxisomal acyl-CoA oxidase [*Mus musculus*] |
| 79 | NP_056544 | 66793429 | acyl-Coenzyme A oxidase 1, palmitoyl [*Mus musculus*] |
| 80 | XP_320717 | 58394415 | ENSANGP00000020118 [*Anopheles gambiae* str. PEST] |
| 81 | AAH21339 | 18204156 | Acox2 protein [*Mus musculus*] |
| 82 | BAE25794 | 74188249 | unnamed protein product [*Mus musculus*] |
| 83 | Q9QXD1 | 17367045 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 84 | XP_320718 | 58394417 | ENSANGP00000020032 [*Anopheles gambiae* str. PEST] |
| 85 | EAT39640 | 108875415 | acyl-CoA oxidase [*Aedes aegypti*] |
| 86 | NP_665713 | 21955130 | acyl-Coenzyme A oxidase 2, branched chain [*Rattus norvegicus*] |
| 87 | XP_625136 | 66556360 | PREDICTED: similar to CG5009-PA, partial [*Apis mellifera*] |
| 88 | CAE63479 | 39592402 | Hypothetical protein CBG07946 [*Caenorhabditis briggsae*] |
| 89 | XP_879996 | 76648809 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 6 [*Bos taurus*] |
| 90 | BAC26167 | 26324826 | unnamed protein product [*Mus musculus*] |
| 91 | XP_592892 | 76648807 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 1 [*Bos taurus*] |
| 92 | AAH47700 | 28839704 | Acyl-Coenzyme A oxidase 2, branched chain [*Homo sapiens*] |
| 93 | XP_541826 | 73985284 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Canis familiaris*] |
| 94 | XP_782824 | 72015136 | PREDICTED: similar to Acyl-coenzyme A oxidase 1, peroxisomal (Palmitoyl-CoA oxidase) (AOX) [*Strongylocentrotus purpuratus*] |
| 95 | EAR95568 | 89297580 | Acyl-CoA oxidase family protein [*Tetrahymena thermophila* SB210] |
| 96 | CAE63477 | 39592400 | Hypothetical protein CBG07944 [*Caenorhabditis briggsae*] |
| 97 | NP_510603 | 17568313 | F59F4.1 [*Caenorhabditis elegans*] |
| 98 | EAT48205 | 108883980 | acyl-CoA oxidase [*Aedes aegypti*] |
| 99 | XP_785210 | 72015040 | PREDICTED: similar to Acyl-coenzyme A oxidase 1, peroxisomal (Palmitoyl-CoA oxidase) (AOX) [*Strongylocentrotus purpuratus*] |
| 100 | O02767 | 17366131 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 101 | AAW78690 | 58531950 | peroxisomal acyl-CoA oxidase 1B [*Lycopersicon esculentum*] |
| 102 | CAE63480 | 39592403 | Hypothetical protein CBG07947 [*Caenorhabditis briggsae*] |
| 103 | EAS31618 | 90301987 | hypothetical protein CIMG_07097 [*Coccidioides immitis* RS] |
| 104 | CAE63476 | 39592399 | Hypothetical protein CBG07943 [*Caenorhabditis briggsae*] |
| 105 | XP_973660 | 91082769 | PREDICTED: similar to CG5009-PA [*Tribolium castaneum*] |
| 106 | CAE69737 | 39596101 | Hypothetical protein CBG16008 [*Caenorhabditis briggsae*] |
| 107 | NP_611264 | 24654595 | CG5009-PA [*Drosophila melanogaster*] |
| 108 | AAF73843 | 8163758 | acyl-CoA oxidase ACX3 [*Arabidopsis thaliana*] |
| 109 | Q9LLH9 | 62286634 | Acyl-coenzyme A oxidase 3, peroxisomal precursor (AOX 3) (Medium-chain acyl-CoA oxidase) (AtCX3) |
| 110 | EAL26359 | 54636956 | GA18591-PA [*Drosophila pseudoobscura*] |
| 111 | AAH54727 | 68262425 | Acox1 protein [*Mus musculus*] |
| 112 | XP_783450 | 72111190 | PREDICTED: similar to acyl-Coenzyme A oxidase 1, palmitoyl [*Strongylocentrotus purpuratus*] |
| 113 | XP_758355 | 71010163 | hypothetical protein UM02208.1 [*Ustilago maydis* 521] |
| 114 | AAL28144 | 16767852 | GH01266p [*Drosophila melanogaster*] |

TABLE 34-continued

Examples of pox2 polypeptides.

| Row | ACCESSION | GI | PROTEIN DESCRIPTION |
|---|---|---|---|
| 115 | NP_001 . . . | 71983346 | F08A8.1a [*Caenorhabditis elegans*] |
| 116 | EAS04704 | 89306716 | Acyl-CoA oxidase family protein [*Tetrahymena thermophila* SB210] |
| 117 | NP_493263 | 17506533 | F08A8.3 [*Caenorhabditis elegans*] |
| 118 | BAC35782 | 74197284 | unnamed protein product [*Mus musculus*] |
| 119 | XP_635946 | 66804335 | hypothetical protein DDBDRAFT_0188674 [*Dictyostelium discoideum* AX4] |
| 120 | NP_493264 | 17506535 | F08A8.4 [*Caenorhabditis elegans*] |
| 121 | CAJ58493 | 85539740 | Hypothetical protein F08A8.1c [*Caenorhabditis elegans*] |
| 122 | NP_001 . . . | 71983355 | F08A8.1b [*Caenorhabditis elegans*] |
| 123 | EAS02716 | 89304728 | Acyl-CoA oxidase family protein [*Tetrahymena thermophila* SB210] |
| 124 | XP_879827 | 76648805 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 5 [*Bos taurus*] |
| 125 | CAH91864 | 55730283 | hypothetical protein [*Pongo pygmaeus*] |
| 126 | NP_499119 | 17552648 | C48B4.1 [*Caenorhabditis elegans*] |
| 127 | ZP_012 . . . | 90587482 | Acyl-CoA oxidase-like:Acyl-CoA dehydrogenase-like:Acyl-CoA dehydrogenase, central region [*Flavobacterium johnsoniae* UW101] |
| 128 | BAE55537 | 83765394 | unnamed protein product [*Aspergillus oryzae*] |
| 129 | XP_637610 | 66807775 | hypothetical protein DDBDRAFT_0187085 [*Dictyostelium discoideum* AX4] |
| 130 | BAF19505 | 113595631 | Os06g0354500 [*Oryza sativa* (*japonica* cultivar-group)] |
| 131 | EAT87650 | 111066530 | hypothetical protein SNOG_05259 [*Phaeosphaeria nodorum* SN15] |
| 132 | CAE65171 | 39590798 | Hypothetical protein CBG10043 [*Caenorhabditis briggsae*] |
| 133 | XP_636605 | 66805767 | hypothetical protein DDBDRAFT_0188084 [*Dictyostelium discoideum* AX4] |
| 134 | XP_664356 | 67541164 | hypothetical protein AN6752.2 [*Aspergillus nidulans* FGSC A4] |
| 135 | EAR99631 | 89301643 | Acyl-CoA oxidase family protein [*Tetrahymena thermophila* SB210] |
| 136 | NP_493262 | 17506531 | F08A8.2 [*Caenorhabditis elegans*] |
| 137 | XP_382463 | 46110811 | hypothetical protein FG02287.1 [*Gibberella zeae* PH-1] |
| 138 | AAL39944 | 17862934 | SD03592p [*Drosophila melanogaster*] |
| 139 | NP_523802 | 17647123 | acyl-Coenzyme A oxidase at 57D proximal CG9707-PA [*Drosophila melanogaster*] |
| 140 | XP_587157 | 76620513 | PREDICTED: similar to Acyl-coenzyme A oxidase 3, peroxisomal (Pristanoyl-CoA oxidase) [*Bos taurus*] |
| 141 | EAR98581 | 89300593 | Acyl-CoA oxidase family protein [*Tetrahymena thermophila* SB210] |
| 142 | Q9LMI7 | 62286635 | Putative acyl-coenzyme A oxidase 3.2, peroxisomal precursor |
| 143 | O65201 | 62286588 | Acyl-coenzyme A oxidase 2, peroxisomal precursor (AOX 2) (Long-chain acyl-CoA oxidase) (AtCX2) |
| 144 | AAC13497 | 3044212 | acyl-CoA oxidase [*Arabidopsis thaliana*] |
| 145 | CAH91120 | 55728762 | hypothetical protein [*Pongo pygmaeus*] |
| 146 | EAR89261 | 89291273 | Acyl-CoA oxidase family protein [*Tetrahymena thermophila* SB210] |
| 147 | XP_646395 | 66826081 | hypothetical protein DDBDRAFT_0216722 [*Dictyostelium discoideum* AX4] |
| 148 | O64894 | 62286587 | Acyl-coenzyme A oxidase, peroxisomal precursor (AOX) (Long-chain acyl-CoA oxidase) |
| 149 | NP_998312 | 47085909 | pristanoyl acyl-Coenzyme A oxidase 3 [*Danio rerio*] |
| 150 | O15254 | 17366151 | Acyl-coenzyme A oxidase 3, peroxisomal (Pristanoyl-CoA oxidase) (Branched-chain acyl-CoA oxidase) (BRCACox) |
| 151 | AAL48010 | 17944231 | LD22081p [*Drosophila melanogaster*] |
| 152 | ZP_012 . . . | 89890388 | acyl-CoA oxidase [*Flavobacteria bacterium* BBFL7] |
| 153 | XP_758113 | 71007469 | hypothetical protein UM01966.1 [*Ustilago maydis* 521] |
| 154 | EAL26647 | 54637244 | GA21980-PA [*Drosophila pseudoobscura*] |
| 155 | NP_109646 | 34328334 | acyl-Coenzyme A oxidase 3, pristanoyl [*Mus musculus*] |
| 156 | YP_290295 | 72162638 | hypothetical protein Tfu_2239 [*Thermobifida fusca* YX] |
| 157 | AAH44725 | 28703869 | Acox3 protein [*Mus musculus*] |
| 158 | NP_445791 | 16758056 | acyl-Coenzyme A oxidase 3, pristanoyl [*Rattus norvegicus*] |
| 159 | YP_445820 | 83816544 | acyl-coenzyme A oxidase I, putative [*Salinibacter ruber DSM* 13855] |
| 160 | AAB67883 | 1575556 | acyl-CoA oxidase homolog [*Phalaenopsis* sp. 'True Lady'] |
| 161 | AAR00586 | 37699750 | acyl-CoA oxidase [*Phalaenopsis* cv. 'True Lady'] |
| 162 | XP_969513 | 91093755 | PREDICTED: similar to pristanoyl acyl-Coenzyme A oxidase 3 [*Tribolium castaneum*] |
| 163 | XP_786025 | 72005645 | PREDICTED: similar to pristanoyl acyl-Coenzyme A oxidase 3 [*Strongylocentrotus purpuratus*] |
| 164 | YP_634556 | 108758121 | putative acyl-CoA dehydrogenase [*Myxococcus xanthus* DK 1622] |
| 165 | EAT87454 | 111066334 | hypothetical protein SNOG_05063 [*Phaeosphaeria nodorum* SN15] |

TABLE 34-continued

| Examples of pox2 polypeptides. | | | |
|---|---|---|---|
| Row | ACCESSION | GI | PROTEIN DESCRIPTION |
| 166 | Q9EPL9 | 17366740 | Acyl-coenzyme A oxidase 3, peroxisomal (Pristanoyl-CoA oxidase) (Branched-chain acyl-CoA oxidase) (BRCACox) |
| 167 | XP_545908 | 73951751 | PREDICTED: similar to Acyl-coenzyme A oxidase 3, peroxisomal (Pristanoyl-CoA oxidase) [*Canis familiaris*] |
| 168 | EAL26648 | 54637245 | GA21981-PA [*Drosophila pseudoobscura*] |
| 169 | BAC26136 | 26324764 | unnamed protein product [*Mus musculus*] |
| 170 | CAA04688 | 2370232 | putative acyl-CoA oxidase [*Hordeum vulgare* subsp. *vulgare*] |
| 171 | BAE42553 | 74143079 | unnamed protein product [*Mus musculus*] |
| 172 | YP_702012 | 111019040 | acyl-CoA oxidase [*Rhodococcus* sp. RHA1] |
| 173 | XP_786081 | 72005647 | PREDICTED: similar to pristanoyl acyl-Coenzyme A oxidase 3 [*Strongylocentrotus purpuratus*] |
| 174 | NP_001 . . . | 79332306 | ACX2 (ACYL-COA OXIDASE 2); acyl-CoA oxidase [*Arabidopsis thaliana*] |
| 175 | NP_572371 | 24640268 | CG4586-PA [*Drosophila melanogaster*] |
| 176 | NP_961035 | 41408199 | hypothetical protein MAP2101 [*Mycobacterium avium subsp. paratuberculosis* K-10] |
| 177 | EAL32329 | 54643586 | GA18278-PA [*Drosophila pseudoobscura*] |
| 178 | ZP_012 . . . | 90205075 | Acyl-CoA oxidase-like:Acyl-CoA dehydrogenase-like:Acyl-CoA dehydrogenase, central region [*Mycobacterium vanbaalenii* PYR-1] |
| 179 | ABA94670 | 108864573 | Acyl-coenzyme A oxidase 2, peroxisomal precursor, putative, expressed [*Oryza sativa* (*japonica* cultivar-group)] |
| 180 | BAE60166 | 83770031 | unnamed protein product [*Aspergillus oryzae*] |
| 181 | ZP_011 . . . | 89339305 | Acyl-CoA oxidase-like:Acyl-CoA dehydrogenase-like:Acyl-CoA dehydrogenase, central region [*Mycobacterium flavescens* PYR-GCK] |
| 182 | NP_609027 | 45550141 | CG9527-PA [*Drosophila melanogaster*] |
| 183 | EAT48670 | 108884445 | acyl-CoA oxidase [*Aedes aegypti*] |
| 184 | ZP_012 . . . | 92908524 | Acyl-CoA oxidase-like:Acyl-CoA dehydrogenase-like:Acyl-CoA dehydrogenase, central region [*Mycobacterium* sp. JLS] |
| 185 | AAH17053 | 16877606 | ACOX3 protein [*Homo sapiens*] |
| 186 | ZP_004 . . . | 66967405 | Acyl-CoA oxidase:Acyl-CoA dehydrogenase, C-terminal [*Arthrobacter sp. FB24*] |
| 187 | NP_508036 | 17560134 | F25C8.1 [*Caenorhabditis elegans*] |
| 188 | ZP_011 . . . | 88854811 | acyl-CoA oxidase [*marine actinobacterium PHSC20C1*] |
| 189 | AAL48950 | 17945806 | RE34879p [*Drosophila melanogaster*] |
| 190 | YP_640598 | 108800401 | acyl-CoA dehydrogenase-like protein [*Mycobacterium* sp. MCS] |
| 191 | NP_724181 | 24585195 | CG17544-PC, isoform C [*Drosophila melanogaster*] |
| 192 | AAL14003 | 16186117 | SD05719p [*Drosophila melanogaster*] |
| 193 | XP_642669 | 66817952 | hypothetical protein DDBDRAFT_0169270 [*Dictyostelium discoideum* AX4] |
| 194 | CAA96917 | 1945301 | POX1 [*Saccharomyces cerevisiae*] |
| 195 | NP_500943 | 17540842 | F58F9.7 [*Caenorhabditis elegans*] |
| 196 | XP_664369 | 67541190 | hypothetical protein AN6765.2 [*Aspergillus nidulans* FGSC A4] |

TABLE 35

| Examples of pox1a polypeptides. | | | |
|---|---|---|---|
| Row | ACCESSION | GI | PROTEIN DESCRIPTION |
| 1 | XP_504703 | 50554589 | YlPOX1 [*Yarrowia lipolytica*]. |
| 2 | O74934 | 59799072 | Acyl-coenzyme A oxidase 1 (Acyl-CoA oxidase 1) |
| 3 | O74936 | 59799074 | Acyl-coenzyme A oxidase 3 (Acyl-CoA oxidase 3) |
| 4 | XP_502199 | 50549457 | YlPOX5 [*Yarrowia lipolytica*] |
| 5 | O74935 | 59799073 | Acyl-coenzyme A oxidase 2 (Acyl-CoA oxidase 2) |
| 6 | XP_503632 | 50552444 | hypothetical protein [*Yarrowia lipolytica*] |
| 7 | XP_504475 | 50554133 | YlPOX4 [*Yarrowia lipolytica*] |
| 8 | XP_760471 | 71020481 | hypothetical protein UM04324.1 [*Ustilago maydis* 521] |
| 9 | XP_571768 | 58269224 | Acyl-coenzyme A oxidase I [*Cryptococcus neoformans* var. *neoformans* JEC21] |
| 10 | XP_717995 | 68475844 | putative fatty-acyl coenzyme A oxidase [*Candida albicans* SC5314] |
| 11 | P08790 | 17373073 | Acyl-coenzyme A oxidase 5 (Acyl-CoA oxidase 5) (PXP-5) |
| 12 | OXCKX5 | 66061 | acyl-CoA oxidase (EC 1.3.3.6) POX5, peroxisomal - yeast (*Candida tropicalis*) |
| 13 | Q9Y7B1 | 60391213 | Acyl-coenzyme A oxidase (Acyl-CoA oxidase) |
| 14 | Q6BRD5 | 59799027 | Acyl-coenzyme A oxidase (Acyl-CoA oxidase) |
| 15 | XP_457726 | 50417804 | hypothetical protein DEHA0C01155g [*Debaryomyces hansenii* CBS767] |
| 16 | AAA34362 | 170912 | acyl-coenzyme A oxidase II precursor |

TABLE 35-continued

Examples of pox1a polypeptides.

| Row | ACCESSION | GI | PROTEIN DESCRIPTION |
|---|---|---|---|
| 17 | XP_459232 | 50421365 | hypothetical protein DEHA0D18667g [*Debaryomyces hansenii* CBS767] |
| 18 | BAA83482 | 5763520 | acyl-CoA oxidase [*Candida tropicalis*] |
| 19 | BAA83483 | 5763522 | acyl-CoA oxidase [*Candida tropicalis*] |
| 20 | OXCKPM | 66060 | acyl-CoA oxidase (EC 1.3.3.6) PXP4, peroxisomal - yeast (*Candida maltosa*) |
| 21 | AAA34361 | 170910 | PXP-2 protein |
| 22 | XP_721610 | 68468582 | putative fatty-acyl coenzyme A oxidase [*Candida albicans* SC5314] |
| 23 | 1306283A | 225549 | oxidase, fatty acyl |
| 24 | P06598 | 17373023 | Acyl-coenzyme A oxidase 4 (Acyl-CoA oxidase 4) (PXP-4) (Peroxisomal fatty acyl-CoA oxidase) |
| 25 | XP_721613 | 68468588 | putative fatty-acyl coenzyme A oxidase [*Candida albicans* SC5314] |
| 26 | Q00468 | 2498206 | Acyl-coenzyme A oxidase 2 (Acyl-CoA oxidase 2) (AOX 2) |
| 27 | Q6CKK7 | 59799028 | Acyl-coenzyme A oxidase (Acyl-CoA oxidase) |
| 28 | Q6FY63 | 59799032 | Acyl-coenzyme A oxidase (Acyl-CoA oxidase) |
| 29 | Q756A9 | 60391210 | Acyl-coenzyme A oxidase (Acyl-CoA oxidase) |
| 30 | NP_011310 | 6321233 | Fatty-acyl coenzyme A oxidase, involved in the fatty acid beta-oxidation pathway; localized to the peroxisomal matrix; Pox1p [*Saccharomyces cerevisiae*] |
| 31 | AAA34891 | 172217 | acyl-coenzyme A oxidase |
| 32 | O65202 | 62286589 | Acyl-coenzyme A oxidase 1, peroxisomal (AOX 1) (Long-chain acyl-CoA oxidase) (AtCX1) |
| 33 | 1W07B | 58177067 | Chain B, Arabidopsis Thaliana Acyl-Coa Oxidase 1 |
| 34 | H71434 | 7488059 | probable apetala2 domain TINY - *Arabidopsis thaliana* |
| 35 | NP_567513 | 18414744 | ACX1 (ACYL-COA OXIDASE 1) [*Arabidopsis thaliana*] |
| 36 | Q9ZQP2 | 62286640 | Putative acyl-coenzyme A oxidase 1.2, peroxisomal |
| 37 | AAL01888 | 15553480 | acyl-CoA oxidase [*Glycine max*] |
| 38 | CAA68660 | 2673 | acyl-coenzyme A oxidase [*Candida tropicalis*] |
| 39 | AAL01887 | 15553478 | acyl-CoA oxidase [*Glycine max*] |
| 40 | BAF18456 | 113594582 | Os06g0103500 [*Oryza sativa* (*japonica* cultivar-group)] |
| 41 | NP_001 . . . | 55741614 | acyl-Coenzyme A oxidase 1, palmitoyl [*Gallus gallus*] |
| 42 | AAH68891 | 46250227 | MGC83074 protein [*Xenopus laevis*] |
| 43 | 2FONC | 109157678 | Chain C, X-Ray Crystal Structure Of Leacx1, An Acyl-Coa Oxidase From *Lycopersicon Esculentum* (Tomato) |
| 44 | NP_001 . . . | 54400372 | hypothetical protein LOC449662 [*Danio rerio*] |
| 45 | AAW78689 | 58531948 | peroxisomal acyl-CoA oxidase 1A [*Lycopersicon esculentum*] |
| 46 | XP_001 . . . | 109118312 | PREDICTED: similar to acyl-Coenzyme A oxidase isoform b [*Macaca mulatta*] |
| 47 | AAW78691 | 58531952 | peroxisomal acyl-CoA oxidase 1A [*Lycopersicon cheesmaniae*] |
| 48 | Q5RC19 | 62286600 | Acyl-coenzyme A oxidase 1, peroxisomal (Palmitoyl-CoA oxidase) (AOX) |
| 49 | ABE83706 | 92875906 | acyl-CoA oxidase [*Medicago truncatula*] |
| 50 | NP_009223 | 30089974 | acyl-Coenzyme A oxidase isoform b [*Homo sapiens*] |
| 51 | Q15067 | 17380467 | Acyl-coenzyme A oxidase 1, peroxisomal (Palmitoyl-CoA oxidase) (AOX) (Straight-chain acyl-CoA oxidase) (SCOX) |
| 52 | AAA18595 | 495475 | peroxisomal fatty acyl-coA oxidase |
| 53 | AAA19113 | 458119 | acyl-CoA oxidase |
| 54 | NP_001 . . . | 78369480 | acyl-Coenzyme A oxidase 1, palmitoyl [*Bos taurus*] |
| 55 | AAH63727 | 39795632 | MGC68531 protein [*Xenopus laevis*] |
| 56 | AAB30019 | 7689914 | peroxisomal acyl-coenzyme A oxidase [*Homo sapiens*] |
| 57 | NP_001 . . . | 62751552 | MGC108278 protein [*Xenopus tropicalis*] |
| 58 | BAA86870 | 6429156 | peroxisomal acyl-CoA oxidase [*Mus musculus*] |
| 59 | Q9R0H0 | 51338830 | Acyl-coenzyme A oxidase 1, peroxisomal (Palmitoyl-CoA oxidase) (AOX) |
| 60 | AAH85743 | 55249685 | Acyl-Coenzyme A oxidase 1, palmitoyl [*Rattus norvegicus*] |
| 61 | AAB62926 | 2253380 | peroxisomal acyl-CoA oxidase [*Mus musculus*] |
| 62 | CAH90691 | 55727877 | hypothetical protein [*Pongo pygmaeus*] |
| 63 | CAJ83302 | 89271321 | acyl-Coenzyme A oxidase 2, branched chain [*Xenopus tropicalis*] |
| 64 | AAH97101 | 67678187 | Zgc: 92584 protein [*Danio rerio*] |
| 65 | NP_004026 | 30089972 | acyl-Coenzyme A oxidase isoform a [*Homo sapiens*] |
| 66 | AAH08767 | 14250616 | Acyl-Coenzyme A oxidase 1, palmitoyl [*Homo sapiens*] |
| 67 | CAD97622 | 31873262 | hypothetical protein [*Homo sapiens*] |
| 68 | B54942 | 1082171 | acyl-CoA oxidase (EC 1.3.3.6), peroxisomal splice form II - human |
| 69 | 2DDHA | 93279231 | Chain A, Crystal Structure Of Acyl-Coa Oxidase Complexed With 3-Oh-Dodecanoate |
| 70 | XP_540441 | 73965013 | PREDICTED: similar to acyl-Coenzyme A oxidase isoform a [*Canis familiaris*] |
| 71 | I38095 | 2117541 | acyl-CoA oxidase (EC 1.3.3.6), peroxisomal - human |
| 72 | AAH10425 | 14714578 | Acyl-Coenzyme A oxidase 1, palmitoyl [*Homo sapiens*] |
| 73 | NP_056544 | 66793429 | acyl-Coenzyme A oxidase 1, palmitoyl [*Mus musculus*] |
| 74 | AAI08648 | 83318302 | Unknown (protein for MGC: 131363) [*Xenopus laevis*] |

TABLE 35-continued

Examples of pox1a polypeptides.

| Row | ACCESSION | GI | PROTEIN DESCRIPTION |
|---|---|---|---|
| 75 | Q9Z1N0 | 17367267 | Acyl-coenzyme A oxidase 1, peroxisomal (Palmitoyl-CoA oxidase) (AOX) |
| 76 | XP_414406 | 50754485 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Gallus gallus*] |
| 77 | Q8HYL8 | 34098564 | Acyl-coenzyme A oxidase 1, peroxisomal (Palmitoyl-CoA oxidase) (AOX) |
| 78 | XP_511690 | 55645995 | PREDICTED: similar to hypothetical protein [*Pan troglodytes*] |
| 79 | AAO15577 | 27462768 | acyl-CoA oxidase type 2 [*Phascolarctos cinereus*] |
| 80 | XP_625136 | 66556360 | PREDICTED: similar to CG5009-PA, partial [*Apis mellifera*] |
| 81 | XP_320717 | 58394415 | ENSANGP00000020118 [*Anopheles gambiae* str. PEST] |
| 82 | EAT39640 | 108875415 | acyl-CoA oxidase [*Aedes aegypti*] |
| 83 | BAC26167 | 26324826 | unnamed protein product [*Mus musculus*] |
| 84 | EAS31618 | 90301987 | hypothetical protein CIMG_07097 [*Coccidioides immitis* RS] |
| 85 | XP_382463 | 46110811 | hypothetical protein FG02287.1 [*Gibberella zeae* PH-1] |
| 86 | XP_320718 | 58394417 | ENSANGP00000020032 [*Anopheles gambiae* str. PEST] |
| 87 | CAE63479 | 39592402 | Hypothetical protein CBG07946 [*Caenorhabditis briggsae*] |
| 88 | AAW78690 | 58531950 | peroxisomal acyl-CoA oxidase 1B [*Lycopersicon esculentum*] |
| 89 | CAE69737 | 39596101 | Hypothetical protein CBG16008 [*Caenorhabditis briggsae*] |
| 90 | AAH21339 | 18204156 | Acox2 protein [*Mus musculus*] |
| 91 | BAE25794 | 74188249 | unnamed protein product [*Mus musculus*] |
| 92 | EAR95568 | 89297580 | Acyl-CoA oxidase family protein [*Tetrahymena thermophila* SB210] |
| 93 | BAE55537 | 83765394 | unnamed protein product [*Aspergillus oryzae*] |
| 94 | Q9QXD1 | 17367045 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 95 | NP_510603 | 17568313 | F59F4.1 [*Caenorhabditis elegans*] |
| 96 | XP_785210 | 72015040 | PREDICTED: similar to Acyl-coenzyme A oxidase 1, peroxisomal (Palmitoyl-CoA oxidase) (AOX) [*Strongylocentrotus purpuratus*] |
| 97 | XP_973660 | 91082769 | PREDICTED: similar to CG5009-PA [*Tribolium castaneum*] |
| 98 | XP_782824 | 72015136 | PREDICTED: similar to Acyl-coenzyme A oxidase 1, peroxisomal (Palmitoyl-CoA oxidase) (AOX) [*Strongylocentrotus purpuratus*] |
| 99 | AAH47700 | 28839704 | Acyl-Coenzyme A oxidase 2, branched chain [*Homo sapiens*] |
| 100 | CAE63480 | 39592403 | Hypothetical protein CBG07947 [*Caenorhabditis briggsae*] |
| 101 | O02767 | 17366131 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 102 | NP_665713 | 21955130 | acyl-Coenzyme A oxidase 2, branched chain [*Rattus norvegicus*] |
| 103 | XP_664356 | 67541164 | hypothetical protein AN6752.2 [*Aspergillus nidulans* FGSC A4] |
| 104 | EAT48205 | 108883980 | acyl-CoA oxidase [*Aedes aegypti*] |
| 105 | CAE63477 | 39592400 | Hypothetical protein CBG07944 [*Caenorhabditis briggsae*] |
| 106 | XP_758355 | 71010163 | hypothetical protein UM02208.1 [*Ustilago maydis* 521] |
| 107 | CAE65171 | 39590798 | Hypothetical protein CBG10043 [*Caenorhabditis briggsae*] |
| 108 | XP_637610 | 66807775 | hypothetical protein DDBDRAFT_0187085 [*Dictyostelium discoideum* AX4] |
| 109 | NP_499119 | 17552648 | C48B4.1 [*Caenorhabditis elegans*] |
| 110 | XP_635946 | 66804335 | hypothetical protein DDBDRAFT_0188674 [*Dictyostelium discoideum* AX4] |
| 111 | XP_592892 | 76648807 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 1 [*Bos taurus*] |
| 112 | XP_879996 | 76648809 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 6 [*Bos taurus*] |
| 113 | XP_783450 | 72111190 | PREDICTED: similar to acyl-Coenzyme A oxidase 1, palmitoyl [*Strongylocentrotus purpuratus*] |
| 114 | XP_541826 | 73985284 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Canis familiaris*] |
| 115 | EAR89261 | 89291273 | Acyl-CoA oxidase family protein [*Tetrahymena thermophila* SB210] |
| 116 | AAH54727 | 68262425 | Acox1 protein [*Mus musculus*] |
| 117 | BAC35782 | 74197284 | unnamed protein product [*Mus musculus*] |
| 118 | NP_493263 | 17506533 | F08A8.3 [*Caenorhabditis elegans*] |
| 119 | AAF14635 | 6503198 | acyl-CoA oxidase [*Petroselinum crispum*] |

TABLE 35-continued

Examples of pox1a polypeptides.

| Row | ACCESSION | GI | PROTEIN DESCRIPTION |
|---|---|---|---|
| 120 | CAE63476 | 39592399 | Hypothetical protein CBG07943 [*Caenorhabditis briggsae*] |
| 121 | AAL39944 | 17862934 | SD03592p [*Drosophila melanogaster*] |
| 122 | NP_523802 | 17647123 | acyl-Coenzyme A oxidase at 57D proximal CG9707-PA [*Drosophila melanogaster*] |
| 123 | ZP_012 . . . | 90587482 | Acyl-CoA oxidase-like:Acyl-CoA dehydrogenase-like:Acyl-CoA dehydrogenase, central region [*Flavobacterium johnsoniae* UW101] |
| 124 | AAR00586 | 37699750 | acyl-CoA oxidase [*Phalaenopsis* cv. 'True Lady'] |
| 125 | XP_758113 | 71007469 | hypothetical protein UM01966.1 [*Ustilago maydis* 521] |
| 126 | AAB67883 | 1575556 | acyl-CoA oxidase homolog [*Phalaenopsis* sp. 'True Lady'] |
| 127 | NP_001 . . . | 71983346 | F08A8.1a [*Caenorhabditis elegans*] |
| 128 | NP_001 . . . | 71983355 | F08A8.1b [*Caenorhabditis elegans*] |
| 129 | CAJ58493 | 85539740 | Hypothetical protein F08A8.1c [*Caenorhabditis elegans*] |
| 130 | AAC13497 | 3044212 | acyl-CoA oxidase [*Arabidopsis thaliana*] |
| 131 | O65201 | 62286588 | Acyl-coenzyme A oxidase 2, peroxisomal precursor (AOX 2) (Long-chain acyl-CoA oxidase) (AtCX2) |
| 132 | EAS04704 | 89306716 | Acyl-CoA oxidase family protein [*Tetrahymena thermophila* SB210] |
| 133 | EAL26359 | 54636956 | GA18591-PA [*Drosophila pseudoobscura*] |
| 134 | XP_636605 | 66805767 | hypothetical protein DDBDRAFT_0188084 [*Dictyostelium discoideum* AX4] |
| 135 | O64894 | 62286587 | Acyl-coenzyme A oxidase, peroxisomal precursor (AOX) (Long-chain acyl-CoA oxidase) |
| 136 | NP_611264 | 24654595 | CG5009-PA [*Drosophila melanogaster*] |
| 137 | NP_493264 | 17506535 | F08A8.4 [*Caenorhabditis elegans*] |
| 138 | AAH44725 | 28703869 | Acox3 protein [*Mus musculus*] |
| 139 | NP_109646 | 34328334 | acyl-Coenzyme A oxidase 3, pristanoyl [*Mus musculus*] |
| 140 | XP_786025 | 72005645 | PREDICTED: similar to pristanoyl acyl-Coenzyme A oxidase 3 [*Strongylocentrotus purpuratus*] |
| 141 | XP_646395 | 66826081 | hypothetical protein DDBDRAFT_0216722 [*Dictyostelium discoideum* AX4] |
| 142 | EAT87650 | 111066530 | hypothetical protein SNOG_05259 [*Phaeosphaeria nodorum* SN15] |
| 143 | NP_998312 | 47085909 | pristanoyl acyl-Coenzyme A oxidase 3 [*Danio rerio*] |
| 144 | YP_634556 | 108758121 | putative acyl-CoA dehydrogenase [*Myxococcus xanthus* DK 1622] |
| 145 | AAL28144 | 16767852 | GH01266p [*Drosophila melanogaster*] |
| 146 | YP_445820 | 83816544 | acyl-coenzyme A oxidase I, putative [*Salinibacter ruber* DSM 13855] |
| 147 | EAL26647 | 54637244 | GA21980-PA [*Drosophila pseudoobscura*] |
| 148 | XP_786081 | 72005647 | PREDICTED: similar to pristanoyl acyl-Coenzyme A oxidase 3 [*Strongylocentrotus purpuratus*] |
| 149 | EAR99631 | 89301643 | Acyl-CoA oxidase family protein [*Tetrahymena thermophila* SB210] |
| 150 | NP_493262 | 17506531 | F08A8.2 [*Caenorhabditis elegans*] |
| 151 | CAH91864 | 55730283 | hypothetical protein [*Pongo pygmaeus*] |
| 152 | Q9LLH9 | 62286634 | Acyl-coenzyme A oxidase 3, peroxisomal precursor (AOX 3) (Medium-chain acyl-CoA oxidase) (AtCX3) |
| 153 | AAF73843 | 8163758 | acyl-CoA oxidase ACX3 [*Arabidopsis thaliana*] |
| 154 | XP_969513 | 91093755 | PREDICTED: similar to pristanoyl acyl-Coenzyme A oxidase 3 [*Tribolium castaneum*] |
| 155 | O15254 | 17366151 | Acyl-coenzyme A oxidase 3, peroxisomal (Pristanoyl-CoA oxidase) (Branched-chain acyl-CoA oxidase) (BRCACox) |
| 156 | Q9EPL9 | 17366740 | Acyl-coenzyme A oxidase 3, peroxisomal (Pristanoyl-CoA oxidase) (Branched-chain acyl-CoA oxidase) (BRCACox) |
| 157 | NP_445791 | 16758056 | acyl-Coenzyme A oxidase 3, pristanoyl [*Rattus norvegicus*] |
| 158 | ABA94670 | 108864573 | Acyl-coenzyme A oxidase 2, peroxisomal precursor, putative, expressed [*Oryza sativa* (*japonica* cultivar-group)] |
| 159 | EAT87454 | 111066334 | hypothetical protein SNOG_05063 [*Phaeosphaeria nodorum* SN15] |
| 160 | EAL26648 | 54637245 | GA21981-PA [*Drosophila pseudoobscura*] |
| 161 | EAR98581 | 89300593 | Acyl-CoA oxidase family protein [*Tetrahymena thermophila* SB210] |
| 162 | BAE42553 | 74143079 | unnamed protein product [*Mus musculus*] |
| 163 | BAC26136 | 26324764 | unnamed protein product [*Mus musculus*] |
| 164 | XP_879827 | 76648805 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 5 [*Bos taurus*] |
| 165 | XP_587157 | 76620513 | PREDICTED: similar to Acyl-coenzyme A oxidase 3, peroxisomal (Pristanoyl-CoA oxidase) [*Bos taurus*] |
| 166 | YP_290295 | 72162638 | hypothetical protein Tfu_2239 [*Thermobifida fusca* YX] |
| 167 | CAH91120 | 55728762 | hypothetical protein [*Pongo pygmaeus*] |
| 168 | EAS02716 | 89304728 | Acyl-CoA oxidase family protein [*Tetrahymena thermophila* SB210] |

TABLE 35-continued

Examples of pox1a polypeptides.

| Row | ACCESSION | GI | PROTEIN DESCRIPTION |
|---|---|---|---|
| 169 | AAL48010 | 17944231 | LD22081p [*Drosophila melanogaster*] |
| 170 | XP_545908 | 73951751 | PREDICTED: similar to Acyl-coenzyme A oxidase 3, peroxisomal (Pristanoyl-CoA oxidase) [*Canis familiaris*] |
| 171 | ZP_011 . . . | 88854811 | acyl-CoA oxidase [*marine actinobacterium* PHSC20C1] |
| 172 | NP_001 . . . | 79332306 | ACX2 (ACYL-COA OXIDASE 2); acyl-CoA oxidase [*Arabidopsis thaliana*] |
| 173 | BAF19505 | 113595631 | Os06g0354500 [*Oryza sativa* (*japonica* cultivar-group)] |
| 174 | EAL32329 | 54643586 | GA18278-PA [*Drosophila pseudoobscura*] |
| 175 | CAA04688 | 2370232 | putative acyl-CoA oxidase [*Hordeum vulgare* subsp. *vulgare*] |
| 176 | ZP_012 . . . | 89890388 | acyl-CoA oxidase [*Flavobacteria bacterium* BBFL7] |
| 177 | Q9LMI7 | 62286635 | Putative acyl-coenzyme A oxidase 3.2, peroxisomal precursor |
| 178 | XP_395486 | 66564429 | PREDICTED: similar to CG9527-PA [*Apis mellifera*] |
| 179 | YP_702012 | 111019040 | acyl-CoA oxidase [*Rhodococcus* sp. RHA1] |
| 180 | ZP_012 . . . | 90205075 | Acyl-CoA oxidase-like:Acyl-CoA dehydrogenase-like:Acyl-CoA dehydrogenase, central region [*Mycobacterium vanbaalenii* PYR-1] |
| 181 | AAL48950 | 17945806 | RE34879p [*Drosophila melanogaster*] |
| 182 | NP_609027 | 45550141 | CG9527-PA [*Drosophila melanogaster*] |
| 183 | ZP_006 . . . | 71369913 | Acyl-CoA oxidase:Acyl-CoA dehydrogenase, C-terminal:Acyl-CoA dehydrogenase, central region:Acyl-CoA dehydrogenase, N-terminal [*Nocardioides* sp. JS614] |
| 184 | ZP_012 . . . | 92908524 | Acyl-CoA oxidase-like:Acyl-CoA dehydrogenase-like:Acyl-CoA dehydrogenase, central region [*Mycobacterium* sp. JLS] |
| 185 | EAT48670 | 108884445 | acyl-CoA oxidase [*Aedes aegypti*] |
| 186 | XP_317446 | 58390030 | ENSANGP00000011863 [*Anopheles gambiae* str. PEST] |
| 187 | EAS36523 | 90306892 | hypothetical protein CIMG_01877 [*Coccidioides immitis* RS] |
| 188 | NP_572371 | 24640268 | CG4586-PA [*Drosophila melanogaster*] |
| 189 | XP_642669 | 66817952 | hypothetical protein DDBDRAFT_0169270 [*Dictyostelium discoideum* AX4] |
| 190 | CAA96917 | 1945301 | PDX1 [*Saccharomyces cerevisiae*] |
| 191 | ZP_011 . . . | 89339305 | Acyl-CoA oxidase-like:Acyl-CoA dehydrogenase-like:Acyl-CoA dehydrogenase, central region [*Mycobacterium flavescens* PYR-GCK] |
| 192 | ZP_003 . . . | 62426247 | COG1960: Acyl-CoA dehydrogenases [*Brevibacterium linens* BL2] |
| 193 | YP_640598 | 108800401 | acyl-CoA dehydrogenase-like protein [*Mycobacterium* sp. MCS] |
| 194 | NP_724181 | 24585195 | CG17544-PC, isoform C [*Drosophila melanogaster*] |
| 195 | AAL14003 | 16186117 | SD05719p [*Drosophila melanogaster*] |
| 196 | AAH17053 | 16877606 | ACOX3 protein [*Homo sapiens*] |
| 197 | EAL32912 | 54644170 | GA21857-PA [*Drosophila pseudoobscura*] |

TABLE 36

Examples of pox4 polypeptides.

| Row | ACCESSION | GI | PROTEIN DESCRIPTION |
|---|---|---|---|
| 1 | XP_504475.1 | 50554133 | YlPOX4 [*Yarrowia lipolytica*] |
| 2 | O74935 | 59799073 | Acyl-coenzyme A oxidase 2 (Acyl-CoA oxidase 2) |
| 3 | O74936 | 59799074 | Acyl-coenzyme A oxidase 3 (Acyl-CoA oxidase 3) |
| 4 | XP_502199 | 50549457 | YlPOX5 [*Yarrowia lipolytica*] |
| 5 | O74934 | 59799072 | Acyl-coenzyme A oxidase 1 (Acyl-CoA oxidase 1) |
| 6 | XP_504703 | 50554589 | YlPOX1 [*Yarrowia lipolytica*] |
| 7 | XP_503632 | 50552444 | hypothetical protein [*Yarrowia lipolytica*] |
| 8 | XP_760471 | 71020481 | hypothetical protein UM04324.1 [*Ustilago maydis* 521] |
| 9 | XP_571768 | 58269224 | Acyl-coenzyme A oxidase I [*Cryptococcus neoformans* var. *neoformans* JEC21] |
| 10 | XP_717995 | 68475844 | putative fatty-acyl coenzyme A oxidase [*Candida albicans* SC5314] |
| 11 | BAA83482 | 5763520 | acyl-CoA oxidase [*Candida tropicalis*] |
| 12 | BAA83483 | 5763522 | acyl-CoA oxidase [*Candida tropicalis*] |
| 13 | OXCKPM | 66060 | acyl-CoA oxidase (EC 1.3.3.6) PXP4, peroxisomal - yeast (*Candida maltosa*) |
| 14 | XP_721610 | 68468582 | putative fatty-acyl coenzyme A oxidase [*Candida albicans* SC5314] |
| 15 | AAA34362 | 170912 | acyl-coenzyme A oxidase II precursor |
| 16 | P08790 | 17373073 | Acyl-coenzyme A oxidase 5 (Acyl-CoA oxidase 5) (PXP-5) |
| 17 | OXCKX5 | 66061 | acyl-CoA oxidase (EC 1.3.3.6) POX5, peroxisomal - yeast (*Candida tropicalis*) |
| 18 | Q6BRD5 | 59799027 | Acyl-coenzyme A oxidase (Acyl-CoA oxidase) |
| 19 | XP_457726 | 50417804 | hypothetical protein DEHA0C01155g [*Debaryomyces hansenii* CBS767] |

TABLE 36-continued

Examples of pox4 polypeptides.

| Row | ACCESSION | GI | PROTEIN DESCRIPTION |
|---|---|---|---|
| 20 | P06598 | 17373023 | Acyl-coenzyme A oxidase 4 (Acyl-CoA oxidase 4) (PXP-4) (Peroxisomal fatty acyl-CoA oxidase) |
| 21 | 1306283A | 225549 | oxidase, fatty acyl |
| 22 | AAA34361 | 170910 | PXP-2 protein |
| 23 | XP_459232 | 50421365 | hypothetical protein DEHA0D18667g [*Debaryomyces hansenii* CBS767] |
| 24 | Q9Y7B1 | 60391213 | Acyl-coenzyme A oxidase (Acyl-CoA oxidase) |
| 25 | XP_721613 | 68468588 | putative fatty-acyl coenzyme A oxidase [*Candida albicans* SC5314] |
| 26 | Q00468 | 2498206 | Acyl-coenzyme A oxidase 2 (Acyl-CoA oxidase 2) (AOX 2) |
| 27 | Q6FY63 | 59799032 | Acyl-coenzyme A oxidase (Acyl-CoA oxidase) |
| 28 | NP_011310 | 6321233 | Fatty-acyl coenzyme A oxidase, involved in the fatty acid beta-oxidation pathway; localized to the peroxisomal matrix; Pox1p [*Saccharomyces cerevisiae*] |
| 29 | AAA34891 | 172217 | acyl-coenzyme A oxidase |
| 30 | Q6CKK7 | 59799028 | Acyl-coenzyme A oxidase (Acyl-CoA oxidase) |
| 31 | Q756A9 | 60391210 | Acyl-coenzyme A oxidase (Acyl-CoA oxidase) |
| 32 | O65202 | 62286589 | Acyl-coenzyme A oxidase 1, peroxisomal (AOX 1) (Long-chain acyl-CoA oxidase) (AtCX1) |
| 33 | CAA68660 | 2673 | acyl-coenzyme A oxidase [*Candida tropicalis*] |
| 34 | 1W07B | 58177067 | Chain B, *Arabidopsis Thaliana* Acyl-Coa Oxidase 1 |
| 35 | AAL01888 | 15553480 | acyl-CoA oxidase [*Glycine max*] |
| 36 | H71434 | 7488059 | probable apetala2 domain TINY - *Arabidopsis thaliana* |
| 37 | NP_567513 | 18414744 | ACX1 (ACYL-COA OXIDASE 1) [*Arabidopsis thaliana*] |
| 38 | AAH63727 | 39795632 | MGC68531 protein [*Xenopus laevis*] |
| 39 | AAL01887 | 15553478 | acyl-CoA oxidase [*Glycine max*] |
| 40 | AAI08648 | 83318302 | Unknown (protein for MGC: 131363) [*Xenopus laevis*] |
| 41 | BAF18456 | 113594582 | Os06g0103500 [*Oryza sativa* (*japonica* cultivar-group)] |
| 42 | Q9ZQP2 | 62286640 | Putative acyl-coenzyme A oxidase 1.2, peroxisomal |
| 43 | NP_001 . . . | 78369480 | acyl-Coenzyme A oxidase 1, palmitoyl [*Bos taurus*] |
| 44 | ABE83706 | 92875906 | acyl-CoA oxidase [*Medicago truncatula*] |
| 45 | NP_001 . . . | 62751552 | MGC108278 protein [*Xenopus tropicalis*] |
| 46 | NP_001 . . . | 55741614 | acyl-Coenzyme A oxidase 1, palmitoyl [*Gallus gallus*] |
| 47 | AAW78689 | 58531948 | peroxisomal acyl-CoA oxidase 1A [*Lycopersicon esculentum*] |
| 48 | 2FONC | 109157678 | Chain C, X-Ray Crystal Structure Of Leacx1, An Acyl-Coa Oxidase From *Lycopersicon Esculentum* (Tomato) |
| 49 | NP_001 . . . | 54400372 | hypothetical protein LOC449662 [*Danio rerio*] |
| 50 | AAW78691 | 58531952 | peroxisomal acyl-CoA oxidase 1A [*Lycopersicon cheesmaniae*] |
| 51 | Q5RC19 | 62286600 | Acyl-coenzyme A oxidase 1, peroxisomal (Palmitoyl-CoA oxidase) (AOX) |
| 52 | XP_001 . . . | 109118312 | PREDICTED: similar to acyl-Coenzyme A oxidase isoform b [*Macaca mulatta*] |
| 53 | Q15067 | 17380467 | Acyl-coenzyme A oxidase 1, peroxisomal (Palmitoyl-CoA oxidase) (AOX) (Straight-chain acyl-CoA oxidase) (SCOX) |
| 54 | NP_009223 | 30089974 | acyl-Coenzyme A oxidase isoform b [*Homo sapiens*] |
| 55 | AAO15577 | 27462768 | acyl-CoA oxidase type 2 [*Phascolarctos cinereus*] |
| 56 | AAB30019 | 7689914 | peroxisomal acyl-coenzyme A oxidase [*Homo sapiens*] |
| 57 | AAH97101 | 67678187 | Zgc: 92584 protein [*Danio rerio*] |
| 58 | XP_414406 | 50754485 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Gallus gallus*] |
| 59 | AAA19113 | 458119 | acyl-CoA oxidase |
| 60 | AAA18595 | 495475 | peroxisomal fatty acyl-coA oxidase |
| 61 | Q9Z1N0 | 17367267 | Acyl-coenzyme A oxidase 1, peroxisomal (Palmitoyl-CoA oxidase) (AOX) |
| 62 | Q8HYL8 | 34098564 | Acyl-coenzyme A oxidase 1, peroxisomal (Palmitoyl-CoA oxidase) (AOX) |
| 63 | AAH85743 | 55249685 | Acyl-Coenzyme A oxidase 1, palmitoyl [*Rattus norvegicus*] |
| 64 | AAH10425 | 14714578 | Acyl-Coenzyme A oxidase 1, palmitoyl [*Homo sapiens*] |
| 65 | CAH90691 | 55727877 | hypothetical protein [*Pongo pygmaeus*] |
| 66 | CAD97622 | 31873262 | hypothetical protein [*Homo sapiens*] |
| 67 | AAH08767 | 14250616 | Acyl-Coenzyme A oxidase 1, palmitoyl [*Homo sapiens*] |
| 68 | NP_004026 | 30089972 | acyl-Coenzyme A oxidase isoform a [*Homo sapiens*] |
| 69 | I38095 | 2117541 | acyl-CoA oxidase (EC 1.3.3.6), peroxisomal - human |
| 70 | BAA86870 | 6429156 | peroxisomal acyl-CoA oxidase [*Mus musculus*] |
| 71 | CAJ83302 | 89271321 | acyl-Coenzyme A oxidase 2, branched chain [*Xenopus tropicalis*] |
| 72 | Q9R0H0 | 51338830 | Acyl-coenzyme A oxidase 1, peroxisomal (Palmitoyl-CoA oxidase) (AOX) |
| 73 | AAB62926 | 2253380 | peroxisomal acyl-CoA oxidase [*Mus musculus*] |
| 74 | B54942 | 1082171 | acyl-CoA oxidase (EC 1.3.3.6), peroxisomal splice form II - human |
| 75 | XP_320717 | 58394415 | ENSANGP00000020118 [*Anopheles gambiae* str. PEST] |
| 76 | BAE25794 | 74188249 | unnamed protein product [*Mus musculus*] |
| 77 | AAH21339 | 18204156 | Acox2 protein [*Mus musculus*] |

TABLE 36-continued

Examples of pox4 polypeptides.

| Row | ACCESSION | GI | PROTEIN DESCRIPTION |
|---|---|---|---|
| 78 | 2DDHA | 93279231 | Chain A, Crystal Structure Of Acyl-Coa Oxidase Complexed With 3-Oh-Dodecanoate |
| 79 | Q9QXD1 | 17367045 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 80 | AAH68891 | 46250227 | MGC83074 protein [*Xenopus laevis*] |
| 81 | XP_540441 | 73965013 | PREDICTED: similar to acyl-Coenzyme A oxidase isoform a [*Canis familiaris*] |
| 82 | XP_320718 | 58394417 | ENSANGP00000020032 [*Anopheles gambiae* str. PEST] |
| 83 | XP_511690 | 55645995 | PREDICTED: similar to hypothetical protein [*Pan troglodytes*] |
| 84 | NP_056544 | 66793429 | acyl-Coenzyme A oxidase 1, palmitoyl [*Mus musculus*] |
| 85 | EAT39640 | 108875415 | acyl-CoA oxidase [*Aedes aegypti*] |
| 86 | XP_783450 | 72111190 | PREDICTED: similar to acyl-Coenzyme A oxidase 1, palmitoyl [*Strongylocentrotus purpuratus*] |
| 87 | NP_665713 | 21955130 | acyl-Coenzyme A oxidase 2, branched chain [*Rattus norvegicus*] |
| 88 | XP_973660 | 91082769 | PREDICTED: similar to CG5009-PA [*Tribolium castaneum*] |
| 89 | CAE63476 | 39592399 | Hypothetical protein CBG07943 [*Caenorhabditis briggsae*] |
| 90 | XP_625136 | 66556360 | PREDICTED: similar to CG5009-PA, partial [*Apis mellifera*] |
| 91 | XP_592892 | 76648807 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 1 [*Bos taurus*] |
| 92 | XP_879996 | 76648809 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 6 [*Bos taurus*] |
| 93 | AAW78690 | 58531950 | peroxisomal acyl-CoA oxidase 1B [*Lycopersicon esculentum*] |
| 94 | AAH47700 | 28839704 | Acyl-Coenzyme A oxidase 2, branched chain [*Homo sapiens*] |
| 95 | CAE69737 | 39596101 | Hypothetical protein CBG16008 [*Caenorhabditis briggsae*] |
| 96 | NP_499119 | 17552648 | C48B4.1 [*Caenorhabditis elegans*] |
| 97 | CAE65171 | 39590798 | Hypothetical protein CBG10043 [*Caenorhabditis briggsae*] |
| 98 | XP_541826 | 73985284 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Canis familiaris*] |
| 99 | NP_510603 | 17568313 | F59F4.1 [*Caenorhabditis elegans*] |
| 100 | NP_001 . . . | 71983346 | F08A8.1a [*Caenorhabditis elegans*] |
| 101 | EAR95568 | 89297580 | Acyl-CoA oxidase family protein [*Tetrahymena thermophila* SB210] |
| 102 | NP_001 . . . | 71983355 | F08A8.1b [*Caenorhabditis elegans*] |
| 103 | CAJ58493 | 85539740 | Hypothetical protein F08A8.1c [*Caenorhabditis elegans*] |
| 104 | EAL26359 | 54636956 | GA18591-PA [*Drosophila pseudoobscura*] |
| 105 | BAC26167 | 26324826 | unnamed protein product [*Mus musculus*] |
| 106 | CAE63479 | 39592402 | Hypothetical protein CBG07946 [*Caenorhabditis briggsae*] |
| 107 | O02767 | 17366131 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 108 | NP_611264 | 24654595 | CG5009-PA [*Drosophila melanogaster*] |
| 109 | CAE63480 | 39592403 | Hypothetical protein CBG07947 [*Caenorhabditis briggsae*] |
| 110 | XP_758355 | 71010163 | hypothetical protein UM02208.1 [*Ustilago maydis* 521] |
| 111 | EAT48205 | 108883980 | acyl-CoA oxidase [*Aedes aegypti*] |
| 112 | XP_782824 | 72015136 | PREDICTED: similar to Acyl-coenzyme A oxidase 1, peroxisomal (Palmitoyl-CoA oxidase) (AOX) [*Strongylocentrotus purpuratus*] |
| 113 | AAL28144 | 16767852 | GH01266p [*Drosophila melanogaster*] |
| 114 | XP_785210 | 72015040 | PREDICTED: similar to Acyl-coenzyme A oxidase 1, peroxisomal (Palmitoyl-CoA oxidase) (AOX) [*Strongylocentrotus purpuratus*] |
| 115 | EAS31618 | 90301987 | hypothetical protein CIMG_07097 [*Coccidioides immitis* RS] |
| 116 | XP_879827 | 76648805 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 5 [*Bos taurus*] |
| 117 | CAH91864 | 55730283 | hypothetical protein [*Pongo pygmaeus*] |
| 118 | NP_493263 | 17506533 | F08A8.3 [*Caenorhabditis elegans*] |
| 119 | Q9LLH9 | 62286634 | Acyl-coenzyme A oxidase 3, peroxisomal precursor (AOX 3) (Medium-chain acyl-CoA oxidase) (AtCX3) |
| 120 | AAF73843 | 8163758 | acyl-CoA oxidase ACX3 [*Arabidopsis thaliana*] |
| 121 | AAL39944 | 17862934 | SD03592p [*Drosophila melanogaster*] |
| 122 | NP_523802 | 17647123 | acyl-Coenzyme A oxidase at 57D proximal CG9707-PA [*Drosophila melanogaster*] |

TABLE 36-continued

Examples of pox4 polypeptides.

| Row | ACCESSION | GI | PROTEIN DESCRIPTION |
|---|---|---|---|
| 123 | AAH54727 | 68262425 | Acox1 protein [*Mus musculus*] |
| 124 | BAC35782 | 74197284 | unnamed protein product [*Mus musculus*] |
| 125 | BAE55537 | 83765394 | unnamed protein product [*Aspergillus oryzae*] |
| 126 | CAE63477 | 39592400 | Hypothetical protein CBG07944 [*Caenorhabditis briggsae*] |
| 127 | XP_636605 | 66805767 | hypothetical protein DDBDRAFT_0188084 [*Dictyostelium discoideum* AX4] |
| 128 | NP_493264 | 17506535 | F08A8.4 [*Caenorhabditis elegans*] |
| 129 | NP_493262 | 17506531 | F08A8.2 [*Caenorhabditis elegans*] |
| 130 | EAL26648 | 54637245 | GA21981-PA [*Drosophila pseudoobscura*] |
| 131 | AAF14635 | 6503198 | acyl-CoA oxidase [*Petroselinum crispum*] |
| 132 | XP_664356 | 67541164 | hypothetical protein AN6752.2 [*Aspergillus nidulans* FGSC A4] |
| 133 | EAL26647 | 54637244 | GA21980-PA [*Drosophila pseudoobscura*] |
| 134 | AAL48010 | 17944231 | LD22081p [*Drosophila melanogaster*] |
| 135 | ZP_012 . . . | 90587482 | Acyl-CoA oxidase-like:Acyl-CoA dehydrogenase-like:Acyl-CoA dehydrogenase, central region [*Flavobacterium johnsoniae* UW101] |
| 136 | CAA04688 | 2370232 | putative acyl-CoA oxidase [*Hordeum vulgare* subsp. *vulgare*] |
| 137 | Q9LMI7 | 62286635 | Putative acyl-coenzyme A oxidase 3.2, peroxisomal precursor |
| 138 | EAR89261 | 89291273 | Acyl-CoA oxidase family protein [*Tetrahymena thermophila* SB210] |
| 139 | YP_290295 | 72162638 | hypothetical protein Tfu_2239 [*Thermobifida fusca* YX] |
| 140 | XP_758113 | 71007469 | hypothetical protein UM01966.1 [*Ustilago maydis* 521] |
| 141 | BAF19505 | 113595631 | Os06g0354500 [*Oryza sativa* (*japonica* cultivar-group)] |
| 142 | XP_317446 | 58390030 | ENSANGP00000011863 [*Anopheles gambiae* str. PEST] |
| 143 | XP_635946 | 66804335 | hypothetical protein DDBDRAFT_0188674 [*Dictyostelium discoideum* AX4] |
| 144 | XP_382463 | 46110811 | hypothetical protein FG02287.1 [*Gibberella zeae* PH-1] |
| 145 | YP_445820 | 83816544 | acyl-coenzyme A oxidase I, putative [*Salinibacter ruber* DSM 13855] |
| 146 | EAR99631 | 89301643 | Acyl-CoA oxidase family protein [*Tetrahymena thermophila* SB210] |
| 147 | EAT87650 | 111066530 | hypothetical protein SNOG_05259 [*Phaeosphaeria nodorum* SN15] |
| 148 | O15254 | 17366151 | Acyl-coenzyme A oxidase 3, peroxisomal (Pristanoyl-CoA oxidase) (Branched-chain acyl-CoA oxidase) (BRCACox) |
| 149 | NP_508036 | 17560134 | F25C8.1 [*Caenorhabditis elegans*] |
| 150 | NP_998312 | 47085909 | pristanoyl acyl-Coenzyme A oxidase 3 [*Danio rerio*] |
| 151 | EAL32329 | 54643586 | GA18278-PA [*Drosophila pseudoobscura*] |
| 152 | EAS02716 | 89304728 | Acyl-CoA oxidase family protein [*Tetrahymena thermophila* SB210] |
| 153 | EAT48670 | 108884445 | acyl-CoA oxidase [*Aedes aegypti*] |
| 154 | CAH91120 | 55728762 | hypothetical protein [*Pongo pygmaeus*] |
| 155 | EAS04704 | 89306716 | Acyl-CoA oxidase family protein [*Tetrahymena thermophila* SB210] |
| 156 | ZP_012 . . . | 89890388 | acyl-CoA oxidase [*Flavobacteria bacterium* BBFL7] |
| 157 | O64894 | 62286587 | Acyl-coenzyme A oxidase, peroxisomal precursor (AOX) (Long-chain acyl-CoA oxidase) |
| 158 | XP_969513 | 91093755 | PREDICTED: similar to pristanoyl acyl-Coenzyme A oxidase 3 [*Tribolium castaneum*] |
| 159 | AAC13497 | 3044212 | acyl-CoA oxidase [*Arabidopsis thaliana*] |
| 160 | O65201 | 62286588 | Acyl-coenzyme A oxidase 2, peroxisomal precursor (AOX 2) (Long-chain acyl-CoA oxidase) (AtCX2) |
| 161 | XP_646395 | 66826081 | hypothetical protein DDBDRAFT_0216722 [*Dictyostelium discoideum* AX4] |
| 162 | YP_634556 | 108758121 | putative acyl-CoA dehydrogenase [*Myxococcus xanthus* DK 1622] |
| 163 | XP_587157 | 76620513 | PREDICTED: similar to Acyl-coenzyme A oxidase 3, peroxisomal (Pristanoyl-CoA oxidase) [*Bos taurus*] |
| 164 | EAR98581 | 89300593 | Acyl-CoA oxidase family protein [*Tetrahymena thermophila* SB210] |
| 165 | XP_637610 | 66807775 | hypothetical protein DDBDRAFT_0187085 [*Dictyostelium discoideum* AX4] |
| 166 | NP_572371 | 24640268 | CG4586-PA [*Drosophila melanogaster*] |
| 167 | EAT87454 | 111066334 | hypothetical protein SNOG_05063 [*Phaeosphaeria nodorum* SN15] |
| 168 | AAB67883 | 1575556 | acyl-CoA oxidase homolog [*Phalaenopsis* sp. 'True Lady'] |
| 169 | NP_961035 | 41408199 | hypothetical protein MAP2101 [*Mycobacterium avium* subsp. *paratuberculosis* K-10] |
| 170 | ABA94670 | 108864573 | Acyl-coenzyme A oxidase 2, peroxisomal precursor, putative, expressed [*Oryza sativa* (*japonica* cultivar-group)] |
| 171 | AAR00586 | 37699750 | acyl-CoA oxidase [*Phalaenopsis* cv. 'True Lady'] |
| 172 | XP_545908 | 73951751 | PREDICTED: similar to Acyl-coenzyme A oxidase 3, peroxisomal (Pristanoyl-CoA oxidase) [*Canis familiaris*] |
| 173 | YP_702012 | 111019040 | acyl-CoA oxidase [*Rhodococcus* sp. RHA1] |

TABLE 36-continued

Examples of pox4 polypeptides.

| Row | ACCESSION | GI | PROTEIN DESCRIPTION |
|---|---|---|---|
| 174 | ZP_012 . . . | 90205075 | Acyl-CoA oxidase-like:Acyl-CoA dehydrogenase-like:Acyl-CoA dehydrogenase, central region [*Mycobacterium vanbaalenii* PYR-1] |
| 175 | EAS36523 | 90306892 | hypothetical protein CIMG_01877 [*Coccidioides immitis* RS] |
| 176 | NP_001 . . . | 79332306 | ACX2 (ACYL-COA OXIDASE 2); acyl-CoA oxidase [*Arabidopsis thaliana*] |
| 177 | CAA68661 | 2674 | 44 kD translation product [*Candida tropicalis*] |
| 178 | ZP_012 . . . | 92908524 | Acyl-CoA oxidase-like:Acyl-CoA dehydrogenase-like:Acyl-CoA dehydrogenase, central region [*Mycobacterium* sp. JLS] |
| 179 | XP_786025 | 72005645 | PREDICTED: similar to pristanoyl acyl-Coenzyme A oxidase 3 [*Strongylocentrotus purpuratus*] |
| 180 | CAA96917 | 1945301 | POX1 [*Saccharomyces cerevisiae*] |
| 181 | BAE60166 | 83770031 | unnamed protein product [*Aspergillus oryzae*] |
| 182 | ZP_011 . . . | 89339305 | Acyl-CoA oxidase-like:Acyl-CoA dehydrogenase-like:Acyl-CoA dehydrogenase, central region [*Mycobacterium flavescens* PYR-GCK] |
| 183 | YP_640598 | 108800401 | acyl-CoA dehydrogenase-like protein [*Mycobacterium* sp. MCS] |
| 184 | ZP_006 . . . | 71369913 | Acyl-CoA oxidase:Acyl-CoA dehydrogenase, C-terminal:Acyl-CoA dehydrogenase, central region:Acyl-CoA dehydrogenase, N-terminal [*Nocardioides* sp. JS614] |
| 185 | AAL14003 | 16186117 | SD05719p [*Drosophila melanogaster*] |
| 186 | NP_724181 | 24585195 | CG17544-PC, isoform C [*Drosophila melanogaster*] |
| 187 | AAH44725 | 28703869 | Acox3 protein [*Mus musculus*] |
| 188 | NP_109646 | 34328334 | acyl-Coenzyme A oxidase 3, pristanoyl [*Mus musculus*] |
| 189 | EAL33335 | 54644594 | GA14550-PA [*Drosophila pseudoobscura*] |
| 190 | ZP_004 . . . | 66967405 | Acyl-CoA oxidase:Acyl-CoA dehydrogenase, C-terminal [*Arthrobacter* sp. FB24] |
| 191 | NP_445791 | 16758056 | acyl-Coenzyme A oxidase 3, pristanoyl [*Rattus norvegicus*] |
| 192 | XP_786081 | 72005647 | PREDICTED: similar to pristanoyl acyl-Coenzyme A oxidase 3 [*Strongylocentrotus purpuratus*] |
| 193 | Q9EPL9 | 17366740 | Acyl-coenzyme A oxidase 3, peroxisomal (Pristanoyl-CoA oxidase) (Branched-chain acyl-CoA oxidase) (BRCACox) |
| 194 | NP_609027 | 45550141 | CG9527-PA [*Drosophila melanogaster*] |
| 195 | ZP_006 . . . | 69287897 | Acyl-CoA dehydrogenase, C-terminal:Acyl-CoA dehydrogenase, central region [*Kineococcus radiotolerans* SRS30216] |
| 196 | BAE47462 | 78483008 | acyl-CoA oxidase [*Arthrobacter ureafaciens*] |

TABLE 37

Examples of pox1 polypeptides.

| Row | ACCESSION | GI | PROTEIN DESCRIPTION |
|---|---|---|---|
| 1 | XP_503632 | 50552444 | hypothetical protein [*Yarrowia lipolytica*]. |
| 2 | O74935 | 59799073 | Acyl-coenzyme A oxidase 2 (Acyl-CoA oxidase 2) |
| 3 | O74936 | 59799074 | Acyl-coenzyme A oxidase 3 (Acyl-CoA oxidase 3) |
| 4 | XP_502199 | 50549457 | YlPOX5 [*Yarrowia lipolytica*] |
| 5 | O74934 | 59799072 | Acyl-coenzyme A oxidase 1 (Acyl-CoA oxidase 1) |
| 6 | XP_504703 | 50554589 | YlPOX1 [*Yarrowia lipolytica*] |
| 7 | XP_504475 | 50554133 | YlPOX4 [*Yarrowia lipolytica*] |
| 8 | XP_760471 | 71020481 | hypothetical protein UM04324.1 [*Ustilago maydis* 521] |
| 9 | XP_571768 | 58269224 | Acyl-coenzyme A oxidase I [*Cryptococcus neoformans* var. *neoformans* JEC21] |
| 10 | AAA34362 | 170912 | acyl-coenzyme A oxidase II precursor |
| 11 | BAA83482 | 5763520 | acyl-CoA oxidase [*Candida tropicalis*] |
| 12 | XP_717995 | 68475844 | putative fatty-acyl coenzyme A oxidase [*Candida albicans* SC5314] |
| 13 | BAA83483 | 5763522 | acyl-CoA oxidase [*Candida tropicalis*] |
| 14 | XP_721610 | 68468582 | putative fatty-acyl coenzyme A oxidase [*Candida albicans* SC5314] |
| 15 | OXCKPM | 66060 | acyl-CoA oxidase (EC 1.3.3.6) PXP4, peroxisomal - yeast (*Candida maltosa*) |
| 16 | P08790 | 17373073 | Acyl-coenzyme A oxidase 5 (Acyl-CoA oxidase 5) (PXP-5) |
| 17 | OXCKX5 | 66061 | acyl-CoA oxidase (EC 1.3.3.6) PDX5, peroxisomal - yeast (*Candida tropicalis*) |
| 18 | XP_721613 | 68468588 | putative fatty-acyl coenzyme A oxidase [*Candida albicans* SC5314] |
| 19 | AAA34361 | 170910 | PXP-2 protein |
| 20 | Q6BRD5 | 59799027 | Acyl-coenzyme A oxidase (Acyl-CoA oxidase) |
| 21 | 1306283A | 225549 | oxidase, fatty acyl |

TABLE 37-continued

Examples of pox1 polypeptides.

| Row | ACCESSION | GI | PROTEIN DESCRIPTION |
|---|---|---|---|
| 22 | P06598 | 17373023 | Acyl-coenzyme A oxidase 4 (Acyl-CoA oxidase 4) (PXP-4) (Peroxisomal fatty acyl-CoA oxidase) |
| 23 | XP_459232 | 50421365 | hypothetical protein DEHA0D18667g [*Debaryomyces hansenii* CBS767] |
| 24 | Q00468 | 2498206 | Acyl-coenzyme A oxidase 2 (Acyl-CoA oxidase 2) (AOX 2) |
| 25 | XP_457726 | 50417804 | hypothetical protein DEHA0C01155g [*Debaryomyces hansenii* CBS767] |
| 26 | Q9Y7B1 | 60391213 | Acyl-coenzyme A oxidase (Acyl-CoA oxidase) |
| 27 | Q6CKK7 | 59799028 | Acyl-coenzyme A oxidase (Acyl-CoA oxidase) |
| 28 | NP_011310 | 6321233 | Fatty-acyl coenzyme A oxidase, involved in the fatty acid beta-oxidation pathway; localized to the peroxisomal matrix; Pox1p [*Saccharomyces cerevisiae*] |
| 29 | AAA34891 | 172217 | acyl-coenzyme A oxidase |
| 30 | Q6FY63 | 59799032 | Acyl-coenzyme A oxidase (Acyl-CoA oxidase) |
| 31 | Q756A9 | 60391210 | Acyl-coenzyme A oxidase (Acyl-CoA oxidase) |
| 32 | CAA68660 | 2673 | acyl-coenzyme A oxidase [*Candida tropicalis*] |
| 33 | 1W07B | 58177067 | Chain B, *Arabidopsis Thaliana* Acyl-Coa Oxidase 1 |
| 34 | O65202 | 62286589 | Acyl-coenzyme A oxidase 1, peroxisomal (AOX 1) (Long-chain acyl-CoA oxidase) (AtCX1) |
| 35 | NP_001 . . . | 55741614 | acyl-Coenzyme A oxidase 1, palmitoyl [*Gallus gallus*] |
| 36 | AAH85743 | 55249685 | Acyl-Coenzyme A oxidase 1, palmitoyl [*Rattus norvegicus*] |
| 37 | XP_414406 | 50754485 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Gallus gallus*] |
| 38 | H71434 | 7488059 | probable apetala2 domain TINY - *Arabidopsis thaliana* |
| 39 | 2DDHA | 93279231 | Chain A, Crystal Structure Of Acyl-Coa Oxidase Complexed With 3-Oh-Dodecanoate |
| 40 | NP_567513 | 18414744 | ACX1 (ACYL-COA OXIDASE 1) [*Arabidopsis thaliana*] |
| 41 | NP_001 . . . | 62751552 | MGC108278 protein [*Xenopus tropicalis*] |
| 42 | AAI08648 | 83318302 | Unknown (protein for MGC: 131363) [*Xenopus laevis*] |
| 43 | AAH97101 | 67678187 | Zgc: 92584 protein [*Danio rerio*] |
| 44 | AAH63727 | 39795632 | MGC68531 protein [*Xenopus laevis*] |
| 45 | NP_001 . . . | 54400372 | hypothetical protein LOC449662 [*Danio rerio*] |
| 46 | AAL01888 | 15553480 | acyl-CoA oxidase [*Glycine max*] |
| 47 | ABE83706 | 92875906 | acyl-CoA oxidase [*Medicago truncatula*] |
| 48 | AAL01887 | 15553478 | acyl-CoA oxidase [*Glycine max*] |
| 49 | BAE25794 | 74188249 | unnamed protein product [*Mus musculus*] |
| 50 | NP_056544 | 66793429 | acyl-Coenzyme A oxidase 1, palmitoyl [*Mus musculus*] |
| 51 | XP_001 . . . | 109118312 | PREDICTED: similar to acyl-Coenzyme A oxidase isoform b [*Macaca mulatta*] |
| 52 | BAA86870 | 6429156 | peroxisomal acyl-CoA oxidase [*Mus musculus*] |
| 53 | Q9R0H0 | 51338830 | Acyl-coenzyme A oxidase 1, peroxisomal (Palmitoyl-CoA oxidase) (AOX) |
| 54 | AAB62926 | 2253380 | peroxisomal acyl-CoA oxidase [*Mus musculus*] |
| 55 | AAA18595 | 495475 | peroxisomal fatty acyl-coA oxidase |
| 56 | Q5RC19 | 62286600 | Acyl-coenzyme A oxidase 1, peroxisomal (Palmitoyl-CoA oxidase) (AOX) |
| 57 | 2FONC | 109157678 | Chain C, X-Ray Crystal Structure Of Leacx1, An Acyl-Coa Oxidase From *Lycopersicon Esculentum* (Tomato) |
| 58 | AAW78689 | 58531948 | peroxisomal acyl-CoA oxidase 1A [*Lycopersicon esculentum*] |
| 59 | AAW78691 | 58531952 | peroxisomal acyl-CoA oxidase 1A [*Lycopersicon cheesmaniae*] |
| 60 | CAH90691 | 55727877 | hypothetical protein [*Pongo pygmaeus*] |
| 61 | NP_009223 | 30089974 | acyl-Coenzyme A oxidase isoform b [*Homo sapiens*] |
| 62 | Q15067 | 17380467 | Acyl-coenzyme A oxidase 1, peroxisomal (Palmitoyl-CoA oxidase) (AOX) (Straight-chain acyl-CoA oxidase) (SCOX) |
| 63 | AAH21339 | 18204156 | Acox2 protein [*Mus musculus*] |
| 64 | NP_004026 | 30089972 | acyl-Coenzyme A oxidase isoform a [*Homo sapiens*] |
| 65 | NP_001 . . . | 78369480 | acyl-Coenzyme A oxidase 1, palmitoyl [*Bos taurus*] |
| 66 | Q9ZQP2 | 62286640 | Putative acyl-coenzyme A oxidase 1.2, peroxisomal |
| 67 | AAH08767 | 14250616 | Acyl-Coenzyme A oxidase 1, palmitoyl [*Homo sapiens*] |
| 68 | AAH68891 | 46250227 | MGC83074 protein [*Xenopus laevis*] |
| 69 | Q8HYL8 | 34098564 | Acyl-coenzyme A oxidase 1, peroxisomal (Palmitoyl-CoA oxidase) (AOX) |
| 70 | XP_540441 | 73965013 | PREDICTED: similar to acyl-Coenzyme A oxidase isoform a [*Canis familiaris*] |
| 71 | AAB30019 | 7689914 | peroxisomal acyl-coenzyme A oxidase [*Homo sapiens*] |
| 72 | CAD97622 | 31873262 | hypothetical protein [*Homo sapiens*] |
| 73 | I38095 | 2117541 | acyl-CoA oxidase (EC 1.3.3.6), peroxisomal - human |
| 74 | BAF18456 | 113594582 | Os06g0103500 [*Oryza sativa* (*japonica* cultivar-group)] |
| 75 | AAH10425 | 14714578 | Acyl-Coenzyme A oxidase 1, palmitoyl [*Homo sapiens*] |
| 76 | AAA19113 | 458119 | acyl-CoA oxidase |
| 77 | B54942 | 1082171 | acyl-CoA oxidase (EC 1.3.3.6), peroxisomal splice form II - human |
| 78 | Q9QXD1 | 17367045 | Acyl-coenzyme A oxidase 2, peroxisomal (3-alpha,7-alpha,12-alpha-trihydroxy-5-beta-cholestanoyl-CoA 24-hydroxylase) (3- |

TABLE 37-continued

Examples of pox1 polypeptides.

| Row | ACCESSION | GI | PROTEIN DESCRIPTION |
|---|---|---|---|
| | | | alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 79 | Q9Z1N0 | 17367267 | Acyl-coenzyme A oxidase 1, peroxisomal (Palmitoyl-CoA oxidase) (AOX) |
| 80 | CAJ83302 | 89271321 | acyl-Coenzyme A oxidase 2, branched chain [*Xenopus tropicalis*] |
| 81 | XP_511690 | 55645995 | PREDICTED: similar to hypothetical protein [*Pan troglodytes*] |
| 82 | XP_592892 | 76648807 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 1 [*Bos taurus*] |
| 83 | XP_879996 | 76648809 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 6 [*Bos taurus*] |
| 84 | AAO15577 | 27462768 | acyl-CoA oxidase type 2 [*Phascolarctos cinereus*] |
| 85 | NP_665713 | 21955130 | acyl-Coenzyme A oxidase 2, branched chain [*Rattus norvegicus*] |
| 86 | XP_320718 | 58394417 | ENSANGP00000020032 [*Anopheles gambiae* str. PEST] |
| 87 | NP_510603 | 17568313 | F59F4.1 [*Caenorhabditis elegans*] |
| 88 | XP_541826 | 73985284 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Canis familiaris*] |
| 89 | CAE69737 | 39596101 | Hypothetical protein CBG16008 [*Caenorhabditis briggsae*] |
| 90 | CAE63479 | 39592402 | Hypothetical protein CBG07946 [*Caenorhabditis briggsae*] |
| 91 | XP_782824 | 72015136 | PREDICTED: similar to Acyl-coenzyme A oxidase 1, peroxisomal (Palmitoyl-CoA oxidase) (AOX) [*Strongylocentrotus purpuratus*] |
| 92 | AAH47700 | 28839704 | Acyl-Coenzyme A oxidase 2, branched chain [*Homo sapiens*] |
| 93 | XP_785210 | 72015040 | PREDICTED: similar to Acyl-coenzyme A oxidase 1, peroxisomal (Palmitoyl-CoA oxidase) (AOX) [*Strongylocentrotus purpuratus*] |
| 94 | EAT39640 | 108875415 | acyl-CoA oxidase [*Aedes aegypti*] |
| 95 | EAS31618 | 90301987 | hypothetical protein CIMG_07097 [*Coccidioides immitis* RS] |
| 96 | O02767 | 17366131 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 97 | NP_998312 | 47085909 | pristanoyl acyl-Coenzyme A oxidase 3 [*Danio rerio*] |
| 98 | XP_783450 | 72111190 | PREDICTED: similar to acyl-Coenzyme A oxidase 1, palmitoyl [*Strongylocentrotus purpuratus*] |
| 99 | EAR95568 | 89297580 | Acyl-CoA oxidase family protein [*Tetrahymena thermophila* SB210] |
| 100 | XP_320717 | 58394415 | ENSANGP00000020118 [*Anopheles gambiae* str. PEST] |
| 101 | NP_493263 | 17506533 | F08A8.3 [*Caenorhabditis elegans*] |
| 102 | AAF73843 | 8163758 | acyl-CoA oxidase ACX3 [*Arabidopsis thaliana*] |
| 103 | BAC26167 | 26324826 | unnamed protein product [*Mus musculus*] |
| 104 | Q9LLH9 | 62286634 | Acyl-coenzyme A oxidase 3, peroxisomal precursor (AOX 3) (Medium-chain acyl-CoA oxidase) (AtCX3) |
| 105 | NP_493264 | 17506535 | F08A8.4 [*Caenorhabditis elegans*] |
| 106 | XP_758355 | 71010163 | hypothetical protein UM02208.1 [*Ustilago maydis 521*] |
| 107 | XP_664356 | 67541164 | hypothetical protein AN6752.2 [*Aspergillus nidulans* FGSC A4] |
| 108 | EAT48205 | 108883980 | acyl-CoA oxidase [*Aedes aegypti*] |
| 109 | XP_879827 | 76648805 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 5 [*Bos taurus*] |
| 110 | NP_499119 | 17552648 | C48B4.1 [*Caenorhabditis elegans*] |
| 111 | O15254 | 17366151 | Acyl-coenzyme A oxidase 3, peroxisomal (Pristanoyl-CoA oxidase) (Branched-chain acyl-CoA oxidase) (BRCACox) |
| 112 | BAE55537 | 83765394 | unnamed protein product [*Aspergillus oryzae*] |
| 113 | XP_625136 | 66556360 | PREDICTED: similar to CG5009-PA, partial [*Apis mellifera*] |
| 114 | CAE63476 | 39592399 | Hypothetical protein CBG07943 [*Caenorhabditis briggsae*] |
| 115 | NP_523802 | 17647123 | acyl-Coenzyme A oxidase at 57D proximal CG9707-PA [*Drosophila melanogaster*] |
| 116 | AAH54727 | 68262425 | Acox1 protein [*Mus musculus*] |
| 117 | BAC35782 | 74197284 | unnamed protein product [*Mus musculus*] |
| 118 | AAW78690 | 58531950 | peroxisomal acyl-CoA oxidase 1B [*Lycopersicon esculentum*] |
| 119 | AAL39944 | 17862934 | SD03592p [*Drosophila melanogaster*] |
| 120 | XP_786081 | 72005647 | PREDICTED: similar to pristanoyl acyl-Coenzyme A oxidase 3 [*Strongylocentrotus purpuratus*] |
| 121 | ZP_012 . . . | 90587482 | Acyl-CoA oxidase-like:Acyl-CoA dehydrogenase-like:Acyl-CoA dehydrogenase, central region [*Flavobacterium johnsoniae* UW101] |

TABLE 37-continued

Examples of pox1 polypeptides.

| Row | ACCESSION | GI | PROTEIN DESCRIPTION |
|---|---|---|---|
| 122 | CAE63477 | 39592400 | Hypothetical protein CBG07944 [*Caenorhabditis briggsae*] |
| 123 | EAR89261 | 89291273 | Acyl-CoA oxidase family protein [*Tetrahymena thermophila* SB210] |
| 124 | CAE65171 | 39590798 | Hypothetical protein CBG10043 [*Caenorhabditis briggsae*] |
| 125 | CAH91120 | 55728762 | hypothetical protein [*Pongo pygmaeus*] |
| 126 | XP_587157 | 76620513 | PREDICTED: similar to Acyl-coenzyme A oxidase 3, peroxisomal (Pristanoyl-CoA oxidase) [*Bos taurus*] |
| 127 | XP_382463 | 46110811 | hypothetical protein FG02287.1 [*Gibberella zeae* PH-1] |
| 128 | XP_973660 | 91082769 | PREDICTED: similar to CG5009-PA [*Tribolium castaneum*] |
| 129 | CAH91864 | 55730283 | hypothetical protein [*Pongo pygmaeus*] |
| 130 | NP_493262 | 17506531 | F08A8.2 [*Caenorhabditis elegans*] |
| 131 | NP_001 . . . | 71983346 | F08A8.1a [*Caenorhabditis elegans*] |
| 132 | NP_109646 | 34328334 | acyl-Coenzyme A oxidase 3, pristanoyl [*Mus musculus*] |
| 133 | AAH44725 | 28703869 | Acox3 protein [*Mus musculus*] |
| 134 | XP_969513 | 91093755 | PREDICTED: similar to pristanoyl acyl-Coenzyme A oxidase 3 [*Tribolium castaneum*] |
| 135 | CAE63480 | 39592403 | Hypothetical protein CBG07947 [*Caenorhabditis briggsae*] |
| 136 | CAJ58493 | 85539740 | Hypothetical protein F08A8.1c [*Caenorhabditis elegans*] |
| 137 | NP_001 . . . | 71983355 | F08A8.1b [*Caenorhabditis elegans*] |
| 138 | XP_635946 | 66804335 | hypothetical protein DDBDRAFT_0188674 [*Dictyostelium discoideum* AX4] |
| 139 | BAF19505 | 113595631 | Os06g0354500 [*Oryza sativa (japonica* cultivar-group)] |
| 140 | XP_786025 | 72005645 | PREDICTED: similar to pristanoyl acyl-Coenzyme A oxidase 3 [*Strongylocentrotus purpuratus*] |
| 141 | NP_611264 | 24654595 | CG5009-PA [*Drosophila melanogaster*] |
| 142 | NP_445791 | 16758056 | acyl-Coenzyme A oxidase 3, pristanoyl [*Rattus norvegicus*] |
| 143 | Q9EPL9 | 17366740 | Acyl-coenzyme A oxidase 3, peroxisomal (Pristanoyl-CoA oxidase) (Branched-chain acyl-CoA oxidase) (BRCACox) |
| 144 | Q9LMI7 | 62286635 | Putative acyl-coenzyme A oxidase 3.2, peroxisomal precursor |
| 145 | BAE42553 | 74143079 | unnamed protein product [*Mus musculus*] |
| 146 | AAL28144 | 16767852 | GH01266p [*Drosophila melanogaster*] |
| 147 | EAT87650 | 111066530 | hypothetical protein SNOG_05259 [*Phaeosphaeria nodorum* SN15] |
| 148 | BAC26136 | 26324764 | unnamed protein product [*Mus musculus*] |
| 149 | XP_545908 | 73951751 | PREDICTED: similar to Acyl-coenzyme A oxidase 3, peroxisomal (Pristanoyl-CoA oxidase) [*Canis familiaris*] |
| 150 | EAR99631 | 89301643 | Acyl-CoA oxidase family protein [*Tetrahymena thermophila* SB210] |
| 151 | AAC13497 | 3044212 | acyl-CoA oxidase [*Arabidopsis thaliana*] |
| 152 | O65201 | 62286588 | Acyl-coenzyme A oxidase 2, peroxisomal precursor (AOX 2) (Long-chain acyl-CoA oxidase) (AtCX2) |
| 153 | AAF14635 | 6503198 | acyl-CoA oxidase [*Petroselinum crispum*] |
| 154 | EAS02716 | 89304728 | Acyl-CoA oxidase family protein [*Tetrahymena thermophila* SB210] |
| 155 | AAR00586 | 37699750 | acyl-CoA oxidase [*Phalaenopsis* cv. 'True Lady'] |
| 156 | EAS04704 | 89306716 | Acyl-CoA oxidase family protein [*Tetrahymena thermophila* SB210] |
| 157 | YP_634556 | 108758121 | putative acyl-CoA dehydrogenase [*Myxococcus xanthus* DK 1622] |
| 158 | O64894 | 62286587 | Acyl-coenzyme A oxidase, peroxisomal precursor (AOX) (Long-chain acyl-CoA oxidase) |
| 159 | AAB67883 | 1575556 | acyl-CoA oxidase homolog [*Phalaenopsis* sp. 'True Lady'] |
| 160 | ZP_012 . . . | 89890388 | acyl-CoA oxidase [*Flavobacteria bacterium* BBFL7] |
| 161 | EAL26359 | 54636956 | GA18591-PA [*Drosophila pseudoobscura*] |
| 162 | EAL26647 | 54637244 | GA21980-PA [*Drosophila pseudoobscura*] |
| 163 | EAR98581 | 89300593 | Acyl-CoA oxidase family protein [*Tetrahymena thermophila* SB210] |
| 164 | AAH17053 | 16877606 | ACOX3 protein [*Homo sapiens*] |
| 165 | XP_636605 | 66805767 | hypothetical protein DDBDRAFT_0188084 [*Dictyostelium discoideum* AX4] |
| 166 | YP_445820 | 83816544 | acyl-coenzyme A oxidase I, putative [*Salinibacter ruber* DSM 13855] |
| 167 | EAT87454 | 111066334 | hypothetical protein SNOG_05063 [*Phaeosphaeria nodorum* SN15] |
| 168 | NP_001 . . . | 79332306 | ACX2 (ACYL-COA OXIDASE 2); acyl-CoA oxidase [*Arabidopsis thaliana*] |
| 169 | YP_290295 | 72162638 | hypothetical protein Tfu_2239 [*Thermobifida fusca* YX] |
| 170 | XP_646395 | 66826081 | hypothetical protein DDBDRAFT_0216722 [*Dictyostelium discoideum* AX4] |
| 171 | XP_317513 | 58390136 | ENSANGP00000010039 [*Anopheles gambiae* str. PEST] |
| 172 | ZP_012 . . . | 90205075 | Acyl-CoA oxidase-like:Acyl-CoA dehydrogenase-like:Acyl-CoA dehydrogenase, central region [*Mycobacterium vanbaalenii* PYR-1] |
| 173 | EAS36523 | 90306892 | hypothetical protein CIMG_01877 [*Coccidioides immitis* RS] |
| 174 | XP_758113 | 71007469 | hypothetical protein UM01966.1 [*Ustilago maydis* 521] |
| 175 | XP_395486 | 66564429 | PREDICTED: similar to CG9527-PA [*Apis mellifera*] |

TABLE 37-continued

| Examples of pox1 polypeptides. | | | |
|---|---|---|---|
| Row | ACCESSION | GI | PROTEIN DESCRIPTION |
| 176 | ABA94670 | 108864573 | Acyl-coenzyme A oxidase 2, peroxisomal precursor, putative, expressed [*Oryza sativa* (*japonica* cultivar-group)] |
| 177 | XP_637610 | 66807775 | hypothetical protein DDBDRAFT_0187085 [*Dictyostelium discoideum* AX4] |
| 178 | ZP_003 . . . | 62426247 | COG1960: Acyl-CoA dehydrogenases [*Brevibacterium linens* BL2] |
| 179 | YP_702012 | 111019040 | acyl-CoA oxidase [*Rhodococcus* sp. RHA1] |
| 180 | NP_500943 | 17540842 | F58F9.7 [*Caenorhabditis elegans*] |
| 181 | EAT39346 | 108875121 | acyl-CoA oxidase [*Aedes aegypti*] |
| 182 | CAA96917 | 1945301 | POX1 [*Saccharomyces cerevisiae*] |
| 183 | NP_609027 | 45550141 | CG9527-PA [*Drosophila melanogaster*] |
| 184 | CAA04688 | 2370232 | putative acyl-CoA oxidase [*Hordeum vulgare* subsp. *vulgare*] |
| 185 | AAL48010 | 17944231 | LD22081p [*Drosophila melanogaster*] |
| 186 | EAL32329 | 54643586 | GA18278-PA [*Drosophila pseudoobscura*] |
| 187 | CAE61577 | 39584202 | Hypothetical protein CBG05491 [*Caenorhabditis briggsae*] |
| 188 | AAL48950 | 17945806 | RE34879p [*Drosophila melanogaster*] |
| 189 | NP_724181 | 24585195 | CG17544-PC, isoform C [*Drosophila melanogaster*] |
| 190 | AAL14003 | 16186117 | SD05719p [*Drosophila melanogaster*] |
| 191 | XP_317446 | 58390030 | ENSANGP00000011863 [*Anopheles gambiae* str. PEST] |
| 192 | ZP_011 . . . | 89339305 | Acyl-CoA oxidase-like:Acyl-CoA dehydrogenase-like:Acyl-CoA dehydrogenase, central region [*Mycobacterium flavescens* PYR-GCK] |
| 193 | ZP_004 . . . | 66967405 | Acyl-CoA oxidase:Acyl-CoA dehydrogenase, C-terminal [*Arthrobacter* sp. FB24] |
| 194 | ZP_011 . . . | 88803915 | acyl-coenzyme A oxidase I, putative [*Robiginitalea biformata* HTCC2501] |
| 195 | EAL32912 | 54644170 | GA21857-PA [*Drosophila pseudoobscura*] |
| 196 | EAL26648 | 54637245 | GA21981-PA [*Drosophila pseudoobscura*] |
| 197 | ZP_012 . . . | 92908524 | Acyl-CoA oxidase-like:Acyl-CoA dehydrogenase-like:Acyl-CoA dehydrogenase, central region [*Mycobacterium* sp. JLS] |

TABLE 38

| Examples of pox3 polypeptides. | | | |
|---|---|---|---|
| Row | ACCESSION | GI | PROTEIN DESCRIPTION |
| 1 | XP_503244 | 50551539 | YlPOX3 [*Yarrowia lipolytica*] |
| 2 | XP_502199 | 50549457 | YlPOX5 [*Yarrowia lipolytica*] |
| 3 | O74935 | 59799073 | Acyl-coenzyme A oxidase 2 (Acyl-CoA oxidase 2) |
| 4 | O74934 | 59799072 | Acyl-coenzyme A oxidase 1 (Acyl-CoA oxidase 1) |
| 5 | XP_504703 | 50554589 | YlPOX1 [*Yarrowia lipolytica*] |
| 6 | XP_504475 | 50554133 | YlPOX4 [*Yarrowia lipolytica*] |
| 7 | XP_503632 | 50552444 | hypothetical protein [*Yarrowia lipolytica*] |
| 8 | XP_571768 | 58269224 | Acyl-coenzyme A oxidase I [*Cryptococcus neoformans* var. *neoformans* JEC21] |
| 9 | XP_760471 | 71020481 | hypothetical protein UM04324.1 [*Ustilago maydis* 521] |
| 10 | XP_717995 | 68475844 | putative fatty-acyl coenzyme A oxidase [*Candida albicans* SC5314] |
| 11 | Q6BRD5 | 59799027 | Acyl-coenzyme A oxidase (Acyl-CoA oxidase) |
| 12 | BAA83482 | 5763520 | acyl-CoA oxidase [*Candida tropicalis*] |
| 13 | OXCKPM | 66060 | acyl-CoA oxidase (EC 1.3.3.6) PXP4, peroxisomal - yeast (*Candida maltosa*) |
| 14 | BAA83483 | 5763522 | acyl-CoA oxidase [*Candida tropicalis*] |
| 15 | AAA34362 | 170912 | acyl-coenzyme A oxidase II precursor |
| 16 | P08790 | 17373073 | Acyl-coenzyme A oxidase 5 (Acyl-CoA oxidase 5) (PXP-5) |
| 17 | OXCKX5 | 66061 | acyl-CoA oxidase (EC 1.3.3.6) POX5, peroxisomal - yeast (*Candida tropicalis*) |
| 18 | XP_721610 | 68468582 | putative fatty-acyl coenzyme A oxidase [*Candida albicans* SC5314] |
| 19 | Q9Y7B1 | 60391213 | Acyl-coenzyme A oxidase (Acyl-CoA oxidase) |
| 20 | XP_457726 | 50417804 | hypothetical protein DEHA0C01155g [*Debaryomyces hansenii* CBS767] |
| 21 | P06598 | 17373023 | Acyl-coenzyme A oxidase 4 (Acyl-CoA oxidase 4) (PXP-4) (Peroxisomal fatty acyl-CoA oxidase) |
| 22 | AAA34361 | 170910 | PXP-2 protein |
| 23 | 1306283A | 225549 | oxidase, fatty acyl |
| 24 | XP_721613 | 68468588 | putative fatty-acyl coenzyme A oxidase [*Candida albicans* SC5314] |
| 25 | XP_459232 | 50421365 | hypothetical protein DEHA0D18667g [*Debaryomyces hansenii* CBS767] |
| 26 | Q00468 | 2498206 | Acyl-coenzyme A oxidase 2 (Acyl-CoA oxidase 2) (AOX 2) |
| 27 | Q6FY63 | 59799032 | Acyl-coenzyme A oxidase (Acyl-CoA oxidase) |

TABLE 38-continued

Examples of pox3 polypeptides.

| Row | ACCESSION | GI | PROTEIN DESCRIPTION |
|---|---|---|---|
| 28 | Q6CKK7 | 59799028 | Acyl-coenzyme A oxidase (Acyl-CoA oxidase) |
| 29 | Q756A9 | 60391210 | Acyl-coenzyme A oxidase (Acyl-CoA oxidase) |
| 30 | NP_011310 | 6321233 | Fatty-acyl coenzyme A oxidase, involved in the fatty acid beta-oxidation pathway; localized to the peroxisomal matrix; Pox1p [*Saccharomyces cerevisiae*] |
| 31 | AAA34891 | 172217 | acyl-coenzyme A oxidase |
| 32 | CAA68660 | 2673 | acyl-coenzyme A oxidase [*Candida tropicalis*] |
| 33 | BAF18456 | 113594582 | Os06g0103500 [*Oryza sativa* (*japonica* cultivar-group)] |
| 34 | O65202 | 62286589 | Acyl-coenzyme A oxidase 1, peroxisomal (AOX 1) (Long-chain acyl-CoA oxidase) (AtCX1) |
| 35 | H71434 | 7488059 | probable apetala2 domain TINY - *Arabidopsis thaliana* |
| 36 | 1W07B | 58177067 | Chain B, *Arabidopsis Thaliana* Acyl-Coa Oxidase 1 |
| 37 | NP_567513 | 18414744 | ACX1 (ACYL-COA OXIDASE 1) [*Arabidopsis thaliana*] |
| 38 | AAH68891 | 46250227 | MGC83074 protein [*Xenopus laevis*] |
| 39 | AAL01888 | 15553480 | acyl-CoA oxidase [*Glycine max*] |
| 40 | ABE83706 | 92875906 | acyl-CoA oxidase [*Medicago truncatula*] |
| 41 | Q9ZQP2 | 62286640 | Putative acyl-coenzyme A oxidase 1.2, peroxisomal |
| 42 | CAJ83302 | 89271321 | acyl-Coenzyme A oxidase 2, branched chain [*Xenopus tropicalis*] |
| 43 | BAE25794 | 74188249 | unnamed protein product [*Mus musculus*] |
| 44 | AAL01887 | 15553478 | acyl-CoA oxidase [*Glycine max*] |
| 45 | AAW78689 | 58531948 | peroxisomal acyl-CoA oxidase 1A [*Lycopersicon esculentum*] |
| 46 | 2FONC | 109157678 | Chain C, X-Ray Crystal Structure Of Leacx1, An Acyl-Coa Oxidase From *Lycopersicon Esculentum* (Tomato) |
| 47 | AAW78691 | 58531952 | peroxisomal acyl-CoA oxidase 1A [*Lycopersicon cheesmaniae*] |
| 48 | AAH21339 | 18204156 | Acox2 protein [*Mus musculus*] |
| 49 | XP_320717 | 58394415 | ENSANGP00000020118 [*Anopheles gambiae* str. PEST] |
| 50 | Q9QXD1 | 17367045 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 51 | XP_414406 | 50754485 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Gallus gallus*] |
| 52 | NP_001 . . . | 54400372 | hypothetical protein LOC449662 [*Danio rerio*] |
| 53 | AAH63727 | 39795632 | MGC68531 protein [*Xenopus laevis*] |
| 54 | EAT39640 | 108875415 | acyl-CoA oxidase [*Aedes aegypti*] |
| 55 | AAH97101 | 67678187 | Zgc: 92584 protein [*Danio rerio*] |
| 56 | NP_001 . . . | 55741614 | acyl-Coenzyme A oxidase 1, palmitoyl [*Gallus gallus*] |
| 57 | NP_001 . . . | 62751552 | MGC108278 protein [*Xenopus tropicalis*] |
| 58 | NP_665713 | 21955130 | acyl-Coenzyme A oxidase 2, branched chain [*Rattus norvegicus*] |
| 59 | XP_320718 | 58394417 | ENSANGP00000020032 [*Anopheles gambiae* str. PEST] |
| 60 | AAI08648 | 83318302 | Unknown (protein for MGC: 131363) [*Xenopus laevis*] |
| 61 | CAE63479 | 39592402 | Hypothetical protein CBG07946 [*Caenorhabditis briggsae*] |
| 62 | Q8HYL8 | 34098564 | Acyl-coenzyme A oxidase 1, peroxisomal (Palmitoyl-CoA oxidase) (AOX) |
| 63 | EAS31618 | 90301987 | hypothetical protein CIMG_07097 [*Coccidioides immitis* RS] |
| 64 | CAH90691 | 55727877 | hypothetical protein [*Pongo pygmaeus*] |
| 65 | Q5RC19 | 62286600 | Acyl-coenzyme A oxidase 1, peroxisomal (Palmitoyl-CoA oxidase) (AOX) |
| 66 | XP_001 . . . | 109118312 | PREDICTED: similar to acyl-Coenzyme A oxidase isoform b [*Macaca mulatta*] |
| 67 | XP_540441 | 73965013 | PREDICTED: similar to acyl-Coenzyme A oxidase isoform a [*Canis familiaris*] |
| 68 | I38095 | 2117541 | acyl-CoA oxidase (EC 1.3.3.6), peroxisomal - human |
| 69 | AAH08767 | 14250616 | Acyl-Coenzyme A oxidase 1, palmitoyl [*Homo sapiens*] |
| 70 | NP_004026 | 30089972 | acyl-Coenzyme A oxidase isoform a [*Homo sapiens*] |
| 71 | CAD97622 | 31873262 | hypothetical protein [*Homo sapiens*] |
| 72 | NP_510603 | 17568313 | F59F4.1 [*Caenorhabditis elegans*] |
| 73 | Q15067 | 17380467 | Acyl-coenzyme A oxidase 1, peroxisomal (Palmitoyl-CoA oxidase) (AOX) (Straight-chain acyl-CoA oxidase) (SCOX) |
| 74 | NP_009223 | 30089974 | acyl-Coenzyme A oxidase isoform b [*Homo sapiens*] |
| 75 | NP_001 . . . | 78369480 | acyl-Coenzyme A oxidase 1, palmitoyl [*Bos taurus*] |
| 76 | B54942 | 1082171 | acyl-CoA oxidase (EC 1.3.3.6), peroxisomal splice form II - human |
| 77 | AAA18595 | 495475 | peroxisomal fatty acyl-coA oxidase |
| 78 | AAA19113 | 458119 | acyl-CoA oxidase |
| 79 | AAB30019 | 7689914 | peroxisomal acyl-coenzyme A oxidase [*Homo sapiens*] |
| 80 | XP_758355 | 71010163 | hypothetical protein UM02208.1 [*Ustilago maydis* 521] |
| 81 | AAH10425 | 14714578 | Acyl-Coenzyme A oxidase 1, palmitoyl [*Homo sapiens*] |
| 82 | CAE65171 | 39590798 | Hypothetical protein CBG10043 [*Caenorhabditis briggsae*] |
| 83 | O02767 | 17366131 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA |

TABLE 38-continued

Examples of pox3 polypeptides.

| Row | ACCESSION | GI | PROTEIN DESCRIPTION |
|---|---|---|---|
| | | | oxidase) (Trihydroxycoprostanoyl-CoA oxidase) (THCCox) (THCA-CoA oxidase) |
| 84 | AAH47700 | 28839704 | Acyl-Coenzyme A oxidase 2, branched chain [*Homo sapiens*] |
| 85 | AAO15577 | 27462768 | acyl-CoA oxidase type 2 [*Phascolarctos cinereus*] |
| 86 | CAE69737 | 39596101 | Hypothetical protein CBG16008 [*Caenorhabditis briggsae*] |
| 87 | 2DDHA | 93279231 | Chain A, Crystal Structure Of Acyl-Coa Oxidase Complexed With 3-Oh-Dodecanoate |
| 88 | NP_499119 | 17552648 | C48B4.1 [*Caenorhabditis elegans*] |
| 89 | XP_625136 | 66556360 | PREDICTED: similar to CG5009-PA, partial [*Apis mellifera*] |
| 90 | XP_879996 | 76648809 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 6 [*Bos taurus*] |
| 91 | XP_592892 | 76648807 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 1 [*Bos taurus*] |
| 92 | XP_782824 | 72015136 | PREDICTED: similar to Acyl-coenzyme A oxidase 1, peroxisomal (Palmitoyl-CoA oxidase) (AOX) [*Strongylocentrotus purpuratus*] |
| 93 | Q9LLH9 | 62286634 | Acyl-coenzyme A oxidase 3, peroxisomal precursor (AOX 3) (Medium-chain acyl-CoA oxidase) (AtCX3) |
| 94 | AAF73843 | 8163758 | acyl-CoA oxidase ACX3 [*Arabidopsis thaliana*] |
| 95 | AAH85743 | 55249685 | Acyl-Coenzyme A oxidase 1, palmitoyl [*Rattus norvegicus*] |
| 96 | XP_785210 | 72015040 | PREDICTED: similar to Acyl-coenzyme A oxidase 1, peroxisomal (Palmitoyl-CoA oxidase) (AOX) [*Strongylocentrotus purpuratus*] |
| 97 | XP_511690 | 55645995 | PREDICTED: similar to hypothetical protein [*Pan troglodytes*] |
| 98 | NP_493263 | 17506533 | F08A8.3 [*Caenorhabditis elegans*] |
| 99 | XP_973660 | 91082769 | PREDICTED: similar to CG5009-PA [*Tribolium castaneum*] |
| 100 | CAE63477 | 39592400 | Hypothetical protein CBG07944 [*Caenorhabditis briggsae*] |
| 101 | NP_056544 | 66793429 | acyl-Coenzyme A oxidase 1, palmitoyl [*Mus musculus*] |
| 102 | Q9Z1N0 | 17367267 | Acyl-coenzyme A oxidase 1, peroxisomal (Palmitoyl-CoA oxidase) (AOX) |
| 103 | EAT48205 | 108883980 | acyl-CoA oxidase [*Aedes aegypti*] |
| 104 | BAA86870 | 6429156 | peroxisomal acyl-CoA oxidase [*Mus musculus*] |
| 105 | Q9R0H0 | 51338830 | Acyl-coenzyme A oxidase 1, peroxisomal (Palmitoyl-CoA oxidase) (AOX) |
| 106 | EAR95568 | 89297580 | Acyl-CoA oxidase family protein [*Tetrahymena thermophila* SB210] |
| 107 | AAB62926 | 2253380 | peroxisomal acyl-CoA oxidase [*Mus musculus*] |
| 108 | AAW78690 | 58531950 | peroxisomal acyl-CoA oxidase 1B [*Lycopersicon esculentum*] |
| 109 | XP_635946 | 66804335 | hypothetical protein DDBDRAFT_0188674 [*Dictyostelium discoideum* AX4] |
| 110 | NP_493264 | 17506535 | F08A8.4 [*Caenorhabditis elegans*] |
| 111 | CAE63480 | 39592403 | Hypothetical protein CBG07947 [*Caenorhabditis briggsae*] |
| 112 | NP_001 . . . | 71983346 | F08A8.1a [*Caenorhabditis elegans*] |
| 113 | CAE63476 | 39592399 | Hypothetical protein CBG07943 [*Caenorhabditis briggsae*] |
| 114 | BAC26167 | 26324826 | unnamed protein product [*Mus musculus*] |
| 115 | XP_541826 | 73985284 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Canis familiaris*] |
| 116 | BAE55537 | 83765394 | unnamed protein product [*Aspergillus oryzae*] |
| 117 | NP_001 . . . | 71983355 | F08A8.1b [*Caenorhabditis elegans*] |
| 118 | CAJ58493 | 85539740 | Hypothetical protein F08A8.1c [*Caenorhabditis elegans*] |
| 119 | EAS04704 | 89306716 | Acyl-CoA oxidase family protein [*Tetrahymena thermophila* SB210] |
| 120 | NP_493262 | 17506531 | F08A8.2 [*Caenorhabditis elegans*] |
| 121 | EAT87650 | 111066530 | hypothetical protein SNOG_05259 [*Phaeosphaeria nodorum* SN15] |
| 122 | O64894 | 62286587 | Acyl-coenzyme A oxidase, peroxisomal precursor (AOX) (Long-chain acyl-CoA oxidase) |
| 123 | XP_664356 | 67541164 | hypothetical protein AN6752.2 [*Aspergillus nidulans* FGSC A4] |
| 124 | XP_783450 | 72111190 | PREDICTED: similar to acyl-Coenzyme A oxidase 1, palmitoyl [*Strongylocentrotus purpuratus*] |
| 125 | BAF19505 | 113595631 | Os06g0354500 [*Oryza sativa* (*japonica* cultivar-group)] |
| 126 | XP_382463 | 46110811 | hypothetical protein FG02287.1 [*Gibberella zeae* PH-1] |
| 127 | XP_879827 | 76648805 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 5 [*Bos taurus*] |
| 128 | Q9LMI7 | 62286635 | Putative acyl-coenzyme A oxidase 3.2, peroxisomal precursor |
| 129 | AAR00586 | 37699750 | acyl-CoA oxidase [*Phalaenopsis* cv. 'True Lady'] |
| 130 | CAH91864 | 55730283 | hypothetical protein [*Pongo pygmaeus*] |
| 131 | NP_998312 | 47085909 | pristanoyl acyl-Coenzyme A oxidase 3 [*Danio rerio*] |

TABLE 38-continued

| Examples of pox3 polypeptides. | | | |
|---|---|---|---|
| Row | ACCESSION | GI | PROTEIN DESCRIPTION |
| 132 | AAL39944 | 17862934 | SD03592p [*Drosophila melanogaster*] |
| 133 | NP_523802 | 17647123 | acyl-Coenzyme A oxidase at 57D proximal CG9707-PA [*Drosophila melanogaster*] |
| 134 | EAR99631 | 89301643 | Acyl-CoA oxidase family protein [*Tetrahymena thermophila* SB210] |
| 135 | AAB67883 | 1575556 | acyl-CoA oxidase homolog [*Phalaenopsis* sp. 'True Lady'] |
| 136 | AAL48010 | 17944231 | LD22081p [*Drosophila melanogaster*] |
| 137 | EAR98581 | 89300593 | Acyl-CoA oxidase family protein [*Tetrahymena thermophila* SB210] |
| 138 | YP_445820 | 83816544 | acyl-coenzyme A oxidase I, putative [*Salinibacter ruber* DSM 13855] |
| 139 | EAL26648 | 54637245 | GA21981-PA [*Drosophila pseudoobscura*] |
| 140 | O65201 | 62286588 | Acyl-coenzyme A oxidase 2, peroxisomal precursor (AOX 2) (Long-chain acyl-CoA oxidase) (AtCX2) |
| 141 | AAC13497 | 3044212 | acyl-CoA oxidase [*Arabidopsis thaliana*] |
| 142 | AAF14635 | 6503198 | acyl-CoA oxidase [*Petroselinum crispum*] |
| 143 | XP_636605 | 66805767 | hypothetical protein DDBDRAFT_0188084 [*Dictyostelium discoideum* AX4] |
| 144 | O15254 | 17366151 | Acyl-coenzyme A oxidase 3, peroxisomal (Pristanoyl-CoA oxidase) (Branched-chain acyl-CoA oxidase) (BRCACox) |
| 145 | XP_758113 | 71007469 | hypothetical protein UM01966.1 [*Ustilago maydis* 521] |
| 146 | NP_611264 | 24654595 | CG5009-PA [*Drosophila melanogaster*] |
| 147 | XP_969513 | 91093755 | PREDICTED: similar to pristanoyl acyl-Coenzyme A oxidase 3 [*Tribolium castaneum*] |
| 148 | NP_109646 | 34328334 | acyl-Coenzyme A oxidase 3, pristanoyl [*Mus musculus*] |
| 149 | XP_637610 | 66807775 | hypothetical protein DDBDRAFT_0187085 [*Dictyostelium discoideum* AX4] |
| 150 | BAC35782 | 74197284 | unnamed protein product [*Mus musculus*] |
| 151 | EAL26647 | 54637244 | GA21980-PA [*Drosophila pseudoobscura*] |
| 152 | AAH44725 | 28703869 | Acox3 protein [*Mus musculus*] |
| 153 | AAH54727 | 68262425 | Acox1 protein [*Mus musculus*] |
| 154 | XP_587157 | 76620513 | PREDICTED: similar to Acyl-coenzyme A oxidase 3, peroxisomal (Pristanoyl-CoA oxidase) [*Bos taurus*] |
| 155 | ZP_012 . . . | 90587482 | Acyl-CoA oxidase-like:Acyl-CoA dehydrogenase-like:Acyl-CoA dehydrogenase, central region [*Flavobacterium johnsoniae* UW101] |
| 156 | CAA04688 | 2370232 | putative acyl-CoA oxidase [*Hordeum vulgare* subsp. *vulgare*] |
| 157 | EAL26359 | 54636956 | GA18591-PA [*Drosophila pseudoobscura*] |
| 158 | AAL28144 | 16767852 | GH01266p [*Drosophila melanogaster*] |
| 159 | CAH91120 | 55728762 | hypothetical protein [*Pongo pygmaeus*] |
| 160 | NP_445791 | 16758056 | acyl-Coenzyme A oxidase 3, pristanoyl [*Rattus norvegicus*] |
| 161 | Q9EPL9 | 17366740 | Acyl-coenzyme A oxidase 3, peroxisomal (Pristanoyl-CoA oxidase) (Branched-chain acyl-CoA oxidase) (BRCACox) |
| 162 | XP_786081 | 72005647 | PREDICTED: similar to pristanoyl acyl-Coenzyme A oxidase 3 [*Strongylocentrotus purpuratus*] |
| 163 | EAR89261 | 89291273 | Acyl-CoA oxidase family protein [*Tetrahymena thermophila* SB210] |
| 164 | ZP_012 . . . | 89890388 | acyl-CoA oxidase [*Flavobacteria bacterium* BBFL7] |
| 165 | XP_646395 | 66826081 | hypothetical protein DDBDRAFT_0216722 [*Dictyostelium discoideum* AX4] |
| 166 | NP_001 . . . | 79332306 | ACX2 (ACYL-COA OXIDASE 2); acyl-CoA oxidase [*Arabidopsis thaliana*] |
| 167 | BAC26136 | 26324764 | unnamed protein product [*Mus musculus*] |
| 168 | BAE42553 | 74143079 | unnamed protein product [*Mus musculus*] |
| 169 | EAS02716 | 89304728 | Acyl-CoA oxidase family protein [*Tetrahymena thermophila* SB210] |
| 170 | ABA94670 | 108864573 | Acyl-coenzyme A oxidase 2, peroxisomal precursor, putative, expressed [*Oryza sativa* (*japonica* cultivar-group)] |
| 171 | YP_290295 | 72162638 | hypothetical protein Tfu_2239 [*Thermobifida fusca* YX] |
| 172 | EAL32329 | 54643586 | GA18278-PA [*Drosophila pseudoobscura*] |
| 173 | EAT87454 | 111066334 | hypothetical protein SNOG_05063 [*Phaeosphaeria nodorum* SN15] |
| 174 | YP_634556 | 108758121 | putative acyl-CoA dehydrogenase [*Myxococcus xanthus* DK 1622] |
| 175 | NP_508036 | 17560134 | F25C8.1 [*Caenorhabditis elegans*] |
| 176 | NP_572371 | 24640268 | CG4586-PA [*Drosophila melanogaster*] |
| 177 | ZP_012 . . . | 90205075 | Acyl-CoA oxidase-like:Acyl-CoA dehydrogenase-like:Acyl-CoA dehydrogenase, central region [*Mycobacterium vanbaalenii* PYR-1] |
| 178 | XP_545908 | 73951751 | PREDICTED: similar to Acyl-coenzyme A oxidase 3, peroxisomal (Pristanoyl-CoA oxidase) [*Canis familiaris*] |
| 179 | YP_702012 | 111019040 | acyl-CoA oxidase [*Rhodococcus* sp. RHA1] |
| 180 | ZP_011 . . . | 89339305 | Acyl-CoA oxidase-like:Acyl-CoA dehydrogenase-like:Acyl-CoA dehydrogenase, central region [*Mycobacterium flavescens* PYR-GCK] |

TABLE 38-continued

| Examples of pox3 polypeptides. | | | |
|---|---|---|---|
| Row | ACCESSION | GI | PROTEIN DESCRIPTION |
| 181 | XP_786025 | 72005645 | PREDICTED: similar to pristanoyl acyl-Coenzyme A oxidase 3 [*Strongylocentrotus purpuratus*] |
| 182 | BAE60166 | 83770031 | unnamed protein product [*Aspergillus oryzae*] |
| 183 | ZP_012 . . . | 92908524 | Acyl-CoA oxidase-like:Acyl-CoA dehydrogenase-like:Acyl-CoA dehydrogenase, central region [*Mycobacterium* sp. JLS] |
| 184 | NP_961035 | 41408199 | hypothetical protein MAP2101 [*Mycobacterium avium* subsp. *paratuberculosis* K-10] |
| 185 | YP_640598 | 108800401 | acyl-CoA dehydrogenase-like protein [*Mycobacterium* sp. MCS] |
| 186 | XP_317446 | 58390030 | ENSANGP00000011863 [*Anopheles gambiae* str. PEST] |
| 187 | EAT48670 | 108884445 | acyl-CoA oxidase [*Aedes aegypti*] |
| 188 | BAE47462 | 78483008 | acyl-CoA oxidase [*Arthrobacter ureafaciens*] |
| 189 | ZP_003 . . . | 62426247 | COG1960: Acyl-CoA dehydrogenases [*Brevibacterium linens* BL2] |
| 190 | AAH17053 | 16877606 | ACOX3 protein [*Homo sapiens*] |
| 191 | ZP_011 . . . | 88854811 | acyl-CoA oxidase [*marine actinobacterium* PHSC20C1] |
| 192 | ZP_006 . . . | 71369913 | Acyl-CoA oxidase:Acyl-CoA dehydrogenase, C-terminal:Acyl-CoA dehydrogenase, central region:Acyl-CoA dehydrogenase, N-terminal [*Nocardioides* sp. JS614] |
| 193 | ZP_009 . . . | 84496319 | hypothetical protein JNB_02330 [*Janibacter* sp. HTCC2649] |
| 194 | ZP_004 . . . | 66967405 | Acyl-CoA oxidase:Acyl-CoA dehydrogenase, C-terminal [*Arthrobacter* sp. FB24] |
| 195 | ZP_011 . . . | 88803915 | acyl-coenzyme A oxidase I, putative [*Robiginitalea biformata* HTCC2501] |
| 196 | CAA68661 | 2674 | 44 kD translation product [*Candida tropicalis*] |

TABLE 39

| Examples of pox5 polypeptides. | | | |
|---|---|---|---|
| Row | ACCESSION | GI | PROTEIN DESCRIPTION |
| 1 | XP_502199 | 50549457 | YlPOX5 [*Yarrowia lipolytica*]. |
| 2 | O74936 | 59799074 | Acyl-coenzyme A oxidase 3 (Acyl-CoA oxidase 3) |
| 3 | O74934 | 59799072 | Acyl-coenzyme A oxidase 1 (Acyl-CoA oxidase 1) |
| 4 | XP_504703 | 50554589 | YlPOX1 [*Yarrowia lipolytica*] |
| 5 | O74935 | 59799073 | Acyl-coenzyme A oxidase 2 (Acyl-CoA oxidase 2) |
| 6 | XP_504475 | 50554133 | YlPOX4 [*Yarrowia lipolytica*] |
| 7 | XP_503632 | 50552444 | hypothetical protein [*Yarrowia lipolytica*] |
| 8 | XP_760471 | 71020481 | hypothetical protein UM04324.1 [*Ustilago maydis* 521] |
| 9 | XP_571768 | 58269224 | Acyl-coenzyme A oxidase I [*Cryptococcus neoformans* var. *neoformans* JEC21] |
| 10 | BAA83482 | 5763520 | acyl-CoA oxidase [*Candida tropicalis*] |
| 11 | BAA83483 | 5763522 | acyl-CoA oxidase [*Candida tropicalis*] |
| 12 | OXCKPM | 66060 | acyl-CoA oxidase (EC 1.3.3.6) PXP4, peroxisomal - yeast (*Candida maltosa*) |
| 13 | P08790 | 17373073 | Acyl-coenzyme A oxidase 5 (Acyl-CoA oxidase 5) (PXP-5) |
| 14 | AAA34362 | 170912 | acyl-coenzyme A oxidase II precursor |
| 15 | OXCKX5 | 66061 | acyl-CoA oxidase (EC 1.3.3.6) POX5, peroxisomal - yeast (*Candida tropicalis*) |
| 16 | XP_717995 | 68475844 | putative fatty-acyl coenzyme A oxidase [*Candida albicans* SC5314] |
| 17 | Q9Y7B1 | 60391213 | Acyl-coenzyme A oxidase (Acyl-CoA oxidase) |
| 18 | XP_721610 | 68468582 | putative fatty-acyl coenzyme A oxidase [*Candida albicans* SC5314] |
| 19 | AAA34361 | 170910 | PXP-2 protein |
| 20 | XP_721613 | 68468588 | putative fatty-acyl coenzyme A oxidase [*Candida albicans* SC5314] |
| 21 | P06598 | 17373023 | Acyl-coenzyme A oxidase 4 (Acyl-CoA oxidase 4) (PXP-4) (Peroxisomal fatty acyl-CoA oxidase) |
| 22 | Q6BRD5 | 59799027 | Acyl-coenzyme A oxidase (Acyl-CoA oxidase) |
| 23 | 1306283A | 225549 | oxidase, fatty acyl |
| 24 | XP_457726 | 50417804 | hypothetical protein DEHA0C01155g [*Debaryomyces hansenii* CBS767] |
| 25 | XP_459232 | 50421365 | hypothetical protein DEHA0D18667g [*Debaryomyces hansenii* CBS767] |
| 26 | Q00468 | 2498206 | Acyl-coenzyme A oxidase 2 (Acyl-CoA oxidase 2) (AOX 2) |
| 27 | Q756A9 | 60391210 | Acyl-coenzyme A oxidase (Acyl-CoA oxidase) |
| 28 | Q6FY63 | 59799032 | Acyl-coenzyme A oxidase (Acyl-CoA oxidase) |
| 29 | NP_011310 | 6321233 | Fatty-acyl coenzyme A oxidase, involved in the fatty acid beta-oxidation pathway; localized to the peroxisomal matrix; Pox1p [*Saccharomyces cerevisiae*] |

TABLE 39-continued

Examples of pox5 polypeptides.

| Row | ACCESSION | GI | PROTEIN DESCRIPTION |
|---|---|---|---|
| 30 | AAA34891 | 172217 | acyl-coenzyme A oxidase |
| 31 | Q6CKK7 | 59799028 | Acyl-coenzyme A oxidase (Acyl-CoA oxidase) |
| 32 | 1W07B | 58177067 | Chain B, *Arabidopsis Thaliana* Acyl-Coa Oxidase 1 |
| 33 | O65202 | 62286589 | Acyl-coenzyme A oxidase 1, peroxisomal (AOX 1) (Long-chain acyl-CoA oxidase) (AtCX1) |
| 34 | CAA68660 | 2673 | acyl-coenzyme A oxidase [*Candida tropicalis*] |
| 35 | NP_567513 | 18414744 | ACX1 (ACYL-COA OXIDASE 1) [*Arabidopsis thaliana*] |
| 36 | H71434 | 7488059 | probable apetala2 domain TINY - *Arabidopsis thaliana* |
| 37 | AAL01888 | 15553480 | acyl-CoA oxidase [*Glycine max*] |
| 38 | AAL01887 | 15553478 | acyl-CoA oxidase [*Glycine max*] |
| 39 | ABE83706 | 92875906 | acyl-CoA oxidase [*Medicago truncatula*] |
| 40 | BAF18456 | 113594582 | Os06g0103500 [*Oryza sativa* (*japonica* cultivar-group)] |
| 41 | 2FONC | 109157678 | Chain C, X-Ray Crystal Structure Of Leacx1, An Acyl-Coa Oxidase From *Lycopersicon Esculentum* (Tomato) |
| 42 | AAW78689 | 58531948 | peroxisomal acyl-CoA oxidase 1A [*Lycopersicon esculentum*] |
| 43 | AAW78691 | 58531952 | peroxisomal acyl-CoA oxidase 1A [*Lycopersicon cheesmaniae*] |
| 44 | Q9ZQP2 | 62286640 | Putative acyl-coenzyme A oxidase 1.2, peroxisomal |
| 45 | NP_001 . . . | 54400372 | hypothetical protein LOC449662 [*Danio rerio*] |
| 46 | XP_592892 | 76648807 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 1 [*Bos taurus*] |
| 47 | XP_879996 | 76648809 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 6 [*Bos taurus*] |
| 48 | AAH68891 | 46250227 | MGC83074 protein [*Xenopus laevis*] |
| 49 | AAH97101 | 67678187 | Zgc: 92584 protein [*Danio rerio*] |
| 50 | XP_414406 | 50754485 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Gallus gallus*] |
| 51 | NP_001 . . . | 55741614 | acyl-Coenzyme A oxidase 1, palmitoyl [*Gallus gallus*] |
| 52 | XP_320717 | 58394415 | ENSANGP00000020118 [*Anopheles gambiae* str. PEST ] |
| 53 | NP_510603 | 17568313 | F59F4.1 [*Caenorhabditis elegans*] |
| 54 | BAE25794 | 74188249 | unnamed protein product [*Mus musculus*] |
| 55 | CAE69737 | 39596101 | Hypothetical protein CBG16008 [*Caenorhabditis briggsae*] |
| 56 | AAH21339 | 18204156 | Acox2 protein [*Mus musculus*] |
| 57 | CAJ83302 | 89271321 | acyl-Coenzyme A oxidase 2, branched chain [*Xenopus tropicalis*] |
| 58 | XP_320718 | 58394417 | ENSANGP00000020032 [*Anopheles gambiae* str. PEST] |
| 59 | Q9QXD1 | 17367045 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 60 | AAH63727 | 39795632 | MGC68531 protein [*Xenopus laevis*] |
| 61 | Q5RC19 | 62286600 | Acyl-coenzyme A oxidase 1, peroxisomal (Palmitoyl-CoA oxidase) (AOX) |
| 62 | AAW78690 | 58531950 | peroxisomal acyl-CoA oxidase 1B [*Lycopersicon esculentum*] |
| 63 | XP_782824 | 72015136 | PREDICTED: similar to Acyl-coenzyme A oxidase 1, peroxisomal (Palmitoyl-CoA oxidase) (AOX) [*Strongylocentrotus purpuratus*] |
| 64 | AAH47700 | 28839704 | Acyl-Coenzyme A oxidase 2, branched chain [*Homo sapiens*] |
| 65 | EAT39640 | 108875415 | acyl-CoA oxidase [*Aedes aegypti*] |
| 66 | NP_001 . . . | 62751552 | MGC108278 protein [*Xenopus tropicalis*] |
| 67 | CAH90691 | 55727877 | hypothetical protein [*Pongo pygmaeus*] |
| 68 | XP_001 . . . | 109118312 | PREDICTED: similar to acyl-Coenzyme A oxidase isoform b [*Macaca mulatta*] |
| 69 | Q15067 | 17380467 | Acyl-coenzyme A oxidase 1, peroxisomal (Palmitoyl-CoA oxidase) (AOX) (Straight-chain acyl-CoA oxidase) (SCOX) |
| 70 | NP_009223 | 30089974 | acyl-Coenzyme A oxidase isoform b [*Homo sapiens*] |
| 71 | AAA19113 | 458119 | acyl-CoA oxidase |
| 72 | AAB30019 | 7689914 | peroxisomal acyl-coenzyme A oxidase [*Homo sapiens*] |
| 73 | XP_785210 | 72015040 | PREDICTED: similar to Acyl-coenzyme A oxidase 1, peroxisomal (Palmitoyl-CoA oxidase) (AOX) [*Strongylocentrotus purpuratus*] |
| 74 | O02767 | 17366131 | Acyl-coenzyme A oxidase 2, peroxisomal (3-alpha,7-alpha,12-alpha-trihydroxy-5-beta-cholestanoyl-CoA 24-hydroxylase) (3-alpha,7-alpha,12-alpha-trihydroxy-5-beta-cholestanoyl-CoA oxidase) (Trihydroxycoprostanoyl-CoA oxidase) (THCCox) (THCA-CoA oxidase) |
| 75 | NP_004026 | 30089972 | acyl-Coenzyme A oxidase isoform a [*Homo sapiens*] |
| 76 | AAA18595 | 495475 | peroxisomal fatty acyl-coA oxidase |
| 77 | I38095 | 2117541 | acyl-CoA oxidase (EC 1.3.3.6), peroxisomal - human |
| 78 | AAH08767 | 14250616 | Acyl-Coenzyme A oxidase 1, palmitoyl [*Homo sapiens*] |

TABLE 39-continued

Examples of pox5 polypeptides.

| Row | ACCESSION | GI | PROTEIN DESCRIPTION |
|---|---|---|---|
| 79 | B54942 | 1082171 | acyl-CoA oxidase (EC 1.3.3.6), peroxisomal splice form II - human |
| 80 | NP_001 . . . | 78369480 | acyl-Coenzyme A oxidase 1, palmitoyl [*Bos taurus*] |
| 81 | NP_499119 | 17552648 | C48B4.1 [*Caenorhabditis elegans*] |
| 82 | NP_665713 | 21955130 | acyl-Coenzyme A oxidase 2, branched chain [*Rattus norvegicus*] |
| 83 | CAD97622 | 31873262 | hypothetical protein [*Homo sapiens*] |
| 84 | BAA86870 | 6429156 | peroxisomal acyl-CoA oxidase [*Mus musculus*] |
| 85 | NP_056544 | 66793429 | acyl-Coenzyme A oxidase 1, palmitoyl [*Mus musculus*] |
| 86 | AAH85743 | 55249685 | Acyl-Coenzyme A oxidase 1, palmitoyl [*Rattus norvegicus*] |
| 87 | 2DDHA | 93279231 | Chain A, Crystal Structure Of Acyl-Coa Oxidase Complexed With 3-Oh-Dodecanoate |
| 88 | Q9R0H0 | 51338830 | Acyl-coenzyme A oxidase 1, peroxisomal (Palmitoyl-CoA oxidase) (AOX) |
| 89 | XP_758355 | 71010163 | hypothetical protein UM02208.1 [*Ustilago maydis* 521] |
| 90 | AAH10425 | 14714578 | Acyl-Coenzyme A oxidase 1, palmitoyl [*Homo sapiens*] |
| 91 | AAB62926 | 2253380 | peroxisomal acyl-CoA oxidase [*Mus musculus*] |
| 92 | CAE65171 | 39590798 | Hypothetical protein CBG10043 [*Caenorhabditis briggsae*] |
| 93 | XP_625136 | 66556360 | PREDICTED: similar to CG5009-PA, partial [*Apis mellifera*] |
| 94 | XP_540441 | 73965013 | PREDICTED: similar to acyl-Coenzyme A oxidase isoform a [*Canis familiaris*] |
| 95 | Q8HYL8 | 34098564 | Acyl-coenzyme A oxidase 1, peroxisomal (Palmitoyl-CoA oxidase) (AOX) |
| 96 | CAE63476 | 39592399 | Hypothetical protein CBG07943 [*Caenorhabditis briggsae*] |
| 97 | AAI08648 | 83318302 | Unknown (protein for MGC: 131363) [*Xenopus laevis*] |
| 98 | XP_879827 | 76648805 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) isoform 5 [*Bos taurus*] |
| 99 | AAF73843 | 8163758 | acyl-CoA oxidase ACX3 [*Arabidopsis thaliana*] |
| 100 | Q9LLH9 | 62286634 | Acyl-coenzyme A oxidase 3, peroxisomal precursor (AOX 3) (Medium-chain acyl-CoA oxidase) (AtCX3) |
| 101 | XP_973660 | 91082769 | PREDICTED: similar to CG5009-PA [*Tribolium castaneum*] |
| 102 | EAS31618 | 90301987 | hypothetical protein CIMG_07097 [*Coccidioides immitis* RS] |
| 103 | EAR95568 | 89297580 | Acyl-CoA oxidase family protein [*Tetrahymena thermophila* SB210] |
| 104 | Q9Z1N0 | 17367267 | Acyl-coenzyme A oxidase 1, peroxisomal (Palmitoyl-CoA oxidase) (AOX) |
| 105 | AAO15577 | 27462768 | acyl-CoA oxidase type 2 [*Phascolarctos cinereus*] |
| 106 | XP_541826 | 73985284 | PREDICTED: similar to Acyl-coenzyme A oxidase 2, peroxisomal (Branched-chain acyl-CoA oxidase) (BRCACox) (Trihydroxycoprostanoyl-CoA oxidase) (THCCox) (THCA-CoA oxidase) [*Canis familiaris*] |
| 107 | CAE63479 | 39592402 | Hypothetical protein CBG07946 [*Caenorhabditis briggsae*] |
| 108 | XP_511690 | 55645995 | PREDICTED: similar to hypothetical protein [*Pan troglodytes*] |
| 109 | BAC26167 | 26324826 | unnamed protein product [*Mus musculus*] |
| 110 | CAE63477 | 39592400 | Hypothetical protein CBG07944 [*Caenorhabditis briggsae*] |
| 111 | NP_493264 | 17506535 | F08A8.4 [*Caenorhabditis elegans*] |
| 112 | Q9LMI7 | 62286635 | Putative acyl-coenzyme A oxidase 3.2, peroxisomal precursor |
| 113 | CAJ58493 | 85539740 | Hypothetical protein F08A8.1c [*Caenorhabditis elegans*] |
| 114 | NP_001 . . . | 71983355 | F08A8.1b [*Caenorhabditis elegans*] |
| 115 | NP_001 . . . | 71983346 | F08A8.1a [*Caenorhabditis elegans*] |
| 116 | BAF19505 | 113595631 | Os06g0354500 [*Oryza sativa* (*japonica* cultivar-group)] |
| 117 | NP_493263 | 17506533 | F08A8.3 [*Caenorhabditis elegans*] |
| 118 | O64894 | 62286587 | Acyl-coenzyme A oxidase, peroxisomal precursor (AOX) (Long-chain acyl-CoA oxidase) |
| 119 | NP_493262 | 17506531 | F08A8.2 [*Caenorhabditis elegans*] |
| 120 | CAE63480 | 39592403 | Hypothetical protein CBG07947 [*Caenorhabditis briggsae*] |
| 121 | AAF14635 | 6503198 | acyl-CoA oxidase [*Petroselinum crispum*] |
| 122 | BAE55537 | 83765394 | unnamed protein product [*Aspergillus oryzae*] |
| 123 | NP_998312 | 47085909 | pristanoyl acyl-Coenzyme A oxidase 3 [*Danio rerio*] |
| 124 | O65201 | 62286588 | Acyl-coenzyme A oxidase 2, peroxisomal precursor (AOX 2) (Long-chain acyl-CoA oxidase) (AtCX2) |
| 125 | AAC13497 | 3044212 | acyl-CoA oxidase [*Arabidopsis thaliana*] |
| 126 | EAT87650 | 111066530 | hypothetical protein SNOG_05259 [*Phaeosphaeria nodorum* SN15] |
| 127 | XP_587157 | 76620513 | PREDICTED: similar to Acyl-coenzyme A oxidase 3, peroxisomal (Pristanoyl-CoA oxidase) [*Bos taurus*] |
| 128 | EAT48205 | 108883980 | acyl-CoA oxidase [*Aedes aegypti*] |
| 129 | EAT87454 | 111066334 | hypothetical protein SNOG_05063 [*Phaeosphaeria nodorum* SN15] |
| 130 | XP_664356 | 67541164 | hypothetical protein AN6752.2 [*Aspergillus nidulans* FGSC A4] |
| 131 | AAB67883 | 1575556 | acyl-CoA oxidase homolog [*Phalaenopsis* sp. 'True Lady'] |
| 132 | AAR00586 | 37699750 | acyl-CoA oxidase [*Phalaenopsis* cv. 'True Lady'] |
| 133 | CAH91864 | 55730283 | hypothetical protein [*Pongo pygmaeus*] |
| 134 | XP_636605 | 66805767 | hypothetical protein DDBDRAFT_0188084 [*Dictyostelium discoideum* AX4] |

TABLE 39-continued

Examples of pox5 polypeptides.

| Row | ACCESSION | GI | PROTEIN DESCRIPTION |
|---|---|---|---|
| 135 | NP_611264 | 24654595 | CG5009-PA [*Drosophila melanogaster*] |
| 136 | EAS04704 | 89306716 | Acyl-CoA oxidase family protein [*Tetrahymena thermophila* SB210] |
| 137 | XP_635946 | 66804335 | hypothetical protein DDBDRAFT_0188674 [*Dictyostelium discoideum* AX4] |
| 138 | O15254 | 17366151 | Acyl-coenzyme A oxidase 3, peroxisomal (Pristanoyl-CoA oxidase) (Branched-chain acyl-CoA oxidase) (BRCACox) |
| 139 | AAL39944 | 17862934 | SD03592p [*Drosophila melanogaster*] |
| 140 | NP_523802 | 17647123 | acyl-Coenzyme A oxidase at 57D proximal CG9707-PA [*Drosophila melanogaster*] |
| 141 | AAL28144 | 16767852 | GH01266p [*Drosophila melanogaster*] |
| 142 | XP_382463 | 46110811 | hypothetical protein FG02287.1 [*Gibberella zeae* PH-1] |
| 143 | EAL26359 | 54636956 | GA18591-PA [*Drosophila pseudoobscura*] |
| 144 | CAA04688 | 2370232 | putative acyl-CoA oxidase [*Hordeum vulgare* subsp. *vulgare*] |
| 145 | XP_783450 | 72111190 | PREDICTED: similar to acyl-Coenzyme A oxidase 1, palmitoyl [*Strongylocentrotus purpuratus*] |
| 146 | AAL48010 | 17944231 | LD22081p [*Drosophila melanogaster*] |
| 147 | CAH91120 | 55728762 | hypothetical protein [*Pongo pygmaeus*] |
| 148 | XP_646395 | 66826081 | hypothetical protein DDBDRAFT_0216722 [*Dictyostelium discoideum* AX4] |
| 149 | XP_758113 | 71007469 | hypothetical protein UM01966.1 [*Ustilago maydis* 521] |
| 150 | EAR99631 | 89301643 | Acyl-CoA oxidase family protein [*Tetrahymena thermophila* SB210] |
| 151 | EAR89261 | 89291273 | Acyl-CoA oxidase family protein [*Tetrahymena thermophila* SB210] |
| 152 | XP_637610 | 66807775 | hypothetical protein DDBDRAFT_0187085 [*Dictyostelium discoideum* AX4] |
| 153 | ABA94670 | 108864573 | Acyl-coenzyme A oxidase 2, peroxisomal precursor, putative, expressed [*Oryza sativa* (*japonica* cultivar-group)] |
| 154 | EAL26647 | 54637244 | GA21980-PA [*Drosophila pseudoobscura*] |
| 155 | ZP_012 . . . | 90587482 | Acyl-CoA oxidase-like:Acyl-CoA dehydrogenase-like:Acyl-CoA dehydrogenase, central region [*Flavobacterium johnsoniae* UW101] |
| 156 | BAC35782 | 74197284 | unnamed protein product [*Mus musculus*] |
| 157 | EAS02716 | 89304728 | Acyl-CoA oxidase family protein [*Tetrahymena thermophila* SB210] |
| 158 | YP_634556 | 108758121 | putative acyl-CoA dehydrogenase [*Myxococcus xanthus* DK 1622] |
| 159 | AAH54727 | 68262425 | Acox1 protein [*Mus musculus*] |
| 160 | YP_445820 | 83816544 | acyl-coenzyme A oxidase I, putative [*Salinibacter ruber* DSM 13855] |
| 161 | AAH44725 | 28703869 | Acox3 protein [*Mus musculus*] |
| 162 | NP_109646 | 34328334 | acyl-Coenzyme A oxidase 3, pristanoyl [*Mus musculus*] |
| 163 | XP_545908 | 73951751 | PREDICTED: similar to Acyl-coenzyme A oxidase 3, peroxisomal (Pristanoyl-CoA oxidase) [*Canis familiaris*] |
| 164 | NP_001 . . . | 79332306 | ACX2 (ACYL-COA OXIDASE 2); acyl-CoA oxidase [*Arabidopsis thaliana*] |
| 165 | EAR98581 | 89300593 | Acyl-CoA oxidase family protein [*Tetrahymena thermophila* SB210] |
| 166 | XP_969513 | 91093755 | PREDICTED: similar to pristanoyl acyl-Coenzyme A oxidase 3 [*Tribolium castaneum*] |
| 167 | ZP_012 . . . | 89890388 | acyl-CoA oxidase [*Flavobacteria bacterium* BBFL7] |
| 168 | YP_290295 | 72162638 | hypothetical protein Tfu_2239 [*Thermobifida fusca* YX] |
| 169 | BAC26136 | 26324764 | unnamed protein product [*Mus musculus*] |
| 170 | BAE42553 | 74143079 | unnamed protein product [*Mus musculus*] |
| 171 | EAL26648 | 54637245 | GA21981-PA [*Drosophila pseudoobscura*] |
| 172 | NP_445791 | 16758056 | acyl-Coenzyme A oxidase 3, pristanoyl [*Rattus norvegicus*] |
| 173 | Q9EPL9 | 17366740 | Acyl-coenzyme A oxidase 3, peroxisomal (Pristanoyl-CoA oxidase) (Branched-chain acyl-CoA oxidase) (BRCACox) |
| 174 | XP_786025 | 72005645 | PREDICTED: similar to pristanoyl acyl-Coenzyme A oxidase 3 [*Strongylocentrotus purpuratus*] |
| 175 | XP_786081 | 72005647 | PREDICTED: similar to pristanoyl acyl-Coenzyme A oxidase 3 [*Strongylocentrotus purpuratus*] |
| 176 | EAL32329 | 54643586 | GA18278-PA [*Drosophila pseudoobscura*] |
| 177 | NP_724181 | 24585195 | CG17544-PC, isoform C [*Drosophila melanogaster*] |
| 178 | AAL14003 | 16186117 | SD05719p [*Drosophila melanogaster*] |
| 179 | CAA68661 | 2674 | 44 kD translation product [*Candida tropicalis*] |
| 180 | NP_572371 | 24640268 | CG4586-PA [*Drosophila melanogaster*] |
| 181 | ZP_011 . . . | 88854811 | acyl-CoA oxidase [*marine actinobacterium* PHSC20C1] |
| 182 | EAL33335 | 54644594 | GA14550-PA [*Drosophila pseudoobscura*] |
| 183 | EAS36523 | 90306892 | hypothetical protein CIMG_01877 [*Coccidioides immitis* RS] |
| 184 | EAT48670 | 108884445 | acyl-CoA oxidase [*Aedes aegypti*] |
| 185 | YP_702012 | 111019040 | acyl-CoA oxidase [*Rhodococcus* sp. RHA1] |
| 186 | ZP_003 . . . | 62426247 | COG1960: Acyl-CoA dehydrogenases [*Brevibacterium linens* BL2] |

TABLE 39-continued

Examples of pox5 polypeptides.

| Row | ACCESSION | GI | PROTEIN DESCRIPTION |
|---|---|---|---|
| 187 | XP_317446 | 58390030 | ENSANGP00000011863 [*Anopheles gambiae* str. PEST] |
| 188 | XP_317513 | 58390136 | ENSANGP00000010039 [*Anopheles gambiae* str. PEST] |
| 189 | AAH17053 | 16877606 | ACOX3 protein [*Homo sapiens*] |
| 190 | ZP_012 . . . | 90205075 | Acyl-CoA oxidase-like:Acyl-CoA dehydrogenase-like:Acyl-CoA dehydrogenase, central region [*Mycobacterium vanbaalenii* PYR-1] |
| 191 | ZP_011 . . . | 88803915 | acyl-coenzyme A oxidase I, putative [*Robiginitalea biformata* HTCC2501] |
| 192 | XP_642669 | 66817952 | hypothetical protein DDBDRAFT_0169270 [*Dictyostelium discoideum* AX4] |
| 193 | NP_508036 | 17560134 | F25C8.1 [*Caenorhabditis elegans*] |
| 194 | ZP_006 . . . | 71369913 | Acyl-CoA oxidase:Acyl-CoA dehydrogenase, C-terminal:Acyl-CoA dehydrogenase, central region:Acyl-CoA dehydrogenase, N-terminal [*Nocardioides* sp. JS614] |
| 195 | BAE65934 | 83775815 | unnamed protein product [*Aspergillus oryzae*] |
| 196 | ZP_012 . . . | 92908524 | Acyl-CoA oxidase-like:Acyl-CoA dehydrogenase-like:Acyl-CoA dehydrogenase, central region [*Mycobacterium* sp. JLS] |

TABLE 40

Examples of triglyceride lipase (tgl4) polypeptides.

| Row | ACCESSION | GI | PROTEIN DESCRIPTION |
|---|---|---|---|
| 1 | XP_505230 | 50555644 | hypothetical protein [*Yarrowia lipolytica*]. |
| 2 | XP_459553 | 50421985 | hypothetical protein DEHA0E06127g [*Debaryomyces hansenii* CBS767] |
| 3 | XP_387731 | 46126355 | hypothetical protein FG07555.1 [*Gibberella zeae* H-1 ] |
| 4 | XP_717704 | 68476486 | putative patatin-like phospholipase [*Candida albicans* SC5314] |
| 5 | XP_958750 | 85091127 | hypothetical protein [*Neurospora crassa* OR74A] |
| 6 | NP_013015 | 6322942 | Triacylglycerol lipase involved in triacylglycerol mobilization and degradation; found in lipid particles; potential Cdc28p substrate; Tgl4p [*Saccharomyces cerevisiae*] |
| 7 | XP_659317 | 67522513 | hypothetical protein AN1713.2 [*Aspergillus nidulans* FGSC A4] |
| 8 | NP_984327 | 45188104 | ADR231Cp [*Eremothecium gossypii*] |
| 9 | CAD60564 | 27764284 | unnamed protein product [*Podospora anserina*] |
| 10 | EAT92134 | 111071014 | hypothetical protein SNOG_00639 [*Phaeosphaeria nodorum* SN15] |
| 11 | BAE59228 | 83769091 | unnamed protein product [*Aspergillus oryzae*] |
| 12 | XP_446465 | 50288073 | unnamed protein product [*Candida glabrata*] |
| 13 | XP_751982 | 70994310 | patatin-like serine hydrolase [*Aspergillus fumigatus* Af293] |
| 14 | XP_451336 | 50302799 | unnamed protein product [*Kluyveromyces lactis*] |
| 15 | EAS30095 | 90300464 | hypothetical protein CIMG_08841 [*Coccidioides immitis* RS] |
| 16 | EAQ83092 | 88175624 | hypothetical protein CHGG_10910 [*Chaetomium globosum* CBS 148.51] |
| 17 | NP_014724 | 6324655 | Triacylglycerol lipase involved in TAG mobilization; localizes to lipid particles; potential Cdc28p substrate; Tgl5p [*Saccharomyces cerevisiae*] |
| 18 | XP_448470 | 50292075 | unnamed protein product [*Candida glabrata*] |
| 19 | ABG79933 | 110628937 | triacylglycerol lipase [*Magnaporthe grisea*] |
| 20 | NP_593197 | 19114109 | hypothetical protein SPAC1A6.05c [*Schizosaccharomyces pombe* 972h- ] |
| 21 | EAR86065 | 89288077 | Patatin-like phospholipase family protein [*Tetrahymena thermophila* SB210] |
| 22 | XP_463448 | 50902030 | P0512C01.22 [*Oryza sativa* (*japonica* cultivar-group)] |
| 23 | BAF06239 | 113533856 | Os01g0762000 [*Oryza sativa* (*japonica* cultivar-group)] |
| 24 | YP_433865 | 83645430 | predicted esterase of the alpha-beta hydrolase superfamily [*Hahella chejuensis* KCTC 2396] |
| 25 | ZP_008 . . . | 77951643 | conserved hypothetical protein [*Marinobacter aquaeolei* VT8] |
| 26 | AAM97135 | 22531263 | putative protein [*Arabidopsis thaliana*] |
| 27 | BAF13581 | 113550138 | Os03g0810900 [*Oryza sativa* (*japonica* cultivar-group)] |
| 28 | ABE78088 | 92867978 | phospholipase, patatin family, putative [*Medicago truncatula*] |
| 29 | YP_693301 | 110834442 | hypothetical protein ABO_1581 [*Alcanivorax borkumensis* SK2] |
| 30 | NP_974449 | 42572707 | unknown protein [*Arabidopsis thaliana*] |
| 31 | BAE56507 | 83766364 | unnamed protein product [*Aspergillus oryzae*] |
| 32 | EAR83738 | 89285729 | Patatin-like phospholipase family protein [*Tetrahymena thermophila* SB210 ] |
| 33 | ABE94194 | 92898449 | Patatin [*Medicago truncatula*] |
| 34 | XP_752278 | 70995024 | patatin-like serine hydrolase [*Aspergillus fumigatus* Af293] |
| 35 | YP_046026 | 50084516 | hypothetical protein ACIAD1335 [*Acinetobacter* sp. ADP1] |
| 36 | ZP_011 . . . | 88794068 | predicted esterase of the alpha-beta hydrolase superfamily protein [*Alteromonas macleodii* 'Deep ecotype'] |

TABLE 40-continued

Examples of triglyceride lipase (tgl4) polypeptides.

| Row | ACCESSION | GI | PROTEIN DESCRIPTION |
|---|---|---|---|
| 37 | XP_380696 | 46107274 | hypothetical protein FG00520.1 [*Gibberella zeae* PH-1] |
| 38 | ZP_011 . . . | 88703608 | Patatin-like phospholipase [gamma proteobacterium KT 71] |
| 39 | EAT85718 | 111064598 | hypothetical protein SNOG_07067 [*Phaeosphaeria nodorum* SN15] |
| 40 | ZP_011 . . . | 88707125 | Patatin-like phospholipase [gamma proteobacterium KT 71] |
| 41 | XP_757164 | 71004996 | hypothetical protein UM01017.1 [*Ustilago maydis* 521] |
| 42 | YP_615253 | 103485692 | Patatin [*Sphingopyxis alaskensis* RB2256] |
| 43 | XP_964502 | 85113293 | hypothetical protein [*Neurospora crassa* OR74A] |
| 44 | NP_594022 | 63054585 | hypothetical protein SPAC31G5.20c [*Schizosaccharomyces pombe* 972h-] |
| 45 | XP_502898 | 50550851 | hypothetical protein [*Yarrowia lipolytica*] |
| 46 | XP_722550 | 68466709 | putative patatin-like phospholipase [*Candida albicans* SC5314] |
| 47 | EAS31687 | 90302056 | hypothetical protein CIMG_07166 [*Coccidioides immitis* RS] |
| 48 | BAE57969 | 83767830 | unnamed protein product [*Aspergillus oryzae*] |
| 49 | XP_722412 | 68466994 | putative patatin-like phospholipase [*Candida albicans* SC5314] |
| 50 | EAQ93362 | 88185894 | hypothetical protein CHGG_01597 [*Chaetomium globosum* CBS 148.51] |
| 51 | ZP_010 . . . | 85708568 | hypothetical protein NAP1_04995 [*Erythrobacter* sp. NAP1] |
| 52 | XP_457141 | 50412575 | hypothetical protein DEHA0B04048g [*Debaryomyces hansenii* CBS767] |
| 53 | XP_658012 | 67516253 | hypothetical protein AN0408.2 [*Aspergillus nidulans* FGSC A4] |
| 54 | EAS33873 | 90304242 | hypothetical protein CIMG_04897 [*Coccidioides immitis* RS] |
| 55 | XP_805126 | 71404931 | hypothetical protein [*Trypanosoma cruzi* strain CL Brener] |
| 56 | CAB88226 | 7630152 | conserved hypothetical protein L5213T.05 [*Leishmania major*] |
| 57 | CAJ06433 | 68127889 | hypothetical protein, conserved [*Leishmania major*] |
| 58 | XP_750246 | 70990794 | patatin-like serine hydrolase [*Aspergillus fumigatus* Af293] |
| 59 | ABG79934 | 110628939 | triacylglycerol lipase [*Magnaporthe grisea*] |
| 60 | XP_386821 | 46124535 | hypothetical protein FG06645.1 [*Gibberella zeae* PH-1] |
| 61 | EAT92413 | 111071293 | hypothetical protein SNOG_00918 [*Phaeosphaeria nodorum* SN15] |
| 62 | NP_588315 | 19075815 | hypothetical protein SPCC1450.16c [*Schizosaccharomyces pombe* 972h-] |
| 63 | EAQ90965 | 88183497 | hypothetical protein CHGG_02900 [*Chaetomium globosum* CBS 148.51] |
| 64 | XP_957267 | 85084210 | hypothetical protein [*Neurospora crassa* OR74A] |
| 65 | XP_451445 | 50303015 | unnamed protein product [*Kluyveromyces lactis*] |
| 66 | CAB11704 | 2388971 | SPAC31G5.20c [*Schizosaccharomyces pombe*] |
| 67 | XP_626587 | 66358818 | hypothetical protein cgd2_4050 [*Cryptosporidium parvum* Iowa II] |
| 68 | XP_665308 | 67588018 | hypothetical protein Chro.20432 [*Cryptosporidium hominis* TU502] |
| 69 | XP_449952 | 50295082 | hypothetical protein CAGL0M13981g [*Candida glabrata* CBS138] |
| 70 | XP_722764 | 68466564 | putative lipid particle triacylglycerol lipase fragment [*Candida albicans* SC5314] |
| 71 | NP_986330 | 45200760 | AGL337Cp [*Eremothecium gossypii*] |
| 72 | CAE84405 | 39722369 | Tgl3 protein [*Kluyveromyces delphensis*] |
| 73 | XP_807283 | 71409928 | hypothetical protein [*Trypanosoma cruzi* strain CL Brener] |
| 74 | XP_807016 | 71409330 | hypothetical protein [*Trypanosoma cruzi* strain CL Brener] |
| 75 | XP_502944 | 50550941 | hypothetical protein [*Yarrowia lipolytica*] |
| 76 | NP_014044 | 6323973 | Triacylglycerol lipase of the lipid particle, responsible for all the TAG lipase activity of the lipid particle; contains the consensus sequence motif GXSXG, which is found in lipolytic enzymes; Tgl3p [*Saccharomyces cerevisiae*] |

TABLE 41

Examples of triglyceride lipase (tgl3) polypeptides.

| Row | ACCESSION | GI | PROTEIN DESCRIPTION |
|---|---|---|---|
| 1 | XP_502944 | 50550941 | hypothetical protein [*Yarrowia lipolytica*]. |
| 2 | XP_752278 | 70995024 | patatin-like serine hydrolase [*Aspergillus fumigatus* Af293] |
| 3 | BAE56507 | 83766364 | unnamed protein product [*Aspergillus oryzae*] |
| 4 | EAT85718 | 111064598 | hypothetical protein SNOG_07067 [*Phaeosphaeria nodorum* SN15] |
| 5 | XP_380696 | 46107274 | hypothetical protein FG00520.1 [*Gibberella zeae* PH-1] |
| 6 | XP_964502 | 85113293 | hypothetical protein [*Neurospora crassa* OR74A] |
| 7 | EAQ93362 | 88185894 | hypothetical protein CHGG_01597 [*Chaetomium globosum* CBS 148.51] |
| 8 | XP_722764 | 68466564 | putative lipid particle triacylglycerol lipase fragment [*Candida albicans* SC5314] |

TABLE 41-continued

Examples of triglyceride lipase (tgl3) polypeptides.

| Row | ACCESSION | GI | PROTEIN DESCRIPTION |
|---|---|---|---|
| 9 | NP_986330 | 45200760 | AGL337Cp [*Eremothecium gossypii*] |
| 10 | CAE84405 | 39722369 | Tgl3 protein [*Kluyveromyces delphensis*] |
| 11 | XP_449952 | 50295082 | hypothetical protein CAGL0M13981g [*Candida glabrata* CBS138] |
| 12 | XP_451445 | 50303015 | unnamed protein product [*Kluyveromyces lactis*] |
| 13 | NP_014044 | 6323973 | Triacylglycerol lipase of the lipid particle, responsible for all the TAG lipase activity of the lipid particle; contains the consensus sequence motif GXSXG, which is found in lipolytic enzymes; Tgl3p [*Saccharomyces cerevisiae*] |
| 14 | EAS31687 | 90302056 | hypothetical protein CIMG_07166 [*Coccidioides immitis* RS] |
| 15 | EAT92134 | 111071014 | hypothetical protein SNOG_00639 [*Phaeosphaeria nodorum* SN15] |
| 16 | XP_387731 | 46126355 | hypothetical protein FG07555.1 [*Gibberella zeae* PH-1] |
| 17 | NP_588315 | 19075815 | hypothetical protein SPCC1450.16c [*Schizosaccharomyces pombe* 972h-] |
| 18 | XP_751982 | 70994310 | patatin-like serine hydrolase [*Aspergillus fumigatus* Af293] |
| 19 | XP_958750 | 85091127 | hypothetical protein [*Neurospora crassa* OR74A] |
| 20 | EAQ83092 | 88175624 | hypothetical protein CHGG_10910 [*Chaetomium globosum* CBS 148.51] |
| 21 | BAE59228 | 83769091 | unnamed protein product [*Aspergillus oryzae*] |
| 22 | YP_693301 | 110834442 | hypothetical protein ABO_1581 [*Alcanivorax borkumensis* SK2] |
| 23 | XP_659317 | 67522513 | hypothetical protein AN1713.2 [*Aspergillus nidulans* FGSC A4] |
| 24 | ZP_011 . . . | 88703608 | Patatin-like phospholipase [gamma proteobacterium KT 71] |
| 25 | BAF06239 | 113533856 | Os01g0762000 [*Oryza sativa* (*japonica* cultivar-group)] |
| 26 | XP_463448 | 50902030 | P0512C01.22 [*Oryza sativa* (*japonica* cultivar-group)] |
| 27 | EAS30095 | 90300464 | hypothetical protein CIMG_08841 [*Coccidioides immitis* RS] |
| 28 | YP_433865 | 83645430 | predicted esterase of the alpha-beta hydrolase superfamily [*Hahella chejuensis* KCTC 2396] |
| 29 | XP_459553 | 50421985 | hypothetical protein DEHA0E06127g [*Debaryomyces hansenii* CBS767] |
| 30 | CAD60564 | 27764284 | unnamed protein product [*Podospora anserina*] |
| 31 | ZP_008 . . . | 77951643 | conserved hypothetical protein [*Marinobacter aquaeolei* VT8] |
| 32 | XP_505230 | 50555644 | hypothetical protein [*Yarrowia lipolytica*] |
| 33 | XP_446465 | 50288073 | unnamed protein product [*Candida glabrata*] |
| 34 | AAM97135 | 22531263 | putative protein [*Arabidopsis thaliana*] |
| 35 | BAF13581 | 113550138 | Os03g0810900 [*Oryza sativa* (*japonica* cultivar-group)] |
| 36 | ABG79933 | 110628937 | triacylglycerol lipase [*Magnaporthe grisea*] |
| 37 | XP_717704 | 68476486 | putative patatin-like phospholipase [*Candida albicans* SC5314] |
| 38 | NP_013015 | 6322942 | Triacylglycerol lipase involved in triacylglycerol mobilization and degradation; found in lipid particles; potential Cdc28p substrate; Tgl4p [*Saccharomyces cerevisiae*] |
| 39 | NP_594022 | 63054585 | hypothetical protein SPAC31G5.20c [*Schizosaccharomyces pombe* 972h-] |
| 40 | EAR83738 | 89285729 | Patatin-like phospholipase family protein [*Tetrahymena thermophila* SB210] |
| 41 | NP_984327 | 45188104 | ADR231Cp [*Eremothecium gossypii*] |
| 42 | EAR86065 | 89288077 | Patatin-like phospholipase family protein [*Tetrahymena thermophila* SB210] |
| 43 | NP_014724 | 6324655 | Triacylglycerol lipase involved in TAG mobilization; localizes to lipid particles; potential Cdc28p substrate; Tgl5p [*Saccharomyces cerevisiae*] |
| 44 | YP_046026 | 50084516 | hypothetical protein ACIAD1335 [*Acinetobacter* sp. ADP1] |
| 45 | XP_451336 | 50302799 | unnamed protein product [*Kluyveromyces lactis*] |
| 46 | ZP_011 . . . | 88794068 | predicted esterase of the alpha-beta hydrolase superfamily protein [*Alteromonas macleodii* 'Deep ecotype'] |
| 47 | XP_722550 | 68466709 | putative patatin-like phospholipase [*Candida albicans* SC5314] |
| 48 | XP_722412 | 68466994 | putative patatin-like phospholipase [*Candida albicans* SC5314] |
| 49 | EAS33873 | 90304242 | hypothetical protein CIMG_04897 [*Coccidioides immitis* RS] |
| 50 | ABG79934 | 110628939 | triacylglycerol lipase [*Magnaporthe grisea*] |
| 51 | ZP_011 . . . | 88707125 | Patatin-like phospholipase [gamma proteobacterium KT 71] |
| 52 | NP_593197 | 19114109 | hypothetical protein SPAC1A6.05c [*Schizosaccharomyces pombe* 972h-] |
| 53 | YP_615253 | 103485692 | Patatin [*Sphingopyxis alaskensis* RB2256] |
| 54 | ZP_010 . . . | 85708568 | hypothetical protein NAP1_04995 [*Erythrobacter* sp. NAP1] |
| 55 | XP_658012 | 67516253 | hypothetical protein AN0408.2 [*Aspergillus nidulans* FGSC A4] |
| 56 | XP_448470 | 50292075 | unnamed protein product [*Candida glabrata*] |
| 57 | XP_807283 | 71409928 | hypothetical protein [*Trypanosoma cruzi* strain CL Brener] |
| 58 | XP_386821 | 46124535 | hypothetical protein FG06645.1 [*Gibberella zeae* PH-1] |

TABLE 42

Examples of acyl-coA-cholesterol polypeptides.

| Row | ACCESSION | GI | PROTEIN DESCRIPTION |
|---|---|---|---|
| 1 | XP_505086.1 | 50555355 | hypothetical protein [*Yarrowia lipolytica*]. |
| 2 | XP_449806 | 50294790 | hypothetical protein CAGL0M10571g [*Candida glabrata* CBS138] |
| 3 | AAO32554 | 28564940 | ARE2 [*Saccharomyces kluyveri*] |
| 4 | XP_461395 | 50425599 | hypothetical protein DEHA0F25652g [*Debaryomyces hansenii* CBS767] |
| 5 | P84285 | 56404462 | Sterol O-acyltransferase 2 (Sterol-ester synthase) (ASAT) |
| 6 | XP_714776 | 68482533 | acyl-CoA cholesterol acyltransferase [*Candida albicans* SC5314] |
| 7 | AAO32474 | 28564191 | ARE2 [*Saccharomyces castellii*] |
| 8 | NP_982606 | 45184888 | AAR065Cp [*Eremothecium gossypii*] |
| 9 | NP_014416 | 6324346 | Acyl-CoA:sterol acyltransferase, isozyme of Are1p; endoplasmic reticulum enzyme that contributes the major sterol esterification activity in the presence of oxygen; Are2p [*Saccharomyces cerevisiae*] |
| 10 | AAC49441 | 1389739 | acyl-CoA:sterol acyltransferase |
| 11 | XP_452607 | 50305295 | unnamed protein product [*Kluyveromyces lactis*] |
| 12 | Q876L2 | 34582301 | Sterol O-acyltransferase 2 (Sterol-ester synthase 2) |
| 13 | Q876L3 | 34582302 | Sterol O-acyltransferase 1 (Sterol-ester synthase 1) |
| 14 | AAT92940 | 51013293 | YCR048W [*Saccharomyces cerevisiae*] |
| 15 | XP_445307 | 50285757 | unnamed protein product [*Candida glabrata*] |
| 16 | NP_593707 | 19114619 | hypothetical protein SPAC13G7.05 [*Schizosaccharomyces pombe* 972h-] |
| 17 | XP_370268 | 39977761 | hypothetical protein MG06765.4 [*Magnaporthe grisea 70-15*] |
| 18 | EAQ84619 | 88177151 | hypothetical protein CHGG_08633 [*Chaetomium globosum* CBS 148.51] |
| 19 | XP_961300 | 85102248 | related to acyl-CoA sterol acyltransferase [*MIPS*] [*Neurospora crassa* OR74A] |
| 20 | XP_750354 | 70991010 | sterol o-acyltransferase APE2 [*Aspergillus fumigatus* Af293] |
| 21 | EAT80792 | 111059672 | hypothetical protein SNOG_11748 [*Phaeosphaeria nodorum* SN15] |
| 22 | XP_661812 | 67527926 | hypothetical protein AN4208.2 [*Aspergillus nidulans* FGSC A4] |
| 23 | BAE54934 | 83764790 | unnamed protein product [*Aspergillus oryzae*] |
| 24 | EAT89521 | 111068401 | predicted protein [*Phaeosphaeria nodorum* SN15] |
| 25 | EAQ86094 | 88178626 | hypothetical protein CHGG_07347 [*Chaetomium globosum* CBS 148.51] |
| 26 | NP_588558 | 19076058 | hypothetical protein SPCP1E11.05c [*Schizosaccharomyces pombe* 972h-] |
| 27 | XP_956576 | 85080625 | hypothetical protein [*Neurospora crassa* OR74A] |
| 28 | EAS32815 | 90303184 | hypothetical protein CIMG_03839 [*Coccidioides immitis* RS] |
| 29 | XP_382192 | 46110268 | hypothetical protein FG02016.1 [*Gibberella zeae* PH-1] |
| 30 | XP_761502 | 71022545 | hypothetical protein UM05355.1 [*Ustilago maydis* 521] |
| 31 | EAL20032 | 50257323 | hypothetical protein CNBF3580 [*Cryptococcus neoformans* var. *neoformans* B-3501A] |
| 32 | XP_571260 | 58268208 | sterol O-acyltransferase [*Cryptococcus neoformans* var. *neoformans* JEC21] |
| 33 | EAR83561 | 89285549 | MBOAT family protein [*Tetrahymena thermophila* SB210] |
| 34 | EAS03424 | 89305436 | MBOAT family protein [*Tetrahymena thermophila* SB210] |
| 35 | AAS72375 | 45642961 | acyl-CoA:cholesterol acyltransferase alpha [*Toxoplasma gondii*] |
| 36 | AAS72376 | 45642963 | acyl-CoA:cholesterol acyltransferase beta [*Toxoplasma gondii*] |
| 37 | XP_640280 | 111226542 | hypothetical protein DDBDRAFT_0205259 [*Dictyostelium discoideum* AX4] |
| 38 | XP_645633 | 66824557 | hypothetical protein DDBDRAFT_0202877 [*Dictyostelium discoideum* AX4] |
| 39 | EAS35506 | 90305875 | hypothetical protein CIMG_00860 [*Coccidioides immitis* RS] |
| 40 | XP_386864 | 46124621 | hypothetical protein FG06688.1 [*Gibberella zeae* PH-1] |
| 41 | NP_649816 | 28571583 | CG8112-PA [*Drosophila melanogaster*] |
| 42 | CAE75170 | 39591950 | Hypothetical protein CBG23107 [*Caenorhabditis briggsae*] |
| 43 | NP_033256 | 84619697 | sterol O-acyltransferase 1 [*Mus musculus*] |
| 44 | BAC34925 | 26342537 | unnamed protein product [*Mus musculus*] |
| 45 | XP_359451 | 39939828 | hypothetical protein MG05326.4 [*Magnaporthe grisea* 70-15] |
| 46 | Q61263 | 18202591 | Sterol O-acyltransferase 1 (Cholesterol acyltransferase 1) (Acyl coenzyme A:cholesterol acyltransferase 1) (ACAT-1) |
| 47 | XP_975142 | 91083363 | PREDICTED: similar to CG31991-PA, isoform A [*Tribolium castaneum*] |
| 48 | EAL28962 | 54639560 | GA20833-PA [*Drosophila pseudoobscura*] |
| 49 | XP_957022 | 85082953 | hypothetical protein [*Neurospora crassa* OR74A] |
| 50 | XP_547445 | 73961286 | PREDICTED: similar to Sterol O-acyltransferase 1 (Cholesterol acyltransferase 1) (Acyl coenzyme A:cholesterol acyltransferase 1) (ACAT-1) [*Canis familiaris*] |
| 51 | EAQ89124 | 88181656 | hypothetical protein CHGG_05743 [*Chaetomium globosum* CBS 148.51] |
| 52 | EAT78735 | 111057615 | hypothetical protein SNOG_13711 [*Phaeosphaeria nodorum* SN15] |
| 53 | Q60457 | 18202585 | Sterol O-acyltransferase 1 (Cholesterol acyltransferase 1) (Acyl coenzyme A:cholesterol acyltransferase 1) (ACAT-1) |

TABLE 42-continued

Examples of acyl-coA-cholesterol polypeptides.

| Row | ACCESSION | GI | PROTEIN DESCRIPTION |
|---|---|---|---|
| 54 | XP_624754 | 110762262 | PREDICTED: similar to midway CG31991-PA, isoform A [*Apis mellifera*] |
| 55 | O70536 | 18202126 | Sterol O-acyltransferase 1 (Cholesterol acyltransferase 1) (Acyl coenzyme A:cholesterol acyltransferase 1) (ACAT-1) |
| 56 | XP_728984 | 82915156 | hypothetical protein PY01256 [*Plasmodium yoelii yoelii* str. 17XNL] |
| 57 | NP_505828 | 71997360 | H19N07.4 [*Caenorhabditis elegans*] |
| 58 | NP_001 . . . | 77735363 | hypothetical protein LOC504287 [*Bos taurus*] |
| 59 | 2201440A | 1585676 | acyl-CoA/cholesterol acyltransferase |
| 60 | XP_663763 | 67539978 | hypothetical protein AN6159.2 [*Aspergillus nidulans* FGSC A4] |
| 61 | CAI13574 | 55960156 | sterol O-acyltransferase (acyl-Coenzyme A: cholesterol acyltransferase) 1 [*Homo sapiens*] |
| 62 | XP_514030 | 55588858 | PREDICTED: hypothetical protein XP_514030 [*Pan troglodytes*] |
| 63 | AAL56227 | 18028942 | cholesterol acyltransferase 1 [*Gorilla gorilla*] |
| 64 | AAL56228 | 18028944 | cholesterol acyltransferase 1 [*Pongo pygmaeus*] |
| 65 | AAC37532 | 4878022 | acyl-coenzyme A: cholesterol acyltransferase [*Homo sapiens*] |
| 66 | EAT47694 | 108883469 | sterol o-acyltransferase [*Aedes aegypti*] |
| 67 | XP_390039 | 46136695 | hypothetical protein FG09863.1 [*Gibberella zeae* PH-1] |
| 68 | BAE01048 | 67969393 | unnamed protein product [*Macaca fascicularis*] |
| 69 | O77761 | 18202178 | Sterol O-acyltransferase 1 (Cholesterol acyltransferase 1) (Acyl coenzyme A:cholesterol acyltransferase 1) (ACAT-1) |
| 70 | AAH06263 | 34782946 | DGAT1 protein [*Homo sapiens*] |
| 71 | XP_317656 | 31226099 | ENSANGP00000002281 [*Anopheles gambiae* str. PEST] |
| 72 | XP_320320 | 58393809 | ENSANGP00000016486 [*Anopheles gambiae* str. PEST] |
| 73 | XP_320321 | 58393811 | ENSANGP00000016512 [*Anopheles gambiae* str. PEST] |
| 74 | BAE65302 | 83775179 | unnamed protein product [*Aspergillus oryzae*] |
| 75 | NP_724017 | 24584734 | midway CG31991-PC, isoform C [*Drosophila melanogaster*] |
| 76 | NP_995724 | 45552403 | midway CG31991-PD, isoform D [*Drosophila melanogaster*] |
| 77 | EAL33593 | 54644853 | GA16599-PA [*Drosophila pseudoobscura*] |
| 78 | NP_586145 | 19074639 | STEROL O-ACYLTRANSFERASE [*Encephalitozoon cuniculi* GB-M1] |
| 79 | XP_502557 | 50550169 | hypothetical protein [*Yarrowia lipolytica*] |
| 80 | XP_885914 | 76617939 | PREDICTED: similar to Sterol O-acyltransferase 2 (Cholesterol acyltransferase 2) (Acyl coenzyme A:cholesterol acyltransferase 2) (ACAT-2) isoform 2 [*Bos taurus*] |
| 81 | XP_591251 | 76617937 | PREDICTED: similar to Sterol O-acyltransferase 2 (Cholesterol acyltransferase 2) (Acyl coenzyme A:cholesterol acyltransferase 2) (ACAT-2) isoform 1 [*Bos taurus*] |
| 82 | XP_624691 | 66564061 | PREDICTED: similar to CG8112-PA [*Apis mellifera*] |
| 83 | O75908 | 18202149 | Sterol O-acyltransferase 2 (Cholesterol acyltransferase 2) (Acyl coenzyme A:cholesterol acyltransferase 2) (ACAT-2) |
| 84 | XP_001 . . . | 109096888 | PREDICTED: sterol O-acyltransferase 2 [*Macaca mulatta*] |
| 85 | AAK48829 | 13898623 | acyl coenzyme A: cholesterol acyltransferase-2 [*Homo sapiens*] |
| 86 | AAH77916 | 50416229 | Soat1-prov protein [*Xenopus laevis*] |
| 87 | AAH96091 | 64654094 | Sterol O-acyltransferase 2 [*Homo sapiens*] |
| 88 | EAT38531 | 108874306 | sterol o-acyltransferase [*Aedes aegypti*] |
| 89 | AAH96090 | 64652990 | Sterol O-acyltransferase 2 [*Homo sapiens*] |
| 90 | NP_001 . . . | 50539976 | hypothetical protein LOC436731 [*Danio rerio*] |
| 91 | NP_714950 | 40254723 | sterol O-acyltransferase 2 [*Rattus norvegicus*] |
| 92 | XP_422267 | 50751122 | PREDICTED: similar to Sterol O-acyltransferase 1 (Cholesterol acyltransferase 1) (Acyl coenzyme A:cholesterol acyltransferase 1) (ACAT-1) [*Gallus gallus*] |
| 93 | O88908 | 18202245 | Sterol O-acyltransferase 2 (Cholesterol acyltransferase 2) (Acyl coenzyme A:cholesterol acyltransferase 2) (ACAT-2) |
| 94 | O77759 | 18202176 | Sterol O-acyltransferase 2 (Cholesterol acyltransferase 2) (Acyl coenzyme A:cholesterol acyltransferase 2) (ACAT-2) |
| 95 | NP_666176 | 22122547 | sterol O-acyltransferase 2 [*Mus musculus*] |
| 96 | BAC00846 | 21392392 | AcylCoA:Cholesterol Acyltransferase 2 [*Rattus norvegicus*] |
| 97 | XP_692855 | 68364838 | PREDICTED: similar to Soatl-prov protein [*Danio rerio*] |
| 98 | XP_543637 | 73996435 | PREDICTED: similar to sterol O-acyltransferase 2 [*Canis familiaris*] |
| 99 | CAG11944 | 47225461 | unnamed protein product [*Tetraodon nigroviridis*] |
| 100 | CAF96514 | 47222847 | unnamed protein product [*Tetraodon nigroviridis*] |
| 101 | CAG10815 | 47219451 | unnamed protein product [*Tetraodon nigroviridis*] |
| 102 | EAR94647 | 89296659 | MBOAT family protein [*Tetrahymena thermophila* SB210] |
| 103 | AAP68322 | 31711932 | At2g19450 [*Arabidopsis thaliana*] |
| 104 | EAR94441 | 89296453 | MBOAT family protein [*Tetrahymena thermophila* SB210] |
| 105 | CAG07990 | 47225647 | unnamed protein product [*Tetraodon nigroviridis*] |
| 106 | XP_788209 | 72085563 | PREDICTED: similar to sterol O-acyltransferase 1 [*Strongylocentrotus purpuratus*] |
| 107 | AAO32475 | 28564193 | ARE2 [*Saccharomyces castellii*] |
| 108 | XP_673128 | 68062248 | hypothetical protein PB300300.00.0 [*Plasmodium berghei* strain ANKA] |

TABLE 43

Examples of phospholipid-diacylglycerol polypeptides.

| Row | ACCESSION | GI | PROTEIN DESCRIPTION |
|---|---|---|---|
| 1 | XP_504038 | 50553256 | hypothetical protein [*Yarrowia lipolytica*]. |
| 2 | XP_458897 | 50420721 | hypothetical protein DEHA0D10868g [*Debaryomyces hansenii* CBS767] |
| 3 | XP_718878 | 68473963 | hypothetical protein CaO19_13439 [*Candida albicans* SC5314] |
| 4 | XP_447501 | 50290139 | hypothetical protein CAGL0I05786g [*Candida glabrata* CBS138] |
| 5 | XP_455369 | 50310695 | unnamed protein product [*Kluyveromyces lactis*] |
| 6 | NP_014405 | 6324335 | Acyltransferase that catalyzes diacylglycerol esterification; one of several acyltransferases that contribute to triglyceride synthesis; putative homolog of human lecithin cholesterol acyltransferase; Lro1p [*Saccharomyces cerevisiae*] |
| 7 | NP_985371 | 45198342 | AFL179Cp [*Eremothecium gossypii*] |
| 8 | BAE57684 | 83767545 | unnamed protein product [*Aspergillus oryzae*] |
| 9 | EAS32928 | 90303297 | hypothetical protein CIMG_03952 [*Coccidioides immitis* RS] |
| 10 | EAT89812 | 111068692 | hypothetical protein SNOG_03081 [*Phaeosphaeria nodorum* SN15] |
| 11 | XP_662596 | 67537644 | hypothetical protein AN4992.2 [*Aspergillus nidulans* FGSC A4] |
| 12 | XP_361017 | 39942960 | hypothetical protein MG03560.4 [*Magnaporthe grisea* 70-15] |
| 13 | CAD60714 | 27803011 | unnamed protein product [*Podospora anserina*] |
| 14 | XP_718980 | 68473754 | hypothetical protein CaO19_6018 [*Candida albicans* SC5314] |
| 15 | XP_386551 | 46123995 | hypothetical protein FG06375.1 [*Gibberella zeae* PH-1] |
| 16 | XP_959598 | 85092964 | hypothetical protein [*Neurospora crassa* OR74A] |
| 17 | XP_754624 | 70999814 | phospholipid:diacylglycerol acyltransferase [*Aspergillus fumigatus* Af293] |
| 18 | O94680 | 21362753 | Phospholipid:diacylglycerol acyltransferase (PDAT) (*Pombe* LRO1 homolog 1) |
| 19 | EAQ92213 | 88184745 | hypothetical protein CHGG_00448 [*Chaetomium globosum* CBS 148.51] |
| 20 | XP_756469 | 71003606 | hypothetical protein UM00322.1 [*Ustilago maydis* 521] |
| 21 | EAL18953 | 50256226 | hypothetical protein CNBI2140 [*Cryptococcus neoformans* var. *neoformans* B-3501A] |
| 22 | XP_568014 | 58261208 | phospholipid:diacylglycerol acyltransferase [*Cryptococcus neoformans* var. *neoformans* JEC21] |
| 23 | AAP47635 | 37785695 | lecithine cholesterol acyltransferase-like protein [*Medicago truncatula*] |
| 24 | AAS79590 | 45935132 | putative phosphatidylcholine-sterol acyltransferase [*Ipomoea trifida*] |
| 25 | BAF25212 | 113631531 | Os09g0444200 [*Oryza sativa* (*japonica* cultivar-group)] |
| 26 | AAK96619 | 15450695 | AT5g13640/MSH12_10 [*Arabidopsis thaliana*] |
| 27 | XP_829379 | 74025626 | phospholipid:diacylglycerol acyltransferase-like protein [*Trypanosoma brucei* TREU927] |
| 28 | XP_816552 | 71655997 | phospholipid:diacylglycerol acyltransferase [*Trypanosoma cruzi* strain CL Brener] |
| 29 | AAO17787 | 37724553 | lecithine cholesterol acyltransferase-like protein [*Arabidopsis thaliana*] |
| 30 | XP_821756 | 71660075 | phospholipid:diacylglycerol acyltransferase [*Trypanosoma cruzi* strain CL Brener] |
| 31 | CAD38153 | 27552462 | putative phosphatidylcholine-sterol acetyltransferase [*Physcomitrella patens*] |
| 32 | NP_190069 | 15230521 | phosphatidylcholine-sterol O-acyltransferase [*Arabidopsis thaliana*] |
| 33 | CAD38155 | 27552466 | putative acetyltransferase [*Physcomitrella patens*] |
| 34 | CAJ02843 | 68124573 | phospholipid:diacylglycerol acyltransferase, putative [*Leishmania major*] |

TABLE 44

Examples of malate dehydrogenase polypeptides.

| Row | ACCESSION | GI | PROTEIN DESCRIPTION |
|---|---|---|---|
| 1 | XP_503933.1 | 50553046 | hypothetical protein [*Yarrowia lipolytica*]. |
| 2 | EAT83219 | 111062099 | predicted protein [*Phaeosphaeria nodorum* SN15] |
| 3 | XP_747556 | 70984070 | malate dehydrogenase, NAD-dependent [*Aspergillus fumigatus* Af293] |
| 4 | BAE61776 | 83771646 | unnamed protein product [*Aspergillus oryzae*] |
| 5 | EAQ89010 | 88181542 | malate dehydrogenase, mitochondrial precursor [*Chaetomium globosum* CBS 148.51] |
| 6 | EAS37226 | 90307595 | hypothetical protein CIMG_02580 [*Coccidioides immitis* RS] |
| 7 | XP_572013 | 58269714 | L-malate dehydrogenase [*Cryptococcus neoformans* var. *neoformans* JEC21] |
| 8 | XP_748936 | 70986899 | malate dehydrogenase, NAD-dependent [*Aspergillus fumigatus* Af293] |

TABLE 44-continued

Examples of malate dehydrogenase polypeptides.

| Row | ACCESSION | GI | PROTEIN DESCRIPTION |
|---|---|---|---|
| 9 | BAE55502 | 83765359 | unnamed protein product [*Aspergillus oryzae*] |
| 10 | EAQ88553 | 88181085 | malate dehydrogenase, mitochondrial precursor [*Chaetomium globosum* CBS 148.51] |
| 11 | ABH10641 | 111606553 | malate dehydrogenase [*Coccidioides posadasii*] |
| 12 | XP_321163 | 58395331 | ENSANGP00000020184 [*Anopheles gambiae* str. PEST] |
| 13 | XP_717047 | 68477790 | putative peroxisomal malate dehydrogenase [*Candida albicans* SC5314] |
| 14 | AAY63978 | 67043759 | mitochondrial malate dehydrogenase [*Lysiphlebus testaceipes*] |
| 15 | AAX19496 | 60393102 | mitochondrial malate dehydrogenase 2b [*Xenopus laevis*] |
| 16 | EAT40089 | 108875864 | malate dehydrogenase [*Aedes aegypti*] |
| 17 | AAI06696 | 76780392 | Mdh2a protein [*Xenopus laevis*] |
| 18 | XP_572038 | 58269764 | malate dehydrogenase [*Cryptococcus neoformans* var. *neoformans* JEC21] |
| 19 | XP_392478 | 66513092 | PREDICTED: similar to mitochondrial malate dehydrogenase precursor isoform 1 [*Apis mellifera*] |
| 20 | XP_973533 | 91085015 | PREDICTED: similar to mitochondrial malate dehydrogenase precursor [*Tribolium castaneum*] |
| 21 | CAG12894 | 47224065 | unnamed protein product [*Tetraodon nigroviridis*] |
| 22 | NP_001 . . . | 58332672 | mitochondrial malate dehydrogenase 2 [*Xenopus tropicalis*] |
| 23 | XP_819104 | 71664243 | malate dehydrogenase [*Trypanosoma cruzi* strain CL Brener] |
| 24 | CAJ07715 | 68129178 | malate dehydrogenase [*Leishmania major*] |
| 25 | EAL29124 | 54639722 | GA20754-PA [*Drosophila pseudoobscura*] |
| 26 | XP_708782 | 68367713 | PREDICTED: similar to malate dehydrogenase, mitochondrial isoform 6 [*Danio rerio*] |
| 27 | XP_708779 | 68367700 | PREDICTED: similar to malate dehydrogenase, mitochondrial isoform 3 [*Danio rerio*] |
| 28 | AAW79319 | 58613465 | malate dehydrogenase [*Isochrysis galbana*] |
| 29 | CAI29601 | 56403598 | hypothetical protein [*Pongo pygmaeus*] |
| 30 | XP_460754 | 50424335 | hypothetical protein DEHA0F09911g [*Debaryomyces hansenii* CBS767] |
| 31 | XP_001 . . . | 109066259 | PREDICTED: similar to mitochondrial malate dehydrogenase precursor [*Macaca mulatta*] |
| 32 | AAK69767 | 14583133 | malate dehydrogenase [*Sphyraena idiastes*] |
| 33 | XP_708778 | 68367696 | PREDICTED: similar to malate dehydrogenase, mitochondrial isoform 2 [*Danio rerio*] |
| 34 | NP_001 . . . | 79327392 | PMDH2 [*Arabidopsis thaliana*] |
| 35 | ABE84799 | 92877831 | Malate dehydrogenase, NAD-dependent, eukaryotes and gamma proteobacteria [*Medicago truncatula*] |
| 36 | AAU29200 | 52139820 | glyoxisomal malate dehydrogenase [*Lycopersicon esculentum*] |
| 37 | AAW27425 | 56758570 | SJCHGC06124 protein [*Schistosoma japonicum*] |
| 38 | XP_708781 | 68367709 | PREDICTED: similar to malate dehydrogenase, mitochondrial isoform 5 [*Danio rerio*] |
| 39 | 1SMKH | 60593494 | Chain H, Mature And Translocatable Forms Of Glyoxysomal Malate Dehydrogenase Have Different Activities And Stabilities But Similar Crystal Structures |
| 40 | XP_822509 | 71746908 | mitochondrial malate dehydrogenase [*Trypanosoma brucei* TREU927] |
| 41 | 1SEVB | 60593476 | Chain B, Mature And Translocatable Forms Of Glyoxysomal Malate Dehydrogenase Have Different Activities And Stabilities But Similar Crystal Structures |
| 42 | XP_708780 | 68367705 | PREDICTED: similar to malate dehydrogenase, mitochondrial isoform 4 [*Danio rerio*] |
| 43 | ABD77290 | 89574129 | mitochondrial malate dehydrogenase 2, NAD [*Homo sapiens*] |
| 44 | ABD77284 | 89574117 | mitochondrial malate dehydrogenase 2, NAD [*Rattus norvegicus*] |
| 45 | ABD77283 | 89574115 | mitochondrial malate dehydrogenase 2, NAD [*Mus musculus*] |
| 46 | ABD77287 | 89574123 | mitochondrial malate dehydrogenase 2, NAD [*Oryctolagus cuniculus*] |
| 47 | ABD77280 | 89574109 | mitochondrial malate dehydrogenase 2, NAD [*Loxodonta africana*] |
| 48 | ABD77288 | 89574125 | mitochondrial malate dehydrogenase 2, NAD [*Lepus europaeus*] |
| 49 | XP_792004 | 72025672 | PREDICTED: similar to mitochondrial malate dehydrogenase precursor [*Strongylocentrotus purpuratus*] |
| 50 | ABD77293 | 89574135 | mitochondrial malate dehydrogenase 2, NAD [*Canis familiaris*] |
| 51 | ABD77294 | 89574137 | mitochondrial malate dehydrogenase 2, NAD [*Felis catus*] |
| 52 | ABD77278 | 89574105 | mitochondrial malate dehydrogenase 2, NAD [*Didelphis virginiana*] |
| 53 | XP_809210 | 71414199 | mitochondrial malate dehydrogenase [*Trypanosoma cruzi* strain CL Brener] |
| 54 | ABD77301 | 89574151 | mitochondrial malate dehydrogenase 2, NAD [*Sus scrofa*] |
| 55 | ABD77286 | 89574121 | mitochondrial malate dehydrogenase 2, NAD [*Mesocricetus auratus*] |

TABLE 44-continued

Examples of malate dehydrogenase polypeptides.

| Row | ACCESSION | GI | PROTEIN DESCRIPTION |
|---|---|---|---|
| 56 | ABD77298 | 89574145 | mitochondrial malate dehydrogenase 2, NAD [*Bos taurus*] |
| 57 | AAT35230 | 47531133 | mitochondrial malate dehydrogenase [*Clonorchis sinensis*] |
| 58 | ABD77281 | 89574111 | mitochondrial malate dehydrogenase 2, NAD [*Dasypus novemcinctus*] |
| 59 | ABD77296 | 89574141 | mitochondrial malate dehydrogenase 2, NAD [*Ceratotherium simum*] |
| 60 | ABA99939 | 108863014 | Malate dehydrogenase, glyoxysomal precursor, putative, expressed [*Oryza sativa* (*japonica* cultivar-group)] |
| 61 | AAU29198 | 52139816 | mitochondrial malate dehydrogenase [*Lycopersicon esculentum*] |
| 62 | ABD77279 | 89574107 | mitochondrial malate dehydrogenase 2, NAD [*Sminthopsis douglasi*] |
| 63 | CAJ07717 | 68129180 | malate dehydrogenase, putative [*Leishmania major*] |
| 64 | XP_519160 | 55628772 | PREDICTED: similar to mitochondrial malate dehydrogenase precursor [*Pan troglodytes*] |
| 65 | ABD72702 | 89473780 | putative mitochondrial malate dehydrogenase [*Acyrthosiphon pisum*] |
| 66 | ABD77299 | 89574147 | mitochondrial malate dehydrogenase 2, NAD [*Balaenoptera physalus*] |
| 67 | BAF23792 | 113623847 | Os08g0434300 [*Oryza sativa* (*japonica* cultivar-group)] |
| 68 | CAI11361 | 57337458 | putative malate dehydrogenase [*Orpinomyces* sp. OUS1] |
| 69 | ABD77289 | 89574127 | mitochondrial malate dehydrogenase 2, NAD [*Tadarida brasiliensis*] |
| 70 | BAF06605 | 113534222 | Os01g0829800 [*Oryza sativa* (*japonica* cultivar-group)] |
| 71 | ABD77292 | 89574133 | mitochondrial malate dehydrogenase 2, NAD [*Tupaia glis*] |
| 72 | ABD77285 | 89574119 | mitochondrial malate dehydrogenase 2, NAD [*Cavia porcellus*] |
| 73 | BAF18303 | 113579940 | Os05g0574400 [*Oryza sativa* (*japonica* cultivar-group)] |
| 74 | ZP_010 . . . | 85712491 | malate dehydrogenase [*Idiomarina baltica* OS145] |
| 75 | XP_539718 | 57097207 | PREDICTED: similar to malate dehydrogenase 2, NAD (mitochondrial) [*Canis familiaris*] |
| 76 | ABD77277 | 89574103 | mitochondrial malate dehydrogenase 2, NAD [*Monodelphis domestica*] |
| 77 | Q5R030 | 62286970 | Malate dehydrogenase |
| 78 | YP_660122 | 109896867 | malate dehydrogenase, NAD-dependent [*Pseudoalteromonas atlantica* T6c] |
| 79 | Q87SU7 | 48428249 | Malate dehydrogenase |
| 80 | ABD77291 | 89574131 | mitochondrial malate dehydrogenase 2, NAD [*Aotus trivirgatus*] |
| 81 | ZP_007 . . . | 75854582 | COG0039: Malate/lactate dehydrogenases [*Vibrio* sp. Ex25] |
| 82 | ZP_011 . . . | 88795318 | malate dehydrogenase [*Alteromonas macleodii* 'Deep ecotype'] |
| 83 | ZP_012 . . . | 91228842 | malate dehydrogenase [*Vibrio alginolyticus* 12G01] |
| 84 | ZP_011 . . . | 89075547 | malate dehydrogenase [*Photobacterium* sp. SKA34] |
| 85 | ZP_012 . . . | 90580811 | malate dehydrogenase [*Vibrio angustum* S14] |
| 86 | YP_671200 | 110643470 | malate dehydrogenase [*Escherichia coli* 536] |
| 87 | ABD77295 | 89574139 | mitochondrial malate dehydrogenase 2, NAD [*Equus caballus*] |
| 88 | Q5E875 | 66774139 | Malate dehydrogenase |
| 89 | ZP_007 . . . | 75209673 | COG0039: Malate/lactate dehydrogenases [*Escherichia coli* B171] |
| 90 | ZP_009 . . . | 84394039 | malate dehydrogenase [*Vibrio splendidus* 12B01] |
| 91 | ZP_007 . . . | 75228638 | COG0039: Malate/lactate dehydrogenases [*Escherichia coli* B7A] |
| 92 | ZP_010 . . . | 86147822 | malate dehydrogenase [*Vibrio* sp. MED222] |
| 93 | BAD30064 | 50508045 | malate dehydrogenase [*Moritella* sp. 36B1] |
| 94 | Q4QL89 | 73621201 | Malate dehydrogenase |
| 95 | YP_404893 | 82778544 | malate dehydrogenase [*Shigella dysenteriae* Sd197] |
| 96 | BAD30059 | 50508035 | malate dehydrogenase [*Moritella* sp. 47A1] |
| 97 | BAD30066 | 50508049 | malate dehydrogenase [*Moritella* sp. 36G1] |
| 98 | ZP_008 . . . | 77958772 | COG0039: Malate/lactate dehydrogenases [*Yersinia bercovieri* ATCC 43970] |
| 99 | BAD30071 | 50508059 | malate dehydrogenase [*Moritella* sp. 38F1] |
| 100 | ZP_008 . . . | 77973999 | COG0039: Malate/lactate dehydrogenases [*Yersinia frederiksenii* ATCC 33641] |
| 101 | ZP_008 . . . | 77977600 | COG0039: Malate/lactate dehydrogenases [*Yersinia intermedia* ATCC 29909] |
| 102 | P48364 | 1346511 | Malate dehydrogenase |
| 103 | BAD30062 | 50508041 | malate dehydrogenase [*Moritella* sp. 16H2] |
| 104 | BAD30069 | 50508055 | malate dehydrogenase [*Moritella* ]sp. 56A1] |
| 105 | ZP_008 . . . | 77961850 | COG0039: Malate/lactate dehydrogenases [*Yersinia mollaretii* ATCC 43969] |
| 106 | ZP_012 . . . | 90411956 | putative malate dehydrogenase [*Photobacterium profundum* 3TCK] |
| 107 | Q6AW21 | 57012891 | Malate dehydrogenase |
| 108 | Q57JA9 | 68052390 | Malate dehydrogenase |
| 109 | ZP_012 . . . | 90407531 | malate dehydrogenase [*Psychromonas* sp. CNPT3] |

TABLE 44-continued

Examples of malate dehydrogenase polypeptides.

| Row | ACCESSION | GI | PROTEIN DESCRIPTION |
|---|---|---|---|
| 110 | BAD36746 | 51172588 | malate dehydrogenase [*Moritella yayanosii*] |
| 111 | Q6AW23 | 57012892 | Malate dehydrogenase |
| 112 | ABG22106 | 108863015 | Malate dehydrogenase, glyoxysomal precursor, putative, expressed [*Oryza sativa* (*japonica* cultivar-group)] |
| 113 | ZP_005 . . . | 68546610 | Malate dehydrogenase, NAD-dependent, eukaryotes and gamma proteobacteria [*Shewanella amazonensis* SB2B] |
| 114 | BAD30060 | 50508037 | malate dehydrogenase [*Moritella* sp. 47B1] |
| 115 | EAL31008 | 54642259 | GA10540-PA [*Drosophila pseudoobscura*] |
| 116 | YP_736674 | 114046124 | malate dehydrogenase, NAD-dependent [*Shewanella* sp. MR-7] |
| 117 | CAJ07716 | 68129179 | malate dehydrogenase, putative [*Leishmania major*] |
| 118 | ZP_009 . . . | 82743617 | Malate dehydrogenase, NAD-dependent, eukaryotes and gamma proteobacteria [*Shewanella* sp. W3-18-1] |
| 119 | Q47VL0 | 83288301 | Malate dehydrogenase |
| 120 | ZP_011 . . . | 88859032 | malate dehydrogenase [*Pseudoalteromonas tunicata* D2] |
| 121 | YP_561838 | 91792187 | malate dehydrogenase, NAD-dependent [*Shewanella denitrificans* OS217] |
| 122 | ZP_005 . . . | 68544347 | Malate dehydrogenase, NAD-dependent, eukaryotes and gamma proteobacteria [*Shewanella baltica* OS155] |
| 123 | ZP_007 . . . | 75429373 | malate dehydrogenase [*Actinobacillus succinogenes* 130Z] |
| 124 | AAW29940 | 56788316 | malate dehydrogenase [*Pasteurella trehalosi*] |
| 125 | BAD30063 | 50508043 | malate dehydrogenase [*Shewanella* sp. T4609] |
| 126 | EAL31009 | 54642260 | GA10541-PA [*Drosophila pseudoobscura*] |
| 127 | ZP_006 . . . | 69950735 | Malate dehydrogenase, NAD-dependent, eukaryotes and gamma proteobacteria [*Shewanella frigidimarina NCIMB* 400] |
| 128 | YP_341148 | 77361573 | malate dehydrogenase [*Pseudoalteromonas haloplanktis* TAC125] |
| 129 | ZP_013 . . . | 106882260 | malate dehydrogenase, NAD-dependent [*Psychromonas ingrahamii* 37] |
| 130 | BAD30068 | 50508053 | malate dehydrogenase [*Shewanella* sp. 33H2] |
| 131 | ZP_008 . . . | 78368581 | Malate dehydrogenase, NAD-dependent, eukaryotes and gamma proteobacteria [*Shewanella* sp. PV-4] |
| 132 | XP_851105 | 74004024 | PREDICTED: similar to malate dehydrogenase, mitochondrial [*Canis familiaris*] |
| 133 | ABD77300 | 89574149 | mitochondrial malate dehydrogenase 2, NAD [*Hippopotamus amphibius*] |
| 134 | XP_816948 | 71656813 | glycosomal malate dehydrogenase [*Trypanosoma cruzi* strain CL Brener] |
| 135 | CAJ19596 | 82655060 | malate dehydrogenase [*Klebsiella pneumoniae*] |
| 136 | AAW29939 | 56788314 | malate dehydrogenase [*Mannheimia glucosida*] |
| 137 | CAJ19583 | 82655034 | malate dehydrogenase [*Klebsiella pneumoniae*] |
| 138 | CAJ19589 | 82655046 | malate dehydrogenase [*Klebsiella pneumoniae*] |
| 139 | CAJ19580 | 82655028 | malate dehydrogenase [*Klebsiella pneumoniae*] |
| 140 | CAJ19591 | 82655050 | malate dehydrogenase [*Klebsiella pneumoniae*] |
| 141 | CAJ19595 | 82655058 | malate dehydrogenase [*Klebsiella pneumoniae*] |
| 142 | CAJ19593 | 82655054 | malate dehydrogenase [*Klebsiella pneumoniae*] |
| 143 | AAW29937 | 56788310 | malate dehydrogenase [*Mannheimia haemolytica*] |
| 144 | XP_812467 | 71423452 | glycosomal malate dehydrogenase [*Trypanosoma cruzi* strain CL Brener] |
| 145 | AAW29938 | 56788312 | malate dehydrogenase [*Mannheimia haemolytica*] |
| 146 | AAW29936 | 56788308 | malate dehydrogenase [*Mannheimia haemolytica*] |
| 147 | XP_849858 | 73993436 | PREDICTED: similar to malate dehydrogenase, mitochondrial [*Canis familiaris*] |
| 148 | AAW28048 | 56718658 | malate dehydrogenase [*Vibrio cholerae*] |
| 149 | AAU88998 | 52856248 | malate dehydrogenase [*Shigella flexneri*] |
| 150 | AAW28041 | 56718644 | malate dehydrogenase [*Vibrio cholerae*] |
| 151 | AAW28047 | 56718656 | malate dehydrogenase [*Vibrio mimicus*] |
| 152 | AAW28045 | 56718652 | malate dehydrogenase [*Vibrio mimicus*] |
| 153 | ABD77282 | 89574113 | mitochondrial malate dehydrogenase 2, NAD [*Tamandua tetradactyla*] |
| 154 | AAU89018 | 52856288 | malate dehydrogenase [*Shigella boydii*] |
| 155 | AAU89003 | 52856258 | malate dehydrogenase [*Escherichia coli*] |
| 156 | AAU88960 | 52856172 | malate dehydrogenase [*Escherichia coli*] |
| 157 | AAU88962 | 52856176 | malate dehydrogenase [*Shigella flexneri*] |
| 158 | AAU88996 | 52856244 | malate dehydrogenase [*Escherichia coli*] |
| 159 | AAU88972 | 52856196 | malate dehydrogenase [*Shigella boydii*] |
| 160 | AAU88969 | 52856190 | malate dehydrogenase [*Shigella boydii*] |
| 161 | ZP_007 . . . | 75822170 | COG0039: Malate/lactate dehydrogenases [*Vibrio cholerae* RC385] |
| 162 | AAU89062 | 52856376 | malate dehydrogenase [*Shigella boydii*] |
| 163 | AAU88982 | 52856216 | malate dehydrogenase [*Shigella dysenteriae*] |
| 164 | AAU88995 | 52856242 | malate dehydrogenase [*Escherichia coli*] |
| 165 | AAU88993 | 52856238 | malate dehydrogenase [*Escherichia coli*] |
| 166 | AAU89044 | 52856340 | malate dehydrogenase [*Shigella flexneri*] |
| 167 | AAU89015 | 52856282 | malate dehydrogenase [*Shigella boydii*] |

TABLE 44-continued

Examples of malate dehydrogenase polypeptides.

| Row | ACCESSION | GI | PROTEIN DESCRIPTION |
|---|---|---|---|
| 168 | AAU88971 | 52856194 | malate dehydrogenase [*Shigella sonnei*] |
| 169 | AAW28034 | 56718629 | malate dehydrogenase [*Vibrio cholerae*] |
| 170 | AAU89011 | 52856274 | malate dehydrogenase [*Shigella flexneri*] |
| 171 | AAU88958 | 52856168 | malate dehydrogenase [*Escherichia coli*] |
| 172 | AAU88976 | 52856204 | malate dehydrogenase [*Shigella dysenteriae*] |
| 173 | AAU88991 | 52856234 | malate dehydrogenase [*Escherichia coli*] |
| 174 | XP_850818 | 73988067 | PREDICTED: similar to mitochondrial malate dehydrogenase precursor [*Canis familiaris*] |
| 175 | AAU86550 | 52697626 | malate dehydrogenase [*Shigella boydii*] |
| 176 | AAU88979 | 52856210 | malate dehydrogenase [*Shigella dysenteriae*] |
| 177 | AAU89005 | 52856262 | malate dehydrogenase [*Escherichia coli*] |
| 178 | AAU89019 | 52856290 | malate dehydrogenase [*Shigella dysenteriae*] |
| 179 | AAU88983 | 52856218 | malate dehydrogenase [*Shigella dysenteriae*] |
| 180 | AAU86549 | 52697624 | malate dehydrogenase [*Escherichia albertii*] |
| 181 | AAX85842 | 62532910 | Mdh [*Escherichia coli*] |
| 182 | AAU89007 | 52856266 | malate dehydrogenase [*Shigella flexneri*] |
| 183 | AAU88980 | 52856212 | malate dehydrogenase [*Shigella flexneri*] |
| 184 | AAU89000 | 52856252 | malate dehydrogenase [*Shigella flexneri*] |
| 185 | AAU88968 | 52856188 | malate dehydrogenase [*Shigella boydii*] |
| 186 | AAU88988 | 52856228 | malate dehydrogenase [*Escherichia coli*] |
| 187 | AAX85856 | 62532938 | Mdh [*Escherichia coli*] |
| 188 | AAU86566 | 52697658 | malate dehydrogenase [*Shigella boydii*] |
| 189 | AAU86571 | 52697668 | malate dehydrogenase [*Escherichia albertii*] |
| 190 | ABF20150 | 94468239 | Mdh [*Escherichia coli*] |
| 191 | AAU89051 | 52856354 | malate dehydrogenase [*Shigella boydii*] |
| 192 | AAU89059 | 52856370 | malate dehydrogenase [*Shigella boydii*] |
| 193 | AAU89057 | 52856366 | malate dehydrogenase [*Shigella boydii*] |
| 194 | AAU89036 | 52856324 | malate dehydrogenase [*Shigella flexneri*] |
| 195 | AAU86559 | 52697644 | malate dehydrogenase [*Shigella boydii*] |
| 196 | ABF20151 | 94468241 | Mdh [*Escherichia coli*] |
| 197 | ABF20142 | 94468223 | Mdh [*Escherichia coli*] |
| 198 | AAU88990 | 52856232 | malate dehydrogenase [*Escherichia coli*] |
| 199 | AAU86567 | 52697660 | malate dehydrogenase [*Shigella boydii*] |
| 200 | AAU89032 | 52856316 | malate dehydrogenase [*Shigella dysenteriae*] |
| 201 | AAU89012 | 52856276 | malate dehydrogenase [*Shigella flexneri*] |

TABLE 45

Examples of glucose-6-phosphate dehydrogenase polypeptides.

| Row | ACCESSION | GI | PROTEIN DESCRIPTION |
|---|---|---|---|
| 1 | XP_504275 | 50553728 | hypothetical protein [*Yarrowia lipolytica*] |
| 2 | XP_365081 | 39965237 | hypothetical protein MG09926.4 [*Magnaporthe grisea* 70-15] |
| 3 | XP_381455 | 46108794 | G6PD_ASPNG Glucose-6-phosphate 1-dehydrogenase (G6PD) [*Gibberella zeae* PH-1] |
| 4 | XP_660585 | 67525047 | glucose-6-phosphate 1-dehydrogenase [*Aspergillus nidulans* FGSC A4] |
| 5 | P48826 | 1346070 | Glucose-6-phosphate 1-dehydrogenase (G6PD) |
| 6 | CAA54840 | 1523782 | glucose-6-phosphate 1-dehydrogenase [*Aspergillus niger*] |
| 7 | EAU38380 | 114196680 | glucose-6-phosphate 1-dehydrogenase [*Aspergillus terreus* NIH2624] |
| 8 | EAT83608 | 111062488 | predicted protein [*Phaeosphaeria nodorum* SN15] |
| 9 | EAS28915 | 90299284 | glucose-6-phosphate 1-dehydrogenase [*Coccidioides immitis* RS] |
| 10 | XP_754767 | 71000100 | glucose-6-phosphate 1-dehydrogenase [*Aspergillus fumigatus* Af293] |
| 11 | XP_958320 | 85090234 | GLUCOSE-6-PHOSPHATE 1-DEHYDROGENASE (G6PD) [*Neurospora crassa* OR74A] |
| 12 | EAQ93370 | 88185902 | glucose-6-phosphate 1-dehydrogenase [*Chaetomium globosum* CBS 148.51] |
| 13 | CAA58825 | 642160 | unnamed protein product [*Emericella nidulans*] |
| 14 | XP_458129 | 50419213 | hypothetical protein DEHA0C11286g [*Debaryomyces hansenii* CBS767] |
| 15 | AAB25541 | 299248 | glucose-6-phosphate dehydrogenase [*Pichia jadinii* = yeast, Peptide, 495 aa] |
| 16 | XP_723251 | 68465104 | putative glucose-6-phosphate dehydrogenase [*Candida albicans* SC5314] |
| 17 | XP_723440 | 68464725 | putative glucose-6-phosphate dehydrogenase [*Candida albicans* SC5314] |
| 18 | XP_453944 | 50307901 | G6PD_KLULA [*Kluyveromyces lactis*] |
| 19 | NP_982741 | 45185024 | ABL206Cp [*Eremothecium gossypii*] |
| 20 | XP_448038 | 50291211 | unnamed protein product [*Candida glabrata*] |

TABLE 45-continued

Examples of glucose-6-phosphate dehydrogenase polypeptides.

| Row | ACCESSION | GI | PROTEIN DESCRIPTION |
|---|---|---|---|
| 21 | XP_572045 | 58269778 | glucose-6-phosphate 1-dehydrogenase [*Cryptococcus neoformans* var. *neoformans* JEC21] |
| 22 | NP_014158 | 6324088 | Glucose-6-phosphate dehydrogenase (G6PD), catalyzes the first step of the pentose phosphate pathway; involved in adapting to oxidatve stress; homolog of the human G6PD which is deficient in patients with hemolytic anemia; Zwf1p [*Saccharomyces cerevisiae*] |
| 23 | AAT93017 | 51013447 | YNL241C [*Saccharomyces cerevisiae*] |
| 24 | AAA34619 | 171545 | glucose-6-phosphate dehydrogenase (ZWF1) (EC 1.1.1.49) |
| 25 | XP_761077 | 71021693 | hypothetical protein UM04930.1 [*Ustilago maydis* 521] |
| 26 | NP_593344 | 63054535 | glucose-6-phosphate 1-dehydrogenase [*Schizosaccharomyces pombe* 972h-] |
| 27 | XP_644814 | 66822919 | glucose 6-phosphate-1-dehydrogenase [*Dictyostelium discoideum* AX4] |
| 28 | ABD72519 | 89357348 | glucose 6-phosphate dehydrogenase [*Trypanosoma cruzi*] |
| 29 | BAE99888 | 110735823 | glucose-6-phosphate dehydrogenase [*Arabidopsis thaliana*] |
| 30 | CAB52675 | 5732197 | glucose-6-phosphate 1-dehydrogenase [*Arabidopsis thaliana*] |
| 31 | CAB08746 | 2104434 | SPAC3A12.18 [*Schizosaccharomyces pombe*] |
| 32 | ABD72517 | 89357344 | glucose 6-phosphate dehydrogenase [*Trypanosoma cruzi*] |
| 33 | ABD72518 | 89357346 | glucose 6-phosphate dehydrogenase [*Trypanosoma cruzi*] |
| 34 | BAB96757 | 21262179 | glucose-6-phosphate dehydrogenase 1 [*Chlorella vulgaris*] |
| 35 | XP_822502 | 71746894 | glucose-6-phosphate 1-dehydrogenase [*Trypanosoma brucei* TREU927] |
| 36 | CAJ07708 | 68129171 | glucose-6-phosphate dehydrogenase [*Leishmania major*] |
| 37 | CAC07816 | 10045209 | glucose-6-phosphate 1-dehydrogenase [*Trypanosoma brucei*] |
| 38 | BAF15046 | 113564703 | Os04g0485300 [*Oryza sativa* (*japonica* cultivar-group)] |
| 39 | AAO37825 | 28261397 | glucose-6-phosphate dehydrogenase [*Leishmania mexicana*] |
| 40 | AAM64228 | 27434608 | glucose-6-phosphate dehydrogenase [*Leishmania mexicana amazonensis*] |
| 41 | XP_001 . . . | 110750934 | PREDICTED: similar to Zwischenferment CG12529-PA, isoform A [*Apis mellifera*] |
| 42 | XP_974096 | 91082561 | PREDICTED: similar to CG12529-PA, isoform A [*Tribolium castaneum*] |
| 43 | ABE83959 | 92876243 | Glucose-6-phosphate dehydrogenase [*Medicago truncatula*] |
| 44 | BAE38077 | 74138546 | unnamed protein product [*Mus musculus*] |
| 45 | NP_001 . . . | 79313844 | G6PD5; glucose-6-phosphate 1-dehydrogenase [*Arabidopsis thaliana*] |
| 46 | CAB52674 | 5732195 | glucose-6-phosphate 1-dehydrogenase [*Arabidopsis thaliana*] |
| 47 | AAD11426 | 4206114 | cytoplasmic glucose-6-phosphate 1-dehydrogenase [*Mesembryanthemum crystallinum*] |
| 48 | Q42919 | 3023815 | Glucose-6-phosphate 1-dehydrogenase, cytoplasmic isoform (G6PD) |
| 49 | AAL79959 | 19071787 | glucose-6-phosphate dehydrogenase [*Oryza sativa* (*japonica* cultivar-group)] |
| 50 | CAE62054 | 39593761 | Hypothetical protein CBG06072 [*Caenorhabditis briggsae*] |
| 51 | EAL31619 | 54642875 | GA11679-PA [*Drosophila pseudoobscura*] |
| 52 | Q00612 | 54037161 | Glucose-6-phosphate 1-dehydrogenase X (G6PD) |
| 53 | AAH75663 | 49523350 | Glucose-6-phosphate dehydrogenase X-linked [*Mus musculus*] |
| 54 | AAB69319 | 2352923 | cytosolic glucose-6-phosphate dehydrogenase 2 [*Petroselinum crispum*] |
| 55 | AAM64230 | 27434612 | glucose-6-phosphate dehydrogenase [*Leishmania guyanensis*] |
| 56 | ABB29564 | 78183137 | putative Zwischenferment [*Drosophila yakuba*] |
| 57 | AAL57688 | 18086470 | AT3g27300/K17E12_12 [*Arabidopsis thaliana*] |
| 58 | NP_728287 | 24643352 | Zwischenferment CG12529-PB, isoform B [*Drosophila melanogaster*] |
| 59 | EAT38627 | 108874402 | glucose-6-phosphate 1-dehydrogenase [*Aedes aegypti*] |
| 60 | AAR26303 | 89214190 | glucose-6-phosphate dehydrogenase [*Populus suaveolens*] |
| 61 | AAA99073 | 1304700 | glucose-6-phosphate 1-dehydrogenase [*Drosophila melanogaster*] |
| 62 | AAK93503 | 15292469 | SD03244p [*Drosophila melanogaster*] |
| 63 | AAB02809 | 1304686 | glucose-6-phosphate 1-dehydrogenase [*Drosophila melanogaster*] |
| 64 | NP_523411 | 24643350 | Zwischenferment CG12529-PA, isoform A [*Drosophila melanogaster*] |
| 65 | AAA99107 | 1305086 | glucose-6-phosphate 1-dehydrogenase [*Drosophila melanogaster*] |
| 66 | ABB29562 | 78183133 | putative Zwischenferment [*Drosophila simulans*] |
| 67 | NP_502129 | 17538218 | B0035.5 [*Caenorhabditis elegans*] |
| 68 | AAZ23850 | 71089991 | glucose-6-phosphate dehydrogenase [*Boophilus microplus*] |
| 69 | P37830 | 585165 | Glucose-6-phosphate 1-dehydrogenase, cytoplasmic isoform (G6PD) |
| 70 | AAB02812 | 1304692 | glucose-6-phosphate 1-dehydrogenase [*Drosophila melanogaster*] |
| 71 | ABB55386 | 81075965 | glucose-6-phosphate 1-dehydrogenase cytoplasmic isoform-like [*Solanum tuberosum*] |

TABLE 45-continued

| Row | ACCESSION | GI | PROTEIN DESCRIPTION |
|---|---|---|---|
| | Examples of glucose-6-phosphate dehydrogenase polypeptides. | | |
| 72 | CAJ83683 | 89273424 | glucose-6-phosphate dehydrogenase [*Xenopus tropicalis*] |
| 73 | NP_001 . . . | 62859893 | glucose-6-phosphate dehydrogenase 2 [*Xenopus tropicalis*] |
| 74 | ABB29563 | 78183135 | putative Zwischenferment [*Drosophila teissieri*] |
| 75 | AAX45785 | 61394184 | glucose-6-phosphate dehydrogenase isoform B [*Ips typographus*] |
| 76 | AAX45784 | 61394183 | glucose-6-phosphate dehydrogenase isoform A [*Ips typographus*] |
| 77 | AAH81820 | 51980296 | Glucose-6-phosphate dehydrogenase X-linked [*Rattus norvegicus*] |
| 78 | XP_311452 | 58381765 | ENSANGP00000018551 [*Anopheles gambiae* str. PEST] |
| 79 | XP_538209 | 74009187 | PREDICTED: similar to Glucose-6-phosphate 1-dehydrogenase (G6PD) [*Canis familiaris*] |
| 80 | AAH59324 | 111185531 | Unknown (protein for MGC: 69058) [*Xenopus laevis*] |
| 81 | ABB29560 | 78183129 | putative Zwischenferment [*Drosophila erecta*] |
| 82 | Q27638 | 3023810 | Glucose-6-phosphate 1-dehydrogenase (G6PD) |
| 83 | Q29492 | 2494652 | Glucose-6-phosphate 1-dehydrogenase (G6PD) |
| 84 | BAF09259 | 113536876 | Os02g0600400 [*Oryza sativa* (*japonica* cultivar-group)] |
| 85 | O55044 | 62510568 | Glucose-6-phosphate 1-dehydrogenase (G6PD) |
| 86 | CAA04993 | 3021510 | glucose-6-phosphate dehydrogenase [*Nicotiana tabacum*] |
| 87 | ABB29561 | 78183131 | putative Zwischenferment [*Drosophila orena*] |
| 88 | BAA97662 | 8918502 | glucose-6-phosphate dehydrogenase [*Triticum aestivum*] |
| 89 | BAD17920 | 46849421 | glucose-6-phosphate 1-dehydrogenase [*Acipenser baerii*] |
| 90 | XP_699168 | 68440567 | PREDICTED: similar to glucose-6-phosphate dehydrogenase [*Danio rerio*] |
| 91 | AAB96363 | 2734869 | glucose-6-phosphate dehydrogenase [*Takifugu rubripes*] |
| 92 | NP_000393 | 109389365 | glucose-6-phosphate dehydrogenase isoform a [*Homo sapiens*] |
| 93 | NP_001 . . . | 108773793 | glucose-6-phosphate dehydrogenase isoform b [*Homo sapiens*] |
| 94 | AAA52500 | 182871 | glucose-6-phosphate dehydrogenase variant A-(EC 1.1.1.49) |
| 95 | P11413 | 120731 | Glucose-6-phosphate 1-dehydrogenase (G6PD) |
| 96 | AAA92653 | 1203978 | G6PD [*Homo sapiens*] |
| 97 | AAX43335 | 61369430 | glucose-6-phosphate dehydrogenase [synthetic construct] |
| 98 | P41571 | 1169799 | Glucose-6-phosphate 1-dehydrogenase (G6PD) (Zwischenferment) |
| 99 | 2BHLB | 66361518 | Chain B, X-Ray Structure Of Human Glucose-6-Phosphate Dehydrogenase (Deletion Variant) Complexed With Glucose-6-Phosphate |
| 100 | ABC74527 | 85700174 | glucose-6-phosphate dehydrogenase [*Populus trichocarpa*] |
| 101 | ABC74528 | 85700176 | glucose-6-phosphate dehydrogenase [*Populus trichocarpa*] |
| 102 | AAA51463 | 157470 | glucose-6-phosphate dehydrogenase |
| 103 | XP_001 . . . | 109132852 | PREDICTED: glucose-6-phosphate dehydrogenase isoform 1 [*Macaca mulatta*] |
| 104 | 1QKIH | 7546530 | Chain H, X-Ray Structure Of Human Glucose 6-Phosphate Dehydrogenase (Variant Canton R4591) Complexed With Structural Nadp+ |
| 105 | XP_001 . . . | 109132850 | PREDICTED: glucose-6-phosphate dehydrogenase isoform 2 [*Macaca mulatta*] |
| 106 | BAA97663 | 8918504 | glucose-6-phosphate dehydrogenase [*Triticum aestivum*] |
| 107 | CAA04992 | 3021508 | glucose-6-phosphate dehydrogenase [*Nicotiana tabacum*] |
| 108 | AAB69318 | 2352921 | cytosolic glucose-6-phosphate dehydrogenase 1 [*Petroselinum crispum*] |
| 109 | XP_307095 | 58375370 | ENSANGP00000012074 [*Anopheles gambiae* str. PEST] |
| 110 | AAA41179 | 204197 | glucose-6-phosphate dehydrogenase |
| 111 | AAA63175 | 182890 | glucose-6-phosphate dehydrogenase [*Homo sapiens*] |
| 112 | BAA97664 | 8918506 | glucose-6-phosphate dehydrogenase [*Triticum aestivum*] |
| 113 | AAW24823 | 56753227 | SJCHGC02527 protein [*Schistosoma japonicum*] |
| 114 | CAA58590 | 5459313 | glucose-6-phosphate 1-dehydrogenase [*Takifugu rubripes*] |
| 115 | CAG07451 | 47228719 | unnamed protein product [*Tetraodon nigroviridis*] |
| 116 | CAJ28912 | 113207852 | glucose-6-phosphate 1-dehydrogenase [*Crassostrea gigas*] |
| 117 | ABC25881 | 83628088 | glucose-6-phosphate 1-dehydrogenase [*Homo sapiens*] |
| 118 | ABC25981 | 83628208 | glucose-6-phosphate 1-dehydrogenase [*Homo sapiens*] |
| 119 | ABC25826 | 83628022 | glucose-6-phosphate 1-dehydrogenase [*Homo sapiens*] |
| 120 | BAD17912 | 46849405 | glucose-6-phosphate 1-dehydrogenase [*Amia calva*] |
| 121 | BAD17877 | 46849335 | glucose-6-phosphate 1-dehydrogenase [*Protopterus annectens*] |
| 122 | BAD17947 | 46849475 | glucose-6-phosphate 1-dehydrogenase [*Callorhinchus callorynchus*] |
| 123 | AAI20828 | 111306848 | Glucose-6-phosphate dehydrogenase 2 [*Mus musculus*] |
| 124 | BAD17927 | 46849435 | glucose-6-phosphate 1-dehydrogenase [*Polypterus ornatipinnis*] |
| 125 | BAD17898 | 46849377 | glucose-6-phosphate 1-dehydrogenase [*Oryzias latipes*] |
| 126 | BAD17891 | 46849363 | glucose-6-phosphate 1-dehydrogenase [*Ambystoma mexicanum*] |
| 127 | BAD17951 | 46849483 | glucose-6-phosphate 1-dehydrogenase [*Lethenteron reissneri*] |
| 128 | AAF19030 | 7629275 | glucose-6-phosphate-1-dehydrogenase; G6PD [*Pimephales promelas*] |

TABLE 45-continued

Examples of glucose-6-phosphate dehydrogenase polypeptides.

| Row | ACCESSION | GI | PROTEIN DESCRIPTION |
|---|---|---|---|
| 129 | BAD17941 | 46849463 | glucose-6-phosphate 1-dehydrogenase [*Potamotrygon motoro*] |
| 130 | BAD17954 | 46849489 | glucose-6-phosphate 1-dehydrogenase [*Branchiostoma belcheri*] |
| 131 | BAD17905 | 46849391 | glucose-6-phosphate 1-dehydrogenase [*Lepisosteus osseus*] |
| 132 | BAD17884 | 46849349 | glucose-6-phosphate 1-dehydrogenase [*Lepidosiren paradoxa*] |
| 133 | BAD17934 | 46849449 | glucose-6-phosphate 1-dehydrogenase [*Cephaloscyllium umbratile*] |
| 134 | ABC74529 | 85700178 | glucose-6-phosphate dehydrogenase [*Populus trichocarpa*] |
| 135 | CAB52685 | 5734379 | plastidic glucose-6-phosphate dehydrogenase [*Dunaliella bioculata*] |
| 136 | Q43793 | 3023817 | Glucose-6-phosphate 1-dehydrogenase, chloroplast precursor (G6PD) |
| 137 | AAF87216 | 9392607 | plastidic glucose 6-phosphate dehydrogenase [*Nicotiana tabacum*] |
| 138 | BAC23041 | 24745908 | glucose 6-phosphate dehydrogenase [*Solanum tuberosum*] |
| 139 | CAB52708 | 5734502 | glucose-6-phosphate 1-dehydrogenase [*Solanum tuberosum*] |
| 140 | BAF21344 | 113610966 | Os07g0406300 [*Oryza sativa* (*japonica* cultivar-group)] |
| 141 | AAQ02671 | 33304517 | putative plastidic glucose-6-phosphate dehydrogenase [*Oryza sativa* (*japonica* cultivar-group)] |
| 142 | AAW82643 | 58803037 | hepatic glucose-6-phosphate dehydrogenase [*Rhabdosargus sarba*] |
| 143 | BAF12270 | 113548827 | Os03g0412800 [*Oryza sativa* (*japonica* cultivar-group)] |
| 144 | AAN72144 | 25083966 | glucose-6-phosphate dehydrogenase [*Arabidopsis thaliana*] |
| 145 | AAB69317 | 2352919 | plastidic glucose-6-phosphate dehydrogenase [*Petroselinum crispum*] |
| 146 | O24357 | 3334193 | Glucose-6-phosphate 1-dehydrogenase, chloroplast precursor (G6PD) |
| 147 | AAO23597 | 27764952 | At1g24280/F3I6_22 [*Arabidopsis thaliana*] |
| 148 | Q8L743 | 25452975 | Glucose-6-phosphate 1-dehydrogenase 3, chloroplast precursor (G6PD3) (G6PDH3) |
| 149 | CAA59011 | 1166405 | glucose-6-phosphate 1-dehydrogenase [*Arabidopsis thaliana*] |
| 150 | CAA59012 | 1174336 | glucose-6-phosphate 1-dehydrogenase [*Arabidopsis thaliana*] |
| 151 | CAC05439 | 9955555 | glucose-6-phosphate 1-dehydrogenase [*Arabidopsis thaliana*] |
| 152 | Q9FY99 | 25452980 | Glucose-6-phosphate 1-dehydrogenase 2, chloroplast precursor (G6PD2) (G6PDH2) |
| 153 | AAL57678 | 18086448 | AT5g13110/T19L5_70 [*Arabidopsis thaliana*] |
| 154 | Q43839 | 3023818 | Glucose-6-phosphate 1-dehydrogenase, chloroplast precursor (G6PD) |
| 155 | CAA04696 | 3021305 | plastidic glucose-6-phosphate dehydrogenase [*Arabidopsis thaliana*] |
| 156 | CAB52681 | 5734372 | glucose-6-phosphate 1-dehydrogenase [*Cyanidium caldarium*] |
| 157 | CAA04994 | 3021532 | glucose-6-phosphate dehydrogenase [*Nicotiana tabacum*] |
| 158 | Q7YS37 | 62510624 | Glucose-6-phosphate 1-dehydrogenase (G6PD) |
| 159 | CAG04059 | 47229307 | unnamed protein product [*Tetraodon nigroviridis*] |
| 160 | CAD28862 | 29149997 | glucose 6 phosphate dehydrogenase [*Acraea encedana*] |
| 161 | CAD28863 | 29149999 | glucose 6 phosphate dehydrogenase [*Acraea encedana*] |
| 162 | AAM64231 | 27434614 | glucose-6-phosphate dehydrogenase [*Leishmania braziliensis*] |
| 163 | AAG28728 | 11066848 | glucose-6-phosphate-dehydrogenase [*Drosophila mauritiana*] |
| 164 | AAG28730 | 11066852 | glucose-6-phosphate-dehydrogenase [*Drosophila sechellia*] |
| 165 | ABF96583 | 108708788 | Glucose-6-phosphate 1-dehydrogenase, chloroplast precursor, putative, expressed [*Oryza sativa* (*japonica* cultivar-group)] |
| 166 | CAA03941 | 2276348 | Glucose-6-phosphate dehydrogenase [*Spinacia oleracea*] |
| 167 | XP_583628 | 76658972 | PREDICTED: similar to Glucose-6-phosphate 1-dehydrogenase (G6PD) [*Bos taurus*] |
| 168 | AAA52499 | 182869 | glucose-6-phosphate dehydrogenase |
| 169 | AAM64229 | 27434610 | glucose-6-phosphate dehydrogenase [*Leishmania mexicana*] |
| 170 | NP_587749 | 19075249 | hypothetical protein SPCC794.01c [*Schizosaccharomyces pombe* 972h-] |
| 171 | AAR12945 | 38156652 | glucose-6-phosphate dehydrogenase [*Drosophila mojavensis*] |
| 172 | AAR12953 | 38156668 | glucose-6-phosphate dehydrogenase [*Drosophila mojavensis*] |
| 173 | AAR12946 | 38156654 | glucose-6-phosphate dehydrogenase [*Drosophila mojavensis*] |
| 174 | AAR12943 | 38156648 | glucose-6-phosphate dehydrogenase [*Drosophila mojavensis*] |
| 175 | AAR12952 | 38156666 | glucose-6-phosphate dehydrogenase [*Drosophila mojavensis*] |
| 176 | BAF11858 | 113548415 | Os03g0318500 [*Oryza sativa* (*japonica* cultivar-group)] |
| 177 | XP_559252 | 57942974 | ENSANGP00000028421 [*Anopheles gambiae* str. PEST] |
| 178 | NP_593614 | 19114526 | hypothetical protein SPAC3C7.13c [*Schizosaccharomyces pombe* 972h-] |
| 179 | BAD94743 | 62321397 | glucose-6-phosphate dehydrogenase [*Arabidopsis thaliana*] |
| 180 | CAJ20381 | 95007160 | glucose-6-phosphate-1-dehydrogenase [*Toxoplasma gondii*] |
| 181 | YP_605437 | 94986073 | glucose-6-phosphate 1-dehydrogenase [*Deinococcus geothermalis* DSM 11300] |
| 182 | CAE51228 | 37651949 | glucose 6 phosphate dehydrogenase [*Adalia bipunctata*] |
| 183 | YP_007820 | 46446455 | putative glucose-6-phosphate [*Candidatus Protochlamydia amoebophila* UWE25] |
| 184 | NP_295319 | 15806604 | glucose-6-phosphate 1-dehydrogenase [*Deinococcus radiodurans* R1] |

TABLE 45-continued

Examples of glucose-6-phosphate dehydrogenase polypeptides.

| Row | ACCESSION | GI | PROTEIN DESCRIPTION |
|---|---|---|---|
| 185 | CAE51222 | 37651937 | glucose 6 phosphate dehydrogenase [*Adalia bipunctata*] |
| 186 | CAE51229 | 37651951 | glucose 6 phosphate dehydrogenase [*Adalia decempunctata*] |
| 187 | ZP_007 . . . | 76260057 | Glucose-6-phosphate dehydrogenase [*Chloroflexus aurantiacus* J-10-fl] |
| 188 | ZP_002 . . . | 47096622 | glucose-6-phosphate 1-dehydrogenase [*Listeria monocytogenes* str. ½a F6854] |
| 189 | ZP_004 . . . | 66965919 | Glucose-6-phosphate dehydrogenase [*Arthrobacter* sp.*FB24*] |
| 190 | ZP_002 . . . | 47093301 | glucose-6-phosphate 1-dehydrogenase [*Listeria monocytogenes* str. 4b H7858] |
| 191 | NP_471419 | 16801151 | hypothetical protein lin2085 [*Listeria innocua* Clip11262] |
| 192 | NP_693860 | 23100393 | glucose-6-phosphate 1-dehydrogenase [*Oceanobacillus iheyensis* HTE831] |
| 193 | NP_829405 | 29840299 | glucose-6-phosphate 1-dehydrogenase [*Chlamydophila caviae* GPIC] |
| 194 | CAJ71041 | 91203388 | strongly similar to glucose-6-phosphate dehydrogenase [*Candidatus Kuenenia stuttgartiensis*] |
| 195 | YP_629214 | 108761123 | glucose-6-phosphate 1-dehydrogenase [*Myxococcus xanthus* DK 1622] |
| 196 | ZP_009 . . . | 84387050 | glucose-6-phosphate 1-dehydrogenase [*Vibrio splendidus* 12B01] |
| 197 | ZP_011 . . . | 88856188 | glucose-6-phosphate 1-dehydrogenase [marine actinobacterium PHSC20C1] |
| 198 | NP_827489 | 29832855 | glucose-6-phosphate 1-dehydrogenase [*Streptomyces avermitilis* MA-4680] |
| 199 | CAH10104 | 88319768 | putative glucose-6-phosphate-1-dehydrogenase [*Streptomyces* sp. SCC 2136] |
| 200 | YP_148187 | 56420869 | glucose-6-phosphate 1-dehydrogenase [*Geobacillus kaustophilus* HTA426] |
| 201 | ZP_006 . . . | 71368421 | Glucose-6-phosphate dehydrogenase [*Nocardioides* sp. JS614] |

TABLE 46

Examples of 6-phosphogluconate dehydrogenase polypeptides.

| Row | ACCESSION | GI | PROTEIN DESCRIPTION |
|---|---|---|---|
| 1 | XP_500938 | 50546937 | hypothetical protein [*Yarrowia lipolytica*]. |
| 2 | XP_458726 | 50420381 | hypothetical protein DEHA0D06820g [*Debaryomyces hansenii* CBS767] |
| 3 | XP_451408 | 50302941 | unnamed protein product [*Kluyveromyces lactis*] |
| 4 | O13287 | 3334110 | 6-phosphogluconate dehydrogenase, decarboxylating |
| 5 | XP_722227 | 68467588 | hypothetical protein CaO19_5024 [*Candida albicans* SC5314] |
| 6 | NP_012053 | 6321977 | 6-phosphogluconate dehydrogenase (decarboxylating), catalyzes an NADPH regenerating reaction in the pentose phosphate pathway; required for growth on D-glucono-delta-lactone and adaptation to oxidative stress; Gnd1p [*Saccharomyces cerevisiae*] |
| 7 | AAO32396 | 28564035 | GND1 [*Saccharomyces bayanus*] |
| 8 | XP_750696 | 70991695 | 6-phosphogluconate dehydrogenase, decarboxylating [*Aspergillus fumigatus* Af293] |
| 9 | CAD80254 | 29409963 | 6-phosphogluconate dehydrogenase [*Aspergillus niger*] |
| 10 | XP_661558 | 67526993 | hypothetical protein AN3954.2 [*Aspergillus nidulans* FGSC A4] |
| 11 | AAO32456 | 28564155 | GND1 [*Saccharomyces servazzii*] |
| 12 | AAO32497 | 28564385 | GND1 [*Saccharomyces castellii*] |
| 13 | BAE57349 | 83767210 | unnamed protein product [*Aspergillus oryzae*] |
| 14 | AAT92830 | 51013073 | YGR256W [*Saccharomyces cerevisiae*] |
| 15 | XP_449923 | 50295024 | hypothetical protein CAGL0M13343g [*Candida glabrata* CBS138] |
| 16 | NP_985676 | 45198647 | AFR129Wp [*Eremothecium gossypii*] |
| 17 | EAS35799 | 90306168 | 6-phosphogluconate dehydrogenase, decarboxylating [*Coccidioides immitis* RS] |
| 18 | XP_758724 | 71014537 | hypothetical protein UM02577.1 [*Ustilago maydis* 521] |
| 19 | O60037 | 12229635 | 6-phosphogluconate dehydrogenase, decarboxylating |
| 20 | XP_964959 | 85115938 | hypothetical protein [*Neurospora crassa* OR74A] |
| 21 | XP_381287 | 46108458 | hypothetical protein FG01111.1 [*Gibberella zeae* PH-1] |
| 22 | EAT76717 | 111055597 | predicted protein [*Phaeosphaeria nodorum* SN15] |
| 23 | XP_369069 | 39975357 | hypothetical protein MG00175.4 [*Magnaporthe grisea* 70-15] |
| 24 | XP_567793 | 58260766 | phosphogluconate dehydrogenase (decarboxylating) [*Cryptococcus neoformans* var. *neoformans* JEC21] |
| 25 | NP_595095 | 19111887 | 6-phosphogluconate dehydrogenase [*Schizosaccharomyces pombe* 972h-] |

TABLE 46-continued

Examples of 6-phosphogluconate dehydrogenase polypeptides.

| Row | ACCESSION | GI | PROTEIN DESCRIPTION |
|---|---|---|---|
| 26 | EAQ92608 | 88185140 | hypothetical protein CHGG_00843 [*Chaetomium globosum* CBS 148.51] |
| 27 | T42523 | 11251352 | probable phosphogluconate dehydrogenase (decarboxylating) (EC 1.1.1.44) - fission yeast (*Schizosaccharomyces pombe*) (fragment) |
| 28 | XP_781394 | 72005545 | PREDICTED: similar to 6-phosphogluconate dehydrogenase, decarboxylating [*Strongylocentrotus purpuratus*] |
| 29 | BAD98151 | 63003720 | 6-phosphogluconate dehydrogenase [*Ascidia sydneiensis samea*] |
| 30 | XP_625090 | 66547531 | PREDICTED: similar to 6-phosphogluconate dehydrogenase, decarboxylating, partial [*Apis mellifera*] |
| 31 | CAG32303 | 53134115 | hypothetical protein [*Gallus gallus*] |
| 32 | 2PGD | 999886 | Chain, 6-Phosphogluconate Dehydrogenase (6-Pgdh) (E.C.1.1.1.44) |
| 33 | NP_001 . . . | 57164179 | 6-phosphogluconate dehydrogenase (decarboxylating) [*Ovis aries*] |
| 34 | XP_911640 | 82896232 | PREDICTED: similar to 6-phosphogluconate dehydrogenase, decarboxylating isoform 6 [*Mus musculus*] |
| 35 | BAE31577 | 74225286 | unnamed protein product [*Mus musculus*] |
| 36 | AAX43359 | 61369608 | phosphogluconate dehydrogenase [synthetic construct] |
| 37 | CAI95751 | 66347393 | phosphogluconate dehydrogenase [*Homo sapiens*] |
| 38 | XP_993478 | 94374014 | PREDICTED: similar to 6-phosphogluconate dehydrogenase, decarboxylating isoform 4 [*Mus musculus*] |
| 39 | AAH11329 | 15030150 | Phosphogluconate dehydrogenase [*Mus musculus*] |
| 40 | AAI02179 | 73586529 | LOC514939 protein [*Bos taurus*] |
| 41 | AAA75302 | 984325 | phosphogluconate dehydrogenase [*Homo sapiens*] |
| 42 | AAH59958 | 37747616 | MGC68486 protein [*Xenopus laevis*] |
| 43 | ZP_005 . . . | 67931108 | 6-phosphogluconate dehydrogenase, decarboxylating [*Solibacter usitatus* Ellin6076] |
| 44 | EAT42557 | 108878332 | 6-phosphogluconate dehydrogenase [*Aedes aegypti*] |
| 45 | XP_535411 | 73950940 | PREDICTED: similar to 6-phosphogluconate dehydrogenase, decarboxylating isoform 1 [*Canis familiaris*] |
| 46 | XP_313091 | 58384192 | ENSANGP00000012857 [*Anopheles gambiae* str. PEST] |
| 47 | CAG07546 | 47228814 | unnamed protein product [*Tetraodon nigroviridis*] |
| 48 | YP_007316 | 46445951 | 6-phosphogluconate dehydrogenase [*Candidatus Protochlamydia amoebophila* UWE25] |
| 49 | NP_998717 | 47087205 | phosphogluconate hydrogenase isoform 2 [*Danio rerio*] |
| 50 | XP_972051 | 91094851 | PREDICTED: similar to phosphogluconate hydrogenase isoform 2 [*Tribolium castaneum*] |
| 51 | CAE70848 | 39594980 | Hypothetical protein CBG17632 [*Caenorhabditis briggsae*] |
| 52 | XP_001 . . . | 94372948 | PREDICTED: similar to 6-phosphogluconate dehydrogenase, decarboxylating isoform 9 [*Mus musculus*] |
| 53 | NP_998618 | 47087439 | phosphogluconate hydrogenase isoform 1 [*Danio rerio*] |
| 54 | AAH95571 | 63102189 | Pgd protein [*Danio rerio*] |
| 55 | XP_993446 | 94374016 | PREDICTED: similar to 6-phosphogluconate dehydrogenase, decarboxylating isoform 3 [*Mus musculus*] |
| 56 | EAL31500 | 54642755 | GA17642-PA [*Drosophila pseudoobscura*] |
| 57 | Q17761 | 74962414 | 6-phosphogluconate dehydrogenase, decarboxylating |
| 58 | P41573 | 1168233 | 6-phosphogluconate dehydrogenase, decarboxylating |
| 59 | AAL90185 | 19528141 | AT26455p [*Drosophila melanogaster*] |
| 60 | NP_476860 | 24639279 | Phosphogluconate dehydrogenase CG3724-PA [*Drosophila melanogaster*] |
| 61 | NP_001 . . . | 114053253 | 6-phosphogluconate dehydrogenase [*Bombyx mori*] |
| 62 | P41570 | 1168228 | 6-phosphogluconate dehydrogenase, decarboxylating |
| 63 | CAJ43391 | 95140247 | 6-phosphogluconate dehydrogenase [*Bactrocera oleae*] |
| 64 | CAJ43390 | 95140245 | 6-phosphogluconate dehydrogenase [*Ceratitis capitata*] |
| 65 | AAP92648 | 33086672 | Cc2-27 [*Rattus norvegicus*] |
| 66 | YP_661682 | 109898427 | 6-phosphogluconate dehydrogenase, decarboxylating [*Pseudoalteromonas atlantica* T6c] |
| 67 | XP_592859 | 76637462 | PREDICTED: similar to 6-phosphogluconate dehydrogenase, decarboxylating [*Bos taurus*] |
| 68 | YP_526109 | 90020282 | 6-phosphogluconate dehydrogenase, decarboxylating [*Saccharophagus degradans* 2-40] |
| 69 | ZP_001 . . . | 53733078 | COG0362: 6-phosphogluconate dehydrogenase [*Haemophilus influenzae* R2846] |
| 70 | NP_761502 | 27365974 | 6-phosphogluconate dehydrogenase [*Vibrio vulnificus* CMCP6] |
| 71 | YP_391484 | 78485559 | 6-phosphogluconate dehydrogenase, decarboxylating [*Thiomicrospira crunogena* XCL-2] |
| 72 | YP_248262 | 68249150 | 6-phosphogluconate dehydrogenase [*Haemophilus influenzae* 86-028NP] |
| 73 | NP_934400 | 37679791 | 6-phosphogluconate dehydrogenase [*Vibrio vulnificus* YJ016] |
| 74 | ZP_007 . . . | 75857693 | COG0362: 6-phosphogluconate dehydrogenase [*Vibrio* sp. Ex25] |
| 75 | NP_798087 | 28898482 | 6-phosphogluconate dehydrogenase [*Vibrio parahaemolyticus* RIMD 2210633] |

TABLE 46-continued

Examples of 6-phosphogluconate dehydrogenase polypeptides.

| Row | ACCESSION | GI | PROTEIN DESCRIPTION |
|---|---|---|---|
| 76 | YP_206428 | 59713653 | 6-phosphogluconate dehydrogenase [*Vibrio fischeri* ES114] |
| 77 | ZP_001 . . . | 53733322 | COG0362: 6-phosphogluconate dehydrogenase [*Haemophilus influenzae* R2866] |
| 78 | ZP_012 . . . | 91224436 | 6-phosphogluconate dehydrogenase [*Vibrio alginolyticus* 12G01] |
| 79 | AAB20377 | 239383 | 6-phosphogluconate dehydrogenase [sheep, Peptide, 466 aa] |
| 80 | ZP_010 . . . | 86145883 | 6-phosphogluconate dehydrogenase [*Vibrio* sp. MED222] |
| 81 | ZP_007 . . . | 75432781 | Phosphogluconate dehydrogenase (decarboxylating) [*Actinobacillus succinogenes* 130Z] |
| 82 | ZP_001 . . . | 46143450 | COG0362: 6-phosphogluconate dehydrogenase [*Actinobacillus pleuropneumoniae serovar* 1 str. 4074] |
| 83 | ZP_012 . . . | 90578957 | 6-phosphogluconate dehydrogenase [*Vibrio angustum* S14] |
| 84 | YP_087205 | 52424068 | 6-phosphogluconate dehydrogenase [*Mannheimia succiniciproducens* MBEL55E] |
| 85 | ZP_011 . . . | 89073009 | 6-phosphogluconate dehydrogenase [*Photobacterium* sp. SKA34] |
| 86 | NP_273081 | 15675963 | 6-phosphogluconate dehydrogenase [*Neisseria meningitidis* MC58] |
| 87 | ZP_007 . . . | 75825242 | COG0362: 6-phosphogluconate dehydrogenase [*Vibrio cholerae* O395] |
| 88 | ZP_007 . . . | 75822319 | COG0362: 6-phosphogluconate dehydrogenase [*Vibrio cholerae* RC385] |
| 89 | ZP_007 . . . | 75831146 | COG0362: 6-phosphogluconate dehydrogenase [*Vibrio cholerae* MO10] |
| 90 | YP_719859 | 113461790 | 6-phosphogluconate dehydrogenase [*Haemophilus somnus* 129PT] |
| 91 | ZP_012 . . . | 90411828 | 6-phosphogluconate dehydrogenase [*Photobacterium profundum* 3TCK] |
| 92 | YP_129657 | 54308637 | 6-phosphogluconate dehydrogenase [*Photobacterium profundum* SS9] |
| 93 | ZP_001 . . . | 53728695 | COG0362: 6-phosphogluconate dehydrogenase [*Haemophilus somnus* 2336] |
| 94 | BAD36766 | 51241757 | 6-phosphogluconate dehydrogenase [*Cyanidioschyzon merolae*] |
| 95 | P70718 | 2492494 | 6-phosphogluconate dehydrogenase, decarboxylating |
| 96 | XP_642122 | 66816225 | 6-phosphogluconate dehydrogenase (decarboxylating) [*Dictyostelium discoideum* AX4] |
| 97 | Q7VMX4 | 71152205 | 6-phosphogluconate dehydrogenase, decarboxylating |
| 98 | NP_283102 | 15793280 | 6-phosphogluconate dehydrogenase [*Neisseria meningitidis* Z2491] |
| 99 | NP_246493 | 15603419 | 6-phosphogluconate dehydrogenase [*Pasteurella multocida* subsp. *multocida* str. Pm70] |
| 100 | AAO19943 | 27573087 | 6-phosphogluconate dehydrogenase, decarboxylating [*Neisseria gonorrhoeae*] |
| 101 | AAO19944 | 27573089 | 6-phosphogluconate dehydrogenase, decarboxylating [*Neisseria gonorrhoeae*] |
| 102 | YP_208939 | 59802227 | 6-phosphogluconate dehydrogenase [*Neisseria gonorrhoeae* FA 1090] |
| 103 | AAO19934 | 27573069 | 6-phosphogluconate dehydrogenase, decarboxylating [*Neisseria gonorrhoeae*] |
| 104 | AAO19942 | 27573085 | 6-phosphogluconate dehydrogenase, decarboxylating [*Neisseria gonorrhoeae*] |
| 105 | ZP_013 . . . | 106881674 | 6-phosphogluconate dehydrogenase, decarboxylating [*Psychromonas ingrahamii* 37] |
| 106 | XP_515670 | 55599346 | PREDICTED: similar to 6-phosphogluconate dehydrogenase, decarboxylating [*Pan troglodytes*] |
| 107 | ZP_010 . . . | 87309497 | 6-phosphogluconate dehydrogenase [*Blastopirellula marina* DSM 3645] |
| 108 | NP_865160 | 32472166 | 6-phosphogluconate dehydrogenase [*Rhodopirellula baltica* SH 1] |
| 109 | AAW29923 | 56788282 | 6-phosphogluconate dehydrogenase [*Mannheimia haemolytica*] |
| 110 | AAW29924 | 56788284 | 6-phosphogluconate dehydrogenase [*Mannheimia glucosida*] |
| 111 | AAW29925 | 56788286 | 6-phosphogluconate dehydrogenase [*Pasteurella trehalosi*] |
| 112 | NP_218771 | 15639322 | 6-phosphogluconate dehydrogenase [*Treponema pallidum* subsp. *pallidum* str. Nichols] |
| 113 | YP_148197 | 56420879 | 6-phosphogluconate dehydrogenase [*Geobacillus kaustophilus* HTA426] |
| 114 | YP_356348 | 77918533 | probable phosphogluconate dehydrogenase (decarboxylating) [*Pelobacter carbinolicus* DSM 2380] |
| 115 | NP_390267 | 50812264 | 6-phosphogluconate dehydrogenase [*Bacillus subtilis* subsp. *subtilis* str. 168] |
| 116 | YP_092134 | 52786305 | 6-phosphogluconate dehydrogenase [*Bacillus licheniformis* ATCC 14580] |
| 117 | ZP_011 . . . | 89099010 | 6-phosphogluconate dehydrogenase [*Bacillus* sp. NRRL B-14911] |

TABLE 46-continued

Examples of 6-phosphogluconate dehydrogenase polypeptides.

| Row | ACCESSION | GI | PROTEIN DESCRIPTION |
|---|---|---|---|
| 118 | NP_691106 | 23097640 | 6-phosphogluconate dehydrogenase [*Oceanobacillus iheyensis* HTE831] |
| 119 | YP_219832 | 62185047 | 6-phosphogluconate dehydrogenase [*Chlamydophila abortus* S26/3] |
| 120 | ZP_002 . . . | 47565365 | 6-phosphogluconate dehydrogenase, decarboxylating [*Bacillus cereus* G9241] |
| 121 | YP_026451 | 49183199 | 6-phosphogluconate dehydrogenase [*Bacillus anthracis* str. Sterne] |
| 122 | YP_034514 | 49476731 | 6-phosphogluconate dehydrogenase [*Bacillus thuringiensis* serovar konkukian str. 97-27] |
| 123 | YP_081773 | 52145056 | 6-phosphogluconate dehydrogenase [*Bacillus cereus* E33L] |
| 124 | YP_515493 | 89898383 | 6-phosphogluconate dehydrogenase [*Chlamydophila felis* Fe/C-56] |
| 125 | NP_814782 | 29375628 | 6-phosphogluconate dehydrogenase [*Enterococcus faecalis* V583] |
| 126 | ZP_003 . . . | 65317607 | COG0362: 6-phosphogluconate dehydrogenase [*Bacillus anthracis* str. A2012] |
| 127 | YP_175422 | 56963691 | 6-phosphogluconate dehydrogenase [*Bacillus clausii* KSM-K16] |
| 128 | ZP_006 . . . | 69247351 | 6-phosphogluconate dehydrogenase, decarboxylating [*Enterococcus faecium* DO] |
| 129 | NP_810135 | 29346632 | 6-phosphogluconate dehydrogenase [*Bacteroides thetaiotaomicron* VPI-5482] |
| 130 | NP_829300 | 29840194 | 6-phosphogluconate dehydrogenase [*Chlamydophila caviae* GPIC] |
| 131 | AAL76325 | 18644678 | 6-phosphogluconate dehydrogenase [*Porphyra yezoensis*] |
| 132 | YP_546705 | 91776949 | 6-phosphogluconate dehydrogenase, decarboxylating [*Methylobacillus flagellatus* KT] |
| 133 | ZP_004 . . . | 67546118 | 6-phosphogluconate dehydrogenase, decarboxylating [*Burkholderia vietnamiensis* G4] |
| 134 | Q9CHU6 | 18202802 | 6-phosphogluconate dehydrogenase, decarboxylating |
| 135 | ZP_006 . . . | 74014955 | 6-phosphogluconate dehydrogenase, decarboxylating [*Burkholderia ambifaria* AMMD] |
| 136 | YP_372936 | 78063028 | 6-phosphogluconate dehydrogenase [*Burkholderia* sp.*383*] |
| 137 | YP_624314 | 107026803 | 6-phosphogluconate dehydrogenase, decarboxylating [*Burkholderia cenocepacia* AU 1054] |
| 138 | NP_928851 | 37525507 | 6-phosphogluconate dehydrogenase [*Photorhabdus luminescens* subsp. *laumondii* TTO1] |
| 139 | ZP_002 . . . | 47095960 | 6-phosphogluconate dehydrogenase, decarboxylating [*Listeria monocytogenes* str. ½a F6854] |
| 140 | YP_438830 | 83717630 | 6-phosphogluconate dehydrogenase, decarboxylating [*Burkholderia thailandensis* E264] |
| 141 | P96789 | 8134294 | 6-phosphogluconate dehydrogenase, decarboxylating |
| 142 | NP_924063 | 37520686 | 6-phosphogluconate dehydrogenase [*Gloeobacter violaceus* PCC 7421] |
| 143 | AAA24207 | 146938 | 6-phosphogluconate dehydrogenase |
| 144 | ZP_009 . . . | 84360352 | COG0362: 6-phosphogluconate dehydrogenase [*Burkholderia dolosa* AUO158] |
| 145 | YP_335987 | 76817886 | 6-phosphogluconate dehydrogenase [*Burkholderia pseudomallei* 1710b] |
| 146 | AAA24495 | 147501 | 6-phosphogluconate dehydrogenase |
| 147 | NP_310857 | 15832084 | 6-phosphogluconate dehydrogenase [*Escherichia coli* O157:H7 str. Sakai] |
| 148 | ZP_009 . . . | 83571257 | COG0362: 6-phosphogluconate dehydrogenase [*Shigella dysenteriae* 1012] |
| 149 | ZP_007 . . . | 75229110 | COG0362: 6-phosphogluconate dehydrogenase [*Escherichia coli* B7A] |
| 150 | ZP_013 . . . | 100915196 | hypothetical protein Bmal10_03003493 [*Burkholderia mallei* 10399] |
| 151 | AAG35219 | 11464518 | 6-phosphogluconate dehydrogenase [*Escherichia coli*] |
| 152 | ZP_013 . . . | 100236192 | hypothetical protein Bpse4_03000697 [*Burkholderia pseudomallei* 406e] |
| 153 | YP_669972 | 110642242 | 6-phosphogluconate dehydrogenase, decarboxylating [*Escherichia coli* 536] |
| 154 | ZP_013 . . . | 100062231 | hypothetical protein BpseP_03002198 [*Burkholderia pseudomallei* Pasteur] |
| 155 | YP_114383 | 53803994 | 6-phosphogluconate dehydrogenase [*Methylococcus capsulatus* str. Bath] |
| 156 | AAA24208 | 146940 | 6-phosphogluconate dehydrogenase |
| 157 | YP_310991 | 74312572 | gluconate-6-phosphate dehydrogenase, decarboxylating [*Shigella sonnei* Ss046] |
| 158 | ZP_003 . . . | 48870455 | COG0362: 6-phosphogluconate dehydrogenase [*Pediococcus pentosaceus* ATCC 25745] |
| 159 | ZP_007 . . . | 75514070 | COG0362: 6-phosphogluconate dehydrogenase [*Escherichia coli* 53638] |

TABLE 46-continued

Examples of 6-phosphogluconate dehydrogenase polypeptides.

| Row | ACCESSION | GI | PROTEIN DESCRIPTION |
|---|---|---|---|
| 160 | YP_049550 | 50120383 | 6-phosphogluconate dehydrogenase [*Erwinia carotovora* subsp. *atroseptica* SCRI1043] |
| 161 | AP_002630 | 89108850 | gluconate-6-phosphate dehydrogenase, decarboxylating [*Escherichia coli* W3110] |
| 162 | ZP_007 . . . | 75259178 | COG0362: 6-phosphogluconate dehydrogenase [*Escherichia coli* E22] |
| 163 | YP_541301 | 91211315 | 6-phosphogluconate dehydrogenase, decarboxylating [*Escherichia coli* UTI89] |
| 164 | YP_013993 | 46907604 | 6-phosphogluconate dehydrogenase [*Listeria monocytogenes* str. 4b F2365] |
| 165 | YP_403788 | 82777439 | gluconate-6-phosphate dehydrogenase [*Shigella dysenteriae* Sd197] |
| 166 | ZP_009 . . . | 83588030 | COG0362: 6-phosphogluconate dehydrogenase [*Escherichia coli* 101-1] |
| 167 | AAD50492 | 5739470 | 6-phosphogluconate dehydrogenase Gnd [*Escherichia coli*] |
| 168 | ZP_006 . . . | 75177157 | COG0362: 6-phosphogluconate dehydrogenase [*Shigella boydii* BS512] |
| 169 | AAA24209 | 146942 | 6-phosphogluconate dehydrogenase |
| 170 | AAG35221 | 11464522 | 6-phosphogluconate dehydrogenase [*Escherichia coli*] |
| 171 | ZP_007 . . . | 75186836 | COG0362: 6-phosphogluconate dehydrogenase [*Escherichia coli* E24377A] |
| 172 | YP_689521 | 110806001 | gluconate-6-phosphate dehydrogenase [*Shigella flexneri* 5 str. 8401] |
| 173 | ZP_008 . . . | 77959279 | COG0362: 6-phosphogluconate dehydrogenase [*Yersinia bercovieri* ATCC 43970] |
| 174 | AAG35224 | 11464528 | 6-phosphogluconate dehydrogenase [*Escherichia coli*] |
| 175 | ZP_007 . . . | 77636293 | COG0362: 6-phosphogluconate dehydrogenase [*Yersinia pestis* Angola] |
| 176 | ZP_008 . . . | 77962467 | COG0362: 6-phosphogluconate dehydrogenase [*Yersinia mollaretii* ATCC 43969] |
| 177 | ZP_008 . . . | 77978861 | COG0362: 6-phosphogluconate dehydrogenase [*Yersinia intermedia* ATCC 29909] |
| 178 | AAG35218 | 11464516 | 6-phosphogluconate dehydrogenase [*Escherichia coli*] |
| 179 | BAA77736 | 4867927 | 6-phosphogluconate dehydrogenase [*Escherichia coli*] |
| 180 | AAA24490 | 147491 | 6-phosphogluconate dehydrogenase |
| 181 | YP_648367 | 108812600 | 6-phosphogluconate dehydrogenase, decarboxylating [*Yersinia pestis* Nepal516] |
| 182 | NP_669932 | 22126509 | 6-phosphogluconate dehydrogenase [*Yersinia pestis* KIM] |
| 183 | AAA23918 | 146232 | 6-phosphogluconate dehydrogenase (EC 1.1.1.44) |
| 184 | CAJ71042 | 91203389 | strongly similar to 6-phosphogluconate dehydrogenase (decarboxylating) [*Candidatus Kuenenia stuttgartiensis*] |
| 185 | AAA24206 | 146936 | 6-phosphogluconate dehydrogenase |
| 186 | AAA24494 | 147499 | 6-phosphogluconate dehydrogenase |
| 187 | AAA24492 | 147495 | 6-phosphogluconate dehydrogenase |
| 188 | YP_099135 | 53713143 | 6-phosphogluconate dehydrogenase [*Bacteroides fragilis* YCH46] |
| 189 | AAA23925 | 146246 | 6-phosphogluconate dehydrogenase |
| 190 | YP_211552 | 60681408 | 6-phosphogluconate dehydrogenase [*Bacteroides fragilis* NCTC 9343] |
| 191 | AAV74381 | 56122509 | Gnd [*Escherichia coli*] |
| 192 | NP_992794 | 45441255 | 6-phosphogluconate dehydrogenase [*Yersinia pestis* biovar *Microtus* str. 91001] |
| 193 | YP_650749 | 108806833 | 6-phosphogluconate dehydrogenase, decarboxylating [*Yersinia pestis* Antiqua] |
| 194 | NP_876643 | 33241702 | 6-phosphogluconate dehydrogenase [*Chlamydophila pneumoniae* TW-183] |
| 195 | NP_357929 | 15902379 | 6-phosphogluconate dehydrogenase [*Streptococcus pneumoniae* R6] |
| 196 | ZP_014 . . . | 111658214 | hypothetical protein SpneT_02000606 [*Streptococcus pneumoniae* TIGR4] |
| 197 | NP_782446 | 28211502 | 6-phosphogluconate dehydrogenase [*Clostridium tetani* E88] |
| 198 | AAG35223 | 11464526 | 6-phosphogluconate dehydrogenase [*Escherichia coli*] |
| 199 | AAA24493 | 147497 | 6-phosphogluconate dehydrogenase |
| 200 | ZP_007 . . . | 75214880 | COG0362: 6-phosphogluconate dehydrogenase [*Escherichia coli* E110019] |

TABLE 47

Examples of Fructose 1,6 bisphosphatase polypeptides.

| Row | ACCESSION | GI | PROTEIN DESCRIPTION |
|---|---|---|---|
| 1 | XP_500111 | 50545147 | hypothetical protein [*Yarrowia lipolytica*]. |
| 2 | AAP85294 | 32492043 | fructose-1,6-bisphosphatase [*Yarrowia lipolytica*] |
| 3 | XP_460410 | 50423651 | hypothetical protein DEHA0F01309g [*Debaryomyces hansenii* CBS767] |
| 4 | CAC69139 | 15528447 | putative fructose-1,6-bisphosphatase [*Pichia anomala*] |
| 5 | XP_447425 | 50289987 | hypothetical protein CAGL0I04048g [*Candida glabrata* CBS138] |
| 6 | NP_986140 | 45199111 | AFR593Cp [*Eremothecium gossypii*] |
| 7 | XP_454003 | 50308005 | F16P_KLULA [*Kluyveromyces lactis*] |
| 8 | EAT78213 | 111057093 | predicted protein [*Phaeosphaeria nodorum* SN15] |
| 9 | XP_710934 | 68490480 | fructose-1,6-bisphosphatase [*Candida albicans* SC5314] |
| 10 | AAT92835 | 51013083 | YLR377C [*Saccharomyces cerevisiae*] |
| 11 | XP_364050 | 39954137 | hypothetical protein MG08895.4 [*Magnaporthe grisea* 70-15] |
| 12 | NP_001... | 68006542 | fructose-1,6-bisphosphatase [*Schizosaccharomyces pombe* 972h-] |
| 13 | NP_595083 | 19111875 | hypothetical protein SPBC1198.14c [*Schizosaccharomyces pombe* 972h-] |
| 14 | XP_751698 | 70993702 | fructose-1,6-bisphosphatase [*Aspergillus fumigatus* Af293] |
| 15 | XP_447010 | 50289161 | unnamed protein product [*Candida glabrata*] |
| 16 | BAE58185 | 83768046 | unnamed protein product [*Aspergillus oryzae*] |
| 17 | EAQ84924 | 88177456 | conserved hypothetical protein [*Chaetomium globosum* CBS 148.51] |
| 18 | AAF34693 | 6980006 | fructose 1,6-bisphosphatase [*Candida albicans*] |
| 19 | BAB12208 | 9955389 | fructose-1,6-bisphosphatase [*Aspergillus oryzae*] |
| 20 | XP_663208 | 67538868 | hypothetical protein AN5604.2 [*Aspergillus nidulans* FGSC A4] |
| 21 | XP_389456 | 46134281 | conserved hypothetical protein [*Gibberella zeae* PH-1] |
| 22 | XP_960423 | 85097320 | hypothetical protein [*Neurospora crassa* OR74A] |
| 23 | EAS36192 | 90306561 | fructose-1,6-bisphosphatase [*Coccidioides immitis* RS] |
| 24 | XP_566475 | 58258125 | fructose-bisphosphatase [*Cryptococcus neoformans* var. *neoformans* JEC21] |
| 25 | XP_758850 | 71015920 | hypothetical protein UM02703.1 [*Ustilago maydis* 521] |
| 26 | P14766 | 119748 | Fructose-1,6-bisphosphatase, cytosolic (D-fructose-1,6-bisphosphate 1-phosphohydrolase) (FBPase) |
| 27 | AAZ86538 | 73811203 | fructose 1,6-bisphosphatase [*Brassica rapa* subsp. *pekinensis*] |
| 28 | Q9MA79 | 75312318 | Fructose-1,6-bisphosphatase, cytosolic (D-fructose-1,6-bisphosphate 1-phosphohydrolase) (FBPase) |
| 29 | Q9SDL8 | 75313310 | Fructose-1,6-bisphosphatase, cytosolic (D-fructose-1,6-bisphosphate 1-phosphohydrolase) (FBPase) |
| 30 | BAD81916 | 56785198 | fructose-1,6-bisphosphatase [*Oryza sativa* (*japonica* cultivar-group)] |
| 31 | P46267 | 1169585 | Fructose-1,6-bisphosphatase, cytosolic (D-fructose-1,6-bisphosphate 1-phosphohydrolase) (FBPase) |
| 32 | P46276 | 1169586 | Fructose-1,6-bisphosphatase, cytosolic (D-fructose-1,6-bisphosphate 1-phosphohydrolase) (FBPase) (CY-F1) |
| 33 | Q8RW99 | 75303233 | Fructose-1,6-bisphosphatase, cytosolic (D-fructose-1,6-bisphosphate 1-phosphohydrolase) (FBPase) |
| 34 | Q43139 | 76363515 | Fructose-1,6-bisphosphatase, cytosolic (D-fructose-1,6-bisphosphate 1-phosphohydrolase) (FBPase) |
| 35 | CAB46084 | 5305145 | fructose-1,6-bisphosphatase [*Pisum sativum*] |
| 36 | BAF06820 | 113534437 | Os01g0866400 [*Oryza sativa* (*japonica* cultivar-group)] |
| 37 | Q42649 | 76789650 | Fructose-1,6-bisphosphatase, cytosolic (D-fructose-1,6-bisphosphate 1-phosphohydrolase) (FBPase) |
| 38 | Q9XF47 | 75315047 | Fructose-1,6-bisphosphatase, cytosolic (D-fructose-1,6-bisphosphate 1-phosphohydrolase) (FBPase) |
| 39 | CAA61409 | 895909 | fructose-1,6-bisphosphatase [*Saccharum* hybrid cultivar H65-7052] |
| 40 | 1906373A | 444324 | cytosolic fructose bisphosphatase |
| 41 | EAR87347 | 89289359 | fructose-1,6-bisphosphatase family protein [*Tetrahymena thermophila* SB210] |
| 42 | NP_915641 | 34908588 | fructose-1,6-bisphosphatase [*Oryza sativa* (*japonica* cultivar-group)] |
| 43 | XP_475314 | 50931573 | putative fructose-1,6-bisphosphatase [*Oryza sativa* (*japonica* cultivar-group)] |
| 44 | NP_491004 | 17508131 | K07A3.1 [*Caenorhabditis elegans*] |
| 45 | XP_782411 | 72013871 | PREDICTED: similar to fructose-1,6-bisphosphatase 1, like [*Strongylocentrotus purpuratus*] |
| 46 | CAE60538 | 39595500 | Hypothetical protein CBG04165 [*Caenorhabditis briggsae*] |
| 47 | NP_610001 | 19921562 | fructose-1,6-bisphosphatase CG31692-PA, isoform A [*Drosophila melanogaster*] |
| 48 | NP_724223 | 45550998 | fructose-1,6-bisphosphatase CG31692-PB, isoform B [*Drosophila melanogaster*] |
| 49 | XP_319937 | 58393257 | ENSANGP00000016841 [*Anopheles gambiae* str. PEST] |
| 50 | AAN31471 | 23394363 | fructose-1 6-biphosphatase [*Phytophthora infestans*] |
| 51 | XP_425040 | 50762393 | PREDICTED: similar to fructose 1,6-bisphosphatase [*Gallus gallus*] |

TABLE 47-continued

Examples of Fructose 1,6 bisphosphatase polypeptides.

| Row | ACCESSION | GI | PROTEIN DESCRIPTION |
|---|---|---|---|
| 52 | EAT47721 | 108883496 | fructose-1,6-bisphosphatase [*Aedes aegypti*] |
| 53 | EAT47722 | 108883497 | fructose-1,6-bisphosphatase [*Aedes aegypti*] |
| 54 | AAH53784 | 32450356 | Fbp-prov protein [*Xenopus laevis*] |
| 55 | YP_001659 | 45657573 | fructose-1,6-bisphosphatase [*Leptospira interrogans* serovar Copenhageni str. Fiocruz L1-130] |
| 56 | NP_989145 | 45361017 | Fructose-1,6-bisphosphatase [*Xenopus tropicalis*] |
| 57 | 1YZ0B | 62738852 | Chain B, R-State Amp Complex Reveals Initial Steps Of The Quaternary Transition Of Fructose-1,6-Bisphosphatase |
| 58 | 1Q9DB | 39654661 | Chain B, Fructose-1,6-Bisphosphatase Complexed With A New Allosteric Site Inhibitor (I-State) |
| 59 | NP_999144 | 47522784 | fructose 1,6-bisphosphatase [*Sus scrofa*] |
| 60 | EAL32807 | 54644065 | GA16400-PA [*Drosophila pseudoobscura*] |
| 61 | XP_848306 | 73946392 | PREDICTED: similar to fructose-1,6-bisphosphatase 1 isoform 3 [*Canis familiaris*] |
| 62 | 1FJ9B | 11514534 | Chain B, Fructose-1,6-Bisphosphatase (Mutant Y57w) ProductsZNAMP Complex (T-State) |
| 63 | 1LEVF | 24987566 | Chain F, Porcine Kidney Fructose-1,6-Bisphosphatase Complexed With An Amp-Site Inhibitor |
| 64 | 1BK4A | 6729708 | Chain A, Crystal Structure Of Rabbit Liver Fructose-1,6-Bisphosphatase At 2.3 Angstrom Resolution |
| 65 | Q3SZB7 | 110808224 | Fructose-1,6-bisphosphatase 1 (D-fructose-1,6-bisphosphate 1-phosphohydrolase 1) (FBPase 1) |
| 66 | AAA41131 | 310111 | fructose-biphosphatase |
| 67 | P46275 | 2506391 | Fructose-1,6-bisphosphatase, chloroplast precursor (D-fructose-1,6-bisphosphate 1-phosphohydrolase) (FBPase) |
| 68 | 2F3HB | 99032142 | Chain B, Mechanism Of Displacement Of A Catalytically Essential Loop From The Active Site Of Fructose-1,6-Bisphosphatase |
| 69 | NP_036690 | 51036635 | fructose-1,6-biphosphatase 1 [*Rattus norvegicus*] |
| 70 | AAC25597 | 3288991 | fructose-1,6-bisphosphatase [*Sus scrofa*] |
| 71 | XP_967802 | 91077758 | PREDICTED: similar to CG31692-PA, isoform A [*Tribolium castaneum*] |
| 72 | AAK59929 | 14318171 | fructose-1,6-bisphosphatase [*Pisum sativum*] |
| 73 | 1DCUD | 6730314 | Chain D, Redox Signaling In The Chloroplast: Structure Of Oxidized Pea Fructose-1,6-Bisphosphate Phosphatase |
| 74 | 1DBZD | 6730306 | Chain D, C153s Mutant Of Pea Fructose-1,6-Bisphosphatase |
| 75 | CAB39759 | 4539148 | fructose-1,6-bisphosphatase [*Pisum sativum*] |
| 76 | P09199 | 20141075 | Fructose-1,6-bisphosphatase 1 (D-fructose-1,6-bisphosphate 1-phosphohydrolase 1) (FBPase 1) |
| 77 | CAA48719 | 20717 | fructose-bisphosphatase [*Pisum sativum*] |
| 78 | 1FPIB | 1633402 | Chain B, Fructose-1,6-Bisphosphatase (D-Fructose-1,6-Bisphosphate 1-Phosphohydrolase) Complexed With Amp, 2,5-Anhydro-D-Glucitol-1,6-Bisphosphate And Potassium Ions (100 Mm) |
| 79 | AAB30523 | 546354 | fructose-1,6-biphosphatase, FBPase {EC 3.1.3.11} [*Pisum sativum* = peas, Lincoln, Peptide Chloroplast, 357 aa] |
| 80 | 1KZ8F | 24987484 | Chain F, Crystal Structure Of Porcine Fructose-1,6-Bisphosphatase Complexed With A Novel Allosteric-Site Inhibitor |
| 81 | AAW25416 | 56754457 | SJCHGC06706 protein [*Schistosoma japonicum*] |
| 82 | 1FRPB | 809402 | Chain B, Fructose-1,6-Bisphosphatase (D-Fructose-1,6-Bisphosphate 1-Phosphohydrolase) (E.C.3.1.3.11) Complexed With Fructose-2,6-Bisphosphate, Adenosine Monophosphate (Amp), And Zinc |
| 83 | XP_425039 | 50762391 | PREDICTED: similar to fructose-1,6-bisphosphatase [*Gallus gallus*] |
| 84 | NP_998297 | 47085885 | fructose-1,6-bisphosphatase 1 [*Danio rerio*] |
| 85 | 1RDZB | 1942591 | Chain B, T-State Structure Of The Arg 243 To Ala Mutant Of Pig Kidney Fructose 1,6-Bisphosphatase Expressed In *E. Coli* |
| 86 | 1FSAB | 2554913 | Chain B, The T-State Structure Of Lys 42 To Ala Mutant Of The Pig Kidney Fructose 1,6-Bisphosphatase Expressed In *E. Coli* |
| 87 | BAE28940 | 74146344 | unnamed protein product [*Mus musculus*] |
| 88 | CAG05216 | 47228396 | unnamed protein product [*Tetraodon nigroviridis*] |
| 89 | NP_956236 | 41053949 | fructose-1,6-bisphosphatase 1, like [*Danio rerio*] |
| 90 | Q07204 | 585118 | Fructose-1,6-bisphosphatase, chloroplast precursor (D-fructose-1,6-bisphosphate 1-phosphohydrolase) (FBPase) |
| 91 | BAF11578 | 113548135 | Os03g0267300 [*Oryza sativa* (*japonica* cultivar-group)] |
| 92 | 2FIXL | 90109451 | Chain L, Structure Of Human Liver Fbpase Complexed With Potent Benzoxazole Allosteric Inhibitiors |
| 93 | 2FHYL | 90109424 | Chain L, Structure Of Human Liver Fpbase Complexed With A Novel Benzoxazole As Allosteric Inhibitor |
| 94 | XP_001 . . . | 109112377 | PREDICTED: fructose-1,6-bisphosphatase 1 isoform 2 [*Macaca mulatta*] |
| 95 | 1FTAD | 1311149 | Chain D, Fructose-1,6-Bisphosphatase(D-Fructose-1,6-Bisphosphate, 1-Phosphohydrolase) (E.C.3.1.3.11) Complexed With The Allosteric Inhibitor Amp |

TABLE 47-continued

| Examples of Fructose 1,6 bisphosphatase polypeptides. | | | |
|---|---|---|---|
| Row | ACCESSION | GI | PROTEIN DESCRIPTION |
| 96 | CAH72692 | 55662224 | fructose-1,6-bisphosphatase 1 [*Homo sapiens*] |
| 97 | CAG08190 | 47221528 | unnamed protein product [*Tetraodon nigroviridis*] |
| 98 | XP_533504 | 73946534 | PREDICTED: similar to Fructose-1,6-bisphosphatase isozyme 2 (D-fructose-1,6-bisphosphate 1-phosphohydrolase) (FBPase) [*Canis familiaris*] |
| 99 | AAC25774 | 3293553 | fructose-1,6-bisphosphatase [*Homo sapiens*] |
| 100 | AAA35817 | 182311 | fructose-1,6-bisphosphatase |
| 101 | AAD12243 | 4218951 | fructose-1,6-bisphosphatase precursor [*Brassica napus*] |
| 102 | NP_001 . . . | 114051459 | hypothetical protein LOC514066 [*Bos taurus*] |
| 103 | P09195 | 119745 | Fructose-1,6-bisphosphatase, chloroplast precursor (D-fructose-1,6-bisphosphate 1-phosphohydrolase) (FBPase) |
| 104 | NP_001 . . . | 57524507 | hypothetical protein LOC445505 [*Danio rerio*] |
| 105 | NP_001. . . | 114051287 | fructose-1,6-bisphosphatase [*Bombyx mori*] |
| 106 | NP_001. . . | 73853862 | hypothetical protein LOC613108 [*Xenopus tropicalis*] |
| 107 | AAD25541 | 4585576 | fructose-1,6-bisphosphatase precursor [*Solanum tuberosum*] |
| 108 | Q9N0J6 | 75067927 | Fructose-1,6-bisphosphatase isozyme 2 (D-fructose-1,6-bisphosphate 1-phosphohydrolase 2) (FBPase 2) |
| 109 | AAN31884 | 23397203 | putative fructose-bisphosphatase precursor [*Arabidopsis thaliana*] |
| 110 | AAH81229 | 51703601 | Unknown (protein for MGC: 85456) [*Xenopus laevis*] |
| 111 | P22418 | 3915687 | Fructose-1,6-bisphosphatase, chloroplast precursor (D-fructose-1,6-bisphosphate 1-phosphohydrolase) (FBPase) |
| 112 | CAA41154 | 11242 | fructose-bisphosphatase [*Arabidopsis thaliana*] |
| 113 | XP_001. . . | 109112375 | PREDICTED: fructose-1,6-bisphosphatase 1 isoform 1 [*Macaca mulatta*] |
| 114 | P70695 | 76363514 | Fructose-1,6-bisphosphatase isozyme 2 (D-fructose-1,6-bisphosphate 1-phosphohydrolase 2) (FBPase 2) (RAE-30) |
| 115 | CAG08189 | 47221527 | unnamed protein product [*Tetraodon nigroviridis*] |
| 116 | AAI13633 | 109731177 | Fructose-1,6-bisphosphatase 2 [*Homo sapiens*] |
| 117 | 1SPID | 999624 | Chain D, Fructose-1,6-Bisphosphatase (D-Fructose-1,6-Bisphosphate 1-Phosphohydrolase) (E.C.3.1.3.11) |
| 118 | AAF72973 | 8118281 | fructose-1,6-bisphosphatase [*Zaocys dhumnades*] |
| 119 | AAH12720 | 15215255 | Fbp2 protein [*Mus musculus*] |
| 120 | O00757 | 76789651 | Fructose-1,6-bisphosphatase isozyme 2 (D-fructose-1,6-bisphosphate 1-phosphohydrolase 2) (FBPase 2) |
| 121 | XP_827196 | 71745132 | fructose-1,6-bisphosphate cytosolic [*Trypanosoma brucei* TREU927] |
| 122 | Q9Z1N1 | 76364186 | Fructose-1,6-bisphosphatase isozyme 2 (D-fructose-1,6-bisphosphate 1-phosphohydrolase 2) (FBPase 2) |
| 123 | BAE40306 | 74212301 | unnamed protein product [*Mus musculus*] |
| 124 | CAC70747 | 15718373 | fructose-1,6-bisphosphatase [*Trypanosoma brucei*] |
| 125 | NP_032020 | 6679761 | fructose bisphosphatase 2 [*Mus musculus*] |
| 126 | AAP79192 | 32307574 | fructose-1,6 bisphosphatase [*Bigelowiella natans*] |
| 127 | ZP_010. . . | 86130901 | fructose-1,6-bisphosphatase [*Cellulophaga* sp. MED134] |
| 128 | YP_422024 | 83311760 | Fructose-1,6-bisphosphatase [*Magnetospirillum magneticum* AMB-1] |
| 129 | YP_679484 | 110639275 | fructose-1,6-bisphosphatase [*Cytophaga hutchinsonii* ATCC 33406] |
| 130 | ZP_000. . . | 23014308 | COG0158: Fructose-1,6-bisphosphatase [*Magnetospirillum magnetotacticum* MS-1] |
| 131 | XP_888627 | 76363832 | *Leishmania major* strain Friedlin cytosolic fructose-1,6-bisphosphatase [*Leishmania major* strain Friedlin] |
| 132 | ZP_009. . . | 83855881 | fructose-1,6-bisphosphatase [*Croceibacter atlanticus* HTCC2559] |
| 133 | YP_437516 | 83649081 | Fructose-1,6-bisphosphatase [*Hahella chejuensis* KCTC 2396] |
| 134 | ZP_011. . . | 88711300 | fructose-1,6-bisphosphatase [*Flavobacteriales bacterium* HTCC2170] |
| 135 | CAC82800 | 16519317 | fructose 1,6-bisphosphatase [*Galdieria sulphuraria*] |
| 136 | ZP_012. . . | 91215105 | fructose-1,6-bisphosphatase [*Psychroflexus torquis* ATCC 700755] |
| 137 | ZP_012. . . | 90591576 | Inositol phosphatase/fructose-1,6-bisphosphatase [*Flavobacterium johnsoniae* UW101] |
| 138 | XP_793452 | 72046390 | PREDICTED: similar to fructose-1,6-bisphosphatase 1, like [*Strongylocentrotus purpuratus*] |
| 139 | CAJ72223 | 91202584 | strongly similar to fructose-1,6-bisphosphatase [*Candidatus Kuenenia stuttgartiensis*] |
| 140 | ZP_011. . . | 88804197 | fructose-1,6-bisphosphatase [*Robiginitalea biformata* HTCC2501] |
| 141 | YP_445598 | 83815956 | fructose-1,6-bisphosphatase [*Salinibacter ruber* DSM 13855] |
| 142 | ZP_007. . . | 75815977 | COG0158: Fructose-1,6-bisphosphatase [*Vibrio cholerae* V52] |
| 143 | ZP_011. . . | 88802508 | fructose-1,6-bisphosphatase [*Polaribacter irgensii* 23-P] |
| 144 | ZP_007. . . | 75827798 | COG0158: Fructose-1,6-bisphosphatase [*Vibrio cholerae* O395] |
| 145 | ZP_011. . . | 88797163 | Fructose-1,6-bisphosphatase [*Reinekea* sp. MED297] |
| 146 | ZP_005. . . | 68553442 | Inositol phosphatase/fructose-1,6-bisphosphatase [*Prosthecochloris aestuarii* DSM 271] |

TABLE 47-continued

Examples of Fructose 1,6 bisphosphatase polypeptides.

| Row | ACCESSION | GI | PROTEIN DESCRIPTION |
|---|---|---|---|
| 147 | ZP_007... | 75830525 | COG0158: Fructose-1,6-bisphosphatase [*Vibrio cholerae* MO10] |
| 148 | Q42796 | 2494415 | Fructose-1,6-bisphosphatase, chloroplast precursor (D-fructose-1,6-bisphosphate 1-phosphohydrolase) (FBPase) |
| 149 | ZP_007... | 75822783 | COG0158: Fructose-1,6-bisphosphatase [*Vibrio cholerae* RC385] |
| 150 | NP_933227 | 37678618 | fructose-1,6-bisphosphatase [*Vibrio vulnificus* YJ016] |
| 151 | XP_812636 | 71423971 | fructose-1,6-bisphosphatase, cytosolic [*Trypanosoma cruzi* strain CL Brener] |
| 152 | ZP_006... | 71480926 | Inositol phosphatase/fructose-1,6-bisphosphatase [*Prosthecochloris vibrioformis* DSM 265] |
| 153 | ZP_007... | 75854570 | COG0158: Fructose-1,6-bisphosphatase [*Vibrio* sp. Ex25] |
| 154 | NP_931714 | 37528369 | fructose-1,6-bisphosphatase [*Photorhabdus luminescens* subsp. *laumondii* TTO1] |
| 155 | XP_805839 | 71406635 | fructose-1,6-bisphosphatase, cytosolic [*Trypanosoma cruzi* strain CL Brener] |
| 156 | YP_374392 | 78186349 | fructose-1,6-bisphosphatase [*Pelodictyon luteolum* DSM 273] |
| 157 | NP_902097 | 34497882 | fructose-1,6-bisphosphatase [*Chromobacterium violaceum* ATCC 12472] |
| 158 | XP_646323 | 66825937 | D-fructose-1,6-bisphosphate 1-phosphohydrolase [*Dictyostelium discoideum* AX4] |
| 159 | ZP_010... | 86147594 | fructose-1,6-bisphosphatase [*Vibrio* sp. MED222] |
| 160 | NP_796691 | 28897086 | fructose-1,6-bisphosphatase [*Vibrio parahaemolyticus* RIMD 2210633] |
| 161 | YP_052014 | 50122847 | fructose-1,6-bisphosphatase [*Erwinia carotovora* subsp. *atroseptica* SCRI1043] |
| 162 | ZP_007... | 77634762 | COG0158: Fructose-1,6-bisphosphatase [*Yersinia pestis* Angola] |
| 163 | ZP_012... | 90406722 | fructose-1,6-bisphosphatase [*Psychromonas* sp. CNPT3] |
| 164 | ZP_006... | 71549000 | Inositol phosphatase/fructose-1,6-bisphosphatase [*Nitrosomonas eutropha* C71] |
| 165 | ZP_013... | 106882698 | Inositol phosphatase/fructose-1,6-bisphosphatase [*Psychromonas ingrahamii* 37] |
| 166 | ZP_008... | 77973994 | COG0158: Fructose-1,6-bisphosphatase [*Yersinia frederiksenii* ATCC 33641] |
| 167 | ZP_012... | 90411963 | fructose-1,6-bisphosphatase [*Photobacterium profundum* 3TCK] |
| 168 | ZP_005... | 67938188 | Inositol phosphatase/fructose-1,6-bisphosphatase [*Chlorobium phaeobacteroides* BS1] |
| 169 | NP_991956 | 45440417 | fructose-1,6-bisphosphatase [*Yersinia pestis* biovar Microtus str. 91001] |
| 170 | NP_840606 | 30248536 | fructose-1,6-bisphosphatase [*Nitrosomonas europaea* ATCC 19718] |
| 171 | YP_649191 | 108813424 | fructose-1,6-bisphosphatase [*Yersinia pestis* Nepal516] |
| 172 | ZP_010... | 86134593 | fructose-1,6-bisphosphatase [*Tenacibaculum* sp. MED152] |
| 173 | ZP_012... | 94268582 | Inositol phosphatase/fructose-1,6-bisphosphatase [delta proteobacterium MLMS-1] |
| 174 | ZP_012... | 94264279 | Inositol phosphatase/fructose-1,6-bisphosphatase [delta proteobacterium MLMS-1] |
| 175 | ZP_005... | 67919158 | Inositol phosphatase/fructose-1,6-bisphosphatase [*Chlorobium limicola* DSM 245] |
| 176 | NP_661262 | 21673197 | fructose-1,6-bisphosphatase [*Chlorobium tepidum* TLS] |
| 177 | YP_128618 | 54307598 | fructose-1,6-bisphosphatase [*Photobacterium profundum* SS9] |
| 178 | YP_378918 | 78188580 | fructose-1,6-bisphosphatase [*Chlorobium chlorochromatii* CaD3] |
| 179 | ZP_005... | 68551142 | Inositol phosphatase/fructose-1,6-bisphosphatase [*Pelodictyon phaeoclathratiforme* BU-1] |
| 180 | YP_445968 | 83814754 | fructose-1,6-bisphosphatase [*Salinibacter ruber* DSM 13855] |
| 181 | ZP_012... | 90580816 | fructose-1,6-bisphosphatase [*Vibrio angustum* S14] |
| 182 | ZP_011... | 89075542 | fructose-1,6-bisphosphatase [*Photobacterium* sp. SKA34] |
| 183 | YP_342093 | 77163568 | fructose-1,6-bisphosphatase [*Nitrosococcus oceani* ATCC 19707] |
| 184 | ZP_009... | 84387793 | fructose-1,6-bisphosphatase [*Vibrio splendidus* 12B01] |
| 185 | ZP_010... | 86141292 | fructose-1,6-bisphosphatase [*Flavobacterium* sp. MED217] |
| 186 | ZP_005... | 67937321 | Inositol phosphatase/fructose-1,6-bisphosphatase [*Chlorobium phaeobacteroides* DSM 266] |
| 187 | ZP_012... | 91228829 | fructose-1,6-bisphosphatase [*Vibrio alginolyticus* 12G01] |
| 188 | ZP_008... | 77961846 | COG0158: Fructose-1,6-bisphosphatase [*Yersinia mollaretii* ATCC 43969] |
| 189 | ZP_008... | 77977605 | COG0158: Fructose-1,6-bisphosphatase [*Yersinia intermedia* ATCC 29909] |
| 190 | YP_203647 | 59710871 | fructose-1,6-bisphosphatase [*Vibrio fischeri* ES114] |
| 191 | ZP_013... | 110596824 | Inositol phosphatase/fructose-1,6-bisphosphatase [*Chlorobium ferrooxidans* DSM 13031] |
| 192 | YP_454036 | 85058334 | fructose-1,6-bisphosphatase [*Sodalis glossinidius* str. 'morsitans'] |

TABLE 47-continued

| Examples of Fructose 1,6 bisphosphatase polypeptides. | | | |
|---|---|---|---|
| Row | ACCESSION | GI | PROTEIN DESCRIPTION |
| 193 | ZP_001... | 32035025 | COG0158: Fructose-1,6-bisphosphatase [*Actinobacillus pleuropneumoniae* serovar 1 str. 4074] |
| 194 | YP_011058 | 46580250 | fructose-1,6-bisphosphatase [*Desulfovibrio vulgaris* subsp. *vulgaris* str. Hildenborough] |
| 195 | YP_219276 | 62182859 | fructose-1,6-bisphosphatase [*Salmonella enterica* subsp. *enterica* serovar Choleraesuis str. SC-B67] |
| 196 | YP_560077 | 91784871 | Inositolphosphatase/fructose-1,6-bisphosphatase [*Burkholderia xenovorans* LB400] |
| 197 | YP_316335 | 74318595 | fructose-1,6-bisphosphatase [*Thiobacillus denitrificans* ATCC 25259] |
| 198 | YP_388561 | 78357112 | fructose-1,6-bisphosphatase [*Desulfovibrio desulfuricans* G20] |
| 199 | NP_313236 | 15834463 | fructose-1,6-bisphosphatase [*Escherichia coli* O157:H7 str. Sakai] |
| 200 | YP_313128 | 74314709 | fructose-bisphosphatase [*Shigella sonnei* Ss046] |
| 201 | ZP_011... | 88801533 | fructose-1,6-bisphosphatase [*Polaribacter irgensii* 23-P] |

TABLE 53

| Examples of squalene epoxidase polypeptides | | | |
|---|---|---|---|
| Row | ACCESSION | GI | PROTEIN DESCRIPTION |
| 1 | XP_503994 | 50553168 | hypothetical protein [*Yarrowia lipolytica*]. |
| 2 | EAS30670 | 90301039 | hypothetical protein CIMG_06149 [*Coccidioides immitis* RS] |
| 3 | XP_753858 | 70998268 | squalene monooxygenase Erg1 [*Aspergillus fumigatus* Af293] |
| 4 | XP_711894 | 68488538 | squalene epoxidase [*Candida albicans* SC5314] |
| 5 | ABD48706 | 88697124 | squalene epoxidase [*Emericella nidulans*] |
| 6 | XP_681020 | 67901528 | hypothetical protein AN7751.2 [*Aspergillus nidulans* FGSC A4] |
| 7 | AAQ18215 | 33415411 | squalene epoxidase [*Trichophyton rubrum*] |
| 8 | BAE62359 | 83772229 | unnamed protein product [*Aspergillus oryzae*] |
| 9 | AAQ18216 | 61807216 | squalene epoxidase [*Trichophyton rubrum*] |
| 10 | AAZ08563 | 70797544 | squalene epoxidase [*Trichophyton rubrum*] |
| 11 | CAJ18281 | 90185988 | squalene epoxidase [*Hypocrea lixii*] |
| 12 | XP_462160 | 50427105 | hypothetical protein DEHA0G15202g [*Debaryomyces hansenii* CBS767] |
| 13 | NP_011691 | 6321614 | Squalene epoxidase, catalyzes the epoxidation of squalene to 2,3-oxidosqualene; plays an essential role in the ergosterol-biosynthesis pathway and is the specific target of the antifungal drug terbinafine; Erg1p [*Saccharomyces cerevisiae*] |
| 14 | AAA34592 | 171471 | squalene epoxidase |
| 15 | O13306 | 51704232 | Squalene monooxygenase (Squalene epoxidase) (SE) |
| 16 | XP_455763 | 50311477 | unnamed protein product [*Kluyveromyces lactis*] |
| 17 | XP_386391 | 46123675 | hypothetical protein FG06215.1 [*Gibberella zeae* PH-1] |
| 18 | EAQ88139 | 88180671 | hypothetical protein CHGG_04758 [*Chaetomium globosum* CBS 148.51] |
| 19 | XP_961806 | 85104779 | hypothetical protein [*Neurospora crassa* OR74A] |
| 20 | XP_758545 | 71012984 | hypothetical protein UM02398.1 [*Ustilago maydis* 521] |
| 21 | XP_369325 | 39975869 | hypothetical protein MG06139.4 [*Magnaporthe grisea* 70-15] |
| 22 | XP_570092 | 58265872 | squalene monooxygenase [*Cryptococcus neoformans* var. *neoformans* JEC21] |
| 23 | Q9C1W3 | 51701448 | Probable squalene monooxygenase (Squalene epoxidase) (SE) |
| 24 | EAT79729 | 111058609 | hypothetical protein SNOG_12929 [*Phaeosphaeria nodorum* SN15] |
| 25 | CAG38355 | 108743007 | squalene epoxidase [*Aspergillus niger*] |
| 26 | BAE73094 | 84579321 | hypothetical protein [*Macaca fascicularis*] |
| 27 | EAU31524 | 114189824 | hypothetical protein ATEG_08351 [*Aspergillus terreus* NIH2624] |
| 28 | NP_003120 | 62865635 | squalene monooxygenase [*Homo sapiens*] |
| 29 | CAI46076 | 57997512 | hypothetical protein [*Homo sapiens*] |
| 30 | BAE37374 | 74200967 | unnamed protein product [*Mus musculus*] |
| 31 | XP_850640 | 73974448 | PREDICTED: similar to squalene monooxygenase isoform 1 [*Canis familiaris*] |
| 32 | Q75F69 | 51701415 | Squalene monooxygenase (Squalene epoxidase) (SE) |
| 33 | AAS60234 | 45388098 | squalene epoxidase 1 [*Aspergillus fumigatus*] |
| 34 | Q14534 | 12644414 | Squalene monooxygenase (Squalene epoxidase) (SE) |
| 35 | XP_001... | 109087424 | PREDICTED: similar to squalene monooxygenase [*Macaca mulatta*] |
| 36 | AAH97330 | 66911977 | Sqle protein [*Rattus norvegicus*] |
| 37 | EAU30782 | 114189082 | hypothetical protein ATEG_08650 [*Aspergillus terreus* NIH2624] |
| 38 | CAF98057 | 47218525 | unnamed protein product [*Tetraodon nigroviridis*] |
| 39 | XP_861944 | 73974450 | PREDICTED: similar to squalene monooxygenase isoform 2 [*Canis familiaris*] |
| 40 | ABF94794 | 108706999 | Squalene monooxygenase, putative, expressed [*Oryza sativa* (*japonica* cultivar-group)] |

TABLE 53-continued

| Examples of squalene epoxidase polypeptides | | | |
|---|---|---|---|
| Row | ACCESSION | GI | PROTEIN DESCRIPTION |
| 41 | BAF11377 | 113547934 | Os03g0231800 [*Oryza sativa* (*japonica* cultivar-group)] |
| 42 | XP_470614 | 50920507 | Putative Squalene monooxygenase [*Oryza sativa* (*japonica* cultivar-group)] |
| 43 | ABF94791 | 108706996 | Squalene monooxygenase, putative, expressed [*Oryza sativa* (*japonica* cultivar-group)] |
| 44 | AAM61384 | 21537043 | squalene epoxidase-like protein [*Arabidopsis thaliana*] |
| 45 | BAE98940 | 110742002 | hypothetical protein [*Arabidopsis thaliana*] |
| 46 | ABE84801 | 92877833 | Helix-turn-helix, AraC type; NAD-binding site; Fumarate lyase [*Medicago truncatula*] |
| 47 | BAE36598 | 74183459 | unnamed protein product [*Mus musculus*] |
| 48 | XP_693698 | 68403773 | PREDICTED: similar to squalene monooxygenase [*Danio rerio*] |
| 49 | CAB80441 | 7270759 | squalene epoxidase-like protein [*Arabidopsis thaliana*] |
| 50 | O48651 | 6685403 | Squalene monooxygenase (Squalene epoxidase) (SE) |
| 51 | AAY22200 | 62945915 | squalene monooxygenase [*Datura innoxia*] |
| 52 | BAD15330 | 46359651 | squalene epoxidase [*Panax ginseng*] |
| 53 | CAD23248 | 27475610 | squalene monooxygenase 2 [*Medicago truncatula*] |
| 54 | ABC94943 | 86371770 | squalene epoxidase [*Medicago sativa*] |
| 55 | CAD23249 | 27475612 | squalene monooxygenase 1 [*Medicago truncatula*] |
| 56 | AAN15558 | 23198062 | squalene monooxygenase, putative [*Arabidopsis thaliana*] |
| 57 | NP_179868 | 15227757 | oxidoreductase [*Arabidopsis thaliana*] |
| 58 | AAG50645 | 12321049 | squalene monooxygenase, putative [*Arabidopsis thaliana*] |
| 59 | XP_629022 | 66800193 | hypothetical protein DDBDRAFT_0192021 [*Dictyostelium discoideum* AX4] |
| 60 | CAK11466 | 94733753 | novel protein similar to vertebrate squalene epoxidase (SQLE) [*Danio rerio*] |
| 61 | AAQ13595 | 33337947 | putative squalene epoxidase [*Lycopersicon esculentum*] |
| 62 | ABF94792 | 108706997 | Squalene monooxygenase, putative, expressed [*Oryza sativa* (*japonica* cultivar-group)] |
| 63 | XP_604908 | 76660360 | PREDICTED: similar to squalene monooxygenase [*Bos taurus*] |
| 64 | BAA11209 | 1483186 | squalene epoxidase [*Homo sapiens*] |
| 65 | NP_197803 | 15237902 | SQP1 [*Arabidopsis thaliana*] |
| 66 | NP_001... | 79328611 | SQP1 [*Arabidopsis thaliana*] |
| 67 | CAA06772 | 3123331 | squalene epoxidase homologue [*Arabidopsis thaliana*] |
| 68 | O65726 | 6685410 | Squalene monooxygenase 1,2 (Squalene epoxidase 1,2) (SE 1,2) |
| 69 | O65727 | 6685411 | Squalene monooxygenase 1,1 (Squalene epoxidase 1,1) (SE 1,1) |
| 70 | NP_197804 | 15237903 | oxidoreductase [*Arabidopsis thaliana*] |
| 71 | CAJ03182 | 68125205 | squalene monooxygenase-like protein [*Leishmania major*] |
| 72 | NP_197802 | 15237900 | SQP2; oxidoreductase [*Arabidopsis thaliana*] |
| 73 | XP_828409 | 71754989 | squalene monooxygenase [*Trypanosoma brucei* TREU927] |
| 74 | XP_808343 | 71412304 | squalene monooxygenase [*Trypanosoma cruzi* strain CL Brener] |
| 75 | XP_789059 | 72038634 | PREDICTED: similar to squalene monooxygenase [*Strongylocentrotus purpuratus*] |
| 76 | XP_796297 | 72133073 | PREDICTED: similar to squalene monooxygenase [*Strongylocentrotus purpuratus*] |
| 77 | AAB69189 | 2352528 | squalene epoxidase [*Candida glabrata*] |
| 78 | XP_813434 | 71649420 | squalene monooxygenase [*Trypanosoma cruzi* strain CL Brener] |
| 79 | XP_796261 | 72133071 | PREDICTED: similar to squalene monooxygenase [*Strongylocentrotus purpuratus*] |
| 80 | XP_793783 | 72114550 | PREDICTED: similar to squalene monooxygenase, partial [*Strongylocentrotus purpuratus*] |
| 81 | XP_789028 | 72038632 | PREDICTED: similar to squalene xygenase [*Strongylocentrotus purpuratus*] |
| 82 | AAT97087 | 51105054 | squalene epoxidase-like protein [*Lymnaea stagnalis*] |
| 83 | XP_804343 | 71402993 | squalene monooxygenase [*Trypanosoma cruzi* strain CL Brener] |
| 84 | YP_115265 | 53803024 | monooxygenase family protein [*Methylococcus capsulatus* str. Bath] |
| 85 | AAM91177 | 22136198 | unknown protein [*Arabidopsis thaliana*] |
| 86 | XP_799134 | 72026766 | PREDICTED: similar to Squalene monooxygenase (Squalene epoxidase) (SE), partial [*Strongylocentrotus purpuratus*] |

TABLE 54

| Examples of ERG1 polypeptides. | | | |
|---|---|---|---|
| Row | ACCESSION | GI | PROTEIN DESCRIPTION |
| 1 | AAA34592 | 171471 | squalene epoxidase |
| 2 | O13306 | 51704232 | Squalene monooxygenase (Squalene epoxidase) (SE) |
| 3 | XP_455763 | 50311477 | unnamed protein product [*Kluyveromyces lactis*] |
| 4 | Q75F69 | 51701415 | Squalene monooxygenase (Squalene epoxidase) (SE) |
| 5 | XP_462160 | 50427105 | hypothetical protein DEHA0G15202g [*Debaryomyces hansenii* CBS767] |
| 6 | XP_711894 | 68488538 | squalene epoxidase [*Candida albicans* SC5314] |
| 7 | XP_503994 | 50553168 | hypothetical protein [*Yarrowia lipolytica*] |
| 8 | AAB69189 | 2352528 | squalene epoxidase [*Candida glabrata*] |

TABLE 54-continued

Examples of ERG1 polypeptides.

| Row | ACCESSION | GI | PROTEIN DESCRIPTION |
|---|---|---|---|
| 9 | AAQ18215 | 33415411 | squalene epoxidase [*Trichophyton rubrum*] |
| 10 | AAQ18216 | 61807216 | squalene epoxidase [*Trichophyton rubrum*] |
| 11 | AAZ08563 | 70797544 | squalene epoxidase [*Trichophyton rubrum*] |
| 12 | EAS30670 | 90301039 | hypothetical protein CIMG_06149 [*Coccidioides immitis* RS] |
| 13 | Q9C1W3 | 51701448 | Probable squalene monooxygenase (Squalene epoxidase) (SE) |
| 14 | XP_758545 | 71012984 | hypothetical protein UM02398.1 [*Ustilago maydis* 521] |
| 15 | XP_681020 | 67901528 | hypothetical protein AN7751.2 [*Aspergillus nidulans* FGSC A4] |
| 16 | ABD48706 | 88697124 | squalene epoxidase [*Emericella nidulans*] |
| 17 | BAE62359 | 83772229 | unnamed protein product [*Aspergillus oryzae*] |
| 18 | XP_753858 | 70998268 | squalene monooxygenase Erg1 [*Aspergillus fumigatus* Af293] |
| 19 | XP_961806 | 85104779 | hypothetical protein [*Neurospora crassa* OR74A] |
| 20 | XP_386391 | 46123675 | hypothetical protein FG06215.1 [*Gibberella zeae* PH-1] |
| 21 | CAJ18281 | 90185988 | squalene epoxidase [*Hypocrea lixii*] |
| 22 | BAE73094 | 84579321 | hypothetical protein [*Macaca fascicularis*] |
| 23 | BAE37374 | 74200967 | unnamed protein product [*Mus musculus*] |
| 24 | XP_570092 | 58265872 | squalene monooxygenase [*Cryptococcus neoformans* var. *neoformans* JEC21] |
| 25 | NP_003120 | 62865635 | squalene monooxygenase [*Homo sapiens*] |
| 26 | EAT79729 | 111058609 | hypothetical protein SNOG_12929 [*Phaeosphaeria nodorum* SN15] |
| 27 | AAH97330 | 66911977 | Sqle protein [*Rattus norvegicus*] |
| 28 | CAI46076 | 57997512 | hypothetical protein [*Homo sapiens*] |
| 29 | CAF98057 | 47218525 | unnamed protein product [*Tetraodon nigroviridis*] |
| 30 | XP_850640 | 73974448 | PREDICTED: similar to squalene monooxygenase isoform 1 [*Canis familiaris*] |
| 31 | XP_369325 | 39975869 | hypothetical protein MG06139.4 [*Magnaporthe grisea* 70-15] |
| 32 | Q14534 | 12644414 | Squalene monooxygenase (Squalene epoxidase) (SE) |
| 33 | XP_001. . . | 109087424 | PREDICTED: similar to squalene monooxygenase [*Macaca mulatta*] |
| 34 | EAQ88139 | 88180671 | hypothetical protein CHGG_04758 [*Chaetomium globosum* CBS 148.51] |
| 35 | XP_693698 | 68403773 | PREDICTED: similar to squalene monooxygenase [*Danio rerio*] |
| 36 | CAG38355 | 108743007 | squalene epoxidase [*Aspergillus niger*] |
| 37 | XP_861944 | 73974450 | PREDICTED: similar to squalene monooxygenase isoform 2 [*Canis familiaris*] |
| 38 | XP_519950 | 55631226 | PREDICTED: similar to squalene epoxidase [*Pan troglodytes*] |
| 39 | AAS60234 | 45388098 | squalene epoxidase 1 [*Aspergillus fumigatus*] |
| 40 | XP_629022 | 66800193 | hypothetical protein DDBDRAFT_0192021 [*Dictyostelium discoideum* AX4] |
| 41 | CAK11466 | 94733753 | novel protein similar to vertebrate squalene epoxidase (SQLE) [*Danio rerio*] |
| 42 | BAE98940 | 110742002 | hypothetical protein [*Arabidopsis thaliana*] |
| 43 | AAM61384 | 21537043 | squalene epoxidase-like protein [*Arabidopsis thaliana*] |
| 44 | ABC94943 | 86371770 | squalene epoxidase [*Medicago sativa*] |
| 45 | CAB80441 | 7270759 | squalene epoxidase-like protein [*Arabidopsis thaliana*] |
| 46 | CAD23248 | 27475610 | squalene monooxygenase 2 [*Medicago truncatula*] |
| 47 | BAE36598 | 74183459 | unnamed protein product [*Mus musculus*] |
| 48 | AAQ13595 | 33337947 | putative squalene epoxidase [*Lycopersicon esculentum*] |
| 49 | AAY22200 | 62945915 | squalene monooxygenase [*Datura innoxia*] |
| 50 | ABF94791 | 108706996 | Squalene monooxygenase, putative, expressed [*Oryza sativa* (*japonica* cultivar-group)] |
| 51 | AAN15558 | 23198062 | squalene monooxygenase, putative [*Arabidopsis thaliana*] |
| 52 | ABF94794 | 108706999 | Squalene monooxygenase, putative, expressed [*Oryza sativa* (*japonica* cultivar-group)] |
| 53 | XP_470614 | 50920507 | Putative Squalene monooxygenase [*Oryza sativa* (*japonica* cultivar-group)] |
| 54 | BAF11377 | 113547934 | Os03g0231800 [*Oryza sativa* (*japonica* cultivar-group)] |
| 55 | CAD23249 | 27475612 | squalene monooxygenase 1 [*Medicago truncatula*] |
| 56 | AAG50645 | 12321049 | squalene monooxygenase, putative [*Arabidopsis thaliana*] |
| 57 | NP_179868 | 15227757 | oxidoreductase [*Arabidopsis thaliana*] |
| 58 | ABE84801 | 92877833 | Helix-turn-helix, AraC type; NAD-binding site; Fumarate lyase [*Medicago truncatula*] |
| 59 | ABF94792 | 108706997 | Squalene monooxygenase, putative, expressed [*Oryza sativa* (*japonica* cultivar-group)] |
| 60 | BAA11209 | 1483186 | squalene epoxidase [*Homo sapiens*] |
| 61 | XP_604908 | 76660360 | PREDICTED: similar to squalene monooxygenase [*Bos taurus*] |
| 62 | XP_828409 | 71754989 | squalene monooxygenase [*Trypanosoma brucei* TREU927] |
| 63 | XP_808343 | 71412304 | squalene monooxygenase [*Trypanosoma cruzi* strain CL Brener] |
| 64 | CAJ03182 | 68125205 | squalene monooxygenase-like protein [*Leishmania major*] |
| 65 | O65726 | 6685410 | Squalene monooxygenase 1,2 (Squalene epoxidase 1,2) (SE 1,2) |
| 66 | NP_197804 | 15237903 | oxidoreductase [*Arabidopsis thaliana*] |
| 67 | O65727 | 6685411 | Squalene monooxygenase 1,1 (Squalene epoxidase 1,1) (SE 1,1) |
| 68 | CAA06772 | 3123331 | squalene epoxidase homologue [*Arabidopsis thaliana*] |
| 69 | NP_001. . . | 79328611 | SQP1 [*Arabidopsis thaliana*] |
| 70 | NP_197803 | 15237902 | SQP1 [*Arabidopsis thaliana*] |
| 71 | NP_197802 | 15237900 | SQP2; oxidoreductase [*Arabidopsis thaliana*] |

TABLE 55

Examples of ERG7 polypeptides.

| Row | ACCESSION | GI | PROTEIN DESCRIPTION |
|---|---|---|---|
| 1 | AAT93062 | 51013537 | YHR072W [*Saccharomyces cerevisiae*] |
| 2 | AAA16975 | 465105 | lanosterol synthase |
| 3 | XP_448182 | 50291499 | unnamed protein product [*Candida glabrata*] |
| 4 | XP_451982 | 50304065 | unnamed protein product [*Kluyveromyces lactis*] |
| 5 | NP_987017 | 45201447 | AGR351Wp [*Eremothecium gossypii*] |
| 6 | XP_457937 | 50418833 | hypothetical protein DEHA0C06501g [*Debaryomyces hansenii* CBS767] |
| 7 | XP_722471 | 68467112 | 2,3-oxidosqualene-lanosterol cyclase [*Candida albicans* SC5314] |
| 8 | XP_722612 | 68466833 | 2,3-oxidosqualene-lanosterol cyclase [*Candida albicans* SC5314] |
| 9 | 1903190A | 383419 | oxidosqualene cyclase |
| 10 | XP_504990 | 50555163 | hypothetical protein [*Yarrowia lipolytica*] |
| 11 | AAB08472 | 1549343 | inactive oxidosqualene-lansoterol cyclase [*Saccharomyces cerevisiae*] |
| 12 | Q96WJ0 | 30913110 | Lanosterol synthase (Oxidosqualene--lanosterol cyclase) (2,3-epoxysqualene--lanosterol cyclase) (OSC) |
| 13 | XP_747936 | 70984860 | oxidosqualene:lanosterol cyclase [*Aspergillus fumigatus* Af293] |
| 14 | BAE61626 | 83771494 | unnamed protein product [*Aspergillus oryzae*] |
| 15 | NP_593702 | 63054562 | lanosterol synthase activity [*Schizosaccharomyces pombe* 972h-] |
| 16 | XP_758387 | 71010409 | hypothetical protein UM02240.1 [*Ustilago maydis* 521] |
| 17 | XP_681529 | 67902546 | hypothetical protein AN8260.2 [*Aspergillus nidulans* FGSC A4] |
| 18 | EAS37438 | 90307807 | hypothetical protein CIMG_02792 [*Coccidioides immitis* RS] |
| 19 | XP_961026 | 85100788 | lanosterol synthase related protein [MIPS] [*Neurospora crassa* OR74A] |
| 20 | XP_751627 | 70993560 | oxidosqualene:lanosterol cyclase [*Aspergillus fumigatus* Af293] |
| 21 | EAQ86439 | 88178971 | hypothetical protein CHGG_07692 [*Chaetomium globosum* CBS 148.51] |
| 22 | XP_386126 | 46123145 | hypothetical protein FG05950.1 [*Gibberella zeae* PH-1] |
| 23 | BAE63415 | 83773288 | unnamed protein product [*Aspergillus oryzae*] |
| 24 | EAS31167 | 90301536 | hypothetical protein CIMG_06646 [*Coccidioides immitis* RS] |
| 25 | EAT81661 | 111060541 | hypothetical protein SNOG_11162 [*Phaeosphaeria nodorum* SN15] |
| 26 | XP_570450 | 58266588 | lanosterol synthase [*Cryptococcus neoformans* var. *neoformans* JEC21] |
| 27 | AAL56020 | 18028346 | oxidosqualene:lanosterol cyclase [*Cephalosporium caerulens*] |
| 28 | BAC37102 | 26346907 | unnamed protein product [*Mus musculus*] |
| 29 | Q8BLN5 | 62286881 | Lanosterol synthase (Oxidosqualene--lanosterol cyclase) (2,3-epoxysqualene--lanosterol cyclase) (OSC) |
| 30 | XP_001... | 109065021 | PREDICTED: lanosterol synthase isoform 2 [*Macaca mulatta*] |
| 31 | 1W6KA | 56966682 | Chain A, Structure Of Human Osc In Complex With Lanosterol |
| 32 | BAC31739 | 26336108 | unnamed protein product [*Mus musculus*] |
| 33 | XP_646246 | 66825783 | hypothetical protein DDB_0191311 [*Dictyostelium discoideum* AX4] |
| 34 | AAF80384 | 8886139 | cycloartenol synthase [*Dictyostelium discoideum*] |
| 35 | CAB42828 | 4808278 | lanosterol synthase [*Homo sapiens*] |
| 36 | 1W6JA | 56966681 | Chain A, Structure Of Human Osc In Complex With Ro 48-8071 |
| 37 | BAA08208 | 639865 | 2,3-oxidosqualene:lanosterol cyclase [*Rattus norvegicus*] |
| 38 | NP_112311 | 13591981 | lanosterol synthase [*Rattus norvegicus*] |
| 39 | NP_001... | 114053041 | lanosterol synthase (2,3-oxidosqualene-lanosterol cyclase) [*Bos taurus*] |
| 40 | P48450 | 62296496 | Lanosterol synthase (Oxidosqualene--lanosterol cyclase) (2,3-epoxysqualene--lanosterol cyclase) (OSC) |
| 41 | NP_001... | 57529773 | lanosterol synthase (2,3-oxidosqualene-lanosterol cyclase) [*Gallus gallus*] |
| 42 | XP_751356 | 70993016 | oxidosqualene cyclase [*Aspergillus fumigatus* Af293] |
| 43 | CAG08284 | 47222029 | unnamed protein product [*Tetraodon nigroviridis*] |
| 44 | BAB83085 | 18147590 | cycloartenol synthase [*Betula platyphylla*] |
| 45 | BAA76902 | 4589852 | cycloartenol synthase [*Glycyrrhiza glabra*] |
| 46 | BAE61719 | 83771588 | unnamed protein product [*Aspergillus oryzae*] |
| 47 | BAA33460 | 3688598 | Cycloartenol Synthase [*Panax ginseng*] |
| 48 | XP_001... | 109065023 | PREDICTED: lanosterol synthase isoform 1 [*Macaca mulatta*] |
| 49 | BAD34644 | 50896401 | cycloartenol synthase [*Cucurbita pepo*] |
| 50 | BAA85266 | 6045133 | cycloartenol synthase [*Luffa aegyptiaca*] |
| 51 | BAB83253 | 18147771 | cycloartenol synthase [*Costus speciosus*] |
| 52 | ABB76767 | 82468805 | cycloartenol synthase [*Ricinus communis*] |
| 53 | BAA23533 | 2627181 | cycloartenol synthase [*Pisum sativum*] |
| 54 | BAD34645 | 50896403 | cucurbitadienol synthase [*Cucurbita pepo*] |
| 55 | BAE53431 | 83016479 | cycloartenol synthase [*Lotus japonicus*] |
| 56 | AAS83469 | 46242746 | cycloartenol synthase [*Bupleurum kaoi*] |
| 57 | A49398 | 541855 | cycloartenol synthase (EC 5.4.99.8) - *Arabidopsis thaliana* |
| 58 | AAN64509 | 24796994 | At2g07050/T4E14.16 [*Arabidopsis thaliana*] |
| 59 | BAD34646 | 50896405 | putative oxidosqualene cyclase [*Cucurbita pepo*] |
| 60 | AAC04931 | 452446 | cycloartenol synthase; (S)-2,3-epoxysqualene mutase [*Arabidopsis thaliana*] |
| 61 | BAE95408 | 108743265 | lanosterol synthase [*Arabidopsis thaliana*] |
| 62 | AAG44096 | 12004573 | cycloartenol synthase [*Abies magnifica*] |
| 63 | AAS01524 | 41387168 | cycloartenol synthase [*Centella asiatica*] |
| 64 | BAB83086 | 18147592 | cycloartenol synthase [*Betula platyphylla*] |
| 65 | AAF03375 | 6090879 | putative cycloartenol synthase [*Oryza sativa*] |
| 66 | BAF07762 | 113535379 | Os02g0139700 [*Oryza sativa* (*japonica* cultivar-group)] |
| 67 | BAE95410 | 108743269 | lanosterol synthase [*Lotus japonicus*] |
| 68 | AAK82995 | 15076959 | lanosterol synthase [*Trypanosoma cruzi*] |
| 69 | XP_820967 | 71668047 | lanosterol synthase [*Trypanosoma cruzi* strain CL Brener] |
| 70 | BAA85267 | 6045135 | oxidosqualene cyclase [*Luffa aegyptiaca*] |
| 71 | NP_190099 | 42565553 | catalytic/lyase [*Arabidopsis thaliana*] |
| 72 | AAT38889 | 47834383 | cycloartenol synthase [*Avena longiglumis*] |

TABLE 55-continued

Examples of ERG7 polypeptides.

| Row | ACCESSION | GI | PROTEIN DESCRIPTION |
|---|---|---|---|
| 73 | BAA86933 | 6456469 | oxidosqualene cyclase [*Taraxacum officinale*] |
| 74 | AAT38891 | 47834387 | cycloartenol synthase [*Avena strigosa*] |
| 75 | CAC84559 | 15866702 | cycloartenol synthase [*Avena strigosa*] |
| 76 | AAT38890 | 47834385 | cycloartenol synthase [*Avena prostrata*] |
| 77 | AAT38888 | 47834381 | cycloartenol synthase [*Avena longiglumis*] |
| 78 | AAT38887 | 47834379 | cycloartenol synthase [*Avena clauda*] |
| 79 | AAT38892 | 47834389 | cycloartenol synthase [*Avena ventricosa*] |
| 80 | XP_819758 | 71665580 | lanosterol synthase [*Trypanosoma cruzi* strain CL Brener] |
| 81 | BAA86930 | 6456434 | lupeol synthase [*Olea europaea*] |
| 82 | CAA61078 | 984145 | lanosterol synthase [*Homo sapiens*] |
| 83 | BAA33462 | 3688602 | Oxidosqualene Cyclase [*Panax ginseng*] |
| 84 | AAG26328 | 11023151 | lanosterol synthase [*Trypanosoma brucei brucei*] |
| 85 | XP_825673 | 71752517 | lanosterol synthase [*Trypanosoma brucei* TREU927] |
| 86 | BAA86932 | 6456467 | lupeol synthase [*Taraxacum officinale*] |
| 87 | CAD23247 | 27475608 | beta-amyrin synthase [*Medicago truncatula*] |
| 88 | BAA97558 | 8918271 | beta-amyrin synthase [*Pisum sativum*] |
| 89 | BAA86931 | 6456465 | cycloartenol synthase [*Olea europaea*] |
| 90 | BAD08587 | 41687978 | lupeol synthase [*Glycyrrhiza glabra*] |
| 91 | BAA84603 | 5922599 | oxidosqualene cyclase [*Allium macrostemon*] |
| 92 | AAO33578 | 28194504 | beta-amyrin synthase [*Medicago truncatula*] |
| 93 | BAB83087 | 18147594 | lupeol synthase [*Betula platyphylla*] |
| 94 | BAB83254 | 18147773 | multifunctional triterpene synthase [*Costus speciosus*] |
| 95 | BAA89815 | 6730969 | beta-amyrin synthase [*Glycyrrhiza glabra*] |
| 96 | BAE53429 | 83016474 | beta-amyrin synthase [*Lotus japonicus*] |
| 97 | AAO33579 | 28194506 | putative beta-amyrin synthase [*Lotus japonicus*] |
| 98 | BAA33461 | 3688600 | beta-Amyrin Synthase [*Panax ginseng*] |
| 99 | CAB72151 | 6911851 | oxidosqualene cyclase-like protein [*Arabidopsis thaliana*] |
| 100 | CAJ02110 | 68124127 | lanosterol synthase, putative [*Leishmania major*] |
| 101 | BAA33722 | 3721856 | beta-Amyrin Synthase [*Panax ginseng*] |
| 102 | AAX14716 | 60203059 | beta-amyrin synthase [*Aster sedifolius*] |
| 103 | BAE53430 | 83016477 | lupeol synthase [*Lotus japonicus*] |
| 104 | ABE91090 | 92892072 | Prenyltransferase/squalene oxidase [*Medicago truncatula*] |
| 105 | XP_681518 | 67902524 | hypothetical protein AN8249.2 [*Aspergillus nidulans* FGSC A4] |
| 106 | AAC17080 | 3152599 | Strong similarity to lupeol synthase gb\|U49919 and cycloartenol synthase gb\|U02555 from *A. thaliana* (the third gene with similar homology). [*Arabidopsis thaliana*] |
| 107 | BAF28067 | 113644926 | Os11g0286800 [*Oryza sativa* (*japonica* cultivar-group)] |
| 108 | NP_683508 | 22330736 | beta-amyrin synthase [*Arabidopsis thaliana*] |
| 109 | AAS83468 | 46242744 | beta-armyrin synthase [*Bupleurum kaoi*] |
| 110 | AAO33580 | 28194508 | multifunctional beta-amyrin synthase [*Lotus japonicus*] |
| 111 | BAE43642 | 73991374 | beta-amyrin synthase [*Euphorbia tirucalli*] |
| 112 | BAB83088 | 18147596 | beta-amyrin synthase [*Betula platyphylla*] |
| 113 | ABB76766 | 82468803 | lupeol synthase [*Ricinus communis*] |
| 114 | ABG22399 | 108864084 | Cycloartenol synthase, putative, expressed [*Oryza sativa* (*japonica* cultivar-group)] |
| 115 | BAF28063 | 113644922 | Os11g0285000 [*Oryza sativa* (*japonica* cultivar-group)] |
| 116 | ABG22398 | 108864083 | Cycloartenol synthase, putative, expressed [*Oryza sativa* (*japonica* cultivar-group)] |
| 117 | NP_849903 | 30699380 | LUP1 (LUPEOL SYNTHASE 1); lupeol synthase [*Arabidopsis thaliana*] |
| 118 | AAB94341 | 2738027 | 2,3-oxidosqualene-triterpenoid cyclase [*Arabidopsis thaliana*] |
| 119 | AAN77001 | 25991999 | 2,3-oxidosqualene-triterpene cyclase [*Arabidopsis thaliana*] |
| 120 | AAT38893 | 47834391 | beta-amyrin synthase [*Avena clauda*] |
| 121 | AAD05032 | 1762150 | lupeol synthase [*Arabidopsis thaliana*] |
| 122 | NP_178017 | 30699377 | ATLUP2; lupeol synthase [*Arabidopsis thaliana*] |
| 123 | ABE88599 | 92887080 | squalene/oxidosqualene cyclases [*Medicago truncatula*] |
| 124 | ABG22449 | 108864253 | Cycloartenol synthase, putative, expressed [*Oryza sativa* (*japonica* cultivar-group)] |
| 125 | BAB68529 | 15787841 | isomultiflorenol synthase [*Luffa aegyptiaca*] |
| 126 | AAT38898 | 47834401 | beta-amyrin synthase [*Avena ventricosa*] |
| 127 | AAT38894 | 47834393 | beta-amyrin synthase [*Avena longiglumis*] |
| 128 | AAT38897 | 47834399 | beta-amyrin synthase [*Avena strigosa*] |
| 129 | NP_178016 | 22330734 | catalytic/lyase [*Arabidopsis thaliana*] |
| 130 | AAT38895 | 47834395 | beta-amyrin synthase [*Avena longiglumis*] |
| 131 | AAT38896 | 47834397 | beta-amyrin synthase [*Avena prostrata*] |
| 132 | BAA97559 | 8918273 | mixed-amyrin synthase [*Pisum sativum*] |
| 133 | AAC98864 | 4090722 | pentacyclic triterpene synthase [*Arabidopsis thaliana*] |
| 134 | BAF28466 | 113645325 | Os11g0562100 [*Oryza sativa* (*japonica* cultivar-group)] |
| 135 | AAG41762 | 11934652 | pentacyclic triterpene synthase [synthetic construct] |
| 136 | XP_480759 | 50942463 | putative Cycloartenol Synthase [*Oryza sativa* (*japonica* cultivar-group)] |
| 137 | BAE43643 | 73991380 | putative oxidosqulene cyclase [*Euphorbia tirucalli*] |
| 138 | AAC17070 | 3152589 | Strong similarity to lupeol synthase gb\|U49919 from *A. thaliana* (second gene in a series of three with similar homologies). [*Arabidopsis thaliana*] |
| 139 | BAD15332 | 46359655 | beta-amyrin synthase [*Panax ginseng*] |
| 140 | AAM23264 | 23428800 | beta-amyrin synthase [*Glycine max*] |
| 141 | ABC33922 | 83638481 | beta-amyrin synthase [*Gypsophila paniculata*] |
| 142 | AAS01523 | 41387158 | putative beta-amyrin synthase [*Centella asiatica*] |

TABLE 55-continued

| Examples of ERG7 polypeptides. | | | |
|---|---|---|---|
| Row | ACCESSION | GI | PROTEIN DESCRIPTION |
| 143 | BAE99758 | 110743847 | cycloartenol synthase [*Arabidopsis thaliana*] |
| 144 | BAB11065 | 10177752 | cycloartenol synthase [*Arabidopsis thaliana*] |
| 145 | NP_177971 | 15218390 | catalytic [*Arabidopsis thaliana*] |
| 146 | CAD39196 | 32526539 | cycloartenol synthase [*Stigmatella aurantiaca*] |
| 147 | ABG22450 | 108864254 | Cycloartenol synthase, putative, expressed [*Oryza sativa* (*japonica* cultivar-group)] |
| 148 | CAA93571 | 1204221 | erg7 [*Schizosaccharomyces pombe*] |
| 149 | NP_567462 | 18414430 | ATPEN1; catalytic/lyase [*Arabidopsis thaliana*] |
| 150 | NP_199612 | 42568386 | catalytic [*Arabidopsis thaliana*] |
| 151 | NP_193272 | 15233798 | catalytic/lyase [*Arabidopsis thaliana*] |
| 152 | ABE88610 | 92887091 | squalene/oxidosqualene cyclases [*Medicago truncatula*] |
| 153 | AAW30034 | 56790234 | At5g42600 [*Arabidopsis thaliana*] |
| 154 | BAF01935 | 110740066 | putative lupeol synthase [*Arabidopsis thaliana*] |
| 155 | NP_198464 | 15239312 | ATPEN3; catalytic [*Arabidopsis thaliana*] |
| 156 | BAB83089 | 18147598 | putative oxidosqualene cyclase [*Betula platyphylla*] |
| 157 | YP_115266 | 53803023 | squalene cyclase family protein [*Methylococcus capsulatus* str. Bath] |
| 158 | CAB78579 | 7268284 | lupeol synthase like protein [*Arabidopsis thaliana*] |
| 159 | CAB78576 | 7268281 | lupeol synthase like protein [*Arabidopsis thaliana*] |

TABLE 56

| Examples of ERG6 polypeptides. | | | |
|---|---|---|---|
| Row | ACCESSION | GI | PROTEIN DESCRIPTION |
| 1 | CAA89944 | 854482 | Erg6p [*Saccharomyces cerevisiae*] |
| 2 | P25087 | 462024 | Sterol 24-C-methyltransferase (Delta(24)-sterol C-methyltransferase) |
| 3 | CAA52308 | 396515 | S-adenosyl-methionine:delta-24-sterol-C-methyltransferase [*Saccharomyces cerevisiae*] |
| 4 | AAB31378 | 619251 | putative S-adenosylmethionine-dependent methyltransferase [*Saccharomyces cerevisiae*] |
| 5 | Q6FRZ7 | 62900214 | Sterol 24-C-methyltransferase (Delta(24)-sterol C-methyltransferase) |
| 6 | AAX73200 | 62178560 | C24 sterol methyltransferase [*Candida glabrata*] |
| 7 | P_446997 | 50289135 | unnamed protein product [*Candida glabrata*] |
| 8 | CAG59930 | 49526306 | unnamed protein product [*Candida glabrata* CBS138] |
| 9 | AAX73199 | 62178558 | C24 sterol methyltransferase [*Candida glabrata*] |
| 10 | Q6CYB3 | 62900210 | Sterol 24-C-methyltransferase (Delta(24)-sterol C-methyltransferase) |
| 11 | P_451076 | 50302283 | unnamed protein product [*Kluyveromyces lactis*] |
| 12 | CAH02664 | 49640207 | unnamed protein product [*Kluyveromyces lactis* NRRL Y-1140] |
| 13 | Q759S7 | 62900245 | Sterol 24-C-methyltransferase (Delta(24)-sterol C-methyltransferase) |
| 14 | P_984292 | 45188069 | ADR196Wp [*Eremothecium gossypii*] |
| 15 | AAS52116 | 44982886 | ADR196Wp [*Ashbya gossypii* ATCC 10895] |
| 16 | CAA37826 | 4122 | unnamed protein product [*Saccharomyces cerevisiae*] |
| 17 | Q875K1 | 62900279 | Sterol 24-C-methyltransferase (Delta(24)-sterol C-methyltransferase) |
| 18 | AAO21936 | 27803704 | S-adenosylmethionine:D24-methyltransferase [*Clavispora lusitaniae*] |
| 19 | Q6BRB7 | 62900203 | Sterol 24-C-methyltransferase (Delta(24)-sterol C-methyltransferase) |
| 20 | P_459253 | 50421405 | hypothetical protein DEHA0D19151g [*Debaryomyces hansenii* CBS767] |
| 21 | CAG87427 | 49654920 | unnamed protein product [*Debaryomyces hansenii* CBS767] |
| 22 | P_721588 | 68468538 | SAM:delta 24-methyltransferase [*Candida albicans* SC5314] |
| 23 | P_721708 | 68468297 | SAM:delta 24-methyltransferase [*Candida albicans* SC5314] |
| 24 | EAL02920 | 46443640 | hypothetical protein CaO19.1631 [*Candida albicans* SC5314] |
| 25 | EAL02792 | 46443511 | hypothetical protein CaO19.9199 [*Candida albicans* SC5314] |
| 26 | O74198 | 6015114 | Sterol 24-C-methyltransferase (Delta(24)-sterol C-methyltransferase) |
| 27 | AAC26626 | 3323500 | sterol transmethylase [*Candida albicans*] |
| 28 | Q6C2D9 | 62900205 | Sterol 24-C-methyltransferase (Delta(24)-sterol C-methyltransferase) |
| 29 | P_505173 | 50555530 | hypothetical protein [*Yarrowia lipolytica*] |
| 30 | CAG77980 | 49651043 | unnamed protein product [*Yarrowia lipolytica* CLIB122] |
| 31 | P_595787 | 19112579 | hypothetical protein SPBC16E9.05 [*Schizosaccharomyces pombe* 972h-] |
| 32 | O14321 | 6166151 | Sterol 24-C-methyltransferase (Delta(24)-sterol C-methyltransferase) |
| 33 | CAB16897 | 2467267 | SPBC16E9.05 [*Schizosaccharomyces pombe*] |
| 34 | EAT84719 | 111063599 | hypothetical protein SNOG_08443 [*Phaeosphaeria nodorum* SN15] |

TABLE 56-continued

Examples of ERG6 polypeptides.

| Row | ACCESSION | GI | PROTEIN DESCRIPTION |
|---|---|---|---|
| 35 | EAS29698 | 90300067 | hypothetical protein CIMG__08444 [*Coccidioides immitis* RS] |
| 36 | EAQ70709 | 86196071 | hypothetical protein MGG__ch7g116 [*Magnaporthe grisea* 70-15] |
| 37 | P__366350 | 39969919 | hypothetical protein MG10568.4 [*Magnaporthe grisea* 70-15] |
| 38 | P__746550 | 70982043 | sterol 24-c-methyltransferase [*Aspergillus fumigatus* Af293] |
| 39 | EAL84512 | 66844173 | sterol 24-c-methyltransferase, putative [*Aspergillus fumigatus* Af293] |
| 40 | BAE64809 | 83774686 | unnamed protein product [*Aspergillus oryzae*] |
| 41 | P__965392 | 85118140 | probable DELTA(24)-STEROL C-METHYLTRANSFERASE [MIPS] [*Neurospora crassa* OR74A] |
| 42 | Q9P3R1 | 62900336 | Sterol 24-C-methyltransferase (Delta(24)-sterol C-methyltransferase) |
| 43 | EAA36156 | 28927200 | probable DELTA(24)-STEROL C-METHYLTRANSFERASE [MIPS] [*Neurospora crassa*] |
| 44 | CAB97289 | 9367272 | probable DELTA(24)-STEROL C-METHYLTRANSFERASE (ERG6) [*Neurospora crassa*] |
| 45 | P__664750 | 67541965 | hypothetical protein AN7146.2 [*Aspergillus nidulans* FGSC A4] |
| 46 | EAA61398 | 40742208 | hypothetical protein AN7146.2 [*Aspergillus nidulans* FGSC A4] |
| 47 | P__382959 | 46111803 | hypothetical protein FG02783.1 [*Gibberella zeae* PH-1] |
| 48 | EAA70778 | 42547935 | hypothetical protein FG02783.1 [*Gibberella zeae* PH-1] |
| 49 | Q96WX4 | 62900323 | Sterol 24-C-methyltransferase (Delta(24)-sterol C-methyltransferase) |
| 50 | AAK54439 | 14192727 | S-adenosyl methionine:sterol methyl transferase [*Pneumocystis carinii*] |
| 51 | EAQ89522 | 88182054 | conserved hypothetical protein [*Chaetomium globosum* CBS 148.51] |
| 52 | BAA13793 | 41688402 | unnamed protein product [*Schizosaccharomyces pombe*] |
| 53 | P__385916 | 46122725 | hypothetical protein FG05740.1 [*Gibberella zeae* PH-1] |
| 54 | EAA75815 | 42552972 | hypothetical protein FG05740.1 [*Gibberella zeae* PH-1] |
| 55 | P__361872 | 39944670 | hypothetical protein MG04346.4 [*Magnaporthe grisea* 70-15] |
| 56 | Q5EN22 | 62900141 | Sterol 24-C-methyltransferase (Delta(24)-sterol C-methyltransferase) |
| 57 | AAX07631 | 59802827 | sterol 24-C-methyltransferase-like protein [*Magnaporthe grisea*] |
| 58 | BAE61033 | 83770900 | unnamed protein product [*Aspergillus oryzae*] |
| 59 | P__759329 | 71018197 | hypothetical protein UM03182.1 [*Ustilago maydis* 521] |
| 60 | EAK84412 | 46099179 | hypothetical protein UM03182.1 [*Ustilago maydis* 521] |
| 61 | AAK00294 | 12642580 | sterol methyl transferase [*Pneumocystis carinii* f. sp. *carinii*] |
| 62 | P__360548 | 39942022 | hypothetical protein MG10860.4 [*Magnaporthe grisea* 70-15] |
| 63 | P__568887 | 58262954 | sterol 24-C-methyltransferase [*Cryptococcus neoformans* var. *neoformans* JEC21] |
| 64 | AAW41580 | 57223537 | sterol 24-C-methyltransferase, putative [*Cryptococcus neoformans* var. *neoformans* JEC21] |
| 65 | EAL22628 | 50259962 | hypothetical protein CNBB2600 [*Cryptococcus neoformans* var. *neoformans* B-3501A] |
| 66 | AAC34951 | 3560474 | S-adenosyl-methionine-sterol-C-methyltransferase [*Nicotiana tabacum*] |
| 67 | AAC04265 | 2909846 | (S)-adenosyl-L-methionine:delta 24-sterol methyltransferase [*Zea mays*] |
| 68 | AAB49338 | 1872473 | delta-24-sterol methyltransferase [*Triticum aestivum*] |
| 69 | Q9LM02 | 62901053 | Cycloartenol-C-24-methyltransferase (24-sterol C-methyltransferase 1) (Sterol C-methyltransferase 1) (Protein STEROL METHYLTRANSFERASE 1) (Protein CEPHALOPOD) |
| 70 | AAN15377 | 23197700 | 24-sterol C-methyltransferase [*Arabidopsis thaliana*] |
| 71 | AAM53274 | 21539443 | 24-sterol C-methyltransferase [*Arabidopsis thaliana*] |
| 72 | P__196875 | 15240691 | SMT1 (STEROL METHYLTRANSFERASE 1) [*Arabidopsis thaliana*] |
| 73 | AAG28462 | 11066105 | sterol methyltransferase SMT1 [*Arabidopsis thaliana*] |
| 74 | BAB08698 | 9758037 | 24-sterol C-methyltransferase [*Arabidopsis thaliana*] |
| 75 | AAF78847 | 8745241 | SAM:cycloartenol-C24-methyltransferase [*Arabidopsis thaliana*] |
| 76 | AAM53553 | 21434843 | cephalopod [*Arabidopsis thaliana*] |
| 77 | AAB70886 | 1899060 | endosperm C-24 sterol methyltransferase [*Zea mays*] |
| 78 | AAB37769 | 1706965 | delta-24-sterol methyltransferase [*Triticum aestivum*] |
| 79 | BAF21068 | 113610690 | Os07g0206700 [*Oryza sativa* (*japonica* cultivar-group)] |
| 80 | Q6ZIX2 | 68566037 | Cycloartenol-C-24-methyltransferase 1 (24-sterol C-methyltransferase 1) (Sterol C-methyltransferase 1) |
| 81 | P__477078 | 50935101 | cycloartenol-C24-methyltransferase [*Oryza sativa* (*japonica* cultivar-group)] |
| 82 | BAC83238 | 34393309 | cycloartenol-C24-methyltransferase [*Oryza sativa* (*japonica* cultivar-group)] |
| 83 | AAB04057 | 1399380 | S-adenosyl-L-methionine:delta24-sterol-C-methyltransferase |
| 84 | AAB62812 | 2246458 | S-adenosyl-methionine-sterol-C-methyltransferase [*Ricinus communis*] |
| 85 | AAC35787 | 3603295 | S-adenosyl-methionine cycloartenol-C24-methyltransferase [*Nicotiana tabacum*] |
| 86 | AAC34988 | 3560531 | cycloartenol-C24-methyltransferase [*Oryza sativa* subsp. *japonica*] |
| 87 | AAZ83345 | 73761691 | 24-sterol C-methyltransferase [*Gossypium hirsutum*] |
| 88 | EAS30660 | 90301029 | hypothetical protein CIMG__06139 [*Coccidioides immitis* RS] |

TABLE 56-continued

Examples of ERG6 polypeptides.

| Row | ACCESSION | GI | PROTEIN DESCRIPTION |
|---|---|---|---|
| 89 | P_470035 | 50919277 | putative endosperm C-24 sterol methyltransferase [*Oryza sativa* (*japonica* cultivar-group)] |
| 90 | AAP21419 | 30103006 | putative endosperm C-24 sterol methyltransferase [*Oryza sativa* (*japonica* cultivar-group)] |
| 91 | AAR92099 | 40806291 | S-adenosyl-L-methionine-C-24-delta-sterol-methyltransferase B [*Leishmania donovani*] |
| 92 | AAR92098 | 40806289 | S-adenosyl-L-methionine-C-24-delta-sterol-methyltransferase A [*Leishmania donovani*] |
| 93 | CAJ09197 | 68129891 | sterol 24-c-methyltransferase, putative [*Leishmania major*] |
| 94 | CAJ09196 | 68129890 | sterol 24-c-methyltransferase, putative [*Leishmania major*] |
| 95 | P_802864 | 71399753 | sterol 24-c-methyltransferase [*Trypanosoma cruzi* strain CL Brener] |
| 96 | EAN81418 | 70865128 | sterol 24-c-methyltransferase, putative [*Trypanosoma cruzi*] |
| 97 | P_802716 | 71399140 | sterol 24-c-methyltransferase [*Trypanosoma cruzi* strain CL Brener] |
| 98 | EAN81270 | 70864663 | sterol 24-c-methyltransferase, putative [*Trypanosoma cruzi*] |
| 99 | P_822930 | 71747750 | sterol 24-c-methyltransferase [*Trypanosoma brucei* TREU927] |
| 100 | AAZ40214 | 71738257 | sterol methyltransferase [*Trypanosoma brucei brucei*] |
| 101 | CAJ16958 | 70908212 | s-adenosyl-L-methionine-c-24-delta-sterol-methyltransferase a, putative [*Trypanosoma brucei*] |
| 102 | EAN78102 | 70832598 | sterol 24-c-methyltransferase, putative [*Trypanosoma brucei*] |
| 103 | P_636481 | 66805519 | hypothetical protein DDBDRAFT_0188166 [*Dictyostelium discoideum* AX4] |
| 104 | EAL62977 | 60464861 | hypothetical protein DDBDRAFT_0188166 [*Dictyostelium discoideum* AX4] |
| 105 | ABF99454 | 108711659 | Cyclopropane-fatty-acyl-phospholipid synthase family protein, expressed [*Oryza sativa* (*japonica* cultivar-group)] |
| 106 | P_802811 | 71399535 | sterol 24-c-methyltransferase [*Trypanosoma cruzi* strain CL Brener] |
| 107 | EAN81365 | 70864963 | sterol 24-c-methyltransferase, putative [*Trypanosoma cruzi*] |
| 108 | ABB90541 | 82780739 | c24-sterol methyltransferase [*Paracoccidioides brasiliensis*] |
| 109 | AAB62807 | 2246452 | S-adenosyl-methionine-sterol-C-methyltransferase homolog [*Nicotiana tabacum*] |
| 110 | Q39227 | 62900893 | 24-methylenesterol C-methyltransferase 2 (24-sterol C-methyltransferase 2) (Sterol-C-methyltransferase 2) |
| 111 | AAM45009 | 21281107 | putative sterol-C-methyltransferase [*Arabidopsis thaliana*] |
| 112 | P_173458 | 15217917 | SMT2 (STEROL METHYLTRANSFERASE 2) [*Arabidopsis thaliana*] |
| 113 | AAK76716 | 15028255 | putative sterol-C-methyltransferase [*Arabidopsis thaliana*] |
| 114 | AAG48780 | 12083242 | putative sterol-C-methyltransferase [*Arabidopsis thaliana*] |
| 115 | AAF88156 | 9558593 | Identical to 24-sterol C-methyltransferase from *Arabidopsis thaliana* gi\|2129517 and is a member of the ubiE/COQ5 methyltransferase family PF\|01209. ESTs gb\|T42228, gb\|T46520, gb\|T41746, gb\|N38458, gb\|AI993515, gb\|AA389843, gb\|AI099890, gb\|AI099653 come f |
| 116 | 2207220A | 1587694 | sterol C-methyltransferase |
| 117 | CAA61966 | 1061040 | sterol-C-methyltransferase [*Arabidopsis thaliana*] |
| 118 | AAN72104 | 25083682 | 24-sterol C-methyltransferase [*Arabidopsis thaliana*] |
| 119 | AAM91592 | 22136020 | 24-sterol C-methyltransferase [*Arabidopsis thaliana*] |
| 120 | Q94JS4 | 67472706 | 24-methylenesterol C-methyltransferase 3 (24-sterol C-methyltransferase 3) (Sterol-C-methyltransferase 3) |
| 121 | AAM47339 | 21360447 | At1g76090/T23E18_40 [*Arabidopsis thaliana*] |
| 122 | P_177736 | 15222955 | SMT3; S-adenosylmethionine-dependent methyltransferase [*Arabidopsis thaliana*] |
| 123 | AAK52981 | 14030613 | At1g76090/T23E18_40 [*Arabidopsis thaliana*] |
| 124 | AAN31890 | 23397216 | putative sterol-C-methyltransferase [*Arabidopsis thaliana*] |
| 125 | AAB62809 | 2246456 | S-adenosyl-methionine-sterol-C-methyltransferase [*Arabidopsis thaliana*] |
| 126 | AAB62808 | 2246454 | S-adenosyl-methionine-sterol-C-methyltransferase [*Nicotiana tabacum*] |
| 127 | AAM63753 | 21555010 | sterol-C-methyltransferase [*Arabidopsis thaliana*] |
| 128 | BAF10805 | 113547362 | Os03g0136200 [*Oryza sativa* (*japonica* cultivar-group)] |
| 129 | ABF93854 | 108706059 | 24-methylenesterol C-methyltransferase 2, putative, expressed [*Oryza sativa* (*japonica* cultivar-group)] |
| 130 | O82427 | 68566013 | 24-methylenesterol C-methyltransferase 2 (24-sterol C-methyltransferase 2) (Sterol-C-methyltransferase 2) |

TABLE 57

Examples of ERG5 polypeptides.

| Row | ACCESSION | GI | PROTEIN DESCRIPTION |
|---|---|---|---|
| 1 | P54781 | 1706693 | Cytochrome P450 61 (C-22 sterol desaturase) |
| 2 | AAB06217 | 1235991 | cytochrome P450 |
| 3 | CAA89116 | 798924 | unknown [*Saccharomyces cerevisiae*] |

TABLE 57-continued

Examples of ERG5 polypeptides.

| Row | ACCESSION | GI | PROTEIN DESCRIPTION |
|---|---|---|---|
| 4 | AAU09769 | 51830482 | YMR015C [*Saccharomyces cerevisiae*] |
| 5 | AAX73198 | 62178556 | C22 sterol desaturase [*Candida glabrata*] |
| 6 | AAX73197 | 62178554 | C22 sterol desaturase [*Candida glabrata*] |
| 7 | P_449681 | 50294540 | hypothetical protein CAGL0M07656g [*Candida glabrata* CBS138] |
| 8 | CAG62657 | 49528995 | unnamed protein product [*Candida glabrata* CBS138] |
| 9 | P_453562 | 50307167 | unnamed protein product [*Kluyveromyces lactis*] |
| 10 | CAH00658 | 49642696 | unnamed protein product [*Kluyveromyces lactis* NRRL Y-1140] |
| 11 | P_982999 | 45185282 | ABR053Cp [*Eremothecium gossypii*] |
| 12 | AAS50823 | 44980940 | ABR053Cp [*Ashbya gossypii* ATCC 10895] |
| 13 | P_458727 | 50420383 | hypothetical protein DEHA0D06842g [*Debaryomyces hansenii* CBS767] |
| 14 | CAG86871 | 49654394 | unnamed protein product [*Debaryomyces hansenii* CBS767] |
| 15 | P_888893 | 77022898 | hypothetical protein CaJ7.0323 [*Candida albicans* SC5314] |
| 16 | BAE44790 | 76573706 | hypothetical protein [*Candida albicans*] |
| 17 | P_716933 | 68478128 | cytochrome P450 [*Candida albicans* SC5314] |
| 18 | P_717000 | 68477993 | hypothetical protein CaO19.5178 [*Candida albicans* SC5314] |
| 19 | EAK98020 | 46438693 | hypothetical protein CaO19.5178 [*Candida albicans* SC5314] |
| 20 | EAK97950 | 46438622 | hypothetical protein CaO19.12645 [*Candida albicans* SC5314] |
| 21 | CAA21953 | 3850153 | cytochrome P450 [*Candida albicans*] |
| 22 | P_500188 | 50545301 | hypothetical protein [*Yarrowia lipolytica*] |
| 23 | CAG84120 | 49646053 | unnamed protein product [*Yarrowia lipolytica* CLIB122] |
| 24 | BAC01142 | 21624361 | sterol C-22 desaturase [*Symbiotaphrina buchneri*] |
| 25 | BAC01140 | 21624354 | sterol C-22 desaturase [*Symbiotaphrina buchneri*] |
| 26 | BAC01141 | 21624359 | sterol C-22 desaturase [*Symbiotaphrina kochii*] |
| 27 | BAC01139 | 21624352 | sterol C22 desaturase [*Symbiotaphrina kochii*] |
| 28 | EAQ88206 | 88180738 | conserved hypothetical protein [*Chaetomium globosum* CBS148.51] |
| 29 | P_961915 | 85105220 | hypothetical protein [*Neurospora crassa* OR74A] |
| 30 | EAA32679 | 28923500 | hypothetical protein [*Neurospora crassa*] |
| 31 | EAS33985 | 90304354 | hypothetical protein CIMG_05009 [*Coccidioides immitis* RS] |
| 32 | P_750145 | 70990592 | cytochrome P450 sterol C-22 desaturase [*Aspergillus fumigatus* Af293] |
| 33 | EAL88107 | 66847777 | cytochrome P450 sterol C-22 desaturase, putative [*Aspergillus fumigatus* Af293] |
| 34 | EAT87119 | 111065999 | hypothetical protein SNOG_06055 [*Phaeosphaeria nodorum* SN15] |
| 35 | BAE58068 | 83767929 | unnamed protein product [*Aspergillus oryzae*] |
| 36 | P_382135 | 46110154 | hypothetical protein FG01959.1 [*Gibberella zeae* PH-1] |
| 37 | EAA68855 | 42546012 | hypothetical protein FG01959.1 [*Gibberella zeae* PH-1] |
| 38 | P_661646 | 67527317 | hypothetical protein AN4042.2 [*Aspergillus nidulans* FGSC A4] |
| 39 | EAA59513 | 40740323 | hypothetical protein AN4042.2 [*Aspergillus nidulans* FGSC A4] |
| 40 | P_383862 | 46115688 | hypothetical protein FG03686.1 [*Gibberella zeae* PH-1] |
| 41 | EAA71499 | 42548656 | hypothetical protein FG03686.1 [*Gibberella zeae* PH-1] |
| 42 | P_369417 | 39976053 | hypothetical protein MG06047.4 [*Magnaporthe grisea* 70-15] |
| 43 | BAE57461 | 83767322 | unnamed protein product [*Aspergillus oryzae*] |
| 44 | P_593788 | 19114700 | hypothetical protein SPAC19A8.04 [*Schizosaccharomyces pombe* 972h-] |
| 45 | CAB11640 | 7007345 | SPAC19A8.04 [*Schizosaccharomyces pombe*] |
| 46 | P_756497 | 71003662 | hypothetical protein UM00350.1 [*Ustilago maydis* 521] |
| 47 | EAK81168 | 46095935 | hypothetical protein UM00350.1 [*Ustilago maydis* 521] |
| 48 | P_571445 | 58268578 | C-22 sterol desaturase [*Cryptococcus neoformans* var. *neoformans* JEC21] |
| 49 | AAW44138 | 57227680 | C-22 sterol desaturase, putative [*Cryptococcus neoformans* var. *neoformans* JEC21] |
| 50 | EAL20298 | 50257593 | hypothetical protein CNBF1100 [*Cryptococcus neoformans* var. *neoformans* B-3501A] |
| 51 | EAQ86140 | 88178672 | hypothetical protein CHGG_07393 [*Chaetomium globosum* CBS 148.51] |
| 52 | AAO48601 | 28864257 | ERG5 [*Clavispora lusitaniae*] |
| 53 | P_647018 | 66827327 | cytochrome P450 family protein [*Dictyostelium discoideum* AX4] |
| 54 | EAL73097 | 60475161 | cytochrome P450 family protein [*Dictyostelium discoideum* AX4] |
| 55 | BAF04287 | 113531904 | Os01g0211200 [*Oryza sativa* (*japonica* cultivar-group)] |
| 56 | P_913287 | 34903880 | unnamed protein product [*Oryza sativa* (*japonica* cultivar-group)] |
| 57 | BAA96196 | 8096624 | putative sterol C-22 desaturase [*Oryza sativa* (*japonica* cultivar-group)] |
| 58 | BAA96154 | 8096581 | putative sterol C-22 desaturase [*Oryza sativa* (*japonica* cultivar-group)] |
| 59 | ABC59097 | 84514177 | cytochrome P450 monooxygenase CYP710A15 [*Medicago truncatula*] |
| 60 | P_180452 | 15226976 | CYP710A4; heme binding/iron ion binding/monooxygenase/ oxygen binding [*Arabidopsis thaliana*] |
| 61 | AAC79590 | 3927833 | putative cytochrome P450 [*Arabidopsis thaliana*] |
| 62 | P_913285 | 34903876 | unnamed protein product [*Oryza sativa* (*japonica* cultivar-group)] |
| 63 | BAA96194 | 8096622 | sterol C-22 desaturase-like [*Oryza sativa* (*japonica* cultivar-group)] |
| 64 | BAA96152 | 8096579 | sterol C-22 desaturase-like [*Oryza sativa* (*japonica* cultivar-group)] |
| 65 | P_913291 | 34903888 | unnamed protein product [*Oryza sativa* (*japonica* cultivar-group)] |
| 66 | BAA96200 | 8096628 | sterol C-22 desaturase-like [*Oryza sativa* (*japonica* cultivar-group)] |
| 67 | BAA96158 | 8096585 | sterol C-22 desaturase-like [*Oryza sativa* (*japonica* cultivar-group)] |

TABLE 57-continued

| Examples of ERG5 polypeptides. | | | |
|---|---|---|---|
| Row | ACCESSION | GI | PROTEIN DESCRIPTION |
| 68 | BAF04286 | 113531903 | Os01g0210900 [*Oryza sativa* (*japonica* cultivar-group)] |
| 69 | P_913284 | 34903874 | unnamed protein product [*Oryza sativa* (*japonica* cultivar-group)] |
| 70 | BAA96193 | 8096621 | sterol C-22 desaturase-like [*Oryza sativa* (*japonica* cultivar-group)] |
| 71 | BAA96151 | 8096578 | sterol C-22 desaturase-like [*Oryza sativa* (*japonica* cultivar-group)] |
| 72 | BAE71351 | 84468537 | CYP710 [*Arabidopsis thaliana*] |
| 73 | AAQ65177 | 34365731 | At2g34500 [*Arabidopsis thaliana*] |
| 74 | AAN72080 | 25083451 | putative cytochrome P450 [*Arabidopsis thaliana*] |
| 75 | AAM14944 | 20197156 | putative cytochrome P450 [*Arabidopsis thaliana*] |
| 76 | P_180997 | 15226758 | CYP710A1; heme binding/iron ion binding/monooxygenase/ oxygen binding [*Arabidopsis thaliana*] |
| 77 | AAC26690 | 3128210 | putative cytochrome P450 [*Arabidopsis thaliana*] |
| 78 | P_180451 | 15226974 | CYP710A3; heme binding/iron ion binding/monooxygenase/ oxygen binding [*Arabidopsis thaliana*] |
| 79 | AAC79589 | 3927832 | putative cytochrome P450 [*Arabidopsis thaliana*] |
| 80 | BAE80316 | 89111285 | CYP710 protein [*Arabidopsis thaliana*] |
| 81 | AAM26664 | 20856398 | At2g34490/T31E10.17 [*Arabidopsis thaliana*] |
| 82 | AAM14945 | 20197157 | putative cytochrome P450 [*Arabidopsis thaliana*] |
| 83 | AAL75888 | 18650637 | At2g34490/T31E10.17 [*Arabidopsis thaliana*] |
| 84 | P_180996 | 15226756 | CYP710A2; heme binding/iron ion binding/monooxygenase/ oxygen binding [*Arabidopsis thaliana*] |
| 85 | AAC26691 | 3128211 | putative cytochrome P450 [*Arabidopsis thaliana*] |
| 86 | AAM62799 | 21553706 | putative cytochrome P450 [*Arabidopsis thaliana*] |
| 87 | BAE93156 | 91204699 | sterol 22-desaturase [*Lycopersicon esculentum*] |

TABLE 58

| Examples of ERG3 polypeptides. | | | |
|---|---|---|---|
| Row | ACCESSION | GI | PROTEIN DESCRIPTION |
| 1 | AAT93015 | 51013443 | YLR056W [*Saccharomyces cerevisiae*] |
| 2 | NP_013157 | 6323085 | C-5 sterol desaturase, catalyzes the introduction of a C-5(6) |
| 3 | BAA20292 | 2143190 | C-5 sterol desaturase [*Saccharomyces cerevisiae*] |
| 4 | CAA64303 | 1181277 | C-5 sterol desaturase [*Saccharomyces cerevisiae*] |
| 5 | P32353 | 416963 | C-5 sterol desaturase (Sterol-C5-desaturase) (Ergosterol delta |
| 6 | AAB39844 | 233331 | C-5 sterol desaturase [*Saccharomyces cerevisiae*] |
| 7 | AAA34595 | 171477 | C-5 sterol desaturase |
| 8 | AAA34594 | 171475 | C-5 sterol desaturase |
| 9 | XP_446050 | 50287241 | unnamed protein product [*Candida glabrata*] |
| 10 | CAG58974 | 49525357 | unnamed protein product [*Candida glabrata* CBS138] |
| 11 | P50860 | 1706691 | C-5 sterol desaturase (Sterol-C5-desaturase) (Ergosterol delta |
| 12 | AAB02330 | 755695 | ERG3 |
| 13 | Q754B9 | 51701406 | C-5 sterol desaturase (Sterol-C5-desaturase) (Ergosterol delta |
| 14 | NP_985698 | 45198669 | AFR151Cp [*Eremothecium gossypii*] |
| 15 | AAS53522 | 44984679 | AFR151Cp [*Ashbya gossypii* ATCC 10895A] |
| 16 | XP_455482 | 50310919 | unnamed protein product [*Kluyveromyces lactis*] |
| 17 | CAG98190 | 49644618 | unnamed protein product [*Kluyveromyces lactis* NRRL Y-1140] |
| 18 | Q8NJ57 | 51701432 | C-5 sterol desaturase (Sterol-C5-desaturase) (Ergosterol delta |
| 19 | CAD13131 | 22022945 | ergosterol delta 5,6 desaturase [*Candida dubliniensis*] |
| 20 | XP_713577 | 68485022 | hypothetical protein CaO19.767 [*Candida albicans* SC5314] |
| 21 | XP_713612 | 68484947 | hypothetical protein CaO19.8387 [*Candida albicans* SC5314] |
| 22 | EAK94507 | 46435118 | hypothetical protein CaO19.8387 [*Candida albicans* SC5314] |
| 23 | EAK94472 | 46435082 | hypothetical protein CaO19.767 [*Candida albicans* SC5314] |
| 24 | O93875 | 51701379 | C-5 sterol desaturase (Sterol-C5-desaturase) (Ergosterol delta |
| 25 | AAC99343 | 4091929 | C5,6 desaturase [*Candida albicans*] |
| 26 | XP_460747 | 50424321 | hypothetical protein DEHA0F09757g [*Debaryomyces hansenii* CBS76 |
| 27 | CAG89088 | 49656416 | unnamed protein product [*Debaryomyces hansenii* CBS767] |
| 28 | XP_503090 | 50551233 | hypothetical protein [*Yarrowia lipolytica*] |
| 29 | CAG81282 | 49648958 | unnamed protein product [*Yarrowia lipolytica* CLIB122] |
| 30 | XP_664110 | 67540672 | hypothetical protein AN6506.2 [*Aspergillus nidulans* FGSC A4] |
| 31 | EAA57846 | 40738656 | hypothetical protein AN6506.2 [*Aspergillus nidulans* FGSC A4] |
| 32 | BAE61784 | 83771654 | unnamed protein product [*Aspergillus oryzae*] |
| 33 | XP_747563 | 70984086 | sterol delta 5,6-desaturase ERG3 [*Aspergillus fumigatus* Af293] |
| 34 | EAL85525 | 66845190 | sterol delta 5,6-desaturase ERG3 [*Aspergillus fumigatus* Af293] |
| 35 | AAU82098 | 52548218 | C-5 sterol desaturase B-like [*Aspergillus fumigatus*] |
| 36 | BAE56076 | 83765933 | unnamed protein product [*Aspergillus oryzae*] |
| 37 | XP_962923 | 85109451 | hypothetical protein [*Neurospora crassa* OR74A] |
| 38 | Q7SBB6 | 51701418 | Probable C-5 sterol desaturase (Sterol-C5-desaturase) (Ergoste |
| 39 | EAA33687 | 28924567 | hypothetical protein [*Neurospora crassa*] |
| 40 | EAS37256 | 90307625 | C-5 sterol desaturase [*Coccidioides immitis* RS] |
| 41 | Q8J207 | 51701428 | C-5 sterol desaturase (Sterol-C5-desaturase) (Ergosterol delta |
| 42 | AAN27998 | 23476431 | sterol delta 5,6-desaturase ERG3 [*Leptosphaeria maculans*] |

TABLE 58-continued

| Examples of ERG3 polypeptides. | | | |
|---|---|---|---|
| Row | ACCESSION | GI | PROTEIN DESCRIPTION |
| 43 | XP_363987 | 39953467 | hypothetical protein MG08832.4 [*Magnaporthe grisea* 70-15] |
| 44 | EAT83541 | 111062421 | hypothetical protein SNOG_09349 [*Phaeosphaeria nodorum* SN15] |
| 45 | O94457 | 51701380 | Probable C-5 sterol desaturase 1 (Sterol-C5-desaturase 1) (Erg |
| 46 | NP_593135 | 19114047 | hypothetical protein SPAC1687.16c [*Schizosaccharomyces pombe 9* |
| 47 | CAA22610 | 4106670 | SPAC1687.16c [*Schizosaccharomyces pombe*] |
| 48 | XP_382678 | 46111241 | hypothetical protein FG02502.1 [*Gibberella zeae* PH-1] |
| 49 | EAA67236 | 42544393 | hypothetical protein FG02502.1 [*Gibberella zeae* PH-1] |
| 50 | BAE65607 | 83775487 | unnamed protein product [*Aspergillus oryzae*] |
| 51 | O13666 | 6015113 | Probable C-5 sterol desaturase 2 (Sterol-C5-desaturase 2) (Erg |
| 52 | CAA16898 | 2853109 | SPBC27B12.03c [*Schizosaccharomyces pombe*] |
| 53 | BAA21457 | 2257565 | C-5 STEROL DESATURASE [*Schizosaccharomyces pombe*] |

TABLE 59

| Examples of ERG2 polypeptides. | | | |
|---|---|---|---|
| Row | ACCESSION | GI | PROTEIN DESCRIPTION |
| 1 | AAS56448 | 45270134 | YMR202W [*Saccharomyces cerevisiae*] |
| 2 | CAA88643 | 736299 | Erg2p [*Saccharomyces cerevisiae*] |
| 3 | P32352 | 416962 | C-8 sterol isomerase (Delta-8--delta-7 sterol isomerase) |
| 4 | AAA34593 | 171473 | C-8 sterol isomerase |
| 5 | P_985369 | 45198340 | AFL181Cp [*Eremothecium gossypii*] |
| 6 | AAS53193 | 44984227 | AFL181Cp [*Ashbya gossypii* ATCC 10895] |
| 7 | P_449233 | 50293643 | unnamed protein product [*Candida glabrata*] |
| 8 | CAG62207 | 49528546 | unnamed protein product [*Candida glabrata* CBS138] |
| 9 | P_455367 | 50310691 | unnamed protein product [*Kluyveromyces lactis*] |
| 10 | CAG98075 | 49644503 | unnamed protein product [*Kluyveromyces lactis* NRRL Y-1140] |
| 11 | P_458891 | 50420709 | hypothetical protein DEHA0D10714g [*Debaryomyces hansenii* CBS767] |
| 12 | CAG87043 | 49654558 | unnamed protein product [*Debaryomyces hansenii* CBS767] |
| 13 | P_718886 | 68473979 | sterol C8-C7 isomerase [*Candida albicans SC5314*] |
| 14 | P_718988 | 68473770 | sterol C8-C7 isomerase [*Candida albicans* SC5314] |
| 15 | EAL00087 | 46440785 | hypothetical protein CaO19.6026 [*Candida albicans* SC5314] |
| 16 | EAK99982 | 46440679 | hypothetical protein CaO19.13447 [*Candida albicans* SC5314] |
| 17 | P_504668 | 50554519 | hypothetical protein [*Yarrowia lipolytica*] |
| 18 | CAG80272 | 49650537 | unnamed protein product [*Yarrowia lipolytica* CLIB122] |
| 19 | P_501006 | 50547073 | hypothetical protein [*Yarrowia lipolytica*] |
| 20 | CAG83259 | 49646872 | unnamed protein product [*Yarrowia lipolytica* CLIB122] |
| 21 | Q92254 | 67476925 | C-8 sterol isomerase (Delta-8--delta-7 sterol isomerase) |
| 22 | CAC28749 | 12718205 | C-8 sterol isomerase erg-1 [*Neurospora crassa*] |
| 23 | AAB09470 | 1575320 | C-8 sterol isomerase |
| 24 | P_658055 | 67516339 | hypothetical protein AN0451.2 [*Aspergillus nidulans* FGSC A4] |
| 25 | EAA66550 | 40747394 | hypothetical protein AN0451.2 [*Aspergillus nidulans* FGSC A4] |
| 26 | P_593324 | 19114236 | hypothetical protein SPAC20G8.07c [*Schizosaccharomyces pombe* 972h-] |
| 27 | P87113 | 3219796 | Probable C-8 sterol isomerase (Delta-8--delta-7 sterol isomerase) |
| 28 | CAB08601 | 2094862 | SPAC20G8.07c [*Schizosaccharomyces pombe*] |
| 29 | P_363040 | 39947737 | hypothetical protein MG08624.4 [*Magnaporthe grisea* 70-15] |
| 30 | P33281 | 462023 | C-8 sterol isomerase (Delta-8--delta-7 sterol isomerase) |
| 31 | CAA80454 | 311322 | C-8 sterol isomerase [*Magnaporthe grisea*] |
| 32 | EAQ85888 | 88178420 | hypothetical protein CHGG_07141 [*Chaetomium globosum* CBS148.51] |
| 33 | P_961312 | 85102300 | C-8 STEROL ISOMERASE (DELTA-8--DELTA-7 STEROL ISOMERASE) [*Neurospora crassa* OR74A] |
| 34 | EAA32076 | 28922855 | C-8 STEROL ISOMERASE (DELTA-8--DELTA-7 STEROL ISOMERASE) [*Neurospora crassa*] |
| 35 | P_844057 | 72387265 | C-8 sterol isomerase, putative [*Trypanosoma brucei*] |
| 36 | P_826540 | 71905267 | C-8 sterol isomerase, putative [*Trypanosoma brucei*] |
| 37 | AAZ10498 | 70800589 | C-8 sterol isomerase, putative [*Trypanosoma brucei*] |
| 38 | AAX80634 | 62360216 | C-8 sterol isomerase, putative [*Trypanosoma brucei*] |
| 39 | P_758081 | 71006989 | C-8 sterol isomerase [*Ustilago maydis* 521] |
| 40 | EAK82388 | 46097155 | ERG2_USTMA C-8 sterol isomerase (Delta-8--delta-7 sterol isomerase) [*Ustilago maydis* 521] |
| 41 | P32360 | 416961 | C-8 sterol isomerase (Delta-8--delta-7 sterol isomerase) |
| 42 | CAA78959 | 2967 | C-8 sterol isomerase [*Ustilago maydis*] |
| 43 | P_567070 | 58259315 | C-8 sterol isomerase [*Cryptococcus neoformans* var. *neoformans* JEC21] |
| 44 | AAW41251 | 57223207 | C-8 sterol isomerase, putative [*Cryptococcus neoformans* var. *neoformans* JEC21] |
| 45 | EAL23045 | 50260386 | hypothetical protein CNBA8120 [*Cryptococcus neoformans* var. *neoformans* B-3501A] |
| 46 | P_821186 | 71658920 | C-8 sterol isomerase [*Trypanosoma cruzi* strain CL Brener] |
| 47 | EAN99335 | 70886558 | C-8 sterol isomerase, putative [*Trypanosoma cruzi*] |

TABLE 59-continued

| Examples of ERG2 polypeptides. | | | |
|---|---|---|---|
| Row | ACCESSION | GI | PROTEIN DESCRIPTION |
| 48 | AAQ18796 | 33439494 | C-8 sterol isomerase [*Trypanosoma cruzi*] |
| 49 | P_847879 | 73536920 | C-8 sterol isomerase-like protein [*Leishmania major* strain Friedlin] |
| 50 | AAZ09671 | 70799755 | C-8 sterol isomerase-like protein [*Leishmania major* strain Friedlin] |

TABLE 60

| Examples of ERG3-like polypeptides. | | | |
|---|---|---|---|
| Row | ACCESSION | GI | PROTEIN DESCRIPTION |
| 1 | BAA33730 | 3721884 | sterol-C5-desaturase [*Mus musculus*] |
| 2 | BAE32506 | 74178504 | unnamed protein product [*Mus musculus*] |
| 3 | AAH24132 | 18848246 | Sterol-C5-desaturase (fungal ERG3, delta-5-desaturase) homolog (*S. cerevisae*) [*Mus musculus*] |
| 4 | NP_766357 | 27777693 | sterol-C5-desaturase (fungal ERG3, delta-5-desaturase) homolog [*Mus musculus*] |
| 5 | BAC36944 | 26346591 | unnamed protein product [*Mus musculus*] |
| 6 | BAC31666 | 26335931 | unnamed protein product [*Mus musculus*] |
| 7 | AAH81704 | 51859106 | Sterol-C5-desaturase (fungal ERG3, delta-5-desaturase) homolog (*S. cerevisae*) [*Rattus norvegicus*] |
| 8 | NP_446094 | 25742651 | sterol-C5-desaturase (fungal ERG3, delta-5-desaturase) homolog [*Rattus norvegicus*] |
| 9 | BAB19798 | 11990472 | sterol C5-desaturase [*Rattus norvegicus*] |
| 10 | XP_853004 | 73955000 | PREDICTED: similar to sterol-C5-desaturase-like [*Canis familiaris*] |
| 11 | XP_508825 | 55637121 | PREDICTED: similar to delta7-sterol-C5-desaturase [*Pan troglodytes*] |
| 12 | NP_001 . . . | 68160945 | sterol-C5-desaturase-like [*Homo sapiens*] |
| 13 | NP_008849 | 68160941 | sterol-C5-desaturase-like [*Homo sapiens*] |
| 14 | BAD96861 | 62897843 | sterol-C5-desaturase (ERG3 delta-5-desaturase homolog, fungal)-like variant [*Homo sapiens*] |
| 15 | BAD96406 | 62896931 | sterol-C5-desaturase (ERG3 delta-5-desaturase homolog, fungal)-like variant [*Homo sapiens*] |
| 16 | AAH50427 | 30046554 | Sterol-C5-desaturase (ERG3 delta-5-desaturase homolog, fungal)-like [*Homo sapiens*] |
| 17 | AAH12333 | 15147389 | Sterol-C5-desaturase (ERG3 delta-5-desaturase homolog, fungal)-like [*Homo sapiens*] |
| 18 | AAF00544 | 6003685 | delta7-sterol-C5-desaturase [*Homo sapiens*] |
| 19 | BAB68218 | 15637108 | sterol C5 desaturase [*Homo sapiens*] |
| 20 | O75845 | 6174975 | Lathosterol oxidase (Lathosterol 5-desaturase) (Delta-7-sterol 5-desaturase) (C-5 sterol desatur |
| 21 | BAA33729 | 3721882 | sterol-C5-desaturase [*Homo sapiens*] |
| 22 | XP_001 . . . | 1.09E+08 | PREDICTED: sterol-C5-desaturase (ERG3 delta-5-desaturase homolog, fungal)-like isoform 2 [*Macaca* |
| 23 | AAH78055 | 50416254 | Sc5d-prov protein [*Xenopus laevis*] |
| 24 | NP_001 . . . | 52219112 | sterol-C5-desaturase (fungal ERG3, delta-5-desaturase) homolog [*Danio rerio*] |
| 25 | AAH81395 | 51859008 | Sterol-C5-desaturase (fungal ERG3, delta-5-desaturase) homolog (*S. cerevisae*) [*Danio rerio*] |
| 26 | BAA18970 | 1906796 | fungal sterol-C5-desaturase homolog [*Homo sapiens*] |
| 27 | XP_001 . . . | 1.09E+08 | PREDICTED: sterol-C5-desaturase (ERG3 delta-5-desaturase homolog, fungal)-like isoform 1 [*Macaca* |
| 28 | XP_793331 | 72159211 | PREDICTED: similar to sterol-C5-desaturase (fungal ERG3, delta-5-desaturase) homolog [*Strongyloc* |
| 29 | NP_001 . . . | 78369462 | hypothetical protein LOC525154 [*Bos taurus*] |
| 30 | AAI03339 | 74353920 | Similar to sterol-C5-desaturase-like [*Bos taurus*] |
| 31 | CAF90498 | 47207599 | unnamed protein product [*Tetraodon nigroviridis*] |

TABLE 61

| Examples of ERG27 polypeptides. | | | |
|---|---|---|---|
| Row | ACCESSION | GI | PROTEIN DESCRIPTION |
| 1 | Q12452 | 60392263 | 3-keto-steroid reductase |
| 2 | CAA97664 | 1360483 | unnamed protein product [*Saccharomyces cerevisiae*] |
| 3 | AAB67544 | 1256850 | Ylr100wp [*Saccharomyces cerevisiae*] |
| 4 | Q6FIV3 | 62286920 | 3-keto-steroid reductase |
| 5 | P_449841 | 50294860 | hypothetical protein CAGL0M11506g [*Candida glabrata* CBS138] |
| 6 | CAG62821 | 49529155 | unnamed protein product [*Candida glabrata* CBS138] |
| 7 | Q6CJC2 | 62286919 | 3-keto-steroid reductase |
| 8 | P_455967 | 50311871 | unnamed protein product [*Kluyveromyces lactis*] |

TABLE 61-continued

| Examples of ERG27 polypeptides. | | | |
|---|---|---|---|
| Row | ACCESSION | GI | PROTEIN DESCRIPTION |
| 9 | CAG98675 | 49645103 | unnamed protein product [*Kluyveromyces lactis* NRRL Y-1140] |
| 10 | Q74ZZ0 | 62286926 | 3-keto-steroid reductase |
| 11 | P_986733 | 45201163 | AGR068Wp [*Eremothecium gossypii*] |
| 12 | AAS54557 | 44985946 | AGR068Wp [*Ashbya gossypii* ATCC 10895] |
| 13 | Q6BNP0 | 62286917 | 3-keto-steroid reductase |
| 14 | P_460180 | 50423199 | hypothetical protein DEHA0E21263g [*Debaryomyces hansenii* CBS |
| 15 | CAG88453 | 49655848 | unnamed protein product [*Debaryomyces hansenii* CBS767] |
| 16 | Q874K0 | 62286935 | 3-keto-steroid reductase |
| 17 | AAN28009 | 29465858 | 3-keto reductase [*Candida albicans*] |
| 18 | P_717865 | 68476112 | 3-keto sterol reductase [*Candida albicans* SC5314] |
| 19 | P_717931 | 68475981 | 3-keto sterol reductase [*Candida albicans* SC5314] |
| 20 | EAK98982 | 46439667 | hypothetical protein CaO19.3240 [*Candida albicans* SC5314] |
| 21 | EAK98915 | 46439599 | hypothetical protein CaO19.10750 [*Candida albicans* SC5314] |
| 22 | Q6CE88 | 62286918 | 3-keto-steroid reductase |
| 23 | P_501024 | 50547109 | hypothetical protein [*Yarrowia lipolytica*] |
| 24 | CAG83277 | 49646890 | unnamed protein product [*Yarrowia lipolytica* CLIB122] |
| 25 | P_595440 | 19112232 | 3-keto sterol reductase [*Schizosaccharomyces pombe* 972h-] |
| 26 | CAA21246 | 3738145 | SPBC1709.07 [*Schizosaccharomyces pombe*] |
| 27 | BAA13878 | 1749642 | unnamed protein product [*Schizosaccharomyces pombe*] |
| 28 | P_751680 | 70993666 | 3-ketosteroid reductase [*Aspergillus fumigatus* Af293] |
| 29 | EAL89642 | 66849314 | 3-ketosteroid reductase [*Aspergillus fumigatus* Af293] |
| 30 | P_958799 | 85091228 | hypothetical protein [*Neurospora crassa* OR74A] |
| 31 | EAA29563 | 28920185 | hypothetical protein [*Neurospora crassa*] |
| 32 | BAE58171 | 83768032 | unnamed protein product [*Aspergillus oryzae*] |
| 33 | EAQ85086 | 88177618 | hypothetical protein CHGG_09100 [*Chaetomium globosum* CBS148 |
| 34 | EAT86025 | 111064905 | hypothetical protein SNOG_06194 [*Phaeosphaeria nodorum* SN15] |
| 35 | P_663189 | 67538830 | hypothetical protein AN5585.2 [*Aspergillus nidulans* FGSC A4] |
| 36 | EAA62228 | 40743038 | hypothetical protein AN5585.2 [*Aspergillus nidulans* FGSC A4] |
| 37 | EAS36221 | 90306590 | hypothetical protein CIMG_01575 [*Coccidioides immitis* RS] |
| 38 | AAO64345 | 29150686 | 3-ketosteroid reductase [*Botryotinia fuckeliana*] |
| 39 | P_796770 | 72131681 | PREDICTED: similar to hydroxysteroid (17-beta) dehydrogenase |
| 40 | P_793145 | 72086766 | PREDICTED: similar to hydroxysteroid (17-beta) dehydrogenase |
| 41 | P_570518 | 58266724 | 3-keto sterol reductase [*Cryptococcus neoformans* var. neofor |
| 42 | AAW43211 | 57226751 | 3-keto sterol reductase, putative [*Cryptococcus neoformans* v |
| 43 | EAL21279 | 50258592 | hypothetical protein CNBD3330 [*Cryptococcus neoformans* var. |
| 44 | AAI00220 | 71681260 | Unknown (protein for MGC: 114978) [*Xenopus laevis*] |
| 45 | BAE06843 | 70720928 | hypothetical protein [*Epichloe festucae*] |
| 46 | P_001 . . . | 62859081 | hydroxysteroid (17-beta) dehydrogenase 7 [*Xenopus tropicalis* |
| 47 | P_851698 | 74006237 | PREDICTED: similar to hydroxysteroid (17-beta) dehydrogenase |
| 48 | CAC88119 | 18077845 | 17beta-hydroxysteroid dehydrogenase type 7 [*Mus musculus*] |
| 49 | AAH11464 | 15079256 | Hsd17b7 protein [*Mus musculus*] |
| 50 | P_034606 | 87162470 | hydroxysteroid (17-beta) dehydrogenase 7 [*Mus musculus*] |
| 51 | BAC25918 | 26390565 | unnamed protein product [*Mus musculus*] |
| 52 | BAC34124 | 26340924 | unnamed protein product [*Mus musculus*] |
| 53 | O88736 | 8134403 | 3-keto-steroid reductase (Estradiol 17-beta-dehydrogenase 7) |
| 54 | CAA75742 | 3319971 | 17-beta-hydroxysteroid dehydrogenase type 7 [*Mus musculus*] |
| 55 | P_695820 | 68440091 | PREDICTED: similar to Hydroxysteroid (17-beta) dehydrogenase |
| 56 | P_058931 | 8393576 | hydroxysteroid (17-beta) dehydrogenase 7 [*Rattus norvegicus*] |
| 57 | Q62904 | 8134405 | 3-keto-steroid reductase (Estradiol 17-beta-dehydrogenase 7) |
| 58 | AAC52623 | 1397235 | ovarian-specific protein |
| 59 | BAC37061 | 26346825 | unnamed protein product [*Mus musculus*] |
| 60 | AAM21211 | 20385196 | 17-beta-hydroxysteroid dehydrogenase type 7 [*Mus musculus*] |
| 61 | P_363377 | 39951321 | hypothetical protein MG01303.4 [*Magnaporthe grisea* 70-15] |
| 62 | P_581467 | 76611932 | PREDICTED: similar to hydroxysteroid (17-beta) dehydrogenase |
| 63 | CAC88111 | 18077843 | 17beta hydroxysteroid dehydrogenase [*Homo sapiens*] |
| 64 | AAX42032 | 61361334 | hydroxysteroid (17-beta) dehydrogenase 7 [synthetic construc |
| 65 | AAX42031 | 61361326 | hydroxysteroid (17-beta) dehydrogenase 7 [synthetic construc |
| 66 | CAI13457 | 55959848 | hydroxysteroid (17-beta) dehydrogenase 7 [*Homo sapiens*] |
| 67 | CAI15947 | 55959770 | hydroxysteroid (17-beta) dehydrogenase 7 [*Homo sapiens*] |
| 68 | AAH65246 | 40807207 | Hydroxysteroid (17-beta) dehydrogenase 7 [*Homo sapiens*] |
| 69 | AAQ89321 | 37183042 | HSD17B7 [*Homo sapiens*] |
| 70 | AAP35738 | 30582989 | hydroxysteroid (17-beta) dehydrogenase 7 [*Homo sapiens*] |
| 71 | AAH07068 | 13937918 | Hydroxysteroid (17-beta) dehydrogenase 7 [*Homo sapiens*] |
| 72 | CAC20418 | 12053691 | 17beta-hydroxysteroid dehydrogenase type 7 [*Homo sapiens*] |
| 73 | P56937 | 8134404 | 3-keto-steroid reductase (Estradiol 17-beta-dehydrogenase 7) |
| 74 | P_057455 | 7705421 | hydroxysteroid (17-beta) dehydrogenase 7 [*Homo sapiens*] |
| 75 | AAF09266 | 6721095 | 17 beta-hydroxysteroid dehydrogenase type VII [*Homo sapiens*] |
| 76 | ABB72853 | 82400271 | 17-beta hydroxysteroid dehydrogenase 7 [*Macaca fascicularis*] |
| 77 | AAX29487 | 60653587 | hydroxysteroid (17-beta) dehydrogenase 7 [synthetic construc |
| 78 | AAP36180 | 30583863 | Homo sapiens hydroxysteroid (17-beta) dehydrogenase 7 [synth |
| 79 | AAF14537 | 6502988 | 17beta-hydroxysteroid dehydrogenase type 7 [*Homo sapiens*] |
| 80 | AAK20950 | 13383374 | 17-beta-hydroxysteroid dehydrogenase type 7 [*Oryctolagus* cun |
| 81 | AAP97275 | 33150794 | ovarian-specific protein; OSP [*Homo sapiens*] |
| 82 | P_422210 | 50750970 | PREDICTED: similar to Estradiol 17 beta-dehydrogenase 7 (17- |

TABLE 62

Examples of ERG26 polypeptides.

| Row | ACCESSION | GI | PROTEIN DESCRIPTION |
|---|---|---|---|
| 1 | AAT93045 | 51013503 | YGL001C [*Saccharomyces cerevisiae*] |
| 2 | P53199 | 1723793 | Sterol-4-alpha-carboxylate 3-dehydrogenase, decarboxylating |
| 3 | CAA96701 | 1322447 | unnamed protein product [*Saccharomyces cerevisiae*] |
| 4 | P_446390 | 50287923 | unnamed protein product [*Candida glabrata*] |
| 5 | CAG59317 | 49525698 | unnamed protein product [*Candida glabrata* CBS138] |
| 6 | P_453025 | 50306127 | unnamed protein product [*Kluyveromyces lactis*] |
| 7 | CAH01876 | 49642158 | unnamed protein product [*Kluyveromyces lactis* NRRL Y-1140] |
| 8 | CAC38016 | 13940379 | putative C-3 sterol dehydrogenase [*Zygosaccharomyces rouxii*] |
| 9 | P_985548 | 45198519 | AFR001Wp [*Eremothecium gossypii*] |
| 10 | AAS53372 | 44984470 | AFR001Wp [*Ashbya gossypii* ATCC 10895] |
| 11 | P_458178 | 50419307 | hypothetical protein DEHA0C12463g [*Debaryomyces hansenii* CBS767] |
| 12 | CAG86252 | 49653844 | unnamed protein product [*Debaryomyces hansenii* CBS767] |
| 13 | P_715564 | 68481045 | C-3 sterol dehydrogenase/C-4 decarboxylase [*Candida albicans* SC53 |
| 14 | P_715620 | 68480934 | C-3 sterol dehydrogenase/C-4 decarboxylase [*Candida albicans* SC53 |
| 15 | EAK96601 | 46437251 | hypothetical protein CaO19.10427 [*Candida albicans* SC5314] |
| 16 | EAK96542 | 46437191 | hypothetical protein CaO19.2909 [*Candida albicans* SC5314] |
| 17 | AAK69617 | 14582743 | C-3 sterol dehydrogenase/C-4 decarboxylase [*Candida albicans*] |
| 18 | P_502124 | 50549307 | hypothetical protein [*Yarrowia lipolytica*] |
| 19 | CAG82444 | 49647991 | unnamed protein product [*Yarrowia lipolytica* CLIB122] |
| 20 | P_596741 | 19113533 | hypothetical protein SPBC3F6.02c [*Schizosaccharomyces pombe* 972h- |
| 21 | CAA17691 | 2924499 | SPBC3F6.02c [*Schizosaccharomyces pombe*] |
| 22 | AAQ88129 | 37039511 | C-3 sterol dehydrogenase [*Cryptococcus neoformans* var. *grubii* H99 |
| 23 | P_381379 | 46108642 | hypothetical protein FG01203.1 [*Gibberella zeae* PH-1] |
| 24 | EAA67667 | 42544824 | hypothetical protein FG01203.1 [*Gibberella zeae* PH-1] |
| 25 | EAQ90884 | 88183416 | conserved hypothetical protein [*Chaetomium globosum* CBS 148.51] |
| 26 | P_640712 | 66813066 | 3beta-hydroxysteroid dehydrogenase [*Dictyostelium discoideum* AX4] |
| 27 | EAL66725 | 60468723 | 3beta-hydroxysteroid dehydrogenase [*Dictyostelium discoideum* AX4] |
| 28 | EAT77489 | 111056369 | hypothetical protein SNOG_15264 [*Phaeosphaeria nodorum* SN15] |
| 29 | P_965466 | 85118539 | hypothetical protein [*Neurospora crassa* OR74A] |
| 30 | CAE76518 | 38567226 | related to C-3 sterol dehydrogenase (C-4 decarboxylase) [Neurospo |
| 31 | EAA36230 | 28927275 | hypothetical protein [*Neurospora crassa*] |
| 32 | P_420279 | 50745878 | PREDICTED: similar to NAD(P) dependent steroid dehydrogenase-like |
| 33 | P_001 . . . | 78369400 | hypothetical protein LOC616694 [*Bos taurus*] |
| 34 | AAI03390 | 73586574 | Similar to NAD(P) dependent steroid dehydrogenase-like [*Bos* tauru |
| 35 | P_001 . . . | 62859757 | hypothetical protein LOC550044 [*Xenopus tropicalis*] |
| 36 | AAH88699 | 56788986 | LOC496236 protein [*Xenopus laevis*] |
| 37 | P_538199 | 74008671 | PREDICTED: similar to NAD(P) dependent steroid dehydrogenase-like |
| 38 | P_853073 | 74008673 | PREDICTED: similar to NAD(P) dependent steroid dehydrogenase-like |
| 39 | AAH52834 | 31127258 | NAD(P) dependent steroid dehydrogenase-like [*Mus musculus*] |
| 40 | P_001 . . . | 109132673 | PREDICTED: similar to NAD(P) dependent steroid dehydrogenase-like |
| 41 | P_001 . . . | 109132671 | PREDICTED: similar to NAD(P) dependent steroid dehydrogenase-like |
| 42 | P_001 . . . | 57164113 | NAD(P) dependent steroid dehydrogenase-like [*Rattus norvegicus*] |
| 43 | AAH87626 | 56388600 | NAD(P) dependent steroid dehydrogenase-like [*Rattus norvegicus*] |
| 44 | BAE24522 | 74187675 | unnamed protein product [*Mus musculus*] |
| 45 | P_035071 | 31982437 | NAD(P) dependent steroid dehydrogenase-like [*Mus musculus*] |
| 46 | Q9R1J0 | 8473695 | Sterol-4-alpha-carboxylate 3-dehydrogenase, decarboxylating |
| 47 | CAA15948 | 7619723 | NAD(P)H steroid dehydrogenase [*Mus musculus*] |
| 48 | AAD38448 | 5052206 | putative NAD(P)H steroid dehydrogenase [*Mus musculus*] |
| 49 | AAH19945 | 18043286 | NAD(P) dependent steroid dehydrogenase-like [*Mus musculus*] |
| 50 | AAH07816 | 14043700 | NAD(P) dependent steroid dehydrogenase-like [*Homo sapiens*] |
| 51 | AAH00245 | 12652969 | NAD(P) dependent steroid dehydrogenase-like [*Homo sapiens*] |
| 52 | Q15738 | 8488997 | Sterol-4-alpha-carboxylate 3-dehydrogenase, decarboxylating (H105 |
| 53 | P_057006 | 8393516 | NAD(P) dependent steroid dehydrogenase-like [*Homo sapiens*] |
| 54 | AAC50558 | 4457237 | H105e3 [*Homo sapiens*] |
| 55 | CAF99107 | 47222951 | unnamed protein product [*Tetraodon nigroviridis*] |
| 56 | P_756075 | 71002788 | C-3 sterol dehydrogenase/C-4 decarboxylase [*Aspergillus fumigatus* |
| 57 | EAL94037 | 66853713 | C-3 sterol dehydrogenase/C-4 decarboxylase [*Aspergillus fumigatus* |
| 58 | P_567299 | 58259773 | C-3 sterol dehydrogenase (C-4 sterol decarboxylase) [*Cryptococcus* |
| 59 | AAW45782 | 57229349 | C-3 sterol dehydrogenase (C-4 sterol decarboxylase), putative [Cr |
| 60 | EAL18383 | 50255650 | hypothetical protein CNBJ3060 [*Cryptococcus neoformans* var. neofo |
| 61 | P_001 . . . | 62955325 | hypothetical protein LOC550369 [*Danio rerio*] |
| 62 | AAH93332 | 62204675 | Zgc: 112474 [*Danio rerio*] |
| 63 | EAS37011 | 90307380 | hypothetical protein CIMG_02365 [*Coccidioides immitis* RS] |
| 64 | P_755836 | 71002310 | C-3 sterol dehydrogenase/C-4 decarboxylase [*Aspergillus fumigatus* |

TABLE 62-continued

| Examples of ERG26 polypeptides. | | | |
|---|---|---|---|
| Row | ACCESSION | GI | PROTEIN DESCRIPTION |
| 65 | EAL93798 | 66853474 | C-3 sterol dehydrogenase/C-4 decarboxylase [*Aspergillus fumigatus* |
| 66 | CAH90815 | 55728130 | hypothetical protein [*Pongo pygmaeus*] |
| 67 | P_760274 | 71020087 | hypothetical protein UM04127.1 [*Ustilago maydis* 521] |
| 68 | EAK85155 | 46099922 | hypothetical protein UM04127.1 [*Ustilago maydis* 521] |
| 69 | P_680844 | 67901176 | hypothetical protein AN7575.2 [*Aspergillus nidulans* FGSC A4] |
| 70 | EAA62155 | 40742965 | hypothetical protein AN7575.2 [*Aspergillus nidulans* FGSC A4] |
| 71 | AAZ14936 | 70906332 | putative sterol dehydrogenase [*Coprinellus disseminatus*] |

TABLE 63

| Examples of ERG25 polypeptides. | | | |
|---|---|---|---|
| Row | ACCESSION | GI | PROTEIN DESCRIPTION |
| 1 | AAS56153 | 45269545 | YGR060W [*Saccharomyces cerevisiae*] |
| 2 | XP_448420 | 50291975 | unnamed protein product [*Candida glabrata*] |
| 3 | XP_451890 | 50303885 | unnamed protein product [*Kluyveromyces lactis*] |
| 4 | NP_986119 | 45199090 | AFR572Wp [*Eremothecium gossypii*] |
| 5 | XP_456861 | 50409318 | hypothetical protein DEHA0A12661g [*Debaryomyces hansenii* CBS767] |
| 6 | XP_713420 | 68485318 | C-4 sterol methyl oxidase [*Candida albicans* SC5314] |
| 7 | XP_461658 | 50426123 | hypothetical protein DEHA0G03124g [*Debaryomyces hansenii* CBS767] |
| 8 | XP_505281 | 50555746 | hypothetical protein [*Yarrowia lipolytica*] |
| 9 | XP_722703 | 68466442 | putative C-4 sterol methyl oxidase [*Candida albicans* SC5314] |
| 10 | XP_722849 | 68466149 | putative C-4 sterol methyl oxidase [*Candida albicans* SC5314] |
| 11 | ABF84061 | 107785180 | C-4 sterol methyl oxidase [*Chaetomium globosum*] |
| 12 | Q9UUH4 | 28558117 | C-4 methylsterol oxidase (Methylsterol monooxygenase) |
| 13 | XP_962240 | 85106720 | hypothetical protein [*Neurospora crassa* OR74A] |
| 14 | EAT84680 | 111063560 | hypothetical protein SNOG_08404 [*Phaeosphaeria nodorum* SN15] |
| 15 | XP_746668 | 70982279 | hypothetical protein Afu4g04820 [*Aspergillus fumigatus* Af293] |
| 16 | XP_390006 | 46136629 | hypothetical protein FG09830.1 [*Gibberella zeae* PH-1] |
| 17 | BAE65381 | 83775259 | unnamed protein product [*Aspergillus oryzae*] |
| 18 | XP_360827 | 39942580 | hypothetical protein MG03370.4 [*Magnaporthe grisea* 70-15] |
| 19 | ABA70590 | 77377695 | hypothetical protein [*Penicillium chrysogenum*] |
| 20 | XP_369331 | 39975881 | hypothetical protein MG06133.4 [*Magnaporthe grisea* 70-15] |
| 21 | EAS29762 | 90300131 | hypothetical protein CIMG_08508 [*Coccidioides immitis* RS] |
| 22 | XP_762027 | 71023595 | hypothetical protein UM05880.1 [*Ustilago maydis* 521] |
| 23 | XP_569526 | 58264740 | C-4 methyl sterol oxidase [*Cryptococcus neoformans* var. *neoformans* JEC21] |
| 24 | EAQ88125 | 88180657 | hypothetical protein CHGG_04744 [*Chaetomium globosum* CBS 148.51] |
| 25 | BAE66491 | 83776372 | unnamed protein product [*Aspergillus oryzae*] |
| 26 | XP_746962 | 70982869 | c-4 methyl sterol oxidase [*Aspergillus fumigatus* Af293] |
| 27 | XP_682176 | 67903840 | hypothetical protein AN8907.2 [*Aspergillus nidulans* FGSC A4] |
| 28 | XP_664577 | 67541619 | hypothetical protein AN6973.2 [*Aspergillus nidulans* FGSC A4] |
| 29 | XP_646277 | 66825845 | hypothetical protein DDBDRAFT_0190553 [*Dictyostelium discoideum* AX4] |
| 30 | NP_998917 | 47523336 | sterol-C4-methyl oxidase-like protein [*Sus scrofa*] |
| 31 | AAI07880 | 79160074 | Sterol-C4-methyl oxidase-like [*Homo sapiens*] |
| 32 | BAE01921 | 67971158 | unnamed protein product [*Macaca fascicularis*] |
| 33 | XP_001 . . . | 109076099 | PREDICTED: sterol-C4-methyl oxidase-like isoform 3 [*Macaca mulatta*] |
| 34 | XP_580615 | 61871492 | PREDICTED: similar to C-4 methylsterol oxidase (Methylsterol monooxygenase) isoform 1 [*Bos taurus*] |
| 35 | CAC24471 | 12311696 | hypothetical protein [*Candida albicans*] |
| 36 | BAE30143 | 74185334 | unnamed protein product [*Mus musculus*] |
| 37 | XP_532714 | 57096891 | PREDICTED: similar to C-4 methylsterol oxidase (Methylsterol monooxygenase) isoform 1 [*Canis familiaris*] |
| 38 | CAF92153 | 47211304 | unnamed protein product [*Tetraodon nigroviridis*] |
| 39 | AAH63155 | 38649308 | Sterol-C4-methyl oxidase-like [*Rattus norvegicus*] |
| 40 | NP_001 . . . | 57530155 | sterol-C4-methyl oxidase-like [*Gallus gallus*] |
| 41 | NP_998518 | 47087009 | sterol-C4-methyl oxidase-like [*Danio rerio*] |
| 42 | NP_563789 | 18390767 | SMO2-2; C-4 methylsterol oxidase [*Arabidopsis thaliana*] |
| 43 | AAI21457 | 111309060 | Unknown (protein for MGC: 146461) [*Xenopus tropicalis*] |
| 44 | AAM64821 | 21592871 | putative C-4 sterol methyl oxidase [*Arabidopsis thaliana*] |
| 45 | AAF79571 | 8778563 | F22G5.23 [*Arabidopsis thaliana*] |
| 46 | AAO13795 | 27448145 | putative sterol 4-alpha-methyl-oxidase [*Gossypium arboreum*] |
| 47 | AAO48604 | 28864263 | ERG25 [*Clavispora lusitaniae*] |
| 48 | AAQ83692 | 34978966 | C-4 sterol methyl oxidase 2 [*Nicotiana benthamiana*] |
| 49 | ABD97153 | 90658509 | C-4 methyl sterol oxidase [*Cryptococcus neoformans* var. *neoformans*] |

TABLE 63-continued

| Examples of ERG25 polypeptides. | | | |
|---|---|---|---|
| Row | ACCESSION | GI | PROTEIN DESCRIPTION |
| 50 | ABD97146 | 90658495 | C-4 methyl sterol oxidase [*Cryptococcus neoformans* var. *grubii*] |
| 51 | ABD97147 | 90658497 | C-4 methyl sterol oxidase [*Cryptococcus neoformans* var. *grubii*] |
| 52 | ABD97134 | 90658471 | C-4 methyl sterol oxidase [*Cryptococcus neoformans* var. *neoformans*] |
| 53 | AAL82576 | 27447203 | putative sterol 4-alpha-methyl-oxidase [*Zea mays*] |
| 54 | NP_850133 | 30684225 | SMO2-1; C-4 methylsterol oxidase [*Arabidopsis thaliana*] |
| 55 | NP_973559 | 42570971 | SMO2-1; C-4 methylsterol oxidase [*Arabidopsis thaliana*] |
| 56 | AAL32287 | 16973432 | sterol 4-alpha-methyl-oxidase [*Arabidopsis thaliana*] |
| 57 | ABE83226 | 92875070 | Sterol desaturase [*Medicago truncatula*] |
| 58 | BAF28920 | 113645779 | Os11g0707600 [*Oryza sativa* (*japonica* cultivar-group)] |
| 59 | BAF20592 | 113610214 | Os07g0101500 [*Oryza sativa* (*japonica* cultivar-group)] |
| 60 | XP_787442 | 72077919 | PREDICTED: similar to C-4 methylsterol oxidase (Methylsterol monooxygenase) [*Strongylocentrotus purpuratus*] |
| 61 | AAM64359 | 21592408 | putative C-4 sterol methyl oxidase [*Arabidopsis thaliana*] |
| 62 | NP_973777 | 42571373 | SMO2-2; C-4 methylsterol oxidase [*Arabidopsis thaliana*] |
| 63 | NP_001 . . . | 62865628 | sterol-C4-methyl oxidase-like isoform 2 [*Homo sapiens*] |
| 64 | AAX95419 | 62733302 | 4-alpha-methyl-sterol C4-methyl-oxidase [*Oryza sativa* (*japonica* cultivar-group)] |
| 65 | XP_883875 | 76638226 | PREDICTED: similar to C-4 methylsterol oxidase (Methylsterol monooxygenase) isoform 3 [*Bos taurus*] |
| 66 | ABE87434 | 92884635 | Sterol desaturase [*Medicago truncatula*] |
| 67 | XP_641553 | 66814748 | hypothetical protein DDBDRAFT_0205936 [*Dictyostelium discoideum* AX4] |
| 68 | AAM65428 | 21593461 | putative C-4 sterol methyl oxidase [*Arabidopsis thaliana*] |
| 69 | NP_567669 | 18416002 | SMO1-3 (STEROL 4-ALPHA METHYL OXIDASE); catalytic [*Arabidopsis thaliana*] |
| 70 | AAM64961 | 21593012 | putative C-4 sterol methyl oxidase [*Arabidopsis thaliana*] |
| 71 | AAN18115 | 23308291 | At4g12110/F16J13_180 [*Arabidopsis thaliana*] |
| 72 | AAK61361 | 27446631 | putative sterol 4-alpha-methyl-oxidase [*Arabidopsis thaliana*] |
| 73 | BAF01201 | 110738551 | hypothetical protein [*Arabidopsis thaliana*] |
| 74 | AAQ13424 | 33337546 | sterol-4-methyl-oxidase [*Arabidopsis thaliana*] |
| 75 | BAF27120 | 113639815 | Os10g0545200 [*Oryza sativa* (*japonica* cultivar-group)] |
| 76 | CAB78254 | 7267912 | putative C-4 sterol methyl oxidase [*Arabidopsis thaliana*] |
| 77 | AAQ94118 | 37591406 | sterol-4-alpha methyl oxidase [*Arabidopsis thaliana*] |
| 78 | AAQ83691 | 34978964 | C-4 sterol methyl oxidase 1 [*Nicotiana benthamiana*] |
| 79 | ABD65536 | 89266491 | sterol-C4-methyl oxidase-like [*Ictalurus punctatus*] |
| 80 | BAC57961 | 28804511 | putative C-4 sterol methyl oxidase [*Aster tripolium*] |

TABLE 64

| Examples of ERG24 polypeptides. | | | |
|---|---|---|---|
| Row | ACCESSION | GI | PROTEIN DESCRIPTION |
| 1 | AAB30203 | 545906 | sterol delta 14 reductase; Erg24p [*Saccharomyces cerevisiae*] |
| 2 | XP_447380 | 50289897 | hypothetical protein CAGL0I02970g [*Candida glabrata* CBS138] |
| 3 | XP_452744 | 50305569 | unnamed protein product [*Kluyveromyces lactis*] |
| 4 | NP_985893 | 45198864 | AFR346Wp [*Eremothecium gossypii*] |
| 5 | XP_710670 | 68491033 | sterol C-14 reductase [*Candida albicans* SC5314] |
| 6 | XP_458371 | 50419687 | hypothetical protein DEHA0C16984g [*Debaryomyces hansenii* CBS767] |
| 7 | XP_501260 | 50547581 | hypothetical protein [*Yarrowia lipolytica*] |
| 8 | XP_566548 | 58258271 | C-14 sterol reductase [*Cryptococcus neoformans* var. *neoformans* JEC21] |
| 9 | NP_596767 | 19113559 | hypothetical protein SPBC16G5.18 [*Schizosaccharomyces pombe* 972h-] |
| 10 | EAL23454 | 50260804 | hypothetical protein CNBA1040 [*Cryptococcus neoformans* var. *neoformans* B-3501A] |
| 11 | XP_759786 | 71019111 | hypothetical protein UM03639.1 [*Ustilago maydis* 521] |
| 12 | XP_386782 | 46124457 | ER24_FUSSO Delta(14)-sterol reductase (C-14 sterol reductase) (Sterol C14-reductase) [*Gibberella zeae* PH-1] |
| 13 | P78575 | 6015106 | Delta(14)-sterol reductase (C-14 sterol reductase) (Sterol C14-reductase) |
| 14 | Q01447 | 3929349 | Delta(14)-sterol reductase (C-14 sterol reductase) (Sterol C14-reductase) |

TABLE 65

Examples of ERG11 polypeptides.

| Row | ACCESSION | GI | PROTEIN DESCRIPTION |
|---|---|---|---|
| 1 | AAA34546 | 171354 | lanosterol 14-demethylase cytochrome P450 |
| 2 | AAA34547 | 171356 | lanosterol 14-demethylase cytochrome P450 |
| 3 | AAY59417 | 66967944 | 14alpha-demethylase [*Candida glabrata*] |
| 4 | XP_454109 | 50308217 | unnamed protein product [*Kluyveromyces lactis*] |
| 5 | Q759W0 | 51701328 | Cytochrome P450 51 (CYPLI) (P450-LIA1) (Sterol 14-alpha demethylase) (Lanosterol 14-alpha demethylase) (P450-14DM) |
| 6 | AAB32679 | 912807 | cyto chrome P-450 lanosterol-alpha-demethylase; P450-L1A1 [*Candida glabrata*] |
| 7 | AAX39316 | 61189834 | lanosterol 14 alpha demethylase [*Candida tropicalis*] |
| 8 | AAF00598 | 6006769 | cytochrome P450 lanosterol 14-alpha demethylase [*Candida albicans*] |
| 9 | XP_716761 | 68478280 | lanosterol 14-alpha-demethylase [*Candida albicans* SC5314] |
| 10 | XP_460143 | 50423125 | hypothetical protein DEHA0E20383g [*Debaryomyces hansenii* CBS767] |
| 11 | ABC41921 | 83728463 | cytochrome P450 lanosterol 14 alpha demethylase [*Candida albicans*] |
| 12 | AAX39315 | 61189832 | lanosterol 14 alpha demethylase [*Candida tropicalis*] |
| 13 | O4CK51 | 65689 | lanosterol 14alpha-demethylase (EC 1.14.14. - ) cytochrome P450 51 - yeast (*Candida albicans*) |
| 14 | XP_716822 | 68478161 | lanosterol 14-alpha-demethylase [*Candida albicans* SC5314] |
| 15 | AAF00603 | 6006774 | cytochrome P450 lanosterol 14-alpha demethylase [*Candida albicans*] |
| 16 | AAF00600 | 6006771 | cytochrome P450 lanosterol 14-alpha demethylase [*Candida albicans*] |
| 17 | BAB03401 | 9558446 | CYP51 variant 3 [*Candida albicans*] |
| 18 | AAK57519 | 14280372 | lanosterol 14-alpha demethylase Erg11p [*Candida dubliniensis*] |
| 19 | AAF00602 | 6006773 | cytochrome P450 lanosterol 14-alpha demethylase [*Candida albicans*] |
| 20 | AAF00601 | 6006772 | cytochrome P450 lanosterol 14-alpha demethylase [*Candida albicans*] |
| 21 | BAB03400 | 9558444 | CYP51 variant 2 [*Candida albicans*] |
| 22 | AAO83898 | 29378393 | cytochrome P-450 lanosterol-alpha-demethylase [*Issatchenkia orientalis*] |
| 23 | AAW50593 | 57341382 | Erg11p [*Candida albicans*] |
| 24 | AAW50592 | 57341380 | Erg11p [*Candida albicans*] |
| 25 | XP_500518 | 50545962 | hypothetical protein [*Yarrowia lipolytica*] |
| 26 | BAC16517 | 23263326 | cytochrome P-450 lanosterol 14alpha-demethylase [*Candida albicans*] |
| 27 | BAC16520 | 23263332 | cytochrome P-450 lanosterol 14alpha-demethylase [*Candida albicans*] |
| 28 | BAC16518 | 23263328 | cytochrome P-450 lanosterol 14alpha-demethylase [*Candida albicans*] |
| 29 | BAC16519 | 23263330 | cytochrome P-450 lanosterol 14alpha-demethylase [*Candida albicans*] |
| 30 | Q02315 | 2493385 | Cytochrome P450 51 (CYPLI) (P450-LIA1) (Sterol 14-alpha demethylase) (Lanosterol 14-alpha demethylase) (P450-14DM) |
| 31 | AAO38776 | 28395121 | lanosterol 14 alpha demethylase; ERG11 [*Pneumocystis carinii*] |
| 32 | ABG91757 | 110816094 | sterol 14alpha-demethylase [*Pneumocystis carinii*] |
| 33 | BAE60239 | 83770104 | unnamed protein product [*Aspergillus oryzae*] |
| 34 | XP_749134 | 70987441 | 14-alpha sterol demethylase Cyp51B [*Aspergillus fumigatus* Af293] |
| 35 | XP_659505 | 67522889 | hypothetical protein AN1901.2 [*Aspergillus nidulans* FGSC A4] |
| 36 | XP_681552 | 67902592 | hypothetical protein AN8283.2 [*Aspergillus nidulans* FGSC A4] |
| 37 | AAK73659 | 14861413 | 14-alpha sterol demethylase [*Aspergillus fumigatus*] |
| 38 | XP_752137 | 70994720 | 14-alpha sterol demethylase Cyp51A [*Aspergillus fumigatus* Af293] |
| 39 | BAE57417 | 83767278 | unnamed protein product [*Aspergillus oryzae*] |
| 40 | AAF79204 | 8778097 | cytochrome P450 sterol 14 alpha-demethylase [*Emericella nidulans*] |
| 41 | CAE18091 | 33300264 | eburicol 14 alpha demethylase [*Blumeria graminis*] |
| 42 | EAS28723 | 90299092 | cytochrome P450 51 [*Coccidioides immitis* RS] |
| 43 | CAE18094 | 33300270 | eburicol 14 alpha demethylase [*Blumeria graminis*] |
| 44 | CAC85624 | 33300256 | eburicol 14alpha demethylase [*Blumeria graminis* f. sp. tritici] |
| 45 | CAE18095 | 33300272 | eburicol 14 alpha demethylase [*Blumeria graminis*] |
| 46 | CAE17515 | 33284834 | eburicol 14 alpha demethylase [*Blumeria graminis* f. sp. *tritici*] |
| 47 | AAU43734 | 52352491 | eburicol 14 alpha-demethylase [*Mycosphaerella graminicola*] |
| 48 | EAS35219 | 90305588 | cytochrome P450 51 [*Coccidioides immitis* RS] |
| 49 | CAE18102 | 33300286 | eburicol 14 alpha demethylase [*Blumeria graminis*] |
| 50 | CAE18103 | 33300288 | eburicol 14 alpha demethylase [*Blumeria graminis*] |
| 51 | CAE18105 | 33300292 | eburicol 14 alpha demethylase [*Blumeria graminis*] |
| 52 | NP_592990 | 19113902 | hypothetical protein SPAC13A11.02c [*Schizosaccharomyces pombe* 972h-] |
| 53 | CAE18100 | 33300282 | eburicol 14 alpha demethylase [*Blumeria graminis*] |
| 54 | AAP79601 | 32330152 | eburicol 14alpha-demethylase [*Mycosphaerella graminicola*] |
| 55 | AAC97606 | 4049645 | eburicol 14alpha demethylase; CYP51; cytochrome P450 sterol 14-demethylase [*Blumeria graminis* f. sp. *hordei*] |
| 56 | CAE18099 | 33300280 | eburicol 14 alpha demethylase [*Blumeria graminis*] |
| 57 | BAE63554 | 83773427 | unnamed protein product [*Aspergillus oryzae*] |
| 58 | XP_381176 | 46108236 | hypothetical protein FG01000.1 [*Gibberella zeae* PH-1] |

TABLE 65-continued

| Examples of ERG11 polypeptides. | | | |
|---|---|---|---|
| Row | ACCESSION | GI | PROTEIN DESCRIPTION |
| 59 | AAF85983 | 9230788 | eburicol 14 alpha-demethylase [*Botryotinia fuckeliana*] |
| 60 | AAP81934 | 32441730 | eburicol 14 alpha-demethylase [*Mycosphaerella graminicola*] |
| 61 | XP_362183 | 39945292 | hypothetical protein MG04628.4 [*Magnaporthe grisea*70-15] |
| 62 | AAP12370 | 30314338 | lanosterol 14 alpha-demethylase; 14 alpha lanosterol demethylase [*Cryptococcus neoformans* var. *grubii*] |
| 63 | AAF74756 | 8347731 | eburicol 14-alpha demethylase [*Mycosphaerella graminicola*] |
| 64 | AAF76464 | 8570176 | 14 alpha-demethylase [*Venturia inaequalis*] |
| 65 | XP_566464 | 58258103 | sterol 14-demethylase [*Cryptococcus neoformans* var. *neoformans* JEC21] |
| 66 | EAQ93417 | 88185949 | conserved hypothetical protein [*Chaetomium globosum* CBS 148.51] |
| 67 | AAL79180 | 18766932 | eburicol 14 alpha-demethylase [*Monilinia fructicola*] |
| 68 | AAU01157 | 51341094 | lanosterol 14-alpha-demethylase [*Coccidioides posadasii*] |
| 69 | CAD27793 | 19572745 | cytochrome P-450 14DM [*Penicillium digitatum*] |
| 70 | XP_384268 | 46116500 | hypothetical protein FG04092.1 [*Gibberella zeae* PH-1] |
| 71 | AAG18433 | 10505323 | eburicol 14 alpha-demethylase [*Botryotinia fuckeliana*] |
| 72 | AAK26391 | 13445823 | eburicol 14 alpha-demethylase [*Botryotinia fuckeliana*] |
| 73 | AAG18431 | 10505318 | eburicol 14 alpha-demethylase [*Botryotinia fuckeliana*] |
| 74 | AAK26386 | 13445813 | eburicol 14 alpha-demethylase [*Botryotinia fuckeliana*] |
| 75 | AAD55135 | 5881952 | eburicol 14-alpha demethylase; cytochrome P450 sterol 14-alpha demethylase; Erg11 [*Uncinula necator*] |
| 76 | AAK26389 | 13445819 | eburicol 14 alpha-demethylase [*Botryotinia fuckeliana*] |
| 77 | CAC85409 | 15864613 | euburicol 14 alpha-demethylase [*Venturia nashicola*] |
| 78 | BAB03659 | 9664027 | cytochrome P-450 14DM [*Penicillium digitatum*] |
| 79 | AAG18435 | 10505329 | eburicol 14 alpha-demethylase [*Botryotinia fuckeliana*] |
| 80 | AAG18434 | 10505326 | eburicol 14 alpha-demethylase [*Botryotinia fuckeliana*] |
| 81 | AAU01158 | 51341096 | lanosterol 14-alpha-demethylase [*Ajellomyces capsulatus*] |
| 82 | AAK26387 | 13445815 | eburicol 14 alpha-demethylase [*Botryotinia fuckeliana*] |
| 83 | AAG18432 | 10505321 | eburicol 14 alpha-demethylase [*Botryotinia fuckeliana*] |
| 84 | AAK26388 | 13445817 | eburicol 14 alpha-demethylase [*Botryotinia fuckeliana*] |
| 85 | XP_391200 | 46139019 | hypothetical protein FG11024.1 [*Gibberella zeae* PH-1] |
| 86 | AAK26390 | 13445821 | eburicol 14 *alpha-demethylase* [*Botryotinia fuckeliana*] |
| 87 | O14442 | 14916976 | Cytochrome P450 51 (CYPLI) (P450-LIA1) (Sterol 14-alpha demethylase) (Eburicol 14-alpha-demethylase) (P450-14DM) |
| 88 | AAG18438 | 10505336 | eburicol 14 alpha-demethylase [*Botryotinia fuckeliana*] |
| 89 | XP_759809 | 71019157 | sterol 14-alpha demethylase [*Ustilago maydis* 521] |
| 90 | AAF18468 | 6581118 | eburicol 14 alpha-demethylase [*Tapesia acuformis*] |
| 91 | AAG18436 | 10505331 | eburicol 14 alpha-demethylase [*Botryotinia fuckeliana*] |
| 92 | AAC49801 | 5733843 | eburicol 14-alpha demethylase [*Uncinula necator*] |
| 93 | ABE01107 | 90823211 | 14alpha demethylase [*Blumeriella jaapii*] |
| 94 | AAG18437 | 10505334 | eburicol 14 alpha-demethylase [*Botryotinia fuckeliana*] |
| 95 | CAD27792 | 19572743 | cytochrome P-450 14DM [*Penicillium digitatum*] |
| 96 | XP_964049 | 85111674 | hypothetical protein [*Neurospora crassa* OR74A] |
| 97 | AAF18469 | 11178694 | eburicol 14 alpha-demethylase [*Tapesia yallundae*] |
| 98 | Q12664 | 2493386 | Cytochrome P450 51 (CYPLI) (P450-LIA1) (Sterol 14-alpha demethylase) (Eburicol 14-alpha-demethylase) (P450-14DM) |
| 99 | AAG44832 | 12006321 | eburicol 14-alpha demethylase [*Tapesia yallundae*] |
| 100 | AAG44831 | 12006319 | eburicol 14-alpha demethylase [*Tapesia yallundae*] |
| 101 | AAN28927 | 23505745 | sterol 14 alpha-demethylase ERG11 [*Leptosphaeria maculans*] |
| 102 | XP_361987 | 39944900 | hypothetical protein MG04432.4 [*Magnaporthe grisea* 70-15] |
| 103 | EAT88907 | 111067787 | hypothetical protein SNOG_03702 [*Phaeosphaeria nodorum* SN15] |
| 104 | AAU01160 | 51341100 | lanosterol 14-alpha-demethylase [*Phanerochaete chrysosporium*] |
| 105 | AAC23550 | 3220152 | cytochrome P450 L1A1 demethylase [*Pichia anomala*] |
| 106 | AAU01159 | 51341098 | lanosterol 14-alpha-demethylase [*Coprinopsis cinerea*] |
| 107 | Q9UVC3 | 12229768 | Cytochrome P450 51 (CYPLI) (P450-LIA1) (Sterol 14-alpha demethylase) (Lanosterol 14-alpha demethylase) (P450-14DM) |
| 108 | AAQ88128 | 37039509 | cytochrome P450 lanosterol 14a-demethylase [*Cryptococcus neoformans* var. *grubii* H99] |
| 109 | NP_064394 | 71061451 | cytochrome P450, family 51 [*Mus musculus*] |
| 110 | EAL24154 | 51094909 | cytochrome P450, family 51, subfamily A, polypeptide 1 [*Homo sapiens*] |
| 111 | Q16850 | 3915660 | Cytochrome P450 51A1 (CYPLI) (P450LI) (Sterol 14-alpha demethylase) (Lanosterol 14-alpha demethylase) (LDM) (P450-14DM) (P45014DM) |
| 112 | NP_999597 | 47523914 | cytochrome P450 51 [*Sus scrofa*] |
| 113 | BAC27231 | 26326975 | unnamed protein product [*Mus musculus*] |
| 114 | Q5RE72 | 83287777 | Cytochrome P450 51A1 (CYPLI) (P450LI) (Sterol 14-alpha demethylase) (Lanosterol 14-alpha demethylase) (LDM) (P450-14DM) (P45014DM) |
| 115 | Q4PJW3 | 75075066 | Cytochrome P450 51A1 (CYPLI) (P450LI) (Sterol 14-alpha demethylase) (Lanosterol 14-alpha demethylase) (LDM) (P450-14DM) (P45014DM) |
| 116 | AAF74562 | 8347236 | lanosterol 14-alpha-demethylase [*Mus musculus*] |
| 117 | AAC50951 | 1698484 | lanosterol 14-alpha demethylase [*Homo sapiens*] |

TABLE 65-continued

| Examples of ERG11 polypeptides. | | | |
|---|---|---|---|
| Row | ACCESSION | GI | PROTEIN DESCRIPTION |
| 118 | XP_532457 | 57095976 | PREDICTED: similar to Cytochrome P450 51A1 (CYPLI) (P450LI) (Sterol 14-alpha demethylase) (Lanosterol 14-alpha demethylase) (LDM) (P450-14DM) (P45014DM) isoform 1 [*Canis familiaris*] |
| 119 | AAF73986 | 8215679 | lanosterol 14-alpha-demethylase [*Mus musculus*] |
| 120 | AAH81210 | 51703589 | MGC84806 protein [*Xenopus laevis*] |
| 121 | AAA87074 | 699396 | lanosterol 14-alpha-demethylase |
| 122 | XP_418650 | 50732469 | PREDICTED: similar to lanosterol 14-demethylase [*Gallus gallus*] |
| 123 | BAE01508 | 67970330 | unnamed protein product [*Macaca fascicularis*] |
| 124 | AAR89624 | 40748287 | 14-alpha demethylase [*Fundulus heteroclitus*] |
| 125 | NP_001 . . . | 50053648 | cytochrome P450, family 51 [*Strongylocentrotus purpuratus*] |
| 126 | AAR89625 | 40748289 | 14-alpha demethylase [*Danio rerio*] |
| 127 | NP_001 . . . | 99028936 | cytochrome P450, family 51 [*Danio rerio*] |
| 128 | CAJ81841 | 89268132 | cytochrome P450, family 51, subfamily A, polypeptide 1 [*Xenopus tropicalis*] |
| 129 | AAR89626 | 40748291 | 14-alpha demethylase [*Abudefduf saxatilis*] |

TABLE 66

| Examples of ERG4 polypeptides. | | | |
|---|---|---|---|
| Row | ACCESSION | GI | PROTEIN DESCRIPTION |
| 1 | AAD13895 | 4261595 | Unknown [*Saccharomyces cerevisiae*] |
| 2 | AAT93224 | 51013861 | YGL012W [*Saccharomyces cerevisiae*] |
| 3 | AAY42962 | 66270055 | C24 sterol reductase [*Candida glabrata*] |
| 4 | XP_451223 | 50302575 | unnamed protein product [*Kluyveromyces lactis*] |
| 5 | NP_986579 | 45201009 | AGL087Cp [*Eremothecium gossypii*] |
| 6 | XP_456709 | 50407411 | hypothetical protein DEHA0A08888g [*Debaryomyces hansenii* CBS767] |
| 7 | XP_717662 | 68476402 | sterol C-24 (28) reductase [*Candida albicans* SC5314] |
| 8 | XP_503021 | 50551095 | hypothetical protein [*Yarrowia lipolytica*] |
| 9 | EAU37607 | 114195907 | Delta(24(24(1)))-sterol reductase [*Aspergillus terreus* NIH2624] |
| 10 | BAE61064 | 83770931 | unnamed protein product [*Aspergillus oryzae*] |
| 11 | NP_594742 | 19115654 | hypothetical protein SPAC20G4.07c [*Schizosaccharomyces pombe* 972h-] |
| 12 | CAA45113 | 5109 | sts1+ [*Schizosaccharomyces pombe*] |
| 13 | XP_662788 | 67538028 | hypothetical protein AN5184.2 [*Aspergillus nidulans* FGSC A4] |
| 14 | XP_750461 | 70991224 | c-24(28) sterol reductase [*Aspergillus fumigatus* Af293] |
| 15 | EAS37114 | 90307483 | hypothetical protein CIMG_02468 [*Coccidioides immitis* RS] |
| 16 | XP_365763 | 39968745 | hypothetical protein MG02465.4 [*Magnaporthe grisea* 70-15] |
| 17 | CAC18223 | 16944336 | probable sterol C-24 reductase [*Neurospora crassa*] |
| 18 | XP_961419 | 85102913 | probable sterol C-24 reductase [MIPS] [*Neurospora crassa* OR74A] |
| 19 | XP_660288 | 67524453 | hypothetical protein AN2684.2 [*Aspergillus nidulans* FGSC A4] |
| 20 | EAU33849 | 114192149 | Delta(24(24(1)))-sterol reductase [*Aspergillus terreus* NIH2624] |
| 21 | XP_753221 | 70996933 | c-24(28) sterolreductase [*Aspergillus fumigatus* Af293] |
| 22 | BAE59624 | 83769489 | unnamed protein product [*Aspergillus oryzae*] |
| 23 | EAT92432 | 111071312 | predicted protein [*Phaeosphaeria nodorum* SN15] |
| 24 | XP_390179 | 46136975 | hypothetical protein FG10003.1 [*Gibberella zeae* PH-1] |
| 25 | XP_757645 | 71005958 | hypothetical protein UM01498.1 [*Ustilago maydis* 521] |
| 26 | EAS37449 | 90307818 | hypothetical protein CIMG_02803 [*Coccidioides immitis* RS] |
| 27 | NP_820201 | 29654509 | c-24(28) sterol reductase, putative [*Coxiella burnetii* RSA 493] |
| 28 | ZP_012 . . . | 94491050 | hypothetical protein CburD_01001859 [*Coxiella burnetii* Dugway 7E9-12] |
| 29 | AAQ88130 | 37039513 | sterol C-24 reductase [*Cryptococcus neoformans* var. *grubii* H99] |
| 30 | XP_569697 | 58265082 | delta24(24-1) sterol reductase [*Cryptococcus neoformans* var. *neoformans* JEC21] |
| 31 | EAQ90721 | 88183253 | hypothetical protein CHGG_02656 [*Chaetomium globosum* CBS 148.51] |
| 32 | BAE55606 | 83765463 | unnamed protein product [*Aspergillus oryzae*] |
| 33 | CAJ06078 | 68128884 | sterol C-24 reductase, putative [*Leishmania major*] |
| 34 | ABD46555 | 88601114 | sterol C-24 reductase-like protein [*Acanthamoeba castellanii*] |
| 35 | XP_638613 | 66809779 | ERG4/ERG24 ergosterol biosynthesis protein family protein [*Dictyostelium discoideum* AX4] |

TABLE 67

| Examples of beta-carotene 15,15'-monooxygenase polypeptides. | | |
|---|---|---|
| ACCESSION | GI | PROTEIN DESCRIPTION |
| AAG15381 | 10242318 | beta, beta-carotene 15,15'-dioxygenase [*Mus musculus*] |
| EDL92648 | 149038288 | beta-carotene 15,15'-monooxygenase [*Rattus norvegicus*] |
| Q91XT5 | 46397349 | Beta,beta-carotene 15,15'-monooxygenase (Beta-carotene dioxygenase 1) |

TABLE 67-continued

Examples of beta-carotene 15,15'-monooxygenase polypeptides.

| ACCESSION | GI | PROTEIN DESCRIPTION |
|---|---|---|
| XP_546815 | 57087275 | PREDICTED: similar to Beta,beta-carotene 15,15-monooxygenase (Beta-carotene dioxygenase 1) [*Canis familiaris*] |
| XP_001 . . . | 149699876 | PREDICTED: similar to beta, beta-carotene 15,15-dioxygenase [*Equus caballus*] |
| EAW95537 | 119615943 | beta-carotene 15,15'-monooxygenase 1, isoform CRA_a [*Homo sapiens*] |
| Q9HAY6 | 41688803 | Beta,beta-carotene 15,15'-monooxygenase (Beta-carotene dioxygenase 1) |
| BAA91776 | 7022941 | unnamed protein product [*Homo sapiens*] |
| BAC35679 | 26344045 | unnamed protein product [*Mus musculus*] |
| NP_001 . . . | 66792910 | beta-carotene 15,15'-monooxygenase 1 [*Bos taurus*] |
| XP_001 . . . | 126303742 | PREDICTED: similar to beta, beta-carotene 15,15-dioxygenase [*Monodelphis domestica*] |
| XP_523435 | 114663815 | PREDICTED: beta-carotene 15,15'-monooxygenase 1 [*Pan troglodytes*] |
| XP_414163 | 50753878 | PREDICTED: beta-carotene 15,15'-monooxygenase 1 [*Gallus gallus*] |
| EAW95538 | 119615944 | beta-carotene 15,15'-monooxygenase 1, isoform CRA_b [*Homo sapiens*] |
| AAH56789 | 34784018 | Zgc: 63614 [*Danio rerio*] |
| NP_571873 | 42476258 | beta-carotene 15,15'-monooxygenase 1 [*Danio rerio*] |
| CAC37566 | 13872740 | putative b,b-carotene-15,15'-dioxygenase [*Danio rerio*] |
| CAF95764 | 47214429 | unnamed protein product [*Tetraodon nigroviridis*] |
| CAF92469 | 47212035 | unnamed protein product [*Tetraodon nigroviridis*] |
| ABQ09267 | 146186430 | beta-carotene 15,15'-monooxygenase 1 [*Oryzias latipes*] |
| CAM14044 | 122890964 | beta-carotene 15,15-dioxygenase 2 [*Danio rerio*] |
| AAI33726 | 126631776 | Bcdo2 protein [*Rattus norvegicus*] |
| CAC37567 | 13872742 | putative b,b-carotene-9',10'-dioxygenase [*Danio rerio*] |
| AAI07007 | 76825286 | Beta-carotene 9',10'-dioxygenase 2 [*Mus musculus*] |
| AAI35025 | 141795614 | Bcdo21 protein [*Danio rerio*] |
| NP_001 . . . | 55741954 | beta-carotene dioxygenase 2 [*Xenopus tropicalis*] |
| XP_417929 | 118102019 | PREDICTED: similar to carotene-9,10-monooxygenase [*Gallus gallus*] |
| Q5RF16 | 75042584 | Beta,beta-carotene 9',10'-dioxygenase (Beta-carotene dioxygenase 2) (B-diox-II) |
| XP_001 . . . | 109108669 | PREDICTED: beta-carotene dioxygenase 2 [*Macaca mulatta*] |
| BAC41782 | 26449309 | hypothetical protein [*Macaca fascicularis*] |
| Q8HXG8 | 47117670 | Beta,beta-carotene 9',10'-dioxygenase (Beta-carotene dioxygenase 2) (B-diox-II) |
| AAI15260 | 92098295 | Beta-carotene 15,15-dioxygenase 2 [*Danio rerio*] |
| AAS20392 | 42560440 | carotene-9',10'-monooxygenase [*Mustela putorius furo*] |
| CAG03680 | 47217728 | unnamed protein product [*Tetraodon nigroviridis*] |
| XP_536572 | 73955144 | PREDICTED: similar to Beta,beta-carotene 9,10-dioxygenase (Beta-carotene dioxygenase 2) (B-diox-II) [*Canis familiaris*] |
| XP_001 . . . | 126327024 | PREDICTED: similar to carotene-9,10-monooxygenase [*Monodelphis domestica*] |
| XP_001 . . . | 114640348 | PREDICTED: beta-carotene dioxygenase 2 isoform 3 [*Pan troglodytes*] |
| XP_001 . . . | 114640346 | PREDICTED: beta-carotene dioxygenase 2 isoform 4 [*Pan troglodytes*] |
| AAK69433 | 14582265 | putative carotene dioxygenase [*Homo sapiens*] |
| Q9BYV7 | 41688802 | Beta,beta-carotene 9',10'-dioxygenase (Beta-carotene dioxygenase 2) (B-diox-II) |
| EAW67194 | 119587598 | beta-carotene dioxygenase 2, isoform CRA_f [*Homo sapiens*] |
| EAW67189 | 119587593 | beta-carotene dioxygenase 2, isoform CRA_a [*Homo sapiens*] |
| XP_001 . . . | 149716895 | PREDICTED: similar to carotene-9,10-monooxygenase [*Equus caballus*] |
| NP_001 . . . | 82617628 | beta-carotene dioxygenase 2 isoform b [*Homo sapiens*] |
| NP_114144 | 82617624 | beta-carotene dioxygenase 2 isoform a [*Homo sapiens*] |
| CAC27994 | 12666531 | putative b,b-carotene-9',10'-dioxygenase [*Homo sapiens*] |
| XP_508757 | 114640350 | PREDICTED: hypothetical protein isoform 5 [*Pan troglodytes*] |
| BAB55379 | 14042749 | unnamed protein product [*Homo sapiens*] |
| EAW67193 | 119587597 | beta-carotene dioxygenase 2, isoform CRA_e [*Homo sapiens*] |
| NP_001 . . . | 147906096 | hypothetical protein LOC791719 [*Danio rerio*] |
| XP_001 . . . | 125824393 | PREDICTED: similar to retinal pigment epithelium 65b [*Danio rerio*] |
| AAH59559 | 37748750 | Zgc: 73213 [*Danio rerio*] |
| AAC14586 | 675485 | retinal pigment epithelium-specific 61 kDa protein [*Homo sapiens*] |
| XP_001 . . . | 109008381 | PREDICTED: retinal pigment epithelium-specific protein 65 kDa [*Macaca mulatta*] |
| NP_001 . . . | 71480121 | retinal pigment epithelium 65b [*Danio rerio*] |
| NP_084263 | 147902089 | retinal pigment epithelium 65 [*Mus musculus*] |
| AAD42042 | 5326773 | retinal pigment epithelium-specific protein RPE65 [*Cercopithecus aethiops*] |
| AAL01119 | 15488446 | RPE65 [*Mus musculus*] |
| CAA46988 | 564 | membrane receptor p63 [*Bos taurus*] |
| AAC37306 | 163657 | retinal pigment epithelium-specific 65 kD protein |
| EDL82582 | 149026339 | retinal pigment epithelium 65 [*Rattus norvegicus*] |
| NP_446014 | 16758332 | retinal pigment epithelium 65 [*Rattus norvegicus*] |
| NP_001 . . . | 148228575 | retinal pigment epithelium-specific protein 65 kDa [*Xenopus laevis*] |
| AAC72356 | 3851555 | retinal pigment epithelium-specific protein RPE65 [*Canis familiaris*] |

TABLE 67-continued

Examples of beta-carotene 15,15'-monooxygenase polypeptides.

| ACCESSION | GI | PROTEIN DESCRIPTION |
|---|---|---|
| CAF98473 | 47220374 | unnamed protein product [*Tetraodon nigroviridis*] |
| NP_001 . . . | 50978910 | retinal pigment epithelium-specific protein 65 kDa [*Canis lupus familiaris*] |
| AAD12758 | 4001821 | RPE65 protein; retinal pigment epithelium 65-protein [*Ambystoma tigrinum*] |
| XP_001 . . . | 126305965 | PREDICTED: similar to membrane receptor p63 [*Monodelphis domestica*] |
| NP_001 . . . | 156120623 | hypothetical protein LOC514135 [*Bos taurus*] |
| Q9YGX2 | 48475042 | Retinal pigment epithelium-specific 65 kDa protein |
| NP_001 . . . | 147906384 | MGC85437 protein [*Xenopus laevis*] |
| NP_001 . . . | 118344140 | beta-carotene-15,15'-monooxygenase [*Ciona intestinalis*] |
| BAC41351 | 26005798 | retinal pigment epithelium abundant protein [*Cynops pyrrhogaster*] |
| XP_001 . . . | 114557125 | PREDICTED: retinal pigment epithelium-specific protein 65 kDa [*Pan troglodytes*] |
| NP_001 . . . | 148230104 | beta-carotene dioxygenase 2 [*Xenopus laevis*] |
| XP_001 . . . | 114640352 | PREDICTED: beta-carotene dioxygenase 2 isoform 2 [*Pan troglodytes*] |
| XP_001 . . . | 115928922 | PREDICTED: similar to beta-carotene 15,15-dioxygenase [*Strongylocentrotus purpuratus*] |
| AAL39096 | 17432605 | RPE65 [*Mus musculus*] |
| XP_001 . . . | 125816256 | PREDICTED: similar to Beta-carotene 15,15-dioxygenase 2 [*Danio rerio*] |
| XP_001 . . . | 156342819 | hypothetical protein NEMVEDRAFT_v1g222532 [*Nematostella vectensis*] |
| XP_001 . . . | 125824367 | PREDICTED: similar to retinal pigment epithelium 65b [*Danio rerio*] |
| XP_001 . . . | 156393603 | predicted protein [*Nematostella vectensis*] |
| XP_001 . . . | 156371447 | predicted protein [*Nematostella vectensis*] |
| AAH67696 | 45767835 | Bcdo2l protein [*Danio rerio*] |
| CAD45010 | 22657452 | retinal pigment epithelium-specific protein [*Canis familiaris*] |
| NP_001 . . . | 118344130 | RPE65 homolog [*Ciona intestinalis*] |
| XP_317319 | 118789286 | ENSANGP00000006854 [*Anopheles gambiae* str. PEST] |
| EAA12399 | 157014990 | AGAP008143-PA [*Anopheles gambiae* str. PEST] |
| AAY85350 | 68132170 | carotenoid 9',10' monoxygenase II [*Rattus norvegicus*] |
| XP_001 . . . | 115969938 | PREDICTED: similar to beta-carotene 15,15-dioxygenase, partial [*Strongylocentrotus purpuratus*] |
| XP_001 . . . | 157135394 | beta-carotene dioxygenase [*Aedes aegypti*] |
| XP_967460 | 91093114 | PREDICTED: similar to CG9347-PA [*Tribolium castaneum*] |
| NP_496729 | 71998242 | Y46G5A.24 [*Caenorhabditis elegans*] |
| XP_001 . . . | 156398339 | predicted protein [*Nematostella vectensis*] |
| XP_394000 | 66523635 | PREDICTED: similar to neither inactivation nor afterpotential B CG9347-PA isoform 1 [*Apis mellifera*] |
| F88115 | 25395537 | protein F53C3.12 [imported] - *Caenorhabditis elegans* |
| AAC67462 | 26251528 | Hypothetical protein F53C3.12 [*Caenorhabditis elegans*] |
| XP_001 . . . | 149709742 | PREDICTED: similar to retinal pigment epithelium abundant protein RPE65 [*Equus caballus*] |
| CAE71494 | 39582162 | Hypothetical protein CBG18419 [*Caenorhabditis briggsae*] |
| CAE71509 | 39582177 | Hypothetical protein CBG18441 [*Caenorhabditis briggsae*] |
| XP_001 . . . | 156555525 | PREDICTED: similar to beta-carotene dioxygenase [*Nasonia vitripennis*] |
| XP_001 . . . | 125824371 | PREDICTED: similar to retinal pigment epithelium 65b [*Danio rerio*] |
| CAF91639 | 47209442 | unnamed protein product [*Tetraodon nigroviridis*] |
| CAG02881 | 47222516 | unnamed protein product [*Tetraodon nigroviridis*] |
| CAG06487 | 47224917 | unnamed protein product [*Tetraodon nigroviridis*] |
| EDL95460 | 149041619 | beta-carotene 9',10'-dioxygenase 2 [*Rattus norvegicus*] |
| YP_001 . . . | 154707125 | putative dioxygenase [*Coxiella burnetii Dugway 7E9-12*] |
| NP_650307 | 24646669 | neither inactivation nor afterpotential B CG9347-PA [*Drosophila melanogaster*] |
| BAA94508 | 7593040 | DRPE65 [*Drosophila melanogaster*] |
| ZP_019 . . . | 153206838 | dioxygenase, putative [*Coxiella burnetii*'MSU Goat Q177'] |
| AAH92162 | 62132948 | Zgc: 110538 [*Danio rerio*] |
| YP_444280 | 83814867 | 15,15' beta carotene dioxygenase [*Salinibacter ruber* DSM 13855] |
| BAB32248 | 12861637 | unnamed protein product [*Mus musculus*] |
| EAW67192 | 119587596 | beta-carotene dioxygenase 2, isoform CRA_d [*Homo sapiens*] |
| XP_001 . . . | 114640354 | PREDICTED: hypothetical protein isoform 1 [*Pan troglodytes*] |
| BAC03747 | 21750237 | unnamed protein product [*Homo sapiens*] |
| EAW67190 | 119587594 | beta-carotene dioxygenase 2, isoform CRA_b [*Homo sapiens*] |
| XP_001 . . . | 125774315 | GA21719-PA [*Drosophila pseudoobscura*] |
| YP_001 . . . | 134096631 | lignostilbene-alpha/beta-dioxygenase [*Saccharopolyspora erythraea* NRRL 2338] |
| EAW67191 | 119587595 | beta-carotene dioxygenase 2, isoform CRA_c [*Homo sapiens*] |
| XP_001 . . . | 149486496 | PREDICTED: similar to b,b-carotene-9,10-dioxygenase, partial [*Ornithorhynchus anatinus*] |
| AAO90531 | 29541592 | dioxygenase, putative [*Coxiella burnetii* RSA 493] |
| XP_001 . . . | 109129384 | PREDICTED: similar to Beta,beta-carotene 15,15-monooxygenase (Beta-carotene dioxygenase 1) [*Macaca mulatta*] |
| CAJ53109 | 109626642 | beta,beta-carotene 9',10'-dioxygenase 2 [*Haloquadratum walsbyi* DSM 16790] |

TABLE 67-continued

Examples of beta-carotene 15,15'-monooxygenase polypeptides.

| ACCESSION | GI | PROTEIN DESCRIPTION |
|---|---|---|
| XP_001 . . . | 109129778 | PREDICTED: similar to Beta,beta-carotene 15,15-monooxygenase (Beta-carotene dioxygenase 1), partial [*Macaca mulatta*] |
| XP_001 . . . | 118109416 | PREDICTED: similar to beta-carotene 15,15-dioxygenase, partial [*Gallus gallus*] |
| ABF70124 | 102139989 | dioxygenase-related protein [*Musa balbisiana*] |
| AAW59435 | 57918684 | decreased apical dominance protein [*Petunia* x *hybrida*] |
| EAY74583 | 125526469 | hypothetical protein OsI_002430 [*Oryza sativa* (*indica* cultivar-group)] |
| AAL66961 | 18377622 | unknown protein [*Arabidopsis thaliana*] |
| EAY74584 | 125526470 | hypothetical protein OsI_002431 [*Oryza sativa* (*indica* cultivar-group)] |
| BAC05598 | 21902049 | putative dioxygenase [*Oryza sativa* (*japonica* cultivar-group)] |
| AAW33596 | 57116144 | Dad1/CCD8 [*Petunia* x *hybrida*] |
| NP_001 . . . | 115439899 | Os01g0746400 [*Oryza sativa* (*japonica* cultivar-group)] |
| EAY75798 | 125527684 | hypothetical protein OsI_003645 [*Oryza sativa* (*indica* cultivar-group)] |
| EAZ13518 | 125572003 | hypothetical protein OsJ_003343 [*Oryza sativa* (*japonica* cultivar-group)] |
| ABQ08577 | 146160696 | beta-carotene 15,15'-monooxygenase 2 [*Oryzias latipes*] |
| BAB63485 | 15289786 | retinal pigment epithelium 65-like [*Oryza sativa* (*japonica* cultivar-group)] |
| AAS66906 | 45504725 | dioxygenase RAMOSUS1 [*Pisum sativum*] |
| ZP_013 . . . | 95927318 | hypothetical protein CburR_01000925 [*Coxiella burnetii* RSA 331] |
| YP_658115 | 110668304 | beta,beta-carotene 15,15'-monooxygenase; beta-carotene dioxygenase 1 [*Haloquadratum walsbyi* DSM 16790] |
| CAL90971 | 121495644 | torulene oxygenase [*Gibberella fujikuroi*] |
| YP_134677 | 55376826 | retinal pigment epithelial membrane protein [*Haloarcula marismortui* ATCC 43049] |
| CAL90970 | 121495642 | torulene oxygenase [*Gibberella fujikuroi*] |
| XP_382801 | 46111487 | hypothetical protein FG02625.1 [*Gibberella zeae* PH-1] |
| XP_001 . . . | 149480289 | PREDICTED: similar to carotene-9,10-monooxygenase, partial [*Ornithorhynchus anatinus*] |
| ABQ76053 | 148508268 | beta,beta-carotene 9',10'-dioxygenase 2 [uncultured haloarchaeon] |
| YP_657779 | 110667968 | beta,beta-carotene 9',10'-dioxygenase 2 [*Haloquadratum walsbyi* DSM 16790] |
| XP_001 . . . | 109149184 | PREDICTED: similar to Beta,beta-carotene 15,15-monooxygenase (Beta-carotene dioxygenase 1), partial [*Macaca mulatta*] |
| AAP92577 | 33086530 | Ab2-079 [*Rattus norvegicus*] |
| ABN50352 | 125662819 | carotenoid cleavage dioxygenase 1 [*Hypocrea jecorina*] |
| EAL93736 | 66853412 | dioxygenase, putative [*Aspergillus fumigatus* Af293] |
| XP_001 . . . | 125876361 | PREDICTED: hypothetical protein, partial [*Danio rerio*] |
| XP_001 . . . | 119481741 | dioxygenase, putative [*Neosartorya fischeri* NRRL 181] |
| XP_001 . . . | 119494253 | retinal pigment epithelial membrane family protein [*Neosartorya fischeri* NRRL 181] |
| XP_958452 | 85090512 | hypothetical protein [*Neurospora crassa* OR74A] |
| EDO64867 | 157069539 | predicted protein [*Neurospora crassa* OR74A] |
| XP_001 . . . | 121716178 | dioxygenase, putative [*Aspergillus clavatus* NRRL 1] |
| CAL64769 | 148353839 | putative carotene oxygenase [*Blakeslea trispora*] |
| BAD79505 | 56686283 | lignostilbene-alpha beta-dioxygenase [*Synechococcus elongatus* PCC 6301] |
| ZP_016 . . . | 119509407 | Retinal pigment epithelial membrane protein [*Nodularia spumigena* CCY9414] |
| BAE56886 | 83766746 | unnamed protein product [*Aspergillus oryzae*] |
| BAE59247 | 83769110 | unnamed protein product [*Aspergillus oryzae*] |
| ECC98172 | 139038333 | hypothetical protein GOS_5249294 [marine metagenome] |
| ZP_017 . . . | 126656631 | Beta-carotene 15,15'-dioxygenase [*Cyanothece* sp. CCY0110] |
| BAC91630 | 35214261 | gll3689 [*Gloeobacter violaceus* PCC 7421] |
| EAT90277 | 111069157 | hypothetical protein SNOG_02065 [*Phaeosphaeria nodorum* SN15] |
| CAB79998 | 7270228 | putative protein [*Arabidopsis thaliana*] |
| CAL49287 | 117557505 | putative carotene-dioxygenase [*Rhizopus oryzae*] |
| XP_659308 | 67522495 | hypothetical protein AN1704.2 [*Aspergillus nidulans* FGSC A4] |
| XP_001 . . . | 125824373 | PREDICTED: similar to retinal pigment epithelium 65b [*Danio rerio*] |
| XP_001 . . . | 119185939 | hypothetical protein CIMG_03017 [*Coccidioides immitis* RS] |
| 2BIWB | 66361521 | Chain B, Crystal Structure Of Apocarotenoid Cleavage Oxygenase From Synechocystis, Native Enzyme |
| ABA20860 | 75701184 | Retinal pigment epithelial membrane protein [*Anabaena variabilis* ATCC 29413] |
| XP_001 . . . | 116207620 | hypothetical protein CHGG_03103 [*Chaetomium globosum* CBS 148.51] |
| XP_001 . . . | 145257182 | hypothetical protein An04g02710 [*Aspergillus niger*] |
| BAB75983 | 17133419 | lignostilbene-alpha,beta-dioxygenase [*Nostoc* sp. PCC 7120] |
| XP_501958 | 50548975 | hypothetical protein [*Yarrowia lipolytica*] |
| XP_001 . . . | 109129782 | PREDICTED: similar to Beta,beta-carotene 15,15-monooxygenase (Beta-carotene dioxygenase 1), partial [*Macaca mulatta*] |
| ZP_016 . . . | 119484919 | Retinal pigment epithelial membrane protein [*Lyngbya* sp. PCC 8106] |
| ZP_017 . . . | 126656882 | Retinal pigment epithelial membrane protein [*Cyanothece* sp. CCY0110] |
| XP_001 . . . | 109149035 | PREDICTED: similar to Beta,beta-carotene 15,15-monooxygenase (Beta-carotene dioxygenase 1), partial [*Macaca mulatta*] |

TABLE 67-continued

| Examples of beta-carotene 15,15'-monooxygenase polypeptides. | | |
|---|---|---|
| ACCESSION | GI | PROTEIN DESCRIPTION |
| CAL49288 | 117557507 | putative carotene-dioxygenase [*Rhizopus oryzae*] |
| ZP_001 . . . | 23130610 | COG3670: Lignostilbene-alpha,beta-dioxygenase and related enzymes [*Nostoc punctiforme* PCC 73102] |
| XP_362433 | 39945792 | hypothetical protein MGG_08016 [*Magnaporthe grisea* 70-15] |
| XP_001 . . . | 115951205 | PREDICTED: hypothetical protein [*Strongylocentrotus purpuratus*] |
| AAC12875 | 3033545 | lignostilbene-alpha,beta-dioxygenase [*Synechococcus* sp. PCC 7942] |
| XP_001 . . . | 154282379 | conserved hypothetical protein [*Ajellomyces capsulatus* NAm1] |
| ABG52331 | 110167791 | Carotenoid oxygenase [*Trichodesmium erythraeum* IMS101] |
| ABC99263 | 86554305 | putative lignostilbene-alpha,beta-dioxygenase [*Synechococcus* sp. JA-3-3Ab] |
| NP_931511 | 37528166 | hypothetical protein plu4336 [*Photorhabdus luminescens* subsp. *laumondii* TTO1] |
| EDD33453 | 143171893 | hypothetical protein GOS_1320815 [marine metagenome] |
| XP_001 . . . | 115387251 | predicted protein [*Aspergillus terreus* NIH2624] |
| YP_885943 | 118467371 | lignostilbene-alpha,beta-dioxygenase [*Mycobacterium smegmatis* str. MC2 155] |

TABLE 68

| Examples of beta-carotene retinol dehydrogenase polypeptides. | | |
|---|---|---|
| ACCESSION | GI | PROTEIN DESCRIPTION |
| AAX33670 | 60678607 | epithelial retinol dehydrogenase [*Mus musculus*] |
| BAC34110 | 26340896 | unnamed protein product [*Mus musculus*] |
| XP_001 . . . | 149730699 | PREDICTED: similar to short-chain dehydrogenase/reductase RETSDR8 [*Equus caballus*] |
| XP_545513 | 74004823 | PREDICTED: similar to NADP-dependent retinol dehydrogenase/reductase [*Canis familiaris*] |
| Q8HYR6 | 75064969 | Dehydrogenase/reductase SDR family member 9 precursor (3-alpha hydroxysteroid dehydrogenase) (3alpha-HSD) (Short-chain dehydrogenase/reductase retSDR8) |
| XP_001 . . . | 114581559 | PREDICTED: NADP-dependent retinol dehydrogenase/reductase isoform 3 [*Pan troglodytes*] |
| XP_001 . . . | 109099963 | PREDICTED: similar to NADP-dependent retinol dehydrogenase/reductase isoform 3 [*Macaca mulatta*] |
| AAL37037 | 17224600 | short-chain dehydrogenase/reductase RETSDR8 [*Homo sapiens*] |
| AAD32458 | 4894382 | retinol dehydrogenase homolog [*Homo sapiens*] |
| XP_001 . . . | 126326289 | PREDICTED: similar to short-chain dehydrogenase/reductase RETSDR8 [*Monodelphis domestica*] |
| XP_001 . . . | 149639643 | PREDICTED: similar to short-chain dehydrogenase/reductase RETSDR8 [*Ornithorhynchus anatinus*] |
| XP_001 . . . | 114581568 | PREDICTED: NADP-dependent retinol dehydrogenase/reductase isoform 1 [*Pan troglodytes*] |
| AAF82748 | 9082139 | retinol dehydrogenase homolog isoform-1 [*Homo sapiens*] |
| XP_001 . . . | 109099969 | PREDICTED: similar to NADP-dependent retinol dehydrogenase/reductase isoform 1 [*Macaca mulatta*] |
| AAY24306 | 62988919 | unknown [*Homo sapiens*] |
| XP_422015 | 118093666 | PREDICTED: similar to short-chain dehydrogenase/reductase RETSDR8 [*Gallus gallus*] |
| XP_001 . . . | 114581566 | PREDICTED: NADP-dependent retinol dehydrogenase/reductase isoform 2 [*Pan troglodytes*] |
| NP_001 . . . | 147905288 | NADP-dependent retinol dehydrogenase/reductase [*Xenopus laevis*] |
| AAH67304 | 45501367 | Dehydrogenase/reductase (SDR family) member 9 [*Xenopus tropicalis*] |
| EDM16447 | 149066574 | rCG60176, isoform CRA_a [*Rattus norvegicus*] |
| AAH62000 | 38303814 | Rdh2 protein [*Rattus norvegicus*] |
| AAC52316 | 1072046 | retinol dehydrogenase type II |
| NP_001 . . . | 148227174 | hypothetical protein LOC398882 [*Xenopus laevis*] |
| NP_033066 | 6677697 | retinol dehydrogenase 16 [*Mus musculus*] |
| NP_001 . . . | 147900576 | hypothetical protein LOC432178 [*Xenopus laevis*] |
| NP_694773 | 23680945 | retinol dehydrogenase 9 [*Mus musculus*] |
| NP_003716 | 19743808 | hydroxysteroid (17-beta) dehydrogenase 6 [*Homo sapiens*] |
| BAE21017 | 74205129 | unnamed protein product [*Mus musculus*] |
| EDL24523 | 148692576 | mCG140848 [*Mus musculus*] |
| AAL14860 | 22651436 | cis-retinol/3alpha hydroxysterol short-chain dehydrogenase-like protein [*Mus musculus*] |
| P55006 | 1710631 | Retinol dehydrogenase 7 (Retinol dehydrogenase type III) (RODH III) |
| AAH82896 | 52354822 | LOC494781 protein [*Xenopus laevis*] |
| XP_001 . . . | 109097334 | PREDICTED: similar to 3-hydroxysteroid epimerase [*Macaca mulatta*] |
| AAI35515 | 134023801 | LOC100124842 protein [*Xenopus tropicalis*] |
| P50169 | 1710629 | Retinol dehydrogenase 3 (Retinol dehydrogenase type I) (RODH I) |
| BAC98304 | 37360649 | cis-retinol/androgen dehydrogenase type 3 [*Mus musculus*] |

TABLE 68-continued

Examples of beta-carotene retinol dehydrogenase polypeptides.

| ACCESSION | GI | PROTEIN DESCRIPTION |
|---|---|---|
| NP_663399 | 21703846 | cis-retinol/3alpha hydroxysterol short-chain dehydrogenase-like [*Mus musculus*] |
| AAB07997 | 841197 | retinol dehydrogenase type I |
| XP_001 . . . | 126343946 | PREDICTED: similar to microsomal NAD+-dependent retinol dehydrogenase 4 [*Monodelphis domestica*] |
| NP_775427 | 27545384 | hydroxysteroid (17-beta) dehydrogenase 6 [*Rattus norvegicus*] |
| EDL24527 | 148692580 | mCG134493 [*Mus musculus*] |
| XP_531641 | 73968454 | PREDICTED: similar to microsomal NAD+-dependent retinol dehydrogenase 4 isoform 1 [*Canis familiaris*] |
| AAH24603 | 19354049 | Retinol dehydrogenase 7 [*Mus musculus*] |
| AAL02134 | 22074192 | retinol dehydrogenase similar protein 2 [*Mus musculus*] |
| NP_536684 | 20147789 | retinol dehydrogenase 1 (all trans) [*Mus musculus*] |
| AAH88104 | 56789874 | Hydroxysteroid (17-beta) dehydrogenase 6 [*Rattus norvegicus*] |
| EDL24532 | 148692585 | hydroxysteroid (17-beta) dehydrogenase 9, isoform CRA_a [*Mus musculus*] |
| ABG81445 | 110665598 | microsomal NAD+-dependent retinol dehydrogenase 4 [*Bos taurus*] |
| EDL24533 | 148692586 | hydroxysteroid (17-beta) dehydrogenase 9, isoform CRA_b [*Mus musculus*] |
| XP_538239 | 73968448 | PREDICTED: similar to 3-hydroxysteroid epimerase isoform 3 [*Canis familiaris*] |
| CAJ81333 | 89272084 | novel retinol dehydrogenase protein [*Xenopus tropicalis*] |
| AAH46694 | 28302191 | Rodh-A-prov protein [*Xenopus laevis*] |
| XP_001 . . . | 149715148 | PREDICTED: similar to microsomal NAD+-dependent retinol dehydrogenase 4 [*Equus caballus*] |
| XP_001 . . . | 109097338 | PREDICTED: similar to microsomal NAD+-dependent retinol dehydrogenase 4 isoform 2 [*Macaca mulatta*] |
| XP_001 . . . | 109097336 | PREDICTED: similar to microsomal NAD+-dependent retinol dehydrogenase 4 isoform 3 [*Macaca mulatta*] |
| XP_858182 | 73968456 | PREDICTED: similar to microsomal NAD+-dependent retinol dehydrogenase 4 isoform 2 [*Canis familiaris*] |
| AAI02627 | 74354657 | Similar to 3-hydroxysteroid epimerase [*Bos taurus*] |
| XP_858059 | 73968446 | PREDICTED: similar to 3-hydroxysteroid epimerase isoform 4 [*Canis familiaris*] |
| AAC39922 | 3372592 | sterol/retinol dehydrogenase [*Homo sapiens*] |
| AAY44823 | 66354281 | retinol dehydrogenase 5 [*Danio rerio*] |
| XP_522604 | 55639443 | PREDICTED: retinol dehydrogenase 16 [*Pan troglodytes*] |
| AAH97151 | 66911361 | Retinol dehydrogenase 5 (11-cis/9-cis) [*Danio rerio*] |
| CAK05049 | 94732559 | novel protein similar to vertebrate retinol dehydrogenase family [*Danio rerio*] |
| NP_990044 | 45382649 | 11-cis retinol dehydrogenase [*Gallus gallus*] |
| EAW96968 | 119617374 | retinol dehydrogenase 16 (all-trans and 13-cis) [*Homo sapiens*] |
| NP_001 . . . | 148233310 | hypothetical protein LOC398939 [*Xenopus laevis*] |
| CAG04959 | 47218630 | unnamed protein product [*Tetraodon nigroviridis*] |
| AAH88014 | 56789076 | Hypothetical LOC496749 [*Xenopus tropicalis*] |
| AAI23192 | 114107846 | Rdh9 protein [*Xenopus laevis*] |
| AAC72923 | 3859946 | retinol dehydrogenase [*Homo sapiens*] |
| AAF82747 | 9082137 | retinol dehydrogenase homolog isoform-2 [*Homo sapiens*] |
| AAH75455 | 49522586 | MGC89248 protein [*Xenopus tropicalis*] |
| AAH59614 | 37590384 | Retinol dehydrogenase 1, like [*Danio rerio*] |
| AAB88252 | 2661211 | oxidative 3 alpha hydroxysteroid dehydrogenase [*Homo sapiens*] |
| EDL24633 | 148692686 | retinol dehydrogenase 5, isoform CRA_b [*Mus musculus*] |
| BAE22435 | 74149341 | unnamed protein product [*Mus musculus*] |
| XP_538220 | 73968269 | PREDICTED: similar to 11-cis retinol dehydrogenase (11-cis RDH) [*Canis familiaris*] |
| NP_001 . . . | 147899633 | MGC84134 protein [*Xenopus laevis*] |
| XP_001 . . . | 109097121 | PREDICTED: retinol dehydrogenase 5 (11-cis and 9-cis) [*Macaca mulatta*] |
| NP_001 . . . | 147905378 | MGC84099 protein [*Xenopus laevis*] |
| CAF92451 | 47210426 | unnamed protein product [*Tetraodon nigroviridis*] |
| XP_522429 | 55638373 | PREDICTED: similar to 11-cis retinol dehydrogenase isoform 2 [*Pan troglodytes*] |
| AAH88529 | 56788840 | Hypothetical LOC496830 [*Xenopus tropicalis*] |
| NP_002896 | 50726952 | retinol dehydrogenase 5 (11-cis and 9-cis) [*Homo sapiens*] |
| CAA57715 | 663171 | 11-cis retinol dehydrogenase [*Bos taurus*] |
| AAH28298 | 20271410 | Retinol dehydrogenase 5 (11-cis/9-cis) [*Homo sapiens*] |
| NP_001 . . . | 148230094 | hypothetical protein LOC399015 [*Xenopus laevis*] |
| AAA80694 | 1054531 | 11-cis-retinol dehydrogenase |
| NP_932335 | 37620196 | retinol dehydrogenase 1 [*Danio rerio*] |
| XP_538240 | 73968424 | PREDICTED: similar to orphan short-chain dehydrogenase/reductase [*Canis familiaris*] |
| AAI34659 | 134024746 | MGC151815 protein [*Bos taurus*] |
| AAH64820 | 40673988 | Orphan short chain dehydrogenase/reductase [*Mus musculus*] |
| EDL24531 | 148692584 | orphan short chain dehydrogenase/reductase [*Mus musculus*] |
| AAB93668 | 1916935 | 9-cis-retinol specific dehydrogenase [*Homo sapiens*] |
| XP_001 . . . | 149715290 | PREDICTED: hypothetical protein [*Equus caballus*] |

TABLE 68-continued

Examples of beta-carotene retinol dehydrogenase polypeptides.

| ACCESSION | GI | PROTEIN DESCRIPTION |
|---|---|---|
| XP_001 . . . | 109482100 | PREDICTED: similar to retinol dehydrogenase similar protein [*Rattus norvegicus*] |
| EAW96967 | 119617373 | orphan short-chain dehydrogenase/reductase [*Homo sapiens*] |
| XP_522439 | 114644207 | PREDICTED: orphan short-chain dehydrogenase/reductase [*Pan troglodytes*] |
| EDL24528 | 148692581 | mCG134494, isoform CRA_a [*Mus musculus*] |
| ABQ09278 | 146186452 | retinol dehydrogenase 1 [*Oryzias latipes*] |
| ABQ09279 | 146186454 | retinol dehydrogenase 5 [*Oryzias latipes*] |
| XP_001 . . . | 109097340 | PREDICTED: similar to microsomal NAD+-dependent retinol dehydrogenase 4 isoform 1 [*Macaca mulatta*] |
| EDM16444 | 149066571 | orphan short chain dehydrogenase/reductase [*Rattus norvegicus*] |
| AAG44849 | 12006418 | microsomal retinol dehydrogenase [*Branchiostoma lanceolatum*] |
| BAE88760 | 90078160 | unnamed protein product [*Macaca fascicularis*] |
| AAG44847 | 12006414 | microsomal retinol dehydrogenase 1 [*Branchiostoma floridae*] |
| XP_782726 | 115665382 | PREDICTED: similar to retinol dehydrogenase type 1, partial [*Strongylocentrotus purpuratus*] |
| XP_001 . . . | 115939186 | PREDICTED: similar to retinol dehydrogenase type 1 [*Strongylocentrotus purpuratus*] |
| XP_001 . . . | 118093664 | PREDICTED: similar to MGC83505 protein [*Gallus gallus*] |
| XP_781379 | 115654644 | PREDICTED: similar to retinol dehydrogenase type 1, partial [*Strongylocentrotus purpuratus*] |
| XP_001 . . . | 115958895 | PREDICTED: similar to retinol dehydrogenase type 1 [*Strongylocentrotus purpuratus*] |
| AAG44848 | 12006416 | microsomal retinol dehydrogenase 2 [*Branchiostoma floridae*] |
| XP_001 . . . | 115960451 | PREDICTED: similar to retinol dehydrogenase type III [*Strongylocentrotus purpuratus*] |
| EDL84786 | 149029615 | rCG42422, isoform CRA_a [*Rattus norvegicus*] |
| AAL14861 | 22651438 | cis-retinol/3alpha hydroxysterol short-chain dehydrogenase-like protein isoform [*Mus musculus*] |
| XP_001 . . . | 156386264 | predicted protein [*Nematostella vectensis*] |
| XP_001 . . . | 156389613 | predicted protein [*Nematostella vectensis*] |
| XP_001 . . . | 156368581 | predicted protein [*Nematostella vectensis*] |
| XP_001 . . . | 156362183 | predicted protein [*Nematostella vectensis*] |
| BAC28142 | 26328807 | unnamed protein product [*Mus musculus*] |
| XP_001 . . . | 156367012 | predicted protein [*Nematostella vectensis*] |
| XP_001 . . . | 156367010 | predicted protein [*Nematostella vectensis*] |
| CAG14527 | 47203967 | unnamed protein product [*Tetraodon nigroviridis*] |
| XP_001 . . . | 156367016 | predicted protein [*Nematostella vectensis*] |
| XP_001 . . . | 156401057 | predicted protein [*Nematostella vectensis*] |
| AAB69884 | 2384782 | Dehydrogenases, short chain protein 16 [*Caenorhabditis elegans*] |
| XP_001 . . . | 156367014 | predicted protein [*Nematostella vectensis*] |
| XP_001 . . . | 156367008 | predicted protein [*Nematostella vectensis*] |
| NP_871815 | 32563809 | DeHydrogenases, Short chain family member (dhs-2) [*Caenorhabditis elegans*] |
| NP_491575 | 17507613 | DeHydrogenases, Short chain family member (dhs-2) [*Caenorhabditis elegans*] |
| NP_505941 | 115534660 | DeHydrogenases, Short chain family member (dhs-20) [*Caenorhabditis elegans*] |
| CAE74886 | 39583813 | Hypothetical protein CBG22749 [*Caenorhabditis briggsae*] |
| XP_001 . . . | 156408325 | predicted protein [*Nematostella vectensis*] |
| XP_001 . . . | 126343453 | PREDICTED: similar to 3-hydroxybutyrate dehydrogenase, type 1 [*Monodelphis domestica*] |
| CAE64533 | 39593064 | Hypothetical protein CBG09275 [*Caenorhabditis briggsae*] |
| XP_001 . . . | 149571441 | PREDICTED: similar to retinol dehydrogenase similar protein, partial [*Ornithorhynchus anatinus*] |
| NP_955017 | 49227085 | truncated cis-retinol/3alpha-hydroxysterol short-chain dehydrogenase [*Mus musculus*] |
| XP_001 . . . | 156363786 | predicted protein [*Nematostella vectensis*] |
| XP_001 . . . | 109097342 | PREDICTED: similar to microsomal NAD+-dependent retinol dehydrogenase 4 [*Macaca mulatta*] |
| NP_001 . . . | 147899736 | hypothetical protein LOC100037356 [*Danio rerio*] |
| XP_001 . . . | 156366980 | predicted protein [*Nematostella vectensis*] |
| XP_001 . . . | 125853068 | PREDICTED: hypothetical protein [*Danio rerio*] |
| AAH11964 | 15080429 | 3-hydroxybutyrate dehydrogenase, type 1 [*Homo sapiens*] |
| XP_345771 | 109480152 | PREDICTED: similar to retinol dehydrogenase 5 [*Rattus norvegicus*] |
| XP_001 . . . | 149731507 | PREDICTED: similar to 3-hydroxybutyrate dehydrogenase, type 1 [*Equus caballus*] |
| NP_976059 | 44680136 | 3-hydroxybutyrate dehydrogenase precursor [*Homo sapiens*] |
| XP_001 . . . | 149633623 | PREDICTED: similar to 3-hydroxybutyrate dehydrogenase, type 1 [*Ornithorhynchus anatinus*] |
| AAH89597 | 58476255 | BC089597 protein [*Mus musculus*] |
| XP_001 . . . | 114591350 | PREDICTED: 3-hydroxybutyrate dehydrogenase isoform 1 [*Pan troglodytes*] |
| XP_516981 | 114591348 | PREDICTED: 3-hydroxybutyrate dehydrogenase isoform 2 [*Pan troglodytes*] |

TABLE 68-continued

| Examples of beta-carotene retinol dehydrogenase polypeptides. | | |
|---|---|---|
| ACCESSION | GI | PROTEIN DESCRIPTION |
| XP_001 . . . | 156405501 | predicted protein [*Nematostella vectensis*] |
| CAG04267 | 47223406 | unnamed protein product [*Tetraodon nigroviridis*] |
| XP_545160 | 74002972 | PREDICTED: similar to 3-hydroxybutyrate dehydrogenase precursor [*Canis familiaris*] |
| AAI03052 | 73587365 | 3-hydroxybutyrate dehydrogenase, type 1 [*Bos taurus*] |
| BAF35260 | 116267595 | 11beta-hydroxysteroid dehydrogenase short form [*Anguilla japonica*] |
| AAH65613 | 41350974 | Hydroxysteroid 11-beta dehydrogenase 2 [*Danio rerio*] |
| AAB59684 | 203921 | D-beta-hydroxybutyrate dehydrogenase |
| BAE27076 | 74226863 | unnamed protein product [*Mus musculus*] |
| NP_446447 | 55742813 | 3-hydroxybutyrate dehydrogenase, type 1 [*Rattus norvegicus*] |
| P29147 | 68837285 | D-beta-hydroxybutyrate dehydrogenase, mitochondrial precursor (BDH) (3-hydroxybutyrate dehydrogenase) |
| EDK97750 | 148665334 | 3-hydroxybutyrate dehydrogenase, type 1 [*Mus musculus*] |
| CAE75331 | 39592111 | Hypothetical protein CBG23309 [*Caenorhabditis briggsae*] |
| BAE23523 | 74206030 | unnamed protein product [*Mus musculus*] |
| BAC36453 | 26345604 | unnamed protein product [*Mus musculus*] |
| ABH02937 | 110931880 | 17-beta hydroxysteroid dehydrogenase 2 [*Bos taurus*] |
| NP_509415 | 17568189 | F55E10.6 [*Caenorhabditis elegans*] |
| XP_546810 | 73957269 | PREDICTED: similar to hydroxysteroid (17-beta) dehydrogenase 2 [*Canis familiaris*] |
| XP_001 . . . | 115925077 | PREDICTED: similar to retinol dehydrogenase type 1 [*Strongylocentrotus purpuratus*] |
| AAA58352 | 177198 | (R)-3-hydroxybutyrate dehydrogenase |
| XP_422703 | 50752249 | PREDICTED: hypothetical protein [*Gallus gallus*] |
| XP_001 . . . | 149640222 | PREDICTED: similar to 17-beta hydroxysteroid dehydrogenase 2 [*Ornithorhynchus anatinus*] |
| XP_511130 | 114663836 | PREDICTED: hydroxysteroid (17-beta) dehydrogenase 2 [*Pan troglodytes*] |
| P37059 | 544152 | Estradiol 17-beta-dehydrogenase 2 (17-beta-HSD 2) (Microsomal 17-beta-hydroxysteroid dehydrogenase) (20 alpha-hydroxysteroid dehydrogenase) (20-alpha-HSD) (E2DH) |
| AAV38556 | 54696368 | hydroxysteroid (17-beta) dehydrogenase 2 [synthetic construct] |
| AAH90448 | 60649586 | Hsd17b2 protein [*Danio rerio*] |
| XP_001 . . . | 118087716 | PREDICTED: hypothetical protein [*Gallus gallus*] |
| NP_001 . . . | 93277072 | hydroxysteroid (17-beta) dehydrogenase 2 [*Danio rerio*] |
| P51658 | 2507561 | Estradiol 17-beta-dehydrogenase 2 (17-beta-HSD 2) (17-beta-hydroxysteroid dehydrogenase 2) |
| BAC76709 | 30844232 | 11-beta-hydroxysteroid dehydrogenase [*Oncorhynchus mykiss*] |
| AAY84567 | 67975199 | 17-beta hydroxysteroid dehydrogenase 2 [*Macaca fascicularis*] |
| BAD96721 | 62897563 | hydroxysteroid (17-beta) dehydrogenase 2 variant [*Homo sapiens*] |
| XP_414168 | 118096516 | PREDICTED: similar to 17 beta hydroxysteroid dehydrogenase type 2 [*Gallus gallus*] |
| CAE66933 | 39589698 | Hypothetical protein CBG12325 [*Caenorhabditis briggsae*] |
| AAK95857 | 22074155 | retinol dehydrogenase similar protein [*Rattus norvegicus*] |
| AAH74144 | 49257832 | MGC81883 protein [*Xenopus laevis*] |
| XP_001 . . . | 125850087 | PREDICTED: hypothetical protein [*Danio rerio*] |
| AAH90181 | 58701977 | Zgc: 113142 [*Danio rerio*] |
| AAA87007 | 755574 | 11-beta-hydroxylsteroid dehydrogenase type 2 |
| Q62730 | 3334165 | Estradiol 17-beta-dehydrogenase 2 (17-beta-HSD 2) (17-beta-hydroxysteroid dehydrogenase 2) |
| XP_001 . . . | 115956172 | PREDICTED: similar to Retinol dehydrogenase 3 (Retinol dehydrogenase type I) (RODH I) [Strongylocentrotus purpuratus] |
| CAA64982 | 1200097 | 17-beta-hydroxysteroid dehydrogenase type II [*Mus musculus*] |
| EDL11587 | 148679640 | hydroxysteroid (17-beta) dehydrogenase 2 [*Mus musculus*] |
| EDL92656 | 149038296 | hydroxysteroid (17-beta) dehydrogenase 2 [*Rattus norvegicus*] |
| XP_001 . . . | 149626583 | PREDICTED: similar to 11 beta-hydroxysteroid dehydrogenase type 2 [*Ornithorhynchus anatinus*] |
| XP_001 . . . | 109482098 | PREDICTED: similar to Retinol dehydrogenase 2 (Retinol dehydrogenase type II) (RODH II) (29 k-protein) [*Rattus norvegicus*] |
| XP_001 . . . | 109128927 | PREDICTED: similar to Corticosteroid 11-beta-dehydrogenase isozyme 2 (11-DH2) (11-beta-hydroxysteroid dehydrogenase type 2) (11-beta-HSD2) (NAD-dependent 11-beta-hydroxysteroid dehydrogenase) [*Macaca mulatta*] |

TABLE 69

| Genes Comprising the SAGA Complex. | |
|---|---|
| *S. cerevisiae* gene | *Y lipolytica* gene |
| SPT3 | YALI0E21417g |
| SPT7 | none identified |
| SPT8 | YALI0E23804g |

TABLE 69-continued

| Genes Comprising the SAGA Complex. | |
|---|---|
| *S. cerevisiae* gene | *Y lipolytica* gene |
| SPT20 | YALI0C04070g |
| ADA2 | YALI0F14443g |
| ADA3 | none identified |

TABLE 69-continued

| Genes Comprising the SAGA Complex. | |
|---|---|
| *S. cerevisiae* gene | *Y lipolytica* gene |
| GCN5 | YALI0E02772g |
| ADA1 | none identified |
| TRA1 | YALI0C02057g |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. An engineered *Y. lipolytica* strain that produces at least one retinolic compound selected from the group consisting of retinol, retinal, retinoic acid, retinyl palmitate and combinations thereof, the strain comprising at least one retinologenic modification selected from the group consisting of increased expression or activity of a beta-carotene 15,15'-monooxygenase polypeptide, increased expression or activity of a retinol dehydrogenase polypeptide, and combinations thereof;

wherein the engineered strain can accumulate lipid to at least about 20% of its dry cell weight; and wherein as a result of genetic engineering, the engineered strain produces the at least one retinolic compound to a level at least about 1% of its dry cell weight.

2. The engineered *Y. lipolytica* strain of claim 1, wherein the strain does not naturally produce the at least one retinolic compound.

3. The engineered *Y. lipolytica* strain of claim 1, further comprising at least one oleaginic modification.

4. The engineered *Y. lipolytica* strain of claim 3, wherein the at least one oleaginic modification increases or decreases expression or activity of at least one oleaginic polypeptide, selected from the group consisting of acetyl-CoA carboxylase polypeptide, pyruvate decarboxylase polypeptide, isocitrate dehydrogenase polypeptide, ATP-citrate lyase polypeptide, malic enzyme polypeptide, AMP deaminase polypeptide, malate dehydrogenase polypeptide, glucose-6-phosphate dehydrogenase polypeptide, 6-phosphogluconate dehydrogenase polypeptide, fructose 1,6 bisphosphatase polypeptide, NADH kinase polypeptide, transhydrogenase polypeptide, acyl-CoA:diacylglycerol acyltransferase polypeptide, phospholipid:diacylglycerol acyltransferase polypeptide, acyl-CoA:cholesterol acyltransferase polypeptide, triglyceride lipase polypeptide, acyl-coenzyme A oxidase polypeptide and combinations thereof.

5. The engineered *Y. lipolytica* strain of claim 3, wherein the at least one oleaginic modification increases or decreases expression or activity of at least one oleaginic polypeptide selected from the group consisting of a polypeptide in any one of Tables 1 through 6 or 31-47.

6. The engineered *Y. lipolytica* strain of claim 1, wherein the at least one retinologenic modification confers to the engineered strain the ability to produce the at least one retinolic compound to a level at least about 1% of its dry cell weight.

7. The engineered *Y. lipolytica* strain of claim 1, wherein the at least one retinologenic modification confers to the engineered strain the ability to produce at least one retinolic compound which a non-engineered strain does not naturally produce.

8. The engineered *Y. lipolytica* strain of claim 1, wherein the at least one retinologenic modification increases expression or activity of beta-carotene 15,15'-monoxygenase or beta carotene retinol dehydrogenase.

9. The engineered *Y. lipolytica* strain of claim 1, wherein the beta-carotene 15,15'-monooxygenase polypeptide is selected from the group consisting of a polypeptide in Table 67.

10. The engineered *Y. lipolytica* strain of claim 1, wherein the at least one retinologenic modification further comprises decreasing the expression or activity of one or more components of the SAGA histone acetyltransferase complex.

11. The engineered *Y. lipolytica* strain of claim 10, wherein the at least one retinologenic modification comprises disruption of the endogenous SPT8 gene.

12. The engineered *Y. lipolytica* strain of claim 10 wherein the one or more components of the SAGA histone acetyltransferase complex are selected from the polypeptides listed in Table 69.

13. The engineered *Y. lipolytica* strain of claim 1, wherein the retinologenic modification further comprises altering the expression or activity of one or more carotenoid biosynthesis polypeptides.

14. The engineered *Y. lipolytica* strain of claim 13, wherein the one or more carotenoid biosynthesis polypeptides are selected from the group consisting of phytoene synthase, phytoene dehydrogenase, lycopene cyclase, carotene ketolase, carotene hydroxylase, astaxanthin synthase, carotenoid epsilon hydroxylase, lycopene cyclase, carotenoid glucosyltransferase, acyl CoA:diacyglycerol acyltransferase, geranylgeranylpyrophosphate synthase, and truncated HMG-CoA reductase.

15. The engineered *Y. lipolytica* strain of claim 13, wherein the one or more carotenoid biosynthesis polypeptides are selected from the sequences provided in Tables 17a-25.

16. A method of producing a retinolic compound, the method comprising steps of:

a. cultivating the fungus of claim 1 under conditions that allow production of the retinolic compound;

b. and isolating the produced retinolic compound.

17. The engineered *Y. lipolytica* strain of claim 1, wherein the at least one retinologenic modification comprises introduction of a gene encoding a heterologous beta-carotene 15,15'-monooxygenase polypeptide, a heterologous retinol dehydrogenase polypeptide, or combinations thereof.

18. The engineered *Y. lipolytica* strain of claim 1, wherein the retinol dehydrogenase polypeptide is selected from the group consisting of a polypeptide in Table 68.

19. An engineered *Y. lipolytica* strain that produces at least one retinolic compound selected from the group consisting of retinol, retinal, retinoic acid, retinyl palmitate and combinations thereof, the strain comprising at least one genetic modification selected from the group consisting of:

increased expression or activity of a beta-carotene 15,15'-monooxygenase polypeptide;

increased expression or activity of a retinol dehydrogenase polypeptide;

increased expression or activity of phytoene synthase;

increased expression or activity of lycopene cyclase;

increased expression or activity of phytoene dehydrogenease;

increased expression or activity of geranylgeranylpyrophosphate synthase;

increased expression or activity of truncated HMG-CoA reductase; and combinations thereof;

wherein the engineered strain can accumulate lipid to at least about 20% of its dry cell weight; and wherein as a result of genetic engineering, the engineered strain produces the at least one retinolic compound to a level at least about 1% of its dry cell weight.

20. The engineered *Y. lipolytica* strain of claim 19, wherein the genetic modification comprises introduction of one or more heterologous genes encoding metabolic enzymes selected from the group consisting of: beta-carotene 15,15'-monooxygenase, phytoene synthase, lycopene cyclase, phytoene dehydrogenease, geranylgeranylpyrophosphate synthase, truncated HMG-CoA reductase, and combinations thereof.

* * * * *

UNITED STATES PATENT AND TRADEMARK OFFICE

CERTIFICATE OF CORRECTION

PATENT NO. : 8,691,555 B2
APPLICATION NO. : 12/443362
DATED : April 8, 2014
INVENTOR(S) : Bailey et al.

It is certified that error appears in the above-identified patent and that said Letters Patent is hereby corrected as shown below:

In the Claims

On the last page of the patent, please correct claim 8 from:

"The engineered *Y. lipolytica* strain of claim 1, wherein the at least one retinologenic modification increases expression or activity of beta-carotene 15,15'-monoxygenase or beta carotene retinol dehydrogenase."

to read:

--The engineered *Y. lipolytica* strain of claim 1, wherein the at least one retinologenic modification increases expression or activity of beta-carotene 15,15'-monoxygenase.--

Signed and Sealed this
Second Day of September, 2014

Michelle K. Lee
*Deputy Director of the United States Patent and Trademark Office*

UNITED STATES PATENT AND TRADEMARK OFFICE

CERTIFICATE OF CORRECTION

PATENT NO. : 8,691,555 B2
APPLICATION NO. : 12/443362
DATED : April 8, 2014
INVENTOR(S) : Bailey et al.

It is certified that error appears in the above-identified patent and that said Letters Patent is hereby corrected as shown below:

In the Claims

Col. 665, lines 21-24,

On the last page of the patent, please correct claim 8 from:

"The engineered *Y. lipolytica* strain of claim 1, wherein the at least one retinologenic modification increases expression or activity of beta-carotene 15,15'-monoxygenase or beta carotene retinol dehydrogenase."

to read:

--The engineered *Y. lipolytica* strain of claim 1, wherein the at least one retinologenic modification increases expression or activity of beta-carotene 15,15'-monoxygenase.--

This certificate supersedes the Certificate of Correction issued September 2, 2014.

Signed and Sealed this
Thirtieth Day of September, 2014

Michelle K. Lee
*Deputy Director of the United States Patent and Trademark Office*

SEQUENCE LISTING

```
<160> NUMBER OF SEQ ID NOS: 219

<210> SEQ ID NO 1
<211> LENGTH: 984
<212> TYPE: DNA
<213> ORGANISM: Yarrowia lipolytica
<220> FEATURE:
<223> OTHER INFORMATION: Gene encoding geranylgeranyl pyrophosphate
      synthase

<400> SEQUENCE: 1

atggattata acagcgcgga tttcaaggag atatggggca aggccgccga caccgcgctg      60

ctgggaccgt acaactacct cgccaacaac cggggccaca acatcagaga acacttgatc     120

gcagcgttcg gagcggttat caaggtggac aagagcgatc tcgagaccat ttcgcacatc     180

accaagattt tgcataactc gtcgctgctt gttgatgacg tggaagacaa ctcgatgctc     240

cgacgaggcc tgccggcagc ccattgtctg tttggagtcc cccaaaccat caactccgcc     300

aactacatgt actttgtggc tctgcaggag gtgctcaagc tcaagtctta tgatgccgtc     360

tccattttca ccgaggaaat gatcaacttg catagaggtc agggtatgga tctctactgg     420

agagaaacac tcacttgccc ctcggaagac gagtatctgg agatggtggt gcacaagacc     480

ggtggactgt ttcggctggc tctgagactt atgctgtcgg tggcatcgaa acaggaggac     540

catgaaaaga tcaactttga tctcacacac cttaccgaca cactgggagt catttaccag     600

attctggatg attacctcaa cctgcagtcc acggaattga ccgagaacaa gggattctgc     660

gaagatatca gcgaaggaaa gttttcgttt ccgctgattc acagcatacg caccaacccg     720

gataaccacg agattctcaa cattctcaaa cagcgaacaa gcgacgcttc actcaaaaag     780

tacgccgtgg actacatgag aacagaaacc aagagtttcg actactgcct caagaggata     840

caggccatgt cactcaaggc aagttcgtac attgatgatc tagcagcagc tggccacgat     900

gtctccaagc tacgagccat tttgcattat tttgtgtcca cctctgactg tgaggagaga     960

aagtactttg aggatgcgca gtga                                            984


<210> SEQ ID NO 2
<211> LENGTH: 327
<212> TYPE: PRT
<213> ORGANISM: Yarrowia lipolytica
<220> FEATURE:
<223> OTHER INFORMATION: Geranylgeranyl pyrophosphate synthase

<400> SEQUENCE: 2

Met Asp Tyr Asn Ser Ala Asp Phe Lys Glu Ile Trp Gly Lys Ala Ala
1               5                   10                  15

Asp Thr Ala Leu Leu Gly Pro Tyr Asn Tyr Leu Ala Asn Asn Arg Gly
            20                  25                  30

His Asn Ile Arg Glu His Leu Ile Ala Ala Phe Gly Ala Val Ile Lys
        35                  40                  45
```

```
Val Asp Lys Ser Asp Leu Glu Thr Ile Ser His Ile Thr Lys Ile Leu
    50                  55                  60

His Asn Ser Ser Leu Leu Val Asp Asp Val Glu Asp Asn Ser Met Leu
65                  70                  75                  80

Arg Arg Gly Leu Pro Ala Ala His Cys Leu Phe Gly Val Pro Gln Thr
                85                  90                  95

Ile Asn Ser Ala Asn Tyr Met Tyr Phe Val Ala Leu Gln Glu Val Leu
            100                 105                 110

Lys Leu Lys Ser Tyr Asp Ala Val Ser Ile Phe Thr Glu Glu Met Ile
        115                 120                 125

Asn Leu His Arg Gly Gln Gly Met Asp Leu Tyr Trp Arg Glu Thr Leu
    130                 135                 140

Thr Cys Pro Ser Glu Asp Glu Tyr Leu Glu Met Val Val His Lys Thr
145                 150                 155                 160

Gly Gly Leu Phe Arg Leu Ala Leu Arg Leu Met Leu Ser Val Ala Ser
                165                 170                 175

Lys Gln Glu Asp His Glu Lys Ile Asn Phe Asp Leu Thr His Leu Thr
            180                 185                 190

Asp Thr Leu Gly Val Ile Tyr Gln Ile Leu Asp Asp Tyr Leu Asn Leu
        195                 200                 205

Gln Ser Thr Glu Leu Thr Glu Asn Lys Gly Phe Cys Glu Asp Ile Ser
    210                 215                 220

Glu Gly Lys Phe Ser Phe Pro Leu Ile His Ser Ile Arg Thr Asn Pro
225                 230                 235                 240

Asp Asn His Glu Ile Leu Asn Ile Leu Lys Gln Arg Thr Ser Asp Ala
                245                 250                 255

Ser Leu Lys Lys Tyr Ala Val Asp Tyr Met Arg Thr Glu Thr Lys Ser
            260                 265                 270

Phe Asp Tyr Cys Leu Lys Arg Ile Gln Ala Met Ser Leu Lys Ala Ser
        275                 280                 285

Ser Tyr Ile Asp Asp Leu Ala Ala Ala Gly His Asp Val Ser Lys Leu
    290                 295                 300

Arg Ala Ile Leu His Tyr Phe Val Ser Thr Ser Asp Cys Glu Glu Arg
305                 310                 315                 320

Lys Tyr Phe Glu Asp Ala Gln
                325
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ctgggtgacc tggaagcctt 20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
aagatcaatc cgtagaagtt cag 23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
aagcgattac aatcttcctt tgg 23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
ccagtccatc aactcagtct ca 22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
gcattgctta ttacgaagac tac 23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
ccactgtcct ccactacaaa cac 23

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
cacaaacgcg ttcactgcgc atcctcaaag t 31

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
cacaatctag acacaaatgg attataacag cgcggat 37

-continued

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
cacaaactag tttgccacct acaagccaga t 31

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
cacaaggtac caatgtgaaa gtgcgcgtga t 31

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
cacaaggtac cagagaccgg gttggcgg 28

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
cacaagcggc cgcgctagca tggggatcga tctcttatat 40

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
cacaagcggc cgcgctagcg aatgattctt atactcagaa g 41

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
cacaagcggc cgcacgcgtg caattaacag atagtttgcc 40

<210> SEQ ID NO 17
<211> LENGTH: 33

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cacaagctag ctggggatgc gatctcttat atc 33

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cacaaacgcg tttaaatggt atttagattt ctcatt 36

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cacaatctag acacaaatgc tgctcaccta catgga 36

<210> SEQ ID NO 20
<211> LENGTH: 1906
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleic acid coding sequence of pMB4628

<400> SEQUENCE: 20
atgctgctca cctacatgga agtccacctc tactacacgc tgcctgtgct gggcgtcctg 60
tcctggctgt cgcggccgta ctacacagcc accgatgcgc tcaaattcaa atttctgaca 120
ctggttgcct tcacgaccgc ctccgcctgg gacaactaca ttgtctacca caaggcgtgg 180
tcctactgcc ccacctgcgt caccgctgtc attggctacg tgcccttgga ggagtacatg 240
ttcttcatca tcatgactct gttgaccgtg gcattcacca atctggtgat gcgctggcac 300
ctgcacagct tctttatcag gcctgaaacg cccgtcatgc agtccgtcct ggtccgtctt 360
gtccccataa cagccttatt aatcactgca tacaaggctt gggtaagcaa acaaacaaat 420
gatgtgccgc atcgcatttt aatattaacc attgcataca cagcatttgg cggtccctgg 480
aaagccactg ttctacggat catgcatttt gtggtacgcc tgtccggttt tggccttatt 540
gtggtttggt gctggcgagt acatgatgcg tcgtccgctg gcggtgctcg tctccattgc 600
gctgcccacg ctgtttctct gctgggtcga tgtcgtcgct attggcgccg gcacatggga 660
catttcgctg gccacaagca ccggcaagtt cgtcgtgccc cacctgcccg tggaggaatt 720
catgttcttt gcgctaatta ataccgtttt ggtatttggt acgtgtgcga tcgatcgcac 780
gatggcgatc ctccacctgt tcaaaaacaa gagtccttat cagcgcccat accagcacag 840
caagtcgttc ctccaccaga tcctcgagat gacctgggcc ttctgtttac ccgaccaagt 900
gctgcattca gacacattcc acgacctgtc cgtcagctgg gacatcctgc gcaaggcctc 960

-continued

```
caagtccttt tacacggcct ctgctgtctt tcccggcgac gtgcgccaag agctcggtgt   1020

gctatacgcc ttttgcagag ccacggacga tctctgcgac aacgagcagg tccctgtgca   1080

gacgcgaaag gagcagctga tactgacaca tcagttcgtc agcgatctgt ttggccaaaa   1140

gacaagcgcg ccgactgcca ttgactggga cttttacaac gaccaactgc ctgcctcgtg   1200

catctctgcc ttcaagtcgt tcacccgttt gcgccatgtg ctggaagctg gagccatcaa   1260

ggaactgctc gacgggtaca agtgggattt ggagcgtcgc tccatcaggg atcaggagga   1320

tctcagatat tactcagctt gtgtcgccag cagtgttggt gaaatgtgca ctcgcatcat   1380

actggcccac gccgacaagc ccgcctcccg ccagcaaaca cagtggatca ttcagcgtgc   1440

gcgtgaaatg ggtctggtac tccaatatac aaacattgca agagacattg tcaccgacag   1500

cgaggaactg ggcagatgct acctgcctca ggattggctt accgagaagg aggtggcgct   1560

gattcaaggc ggccttgccc gagaaattgg cgaggagcga ttgctctcac tgtcgcatcg   1620

cctcatctac caggcagacg agctcatggt ggttgccaac aagggcatcg acaagctgcc   1680

cagccattgt caaggcggcg tgcgtgcggc ctgcaacgtc tatgcttcca ttggcaccaa   1740

gctcaagtct tacaagcacc actatcccag cagagcacat gtcggcaatt cgaaacgagt   1800

ggaaattgct cttcttagcg tatacaacct ttacaccgcg ccaattgcga ctagtagtac   1860

cacacattgc agacagggaa aaatgagaaa tctaaatacc atttaa                  1906
```

<210> SEQ ID NO 21
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CarRP protein

<400> SEQUENCE: 21

```
Met Leu Leu Thr Tyr Met Glu Val His Leu Tyr Tyr Thr Leu Pro Val
1               5                   10                  15

Leu Gly Val Leu Ser Trp Leu Ser Arg Pro Tyr Tyr Thr Ala Thr Asp
            20                  25                  30

Ala Leu Lys Phe Lys Phe Leu Thr Leu Val Ala Phe Thr Thr Ala Ser
        35                  40                  45

Ala Trp Asp Asn Tyr Ile Val Tyr His Lys Ala Trp Ser Tyr Cys Pro
    50                  55                  60

Thr Cys Val Thr Ala Val Ile Gly Tyr Val Pro Leu Glu Glu Tyr Met
65                  70                  75                  80

Phe Phe Ile Ile Met Thr Leu Leu Thr Val Ala Phe Thr Asn Leu Val
                85                  90                  95

Met Arg Trp His Leu His Ser Phe Phe Ile Arg Pro Glu Thr Pro Val
            100                 105                 110

Met Gln Ser Val Leu Val Arg Leu Val Pro Ile Thr Ala Leu Leu Ile
        115                 120                 125

Thr Ala Tyr Lys Ala Trp His Leu Ala Val Pro Gly Lys Pro Leu Phe
    130                 135                 140

Tyr Gly Ser Cys Ile Leu Trp Tyr Ala Cys Pro Val Leu Ala Leu Leu
145                 150                 155                 160

Trp Phe Gly Ala Gly Glu Tyr Met Met Arg Arg Pro Leu Ala Val Leu
                165                 170                 175

Val Ser Ile Ala Leu Pro Thr Leu Phe Leu Cys Trp Val Asp Val Val
```

```
            180                 185                 190

Ala Ile Gly Ala Gly Thr Trp Asp Ile Ser Leu Ala Thr Ser Thr Gly
        195                 200                 205

Lys Phe Val Val Pro His Leu Pro Val Glu Glu Phe Met Phe Phe Ala
    210                 215                 220

Leu Ile Asn Thr Val Leu Val Phe Gly Thr Cys Ala Ile Asp Arg Thr
225                 230                 235                 240

Met Ala Ile Leu His Leu Phe Lys Asn Lys Ser Pro Tyr Gln Arg Pro
                245                 250                 255

Tyr Gln His Ser Lys Ser Phe Leu His Gln Ile Leu Glu Met Thr Trp
            260                 265                 270

Ala Phe Cys Leu Pro Asp Gln Val Leu His Ser Asp Thr Phe His Asp
        275                 280                 285

Leu Ser Val Ser Trp Asp Ile Leu Arg Lys Ala Ser Lys Ser Phe Tyr
    290                 295                 300

Thr Ala Ser Ala Val Phe Pro Gly Asp Val Arg Gln Glu Leu Gly Val
305                 310                 315                 320

Leu Tyr Ala Phe Cys Arg Ala Thr Asp Asp Leu Cys Asp Asn Glu Gln
                325                 330                 335

Val Pro Val Gln Thr Arg Lys Glu Gln Leu Ile Leu Thr His Gln Phe
            340                 345                 350

Val Ser Asp Leu Phe Gly Gln Lys Thr Ser Ala Pro Thr Ala Ile Asp
        355                 360                 365

Trp Asp Phe Tyr Asn Asp Gln Leu Pro Ala Ser Cys Ile Ser Ala Phe
    370                 375                 380

Lys Ser Phe Thr Arg Leu Arg His Val Leu Glu Ala Gly Ala Ile Lys
385                 390                 395                 400

Glu Leu Leu Asp Gly Tyr Lys Trp Asp Leu Glu Arg Arg Ser Ile Arg
                405                 410                 415

Asp Gln Glu Asp Leu Arg Tyr Tyr Ser Ala Cys Val Ala Ser Ser Val
            420                 425                 430

Gly Glu Met Cys Thr Arg Ile Ile Leu Ala His Ala Asp Lys Pro Ala
        435                 440                 445

Ser Arg Gln Gln Thr Gln Trp Ile Ile Gln Arg Ala Arg Glu Met Gly
    450                 455                 460

Leu Val Leu Gln Tyr Thr Asn Ile Ala Arg Asp Ile Val Thr Asp Ser
465                 470                 475                 480

Glu Glu Leu Gly Arg Cys Tyr Leu Pro Gln Asp Trp Leu Thr Glu Lys
                485                 490                 495

Glu Val Ala Leu Ile Gln Gly Gly Leu Ala Arg Glu Ile Gly Glu Glu
            500                 505                 510

Arg Leu Leu Ser Leu Ser His Arg Leu Ile Tyr Gln Ala Asp Glu Leu
        515                 520                 525

Met Val Val Ala Asn Lys Gly Ile Asp Lys Leu Pro Ser His Cys Gln
    530                 535                 540

Gly Gly Val Arg Ala Ala Cys Asn Val Tyr Ala Ser Ile Gly Thr Lys
545                 550                 555                 560

Leu Lys Ser Tyr Lys His His Tyr Pro Ser Arg Ala His Val Gly Asn
                565                 570                 575

Ser Lys Arg Val Glu Ile Ala Leu Leu Ser Val Tyr Asn Leu Tyr Thr
            580                 585                 590

Ala Pro Ile Ala Thr Ser Ser Thr Thr His Cys Arg Gln Gly Lys Met
        595                 600                 605
```

Arg Asn Leu Asn Thr Ile
    610

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer M04318

<400> SEQUENCE: 22
gtaaaacgac ggccagt                                                    17

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4644

<400> SEQUENCE: 23
cacacggtct catgccaagc cttgtatgca gtgattaa                             38

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4639

<400> SEQUENCE: 24
ccactgtgtt tgctggcgg                                                  19

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4644

<400> SEQUENCE: 25
cacacggtct ctggcatttg gcggtccctg gaaa                                 34

<210> SEQ ID NO 26
<211> LENGTH: 1845
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Intronless nucleic acid coding sequence of
      pMB4705

<400> SEQUENCE: 26
atgctgctca cctacatgga agtccacctc tactacacgc tgcctgtgct gggcgtcctg     60
tcctggctgt cgcggccgta ctacacagcc accgatgcgc tcaaattcaa atttctgaca    120

```
ctggttgcct tcacgaccgc ctccgcctgg gacaactaca ttgtctacca caaggcgtgg    180

tcctactgcc ccacctgcgt caccgctgtc attggctacg tgcccttgga ggagtacatg    240

ttcttcatca tcatgactct gttgaccgtg gcattcacca atctggtgat gcgctggcac    300

ctgcacagct tctttatcag gcctgaaacg cccgtcatgc agtccgtcct ggtccgtctt    360

gtccccataa cagccttatt aatcactgca tacaaggctt ggcatttggc ggtccctgga    420

aagccactgt tctacggatc atgcattttg tggtacgcct gtccggtttt ggccttattg    480

tggtttggtg ctggcgagta catgatgcgt cgtccgctgg cggtgctcgt ctccattgcg    540

ctgcccacgc tgtttctctg ctgggtcgat gtcgtcgcta ttggcgccgg cacatgggac    600

atttcgctgg ccacaagcac cggcaagttc gtcgtgcccc acctgcccgt ggaggaattc    660

atgttctttg cgctaattaa taccgttttg gtatttggta cgtgtgcgat cgatcgcacg    720

atggcgatcc tccacctgtt caaaaacaag agtccttatc agcgcccata ccagcacagc    780

aagtcgttcc tccaccagat cctcgagatg acctgggcct tctgtttacc cgaccaagtg    840

ctgcattcag acacattcca cgacctgtcc gtcagctggg acatcctgcg caaggcctcc    900

aagtcctttt acacggcctc tgctgtcttt cccggcgacg tgcgccaaga gctcggtgtg    960

ctatacgcct tttgcagagc cacggacgat ctctgcgaca acgagcaggt ccctgtgcag   1020

acgcgaaagg agcagctgat actgacacat cagttcgtca gcgatctgtt tggccaaaag   1080

acaagcgcgc cgactgccat tgactgggac ttttacaacg accaactgcc tgcctcgtgc   1140

atctctgcct tcaagtcgtt cacccgtttg cgccatgtgc tggaagctgg agccatcaag   1200

gaactgctcg acgggtacaa gtgggatttg gagcgtcgct ccatcaggga tcaggaggat   1260

ctcagatatt actcagcttg tgtcgccagc agtgttggtg aaatgtgcac tcgcatcata   1320

ctggcccacg ccgacaagcc cgcctcccgc cagcaaacac agtggatcat tcagcgtgcg   1380

cgtgaaatgg gtctggtact ccaatataca aacattgcaa gagacattgt caccgacagc   1440

gaggaactgg gcagatgcta cctgcctcag gattggctta ccgagaagga ggtggcgctg   1500

attcaaggcg gccttgcccg agaaattggc gaggagcgat tgctctcact gtcgcatcgc   1560

ctcatctacc aggcagacga gctcatggtg gttgccaaca agggcatcga caagctgccc   1620

agccattgtc aaggcggcgt gcgtgcggcc tgcaacgtct atgcttccat tggcaccaag   1680

ctcaagtctt acaagcacca ctatcccagc agagcacatg tcggcaattc gaaacgagtg   1740

gaaattgctc ttcttagcgt atacaacctt tacaccgcgc caattgcgac tagtagtacc   1800

acacattgca gacagggaaa aatgagaaat ctaaatacca tttaa                   1845
```

```
<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4530

<400> SEQUENCE: 27

cacaaacgcg tttaaatgac attagagtta tgaac                                 35


<210> SEQ ID NO 28
<211> LENGTH: 37
<212> TYPE: DNA
<213> ORGANISM: Artificial Sequence
<220> FEATURE:
```

-continued

<223> OTHER INFORMATION: Description of Artificial Sequence: Synthetic
      oligonucleotide
<220> FEATURE:
<223> OTHER INFORMATION: PCR primer MO4542

<400> SEQUENCE: 28
cacaatctag acacaaatgt ccaagaaaca cattgtc 37

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4318

<400> SEQUENCE: 29
gtaaaacgac ggccagt 17

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4648

<400> SEQUENCE: 30
cacaaggtct caagcacgca tcccggaact g 31

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4646

<400> SEQUENCE: 31
cacacggtct caggcatgtc gccctacgat gc 32

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4647

<400> SEQUENCE: 32
cacacggtct catgcttgca cccacaaaga atagg 35

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4343

-continued

<400> SEQUENCE: 33
caggaaacag ctatgac 17

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO4645

<400> SEQUENCE: 34
cacacggtct cttgcccata tacatggtct gaaacg 36

<210> SEQ ID NO 35
<211> LENGTH: 1740
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleic acid coding sequence of CarB of pMB4638

<400> SEQUENCE: 35
atgtccaaga aacacattgt cattatcggt gctggcgtgg gtggcacggc tacagctgct 60
cgtttggccc gcgaaggctt caaggtcact gtggtggaga aaaacgactt tggtggcggc 120
cgctgctcct tgatccatca ccagggccat cgctttgatc agggcccgtc gctctacctg 180
atgcccaagt actttgagga cgcctttgcc gatctggacg agcgcattca agaccacctg 240
gagctgctgc gatgcgacaa caactacaag gtgcactttg acgacggtga gtcgatccag 300
ctgtcgtctg acttgacacg catgaaggct gaattggacc gcgtggaggg ccccccttggt 360 tttggccgat tcctggattt catgaaagag acacacatcc actacgaaag cggcaccctg 420
attgcgctca agaagaattt cgaatccatc tgggacctga ttcgcatcaa gtacgctcca 480
gagatctttc gcttgcacct gtttggcaag atctacgacc gcgcttccaa gtacttcaag 540
accaagaaga tgcgcatggc attcacgttt cagaccatgt atatgggcat gtcgccctac 600
gatgcgcctg ctgtctacag cctgttgcag tacaccgagt tcgctgaagg catctggtat 660
ccccgtggcg gcttcaacat ggtggttcag aagctagagg cgattgcaaa gcaaaagtac 720
gatgccgagt ttatctacaa tgcgcctgtt gccaagatta acaccgatga tgccaccaaa 780
caagtgacag gtgtaacctt ggaaaatggc cacatcatcg atgccgatgc ggttgtgtgt 840
aacgcagatc tggtctatgc ttatcacaat ctgttgcctc cctgccgatg gacgcaaaac 900
acactggctt ccaagaaatt gacgtcttct tccatttcct tctactggtc catgtccacc 960
aaggtgcctc aattggacgt gcacaacatc tttttggccg aggcttatca ggagagcttt 1020
gacgaaatct tcaaggactt tggcctgcct tctgaagcct ccttctacgt caatgtgccc 1080
tctcgcatcg atccttctgc tgctcccgac ggcaaggact ctgtcattgt cttggtgcct 1140
attggtcata tgaagagcaa gacgggcgat gcttccaccg agaactaccc ggccatggtg 1200
gacaaggcac gcaagatggt gctggctgtg attgagcgtc gtctgggcat gtcgaatttc 1260
gccgacttga ttgagcatga gcaagtcaat gatcccgctg tatggcagag caagttcaat 1320
ctgtggagag gctcaattct gggtttgtct catgatgtgc ttcaggtgct gtggttccgt 1380
cccagcacaa aggattctac cggtcgttat gataacctat tctttgtggg tgcaagcacg 1440

```
catcccggaa ctggtgttcc cattgtcctt gcaggaagca agctcacctc tgaccaagtt   1500

gtcaagagct ttggaaagac gcccaagcca agaaagatcg agatggagaa cacgcaagca   1560

cctttggagg agcctgatgc tgaatcgaca ttccctgtgt ggttctggtt gcgcgctgcc   1620

ttttgggtca tgtttatgtt cttttacttc ttccctcaat ccaatggcca aacgcccgca   1680

tcttttatca ataatttgtt acctgaagta ttccgcgttc ataactctaa tgtcatttaa   1740


<210> SEQ ID NO 36
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CarB protein

<400> SEQUENCE: 36

Met Ser Lys Lys His Ile Val Ile Ile Gly Ala Gly Val Gly Gly Thr
1               5                   10                  15

Ala Thr Ala Ala Arg Leu Ala Arg Glu Gly Phe Lys Val Thr Val Val
            20                  25                  30

Glu Lys Asn Asp Phe Gly Gly Gly Arg Cys Ser Leu Ile His His Gln
        35                  40                  45

Gly His Arg Phe Asp Gln Gly Pro Ser Leu Tyr Leu Met Pro Lys Tyr
    50                  55                  60

Phe Glu Asp Ala Phe Ala Asp Leu Asp Glu Arg Ile Gln Asp His Leu
65                  70                  75                  80

Glu Leu Leu Arg Cys Asp Asn Asn Tyr Lys Val His Phe Asp Asp Gly
                85                  90                  95

Glu Ser Ile Gln Leu Ser Ser Asp Leu Thr Arg Met Lys Ala Glu Leu
            100                 105                 110

Asp Arg Val Glu Gly Pro Leu Gly Phe Gly Arg Phe Leu Asp Phe Met
        115                 120                 125

Lys Glu Thr His Ile His Tyr Glu Ser Gly Thr Leu Ile Ala Leu Lys
    130                 135                 140

Lys Asn Phe Glu Ser Ile Trp Asp Leu Ile Arg Ile Lys Tyr Ala Pro
145                 150                 155                 160

Glu Ile Phe Arg Leu His Leu Phe Gly Lys Ile Tyr Asp Arg Ala Ser
                165                 170                 175

Lys Tyr Phe Lys Thr Lys Lys Met Arg Met Ala Phe Thr Phe Gln Thr
            180                 185                 190

Met Tyr Met Gly Met Ser Pro Tyr Asp Ala Pro Ala Val Tyr Ser Leu
        195                 200                 205

Leu Gln Tyr Thr Glu Phe Ala Glu Gly Ile Trp Tyr Pro Arg Gly Gly
    210                 215                 220

Phe Asn Met Val Val Gln Lys Leu Glu Ala Ile Ala Lys Gln Lys Tyr
225                 230                 235                 240

Asp Ala Glu Phe Ile Tyr Asn Ala Pro Val Ala Lys Ile Asn Thr Asp
                245                 250                 255

Asp Ala Thr Lys Gln Val Thr Gly Val Thr Leu Glu Asn Gly His Ile
            260                 265                 270

Ile Asp Ala Asp Ala Val Val Cys Asn Ala Asp Leu Val Tyr Ala Tyr
        275                 280                 285

His Asn Leu Leu Pro Pro Cys Arg Trp Thr Gln Asn Thr Leu Ala Ser
    290                 295                 300
```

```
Lys Lys Leu Thr Ser Ser Ser Ile Ser Phe Tyr Trp Ser Met Ser Thr
305                 310                 315                 320

Lys Val Pro Gln Leu Asp Val His Asn Ile Phe Leu Ala Glu Ala Tyr
                325                 330                 335

Gln Glu Ser Phe Asp Glu Ile Phe Lys Asp Phe Gly Leu Pro Ser Glu
            340                 345                 350

Ala Ser Phe Tyr Val Asn Val Pro Ser Arg Ile Asp Pro Ser Ala Ala
        355                 360                 365

Pro Asp Gly Lys Asp Ser Val Ile Val Leu Val Pro Ile Gly His Met
    370                 375                 380

Lys Ser Lys Thr Gly Asp Ala Ser Thr Glu Asn Tyr Pro Ala Met Val
385                 390                 395                 400

Asp Lys Ala Arg Lys Met Val Leu Ala Val Ile Glu Arg Arg Leu Gly
                405                 410                 415

Met Ser Asn Phe Ala Asp Leu Ile Glu His Glu Gln Val Asn Asp Pro
            420                 425                 430

Ala Val Trp Gln Ser Lys Phe Asn Leu Trp Arg Gly Ser Ile Leu Gly
        435                 440                 445

Leu Ser His Asp Val Leu Gln Val Leu Trp Phe Arg Pro Ser Thr Lys
    450                 455                 460

Asp Ser Thr Gly Arg Tyr Asp Asn Leu Phe Phe Val Gly Ala Ser Thr
465                 470                 475                 480

His Pro Gly Thr Gly Val Pro Ile Val Leu Ala Gly Ser Lys Leu Thr
                485                 490                 495

Ser Asp Gln Val Val Lys Ser Phe Gly Lys Thr Pro Lys Pro Arg Lys
            500                 505                 510

Ile Glu Met Glu Asn Thr Gln Ala Pro Leu Glu Glu Pro Asp Ala Glu
        515                 520                 525

Ser Thr Phe Pro Val Trp Phe Trp Leu Arg Ala Ala Phe Trp Val Met
    530                 535                 540

Phe Met Phe Phe Tyr Phe Phe Pro Gln Ser Asn Gly Gln Thr Pro Ala
545                 550                 555                 560

Ser Phe Ile Asn Asn Leu Leu Pro Glu Val Phe Arg Val His Asn Ser
                565                 570                 575

Asn Val Ile
```

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO4684

<400> SEQUENCE: 37
cattcactag tggtgtgttc tgtggagcat tc 32

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO4685

<400> SEQUENCE: 38
cacacggtct catcgaggtg tagtggtagt gcagtg 36

<210> SEQ ID NO 39
<211> LENGTH: 1740
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Nucleic acid coding sequence of CarB(i) of
pMB4660

<400> SEQUENCE: 39
atgtccaaga aacacattgt cattatcggt gctggcgtgg gtggcacggc tacagctgct 60
cgtttggccc gcgaaggctt caaggtcact gtggtggaga aaaacgactt tggtggcggc 120
cgctgctcct tgatccatca ccagggccat cgctttgatc agggcccgtc gctctacctg 180
atgcccaagt actttgagga cgcctttgcc gatctggacg agcgcattca agaccacctg 240
gagctgctgc gatgcgacaa caactacaag gtgcactttg acgacggtga gtcgatccag 300
ctgtcgtctg acttgacacg catgaaggct gaattggacc gcgtggaggg cccccttggt 360
tttggccgat tcctggattt catgaaagag acacacatcc actacgaaag cggcaccctg 420
attgcgctca agaagaattt cgaatccatc tgggacctga ttcgcatcaa gtacgctcca 480
gagatctttc gcttgcacct gtttggcaag atctacgacc gcgcttccaa gtacttcaag 540
accaagaaga tgcgcatggc attcacgttt cagaccatgt atatgggcat gtcgccctac 600
gatgcgcctg ctgtctacag cctgttgcag tacaccgagt tcgctgaagg catctggtat 660
ccccgtggcg gcttcaacat ggtggttcag aagctagagg cgattgcaaa gcaaaagtac 720
gatgccgagt ttatctacaa tgcgcctgtt gccaagatta acaccgatga tgccaccaaa 780
caagtgacag gtgtaacctt ggaaaatggc cacatcatcg atgccgatgc ggttgtgtgt 840
aacgcagatc tggtctatgc ttatcacaat ctgttgcctc cctgccgatg gacgcaaaac 900
acactggctt ccaagaaatt gacgtcttct tccatttcct tctactggtc catgtccacc 960
aaggtgcctc aattggacgt gcacaacatc tttttggccg aggcttatca ggagagcttt 1020
gacgaaatct tcaaggactt tggcctgcct tctgaagcct ccttctacgt caatgtgccc 1080
tctcgcatcg atccttctgc tgctcccgac ggcaaggact ctgtcattgt cttggtgcct 1140
attggtcata tgaagagcaa gacgggcgat gcttccaccg agaactaccc ggccatggtg 1200
gacaaggcac gcaagatggt gctggctgtg attgagcgtc gtctgggcat gtcgaatttc 1260
gccgacttga ttgagcatga gcaagtcaat gatcccgctg tatggcagag caagttcaat 1320
ctgtggagag gctcaattct gggtttgtct catgatgtgc ttcaggtgct gtggttccgt 1380
cccagcacaa aggattctac cggtcgttat gataacctat tctttgtggg tgcaagcacg 1440
catcccggaa ctggtgttcc cattgtcctt gcaggaagca agctcacctc tgaccaagtt 1500
gtcaagagct ttggaaagac gcccaagcca agaaagatcg agatggagaa cacgcaagca 1560
cctttggagg agcctgatgc tgaatcgaca ttccctgtgt ggttctggtt gcgcgctgcc 1620
ttttgggtca tgtttatgtt cttttacttc ttccctcaat ccaatggcca aacgcccgca 1680
tcttttatca ataatttgtt acctgaagta ttccgcgttc ataactctaa tgtcatttaa 1740

<210> SEQ ID NO 40
<211> LENGTH: 579
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CarB(i) protein

<400> SEQUENCE: 40

```
Met Ser Lys Lys His Ile Val Ile Ile Gly Ala Gly Val Gly Gly Thr
1               5                   10                  15

Ala Thr Ala Ala Arg Leu Ala Arg Glu Gly Phe Lys Val Thr Val Val
            20                  25                  30

Glu Lys Asn Asp Phe Gly Gly Gly Arg Cys Ser Leu Ile His His Gln
        35                  40                  45

Gly His Arg Phe Asp Gln Gly Pro Ser Leu Tyr Leu Met Pro Lys Tyr
    50                  55                  60

Phe Glu Asp Ala Phe Ala Asp Leu Asp Glu Arg Ile Gln Asp His Leu
65                  70                  75                  80

Glu Leu Leu Arg Cys Asp Asn Asn Tyr Lys Val His Phe Asp Asp Gly
                85                  90                  95

Glu Ser Ile Gln Leu Ser Ser Asp Leu Thr Arg Met Lys Ala Glu Leu
            100                 105                 110

Asp Arg Val Glu Gly Pro Leu Gly Phe Gly Arg Phe Leu Asp Phe Met
        115                 120                 125

Lys Glu Thr His Ile His Tyr Glu Ser Gly Thr Leu Ile Ala Leu Lys
    130                 135                 140

Lys Asn Phe Glu Ser Ile Trp Asp Leu Ile Arg Ile Lys Tyr Ala Pro
145                 150                 155                 160

Glu Ile Phe Arg Leu His Leu Phe Gly Lys Ile Tyr Asp Arg Ala Ser
                165                 170                 175

Lys Tyr Phe Lys Thr Lys Lys Met Arg Met Ala Phe Thr Phe Gln Thr
            180                 185                 190

Met Tyr Met Gly Met Ser Pro Tyr Asp Ala Pro Ala Val Tyr Ser Leu
        195                 200                 205

Leu Gln Tyr Thr Glu Phe Ala Glu Gly Ile Trp Tyr Pro Arg Gly Gly
    210                 215                 220

Phe Asn Met Val Val Gln Lys Leu Glu Ala Ile Ala Lys Gln Lys Tyr
225                 230                 235                 240

Asp Ala Glu Phe Ile Tyr Asn Ala Pro Val Ala Lys Ile Asn Thr Asp
                245                 250                 255

Asp Ala Thr Lys Gln Val Thr Gly Val Thr Leu Glu Asn Gly His Ile
            260                 265                 270

Ile Asp Ala Asp Ala Val Val Cys Asn Ala Asp Leu Val Tyr Ala Tyr
        275                 280                 285

His Asn Leu Leu Pro Pro Cys Arg Trp Thr Gln Asn Thr Leu Ala Ser
    290                 295                 300

Lys Lys Leu Thr Ser Ser Ser Ile Ser Phe Tyr Trp Ser Met Ser Thr
305                 310                 315                 320

Lys Val Pro Gln Leu Asp Val His Asn Ile Phe Leu Ala Glu Ala Tyr
                325                 330                 335

Gln Glu Ser Phe Asp Glu Ile Phe Lys Asp Phe Gly Leu Pro Ser Glu
            340                 345                 350

Ala Ser Phe Tyr Val Asn Val Pro Ser Arg Ile Asp Pro Ser Ala Ala
        355                 360                 365

Pro Asp Gly Lys Asp Ser Val Ile Val Leu Val Pro Ile Gly His Met
    370                 375                 380
```

```
Lys Ser Lys Thr Gly Asp Ala Ser Thr Glu Asn Tyr Pro Ala Met Val
385                 390                 395                 400

Asp Lys Ala Arg Lys Met Val Leu Ala Val Ile Glu Arg Arg Leu Gly
                405                 410                 415

Met Ser Asn Phe Ala Asp Leu Ile Glu His Glu Gln Val Asn Asp Pro
            420                 425                 430

Ala Val Trp Gln Ser Lys Phe Asn Leu Trp Arg Gly Ser Ile Leu Gly
        435                 440                 445

Leu Ser His Asp Val Leu Gln Val Leu Trp Phe Arg Pro Ser Thr Lys
    450                 455                 460

Asp Ser Thr Gly Arg Tyr Asp Asn Leu Phe Phe Val Gly Ala Ser Thr
465                 470                 475                 480

His Pro Gly Thr Gly Val Pro Ile Val Leu Ala Gly Ser Lys Leu Thr
                485                 490                 495

Ser Asp Gln Val Val Lys Ser Phe Gly Lys Thr Pro Lys Pro Arg Lys
            500                 505                 510

Ile Glu Met Glu Asn Thr Gln Ala Pro Leu Glu Glu Pro Asp Ala Glu
        515                 520                 525

Ser Thr Phe Pro Val Trp Phe Trp Leu Arg Ala Ala Phe Trp Val Met
    530                 535                 540

Phe Met Phe Phe Tyr Phe Phe Pro Gln Ser Asn Gly Gln Thr Pro Ala
545                 550                 555                 560

Ser Phe Ile Asn Asn Leu Leu Pro Glu Val Phe Arg Val His Asn Ser
                565                 570                 575

Asn Val Ile
```

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: PCR primer O

<400> SEQUENCE: 41
ttctagacac aaaaatggct gcagaccaat tggtga 36

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: PCR primer P

<400> SEQUENCE: 42
cattaattct tctaaaggac gtattttctt atc 33

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: PCR primer Q

<400> SEQUENCE: 43

-continued gttctctgga cgacctagag g 21

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO4658

<400> SEQUENCE: 44
cacacacgcg tacacctatg accgtatgca aat 33

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO4657

<400> SEQUENCE: 45
cacactctag acacaaaaat gacccagtct gtgaaggtgg 40

<210> SEQ ID NO 46
<211> LENGTH: 1503
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleic acid coding sequence of Hmg1 of pMB4714

<400> SEQUENCE: 46
atgacccagt ctgtgaaggt ggttgagaag cacgttccta tcgtcattga gaagcccagc 60
gagaaggagg aggacacctc ttctgaagac tccattgagc tgactgtcgg aaagcagccc 120
aagcccgtga ccgagacccg ttctctggac gacctagagg ctatcatgaa ggcaggtaag 180
accaagcttc tggaggacca cgaggttgtc aagctctctc tcgagggcaa gcttcctttg 240
tatgctcttg agaagcagct tggtgacaac acccgagctg ttggcatccg acgatctatc 300
atctcccagc agtctaatac caagacttta gagacctcaa agcttcctta cctgcactac 360
gactacgacc gtgtttttgg agcctgttgc gagaacgtta ttggttacat gcctctcccc 420
gttggtgttg ctggccccat gaacattgat ggcaagaact accacattcc tatggccacc 480
actgagggtt gtcttgttgc ctcaaccatg cgaggttgca aggccatcaa cgccggtggc 540
ggtgttacca ctgtgcttac tcaggacggt atgacacgag gtccttgtgt ttccttcccc 600
tctctcaagc gggctggagc cgctaagatc tggcttgatt ccgaggaggg tctcaagtcc 660
atgcgaaagg ccttcaactc cacctctcga tttgctcgtc tccagtctct tcactctacc 720
cttgctggta acctgctgtt tattcgattc cgaaccacca ctggtgatgc catgggcatg 780
aacatgatct ccaagggcgt cgaacactct ctggccgtca tggtcaagga gtacggcttc 840
cctgatatgg acattgtgtc tgtctcgggt aactactgca ctgacaagaa gcccgcagcg 900
atcaactgga tcgaaggccg aggcaagagt gttgttgccg aagccaccat ccctgctcac 960
attgtcaagt ctgttctcaa aagtgaggtt gacgctcttg ttgagctcaa catcagcaag 1020

-continued aatctgatcg gtagtgccat ggctggctct gtgggaggtt tcaatgcaca cgccgcaaac 1080
ctggtgaccg ccatctacct tgccactggc caggatcctg ctcagaatgt cgagtcttcc 1140
aactgcatca cgctgatgag caacgtcgac ggtaacctgc tcatctccgt ttccatgcct 1200
tctatcgagg tcggtaccat tggtggaggt actattttgg agccccaggg ggctatgctg 1260
gagatgcttg gcgtgcgagg tcctcacatc gagacccccg gtgccaacgc ccaacagctt 1320
gctcgcatca ttgcttctgg agttcttgca gcggagcttt cgctgtgttc tgctcttgct 1380
gccggccatc ttgtgcaaag tcatatgacc cacaaccggt cccaggctcc tactccggcc 1440
aagcagtctc aggccgatct gcagcgtcta caaaacggtt cgaatatttg catacggtca 1500
tag 1503

<210> SEQ ID NO 47
<211> LENGTH: 500
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Hmg1 protein

<400> SEQUENCE: 47

Met Thr Gln Ser Val Lys Val Val Glu Lys His Val Pro Ile Val Ile
1 5 10 15

Glu Lys Pro Ser Glu Lys Glu Glu Asp Thr Ser Ser Glu Asp Ser Ile
20 25 30

Glu Leu Thr Val Gly Lys Gln Pro Lys Pro Val Thr Glu Thr Arg Ser
35 40 45

Leu Asp Asp Leu Glu Ala Ile Met Lys Ala Gly Lys Thr Lys Leu Leu
50 55 60

Glu Asp His Glu Val Val Lys Leu Ser Leu Glu Gly Lys Leu Pro Leu
65 70 75 80

Tyr Ala Leu Glu Lys Gln Leu Gly Asp Asn Thr Arg Ala Val Gly Ile
85 90 95

Arg Arg Ser Ile Ile Ser Gln Gln Ser Asn Thr Lys Thr Leu Glu Thr
100 105 110

Ser Lys Leu Pro Tyr Leu His Tyr Asp Tyr Asp Arg Val Phe Gly Ala
115 120 125

Cys Cys Glu Asn Val Ile Gly Tyr Met Pro Leu Pro Val Gly Val Ala
130 135 140

Gly Pro Met Asn Ile Asp Gly Lys Asn Tyr His Ile Pro Met Ala Thr
145 150 155 160

Thr Glu Gly Cys Leu Val Ala Ser Thr Met Arg Gly Cys Lys Ala Ile
165 170 175

Asn Ala Gly Gly Gly Val Thr Thr Val Leu Thr Gln Asp Gly Met Thr
180 185 190

Arg Gly Pro Cys Val Ser Phe Pro Ser Leu Lys Arg Ala Gly Ala Ala
195 200 205

Lys Ile Trp Leu Asp Ser Glu Glu Gly Leu Lys Ser Met Arg Lys Ala
210 215 220

Phe Asn Ser Thr Ser Arg Phe Ala Arg Leu Gln Ser Leu His Ser Thr
225 230 235 240

Leu Ala Gly Asn Leu Leu Phe Ile Arg Phe Arg Thr Thr Thr Gly Asp
245 250 255

Ala Met Gly Met Asn Met Ile Ser Lys Gly Val Glu His Ser Leu Ala

```
        260                 265                 270

Val Met Val Lys Glu Tyr Gly Phe Pro Asp Met Asp Ile Val Ser Val
    275                 280                 285

Ser Gly Asn Tyr Cys Thr Asp Lys Lys Pro Ala Ala Ile Asn Trp Ile
    290                 295                 300

Glu Gly Arg Gly Lys Ser Val Val Ala Glu Ala Thr Ile Pro Ala His
305                 310                 315                 320

Ile Val Lys Ser Val Leu Lys Ser Glu Val Asp Ala Leu Val Glu Leu
                325                 330                 335

Asn Ile Ser Lys Asn Leu Ile Gly Ser Ala Met Ala Gly Ser Val Gly
            340                 345                 350

Gly Phe Asn Ala His Ala Ala Asn Leu Val Thr Ala Ile Tyr Leu Ala
        355                 360                 365

Thr Gly Gln Asp Pro Ala Gln Asn Val Glu Ser Ser Asn Cys Ile Thr
    370                 375                 380

Leu Met Ser Asn Val Asp Gly Asn Leu Leu Ile Ser Val Ser Met Pro
385                 390                 395                 400

Ser Ile Glu Val Gly Thr Ile Gly Gly Gly Thr Ile Leu Glu Pro Gln
                405                 410                 415

Gly Ala Met Leu Glu Met Leu Gly Val Arg Gly Pro His Ile Glu Thr
            420                 425                 430

Pro Gly Ala Asn Ala Gln Gln Leu Ala Arg Ile Ile Ala Ser Gly Val
        435                 440                 445

Leu Ala Ala Glu Leu Ser Leu Cys Ser Ala Leu Ala Ala Gly His Leu
    450                 455                 460

Val Gln Ser His Met Thr His Asn Arg Ser Gln Ala Pro Thr Pro Ala
465                 470                 475                 480

Lys Gln Ser Gln Ala Asp Leu Gln Arg Leu Gln Asn Gly Ser Asn Ile
                485                 490                 495

Cys Ile Arg Ser
            500
```

```
<210> SEQ ID NO 48
<211> LENGTH: 551
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: crtZ sequence of Novosphingobium
      aromaticivorans, using Y. lipolytica codon bias

<400> SEQUENCE: 48

ttctagacac aaaaatgggt ggagccatgc agaccctcgc tgctatcctg atcgtcctcg      60

gtacagtgct cgctatggag tttgtcgctt ggtcttctca taagtatatc atgcatggct     120

tcggatgggg atggcataga gaccatcacg agccccatga gggatttctt gagaagaatg     180

acttatacgc catcgttggc gctgccctct cgatactcat gtttgccctc ggctctccca     240

tgatcatggg cgctgacgcc tggtggcccg gaacctggat cggactcggt gtcctcttct     300

atggtgtcat ctataccctc gtgcacgacg gtctggtgca ccaacgatgg tttagatggg     360

tgcctaaacg aggttacgcc aaacgactcg tgcaggccca taagctgcac cacgccacca     420

ttggcaagga aggaggcgtc tcattcggtt tcgtgttcgc ccgagatccc gccgttctga     480

agcaggagct tcgagctcaa cgagaagcag gtatcgccgt gctgcgagag gctgtggacg     540

gctagacgcg t                                                          551
```

<210> SEQ ID NO 49
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CrtZ protein

<400> SEQUENCE: 49

```
Met Gly Gly Ala Met Gln Thr Leu Ala Ala Ile Leu Ile Val Leu Gly
1               5                   10                  15

Thr Val Leu Ala Met Glu Phe Val Ala Trp Ser Ser His Lys Tyr Ile
            20                  25                  30

Met His Gly Phe Gly Trp Gly Trp His Arg Asp His His Glu Pro His
        35                  40                  45

Glu Gly Phe Leu Glu Lys Asn Asp Leu Tyr Ala Ile Val Gly Ala Ala
    50                  55                  60

Leu Ser Ile Leu Met Phe Ala Leu Gly Ser Pro Met Ile Met Gly Ala
65                  70                  75                  80

Asp Ala Trp Trp Pro Gly Thr Trp Ile Gly Leu Gly Val Leu Phe Tyr
                85                  90                  95

Gly Val Ile Tyr Thr Leu Val His Asp Gly Leu Val His Gln Arg Trp
            100                 105                 110

Phe Arg Trp Val Pro Lys Arg Gly Tyr Ala Lys Arg Leu Val Gln Ala
        115                 120                 125

His Lys Leu His His Ala Thr Ile Gly Lys Glu Gly Gly Val Ser Phe
    130                 135                 140

Gly Phe Val Phe Ala Arg Asp Pro Ala Val Leu Lys Gln Glu Leu Arg
145                 150                 155                 160

Ala Gln Arg Glu Ala Gly Ile Ala Val Leu Arg Glu Ala Val Asp Gly
                165                 170                 175
```

<210> SEQ ID NO 50
<211> LENGTH: 815
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CrtW sequence based on Sargasso Sea
      environmental sequence

<400> SEQUENCE: 50

```
ttctagacac aaaaatgact cgatctattt cctggccttc cacctactgg cacctccagc     60

cctcctgttc ttcttgggtc gcaaacgaat tctctcctca agcccgaaaa ggtctcgtcc    120

tcgctggtct cattggttcc gcttggctgc ttactctcgg acttggcttt tcccttcccc    180

tccatcaaac gagctggctt ctcatcggtt gtctcgttct ccttagatct ttcctgcaca    240

ccggactttt tatcgttgcc catgacgcta tgcacgcttc tcttgttcct gaccaccctg    300

gccttaaccg ttggattgga cgtgtctgtc ttctcatgta tgctggactc tcctacaaaa    360

gatgctgccg aaatcaccgt cgacaccacc aagcccctga aacagttgaa gaccctgact    420

accaacgatg cactaacaac aatatcctcg actggtacgt tcactttatg ggaaattacc    480

tcggatggca acaattgctt aatctctctt gcgtttggct cgctctcacc ttccgtgttt    540

ctgactactc tgctcaattc ttccacctgc tccttttctc tgtccttcct ctcatcgtct    600
```

```
cctcctgtca actcttcctc gtgggaacct ggctgccaca ccgacgaggc gctactactc    660

gacccggcgt taccactcga tccctgaact tccaccctgc tctttccttc gctgcttgct    720

accacttcgg ttaccaccgt gaacaccatg aatctccctc tactccttgg ttccaacttc    780

ctaaactccg agaaggttct ctcatctaaa cgcgt                               815


<210> SEQ ID NO 51
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CrtW protein

<400> SEQUENCE: 51

Met Thr Arg Ser Ile Ser Trp Pro Ser Thr Tyr Trp His Leu Gln Pro
1               5                   10                  15

Ser Cys Ser Ser Trp Val Ala Asn Glu Phe Ser Pro Gln Ala Arg Lys
            20                  25                  30

Gly Leu Val Leu Ala Gly Leu Ile Gly Ser Ala Trp Leu Leu Thr Leu
        35                  40                  45

Gly Leu Gly Phe Ser Leu Pro Leu His Gln Thr Ser Trp Leu Leu Ile
    50                  55                  60

Gly Cys Leu Val Leu Leu Arg Ser Phe Leu His Thr Gly Leu Phe Ile
65                  70                  75                  80

Val Ala His Asp Ala Met His Ala Ser Leu Val Pro Asp His Pro Gly
                85                  90                  95

Leu Asn Arg Trp Ile Gly Arg Val Cys Leu Leu Met Tyr Ala Gly Leu
            100                 105                 110

Ser Tyr Lys Arg Cys Cys Arg Asn His Arg Arg His His Gln Ala Pro
        115                 120                 125

Glu Thr Val Glu Asp Pro Asp Tyr Gln Arg Cys Thr Asn Asn Asn Ile
    130                 135                 140

Leu Asp Trp Tyr Val His Phe Met Gly Asn Tyr Leu Gly Trp Gln Gln
145                 150                 155                 160

Leu Leu Asn Leu Ser Cys Val Trp Leu Ala Leu Thr Phe Arg Val Ser
                165                 170                 175

Asp Tyr Ser Ala Gln Phe Phe His Leu Leu Leu Phe Ser Val Leu Pro
            180                 185                 190

Leu Ile Val Ser Ser Cys Gln Leu Phe Leu Val Gly Thr Trp Leu Pro
        195                 200                 205

His Arg Arg Gly Ala Thr Thr Arg Pro Gly Val Thr Thr Arg Ser Leu
    210                 215                 220

Asn Phe His Pro Ala Leu Ser Phe Ala Ala Cys Tyr His Phe Gly Tyr
225                 230                 235                 240

His Arg Glu His His Glu Ser Pro Ser Thr Pro Trp Phe Gln Leu Pro
                245                 250                 255

Lys Leu Arg Glu Gly Ser Leu Ile
            260


<210> SEQ ID NO 52
<211> LENGTH: 968
<212> TYPE: DNA
<213> ORGANISM: Artificial Sequence
<220> FEATURE:
<223> OTHER INFORMATION: Description of Artificial Sequence: Synthetic
```

polynucleotide
<220> FEATURE:
<223> OTHER INFORMATION: CrtW sequence based on Aurantimonas sp. SI85-9A1, using Y. lipolytica codon bias

<400> SEQUENCE: 52

```
ctctagacac aaaaatgtct tcctttgccc ctatgaatga tgttgctatt cctgccggtc     60

aagctccttt ctctgcctgt actagaaaac ctgtcctgag accttttcaa gctgccatcg    120

gtcttacact cgccggatgt gttatctctg cttggattgc aatccacgtt ggagctgtct    180

ttttcctcga tgtcggttgg cgaacccttc ctgttgttcc tgtcctcatt gccgttcagt    240

gctggctcac ggtcggtctt tttattgtcg cacacgatgc tatgcacggc tccctcgctc    300

ctggttggcc acgacttaac gctcgaattg gtgccttcat cctcaccatc tacgctggat    360

tcgcttggag acgtgtccga ggagctcaca tggcccatca cgacgcccct ggtactgccg    420

atgaccctga cttctttgtt gatgaacctg accgattttg gccttggttt cgagctttct    480

tccttagata ttttggacgt cgatctattc tctttgtttg cacagttgtc accgtttaca    540

ttctggtcct tggagcccct gttcttaatg ttgttctctt ttacggtctt ccttcccttc    600

tgtcttctct tcaactcttt tactttggaa cttttcgtcc tcaccgtcat gaagaagatg    660

atttcgttga cgcccataat gcccgatcta atgaatttgg ttacatcgcc tccctccttt    720

cttgctttca ctttggatac catcacgaac atcatgccga gccgtgggtc ccttggtggg    780

gtcttccttc tcaatggcgc cagagacaag cctcttcttc ccgacaggtc ccgggcggcc    840

gagacgctgc tgacgccgct ggagcatctc gacaacctgc cggacgatac cgatctgttt    900

cttctcgagg tcgaaatcag gcccgttctc ccgcttctgg tcgaaacgaa caaatgagat    960

aaacgcgt                                                             968
```

<210> SEQ ID NO 53
<211> LENGTH: 315
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CrtW protein

<400> SEQUENCE: 53

```
Met Ser Ser Phe Ala Pro Met Asn Asp Val Ala Ile Pro Ala Gly Gln
1               5                   10                  15

Ala Pro Phe Ser Ala Cys Thr Arg Lys Pro Val Leu Arg Pro Phe Gln
            20                  25                  30

Ala Ala Ile Gly Leu Thr Leu Ala Gly Cys Val Ile Ser Ala Trp Ile
        35                  40                  45

Ala Ile His Val Gly Ala Val Phe Phe Leu Asp Val Gly Trp Arg Thr
    50                  55                  60

Leu Pro Val Val Pro Val Leu Ile Ala Val Gln Cys Trp Leu Thr Val
65                  70                  75                  80

Gly Leu Phe Ile Val Ala His Asp Ala Met His Gly Ser Leu Ala Pro
                85                  90                  95

Gly Trp Pro Arg Leu Asn Ala Arg Ile Gly Ala Phe Ile Leu Thr Ile
            100                 105                 110

Tyr Ala Gly Phe Ala Trp Arg Arg Val Arg Gly Ala His Met Ala His
        115                 120                 125

His Asp Ala Pro Gly Thr Ala Asp Asp Pro Asp Phe Phe Val Asp Glu
    130                 135                 140
```

```
Pro Asp Arg Phe Trp Pro Trp Phe Arg Ala Phe Phe Leu Arg Tyr Phe
145                 150                 155                 160

Gly Arg Arg Ser Ile Leu Phe Val Cys Thr Val Val Thr Val Tyr Ile
                165                 170                 175

Leu Val Leu Gly Ala Pro Val Leu Asn Val Val Leu Phe Tyr Gly Leu
            180                 185                 190

Pro Ser Leu Leu Ser Ser Leu Gln Leu Phe Tyr Phe Gly Thr Phe Arg
        195                 200                 205

Pro His Arg His Glu Glu Asp Asp Phe Val Asp Ala His Asn Ala Arg
    210                 215                 220

Ser Asn Glu Phe Gly Tyr Ile Ala Ser Leu Leu Ser Cys Phe His Phe
225                 230                 235                 240

Gly Tyr His His Glu His His Ala Glu Pro Trp Val Pro Trp Trp Gly
                245                 250                 255

Leu Pro Ser Gln Trp Arg Gln Arg Gln Ala Ser Ser Ser Arg Gln Val
            260                 265                 270

Pro Gly Gly Arg Asp Ala Ala Asp Ala Ala Gly Ala Ser Arg Gln Pro
        275                 280                 285

Ala Gly Arg Tyr Arg Ser Val Ser Ser Arg Gly Arg Asn Gln Ala Arg
    290                 295                 300

Ser Pro Ala Ser Gly Arg Asn Glu Gln Met Arg
305                 310                 315
```

<210> SEQ ID NO 54
<211> LENGTH: 811
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CrtW sequence based on protein sequence of Parvularcula bermudensis, using Y. lipolytica codon bias

<400> SEQUENCE: 54

```
ctctagacac aaaaatggac cctaccggag acgttactgc tagccctcga cctcaaacca     60

ccattcctgt ccgacaagca ctctggggac ttagccttgc tggagccatc atcgccgcat    120

gggtttttat gcacattggt ttcgtttttt ttgcccccct tgatcctatc gttctcgccc    180

tcgccccagt tattattctt cttcaatcct ggctttctgt tggtcttttt attatttctc    240

acgacgcaat tcacggttcc ctcgcccctg gacgacccgc ctttaataga gccatgggac    300

gactctgcat gacactttac gccggtttcg actttgaccg tatggccgct gcacatcacc    360

gacatcacag atcccctgga accgccgctg accccgattt ttctgttgac tcccctgatc    420

gacctctccc ttggtttgga gctttcttcc gacgttactt tggctggaga ccttttctta    480

ccgttaacgc tgtcgtcttt acctactggc ttgttcttgg agctaaccct gttaatattg    540

ttctctttta tggcgttcct gcactccttt ccgccggaca gctcttttac tttggtacat    600

ttctccctca ccgacacgaa cgacaaggct ttgctgatca ccaccgagca cgatccgtcc    660

gatcccctta catgctttct cttgttactt gttaccactt tggaggctat catcacgaac    720

atcatctctt tccacacgaa ccctggtggc gcctgcctca acgaggaggt tgggaacgtg    780

acagacgaaa gagaaccggc ccttaacgcg t                                   811
```

<210> SEQ ID NO 55
<211> LENGTH: 263
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CrtW protein

<400> SEQUENCE: 55

```
Met Asp Pro Thr Gly Asp Val Thr Ala Ser Pro Arg Pro Gln Thr Thr
1               5                   10                  15

Ile Pro Val Arg Gln Ala Leu Trp Gly Leu Ser Leu Ala Gly Ala Ile
            20                  25                  30

Ile Ala Ala Trp Val Phe Met His Ile Gly Phe Val Phe Phe Ala Pro
        35                  40                  45

Leu Asp Pro Ile Val Leu Ala Leu Ala Pro Val Ile Ile Leu Leu Gln
    50                  55                  60

Ser Trp Leu Ser Val Gly Leu Phe Ile Ile Ser His Asp Ala Ile His
65                  70                  75                  80

Gly Ser Leu Ala Pro Gly Arg Pro Ala Phe Asn Arg Ala Met Gly Arg
                85                  90                  95

Leu Cys Met Thr Leu Tyr Ala Gly Phe Asp Phe Asp Arg Met Ala Ala
            100                 105                 110

Ala His His Arg His His Arg Ser Pro Gly Thr Ala Ala Asp Pro Asp
        115                 120                 125

Phe Ser Val Asp Ser Pro Asp Arg Pro Leu Pro Trp Phe Gly Ala Phe
    130                 135                 140

Phe Arg Arg Tyr Phe Gly Trp Arg Pro Phe Leu Thr Val Asn Ala Val
145                 150                 155                 160

Val Phe Thr Tyr Trp Leu Val Leu Gly Ala Asn Pro Val Asn Ile Val
                165                 170                 175

Leu Phe Tyr Gly Val Pro Ala Leu Leu Ser Ala Gly Gln Leu Phe Tyr
            180                 185                 190

Phe Gly Thr Phe Leu Pro His Arg His Glu Arg Gln Gly Phe Ala Asp
        195                 200                 205

His His Arg Ala Arg Ser Val Arg Ser Pro Tyr Met Leu Ser Leu Val
    210                 215                 220

Thr Cys Tyr His Phe Gly Gly Tyr His His Glu His His Leu Phe Pro
225                 230                 235                 240

His Glu Pro Trp Trp Arg Leu Pro Gln Arg Gly Gly Trp Glu Arg Asp
                245                 250                 255

Arg Arg Lys Arg Thr Gly Pro
            260
```

<210> SEQ ID NO 56
<211> LENGTH: 575
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CrtZ sequence wbased on protein sequence of
Parvularcula bermudensis, using Y. lipolytica codon bias

<400> SEQUENCE: 56

```
ctctagacac aaaaatgact ctcgctctct ggcaaaagat caccctcgtc cttggttccg      60

ctgctctgat ggaaggattt gcttggtggg cccatagata tattatgcac ggttggggat     120

gggcttggca tagagatcat catgaacctc acgacaaagt ttttgaaaaa aatgacctgt     180
```

ttgctgtggt ttttggctcg ttcgcatttg gtttgttcat cgtcggttac ctttattggc 240
cacctgtttg gtacgttgct gctggcatca ctctttacgg acttctttac gcatttgttc 300
atgacggttt ggttcatcaa cgttggccct ggcatttcat gcctaaacga ggatacctcc 360
gaagactggt tcaagctcac aaacttcatc atgctgttac aacacaaggc ggaaatgttt 420
cgtttggatt cgtccttgcc cctgacccta gacatcttag agaaaaactt agacaatttc 480
gtgctgaaag acatcgtgcc cttgccgccg aaggtgcttc ctcctctgac cctcgtgttc 540
ccccttttcg aaaagttcaa gacgtttaaa cgcgt 575

<210> SEQ ID NO 57
<211> LENGTH: 184
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CrtZ protein

<400> SEQUENCE: 57

Met Thr Leu Ala Leu Trp Gln Lys Ile Thr Leu Val Leu Gly Ser Ala
1 5 10 15

Ala Leu Met Glu Gly Phe Ala Trp Trp Ala His Arg Tyr Ile Met His
20 25 30

Gly Trp Gly Trp Ala Trp His Arg Asp His His Glu Pro His Asp Lys
35 40 45

Val Phe Glu Lys Asn Asp Leu Phe Ala Val Val Phe Gly Ser Phe Ala
50 55 60

Phe Gly Leu Phe Ile Val Gly Tyr Leu Tyr Trp Pro Pro Val Trp Tyr
65 70 75 80

Val Ala Ala Gly Ile Thr Leu Tyr Gly Leu Leu Tyr Ala Phe Val His
85 90 95

Asp Gly Leu Val His Gln Arg Trp Pro Trp His Phe Met Pro Lys Arg
100 105 110

Gly Tyr Leu Arg Arg Leu Val Gln Ala His Lys Leu His His Ala Val
115 120 125

Thr Thr Gln Gly Gly Asn Val Ser Phe Gly Phe Val Leu Ala Pro Asp
130 135 140

Pro Arg His Leu Arg Glu Lys Leu Arg Gln Phe Arg Ala Glu Arg His
145 150 155 160

Arg Ala Leu Ala Ala Glu Gly Ala Ser Ser Ser Asp Pro Arg Val Pro
165 170 175

Pro Phe Arg Lys Val Gln Asp Val
180

<210> SEQ ID NO 58
<211> LENGTH: 521
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CrtZ sequence based on protein sequence of Erythrobacter litoralis, using Y. lipolytica codon bias

<400> SEQUENCE: 58
ctctagacac aaaaatgagc tggtgggcta tcgctcttat tgtctttggt gctgtcgttg 60
gaatggaatt ttttgcttgg ttcgctcata agtacattat gcatggttgg ggatggagct 120

```
ggcaccgaga tcatcacgaa cctcacgata atactcttga aaaaaacgac cttttcgccg    180

ttgtctttgg ctcggttgcc gcacttctgt ttgttattgg agctctctgg tctgatcctc    240

tctggtgggc agcagttggt attacattgt atggcgtcat ttacactctg gttcacgacg    300

gacttgttca tcaacgttac tggcgttgga cccctaagcg aggttatgct aagagacttg    360

tccaggccca tcgacttcat cacgctactg ttggaaagga aggaggtgtt tcttttggtt    420

ttgtgttcgc ccgagatcct gctaagttga aagccgaatt gaaacaacaa agagaacagg    480

gacttgccgt cgttcgagat tctatgggag cataaacgcg t                        521
```

<210> SEQ ID NO 59
<211> LENGTH: 166
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CrtZ protein

<400> SEQUENCE: 59

```
Met Ser Trp Trp Ala Ile Ala Leu Ile Val Phe Gly Ala Val Val Gly
1               5                   10                  15

Met Glu Phe Phe Ala Trp Phe Ala His Lys Tyr Ile Met His Gly Trp
            20                  25                  30

Gly Trp Ser Trp His Arg Asp His His Glu Pro His Asp Asn Thr Leu
        35                  40                  45

Glu Lys Asn Asp Leu Phe Ala Val Val Phe Gly Ser Val Ala Ala Leu
    50                  55                  60

Leu Phe Val Ile Gly Ala Leu Trp Ser Asp Pro Leu Trp Trp Ala Ala
65                  70                  75                  80

Val Gly Ile Thr Leu Tyr Gly Val Ile Tyr Thr Leu Val His Asp Gly
                85                  90                  95

Leu Val His Gln Arg Tyr Trp Arg Trp Thr Pro Lys Arg Gly Tyr Ala
            100                 105                 110

Lys Arg Leu Val Gln Ala His Arg Leu His His Ala Thr Val Gly Lys
        115                 120                 125

Glu Gly Gly Val Ser Phe Gly Phe Val Phe Ala Arg Asp Pro Ala Lys
    130                 135                 140

Leu Lys Ala Glu Leu Lys Gln Gln Arg Glu Gln Gly Leu Ala Val Val
145                 150                 155                 160

Arg Asp Ser Met Gly Ala
                165
```

<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO5017

<400> SEQUENCE: 60

```
ctagacacaa aaatgtacga ctacgccttc gt                                   32
```

<210> SEQ ID NO 61
<211> LENGTH: 32
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO5018

<400> SEQUENCE: 61

gcacctgaag ttcaccgtgc ccgcggttcc aa                                32


<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO5019

<400> SEQUENCE: 62

gtgcacgaag gcgtagtcgt acatttttgt gt                                32


<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO5020

<400> SEQUENCE: 63

cgcgttggaa ccgcgggcac ggtgaacttc ag                                32


<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO5016

<400> SEQUENCE: 64

cccgcggcgg tacttct                                                 17


<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO5013

<400> SEQUENCE: 65

ccgtctctac agcaggatca ggtcaatgc                                    29


<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: PCR primer MO5014

<400> SEQUENCE: 66
ccgtctcact gtactccttc tgtcgcctg 29

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MO5015

<400> SEQUENCE: 67
cacgcgtcta ctgctcatac aacgccct 28

<210> SEQ ID NO 68
<211> LENGTH: 1809
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleic acid coding sequence of al-2

<400> SEQUENCE: 68
atgtacgact acgccttcgt gcacctgaag ttcaccgtgc ccgcggcggt acttctcacc 60
gctatcgcct accccattct caacaggata catctcatcc aaacaggctt cctcgtcgtc 120
gtcgccttta ccgccgctct gccatgggat gcctacttga ttaagcacaa agtatggtct 180
tacccaccag aagccattgt tgggccgcgt ttgcttggaa ttccctttga agagctgttc 240
ttctttgtga tacagactta catcacggcg ctcgtataca tcctcttcaa caagccggtg 300
ctgcacgcgt tgcacctcaa caatcaacaa aacccgccag catggatgag ggttgtcaag 360
gttaccggcc aggtagtcct cgtagccttg tcggtatggg gatggaatgc cgctcaggtt 420
catcaggaaa caagctatct cggcttgatc cttgtttggg cttgtccgtt cttactggct 480
atctggaccc tcgctgggcg cttcattctc agcctaccct ggtacgcgac ggtgctcccg 540
atgttcctac ccaccttcta tctttgggcg gtagacgagt ttgccttgca caggggtact 600
tggtccatcg gatcggggac gaagctcgat tttgtctgt ttggcaagtt ggacattgaa 660
gaagccacgt tcttcctggt gaccaacatg ctcatcgttg gcggtatggc cgcgttcgat 720
caatatctgg ccgtcattta cgctttccca actctgttcc ccaaggtcaa ccggtatccg 780
acaactcata tgcttcttca aagccgtctt atcaacactt ccaggtacga tcttgagcgc 840
attgagggcc tgagagaagc ggtcgagaga ctgcgcctga agagcaggag tttttacctg 900
gccaattcgc tcttttctgg tcgactccgc attgacctga tcctgctgta ctccttctgt 960
cgcctggctg atgatctagt cgacgacgcc aaatctcgcc gtgaggtctt gtcctggacc 1020
gcgaagctga accacttcct tgatctgcac tacaaggacg cggacgccac cgaggacccc 1080
aagaaaaagg cggagcgaat cgacgcctac atcaagacag cgttccctcc ctgtgcctac 1140
caagccctcc acctcctgcc cactcacatt cttcctccca agcctcttta cgatctcatc 1200
aagggtttcg agatggactc tcaattcacc ttccacggta cttccgactc tacggatctc 1260
caatacccca tcgccgacga caaggacctt gagaactacg ctatctatgt cgccggtacc 1320
gtcggcgagc tctgcatcgc cctcatcatc taccactgcc tgccagacat gtcggacact 1380

-continued

```
cagaagcgcg agctcgagac cgccgcgtgc cggatgggca tcgcgctgca gtacgtcaac   1440

atcgctcgtg acatcgtcgt cgacgcacgt atcgggcgcg tttacttgcc taccacctgg   1500

ctcaagaagg aagggttgac gcacaagatg gtcttggaga accccgaggg tcccgaggtc   1560

attgagcgga tgagaagacg gcttttggaa aatgcgtttg agctgtatgg gggcgcgagg   1620

cctgagatgc aacggatacc gagcgaggct aggggcccga tgattggtgc cgttgaaaat   1680

tacatggcga ttggaagggt gttgagggag aggaaggagg ggacggtgtt tgtgaggatg   1740

gaggggaggg ctacggtccc gaagcgaagg aggttgagca cgctgttgag ggcgttgtat   1800

gagcagtag                                                           1809
```

```
<210> SEQ ID NO 69
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: al-2 protein

<400> SEQUENCE: 69

Met Tyr Asp Tyr Ala Phe Val His Leu Lys Phe Thr Val Pro Ala Ala
1               5                   10                  15

Val Leu Leu Thr Ala Ile Ala Tyr Pro Ile Leu Asn Arg Ile His Leu
            20                  25                  30

Ile Gln Thr Gly Phe Leu Val Val Val Ala Phe Thr Ala Ala Leu Pro
        35                  40                  45

Trp Asp Ala Tyr Leu Ile Lys His Lys Val Trp Ser Tyr Pro Pro Glu
    50                  55                  60

Ala Ile Val Gly Pro Arg Leu Leu Gly Ile Pro Phe Glu Glu Leu Phe
65                  70                  75                  80

Phe Phe Val Ile Gln Thr Tyr Ile Thr Ala Leu Val Tyr Ile Leu Phe
                85                  90                  95

Asn Lys Pro Val Leu His Ala Leu His Leu Asn Asn Gln Gln Asn Pro
            100                 105                 110

Pro Ala Trp Met Arg Val Val Lys Val Thr Gly Gln Val Val Leu Val
        115                 120                 125

Ala Leu Ser Val Trp Gly Trp Asn Ala Ala Gln Val His Gln Glu Thr
    130                 135                 140

Ser Tyr Leu Gly Leu Ile Leu Val Trp Ala Cys Pro Phe Leu Leu Ala
145                 150                 155                 160

Ile Trp Thr Leu Ala Gly Arg Phe Ile Leu Ser Leu Pro Trp Tyr Ala
                165                 170                 175

Thr Val Leu Pro Met Phe Leu Pro Thr Phe Tyr Leu Trp Ala Val Asp
            180                 185                 190

Glu Phe Ala Leu His Arg Gly Thr Trp Ser Ile Gly Ser Gly Thr Lys
        195                 200                 205

Leu Asp Phe Cys Leu Phe Gly Lys Leu Asp Ile Glu Glu Ala Thr Phe
    210                 215                 220

Phe Leu Val Thr Asn Met Leu Ile Val Gly Gly Met Ala Ala Phe Asp
225                 230                 235                 240

Gln Tyr Leu Ala Val Ile Tyr Ala Phe Pro Thr Leu Phe Pro Lys Val
                245                 250                 255

Asn Arg Tyr Pro Thr Thr His Met Leu Leu Gln Ser Arg Leu Ile Asn
            260                 265                 270
```

```
Thr Ser Arg Tyr Asp Leu Glu Arg Ile Glu Gly Leu Arg Glu Ala Val
        275                 280                 285

Glu Arg Leu Arg Leu Lys Ser Arg Ser Phe Tyr Leu Ala Asn Ser Leu
    290                 295                 300

Phe Ser Gly Arg Leu Arg Ile Asp Leu Ile Leu Leu Tyr Ser Phe Cys
305                 310                 315                 320

Arg Leu Ala Asp Asp Leu Val Asp Asp Ala Lys Ser Arg Arg Glu Val
                325                 330                 335

Leu Ser Trp Thr Ala Lys Leu Asn His Phe Leu Asp Leu His Tyr Lys
            340                 345                 350

Asp Ala Asp Ala Thr Glu Asp Pro Lys Lys Lys Ala Glu Arg Ile Asp
        355                 360                 365

Ala Tyr Ile Lys Thr Ala Phe Pro Pro Cys Ala Tyr Gln Ala Leu His
    370                 375                 380

Leu Leu Pro Thr His Ile Leu Pro Pro Lys Pro Leu Tyr Asp Leu Ile
385                 390                 395                 400

Lys Gly Phe Glu Met Asp Ser Gln Phe Thr Phe His Gly Thr Ser Asp
                405                 410                 415

Ser Thr Asp Leu Gln Tyr Pro Ile Ala Asp Asp Lys Asp Leu Glu Asn
            420                 425                 430

Tyr Ala Ile Tyr Val Ala Gly Thr Val Gly Glu Leu Cys Ile Ala Leu
        435                 440                 445

Ile Ile Tyr His Cys Leu Pro Asp Met Ser Asp Thr Gln Lys Arg Glu
    450                 455                 460

Leu Glu Thr Ala Ala Cys Arg Met Gly Ile Ala Leu Gln Tyr Val Asn
465                 470                 475                 480

Ile Ala Arg Asp Ile Val Val Asp Ala Arg Ile Gly Arg Val Tyr Leu
                485                 490                 495

Pro Thr Thr Trp Leu Lys Lys Glu Gly Leu Thr His Lys Met Val Leu
            500                 505                 510

Glu Asn Pro Glu Gly Pro Glu Val Ile Glu Arg Met Arg Arg Arg Leu
        515                 520                 525

Leu Glu Asn Ala Phe Glu Leu Tyr Gly Gly Ala Arg Pro Glu Met Gln
    530                 535                 540

Arg Ile Pro Ser Glu Ala Arg Gly Pro Met Ile Gly Ala Val Glu Asn
545                 550                 555                 560

Tyr Met Ala Ile Gly Arg Val Leu Arg Glu Arg Lys Glu Gly Thr Val
                565                 570                 575

Phe Val Arg Met Glu Gly Arg Ala Thr Val Pro Lys Arg Arg Arg Leu
            580                 585                 590

Ser Thr Leu Leu Arg Ala Leu Tyr Glu Gln
        595                 600
```

<210> SEQ ID NO 70
<211> LENGTH: 521
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CrtZ sequence based on protein sequence of Erythrobacter sp. NAP1, using Y. lipolytica codon bias

<400> SEQUENCE: 70

```
ctctagacac aaaaatgtct tggcctgccg ctattgcagt tacacttggt gcccttattt     60

ttatggaatt ctttgcttgg tacgctcaca aatacattat gcatggatgg ggatggggtt    120
```

```
ggcacagaga ccatcacgaa cctcacgaca acaaactgga aaaaaatgac ctgttcgctg    180

tggttttcgg aacaattaac gctggtatgt atatttttgg tgctctttat tgggatgctt    240

tgtggtgggc tgcacttgga gttaatcttt acggagtgat ttacgccctt gttcatgacg    300

gactggttca tcaaagattt ggaagatacg tccctaaaaa cgcatacgct aaacgacttg    360

ttcaagcaca cagattgcat cacgctacta tcggtaaaga aggaggagtg tccttcggat    420

tcgttcttgc tcgagaccct gctaaactta aagccgaact taaacgacaa tctcaatccg    480

gagaagctat tgttcgagaa tccgccggag cctaaacgcg t                        521
```

```
<210> SEQ ID NO 71
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CrtZ protein

<400> SEQUENCE: 71

Met Ser Trp Pro Ala Ala Ile Ala Val Thr Leu Gly Ala Leu Ile Phe
1               5                   10                  15

Met Glu Phe Phe Ala Trp Tyr Ala His Lys Tyr Ile Met His Gly Trp
            20                  25                  30

Gly Trp Gly Trp His Arg Asp His His Glu Pro His Asp Asn Lys Leu
        35                  40                  45

Glu Lys Asn Asp Leu Phe Ala Val Val Phe Gly Thr Ile Asn Ala Gly
    50                  55                  60

Met Tyr Ile Phe Gly Ala Leu Tyr Trp Asp Ala Leu Trp Trp Ala Ala
65                  70                  75                  80

Leu Gly Val Asn Leu Tyr Gly Val Ile Tyr Ala Leu Val His Asp Gly
                85                  90                  95

Leu Val His Gln Arg Phe Gly Arg Tyr Val Pro Lys Asn Ala Tyr Ala
            100                 105                 110

Lys Arg Leu Val Gln Ala His Arg Leu His His Ala Thr Ile Gly Lys
        115                 120                 125

Glu Gly Gly Val Ser Phe Gly Phe Val Leu Ala Arg Asp Pro Ala Lys
    130                 135                 140

Leu Lys Ala Glu Leu Lys Arg Gln Ser Gln Ser Gly Glu Ala Ile Val
145                 150                 155                 160

Arg Glu Ser Ala Gly Ala
                165


<210> SEQ ID NO 72
<211> LENGTH: 623
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CrtZ sequence based on protein sequence of
      Sphingopyxis alaskensis, using Y. lipolytica codon bias

<400> SEQUENCE: 72

ctctagacac aaaaatgagc caccgaagag atccaggact tagaagagac gacgcacgat     60

ctatggcctc ctgtctcaga cgagcttaca acccccacat gtccctgcct gcaattttgt    120

ttttggttct tgctactgtc attgcaatgg aaggagtcgc ctgggcatcc cacaaataca    180
```

```
tcatgcacgg atttggatgg gcctggcaca gagaccacca tgaaccccac gacaatcgac    240

tcgagaaaaa cgacctgttt gccctgttcg gagccgctat gtctatttct gccttcgcta    300

ttggttctcc tatgattatg ggtgcagctg cctggaagcc tggaacttgg attggacttg    360

gtattcttct ttacggtatt atctacacac tcgttcacga cggccttgtg caccaaagat    420

actttcgatg ggtcccacga cgaggttacg caaaacgact tgttcaagca cacaaacttc    480

atcacgctac aatcggaaaa gagggaggag tttctttcgg atttgttttt gctcgtgacc    540

ctgctaaact taaagccgaa ctgaaagcac aacgagaagc tggtattgca gtcgtcagag    600

aagcccttgc tgactaaacg cgt                                             623
```

```
<210> SEQ ID NO 73
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CrtZ protein

<400> SEQUENCE: 73

Met Ser His Arg Arg Asp Pro Gly Leu Arg Arg Asp Asp Ala Arg Ser
1               5                   10                  15

Met Ala Ser Cys Leu Arg Arg Ala Tyr Asn Pro His Met Ser Leu Pro
            20                  25                  30

Ala Ile Leu Phe Leu Val Leu Ala Thr Val Ile Ala Met Glu Gly Val
        35                  40                  45

Ala Trp Ala Ser His Lys Tyr Ile Met His Gly Phe Gly Trp Ala Trp
    50                  55                  60

His Arg Asp His His Glu Pro His Asp Asn Arg Leu Glu Lys Asn Asp
65                  70                  75                  80

Leu Phe Ala Leu Phe Gly Ala Ala Met Ser Ile Ser Ala Phe Ala Ile
                85                  90                  95

Gly Ser Pro Met Ile Met Gly Ala Ala Ala Trp Lys Pro Gly Thr Trp
            100                 105                 110

Ile Gly Leu Gly Ile Leu Leu Tyr Gly Ile Ile Tyr Thr Leu Val His
        115                 120                 125

Asp Gly Leu Val His Gln Arg Tyr Phe Arg Trp Val Pro Arg Arg Gly
    130                 135                 140

Tyr Ala Lys Arg Leu Val Gln Ala His Lys Leu His His Ala Thr Ile
145                 150                 155                 160

Gly Lys Glu Gly Gly Val Ser Phe Gly Phe Val Phe Ala Arg Asp Pro
                165                 170                 175

Ala Lys Leu Lys Ala Glu Leu Lys Ala Gln Arg Glu Ala Gly Ile Ala
            180                 185                 190

Val Val Arg Glu Ala Leu Ala Asp
        195                 200


<210> SEQ ID NO 74
<211> LENGTH: 482
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CrtZ sequence from Robiginitalea biformata
```

<400> SEQUENCE: 74
cacaatctag acacaaaaat gacagtcttg atttggatcg caattttcct ggccaccttc 60
tgcttcatgg aattcatggc ctggtttacg cataaatata tcatgcacgg tttcctctgg 120
agccttcata aggaccacca taaaaaggac cacgacagtt ggtttgagcg aaacgacgcc 180
ttctttctat tttatgcgat agtctccatg tcctttatcg ggccgccgt gaacacggga 240 ttctggcagg ggtggcccat cggcctgggc atcctcgctt acgggattgc ctactttatc 300
gtacacgata tctttatcca tcagcggttc aagctctttc gcaatgcgaa taactggtac 360
gcgcggggta tccgcagggc ccataaaatc caccacaagc acctgggaaa agaggaaggg 420
gaatgcttcg ggatgctgtt tgtcccattt aagtacttcc ggaagacctg aacgcgtttg 480
tg 482

<210> SEQ ID NO 75
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: CrtZ protein

<400> SEQUENCE: 75

Met Thr Val Leu Ile Trp Ile Ala Ile Phe Leu Ala Thr Phe Cys Phe
1 5 10 15

Met Glu Phe Met Ala Trp Phe Thr His Lys Tyr Ile Met His Gly Phe
20 25 30

Leu Trp Ser Leu His Lys Asp His His Lys Lys Asp His Asp Ser Trp
35 40 45

Phe Glu Arg Asn Asp Ala Phe Phe Leu Phe Tyr Ala Ile Val Ser Met
50 55 60

Ser Phe Ile Gly Ala Ala Val Asn Thr Gly Phe Trp Gln Gly Trp Pro
65 70 75 80

Ile Gly Leu Gly Ile Leu Ala Tyr Gly Ile Ala Tyr Phe Ile Val His
85 90 95

Asp Ile Phe Ile His Gln Arg Phe Lys Leu Phe Arg Asn Ala Asn Asn
100 105 110

Trp Tyr Ala Arg Gly Ile Arg Arg Ala His Lys Ile His His Lys His
115 120 125

Leu Gly Lys Glu Glu Gly Glu Cys Phe Gly Met Leu Phe Val Pro Phe
130 135 140

Lys Tyr Phe Arg Lys Thr
145 150

<210> SEQ ID NO 76
<211> LENGTH: 536
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: CrtZ sequence as amplified from genomic DNA extracted from Xanthobacter autotrophicus

<400> SEQUENCE: 76
cacaatctag acacaaaaat gtccaccagc ctcgccttcc tcgtcaacgc gctcatcgtg 60
atcgccacgg tcgccgccat ggaaggggtg gcctgggccg cgcacaaata tgtcatgcac 120
ggcttcggct ggggctggca caagtcccac cacgagccgc gcgagggcgt gttcgagcgc 180
aacgaccttt atgcgctgct gttcgcaggc atcgccatcg ccctcatcta cgcgttccgc 240
aatggcggcg cgctgctgtg ggtgggcgtg gggatgacgg tctacggctt cctttatttc 300
ttcgtgcacg acggcatcac ccaccagcgc tggccgttcc gctacgtgcc gcgcaacggc 360
tatctcaagc gcctggtgca ggcccaccgg ctgcaccatg cggtggatgg caaggagggc 420
tgcgtctcct tcggcttcat ctatgccccg ccgcctgccg acctgaaggc caagctgaag 480
aagctgcacg gcggcagcct gaagcagaac gaggcggcgg aatagacgcg tttgtg 536

<210> SEQ ID NO 77
<211> LENGTH: 168
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: CrtZ protein

<400> SEQUENCE: 77

Met Ser Thr Ser Leu Ala Phe Leu Val Asn Ala Leu Ile Val Ile Ala
1 5 10 15

Thr Val Ala Ala Met Glu Gly Val Ala Trp Ala Ala His Lys Tyr Val
20 25 30

Met His Gly Phe Gly Trp Gly Trp His Lys Ser His His Glu Pro Arg
35 40 45

Glu Gly Val Phe Glu Arg Asn Asp Leu Tyr Ala Leu Leu Phe Ala Gly
50 55 60

Ile Ala Ile Ala Leu Ile Tyr Ala Phe Arg Asn Gly Gly Ala Leu Leu
65 70 75 80

Trp Val Gly Val Gly Met Thr Val Tyr Gly Phe Leu Tyr Phe Phe Val
85 90 95

His Asp Gly Ile Thr His Gln Arg Trp Pro Phe Arg Tyr Val Pro Arg
100 105 110

Asn Gly Tyr Leu Lys Arg Leu Val Gln Ala His Arg Leu His His Ala
115 120 125

Val Asp Gly Lys Glu Gly Cys Val Ser Phe Gly Phe Ile Tyr Ala Pro
130 135 140

Pro Pro Ala Asp Leu Lys Ala Lys Leu Lys Lys Leu His Gly Gly Ser
145 150 155 160

Leu Lys Gln Asn Glu Ala Ala Glu
165

<210> SEQ ID NO 78
<211> LENGTH: 502
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: CrtZ sequence amplified from genomic DNA
extracted from Pseudomonas putida

<400> SEQUENCE: 78
tctctctaga cacaaaaatg gtgttcaatc tcgccatatt gttcggcacc ctggtggcca 60
tggagggcgt tggtacgctg gctcacaagt acatcatgca tggctggggc tggtggctgc 120
accgatcgca ccatgagcca cacctgggca tgctcgaaac caacgacctg tacctggtgg 180

```
ccctggggct gatcgccacg gcgctggtgg cgctgggcaa aagtggttat gcgcctttgc    240

agtgggtggg cggtggtgtg gcaggctatg gagcactgta tgtactggcc cacgacggtt    300

tctttcaccg gcactggccg cgcaagccgc ggccggtcaa ccgctacctg aaacgcttgc    360

accgcgcgca ccgcttgcac catgcggtga aggggcgcac ggggagcgtg tcgttcgggt    420

tcttctatgc gccgccgctg aaggtgttga agcagcaatt gcgcagcagg cgcagccaat    480

cgtgaacgcg tgagacgttg tg                                             502
```

```
<210> SEQ ID NO 79
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CrtZ protein

<400> SEQUENCE: 79

Met Val Phe Asn Leu Ala Ile Leu Phe Gly Thr Leu Val Ala Met Glu
1               5                   10                  15

Gly Val Gly Thr Leu Ala His Lys Tyr Ile Met His Gly Trp Gly Trp
            20                  25                  30

Trp Leu His Arg Ser His His Glu Pro His Leu Gly Met Leu Glu Thr
        35                  40                  45

Asn Asp Leu Tyr Leu Val Ala Leu Gly Leu Ile Ala Thr Ala Leu Val
    50                  55                  60

Ala Leu Gly Lys Ser Gly Tyr Ala Pro Leu Gln Trp Val Gly Gly Gly
65                  70                  75                  80

Val Ala Gly Tyr Gly Ala Leu Tyr Val Leu Ala His Asp Gly Phe Phe
                85                  90                  95

His Arg His Trp Pro Arg Lys Pro Arg Pro Val Asn Arg Tyr Leu Lys
            100                 105                 110

Arg Leu His Arg Ala His Arg Leu His His Ala Val Lys Gly Arg Thr
        115                 120                 125

Gly Ser Val Ser Phe Gly Phe Phe Tyr Ala Pro Pro Leu Lys Val Leu
    130                 135                 140

Lys Gln Gln Leu Arg Ser Arg Arg Ser Gln Ser
145                 150                 155


<210> SEQ ID NO 80
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Partial intron sequence

<400> SEQUENCE: 80

acaaacaaat gatgtgccgc atcgcatttt aatattaacc attgcataca cag            53


<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: Predicted partial amino acid sequence of
      unspliced intron

<400> SEQUENCE: 81

Val Ser Lys Gln Thr Asn Asp Val Pro His Arg Ile Leu Ile Pro Leu
1               5                   10                  15

His Thr Gln


<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Y. lipolytica ERG9

<400> SEQUENCE: 82

gatctcgttc tgctcgggta gatc                                            24


<210> SEQ ID NO 83
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Y. lipolytica ERG9

<400> SEQUENCE: 83

gtgctctgcg gtaagatcga ctagtggtgt gttctgtgga gcattc                    46


<210> SEQ ID NO 84
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Y. lipolytica ERG9

<400> SEQUENCE: 84

ccaccactgc actaccacta cacctcgagc atgcatcagg aaggactctc cctgtggt       58


<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Y. lipolytica ERG9

<400> SEQUENCE: 85

gtgttatggc tctacgtgaa ggggccc                                         27


<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Y. Lipolytica ERG9
```

<400> SEQUENCE: 86
cccgacgtta tccagaagaa c 21

<210> SEQ ID NO 87
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: P. marcusii primer

<400> SEQUENCE: 87
cacaccgtct caaatgacca atttcctgat cgtcgtc 37

<210> SEQ ID NO 88
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: P. marcusii primer

<400> SEQUENCE: 88
cacacagatc tcacgtgcgc tcctgcgcc 29

<210> SEQ ID NO 89
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: P. marcusii primer

<400> SEQUENCE: 89
cacaccctag gccatgagcg cacatgccct gc 32

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: P. marcusii primer

<400> SEQUENCE: 90
cacacaagct ttcatgcggt gtcccccttg 30

<210> SEQ ID NO 91
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: phosphorylated oligonucleotide adaptor

<400> SEQUENCE: 91
aattcgcggc cgct 14

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: phosphorylated oligonucleotide adaptor

<400> SEQUENCE: 92
agcggccgcg 10

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer K

<400> SEQUENCE: 93
ccttctagtc gtacgtagtc agc 23

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer L

<400> SEQUENCE: 94
ccactgatct agaatctctt tctgg 25

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer M

<400> SEQUENCE: 95
ggctcattgc gcatgctaac atcg 24

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer N

<400> SEQUENCE: 96
cgacgatgct atgagcttct agacg 25

<210> SEQ ID NO 97
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer 1fwd

<400> SEQUENCE: 97
cacacggatc ctataatgcc ttccgcaacg accg 34

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer 1rev

<400> SEQUENCE: 98
cacacactag ttaaatttgg acctcaacac gaccc 35

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer 2fwd

<400> SEQUENCE: 99
cacacggatc caatataaat gtctgcgaag agcatcctcg 40

<210> SEQ ID NO 100
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer 2rev

<400> SEQUENCE: 100
cacacgcatg cttaagcttg gaactccacc gcac 34

<210> SEQ ID NO 101
<211> LENGTH: 47
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer gal10

<400> SEQUENCE: 101
cacacggatc caattttcaa aaattcttac tttttttttg gatggac 47

<210> SEQ ID NO 102
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer gal1

<400> SEQUENCE: 102
cacacggatc ctttttctc cttgacgtta aagtatagag g 41

<210> SEQ ID NO 103
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer AMD1FWD

<400> SEQUENCE: 103
cacacgagct caaaaatgga caatcaggct acacagag 38

<210> SEQ ID NO 104
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer AMD1rev

<400> SEQUENCE: 104
cacaccctag gtcacttttc ttcaatggtt ctcttgaaat tg 42

<210> SEQ ID NO 105
<211> LENGTH: 46
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer gal7prox

<400> SEQUENCE: 105
cacacgagct cggaatattc aactgttttt ttttatcatg ttgatg 46

<210> SEQ ID NO 106
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer gal7dist

<400> SEQUENCE: 106
cacacggatc cttcttgaaa atatgcactc tatatctttt ag 42

<210> SEQ ID NO 107
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MAEfwd

<400> SEQUENCE: 107
cacacgctag ctacaaaatg ttgtcactca aacgcatagc aac 43

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: PCR primer MAErev

<400> SEQUENCE: 108
cacacgtcga cttaatgatc tcggtatacg agaggaac 38

<210> SEQ ID NO 109
<211> LENGTH: 960
<212> TYPE: DNA
<213> ORGANISM: Yarrowia lipolytica
<220> FEATURE:
<223> OTHER INFORMATION: Met2 promoter

<400> SEQUENCE: 109
cctctcactt tgtgaatcgt gaaacatgaa tcttcaagcc aagaatgtta ggcaggggaa 60
gctttctttc agactttttg gaattggtcc tcttttggac attattgacg atattattat 120
tttttccccg tccaatgttg acccttgtaa gccattccgg ttctggagcg catctcgtct 180
gaaggagtct tcgtgtggct ataactacaa gcgttgtatg gtggatccta tgaccgtcta 240
tatagggcaa cttttgctct tgttcttccc cctccttgag ggacgtatgg caatggctat 300
gacaactatc gtagtgagcc tctataaccc attgaagtac aagtcctcca ccttgctgcc 360
aaactcgcga gaaaaaaagt ccaccaactc cgcccgggaaa tactggagaa cacctctaag 420
acgtgggctt ctgcacctgt gtggcttggg tctgggtttt gcgagctctg agccacaacc 480
taaggacggt gtgattggga gataagtagt cgttggtttt ctaatcgcac gtgatatgca 540
agccacactt ataacacaat gaagacaggc cgatgaactg catgtcattg tacaggtgcg 600
gagagcaaga aactctgggg cggaggtgaa agatgagaca aaaagcctca ggtgcaaggt 660
agggagttga tcaacgtcaa acacaaataa tctaggttgt taggcagcta aacatgtata 720
taactgggct gccaccgagt gttacttgtc attaacgtcg cattttcgcc tacacaaaat 780
ttgggttact cgccactaca ctgctcaaat ctttcagctg tgcaacaagc tttcaggtca 840
cacatagact cgcataagga cccgggtcat ctgttattct ccactggtaa accaatagtc 900
ctagctgatt tgggtacaga agctcacttt cacatctttt catcttcttc tacaaccatc 960

<210> SEQ ID NO 110
<211> LENGTH: 855
<212> TYPE: DNA
<213> ORGANISM: Yarrowia lipolytica
<220> FEATURE:
<223> OTHER INFORMATION: Met3 promoter

<400> SEQUENCE: 110
atctgtgagg agcccctggc gtcactgtcg actgtgccgg catttctgat ggtatttcca 60
gccccgcagt tctcgagacc cccgaacaaa tgtgccacac ccttgccaaa atgacgaata 120
cacggcgtcg cggccgggaa tcgaactctt ggcaccgcca caggagtgaa atttgaaatt 180
tgaaatttga aaaataattc acattttgag tttcaataat atatcgatga ccctcccaaa 240
agacccaagt cgagacgcaa aaaaacaccc agacgacatg gatgcggtca cgtgaccgca 300
aaaaccgccc cggaaatccg tttgtgacgt gttcaattcc atctctatgt ttttctgcgg 360
tttctacgat gccgcaatgg tggccaatgt gcgtttcact gccgtagtgg ctggaacaag 420
ccacaggggg tcgtcgggcc aatcagacgg tccctgacat ggttctgcgc cctaacccgg 480
gaactctaac ccccgtggtg gcgcaatcgc tgtcttcatg tgctttatct cacgtgacgg 540
ctggaatctg gcagaagacg gagtatgtac attttgtcgt tggtcacgtt atccctaaaa 600
cgtggtgttt aaactggtcg aatgcttggc ccagaacaca agaagaaaaa aacgagacaa 660
cttgatcagt ttcaacgcca cagcaagctt gtcttcactg tggttggtct tctccacgcc 720
acaagcaaca cgtacatgtc aattacgtca gggtctttta agttctgtgg cttttgaacc 780
agttataaag aaccaaccac cctttttttca aagctaatca agacggggaa attttttttt 840
tgatattttt cgaca 855

<210> SEQ ID NO 111
<211> LENGTH: 897
<212> TYPE: DNA
<213> ORGANISM: Yarrowia lipolytica
<220> FEATURE:
<223> OTHER INFORMATION: Met6 promoter

<400> SEQUENCE: 111
gatactgcag acggtgcatt acttacccgt gtcgactgag agtctacttg gtacttggcc 60
ctgtggctaa gcagtatttg agcaacaatg caatgcagtt gctgactcgg ttccagatcc 120
ccttgccccg atgtgtggaa gcgttgtttt tggggcaagg gcatgtgggg gctgcatcat 180
actgtggctg gggccgttgg aagagccgtc ggcagcgagc ctgagtcgct tctcggggcc 240
ttattccccc cgcctctagg tcagcggcgg ccgaagtgtc gtactcagct cgcctgtaca 300
gtatgacgtg accgaatagc ctctggaagg ttggagaagt acagtgcaaa aaaaagttgc 360
aaaatttcat tttagcgttc gatccgacgt ggcagttgga caatgaatcg atggagacat 420
gatcatgggc agaaatagaa ggtctccatg ttcaatggca gtaccaattg agcaacagac 480
gggtcgacag gcggcgggca caccatccgc cctccacatg gcgcaatcgt cagtgcagcg 540
attcgtactc ggattgcatc atgttgcacc gaaagttggg gcccgcacgt tggagaggcg 600
aggagccagg gttagctttg gtggggtcct ttgttgtcac gtggcatcag cgaatggcgt 660
cctccaatca gggccgtcag cgaagtcggc gtgtgatagt gcgtggggag cgaatagagt 720
ttctgggggg gggcggccca aaacgtgaaa tccgagtacg catgtagagt gtaaattggg 780
tgtatagtga cattgtttga ctctgaccct gagagtaata tataatgtgt acgtgtcccc 840
ctccgttggt cttctttttt tctcctttct cctaaccaac acccaaacta atcaatc 897

<210> SEQ ID NO 112
<211> LENGTH: 972
<212> TYPE: DNA
<213> ORGANISM: Yarrowia lipolytica
<220> FEATURE:
<223> OTHER INFORMATION: Met25 promoter

<400> SEQUENCE: 112
aagtcgtatt aacataactt tccttacatt tttttaaagc acgtcactat ccacgtgacc 60
tagccacgcg ataccaagta ttcatccata atgacacact catgacgtcc ggaggacgtc 120
atcatcgtcc agtcacgtgc caaggcacat gactaatcat aacaccttat gactagcttc 180
tgaatcgcta cacagttcca attcgcaaat aaactcgaaa tgacgaaatg ccataataaa 240
aatgacgaaa ctcgagattg agagcagcac atgcactgaa gtggtggaca accagcgtat 300
ccggagacac gacggatcca gcaccatgga agctggccga aaaagagatc cccagcacat 360
tgagcaacca agtcagctca attgagtaac atcacacact cagatcgagt ctgatggtgg 420

-continued

```
tccccttttg ttccttcact tgaaaaataa ttgaaaataa caataacaat aaaaataaaa    480

acaaaataaa aataaaaata aaaataaaaa taaaaaaata aaaaaacctt gccgcattta    540

gcgtcagcca ccccccgcat tgacctgagt acgttggatt gaccccgatc ctgcacgtcg    600

agcgtggtcg gccaaaaagc gcccgtggct ggtgagtcag aaatagcagg gttgcaagag    660

agagctgcgc aacgagcaat aaacggtgtt tttttcgctt ctgtgctgct tagagtggag    720

agccgaccct cgccatgctc acgtgaccat tcacgtggtt gcaaactcca ccttagtata    780

gccgtgtccc tctcgctacc cattatcgca tcgtactcca gccacatttt tttgttcccc    840

gctaaatccg gaaccttatc tgggtcacgt gaaattgcaa tctcgacagg aggttatact    900

tatagagtga gacactccac gcaaggtgtt gcaagtcaat tgacaccacc tcacctcaga    960

ctaacatcca ca                                                         972


<210> SEQ ID NO 113
<211> LENGTH: 1425
<212> TYPE: DNA
<213> ORGANISM: Yarrowia lipolytica
<220> FEATURE:
<223> OTHER INFORMATION: Pox2 promoter

<400> SEQUENCE: 113

gaatctgccc ccacatttta tctccgcttt tgactgtttt tctccccct ttcacactct      60

gcttttggct acataaaccc cgcaccgttt ggaactctgt tggtccgggg aagccgccgt    120

taggtgtgtc agatggagag cgccagacga gcagaaccga gggacagcgg atcgggggag    180

ggctgtcacg tgacgaaggg cactgttgac gtggtgaatg tcgcccgttc tcacgtgacc    240

cgtctcctct atatgtgtat ccgcctcttt gtttggtttt ttttctgctt cccccccccc    300

ccccccaccc caatcacatg ctcagaaagt agacatctgc atcgtcctgc atgccatccc    360

acaagacgaa caagtgatag gccgagagcc gaggacgagg tggagtgcac aaggggtagg    420

cgaatggtac gattccgcca agtgagactg gcgatcggga gaagggttgg tggtcatggg    480

ggatagaatt tgtacaagtg gaaaaaccac tacgagtagc ggatttgata ccacaagtag    540

cagagatata cagcaatggt gggagtgcaa gtatcggaat gtactgtacc tcctgtactc    600

gtactcgtac ggcactcgta gaaacggggc aatacggggg agaagcgatc gcccgtctgt    660

tcaatcgcca caagtccgag taatgctcga gtatcgaagt cttgtacctc cctgtcaatc    720

atggcaccac tggtcttgac ttgtctattc atactggaca agcgccagag ttaagcttgt    780

agcgaatttc gccctcggac atcaccccat acgacggaca cacatgcccg acaaacagcc    840

tctcttattg tagctgaaag tatattgaat gtgaacgtgt acaatatcag gtaccagcgg    900

gaggttacgg ccaaggtgat accggaataa ccctggcttg gagatggtcg gtccattgta    960

ctgaagtgtc cgtgtcgttt ccgtcactgc cccaattgga catgtttgtt tttccgatct   1020

ttcgggcgcc ctctccttgt ctccttgtct gtctcctgga ctgttgctac cccatttctt   1080

tggcctccat tggttcctcc ccgtctttca cgtcgtctat ggttgcatgg tttcccttat   1140

acttttcccc acagtcacat gttatggagg ggtctagatg gaggcctaat tttgacgtgc   1200

aaggggcgaa ttggggcgag aaacacgtcg tggacatggt gcaaggcccg cagggttgat   1260

tcgacgcttt tccgcgaaaa aaacaagtcc aaataccccc gtttattctc cctcggctct   1320

cggtatttca catgaaaact ataacctaga ctacacgggc aaccttaacc ccagagtata   1380

cttatatacc aaagggatgg gtcctcaaaa atcacacaag caacg                    1425
```

<210> SEQ ID NO 114
<211> LENGTH: 500
<212> TYPE: DNA
<213> ORGANISM: Yarrowia lipolytica
<220> FEATURE:
<223> OTHER INFORMATION: Yef3 promoter
<300> PUBLICATION INFORMATION:
<308> DATABASE ACCESSION NUMBER: YALI0E13277g

<400> SEQUENCE: 114
cgccattcgg ttccttccag accattccag atcaatccac ctcttcttat ctcaggtggg 60
tgtgctgaca tcagaccccg tagcccttct cccagtggcg aacagcaggc ataaaacagg 120
gccattgagc agagcaaaca aggtcggtga aatcgtcgaa aaagtcggaa aacggttgca 180
agaaattgga gcgtcacctg ccaccctcca ggctctatat aaagcattgc cccaattgct 240
aacgcttcat atttacacct ttggcacccc agtccatccc tccaataaaa tgtactacat 300
gggacacaac aagagaggat gcgcgcccaa accctaacct agcacatgca cgatgattct 360
ctttgtctgt gaaaaaattt ttccaccaaa atttccccat tgggatgaaa ccctaaccgc 420
aaccaaaagt ttttaactat catcttgtac gtcacggttt ccgattcttc tcttctcttt 480
catcatcatc acttgtgacc 500

<210> SEQ ID NO 115
<211> LENGTH: 494
<212> TYPE: DNA
<213> ORGANISM: Yarrowia lipolytica
<220> FEATURE:
<223> OTHER INFORMATION: Cam1 promoter
<300> PUBLICATION INFORMATION:
<308> DATABASE ACCESSION NUMBER: YALI0C24420g

<400> SEQUENCE: 115
aactaccata aagtaccgag aaatataggc aattgtacaa attgtccacc tccttcactt 60
acattaccga accatggcca tatcaccaaa ataccccgag tgctaaaaca cctccctcca 120
aatgttctct taccttccac cgaaaaccga tcttattatc ccaacgcttg ttgtggcttg 180
acgcgccgca cccgctgggc ttgccatttc gataccaatc caagaggaaa agctcatgag 240
aaacaatcgg aatatcacga gaacggcctg gcgaaccaac aggatatttt tgaatataat 300 taccccctcga atctagtcat atctatgtct actgtagact tgggcggcat catgatgtac 360
attattttag cgtctggaac cctaaagttc acgtacaatc atgtgacaaa cgaggctaaa 420
aaatgtcaat ttcgtatatt agtgttatta cgtggctcac atttccgaat catctaccac 480
cccccaccta aaaa 494

<210> SEQ ID NO 116
<211> LENGTH: 440
<212> TYPE: DNA
<213> ORGANISM: Yarrowia lipolytica
<220> FEATURE:
<223> OTHER INFORMATION: Promoter
<300> PUBLICATION INFORMATION:
<308> DATABASE ACCESSION NUMBER: YALI0D16467g

<400> SEQUENCE: 116 ttttttttaat tttcatattt attttcatat ttattttcat atttattttc atttatttat 60
tcatgtattt atttattact ttttaagtat tttaaactcc tcactaaacc gtcgattgca 120
caatattaac cttcattaca cctgcagcgt ggtttttgtg gtcgttagcc gaagtcttcc 180
aacgtgggta taagtaggaa caattgggcc gatttttga gccgtctaaa tctctcgact 240
caattgatct gctgtcgaaa atccggctct ctagctcctt ttccccgtcc gctggagctc 300

-continued

```
ctcttcattg tgccgttttt ccaacattta actttgccac ccaccaccac ccccactacc    360

atcacccact cgatctctgt tcgtgtcacc acgactttgt cttctcacac atactctgtt    420

tgtgcaccac acattgcgaa                                                440
```

<210> SEQ ID NO 117
<211> LENGTH: 434
<212> TYPE: DNA
<213> ORGANISM: Yarrowia lipolytica
<220> FEATURE:
<223> OTHER INFORMATION: Tef4 promoter
<300> PUBLICATION INFORMATION:
<308> DATABASE ACCESSION NUMBER: YALI0B12562g

<400> SEQUENCE: 117

```
gctacaatag ctttattggc cctattgagc acgctacaat tcggtccagt atgtacaacg     60

tctatgcgca ctaacggcca tacagtgagt tacagcacac ccaaaagtaa ccctgcctga    120

cctgtctgcc tgagacagga agattaactc ttgtagtgac cgagctcgat aagactcaag    180

ccacacaatt tttttatagc cttgcttcaa gagtcgccaa aatgacatta cacaactcca    240

cggaccgtcg gttccatgtc cacacccttg gatgggtaag cgctccacgc acgtaccacg    300

tgcattgagt ttaaccacaa acataggtct gtgtcccaga gttaccctgc tgcatcagcc    360

aagtcttgaa agcaaaattt cttgcacaat ttttcctctt cttttcttca ctgatcgcag    420

tccaaacaca aaca                                                      434
```

<210> SEQ ID NO 118
<211> LENGTH: 752
<212> TYPE: DNA
<213> ORGANISM: Yarrowia lipolytica
<220> FEATURE:
<223> OTHER INFORMATION: promoter
<300> PUBLICATION INFORMATION:
<308> DATABASE ACCESSION NUMBER: YALI0D12903g

<400> SEQUENCE: 118

```
gcgctctgat ccacttgtat ggctccaagt tcagtgtacc aagtagttgg tgatgcaggg     60

agggatgtct ctatccacca ataatgaact catgggcgaa attgtttctg ttaaacactc    120

caactgtcgt tttaaatctc attctctttg catttggact ccattcgctt ccgttgggcc    180

aatataatcc atcgtaacgt actttagatg gaaatttagt tacctgctac ttgtctcaac    240

accccaacag gggctgttcg acagaggtaa tagagcgtca atgggttaat aaaaacacac    300

tgtcgatttt cactcattgt ctttatgata ttacctgttt tccgctgtta tcaatgccga    360

gcatcgtgtt atatcttcca ccccaactac ttgcatttac ttaactatta cctcaactat    420

ttacaccccg aattgttacc tcccaataag taactttatt tcaaccaatg ggacgagagc    480

atctctgaga acatcgatct atctctgtca atattgccca gaatcgttcg aaaaaaaaca    540

ccaaaaggtt tacagcgcca ttataaatat aaattcgttg tcaattcccc cgcaatgtct    600

gttgaaatct cattttgaga ccttccaaca ttaccctctc tcccgtctgg tcacatgacg    660

tgactgcttc ttcccaaaac gaacactccc aactcttccc ccccgtcagt gaaaagtata    720

catccgacct ccaaatcttt tcttcactca ac                                  752
```

<210> SEQ ID NO 119
<211> LENGTH: 402
<212> TYPE: DNA
<213> ORGANISM: Yarrowia lipolytica
<220> FEATURE:
<223> OTHER INFORMATION: Tef1 promoter <300> PUBLICATION INFORMATION:
<308> DATABASE ACCESSION NUMBER: YALI0C09141g

<400> SEQUENCE: 119

```
agagacgggt tggcggcgta tttgtgtccc aaaaaacagc cccaattgcc ccaattgacc     60

ccaaattgac ccagtagcgg gcccaacccc ggcgagagcc cccttcaccc cacatatcaa    120

acctcccccg gttcccacac ttgccgttaa gggcgtaggg tactgcagtc tggaatctac    180

gcttgttcag actttgtact agtttctttg tctggccatc cgggtaaccc atgccggacg    240

caaaatagac tactgaaaat ttttttgctt tgtggttggg actttagcca agggtataaa    300

agaccaccgt ccccgaatta cctttcctct tcttttctct ctctccttgt caactcacac    360

ccgaaatcgt taagcatttc cttctgagta taagaatcat tc                       402
```

<210> SEQ ID NO 120
<211> LENGTH: 491
<212> TYPE: DNA
<213> ORGANISM: Yarrowia lipolytica
<220> FEATURE:
<223> OTHER INFORMATION: Fba1 promoter
<300> PUBLICATION INFORMATION:
<308> DATABASE ACCESSION NUMBER: YALI0E26004g

<400> SEQUENCE: 120

```
gctgcgctga tctggacacc acagaggttc cgagcacttt aggttgcacc aaatgtccca     60

ccaggtgcag gcagaaaacg ctggaacagc gtgtacagtt tgtcttagca aaaagtgaag    120

gcgctgaggt cgagcagggt ggtgtgactt gttatagcct ttagagctgc gaaagcgcgt    180

atggatttgg ctcatcaggc cagattgagg gtctgtggac acatgtcatg ttagtgtact    240

tcaatcgccc cctggatata gccccgacaa taggccgtgg cctcattttt ttgccttccg    300

cacatttcca ttgctcggta cccacacctt gcttctcctg cacttgccaa ccttaatact    360

ggtttacatt gaccaacatc ttacaagcgg ggggcttgtc tagggtatat ataaacagtg    420

gctctcccaa tcggttgcca gtctcttttt tcctttcttt ccccacagat tcgaaatcta    480

aactacacat c                                                         491
```

<210> SEQ ID NO 121
<211> LENGTH: 1213
<212> TYPE: DNA
<213> ORGANISM: Yarrowia lipolytica
<220> FEATURE:
<223> OTHER INFORMATION: Pox2 terminator

<400> SEQUENCE: 121

```
gatgaggaat agacaagcgg gtatttattg tatgaataaa gattatgtat tgattgcaaa     60

aaagtgcatt tgtagatgtg gtttattgta gagagtacgg tatgtactgt acgaacatta    120

ggagctactt ctacaagtag attttcttaa caagggtgaa atttactagg aagtacatgc    180

atatttcgtt agtagaatca caaaagaaat gtacaagcac gtactacttg tactccacaa    240

tgtggagtgg gagcaaaaaa attggacgac accggaatcg aaccggggac ctcgcgcatg    300

ctaagcgcat gtgataacca actacaccag acgcccaaga actttcttgg tgattatgga    360

atacgtggtc tgctatatct caattttgct gtaatgaatc attagaatta aaaaaaaaac    420

cccattttttg tgtgattgtc ggccaagaga tggaacagga agaatacgtg aacaagcgag    480

cacgaatgcc atatgctctt ctgaacaacc gagtccgaat ccgatttgtg ggtatcacat    540

gtctcaagta gctgaaatgt atttcgctag aataaaataa atgagattaa gaattaaaaa    600

tattggaata tattttccta gaatagaaac tttggatttt ttttcggcta ttacagtctg    660
```

```
aactggacaa acggctgact atatataaat attattgggt ctgttttctt gtttatgtcg    720

aaattatctg ggttttacta ctgtgtcgtc gagtatagag tggcctgact ggagaaaatg    780

cagtagtatg gacagtaggt actgccagcc agagaagttt ttggaattga tacttgagtc    840

atttttccat tccccattcc ccattccaac acaatcaact gtttctgaac attttccaaa    900

acgcggagat gtatgtcact tggcactgca agtctcgatt caaaatgcat ctctttcaga    960

ccaaagtgtc atcagctttg tttggcccca aattaccgca aatacttgtc gaaattgaag   1020

tgcaatacgg cctcgtctgc catgaaacct gcctattctc ttcaaattgg cgtcaggttt   1080

cacgtccagc attcctcgcc cagacagagt tgctatggtt gaatcgtgta ctgttaatat   1140

atgtatgtat tatactcgta ctacgatata ctgttcaata gagtctctta taatcgtacg   1200

acgattctgg gca                                                      1213
```

```
<210> SEQ ID NO 122
<211> LENGTH: 1341
<212> TYPE: DNA
<213> ORGANISM: Yarrowia lipolytica
<300> PUBLICATION INFORMATION:
<308> DATABASE ACCESSION NUMBER: YALI0F30481g

<400> SEQUENCE: 122

atgtcgcaac cccagaacgt tggaatcaaa gccctcgaga tctacgtgcc ttctcgaatt     60

gtcaaccagg ctgagctcga gaagcacgac ggtgtcgctg ctggcaagta caccattggt    120

cttggtcaga ccaacatggc ctttgtcgac gacagagagg acatctattc ctttgccctg    180

accgccgtct ctcgactgct caagaacaac aacatcgacc ctgcatctat tggtcgaatc    240

gaggttggta ctgaaaccct tctggacaag tccaagtccg tcaagtctgt gctcatgcag    300

ctctttggcg agaacagcaa cattgagggt gtggacaacg tcaacgcctg ctacggagga    360

accaacgccc tgttcaacgc tatcaactgg gttgagggtc gatcttggga cggccgaaac    420

gccatcgtcg ttgccggtga cattgccctc tacgcaaagg gcgctgcccg acccaccgga    480

ggtgccggct gtgttgccat gctcattggc cccgacgctc ccctggttct tgacaacgtc    540

cacggatctt acttcgagca tgcctacgat ttctacaagc ctgatctgac ctccgagtac    600

ccctatgttg atggccacta ctccctgacc tgttacacaa aggccctcga caaggcctac    660

gctgcctaca acgcccgagc cgagaaggtc ggtctgttca aggactccga caagaagggt    720

gctgaccgat ttgactactc tgccttccac gtgcccacct gcaagcttgt caccaagtct    780

tacgctcgac ttctctacaa cgactacctc aacgacaaga gcctgtacga gggccaggtc    840

cccgaggagg ttgctgccgt ctcctacgat gcctctctca ccgacaagac cgtcgagaag    900

accttccttg gtattgccaa ggctcagtcc gccgagcgaa tggctccttc tctccaggga    960

cccaccaaca ccggtaacat gtacaccgcc tctgtgtacg cttctctcat ctctctgctg   1020

acttttgtcc ccgctgagca gctgcagggc aagcgaatct ctctcttctc ttacggatct   1080

ggtcttgctt ccactctttt ctctctgacc gtcaagggag acatttctcc catcgtcaag   1140

gcctgcgact tcaaggctaa gctcgatgac cgatccaccg agactcccgt cgactacgag   1200

gctgccaccg atctccgaga gaaggcccac ctcaagaaga actttgagcc ccagggagac   1260

atcaagcaca tcaagtctgg cgtctactac ctcaccaaca tcgatgacat gttccgacga   1320

aagtacgaga tcaagcagta g                                             1341

<210> SEQ ID NO 123
<211> LENGTH: 446
```

<212> TYPE: PRT
<213> ORGANISM: Yarrowia lipolytica
<300> PUBLICATION INFORMATION:
<308> DATABASE ACCESSION NUMBER: YALI0F30481g

<400> SEQUENCE: 123

```
Met Ser Gln Pro Gln Asn Val Gly Ile Lys Ala Leu Glu Ile Tyr Val
1               5                   10                  15

Pro Ser Arg Ile Val Asn Gln Ala Glu Leu Glu Lys His Asp Gly Val
            20                  25                  30

Ala Ala Gly Lys Tyr Thr Ile Gly Leu Gly Gln Thr Asn Met Ala Phe
        35                  40                  45

Val Asp Asp Arg Glu Asp Ile Tyr Ser Phe Ala Leu Thr Ala Val Ser
    50                  55                  60

Arg Leu Leu Lys Asn Asn Asn Ile Asp Pro Ala Ser Ile Gly Arg Ile
65                  70                  75                  80

Glu Val Gly Thr Glu Thr Leu Leu Asp Lys Ser Lys Ser Val Lys Ser
                85                  90                  95

Val Leu Met Gln Leu Phe Gly Glu Asn Ser Asn Ile Glu Gly Val Asp
            100                 105                 110

Asn Val Asn Ala Cys Tyr Gly Gly Thr Asn Ala Leu Phe Asn Ala Ile
        115                 120                 125

Asn Trp Val Glu Gly Arg Ser Trp Asp Gly Arg Asn Ala Ile Val Val
    130                 135                 140

Ala Gly Asp Ile Ala Leu Tyr Ala Lys Gly Ala Ala Arg Pro Thr Gly
145                 150                 155                 160

Gly Ala Gly Cys Val Ala Met Leu Ile Gly Pro Asp Ala Pro Leu Val
                165                 170                 175

Leu Asp Asn Val His Gly Ser Tyr Phe Glu His Ala Tyr Asp Phe Tyr
            180                 185                 190

Lys Pro Asp Leu Thr Ser Glu Tyr Pro Tyr Val Asp Gly His Tyr Ser
        195                 200                 205

Leu Thr Cys Tyr Thr Lys Ala Leu Asp Lys Ala Tyr Ala Ala Tyr Asn
    210                 215                 220

Ala Arg Ala Glu Lys Val Gly Leu Phe Lys Asp Ser Asp Lys Lys Gly
225                 230                 235                 240

Ala Asp Arg Phe Asp Tyr Ser Ala Phe His Val Pro Thr Cys Lys Leu
                245                 250                 255

Val Thr Lys Ser Tyr Ala Arg Leu Leu Tyr Asn Asp Tyr Leu Asn Asp
            260                 265                 270

Lys Ser Leu Tyr Glu Gly Gln Val Pro Glu Glu Val Ala Ala Val Ser
        275                 280                 285

Tyr Asp Ala Ser Leu Thr Asp Lys Thr Val Glu Lys Thr Phe Leu Gly
    290                 295                 300

Ile Ala Lys Ala Gln Ser Ala Glu Arg Met Ala Pro Ser Leu Gln Gly
305                 310                 315                 320

Pro Thr Asn Thr Gly Asn Met Tyr Thr Ala Ser Val Tyr Ala Ser Leu
                325                 330                 335

Ile Ser Leu Leu Thr Phe Val Pro Ala Glu Gln Leu Gln Gly Lys Arg
            340                 345                 350

Ile Ser Leu Phe Ser Tyr Gly Ser Gly Leu Ala Ser Thr Leu Phe Ser
        355                 360                 365

Leu Thr Val Lys Gly Asp Ile Ser Pro Ile Val Lys Ala Cys Asp Phe
    370                 375                 380

Lys Ala Lys Leu Asp Asp Arg Ser Thr Glu Thr Pro Val Asp Tyr Glu
```

```
385                 390                 395                 400

Ala Ala Thr Asp Leu Arg Glu Lys Ala His Leu Lys Lys Asn Phe Glu
                405                 410                 415

Pro Gln Gly Asp Ile Lys His Ile Lys Ser Gly Val Tyr Tyr Leu Thr
            420                 425                 430

Asn Ile Asp Asp Met Phe Arg Arg Lys Tyr Glu Ile Lys Gln
        435                 440                 445


<210> SEQ ID NO 124
<211> LENGTH: 1350
<212> TYPE: DNA
<213> ORGANISM: Yarrowia lipolytica
<300> PUBLICATION INFORMATION:
<308> DATABASE ACCESSION NUMBER: YALI0B16038g

<400> SEQUENCE: 124

atggactaca tcatttcggc gccaggcaaa gtgattctat ttggtgaaca tgccgctgtg      60

tttggtaagc ctgcgattgc agcagccatc gacttgcgaa catacctgct tgtcgaaacc     120

acaacatccg acaccccgac agtcacgttg gagtttccag acatccactt gaacttcaag     180

gtccaggtgg acaagctggc atctctcaca gcccagacca aggccgacca tctcaattgg     240

tcgactccca aaactctgga taagcacatt ttcgacagct tgtctagctt ggcgcttctg     300

gaagaacctg ggctcactaa ggtccagcag gccgctgttg tgtcgttctt gtacctctac     360

atccacctat gtccccttc tgtgtgcgaa gattcatcaa actgggtagt tcgatcaacg     420

ctgcctatcg gcgcgggcct gggctcttcc gcatccattt gtgtctgttt ggctgcaggt     480

cttctggttc tcaacggcca gctgagcatt gaccaggcaa gagatttcaa gtccctgacc     540

gagaagcagc tgtctctggt ggacgactgg tccttcgtcg gtgaaatgtg cattcacggc     600

aacccgtcgg gcatcgacaa tgctgtggct actcagggag gtgctctgtt gttccagcga     660

cctaacaacc gagtccctct tgttgacatt cccgagatga agctgctgct taccaatacg     720

aagcatcctc gatctaccgc agacctggtt ggtggagtcg gagttctcac taaagagttt     780

ggctccatca tggatcccat catgacttca gtaggcgaga tttccaacca ggccatggag     840

atcatttcta gaggcaagaa gatggtggac cagtctaacc ttgagattga gcagggtatc     900

ttgcctcaac ccacctctga ggatgcctgc aacgtgatgg aagatggagc tactcttcaa     960

aagttgagag atatcggttc ggaaatgcag catctagtga gaatcaatca cggcctgctt    1020

atcgctatgg gtgtttccca cccgaagctc gaaatcattc gaactgcctc cattgtccac    1080

aacctgggtg agaccaagct cactggtgct ggaggaggag gttgcgccat cactctagtc    1140

acttctaaag acaagactgc gacccagctg gaggaaaatg tcattgcttt cacagaggag    1200

atggctaccc atggcttcga ggtgcacgag actactattg gtgccagagg agttggtatg    1260

tgcattgacc atccctctct caagactgtt gaagccttca agaaggtgga gcgggcggat    1320

ctcaaaaaca tcggtccctg gacccattag                                     1350


<210> SEQ ID NO 125
<211> LENGTH: 449
<212> TYPE: PRT
<213> ORGANISM: Yarrowia lipolytica
<300> PUBLICATION INFORMATION:
<308> DATABASE ACCESSION NUMBER: YALI0B16038g

<400> SEQUENCE: 125

Met Asp Tyr Ile Ile Ser Ala Pro Gly Lys Val Ile Leu Phe Gly Glu
1               5                   10                  15
```

```
His Ala Ala Val Phe Gly Lys Pro Ala Ile Ala Ala Ala Ile Asp Leu
            20                  25                  30

Arg Thr Tyr Leu Leu Val Glu Thr Thr Thr Ser Asp Thr Pro Thr Val
        35                  40                  45

Thr Leu Glu Phe Pro Asp Ile His Leu Asn Phe Lys Val Gln Val Asp
    50                  55                  60

Lys Leu Ala Ser Leu Thr Ala Gln Thr Lys Ala Asp His Leu Asn Trp
65                  70                  75                  80

Ser Thr Pro Lys Thr Leu Asp Lys His Ile Phe Asp Ser Leu Ser Ser
                85                  90                  95

Leu Ala Leu Leu Glu Glu Pro Gly Leu Thr Lys Val Gln Gln Ala Ala
            100                 105                 110

Val Val Ser Phe Leu Tyr Leu Tyr Ile His Leu Cys Pro Pro Ser Val
        115                 120                 125

Cys Glu Asp Ser Ser Asn Trp Val Val Arg Ser Thr Leu Pro Ile Gly
    130                 135                 140

Ala Gly Leu Gly Ser Ser Ala Ser Ile Cys Val Cys Leu Ala Ala Gly
145                 150                 155                 160

Leu Leu Val Leu Asn Gly Gln Leu Ser Ile Asp Gln Ala Arg Asp Phe
                165                 170                 175

Lys Ser Leu Thr Glu Lys Gln Leu Ser Leu Val Asp Asp Trp Ser Phe
            180                 185                 190

Val Gly Glu Met Cys Ile His Gly Asn Pro Ser Gly Ile Asp Asn Ala
        195                 200                 205

Val Ala Thr Gln Gly Gly Ala Leu Leu Phe Gln Arg Pro Asn Asn Arg
    210                 215                 220

Val Pro Leu Val Asp Ile Pro Glu Met Lys Leu Leu Leu Thr Asn Thr
225                 230                 235                 240

Lys His Pro Arg Ser Thr Ala Asp Leu Val Gly Gly Val Gly Val Leu
                245                 250                 255

Thr Lys Glu Phe Gly Ser Ile Met Asp Pro Ile Met Thr Ser Val Gly
            260                 265                 270

Glu Ile Ser Asn Gln Ala Met Glu Ile Ile Ser Arg Gly Lys Lys Met
        275                 280                 285

Val Asp Gln Ser Asn Leu Glu Ile Glu Gln Gly Ile Leu Pro Gln Pro
    290                 295                 300

Thr Ser Glu Asp Ala Cys Asn Val Met Glu Asp Gly Ala Thr Leu Gln
305                 310                 315                 320

Lys Leu Arg Asp Ile Gly Ser Glu Met Gln His Leu Val Arg Ile Asn
                325                 330                 335

His Gly Leu Leu Ile Ala Met Gly Val Ser His Pro Lys Leu Glu Ile
            340                 345                 350

Ile Arg Thr Ala Ser Ile Val His Asn Leu Gly Glu Thr Lys Leu Thr
        355                 360                 365

Gly Ala Gly Gly Gly Gly Cys Ala Ile Thr Leu Val Thr Ser Lys Asp
    370                 375                 380

Lys Thr Ala Thr Gln Leu Glu Glu Asn Val Ile Ala Phe Thr Glu Glu
385                 390                 395                 400

Met Ala Thr His Gly Phe Glu Val His Glu Thr Thr Ile Gly Ala Arg
                405                 410                 415

Gly Val Gly Met Cys Ile Asp His Pro Ser Leu Lys Thr Val Glu Ala
            420                 425                 430

Phe Lys Lys Val Glu Arg Ala Asp Leu Lys Asn Ile Gly Pro Trp Thr
        435                 440                 445
```

His

<210> SEQ ID NO 126
<211> LENGTH: 1257
<212> TYPE: DNA
<213> ORGANISM: Yarrowia lipolytica
<300> PUBLICATION INFORMATION:
<308> DATABASE ACCESSION NUMBER: YALI0E06193g

<400> SEQUENCE: 126
atgaccacct attcggctcc gggaaaggcc ctcctttgcg gcggttattt ggttattgat 60
ccggcgtatt cagcatacgt cgtgggcctc tcggcgcgta tttacgcgac agtttcggct 120
tccgaggcct ccaccacctc tgtccatgtc gtctctccgc agtttgacaa gggtgaatgg 180
acctacaact acacgaacgg ccagctgacg gccatcggac acaacccatt tgctcacgcg 240
gccgtcaaca ccgttctgca ttacgttcct cctcgaaacc tccacatcaa catcagcatc 300
aaaagtgaca acgcgtacca ctcgcaaatt gacagcacgc agagaggcca gtttgcatac 360
cacaaaaagg cgatccacga ggtgcctaaa acgggcctcg gtagctccgc tgctcttacc 420
accgttcttg tggcagcttt gctcaagtca tacggcattg atcccttgca taacacccac 480
ctcgttcaca acctgtccca ggttgcacac tgctcggcac agaagaagat tgggtctgga 540
tttgacgtgg cttcggccgt ttgtggctct ctagtctata gacgtttccc ggcggagtcc 600
gtgaacatgg tcattgcagc tgaagggacc tccgaatacg gggctctgtt gagaactacc 660
gttaatcaaa agtggaaggt gactctggaa ccatccttct tgccgccggg aatcagcctg 720
cttatgggag acgtccaggg aggatctgag actccaggta tggtggccaa ggtgatggca 780
tggcgaaaag caaagccccg agaagccgag atggtgtgga gagatctcaa cgctgccaac 840
atgctcatgg tcaagttgtt caacgacctg cgcaagctct ctctcactaa caacgaggcc 900
tacgaacaac ttttggccga ggctgctcct ctcaacgctc taaagatgat aatgttgcag 960
aaccctctcg gagaactagc acgatgcatt atcactattc gaaagcatct caagaagatg 1020
acacgggaga ctggtgctgc tattgagccg gatgagcagt ctgcattgct caacaagtgc 1080
aacacttata gtggagtcat tggaggtgtt gtgcctggag caggaggcta cgatgctatt 1140
tctcttctgg tgatcagctc tacggtgaac aatgtcaagc gagagagcca gggagtccaa 1200
tggatggagc tcaaggagga gaacgagggt ctgcggctcg agaaggggtt caagtag 1257

<210> SEQ ID NO 127
<211> LENGTH: 418
<212> TYPE: PRT
<213> ORGANISM: Yarrowia lipolytica
<300> PUBLICATION INFORMATION:
<308> DATABASE ACCESSION NUMBER: YALI0E06193g

<400> SEQUENCE: 127

Met Thr Thr Tyr Ser Ala Pro Gly Lys Ala Leu Leu Cys Gly Gly Tyr
1 5 10 15

Leu Val Ile Asp Pro Ala Tyr Ser Ala Tyr Val Val Gly Leu Ser Ala
20 25 30

Arg Ile Tyr Ala Thr Val Ser Ala Ser Glu Ala Ser Thr Thr Ser Val
35 40 45

His Val Val Ser Pro Gln Phe Asp Lys Gly Glu Trp Thr Tyr Asn Tyr
50 55 60

Thr Asn Gly Gln Leu Thr Ala Ile Gly His Asn Pro Phe Ala His Ala
65 70 75 80

```
Ala Val Asn Thr Val Leu His Tyr Val Pro Pro Arg Asn Leu His Ile
                85                  90                  95

Asn Ile Ser Ile Lys Ser Asp Asn Ala Tyr His Ser Gln Ile Asp Ser
            100                 105                 110

Thr Gln Arg Gly Gln Phe Ala Tyr His Lys Lys Ala Ile His Glu Val
        115                 120                 125

Pro Lys Thr Gly Leu Gly Ser Ser Ala Ala Leu Thr Thr Val Leu Val
    130                 135                 140

Ala Ala Leu Leu Lys Ser Tyr Gly Ile Asp Pro Leu His Asn Thr His
145                 150                 155                 160

Leu Val His Asn Leu Ser Gln Val Ala His Cys Ser Ala Gln Lys Lys
                165                 170                 175

Ile Gly Ser Gly Phe Asp Val Ala Ser Ala Val Cys Gly Ser Leu Val
            180                 185                 190

Tyr Arg Arg Phe Pro Ala Glu Ser Val Asn Met Val Ile Ala Ala Glu
        195                 200                 205

Gly Thr Ser Glu Tyr Gly Ala Leu Leu Arg Thr Thr Val Asn Gln Lys
    210                 215                 220

Trp Lys Val Thr Leu Glu Pro Ser Phe Leu Pro Pro Gly Ile Ser Leu
225                 230                 235                 240

Leu Met Gly Asp Val Gln Gly Gly Ser Glu Thr Pro Gly Met Val Ala
                245                 250                 255

Lys Val Met Ala Trp Arg Lys Ala Lys Pro Arg Glu Ala Glu Met Val
            260                 265                 270

Trp Arg Asp Leu Asn Ala Ala Asn Met Leu Met Val Lys Leu Phe Asn
        275                 280                 285

Asp Leu Arg Lys Leu Ser Leu Thr Asn Asn Glu Ala Tyr Glu Gln Leu
    290                 295                 300

Leu Ala Glu Ala Ala Pro Leu Asn Ala Leu Lys Met Ile Met Leu Gln
305                 310                 315                 320

Asn Pro Leu Gly Glu Leu Ala Arg Cys Ile Ile Thr Ile Arg Lys His
                325                 330                 335

Leu Lys Lys Met Thr Arg Glu Thr Gly Ala Ala Ile Glu Pro Asp Glu
            340                 345                 350

Gln Ser Ala Leu Leu Asn Lys Cys Asn Thr Tyr Ser Gly Val Ile Gly
        355                 360                 365

Gly Val Val Pro Gly Ala Gly Gly Tyr Asp Ala Ile Ser Leu Leu Val
    370                 375                 380

Ile Ser Ser Thr Val Asn Asn Val Lys Arg Glu Ser Gln Gly Val Gln
385                 390                 395                 400

Trp Met Glu Leu Lys Glu Glu Asn Glu Gly Leu Arg Leu Glu Lys Gly
                405                 410                 415

Phe Lys
```

<210> SEQ ID NO 128
<211> LENGTH: 1164
<212> TYPE: DNA
<213> ORGANISM: Yarrowia lipolytica
<300> PUBLICATION INFORMATION:
<308> DATABASE ACCESSION NUMBER: YALI0F05632g

<400> SEQUENCE: 128

```
atgatccacc aggcctccac caccgctccg gtgaacattg cgacactcaa gtactggggc     60

aagcgagacc ctgctctcaa tctgcccact aacaactcca tctccgtgac tttgtcgcag    120

gatgatctgc ggaccctcac cacagcctcg tgttcccctg atttcaccca ggacgagctg    180
```

-continued

```
tggctcaatg gcaagcagga ggacgtgagc ggcaaacgtc tggttgcgtg tttccgagag    240

ctgcgggctc tgcgacacaa aatggaggac tccgactctt ctctgcctaa gctggccgat    300

cagaagctca agatcgtgtc cgagaacaac ttccccaccg ccgctggtct cgcctcatcg    360

gctgctggct ttgccgccct gatccgagcc gttgcaaatc tctacgagct ccaggagacc    420

cccgagcagc tgtccattgt ggctcgacag ggctctggat ccgcctgtcg atctctctac    480

ggaggctacg tggcatggga aatgggcacc gagtctgacg gaagcgactc gcgagcggtc    540

cagatcgcca ccgccgacca ctggcccgag atgcgagccg ccatcctcgt tgtctctgcc    600

gacaagaagg acacgtcgtc cactaccggt atgcaggtga ctgtgcacac ttctcccctc    660

ttcaaggagc gagtcaccac tgtggttccc gagcggtttg cccagatgaa gaagtcgatt    720

ctggaccgag acttccccac ctttgccgag ctcaccatgc gagactcaaa ccagttccac    780

gccacctgtc tggactcgta tcctcccatt ttctacctca acgacgtgtc gcgagcctcc    840

attcgggtag ttgaggccat caacaaggct gccggagcca ccattgccgc ctacaccttt    900

gatgctggac ccaactgtgt catctactac gaggacaaga acgaggagct ggttctgggt    960

gctctcaagg ccattctggg ccgtgtggag ggatgggaga agcaccagtc tgtggacgcc   1020

aagaagattg atgttgacga gcggtgggag tccgagctgg ccaacggaat tcagcgggtg   1080

atccttacca aggttggagg agatcccgtg aagaccgctg agtcgcttat caacgaggat   1140

ggttctctga agaacagcaa gtag                                          1164
```

<210> SEQ ID NO 129
<211> LENGTH: 387
<212> TYPE: PRT
<213> ORGANISM: Yarrowia lipolytica
<300> PUBLICATION INFORMATION:
<308> DATABASE ACCESSION NUMBER: YALI0F05632g

<400> SEQUENCE: 129

```
Met Ile His Gln Ala Ser Thr Thr Ala Pro Val Asn Ile Ala Thr Leu
1               5                   10                  15

Lys Tyr Trp Gly Lys Arg Asp Pro Ala Leu Asn Leu Pro Thr Asn Asn
            20                  25                  30

Ser Ile Ser Val Thr Leu Ser Gln Asp Asp Leu Arg Thr Leu Thr Thr
        35                  40                  45

Ala Ser Cys Ser Pro Asp Phe Thr Gln Asp Glu Leu Trp Leu Asn Gly
    50                  55                  60

Lys Gln Glu Asp Val Ser Gly Lys Arg Leu Val Ala Cys Phe Arg Glu
65                  70                  75                  80

Leu Arg Ala Leu Arg His Lys Met Glu Asp Ser Asp Ser Ser Leu Pro
                85                  90                  95

Lys Leu Ala Asp Gln Lys Leu Lys Ile Val Ser Glu Asn Asn Phe Pro
            100                 105                 110

Thr Ala Ala Gly Leu Ala Ser Ser Ala Ala Gly Phe Ala Ala Leu Ile
        115                 120                 125

Arg Ala Val Ala Asn Leu Tyr Glu Leu Gln Glu Thr Pro Glu Gln Leu
    130                 135                 140

Ser Ile Val Ala Arg Gln Gly Ser Gly Ser Ala Cys Arg Ser Leu Tyr
145                 150                 155                 160

Gly Gly Tyr Val Ala Trp Glu Met Gly Thr Glu Ser Asp Gly Ser Asp
                165                 170                 175

Ser Arg Ala Val Gln Ile Ala Thr Ala Asp His Trp Pro Glu Met Arg
            180                 185                 190
```

```
Ala Ala Ile Leu Val Val Ser Ala Asp Lys Lys Asp Thr Ser Ser Thr
        195                 200                 205

Thr Gly Met Gln Val Thr Val His Thr Ser Pro Leu Phe Lys Glu Arg
    210                 215                 220

Val Thr Thr Val Val Pro Glu Arg Phe Ala Gln Met Lys Lys Ser Ile
225                 230                 235                 240

Leu Asp Arg Asp Phe Pro Thr Phe Ala Glu Leu Thr Met Arg Asp Ser
                245                 250                 255

Asn Gln Phe His Ala Thr Cys Leu Asp Ser Tyr Pro Pro Ile Phe Tyr
            260                 265                 270

Leu Asn Asp Val Ser Arg Ala Ser Ile Arg Val Val Glu Ala Ile Asn
        275                 280                 285

Lys Ala Ala Gly Ala Thr Ile Ala Ala Tyr Thr Phe Asp Ala Gly Pro
    290                 295                 300

Asn Cys Val Ile Tyr Tyr Glu Asp Lys Asn Glu Glu Leu Val Leu Gly
305                 310                 315                 320

Ala Leu Lys Ala Ile Leu Gly Arg Val Glu Gly Trp Glu Lys His Gln
                325                 330                 335

Ser Val Asp Ala Lys Lys Ile Asp Val Asp Glu Arg Trp Glu Ser Glu
            340                 345                 350

Leu Ala Asn Gly Ile Gln Arg Val Ile Leu Thr Lys Val Gly Gly Asp
        355                 360                 365

Pro Val Lys Thr Ala Glu Ser Leu Ile Asn Glu Asp Gly Ser Leu Lys
    370                 375                 380

Asn Ser Lys
385
```

<210> SEQ ID NO 130
<211> LENGTH: 813
<212> TYPE: DNA
<213> ORGANISM: Yarrowia lipolytica
<300> PUBLICATION INFORMATION:
<308> DATABASE ACCESSION NUMBER: YALI0F04015g

<400> SEQUENCE: 130

```
atgacgacgt cttacagcga caaaatcaag agtatcagcg tgagctctgt ggctcagcag      60

tttcctgagg tggcgccgat tgcggacgtg tccaaggcta gccggcccag cacggagtcg     120

tcggactcgt cggccaagct atttgatggc cacgacgagg agcagatcaa gctgatggac     180

gagatctgtg tggtgctgga ctgggacgac aagccgattg gcggcgcgtc caaaaagtgc     240

tgtcatctga tggacaacat caacgacgga ctggtgcatc gggccttttc cgtgttcatg     300

ttcaacgacc gcggtgagct gcttctgcag cagcgggcgg cggaaaaaat cacctttgcc     360

aacatgtgga ccaacacgtg ctgctcgcat cctctggcgg tgcccagcga gatgggcggg     420

ctggatctgg agtcccggat ccagggcgcc aaaaacgccg cggtccggaa gcttgagcac     480

gagctgggaa tcgaccccaa ggccgttccg gcagacaagt tccatttcct cacccggatc     540

cactacgccg cgccctcctc gggcccctgg ggcgagcacg agattgacta cattctgttt     600

gtccggggcg accccgagct caaggtggtg gccaacgagg tccgcgatac cgtgtgggtg     660

tcgcagcagg gactcaagga catgatggcc gatcccaagc tggttttcac cccttggttc     720

cggctcattt gtgagcaggc gctgtttccc tggtgggacc agttggacaa tctgcccgcg     780

ggcgatgacg agattcggcg gtggatcaag tag                                  813
```

<210> SEQ ID NO 131

-continued

<211> LENGTH: 270
<212> TYPE: PRT
<213> ORGANISM: Yarrowia lipolytica
<300> PUBLICATION INFORMATION:
<308> DATABASE ACCESSION NUMBER: YALI0F04015g

<400> SEQUENCE: 131

```
Met Thr Thr Ser Tyr Ser Asp Lys Ile Lys Ser Ile Ser Val Ser Ser
1               5                   10                  15

Val Ala Gln Gln Phe Pro Glu Val Ala Pro Ile Ala Asp Val Ser Lys
            20                  25                  30

Ala Ser Arg Pro Ser Thr Glu Ser Ser Asp Ser Ser Ala Lys Leu Phe
        35                  40                  45

Asp Gly His Asp Glu Glu Gln Ile Lys Leu Met Asp Glu Ile Cys Val
    50                  55                  60

Val Leu Asp Trp Asp Asp Lys Pro Ile Gly Gly Ala Ser Lys Lys Cys
65                  70                  75                  80

Cys His Leu Met Asp Asn Ile Asn Asp Gly Leu Val His Arg Ala Phe
                85                  90                  95

Ser Val Phe Met Phe Asn Asp Arg Gly Glu Leu Leu Leu Gln Gln Arg
            100                 105                 110

Ala Ala Glu Lys Ile Thr Phe Ala Asn Met Trp Thr Asn Thr Cys Cys
        115                 120                 125

Ser His Pro Leu Ala Val Pro Ser Glu Met Gly Gly Leu Asp Leu Glu
    130                 135                 140

Ser Arg Ile Gln Gly Ala Lys Asn Ala Ala Val Arg Lys Leu Glu His
145                 150                 155                 160

Glu Leu Gly Ile Asp Pro Lys Ala Val Pro Ala Asp Lys Phe His Phe
                165                 170                 175

Leu Thr Arg Ile His Tyr Ala Ala Pro Ser Ser Gly Pro Trp Gly Glu
            180                 185                 190

His Glu Ile Asp Tyr Ile Leu Phe Val Arg Gly Asp Pro Glu Leu Lys
        195                 200                 205

Val Val Ala Asn Glu Val Arg Asp Thr Val Trp Val Ser Gln Gln Gly
    210                 215                 220

Leu Lys Asp Met Met Ala Asp Pro Lys Leu Val Phe Thr Pro Trp Phe
225                 230                 235                 240

Arg Leu Ile Cys Glu Gln Ala Leu Phe Pro Trp Trp Asp Gln Leu Asp
                245                 250                 255

Asn Leu Pro Ala Gly Asp Asp Glu Ile Arg Arg Trp Ile Lys
            260                 265                 270
```

<210> SEQ ID NO 132
<211> LENGTH: 1035
<212> TYPE: DNA
<213> ORGANISM: Yarrowia lipolytica
<300> PUBLICATION INFORMATION:
<308> DATABASE ACCESSION NUMBER: YALI0E05753

<400> SEQUENCE: 132

```
atgtccaagg cgaaattcga aagcgtgttc ccccgaatct ccgaggagct ggtgcagctg      60

ctgcgagacg agggtctgcc ccaggatgcc gtgcagtggt tttccgactc acttcagtac     120

aactgtgtgg gtggaaagct caaccgaggc ctgtctgtgg tcgacaccta ccagctactg     180

accggcaaga aggagctcga tgacgaggag tactaccgac tcgcgctgct cggctggctg     240

attgagctgc tgcaggcgtt tttcctcgtg tcggacgaca ttatggatga gtccaagacc     300

cgacgaggcc agccctgctg gtacctcaag cccaaggtcg gcatgattgc catcaacgat     360
```

```
gctttcatgc tagagagtgg catctacatt ctgcttaaga agcatttccg acaggagaag    420

tactacattg accttgtcga gctgttccac gacatttcgt tcaagaccga gctgggccag    480

ctggtggatc ttctgactgc ccccgaggat gaggttgatc tcaaccggtt ctctctggac    540

aagcactcct ttattgtgcg atacaagact gcttactact ccttctacct gcccgttgtt    600

ctagccatgt acgtggccgg cattaccaac cccaaggacc tgcagcaggc catggatgtg    660

ctgatccctc tcggagagta cttccaggtc caggacgact accttgacaa ctttggagac    720

cccgagttca ttggtaagat cggcaccgac atccaggaca acaagtgctc ctggctcgtt    780

aacaaagccc ttcagaaggc cacccccgag cagcgacaga tcctcgagga caactacggc    840

gtcaaggaca agtccaagga gctcgtcatc aagaaactgt atgatgacat gaagattgag    900

caggactacc ttgactacga ggaggaggtt gttggcgaca tcaagaagaa gatcgagcag    960

gttgacgaga gccgaggctt caagaaggag gtgctcaacg ctttcctcgc caagatttac   1020

aagcgacaga agtag                                                    1035
```

<210> SEQ ID NO 133
<211> LENGTH: 344
<212> TYPE: PRT
<213> ORGANISM: Yarrowia lipolytica
<300> PUBLICATION INFORMATION:
<308> DATABASE ACCESSION NUMBER: YALI0E05753

<400> SEQUENCE: 133

```
Met Ser Lys Ala Lys Phe Glu Ser Val Phe Pro Arg Ile Ser Glu Glu
1               5                   10                  15

Leu Val Gln Leu Leu Arg Asp Glu Gly Leu Pro Gln Asp Ala Val Gln
            20                  25                  30

Trp Phe Ser Asp Ser Leu Gln Tyr Asn Cys Val Gly Gly Lys Leu Asn
        35                  40                  45

Arg Gly Leu Ser Val Val Asp Thr Tyr Gln Leu Leu Thr Gly Lys Lys
    50                  55                  60

Glu Leu Asp Asp Glu Glu Tyr Tyr Arg Leu Ala Leu Leu Gly Trp Leu
65                  70                  75                  80

Ile Glu Leu Leu Gln Ala Phe Phe Leu Val Ser Asp Asp Ile Met Asp
                85                  90                  95

Glu Ser Lys Thr Arg Arg Gly Gln Pro Cys Trp Tyr Leu Lys Pro Lys
            100                 105                 110

Val Gly Met Ile Ala Ile Asn Asp Ala Phe Met Leu Glu Ser Gly Ile
        115                 120                 125

Tyr Ile Leu Leu Lys Lys His Phe Arg Gln Glu Lys Tyr Tyr Ile Asp
    130                 135                 140

Leu Val Glu Leu Phe His Asp Ile Ser Phe Lys Thr Glu Leu Gly Gln
145                 150                 155                 160

Leu Val Asp Leu Leu Thr Ala Pro Glu Asp Glu Val Asp Leu Asn Arg
                165                 170                 175

Phe Ser Leu Asp Lys His Ser Phe Ile Val Arg Tyr Lys Thr Ala Tyr
            180                 185                 190

Tyr Ser Phe Tyr Leu Pro Val Val Leu Ala Met Tyr Val Ala Gly Ile
        195                 200                 205

Thr Asn Pro Lys Asp Leu Gln Gln Ala Met Asp Val Leu Ile Pro Leu
    210                 215                 220

Gly Glu Tyr Phe Gln Val Gln Asp Asp Tyr Leu Asp Asn Phe Gly Asp
225                 230                 235                 240
```

```
Pro Glu Phe Ile Gly Lys Ile Gly Thr Asp Ile Gln Asp Asn Lys Cys
                245                 250                 255

Ser Trp Leu Val Asn Lys Ala Leu Gln Lys Ala Thr Pro Glu Gln Arg
            260                 265                 270

Gln Ile Leu Glu Asp Asn Tyr Gly Val Lys Asp Lys Ser Lys Glu Leu
        275                 280                 285

Val Ile Lys Lys Leu Tyr Asp Asp Met Lys Ile Glu Gln Asp Tyr Leu
    290                 295                 300

Asp Tyr Glu Glu Glu Val Val Gly Asp Ile Lys Lys Lys Ile Glu Gln
305                 310                 315                 320

Val Asp Glu Ser Arg Gly Phe Lys Lys Glu Val Leu Asn Ala Phe Leu
                325                 330                 335

Ala Lys Ile Tyr Lys Arg Gln Lys
            340
```

<210> SEQ ID NO 134
<211> LENGTH: 1890
<212> TYPE: DNA
<213> ORGANISM: Yarrowia lipolytica
<300> PUBLICATION INFORMATION:
<308> DATABASE ACCESSION NUMBER: YALI0E18634g

<400> SEQUENCE: 134

```
atgttacgac tacgaaccat gcgacccaca cagaccagcg tcagggcggc gcttgggccc     60

accgccgcgg cccgaaacat gtcctcctcc agcccctcca gcttcgaata ctcgtcctac    120

gtcaagggca cgcgggaaat cggccaccga aaggcgccca caacccgtct gtcggttgag    180

ggccccatct acgtgggctt cgacggcatt cgtcttctca acctgccgca tctcaacaag    240

ggctcgggat tccccctcaa cgagcgacgg gaattcagac tcagtggtct tctgccctct    300

gccgaagcca ccctggagga acaggtcgac cgagcatacc aacaattcaa aaagtgtggc    360

actcccttag ccaaaaacgg gttctgcacc tcgctcaagt tccaaaacga ggtgctctac    420

tacgccctgc tgctcaagca cgttaaggag gtcttcccca tcatctatac accgactcag    480

ggagaagcca ttgaacagta ctcgcggctg ttccggcggc ccgaaggctg cttcctcgac    540

atcaccagtc cctacgacgt ggaggagcgt ctgggagcgt ttggagacca tgacgacatt    600

gactacattg tcgtgactga ctccgagggt attctcggaa ttggagacca aggagtgggc    660

ggtattggta tttccatcgc caagctggct ctcatgactc tatgtgctgg agtcaacccc    720

tcacgagtca ttcctgtggt tctggatacg ggaaccaaca accaggagct gctgcacgac    780

cccctgtatc tcggccgacg aatgccccga gtgcgaggaa agcagtacga cgacttcatc    840

gacaactttg tgcagtctgc ccgaaggctg tatcccaagg cggtgatcca tttcgaggac    900

tttgggctcg ctaacgcaca caagatcctc gacaagtatc gaccggagat cccctgcttc    960

aacgacgaca tccagggcac tggagccgtc actttggcct ccatcacggc cgctctcaag   1020

gtgctgggca aaaatatcac agatactcga attctcgtgt acggagctgg ttcggccggc   1080

atgggtattg ctgaacaggt ctatgataac ctggttgccc agggtctcga cgacaagact   1140

gcgcgacaaa acatctttct catggaccga ccgggtctac tgaccaccgc acttaccgac   1200

gagcagatga gcgacgtgca gaagccgttt gccaaggaca aggccaatta cgagggagtg   1260

gacaccaaga ctctggagca cgtggttgct gccgtcaagc cccatattct cattggatgt   1320

tccactcagc ccggcgcctt taacgagaag gtcgtcaagg agatgctcaa acacacccct   1380

cgacccatca ttctccctct ttccaacccc acacgtcttc atgaggctgt ccctgcagat   1440

ctgtacaagt ggaccgacgg caaggctctg gttgccaccg gctcgccctt tgacccagtc   1500
```

```
aacggcaagg agacgtctga gaacaataac tgctttgttt tccccggaat cgggctggga   1560

gccattctgt ctcgatcaaa gctcatcacc aacaccatga ttgctgctgc catcgagtgc   1620

ctcgccgaac aggcccccat tctcaagaac cacgacgagg gagtacttcc cgacgtagct   1680

ctcatccaga tcatttcggc ccgggtggcc actgccgtgg ttcttcaggc caaggctgag   1740

ggcctagcca ctgtcgagga agagctcaag cccggcacca aggaacatgt gcagattccc   1800

gacaactttg acgagtgtct cgcctgggtc gagactcaga tgtggcggcc cgtctaccgg   1860

cctctcatcc atgtgcggga ttacgactag                                    1890


<210> SEQ ID NO 135
<211> LENGTH: 629
<212> TYPE: PRT
<213> ORGANISM: Yarrowia lipolytica
<300> PUBLICATION INFORMATION:
<308> DATABASE ACCESSION NUMBER: YALI0E18634g

<400> SEQUENCE: 135

Met Leu Arg Leu Arg Thr Met Arg Pro Thr Gln Thr Ser Val Arg Ala
1               5                   10                  15

Ala Leu Gly Pro Thr Ala Ala Ala Arg Asn Met Ser Ser Ser Ser Pro
            20                  25                  30

Ser Ser Phe Glu Tyr Ser Ser Tyr Val Lys Gly Thr Arg Glu Ile Gly
        35                  40                  45

His Arg Lys Ala Pro Thr Thr Arg Leu Ser Val Glu Gly Pro Ile Tyr
    50                  55                  60

Val Gly Phe Asp Gly Ile Arg Leu Leu Asn Leu Pro His Leu Asn Lys
65                  70                  75                  80

Gly Ser Gly Phe Pro Leu Asn Glu Arg Arg Glu Phe Arg Leu Ser Gly
                85                  90                  95

Leu Leu Pro Ser Ala Glu Ala Thr Leu Glu Glu Gln Val Asp Arg Ala
            100                 105                 110

Tyr Gln Gln Phe Lys Lys Cys Gly Thr Pro Leu Ala Lys Asn Gly Phe
        115                 120                 125

Cys Thr Ser Leu Lys Phe Gln Asn Glu Val Leu Tyr Tyr Ala Leu Leu
    130                 135                 140

Leu Lys His Val Lys Glu Val Phe Pro Ile Ile Tyr Thr Pro Thr Gln
145                 150                 155                 160

Gly Glu Ala Ile Glu Gln Tyr Ser Arg Leu Phe Arg Arg Pro Glu Gly
                165                 170                 175

Cys Phe Leu Asp Ile Thr Ser Pro Tyr Asp Val Glu Glu Arg Leu Gly
            180                 185                 190

Ala Phe Gly Asp His Asp Asp Ile Asp Tyr Ile Val Val Thr Asp Ser
        195                 200                 205

Glu Gly Ile Leu Gly Ile Gly Asp Gln Gly Val Gly Gly Ile Gly Ile
    210                 215                 220

Ser Ile Ala Lys Leu Ala Leu Met Thr Leu Cys Ala Gly Val Asn Pro
225                 230                 235                 240

Ser Arg Val Ile Pro Val Val Leu Asp Thr Gly Thr Asn Asn Gln Glu
                245                 250                 255

Leu Leu His Asp Pro Leu Tyr Leu Gly Arg Arg Met Pro Arg Val Arg
            260                 265                 270

Gly Lys Gln Tyr Asp Asp Phe Ile Asp Asn Phe Val Gln Ser Ala Arg
        275                 280                 285

Arg Leu Tyr Pro Lys Ala Val Ile His Phe Glu Asp Phe Gly Leu Ala
```

-continued

```
    290                 295                 300

Asn Ala His Lys Ile Leu Asp Lys Tyr Arg Pro Glu Ile Pro Cys Phe
305                 310                 315                 320

Asn Asp Asp Ile Gln Gly Thr Gly Ala Val Thr Leu Ala Ser Ile Thr
                325                 330                 335

Ala Ala Leu Lys Val Leu Gly Lys Asn Ile Thr Asp Thr Arg Ile Leu
            340                 345                 350

Val Tyr Gly Ala Gly Ser Ala Gly Met Gly Ile Ala Glu Gln Val Tyr
        355                 360                 365

Asp Asn Leu Val Ala Gln Gly Leu Asp Asp Lys Thr Ala Arg Gln Asn
    370                 375                 380

Ile Phe Leu Met Asp Arg Pro Gly Leu Leu Thr Thr Ala Leu Thr Asp
385                 390                 395                 400

Glu Gln Met Ser Asp Val Gln Lys Pro Phe Ala Lys Asp Lys Ala Asn
                405                 410                 415

Tyr Glu Gly Val Asp Thr Lys Thr Leu Glu His Val Val Ala Ala Val
            420                 425                 430

Lys Pro His Ile Leu Ile Gly Cys Ser Thr Gln Pro Gly Ala Phe Asn
        435                 440                 445

Glu Lys Val Val Lys Glu Met Leu Lys His Thr Pro Arg Pro Ile Ile
    450                 455                 460

Leu Pro Leu Ser Asn Pro Thr Arg Leu His Glu Ala Val Pro Ala Asp
465                 470                 475                 480

Leu Tyr Lys Trp Thr Asp Gly Lys Ala Leu Val Ala Thr Gly Ser Pro
                485                 490                 495

Phe Asp Pro Val Asn Gly Lys Glu Thr Ser Glu Asn Asn Asn Cys Phe
            500                 505                 510

Val Phe Pro Gly Ile Gly Leu Gly Ala Ile Leu Ser Arg Ser Lys Leu
        515                 520                 525

Ile Thr Asn Thr Met Ile Ala Ala Ala Ile Glu Cys Leu Ala Glu Gln
    530                 535                 540

Ala Pro Ile Leu Lys Asn His Asp Glu Gly Val Leu Pro Asp Val Ala
545                 550                 555                 560

Leu Ile Gln Ile Ile Ser Ala Arg Val Ala Thr Ala Val Val Leu Gln
                565                 570                 575

Ala Lys Ala Glu Gly Leu Ala Thr Val Glu Glu Glu Leu Lys Pro Gly
            580                 585                 590

Thr Lys Glu His Val Gln Ile Pro Asp Asn Phe Asp Glu Cys Leu Ala
        595                 600                 605

Trp Val Glu Thr Gln Met Trp Arg Pro Val Tyr Arg Pro Leu Ile His
    610                 615                 620

Val Arg Asp Tyr Asp
625
```

<210> SEQ ID NO 136
<211> LENGTH: 2610
<212> TYPE: DNA
<213> ORGANISM: Yarrowia lipolytica
<300> PUBLICATION INFORMATION:
<308> DATABASE ACCESSION NUMBER: YALI0E11495g

<400> SEQUENCE: 136

```
atgccgcagc aagcaatgga tatcaagggc aaggccaagt ctgtgcccat gcccgaagaa      60

gacgacctgg actcgcattt tgtgggtccc atctctcccc gacctcacgg agcagacgag     120

attgctggct acgtgggctg cgaagacgac gaagacgagc ttgaagaact gggaatgctg     180
```

-continued

```
ggccgatctg cgtccaccca cttctcttac gcggaagaac gccacctcat cgaggttgat    240
gccaagtaca gagctcttca tggccatctg cctcatcagc actctcagag tcccgtgtcc    300
agatcttcgt catttgtgcg ggccgaaatg aaccaccccc ctccccccacc ctccagccac    360
acccaccaac agccagagga cgatgacgca tcttccactc gatctcgatc gtcgtctcga    420
gcttctggac gcaagttcaa cagaaacaga accaagtctg gatcttcgct gagcaagggt    480
ctccagcagc tcaacatgac cggatcgctc gaagaagagc cctacgagag cgatgacgat    540
gcccgactat ctgcggaaga cgacattgtc tatgatgcta cccagaaaga cacctgcaag    600
cccatatctc ctactctcaa acgcacccgc accaaggacg acatgaagaa catgtccatc    660
aacgacgtca aaatcaccac caccacagaa gatcctcttg tggcccagga gctgtccatg    720
atgttcgaaa aggtgcagta ctgccgagac ctccgagaca agtaccaaac cgtgtcgcta    780
cagaaggacg gagacaaccc caaggatgac aagacacact ggaaaattta ccccgagcct    840
ccaccaccct cctggcacga gaccgaaaag cgattccgag gctcgtccaa aaaggagcac    900
caaaagaaag acccgacaat ggatgaattc aaattcgagg actgcgaaat ccccggaccc    960
aacgacatgg tcttcaagcg agatcctacc tgtgtctatc aggtctatga ggatgaaagc   1020
tctctcaacg aaaataagcc gtttgttgcc atcccctcaa tccgagatta ctacatggat   1080
ctggaggatc tcattgtggc ttcgtctgac ggacctgcca agtcttttgc tttccgacga   1140
ctgcaatatc tagaagccaa gtggaacctc tactacctgc tcaacgagta cacggagaca   1200
accgagtcca agaccaaccc ccatcgagac ttttacaacg tacgaaaggt cgacacccac   1260
gttcaccact ctgcctgcat gaaccagaag catctgctgc gattcatcaa atacaagatg   1320
aagaactgcc ctgatgaagt tgtcatccac cgagacggtc gggagctgac actctcccag   1380
gtgtttgagt cacttaactt gactgcctac gacctgtcta tcgataccct tgatatgcat   1440
gctcacaagg actcgttcca tcgatttgac aagttcaacc tcaagtacaa ccctgtcggt   1500
gagtctcgac tgcgagaaat cttcctaaag accgacaact acatccaggg tcgataccta   1560
gctgagatca caaaggaggt gttccaggat ctcgagaact cgaagtacca gatggcggag   1620
taccgtattt ccatctacgg tcggtccaag gacgagtggg acaagctggc tgcctgggtg   1680
ctggacaaca aactgttttc gcccaatgtt cggtggttga tccaggtgcc tcgactgtac   1740
gacatttaca agaaggctgg tctggttaac acctttgccg acattgtgca gaacgtcttt   1800
gagcctcttt tcgaggtcac caaggatccc agtacccatc ccaagctgca cgtgttcctg   1860
cagcgagttg tgggctttga ctctgtcgat gacgagtcga agctggaccg acgtttccac   1920
cgaaagttcc caactgcagc atactgggac agcgcacaga accctcccta ctcgtactgg   1980
cagtactatc tatacgccaa catggcctcc atcaacacct ggagacagcg tttgggctat   2040
aatacttttg agttgcgacc ccatgctgga gaggctggtg acccagagca tcttctgtgc   2100
acttatctgg ttgctcaggg tatcaaccac ggtattctgt tgcgaaaggt gcccttcatt   2160
cagtaccttt actacctgga ccagatcccc attgccatgt ctcctgtgtc caacaatgcg   2220
ctgttcctca cgttcgacaa gaacccctc tactcatact tcaagcgggg tctcaacgtg    2280
tccttgtcat cggatgatcc tctgcagttt gcttacacta aggaggctct gattgaggag   2340
tactctgtgg ctgcgctcat ttacaagctt tccaacgtgg atatgtgtga gcttgctcga   2400
aactcggtac tgcaatctgg ctttgagcga atcatcaagg agcattggat cggcgaaaac   2460
tacgagatcc atggccccga gggcaacacc atccagaaga caaacgtgcc caatgtgcgt   2520
ctggccttcc gagacgagac tttgacccac gagcttgctc tggtggacaa gtacaccaat   2580
```

```
cttgaggagt ttgagcggct gcatggttaa                                    2610


<210> SEQ ID NO 137
<211> LENGTH: 869
<212> TYPE: PRT
<213> ORGANISM: Yarrowia lipolytica
<300> PUBLICATION INFORMATION:
<308> DATABASE ACCESSION NUMBER: YALI0E11495g

<400> SEQUENCE: 137

Met Pro Gln Gln Ala Met Asp Ile Lys Gly Lys Ala Lys Ser Val Pro
1               5                   10                  15

Met Pro Glu Glu Asp Asp Leu Asp Ser His Phe Val Gly Pro Ile Ser
            20                  25                  30

Pro Arg Pro His Gly Ala Asp Glu Ile Ala Gly Tyr Val Gly Cys Glu
        35                  40                  45

Asp Asp Glu Asp Glu Leu Glu Glu Leu Gly Met Leu Gly Arg Ser Ala
    50                  55                  60

Ser Thr His Phe Ser Tyr Ala Glu Glu Arg His Leu Ile Glu Val Asp
65                  70                  75                  80

Ala Lys Tyr Arg Ala Leu His Gly His Leu Pro His Gln His Ser Gln
                85                  90                  95

Ser Pro Val Ser Arg Ser Ser Ser Phe Val Arg Ala Glu Met Asn His
            100                 105                 110

Pro Pro Pro Pro Pro Ser Ser His Thr His Gln Gln Pro Glu Asp Asp
        115                 120                 125

Asp Ala Ser Ser Thr Arg Ser Arg Ser Ser Ser Arg Ala Ser Gly Arg
    130                 135                 140

Lys Phe Asn Arg Asn Arg Thr Lys Ser Gly Ser Ser Leu Ser Lys Gly
145                 150                 155                 160

Leu Gln Gln Leu Asn Met Thr Gly Ser Leu Glu Glu Glu Pro Tyr Glu
                165                 170                 175

Ser Asp Asp Asp Ala Arg Leu Ser Ala Glu Asp Asp Ile Val Tyr Asp
            180                 185                 190

Ala Thr Gln Lys Asp Thr Cys Lys Pro Ile Ser Pro Thr Leu Lys Arg
        195                 200                 205

Thr Arg Thr Lys Asp Asp Met Lys Asn Met Ser Ile Asn Asp Val Lys
    210                 215                 220

Ile Thr Thr Thr Thr Glu Asp Pro Leu Val Ala Gln Glu Leu Ser Met
225                 230                 235                 240

Met Phe Glu Lys Val Gln Tyr Cys Arg Asp Leu Arg Asp Lys Tyr Gln
                245                 250                 255

Thr Val Ser Leu Gln Lys Asp Gly Asp Asn Pro Lys Asp Asp Lys Thr
            260                 265                 270

His Trp Lys Ile Tyr Pro Glu Pro Pro Pro Pro Ser Trp His Glu Thr
        275                 280                 285

Glu Lys Arg Phe Arg Gly Ser Ser Lys Lys Glu His Gln Lys Lys Asp
    290                 295                 300

Pro Thr Met Asp Glu Phe Lys Phe Glu Asp Cys Glu Ile Pro Gly Pro
305                 310                 315                 320

Asn Asp Met Val Phe Lys Arg Asp Pro Thr Cys Val Tyr Gln Val Tyr
                325                 330                 335

Glu Asp Glu Ser Ser Leu Asn Glu Asn Lys Pro Phe Val Ala Ile Pro
            340                 345                 350

Ser Ile Arg Asp Tyr Tyr Met Asp Leu Glu Asp Leu Ile Val Ala Ser
```

-continued

```
        355                 360                 365

Ser Asp Gly Pro Ala Lys Ser Phe Ala Phe Arg Arg Leu Gln Tyr Leu
    370                 375                 380

Glu Ala Lys Trp Asn Leu Tyr Tyr Leu Leu Asn Glu Tyr Thr Glu Thr
385                 390                 395                 400

Thr Glu Ser Lys Thr Asn Pro His Arg Asp Phe Tyr Asn Val Arg Lys
                405                 410                 415

Val Asp Thr His Val His His Ser Ala Cys Met Asn Gln Lys His Leu
            420                 425                 430

Leu Arg Phe Ile Lys Tyr Lys Met Lys Asn Cys Pro Asp Glu Val Val
        435                 440                 445

Ile His Arg Asp Gly Arg Glu Leu Thr Leu Ser Gln Val Phe Glu Ser
    450                 455                 460

Leu Asn Leu Thr Ala Tyr Asp Leu Ser Ile Asp Thr Leu Asp Met His
465                 470                 475                 480

Ala His Lys Asp Ser Phe His Arg Phe Asp Lys Phe Asn Leu Lys Tyr
                485                 490                 495

Asn Pro Val Gly Glu Ser Arg Leu Arg Glu Ile Phe Leu Lys Thr Asp
            500                 505                 510

Asn Tyr Ile Gln Gly Arg Tyr Leu Ala Glu Ile Thr Lys Glu Val Phe
        515                 520                 525

Gln Asp Leu Glu Asn Ser Lys Tyr Gln Met Ala Glu Tyr Arg Ile Ser
    530                 535                 540

Ile Tyr Gly Arg Ser Lys Asp Glu Trp Asp Lys Leu Ala Ala Trp Val
545                 550                 555                 560

Leu Asp Asn Lys Leu Phe Ser Pro Asn Val Arg Trp Leu Ile Gln Val
                565                 570                 575

Pro Arg Leu Tyr Asp Ile Tyr Lys Lys Ala Gly Leu Val Asn Thr Phe
            580                 585                 590

Ala Asp Ile Val Gln Asn Val Phe Glu Pro Leu Phe Glu Val Thr Lys
        595                 600                 605

Asp Pro Ser Thr His Pro Lys Leu His Val Phe Leu Gln Arg Val Val
    610                 615                 620

Gly Phe Asp Ser Val Asp Asp Glu Ser Lys Leu Asp Arg Arg Phe His
625                 630                 635                 640

Arg Lys Phe Pro Thr Ala Ala Tyr Trp Asp Ser Ala Gln Asn Pro Pro
                645                 650                 655

Tyr Ser Tyr Trp Gln Tyr Tyr Leu Tyr Ala Asn Met Ala Ser Ile Asn
            660                 665                 670

Thr Trp Arg Gln Arg Leu Gly Tyr Asn Thr Phe Glu Leu Arg Pro His
        675                 680                 685

Ala Gly Glu Ala Gly Asp Pro Glu His Leu Leu Cys Thr Tyr Leu Val
    690                 695                 700

Ala Gln Gly Ile Asn His Gly Ile Leu Leu Arg Lys Val Pro Phe Ile
705                 710                 715                 720

Gln Tyr Leu Tyr Tyr Leu Asp Gln Ile Pro Ile Ala Met Ser Pro Val
                725                 730                 735

Ser Asn Asn Ala Leu Phe Leu Thr Phe Asp Lys Asn Pro Phe Tyr Ser
            740                 745                 750

Tyr Phe Lys Arg Gly Leu Asn Val Ser Leu Ser Ser Asp Asp Pro Leu
        755                 760                 765

Gln Phe Ala Tyr Thr Lys Glu Ala Leu Ile Glu Glu Tyr Ser Val Ala
    770                 775                 780
```

```
Ala Leu Ile Tyr Lys Leu Ser Asn Val Asp Met Cys Glu Leu Ala Arg
785                 790                 795                 800

Asn Ser Val Leu Gln Ser Gly Phe Glu Arg Ile Ile Lys Glu His Trp
                805                 810                 815

Ile Gly Glu Asn Tyr Glu Ile His Gly Pro Glu Gly Asn Thr Ile Gln
            820                 825                 830

Lys Thr Asn Val Pro Asn Val Arg Leu Ala Phe Arg Asp Glu Thr Leu
        835                 840                 845

Thr His Glu Leu Ala Leu Val Asp Lys Tyr Thr Asn Leu Glu Glu Phe
    850                 855                 860

Glu Arg Leu His Gly
865
```

<210> SEQ ID NO 138
<211> LENGTH: 1017
<212> TYPE: DNA
<213> ORGANISM: Yarrowia lipolytica
<300> PUBLICATION INFORMATION:
<308> DATABASE ACCESSION NUMBER: YALI0D16753g

<400> SEQUENCE: 138

```
atgttccgaa cccgagttac cggctccacc ctgcgatcct tctccacctc cgctgcccga      60

cagcacaagg ttgtcgtcct tggcgccaac ggaggcattg gccagcccct gtctctgctg     120

ctcaagctca acaagaacgt gaccgacctc ggtctgtacg atctgcgagg cgcccccggc     180

gttgctgccg atgtctccca catccccacc aactccaccg tggccggcta ctctcccgac     240

aacaacggca ttgccgaggc cctcaagggc gccaagctgg tgctgatccc cgccggtgtc     300

ccccgaaagc ccggcatgac ccgagacgat ctgttcaaca ccaacgcctc cattgtgcga     360

gacctggcca aggccgtcgg tgagcacgcc cccgacgcct ttgtcggagt cattgctaac     420

cccgtcaact ccaccgtccc cattgtcgcc gaggtgctca agtccaaggg caagtacgac     480

cccaagaagc tcttcggtgt caccaccctc gacgtcatcc gagccgagcg attcgtctcc     540

cagctcgagc acaccaaccc caccaaggag tacttccccg ttgttggcgg ccactccggt     600

gtcaccattg tcccccctcgt gtcccagtcc gaccaccccg acattgccgg tgaggctcga     660

gacaagcttg tccaccgaat ccagtttggc ggtgacgagg ttgtcaaggc caaggacggt     720

gccggatccg ccacccttc catggcccag gctgccgccc gattcgccga ctctctcctc     780

cgaggtgtca acggcgagaa ggacgttgtt gagcccactt tcgtcgactc tcctctgttc     840

aagggtgagg gcatcgactt cttctccacc aaggtcactc ttggccctaa cggtgttgag     900

gagatccacc ccatcggaaa ggtcaacgag tacgaggaga agctcatcga ggctgccaag     960

gccgatctca agaagaacat tgagaagggt gtcaactttg tcaagcagaa cccttaa       1017
```

<210> SEQ ID NO 139
<211> LENGTH: 338
<212> TYPE: PRT
<213> ORGANISM: Yarrowia lipolytica
<300> PUBLICATION INFORMATION:
<308> DATABASE ACCESSION NUMBER: YALI0D16753g

<400> SEQUENCE: 139

```
Met Phe Arg Thr Arg Val Thr Gly Ser Thr Leu Arg Ser Phe Ser Thr
1               5                   10                  15

Ser Ala Ala Arg Gln His Lys Val Val Val Leu Gly Ala Asn Gly Gly
            20                  25                  30

Ile Gly Gln Pro Leu Ser Leu Leu Leu Lys Leu Asn Lys Asn Val Thr
        35                  40                  45
```

```
Asp Leu Gly Leu Tyr Asp Leu Arg Gly Ala Pro Gly Val Ala Ala Asp
    50                  55                  60

Val Ser His Ile Pro Thr Asn Ser Thr Val Ala Gly Tyr Ser Pro Asp
65                  70                  75                  80

Asn Asn Gly Ile Ala Glu Ala Leu Lys Gly Ala Lys Leu Val Leu Ile
                85                  90                  95

Pro Ala Gly Val Pro Arg Lys Pro Gly Met Thr Arg Asp Asp Leu Phe
            100                 105                 110

Asn Thr Asn Ala Ser Ile Val Arg Asp Leu Ala Lys Ala Val Gly Glu
        115                 120                 125

His Ala Pro Asp Ala Phe Val Gly Val Ile Ala Asn Pro Val Asn Ser
    130                 135                 140

Thr Val Pro Ile Val Ala Glu Val Leu Lys Ser Lys Gly Lys Tyr Asp
145                 150                 155                 160

Pro Lys Lys Leu Phe Gly Val Thr Thr Leu Asp Val Ile Arg Ala Glu
                165                 170                 175

Arg Phe Val Ser Gln Leu Glu His Thr Asn Pro Thr Lys Glu Tyr Phe
            180                 185                 190

Pro Val Val Gly Gly His Ser Gly Val Thr Ile Val Pro Leu Val Ser
        195                 200                 205

Gln Ser Asp His Pro Asp Ile Ala Gly Glu Ala Arg Asp Lys Leu Val
    210                 215                 220

His Arg Ile Gln Phe Gly Gly Asp Glu Val Val Lys Ala Lys Asp Gly
225                 230                 235                 240

Ala Gly Ser Ala Thr Leu Ser Met Ala Gln Ala Ala Ala Arg Phe Ala
                245                 250                 255

Asp Ser Leu Leu Arg Gly Val Asn Gly Glu Lys Asp Val Val Glu Pro
            260                 265                 270

Thr Phe Val Asp Ser Pro Leu Phe Lys Gly Glu Gly Ile Asp Phe Phe
        275                 280                 285

Ser Thr Lys Val Thr Leu Gly Pro Asn Gly Val Glu Glu Ile His Pro
    290                 295                 300

Ile Gly Lys Val Asn Glu Tyr Glu Glu Lys Leu Ile Glu Ala Ala Lys
305                 310                 315                 320

Ala Asp Leu Lys Lys Asn Ile Glu Lys Gly Val Asn Phe Val Lys Gln
                325                 330                 335

Asn Pro


<210> SEQ ID NO 140
<211> LENGTH: 1107
<212> TYPE: DNA
<213> ORGANISM: Yarrowia lipolytica
<300> PUBLICATION INFORMATION:
<308> DATABASE ACCESSION NUMBER: YALI0D16247g

<400> SEQUENCE: 140

atgacacaaa cgcacaatct gttttcgcca atcaaagtgg gctcttcgga gctccagaac      60

cggatcgttc tcgcaccctt gactcgaacc agagctctgc ccggaaacgt gccctcggat     120

cttgccacag agtactacgc acaaagagca gcatctccag gcactctcct catcaccgag     180

gccacataca tctcccccgg atctgctgga gtgcccattc caggagacgg aatcgttccg     240

ggcatctgga gtgacgagca gctcgaagca tggaaaaagg tgttcaaggc cgtgcacgac     300

cgaggatcca aaatctacgt ccagctgtgg gacattggac gtgtcgcatg gtaccacaag     360

ctgcaggaac tgggcaacta cttccctaca ggcccctcag ctatccccat gaagggagag     420
```

```
gagagcgagc atctcaaggc tctgactcac tgggagatca agggcaaggt ggccctctac    480

gtcaacgctg ccaagaacgc cattgccgca ggcgctgatg gcgtcgagat ccactcggcc    540

aacggctacc ttcccgacac atttctgaga agcgcctcca accaacgaac agacgaatat    600

ggaggaagca tcgagaaccg ggcccgattc tcgctggaga ttgtcgacgc tatcaccgag    660

gccattggag cagacaaaac cgccatccgt ctgtctccct ggtccacttt ccaggacatt    720

gaggtgaatg acaccgagac ccccgcacag ttcacatacc tgtttgagca gctgcagaag    780

cgagccgacg agggaaagca gctggcctac gtgcatgtag ttgagccccg actgtttggt    840

ccccccgagc cctgggccac caatgagcct ttcagaaaaa tttggaaggg taacttcatt    900

agagcaggtg gatacgatag agagactgct cttgaggatg cagacaagtc agacaacacc    960

ctgattgcct ttggtcgaga cttcattgcc aatcctgatc tcgtccaacg cctcaagaat   1020

aacgagcctt tggccaagta cgacagaaca accttctacg ttccaggtgc caagggctac   1080

actgattacc ctgcgtacaa gatgtaa                                       1107


<210> SEQ ID NO 141
<211> LENGTH: 368
<212> TYPE: PRT
<213> ORGANISM: Yarrowia lipolytica
<300> PUBLICATION INFORMATION:
<308> DATABASE ACCESSION NUMBER: YALI0D16247g

<400> SEQUENCE: 141

Met Thr Gln Thr His Asn Leu Phe Ser Pro Ile Lys Val Gly Ser Ser
1               5                   10                  15

Glu Leu Gln Asn Arg Ile Val Leu Ala Pro Leu Thr Arg Thr Arg Ala
            20                  25                  30

Leu Pro Gly Asn Val Pro Ser Asp Leu Ala Thr Glu Tyr Tyr Ala Gln
        35                  40                  45

Arg Ala Ala Ser Pro Gly Thr Leu Leu Ile Thr Glu Ala Thr Tyr Ile
    50                  55                  60

Ser Pro Gly Ser Ala Gly Val Pro Ile Pro Gly Asp Gly Ile Val Pro
65                  70                  75                  80

Gly Ile Trp Ser Asp Glu Gln Leu Glu Ala Trp Lys Lys Val Phe Lys
                85                  90                  95

Ala Val His Asp Arg Gly Ser Lys Ile Tyr Val Gln Leu Trp Asp Ile
            100                 105                 110

Gly Arg Val Ala Trp Tyr His Lys Leu Gln Glu Leu Gly Asn Tyr Phe
        115                 120                 125

Pro Thr Gly Pro Ser Ala Ile Pro Met Lys Gly Glu Glu Ser Glu His
    130                 135                 140

Leu Lys Ala Leu Thr His Trp Glu Ile Lys Gly Lys Val Ala Leu Tyr
145                 150                 155                 160

Val Asn Ala Ala Lys Asn Ala Ile Ala Ala Gly Ala Asp Gly Val Glu
                165                 170                 175

Ile His Ser Ala Asn Gly Tyr Leu Pro Asp Thr Phe Leu Arg Ser Ala
            180                 185                 190

Ser Asn Gln Arg Thr Asp Glu Tyr Gly Gly Ser Ile Glu Asn Arg Ala
        195                 200                 205

Arg Phe Ser Leu Glu Ile Val Asp Ala Ile Thr Glu Ala Ile Gly Ala
    210                 215                 220

Asp Lys Thr Ala Ile Arg Leu Ser Pro Trp Ser Thr Phe Gln Asp Ile
225                 230                 235                 240
```

```
Glu Val Asn Asp Thr Glu Thr Pro Ala Gln Phe Thr Tyr Leu Phe Glu
                245                 250                 255

Gln Leu Gln Lys Arg Ala Asp Glu Gly Lys Gln Leu Ala Tyr Val His
            260                 265                 270

Val Val Glu Pro Arg Leu Phe Gly Pro Pro Glu Pro Trp Ala Thr Asn
        275                 280                 285

Glu Pro Phe Arg Lys Ile Trp Lys Gly Asn Phe Ile Arg Ala Gly Gly
    290                 295                 300

Tyr Asp Arg Glu Thr Ala Leu Glu Asp Ala Asp Lys Ser Asp Asn Thr
305                 310                 315                 320

Leu Ile Ala Phe Gly Arg Asp Phe Ile Ala Asn Pro Asp Leu Val Gln
                325                 330                 335

Arg Leu Lys Asn Asn Glu Pro Leu Ala Lys Tyr Asp Arg Thr Thr Phe
            340                 345                 350

Tyr Val Pro Gly Ala Lys Gly Tyr Thr Asp Tyr Pro Ala Tyr Lys Met
        355                 360                 365


<210> SEQ ID NO 142
<211> LENGTH: 1017
<212> TYPE: DNA
<213> ORGANISM: Yarrowia lipolytica
<300> PUBLICATION INFORMATION:
<308> DATABASE ACCESSION NUMBER: YALI0A15972g

<400> SEQUENCE: 142

atggaagcca accccgaagt ccagaccgat atcatcacgc tgacccggtt cattctgcag     60

gaacagaaca aggtgggcgc gtcgtccgca atccccaccg gagacttcac tctgctgctc    120

aactcgctgc agtttgcctt caagttcatt gcccacaaca tccgacgatc gaccctggtc    180

aacctgattg gcctgtcggg aaccgccaac tccaccggcg acgaccagaa gaagctggac    240

gtgatcggag acgagatctt catcaacgcc atgaaggcct ccggtaaggt caagctggtg    300

gtgtccgagg agcaggagga cctcattgtg tttgagggcg acggccgata cgccgtggtc    360

tgcgacccca tcgacggatc ctccaacctc gacgccggcg tctccgtcgg caccattttc    420

ggcgtctaca agctccccga gggctcctcc ggatccatca aggacgtgct ccgacccgga    480

aaggagatgg ttgccgccgg ctacaccatg tacggtgcct ccgccaacct ggtgctgtcc    540

accggaaacg gctgcaacgg cttcactctc gatgaccctc tgggagagtt catcctgacc    600

caccccgatc tcaagctccc cgatctgcga tccatctact ccgtcaacga gggtaactcc    660

tccctgtggt ccgacaacgt caaggactac ttcaaggccc tcaagttccc cgaggacggc    720

tccaagccct actcggcccg atacattggc tccatggtcg ccgacgtgca ccgaaccatt    780

ctctacggag gtatgtttgc ctaccccgcc gactccaagt ccaagaaggg caagctccga    840

cttttgtacg agggtttccc catggcctac atcattgagc aggccggcgg tcttgccatc    900

aacgacaacg gcgagcgaat cctcgatctg gtccccaccg agatccacga gcgatccggc    960

gtctggctgg gctccaaggg cgagattgag aaggccaaga agtaccttct gaaatga      1017


<210> SEQ ID NO 143
<211> LENGTH: 338
<212> TYPE: PRT
<213> ORGANISM: Yarrowia lipolytica
<300> PUBLICATION INFORMATION:
<308> DATABASE ACCESSION NUMBER: YALI0A15972g

<400> SEQUENCE: 143

Met Glu Ala Asn Pro Glu Val Gln Thr Asp Ile Ile Thr Leu Thr Arg
1               5                   10                  15
```

-continued

```
Phe Ile Leu Gln Glu Gln Asn Lys Val Gly Ala Ser Ser Ala Ile Pro
            20                  25                  30

Thr Gly Asp Phe Thr Leu Leu Leu Asn Ser Leu Gln Phe Ala Phe Lys
        35                  40                  45

Phe Ile Ala His Asn Ile Arg Arg Ser Thr Leu Val Asn Leu Ile Gly
    50                  55                  60

Leu Ser Gly Thr Ala Asn Ser Thr Gly Asp Asp Gln Lys Lys Leu Asp
65                  70                  75                  80

Val Ile Gly Asp Glu Ile Phe Ile Asn Ala Met Lys Ala Ser Gly Lys
                85                  90                  95

Val Lys Leu Val Val Ser Glu Glu Gln Glu Asp Leu Ile Val Phe Glu
            100                 105                 110

Gly Asp Gly Arg Tyr Ala Val Val Cys Asp Pro Ile Asp Gly Ser Ser
        115                 120                 125

Asn Leu Asp Ala Gly Val Ser Val Gly Thr Ile Phe Gly Val Tyr Lys
    130                 135                 140

Leu Pro Glu Gly Ser Ser Gly Ser Ile Lys Asp Val Leu Arg Pro Gly
145                 150                 155                 160

Lys Glu Met Val Ala Ala Gly Tyr Thr Met Tyr Gly Ala Ser Ala Asn
                165                 170                 175

Leu Val Leu Ser Thr Gly Asn Gly Cys Asn Gly Phe Thr Leu Asp Asp
            180                 185                 190

Pro Leu Gly Glu Phe Ile Leu Thr His Pro Asp Leu Lys Leu Pro Asp
        195                 200                 205

Leu Arg Ser Ile Tyr Ser Val Asn Glu Gly Asn Ser Ser Leu Trp Ser
    210                 215                 220

Asp Asn Val Lys Asp Tyr Phe Lys Ala Leu Lys Phe Pro Glu Asp Gly
225                 230                 235                 240

Ser Lys Pro Tyr Ser Ala Arg Tyr Ile Gly Ser Met Val Ala Asp Val
                245                 250                 255

His Arg Thr Ile Leu Tyr Gly Gly Met Phe Ala Tyr Pro Ala Asp Ser
            260                 265                 270

Lys Ser Lys Lys Gly Lys Leu Arg Leu Leu Tyr Glu Gly Phe Pro Met
        275                 280                 285

Ala Tyr Ile Ile Glu Gln Ala Gly Gly Leu Ala Ile Asn Asp Asn Gly
    290                 295                 300

Glu Arg Ile Leu Asp Leu Val Pro Thr Glu Ile His Glu Arg Ser Gly
305                 310                 315                 320

Val Trp Leu Gly Ser Lys Gly Glu Ile Glu Lys Ala Lys Lys Tyr Leu
                325                 330                 335

Leu Lys
```

<210> SEQ ID NO 144
<211> LENGTH: 1194
<212> TYPE: DNA
<213> ORGANISM: Yarrowia lipolytica
<300> PUBLICATION INFORMATION:
<308> DATABASE ACCESSION NUMBER: YALI0E11099g

<400> SEQUENCE: 144

```
atgcgactca ctctgccccg acttaacgcc gcctacattg taggagccgc ccgaactcct      60

gtcggcaagt tcaacggagc cctcaagtcc gtgtctgcca ttgacctcgg tatcaccgct     120

gccaaggccg ctgtccagcg atccaaggtc cccgccgacc agattgacga gtttctgttt     180

ggccaggtgc tgaccgccaa ctccggccag gcccccgccc gacaggtggt tatcaagggt     240
```

```
ggtttccccg agtccgtcga ggccaccacc atcaacaagg tgtgctcttc cggcctcaag    300

accgtggctc tggctgccca ggccatcaag gccggcgacc gaaacgttat cgtggccggt    360

ggaatggagt ccatgtccaa cacccctac tactccggtc gaggtcttgt tttcggcaac    420

cagaagctcg aggactccat cgtcaaggac ggtctctggg acccctacaa caacatccac    480

atgggcaact gctgcgagaa caccaacaag cgagacggca tcacccgaga gcagcaggac    540

gagtacgcca tcgagtccta ccgacgggcc aacgagtcca tcaagaacgg cgccttcaag    600

gatgagattg tccccgttga gatcaagacc cgaaagggca ccgtgactgt ctccgaggac    660

gaggagccca agggagccaa cgccgagaag ctcaagggcc tcaagcctgt ctttgacaag    720

cagggctccg tcactgccgg taacgcctcc cccatcaacg atggtgcttc tgccgttgtc    780

gttgcctctg gcaccaaggc caaggagctc ggtacccccg tgctcgccaa gattgtctct    840

tacgcagacg ccgccaccgc ccccattgac tttaccattg ctccctctct ggccattccc    900

gccgccctca agaaggctgg ccttaccaag gacgacattg ccctctggga gatcaacgag    960

gccttctccg gtgtcgctct cgccaacctc atgcgactcg gaattgacaa gtccaaggtc   1020

aacgtcaagg gtggagctgt tgctctcggc caccccattg gtgcctccgg taaccgaatc   1080

tttgtgactt tggtcaacgc cctcaaggag ggcgagtacg gagttgccgc catctgcaac   1140

ggtggaggag cttccaccgc catcgtcatc aagaaggtct cttctgtcga gtag         1194
```

<210> SEQ ID NO 145
<211> LENGTH: 397
<212> TYPE: PRT
<213> ORGANISM: Yarrowia lipolytica
<300> PUBLICATION INFORMATION:
<308> DATABASE ACCESSION NUMBER: YALI0E11099g

<400> SEQUENCE: 145

```
Met Arg Leu Thr Leu Pro Arg Leu Asn Ala Ala Tyr Ile Val Gly Ala
1               5                   10                  15

Ala Arg Thr Pro Val Gly Lys Phe Asn Gly Ala Leu Lys Ser Val Ser
            20                  25                  30

Ala Ile Asp Leu Gly Ile Thr Ala Ala Lys Ala Ala Val Gln Arg Ser
        35                  40                  45

Lys Val Pro Ala Asp Gln Ile Asp Glu Phe Leu Phe Gly Gln Val Leu
    50                  55                  60

Thr Ala Asn Ser Gly Gln Ala Pro Ala Arg Gln Val Val Ile Lys Gly
65                  70                  75                  80

Gly Phe Pro Glu Ser Val Glu Ala Thr Thr Ile Asn Lys Val Cys Ser
                85                  90                  95

Ser Gly Leu Lys Thr Val Ala Leu Ala Ala Gln Ala Ile Lys Ala Gly
            100                 105                 110

Asp Arg Asn Val Ile Val Ala Gly Gly Met Glu Ser Met Ser Asn Thr
        115                 120                 125

Pro Tyr Tyr Ser Gly Arg Gly Leu Val Phe Gly Asn Gln Lys Leu Glu
    130                 135                 140

Asp Ser Ile Val Lys Asp Gly Leu Trp Asp Pro Tyr Asn Asn Ile His
145                 150                 155                 160

Met Gly Asn Cys Cys Glu Asn Thr Asn Lys Arg Asp Gly Ile Thr Arg
                165                 170                 175

Glu Gln Gln Asp Glu Tyr Ala Ile Glu Ser Tyr Arg Arg Ala Asn Glu
            180                 185                 190

Ser Ile Lys Asn Gly Ala Phe Lys Asp Glu Ile Val Pro Val Glu Ile
```

```
        195                 200                 205

Lys Thr Arg Lys Gly Thr Val Thr Val Ser Glu Asp Glu Glu Pro Lys
    210                 215                 220

Gly Ala Asn Ala Glu Lys Leu Lys Gly Leu Lys Pro Val Phe Asp Lys
225                 230                 235                 240

Gln Gly Ser Val Thr Ala Gly Asn Ala Ser Pro Ile Asn Asp Gly Ala
                245                 250                 255

Ser Ala Val Val Val Ala Ser Gly Thr Lys Ala Lys Glu Leu Gly Thr
            260                 265                 270

Pro Val Leu Ala Lys Ile Val Ser Tyr Ala Asp Ala Ala Thr Ala Pro
        275                 280                 285

Ile Asp Phe Thr Ile Ala Pro Ser Leu Ala Ile Pro Ala Ala Leu Lys
    290                 295                 300

Lys Ala Gly Leu Thr Lys Asp Asp Ile Ala Leu Trp Glu Ile Asn Glu
305                 310                 315                 320

Ala Phe Ser Gly Val Ala Leu Ala Asn Leu Met Arg Leu Gly Ile Asp
                325                 330                 335

Lys Ser Lys Val Asn Val Lys Gly Gly Ala Val Ala Leu Gly His Pro
            340                 345                 350

Ile Gly Ala Ser Gly Asn Arg Ile Phe Val Thr Leu Val Asn Ala Leu
        355                 360                 365

Lys Glu Gly Glu Tyr Gly Val Ala Ala Ile Cys Asn Gly Gly Gly Ala
    370                 375                 380

Ser Thr Ala Ile Val Ile Lys Lys Val Ser Ser Val Glu
385                 390                 395


<210> SEQ ID NO 146
<211> LENGTH: 1953
<212> TYPE: DNA
<213> ORGANISM: Yarrowia lipolytica
<300> PUBLICATION INFORMATION:
<308> DATABASE ACCESSION NUMBER: YALI0E34793g

<400> SEQUENCE: 146

atgtctgcca acgagaacat ctcccgattc gacgcccctg tgggcaagga gcaccccgcc      60

tacgagctct tccataacca cacacgatct ttcgtctatg gtctccagcc tcgagcctgc     120

cagggtatgc tggacttcga cttcatctgt aagcgagaga acccctccgt ggccggtgtc     180

atctatccct tcggcggcca gttcgtcacc aagatgtact ggggcaccaa ggagactctt     240

ctccctgtct accagcaggt cgagaaggcc gctgccaagc accccgaggt cgatgtcgtg     300

gtcaactttg cctcctctcg atccgtctac tcctctacca tggagctgct cgagtacccc     360

cagttccgaa ccatcgccat tattgccgag ggtgtccccg agcgacgagc ccgagagatc     420

ctccacaagg cccagaagaa gggtgtgacc atcattggtc ccgctaccgt cggaggtatc     480

aagcccggtt gcttcaaggt tggaaacacc ggaggtatga tggacaacat tgtcgcctcc     540

aagctctacc gacccggctc cgttgcctac gtctccaagt ccggaggaat gtccaacgag     600

ctgaacaaca ttatctctca caccaccgac ggtgtctacg agggtattgc tattggtggt     660

gaccgatacc ctggtactac cttcattgac catatcctgc gatacgaggc cgaccccaag     720

tgtaagatca tcgtcctcct tggtgaggtt ggtggtgttg aggagtaccg agtcatcgag     780

gctgttaaga acggccagat caagaagccc atcgtcgctt gggccattgg tacttgtgcc     840

tccatgttca agactgaggt tcagttcggc cacgccggct ccatggccaa ctccgacctg     900

gagactgcca aggctaagaa cgccgccatg aagtctgctg gcttctacgt ccccgatacc     960
```

```
ttcgaggaca tgcccgaggt ccttgccgag ctctacgaga agatggtcgc caagggcgag   1020

ctgtctcgaa tctctgagcc tgaggtcccc aagatcccca ttgactactc ttgggcccag   1080

gagcttggtc ttatccgaaa gcccgctgct ttcatctcca ctatttccga tgaccgaggc   1140

caggagcttc tgtacgctgg catgcccatt tccgaggttt tcaaggagga cattggtatc   1200

ggcggtgtca tgtctctgct gtggttccga cgacgactcc ccgactacgc ctccaagttt   1260

cttgagatgg ttctcatgct tactgctgac cacggtcccg ccgtatccgg tgccatgaac   1320

accattatca ccacccgagc tggtaaggat ctcatttctt ccctggttgc tggtctcctg   1380

accattggta cccgattcgg aggtgctctt gacggtgctg ccaccgagtt caccactgcc   1440

tacgacaagg gtctgtcccc ccgacagttc gttgatacca tgcgaaagca gaacaagctg   1500

attcctggta ttggccatcg agtcaagtct cgaaacaacc ccgatttccg agtcgagctt   1560

gtcaaggact ttgttaagaa gaacttcccc tccacccagc tgctcgacta cgcccttgct   1620

gtcgaggagg tcaccacctc caagaaggac aacctgattc tgaacgttga cggtgctatt   1680

gctgtttctt ttgtcgatct catgcgatct tgcggtgcct ttactgtgga ggagactgag   1740

gactacctca agaacggtgt tctcaacggt ctgttcgttc tcggtcgatc cattggtctc   1800

attgcccacc atctcgatca gaagcgactc aagaccggtc tgtaccgaca tccttgggac   1860

gatatcacct acctggttgg ccaggaggct atccagaaga agcgagtcga gatcagcgcc   1920

ggcgacgttt ccaaggccaa gactcgatca tag                                1953
```

<210> SEQ ID NO 147
<211> LENGTH: 650
<212> TYPE: PRT
<213> ORGANISM: Yarrowia lipolytica
<300> PUBLICATION INFORMATION:
<308> DATABASE ACCESSION NUMBER: YALI0E34793g

<400> SEQUENCE: 147

```
Met Ser Ala Asn Glu Asn Ile Ser Arg Phe Asp Ala Pro Val Gly Lys
1               5                   10                  15

Glu His Pro Ala Tyr Glu Leu Phe His Asn His Thr Arg Ser Phe Val
            20                  25                  30

Tyr Gly Leu Gln Pro Arg Ala Cys Gln Gly Met Leu Asp Phe Asp Phe
        35                  40                  45

Ile Cys Lys Arg Glu Asn Pro Ser Val Ala Gly Val Ile Tyr Pro Phe
    50                  55                  60

Gly Gly Gln Phe Val Thr Lys Met Tyr Trp Gly Thr Lys Glu Thr Leu
65                  70                  75                  80

Leu Pro Val Tyr Gln Gln Val Glu Lys Ala Ala Ala Lys His Pro Glu
                85                  90                  95

Val Asp Val Val Val Asn Phe Ala Ser Ser Arg Ser Val Tyr Ser Ser
            100                 105                 110

Thr Met Glu Leu Leu Glu Tyr Pro Gln Phe Arg Thr Ile Ala Ile Ile
        115                 120                 125

Ala Glu Gly Val Pro Glu Arg Arg Ala Arg Glu Ile Leu His Lys Ala
    130                 135                 140

Gln Lys Lys Gly Val Thr Ile Ile Gly Pro Ala Thr Val Gly Gly Ile
145                 150                 155                 160

Lys Pro Gly Cys Phe Lys Val Gly Asn Thr Gly Gly Met Met Asp Asn
                165                 170                 175

Ile Val Ala Ser Lys Leu Tyr Arg Pro Gly Ser Val Ala Tyr Val Ser
            180                 185                 190
```

```
Lys Ser Gly Gly Met Ser Asn Glu Leu Asn Asn Ile Ile Ser His Thr
        195                 200                 205

Thr Asp Gly Val Tyr Glu Gly Ile Ala Ile Gly Gly Asp Arg Tyr Pro
    210                 215                 220

Gly Thr Thr Phe Ile Asp His Ile Leu Arg Tyr Glu Ala Asp Pro Lys
225                 230                 235                 240

Cys Lys Ile Ile Val Leu Leu Gly Glu Val Gly Gly Val Glu Glu Tyr
                245                 250                 255

Arg Val Ile Glu Ala Val Lys Asn Gly Gln Ile Lys Lys Pro Ile Val
            260                 265                 270

Ala Trp Ala Ile Gly Thr Cys Ala Ser Met Phe Lys Thr Glu Val Gln
        275                 280                 285

Phe Gly His Ala Gly Ser Met Ala Asn Ser Asp Leu Glu Thr Ala Lys
    290                 295                 300

Ala Lys Asn Ala Ala Met Lys Ser Ala Gly Phe Tyr Val Pro Asp Thr
305                 310                 315                 320

Phe Glu Asp Met Pro Glu Val Leu Ala Glu Leu Tyr Glu Lys Met Val
                325                 330                 335

Ala Lys Gly Glu Leu Ser Arg Ile Ser Glu Pro Glu Val Pro Lys Ile
            340                 345                 350

Pro Ile Asp Tyr Ser Trp Ala Gln Glu Leu Gly Leu Ile Arg Lys Pro
        355                 360                 365

Ala Ala Phe Ile Ser Thr Ile Ser Asp Asp Arg Gly Gln Glu Leu Leu
    370                 375                 380

Tyr Ala Gly Met Pro Ile Ser Glu Val Phe Lys Glu Asp Ile Gly Ile
385                 390                 395                 400

Gly Gly Val Met Ser Leu Leu Trp Phe Arg Arg Arg Leu Pro Asp Tyr
                405                 410                 415

Ala Ser Lys Phe Leu Glu Met Val Leu Met Leu Thr Ala Asp His Gly
            420                 425                 430

Pro Ala Val Ser Gly Ala Met Asn Thr Ile Ile Thr Thr Arg Ala Gly
        435                 440                 445

Lys Asp Leu Ile Ser Ser Leu Val Ala Gly Leu Leu Thr Ile Gly Thr
    450                 455                 460

Arg Phe Gly Gly Ala Leu Asp Gly Ala Ala Thr Glu Phe Thr Thr Ala
465                 470                 475                 480

Tyr Asp Lys Gly Leu Ser Pro Arg Gln Phe Val Asp Thr Met Arg Lys
                485                 490                 495

Gln Asn Lys Leu Ile Pro Gly Ile Gly His Arg Val Lys Ser Arg Asn
            500                 505                 510

Asn Pro Asp Phe Arg Val Glu Leu Val Lys Asp Phe Val Lys Lys Asn
        515                 520                 525

Phe Pro Ser Thr Gln Leu Leu Asp Tyr Ala Leu Ala Val Glu Glu Val
    530                 535                 540

Thr Thr Ser Lys Lys Asp Asn Leu Ile Leu Asn Val Asp Gly Ala Ile
545                 550                 555                 560

Ala Val Ser Phe Val Asp Leu Met Arg Ser Cys Gly Ala Phe Thr Val
                565                 570                 575

Glu Glu Thr Glu Asp Tyr Leu Lys Asn Gly Val Leu Asn Gly Leu Phe
            580                 585                 590

Val Leu Gly Arg Ser Ile Gly Leu Ile Ala His His Leu Asp Gln Lys
        595                 600                 605

Arg Leu Lys Thr Gly Leu Tyr Arg His Pro Trp Asp Asp Ile Thr Tyr
    610                 615                 620
```

Leu Val Gly Gln Glu Ala Ile Gln Lys Lys Arg Val Glu Ile Ser Ala
625 630 635 640

Gly Asp Val Ser Lys Ala Lys Thr Arg Ser
645 650

<210> SEQ ID NO 148
<211> LENGTH: 1494
<212> TYPE: DNA
<213> ORGANISM: Yarrowia lipolytica
<300> PUBLICATION INFORMATION:
<308> DATABASE ACCESSION NUMBER: YALI0D24431g

<400> SEQUENCE: 148
atgtcagcga aatccattca cgaggccgac ggcaaggccc tgctcgcaca ctttctgtcc 60
aaggcgcccg tgtgggccga gcagcagccc atcaacacgt ttgaaatggg cacacccaag 120
ctggcgtctc tgacgttcga ggacggcgtg gcccccgagc agatcttcgc cgccgctgaa 180
aagacctacc cctggctgct ggagtccggc gccaagtttg tggccaagcc cgaccagctc 240
atcaagcgac gaggcaaggc cggcctgctg gtactcaaca agtcgtggga ggagtgcaag 300
ccctggatcg ccgagcgggc cgccaagccc atcaacgtgg agggcattga cggagtgctg 360
cgaacgttcc tggtcgagcc ctttgtgccc cacgaccaga agcacgagta ctacatcaac 420
atccactccg tgcgagaggg cgactggatc ctcttctacc acgagggagg agtcgacgtc 480
ggcgacgtgg acgccaaggc cgccaagatc ctcatccccg ttgacattga gaacgagtac 540
ccctccaacg ccacgctcac caaggagctg ctggcacacg tgcccgagga ccagcaccag 600
accctgctcg acttcatcaa ccggctctac gccgtctacg tcgatctgca gtttacgtat 660
ctggagatca accccctggt cgtgatcccc accgcccagg gcgtcgaggt ccactacctg 720
gatcttgccg gcaagctcga ccagaccgca gagtttgagt gcggccccaa gtgggctgct 780
gcgcggtccc ccgccgctct gggccaggtc gtcaccattg acgccggctc caccaaggtg 840
tccatcgacg ccggccccgc catggtcttc cccgctcctt tcggtcgaga gctgtccaag 900
gaggaggcgt acattgcgga gctcgattcc aagaccggag cttctctgaa gctgactgtt 960
ctcaatgcca agggccgaat ctggaccctt gtggctggtg gaggagcctc cgtcgtctac 1020
gccgacgcca ttgcgtctgc cggctttgct gacgagctcg ccaactacgg cgagtactct 1080
ggcgctccca acgagaccca gacctacgag tacgccaaaa ccgtactgga tctcatgacc 1140
cggggcgacg ctcaccccga gggcaaggta ctgttcattg gcggaggaat cgccaacttc 1200
acccaggttg gatccacctt caagggcatc atccgggcct tccgggacta ccagtcttct 1260
ctgcacaacc acaaggtgaa gatttacgtg cgacgaggcg gtcccaactg gcaggagggt 1320
ctgcggttga tcaagtcggc tggcgacgag ctgaatctgc ccatggagat ttacggcccc 1380
gacatgcacg tgtcgggtat tgttcctttg gctctgcttg gaaagcggcc caagaatgtc 1440
aagccttttg gcaccggacc ttctactgag gcttccactc ctctcggagt ttaa 1494

<210> SEQ ID NO 149
<211> LENGTH: 497
<212> TYPE: PRT
<213> ORGANISM: Yarrowia lipolytica
<300> PUBLICATION INFORMATION:
<308> DATABASE ACCESSION NUMBER: YALI0D24431g

<400> SEQUENCE: 149

Met Ser Ala Lys Ser Ile His Glu Ala Asp Gly Lys Ala Leu Leu Ala
1 5 10 15

-continued

```
His Phe Leu Ser Lys Ala Pro Val Trp Ala Glu Gln Gln Pro Ile Asn
            20                  25                  30

Thr Phe Glu Met Gly Thr Pro Lys Leu Ala Ser Leu Thr Phe Glu Asp
        35                  40                  45

Gly Val Ala Pro Glu Gln Ile Phe Ala Ala Ala Glu Lys Thr Tyr Pro
    50                  55                  60

Trp Leu Leu Glu Ser Gly Ala Lys Phe Val Ala Lys Pro Asp Gln Leu
65                  70                  75                  80

Ile Lys Arg Arg Gly Lys Ala Gly Leu Leu Val Leu Asn Lys Ser Trp
                85                  90                  95

Glu Glu Cys Lys Pro Trp Ile Ala Glu Arg Ala Ala Lys Pro Ile Asn
            100                 105                 110

Val Glu Gly Ile Asp Gly Val Leu Arg Thr Phe Leu Val Glu Pro Phe
        115                 120                 125

Val Pro His Asp Gln Lys His Glu Tyr Tyr Ile Asn Ile His Ser Val
    130                 135                 140

Arg Glu Gly Asp Trp Ile Leu Phe Tyr His Glu Gly Gly Val Asp Val
145                 150                 155                 160

Gly Asp Val Asp Ala Lys Ala Ala Lys Ile Leu Ile Pro Val Asp Ile
                165                 170                 175

Glu Asn Glu Tyr Pro Ser Asn Ala Thr Leu Thr Lys Glu Leu Leu Ala
            180                 185                 190

His Val Pro Glu Asp Gln His Gln Thr Leu Leu Asp Phe Ile Asn Arg
        195                 200                 205

Leu Tyr Ala Val Tyr Val Asp Leu Gln Phe Thr Tyr Leu Glu Ile Asn
    210                 215                 220

Pro Leu Val Val Ile Pro Thr Ala Gln Gly Val Glu Val His Tyr Leu
225                 230                 235                 240

Asp Leu Ala Gly Lys Leu Asp Gln Thr Ala Glu Phe Glu Cys Gly Pro
                245                 250                 255

Lys Trp Ala Ala Ala Arg Ser Pro Ala Ala Leu Gly Gln Val Val Thr
            260                 265                 270

Ile Asp Ala Gly Ser Thr Lys Val Ser Ile Asp Ala Gly Pro Ala Met
        275                 280                 285

Val Phe Pro Ala Pro Phe Gly Arg Glu Leu Ser Lys Glu Glu Ala Tyr
    290                 295                 300

Ile Ala Glu Leu Asp Ser Lys Thr Gly Ala Ser Leu Lys Leu Thr Val
305                 310                 315                 320

Leu Asn Ala Lys Gly Arg Ile Trp Thr Leu Val Ala Gly Gly Gly Ala
                325                 330                 335

Ser Val Val Tyr Ala Asp Ala Ile Ala Ser Ala Gly Phe Ala Asp Glu
            340                 345                 350

Leu Ala Asn Tyr Gly Glu Tyr Ser Gly Ala Pro Asn Glu Thr Gln Thr
        355                 360                 365

Tyr Glu Tyr Ala Lys Thr Val Leu Asp Leu Met Thr Arg Gly Asp Ala
    370                 375                 380

His Pro Glu Gly Lys Val Leu Phe Ile Gly Gly Gly Ile Ala Asn Phe
385                 390                 395                 400

Thr Gln Val Gly Ser Thr Phe Lys Gly Ile Ile Arg Ala Phe Arg Asp
                405                 410                 415

Tyr Gln Ser Ser Leu His Asn His Lys Val Lys Ile Tyr Val Arg Arg
            420                 425                 430

Gly Gly Pro Asn Trp Gln Glu Gly Leu Arg Leu Ile Lys Ser Ala Gly
        435                 440                 445
```

Asp Glu Leu Asn Leu Pro Met Glu Ile Tyr Gly Pro Asp Met His Val
450 455 460

Ser Gly Ile Val Pro Leu Ala Leu Leu Gly Lys Arg Pro Lys Asn Val
465 470 475 480

Lys Pro Phe Gly Thr Gly Pro Ser Thr Glu Ala Ser Thr Pro Leu Gly
485 490 495

Val

<210> SEQ ID NO 150
<211> LENGTH: 1458
<212> TYPE: DNA
<213> ORGANISM: Yarrowia lipolytica
<300> PUBLICATION INFORMATION:
<308> DATABASE ACCESSION NUMBER: YALI0E14190g

<400> SEQUENCE: 150
atggttatta tgtgtgtggg acctcagcac acgcatcatc ccaacacagg gtgcagtata 60
tatagacaga cgtgttcctt cgcaccgttc ttcacatatc aaaacactaa caaattcaaa 120
agtgagtatc atggtgggag tcaattgatt gctcggggag ttgaacaggc aacaatggca 180
tgcacagggc cagtgaaggc agactgcagt cgctgcacat ggatcgtggt tctgaggcgt 240
tgctatcaaa agggtcaatt acctcacgaa acacagctgg atgttgtgca atcgtcaatt 300
gaaaaacccg acacaatgca agatctcttt gcgcgcattg ccatcgctgt tgccatcgct 360
gtcgccatcg ccaatgccgc tgcggattat tatccctacc ttgttccccg cttccgcaca 420
accggcgatg tctttgtatc atgaactctc gaaactaact cagtggttaa agctgtcgtt 480
gccggagccg ctggtggtat tggccagccc ctttctcttc tcctcaaact ctctccttac 540
gtgaccgagc ttgctctcta cgatgtcgtc aactccccccg gtgttgccgc tgacctctcc 600
cacatctcca ccaaggctaa ggtcactggc tacctcccca aggatgacgg tctcaagaac 660
gctctgaccg gcgccaacat tgtcgttatc cccgccggta tcccccgaaa gcccggtatg 720
acccgagacg atctgttcaa gatcaacgct ggtatcgtcc gagatctcgt caccggtgtc 780
gcccagtacg cccctgacgc ctttgtgctc atcatctcca accccgtcaa ctctaccgtc 840
cctattgctg ccgaggtcct caagaagcac aacgtcttca accctaagaa gctcttcggt 900
gtcaccaccc ttgacgttgt ccgagcccag accttcaccg ccgctgttgt tggcgagtct 960
gaccccacca agctcaacat ccccgtcgtt ggtggccact ccggagacac cattgtccct 1020
ctcctgtctc tgaccaagcc taaggtcgag atccccgccg acaagctcga cgacctcgtc 1080
aagcgaatcc agtttggtgg tgacgaggtt gtccaggcta aggacggtct tggatccgct 1140
accctctcca tggcccaggc tggtttccga tttgccgagg ctgtcctcaa gggtgccgct 1200
ggtgagaagg gcatcatcga gcccgcctac atctaccttg acggtattga tggcacctcc 1260
gacatcaagc gagaggtcgg tgtcgccttc ttctctgtcc ctgtcgagtt cggccctgag 1320
ggtgccgcta aggcttacaa catccttccc gaggccaacg actacgagaa gaagcttctc 1380
aaggtctcca tcgacggtct ttacggcaac attgccaagg gcgaggagtt cattgttaac 1440
cctcctcctg ccaagtaa 1458

<210> SEQ ID NO 151
<211> LENGTH: 1937
<212> TYPE: DNA
<213> ORGANISM: Yarrowia lipolytica
<300> PUBLICATION INFORMATION:
<308> DATABASE ACCESSION NUMBER: YALI0E22649g

<400> SEQUENCE: 151

```
atgactggca ccttacccaa gttcggcgac ggaaccacca ttgtggttct tggagcctcc     60
ggcgacctcg ctaagaagaa gaccgtgagt attgaaccag actgaggtca attgaagagt    120
aggagagtct gagaacattc gacggacctg attgtgctct ggaccactca attgactcgt    180
tgagagcccc aatgggtctt ggctagccga gtcgttgact tgttgacttg ttgagcccag    240
aacccccaac ttttgccacc atacaccgcc atcaccatga cacccagatg tgcgtgcgta    300
tgtgagagtc aattgttccg tggcaaggca cagcttattc caccgtgttc cttgcacagg    360
tggtctttac gctctcccac tctatccgag caataaaagc ggaaaaacag cagcaagtcc    420
caacagactt ctgctccgaa taaggcgtct agcaagtgtg cccaaaactc aattcaaaaa    480
tgtcagaaac ctgatatcaa cccgtcttca aaagctaacc ccagttcccc gccctcttcg    540
gcctttaccg aaacggcctg ctgcccaaaa atgttgaaat catcggctac gcacggtcga    600
aaatgactca ggaggagtac cacgagcgaa tcagccacta cttcaagacc cccgacgacc    660
agtccaagga gcaggccaag aagttccttg agaacacctg ctacgtccag ggcccttacg    720
acggtgccga gggctaccag cgactgaatg aaaagattga ggagtttgag aagaagaagc    780
ccgagcccca ctaccgtctt ttctacctgg ctctgccccc cagcgtcttc cttgaggctg    840
ccaacggtct gaagaagtat gtctaccccg gcgagggcaa ggcccgaatc atcatcgaga    900
agccctttgg ccacgacctg gcctcgtcac gagagctcca ggacggcctt gctcctctct    960
ggaaggagtc tgagatcttc cgaatcgacc actacctcgg aaaggagatg gtcaagaacc   1020
tcaacattct gcgatttggc aaccagttcc tgtccgccgt gtgggacaag aacaccattt   1080
ccaacgtcca gatctccttc aaggagccct ttggcactga gggccgaggt ggatacttca   1140
acgacattgg aatcatccga gacgttattc agaaccatct gttgcaggtt ctgtccattc   1200
tagccatgga gcgacccgtc actttcggcg ccgaggacat tcgagatgag aaggtcaagg   1260
tgctccgatg tgtcgacatt ctcaacattg acgacgtcat tctcggccag tacggcccct   1320
ctgaagacgg aaagaagccc ggatacaccg atgacgatgg cgttcccgat gactcccgag   1380
ctgtgacctt tgctgctctc catctccaga tccacaacga cagatgggag ggtgttcctt   1440
tcatcctccg agccggtaag gctctggacg agggcaaggt cgagatccga gtgcagttcc   1500
gagacgtgac caagggcgtt gtggaccatc tgcctcgaaa tgagctcgtc atccgaatcc   1560
agccctccga gtccatctac atgaagatga actccaagct gcctggcctt actgccaaga   1620
acattgtcac cgacctggat ctgacctaca accgacgata ctcggacgtg cgaatccctg   1680
aggcttacga gtctctcatt ctggactgcc tcaagggtga ccacaccaac tttgtgcgaa   1740
acgacgagct ggacatttcc tggaagattt tcaccgatct gctgcacaag attgacgagg   1800
acaagagcat tgtgcccgag aagtacgcct acggctctcg tggccccgag cgactcaagc   1860
agtggctccg agaccgaggc tacgtgcgaa acggcaccga gctgtaccaa tggcctgtca   1920
ccaagggctc ctcgtga                                                  1937
```

<210> SEQ ID NO 152
<211> LENGTH: 331
<212> TYPE: PRT
<213> ORGANISM: Yarrowia lipolytica
<300> PUBLICATION INFORMATION:
<308> DATABASE ACCESSION NUMBER: YALI0E14190g

<400> SEQUENCE: 152

```
Val Val Lys Ala Val Val Ala Gly Ala Ala Gly Gly Ile Gly Gln Pro
1               5                   10                  15
```

```
Leu Ser Leu Leu Leu Lys Leu Ser Pro Tyr Val Thr Glu Leu Ala Leu
            20                  25                  30

Tyr Asp Val Val Asn Ser Pro Gly Val Ala Ala Asp Leu Ser His Ile
        35                  40                  45

Ser Thr Lys Ala Lys Val Thr Gly Tyr Leu Pro Lys Asp Asp Gly Leu
    50                  55                  60

Lys Asn Ala Leu Thr Gly Ala Asn Ile Val Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Thr Gly Val Ala Gln Tyr Ala Pro Asp
            100                 105                 110

Ala Phe Val Leu Ile Ile Ser Asn Pro Val Asn Ser Thr Val Pro Ile
        115                 120                 125

Ala Ala Glu Val Leu Lys Lys His Asn Val Phe Asn Pro Lys Lys Leu
    130                 135                 140

Phe Gly Val Thr Thr Leu Asp Val Val Arg Ala Gln Thr Phe Thr Ala
145                 150                 155                 160

Ala Val Val Gly Glu Ser Asp Pro Thr Lys Leu Asn Ile Pro Val Val
                165                 170                 175

Gly Gly His Ser Gly Asp Thr Ile Val Pro Leu Leu Ser Leu Thr Lys
            180                 185                 190

Pro Lys Val Glu Ile Pro Ala Asp Lys Leu Asp Asp Leu Val Lys Arg
        195                 200                 205

Ile Gln Phe Gly Gly Asp Glu Val Val Gln Ala Lys Asp Gly Leu Gly
    210                 215                 220

Ser Ala Thr Leu Ser Met Ala Gln Ala Gly Phe Arg Phe Ala Glu Ala
225                 230                 235                 240

Val Leu Lys Gly Ala Ala Gly Glu Lys Gly Ile Ile Glu Pro Ala Tyr
                245                 250                 255

Ile Tyr Leu Asp Gly Ile Asp Gly Thr Ser Asp Ile Lys Arg Glu Val
            260                 265                 270

Gly Val Ala Phe Phe Ser Val Pro Val Glu Phe Gly Pro Glu Gly Ala
        275                 280                 285

Ala Lys Ala Tyr Asn Ile Leu Pro Glu Ala Asn Asp Tyr Glu Lys Lys
    290                 295                 300

Leu Leu Lys Val Ser Ile Asp Gly Leu Tyr Gly Asn Ile Ala Lys Gly
305                 310                 315                 320

Glu Glu Phe Ile Val Asn Pro Pro Pro Ala Lys
                325                 330
```

<210> SEQ ID NO 153
<211> LENGTH: 498
<212> TYPE: PRT
<213> ORGANISM: Yarrowia lipolytica
<300> PUBLICATION INFORMATION:
<308> DATABASE ACCESSION NUMBER: YALI0E22649g

<400> SEQUENCE: 153

```
Met Thr Gly Thr Leu Pro Lys Phe Gly Asp Gly Thr Thr Ile Val Val
1               5                   10                  15

Leu Gly Ala Ser Gly Asp Leu Ala Lys Lys Lys Thr Phe Pro Ala Leu
            20                  25                  30

Phe Gly Leu Tyr Arg Asn Gly Leu Leu Pro Lys Asn Val Glu Ile Ile
        35                  40                  45
```

```
Gly Tyr Ala Arg Ser Lys Met Thr Gln Glu Glu Tyr His Glu Arg Ile
    50                  55                  60

Ser His Tyr Phe Lys Thr Pro Asp Asp Gln Ser Lys Glu Gln Ala Lys
65                  70                  75                  80

Lys Phe Leu Glu Asn Thr Cys Tyr Val Gln Gly Pro Tyr Asp Gly Ala
                85                  90                  95

Glu Gly Tyr Gln Arg Leu Asn Glu Lys Ile Glu Glu Phe Glu Lys Lys
            100                 105                 110

Lys Pro Glu Pro His Tyr Arg Leu Phe Tyr Leu Ala Leu Pro Pro Ser
        115                 120                 125

Val Phe Leu Glu Ala Ala Asn Gly Leu Lys Lys Tyr Val Tyr Pro Gly
    130                 135                 140

Glu Gly Lys Ala Arg Ile Ile Ile Glu Lys Pro Phe Gly His Asp Leu
145                 150                 155                 160

Ala Ser Ser Arg Glu Leu Gln Asp Gly Leu Ala Pro Leu Trp Lys Glu
                165                 170                 175

Ser Glu Ile Phe Arg Ile Asp His Tyr Leu Gly Lys Glu Met Val Lys
            180                 185                 190

Asn Leu Asn Ile Leu Arg Phe Gly Asn Gln Phe Leu Ser Ala Val Trp
        195                 200                 205

Asp Lys Asn Thr Ile Ser Asn Val Gln Ile Ser Phe Lys Glu Pro Phe
    210                 215                 220

Gly Thr Glu Gly Arg Gly Gly Tyr Phe Asn Asp Ile Gly Ile Ile Arg
225                 230                 235                 240

Asp Val Ile Gln Asn His Leu Leu Gln Val Leu Ser Ile Leu Ala Met
                245                 250                 255

Glu Arg Pro Val Thr Phe Gly Ala Glu Asp Ile Arg Asp Glu Lys Val
            260                 265                 270

Lys Val Leu Arg Cys Val Asp Ile Leu Asn Ile Asp Asp Val Ile Leu
        275                 280                 285

Gly Gln Tyr Gly Pro Ser Glu Asp Gly Lys Lys Pro Gly Tyr Thr Asp
    290                 295                 300

Asp Asp Gly Val Pro Asp Asp Ser Arg Ala Val Thr Phe Ala Ala Leu
305                 310                 315                 320

His Leu Gln Ile His Asn Asp Arg Trp Glu Gly Val Pro Phe Ile Leu
                325                 330                 335

Arg Ala Gly Lys Ala Leu Asp Glu Gly Lys Val Glu Ile Arg Val Gln
            340                 345                 350

Phe Arg Asp Val Thr Lys Gly Val Val Asp His Leu Pro Arg Asn Glu
        355                 360                 365

Leu Val Ile Arg Ile Gln Pro Ser Glu Ser Ile Tyr Met Lys Met Asn
    370                 375                 380

Ser Lys Leu Pro Gly Leu Thr Ala Lys Asn Ile Val Thr Asp Leu Asp
385                 390                 395                 400

Leu Thr Tyr Asn Arg Arg Tyr Ser Asp Val Arg Ile Pro Glu Ala Tyr
                405                 410                 415

Glu Ser Leu Ile Leu Asp Cys Leu Lys Gly Asp His Thr Asn Phe Val
            420                 425                 430

Arg Asn Asp Glu Leu Asp Ile Ser Trp Lys Ile Phe Thr Asp Leu Leu
        435                 440                 445

His Lys Ile Asp Glu Asp Lys Ser Ile Val Pro Glu Lys Tyr Ala Tyr
    450                 455                 460

Gly Ser Arg Gly Pro Glu Arg Leu Lys Gln Trp Leu Arg Asp Arg Gly
465                 470                 475                 480
```

-continued

Tyr Val Arg Asn Gly Thr Glu Leu Tyr Gln Trp Pro Val Thr Lys Gly
485 490 495

Ser Ser

<210> SEQ ID NO 154
<211> LENGTH: 2202
<212> TYPE: DNA
<213> ORGANISM: Yarrowia lipolytica
<300> PUBLICATION INFORMATION:
<308> DATABASE ACCESSION NUMBER: YALI0B15598g

<400> SEQUENCE: 154
atgactgaca cttcaaacat caagtgagta ttgccgcaca caattgcaat caccgccggg 60
ctctacctcc tcagctctcg acgtcaatgg gccagcagcc gccatttgac cccaattaca 120
ctggttgtgt aaaaccctca accacaatcg cttatgctca ccacagacta cgacttaacc 180
aagtcatgtc acaggtcaaa gtaaagtcag cgcaacaccc cctcaatctc aacacacttt 240
tgctaactca ggcctgtcgc tgacattgcc ctcatcggtc tcgccgtcat gggccagaac 300
ctgatcctca acatggccga ccacggtaag tatcaattga ctcaagacgc accagcaaga 360
tacagagcat acccagcaat cgctcctctg ataatcgcca ttgtaacact acgttggtta 420
gattgatcta aggtcgttgc tggttccatg cacttccact tgctcatatg aagggagtca 480
aactctattt tgatagtgtc ctctcccatc cccgaaatgt cgcattgttg ctaacaatag 540
gctacgaggt tgttgcctac aaccgaacca cctccaaggt cgaccacttc ctcgagaacg 600
aggccaaggg tgagtatccg tccagctatg ctgtttacag ccattgaccc caccttcccc 660
cacaattgct acgtcaccat taaaaaacaa aattaccggt atcggcaagc tagactttca 720
tgcaacctac gcagggtaac aagttgagtt tcagccgtgc accttacagg aaaaccagtc 780
atacgccgag gcagtgtgaa agcgaaagca cacagcctac ggtgattgat tgcatttttt 840
tgacatagga gggaaacacg tgacatggca agtgcccaac acgaatacta acaaacagga 900
aagtccatta ttggtgctca ctctatcaag gagctgtgtg ctctgctgaa gcgaccccga 960
cgaatcattc tgctcgttaa ggccggtgct gctgtcgatt ctttcatcga acagctcctg 1020
ccctatctcg ataagggtga tatcatcatt gacggtggta actcccactt ccccgactcc 1080
aaccgacgat acgaggagct taacgagaag ggaatcctct ttgttggttc cggtgtttcc 1140
ggcggtgagg agggtgcccg atacggtccc tccatcatgc ccggtggaaa caaggaggcc 1200
tggccccaca ttaagaagat tttccaggac atctctgcta aggctgatgg tgagccctgc 1260
tgtgactggg tcggtgacgc tggtgccggc cactttgtca agatggttca caacggtatt 1320
gagtatggtg acatgcagct tatctgcgag gcttacgacc tcatgaagcg aggtgctggt 1380
ttcaccaatg aggagattgg agacgttttc gccaagtgga acaacggtat cctcgactcc 1440
ttcctcattg agatcacccg agacatcttc aagtacgacg acggctctgg aactcctctc 1500
gttgagaaga tctccgacac tgctggccag aagggtactg gaaagtggac cgctatcaac 1560
gctcttgacc ttggtatgcc cgtcaccctg atcggtgagg ccgtcttcgc tcgatgcctt 1620
tctgccctca agcaggagcg tgtccgagct tccaaggttc ttgatggccc cgagcccgtc 1680
aagttcactg gtgacaagaa ggagtttgtc gaccagctcg agcaggccct ttacgcctcc 1740
aagatcatct cttacgccca gggtttcatg cttatccgag aggccgccaa gacctacggc 1800
tgggagctca acaacgccgg tattgccctc atgtggcgag gtggttgcat catccgatcc 1860
gtcttccttg ctgacatcac caaggcttac cgacaggacc ccaacctcga gaacctgctg 1920

-continued

```
ttcaacgact tcttcaagaa cgccatctcc aaggccaacc cctcttggcg agctaccgtg   1980

gccaaggctg tcacctgggg tgttcccact cccgcctttg cctcggctct ggctttctac   2040

gacggttacc gatctgccaa gctccccgct aacctgctcc aggcccagcg agactacttc   2100

ggcgcccaca cctaccagct cctcgatggt gatggaaagt ggatccacac caactggacc   2160

ggccgaggtg gtgaggtttc ttcttccact tacgatgctt aa                      2202
```

<210> SEQ ID NO 155
<211> LENGTH: 489
<212> TYPE: PRT
<213> ORGANISM: Yarrowia lipolytica
<300> PUBLICATION INFORMATION:
<308> DATABASE ACCESSION NUMBER: YALI0B15598g

<400> SEQUENCE: 155

```
Met Thr Asp Thr Ser Asn Ile Lys Pro Val Ala Asp Ile Ala Leu Ile
1               5                   10                  15

Gly Leu Ala Val Met Gly Gln Asn Leu Ile Leu Asn Met Ala Asp His
            20                  25                  30

Gly Tyr Glu Val Val Ala Tyr Asn Arg Thr Thr Ser Lys Val Asp His
        35                  40                  45

Phe Leu Glu Asn Glu Ala Lys Gly Lys Ser Ile Ile Gly Ala His Ser
    50                  55                  60

Ile Lys Glu Leu Cys Ala Leu Leu Lys Arg Pro Arg Arg Ile Ile Leu
65                  70                  75                  80

Leu Val Lys Ala Gly Ala Ala Val Asp Ser Phe Ile Glu Gln Leu Leu
                85                  90                  95

Pro Tyr Leu Asp Lys Gly Asp Ile Ile Ile Asp Gly Gly Asn Ser His
            100                 105                 110

Phe Pro Asp Ser Asn Arg Arg Tyr Glu Glu Leu Asn Glu Lys Gly Ile
        115                 120                 125

Leu Phe Val Gly Ser Gly Val Ser Gly Gly Glu Glu Gly Ala Arg Tyr
    130                 135                 140

Gly Pro Ser Ile Met Pro Gly Gly Asn Lys Glu Ala Trp Pro His Ile
145                 150                 155                 160

Lys Lys Ile Phe Gln Asp Ile Ser Ala Lys Ala Asp Gly Glu Pro Cys
                165                 170                 175

Cys Asp Trp Val Gly Asp Ala Gly Ala Gly His Phe Val Lys Met Val
            180                 185                 190

His Asn Gly Ile Glu Tyr Gly Asp Met Gln Leu Ile Cys Glu Ala Tyr
        195                 200                 205

Asp Leu Met Lys Arg Gly Ala Gly Phe Thr Asn Glu Glu Ile Gly Asp
    210                 215                 220

Val Phe Ala Lys Trp Asn Asn Gly Ile Leu Asp Ser Phe Leu Ile Glu
225                 230                 235                 240

Ile Thr Arg Asp Ile Phe Lys Tyr Asp Asp Gly Ser Gly Thr Pro Leu
                245                 250                 255

Val Glu Lys Ile Ser Asp Thr Ala Gly Gln Lys Gly Thr Gly Lys Trp
            260                 265                 270

Thr Ala Ile Asn Ala Leu Asp Leu Gly Met Pro Val Thr Leu Ile Gly
        275                 280                 285

Glu Ala Val Phe Ala Arg Cys Leu Ser Ala Leu Lys Gln Glu Arg Val
    290                 295                 300

Arg Ala Ser Lys Val Leu Asp Gly Pro Glu Pro Val Lys Phe Thr Gly
305                 310                 315                 320
```

-continued

```
Asp Lys Lys Glu Phe Val Asp Gln Leu Glu Gln Ala Leu Tyr Ala Ser
                325                 330                 335

Lys Ile Ile Ser Tyr Ala Gln Gly Phe Met Leu Ile Arg Glu Ala Ala
            340                 345                 350

Lys Thr Tyr Gly Trp Glu Leu Asn Asn Ala Gly Ile Ala Leu Met Trp
        355                 360                 365

Arg Gly Gly Cys Ile Ile Arg Ser Val Phe Leu Ala Asp Ile Thr Lys
    370                 375                 380

Ala Tyr Arg Gln Asp Pro Asn Leu Glu Asn Leu Leu Phe Asn Asp Phe
385                 390                 395                 400

Phe Lys Asn Ala Ile Ser Lys Ala Asn Pro Ser Trp Arg Ala Thr Val
                405                 410                 415

Ala Lys Ala Val Thr Trp Gly Val Pro Thr Pro Ala Phe Ala Ser Ala
            420                 425                 430

Leu Ala Phe Tyr Asp Gly Tyr Arg Ser Ala Lys Leu Pro Ala Asn Leu
        435                 440                 445

Leu Gln Ala Gln Arg Asp Tyr Phe Gly Ala His Thr Tyr Gln Leu Leu
    450                 455                 460

Asp Gly Asp Gly Lys Trp Ile His Thr Asn Trp Thr Gly Arg Gly Gly
465                 470                 475                 480

Glu Val Ser Ser Ser Thr Tyr Asp Ala
                485
```

<210> SEQ ID NO 156
<211> LENGTH: 1742
<212> TYPE: DNA
<213> ORGANISM: Yarrowia lipolytica
<300> PUBLICATION INFORMATION:
<308> DATABASE ACCESSION NUMBER: YALI0D06303g

<400> SEQUENCE: 156

```
atgctcaacc ttagaaccgc ccttcgagct gtgcgacccg tcactctggt gagtatctcg     60

gagcccggga cggctaccaa cacacaagca agatgcaaca gaaaccggac tttttaaatg    120

cggattgcgg aaaatttgca tggcggcaac gactcggaga aggagcggga caattgcaat    180

ggcaggatgc cattgacgaa ctgagggtga tgagagaccg ggcctccgat gacgtggtgg    240

tgacgacagc ccggctggtg ttgccgggac tgtctctgaa aagcaatttc tctatctccg    300

gtctcaacag actccccttc tctagctcaa ttggcattgt cttcagaagg tgtcttagtg    360

gtatccccat tgttatcttc ttttccccaa tgtcaatgtc aatgtcaatg gctccgacct    420

ctttcacatt aacacggcgc aaacacagat accacggaac cgactcaaac aaatccaaag    480

agacgcagcg gaataattgg catcaacgaa cgatttggga tactctggcg agaatgccga    540

aatatttcgc ttgtcttgtt gtttctcttg agtgagttgt ttgtgaagtc gtttggaaga    600

aggttcccaa tgtcacaaac cataccaact cgttacagcc agcttgtaat cccccacctc    660

ttcaatacat actaacgcag acccgatcct acgccacttc cgtggcctct ttcaccggcc    720

agaagaactc caacggcaag tacactgtgt ctctgattga gggagacggt atcggaaccg    780

agatctccaa ggctgtcaag gacatctacc atgccgccaa ggtccccatc gactgggagg    840

ttgtcgacgt cacccccact ctggtcaacg gcaagaccac catccccgac agcgccattg    900

agtccatcaa ccgaaacaag gttgccctca agggtcccct cgccaccccc atcggtaagg    960

gccacgtttc catgaacctg actctgcgac gaaccttcaa cctgttcgcc aacgtccgac   1020

cttgcaagtc cgtcgtgggc tacaagaccc cttacgagaa cgtcgacacc ctgctcatcc   1080

gagagaacac tgagggtgag tactccggta tcgagcacac cgtcgtcccc ggtgtcgttc   1140
```

```
agtccatcaa gctgatcacc cgagaggctt ccgagcgagt catccggtac gcttacgagt   1200

acgccctgtc ccgaggcatg aagaaggtcc ttgttgtcca caaggcctct attatgaagg   1260

tctccgatgg tcttttcctt gaggttgctc gagagctcgc caaggagtac ccctccattg   1320

acctttccgt cgagctgatc gacaacacct gtctgcgaat ggtccaggac cccgctctct   1380

accgagatgt cgtcatggtc atgcccaacc tttacggtga cattctgtcc gatcttgcct   1440

ccggtcttat cggtggtctt ggtctgaccc cctccggtaa catgggtgac gaggtctcca   1500

tcttcgaggc cgtccacgga tccgctcccg acattgctgg caagggtctt gctaacccca   1560

ctgctctgct gctctcctcc gtgatgatgc tgcgacacat gggtctcaac gacaacgcca   1620

ccaacatcga gcaggccgtc tttggcacca ttgcttccgg ccccgagaac cgaaccaagg   1680

atcttaaggg taccgccacc acttctcact ttgctgagca gattatcaag cgactcaagt   1740

ag                                                                  1742
```

```
<210> SEQ ID NO 157
<211> LENGTH: 369
<212> TYPE: PRT
<213> ORGANISM: Yarrowia lipolytica
<300> PUBLICATION INFORMATION:
<308> DATABASE ACCESSION NUMBER: YALI0D06303g

<400> SEQUENCE: 157

Met Leu Asn Leu Arg Thr Ala Leu Arg Ala Val Arg Pro Val Thr Leu
1               5                   10                  15

Thr Arg Ser Tyr Ala Thr Ser Val Ala Ser Phe Thr Gly Gln Lys Asn
            20                  25                  30

Ser Asn Gly Lys Tyr Thr Val Ser Leu Ile Glu Gly Asp Gly Ile Gly
        35                  40                  45

Thr Glu Ile Ser Lys Ala Val Lys Asp Ile Tyr His Ala Ala Lys Val
    50                  55                  60

Pro Ile Asp Trp Glu Val Val Asp Val Thr Pro Thr Leu Val Asn Gly
65                  70                  75                  80

Lys Thr Thr Ile Pro Asp Ser Ala Ile Glu Ser Ile Asn Arg Asn Lys
                85                  90                  95

Val Ala Leu Lys Gly Pro Leu Ala Thr Pro Ile Gly Lys Gly His Val
            100                 105                 110

Ser Met Asn Leu Thr Leu Arg Arg Thr Phe Asn Leu Phe Ala Asn Val
        115                 120                 125

Arg Pro Cys Lys Ser Val Val Gly Tyr Lys Thr Pro Tyr Glu Asn Val
    130                 135                 140

Asp Thr Leu Leu Ile Arg Glu Asn Thr Glu Gly Glu Tyr Ser Gly Ile
145                 150                 155                 160

Glu His Thr Val Val Pro Gly Val Val Gln Ser Ile Lys Leu Ile Thr
                165                 170                 175

Arg Glu Ala Ser Glu Arg Val Ile Arg Tyr Ala Tyr Glu Tyr Ala Leu
            180                 185                 190

Ser Arg Gly Met Lys Lys Val Leu Val Val His Lys Ala Ser Ile Met
        195                 200                 205

Lys Val Ser Asp Gly Leu Phe Leu Glu Val Ala Arg Glu Leu Ala Lys
    210                 215                 220

Glu Tyr Pro Ser Ile Asp Leu Ser Val Glu Leu Ile Asp Asn Thr Cys
225                 230                 235                 240

Leu Arg Met Val Gln Asp Pro Ala Leu Tyr Arg Asp Val Val Met Val
                245                 250                 255
```

```
Met Pro Asn Leu Tyr Gly Asp Ile Leu Ser Asp Leu Ala Ser Gly Leu
            260                 265                 270

Ile Gly Gly Leu Gly Leu Thr Pro Ser Gly Asn Met Gly Asp Glu Val
        275                 280                 285

Ser Ile Phe Glu Ala Val His Gly Ser Ala Pro Asp Ile Ala Gly Lys
    290                 295                 300

Gly Leu Ala Asn Pro Thr Ala Leu Leu Leu Ser Ser Val Met Met Leu
305                 310                 315                 320

Arg His Met Gly Leu Asn Asp Asn Ala Thr Asn Ile Glu Gln Ala Val
                325                 330                 335

Phe Gly Thr Ile Ala Ser Gly Pro Glu Asn Arg Thr Lys Asp Leu Lys
            340                 345                 350

Gly Thr Ala Thr Thr Ser His Phe Ala Glu Gln Ile Ile Lys Arg Leu
        355                 360                 365

Lys


<210> SEQ ID NO 158
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR Primer MO5651

<400> SEQUENCE: 158

cacaaactag tgtcaggaat atgaaaccag g                                    31


<210> SEQ ID NO 159
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO5652

<400> SEQUENCE: 159

cacaaactag tgcatgtgat aggaaggagg a                                    31


<210> SEQ ID NO 160
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4814

<400> SEQUENCE: 160

cacaacgtct ctctagacac aaaaatgagc t                                    31


<210> SEQ ID NO 161
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: PCR primer MO4816
```

-continued

<400> SEQUENCE: 161
cacaacgtct cagccggcac ctgctcccat agaatctcg 39

<210> SEQ ID NO 162
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: PCR primer MO5060

<400> SEQUENCE: 162
cacaagaaga caacggcgca ggagccatgg accctaccgg agacg 45

<210> SEQ ID NO 163
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: PCR primer MO5061

<400> SEQUENCE: 163
cacaagaaga caacgcgttt aagggccggt tctctttc 38

<210> SEQ ID NO 164
<211> LENGTH: 1326
<212> TYPE: DNA
<213> ORGANISM: Ostreococcus lucimarinus

<400> SEQUENCE: 164
atgaaggatg atcgcgaatg gattgcgttt caacagcgca aggtgtttag tgagcaaaag 60
caaatcaaag agtacctcag tgctttgaac gaccgcgaca aggtcgacgt tctcgttgtc 120
ggtgcgggcc ccgcaggtct ggcgatcgca gcggagacgg cgaagaaggg tctttctgtt 180
ggtctcgtcg caccagacac cccgttcgtg aacaactacg gagtatggct cgacgagttc 240
aaagatctag ggctcgaaca ctgcttgctt cataagtatg acgacgcatt ggtttggttc 300
gatgattctg atcctgcgag tggaactgaa ctcggtcgac cttacggtca agtgtgccgc 360
aggcgtcttc gcgaccattt gttgaaggag tgcgcggcgg ctggcgtcaa gtatttacca 420
ggcctggtag attttgtgcg tcacggtgac gtcgaaaaga acgagttagc cgaagcaaac 480
agaggccagc aattcacgtt gaattcgcgt ctcgtcgttg ccggcaccgg tcacaaccgc 540
gacatgctca gctacgaaga gggtgcgccg ccgggctggc agactgcgta tggcgttgag 600
gtgcgcattc cgaaccacgg ttttcccgtg aacaaggccg tgttcatgga ttttcgtcaa 660
agcgatccgg aggcgatgaa agaggaacaa gacgagggcg tttggcgcgt gccgtctttc 720
ctttacgtgt tacccgtgga caaggatgtg gtgttcgtcg aggagacgtg cctcgtcgcg 780
cgcgtacaag tgccgttcga tgaactcaaa cggcgattgt atcgtcgtat gaagcggatg 840
ggtatggaaa tcgtcgaaga agacatcttg gaagtcgagg cgagttggat tccactgggc 900
ggtaccccgc cggttgcccc gcaacgcacc atcgcgtacg gtgcagcagc cggcatggtc 960
caccctgcgt ctggctactc cgtcgtaaac agtattagca aagctccgcg tgttgcgacg 1020
gccatggccg aaggcttgaa ggagggtggc gagattgagg cgagccgaag agcgtgggaa 1080
atcctttggg gtgcggagcc acgaagacaa atcggtttct accagttcgg tatggagctt 1140

```
ctcatgtcgc ttcgcatcga gcagatgcgc aacttcttta gtaccttctt tgcgcttcca   1200

acaaatctga gcagaggatt tttgggtaac agattgtcga gctcagagtt gatcatgttt   1260

gctctcacta cgttcgcaat tggtaacaac gaacttcgtg ggttgttgct cgctcacctg   1320

gtttca                                                              1326


<210> SEQ ID NO 165
<211> LENGTH: 442
<212> TYPE: PRT
<213> ORGANISM: Ostreococcus lucimarinus

<400> SEQUENCE: 165

Met Lys Asp Asp Arg Glu Trp Ile Ala Phe Gln Gln Arg Lys Val Phe
1               5                   10                  15

Ser Glu Gln Lys Gln Ile Lys Glu Tyr Leu Ser Ala Leu Asn Asp Arg
            20                  25                  30

Asp Lys Val Asp Val Leu Val Val Gly Ala Gly Pro Ala Gly Leu Ala
        35                  40                  45

Ile Ala Ala Glu Thr Ala Lys Lys Gly Leu Ser Val Gly Leu Val Ala
    50                  55                  60

Pro Asp Thr Pro Phe Val Asn Asn Tyr Gly Val Trp Leu Asp Glu Phe
65                  70                  75                  80

Lys Asp Leu Gly Leu Glu His Cys Leu Leu His Lys Tyr Asp Asp Ala
                85                  90                  95

Leu Val Trp Phe Asp Asp Ser Asp Pro Ala Ser Gly Thr Glu Leu Gly
            100                 105                 110

Arg Pro Tyr Gly Gln Val Cys Arg Arg Arg Leu Arg Asp His Leu Leu
        115                 120                 125

Lys Glu Cys Ala Ala Ala Gly Val Lys Tyr Leu Pro Gly Leu Val Asp
    130                 135                 140

Phe Val Arg His Gly Asp Val Glu Lys Asn Glu Leu Ala Glu Ala Asn
145                 150                 155                 160

Arg Gly Gln Gln Phe Thr Leu Asn Ser Arg Leu Val Val Ala Gly Thr
                165                 170                 175

Gly His Asn Arg Asp Met Leu Ser Tyr Glu Glu Gly Ala Pro Pro Gly
            180                 185                 190

Trp Gln Thr Ala Tyr Gly Val Glu Val Arg Ile Pro Asn His Gly Phe
        195                 200                 205

Pro Val Asn Lys Ala Val Phe Met Asp Phe Arg Gln Ser Asp Pro Glu
    210                 215                 220

Ala Met Lys Glu Glu Gln Asp Glu Gly Val Trp Arg Val Pro Ser Phe
225                 230                 235                 240

Leu Tyr Val Leu Pro Val Asp Lys Asp Val Val Phe Val Glu Glu Thr
                245                 250                 255

Cys Leu Val Ala Arg Val Gln Val Pro Phe Asp Glu Leu Lys Arg Arg
            260                 265                 270

Leu Tyr Arg Arg Met Lys Arg Met Gly Met Glu Ile Val Glu Glu Asp
        275                 280                 285

Ile Leu Glu Val Glu Ala Ser Trp Ile Pro Leu Gly Gly Thr Pro Pro
    290                 295                 300

Val Ala Pro Gln Arg Thr Ile Ala Tyr Gly Ala Ala Ala Gly Met Val
305                 310                 315                 320

His Pro Ala Ser Gly Tyr Ser Val Val Asn Ser Ile Ser Lys Ala Pro
                325                 330                 335

Arg Val Ala Thr Ala Met Ala Glu Gly Leu Lys Glu Gly Gly Glu Ile
```

```
        340                 345                 350

Glu Ala Ser Arg Arg Ala Trp Glu Ile Leu Trp Gly Ala Glu Pro Arg
        355                 360                 365

Arg Gln Ile Gly Phe Tyr Gln Phe Gly Met Glu Leu Leu Met Ser Leu
    370                 375                 380

Arg Ile Glu Gln Met Arg Asn Phe Phe Ser Thr Phe Phe Ala Leu Pro
385                 390                 395                 400

Thr Asn Leu Ser Arg Gly Phe Leu Gly Asn Arg Leu Ser Ser Ser Glu
                405                 410                 415

Leu Ile Met Phe Ala Leu Thr Thr Phe Ala Ile Gly Asn Asn Glu Leu
            420                 425                 430

Arg Gly Leu Leu Leu Ala His Leu Val Ser
        435                 440
```

<210> SEQ ID NO 166
<211> LENGTH: 642
<212> TYPE: DNA
<213> ORGANISM: Diospyros kaki
<220> FEATURE:
<223> OTHER INFORMATION: Lycopene epsilon cyclase

<400> SEQUENCE: 166

```
actacggcgt atgggaggat gaatttagag atcttggact tgaaaggtgt attgaacatg      60

tttggagaga cacaattgta tatcttgatg acaatgatcc cattctgatt ggtcgtgctt     120

atggacgagt tagtcgtcac ttgctccacg aggagctatt aagaaggtgt gtggagtcag     180

gtgtttcata tttgagctca aaagtggaaa gaattattga aactacgaat gggcagagtc     240

tcatagagtg cggaactgat gttgttgtcc catgcaggct tgctactgtt gcttcgggag     300

cagcttctgg gaaacttttg aagtttgagg tgggaggacc cagagtttct gttcaaacag     360

cttatggtgt ggaggttgag gtggaaaaca atccatatga ccccaacttg atggttttca     420

tggattacag agactatgcc aaacaaaaag ttcagccttt ggaagcacaa tatccaacat     480

ttctttatgc catgcctatg tcccctacaa gagtcttctt tgaggaaact tgtttggctt     540

caaaggatgc catgcctttt gatctattaa agaggaaact catggacaga ttagagacaa     600

tgggagtcca tgttctaaaa acgtatgagg aggaatggtc tt                        642
```

<210> SEQ ID NO 167
<211> LENGTH: 213
<212> TYPE: PRT
<213> ORGANISM: Diospyros kaki
<220> FEATURE:
<223> OTHER INFORMATION: Lycopene epsilon cyclase

<400> SEQUENCE: 167

```
Tyr Gly Val Trp Glu Asp Glu Phe Arg Asp Leu Gly Leu Glu Arg Cys
1               5                   10                  15

Ile Glu His Val Trp Arg Asp Thr Ile Val Tyr Leu Asp Asp Asn Asp
            20                  25                  30

Pro Ile Leu Ile Gly Arg Ala Tyr Gly Arg Val Ser Arg His Leu Leu
        35                  40                  45

His Glu Glu Leu Leu Arg Arg Cys Val Glu Ser Gly Val Ser Tyr Leu
    50                  55                  60

Ser Ser Lys Val Glu Arg Ile Ile Glu Thr Thr Asn Gly Gln Ser Leu
65                  70                  75                  80

Ile Glu Cys Gly Thr Asp Val Val Val Pro Cys Arg Leu Ala Thr Val
                85                  90                  95
```

```
Ala Ser Gly Ala Ala Ser Gly Lys Leu Leu Lys Phe Glu Val Gly Gly
            100                 105                 110

Pro Arg Val Ser Val Gln Thr Ala Tyr Gly Val Glu Val Glu Val Glu
        115                 120                 125

Asn Asn Pro Tyr Asp Pro Asn Leu Met Val Phe Met Asp Tyr Arg Asp
    130                 135                 140

Tyr Ala Lys Gln Lys Val Gln Pro Leu Glu Ala Gln Tyr Pro Thr Phe
145                 150                 155                 160

Leu Tyr Ala Met Pro Met Ser Pro Thr Arg Val Phe Phe Glu Glu Thr
                165                 170                 175

Cys Leu Ala Ser Lys Asp Ala Met Pro Phe Asp Leu Leu Lys Arg Lys
            180                 185                 190

Leu Met Asp Arg Leu Glu Thr Met Gly Val His Val Leu Lys Thr Tyr
        195                 200                 205

Glu Glu Glu Trp Ser
    210


<210> SEQ ID NO 168
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Ostreococcus lucimarinus sequence

<400> SEQUENCE: 168

ttctagaaca aaatgaagga cgaccgagag tggatcgcct tccagcagcg aaaggtgttc     60

tctgagcaga agcagatcaa ggagtacctg tctgccctga acgaccgaga caaggtggac    120

gtgctggtgg tgggcgccgg ccccgccggc ctggccatcg ccgccgagac cgccaagaag    180

ggcctgtctg tgggcctggt ggcccccgac accccccttcg tgaacaacta cggcgtgtgg    240

ctggacgagt tcaaggacct gggcctggag cactgtctgc tgcacaagta cgacgacgcc    300

ctggtgtggt tcgacgactc tgaccccgcc tctggcaccg agctgggccg accctacggc    360

caggtgtgtc gacgacgact gcgagaccac ctgctgaagg agtgtgccgc cgccggcgtg    420

aagtacctgc ccggcctggt ggacttcgtg cgacacggcg acgtggagaa gaacgagctg    480

gccgaggcca accgaggcca gcagttcacc ctgaactctc gactggtggt ggccggcacc    540

ggccacaacc gagacatgct gtcttacgag gagggcgccc cccccggctg gcagaccgcc    600

tacggcgtgg aggtgcgaat ccccaaccac ggcttccccg tgaacaaggc cgtgttcatg    660

gacttccgac agtctgaccc cgaggccatg aaggaggagc aggacgaggg cgtgtggcga    720

gtgccctctt tcctgtacgt gctgcccgtg gacaaggacg tggtgttcgt ggaggagacc    780

tgtctggtgg cccgagtgca ggtgcccttc gacgagctga agcgacgact gtaccgacga    840

atgaagcgaa tgggcatgga gatcgtggag gaggacatcc tggaggtgga ggcctcttgg    900

atccccctgg gcggcacccc ccccgtggcc ccccagcgaa ccatcgccta cggcgccgcc    960

gccggcatgg tgcaccccgc ctctggctac tctgtggtga actctatctc taaggccccc   1020

cgagtggcca ccgccatggc cgagggcctg aaggagggcg gcgagatcga ggcctctcga   1080

cgagcctggg agatcctgtg ggcgccgag ccccgacgac agatcggctt ctaccagttc   1140

ggcatggagc tgctgatgtc tctgcgaatc gagcagatgc gaaacttctt ctctaccttc   1200

ttcgccctgc ccaccaacct gtctcgaggc ttcctgggca accgactgtc ttcttctgag   1260

ctgatcatgt tcgccctgac caccttcgcc atcggcaaca acgagctgcg aggcctgctg   1320
```

ctggcccacc tggtgtctta aacgcgt 1347

<210> SEQ ID NO 169
<211> LENGTH: 1605
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Ostreococcus lucimarinus sequence

<400> SEQUENCE: 169
ttctagaaca aaatgcgagc ccgacgagcc cccgccgccc gagtgacccg agccatccga 60
gcccgaggcg acgccggcac ccgagcccga gacgtggccc ccggcgccac ccgacgaggc 120
gcctctgcca ccccccgagc cacccgacga ccctctgccc gagagacccg acccgagctg 180
tacggcctgg acgcctcttg ggaccccctg acctctggcg accgacgaga gtctgaggag 240
tctcgaaccc ccctgcccga gaccctgccc aacgtgcgat ggggcacctc tgcctctgag 300
gcctacgacc tggtgatcgt gggctgtggc cccgccggcc tgaccgccgc cgacgaggcc 360
tctaagcgag gcctgcgagt ggccctgatg gacccctctc ccctggcccc ctggatgaac 420
aactacggcg tgtggtgtga cgagttcaag tctctgggct tcgacgactg ttaccgagcc 480
gtgtggaaca aggcccgagt gatcatcgac gacggcgacg ccgacggcaa gatgctggac 540
cgagcctacg cccaggtgga ccgaaagaag ctgaagcaga agctgatcgc ccgatctgtg 600
acccagggcg tggagttcgg catcgccgcc gtggactctt gtgacaactc tgaccccaac 660
cactctgtgg tgaccctgtc tgacggccga aaggtgtacg ccaagatggt gctggacgcc 720
accggccact ctcgaaagct ggtggacttc gaccgagact tcacccccgg ctaccaggcc 780
gccttcggca tcgtgtgtac cgtggagaag cacgacttcc ccctggacac catgctgttc 840
atggactggc gagacgagca cctgtctccc gagttcaagc gagccaacga ccgactgccc 900
accttcctgt acgccatgcc cttctctgag accgaggtgt tcctggagga gacctctctg 960
gtggcccgac ccggcctgga gttcgacgac ctgaagctga agctgaagga gcgactggac 1020
tacctgggcg tgaaggtgac caaggtgcac gaggaggagt actgtctgat ccccatgggc 1080
ggcgtgctgc ccaccttccc ccagcgaacc ctgggcatcg gcggcaccgc cggcatggtg 1140
cacccctcta ccggcttcat ggtggccaag accatgctgt gtgtgcgaac cctggtgggc 1200
accctggacg aggccctgaa ggccggcaag cgaggcgaca tcaccggcgc cctggaggcc 1260
gccgaggccg cccagatgaa caacggcaag ttcgacgccg acgccaccgc cgccctggtg 1320
tggaactcta tctggcccga gaacgacctg cgaatgcgaa ccttcatgtg tttcggcatg 1380
gagaccctga tgcagctgga catcgacggc acccgacagt tcttcgacac cttcttcgac 1440
ctgcccaagg acgtgtgggc cggcttcctg tcttggcgaa tccagcccgt gggcctgctg 1500
tctctgggcg tgaacctgtt cgccctgttc tctaactaca tgcgagtgaa cttcgtgaag 1560
tctgccctgc ccttcatggg ctctttcttc gccaactaaa cgcgt 1605

<210> SEQ ID NO 170
<211> LENGTH: 915
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Y. lipolytica codon biased putative carotene epsilon hydroxylase from Ostreococcus tauri

<400> SEQUENCE: 170

```
ttctagaaca aaatgaagga cggccaggac gaggactctg acgagatctg gggcggccag     60
cgacacgcct ctgagatgaa gacccccacc cgacgaaagg cccgaaccaa ggccgagcga    120
gaggcctctg ccgcctctta cgagtggtct gcctgggcct cttcttgtgg cgtgatctct    180
gtggccatca ccgccaccta cttccgaatc ctgcgagagg tggacgtgaa cggcggcgtg    240
ttccccgtgg ccgagctggt ggcccagctg gccctgatcg ccggcgccgc cgtgggcatg    300
gagttctacg cccgatacgc ccacaagcac ctgtggcacg gctcttggtg gaccatgtct    360
aacaagtacc gacaggagtg gaaccgaccc atctggctgc tgcacgagtc tcaccacctg    420
ccccgagagg gcgccttcga ggccaacgac gtgttcgccc tgatgaacgg cgtgcccgcc    480
ttcgccctgt gtgccttcgg cttcttcacc cccggcgtgt tcggcggcct gtgtttcggc    540
gccggcctgg gcatcaccct gttcggcatc gcctacatgt acgtgcacga cggcctggtg    600
cacaagcgat tccccaccgg ccccctgggc aagctgcccg tgatgcgacg aatcgccgcc    660
ggccacacca tccaccacac cgaggccttc gagggcgtgc cctggggcct gttcctgggc    720
atccaggagc tggccgccgt gcccggcggc ctggaggagc tggagaaggt ggtgatcgcc    780
gccgagcgaa aggagaagcg agacgagctg gagctggccc gacgagcctc tgtgggcctg    840
gtgaccgagg gcgcccacat cccctctatg aaggaggccc cccagtgtaa gctgcccgag    900
gacccctaaa cgcgt                                                     915
```

<210> SEQ ID NO 171
<211> LENGTH: 34
<212> TYPE: PRT
<213> ORGANISM: Yarrowia lipolytica

<400> SEQUENCE: 171

```
Met Leu Ser Arg Asn Leu Ser Lys Phe Ala Arg Ala Gly Leu Ile Arg
1               5                   10                  15

Pro Ala Thr Thr Ser Thr His Thr Arg Leu Phe Ser Val Ser Ala Arg
            20                  25                  30

Arg Leu
```

<210> SEQ ID NO 172
<211> LENGTH: 32
<212> TYPE: PRT
<213> ORGANISM: Yarrowia lipolytica

<400> SEQUENCE: 172

```
Met Leu Arg Leu Ile Arg Pro Arg Leu Ala Ala Leu Ala Arg Pro Thr
1               5                   10                  15

Thr Arg Ala Pro Gln Ala Leu Asn Ala Arg Thr His Ile Val Ser Val
            20                  25                  30
```

<210> SEQ ID NO 173
<211> LENGTH: 53
<212> TYPE: PRT
<213> ORGANISM: Saccharomyces cerevisiae

<400> SEQUENCE: 173

```
Met Phe Gln Arg Ser Gly Ala Ala His His Ile Lys Leu Ile Ser Ser
1               5                   10                  15

Arg Arg Cys Arg Phe Lys Ser Ser Phe Ala Val Ala Leu Asn Ala Ala
            20                  25                  30
```

```
Ser Lys Leu Val Thr Pro Lys Ile Leu Trp Asn Asn Pro Ile Ser Leu
        35                  40                  45

Val Ser Lys Glu Met
    50


<210> SEQ ID NO 174
<211> LENGTH: 77
<212> TYPE: PRT
<213> ORGANISM: Yarrowia lipolytica

<400> SEQUENCE: 174

Met Leu Arg Val Gly Arg Ile Gly Thr Lys Thr Leu Ala Ser Ser Ser
1               5                   10                  15

Leu Arg Phe Val Ala Gly Ala Arg Pro Lys Ser Thr Leu Thr Glu Ala
            20                  25                  30

Val Leu Glu Thr Thr Gly Leu Leu Lys Thr Thr Pro Gln Asn Pro Glu
        35                  40                  45

Trp Ser Gly Ala Val Lys Gln Ala Ser Arg Leu Val Glu Thr Asp Thr
    50                  55                  60

Pro Ile Arg Asp Pro Phe Ser Ile Val Ser Gln Glu Met
65                  70                  75


<210> SEQ ID NO 175
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric sequence containing Parvularcula
      bermudensis sequence

<400> SEQUENCE: 175

Met Ser Trp Trp Ala Ile Ala Leu Ile Val Phe Gly Ala Val Val Gly
1               5                   10                  15

Met Glu Phe Phe Ala Trp Phe Ala His Lys Tyr Ile Met His Gly Trp
            20                  25                  30

Gly Trp Ser Trp His Arg Asp His His Glu Pro His Asp Asn Thr Leu
        35                  40                  45

Glu Lys Asn Asp Leu Phe Ala Val Val Phe Gly Ser Val Ala Ala Leu
    50                  55                  60

Leu Phe Val Ile Gly Ala Leu Trp Ser Asp Pro Leu Trp Trp Ala Ala
65                  70                  75                  80

Val Gly Ile Thr Leu Tyr Gly Val Ile Tyr Thr Leu Val His Asp Gly
                85                  90                  95

Leu Val His Gln Arg Tyr Trp Arg Trp Thr Pro Lys Arg Gly Tyr Ala
            100                 105                 110

Lys Arg Leu Val Gln Ala His Arg Leu His His Ala Thr Val Gly Lys
        115                 120                 125

Glu Gly Gly Val Ser Phe Gly Phe Val Phe Ala Arg Asp Pro Ala Lys
    130                 135                 140

Leu Lys Ala Glu Leu Lys Gln Gln Arg Glu Gln Gly Leu Ala Val Val
145                 150                 155                 160

Arg Asp Ser Met Gly Ala Gly Ala Gly Ala Gly Ala Met Asp Pro Thr
                165                 170                 175

Gly Asp Val Thr Ala Ser Pro Arg Pro Gln Thr Thr Ile Pro Val Arg
            180                 185                 190

Gln Ala Leu Trp Gly Leu Ser Leu Ala Gly Ala Ile Ile Ala Ala Trp
```

```
        195                 200                 205

Val Phe Met His Ile Gly Phe Val Phe Phe Ala Pro Leu Asp Pro Ile
    210                 215                 220

Val Leu Ala Leu Ala Pro Val Ile Ile Leu Leu Gln Ser Trp Leu Ser
225                 230                 235                 240

Val Gly Leu Phe Ile Ile Ser His Asp Ala Ile His Gly Ser Leu Ala
                245                 250                 255

Pro Gly Arg Pro Ala Phe Asn Arg Ala Met Gly Arg Leu Cys Met Thr
            260                 265                 270

Leu Tyr Ala Gly Phe Asp Phe Asp Arg Met Ala Ala Ala His His Arg
        275                 280                 285

His His Arg Ser Pro Gly Thr Ala Ala Asp Pro Asp Phe Ser Val Asp
    290                 295                 300

Ser Pro Asp Arg Pro Leu Pro Trp Phe Gly Ala Phe Phe Arg Arg Tyr
305                 310                 315                 320

Phe Gly Trp Arg Pro Phe Leu Thr Val Asn Ala Val Val Phe Thr Tyr
                325                 330                 335

Trp Leu Val Leu Gly Ala Asn Pro Val Asn Ile Val Leu Phe Tyr Gly
            340                 345                 350

Val Pro Ala Leu Leu Ser Ala Gly Gln Leu Phe Tyr Phe Gly Thr Phe
        355                 360                 365

Leu Pro His Arg His Glu Arg Gln Gly Phe Ala Asp His His Arg Ala
    370                 375                 380

Arg Ser Val Arg Ser Pro Tyr Met Leu Ser Leu Val Thr Cys Tyr His
385                 390                 395                 400

Phe Gly Gly Tyr His His Glu His His Leu Phe Pro His Glu Pro Trp
                405                 410                 415

Trp Arg Leu Pro Gln Arg Gly Gly Trp Glu Arg Asp Arg Arg Lys Arg
            420                 425                 430

Thr Gly Pro
        435


<210> SEQ ID NO 176
<211> LENGTH: 1124
<212> TYPE: PRT
<213> ORGANISM: Aspergillus nidulans

<400> SEQUENCE: 176

Met Ala Ser Val Leu Ile Arg Arg Lys Phe Gly Thr Glu Gly Gly Ser
1               5                   10                  15

Asp Ala Glu Pro Ser Trp Leu Lys Arg Gln Val Thr Gly Cys Leu Gln
            20                  25                  30

Ser Ile Ser Arg Arg Ala Cys Ile His Pro Ile His Thr Ile Val Val
        35                  40                  45

Ile Ala Leu Leu Ala Ser Thr Thr Tyr Val Gly Leu Leu Glu Gly Ser
    50                  55                  60

Leu Phe Asp Ser Phe Arg Asn Ser Asn Asn Val Ala Gly His Val Asp
65                  70                  75                  80

Val Asp Ser Leu Leu Leu Gly Asn Arg Ser Leu Arg Leu Gly Glu Gly
                85                  90                  95

Thr Ser Trp Lys Trp Gln Val Glu Asp Ser Leu Asn Gln Asp Asp Gln
            100                 105                 110

Lys Val Gly Asn Pro Glu Leu Lys Arg Glu Val Asp Gln His Leu Ala
        115                 120                 125

Leu Thr Thr Leu Ile Phe Pro Asp Ser Ile Ser Lys Ser Ala Ser Thr
```

```
    130                 135                 140

Ala Pro Ala Ala Asp Ala Leu Pro Val Pro Ala Asn Ala Ser Ala Gln
145                 150                 155                 160

Leu Leu Pro His Thr Pro Asn Leu Phe Ser Pro Phe Ser His Asp Ser
                165                 170                 175

Ser Leu Val Phe Thr Leu Pro Phe Asp Gln Val Pro Gln Phe Leu Arg
            180                 185                 190

Ala Val Gln Glu Leu Pro Asp Pro Thr Leu Glu Asp Asp Glu Gly Glu
        195                 200                 205

Gln Lys Arg Trp Ile Met Arg Ala Thr Arg Gly Pro Val Ser Gly Pro
    210                 215                 220

Asn Gly Thr Ile Ser Ser Trp Leu Ser Asp Ala Trp Ser Ser Phe Val
225                 230                 235                 240

Asp Leu Ile Lys His Ala Glu Thr Ile Asp Ile Ile Ile Met Thr Leu
                245                 250                 255

Gly Tyr Leu Ala Met Tyr Leu Ser Phe Ala Ser Leu Glu Phe Ser Met
            260                 265                 270

Lys Gln Leu Gly Ser Lys Phe Trp Leu Ala Thr Thr Val Leu Phe Ser
        275                 280                 285

Gly Met Phe Ala Phe Leu Phe Gly Leu Leu Val Thr Thr Lys Phe Gly
    290                 295                 300

Val Pro Leu Asn Leu Leu Leu Leu Ser Glu Gly Leu Pro Glu Leu Val
305                 310                 315                 320

Thr Thr Ile Gly Phe Glu Lys Pro Ile Ile Leu Thr Arg Ala Val Leu
                325                 330                 335

Ser Ala Ser Ile Asp Lys Lys Arg Gln Gly Ser Ala Thr Ser Thr Pro
            340                 345                 350

Ser Ser Ile Gln Asp Ser Ile Gln Thr Ala Ile Arg Glu Gln Gly Phe
        355                 360                 365

Glu Ile Ile Arg Asp Tyr Cys Ile Glu Ile Ser Ile Leu Ile Ala Gly
    370                 375                 380

Ala Ala Ser Gly Val Gln Gly Gly Leu Gln Gln Phe Cys Phe Leu Ala
385                 390                 395                 400

Ala Trp Ile Leu Phe Phe Asp Cys Ile Leu Leu Phe Thr Phe Tyr Thr
                405                 410                 415

Thr Ile Leu Cys Ile Lys Leu Glu Ile Thr Arg Ile Arg Arg His Val
            420                 425                 430

Thr Leu Arg Lys Ala Leu Glu Glu Asp Gly Thr Thr Gln Ser Val Ala
        435                 440                 445

Glu Lys Val Ala Ser Ser Asn Asp Trp Phe Gly Ala Gly Ser Asp Asn
    450                 455                 460

Ser Asp Ala Asp Asp Ala Ser Val Phe Gly Arg Lys Ile Lys Ser Asn
465                 470                 475                 480

Asn Val Arg Arg Phe Lys Phe Leu Met Val Gly Gly Phe Val Leu Val
                485                 490                 495

Asn Val Val Asn Met Thr Ala Ile Pro Phe Arg Asn Ser Ser Leu Ser
            500                 505                 510

Pro Leu Cys Asn Val Phe Ser Pro Thr Pro Ile Asp Pro Phe Lys Val
        515                 520                 525

Ala Glu Asn Gly Leu Asp Ala Thr Tyr Val Ser Ala Lys Ser Gln Lys
    530                 535                 540

Leu Glu Leu Val Thr Val Val Pro Pro Ile Lys Val Lys Leu Glu Tyr
545                 550                 555                 560
```

-continued

```
Pro Ser Val His Tyr Ala Lys Leu Gly Glu Ser Gln Ser Ile Glu Ile
                565                 570                 575

Glu Tyr Thr Asp Gln Leu Leu Asp Ala Val Gly Gly His Val Leu Asn
            580                 585                 590

Gly Val Leu Lys Ser Ile Glu Asp Pro Val Ile Ser Lys Trp Ile Thr
        595                 600                 605

Ala Val Leu Thr Ile Ser Ile Val Leu Asn Gly Tyr Leu Phe Asn Ala
    610                 615                 620

Ala Arg Trp Ser Ile Lys Glu Pro Gln Ala Ala Pro Ala Pro Lys Glu
625                 630                 635                 640

Pro Ala Lys Pro Lys Val Tyr Pro Lys Thr Asp Leu Asn Ala Gly Pro
                645                 650                 655

Lys Arg Ser Met Glu Glu Cys Glu Ala Met Leu Lys Ala Lys Lys Ala
            660                 665                 670

Ala Tyr Leu Ser Asp Glu Leu Leu Ile Glu Leu Ser Leu Ser Gly Lys
        675                 680                 685

Leu Pro Gly Tyr Ala Leu Leu Lys Ser Leu Glu Asn Glu Glu Leu Met
    690                 695                 700

Ser Arg Val Asp Ala Phe Leu Arg Ala Val Lys Leu Arg Arg Ala Val
705                 710                 715                 720

Val Ser Arg Thr Pro Ala Thr Ser Ala Val Thr Ser Ser Leu Glu Thr
                725                 730                 735

Ser Lys Leu Pro Tyr Lys Asp Tyr Asn Tyr Ala Leu Val His Gly Ala
            740                 745                 750

Cys Cys Glu Asn Val Ile Gly Thr Leu Pro Leu Pro Leu Gly Val Ala
        755                 760                 765

Gly Pro Leu Val Thr Asp Gly Gln Ser Tyr Phe Ile Pro Met Ala Thr
    770                 775                 780

Ile Glu Gly Val Leu Val Ala Ser Ala Ser Arg Gly Ala Lys Ala Ile
785                 790                 795                 800

Asn Ala Gly Gly Gly Ala Val Ile Val Leu Thr Gly Asp Gly Met Thr
                805                 810                 815

Arg Gly Pro Cys Val Gly Phe Pro Thr Leu Ala Arg Ala Ala Ala Ala
            820                 825                 830

Lys Val Trp Leu Asp Ser Glu Glu Gly Lys Ser Val Met Thr Ala Ala
        835                 840                 845

Phe Asn Ser Thr Ser Arg Phe Ala Arg Leu Gln His Leu Lys Thr Ala
    850                 855                 860

Leu Ala Gly Thr Tyr Leu Tyr Ile Arg Phe Lys Thr Thr Thr Gly Asp
865                 870                 875                 880

Ala Met Gly Met Asn Met Ile Ser Lys Gly Val Glu Lys Ala Leu His
                885                 890                 895

Val Met Ala Thr Glu Cys Gly Phe Asp Asp Met Ala Thr Ile Ser Val
            900                 905                 910

Ser Gly Asn Phe Cys Thr Asp Lys Lys Ala Ala Ala Leu Asn Trp Ile
        915                 920                 925

Asp Gly Arg Gly Lys Ser Val Val Ala Glu Ala Ile Ile Pro Gly Asp
    930                 935                 940

Val Val Arg Asn Val Leu Lys Ser Asp Val Asp Ala Leu Val Glu Leu
945                 950                 955                 960

Asn Thr Ser Lys Asn Leu Ile Gly Ser Ala Met Ala Gly Ser Leu Gly
                965                 970                 975

Gly Phe Asn Ala His Ala Ser Asn Ile Val Thr Ala Ile Phe Leu Ala
            980                 985                 990
```

```
Thr Gly Asp Pro Ala Gln Asn Val  Glu Ser Ser Ser Cys  Ile Thr Thr
        995                 1000                 1005

Met Lys  Asn Thr Asn Gly Asn  Leu Gln Thr Ala Val  Ser Met Pro
    1010                 1015                 1020

Ser Ile  Glu Val Gly Thr Ile  Gly Gly Gly Thr Ile  Leu Glu Ala
    1025                 1030                 1035

Gln Gly  Ala Met Ile Leu Asp  Ile Leu Gly Val Arg  Gly Ser His
    1040                 1045                 1050

Pro Thr  Asn Pro Gly Asp Asn  Ala Arg Gln Leu Ala  Arg Ile Val
    1055                 1060                 1065

Ala Ala  Ala Val Leu Ala Gly  Phe Leu Ser Leu Cys  Ser Ala Leu
    1070                 1075                 1080

Ala Ala  Gly His Leu Val Arg  Ala His Met Ala His  Asn Arg Ser
    1085                 1090                 1095

Ala Ala  Pro Thr Arg Ser Ala  Thr Pro Val Ser Ala  Ala Val Gly
    1100                 1105                 1110

Ala Thr  Arg Gly Leu Ser Met  Thr Ser Ser Arg
    1115                 1120


<210> SEQ ID NO 177
<211> LENGTH: 1210
<212> TYPE: PRT
<213> ORGANISM: Gibberella zeae

<400> SEQUENCE: 177

Met Ala Ser Ile Leu Leu Pro Lys Lys Phe Arg Gly Glu Thr Ala Pro
1               5                   10                  15

Ala Glu Lys Thr Thr Pro Ser Trp Ala Ser Lys Arg Leu Thr Pro Ile
            20                  25                  30

Ala Gln Phe Ile Ser Arg Leu Ala Cys Ser His Pro Ile His Thr Val
        35                  40                  45

Val Leu Val Ala Val Leu Ala Ser Thr Ser Tyr Val Gly Leu Leu Gln
    50                  55                  60

Glu Ser Phe Phe Ser Thr Asp Leu Pro Thr Val Gly Lys Ala Asp Trp
65                  70                  75                  80

Ser Ser Leu Val Glu Gly Ser Arg Val Leu Arg Ala Gly Pro Glu Thr
                85                  90                  95

Ala Trp Asn Trp Lys Ala Ile Glu Gln Asp Ser Ile Gln His Ala Gly
            100                 105                 110

Ala Asp Ala Asp His Leu Ala Leu Leu Thr Leu Val Phe Pro Asp Thr
        115                 120                 125

His Ser Ala Glu Ser Ser Ser Thr Ala Pro Arg Ser Ser His Val Pro
    130                 135                 140

Val Pro Gln Asn Leu Ser Ile Thr Pro Leu Pro Ser Thr Lys Asn Ser
145                 150                 155                 160

Phe Thr Ala Tyr Ser Gln Asp Ser Ile Leu Ala Tyr Ser Leu Pro Tyr
                165                 170                 175

Ala Glu Gly Pro Asp Val Val Gln Trp Ala Asn Asn Ala Trp Thr Glu
            180                 185                 190

Phe Leu Asp Leu Leu Lys Asn Ala Glu Thr Leu Asp Ile Val Ile Met
        195                 200                 205

Phe Leu Gly Tyr Thr Ala Met His Leu Thr Phe Val Ser Leu Phe Leu
    210                 215                 220

Ser Met Arg Lys Ile Gly Ser Lys Phe Trp Leu Gly Ile Cys Thr Leu
225                 230                 235                 240
```

```
Phe Ser Ser Val Phe Ala Phe Leu Phe Gly Leu Ile Val Thr Thr Lys
                245                 250                 255

Leu Gly Val Pro Ile Ser Val Ile Leu Leu Ser Glu Gly Leu Pro Phe
            260                 265                 270

Leu Val Val Thr Ile Gly Phe Glu Lys Asn Ile Val Leu Thr Arg Ala
        275                 280                 285

Val Met Ser His Ala Ile Glu His Arg Arg Gln Ile Gln Asn Ser Lys
    290                 295                 300

Ser Gly Lys Gly Ser Pro Glu Arg Ser Met Gln Asn Val Ile Gln Tyr
305                 310                 315                 320

Ala Val Gln Ser Ala Ile Lys Glu Lys Gly Phe Glu Ile Met Arg Asp
                325                 330                 335

Tyr Ala Ile Glu Ile Val Ile Leu Ala Leu Gly Ala Ala Ser Gly Val
            340                 345                 350

Gln Gly Gly Leu Gln His Phe Cys Phe Leu Ala Ala Trp Thr Leu Phe
        355                 360                 365

Phe Asp Phe Ile Leu Leu Phe Thr Phe Tyr Thr Ala Ile Leu Ser Ile
    370                 375                 380

Lys Leu Glu Ile Asn Arg Ile Lys Arg His Val Asp Met Arg Met Ala
385                 390                 395                 400

Leu Glu Asp Asp Gly Val Ser Arg Arg Val Ala Glu Asn Val Ala Lys
                405                 410                 415

Ser Asp Gly Asp Trp Thr Arg Val Lys Gly Asp Ser Ser Leu Phe Gly
            420                 425                 430

Arg Lys Ser Ser Ser Val Pro Thr Phe Lys Val Leu Met Ile Leu Gly
        435                 440                 445

Phe Ile Phe Val Asn Ile Val Asn Ile Cys Ser Ile Pro Phe Arg Asn
    450                 455                 460

Pro Arg Ser Leu Ser Thr Ile Arg Thr Trp Ala Ser Ser Leu Gly Gly
465                 470                 475                 480

Val Val Ala Pro Leu Ser Val Asp Pro Phe Lys Val Ala Ser Asn Gly
                485                 490                 495

Leu Asp Ala Ile Leu Ala Ala Ala Lys Ser Asn Asn Arg Pro Thr Leu
            500                 505                 510

Val Thr Val Leu Thr Pro Ile Lys Tyr Glu Leu Glu Tyr Pro Ser Ile
        515                 520                 525

His Tyr Ala Leu Gly Ser Ala Ile Asn Gly Asn Asn Ala Glu Tyr Thr
    530                 535                 540

Asp Ala Phe His His His Phe Gln Gly Tyr Gly Val Gly Gly Arg Met
545                 550                 555                 560

Val Gly Gly Ile Leu Lys Ser Leu Glu Asp Pro Val Leu Ser Lys Trp
                565                 570                 575

Ile Val Ile Ala Leu Ala Leu Ser Val Ala Leu Asn Gly Tyr Leu Phe
            580                 585                 590

Asn Val Ala Arg Trp Gly Ile Lys Asp Pro Asn Val Pro Glu His Asn
        595                 600                 605

Ile Asp Arg Asn Glu Leu Ala Arg Ala Gln Gln Phe Asn Asp Thr Gly
    610                 615                 620

Ser Ala Thr Leu Pro Leu Gly Glu Tyr Val Pro Pro Thr Pro Met Arg
625                 630                 635                 640

Thr Glu Pro Ser Thr Pro Ala Ile Thr Asp Asp Glu Ala Glu Gly Leu
                645                 650                 655

Gln Met Thr Lys Ala Arg Ser Asp Lys Leu Pro Asn Arg Pro Asn Glu
```

```
            660                 665                 670

Glu Leu Glu Lys Leu Leu Ala Glu Lys Arg Val Lys Glu Met Ser Asp
        675                 680                 685

Glu Glu Leu Val Ser Leu Ser Met Arg Cys Lys Ile Pro Gly Tyr Ala
    690                 695                 700

Leu Leu Lys Thr Leu Gly Asp Phe Thr Arg Ala Val Lys Ile Arg Arg
705                 710                 715                 720

Ser Ile Ile Ala Arg Asn Arg Ala Thr Ser Asp Leu Thr His Ser Leu
                725                 730                 735

Glu Arg Ser Lys Leu Pro Phe Glu Lys Tyr Asn Trp Glu Arg Val Phe
            740                 745                 750

Cys Ala Cys Cys Glu Asn Val Ile Gly Tyr Met Pro Leu Pro Val Gly
        755                 760                 765

Val Ala Gly Arg Leu Val Thr Asp Gly Gln Ser Tyr Phe Ile Pro Met
    770                 775                 780

Ala Thr Thr Glu Gly Val Leu Val Ala Ser Ala Ser Arg Gly Cys Lys
785                 790                 795                 800

Ala Ile Asn Ala Gly Gly Gly Ala Val Thr Val Leu Thr Ala Asp Gly
                805                 810                 815

Met Thr Arg Gly Pro Cys Val Ala Phe Glu Thr Leu Glu Arg Ala Gly
            820                 825                 830

Ala Ala Lys Leu Trp Ile Asp Ser Glu Ala Gly Ser Asp Ile Met Lys
        835                 840                 845

Lys Ala Phe Asn Ser Thr Ser Arg Phe Ala Arg Leu Gln Ser Met Lys
    850                 855                 860

Thr Ala Leu Ala Gly Thr Asn Leu Tyr Ile Arg Phe Lys Thr Thr Thr
865                 870                 875                 880

Gly Asp Ala Met Gly Met Asn Ile Ile Ser Lys Gly Val Glu His Ala
                885                 890                 895

Leu Ser Val Met Ser Asn Glu Ala Gly Phe Asp Asp Met Gln Ile Val
            900                 905                 910

Ser Val Ser Gly Asn Tyr Cys Thr Asp Lys Lys Ala Ala Ala Leu Asn
        915                 920                 925

Trp Ile Asp Gly Arg Gly Lys Gly Val Val Ala Glu Ala Ile Ile Pro
    930                 935                 940

Gly Asp Val Val Arg Ser Val Leu Lys Ser Asp Val Asp Ala Leu Val
945                 950                 955                 960

Glu Leu Asn Ile Ser Lys Asn Ile Ile Gly Ser Ala Met Ala Gly Ser
                965                 970                 975

Val Gly Gly Phe Asn Ala His Ala Ala Asn Ile Val Ala Ala Ile Phe
            980                 985                 990

Leu Ala Thr Gly Gln Asp Pro Ala  Gln Val Val Glu Ser  Ala Asn Cys
        995                 1000                 1005

Ile Thr  Leu Met Lys Asn Leu  Arg Gly Ala Leu Gln  Thr Ser Val
    1010                 1015                 1020

Ser Met  Pro Ser Leu Glu Val  Gly Thr Leu Gly Gly  Gly Thr Ile
    1025                 1030                 1035

Leu Glu  Pro Gln Ser Ala Met  Leu Asp Leu Leu Gly  Val Arg Gly
    1040                 1045                 1050

Ser His  Pro Thr Asn Pro Gly  Asp Asn Ser Arg Arg  Leu Ala Arg
    1055                 1060                 1065

Ile Ile  Gly Ala Ser Val Leu  Ala Gly Glu Leu Ser  Leu Cys Ser
    1070                 1075                 1080
```

```
Ala Leu  Ala Ala Gly His Leu  Val Arg Ala His Met  Gln His Asn
    1085                 1090                 1095

Arg Ser  Ala Ala Pro Ser Arg  Ser Thr Thr Pro Ala  Pro Met Thr
    1100                 1105                 1110

Pro Val  Arg Ser Phe Asp Thr  Lys Val Arg Cys Gln  Pro Asn Asn
    1115                 1120                 1125

Lys Asp  Ile Arg Asn Ile Leu  Leu Thr Gln His Pro  Ser Lys Pro
    1130                 1135                 1140

Thr Ile  Thr Tyr Ser Lys Arg  Val Ile Lys Ser Thr  Ile His Leu
    1145                 1150                 1155

Asn Pro  Leu Ile Leu Ala Leu  Phe Asp Asn Ser Val  Gln Thr Arg
    1160                 1165                 1170

Asp Val  Gln Leu Gly Asp Gln  Val Ser Thr Arg Gly  Thr Leu Asp
    1175                 1180                 1185

Ala Val  Gly Gly Pro Gln Gly  Gly Gly Val Ala Ala  Gly Gly Val
    1190                 1195                 1200

Ala Arg  Arg Val Val Gly Ser
    1205                 1210


<210> SEQ ID NO 178
<211> LENGTH: 1173
<212> TYPE: PRT
<213> ORGANISM: Neurospora crassa

<400> SEQUENCE: 178

Met Ile Ala Ser Ser Leu Leu Pro Ser Lys Phe Arg Gly Glu Gln Pro
1               5                   10                  15

Ala Thr Gln Ala Ala Thr Pro Ser Trp Ile Asn Lys Lys Val Thr Pro
            20                  25                  30

Pro Leu Gln Lys Leu Ser Lys Ile Thr Ser Ser Asn Pro Ile His Thr
        35                  40                  45

Ile Val Ile Val Ala Leu Leu Ala Ser Ser Ser Tyr Ile Gly Leu Leu
    50                  55                  60

Gln Asn Ser Leu Phe Asn Val Thr Arg Ser Val Arg Lys Ala Glu Trp
65                  70                  75                  80

Glu Ser Leu Gln Ala Gly Ser Arg Met Leu Arg Ala Gly Ala Asn Thr
                85                  90                  95

Glu Trp Asn Trp Gln Asn His Asp Pro Glu Ala Pro Val Pro Ala Asn
            100                 105                 110

Ala Asn His Leu Ala Leu Leu Thr Leu Val Phe Pro Asp Thr Ala Glu
        115                 120                 125

Ser Gly Pro Val Val Ala Gln Thr Asn Thr Val Pro Leu Pro Ser Asn
    130                 135                 140

Leu Ser Thr Thr Pro Leu Pro Ser Thr Ala Ile Ser Phe Thr Tyr Ser
145                 150                 155                 160

Gln Asp Ser Ala Leu Ala Phe Ser Leu Pro Tyr Ser Gln Ala Pro Glu
                165                 170                 175

Phe Leu Ala Asn Ala Gln Glu Ile Pro Asn Ala Val Ser Ser Gln Glu
            180                 185                 190

Thr Ile Glu Thr Glu Arg Gly His Glu Lys Lys Met Trp Ile Met Lys
        195                 200                 205

Ala Ala Arg Val Gln Thr Arg Ser Ser Thr Val Lys Trp Val Gln Asn
    210                 215                 220

Ala Trp Val Glu Phe Thr Asp Leu Leu Arg Asn Ala Glu Thr Leu Asp
225                 230                 235                 240
```

-continued

```
Ile Ile Ile Met Ala Leu Gly Tyr Ile Ser Met His Leu Thr Phe Val
                245                 250                 255

Ser Leu Phe Leu Ser Met Arg Arg Met Gly Ser Asn Phe Trp Leu Ala
            260                 265                 270

Thr Ser Val Ile Phe Ser Ser Ile Phe Ala Phe Leu Phe Gly Leu Leu
        275                 280                 285

Val Thr Thr Lys Leu Gly Val Pro Met Asn Met Val Leu Leu Ser Glu
    290                 295                 300

Gly Leu Pro Phe Leu Val Val Thr Ile Gly Phe Glu Lys Asn Ile Val
305                 310                 315                 320

Leu Thr Arg Ala Val Leu Ser His Ala Ile Asp His Arg Arg Pro Thr
                325                 330                 335

Glu Lys Ser Gly Lys Pro Ser Lys Gln Ala Asp Ser Ala His Ser Ile
            340                 345                 350

Gln Ser Ala Ile Gln Leu Ala Ile Lys Glu Lys Gly Phe Asp Ile Val
        355                 360                 365

Lys Asp Tyr Ala Ile Glu Ala Gly Ile Leu Val Leu Gly Ala Ala Ser
    370                 375                 380

Gly Val Gln Gly Gly Leu Gln Gln Phe Cys Phe Leu Ala Ala Trp Ile
385                 390                 395                 400

Leu Phe Phe Asp Cys Ile Leu Leu Phe Ser Phe Tyr Thr Ala Ile Leu
                405                 410                 415

Cys Ile Lys Leu Phe Ile Asn Arg Ile Lys Arg His Val Gln Met Arg
            420                 425                 430

Lys Ala Leu Glu Glu Asp Gly Val Ser Arg Arg Val Ala Glu Lys Val
        435                 440                 445

Ala Gln Ser Asn Asp Trp Pro Arg Ala Asp Gly Lys Asp Gln Pro Gly
    450                 455                 460

Thr Thr Ile Phe Gly Arg Gln Leu Lys Ser Thr His Ile Pro Lys Phe
465                 470                 475                 480

Lys Val Met Met Val Thr Gly Phe Val Leu Ile Asn Val Leu Asn Leu
                485                 490                 495

Cys Thr Ile Pro Phe Arg Ser Ala Asn Ser Ile Ser Ser Ile Ser Ser
            500                 505                 510

Trp Ala Arg Gly Leu Gly Gly Val Val Thr Pro Pro Pro Val Asp Pro
        515                 520                 525

Phe Lys Val Ala Ser Asn Gly Leu Asp Ile Ile Leu Glu Ala Ala Arg
    530                 535                 540

Ala Asp Gly Arg Glu Thr Thr Val Thr Val Leu Thr Pro Ile Arg Tyr
545                 550                 555                 560

Glu Leu Glu Tyr Pro Ser Thr His Tyr Asp Leu Pro Gln Lys Ser Ala
                565                 570                 575

Glu Val Glu Gly Gly Asp Tyr Ala Asn Leu Gly Gly Tyr Gly Gly Arg
            580                 585                 590

Met Val Gly Ser Ile Leu Lys Ser Leu Glu Asp Pro Thr Leu Ser Lys
        595                 600                 605

Trp Ile Val Val Ala Leu Ala Leu Ser Val Ala Leu Asn Gly Tyr Leu
    610                 615                 620

Phe Asn Ala Ala Arg Trp Gly Ile Lys Asp Pro Asn Val Pro Asp His
625                 630                 635                 640

Pro Ile Asn Pro Lys Glu Leu Asp Glu Ala Gln Lys Phe Asn Asp Thr
                645                 650                 655

Ala Ser Ala Thr Leu Pro Leu Gly Glu Tyr Met Lys Pro Thr Ala Pro
            660                 665                 670
```

```
Ser Ser Pro Val Ala Pro Leu Thr Pro Ser Ser Thr Asp Asp Glu Asn
        675                 680                 685

Asp Ala Gln Ala Lys Glu Asn Arg Ala Val Thr Leu Ala Ala Gln Arg
    690                 695                 700

Ala Thr Thr Ile Arg Ser Gln Gly Glu Leu Asp Lys Met Thr Ala Glu
705                 710                 715                 720

Lys Arg Thr His Glu Leu Asn Asp Glu Glu Thr Val His Leu Ser Leu
                725                 730                 735

Lys Gly Lys Ile Pro Gly Tyr Ala Leu Glu Lys Thr Leu Lys Asp Phe
            740                 745                 750

Thr Arg Ala Val Lys Val Arg Arg Ser Ile Ile Ser Arg Thr Lys Ala
        755                 760                 765

Thr Thr Glu Leu Thr Asn Ile Leu Asp Arg Ser Lys Leu Pro Tyr Gln
    770                 775                 780

Asn Val Asn Trp Ala Gln Val His Gly Ala Cys Cys Glu Asn Val Ile
785                 790                 795                 800

Gly Tyr Met Pro Leu Pro Val Gly Val Ala Gly Pro Leu Val Thr Asp
                805                 810                 815

Gly Gln Ser Phe Phe Val Pro Met Ala Thr Thr Glu Gly Val Leu Val
            820                 825                 830

Ala Ser Thr Ser Arg Gly Cys Lys Ala Ile Asn Ser Gly Gly Gly Ala
        835                 840                 845

Val Thr Val Leu Thr Ala Asp Gly Met Thr Arg Gly Pro Cys Val Gln
    850                 855                 860

Phe Glu Thr Leu Glu Arg Ala Gly Ala Ala Lys Leu Trp Leu Asp Ser
865                 870                 875                 880

Glu Lys Gly Gln Ser Ile Met Lys Lys Ala Phe Asn Ser Thr Ser Arg
                885                 890                 895

Phe Arg Ala Leu Glu Thr Met Lys Thr Ala Met Ala Gly Thr Asn Leu
            900                 905                 910

Tyr Ile Arg Phe Lys Ile Thr Thr Gly Asp Ala Met Gly Met Asn Met
        915                 920                 925

Ile Ser Lys Gly Val Glu His Ala Leu Ser Val Met Tyr Asn Glu Gly
    930                 935                 940

Phe Glu Asp Met Asn Ile Val Ser Leu Ser Gly Asn Tyr Cys Thr Asp
945                 950                 955                 960

Lys Lys Ala Ala Ala Ile Asn Val Ile Asp Gly Arg Gly Lys Ser Val
                965                 970                 975

Val Ala Glu Ala Ile Ile Pro Ala Asp Val Val Lys Asn Val Leu Lys
            980                 985                 990

Thr Asp Val Asp Thr Leu Val Glu  Leu Asn Val Asn Lys  Asn Thr Ile
        995                 1000                1005

Gly Ser  Ala Met Ala Gly Ser  Met Gly Gly Phe Asn  Ala His Ala
    1010                1015                1020

Ala Asn  Ile Val Ala Ala Ile  Phe Leu Ala Thr Gly  Gln Asp Pro
    1025                1030                1035

Ala Gln  Val Val Glu Ser Ala  Asn Cys Ile Thr Leu  Met Arg Asn
    1040                1045                1050

Leu Arg  Gly Asn Leu Gln Ile  Ser Val Ser Met Pro  Ser Ile Glu
    1055                1060                1065

Val Gly  Thr Leu Gly Gly Gly  Thr Ile Leu Glu Pro  Gln Ser Ala
    1070                1075                1080

Met Leu  Asp Met Leu Gly Val  Arg Gly Pro His Pro  Thr Asn Pro
```

```
    1085                1090                1095

Gly Glu  Asn Ala Arg Arg Leu  Ala Arg Ile Val Ala  Ala Ala Val
    1100                1105                1110

Leu Ala  Gly Glu Leu Ser Leu  Cys Ser Ala Leu Ala  Ala Gly His
    1115                1120                1125

Leu Val  Lys Ala His Met Ala  His Asn Arg Ser Ala  Pro Pro Thr
    1130                1135                1140

Arg Thr  Ser Thr Pro Ala Pro  Ala Ala Ala Ala Gly  Leu Thr Met
    1145                1150                1155

Thr Ser  Ser Asn Pro Asn Ala  Ala Ala Val Glu Arg  Ser Arg Arg
    1160                1165                1170


<210> SEQ ID NO 179
<211> LENGTH: 1045
<212> TYPE: PRT
<213> ORGANISM: Saccharomyces cerevisiae

<400> SEQUENCE: 179

Met Ser Leu Pro Leu Lys Thr Ile Val His Leu Val Lys Pro Phe Ala
1               5                   10                  15

Cys Thr Ala Arg Phe Ser Ala Arg Tyr Pro Ile His Val Ile Val Val
            20                  25                  30

Ala Val Leu Leu Ser Ala Ala Ala Tyr Leu Ser Val Thr Gln Ser Tyr
        35                  40                  45

Leu Asn Glu Trp Lys Leu Asp Ser Asn Gln Tyr Ser Thr Tyr Leu Ser
    50                  55                  60

Ile Lys Pro Asp Glu Leu Phe Glu Lys Cys Thr His Tyr Tyr Arg Ser
65                  70                  75                  80

Pro Val Ser Asp Thr Trp Lys Leu Leu Ser Ser Lys Glu Ala Ala Asp
                85                  90                  95

Ile Tyr Thr Pro Phe His Tyr Tyr Leu Ser Thr Ile Ser Phe Gln Ser
            100                 105                 110

Lys Asp Asn Ser Thr Thr Leu Pro Ser Leu Asp Asp Val Ile Tyr Ser
        115                 120                 125

Val Asp His Thr Arg Tyr Leu Leu Ser Glu Glu Pro Lys Ile Pro Thr
    130                 135                 140

Glu Leu Val Ser Glu Asn Gly Thr Lys Trp Arg Leu Arg Asn Asn Ser
145                 150                 155                 160

Asn Phe Ile Leu Asp Leu His Asn Ile Tyr Arg Asn Met Val Lys Gln
                165                 170                 175

Phe Ser Asn Lys Thr Ser Glu Phe Asp Gln Phe Asp Leu Phe Ile Ile
            180                 185                 190

Leu Ala Ala Tyr Leu Thr Leu Phe Tyr Thr Leu Cys Cys Leu Phe Asn
        195                 200                 205

Asp Met Arg Lys Ile Gly Ser Lys Phe Trp Leu Ser Phe Ser Ala Leu
    210                 215                 220

Ser Asn Ser Ala Cys Ala Leu Tyr Leu Ser Leu Tyr Thr Thr His Ser
225                 230                 235                 240

Leu Leu Lys Lys Pro Ala Ser Leu Leu Ser Leu Val Ile Gly Leu Pro
                245                 250                 255

Phe Thr Val Val Ile Ile Gly Glu Lys His Lys Val Arg Leu Ala Ala
            260                 265                 270

Phe Ser Leu Gln Lys Phe His Arg Ile Ser Ile Asp Lys Lys Ile Thr
        275                 280                 285

Val Ser Asn Ile Ile Tyr Glu Ala Met Phe Gln Glu Gly Ala Tyr Leu
```

-continued

```
    290                 295                 300

Ile Arg Asp Tyr Leu Phe Tyr Ile Ser Ser Phe Ile Gly Cys Ala Ile
305                 310                 315                 320

Tyr Ala Arg His Leu Pro Gly Leu Val Asn Phe Cys Ile Leu Ser Thr
                325                 330                 335

Phe Met Leu Val Phe Asp Leu Leu Leu Ser Ala Thr Phe Tyr Ser Ala
            340                 345                 350

Ile Leu Ser Met Lys Leu Phe Ile Asn Ile Ile His Arg Ser Thr Val
        355                 360                 365

Ile Arg Gln Thr Leu Glu Glu Asp Gly Val Val Pro Thr Thr Ala Asp
    370                 375                 380

Ile Ile Tyr Lys Asp Glu Thr Ala Ser Glu Pro His Phe Leu Arg Ser
385                 390                 395                 400

Asn Val Ala Ile Ile Leu Gly Lys Ala Ser Val Ile Gly Leu Leu Leu
                405                 410                 415

Leu Ile Asn Leu Tyr Val Phe Thr Asp Lys Leu Asn Ala Thr Ile Leu
            420                 425                 430

Asn Thr Val Tyr Phe Asp Ser Thr Ile Tyr Ser Leu Pro Asn Phe Ile
        435                 440                 445

Asn Tyr Lys Asp Ile Gly Asn Leu Ser Asn Gln Val Ile Ile Ser Val
    450                 455                 460

Leu Pro Lys Gln Tyr Tyr Thr Pro Leu Lys Lys Tyr His Gln Ile Glu
465                 470                 475                 480

Asp Ser Val Leu Leu Ile Ile Asp Ser Val Ser Asn Ala Ile Arg Asp
                485                 490                 495

Gln Phe Ile Ser Lys Leu Leu Phe Phe Ala Phe Ala Val Ser Ile Ser
            500                 505                 510

Ile Asn Val Tyr Leu Leu Asn Ala Ala Lys Ile His Thr Gly Tyr Met
        515                 520                 525

Asn Phe Gln Pro Gln Ser Asn Lys Ile Asp Asp Leu Val Val Gln Gln
    530                 535                 540

Lys Ser Ala Thr Ile Glu Phe Ser Glu Thr Arg Ser Met Pro Leu Ala
545                 550                 555                 560

Ser Gly Leu Glu Thr Pro Val Thr Ala Lys Asp Ile Ile Ile Ser Glu
                565                 570                 575

Glu Ile Gln Asn Asn Glu Cys Val Tyr Ala Leu Ser Ser Gln Asp Glu
            580                 585                 590

Pro Ile Arg Pro Leu Ser Asn Leu Val Glu Leu Met Glu Lys Glu Gln
        595                 600                 605

Leu Lys Asn Met Asn Asn Thr Glu Val Ser Asn Leu Val Val Asn Gly
    610                 615                 620

Lys Leu Pro Leu Tyr Ser Leu Glu Lys Lys Leu Glu Asp Thr Leu Arg
625                 630                 635                 640

Ala Val Leu Val Arg Arg Lys Ala Leu Ser Thr Leu Ala Glu Ser Pro
                645                 650                 655

Ile Leu Val Ser Glu Lys Leu Pro Phe Arg Asn Tyr Asp Tyr Asp Arg
            660                 665                 670

Val Phe Gly Ala Cys Cys Glu Asn Val Ile Gly Tyr Met Pro Ile Pro
        675                 680                 685

Val Gly Val Ile Gly Pro Leu Ile Thr Asp Gly Thr Ser Tyr His Ile
    690                 695                 700

Pro Met Ala Thr Thr Glu Gly Cys Leu Val Ala Ser Ala Met Pro Gly
705                 710                 715                 720
```

```
Cys Lys Ala Ile Asn Ala Gly Gly Gly Ala Thr Thr Val Leu Thr Lys
                725                 730                 735

Asp Gly Met Thr Arg Gly Pro Val Val Arg Phe Pro Thr Leu Ile Arg
            740                 745                 750

Ser Gly Ala Cys Lys Ile Trp Leu Asp Ser Glu Glu Gly Gln Asn Ser
        755                 760                 765

Ile Lys Lys Ala Phe Asn Ser Thr Ser Arg Phe Ala Arg Leu Gln His
    770                 775                 780

Thr Gln Thr Cys Leu Ala Gly Asp Leu Leu Phe Met Arg Phe Arg Thr
785                 790                 795                 800

Thr Thr Gly Asp Ala Met Gly Met Asn Met Ile Ser Lys Gly Val Glu
                805                 810                 815

Tyr Ser Leu Lys Gln Met Val Glu Glu Tyr Gly Trp Glu Asp Met Glu
            820                 825                 830

Val Val Ser Val Ser Gly Asn Tyr Cys Thr Asp Lys Lys Pro Ala Ala
        835                 840                 845

Ile Asn Trp Ile Glu Gly Arg Gly Lys Ser Val Val Ala Glu Ala Thr
    850                 855                 860

Ile Pro Gly Asp Val Val Lys Ser Val Leu Lys Ser Asp Val Ser Ala
865                 870                 875                 880

Leu Val Glu Leu Asn Ile Ser Lys Asn Ile Val Gly Ser Ala Met Ala
                885                 890                 895

Gly Ser Val Gly Gly Phe Asn Ala His Ala Ala Asn Leu Val Thr Ala
            900                 905                 910

Leu Phe Leu Ala Leu Gly Gln Asp Pro Ala Gln Asn Val Glu Ser Ser
        915                 920                 925

Asn Cys Ile Thr Leu Met Lys Glu Val Asp Gly Asp Leu Arg Ile Ser
    930                 935                 940

Val Ser Met Pro Ser Ile Glu Val Gly Thr Ile Gly Gly Gly Thr Val
945                 950                 955                 960

Leu Glu Pro Gln Gly Ala Met Leu Asp Leu Leu Gly Val Arg Gly Pro
                965                 970                 975

His Pro Thr Glu Pro Gly Ala Asn Ala Arg Gln Leu Ala Arg Ile Ile
            980                 985                 990

Ala Cys Ala Val Leu Ala Gly Glu  Leu Ser Leu Cys Ser  Ala Leu Ala
        995                 1000                1005

Ala Gly  His Leu Val Gln Ser  His Met Thr His Asn  Arg Lys Thr
    1010                1015                1020

Asn Lys  Ala Asn Glu Leu Pro  Gln Pro Ser Asn Lys  Gly Pro Pro
    1025                1030                1035

Cys Lys  Thr Ser Ala Leu Leu
    1040                1045


<210> SEQ ID NO 180
<211> LENGTH: 1052
<212> TYPE: PRT
<213> ORGANISM: Saccharomyces cerevisiae

<400> SEQUENCE: 180

Met Pro Pro Leu Phe Lys Gly Leu Lys Gln Met Ala Lys Pro Leu Ala
1               5                   10                  15

Tyr Val Ser Arg Phe Ser Ala Lys Pro Pro Ile His Ile Ile Leu Phe
            20                  25                  30

Ser Leu Ile Ile Ser Ala Phe Ala Tyr Leu Ser Val Ile Gln Tyr Tyr
        35                  40                  45
```

-continued

```
Phe Asn Gly Trp Gln Leu Asp Ser Asn Ser Val Phe Glu Thr Ala Pro
    50                  55                  60

Asn Lys Asp Ser Asn Thr Leu Phe Gln Glu Cys Ser His Tyr Tyr Arg
65                  70                  75                  80

Asp Ser Ser Leu Asp Gly Trp Val Ser Ile Thr Ala His Glu Ala Ser
                85                  90                  95

Glu Leu Pro Ala Pro His His Tyr Tyr Leu Leu Asn Leu Asn Phe Ser
            100                 105                 110

Pro Asn Glu Thr Asp Ser Ile Pro Glu Leu Ala Asn Thr Val Phe Glu
        115                 120                 125

Lys Asp Asn Thr Lys Tyr Leu Leu Gln Glu Asp Leu Ser Val Ser Lys
    130                 135                 140

Glu Thr Ser Ser Thr Asp Gly Thr Lys Trp Arg Leu Arg Ser Asp Arg
145                 150                 155                 160

Lys Ser Leu Phe Asp Val Lys Thr Leu Ala Tyr Ser Leu Tyr Asp Val
                165                 170                 175

Phe Ser Glu Asn Val Thr Gln Ala Asp Pro Phe Asp Val Leu Ile Met
            180                 185                 190

Val Thr Ala Tyr Leu Met Met Phe Tyr Thr Ile Phe Gly Leu Phe Asn
        195                 200                 205

Asp Met Arg Lys Thr Gly Ser Asn Phe Trp Leu Ser Ala Ser Thr Val
    210                 215                 220

Val Asn Ser Ala Ser Ser Leu Phe Leu Ala Leu Tyr Val Thr Gln Cys
225                 230                 235                 240

Ile Leu Gly Lys Glu Val Ser Ala Leu Thr Leu Phe Glu Gly Leu Pro
                245                 250                 255

Phe Leu Val Val Val Val Gly Phe Lys His Lys Ile Lys Ile Ala Gln
            260                 265                 270

Tyr Ala Leu Glu Lys Phe Glu Arg Val Gly Leu Ser Lys Arg Ile Thr
        275                 280                 285

Thr Asp Glu Ile Val Phe Glu Ser Val Ser Glu Glu Gly Gly Arg Leu
    290                 295                 300

Ile Gln Asp His Leu Leu Cys Ile Phe Ala Phe Ile Gly Cys Met Tyr
305                 310                 315                 320

Ala His Gln Leu Lys Thr Leu Thr Asn Phe Cys Ile Leu Ser Ala Phe
                325                 330                 335

Ile Leu Ile Phe Glu Leu Ile Leu Thr Pro Thr Phe Tyr Ser Ala Ile
            340                 345                 350

Leu Ala Leu Arg Leu Glu Met Asn Val Ile His Arg Ser Thr Ile Ile
        355                 360                 365

Ile Gly Gln Thr Leu Glu Glu Asp Gly Val Val Pro Ser Thr Ala Arg
    370                 375                 380

Ile Ile Ser Lys Ala Glu Lys Lys Ser Val Ser Ser Phe Leu Asn Leu
385                 390                 395                 400

Ser Val Val Val Ile Thr Met Lys Leu Ser Val Ile Leu Leu Phe Val
                405                 410                 415

Phe Ile Asn Phe Tyr Asn Phe Gly Ala Asn Trp Val Asn Asp Ala Phe
            420                 425                 430

Asn Ser Leu Tyr Phe Asp Lys Glu Arg Val Ser Leu Pro Asp Phe Ile
        435                 440                 445

Thr Ser Asn Ala Ser Glu Asn Phe Lys Glu Gln Ala Ile Val Ser Val
    450                 455                 460

Thr Pro Leu Leu Tyr Tyr Lys Pro Ile Lys Ser Tyr Gln Arg Ile Glu
465                 470                 475                 480
```

```
Asp Met Val Leu Leu Leu Leu Arg Asn Val Ser Val Ala Ile Arg Asp
                485                 490                 495

Arg Phe Val Ser Lys Leu Val Leu Ser Ala Leu Val Cys Ser Ala Val
            500                 505                 510

Ile Asn Val Tyr Leu Leu Asn Ala Ala Arg Ile His Thr Ser Tyr Thr
        515                 520                 525

Ala Asp Gln Leu Val Lys Thr Glu Val Thr Lys Lys Ser Phe Thr Ala
    530                 535                 540

Pro Val Gln Lys Ala Ser Thr Pro Val Leu Thr Asn Lys Thr Val Ile
545                 550                 555                 560

Ser Gly Ser Lys Val Lys Ser Leu Ser Ser Ala Gln Ser Ser Ser Ser
                565                 570                 575

Gly Pro Ser Ser Ser Ser Glu Glu Asp Asp Ser Arg Asp Ile Glu Ser
            580                 585                 590

Leu Asp Lys Lys Ile Arg Pro Leu Glu Glu Leu Glu Ala Leu Leu Ser
        595                 600                 605

Ser Gly Asn Thr Lys Gln Leu Lys Asn Lys Glu Val Ala Ala Leu Val
    610                 615                 620

Thr His Gly Lys Leu Pro Leu Tyr Ala Leu Glu Lys Lys Leu Gly Asp
625                 630                 635                 640

Thr Thr Arg Ala Val Ala Val Arg Arg Lys Ala Leu Ser Ile Leu Ala
                645                 650                 655

Glu Ala Pro Val Leu Ala Ser Asp Arg Leu Pro Tyr Lys Asn Tyr Asp
            660                 665                 670

Tyr Asp Arg Val Phe Gly Ala Cys Cys Glu Asn Val Ile Gly Tyr Met
        675                 680                 685

Pro Leu Pro Val Gly Val Ile Gly Pro Leu Val Thr Asp Gly Thr Ser
    690                 695                 700

Tyr His Ile Pro Met Ala Thr Thr Glu Gly Cys Leu Val Ala Ser Ala
705                 710                 715                 720

Met Arg Gly Cys Lys Ala Ile Asn Ala Gly Gly Gly Ala Thr Thr Val
                725                 730                 735

Leu Thr Lys Asp Gly Met Ile Arg Gly Pro Val Val Arg Phe Pro Thr
            740                 745                 750

Leu Lys Arg Ser Gly Ala Cys Lys Ile Trp Leu Asp Ser Glu Glu Gly
        755                 760                 765

Gln Asn Ala Ile Lys Lys Ala Phe Asn Ser Thr Ser Arg Phe Ala Arg
    770                 775                 780

Leu Gln His Ile Gln Thr Cys Leu Ala Gly Asp Leu Leu Phe Met Arg
785                 790                 795                 800

Phe Arg Thr Thr Thr Ser Asp Ala Met Gly Met Asn Met Ile Ser Lys
                805                 810                 815

Gly Val Glu Tyr Ser Leu Lys Gln Met Val Glu Glu Tyr Gly Trp Glu
            820                 825                 830

Asp Met Glu Val Val Ser Val Ser Gly Asn Tyr Cys Thr Asp Lys Lys
        835                 840                 845

Pro Ala Ala Ile Asn Trp Ile Glu Gly Arg Gly Lys Ser Val Val Ala
    850                 855                 860

Glu Ala Thr Ile Pro Gly Asp Val Val Arg Lys Val Leu Lys Ser Asp
865                 870                 875                 880

Val Ser Ala Leu Val Glu Leu Asn Ile Ala Lys Asn Leu Val Gly Ser
                885                 890                 895

Ala Met Ala Gly Ser Val Gly Gly Glu Asn Ala His Ala Ala Asn Leu
```

-continued

```
            900                 905                 910

Val Thr Ala Val Phe Leu Ala Leu Gly Asp Pro Ala Gln Asn Val Glu
        915                 920                 925

Ser Ser Asn Cys Ile Thr Leu Met Lys Glu Val Asp Gly Asp Leu Arg
    930                 935                 940

Ile Ser Val Ser Met Pro Ser Ile Glu Val Gly Thr Ile Gly Gly Gly
945                 950                 955                 960

Thr Val Leu Glu Pro Gln Gly Ala Met Leu Asp Leu Leu Ser Val Arg
                965                 970                 975

Gly Pro His Ala Thr Ala Pro Gly Thr Asn Ala Arg Gln Leu Ala Arg
            980                 985                 990

Ile Val Ala Cys Ala Val Leu Ala  Gly Glu Leu Ser Leu  Cys Ala Ala
        995                 1000                1005

Leu Ala  Ala Gly His Leu Val  Gln Ser His Met Thr  His Asn Arg
    1010                1015                1020

Lys Pro  Ala Glu Pro Thr Lys  Pro Asn Asn Leu Asp  Ala Thr Asp
    1025                1030                1035

Ile Asn  Arg Leu Lys Asp Gly  Ser Val Thr Cys Ile  Lys Ser
    1040                1045                1050


<210> SEQ ID NO 181
<211> LENGTH: 999
<212> TYPE: PRT
<213> ORGANISM: Yarrowia lipolytica

<400> SEQUENCE: 181

Met Leu Gln Ala Ala Ile Gly Lys Ile Val Gly Phe Ala Val Asn Arg
1               5                   10                  15

Pro Ile His Thr Val Val Leu Thr Ser Ile Val Ala Ser Thr Ala Tyr
            20                  25                  30

Leu Ala Leu Leu Asp Ile Ala Ile Pro Gly Glu Glu Gly Thr Gln Pro
        35                  40                  45

Ile Ser Tyr Tyr His Pro Ala Ala Lys Ser Tyr Asp Asn Pro Ala Asp
    50                  55                  60

Trp Thr His Ile Ala Glu Ala Asp Ile Pro Ser Asp Ala Tyr Arg Leu
65                  70                  75                  80

Ala Phe Ala Gln Ile Arg Val Ser Asp Val Gln Gly Gly Glu Ala Pro
                85                  90                  95

Thr Ile Pro Gly Ala Val Ala Val Ser Asp Leu Asp His Arg Ile Val
            100                 105                 110

Met Asp Tyr Lys Gln Trp Ala Pro Trp Thr Ala Ser Asn Glu Gln Ile
        115                 120                 125

Ala Ser Glu Asn His Ile Trp Lys His Ser Phe Lys Asp His Val Ala
    130                 135                 140

Phe Ser Trp Ile Lys Trp Phe Arg Trp Ala Tyr Leu Arg Leu Ser Thr
145                 150                 155                 160

Leu Ile Gln Gly Ala Asp Asn Phe Asp Ile Ala Val Val Ala Leu Gly
                165                 170                 175

Tyr Leu Ala Met His Tyr Thr Phe Phe Ser Leu Phe Arg Ser Lys Arg
            180                 185                 190

Lys Val Gly Ser His Phe Trp Leu Ala Ser Met Ala Leu Val Ser Ser
        195                 200                 205

Phe Phe Ala Phe Leu Leu Ala Val Val Ala Ser Ser Ser Leu Gly Tyr
    210                 215                 220

Arg Pro Ser Met Ile Thr Met Ser Glu Gly Leu Pro Phe Leu Val Val
```

-continued

```
225                 230                 235                 240

Ala Ile Gly Phe Asp Arg Lys Val Asn Leu Ala Ser Glu Val Leu Thr
                245                 250                 255

Ser Lys Ser Ser Gln Leu Ala Pro Met Val Gln Val Ile Thr Lys Ile
            260                 265                 270

Ala Ser Lys Ala Leu Phe Glu Tyr Ser Leu Glu Val Ala Ala Leu Phe
        275                 280                 285

Ala Gly Ala Tyr Thr Gly Val Pro Arg Leu Ser Gln Phe Cys Phe Leu
    290                 295                 300

Ser Ala Trp Ile Leu Ile Phe Asp Tyr Met Phe Leu Leu Thr Phe Tyr
305                 310                 315                 320

Ser Ala Val Ile Ala Ile Lys Phe Leu Ile Asn His Ile Lys Phe Asn
                325                 330                 335

Arg Met Ile Gln Asp Ala Leu Lys Glu Asp Gly Val Ser Ala Ala Val
            340                 345                 350

Ala Glu Lys Val Ala Asp Ser Ser Pro Asp Ala Lys Leu Asp Arg Lys
        355                 360                 365

Ser Asp Val Ser Leu Phe Gly Ala Ser Gly Ala Ile Ala Val Phe Lys
    370                 375                 380

Ile Phe Met Val Leu Gly Phe Leu Gly Leu Asn Leu Ile Asn Leu Thr
385                 390                 395                 400

Ala Ile Pro His Leu Gly Lys Ala Ala Ala Ala Ala Gln Ser Val Thr
                405                 410                 415

Pro Ile Thr Leu Ser Pro Glu Leu Leu His Ala Ile Pro Ala Ser Val
            420                 425                 430

Pro Val Val Val Thr Phe Val Pro Ser Val Val Tyr Glu His Ser Gln
        435                 440                 445

Leu Ile Leu Gln Leu Glu Asp Ala Leu Thr Phe Phe Leu Ala Ala Cys
    450                 455                 460

Ser Lys Thr Ile Gly Asp Pro Val Ile Ser Lys Tyr Ile Phe Leu Cys
465                 470                 475                 480

Leu Met Val Ser Thr Ala Leu Asn Val Tyr Leu Phe Gly Ala Thr Arg
                485                 490                 495

Glu Val Val Arg Thr Gln Ser Val Lys Val Val Glu Lys His Val Pro
            500                 505                 510

Ile Val Ile Glu Lys Pro Ser Glu Lys Glu Glu Asp Thr Ser Ser Glu
        515                 520                 525

Asp Ser Ile Glu Leu Thr Val Gly Lys Gln Pro Lys Pro Val Thr Glu
    530                 535                 540

Thr Arg Ser Leu Asp Asp Leu Glu Ala Thr Met Lys Ala Gly Lys Thr
545                 550                 555                 560

Lys Leu Leu Glu Asp His Glu Val Val Lys Leu Ser Leu Glu Gly Lys
                565                 570                 575

Leu Pro Leu Tyr Ala Leu Phe Lys Gln Leu Gly Asp Asn Thr Arg Ala
            580                 585                 590

Val Gly Ile Arg Arg Ser Ile Ile Ser Gln Gln Ser Asn Thr Lys Thr
        595                 600                 605

Leu Glu Thr Ser Lys Leu Pro Tyr Leu His Tyr Asp Tyr Asp Arg Val
    610                 615                 620

Phe Gly Ala Cys Cys Glu Asn Val Ile Gly Tyr Met Pro Leu Pro Val
625                 630                 635                 640

Gly Val Ala Gly Pro Met Asn Thr Asp Gly Lys Asn Tyr His Ile Pro
                645                 650                 655
```

```
Met Ala Thr Thr Glu Gly Cys Leu Val Ala Ser Thr Met Arg Gly Cys
            660                 665                 670

Lys Ala Ile Asn Ala Gly Gly Gly Val Thr Thr Val Leu Thr Gln Asp
        675                 680                 685

Gly Met Thr Arg Gly Pro Cys Val Ser Phe Pro Ser Leu Lys Arg Ala
    690                 695                 700

Gly Ala Ala Lys Ile Trp Leu Asp Glu Ser Glu Gly Leu Lys Ser Met
705                 710                 715                 720

Arg Lys Ala Phe Asn Ser Thr Ser Arg Phe Ala Arg Leu Gln Ser Leu
                725                 730                 735

His Ser Thr Leu Ala Gly Asn Leu Leu Phe Ile Arg Phe Arg Thr Thr
            740                 745                 750

Thr Gly Asp Ala Met Gly Met Asn Met Ile Ser Lys Gly Val Glu His
        755                 760                 765

Ser Leu Ala Val Met Val Lys Glu Tyr Gly Phe Pro Leu Met Asp Ile
    770                 775                 780

Val Ser Val Ser Gly Asn Tyr Cys Thr Asp Lys Lys Pro Ala Ala Ile
785                 790                 795                 800

Asn Trp Ile Glu Gly Arg Gly Lys Ser Val Val Ala Glu Ala Thr Ile
                805                 810                 815

Pro Ala His Ile Val Lys Ser Val Leu Lys Ser Glu Val Asp Ala Leu
            820                 825                 830

Val Glu Leu Asn Ile Ser Lys Asn Leu Ile Gly Ser Ala Met Ala Gly
        835                 840                 845

Ser Val Gly Gly Phe Asn Ala His Ala Ala Asn Leu Val Thr Ala Ile
    850                 855                 860

Tyr Leu Ala Thr Gly Gln Asp Pro Ala Gln Asn Val Glu Ser Ser Asn
865                 870                 875                 880

Cys Ile Thr Leu Met Ser Asn Val Asp Gly Asn Leu Leu Ile Ser Val
                885                 890                 895

Ser Met Pro Ser Ile Glu Val Gly Thr Ile Gly Gly Gly Thr Ile Leu
            900                 905                 910

Glu Pro Gln Gly Ala Met Leu Glu Met Leu Gly Val Arg Gly Pro His
        915                 920                 925

Ile Glu Thr Pro Gly Ala Asn Ala Gln Gln Leu Ala Arg Ile Ile Ala
    930                 935                 940

Ser Gly Val Leu Ala Ala Glu Leu Ser Leu Cys Ser Ala Leu Ala Ala
945                 950                 955                 960

Gly His Leu Val Gln Ser His Met Thr His Asn Arg Ser Gln Ala Pro
                965                 970                 975

Thr Pro Ala Lys Gln Ser Gln Ala Asp Leu Gln Arg Leu Gln Asn Gly
            980                 985                 990

Ser Asn Ile Cys Ile Arg Ser
        995
```

<210> SEQ ID NO 182
<211> LENGTH: 1289
<212> TYPE: PRT
<213> ORGANISM: Artificial Sequence
<220> FEATURE:
<223> OTHER INFORMATION: Description of Artificial Sequence: Synthetic
consensus polypeptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (5)..(5)
<223> OTHER INFORMATION: Any naturally occurring amino acid
<220> FEATURE:
<221> NAME/KEY: MOD_RES
<222> LOCATION: (8)..(9)
<223> OTHER INFORMATION: Any naturally occurring amino acid
<220> FEATURE:
<221> NAME/KEY: MOD_RES
<222> LOCATION: (12)..(13)
<223> OTHER INFORMATION: Any naturally occurring amino acid
<220> FEATURE:
<221> NAME/KEY: MOD_RES
<222> LOCATION: (15)..(20)
<223> OTHER INFORMATION: Any naturally occurring amino acid
<220> FEATURE:
<221> NAME/KEY: MOD_RES
<222> LOCATION: (22)..(22)
<223> OTHER INFORMATION: Any naturally occurring amino acid
<220> FEATURE:
<221> NAME/KEY: MOD_RES
<222> LOCATION: (26)..(27)
<223> OTHER INFORMATION: Any naturally occurring amino acid
<220> FEATURE:
<221> NAME/KEY: MOD_RES
<222> LOCATION: (29)..(29)
<223> OTHER INFORMATION: Any naturally occurring amino acid
<220> FEATURE:
<221> NAME/KEY: MOD_RES
<222> LOCATION: (32)..(32)
<223> OTHER INFORMATION: Any naturally occurring amino acid
<220> FEATURE:
<221> NAME/KEY: MOD_RES
<222> LOCATION: (36)..(36)
<223> OTHER INFORMATION: Any naturally occurring amino acid
<220> FEATURE:
<221> NAME/KEY: MOD_RES
<222> LOCATION: (43)..(43)
<223> OTHER INFORMATION: Any naturally occurring amino acid
<220> FEATURE:
<221> NAME/KEY: MOD_RES
<222> LOCATION: (66)..(66)
<223> OTHER INFORMATION: Any naturally occurring amino acid
<220> FEATURE:
<221> NAME/KEY: MOD_RES
<222> LOCATION: (70)..(70)
<223> OTHER INFORMATION: Any naturally occurring amino acid
<220> FEATURE:
<221> NAME/KEY: MOD_RES
<222> LOCATION: (72)..(72)
<223> OTHER INFORMATION: Any naturally occurring amino acid
<220> FEATURE:
<221> NAME/KEY: MOD_RES
<222> LOCATION: (74)..(74)
<223> OTHER INFORMATION: Any naturally occurring amino acid
<220> FEATURE:
<221> NAME/KEY: MOD_RES
<222> LOCATION: (77)..(82)
<223> OTHER INFORMATION: Any naturally occurring amino acid
<220> FEATURE:
<221> NAME/KEY: MOD_RES
<222> LOCATION: (84)..(84)
<223> OTHER INFORMATION: Any naturally occurring amino acid
<220> FEATURE:
<221> NAME/KEY: MOD_RES
<222> LOCATION: (88)..(89)
<223> OTHER INFORMATION: Any naturally occurring amino acid
<220> FEATURE:
<221> NAME/KEY: MOD_RES
<222> LOCATION: (93)..(93)
<223> OTHER INFORMATION: Any naturally occurring amino acid
<220> FEATURE:
<221> NAME/KEY: MOD_RES
<222> LOCATION: (96)..(96)
<223> OTHER INFORMATION: Any naturally occurring amino acid
<220> FEATURE:
<221> NAME/KEY: MOD_RES
<222> LOCATION: (98)..(99)
<223> OTHER INFORMATION: Any naturally occurring amino acid
<220> FEATURE:
<221> NAME/KEY: MOD_RES
<222> LOCATION: (101)..(101)
<223> OTHER INFORMATION: Any naturally occurring amino acid
<220> FEATURE:
<221> NAME/KEY: MOD_RES
<222> LOCATION: (105)..(106)
<223> OTHER INFORMATION: Any naturally occurring amino acid
<220> FEATURE:
<221> NAME/KEY: MOD_RES
<222> LOCATION: (109)..(111)
<223> OTHER INFORMATION: Any naturally occurring amino acid
<220> FEATURE:
<221> NAME/KEY: MOD_RES
<222> LOCATION: (113)..(123)
<223> OTHER INFORMATION: Any naturally occurring amino acid
<220> FEATURE:
<221> NAME/KEY: MOD_RES
<222> LOCATION: (128)..(128)
<223> OTHER INFORMATION: Any naturally occurring amino acid
<220> FEATURE:
<221> NAME/KEY: MOD_RES
<222> LOCATION: (133)..(133)
<223> OTHER INFORMATION: Any naturally occurring amino acid
<220> FEATURE:
<221> NAME/KEY: MOD_RES
<222> LOCATION: (143)..(143)
<223> OTHER INFORMATION: Any naturally occurring amino acid
<220> FEATURE:
<221> NAME/KEY: MOD_RES
<222> LOCATION: (145)..(145)
<223> OTHER INFORMATION: Any naturally occurring amino acid
<220> FEATURE:
<221> NAME/KEY: MOD_RES
<222> LOCATION: (151)..(151)
<223> OTHER INFORMATION: Any naturally occurring amino acid
<220> FEATURE:
<221> NAME/KEY: MOD_RES
<222> LOCATION: (153)..(154)
<223> OTHER INFORMATION: Any naturally occurring amino acid
<220> FEATURE:
<221> NAME/KEY: MOD_RES
<222> LOCATION: (159)..(159)
<223> OTHER INFORMATION: Any naturally occurring amino acid
<220> FEATURE:
<221> NAME/KEY: MOD_RES
<222> LOCATION: (161)..(161)
<223> OTHER INFORMATION: Any naturally occurring amino acid
<220> FEATURE:
<221> NAME/KEY: MOD_RES
<222> LOCATION: (164)..(164)
<223> OTHER INFORMATION: Any naturally occurring amino acid
<220> FEATURE:
<221> NAME/KEY: MOD_RES
<222> LOCATION: (168)..(168)
<223> OTHER INFORMATION: Any naturally occurring amino acid
<220> FEATURE:
<221> NAME/KEY: MOD_RES
<222> LOCATION: (170)..(171)
<223> OTHER INFORMATION: Any naturally occurring amino acid
<220> FEATURE:
<221> NAME/KEY: MOD_RES
<222> LOCATION: (175)..(175)
<223> OTHER INFORMATION: Any naturally occurring amino acid
<220> FEATURE:
<221> NAME/KEY: MOD_RES
<222> LOCATION: (183)..(183)
<223> OTHER INFORMATION: Any naturally occurring amino acid
<220> FEATURE:
<221> NAME/KEY: MOD_RES
<222> LOCATION: (190)..(233)
<223> OTHER INFORMATION: Any naturally occurring amino acid
<220> FEATURE:
<221> NAME/KEY: MOD_RES
<222> LOCATION: (237)..(237)
<223> OTHER INFORMATION: Any naturally occurring amino acid
<220> FEATURE:
<221> NAME/KEY: MOD_RES
<222> LOCATION: (239)..(240)
<223> OTHER INFORMATION: Any naturally occurring amino acid
<220> FEATURE:
<221> NAME/KEY: MOD_RES
<222> LOCATION: (244)..(245)
<223> OTHER INFORMATION: Any naturally occurring amino acid
<220> FEATURE:
<221> NAME/KEY: MOD_RES
<222> LOCATION: (262)..(262)
<223> OTHER INFORMATION: Any naturally occurring amino acid
<220> FEATURE:
<221> NAME/KEY: MOD_RES
<222> LOCATION: (273)..(273)
<223> OTHER INFORMATION: Any naturally occurring amino acid
<220> FEATURE:
<221> NAME/KEY: MOD_RES
<222> LOCATION: (277)..(277)
<223> OTHER INFORMATION: Any naturally occurring amino acid
<220> FEATURE:
<221> NAME/KEY: MOD_RES
<222> LOCATION: (292)..(292)
<223> OTHER INFORMATION: Any naturally occurring amino acid
<220> FEATURE:
<221> NAME/KEY: MOD_RES
<222> LOCATION: (312)..(312)
<223> OTHER INFORMATION: Any naturally occurring amino acid
<220> FEATURE:
<221> NAME/KEY: MOD_RES
<222> LOCATION: (346)..(346)
<223> OTHER INFORMATION: Any naturally occurring amino acid
<220> FEATURE:
<221> NAME/KEY: MOD_RES
<222> LOCATION: (350)..(350)
<223> OTHER INFORMATION: Any naturally occurring amino acid
<220> FEATURE:
<221> NAME/KEY: MOD_RES
<222> LOCATION: (353)..(366)
<223> OTHER INFORMATION: Any naturally occurring amino acid
<220> FEATURE:
<221> NAME/KEY: MOD_RES
<222> LOCATION: (368)..(370)
<223> OTHER INFORMATION: Any naturally occurring amino acid
<220> FEATURE:
<221> NAME/KEY: MOD_RES
<222> LOCATION: (374)..(374)
<223> OTHER INFORMATION: Any naturally occurring amino acid
<220> FEATURE:
<221> NAME/KEY: MOD_RES
<222> LOCATION: (378)..(378)
<223> OTHER INFORMATION: Any naturally occurring amino acid
<220> FEATURE:
<221> NAME/KEY: MOD_RES
<222> LOCATION: (383)..(383)
<223> OTHER INFORMATION: Any naturally occurring amino acid
<220> FEATURE:
<221> NAME/KEY: MOD_RES
<222> LOCATION: (410)..(410)
<223> OTHER INFORMATION: Any naturally occurring amino acid
<220> FEATURE:
<221> NAME/KEY: MOD_RES
<222> LOCATION: (412)..(412)
<223> OTHER INFORMATION: Any naturally occurring amino acid
<220> FEATURE:
<221> NAME/KEY: MOD_RES
<222> LOCATION: (426)..(426)
<223> OTHER INFORMATION: Any naturally occurring amino acid
<220> FEATURE:
<221> NAME/KEY: MOD_RES
<222> LOCATION: (454)..(454)
<223> OTHER INFORMATION: Any naturally occurring amino acid
<220> FEATURE:
<221> NAME/KEY: MOD_RES
<222> LOCATION: (463)..(463)
<223> OTHER INFORMATION: Any naturally occurring amino acid
<220> FEATURE:
<221> NAME/KEY: MOD_RES
<222> LOCATION: (474)..(474)
<223> OTHER INFORMATION: Any naturally occurring amino acid
<220> FEATURE:
<221> NAME/KEY: MOD_RES
<222> LOCATION: (477)..(479)
<223> OTHER INFORMATION: Any naturally occurring amino acid
<220> FEATURE:
<221> NAME/KEY: MOD_RES
<222> LOCATION: (485)..(485)
<223> OTHER INFORMATION: Any naturally occurring amino acid
<220> FEATURE:
<221> NAME/KEY: MOD_RES
<222> LOCATION: (487)..(496)
<223> OTHER INFORMATION: Any naturally occurring amino acid
<220> FEATURE:
<221> NAME/KEY: MOD_RES
<222> LOCATION: (499)..(499)
<223> OTHER INFORMATION: Any naturally occurring amino acid
<220> FEATURE:
<221> NAME/KEY: MOD_RES
<222> LOCATION: (502)..(502)
<223> OTHER INFORMATION: Any naturally occurring amino acid
<220> FEATURE:
<221> NAME/KEY: MOD_RES
<222> LOCATION: (527)..(527)
<223> OTHER INFORMATION: Any naturally occurring amino acid
<220> FEATURE:
<221> NAME/KEY: MOD_RES
<222> LOCATION: (529)..(529)
<223> OTHER INFORMATION: Any naturally occurring amino acid
<220> FEATURE:
<221> NAME/KEY: MOD_RES
<222> LOCATION: (531)..(540)
<223> OTHER INFORMATION: Any naturally occurring amino acid
<220> FEATURE:
<221> NAME/KEY: MOD_RES
<222> LOCATION: (542)..(542)
<223> OTHER INFORMATION: Any naturally occurring amino acid
<220> FEATURE:
<221> NAME/KEY: MOD_RES
<222> LOCATION: (545)..(545)
<223> OTHER INFORMATION: Any naturally occurring amino acid
<220> FEATURE:
<221> NAME/KEY: MOD_RES
<222> LOCATION: (548)..(549)
<223> OTHER INFORMATION: Any naturally occurring amino acid
<220> FEATURE:
<221> NAME/KEY: MOD_RES
<222> LOCATION: (557)..(557)
<223> OTHER INFORMATION: Any naturally occurring amino acid
<220> FEATURE:
<221> NAME/KEY: MOD_RES
<222> LOCATION: (564)..(564)
<223> OTHER INFORMATION: Any naturally occurring amino acid
<220> FEATURE:
<221> NAME/KEY: MOD_RES
<222> LOCATION: (571)..(571)
<223> OTHER INFORMATION: Any naturally occurring amino acid
<220> FEATURE:
<221> NAME/KEY: MOD_RES
<222> LOCATION: (594)..(594)
<223> OTHER INFORMATION: Any naturally occurring amino acid
<220> FEATURE:
<221> NAME/KEY: MOD_RES
<222> LOCATION: (596)..(598)
<223> OTHER INFORMATION: Any naturally occurring amino acid
<220> FEATURE:
<221> NAME/KEY: MOD_RES
<222> LOCATION: (600)..(608)
<223> OTHER INFORMATION: Any naturally occurring amino acid
<220> FEATURE:
<221> NAME/KEY: MOD_RES
<222> LOCATION: (610)..(617)
<223> OTHER INFORMATION: Any naturally occurring amino acid
<220> FEATURE:
<221> NAME/KEY: MOD_RES
<222> LOCATION: (619)..(619)
<223> OTHER INFORMATION: Any naturally occurring amino acid
<220> FEATURE:
<221> NAME/KEY: MOD_RES
<222> LOCATION: (622)..(622)
<223> OTHER INFORMATION: Any naturally occurring amino acid
<220> FEATURE:
<221> NAME/KEY: MOD_RES
<222> LOCATION: (661)..(661)
<223> OTHER INFORMATION: Any naturally occurring amino acid
<220> FEATURE:
<221> NAME/KEY: MOD_RES -continued
<222> LOCATION: (668)..(672)
<223> OTHER INFORMATION: Any naturally occurring amino acid
<220> FEATURE:
<221> NAME/KEY: MOD_RES
<222> LOCATION: (675)..(675)
<223> OTHER INFORMATION: Any naturally occurring amino acid
<220> FEATURE:
<221> NAME/KEY: MOD_RES
<222> LOCATION: (678)..(680)
<223> OTHER INFORMATION: Any naturally occurring amino acid
<220> FEATURE:
<221> NAME/KEY: MOD_RES
<222> LOCATION: (682)..(683)
<223> OTHER INFORMATION: Any naturally occurring amino acid
<220> FEATURE:
<221> NAME/KEY: MOD_RES
<222> LOCATION: (685)..(687)
<223> OTHER INFORMATION: Any naturally occurring amino acid
<220> FEATURE:
<221> NAME/KEY: MOD_RES
<222> LOCATION: (690)..(690)
<223> OTHER INFORMATION: Any naturally occurring amino acid
<220> FEATURE:
<221> NAME/KEY: MOD_RES
<222> LOCATION: (692)..(696)
<223> OTHER INFORMATION: Any naturally occurring amino acid
<220> FEATURE:
<221> NAME/KEY: MOD_RES
<222> LOCATION: (698)..(699)
<223> OTHER INFORMATION: Any naturally occurring amino acid
<220> FEATURE:
<221> NAME/KEY: MOD_RES
<222> LOCATION: (701)..(709)
<223> OTHER INFORMATION: Any naturally occurring amino acid
<220> FEATURE:
<221> NAME/KEY: MOD_RES
<222> LOCATION: (713)..(713)
<223> OTHER INFORMATION: Any naturally occurring amino acid
<220> FEATURE:
<221> NAME/KEY: MOD_RES
<222> LOCATION: (718)..(719)
<223> OTHER INFORMATION: Any naturally occurring amino acid
<220> FEATURE:
<221> NAME/KEY: MOD_RES
<222> LOCATION: (721)..(722)
<223> OTHER INFORMATION: Any naturally occurring amino acid
<220> FEATURE:
<221> NAME/KEY: MOD_RES
<222> LOCATION: (724)..(727)
<223> OTHER INFORMATION: Any naturally occurring amino acid
<220> FEATURE:
<221> NAME/KEY: MOD_RES
<222> LOCATION: (729)..(729)
<223> OTHER INFORMATION: Any naturally occurring amino acid
<220> FEATURE:
<221> NAME/KEY: MOD_RES
<222> LOCATION: (732)..(737)
<223> OTHER INFORMATION: Any naturally occurring amino acid
<220> FEATURE:
<221> NAME/KEY: MOD_RES
<222> LOCATION: (755)..(755)
<223> OTHER INFORMATION: Any naturally occurring amino acid
<220> FEATURE:
<221> NAME/KEY: MOD_RES
<222> LOCATION: (757)..(757)
<223> OTHER INFORMATION: Any naturally occurring amino acid
<220> FEATURE:
<221> NAME/KEY: MOD_RES
<222> LOCATION: (763)..(763)
<223> OTHER INFORMATION: Any naturally occurring amino acid
<220> FEATURE:
<221> NAME/KEY: MOD_RES
<222> LOCATION: (767)..(767)
<223> OTHER INFORMATION: Any naturally occurring amino acid
<220> FEATURE:
<221> NAME/KEY: MOD_RES
<222> LOCATION: (781)..(789)
<223> OTHER INFORMATION: Any naturally occurring amino acid
<220> FEATURE:
<221> NAME/KEY: MOD_RES
<222> LOCATION: (805)..(806)
<223> OTHER INFORMATION: Any naturally occurring amino acid
<220> FEATURE:
<221> NAME/KEY: MOD_RES
<222> LOCATION: (813)..(813)
<223> OTHER INFORMATION: Any naturally occurring amino acid
<220> FEATURE:
<221> NAME/KEY: MOD_RES
<222> LOCATION: (903)..(903)
<223> OTHER INFORMATION: Any naturally occurring amino acid
<220> FEATURE:
<221> NAME/KEY: MOD_RES
<222> LOCATION: (908)..(908)
<223> OTHER INFORMATION: Any naturally occurring amino acid
<220> FEATURE:
<221> NAME/KEY: MOD_RES
<222> LOCATION: (924)..(924)
<223> OTHER INFORMATION: Any naturally occurring amino acid
<220> FEATURE:
<221> NAME/KEY: MOD_RES
<222> LOCATION: (981)..(981)
<223> OTHER INFORMATION: Any naturally occurring amino acid
<220> FEATURE:
<221> NAME/KEY: MOD_RES
<222> LOCATION: (1186)..(1186)
<223> OTHER INFORMATION: Any naturally occurring amino acid
<220> FEATURE:
<221> NAME/KEY: MOD_RES
<222> LOCATION: (1189)..(1190)
<223> OTHER INFORMATION: Any naturally occurring amino acid
<220> FEATURE:
<221> NAME/KEY: MOD_RES
<222> LOCATION: (1192)..(1198)
<223> OTHER INFORMATION: Any naturally occurring amino acid
<220> FEATURE:
<221> NAME/KEY: MOD_RES
<222> LOCATION: (1200)..(1200)
<223> OTHER INFORMATION: Any naturally occurring amino acid
<220> FEATURE:
<221> NAME/KEY: MOD_RES
<222> LOCATION: (1202)..(1202)
<223> OTHER INFORMATION: Any naturally occurring amino acid
<220> FEATURE:
<221> NAME/KEY: MOD_RES
<222> LOCATION: (1204)..(1289)
<223> OTHER INFORMATION: Any naturally occurring amino acid

<400> SEQUENCE: 182

```
Xaa Met Ala Ser Xaa Leu Leu Xaa Xaa Arg Phe Xaa Xaa Glu Xaa Xaa
1               5                   10                  15

Xaa Xaa Xaa Xaa Ala Xaa Pro Ser Trp Xaa Xaa Lys Xaa Leu Thr Xaa
            20                  25                  30

Pro Ile Gln Xaa Ile Ser Arg Phe Ala Ala Xaa His Pro Ile His Thr
        35                  40                  45

Ile Val Leu Val Ala Leu Leu Ala Ser Thr Ala Tyr Leu Gly Leu Leu
    50                  55                  60

Gln Xaa Ser Leu Phe Xaa Trp Xaa Leu Xaa Ser Asn Xaa Xaa Xaa Xaa
65                  70                  75                  80

Xaa Xaa Asp Xaa Thr Ser Leu Xaa Xaa Gly Ser Arg Xaa Leu Arg Xaa
                85                  90                  95

Gly Xaa Xaa Thr Xaa Trp Arg Trp Xaa Xaa Ile Asp Xaa Xaa Xaa Ile
            100                 105                 110

Xaa Xaa Xaa Xaa Xaa Xaa Xaa Xaa Xaa Xaa Xaa Ala Ala Asp Ala Xaa
        115                 120                 125

His Leu Ala Leu Xaa Thr Leu Val Phe Pro Asp Thr Gln Ser Xaa Glu
    130                 135                 140

Xaa Ala Ser Thr Ile Pro Xaa Ala Xaa Xaa Val Pro Val Pro Xaa Asn
145                 150                 155                 160

Xaa Ser Ile Xaa Leu Leu Pro Xaa Thr Xaa Xaa Ile Phe Thr Xaa Tyr
```

```
                165                 170                 175

Ser Gln Asp Ser Ser Leu Xaa Phe Ser Leu Pro Tyr Ser Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Asp Ile Val Xaa Trp Xaa Xaa
225                 230                 235                 240

Asn Ala Trp Xaa Xaa Phe Ser Asp Leu Ile Lys Asn Ala Asp Thr Phe
                245                 250                 255

Asp Ile Ile Ile Met Xaa Leu Gly Tyr Leu Ala Met His Tyr Thr Phe
            260                 265                 270

Xaa Ser Leu Phe Xaa Ser Met Arg Lys Leu Gly Ser Lys Phe Trp Leu
        275                 280                 285

Ala Thr Ser Xaa Leu Phe Ser Ser Ile Phe Ala Phe Leu Leu Gly Leu
    290                 295                 300

Leu Val Thr Thr Lys Leu Gly Xaa Val Pro Ile Ser Met Leu Leu Leu
305                 310                 315                 320

Ser Glu Gly Leu Pro Phe Leu Val Val Thr Ile Gly Phe Glu Lys Lys
                325                 330                 335

Ile Val Leu Thr Arg Ala Val Leu Ser Xaa Ala Ile Asp Xaa Arg Arg
            340                 345                 350

Xaa Xaa Xaa Xaa Xaa Xaa Xaa Xaa Xaa Xaa Xaa Xaa Xaa Xaa Ser Xaa
        355                 360                 365

Xaa Xaa Ser Ile Gln Xaa Ala Ile Gln Xaa Ala Ile Lys Glu Xaa Gly
    370                 375                 380

Phe Glu Ile Ile Arg Asp Tyr Ala Ile Glu Ile Ser Ile Leu Ile Ala
385                 390                 395                 400

Gly Ala Ala Ser Gly Val Gln Gly Gly Xaa Leu Xaa Gln Phe Cys Phe
                405                 410                 415

Leu Ala Ala Trp Ile Leu Phe Phe Asp Xaa Ile Leu Leu Phe Thr Phe
            420                 425                 430

Tyr Ser Ala Ile Leu Ala Ile Lys Leu Glu Ile Asn Arg Ile Lys Arg
        435                 440                 445

His Val Ile Ile Arg Xaa Ala Leu Glu Glu Asp Gly Val Ser Xaa Ser
    450                 455                 460

Val Ala Glu Lys Val Ala Lys Ser Glu Xaa Asp Trp Xaa Xaa Xaa Lys
465                 470                 475                 480

Gly Ser Asp Ser Xaa Phe Xaa Xaa Xaa Xaa Xaa Xaa Xaa Xaa Xaa Xaa
                485                 490                 495

Lys Ser Xaa Ala Ile Xaa Ile Phe Lys Val Leu Met Ile Leu Gly Phe
            500                 505                 510

Val Leu Ile Asn Leu Val Asn Leu Thr Ala Ile Pro Phe Arg Xaa Ala
        515                 520                 525

Xaa Ser Xaa Xaa Xaa Xaa Xaa Xaa Xaa Xaa Xaa Xaa Leu Xaa Gly Val
    530                 535                 540

Xaa Ser Pro Xaa Xaa Val Asp Pro Phe Lys Val Ala Xaa Asn Leu Leu
545                 550                 555                 560

Asp Ala Ile Xaa Ala Ala Ala Lys Ser Asn Xaa Arg Glu Thr Leu Val
                565                 570                 575

Thr Val Val Thr Pro Ile Lys Tyr Glu Leu Glu Tyr Pro Ser Ile His
            580                 585                 590
```

-continued

```
Tyr Xaa Glu Xaa Xaa Xaa Ser Xaa Xaa Xaa Xaa Xaa Xaa Xaa Xaa Xaa
        595                 600                 605

Leu Xaa Xaa Xaa Xaa Xaa Xaa Xaa Xaa Gly Xaa Gly Gly Xaa Met Leu
    610                 615                 620

Gly Ser Val Ser Lys Ser Ile Glu Asp Pro Val Ile Ser Lys Trp Ile
625                 630                 635                 640

Val Ile Ala Leu Ala Leu Ser Ile Ala Leu Asn Val Tyr Leu Phe Asn
                645                 650                 655

Ala Ala Arg Trp Xaa Ile Lys Asp Pro Asn Val Xaa Xaa Xaa Xaa Xaa
            660                 665                 670

Glu Val Xaa Glu Leu Xaa Xaa Xaa Gln Xaa Xaa Asn Xaa Xaa Xaa Ser
        675                 680                 685

Ala Xaa Leu Xaa Xaa Xaa Xaa Xaa Ile Xaa Xaa Thr Xaa Xaa Xaa Xaa
    690                 695                 700

Xaa Xaa Xaa Xaa Xaa Thr Pro Ala Xaa Thr Asp Asp Glu Xaa Xaa Ser
705                 710                 715                 720

Xaa Xaa Ser Xaa Xaa Xaa Xaa Val Xaa Lys Ile Xaa Xaa Xaa Xaa Xaa
                725                 730                 735

Xaa Ile Arg Ser Leu Glu Glu Leu Glu Ala Leu Leu Ala Ala Lys Lys
            740                 745                 750

Thr Lys Xaa Leu Xaa Asp Glu Glu Val Val Xaa Leu Ser Leu Xaa Gly
        755                 760                 765

Lys Leu Pro Leu Tyr Ala Leu Glu Lys Thr Leu Gly Xaa Xaa Xaa Xaa
    770                 775                 780

Xaa Xaa Xaa Xaa Xaa Asp Phe Thr Arg Ala Val Lys Ile Arg Arg Ser
785                 790                 795                 800

Ile Ile Ser Arg Xaa Xaa Ala Thr Ser Ala Leu Thr Xaa Ser Leu Glu
                805                 810                 815

Ser Ser Lys Leu Pro Tyr Lys Asn Tyr Asn Tyr Asp Arg Val Phe Gly
            820                 825                 830

Ala Cys Cys Glu Asn Val Ile Gly Tyr Met Pro Leu Pro Val Gly Val
        835                 840                 845

Ala Gly Pro Leu Val Ile Asp Gly Gln Ser Tyr His Ile Pro Met Ala
    850                 855                 860

Thr Thr Glu Gly Val Leu Val Ala Ser Ala Ser Arg Gly Cys Lys Ala
865                 870                 875                 880

Ile Asn Ala Gly Gly Gly Ala Val Thr Val Leu Thr Ala Asp Gly Met
                885                 890                 895

Thr Arg Gly Pro Cys Val Xaa Phe Pro Thr Leu Xaa Arg Ala Gly Ala
            900                 905                 910

Ala Lys Ile Trp Leu Asp Ser Glu Glu Gly Gln Xaa Ser Met Lys Lys
        915                 920                 925

Ala Phe Asn Ser Thr Ser Arg Phe Ala Arg Leu Gln His Ile Lys Thr
    930                 935                 940

Ala Leu Ala Gly Thr Leu Leu Phe Ile Arg Phe Lys Thr Thr Thr Gly
945                 950                 955                 960

Asp Ala Met Gly Met Asn Met Ile Ser Lys Gly Val Glu His Ala Leu
                965                 970                 975

Ser Val Met Val Xaa Glu Tyr Gly Phe Glu Asp Met Glu Ile Val Ser
            980                 985                 990

Val Ser Gly Asn Tyr Cys Thr Asp  Lys Lys Pro Ala Ala  Ile Asn Trp
        995                 1000                 1005

Ile Asp  Gly Arg Gly Lys Ser  Val Val Ala Glu Ala  Thr Ile Pro
    1010                 1015                 1020
```

```
Gly Asp  Val Val Lys Ser Val  Leu Lys Ser Asp Val  Asp Ala Leu
    1025                 1030                 1035

Val Glu  Leu Asn Ile Ser Lys  Asn Leu Ile Gly Ser  Ala Met Ala
    1040                 1045                 1050

Gly Ser  Val Gly Gly Phe Asn  Ala His Ala Ala Asn  Ile Val Thr
    1055                 1060                 1065

Ala Ile  Phe Leu Ala Thr Gly  Gln Asp Pro Ala Gln  Asn Val Glu
    1070                 1075                 1080

Ser Ser  Asn Cys Ile Thr Leu  Met Lys Asn Val Asp  Gly Asn Leu
    1085                 1090                 1095

Gln Ile  Ser Val Ser Met Pro  Ser Ile Glu Val Gly  Thr Ile Gly
    1100                 1105                 1110

Gly Gly  Thr Ile Leu Glu Pro  Gln Gly Ala Met Leu  Asp Leu Leu
    1115                 1120                 1125

Gly Val  Arg Gly Pro His Pro  Thr Asn Pro Gly Asp  Asn Ala Arg
    1130                 1135                 1140

Gln Leu  Ala Arg Ile Ile Ala  Ala Ala Val Leu Ala  Gly Glu Leu
    1145                 1150                 1155

Ser Leu  Cys Ser Ala Leu Ala  Ala Gly His Leu Val  Gln Ala His
    1160                 1165                 1170

Met Thr  His Asn Arg Ser Ala  Ala Pro Thr Arg Ser  Xaa Thr Pro
    1175                 1180                 1185

Xaa Xaa  Ala Xaa Xaa Xaa Xaa  Xaa Xaa Xaa Thr Xaa  Ile Xaa Ser
    1190                 1195                 1200

Xaa Xaa  Xaa Xaa Xaa Xaa Xaa  Xaa Xaa Xaa Xaa Xaa  Xaa Xaa Xaa
    1205                 1210                 1215

Xaa Xaa  Xaa Xaa Xaa Xaa Xaa  Xaa Xaa Xaa Xaa Xaa  Xaa Xaa Xaa
    1220                 1225                 1230

Xaa Xaa  Xaa Xaa Xaa Xaa Xaa  Xaa Xaa Xaa Xaa Xaa  Xaa Xaa Xaa
    1235                 1240                 1245

Xaa Xaa  Xaa Xaa Xaa Xaa Xaa  Xaa Xaa Xaa Xaa Xaa  Xaa Xaa Xaa
    1250                 1255                 1260

Xaa Xaa  Xaa Xaa Xaa Xaa Xaa  Xaa Xaa Xaa Xaa Xaa  Xaa Xaa Xaa
    1265                 1270                 1275

Xaa Xaa  Xaa Xaa Xaa Xaa Xaa  Xaa Xaa Xaa Xaa
    1280                 1285
```

<210> SEQ ID NO 183
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
ctctagacac aaaaatgtcg caaccccaga acgt 34

<210> SEQ ID NO 184
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
cacgcgtcta ctgcttgatc tcgtact 27

<210> SEQ ID NO 185
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
cgctagccac aaaaatggac tacatcattt cggcgc 36

<210> SEQ ID NO 186
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186
cacgcgtcta atgggtccag ggaccga 27

<210> SEQ ID NO 187
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 187
ctctagacac aaaaatgacc acctattcgg ctccg 35

<210> SEQ ID NO 188
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 188
cggcgcgccc tacttgaacc ccttctcga 29

<210> SEQ ID NO 189
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 189
ctctagacac aaaaatgatc caccaggcct ccacca 36

<210> SEQ ID NO 190
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 190
cacgcgtcta cttgctgttc ttcagag 27

<210> SEQ ID NO 191
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ctctagacac aaaaatgacg acgtcttaca gcga 34

<210> SEQ ID NO 192
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cacgcgtcta cttgatccac cgccgaa 27

<210> SEQ ID NO 193
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
ctctagacac aaaaatgtcc aaggcgaaat tcgaa 35

<210> SEQ ID NO 194
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
cacgcgtcta cttctgtcgc ttgtaaa 27

<210> SEQ ID NO 195
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
ctctagacac aaaaatgtta cgactacgaa ccat 34

<210> SEQ ID NO 196
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cacgcgtcta gtcgtaatcc cgcacat 27

<210> SEQ ID NO 197
<211> LENGTH: 34

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
cgctagccac aaaaatgccg cagcaagcaa tgga 34

<210> SEQ ID NO 198
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
cacgcgttta accatgcagc cgctcaa 27

<210> SEQ ID NO 199
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
ctctagacac aaaaatgttc cgaacccgag ttac 34

<210> SEQ ID NO 200
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
cacgcgttta agggttctgc ttgacaa 27

<210> SEQ ID NO 201
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
ctctagacac aaaaatgaca caaacgcaca atct 34

<210> SEQ ID NO 202
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
cacgcgttta catcttgtac gcagggt 27

<210> SEQ ID NO 203
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
ctctagacac aaaaatggaa gccaaccccg aagt 34

<210> SEQ ID NO 204
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
cacgcgttca tttcagaagg tacttct 27

<210> SEQ ID NO 205
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
ctctagacac aaaaatgcga ctcactctgc cc 32

<210> SEQ ID NO 206
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 206
cacgcgtcta ctcgacagaa gagaccttc 29

<210> SEQ ID NO 207
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
ttctagaccc aaaaatgtct gccaacgaga acatctc 37

<210> SEQ ID NO 208
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 208
aacgcgtcta tgatcgagtc ttggccttg 29

<210> SEQ ID NO 209
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 209
ttctagacac aaaaatgtca gcgaaatcca ttcacga 37

<210> SEQ ID NO 210
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 210
cacgcgttaa actccgagag gagtgg 26

<210> SEQ ID NO 211
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 211
ctctagacac aaaagtggtt aaagctgtcg ttgc 34

<210> SEQ ID NO 212
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 212
cacgcgttta cttggcagga ggagggt 27

<210> SEQ ID NO 213
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 213
ctctagacac aaaaatgact ggcaccttac ccaa 34

<210> SEQ ID NO 214
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 214
cacgcgttca cgaggagccc ttggtga 27

<210> SEQ ID NO 215
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 215

ctctagacac aaaaatgact gacacttcaa acat                              34


<210> SEQ ID NO 216
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216

cacgcgttta agcatcgtaa gtggaag                                      27


<210> SEQ ID NO 217
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217

ctctagacac aaaaatgctc aaccttagaa ccgc                              34


<210> SEQ ID NO 218
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218

cacgcgtcta cttgagtcgc ttgataa                                      27


<210> SEQ ID NO 219
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Lys Ala Trp Val Ser Lys Gln Thr Asn Asp Val Pro His Arg Ile Leu
1               5                   10                  15

Ile Pro Leu His Thr Gln His Leu Ala
            20                  25
```